(12) United States Patent
Weiss et al.

(10) Patent No.: US 9,776,995 B2
(45) Date of Patent: Oct. 3, 2017

(54) BICYCLIC SULFONAMIDE COMPOUNDS AS SODIUM CHANNEL INHIBITORS

(71) Applicant: AMGEN INC., Thousand Oaks, CA (US)

(72) Inventors: Matthew Weiss, Boston, MA (US); Erin F. DiMauro, Cambridge, MA (US); Thomas Dineen, Somerville, MA (US); Russell Graceffa, Hampton, NH (US); Angel Guzman-Perez, Belmont, MA (US); Hongbing Huang, Brighton, MA (US); Charles Kreiman, Hopkinton, MA (US); Isaac E. Marx, Arlington, MA (US); Hanh Nho Nguyen, Jupiter, FL (US); Emily Anne Peterson, Cambridge, MA (US); Holly L. Deak, Brookline, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/898,070

(22) PCT Filed: Jun. 11, 2014

(86) PCT No.: PCT/US2014/041998
§ 371 (c)(1),
(2) Date: Dec. 11, 2015

(87) PCT Pub. No.: WO2014/201173
PCT Pub. Date: Dec. 18, 2014

(65) Prior Publication Data
US 2016/0137636 A1 May 19, 2016

Related U.S. Application Data

(60) Provisional application No. 61/983,958, filed on Apr. 24, 2014, provisional application No. 61/834,273, filed on Jun. 12, 2013.

(51) Int. Cl.
| | | |
|---|---|---|
| *C07D 417/14* | (2006.01) |
| *C07D 471/04* | (2006.01) |
| *C07D 413/12* | (2006.01) |
| *C07D 401/12* | (2006.01) |
| *C07D 413/14* | (2006.01) |
| *C07D 417/12* | (2006.01) |
| *C07C 53/18* | (2006.01) |
| *C07D 215/227* | (2006.01) |
| *C07D 403/12* | (2006.01) |
| *C07D 215/36* | (2006.01) |
| *C07D 241/44* | (2006.01) |
| *C07D 401/14* | (2006.01) |

(52) U.S. Cl.
CPC ............ *C07D 417/14* (2013.01); *C07C 53/18* (2013.01); *C07D 215/227* (2013.01); *C07D 215/36* (2013.01); *C07D 241/44* (2013.01); *C07D 401/12* (2013.01); *C07D 401/14* (2013.01); *C07D 403/12* (2013.01); *C07D 413/12* (2013.01); *C07D 413/14* (2013.01); *C07D 417/12* (2013.01); *C07D 471/04* (2013.01)

(58) Field of Classification Search
CPC ..................................................... C07D 400/01
See application file for complete search history.

(56) References Cited

U.S. PATENT DOCUMENTS 8,101,647 B2   1/2012   Chafeev et al.

FOREIGN PATENT DOCUMENTS

| WO | 2006/122014 A2 | 11/2006 |
| WO | 2013/025883 A1 | 2/2013 |
| WO | 2013/086229 A1 | 6/2013 |

OTHER PUBLICATIONS

Pinedo et al. (2000).*
McMahon et al. (2000).*
Halford, B., "Changing the Channel", *C & E News*, 92(12):10-14 (2014).
Goldin, A. L, *Ann Rev Physiol* 63:871-894, (2001).
Wood, J. N. and, Boorman, J. *Curr. Top Med. Chem.* 5:529-537, (2005).
Raymond, C.K., et al., J. Biol.Chem. (2004) 279 (44) :46234-41.
Yu, F.H., et al., Nat. Neuroscience (2006), 9 (9) 1142-1149.
Haim, B.D., et al., J. Neuroscience (2003) 23(26):8881-8892.
Tamaoka A., Internal Medicine (2003), (9):769-770.
Liu, H., et al., Am. J. Pharmacogenomics (2003), 3(3):173-179.
Dib-Hajj, S.D., et al., Proc. Natl. Acad. Sci. USA (1998), 95(15):8963-8968.
Fertleman C. R., et al., *Neuron* 52:767-774, (2006).
Yang Y., et al., J. Med. Genet. 41:171-174, (2004).
Drenth J. P. H., et al., *J Invest Dermatol* 124:1333-1338, (2005).
Cox J.J., et al., *Nature* 444:894-898, (2006).

(Continued)

*Primary Examiner* — Paul V Ward
(74) *Attorney, Agent, or Firm* — Elsa D. Lemoine

(57) ABSTRACT

The present invention provides compounds of Formula I or pharmaceutically acceptable salts thereof, that are inhibitors of voltage-gated sodium channels, in particular Nav1.7. The compounds are useful for the treatment of diseases treatable by inhibition of sodium channels such as pain disorders. Also provided are pharmaceutical compositions containing compounds of the present invention.

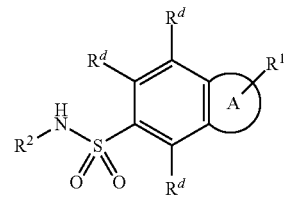

24 Claims, No Drawings

(56) References Cited

OTHER PUBLICATIONS

Goldberg Y. P., et al. *Clin Genet* 71:311-319, (2007).
Morinville et al., *J Comp Neurol.*, 504:680-689 (2007).
Ettinger and Argoff, *Neurotherapeutics*, 4:75-83 (2007).
Gonzalez, E. J.., et. al., "Small Molecule Blockers of Voltage-gated Sodium Channels." Voltage-Gated Ion Channels as Drug Targets. Ed. D. Triggle. Weinheim: WILEY-VCH Verlag GmbH & Co. KGaA, 2006. 168-192. Print.
Waxman, S. G., Nat Rev Neurosci. Dec. 2006; 7(12):932-41.
Do, M. T. H. et. al., *Neuron* 39 :109-120 (2003).
Puopolo et. al., *J. Neurosci.* 27(3) :645-656 (2007).
Hamann M., et. al., *Exp. Neurol.* 184:830-838, (2003).
McKinney B. C, et. al., *Genes Brain Behav.* 7:629-638, (2008).
Woodruff-Pak D. S., et. al., *Behav. Neurosci.* 120(2):229-240, (2006).
Haufe V., et. al., *.J Mol. Cell Cardiol.* 42:469-477, (2007).
Johannessen L. C., *CNS Drugs* 22(1)27-47, (2008).
Kim D. Y., et. al., *Nat. Cell. Biol.* 9(7):755-764, (2007).
Gillet L., et. al.,*J Biol Chem*, 284(13):8680-8691, (2009).
S. M. Berge, et al., "Pharmaceutical Salts," J Pharm Sci, 66(1): 1-19 (1977).
Higuchi, T., and Stella, W., "Pro-drugs as Novel Delivery Systems," vol. 14 of the A.C.S. Symposium Series, (1975).

\* cited by examiner

BICYCLIC SULFONAMIDE COMPOUNDS AS SODIUM CHANNEL INHIBITORS

RELATED APPLICATIONS

This application is a 35 U.S.C. §371 national application from PCT/US2014/041998, filed Jun. 11, 2014, which claims the benefit of U.S. Provisional Patent Application Nos. 61/834,273, filed on Jun. 12, 2013 and 61/983,958, filed on Apr. 24, 2014, which specifications are hereby incorporated herein by reference in their entireties.

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the U.S., roughly 30 of the population, suffer from chronic pain (*C & E News*, Bethany Halford, "Changing the Channel", published Mar. 24, 2014). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., $3^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential" *Curr. Top Med. Chem.* 5:529-537, 2005).

Nav1.1 and Nav1.2 are highly expressed in the brain (Raymond, C. K., et al., J. Biol. Chem. (2004) 279 (44): 46234-41) and are vital to normal brain function. Some loss of function due to Nav 1.1 mutations in humans, have resulted in epilepsy, presumably as these channels are expressed in inhibitory neurons (Yu, F. H., et al., Nat. Neuroscience (2006), 9 (9) 1142-1149). Nav1.1 is also expressed in the peripheral nervous system and inhibition of Nav1.1 in the periphery may provide relief of pain. Hence, while inhibiting Nav1.1 may provide use for treating pain, it may also be undesirable possibly leading to anxiety and over excitability. Nav1.3 is expressed primarily in the fetal central nervous system, and expression was found to be upregulated after nerve injury in rats (Hains, B. D., et al., J. Neuroscience (2030) 23(26):8881-8892). Nav1.4 is epressed primarily in skeletal muscle. Mutations of the gene and its' product have significant impact on muscle function, including paralysis (Tamaoka A., Internal Medicine (2003), (9): 769-770). Nav1.5 is expressed mainly in cardiac myocytes, including atria, ventricles, the sino-atrial node, atrio-ventricular node and cardiac Purkinje fibers. The rapid upstroke of the cardiac action potential and the rapid impulse condution through cardiac tissue is due to the opening of the Nav1.5 channel. Mutations of the Nav1.5 channel have resulted in arrhythmic syndromes, including QTc prolongation, Brugada syndrome (BS), sudden unexpected nocturnal death sybdrome (SUNDS) and sudden infant death syndrome (SIDS) (Liu, H., et al., Am. J. Pharmacogenomics (2003), 3(3):173-179). Nav1.6 is widely distributed voltage-gated sodium channel expressed throughout the central and peripheral nervous system. Nav1.8 is expressed primarily in sensory ganglia of the peripheral nervous system, such as the dorsal root ganglia. There are no identified Nav1.8 mutations that produce varied pain responses in humans. Nav1.8 differs from most neuronal Nav isotypes in that it is insensitive to inhibition by tetrodotoxin. Nav1.9, similar to nav1.8, is also a tetrodotoxin insensitive sodium cahnngel expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., to Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic doctors use for minor surgery. So is the dentists office staple novocaine. But these compounds don't distinguish between the various sodium channel subtypes, making them unsuitable for use as systemic pain killers. "If you give a drug that blocks Nav1.7 but also blocks Nav1.5, the patient will die of heart failure," says Glenn F. King, a professor at Australia's University of Queensland who studies venoms that block ion channels. "It will be a completely painless death, but the patient will die nonetheless." Thus, selectivity for Nav1.7 is desired, particularly over Nav1.5. Researchers have tailored their efforts to find a molecule that inhibitors or block the activity of only Nav1.7. To compound this problem, the identity, every location, every function and/or the tertiary structures of each subtype of voltage gated sodium channel proteins are not known or completely understood.

Consequently, a number of researchers are attempting to identify small molecule inhibitors of Nav1.7. For example, Chafeev et al disclose spiro-oxindole compound for the treatment and/or prevention of sodium channel-mediated diseases, such as pain, in U.S. Pat. No. 8,101,647. Thus, there is a need to identify Nav1.7 inhibitors selective over at least Nav1.5 to treat pain. The present invention provides compounds that are inhibitors of Nav 1.7.

SUMMARY OF THE INVENTION

In embodiment 1, the present invention provides of Formula I, or a pharmaceutically acceptable salt thereof,

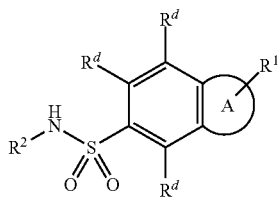

I wherein:

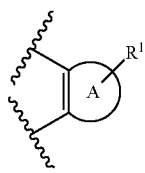

is

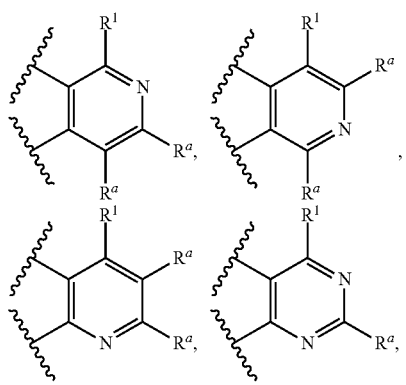

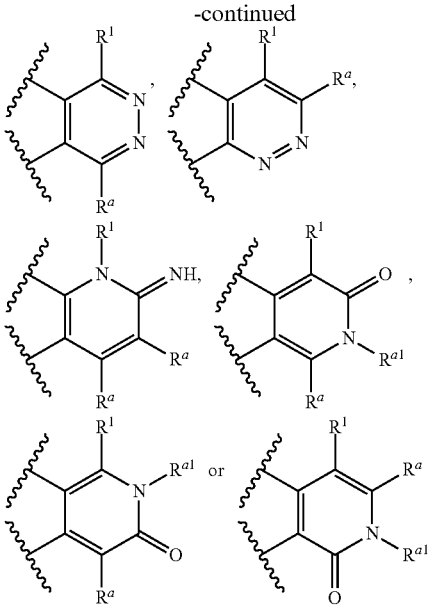

wherein each $R^a$ is independently H, halo, —$NR^cR^c$, —OH, hydroxy$C_{1-6}$alkyl, —$C_{1-6}$alkyl, —$OC_{1-6}$alkyl, —$C_{1-6}$haloalkyl, —$OC_{1-6}$haloalkyl or —CN, and $R^{a1}$ is H, —$C_{1-6}$alkyl or acetyl;

$R^1$ is a 6 membered aryl or heteroaryl, wherein the aryl or heteroaryl is substituted with from 1 to 4 substituents independently selected from A, halo, OH, —$NR^bR^b$, —$C_{1-6}$alkyl, —$OC_{1-6}$alkyl, —$OC_{1-6}$alkylCF_3, —$OC_{1-6}$alkylCN, —$(CR^eR^e)_mCN$, —$C_{1-6}$alkyl$OC_{1-6}$alkyl, —$CF_3$, —$CHF_2$, —$CH_2F$, —$OCF_3$, —$OCHF_2$, —$OCH_2F$, —$(CR^eR^e)_mA$, —$N(R^e)(CR^eR^e)_mA$, —$O(CR^eR^e)_mA$, —$O(CR^eR^e)_mOA$ or —$C(=O)A$, provided at least one substituent on $R^1$ is —$(CR^eR^e)_mA$, —$N(R^e)(CR^eR^e)_mA$, —$O(CR^eR^e)_mA$, —$O(CR^eR^e)_mOA$ or —$C(=O)A$;

A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —$NR^bR^b$, —$C_{1-6}$alkyl, —$OC_{1-6}$alkyl, —$(CR^eR^e)_mOH$, hydroxy$C_{1-6}$alkyl, —$CF_3$, —$CHF_2$, —$CH_2F$, —$OCF_3$, —$OCHF_2$, —$OCH_2F$, —CN, —$C(=O)NR^bR^b$, —$O(CR^eR^e)_mB$ or —$(CR^eR^e)_mB$;

B is a 3 to 5 membered cycloalkyl group that can be unsubstituted or substituted with from 1 to 4 substituents independently selected from Cl, F, Br, —$NHCH_3$, —$N(CH_3)_2$, —$C_{1-4}$alkyl, —$OC_{1-4}$alkyl, —$CF_3$, —$CHF_2$, —$CH_2F$, —$OCF_3$, —$OCHF_2$, —$OCH_2F$ or —CN;

$R^2$ is a 5 to 6 membered aryl or heteroaryl, where the heteroaryl can have from 1 to 3 heteroatoms independently selected from O, N or S, and the aryl and heteroaryl group can be unsubstituted or substituted with from 1 to 4 substituents independently selected from halo, —$NR^bR^b$, —$C_{1-6}$alkyl, —$OC_{1-6}$alkyl, —$(CR^eR^e)_nNR^bR^b$, —$CF_3$, —$CHF_2$, —$CH_2F$, —$OCF_3$, —$OCHF_2$, —$OCH_2F$, —CN or —$C(=O)NR^bR^b$;

each $R^b$ is independently H or —$C_{1-6}$alkyl;

each $R^d$ is independently H, halo, —CN, —$NR^cR^c$, —OH, —$C_{1-6}$alkyl, —$C_{1-6}$haloalkyl, —$OC_{1-6}$haloalkyl or —$OC_{1-6}$alkyl;

each $R^e$ is independently H or —$C_{1-6}$alkyl; and
each $R^e$ is independently H, halo, —CN, —$NR^cR^c$, —OH, —$C_{1-6}$alkyl or —$OC_{1-6}$alkyl;
each n is independently 0, 1, 2, 3 or 4;
each m is independently 0, 1, 2, 3 or 4;
provided that the compound is not
1-(4-fluoro-2-(pyrimidin-5-yl)phenyl)-N-(thiazol-2-yl)isoquinoline-6-sulfonamide;
1-(4-fluoro-2-(pyrimidin-2-yloxy)phenyl)-N-(thiazol-2-yl)isoquinoline-6-sulfonamide;
5-methoxy-4-(2-methoxy-4-(trifluoromethyl)phenyl)-N-(thiazol-2-yl)quinoline-7-sulfonamide;
N-3-isoxazolyl-1-(3-methoxy-1-phenyl-1H-pyrazol-4-yl)-6-isoquinolinesulfonamide;
1-(2-methoxy-6-(tetrahydro-2H-pyran-4-yloxy)-3-pyridinyl)-N-4-pyrimidinyl-6-isoquinolinesulfonamide;
1-(2-(cyclohexylamino)-6-methoxy-3-pyridinyl)-N-4-pyrimidinyl-6-isoquinolinesulfonamide;
1-(2-((4,4-difluorocyclohexyl)amino)-6-methoxy-3-pyridinyl)-N-4-pyrimidinyl-6-isoquinolinesulfonamide;
1-(2-methoxy-6-(tetrahydro-2H-pyran-4-ylamino)-3-pyridinyl)-N-4-pyrimidinyl-6-isoquinolinesulfonamide;
1-(2-(4,4-difluoro-1-piperidinyl)-6-methoxy-3-pyridinyl)-N-4-pyrimidinyl-6-isoquinolinesulfonamide;
1-(6-methoxy-2-(1-pyrrolidinyl)-3-pyridinyl)-N-4-pyrimidinyl-6-isoquinolinesulfonamide;
1-(2-methoxy-6-(4-morpholinyl)-3-pyridinyl)-N-4-pyrimidinyl-6-isoquinolinesulfonamide;
1-(6-methoxy-2-(4-morpholinyl)-3-pyridinyl)-N-4-pyrimidinyl-6-isoquinolinesulfonamide;
1-(6-methoxy-2-(1-piperidinyl)-3-pyridinyl)-N-4-pyrimidinyl-6-isoquinolinesulfonamide;
1-(6-methoxy-2-(tetrahydro-2H-pyran-4-ylamino)-3-pyridinyl)-N-4-pyrimidinyl-6-isoquinolinesulfonamide;
1-(3',5'-difluoro-3-methoxy-4-biphenylyl)-N-(5-methoxy-4-pyrimidinyl)-6-isoquinolinesulfonamide; or
1-(2-methyl-5-(3-oxetanylmethoxy)phenyl)-N-4-pyrimidinyl-6-isoquinolinesulfonamide.

In embodiment 1a, the present invention provides compounds of Formula Ia, and pharmaceutically acceptable salts thereof,

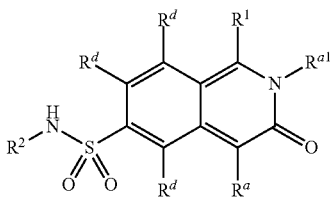

Ia wherein:
$R^a$ is H, halo, —$NR^cR^c$, —OH, hydroxy$C_{1-6}$alkyl, —$C_{1-6}$alkyl, —$OC_{1-6}$alkyl, —$C_{1-6}$haloalkyl, —$OC_{1-6}$haloalkyl or —CN;
$R^{a1}$ is H, —$C_{1-6}$alkyl or acetyl;
$R^1$ is a 6 membered aryl or heteroaryl, wherein the aryl or heteroaryl is substituted with from 1 to 4 substituents independently selected from A, halo, OH, —$NR^bR^b$, —$C_{1-6}$alkyl, —$OC_{1-6}$alkyl, —$OC_{1-6}$alkylCF$_3$, —$OC_{1-6}$alkylCN, —(CR$^e$R$^e$)$_m$CN, —$C_{1-6}$alkylOC$_{1-6}$alkyl, —CF$_3$, —CHF$_2$, —CH$_2$F, —OCF$_3$, —OCHF$_2$, —OCH$_2$F, —(CR$^e$R$^e$)$_m$A, —N(R$^e$)(CR$^e$R$^e$)$_m$A, —O(CR$^e$R$^e$)$_m$A, —O(CR$^e$R$^e$)$_m$OA or —C(═O)A, provided at least one substituent on $R^1$ is —(CR$^e$R$^e$)$_m$A, —N(R$^e$)(CR$^e$R$^e$)$_m$A, —O(CR$^e$R$^e$)$_m$A, —O(CR$^e$R$^e$)$_m$OA or —C(═O)A;

A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —$NR^bR^b$, —$C_{1-6}$alkyl, —$OC_{1-6}$alkyl, —(CR$^e$R$^e$)$_m$OH, hydroxy$C_{1-6}$alkyl, —CF$_3$, —CHF$_2$, —CH$_2$F, —OCF$_3$, —OCHF$_2$, —OCH$_2$F, —CN, —C(═O)NR$^b$R$^b$, —O(CR$^e$R$^e$)$_m$B or —(CR$^e$R$^e$)$_m$B;

B is a 3 to 5 membered cycloalkyl group that can be unsubstituted or substituted with from 1 to 4 substituents independently selected from Cl, F, Br, —NHCH$_3$, —N(CH$_3$)$_2$, —$C_{1-4}$alkyl, —$OC_{1-4}$alkyl, —CF$_3$, —CHF$_2$, —CH$_2$F, —OCF$_3$, —OCHF$_2$, —OCH$_2$F or —CN;

$R^2$ is a 5 to 6 membered aryl or heteroaryl, where the heteroaryl can have from 1 to 3 heteroatoms independently selected from O, N or S, and the aryl and heteroaryl group can be unsubstituted or substituted with from 1 to 4 substituents independently selected from halo, —$NR^bR^b$, —$C_{1-6}$alkyl, —$OC_{1-6}$alkyl, —(CR$^e$R$^e$)$_n$NR$^b$R$^b$, —CF$_3$, —CHF$_2$, —CH$_2$F, —OCF$_3$, —OCHF$_2$, —OCH$_2$F, —CN or —C(═O)NR$^b$R$^b$;

each $R^b$ is independently H or —$C_{1-6}$alkyl;
each $R^c$ is independently H or —$C_{1-6}$alkyl; and
each $R^d$ is independently H, halo, —CN, —$NR^cR^c$, —OH, —$C_{1-6}$alkyl, —$C_{1-6}$haloalkyl, —$OC_{1-6}$haloalkyl or —$OC_{1-6}$alkyl;
each $R^e$ is independently H, halo, —CN, —$NR^cR^c$, —OH, —$C_{1-6}$alkyl or —$OC_{1-6}$alkyl;
each n is independently 0, 1, 2, 3 or 4; and
each m is independently 0, 1, 2, 3 or 4.

In embodiment 1b, the present invention provides compounds of Formula Ib, and pharmaceutically acceptable salts thereof,

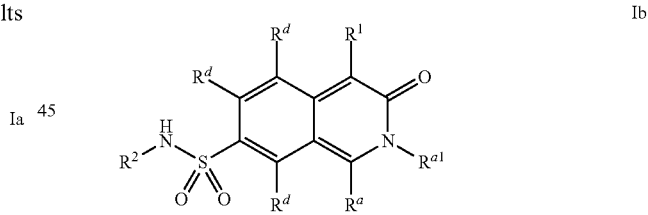

Ib wherein:
$R^a$ is independently H, halo, —$NR^cR^c$, —OH, hydroxy$C_{1-6}$alkyl, —$C_{1-6}$alkyl, —$OC_{1-6}$alkyl, —$C_{1-6}$haloalkyl, —$OC_{1-6}$haloalkyl or —CN,
$R^{a1}$ is H, —$C_{1-6}$alkyl or acetyl;
$R^1$ is a 6 membered aryl or heteroaryl, wherein the aryl or heteroaryl is substituted with from 1 to 4 substituents independently selected from A, halo, OH, —$NR^bR^b$, —$C_{1-6}$alkyl, —$OC_{1-6}$alkyl, —$OC_{1-6}$alkylCF$_3$, —$OC_{1-6}$alkylCN, —(CR$^e$R$^e$)$_m$CN, —$C_{1-6}$alkylOC$_{1-6}$alkyl, —CF$_3$, —CHF$_2$, —CH$_2$F, —OCF$_3$, —OCHF$_2$, —OCH$_2$F, —(CR$^e$R$^e$)$_m$A, —N(R$^e$)(CR$^e$R$^e$)$_m$A, —O(CR$^e$R$^e$)$_m$A, —O(CR$^e$R$^e$)$_m$OA or —C(═O)A, provided at least one substituent on $R^1$ is —(CR$^e$R$^e$)$_m$A, —N(R$^e$)(CR$^e$R$^e$)$_m$A, —O(CR$^e$R$^e$)$_m$A, —O(CR$^e$R$^e$)$_m$OA or —C(═O)A;

A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —NR$^b$R$^b$, —C$_{1-6}$alkyl, —OC$_{1-6}$alkyl, —(CR$^e$R$^e$)$_m$OH, hydroxyC$_{1-6}$alkyl, —CF$_3$, —CHF$_2$, —CH$_2$F, —OCF$_3$, —OCHF$_2$, —OCH$_2$F, —CN, —C(=O)NR$^b$R$^b$, —O(CR$^e$R$^e$)$_m$B or —(CR$^e$R$^e$)$_m$B;

B is a 3 to 5 membered cycloalkyl group that can be unsubstituted or substituted with from 1 to 4 substituents independently selected from Cl, F, Br, —NHCH$_3$, —N(CH$_3$)$_2$, —C$_{1-4}$alkyl, —OC$_{1-4}$alkyl, —CF$_3$, —CHF$_2$, —CH$_2$F, —OCF$_3$, —OCHF$_2$, —OCH$_2$F or —CN;

R$^2$ is a 5 to 6 membered aryl or heteroaryl, where the heteroaryl can have from 1 to 3 heteroatoms independently selected from O, N or S, and the aryl and heteroaryl group can be unsubstituted or substituted with from 1 to 4 substituents independently selected from halo, —NR$^b$R$^b$, —C$_{1-6}$alkyl, —OC$_{1-6}$alkyl, —(CR$^c$R$^c$)—NR$^b$R$^b$, —CF$_3$, —CHF$_2$, —CH$_2$F, —OCF$_3$, —OCHF$_2$, —OCH$_2$F, —CN or —C(=O)NR$^b$R$^b$;

each R$^b$ is independently H or —C$_{1-6}$alkyl;

each R$^e$ is independently H or —C$_{1-6}$alkyl; and each R$^d$ is independently H, halo, —CN, —NR$^e$R$^e$, —OH, —C$_{1-6}$alkyl, —C$_{1-6}$haloalkyl, —OC$_{1-6}$haloalkyl or —OC$_{1-6}$alkyl;

each R$^e$ is independently H, halo, —CN, —NR$^e$R$^e$, —OH, —C$_{1-6}$alkyl or —OC$_{1-6}$alkyl;

each n is independently 0, 1, 2, 3 or 4;

each m is independently 0, 1, 2, 3 or 4;

In embodiment 1d, the present invention provides compounds, and pharmaceutically acceptable salts thereof, wherein ring A comprises an atom that is CR$^a$, wherein R$^a$ is —OH. Thus, the invention also includes tautomers of Formula I, having the following general structure

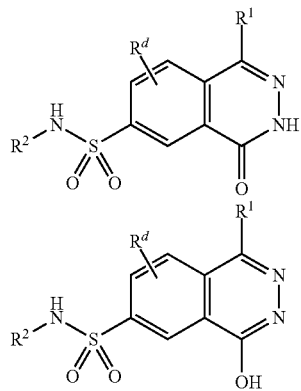

wherein R$^1$, R$^d$ and R$^2$ are as defined herein above or below.

In embodiment 1e, the present invention provides compounds in accordance with embodiment 1, or a pharmaceutically acceptable salt thereof, wherein

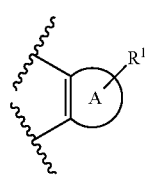

is

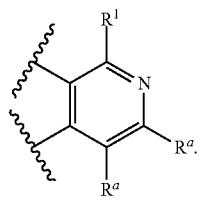

In embodiment 1f, the present invention provides compounds in accordance with embodiment 1, or a pharmaceutically acceptable salt thereof, wherein

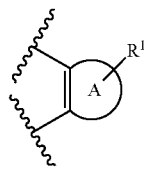

is

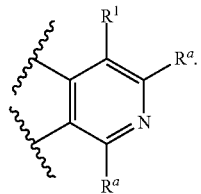

In embodiment 1 g, the present invention provides compounds in accordance with embodiment 1, or a pharmaceutically acceptable salt thereof, wherein

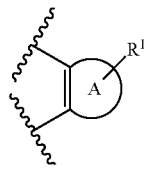

is

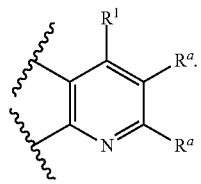

In embodiment 1h, the present invention provides compounds in accordance with embodiment 1, or a pharmaceutically acceptable salt thereof, wherein

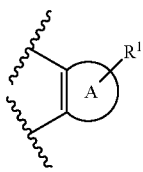

is

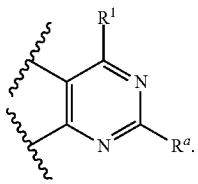

In embodiment 1i, the present invention provides compounds in accordance with embodiment 1, or a pharmaceutically acceptable salt thereof, wherein

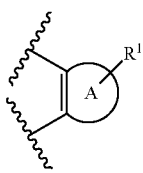

is

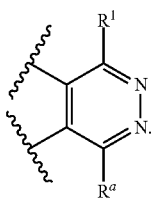

In embodiment 1j, the present invention provides compounds in accordance with embodiment 1, or a pharmaceutically acceptable salt thereof, wherein

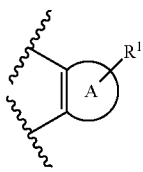

is

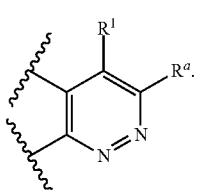

In embodiment 1k, the present invention provides compounds in accordance with embodiment 1, or a pharmaceutically acceptable salt thereof, wherein

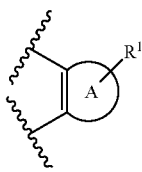

is

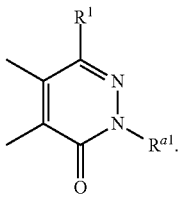

In embodiment 1-m, the present invention provides compounds in accordance with embodiment 1, or a pharmaceutically acceptable salt thereof, wherein

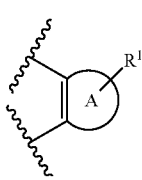

is

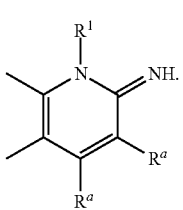

In embodiment 1n, the present invention provides compounds in accordance with embodiment 1, or a pharmaceutically acceptable salt thereof, wherein

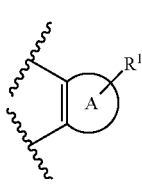

is

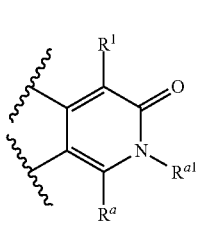

and wherein $R^{a1}$ is —$C_{1-6}$alkyl.

In embodiment 1o, the present invention provides compounds in accordance with embodiment 1, or a pharmaceutically acceptable salt thereof, wherein

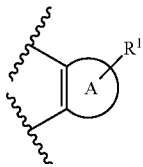

is

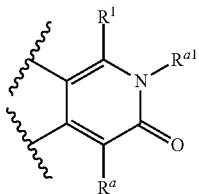

and wherein $R^{a1}$ is —$C_{1-6}$alkyl.

In embodiment 1p, the present invention provides compounds in accordance with embodiment 1, or a pharmaceutically acceptable salt thereof, wherein

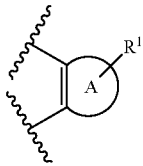

is

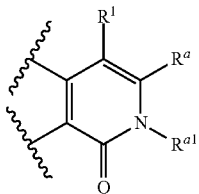

and wherein $R^{a1}$ is —$C_{1-6}$alkyl.

In embodiment 1q, the present invention provides compounds in accordance with embodiment 1, or a pharmaceutically acceptable salt thereof, wherein

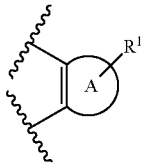

is

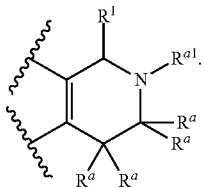

In embodiment 2, the present invention provides compounds in accordance with any one of embodiments 1, 1a to 1q, or pharmaceutically acceptable salts thereof, wherein each $R^d$ is independently H, F or Cl.

In embodiment 2a, the present invention provides compounds in accordance with any one of embodiments 1, 1a to 1q, or pharmaceutically acceptable salts thereof, wherein each $R^d$ is independently H or F.

In embodiment 2b, the present invention provides compounds in accordance with any one of embodiments 1, 1a to 1q, or pharmaceutically acceptable salts thereof, wherein each $R^d$ is independently H.

In embodiment 3, the present invention provides compounds in accordance with any one of embodiments 1, 1a-1q and 2, 2a-2b, or pharmaceutically acceptable salts thereof, wherein $R^1$ is a ring selected from phenyl, pyridinyl or pyrimidinyl, wherein the ring is substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, CN, —C(=O)$NR^bR^b$, —C(=O)$OR^b$, —OA or A, provided at least one substituent on $R^1$ is A or —OA; and A is a 5 to 6 membered aryl or heteroaryl group, or a 4 to 6 membered N-linked heterocycloalkyl group, or a 3 to 6 membered cycloalkyl group, where the heteroaryl can have from 1 to 3 heteroatoms independently selected from O, N or S, the N-linked heterocycloalkyl can have 1 additional heteroatom independently selected from O, N or S, and the aryl, heteroaryl, heterocyclic and cycloalkyl group can be unsubstituted or substituted with from 1 to 4 substituents independently selected from halo, —$C_{1-6}$alkyl, hydroxy-$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

In embodiment 4, the present invention provides compounds in accordance with any one of embodiments 1, 1a-1q 2, 2a-2b and 3, or pharmaceutically acceptable salts thereof, wherein $R^1$ is a phenyl ring or pyridyl ring, wherein the ring is substituted with from 1 to 4 substituents independently selected from halo, —$C_{1-6}$alkyl, $OC_{1-6}$alkyl, hydroxy $C_{1-6}$alkyl, —$CF_3$, —$CHF_2$, —$CH_2F$, —$OCF_3$, —$OCHF_2$, —$OCH_2F$, CN, —C(=O)$NR^bR^b$ —C(=O)$OR^b$, —OA or A, provided at least one substituent on $R^1$ is A or —OA.

In embodiment 5, the present invention provides compounds in accordance with any one of embodiments 1, 1a-1q 2, 2a-2b and 3-4, or pharmaceutically acceptable salts thereof, wherein A is a ring selected from phenyl, cyclopropyl, cyclopentyl, cyclohexyl, piperidinyl, piperazinyl, pyrrolidinyl, azetidinyl, pyridyl, pyrimidinyl, pyrazinyl or pyridazinyl, wherein the ring can be unsubstituted or substituted with from 1 to 4 substituents independently selected from halo, —$C_{1-6}$alkyl, $OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

In embodiment 6, the present invention provides compounds in accordance with any one of embodiments 1, 1a-1q, 2, 2a-2b and 3 to 5, or pharmaceutically acceptable salts thereof, wherein $R^1$ is a phenyl ring or pyridyl ring, wherein the ring is substituted with from 1 to 4 substituents independently selected from halo, —$C_{1-6}$alkyl, —$OC_{1-6}$alkyl, hydroxy $C_{1-6}$alkyl, —$CF_3$, —$CHF_2$, —$CH_2F$, —$OCF_3$, —$OCHF_2$, —$OCH_2F$, CN, —C(=O)$NR^bR^b$ —C(=O)$OR^b$, —OA or A, provided at least one substituent on $R^1$ is A or —OA; and A is a ring selected from phenyl, piperidinyl, piperazinyl, pyrrolidinyl, azetidinyl, cyclopentyl, pyridyl, pyrimidinyl, pyrazolyl or pyridazolyl, wherein the ring can be unsubstituted or substituted with from 1 to 4 substituents independently selected from halo, —$C_{1-6}$alkyl, $OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

In embodiment 7, the present invention provides compounds in accordance with any one of embodiments 1, 1a-1q, 2, 2a-2b and 3 to 6, or pharmaceutically acceptable salts thereof, wherein A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

In embodiment 10, the present invention provides compounds in accordance with any one of embodiments 1, 1a-1q, 2, 2a-2b and 3 to 7, or pharmaceutically acceptable salts thereof, wherein R$^1$ is a phenyl ring or pyridyl ring, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on R$^1$ is A or —OA; and A is a ring selected from phenyl, piperidinyl, pyrrolidinyl, azetidinyl, cyclopentyl, pyridyl, pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN or —C(=O)NR$^b$R$^b$.

In embodiment 11, the present invention provides compounds in accordance with any one of embodiments 1, 1a-1q and 2 to 7, or pharmaceutically acceptable salts thereof, wherein one substituent on R$^1$ is —O(CR$^e$R$^e$)$_m$A.

In embodiment 12, the present invention provides compounds in accordance with any one of embodiments 1, 1a-1q, 2, 2a-2b and 3 to 11, or pharmaceutically acceptable salts thereof, wherein R$^2$ is a 5 to 6 membered aryl or heteroaryl, where the heteroaryl can have from 1 to 3 heteroatoms independently selected from O, N or S, and the aryl or heteroaryl can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$.

In embodiment 13, the present invention provides compounds in accordance with any one of embodiments 1, 1a-1q, 2, 2a-2b and 3 to 12, or pharmaceutically acceptable salts thereof, wherein R$^2$ is thiadiazolyl, substituted thiadiazolyl, thiazolyl, substituted thiazolyl, oxazolyl, substituted oxazolyl, oxadiazolyl, substituted oxadiazolyl, pyrimidinyl, substituted pyrimidinyl, isoxazolyl, substituted isoxazolyl, pyrazolyl, substituted pyrazolyl, pyridyl, substituted pyridyl, pyridazinyl, substituted pyridazinyl, pyrazinyl or substituted pyrazinyl.

In embodiment 14, the present invention provides compounds in accordance with any one of embodiments 1, 1a-1q, 2, 2a-2b and 3 to 13, or pharmaceutically acceptable salts thereof, wherein R$^2$ is a ring selected from 3-oxazolyl, 3-oxadiazolyl, 3-isoxazolyl, 2-thiazolyl, 4-thiazolyl, 2-thiadiazolyl, 3-isothiazolyl, 2-pyrimidinyl, 4-pyrimidinyl or 3-pyridazinyl, where the ring can be unsubstituted or substituted with from 1 to 4 substituents independently selected from F, Cl, —NH(CH$_3$), —CH$_3$, —CH$_2$CH$_3$, propyl, isopropyl, —OCH$_3$, —OCH$_2$CH$_3$, propoxyl, —CF$_3$, —CHF$_2$, —CH$_2$F, —OCF$_3$, —OCHF$_2$, —OCH$_2$F or —CN.

In embodiment 24, the present invention provides compounds in accordance with any one of embodiments 1, 1a-1q, 2, 2a-2b and 3 to 23, or pharmaceutically acceptable salts thereof, wherein each R$^d$ is independently H.

In embodiment 25, the present invention provides compounds in accordance with any one of embodiments 1, 1a, 1b or 1n-1p, or pharmaceutically acceptable salts thereof, wherein

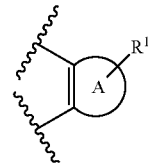

is

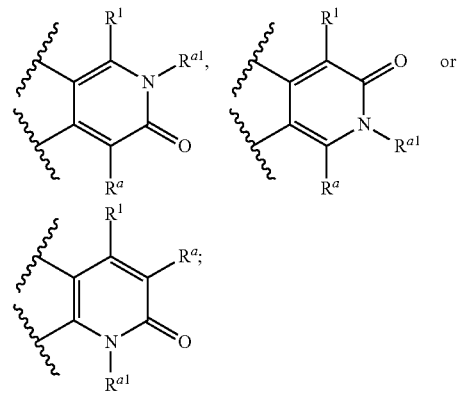

R$^a$ is H, halo, —C$_{1-6}$alkyl, —OC$_{1-6}$alkyl, —C$_{1-6}$haloalkyl, —OC$_{1-6}$haloalkyl or —CN;

R$^{a1}$ is H, —C$_{1-6}$alkyl or acetyl;

R$^1$ is a ring selected from phenyl or pyridyl, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on R$^1$ is A or —OA;

A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN or —C(=O)NR$^b$R$^b$;

R$^2$ is a ring selected from thiazolyl, isothiazolyl, thiadiazolyl, oxazolyl, isoxazolyl, oxadiazolyl, pyrazolyl, pyrimidinyl, pyridyl, pyridazinyl or pyrazinyl, where the ring can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F or —CN; and each R$^d$ is independently H.

In embodiment 26, the present invention provides compounds in accordance with any one of embodiments 1 or 1h, or pharmaceutically acceptable salts thereof, wherein

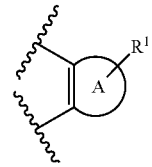

is

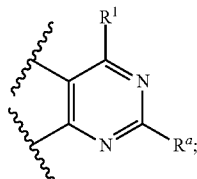

$R^a$ is H, halo, —C$_{1-6}$alkyl, —OC$_{1-6}$alkyl, —C$_{1-6}$haloalkyl, —OC$_{1-6}$haloalkyl or —CN;

$R^1$ is a ring selected from phenyl or pyridyl, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on $R^1$ is A or —OA;

A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, C$_{3-6}$cycloalkyl or —C(=O)NR$^b$R$^b$; and $R^2$ is a ring selected from thiazolyl, isothiazolyl, thiadiazolyl, oxazolyl, isoxazolyl, oxadiazolyl, pyrazolyl, pyrimidinyl, pyridyl, pyridazinyl or pyrazinyl, where the ring can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F or —CN; and each $R^d$ is independently H.

In embodiment 27, the present invention provides compounds in accordance with any one of embodiments 1 or 1i, or pharmaceutically acceptable salts, wherein

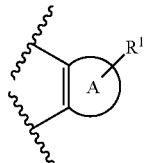

is

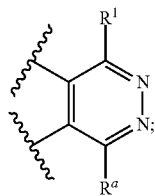

$R^a$ is H, halo, —C$_{1-6}$alkyl, —OC$_{1-6}$alkyl, —C$_{1-6}$haloalkyl, —OC$_{1-6}$haloalkyl or —CN;

$R^1$ is a ring selected from phenyl or pyridyl, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on $R^1$ is A or —OA;

A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN or —C(=O)NR$^b$R$^b$; and $R^2$ is a ring selected from thiazolyl, isothiazolyl, thiadiazolyl, oxazolyl, isoxazolyl, oxadiazolyl, pyrazolyl, pyrimidinyl, pyridyl, pyridazinyl or pyrazinyl, where the ring can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F or —CN; and each $R^d$ is independently H.

In embodiment 28, the present invention provides a compound, or a pharmaceutically acceptable salt thereof, selected from:

1-(2-chloro-3'-fluoro-5-methoxy-4-biphenylyl)-7-fluoro-N-3-isoxazolyl-6-isoquinolinesulfonamide;
7-fluoro-1-(3'-fluoro-3-methoxy-4-biphenylyl)-N-1,2,4-thiadiazol-5-yl-6-isoquinolinesulfonamide;
N-3-isoxazolyl-1-(3-methoxy-4-biphenylyl)-6-isoquinolinesulfonamide;
1-(3-methoxy-4-biphenylyl)-N-1,3,4-thiadiazol-2-yl-6-isoquinolinesulfonamide;
1-(6-(cyclohexylmethoxy)-2-methoxy-3-pyridinyl)-N-4-pyrimidinyl-6-isoquinolinesulfonamide;
1-(6-((4,4-difluorocyclohexyl)methoxy)-2-methoxy-3-pyridinyl)-N-4-pyrimidinyl-6-isoquinolinesulfonamide;
1-(6-(cyclohexylamino)-2-methoxy-3-pyridinyl)-N-4-pyrimidinyl-6-isoquinolinesulfonamide;
1-(4'-chloro-2-cyano-3'-fluoro-5-methoxy-4-biphenylyl)-N-3-isoxazolyl-6-isoquinolinesulfonamide;
1-(2-cyano-3'-fluoro-5-methoxy-5'-methyl-4-biphenylyl)-N-3-isoxazolyl-6-isoquinolinesulfonamide;
1-(3'-chloro-2-cyano-5-methoxy-4'-methyl-4-biphenylyl)-N-3-isoxazolyl-6-isoquinolinesulfonamide;
1-(2-cyano-5-methoxy-2'-methyl-4-biphenylyl)-N-3-isoxazolyl-6-isoquinolinesulfonamide;
1-(2-cyano-3',4'-difluoro-5-methoxy-4-biphenylyl)-N-3-isoxazolyl-6-isoquinolinesulfonamide;
1-(2-cyano-3'-fluoro-5-methoxy-4'-methyl-4-biphenylyl)-N-3-isoxazolyl-6-isoquinolinesulfonamide;
1-(4'-chloro-2-cyano-5-methoxy-3'-methyl-4-biphenylyl)-N-3-isoxazolyl-6-isoquinolinesulfonamide;
1-(5-cyano-4-(5-fluoro-2-methoxy-3-pyridinyl)-2-methoxyphenyl)-N-3-isoxazolyl-6-isoquinolinesulfonamide;
1-(3'-chloro-2-cyano-4'-fluoro-5-methoxy-4-biphenylyl)-N-3-isoxazolyl-6-isoquinolinesulfonamide;
1-(2-cyano-4'-fluoro-5-methoxy-3'-methyl-4-biphenylyl)-N-3-isoxazolyl-6-isoquinolinesulfonamide;
1-(3'-chloro-2-cyano-5'-fluoro-5-methoxy-4-biphenylyl)-N-3-isoxazolyl-6-isoquinolinesulfonamide;
1-(4'-chloro-2-fluoro-5-methoxy-3'-methyl-4-biphenylyl)-N-3-pyridazinyl-6-isoquinolinesulfonamide;
1-(4'-chloro-2-fluoro-5-methoxy-3'-methyl-4-biphenylyl)-N-2-pyrimidinyl-6-isoquinolinesulfonamide;
1-(2,4'-difluoro-5-methoxy-3'-methyl-4-biphenylyl)-N-3-isoxazolyl-6-isoquinolinesulfonamide;
1-(4'-chloro-2-fluoro-5-methoxy-3'-methyl-4-biphenylyl)-N-3-isoxazolyl-6-isoquinolinesulfonamide;
1-(3'-chloro-2-fluoro-5-methoxy-4'-methyl-4-biphenylyl)-N-3-isoxazolyl-6-isoquinolinesulfonamide;
1-(5-fluoro-4-(5-fluoro-2-methoxy-3-pyridinyl)-2-methoxyphenyl)-N-2-pyrimidinyl-6-isoquinolinesulfonamide;

1-(5-fluoro-4-(5-fluoro-2-methoxy-3-pyridinyl)-2-methoxyphenyl)-N-3-isoxazolyl-6-isoquinolinesulfonamide;
1-(2-chloro-4'-fluoro-5-methoxy-3'-methyl-4-biphenylyl)-N-3-isoxazolyl-6-isoquinolinesulfonamide;
1-(4'-chloro-2,3'-difluoro-5-methoxy-4-biphenylyl)-N-3-isoxazolyl-6-isoquinolinesulfonamide;
1-(2,3'-dichloro-5-methoxy-4'-methyl-4-biphenylyl)-N-3-isoxazolyl-6-isoquinolinesulfonamide;
1-(3'-chloro-2-fluoro-5-methoxy-4-biphenyl-N-2-pyrimidinyl-6-isoquinolinesulfonamide;
N-3-isoxazolyl-1-(2,3',5'-trifluoro-5-methoxy-4-biphenylyl)-6-isoquinolinesulfonamide;
1-(5-fluoro-4-(5-fluoro-2-methoxy-3-pyridinyl)-2-methoxyphenyl)-N-3-isothiazolyl-6-isoquinolinesulfonamide;
1-(2,4'-dichloro-3'-fluoro-5-methoxy-4-biphenylyl)-N-3-isoxazolyl-6-isoquinolinesulfonamide
1-(3',5'-difluoro-3-(1-methyl-1H-pyrazol-5-yl)-4-biphenylyl)-N-3-isoxazolyl-6-isoquinolinesulfonamide;
1-(5-chloro-4-(5-fluoro-2-methoxy-3-pyridinyl)-2-methoxyphenyl)-N-3-isoxazolyl-6-isoquinolinesulfonamide;
1-(2-cyano-4'-fluoro-5-methoxy-4-biphenylyl)-N-3-isoxazolyl-6-isoquinolinesulfonamide;
1-(2-cyano-3',5'-difluoro-5-methoxy-4-biphenylyl)-N-2-pyrimidinyl-6-isoquinolinesulfonamide;
1-(3',5'-difluoro-3-methoxy-4-biphenylyl)-N-3-isothiazolyl-6-isoquinolinesulfonamide;
N-3-isoxazolyl-1-(3-methoxy-3'-(trifluoromethyl)-4-biphenylyl)-6-isoquinolinesulfonamide;
1-(2-chloro-3'-fluoro-5-methoxy-4-biphenylyl)-N-2-pyrimidinyl-6-isoquinolinesulfonamide;
1-(2-cyano-3'-fluoro-5-methoxy-4-biphenylyl)-N-2-pyrimidinyl-6-isoquinolinesulfonamide;
1-(6-chloro-3'-fluoro-4-methoxy-3-biphenylyl)-N-1,3,4-thiadiazol-2-yl-6-isoquinolinesulfonamide;
1-(3'-chloro-2-cyano-5-methoxy-4-biphenylyl)-N-3-isoxazolyl-6-isoquinolinesulfonamide;
1-(2-cyano-5-methoxy-3'-methyl-4-biphenylyl)-N-3-isoxazolyl-6-isoquinolinesulfonamide;
1-(3'-chloro-2-cyano-5-methoxy-5'-methyl-4-biphenylyl)-N-3-isoxazolyl-6-isoquinolinesulfonamide;
1-(2-fluoro-5-methoxy-3'-(trifluoromethyl)-4-biphenylyl)-N-3-isoxazolyl-6-isoquinolinesulfonamide;
1-(3'-chloro-2-fluoro-5-methoxy-4-biphenylyl)-N-3-isoxazolyl-6-isoquinolinesulfonamide;
1-(4-bromo-5-chloro-2-methoxyphenyl)-N-3-isoxazolyl-6-isoquinolinesulfonamide;
1-(2-cyano-5-methoxy-3'-(trifluoromethyl)-4-biphenylyl)-N-1,2,4-oxadiazol-3-yl-6-isoquinolinesulfonamide;
1-(2,4'-dichloro-5-methoxy-3'-methyl-4-biphenylyl)-N-3-isoxazolyl-6-isoquinolinesulfonamide;
1-(2-chloro-3'-fluoro-5-methoxy-4-biphenylyl)-N-3-pyridazinyl-6-isoquinolinesulfonamide;
1-(6-chloro-3'-fluoro-4-methoxy-3-biphenylyl)-N-3-isoxazolyl-6-isoquinolinesulfonamide;
1-(2-chloro-3'-fluoro-5-methoxy-4-biphenylyl)-N-1,2,4-oxadiazol-3-yl-6-isoquinolinesulfonamide;
1-(6-chloro-3'-fluoro-4-methoxy-3-biphenylyl)-N-2-pyrimidinyl-6-isoquinolinesulfonamide;
1-(3',5'-difluoro-3-methoxy-4-biphenylyl)-N-2-pyrimidinyl-6-isoquinolinesulfonamide;
1-(3',5'-difluoro-3-methoxy-4-biphenylyl)-N-1,2,4-oxadiazol-3-yl-6-isoquinolinesulfonamide;
1-(3',5'-difluoro-3-methoxy-4-biphenylyl)-N-(5-fluoro-2-pyrimidinyl)-6-isoquinolinesulfonamide;
1-(3',5'-difluoro-3-methoxy-4-biphenylyl)-N-3-pyridazinyl-6-isoquinolinesulfonamide;
1-(3',5'-difluoro-3-methoxy-4-biphenylyl)-N-3-isoxazolyl-6-isoquinolinesulfonamide;
1-(2-cyano-3'-fluoro-5-methoxy-4-biphenylyl)-N-4-pyrimidinyl-6-isoquinolinesulfonamide;
1-(3-(hydroxymethyl)-3'-(trifluoromethyl)-4-biphenylyl)-N-3-isoxazolyl-6-isoquinolinesulfonamide;
1-(2-cyano-5-methoxy-4'-(trifluoromethyl)-4-biphenylyl)-N-3-isoxazolyl-6-isoquinolinesulfonamide;
1-(4-methoxy-4'-(trifluoromethyl)-3-biphenylyl)-N-4-pyrimidinyl-6-isoquinolinesulfonamide;
1-(2-cyano-5-methoxy-3'-(trifluoromethyl)-4-biphenylyl)-N-3-isoxazolyl-6-isoquinolinesulfonamide;
1-(4'-chloro-2-cyano-3'-fluoro-5-methoxy-4-biphenylyl)-N-4-pyrimidinyl-6-isoquinolinesulfonamide;
1-(2-cyano-4'-fluoro-5-methoxy-3'-methyl-4-biphenylyl)-N-4-pyrimidinyl-6-isoquinolinesulfonamide;
1-(2-cyano-5-methoxy-3'-methyl-4-biphenylyl)-N-4-pyrimidinyl-6-isoquinolinesulfonamide;
1-(2-cyano-5-methoxy-2'-methyl-4-biphenylyl)-N-4-pyrimidinyl-6-isoquinolinesulfonamide;
1-(3'-chloro-2-cyano-4'-fluoro-5-methoxy-4-biphenylyl)-N-4-pyrimidinyl-6-isoquinolinesulfonamide;
1-(3'-chloro-2-cyano-5-methoxy-4'-methyl-4-biphenylyl)-N-4-pyrimidinyl-6-isoquinolinesulfonamide;
1-(3'-chloro-2-cyano-5-methoxy-5'-methyl-4-biphenylyl)-N-4-pyrimidinyl-6-isoquinolinesulfonamide;
1-(4'-chloro-2-cyano-5-methoxy-3'-methyl-4-biphenylyl)-N-4-pyrimidinyl-6-isoquinolinesulfonamide;
1-(2-cyano-3'-fluoro-5-methoxy-4'-methyl-4-biphenylyl)-N-4-pyrimidinyl-6-isoquinolinesulfonamide;
1-(2-cyano-3'-fluoro-5-methoxy-5'-methyl-4-biphenylyl)-N-4-pyrimidinyl-6-isoquinolinesulfonamide;
1-(2-cyano-5-methoxy-2',4',5'-trimethyl-4-biphenylyl)-N-4-pyrimidinyl-6-isoquinolinesulfonamide;
1-(2-cyano-3',5'-difluoro-5-methoxy-4-biphenylyl)-N-4-pyrimidinyl-6-isoquinolinesulfonamide;
1-(4-(5-fluoro-2-methoxy-3-pyridinyl)-2-methoxyphenyl)-N-1,3,4-thiadiazol-2-yl-6-isoquinolinesulfonamide;
1-(5-chloro-4-(difluoromethyl)-2-methoxyphenyl)-N-3-isoxazolyl-6-isoquinolinesulfonamide;
1-(2-methoxy-4-(2-methylphenoxy)phenyl)-N-4-pyrimidinyl-6-isoquinolinesulfonamide;
1-(3',4'-difluoro-5-methoxy-2-methyl-4-biphenylyl)-N-1,3,4-thiadiazol-2-yl-6-isoquinolinesulfonamide;
1-(3',5'-difluoro-5-methoxy-2-methyl-4-biphenylyl)-N-1,3,4-thiadiazol-2-yl-6-isoquinolinesulfonamide;
1-(4-(4-fluorophenoxy)-2-methoxyphenyl)-N-1,3,4-thiadiazol-2-yl-6-isoquinolinesulfonamide;
1-(4-(3,4-difluorophenoxy)-2-methoxyphenyl)-N-4-pyrimidinyl-6-isoquinolinesulfonamide;
1-(4-(3,4-dimethylphenoxy)-2-methoxyphenyl)-N-4-pyrimidinyl-6-isoquinolinesulfonamide;
1-(4-(3-fluoro-4-methylphenoxy)-2-methoxyphenyl)-N-4-pyrimidinyl-6-isoquinolinesulfonamide;
1-(4-(3-fluoro-5-methylphenoxy)-2-methoxyphenyl)-N-4-pyrimidinyl-6-isoquinolinesulfonamide;
1-(2-methoxy-4-(3-methylphenoxy)phenyl)-N-4-pyrimidinyl-6-isoquinolinesulfonamide;
1-(2-methoxy-4-(3-methoxyphenoxy)phenyl)-N-4-pyrimidinyl-6-isoquinolinesulfonamide;
1-(2-cyano-5-methoxy-3'-(trifluoromethyl)-4-biphenylyl)-N-4-pyrimidinyl-6-isoquinolinesulfonamide;
1-(2-cyano-5-methoxy-4'-(trifluoromethyl)-4-biphenylyl)-N-4-pyrimidinyl-6-isoquinolinesulfonamide;

1-(2-cyano-4'-fluoro-5-methoxy-4-biphenylyl)-N-4-pyrimidinyl-6-isoquinolinesulfonamide;
1-(4-(2,5-difluorophenoxy)-2-methoxyphenyl)-N-1,3,4-thiadiazol-2-yl-6-isoquinolinesulfonamide;
1-(2-methoxy-4-(2-methoxy-5-methyl-3-pyridinyl)phenyl)-N-1,3,4-thiadiazol-2-yl-6-isoquinolinesulfonamide;
1-(4-(1H-indol-1-yl)-2-methoxyphenyl)-N-1,3,4-thiadiazol-2-yl-6-isoquinolinesulfonamide;
1-(4-(2-fluoro-5-methylphenoxy)-2-methoxyphenyl)-N-1,3,4-thiadiazol-2-yl-6-isoquinolinesulfonamide;
1-(4-(5-fluoro-2-methoxy-3-pyridinyl)-2-methoxyphenyl)-N-3-isoxazolyl-6-isoquinolinesulfonamide;
1-(4-(3-fluoro-4-methylphenoxy)-2-methoxyphenyl)-N-1,3,4-thiadiazol-2-yl-6-isoquinolinesulfonamide;
1-(4-(3-fluoro-5-methylphenoxy)-2-methoxyphenyl)-N-1,3,4-thiadiazol-2-yl-6-isoquinolinesulfonamide;
1-(2-cyano-3',4'-difluoro-5-methoxy-4-biphenylyl)-N-4-pyrimidinyl-6-isoquinolinesulfonamide;
1-(3-(cyanomethoxy)-3'-fluoro-4-biphenylyl)-N-4-pyrimidinyl-6-isoquinolinesulfonamide;
1-(2-cyano-5-methoxy-3'-methyl-4-biphenylyl)-N-1,3,4-thiadiazol-2-yl-6-isoquinolinesulfonamide;
1-(2-cyano-3'-fluoro-5-methoxy-4'-methyl-4-biphenylyl)-N-1,3,4-thiadiazol-2-yl-6-isoquinolinesulfonamide;
1-(2-cyano-5-methoxy-4'-(trifluoromethyl)-4-biphenylyl)-N-1,3,4-thiadiazol-2-yl-6-isoquinolinesulfonamide;
1-(2-cyano-4'-fluoro-5-methoxy-4-biphenylyl)-N-1,3,4-thiadiazol-2-yl-6-isoquinolinesulfonamide;
1-(2-cyano-5-methoxy-2'-methyl-4-biphenylyl)-N-1,3,4-thiadiazol-2-yl-6-isoquinolinesulfonamide;
1-(3'-chloro-2-cyano-4'-fluoro-5-methoxy-4-biphenylyl)-N-1,3,4-thiadiazol-2-yl-6-isoquinolinesulfonamide;
1-(2-chloro-3'-fluoro-5-methoxy-4-biphenylyl)-4-hydroxy-N-3-isoxazolyl-6-isoquinolinesulfonamide;
1-(2-cyano-3'-fluoro-5-methoxy-5'-methyl-4-biphenylyl)-N-1,3,4-thiadiazol-2-yl-6-isoquinolinesulfonamide;
1-(5-cyano-4-(5-fluoro-2-methoxy-3-pyridinyl)-2-methoxyphenyl)-N-1,3,4-thiadiazol-2-yl-6-isoquinolinesulfonamide;
1-(4'-chloro-2-cyano-3'-fluoro-5-methoxy-4-biphenylyl)-N-1,3,4-thiadiazol-2-yl-6-isoquinolinesulfonamide;
1-(3'-chloro-2-cyano-5-methoxy-5'-methyl-4-biphenylyl)-N-1,3,4-thiadiazol-2-yl-6-isoquinolinesulfonamide;
1-(4'-chloro-2-cyano-5-methoxy-3'-methyl-4-biphenylyl)-N-1,3,4-thiadiazol-2-yl-6-isoquinolinesulfonamide;
1-(3'-chloro-2-cyano-5-methoxy-4'-methyl-4-biphenylyl)-N-1,3,4-thiadiazol-2-yl-6-isoquinolinesulfonamide;
1-(2-cyano-4'-fluoro-5-methoxy-3'-methyl-4-biphenylyl)-N-1,3,4-thiadiazol-2-yl-6-isoquinolinesulfonamide;
1-(3-(cyanomethoxy)-3'-fluoro-4-biphenylyl)-N-3-isoxazolyl-6-isoquinolinesulfonamide;
1-(3-(cyanomethoxy)-3'-fluoro-4-biphenylyl)-N-1,3,4-thiadiazol-2-yl-6-isoquinolinesulfonamide;
1-(2-chloro-3'-fluoro-5-methoxy-4-biphenylyl)-4-cyano-N-3-isoxazolyl-6-isoquinolinesulfonamide;
1-(4-chloro-2-methoxy-5-methylphenyl)-N-3-isoxazolyl-6-isoquinolinesulfonamide;
1-(5-chloro-2-methoxy-4-(trifluoromethyl)phenyl)-N-3-isoxazolyl-6-isoquinolinesulfonamide;
1-(4'-chloro-5-methoxy-2,3'-dimethyl-4-biphenylyl)-N-3-isoxazolyl-6-isoquinolinesulfonamide;
1-(2-chloro-3'-fluoro-5-methoxy-4-biphenylyl)-N-3-isothiazolyl-6-isoquinolinesulfonamide;
1-(2-chloro-3'-fluoro-5-methoxy-4-biphenylyl)-N-1,3-oxazol-2-yl-6-isoquinolinesulfonamide;
N-3-isoxazolyl-1-(2-methoxy-5-methyl-4-(trifluoromethyl)phenyl)-6-isoquinolinesulfonamide;
1-(3',5'-difluoro-5-methoxy-2-methyl-4-biphenylyl)-N-3-isoxazolyl-6-isoquinolinesulfonamide;
1-(3',4'-difluoro-5-methoxy-2-methyl-4-biphenylyl)-N-3-isoxazolyl-6-isoquinolinesulfonamide;
1-(3'-fluoro-5-methoxy-2,5'-dimethyl-4-biphenylyl)-N-3-isoxazolyl-6-isoquinolinesulfonamide;
1-(4'-fluoro-5-methoxy-2,3'-dimethyl-4-biphenylyl)-N-3-isoxazolyl-6-isoquinolinesulfonamide;
N-3-isoxazolyl-1-(5-methoxy-2,2',4',5'-tetramethyl-4-biphenylyl)-6-isoquinolinesulfonamide;
N-3-isoxazolyl-1-(5-methoxy-2,3'-dimethyl-4-biphenylyl)-6-isoquinolinesulfonamide;
1-(3'-chloro-5-methoxy-2-methyl-4-biphenylyl)-N-3-isoxazolyl-6-isoquinolinesulfonamide;
N-3-isoxazolyl-1-(5-methoxy-2-methyl-3'-(trifluoromethyl)-4-biphenylyl)-6-isoquinolinesulfonamide;
1-(4-(5-fluoro-2-methoxy-3-pyridinyl)-2-methoxy-5-methylphenyl)-N-3-isoxazolyl-6-isoquinolinesulfonamide;
1-(5'-fluoro-2',5-dimethoxy-2-methyl-4-biphenylyl)-N-3-isoxazolyl-6-isoquinolinesulfonamide;
1-(5'-chloro-2',5-dimethoxy-2-methyl-4-biphenylyl)-N-3-isoxazolyl-6-isoquinolinesulfonamide;
1-(3'-chloro-5-methoxy-2,4'-dimethyl-4-biphenylyl)-N-3-isoxazolyl-6-isoquinolinesulfonamide;
1-(3'-chloro-5-methoxy-2,5'-dimethyl-4-biphenylyl)-N-3-isoxazolyl-6-isoquinolinesulfonamide;
1-(3'-chloro-4'-fluoro-5-methoxy-2-methyl-4-biphenylyl)-N-3-isoxazolyl-6-isoquinolinesulfonamide;
1-(3'-chloro-5'-fluoro-5-methoxy-2-methyl-4-biphenylyl)-N-3-isoxazolyl-6-isoquinolinesulfonamide;
1-(4'-chloro-3'-fluoro-5-methoxy-2-methyl-4-biphenylyl)-N-3-isoxazolyl-6-isoquinolinesulfonamide;
1-(3'-chloro-3-methoxy-4'-methyl-4-biphenylyl)-N-3-isoxazolyl-6-isoquinolinesulfonamide;
1-(4'-chloro-3-methoxy-3'-methyl-4-biphenylyl)-N-3-isoxazolyl-6-isoquinolinesulfonamide;
1-(4'-chloro-3'-fluoro-3-methoxy-4-biphenylyl)-N-3-isoxazolyl-6-isoquinolinesulfonamide; or
3-cyano-1-(2,3'-difluoro-5-methoxy-4-biphenylyl)-N-3-isoxazolyl-6-isoquinolinesulfonamide.

In embodiment 29, the present invention provides a compound, or a pharmaceutically acceptable salt thereof, selected from:
1-(2-fluoro-5-methoxy-3'-(trifluoromethyl)-4-biphenylyl)-N-3-isoxazolyl-6-phthalazinesulfonamide;
4-(2-fluoro-5-methoxy-3'-(trifluoromethyl)-4-biphenylyl)-N-3-isoxazolyl-7-quinazolinesulfonamide;
4-(4'-chloro-2-fluoro-5-methoxy-3'-methyl-4-biphenylyl)-N-3-isoxazolyl-7-quinazolinesulfonamide;
4-(3'-chloro-2-fluoro-5-methoxy-4-biphenylyl)-N-3-isoxazolyl-7-quinazolinesulfonamide;
1-(2-chloro-3'-fluoro-5-methoxy-4-biphenylyl)-N-3-isoxazolyl-6-phthalazinesulfonamide;
1-(2-chloro-3'-fluoro-5-methoxy-4-biphenylyl)-N-2-pyrimidinyl-6-phthalazinesulfonamide;
1-(2-chloro-3'-fluoro-5-methoxy-4-biphenylyl)-N-1,3,4-thiadiazol-2-yl-6-phthalazinesulfonamide;
4-(5'-fluoro-2',5-dimethoxy-2-methyl-4-biphenylyl)-N-3-isoxazolyl-7-quinazolinesulfonamide;
4-(4-(5-fluoro-6-methyl-2-pyridinyl)-2-methoxy-5-methylphenyl)-N-3-isoxazolyl-7-quinazolinesulfonamide;
4-(4-(5-fluoro-2-methoxy-3-pyridinyl)-2-methoxy-5-methylphenyl)-N-3-isoxazolyl-7-quinazolinesulfonamide;
4-(3',4'-difluoro-5-methoxy-2-methyl-4-biphenylyl)-N-3-isoxazolyl-7-quinazolinesulfonamide;
4-(5-cyano-4-(5-fluoro-2-methoxy-3-pyridinyl)-2-methoxyphenyl)-N-3-isoxazolyl-7-quinazolinesulfonamide;

4-(2-chloro-3'-fluoro-5-methoxy-4-biphenylyl)-N-3-pyridazinyl-7-quinazolinesulfonamide;
4-(2-cyano-3',5'-difluoro-5-methoxy-4-biphenylyl)-N-3-isoxazolyl-7-quinazolinesulfonamide;
4-(2-cyano-3'-fluoro-5-methoxy-4-biphenylyl)-N-3-isoxazolyl-7-quinazolinesulfonamide;
4-(2,3'-dichloro-4'-fluoro-5-methoxy-4-biphenylyl)-N-3-isoxazolyl-7-quinazolinesulfonamide;
4-(5-cyano-4-(5-fluoro-2-methoxy-3-pyridinyl)-2-methoxyphenyl)-N-1,3,4-thiadiazol-2-yl-7-quinazolinesulfonamide;
4-(2,4'-dichloro-5-methoxy-3'-methyl-4-biphenylyl)-N-3-isoxazolyl-7-quinazolinesulfonamide;
4-(2-chloro-3',5'-difluoro-5-methoxy-4-biphenylyl)-N-3-isoxazolyl-7-quinazolinesulfonamide;
4-(2-chloro-3'-fluoro-5-methoxy-4-biphenylyl)-N-1,2,5-thiadiazol-3-yl-7-quinazolinesulfonamide;
4-(2-cyano-5-methoxy-3'-(trifluoromethyl)-4-biphenylyl)-N-3-isoxazolyl-7-quinazolinesulfonamide;
4-(2-chloro-4'-fluoro-5-methoxy-3'-methyl-4-biphenylyl)-N-3-isoxazolyl-7-quinazolinesulfonamide;
4-(5-chloro-4-(5-fluoro-2-methoxy-3-pyridinyl)-2-methoxyphenyl)-N-3-isoxazolyl-7-quinazolinesulfonamide;
4-(2-cyano-3',5'-difluoro-5-methoxy-4-biphenylyl)-N-1,3,4-thiadiazol-2-yl-7-quinazolinesulfonamide;
4-(2-cyano-5-methoxy-3'-(trifluoromethyl)-4-biphenylyl)-N-1,3,4-thiadiazol-2-yl-7-quinazolinesulfonamide;
4-(2-chloro-3'-fluoro-5-methoxy-4-biphenylyl)-N-3-isoxazolyl-7-quinazolinesulfonamide;
4-(2-chloro-3'-fluoro-5-methoxy-4-biphenylyl)-N-1,2,4-oxadiazol-3-yl-7-quinazolinesulfonamide;
4-(2-cyano-3'-fluoro-5-methoxy-4-biphenylyl)-N-1,3,4-thiadiazol-2-yl-7-quinazolinesulfonamide;
4-(2-chloro-3'-fluoro-5-methoxy-4-biphenylyl)-N-2-pyrimidinyl-7-quinazolinesulfonamide;
1-(2,4'-dichloro-5-methoxy-3'-methyl-4-biphenylyl)-N-3-isoxazolyl-6-phthalazinesulfonamide;
1-(2,3'-dichloro-5-methoxy-4'-methyl-4-biphenylyl)-N-3-isoxazolyl-6-phthalazinesulfonamide;
4-(4-chloro-2-methoxy-5-methylphenyl)-N-3-isoxazolyl-7-quinazolinesulfonamide;
4-(4'-chloro-5-methoxy-2,3'-dimethyl-4-biphenylyl)-N-3-isoxazolyl-7-quinazolinesulfonamide;
1-(2-chloro-3'-fluoro-5-methoxy-4-biphenylyl)-N-3-isoxazolyl-4-methoxy-6-phthalazinesulfonamide;
1-(2,4'-dichloro-5-methoxy-3'-methyl-4-biphenylyl)-N-3-isothiazolyl-6-phthalazinesulfonamide;
1-(2-chloro-3',5'-difluoro-5-methoxy-4-biphenylyl)-N-3-isothiazolyl-6-phthalazinesulfonamide;
4-(5-chloro-2-methoxy-4-(trifluoromethyl)phenyl)-N-3-isoxazolyl-7-quinazolinesulfonamide;
4-(3',5'-difluoro-5-methoxy-2-methyl-4-biphenylyl)-N-3-isoxazolyl-7-quinazolinesulfonamide;
4-(3'-fluoro-5-methoxy-2,5'-dimethyl-4-biphenylyl)-N-3-isoxazolyl-7-quinazolinesulfonamide;
4-(4'-fluoro-5-methoxy-2,3'-dimethyl-4-biphenylyl)-N-3-isoxazolyl-7-quinazolinesulfonamide;
N-3-isoxazolyl-4-(5-methoxy-2,2',4',5'-tetramethyl-4-biphenylyl)-7-quinazolinesulfonamide;
N-3-isoxazolyl-4-(5-methoxy-2,3'-dimethyl-4-biphenylyl)-7-quinazolinesulfonamide;
4-(3'-chloro-5-methoxy-2-methyl-4-biphenylyl)-N-3-isoxazolyl-7-quinazolinesulfonamide;
N-3-isoxazolyl-4-(5-methoxy-2-methyl-3'-(trifluoromethyl)-4-biphenylyl)-7-quinazolinesulfonamide;
4-(5'-chloro-2',5-dimethoxy-2-methyl-4-biphenylyl)-N-3-isoxazolyl-7-quinazolinesulfonamide;
4-(3'-chloro-5-methoxy-2,4'-dimethyl-4-biphenylyl)-N-3-isoxazolyl-7-quinazolinesulfonamide;
4-(3'-chloro-5-methoxy-2,5'-dimethyl-4-biphenylyl)-N-3-isoxazolyl-7-quinazolinesulfonamide;
4-(3'-chloro-4'-fluoro-5-methoxy-2-methyl-4-biphenylyl)-N-3-isoxazolyl-7-quinazolinesulfonamide;
4-(3'-chloro-5'-fluoro-5-methoxy-2-methyl-4-biphenylyl)-N-3-isoxazolyl-7-quinazolinesulfonamide;
4-(4'-chloro-3'-fluoro-5-methoxy-2-methyl-4-biphenylyl)-N-3-isoxazolyl-7-quinazolinesulfonamide; or
4-(2-chloro-3'-fluoro-5-methoxy-4-biphenylyl)-N-(5-fluoro-2-pyrimidinyl)-7-quinazolinesulfonamide.

In embodiment 30, the present invention provides a compound, or a pharmaceutically acceptable salt thereof, selected from:
4-(2-fluoro-5-methoxy-3'-(trifluoromethyl)-4-biphenylyl)-N-3-isoxazolyl-7-quinazolinesulfonamide;
4-(4'-chloro-2-fluoro-5-methoxy-3'-methyl-4-biphenylyl)-N-3-isoxazolyl-7-quinazolinesulfonamide;
4-(3'-chloro-2-fluoro-5-methoxy-4-biphenylyl)-N-3-isoxazolyl-7-quinazolinesulfonamide;
4-(5'-fluoro-2',5-dimethoxy-2-methyl-4-biphenylyl)-N-3-isoxazolyl-7-quinazolinesulfonamide;
4-(4-(5-fluoro-6-methyl-2-pyridinyl)-2-methoxy-5-methylphenyl)-N-3-isoxazolyl-7-quinazolinesulfonamide;
4-(4-(5-fluoro-2-methoxy-3-pyridinyl)-2-methoxy-5-methylphenyl)-N-3-isoxazolyl-7-quinazolinesulfonamide;
4-(3',4'-difluoro-5-methoxy-2-methyl-4-biphenylyl)-N-3-isoxazolyl-7-quinazolinesulfonamide;
4-(5-cyano-4-(5-fluoro-2-methoxy-3-pyridinyl)-2-methoxyphenyl)-N-3-isoxazolyl-7-quinazolinesulfonamide;
4-(2-chloro-3'-fluoro-5-methoxy-4-biphenylyl)-N-3-pyridazinyl-7-quinazolinesulfonamide;
4-(2-cyano-3',5'-difluoro-5-methoxy-4-biphenylyl)-N-3-isoxazolyl-7-quinazolinesulfonamide;
4-(2-cyano-3'-fluoro-5-methoxy-4-biphenylyl)-N-3-isoxazolyl-7-quinazolinesulfonamide;
4-(2,3'-dichloro-4'-fluoro-5-methoxy-4-biphenylyl)-N-3-isoxazolyl-7-quinazolinesulfonamide;
4-(5-cyano-4-(5-fluoro-2-methoxy-3-pyridinyl)-2-methoxyphenyl)-N-1,3,4-thiadiazol-2-yl-7-quinazolinesulfonamide;
4-(2,4'-dichloro-5-methoxy-3'-methyl-4-biphenylyl)-N-3-isoxazolyl-7-quinazolinesulfonamide;
4-(2-chloro-3',5'-difluoro-5-methoxy-4-biphenylyl)-N-3-isoxazolyl-7-quinazolinesulfonamide;
4-(2-chloro-3'-fluoro-5-methoxy-4-biphenylyl)-N-1,2,5-thiadiazol-3-yl-7-quinazolinesulfonamide;
4-(2-cyano-5-methoxy-3'-(trifluoromethyl)-4-biphenylyl)-N-3-isoxazolyl-7-quinazolinesulfonamide;
4-(2-chloro-4'-fluoro-5-methoxy-3'-methyl-4-biphenylyl)-N-3-isoxazolyl-7-quinazolinesulfonamide;
4-(5-chloro-4-(5-fluoro-2-methoxy-3-pyridinyl)-2-methoxyphenyl)-N-3-isoxazolyl-7-quinazolinesulfonamide;
4-(2-cyano-3',5'-difluoro-5-methoxy-4-biphenylyl)-N-1,3,4-thiadiazol-2-yl-7-quinazolinesulfonamide;
4-(2-cyano-5-methoxy-3'-(trifluoromethyl)-4-biphenylyl)-N-1,3,4-thiadiazol-2-yl-7-quinazolinesulfonamide;
4-(2-chloro-3'-fluoro-5-methoxy-4-biphenylyl)-N-3-isoxazolyl-7-quinazolinesulfonamide;
4-(2-chloro-3'-fluoro-5-methoxy-4-biphenylyl)-N-1,2,4-oxadiazol-3-yl-7-quinazolinesulfonamide;
4-(2-cyano-3'-fluoro-5-methoxy-4-biphenylyl)-N-1,3,4-thiadiazol-2-yl-7-quinazolinesulfonamide;

4-(2-chloro-3'-fluoro-5-methoxy-4-biphenylyl)-N-2-pyrimidinyl-7-quinazolinesulfonamide;
4-(4-chloro-2-methoxy-5-methylphenyl)-N-3-isoxazolyl-7-quinazolinesulfonamide;
4-(4'-chloro-5-methoxy-2,3'-dimethyl-4-biphenylyl)-N-3-isoxazolyl-7-quinazolinesulfonamide;
4-(5-chloro-2-methoxy-4-(trifluoromethyl)phenyl)-N-3-isoxazolyl-7-quinazolinesulfonamide;
4-(3',5'-difluoro-5-methoxy-2-methyl-4-biphenylyl)-N-3-isoxazolyl-7-quinazolinesulfonamide;
4-(3'-fluoro-5-methoxy-2,5'-dimethyl-4-biphenylyl)-N-3-isoxazolyl-7-quinazolinesulfonamide;
4-(4'-fluoro-5-methoxy-2,3'-dimethyl-4-biphenylyl)-N-3-isoxazolyl-7-quinazolinesulfonamide;
N-3-isoxazolyl-4-(5-methoxy-2,2',4',5'-tetramethyl-4-biphenylyl)-7-quinazolinesulfonamide;
N-3-isoxazolyl-4-(5-methoxy-2,3'-dimethyl-4-biphenylyl)-7-quinazolinesulfonamide;
4-(3'-chloro-5-methoxy-2-methyl-4-biphenylyl)-N-3-isoxazolyl-7-quinazolinesulfonamide;
N-3-isoxazolyl-4-(5-methoxy-2-methyl-3'-(trifluoromethyl)-4-biphenylyl)-7-quinazolinesulfonamide;
4-(5'-chloro-2',5-dimethoxy-2-methyl-4-biphenylyl)-N-3-isoxazolyl-7-quinazolinesulfonamide;
4-(3'-chloro-5-methoxy-2,4'-dimethyl-4-biphenylyl)-N-3-isoxazolyl-7-quinazolinesulfonamide;
4-(3'-chloro-5-methoxy-2,5'-dimethyl-4-biphenylyl)-N-3-isoxazolyl-7-quinazolinesulfonamide;
4-(3'-chloro-4'-fluoro-5-methoxy-2-methyl-4-biphenylyl)-N-3-isoxazolyl-7-quinazolinesulfonamide;
4-(3'-chloro-5'-fluoro-5-methoxy-2-methyl-4-biphenylyl)-N-3-isoxazolyl-7-quinazolinesulfonamide;
4-(4'-chloro-3'-fluoro-5-methoxy-2-methyl-4-biphenylyl)-N-3-isoxazolyl-7-quinazolinesulfonamide; or
4-(2-chloro-3'-fluoro-5-methoxy-4-biphenylyl)-N-(5-fluoro-2-pyrimidinyl)-7-quinazolinesulfonamide.

In embodiment 31, the present invention provides a compound, or a pharmaceutically acceptable salt thereof, selected from:
1-(2-fluoro-5-methoxy-3'-(trifluoromethyl)-4-biphenylyl)-N-3-isoxazolyl-6-phthalazinesulfonamide;
1-(2-chloro-3'-fluoro-5-methoxy-4-biphenylyl)-N-3-isoxazolyl-6-phthalazinesulfonamide;
1-(2-chloro-3'-fluoro-5-methoxy-4-biphenylyl)-N-2-pyrimidinyl-6-phthalazinesulfonamide;
1-(2-chloro-3'-fluoro-5-methoxy-4-biphenylyl)-N-1,3,4-thiadiazol-2-yl-6-phthalazinesulfonamide;
1-(2,4'-dichloro-5-methoxy-3'-methyl-4-biphenylyl)-N-3-isoxazolyl-6-phthalazinesulfonamide;
1-(2,3'-dichloro-5-methoxy-4'-methyl-4-biphenylyl)-N-3-isoxazolyl-6-phthalazinesulfonamide;
1-(2-chloro-3'-fluoro-5-methoxy-4-biphenylyl)-N-3-isoxazolyl-4-methoxy-6-phthalazinesulfonamide;
1-(2,4'-dichloro-5-methoxy-3'-methyl-4-biphenylyl)-N-3-isothiazolyl-6-phthalazinesulfonamide; or
1-(2-chloro-3',5'-difluoro-5-methoxy-4-biphenylyl)-N-3-isothiazolyl-6-phthalazinesulfonamide.

In embodiment 32, the present invention provides a compound, or a pharmaceutically acceptable salt thereof, selected from each compound exemplified herein, either individually or collectively, in examples 1-311, disclosed herein in Table 1.

In various other embodiments, the present invention provides one or more compounds, or pharmaceutically acceptable salts thereof, selected from examples 1, 2, 4-6, 13, 24, 27, 31-32, 39, 43, 44, 47, 49, 50, 58, 60, 61, 66, 69, 71, 73-99, 101, 105-123, 125, 127, 129, 135, 137-138, 140-142, 144, 146-148, 151, 154-166, 169-172, 174-177, 179-190, 194-197, 208-210, 212, 217-225, 228-231, 236-240, 244, 249-251, 253-254, 257-258, 272-288, 290 and examples 3, 9-10, 14-15, 18-20, 25-26, 33, 55, 59, 103-104, 113, 191, 198-199, 201-204, 206-207, 211, 213-216, 226-227, 232-235, 241, 243, 245-247, 252, 255-256, 260-271 and 289.

In embodiment 33, the present invention provides multiple compounds, or their pharmaceutically acceptable salts thereof, selected from examples 1, 2, 4-6, 13, 24, 27, 31-32, 39, 43, 44, 47, 49, 50, 58, 60, 61, 66, 69, 71, 73-99, 101, 105-123, 125, 127, 129, 135, 137-138, 140-142, 144, 146-148, 151, 154-166, 169-172, 174-177, 179-190, 194-197, 208-210, 212, 217-225, 228-231, 236-240, 244, 249-251, 253-254, 257-258, 272-288 and 290.

In embodiment 34, the present invention provides a compound, or a pharmaceutically acceptable salt thereof, individually selected from examples 3, 9-10, 14-15, 18-20, 25-26, 33, 55, 59, 103-104, 113, 191, 198-199, 201-204, 206-207, 211, 213-216, 226-227, 232-235, 241, 243, 245-247, 252, 255-256, 260-271 and 289.

In various other embodiments, the present invention provides one or more compounds, or pharmaceutically acceptable salts thereof, selected from examples 14, 18, 21, 25, 42, 51, 52, 53-A, 53-B, 57, 124, 215, 232-235 and 298.

In embodiment 35, the present invention provides methods of treating pain, the methods comprising administering to a patient in need thereof a therapeutically effective amount of a compound in accordance with any one of embodiments 1, 1a-1p, 2, 2a-2b and 3 to 46, or a pharmaceutically acceptable salt thereof.

In embodiment 36, the present invention provides methods of embodiment 48 wherein the treatment is for chronic pain, acute pain, neuropathic pain, pain associated with rheumatoid arthritis, pain associated with osteoarthritis or pain associated with cancer.

In embodiment 37, the present invention provides pharmaceutical compositions comprising a compound in accordance with any one of embodiments 1, 1a-1p, 2, 2a-2b and 3 to 46, or a pharmaceutically acceptable salt thereof, and a pharmaceutically acceptable excipient.

In embodiment 38, the present invention provides compounds of Formula I, or pharmaceutically acceptable salts thereof,

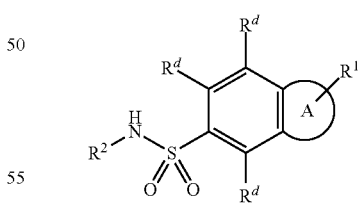

wherein:

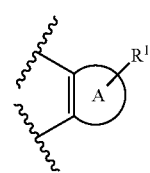

is

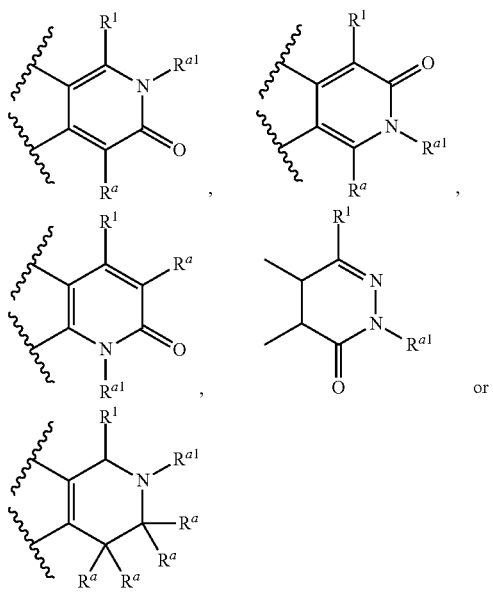

wherein each $R^a$ is independently H, halo, —OH, —NR$^b$R$^b$, —C$_{1-6}$alkyl, —OC$_{1-6}$alkyl, —C$_{1-6}$haloalkyl, —OC$_{1-6}$haloalkyl or —CN, and
$R^{a1}$ is H, —C$_{1-6}$alkyl, acetyl or —CN;
$R^1$ is

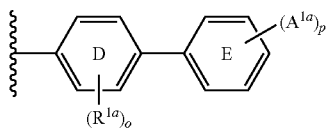

wherein ring D and ring E are both a 6 membered aryl or heteroaryl, where the heteroaryl can have from 1 to 2 nitrogen atoms;
each $R^{1a}$, independently, is halo, —NR$^b$R$^b$, —C$_{1-6}$alkyl, —OC$_{1-6}$alkyl, —OC$_{1-6}$alkylCF$_3$, —OC$_{1-6}$alkylCN, —C$_{1-6}$alkylOC$_{1-6}$alkyl, —(SO$_2$)C$_{1-6}$alkyl, —(SO$_2$)NR$^b$R$^b$, hydroxyC$_{1-6}$alkyl, —CF$_3$, —CHF$_2$, —CH$_2$F, —OCF$_3$, —OCHF$_2$, —OCH$_2$F, —(CR$^e$R$^e$)$_m$CN, —C(=O)NR$^b$R$^b$, —C(=O)OR$^b$ or —(C=N)OC$_{1-6}$alkyl;
each $A^{a1}$, independently, is halo, —NR$^b$R$^b$, —C$_{1-6}$alkyl, —OC$_{1-6}$alkyl, —(CR$^e$R$^e$)$_m$OH, hydroxyC$_{1-6}$alkyl, —CF$_3$, —CHF$_2$, —CH$_2$F, —OCF$_3$, —OCHF$_2$, —OCH$_2$F, —CN, —C(=O)NR$^b$R$^b$, —O(CR$^e$R$^e$)$_m$B or —(CR$^e$R$^e$)$_m$B;
$R^2$ is —(C=O)C$_{1-6}$alkyl, —(C=O)C$_{1-6}$haloalkyl or a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^e$R$^e$)$_n$NR$^b$R$^b$, —CF$_3$, —CHF$_2$, —OCF$_3$, —OCHF$_2$, —OCH$_2$F, —CN or —C(=O)NR$^b$R$^b$;
each $R^b$ is independently H or —C$_{1-6}$alkyl;
each $R^c$ is independently H or —C$_{1-6}$alkyl; and
each $R^d$ is independently H, halo, —CN, —NR$^c$R$^c$, —OH, —C$_{1-6}$alkyl, —C$_{1-6}$haloalkyl, —OC$_{1-6}$haloalkyl or —OC$_{1-6}$alkyl;
each $R^e$ is independently H, halo, —CN, —NR$^c$R$^c$, —OH, —C$_{1-6}$alkyl, —OC$_{1-6}$alkyl or a 5 to 6 membered heterocycloalkyl group having from 1 to 3 heteroatoms independently selected from O, N or S;
each n is independently 0, 1, 2, 3 or 4;
each m is independently 0, 1, 2, 3 or 4;
o is 0, 1, 2 or 3;
p is 0, 1, 2 or 3;
provided that the compound is not
1-(4-fluoro-2-(pyrimidin-5-yl)phenyl)-N-(thiazol-2-yl)isoquinoline-6-sulfonamide; or
1-(3',5'-difluoro-3-methoxy-4-biphenylyl)-N-(5-methoxy-4-pyrimidinyl)-6-isoquinolinesulfonamide.

DETAILED DESCRIPTION OF THE INVENTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as pain, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as C$_{1-8}$alkyl.

The term "hydroxyC$_{1-6}$alkyl" means a straight or branched alkyl chain having one to six carbons and substituted with one or more hydroxyl groups. Representative examples of hydroxyC$_{1-6}$alkyl groups include hydroxymethyl (—CH$_2$OH), 2-hydroxyethyl, 3-hydroxypropyl, 2,3-dihydroxypropyl (—CH$_2$CH(OH)CH$_2$OH), 3-hydroxyisopropyl, 4-hydroxybutyl and the like. Typical alkyl groups are alkyl groups having from 1 to 8 carbon atoms, which groups are commonly represented as C$_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are C$_{1-8}$alkoxy.

The term "halogen" or "halo" means chlorine, fluorine, bromine or iodine. The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are C$_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are C$_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl.

A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are C$_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1 H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo $C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent. Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptoms of a particular disease or condition, or prevents or delays the onset of one of more symptoms of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. Thus, in one embodiment, the invention provides a pharmaceutical composition comprising a compound of the invention, such the compound of any one of embodiments 1-39 described herein or a pharmaceutically acceptable salt thereof, and a pharmaceutically acceptable excipient. The invention also contemplates medicaments, as analogous to pharmaceutical compositions as defined herein. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, Jan. 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat obesity and facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art.

They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O(C$_1$-C$_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O(C$_1$-C$_6$)alkyl)$_2$ or —CH$_2$OC(O)(C$_1$-C$_6$) alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls that are stereoisomeric due to hindered rotations around a bond).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Other examples of tautomerism are as follows:

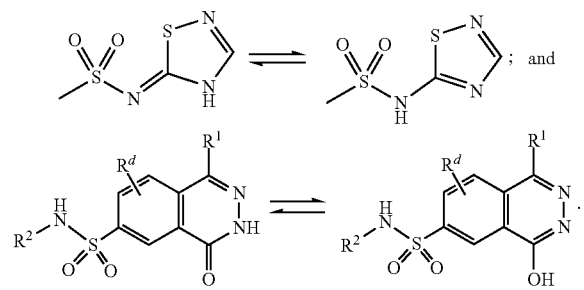

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 µm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, Calif.). Silica gel chromatography was generally performed with prepacked silica gel cartidges (Biotage, Uppsala, Sweden or Teledyne-Isco, Lincoln, Nebr.). $^1H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
ACN acetonitrile
AcOH acetic acid
aq or aq. aqueous
BOC or Boc tert-butyloxycarbonyl
DAST diethylaminosulfur trifluoride
DCM dichloromethane
DMAP 4-dimethylaminopyridine
DMB dimethoxybenzyl
DME dimethoxyethane
DMF N,N-dimethylformamide
DMSO dimethyl sulfoxide
Dppf, DPPF or dppf 1,1'-bis(diphenylphosphino)ferrocene
ESI or ES electrospray ionization
Et ethyl
$Et_2O$ diethyl ether
TEA or $Et_3N$ triethylamine
EtOAc ethyl acetate
eq or eq. equivalent
g grams
h or hr hour
HPLC high pressure liquid chromatography
iPr isopropyl
$iPr_2NEt$ N-ethyl diisopropylamine (Hunig's base)
KOAc potassium acetate
KHMDS potassium hexamethyldisilazide
LC MS, LCMS, LC-MS or LC/MS liquid chromatography mass spectroscopy
LHMDS or LiHMDS lithium hexamethyldisilazide
m/z mass divided by charge
Me methyl
MeOH methanol
MeCN or ACN acetonitrile
mg milligrams
min minutes
mL milliliters
MPLC medium pressure liquid chromatography
MS mass spectra
NaHMDS sodium hexamethyldisilazide
NBS N-bromosuccinimide
NCS N-chlorosuccinimide
n-BuLi n-butyllithium
NMR nuclear magnetic resonance
$Pd_2(dba)_3$ tris(dibenzylideneacetone)dipalladium(0)
Ph phenyl
PMB p-methoxybenzyl
Pr or PR or PG protecting group
RBF or rbf round bottom flask
RT or rt room temperature
SCX strong cation exchange
SEM 2-(trimethylsilyl)ethoxymethyl
SFC supercritical fluid chromatography
TBAF tetra-n-butylammonium fluoride
t-BuOH tert-butanol
TIPS-Cl triisopropylsilyl chloride
TFA trifluoroacetic acid
THF tetrahydrofuran
UV ultraviolet
xantphos 4,5-bis(diphenylphosphino)-9,9-dimethylxanthene
X-Phos 2-dicyclohexylphosphino-2',4',6'-triisopropyl-1,1'-biphenyl

EXAMPLES

General Synthetic Schemes

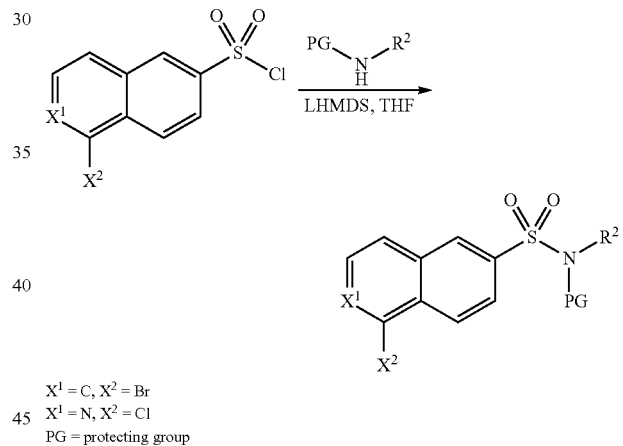

$X^1 = C, X^2 = Br$
$X^1 = N, X^2 = Cl$
PG = protecting group

Amine coupling with a sulfonyl chloride can be performed with a base (such as LHMDS, NaHMDS, KHMDS, $Cs_2CO_3$, $K_2CO_3$, $K_3PO_4$ or $Na_2CO_3$) and an amine which may be protected with a benzyl, DMB, PMB, SEM or allyl group (PG is a protecting group). This reaction can be performed in various solvents such as THF, diethyl ether, DME or dioxane. It is also possible to perform this chemistry without protecting groups in appropriate cases.

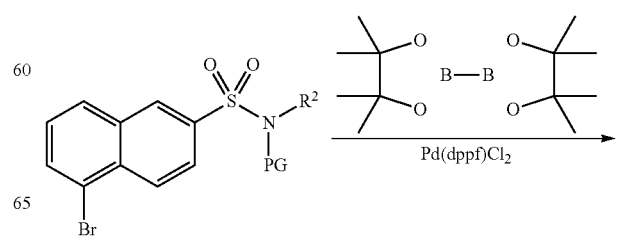

-continued

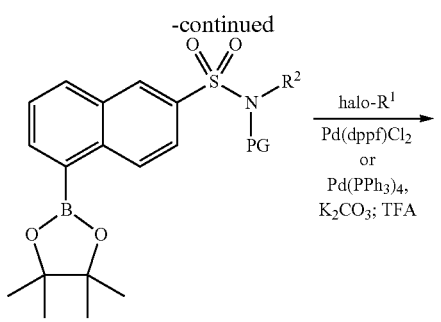

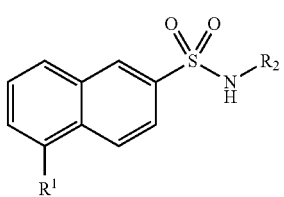

Boronic ester intermediates can be constructed through a Pd-catalyzed coupling with a boron source such as bis(pinacolato)diboron, a catalyst (such as Pd (AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The resulting boronic ester or acid can subsequently be coupled employing a catalyst (such as Pd (AmPhos)$_2$Cl$_2$, Pd(dppf)Cl$_2$ or Pd(PPh$_3$)$_4$) in the presence of a base (such as Cs$_2$CO$_3$, K$_2$CO$_3$, K$_3$PO$_4$ or Na$_2$CO$_3$), and solvents (such as aqueous 1,4-dioxane, DME, EtOH, DMF or t-BuOH). The removal of the protecting group can be done thermally during the coupling reaction or by using acid or reductive conditions (such as TFA, HCl, Pd/C in hydrogen atmosphere, etc.).

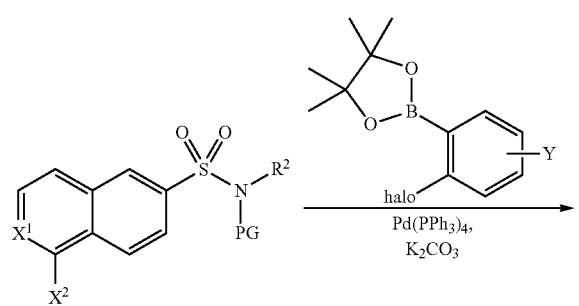

$X^1 = C, X^2 = Br$
$X^1 = N, X^2 = Cl$

The Suzuki reaction can be achieved using a variety of bases (such as Cs$_2$CO$_3$, K$_2$CO$_3$, K$_3$PO$_4$ or Na$_2$CO$_3$), catalysts (such as Pd (AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The subsequent coupling can be performed with various reaction partners (M) to install a R$^e$ group (such as boronic acids, stannanes, Grignard or zinc reagents) and catalysts (such as Pd (AmPhos)$_2$Cl$_2$, Pd(dppf)Cl$_2$ or Pd(PPh$_3$)$_4$). The removal of the protecting group can be done thermally during the coupling reaction or by using acid or reductive conditions (such as TFA, HCl, Pd/C in hydrogen atmosphere, etc.).

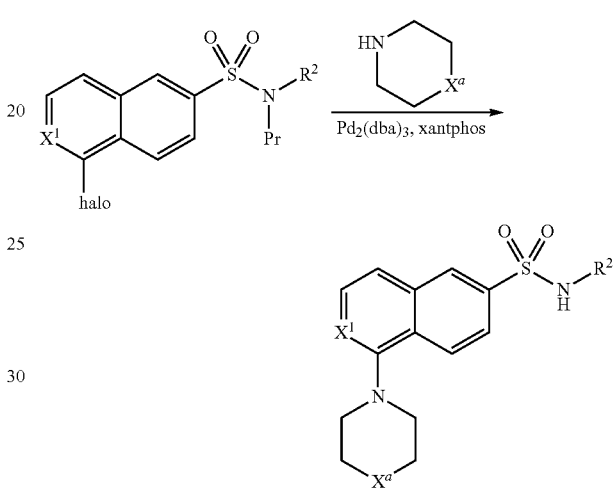

Naphthalenes (X$^1$=CH) or isoquinolines (X$^1$=N) can be substituted through coupling with cyclic amines employing catalysts (such as Pd$_2$(dba)$_3$/xantphos, Pd (AmPhos)$_2$Cl$_2$, Pd(dppf)Cl$_2$ or Pd(PPh$_3$)$_4$) in solvents (such as 1,4-dioxane, DME, DMF or toluene). X$^a$ can be O or NR.

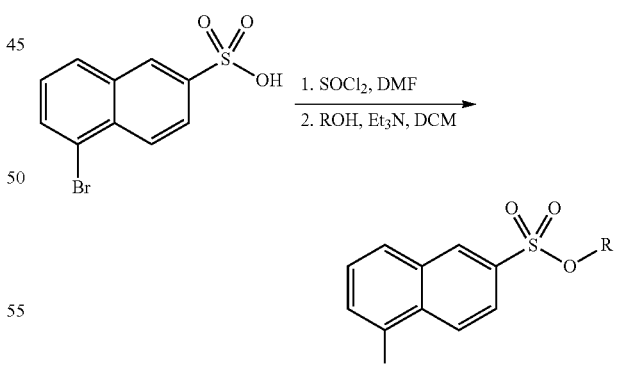

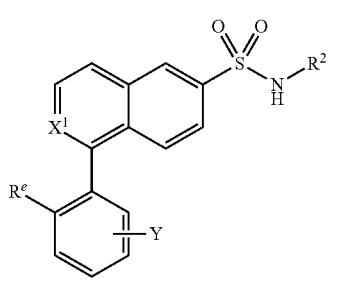

Naphthalene sulfonic acid can be converted to sulfonyl chloride employing a chlorinating agent (such as SO$_2$Cl$_2$, ClSO$_3$H, POCl$_3$, PCl$_5$ or cyanuric trichloride) in various solvents (such as DCM, DCE or DMF). The resulting sulfonyl chloride can be converted into a sulfonic ester with an alcohol (ROH) (such as pentafluorophenol or trifluoroethanol).

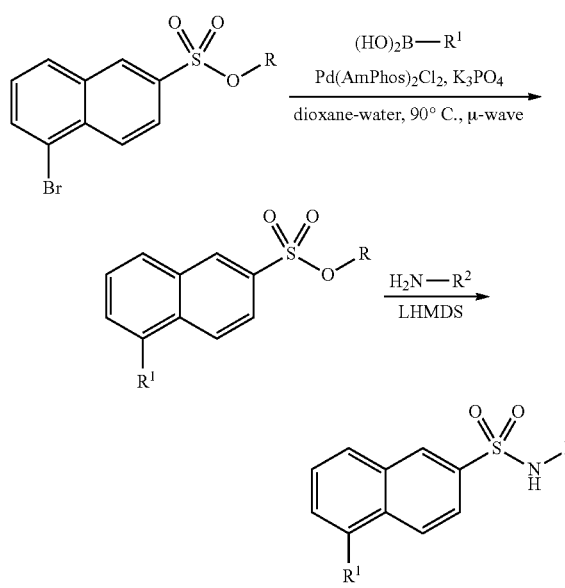

The Suzuki reaction can be achieved using a variety of bases (such as $Cs_2CO_3$, $K_2CO_3$, $K_3PO_4$ or $Na_2CO_3$), catalysts (such as Pd (AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). Amine coupling with a sulfonic ester can be performed with a base (such as LHMDS, NaHMDS, KHMDS, $Cs_2CO_3$, $K_2CO_3$, $K_3PO_4$ or $Na_2CO_3$). Alternatively, the sulfonic ester can be hydrolyzed with a base (such as LiOH, KOH or NaOH) which can be converted to the sulfonyl chloride as stated above. Amine coupling with the resulting sulfonyl chloride can be performed with a base (such as LHMDS, NaHMDS, KHMDS, $Cs_2CO_3$, $K_2CO_3$, $K_3PO_4$ or $Na_2CO_3$).

The following compounds presented herein, as examples of the present invention, and intermediates thereof as building blocks to prepare compounds provided by the invention, may be made by the various methods and synthetic strategies taught hereinbelow. These compounds, and others provided by the invention, may also be prepared using methods described in PCT/US2012/068297, filed Dec. 6, 2012, which specification is incorporated herein by reference in its entirety.

Intermediate A

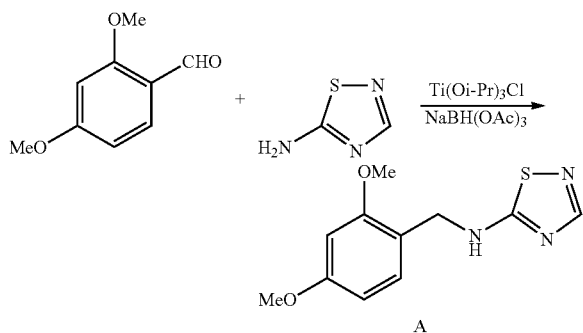

Intermediate A

N-(2,4-DIMETHOXYBENZYL)-1,2,4-THIADIAZOL-5-AMINE

To a solution of 1,2,4-thiadiazol-5-amine (150 g, 1.48 mol, 1.1 eq.) and 2,4-dimethoxybenzaldehyde (224.1 g, 1.35 mol, 1 eq.) in anhydrous DCM (6 L) was added chlorotitanium triisopropoxide (771.3 g, 2.96 mol, 2.2 eq.) slowly over 15 minutes. The resulting yellow solution was stirred for 30 min and then treated with sodium triacetoxyborohydride (715.3 g, 3.38 mol, 2.5 eq.) portionwise (Note: the reaction temperature increased from RT to 34° C.). After 2 hours, LC/MS analysis showed that Intermediate A was formed as the major product. The reaction mixture was cooled using an ice and water bath and neutralized with saturated aqueous $NaHCO_3$ to a pH of about 7. The resulting thick slurry was passed through diatomaceous Earth® (diatomaceous earth) and washed with DCM. The white solid left on the diatomaceous Earth® (diatomaceous earth) was collected, put into a flask, charged with DCM and water and then stirred well. The resulting slurry was again passed through diatomaceous Earth® (diatomaceous earth) and washed with DCM. All the filtrates were combined. The organic layer was separated, dried, filtered and concentrated. The oily residue was purified by column chromatography using silica gel (40 to 63 µm, 23-400 mesh) eluting with 5-10% EtOAc in Hexanes-DCM (1:1), to afford Intermediate A (160 g) as a white solid. MS (ESI, positive ion) m/z: 252.3. $^1$H NMR (400 MHz, DMSO-d$_6$): δ ppm 8.68 (s, 1 H), 7.89 (s, 1 H), 7.17 (d, J=8.2 Hz, 1 H), 6.57 (s, 1 H), 6.49 (d, J=8.3 Hz, 1 H), 4.37 (d, J=5.2 Hz, 2 H), 3.80 (s, 3 H), 3.75 (s, 3 H).

Intermediates B, C, D and E

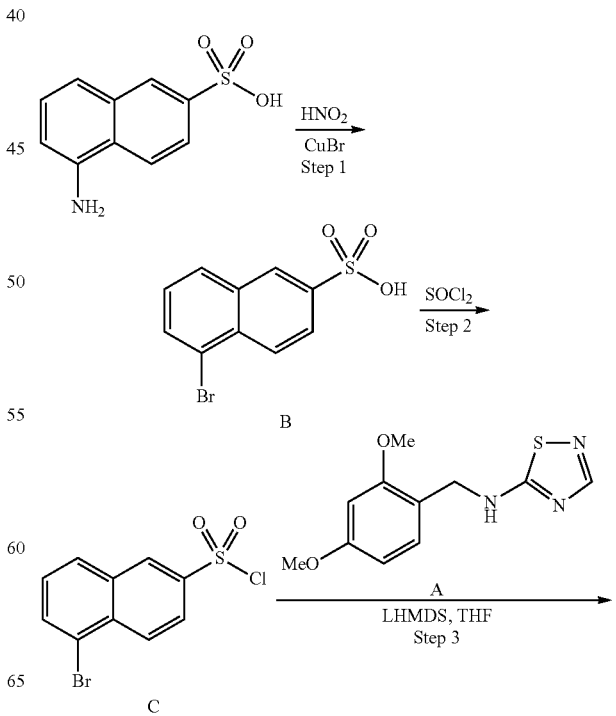

-continued

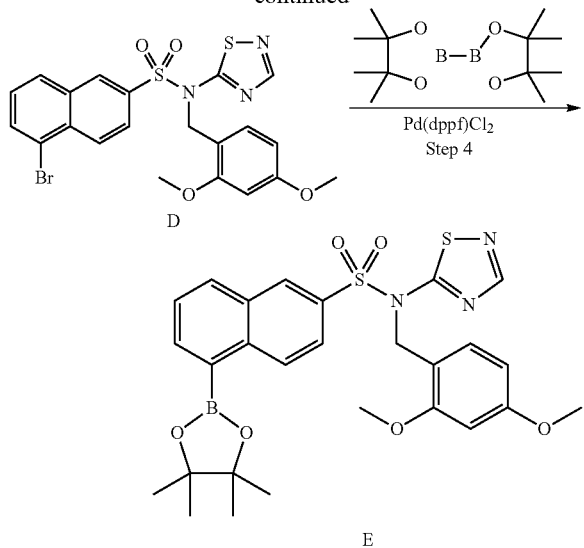

E

Intermediate B

5-BROMONAPHTHALENE-2-SULFONIC ACID

Step 1: To a cold solution of 5-aminonaphthalene-2-sulfonic acid (380 g, 1.70 mol, 1 eq.; Alfa Aesar, Ward Hill, Mass.) in aqueous NaOH (0.85 M, 2.4 L, 2.04 mol, 1.2 eq.) was added aqueous HBr (48%, 519 mL, 4.59 mol, 2.7 eq.) slowly. The resulting suspension was cooled to −5° C. and a solution of $NaNO_2$ (129 g, 1.87 mol, 1.1 eq) in water (280 mL) was added dropwise with stirring, keeping the internal temperature below 0° C. The reaction mixture was stirred at −5 to 0° C. for 30 min (Note: The formation of the diazonium salt could be detected by LC/MS) and urea (12.3 g, 0.20 mol, 0.12 eq.) was added to decompose excess nitrite. The diazonium salt was added dropwise (1 h) with stirring to a heated (70° C.) solution of CuBr (243.9 g, 1.70 mol, 1 eq.) in aqueous HBr (48%, 1038.5 mL, 9.18 mol, 5.4 eq.). The mixture was then stirred at 80° C. for 30 min LC/MS analysis showed that Intermediate B was formed as the major product. The mixture was cooled to room temperature and stirred overnight. The precipitate was filtered, washed with water, and dried under a vacuum, affording Intermediate B (370 g) as a grey solid. MS (ESI): 286.9 $[M]^+$; $^1H$ NMR (300 MHz, DMSO-$d_6$) δ ppm 8.23 (brs, 1 H), 8.09 (t, J=9.0 Hz, 2 H), 7.90 (d, J=9.0 Hz, 2 H), 7.47 (t, J=9.0 Hz, 2 H).

Intermediate C

5-BROMONAPHTHALENE-2-SULFONYL CHLORIDE

Step 2: To a suspension of Intermediate B (287.1 g, 1.0 mol, 1 eq) in anhydrous DMF (1 L) was added $SOCl_2$ (145.9 mL, 2 mol, 2 eq) dropwise keeping the temperature below 30° C. The resulting yellow solution was stirred at RT for 1.5 h (LC/MS analysis showed that Intermediate B was consumed), diluted with DCM (4 L), treated with ice water (4 Kg), and then stirred well. The DCM layer was separated, washed with water (2 L×3), dried, filtered and concentrated to give Intermediate C (220 g) as a yellow solid.

Intermediate D

5-BROMO-N-(2,4-DIMETHOXYBENZYL)-N-(1,2,4-THIADIAZOL-5-YL)NAPHTHALENE-2-SULFONAMIDE

Step 3: A solution of Intermediate C (160 g, 0.64 mol, 1.0 eq) in anhydrous THF (3 L) was cooled to −40° C. and charged with LHMDS (1M in THF, 0.96 L, 0.96 mol, 1.5 eq.) dropwise, keeping the temperature below 0° C. The resulting mixture was stirred at 0° C. for 10 min and then cooled to −40° C. To it was added a solution of Intermediate A (214 g, 0.70 mol, 1.1 eq) in anhydrous THF (300 mL) dropwise, keeping the temperature below 0° C. The mixture was allowed to warm to RT gradually. LC/MS analysis showed that Intermediate D was formed as the major product. The reaction mixture was quenched with 1 N HCl to pH 5. Phases were separated. The aqueous layer was extracted with EtOAc (500 mL×2). The organic layers were combined, washed with 1 M NaOH (500 mL×2) and brine to remove sulfonic acid Intermediate B generated from excess Intermediate C, dried, and concentrated. The residue was crystallized from hot acetone affording Intermediate D (182 g) as an off-white solid. MS (ESI): 542.0 $[M+Na]^+$; $^1H$ NMR (300 MHz, DMSO-$d_6$) δ ppm 8.65 (d, J=1.8 Hz, 1 H), 8.41 (s, 1 H), 8.28 (d, J=8.7 Hz, 1 H), 8.25 (d, J=8.7 Hz, 1 H), 8.13 (d, J=7.5 Hz, 1 H), 7.96 (dd, J=9.0, 1.8 Hz, 1 H), 7.63 (t, J=8.8 Hz, 1 H), 7.00 (d, J=8.4 Hz, 1 H), 6.35 (d, J=8.4 Hz, 1 H), 6.33 (s, 1 H), 5.21 (s, 2 H), 3.66 (s, 3 H), 3.63 (s, 3 H).

Intermediate E

N-(2,4-DIMETHOXYBENZYL)-5-(4,4,5,5-TETRAMETHYL-1,3,2-DIOXABOROLAN-2-YL)-N-(1,2,4-THIADIAZOL-5-YL)NAPHTHALENE-2-SULFONAMIDE

Step 4: A mixture of Intermediate D (100 g, 0.19 mol, 1 eq.), bis(pinacolato)diboron (73.2 g, 0.29 mol, 1.5 eq.), KOAc (55.9 g, 0.57 mol, 3 eq.) and Pd(dppf)$Cl_2$.DCM (7.76 g, 0.0095 mol, 0.05 eq) in anhydrous 1,4-dioxane (500 mL) was degassed with $N_2$ for 10 min and then heated at 80° C. for 5 hours. LC/MS analysis showed that Intermediate D was consumed. The reaction mixture was cooled to RT, quenched with brine (400 mL), and stirred well. Phases were separated. The aqueous layer was extracted with DCM (500 mL×2). The organic layers were combined, washed with brine, dried and concentrated. The residue was passed through a short silica gel pad to remove Pd and other polar impurities by washing with DCM. The DCM solution was concentrated and the residue was triturated with MeOH, affording Intermediate E (102 g) as a white solid. MS (ESI): 568.2 $[M+H]^+$; $^1H$ NMR (300 MHz, DMSO-$d_6$) δ ppm 8.80 (d, J=8.7 Hz, 1 H), 8.63 (d, J=1.8 Hz, 1 H), 8.38 (s, 1 H), 8.34 (d, J=8.1 Hz, 1 H), 8.19 (dd, J=6.9, 1.2 Hz, 1 H), 7.91 (dd, J=8.7, 1.8 Hz, 1 H), 7.43 (dt, J=8.1, 1.8 Hz, 1 H), 7.02

(d, J=8.7 Hz, 1 H), 6.40 (s, 1 H), 6.39 (d, J=8.1 Hz, 1 H), 5.18 (s, 2 H), 3.70 (s, 3 H), 3.66 (s, 3 H), 1.38 (s, 12 H).

Intermediates F and G

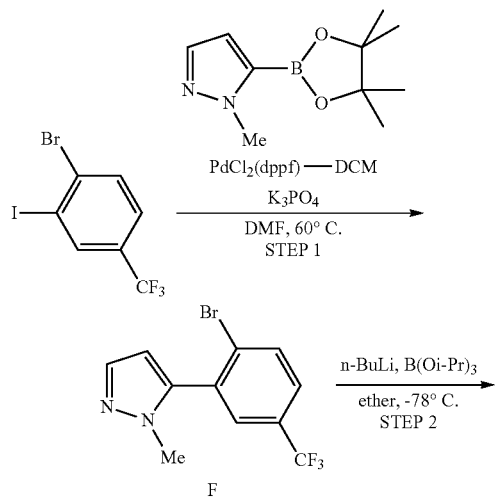

Intermediate F 5-(2-BROMO-5-(TRIFLUOROMETHYL)PHE-NYL)-1-METHYL-1H-PYRAZOLE

Step 1: A round-bottom flask was charged with 1-bromo-2-iodo-4-(trifluoromethyl)benzene (5.00 g, 14.25 mmol; Combi-blocks, San Diego, Calif.), 1-methyl-1H-pyrazole-5-boronic acid pinacol ester (3.41 g, 16.39 mmol), potassium phosphate (6.05 g, 28.5 mmol) and Pd(dppf)Cl$_2$·CH$_2$Cl$_2$ (1.164 g, 1.425 mmol). The flask was flushed with Ar, and DMF (47.5 mL) was then added. The flask was sealed, heated to 60° C. for 12 h, and then stirred at room temperature for 48 h. The mixture was diluted with water and extracted with EtOAc (three times). The combined organics were washed with brine, dried and concentrated under a vacuum. The product was purified by chromatography using silica gel (0 to 100% EtOAc/Heptane) to yield 5-(2-bromo-5-(trifluoromethyl)phenyl)-1-methyl-1H-pyrazole (2.956 g, 9.69 mmol) as a brown solid. $^1$H NMR (400 MHz, DMSO-d$_6$) δ ppm=8.06 (td, J=0.7, 8.1 Hz, 1 H), 7.86-7.73 (m, 2 H), 7.53 (d, J=2.0 Hz, 1 H), 6.41 (d, J=2.0 Hz, 1 H), 3.64 (s, 3 H); m/z (ESI) 305.0 (M+H)$^+$.

Intermediate G (2-(1-METHYL-1H-PYRAZOL-5-YL)-4-(TRIFLUOROMETHYL)PHENYL)BORONIC ACID Step 2: An 250 mL round-bottom flask was charged with 5-(2-bromo-5-(trifluoromethyl)phenyl)-1-methyl-1H-pyrazole (Intermediate F) (2.956 g, 9.69 mmol), diethyl ether (74.5 mL), and triisopropyl borate (2.70 mL, 11.63 mmol). The flask was cooled to −78° C. for 10 min, after which butyllithium (2.5M in hexanes) (4.65 mL, 11.63 mmol) was added dropwise. The mixture was stirred for 30 min, and then warmed to room temperature. A 2N aq. NaOH solution (100 mL) was added, and the resulting biphasic mixture was stirred vigorously for 1 h. The mixture was diluted with water, and the layers separated. The ethereal layer was extracted with water (twice) and the water layers were combined and washed with diethyl ether. The ether layers were back-extracted once more, and all aqueous layers combined and acidified to a pH of about 2 with 6N aq. HCl to give a clear solution. The aqueous layer was extracted with ethyl acetate (twice), and the combined organics were dried over sodium sulfate, filtered and concentrated. The residue was concentrated from DCM to give (2-(1-methyl-1H-pyrazol-5-yl)-4-(trifluoromethyl)phenyl)boronic acid (2.36 g, 8.74 mmol) as a yellow solid. m/z (ESI) 271.2 (M+H)$^+$.

Intermediate AA (2-(PYRIDIN-4-YL)-4-(TRIFLUOROMETHYL)PHENYL)BORONIC ACID

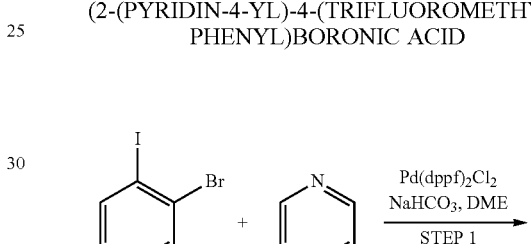

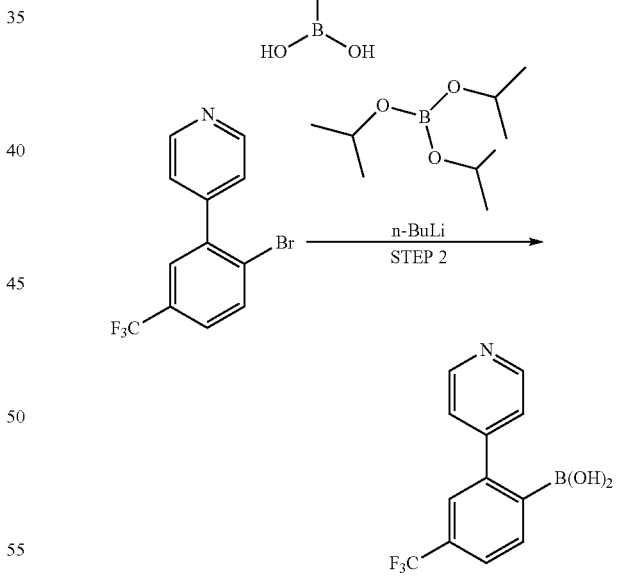

STEP 1: 4-(2-BROMO-5-(TRIFLUOROMETHYL)PHENYL)PYRIDINE

To a solution of compound 1-bromo-2-iodo-4-(trifluoromethyl)benzene (10 g, 28.4 mmol) and pyridin-4-ylboronic acid (7 g, 34.1 mmol) in dimethoxyethane (150 mL) and water (50 mL), sodium bicarbonate (9.54 g, 113.6 mmol) was added. The reaction mixture was purged with nitrogen for 15 minutes and Pd(dppf)$_2$Cl$_2$ (2.3 g, 2.84 mmol)

was added. The reaction was stirred at 90° C. for 5 h. Then the reaction mixture was diluted with water (500 mL) extracted with ethyl acetate (2×200 mL). Organic layer was combined, dried over sodium sulfate, filtered and concentrated under a vacuum to give the compound which was further purified by column chromatography using silica gel (100 to 200 mesh) and 0% to 30% ethyl acetate/hexane as eluent to obtain 4-(2-bromo-5-(trifluoromethyl)phenyl)pyridine (6.7 g, 77.6%) as an off white solid. MS (ESI, positive ion) [M+1]$^+$: 301.98; $^1$H NMR (400 MHz, DMSO) δ 8.71 (d, J=5.9 Hz, 2H), 8.05 (d, J=8.2 Hz, 1H), 7.84-7.75 (d, J=11.3 Hz, 2H), 7.50 (d, J=5.9 Hz, 2H).

STEP 2: (2-(PYRIDIN-4-YL)-4-(TRIFLUOROMETHYL)PHENYL)BORONIC ACID

A round bottom flask was charged with 4-(2-bromo-5-(trifluoromethyl)phenyl)pyridine (2.0 g, 6.62 mmol), diethyl ether (50.9 ml), and triisopropyl borate (1.845 ml, 7.94 mmol). The flask was cooled to −78° C. for 10 minutes after which butyllithium (1.7 M in hexanes) (4.67 ml, 7.94 mmol) was added dropwise. The reaction was stirred for 30 minutes. The dry-ice bath was removed and 2N aqueous NaOH solution (50 mL) was added. The resulting biphasic mixture was stirred vigorously for one hour. The mixture was diluted with water, and the layers were separated. The diethyl ether was then extracted with water (×2) and the water layers were combined and washed twice with diethyl ether. The aqueous layer was neutralized to about pH 7 with 1N aqueous HCl solution and extracted with ethyl acetate (three times). The combined organic layers were dried over sodium sulfate, filtered and concentrated to afford (2-(pyridin-4-yl)-4-(trifluoromethyl)phenyl)boronic acid as an off-white solid. m/z (ESI) 268.1 (M+H)$^+$.

Intermediate AAA

1-CHLOROISOQUINOLINE-6-SULFONYL CHLORIDE

A 1 L round bottom flask was charged with 6-bromo-1-chloro-isoquinoline (10.1 g, 41.6 mmol) and diethyl ether (416 mL) and THF (41.6 mL, 41.6 mmol) to give a light yellow solution. The flask was cooled in a dry ice and acetone bath for 20 min, then 2.5 M n-butyllithium in hexanes (18.3 mL, 43.6 mmol) was added dropwise over 5 min to give a dark solution. After 10 min, LC/MS of an aliquot in MeOH showed conversion of 6-bromo-1-chloro-isoquinoline to mainly 1-chloroisoquinoline. Sulfur dioxide (g) was condensed into the reaction mixture from a lecture bottle (warmed by a warm water bath to make sure there was a positive pressure of SO$_2$(g) which was monitored by an oil bubbler) using a needle for 15 min to give a yellow suspension. After 20 min, LC/MS of an aliquot in MeOH showed consumption of 6-bromo-1-chloro-isoquinoline to 1-chloroisoquinoline-6-sulfinic acid. The chlorination step should be performed at −78° C. Solid n-chlorosuccinimide (5.55 g, 41.6 mmol) was added in three portions at −78° C. The cold bath was removed and the mixture was warmed to room temperature. After 2 hours, 1.2 g of NCS and 100 mL of THF were added at room temperature. After stirring for another 30 min at room temperature, LC/MS of an aliquot in MeOH showed mainly sulfonyl chloride product. After another 30 min, the solid was filtered with an aid of 100 mL of THF. The yellow filtrate was concentrated and placed under vacuum overnight to afford a yellow solid. The next day, the solid was triturated with i-PrOH (30 mL) at room temperature, filtered quickly (left on the frit for less than 3 min), and dried under a vacuum to give a beige solid. The filtrate was concentrated, absorbed onto a plug of silica gel, and purified by chromatography through a silica gel column (120 g), eluting with a gradient of 0% to 20% EtOAc in heptane, to provide a second batch. MS (ESI): 262 [M+H]$^1$; $^1$H NMR (400 MHz, CDCl$_3$) ppm 7.82 (d, J=5.2 Hz, 1 H), 8.23 (dd, J=9.00, 1.96 Hz, 1H), 8.53 (d, J=5.67 Hz, 1 H), 8.58-8.65 (m, 2 H).

Intermediates BB, CC and DD

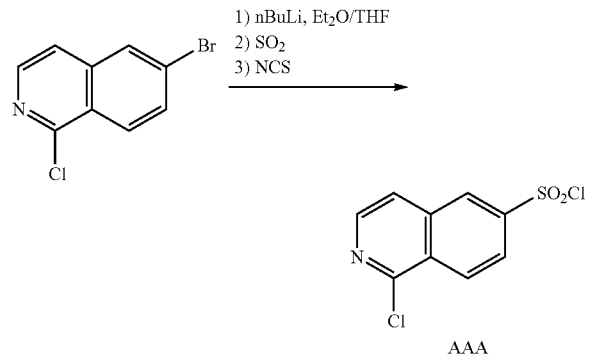

Intermediate AAA

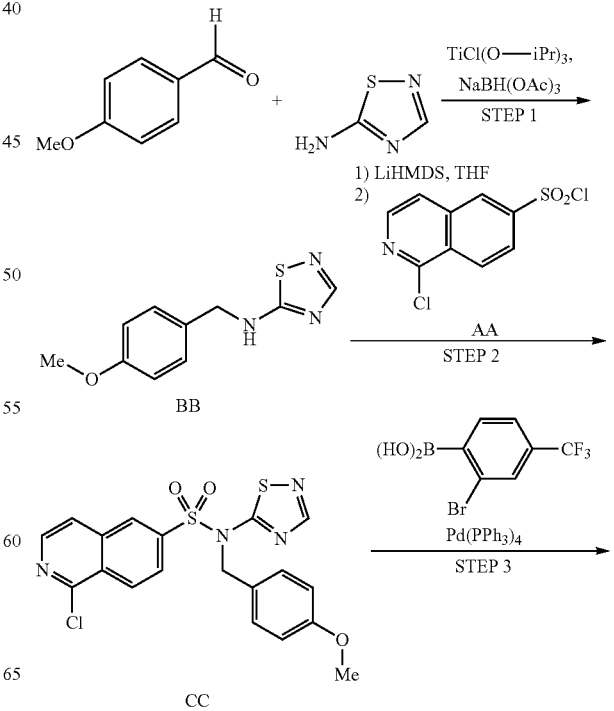

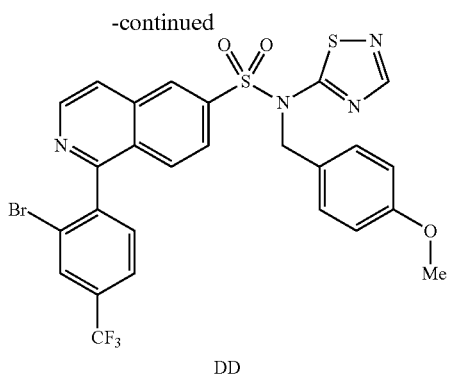

DD

Intermediate BB

N-(4-METHOXYBENZYL)-1,2,4-THIADIAZOL-5-AMINE

Step 1: To a suspension of 4-methoxybenzaldehyde (10.0 g, 73.4 mmol) and 1,2,4-thiadiazol-5-amine (7.40 g, 73.4 mmol) in dichloromethane (200 mL) was added chlorotitanium triisopropoxide (28.6 g, 110 mmol) portionwise over 5 min. After stirring for 3 hours, sodium triacetoxyborohydride (38.9 g, 184 mmol) was added portionwise at 0° C. and allowed to stir for additional 1 hour. The reaction was cooled in an ice and water mixture, quenched with saturated NaHCO$_3$ solution (300 mL) and extracted with dichloromethane (2×300 mL). The organic layer was separated, dried over Na$_2$SO$_4$, filtered and concentrated to obtain the product, which was purified by column chromatography using silica gel (100 to 200 mesh) and 0 to 30% ethyl acetate in hexane to give 5.5 g of as an off-white solid. MS (ESI, positive) m/z: 222.1; $^1$H NMR (400 MHz, DMSO-d$_6$) δ 8.89 (s, 1 H), 7.92 (s, 1 H), 7.27 (d, J=8.5 Hz, 2 H), 6.91 (d, J=8.5 Hz, 2 H), 4.42 (d, J=5.4 Hz, 2 H), 3.73 (s, 3 H).

Intermediate CC

1-CHLORO-N-(4-METHOXYBENZYL)-N-(1,2,4-THIADIAZOL-5-YL)ISOQUINOLINE-6-SULFONAMIDE

Step 2: To a solution of N-(4-methoxybenzyl)-1,2,4-thiadiazol-5-amine (1.40 g, 6.33 mmol) in THF (42.2 mL) at −70° C. under an argon atmosphere was added lithium bis(trimethylsilyl)amide, 1.0 M solution in tetrahydrofuran (6.96 mL, 6.96 mmol) dropwise. The reaction mixture was removed from cooling and stirred for 45 min. The mixture was again cooled to −70° C. (internal temperature) to give a yellow suspension. Then solid 1-chloroisoquinoline-6-sulfonyl chloride (1.82 g, 6.96 mmol) was added in one portion. After 15 min, the mixture was warmed to room temperature and concentrated. The residue was absorbed onto a plug of silica gel and purified by chromatography through a silica gel column (80 g), eluting with a gradient of 0% to 50% EtOAc in hexane, to provide 1-chloro-N-(4-methoxybenzyl)-N-(1,2,4-thiadiazol-5-yl)isoquinoline-6-sulfonamide (0.73 g, 1.633 mmol) as an orange solid. MS (ESI): 447.0 [M+H]; $^1$H NMR (500 MHz, DMSO-d6) ppm 3.65 (s, 3H), 5.24 (s, 2 H), 6.77 (m, J=8.66 Hz, 2 H), 7.28 (m, J=8.66 Hz, 2 H), 8.10 (dd, J=5.9, 10.8 Hz, 1 H), 8.15 (d, J=6.4 Hz, 1 H), 8.42 (d, J=8.6 Hz, 1 H), 8.45 (s, 1H), 8.50 (d, J=5.56 Hz, 1 H), 8.77 (d, J=1.71 Hz, 1 H).

Intermediate DD

1-(2-BROMO-4-(TRIFLUOROMETHYL)PHENYL)-N-(4-METHOXYBENZYL)-N-(1,2,4-THIADIAZOL-5-YL)ISOQUINOLINE-6-SULFONAMIDE

Step 3: A glass pressure tube was charged with 1-chloro-N-(4-methoxybenzyl)-N-(1,2,4-thiadiazol-5-yl)isoquinoline-6-sulfonamide (690 mg, 1.54 mmol), potassium carbonate (107 mg, 7.72 mmol), 2-bromo-4-(trifluoromethyl)phenylboronic acid (498 mg, 1.85 mmol), tetrakis(triphenylphosphine)palladium(0) (178 mg, 0.154 mmol) in dioxane (10.300 mL) and water (5.15 mL). The reaction was purged with argon. The tube was sealed and heated in an oil bath at 100° C. After 35 min, the reaction was cooled down to room temperature. The mixture was extracted with EtOAc (3×30 mL). The organic layers were separated, combined, dried over MgSO$_4$, filtered and concentrated to afford a yellow residue. The residue was absorbed onto a plug of silica gel and purified by chromatography through a silica gel column (40 g), eluting with a gradient of 0% to 20% DCM in heptane to remove PPh$_3$ and then 20 to 90% DCM in heptane to provide 1-(2-bromo-4-(trifluoromethyl)phenyl)-N-(4-methoxybenzyl)-N-(1,2,4-thiadiazol-5-yl)isoquinoline-6-sulfonamide (0.86 g, 1.353 mmol) as a yellow solid. MS (ESI): 634.0 [M+H]$^+$; $^1$H NMR (400 MHz, DMSO-d$_6$) ppm 3.64 (s, 3 H), 5.24 (s, 2 H), 6.78 (d, J=8.90 Hz, 2 H), 7.27 (d, J=8.80 Hz, 2 H), 7.69 (d, J=10 Hz, 1 H), 7.75 (d, J=8 Hz, 1 H), 7.91-7.99 (m, 2H), 8.23-8.26 (m, 2H), 8.46 (s, 1H), 8.81-8.84 (m, 2H).

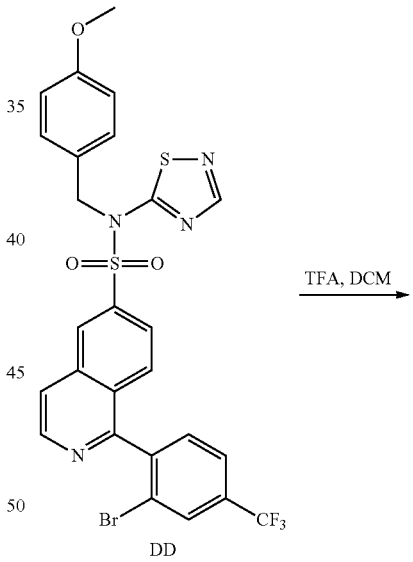

DD

TFA, DCM →

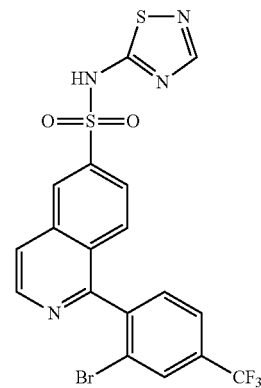

Example 50

1-(2-BROMO-4-(TRIFLUOROMETHYL)PHE-NYL)-N-(1,2,4-THIADIAZOL-5-YL)ISOQUINO-LINE-6-SULFONAMIDE

To a solution of 1-(2-bromo-4-(trifluoromethyl)phenyl)-N-(4-methoxybenzyl)-N-(1,2,4-thiadiazol-5-yl)isoquinoline-6-sulfonamide (INTERMEDIATE DD, 100 mg, 0.157 mmol) in DCM (1574 µl) was added TFA (60.6 µl, 0.787 mmol). The mixture was stirred at room temperature. After 2 h, LC/MS showed mainly the desired product. The reaction mixture was concentrated and dissolved in 3 ml of DMSO. This solution was injected onto the reverse phase HPLC (Xbridge 10 µm, C18, 19×100 mm column eluting with 0.1% NH$_4$OH in ACN and water as the mobile phase) ultimately affording 1-(2-bromo-4-(trifluoromethyl)phenyl)-N-(1,2,4-thiadiazol-5-yl)isoquinoline-6-sulfonamide (10.6 mg, 0.021 mmol). MS (ESI): 514.8 [M+H]$^+$; $^1$H NMR (500 MHz, DMSO-d6) ppm 7.68 (d, J=8.87 Hz, 1 H), 7.76 (d, J=7.80 Hz, 1 H), 7.90-7.98 (m, 2 H), 8.22-8.26 (m, 2 H), 8.48 (s, 1 H), 8.65 (m, 1 H), 8.76 (d, J=5.66 Hz, 1 H).

Intermediate EE

1-CHLORO-N-(THIAZOL-2-YL)ISOQUINOLINE-6-SULFONAMIDE

Step 1: Potassium carbonate (7.97 g, 57.7 mmol) was added to solution of thiazol-2-amine (0.963 g, 9.61 mmol) in acetonitrile (48.1 mL). After stirring for 5 min at room temperature, 1-chloroisoquinoline-6-sulfonyl chloride (2.52 g, 9.61 mmol) was added. After 2 days, a suspension was formed and an LC/MS of an aliquot in DCM showed consumption of starting material and formation of product. The solid was filtered off with the aid of DCM (50 mL) to provide ((1-chloroisoquinolin-6-yl)sulfonyl)(thiazol-2-yl)amide that was carried on to the next step. MS (ESI): 325.8 [M+Na]$^+$.

Intermediate FF

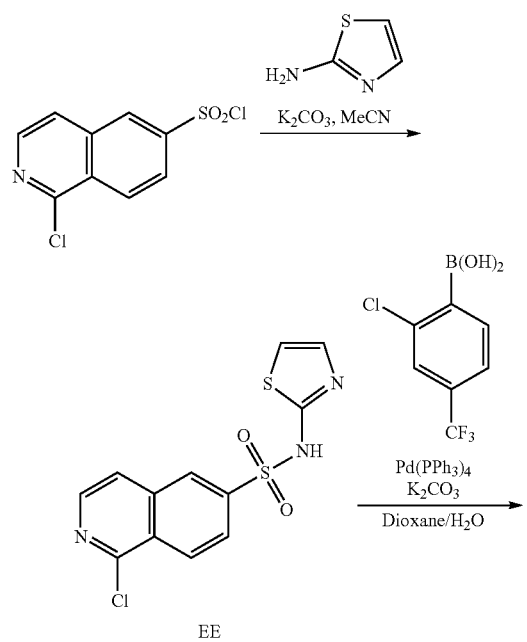

Intermediate EE

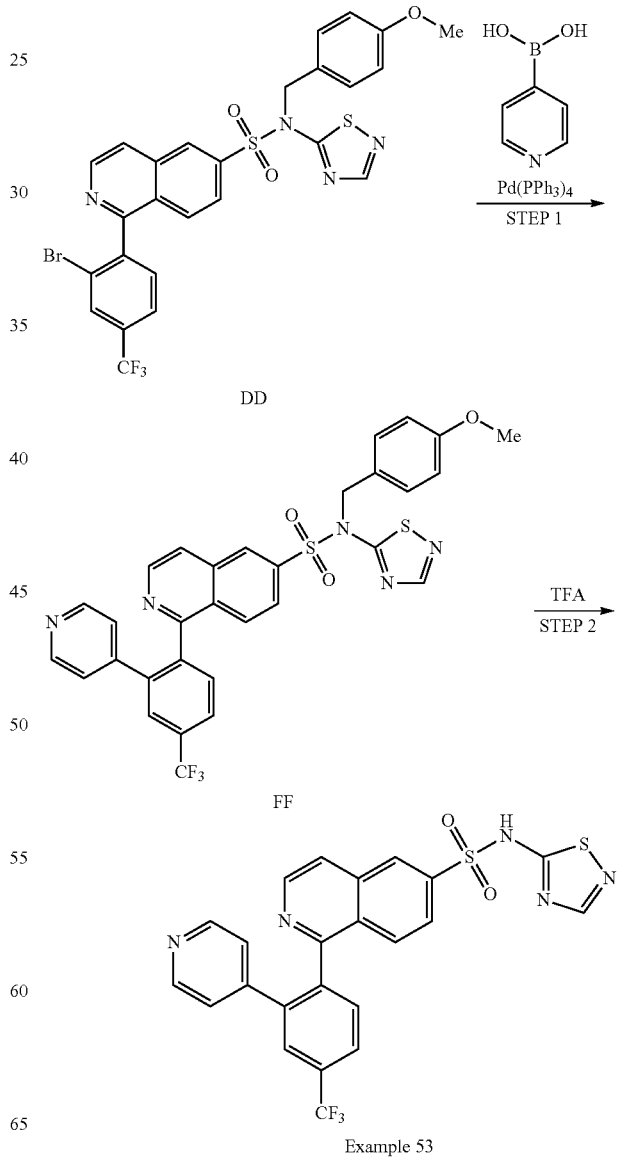

Example 51

Example 53

Intermediate FF

N-(4-METHOXYBENZYL)-1-(2-(PYRIDIN-4-YL)-4-(TRIFLUOROMETHYL)PHENYL)-N-(1,2,4-THIADIAZOL-5-YL)ISOQUINOLINE-6-SULFONAMIDE

Step 1: A microwave vial was charged with 1-(2-bromo-4-(trifluoromethyl)phenyl)-N-(4-methoxybenzyl)-N-(1,2,4-thiadiazol-5-yl)isoquinoline-6-sulfonamide (100 mg, 0.157 mmol), potassium carbonate (109 mg, 0.787 mmol), 4-pyridineboronic acid (77 mg, 0.629 mmol), tetrakis(triphenylphosphine)palladium(0) (18.18 mg, 0.016 mmol), dioxane (1049 µl) and water (525 µl). The vial was purged with argon, sealed and heated in a microwave at 100° C. for 35 min. The reaction was cooled to room temperature, diluted with 60 mL of EtOAc, dried over MgSO₄, filtered and concentrated. The material was absorbed onto a plug of silica gel and purified by chromatography through a silica gel column (40 g), eluting with a gradient of 0% to 100% (90:10 MeOH:DCM) in DCM, to provide a yellow glass, N-(4-methoxybenzyl)-1-(2-(pyridin-4-yl)-4-(trifluoromethyl)phenyl)-N-(1,2,4-thiadiazol-5-yl)isoquinoline-6-sulfonamide (100 mg, 0.158 mmol). This material was carried on to the next step. MS (ESI): 634.0 [M+H]⁺.

Intermediate GG

1-CHLORO-N-(PYRIMIDIN-4-YL)ISOQUINOLINE-6-SULFONAMIDE

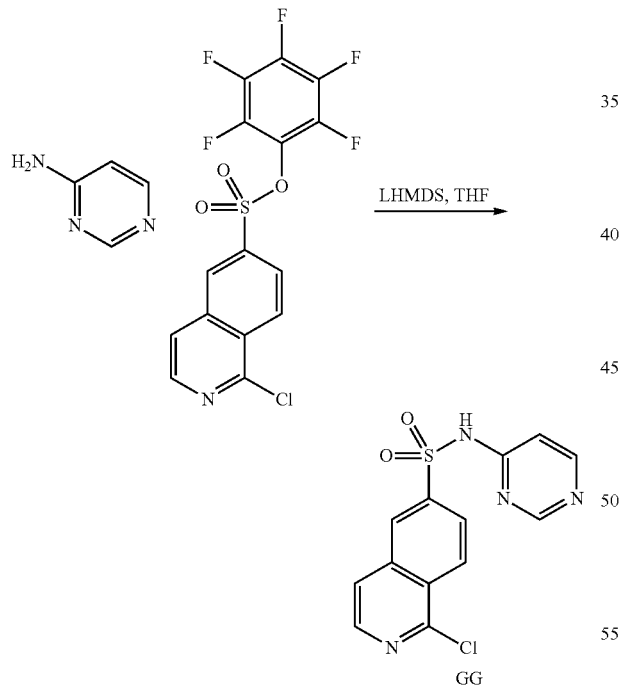

A 50 mL round-bottom flask was charged with perfluorophenyl 1-chloroisoquinoline-6-sulfonate (660 mg, 1.611 mmol), pyrimidin-4-amine (169 mg, 1.772 mmol), and THF (8054 µl) to give an orange solution. The flask was cooled in an ice bath for 5 min, then lithium bis(trimethylsilyl)amide (1M in THF) (3544 µl, 3.54 mmol) was added at a rapid, dropwise rate. After 20 min, the mixture was quenched by the addition of glacial acetic acid (0.5 mL), resulting in a thick slurry. The mixture was diluted with THF and MeOH and concentrated, and the residue was concentrated from EtOAc (three times). The residue was then suspended in EtOAc, sonicated for 1 min, then filtered. The collected solid was washed with EtOAc (once), then dried under a stream of N₂ (g), then under a vacuum to give 676.5 mg of a tan solid. The material was taken up in DCM, sonicated for 30 s, then filtered. The collected solid was washed with DCM (twice), dried under a stream of N₂ (g), then dried under a high vacuum to give 583 mg of a tan solid. The mixture was taken up in boiling methanol, cooled to room temperature, then filtered. The collected solid was washed with methanol, then dried to give 1-chloro-N-(pyrimidin-4-yl)isoquinoline-6-sulfonamide (154.84 mg, 0.483 mmol) as a tan solid. An additional crop of product was obtained by chromatographic purification of the mother liquor on silica gel (0 to 10% MeOH/DCM) to give an additional 110 mg of product as s tan solid. ¹H NMR (400 MHz, DMSO-d₆) δ=13.58-12.66 (br s., 1 H), 8.75-8.66 (m, 1 H), 8.55 (s, 1 H), 8.47-8.37 (m, 2 H), 8.26-8.11 (m, 3 H), 7.07-6.90 (m, 1 H). m/z (ESI) 321.2 (M+H)⁺.

Intermediate LL

PERFLUOROPHENYL 5-(1-BENZYLPYRROLIDIN-2-YL)NAPHTHALENE-2-SULFONATE

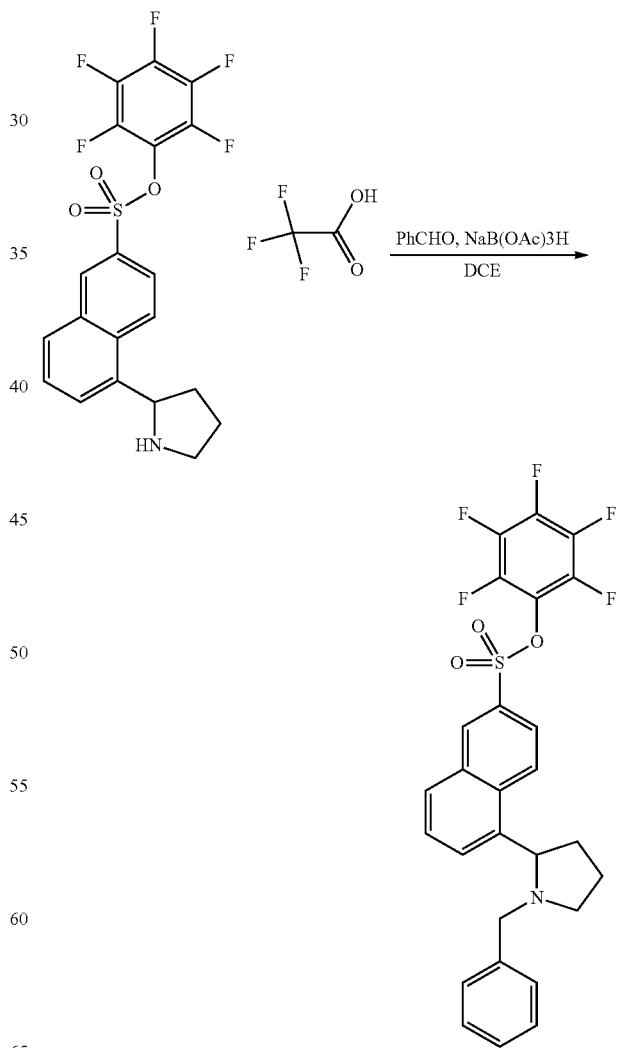

Intermediate LL

A 10-mL round-bottom flask was charged with perfluorophenyl 5-(pyrrolidin-2-yl)naphthalene-2-sulfonate 2,2,2-trifluoroacetate (from STEP 2 of INTERMEDIATE KK) (56.79 mg, 0.102 mmol), DCE (509 μl), and benzaldehyde (31.0 μl, 0.306 mmol) to give a suspension. Sodium triacetoxyborohydride (43.2 mg, 0.204 mmol) was added, followed by an additional portion of DCE (509 μl) to thin the mixture. After 1 h, a saturated aq. Rochelle's salt solution (3 mL) and DCM (2 mL) were added, and the resulting mixture was stirred vigorously for 3 h. The mixture was diluted with water and extracted with DCM (3×). The combined organic extracts were dried over sodium sulfate, filtered, and concentrated. The residue was purified by chromatography on a 12-g with 0 to 40% EtOAc/Heptane to give perfluorophenyl 5-(1-benzylpyrrolidin-2-yl)naphthalene-2-sulfonate (52.93 mg, 0.099 mmol, 97% yield) as a clear oil: $^1$H NMR (400 MHz, DMSO-d$_6$) δ ppm=8.86-8.70 (m, 2 H), 8.22-8.10 (m, 2 H), 8.00 (dd, J=2.2, 9.1 Hz, 1 H), 7.81-7.73 (m, 1 H), 7.33-7.26 (m, 4 H), 7.25-7.17 (m, 1 H), 4.20 (t, J=8.2 Hz, 1 H), 3.77 (d, J=13.2 Hz, 1 H), 3.20 (d, J=13.2 Hz, 1 H), 3.13-3.02 (m, 1 H), 2.48-2.40 (m, 1 H), 2.33 (q, J=9.2 Hz, 1 H), 1.93-1.82 (m, 2 H), 1.78-1.60 (m, 1 H); m/z (ESI) 534.4 (M+H)$^+$.

Intermediate OO

N-(4-METHOXYBENZYL)PYRIMIDIN-4-AMINE

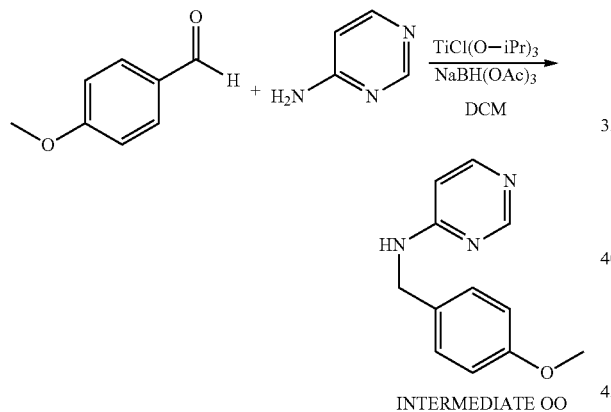

INTERMEDIATE OO p-Anisaldehyde (320 g, 2.35 mol, 1.0 equiv; Aldrich, St. Louis, Mo.) and 4-aminopyrimidine (246 g, 2.58 mol, 1.1 equiv; AK Scientific, Inc., Union City, Calif.) were dissolved in anhydrous DCM (8.0 L). To this solution under N$_2$ atmosphere at room temperature was added a solution of Ti(Oi-Pr)$_3$Cl (1348 g, 5.17 mol, 2.2 equiv; Aldrich) in anhydrous DCM (1 L) in one portion and the reaction mixture was stirred at room temperature for 30 minutes. The reaction mixture was then cooled to 10° C. and NaBH(OAc)$_3$ (1495 g, 7.05 mol, 3.0 equiv; Aldrich) was added in portions over 30 min followed by the addition of acetic acid (10 mL). (Note: A mild exotherm of 10-19° C. was observed). Upon completion of the addition, the reaction mixture was allowed to warm up to room temperature and stirred overnight. The reaction was monitored using LC/MS. Product formation was observed along with many other peaks. Upon completion the reaction mixture was quenched slowly and carefully pouring over a well-stirred saturated aqueous NaHCO$_3$ (30 L). The crude product was then extracted with dichloromethane (3×12 L) and the organic extracts were combined, washed with brine (5 L), dried over Na$_2$SO$_4$, and concentrated under reduced pressure. The crude residue was initially triturated with hexanes to obtain a solid. The crude solid was further triturated with MTBE to remove most of the impurities. The crude product was purified using column chromatography eluting with MeOH/ethyl acetate (2:98 to 5:95) to afford N-(4-methoxybenzyl)pyrimidin-4-amine (INTERMEDIATE OO) as a white solid with >99% purity (129 g, 26% yield). $^1$H NMR (400 MHz, DMSO) δ ppm 8.40 (s, 1H), 8.02 (d, J=6.1 Hz, 1H), 7.82 (t, J=6.0 Hz, 1H), 7.24 (d, J=8.0 Hz, 2H), 6.98-6.77 (m, 2H), 6.48 (s, 1H), 4.43 (s, 2H), 3.72 (s, 3H). m/z (ESI) 216.0 (M+H)$^+$ Intermediate RR TERT-BUTYL 5-FLUORO-2-(4,4,5,5-TETRAMETHYL-1,3,2-DIOXABOROLAN-2-YL)-1H-INDOLE-1-CARBOXYLATE

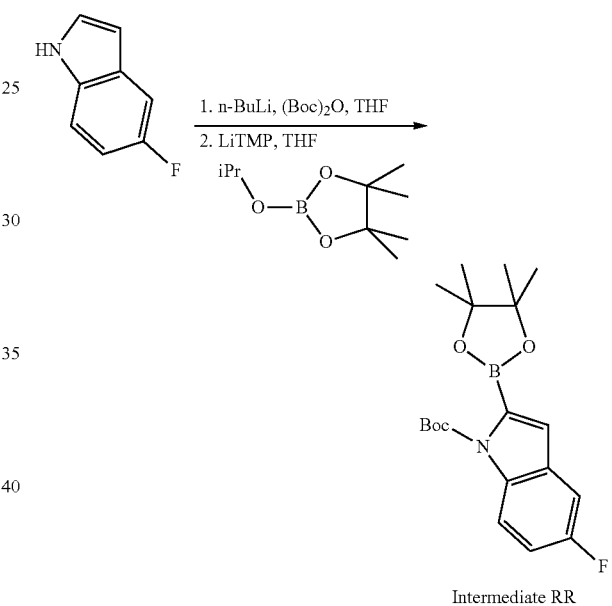

Intermediate RR

A solution of 5-fluoro-1H-indole (1.300 g, 9.62 mmol) in 10 mL THF was cooled to −10° C. and was treated with n-butyllithium (4.23 ml, 10.58 mmol). After stirring for 10 minutes, the reaction mixture was treated with di-tert-butyl dicarbonate (1N in THF) (9.62 ml, 9.62 mmol) and was allowed to stir at room temperature for one hour. LC/MS showed mostly product. A separate solution of 2,2,6,6-tetramethylpiperidine (2.59 ml, 14.43 mmol) in 15 mL of THF was cooled to 0° C. and was treated with n-butyllithium (5.77 ml, 14.43 mmol) After stirring for 20 minutes, this solution was charged to an addition funnel. The original reaction mixture was treated with 2-isopropoxy-4,4,5,5-tetramethyl-1,3,2-dioxaborolane (2.68 ml, 14.43 mmol) followed by drop wise addition of the LiTMP solution at room temperature. After stirring for one hour, LC/MS showed exclusively product, so the reaction mixture was poured into a solution of brine and 1N citric acid (~1:1) and was extracted with DCM. The organics were dried over MgSO4 and concentrated. Purification of the crude residue by column chromatography (0-50% EtOAc/heptane) gave tert-butyl 5-fluoro-2-(4,4,5,5-tetramethyl-1,3,2-dioxaborolan-2- yl)-1H-indole-1-carboxylate (INTERMEDIATE RR; 1.636 g, 4.53 mmol, 47.1% yield). m/z (ESI) 384.3 (M+Na)+.

Intermediate VV

TERT-BUTYL 4-(2-(4,4,5,5-TETRAMETHYL-1,3,2-DIOXABOROLAN-2-YL)-5-(TRIFLUOROMETHYL)PHENYL)-5,6-DIHYDROPYRIDINE-1(2H)-CARBOXYLATE

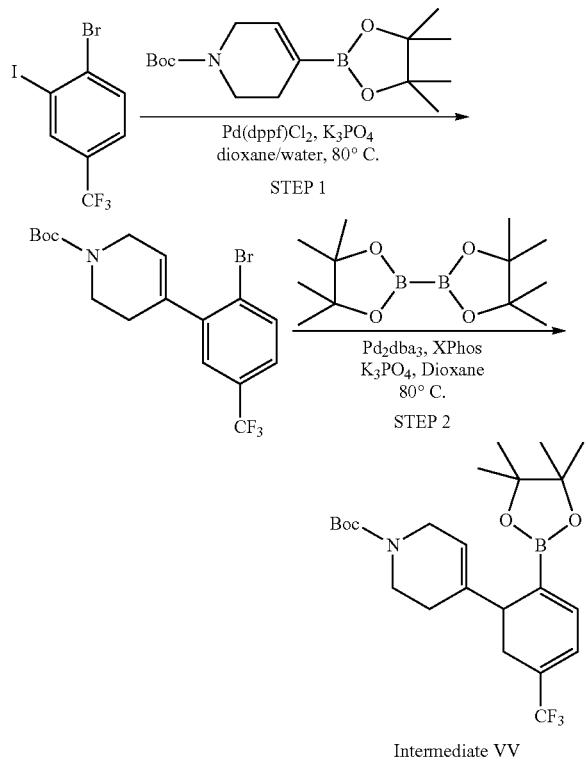

Intermediate VV

STEP 1: TERT-BUTYL 4-(2-BROMO-5-(TRIFLUOROMETHYL)PHENYL)-5,6-DIHYDROPYRIDINE-1(2H)-CARBOXYLATE

A solution of $PdCl_2$(dppf)-$CH_2Cl_2$ adduct (0.582 g, 0.712 mmol), tert-butyl 4-(4,4,5,5-tetramethyl-1,3,2-dioxaborolan-2-yl)-5,6-dihydropyridine-1(2H)-carboxylate (4.63 g, 14.96 mmol), 1-bromo-2-iodo-4-(trifluoromethyl)benzene (2.298 ml, 14.25 mmol), and potassium phosphate (9.07 g, 42.7 mmol) in 50 mL dioxane/25 mL water was heated to 80° C. for 2 hours. LC/MS showed mostly product, so the reaction mixture was poured into water and was extracted with DCM. The organics were dried over $MgSO_4$ and concentrated. Purification of the crude residue by silica gel column chromatography (0-30% EtOAc/heptane) gave tert-butyl 4-(2-bromo-5-(trifluoromethyl)phenyl)-5,6-dihydropyridine-1(2H)-carboxylate (4.05 g, 9.97 mmol, 70.0% yield) as a clear oil. m/z (ESI) 430.2 (M+Na)+.

STEP 2 TERT-BUTYL 4-(2-(4,4,5,5-TETRAMETHYL-1,3,2-DIOXABOROLAN-2-YL)-5-(TRIFLUOROMETHYL)PHENYL)-5,6-DIHYDROPYRIDINE-1(2H)-CARBOXYLATE

A flask charged with XPhos (1.498 g, 3.14 mmol), $Pd_2$(dba)$_3$ (0.959 g, 1.048 mmol), bis(pinacolato)diboron (10.64 g, 41.9 mmol), tert-butyl 4-(2-bromo-5-(trifluoromethyl)phenyl)-5,6-dihydropyridine-1(2H)-carboxylate (8.513 g, 20.96 mmol), potassium phosphate (17.79 g, 84 mmol), and 100 mL dioxane was degassed and heated to 80° C. overnight. LC/MS showed mostly product, so the reaction mixture was diluted with heptane, filtered, and concentrated. Purification of the crude residue by silica gel column chromatography (0 to 15% EtOAc/heptane) gave tert-butyl 4-(2-(4,4,5,5-tetramethyl-1,3,2-dioxaborolan-2-yl)-5-(trifluoromethyl)phenyl)-5,6-dihydropyridine-1(2H)-carboxylate (10.64 g, 23.47 mmol, 112% yield). m/z (ESI) 476.1 (M+Na)+.

Intermediate WW 4-(2-BROMO-5-(TRIFLUOROMETHYL)PHENYL)-1-METHYLPIPERIDINE

Intermediate WW

STEP 1: 4-(2-BROMO-5-(TRIFLUOROMETHYL)PHENYL)-1-METHYL-1,2,3,6-TETRAHYDROPYRIDINE

A solution of Pd(Ph$_3$P)$_4$ (0.986 g, 0.854 mmol), 1-methyl-4-(4,4,5,5-tetramethyl-1,3,2-dioxaborolan-2-yl)-1,2,3,6-tetrahydropyridine (2.000 g, 8.96 mmol), 1-bromo-2-iodo-4-(trifluoromethyl)benzene (1.377 ml, 8.54 mmol), and potassium phosphate (5.44 g, 25.6 mmol) in 20 mL dioxane 10 mL water was heated to 90° C. for one hour. LC/MS showed mostly product, so the reaction mixture was poured into water and extracted with DCM. The organics were dried over $MgSO_4$ and concentrated. Purification of the crude residue by silica gel column chromatography (0 to 97% EtOAc/heptane, 3% MeOH) gave 4-(2-bromo-5-(trifluoromethyl)phenyl)-1-methyl-1,2,3,6-tetrahydropyridine. m/z (ESI) 320.1 (M+H)+.

STEP 2: 4-(2-BROMO-5-(TRIFLUOROMETHYL) PHENYL)-1-METHYLPIPERIDINE (INTERMEDIATE WW)

4-(2-Bromo-5-(trifluoromethyl)phenyl)-1-methyl-1,2,3,6-tetrahydropyridine was dissolved in 20 mL ethanol and the solution was treated with platinum (iv) oxide (0.194 g, 0.854 mmol), and was placed under 45 psi H$_2$ for one hour. LC/MS showed product and debrominated product, so the reaction mixture was diluted with DCM, filtered through a plug of diatomaceous earth and was concentrated. Purification of the crude residue by silica gel column chromatography (0 to 97% EtOAc/heptane, 3% MeOH) gave 4-(2-bromo-5-(trifluoromethyl)phenyl)-1-methylpiperidine (0.065 g, 0.202 mmol, 2.363% yield). m/z (ESI) 322.0 (M+Na)+;

Intermediate XX

5-(2-BROMO-5-(TRIFLUOROMETHYL)PHENYL)-1-METHYL-1H-IMIDAZOLE

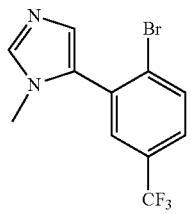 [SMILES: Cn1cncc1-c1cc(C(F)(F)F)ccc1Br]

A solution of PdCl$_2$(dppf)-CH$_2$Cl$_2$ adduct (0.233 g, 0.285 mmol), 1-methyl-2-(tributylstannyl)imidazole (2.189 ml, 6.84 mmol), 1-bromo-2-iodo-4-(trifluoromethyl)benzene (0.919 ml, 5.70 mmol), and potassium fluoride (1.656 g, 28.5 mmol) in 6 mL DMF was heated to 80° C. overnight. LC/MS showed product, so the reaction mixture was poured into water and was extracted with DCM. The organics were dried over MgSO$_4$ and concentrated. Purification of the crude residue by silica gel column chromatography (0 to 100% EtOAc/heptane) gave 2-(2-bromo-5-(trifluoromethyl)phenyl)-1-methyl-1H-imidazole (1.122 g, 3.68 mmol, 64.5% yield). m/z (ESI) 307.2 (M+H)+.

Intermediate YY

2-(2-BROMO-5-(TRIFLUOROMETHYL)PHENYL)-1-METHYL-1H-IMIDAZOLE

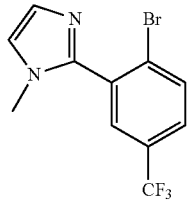

Intermediate YY was synthesized in a similar manner to INTERMEDIATE XX, using 1-methyl-5-(tributylstannyl)-1H-imidazole instead of 1-methyl-2-(tributylstannyl)imidazole to yield 5-(2-bromo-5-(trifluoromethyl)phenyl)-1-methyl-1H-imidazole (1.500 g, 4.92 mmol, 86% yield). m/z (ESI) 307.2 (M+H)+;

Intermediate ZZ

1-(2-BROMO-5-(TRIFLUOROMETHYL)PHENYL)-1H-IMIDAZOLE

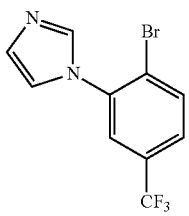 [SMILES: FC(F)(F)c1ccc(Br)c(-n2ccnc2)c1]

A microwave vial charged with potassium tert-butoxide (1.108 g, 9.88 mmol), 1H-imidazole (0.672 g, 9.88 mmol), 1-bromo-2-fluoro-4-(trifluoromethyl)benzene (1.180 ml, 8.23 mmol), and 10 mL dioxane was heated to 180° C. in the microwave for 2 hours. LC/MS showed mostly product, so the reaction mixture was poured into water and was extracted with DCM. The organics were dried over MgSO4 and concentrated. The crude residue was purified by silica gel column chromatography (0 to 100% EtOAc/heptane) yielding 1-(2-bromo-5-(trifluoromethyl)phenyl)-1H-imidazole (1.277 g, 4.39 mmol, 53.3% yield). m/z (ESI) 291.9 (M+H)+.

Intermediate BBB

TERT-BUTYL 4-(2-BROMO-5-(TRIFLUOROMETHYL)PHENYL)PIPERIDINE-1-CARBOXYLATE

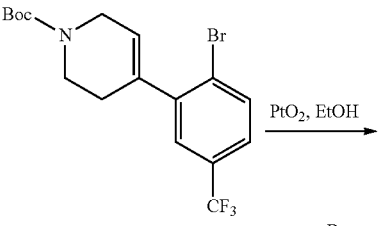

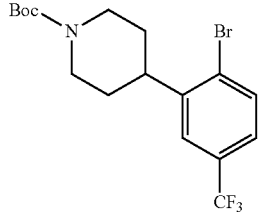

A solution of tert-butyl 4-(2-bromo-5-(trifluoromethyl)phenyl)-5,6-dihydropyridine-1(2H)-carboxylate (from Step 1 of Intermediate VV; 2.435 g, 5.99 mmol) in 20 mL EtOH was treated with platinum(iv) oxide (0.136 g, 0.599 mmol) and was placed under 45 psi H2 for one hour. LC/MS showed mostly product and de-brominated product. The reaction mixture was diluted with DCM and was filtered through diatomaceous earth. The filtrate was concentrated then purified directly by column chromatography (0 to 15% EtOAc/heptane) yielding tert-butyl 4-(2-bromo-5-(trifluoromethyl)phenyl)piperidine-1-carboxylate (0.970 g, 2.376 mmol, 39.6% yield). m/z (ESI) 431.0 (M+Na)+.

Intermediate EEE

1-BROMO-2-(METHYLSULFONYL)-4-(TRIF-LUOROMETHYL)BENZENE

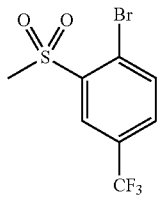

A solution of 1-bromo-2-iodo-4-(trifluoromethyl)benzene (1.608 ml, 9.97 mmol) in 20 mL THF was treated with isopropylmagnesium chloride (2N in diethyl ether) (4.99 ml, 9.97 mmol) and was allowed to stir for 30 minutes. The reaction mixture was cooled to 0° C. and was quenched with mesyl-Cl (0.777 ml, 9.97 mmol). After stirring for one hour, the reaction mixture was concentrated. Purification of the crude residue by reverse phase column chromatography [10 to 100% (0.1% NH4OH in MeOH)/(0.1% NH4OH in water)] gave 1-bromo-2-(methylsulfonyl)-4-(trifluoromethyl)benzene (1.36 g, 4.49 mmol, 45.0% yield). m/z (ESI) 305.1 (M+H)+.

Intermediate FFF

TERT-BUTYL 3-(2-BROMO-5-(TRIFLUOROMETHYL)PHENYL)-3-FLUOROAZETIDINE-1-CARBOXYLATE

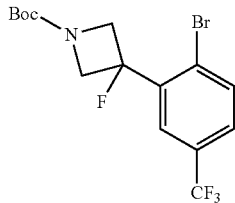 [SMILES: CC(C)(C)OC(=O)N1CC(F)(c2cc(C(F)(F)F)ccc2Br)C1]

A solution of 1-bromo-2-iodo-4-(trifluoromethyl)benzene (1.608 ml, 9.97 mmol) in 20 mL THF was treated with isopropylmagnesium chloride 2N in diethyl ether (4.99 ml, 9.97 mmol) and was allowed to stir for 30 minutes. The reaction mixture was cooled to 0° C. and was quenched with tert-butyl 3-oxoazetidine-1-carboxylate (2.049 g, 11.97 mmol). After stirring for an additional 30 minutes, the reaction mixture was poured into 1N citric acid solution and was extracted with DCM. The organics were dried over MgSO4 and concentrated. The crude residue was dissolved in 20 mL THF, was cooled to −10° C., and was treated with deoxofluor (2.023 ml, 10.97 mmol). The reaction mixture was allowed to warm to room temperature overnight. LC/MS showed product, so the reaction mixture was poured into saturated NaHCO3 solution and was extracted with DCM. The organics were dried over MgSO4 and concentrated. Purification of the crude residue by silica gel column chromatography (0 to 50% EtOAc/heptane) gave tert-butyl 3-(2-bromo-5-(trifluoromethyl)phenyl)-3-fluoroazetidine-1-carboxylate (0.600 g, 1.507 mmol, 15.11% yield).

Intermediate GGG

TERT-BUTYL 3-(2-BROMO-5-(TRIFLUOROMETHYL)PHENYL)-2,5-DIHYDRO-1H-PYRROLE-1-CARBOXYLATE

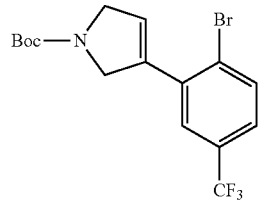 [SMILES: CC(C)(C)OC(=O)N1CC=C(c2cc(C(F)(F)F)ccc2Br)C1]

A solution of PdCl2(dppf)-CH2Cl2 adduct (0.349 g, 0.427 mmol), 1-bromo-2-iodo-4-(trifluoromethyl)benzene (1.500 g, 4.27 mmol), tert-butyl 3-(4,4,5,5-tetramethyl-1,3,2-dioxaborolan-2-yl)-2,5-dihydro-1H-pyrrole-1-carboxylate (ASW MedChem, Inc., New Brunswick, N.J., 1.893 g, 6.41 mmol), and potassium carbonate (3.54 g, 25.6 mmol) in 15 mL dioxane/7.5 mL water was heated to 100° C. for 1 hour. LC/MS showed product, so the reaction mixture was cooled to room temperature and the aqueous layer was removed. The organics were concentrated then purified directly by reverse phase column chromatography [Redisep Gold C18, 20-100% (0.1% NH4OH in MeOH)/(0.1% NH4OH in water)] yielding tert-butyl 3-(2-bromo-5-(trifluoromethyl)phenyl)-2,5-dihydro-1H-pyrrole-1-carboxylate (1.040 g, 2.65 mmol, 62.0% yield). m/z (ESI) 413.9 (M+Na)+.

Intermediate HHH

5-(2-BROMO-5-(TRIFLUOROMETHYL)PHENYL)-1-METHYL-1,2,3,6-TETRAHYDROPYRIDINE

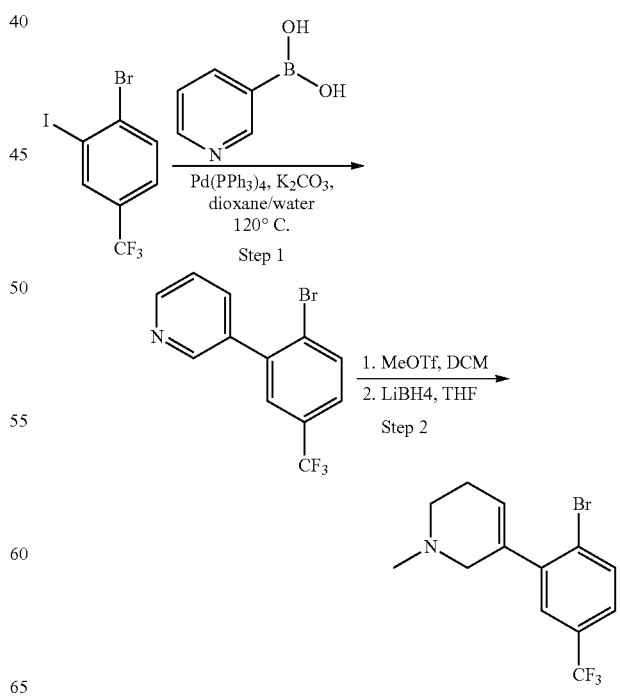

Intermediate HHH

STEP 1: 3-(2-BROMO-5-(TRIFLUOROMETHYL)PHENYL)PYRIDINE

A solution of Pd(Ph₃P)₄ (1.410 g, 1.220 mmol), 1-bromo-2-iodo-4-(trifluoromethyl)benzene (3.94 ml, 24.41 mmol), pyridin-3-ylboronic acid (3.00 g, 24.41 mmol), and potassium carbonate (13.49 g, 98 mmol) in 32 mL dioxane and 16 mL water was heated to 120° C. overnight. LC/MS showed incomplete conversion, so an additional portion of pyridin-3-ylboronic acid (3.00 g, 24.41 mmol) and potassium carbonate (13.49 g, 98 mmol) were added and the reaction mixture was heated to 120° C. for 3 hours. LC/MS showed no further conversion, so the reaction mixture was poured into water and was extracted with DCM. The organics were then concentrated. Purification of the crude residue by column chromatography (0-100% EtOAc/heptane) gave 3-(2-bromo-5-(trifluoromethyl)phenyl)pyridine (5.150 g, 17.05 mmol, 69.8% yield) as a yellow solid. m/z (ESI) 303.9 (M+H)+.

STEP 2: 5-(2-BROMO-5-(TRIFLUOROMETHYL)PHENYL)-1-METHYL-1,2,3,6-TETRAHYDROPYRIDINE

A solution of 3-(2-bromo-5-(trifluoromethyl)phenyl)pyridine (2.000 g, 6.62 mmol) in 13 mL DCM was treated with methyl trifluoromethanesulfonate (0.802 ml, 7.28 mmol) and was allowed to stir at room temperature for one hour. LC/MS showed mostly product so the reaction mixture was treated with sodium triacetoxyborohydride (4.21 g, 19.86 mmol) and was allowed to stir at room temperature overnight. LC/MS showed only a small amount of product, so the reaction mixture was concentrated then taken back up in 12 mL THF and cooled to 0° C. lithium borohydride (3.31 ml, 6.62 mmol) was added, and the reaction mixture was allowed to stir for one hour. LC/MS showed mostly product, so the reaction mixture was quenched with 7N ammonia in MeOH and was allowed to stir over the weekend. The reaction mixture was poured into water and was extracted with DCM. The organics were concentrated the purified directly by reverse phase column chromatography yielding 5-(2-bromo-5-(trifluoromethyl)phenyl)-1-methyl-1,2,3,6-tetrahydropyridine (0.860 g, 2.69 mmol, 40.6% yield) with impurities. m/z (ESI) 321.9 (M+H)+.

Intermediate III 2-(4-CYCLOPROPYL-2-METHOXYPHENYL)-4,4,5,5-TETRAMETHYL-1,3,2-DIOXABOROLANE

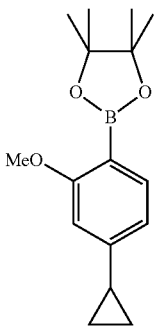 [SMILES: COc1cc(C2CC2)ccc1B1OC(C)(C)C(C)(C)O1]

A solution of PdCl₂(dppf)-CH₂Cl₂ adduct (1.391 g, 1.703 mmol), cyclopropylboronic acid (4.39 g, 51.1 mmol), 1-bromo-4-iodo-2-methoxybenzene (10.66 g, 34.1 mmol), and potassium carbonate (18.83 g, 136 mmol) in 100 mL dioxane/50 mL water was heated to 120° C. for 8 hours. LC/MS showed mostly product, so the reaction mixture was diluted with heptane and was washed with saturated NaHCO₃ solution. The organics were dried over MgSO₄ and concentrated. The crude residue was taken up in 100 mL dioxane, was treated with Pd₂(dba)₃ (0.399 g, 1.703 mmol), dicyclohexyl(2',4',6'-triisopropyl-[1,1'-biphenyl]-2-yl)phosphine (4.06 g, 8.52 mmol), bis(pinacolato)diboron (12.98 g, 51.1 mmol), and potassium phosphate (28.9 g, 136 mmol) and was heated to 120° C. overnight. LC/MS showed product, so the reaction mixture was diluted with heptane then filtered through a plug of diatomaceous earth. The filtrate was concentrated then purified directly by silica gel column chromatography (0-25% EtOAc/heptane) yielding 2-(4-cyclopropyl-2-methoxyphenyl)-4,4,5,5-tetramethyl-1,3,2-dioxaborolane (2.68 g, 9.78 mmol, 28.7% yield). m/z (ESI) 297.3 (M+Na)+

Intermediates JJJ and KKK 1-chloro-N-(4-methoxybenzyl)-N-(thiazol-2-yl)isoquinoline-6-sulfonamide & 1-(2-bromo-4-fluorophenyl)-N-(4-methoxybenzyl)-N-(thiazol-2-yl)isoquinoline-6-sulfonamide

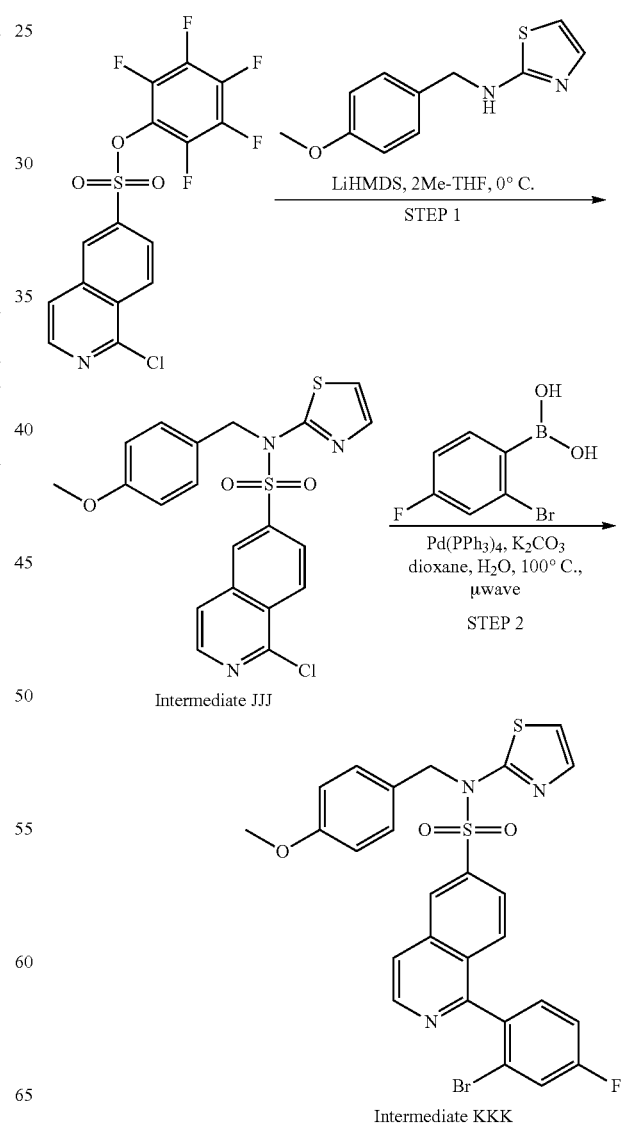

STEP 1: 1-CHLORO-N-(4-METHOXYBENZYL)-N-(THIAZOL-2-YL)ISOQUINOLINE-6-SULFONAMIDE

To a flask containing an ice cold suspension of N-(4-methoxybenzyl)thiazol-2-amine (0.423 g, 1.922 mmol) in 2Me-THF (7.04 ml) was added lithium bis(trimethylsilyl)amide (2.014 ml, 2.014 mmol) dropwise over 10 min. The mixture was stirred for 15 min prior to the addition of a solution of perfluorophenyl 1-chloroisoquinoline-6-sulfonate (see Example 73, Step 1) (0.750 g, 1.831 mmol) in 2Me-THF (3.5 ml). After 1 hr of stirring (ice melt) LC-MS indicated about 65% conversion to product with starting ester and amine present. The mixture was re-cooled to 0° C. and additional LiHMDS (0.5 eq) was added. The mixture was allowed to stir and slowly warm to room temperature overnight. LC-MS indicated about 90% conversion to desired product. The reaction was quenched by the addition of acetic acid (~2 ml) and the resulting mixture (some precipitate formation) was dried under reduced pressure and purified with a 40 g silicycle HP column ramping EtOAc in heptane (0 to 50%) providing product 1-chloro-N-(4-methoxybenzyl)-N-(thiazol-2-yl)isoquinoline-6-sulfonamide (Intermediate JJJ) (0.530 g, 1.188 mmol, 64.9% yield) as a white foam. $^1$H NMR (400 MHz, CHLOROFORM-d) δ ppm 3.71 (s, 3 H) 5.11 (s, 2 H) 6.69-6.76 (m, 2 H) 7.04 (d, J=3.62 Hz, 1 H) 7.26-7.33 (m, 2 H) 7.42 (d, J=3.62 Hz, 1 H) 7.59-7.64 (m, 1 H) 7.85 (dd, J=8.95, 1.81 Hz, 1 H) 8.21 (d, J=1.76 Hz, 1 H) 8.33-8.41 (m, 2 H). m/z (ESI) 446.1 (M+H)$^+$.

STEP 2: 1-(2-BROMO-4-FLUOROPHENYL)-N-(4-METHOXYBENZYL)-N-(THIAZOL-2-YL)ISOQUINOLINE-6-SULFONAMIDE

To a microwave vial charged with 1-chloro-N-(4-methoxybenzyl)-N-(thiazol-2-yl)isoquinoline-6-sulfonamide (0.053 g, 0.119 mmol) was added (2-bromo-4-fluorophenyl)boronic acid (Combi-Blocks, San Diego, Calif.) (0.042 g, 0.190 mmol), potassium carbonate (0.082 g, 0.594 mmol), dioxane (0.594 ml) and water (0.198 ml). The mixture was purged with argon prior to the addition of Pd(PPh$_3$)$_4$ (0.014 g, 0.012 mmol). The vessel was sealed and irradiated at 100° C. for 30 mins affording fairly clean conversion to desired product. The organic phase was decanted, the aqueous rinsed with EtOAc and the EtOAc decanted. The combined organics were dried under reduced pressure and purified with a 25 g HP silicycle column ramping EtOAc in heptane (0-45%, then isocratic at 45%) to provide product as an off-white foam 1-(2-bromo-4-fluorophenyl)-N-(4-methoxybenzyl)-N-(thiazol-2-yl)isoquinoline-6-sulfonamide (Intermediate KKK) (54 mg, 0.092 mmol, 78% yield) with minor impurities according to LC/MS and NMR (~20% impurity). m/z (ESI) 582.2/584.2 (M+H)$^+$.

Intermediate LLL

PERFLUOROPHENYL 1-(2-METHOXY-4-(TRIFLUOROMETHYL)PHENYL)ISOQUINOLINE-6-SULFONATE

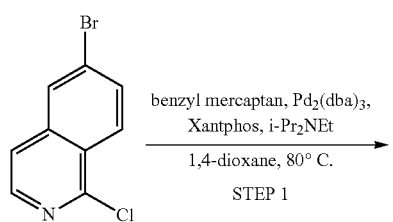

STEP 1: 6-(BENZYLTHIO)-1-CHLOROISOQUINOLINE

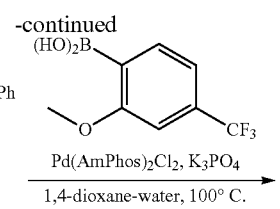

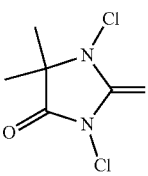

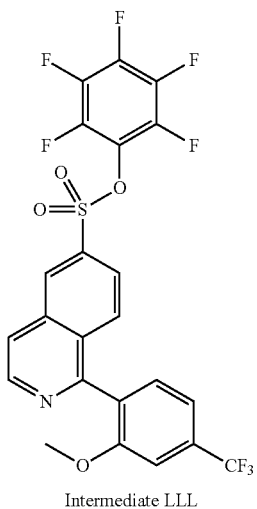

Intermediate LLL

STEP 1: 6-(BENZYLTHIO)-1-CHLOROISOQUINOLINE

A round-bottom flask was charged with 6-bromo-1-chloro-isoquinoline (1.574 ml, 10.86 mmol), Xantphos (0.314 g, 0.543 mmol), and Pd$_2$(dba)$_3$ (0.249 g, 0.271 mmol). The flask was flushed with Ar (g), then 1,4-dioxane (21.72 ml), n,n-diisopropylethylamine (3.79 ml, 21.72 mmol), and benzyl mercaptan (1.349 ml, 11.40 mmol) were added in sequence. The flask was fitted with a reflux condenser and heated to 80° C. for 1 h. The mixture was cooled and concentrated under a vacuum. The crude product was purified by chromatography on silica gel (80-g Redi-Sep Gold column, 25-g silica gel loading column, 0-40% EtOAc/Heptane) to give a yellow solid. The solid was suspended in heptane, sonicated, and filtered. The collected solid was washed with heptane, dried under a stream of N2 (g), then dried under vacuum for to give 6-(benzylthio)-1-chloroisoquinoline as an off-white powder: $^1$H NMR (400 MHz, CHLOROFORM-d) δ ppm=8.26-8.10 (m, 2 H), 7.63-7.51 (m, 2 H), 7.46-7.39 (m, 3 H), 7.37-7.28 (m, 3 H), 4.31 (s, 2 H); m/z (ESI) 286.2 (M+H)+.

STEP 2: 6-(BENZYLTHIO)-1-(2-METHOXY-4-(TRIFLUOROMETHYL)PHENYL)ISOQUINOLINE

A RBF was charged with 6-(benzylthio)-1-chloroisoquinoline (3.101 g, 10.85 mmol), (2-methoxy-4-(trifluoromethyl)phenyl)boronic acid (2.86 g, 13.02 mmol), Pd(AmPhos)2Cl2 (0.384 g, 0.543 mmol), potassium phosphate (6.91 g, 32.6 mmol), 1,3-dioxane (27.1 ml), and water (9.04 ml). The vial was flushed with Ar (g), fitted with a reflux condenser, and placed in a 100° C. heating bath for 45 min. The mixture was cooled to room temperature, then diluted with water and extracted with EtOAc (2×). The combined organic extracts were dried over sodium sulfate, filtered, and concentrated. The crude product was purified by chromatography on silica gel (120-g, 10 to 40% EtOAc/Heptane) to give 6-(benzylthio)-1-(2-methoxy-4-(trifluoromethyl)phenyl)isoquinoline (4.47 g, 10.51 mmol, 97% yield) as a light-yellow solid: $^1$H NMR (400 MHz, CHLOROFORM-d) δ ppm=8.58 (d, J=5.8 Hz, 1 H), 7.66 (d, J=1.8 Hz, 1 H), 7.56-7.47 (m, 3 H), 7.45-7.26 (m, 8 H), 4.31 (s, 2 H), 3.76 (s, 3 H); m/z (ESI) 426.2 (M+H)+.

STEP 3: PERFLUOROPHENYL 1-(2-METHOXY-4-(TRIFLUOROMETHYL)PHENYL)ISOQUINOLINE-6-SULFONATE

A round-bottom flask was charged with 6-(benzylthio)-1-(2-methoxy-4-(trifluoromethyl)phenyl)isoquinoline (4.47 g, 10.51 mmol), acetonitrile (99 ml), acetic acid (3.71 ml), and water (2.472 ml) to give a thin suspension. The flask was cooled in an ice-bath for 15 min, then 1,3-dichloro-5,5-dimethylimidazolidine-2,4-dione (4.14 g, 21.01 mmol) was added in one portion, leading to a solution (12:40 am). After 1 h, 2,3,4,5,6-pentafluorophenol (2.321 g, 12.61 mmol) and triethylamine (2.197 ml, 15.76 mmol) were added in sequence (the base was added dropwise), and the cooling bath was removed. After 1 h, additional portions of 2,3,4,5,6-pentafluorophenol (0.967 g, 5.25 mmol) and triethylamine (0.732 ml, 5.25 mmol) were added. After another 1 h, an additional portion of triethylamine (0.732 ml, 5.25 mmol) was added. The mixture was stirred for 10 more min, then concentrated under a vacuum. The residue was dissolved in DCM and loaded onto a 25-g silica gel loading column. The column was briefly dried under vacuum, then eluted onto a pre-equilibrated 120-g Redi-Sep Gold column with 0-30% EtOAc/Heptane to give perfluorophenyl 1-(2-methoxy-4-(trifluoromethyl)phenyl)isoquinoline-6-sulfonate (5.45 g, 9.92 mmol, 94% yield) as a white foam: $^1$H NMR (400 MHz, DMSO-d$_6$) δ ppm=8.94 (d, J=2.0 Hz, 1 H), 8.84 (d, J=5.7 Hz, 1 H), 8.23 (dd, J=0.5, 5.7 Hz, 1 H), 8.05 (dd, J=2.0, 8.9 Hz, 1 H), 7.90 (d, J=9.0 Hz, 1 H), 7.66 (d, J=7.5 Hz, 1 H), 7.59-7.49 (m, 2 H), 3.76 (s, 3 H); m/z (ESI) 550.2 (M+H)+.

Intermediate LLL-ALTERNATIVE PROCEDURE

PERFLUOROPHENYL 1-(2-METHOXY-4-(TRIFLUOROMETHYL)PHENYL)ISOQUINOLINE-6-SULFONATE

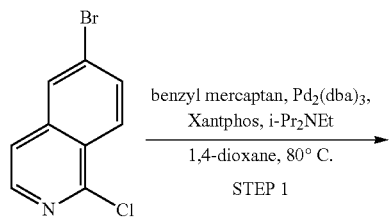

STEP 1

STEP 2

STEP 3

Intermediate LLL

STEP 1: 6-(BENZYLTHIO)-1-CHLOROISOQUINOLINE

A three-neck 2 L flask equipped with an overhead stirrer, a thermocouple and a nitrogen inlet was charged with 6-bromo-1-chloroisoquinoline (60.0 g, 247 mmol), xantphos (7.16 g, 12.4 mmol) and Pd$_2$(dba)$_3$ (5.66 g, 6.19 mmol) in that order. The flask was evacuated. To the reaction flask was charged sparged dioxane (540 mL) and DIPEA (64.8 mL, 371 mmol). The flask was purged with N2 and warmed to 63° C. upon which a solution of phenylmethanethiol (30.5 mL, 260 mmol) in 180 mL of sparged dioxane was charged to the reaction mixture dropwise over 1 hr. The reaction was completed according to LC/MS. The solids were filtered off. The filtrate was concentrated down to a low volume. 500 mL of isopropanol was added into a separate flask. The concentrated product solution was charged slowly to the flask containing isopropanol. The product crystallized out of the solution. The resulting slurry was stirred at RT for 2 hours. The slurry was cooled to 0° C., filtered, washed with 50% IPA/heptanes, and dried under a vacuum with nitrogen sweep. The product was obtained as yellow solids (44.3 g;

63% isolated yield). ¹H NMR (400 MHz, CHLOROFORM-d) δ ppm=8.26-8.10 (m, 2 H), 7.63-7.51 (m, 2 H), 7.46-7.39 (m, 3 H), 7.37-7.28 (m, 3 H), 4.31 (s, 2 H); m/z (ESI) 286.2 (M+H)+.

STEP 2: 6-(BENZYLTHIO)-1-(2-METHOXY-4-(TRIFLUOROMETHYL)PHENYL)ISOQUINO-LINE

A three-neck 2 L flask equipped with an overhead stirrer, a thermocouple, a condenser and a nitrogen inlet was charged with 6-(benzylthio)-1-chloroisoquinoline (23 g, 80 mmol), (2-methoxy-4-(trifluoromethyl)phenyl)boronic acid (22.1 g, 101 mmol), potassium phosphate (51.2 g, 241 mmol) and Amphos (2.85 g, 4.02 mmol) in that order. The flask was evacuated. In a separate flask was charged with dioxane (230 mL) and water (57.5 mL). The solvent solution was sparged with nitrogen and charged to the reaction flask. The reaction flask was purged with nitrogen and warmed to reflux. After 1 hr, the reaction was complete according to LC/MS. The whole was cooled to 0° C., charged with DCM and water. The organic layer was separated, dried over sodium sulfate, filtered, and concentrated down to afford black oil. Isopropanol was added into the black oil and the whole was concentrated again to fully remove DCM and dioxane. The black residue was charged with 200 mL of isopropanol. The product crystallized out of solution. The slurry was stirred for 2 hrs at RT and cooled to 0° C. for 1 hr. The product was filtered off, washed with 30% isopropanol/heptane solution, and dried under vacuum with a nitrogen sweep. The product was obtained as gray solids (24.1 g, 70.4%; >99% purity via LC/MS at 215 nm). ¹H NMR (400 MHz, CHLOROFORM-d) δ ppm=8.58 (d, J=5.8 Hz, 1 H), 7.66 (d, J=1.8 Hz, 1 H), 7.56-7.47 (m, 3 H), 7.45-7.26 (m, 8 H), 4.31 (s, 2 H), 3.76 (s, 3 H); m/z (ESI) 426.2 (M+H)+.

STEP 3: PERFLUOROPHENYL 1-(2-METHOXY-4-(TRIFLUOROMETHYL)PHENYL)ISOQUINO-LINE-6-SULFONATE

A three-neck 2 L flask equipped with an overhead stirrer, a thermocouple and a nitrogen inlet was charged with 6-(benzylthio)-1-(2-methoxy-4-(trifluoromethyl)phenyl) isoquinoline (24.1 g, 56.6 mmol), acetonitrile (241 mL), AcOH (29.9 mL) and water (19.8 mL). The resulting mixture was cooled to 0 to 5° C. upon which solid 1,3-dichloro-5,5-dimethylimidazolidine-2,4-dione (22.3 g, 113 mmol) was charged portionwise while maintaining temperature <5° C. Addition was exothermic. After stirring for 1 hr at 0° C., LCMS indicated that the reaction was complete. 2,3,4,5,6-Pentafluorophenol (20.9 g, 113 mmol) was added into the reaction as a solution in 20 mL ACN. Then triethylamine (21.7 mL, 156 mmol) was added dropwise via syringe over 2 hrs. When the reaction was completed according to LCMS, the whole was diluted with DCM and water. The organic layer was separated, dried over sodium sulfate, filtered, and concentrated to dryness. The product was purified via silica gel column chromatography eluting with DCM. Fractions containing the product were collected, combined and concentrated to afford the desired product as amorphous foam (23.8 g; 76% yield, 95% purity at 254 nm). ¹H NMR (400 MHz, DMSO-d₆) δ ppm=8.94 (d, J=2.0 Hz, 1 H), 8.84 (d, J=5.7 Hz, 1 H), 8.23 (dd, J=0.5, 5.7 Hz, 1 H), 8.05 (dd, J=2.0, 8.9 Hz, 1 H), 7.90 (d, J=9.0 Hz, 1 H), 7.66 (d, J=7.5 Hz, 1 H), 7.59-7.49 (m, 2 H), 3.76 (s, 3 H); m/z (ESI) 550.2 (M+H)+.

Intermediate MMM

5-FLUORO-N-(4-METHOXYBENZYL)THIAZOL-2-AMINE

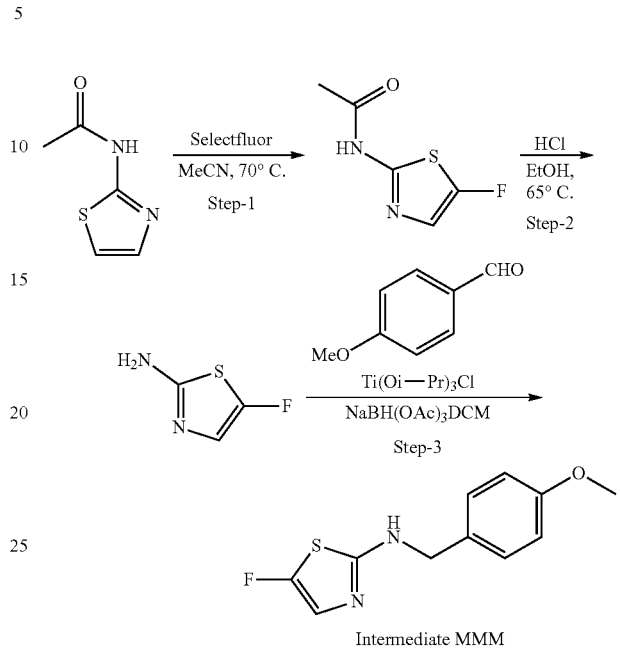

Intermediate MMM

STEP 1: N-(5-FLUOROTHIAZOL-2-YL)ACETAMIDE

To a solution of N-(thiazol-2-yl)acetamide (150 g, 1056 mmol, Combi-Blocks, San Diego, Calif.) in acetonitrile (3 L) was added 1-chloromethyl-4-fluoro-1,4-diazoniabicyclo[2.2.2]octane bis(tetrafluoroborate) (Selectfluor®) (486 g, 1373 mmol, Air Products, Allentown, Pa.) and the mixture was heated at 80° C. for 4 h. The reaction mixture was cooled to room temperature, concentrated under reduced pressure and water (2 L) was added. The mixture was extracted with ethyl acetate (2×1.5 L). The combined organic extract was washed with saturated aqueous NaHCO₃ (1.5 L) and 2N HCl (1 L). The organic layer was dried over sodium sulfate, filtered and concentrated under reduced pressure to obtain the crude N-(5-fluorothiazol-2-yl)acetamide (70.0 g, crude) which was used for next reaction without any purification. m/z (ESI) 161.0 (M+H)+

STEP 2: 5-FLUOROTHIAZOL-2-AMINE

To a solution of N-(5-fluorothiazol-2-yl)acetamide (70.0 g, 437 mmol) in ethanol (500 mL), conc. HCl (300 mL) was added and the reaction mixture was stirred at 80° C. for 16 h. The reaction mixture was concentrated under reduced pressure and the residue was dissolved in water. The mixture was neutralized with aqueous saturated NaHCO₃ solution (500 mL) and extracted with ethyl acetate (2×1000 mL). The combined organic extract was dried over sodium sulfate, filtered and concentrated under reduced pressure to obtain the crude 5-fluorothiazol-2-amine (15.0 g, crude) which was used for next reaction without any purification. m/z (ESI) 119.0 (M+H)+.

STEP 3: 5-FLUORO-N-(4-METHOXYBENZYL)THIAZOL-2-AMINE

To a solution of 5-fluorothiazol-2-amine (15.0 g, 127 mmol) and 4-methoxybenzaldehyde (17.3 g, 127 mmol, Spectrochem) in dichloromethane (1.0 L) was added TiCl(O-$^i$Pr)$_3$ (66.1 g, 254 mmol, Aldrich). The mixture was stirred at room temperature for 3 h. The reaction mixture was cooled to 0° C. and NaBH(OAc)$_3$ (108 g, 508 mmol) was added in portions and stirred at room temperature for 16 h. The reaction mixture (in portions of 200 mL) was quenched with saturated NaHCO$_3$ solution (100 mL) and extracted with dichloromethane (2×500 mL). The combined organic layer was dried over sodium sulfate, filtered and concentrated under reduced pressure to obtain the crude material which was further purified by column chromatography (silica gel 100 to 200 mesh and 50 to 100% dichloromethane in hexanes) to obtain 5-fluoro-N-(4-methoxybenzyl)thiazol-2-amine (20.0 g, 45%) as brown solid. $^1$H NMR (400 MHz, DMSO) δ 7.84 (t, J=5.7 Hz, 1H), 7.37-7.13 (m, 2H), 6.89 (dd, J=6.4, 2.2 Hz, 2H), 6.77 (d, J=2.4 Hz, 1H), 4.28 (d, J=5.6 Hz, 2H), 3.73 (s, 3H). m/z (ESI) 239.0 (M+H)+.

Intermediate NNN

PERFLUOROPHENYL 1-(4-CHLORO-2-METHOXYPHENYL)ISOQUINOLINE-6-SULFONATE

STEP 1: 6-(BENZYLTHIO)-1-(4-CHLORO-2-METHOXYPHENYL)ISOQUINOLINE

A RBF was charged with 6-(benzylthio)-1-chloroisoquinoline (from STEP 1 of INTERMEDIATE LLL) (688.23 mg, 2.408 mmol), (4-chloro-2-methoxyphenyl)boronic acid (494 mg, 2.65 mmol), Pd(AmPhos)$_2$Cl$_2$ (85 mg, 0.120 mmol), potassium phosphate (1534 mg, 7.22 mmol), dioxane (6020 µl), and water (2007 µl). The vial was flushed with Ar (g), then 1,4-dioxane (6020 µl) and water (2007 µl) were added. The vial was sealed and heated in a Biotage Initiator microwave reactor for 30 min at 100° C. The mixture was cooled to room temperature, then diluted with water and extracted with EtOAc (2×). The combined organic extracts were dried over sodium sulfate, filtered, and concentrated. The crude product was purified by chromatography on silica gel (40-g, 10 to 40%, then 40-70% EtOAc/Heptane, 25-g silica gel loading column) to give 6-(benzylthio)-1-(4-chloro-2-methoxyphenyl)isoquinoline (704.36 mg, 1.797 mmol, 74.6% yield) as a light-yellow foam: $^1$H NMR (400 MHz, CHLOROFORM-d) δ ppm=8.56 (d, J=5.8 Hz, 1 H), 7.65 (d, J=1.9 Hz, 1 H), 7.55-7.48 (m, 2 H), 7.44-7.39 (m, 2 H), 7.38-7.27 (m, 5 H), 7.11 (dd, J=1.9, 8.1 Hz, 1 H), 7.04 (d, J=1.9 Hz, 1 H), 4.30 (s, 2 H), 3.70 (s, 3 H); m/z (ESI) 392.2 (M+H)+.

STEP 2: PERFLUOROPHENYL 1-(4-CHLORO-2-METHOXYPHENYL)ISOQUINOLINE-6-SULFONATE

A round-bottom flask was charged with 6-(benzylthio)-1-(4-chloro-2-methoxyphenyl)isoquinoline (700 mg, 1.786 mmol), acetonitrile (1.68E+04 µl), acetic acid (630 µl), and water (420 µl) to give a thin suspension. The flask was cooling in an ice-bath for 15 min, then 1,3-dichloro-5,5-dimethylimidazolidine-2,4-dione (704 mg, 3.57 mmol) was added in one portion, leading to an solution. After 20 min, 2,3,4,5,6-pentafluorophenol (493 mg, 2.68 mmol) and triethylamine (1245 µl, 8.93 mmol) were added in sequence. The cooling bath was removed after a few minutes, and the mixture was warmed to room temperature. The mixture was treated with silica gel then concentrated. More silica gel was added, and the mixture was concentrated from DCM. The impregnated silica gel was eluted onto a pre-equilibrated 40-g column with 0 to 50% EtOAc/Heptane to give perfluorophenyl 1-(4-chloro-2-methoxyphenyl)isoquinoline-6-sulfonate (Intermediate NNN; 432 mg, 0.837 mmol, 46.9% yield) as a white foam. NMR and LC/MS indicated the material was about 82% pure. m/z (ESI) 516.0 (M+H)+.

Intermediate OOO

1-CHLORO-N-(2,4-DIMETHOXYBENZYL)-N-(THIAZOL-2-YL)ISOQUINOLINE-6-SULFONAMIDE

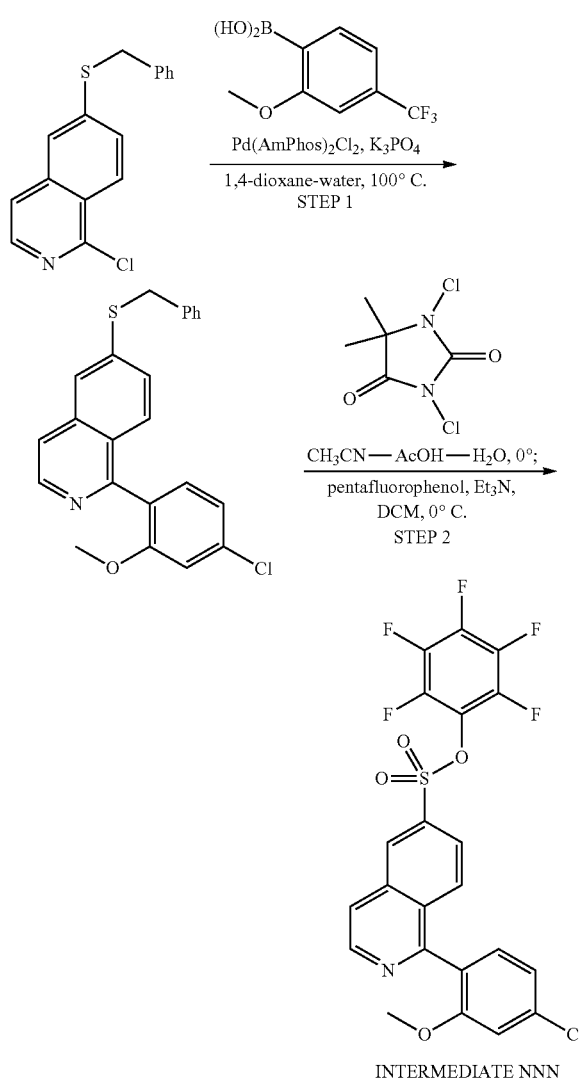

INTERMEDIATE NNN

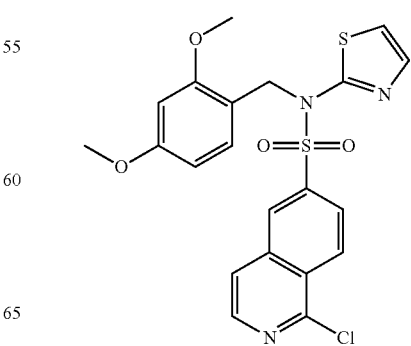

A solution of N-(2,4-dimethoxybenzyl)thiazol-2-amine (0.642 g, 2.56 mmol) in tetrahydrofuran (9.39 ml) was cooled in a dry ice-acetone bath for 5 min. Lithium bis(trimethylsilyl)amide (1M in THF) (2.68 ml, 2.68 mmol) was added drop wise, then the flask was removed from the cooling bath for 5 min. The flask was again cooled into a dry ice-acetone bath for 20 min, resulting in the formation of a thick slurry. A solution of perfluorophenyl 1-chloroisoquinoline-6-sulfonate (see Example 73, Step 1; 1.0 g, 2.441 mmol) in THF (5 mL) was added drop wise, and the reaction was stirred for 30 minutes. The reaction was warmed to room temperature and quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by chromatography on an 80-g with 0 to 50% EtOAc/Heptane to afford 1-chloro-N-(2,4-dimethoxybenzyl)-N-(thiazol-2-yl)isoquinoline-6-sulfonamide (INTERMEDIATE 000) as a white solid. (ESI) 498.2 (M+Na)+.

Intermediate PPP

1-CHLORO-N-(2,4-DIMETHOXYBENZYL)-4-FLUORO-N-(THIAZOL-2-YL)ISOQUINOLINE-6-SULFONAMIDE

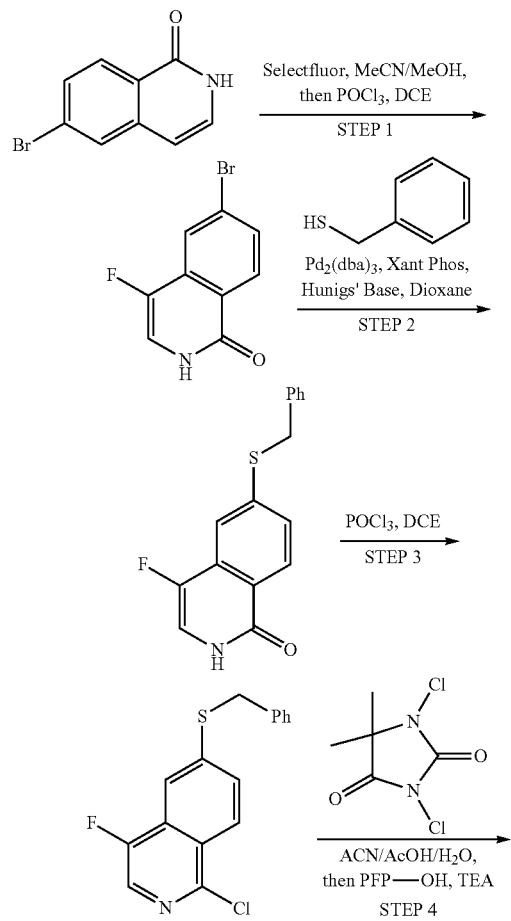

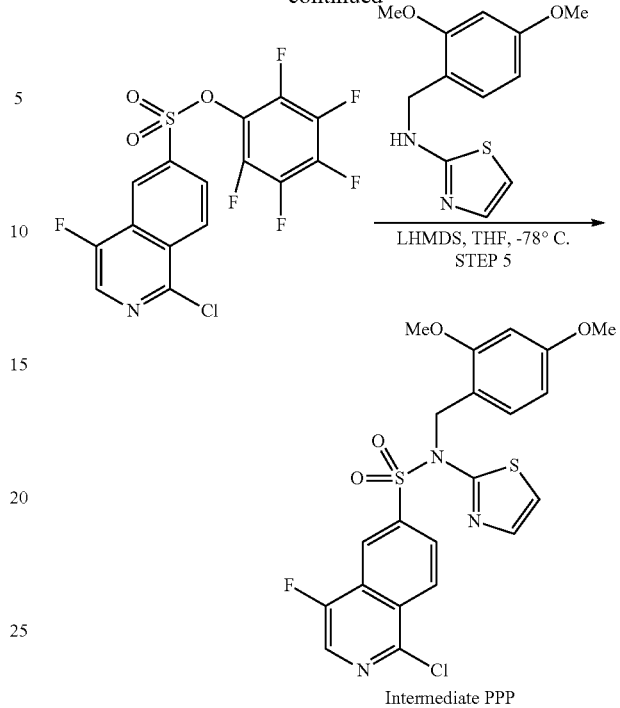

Intermediate PPP

STEP 1: 6-BROMO-4-FLUOROISOQUINOLIN-1(2H)-ONE

A round bottom flask was charged with 6-bromo-2h-isoquinolin-1-one (5.0 g, 22.32 mmol) and 1-chloromethyl-4-fluoro-1,4-diazoniabicyclo[2.2.2]octane bis(tetrafluoroborate) (Selectfluor®) (9.49 g, 26.8 mmol, Air Products, Allentown, Pa.). Methanol (55.8 ml) and acetonitrile (55.8 ml) were added and the reaction was heated to 50° C. and stirred for one hour. The reaction was concentrated, dissolved in DCE (110 mL), and POCl$_3$ (4.16 ml, 44.6 mmol) was added. The reaction was stirred at 50° C. for one hour. The reaction was quenched into ice water and extracted with ethyl acetate. The combined organic layers were dried with sodium sulfate, filtered, and concentrated to afford crude 6-bromo-4-fluoroisoquinolin-1(2H)-one as a light pink solid. (ESI) 242.1 (M+H)+.

STEP 2: 6-(BENZYLTHIO)-4-FLUOROISOQUINOLIN-1(2H)-ONE

A vial was charged with 6-bromo-4-fluoroisoquinolin-1 (2H)-one (3.88 g, 16.03 mmol), Xantphos (0.464 g, 0.802 mmol), and Pd$_2$(dba)$_3$ (0.367 g, 0.401 mmol). The flask was flushed with Ar (g), then dioxane (32.1 ml), benzyl mercaptan (2.086 ml, 17.63 mmol), and n,n-diisopropylethylamine (5.60 ml, 32.1 mmol) were added in sequence. The reaction was heated to 110° C. and stirred for one hour. The reaction was diluted with water and stirred for 30 minutes. The solution was filtered and the solids were washed with water and dried under a nitrogen blanket overnight. The solids were triturated in ethyl acetate, stirred for two hours, and filtered. The solids were washed with ethyl acetate and vacuum dried to afford 6-(benzylthio)-4-fluoroisoquinolin-1(2H)-one as a yellow/green solid. (ESI) 286.2 (M+H)+.

STEP 3: 6-(BENZYLTHIO)-1-CHLORO-4-FLUOROISOQUINOLINE

A vial was charged with 6-(benzylthio)-4-fluoroisoquinolin-1(2H)-one (0.083 g, 0.291 mmol) and DCE (1.454 ml). POCl$_3$ (0.136 ml, 1.454 mmol) was added and the reaction was stirred overnight at 90° C. The reaction was quenched into ice water and extracted with ethyl acetate. The aqueous layer was extracted with ethyl acetate, and the combined organic layers were dried with sodium sulfate, filtered, and concentrated to afford crude 6-(benzylthio)-1-chloro-4-fluoroisoquinoline as a light yellow solid. The material was carried forward without further purification. (ESI) 304.1 (M+H)$^+$.

STEP 4: PERFLUOROPHENYL 1-CHLORO-4-FLUOROISOQUINOLINE-6-SULFONATE

A round-bottom flask was charged with 6-(benzylthio)-1-chloro-4-fluoroisoquinoline (0.088 g, 0.290 mmol), acetonitrile (2.73 ml), acetic acid (0.102 ml), and water (0.068 ml) to give a thin suspension. The flask was cooled in an ice-bath for 10 min, then 1,3-dichloro-5,5-dimethylimidazolidine-2,4-dione (0.114 g, 0.579 mmol) was added in one portion, leading to a solution. The reaction was stirred for 30 minutes. 2,3,4,5,6-pentafluorophenol (0.061 ml, 0.579 mmol) was added followed by drop wise addition of triethylamine (0.101 ml, 0.724 mmol). The reaction was stirred for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (12 g, gradient elution 0 to 25% EtOAc:Heptane) to afford perfluorophenyl 1-chloro-4-fluoroisoquinoline-6-sulfonate as a clear colorless oil. (ESI) 428.1 (M+H)$^+$.

STEP 5: 1-CHLORO-N-(2,4-DIMETHOXYBENZYL)-4-FLUORO-N-(THIAZOL-2-YL)ISOQUINOLINE-6-SULFONAMIDE

A solution of N-(2,4-dimethoxybenzyl)thiazol-2-amine (0.031 g, 0.123 mmol) in tetrahydrofuran (0.450 ml) was cooled in a dry ice-acetone bath for 5 min. Lithium bis(trimethylsilyl)amide (1M in THF) (0.129 ml, 0.129 mmol) was added drop wise, then the flask was removed from the cooling bath for 5 min. The flask was again cooled into a dry ice-acetone bath for 20 min, resulting in the formation of a thick slurry. A solution of perfluorophenyl 1-chloro-4-fluoroisoquinoline-6-sulfonate (0.050 g, 0.117 mmol) in THF (0.25 mL) was added drop wise, and the reaction was stirred for 30 minutes. The reaction was warmed to room temperature and quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by chromatography on a 12-g column with 0 to 100% EtOAc/Heptane to afford 1-chloro-N-(2,4-dimethoxybenzyl)-4-fluoro-N-(thiazol-2-yl)isoquinoline-6-sulfonamide (INTERMEDIATE PPP) as an oily solid. (ESI) 516.2 (M+H)$^+$.

Intermediate QQQ

1-CHLORO-4-FLUORO-N-(4-METHOXYBENZYL)-N-(PYRIMIDIN-4-YL)ISOQUINOLINE-6-SULFONAMIDE

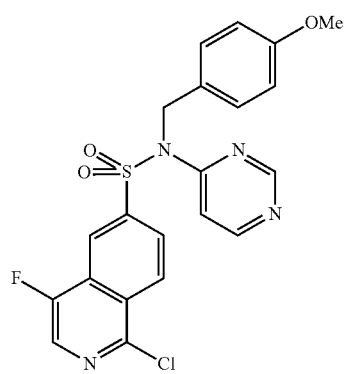 [SMILES: COc1ccc(CN(c2ccncn2)S(=O)(=O)c2ccc3c(Cl)ncc(F)c3c2)cc1]

Intermediate QQQ was prepared in a similar manner to Intermediate PPP, except that N-(4-methoxybenzyl)pyrimidin-4-amine was used instead of N-(2,4-dimethoxybenzyl)thiazol-2-amine in step 5. The final compound was purified via column chromatography (40 g silica gel column, gradient elution 0 to 75% EtOAc:Heptane) to afford 1-chloro-4-fluoro-N-(4-methoxybenzyl)-N-(pyrimidin-4-yl)isoquinoline-6-sulfonamide as a white oily solid. (ESI) 459.2 (M+H)$^+$.

Intermediate RRR

3-CHLORO-1-(2-METHOXY-4-(TRIFLUOROMETHYL)PHENYL)-N-(4-METHOXYBENZYL)-N-(THIAZOL-2-YL)ISOQUINOLINE-6-SULFONAMIDE

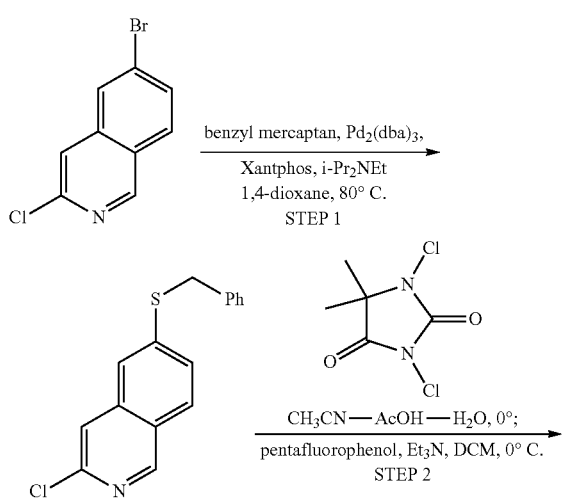

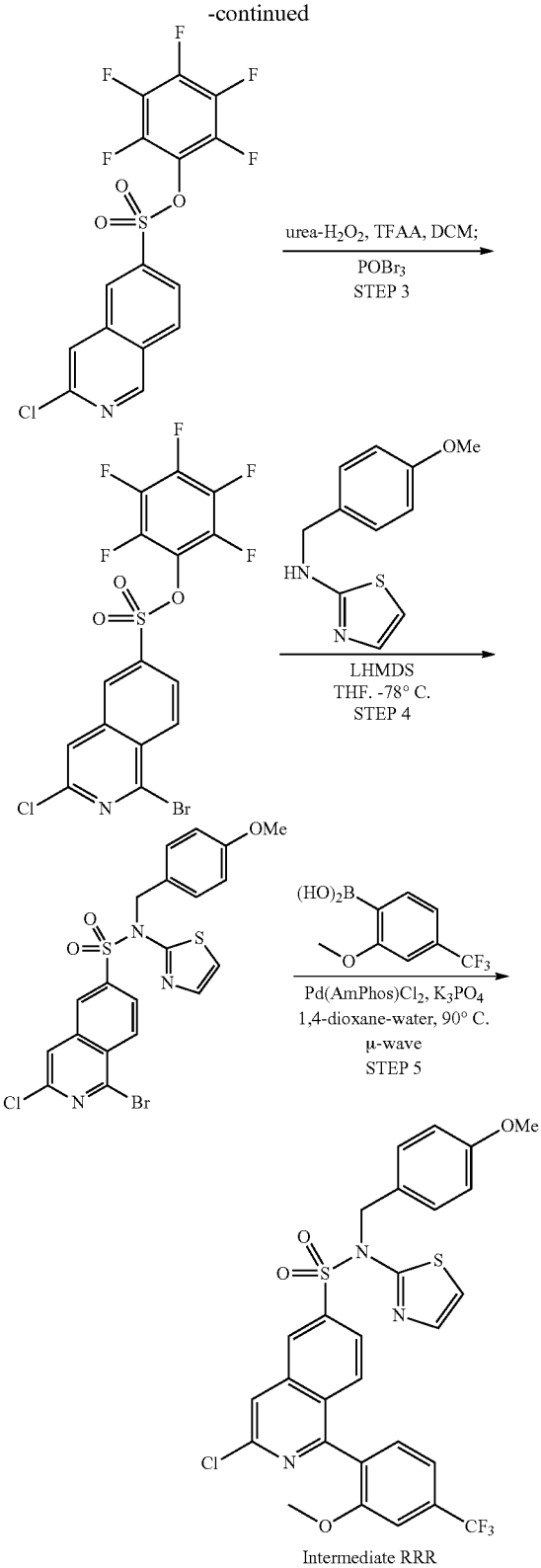

STEP 1: 6-(BENZYLTHIO)-3-CHLOROISOQUINOLINE

A pressure vessel was charged with 6-bromo-3-chloroisoquinoline (1.3307 g, 5.49 mmol), Xantphos (0.159 g, 0.274 mmol), and Pd$_2$(dba)$_3$ (0.126 g, 0.137 mmol). The vessel was flushed with Ar (g), then 1,4-dioxane (10.97 ml), N,N-diisopropylethylamine (1.917 ml, 10.97 mmol), and benzyl mercaptan (0.682 ml, 5.76 mmol) were added in sequence. The vessel was sealed and heated in an 80° C. heating bath for 16 h. The mixture was cooled, diluted with EtOAc, and filtered through diatomaceous earth. The filtrate was concentrated, and the residue was purified by chromatography on silica gel (25-g silica gel loading column, 0 to 30% EtOAC/Heptane) to give 6-(benzylthio)-3-chloroisoquinoline (1.398 g, 4.89 mmol, 89% yield) as a light-yellow solid: $^1$H NMR (400 MHz, CHLOROFORM-d) δ ppm=8.94 (s, 1 H), 7.81 (d, J=8.6 Hz, 1 H), 7.55 (d, J=0.2 Hz, 1 H), 7.50-7.39 (m, 4 H), 7.38-7.28 (m, 3 H), 4.30 (s, 2 H); m/z (ESI) 286.2 (M+H)+.

STEP 2: PERFLUOROPHENYL 3-CHLOROISOQUINOLINE-6-SULFONATE

A round-bottom flask was charged with 6-(benzylthio)-3-chloroisoquinoline (1.363 g, 4.77 mmol), acetonitrile (44.9 ml), and acetic acid (1.683 ml) to give a suspension. The flask was sonicated for 10 min to give an opaque yellow mixture. Water (1.122 ml) was added, and the mixture became a thin suspension. The flask was cooled in an ice-water bath for 20 min, then 1,3-dichloro-5,5-dimethylimidazolidine-2,4-dione (1.879 g, 9.54 mmol) was added in one portion, resulting in the formation of a clear solution within 20 sec. After 15 min, 2,3,4,5,6-pentafluorophenol (1.756 g, 9.54 mmol) and triethylamine (2.66 ml, 19.08 mmol) were added in sequence. After another 25 min of stirring, the mixture was diluted with EtOAc (50 mL) and washed with water (2×50 ml), washed with brine, dried over sodium sulfate, filtered, and concentrated. The residue was dissolved in DCM and purified by chromatography on silica gel (40-g column, 25-g silica gel loading column, 0 to 30% EtOAc/Heptane) to give perfluorophenyl 3-chloroisoquinoline-6-sulfonate (1.69522 g, 4.14 mmol, 87% yield) as a clear oil contaminated with some pentafluorophenol: m/z (ESI) 286.2 (M+H)+.

STEP 3: PERFLUOROPHENYL 1-BROMO-3-CHLOROISOQUINOLINE-6-SULFONATE

A round-bottom flask was charged with perfluorophenyl 3-chloroisoquinoline-6-sulfonate (1.21 g, 2.95 mmol) and DCM (11.81 ml) to give a clear solution. Urea compound with hydrogen peroxide (1:1) (0.556 g, 5.91 mmol) was added, resulting in a suspension. The flask was cooled in an ice-water bath for 10 min, then 2,2,2-trifluoroacetic anhydride (0.834 ml, 5.91 mmol) was added over 20 s. The cooling bath was removed, the flask was sealed, and the mixture was stirred overnight for 15 h. An additional portion of TFAA (0.3 mL) was added, and the mixture was stirred for 5 h. The mixture was carefully quenched with saturated aq. sodium bicarbonate solution (50 mL), then diluted with water and extracted with DCM (3×). The cloudy organic layer was stirred over sodium sulfate for 2 min, which resulted in the formation of an orange solution. The mixture was filtered, and the filtrate was concentrated under a vacuum. The residue was dissolved in DCM (5 mL) to give an orange solution. Phosphoryl tribromide (1.693 g, 5.91 mmol) was added in one portion, and the mixture was stirred further at room temperature. After 1 h, the mixture was poured into ice, then diluted with water and DCM. When it had achieved room temperature, the layers were separated.

The aq. layer was extracted with DCM (2x), and the combined organic extracts were dried over sodium sulfate, filtered, and concentrated. The aq. layer was further diluted with water and extracted with DCM (2x). The combined organic extracts were dried over sodium sulfate, filtered, and concentrated with residue from the first organic extraction. The combined residue was purified by chromatography on silica gel (40-g Redi-Sep Gold column, 25-g loading column, 0-40% EtOAc/Heptane) to give perfluorophenyl 1-bromo-3-chloroisoquinoline-6-sulfonate (0.482 g, 0.986 mmol, 33.4% yield) as a white solid: m/z (ESI) 488.0 (M+H)+.

STEP 4: 1-BROMO-3-CHLORO-N-(4-METHOXYBENZYL)-N-(THIAZOL-2-YL)ISOQUINOLINE-6-SULFONAMIDE

A round-bottom flask was charged with N-(4-methoxybenzyl)thiazol-2-amine (238 mg, 1.081 mmol) and THF (4912 µl) to give an opaque solution. The flask was cooled in a dry ice-acetone bath for 5 min to give a milky suspension, then lithium bis(trimethylsilyl)amide (1M in THF) (1081 µl, 1.081 mmol) was added. The flask was removed from the bath for 2 min to give a clear solution, then resubmerged. The mixture appeared to remain a solution. After 5 min, a solution of perfluorophenyl 1-bromo-3-chloroisoquinoline-6-sulfonate (480 mg, 0.982 mmol) in THF (3 mL with a 2 mL wash) was added drop wise. After 25 min, the mixture was diluted with saturated aq. ammonium chloride solution and warmed to room temperature. The mixture was diluted with water and extracted with EtOAc. The organic extract was dried over sodium sulfate, filtered, and concentrated. The residue was purified by chromatography on silica gel (0 to 40% EtOAc/Heptane) to give 1-bromo-3-chloro-N-(4-methoxybenzyl)-N-(thiazol-2-yl)isoquinoline-6-sulfonamide (481 mg, 0.916 mmol, 93% yield) as a white foam: $^1$H NMR (400 MHz, CHLOROFORM-d) δ ppm=8.32 (d, J=9.0 Hz, 1 H), 8.04 (d, J=1.8 Hz, 1 H), 7.83 (dd, J=1.9, 9.0 Hz, 1 H), 7.67 (s, 1 H), 7.44 (d, J=3.6 Hz, 1 H), 7.30 (d, J=8.8 Hz, 2 H), 7.07 (d, J=3.5 Hz, 1 H), 6.75-6.71 (m, 2 H), 5.12 (s, 2 H), 3.74 (s, 3 H). m/z (ESI) 546.0 (M+H)+.

STEP 5: 3-CHLORO-1-(2-METHOXY-4-(TRIFLUOROMETHYL)PHENYL)-N-(4-METHOXYBENZYL)-N-(THIAZOL-2-YL)ISOQUINOLINE-6-SULFONAMIDE

This reaction was conducted in two separate vials. For the first reaction, a vial was charged with 1-bromo-3-chloro-N-(4-methoxybenzyl)-N-(thiazol-2-yl)isoquinoline-6-sulfonamide (57.11 mg, 0.109 mmol), (2-methoxy-4-(trifluoromethyl)phenyl)boronic acid (25.1 mg, 0.114 mmol), Pd(AmPhos)$_2$Cl$_2$ (3.85 mg, 5.44 µmol), potassium phosphate (69.3 mg, 0.326 mmol), 1,4-dioxane (408µl), and water (136µl). The vial was flushed with Ar (g), then sealed and heated in a microwave reactor for 15 min at 90° C. A second vial was charged with 1-bromo-3-chloro-N-(4-methoxybenzyl)-N-(thiazol-2-yl)isoquinoline-6-sulfonamide (422 mg, 0.804 mmol), (2-methoxy-4-(trifluoromethyl)phenyl)boronic acid (186 mg, 0.844 mmol), Pd(AmPhos)$_2$Cl$_2$ (28.5 mg, 0.040 mmol), potassium phosphate (512 mg, 2.412 mmol), 1,4-dioxane (3015 µl) and water (1005 µl). The vial was flushed with Ar (g), then sealed and heated in a Biotage Initiator microwave reactor for 15 min at 90° C. The reaction mxitures from each vial were combined, and the combined mixture was extracted with EtOAc (3x). The combined organic extracts were concentrated, and the residue was purified by chromatography on silica gel (40-g column, 20 to 60% EtOAc/Heptane) to give 3-chloro-1-(2-methoxy-4-(trifluoromethyl)phenyl)-N-(4-methoxybenzyl)-N-(thiazol-2-yl)isoquinoline-6-sulfonamide (Intermediate RRR; 500.9 mg, 0.808 mmol, 89% yield) as an off-white foam: $^1$H NMR (400 MHz, CHLOROFORM-d) δ ppm=8.15 (t, J=1.1 Hz, 1 H), 7.77 (s, 1 H), 7.68-7.65 (m, 2 H), 7.50 (s, 1 H), 7.44-7.38 (m, 2 H), 7.30 (d, J=8.8 Hz, 2 H), 7.27 (s, 1 H), 7.04 (d, J=3.6 Hz, 1 H), 6.73 (d, J=8.8 Hz, 2 H), 5.11 (s, 2 H), 3.76 (s, 3 H), 3.73 (s, 3 H); m/z (ESI) 620.2 (M+H)+.

Intermediate SSS

1-CHLORO-N-(THIAZOL-2-YL)-N-((2-(TRIMETHYLSILYL)ETHOXY)METHYL)ISOQUINOLINE-6-SULFONAMIDE

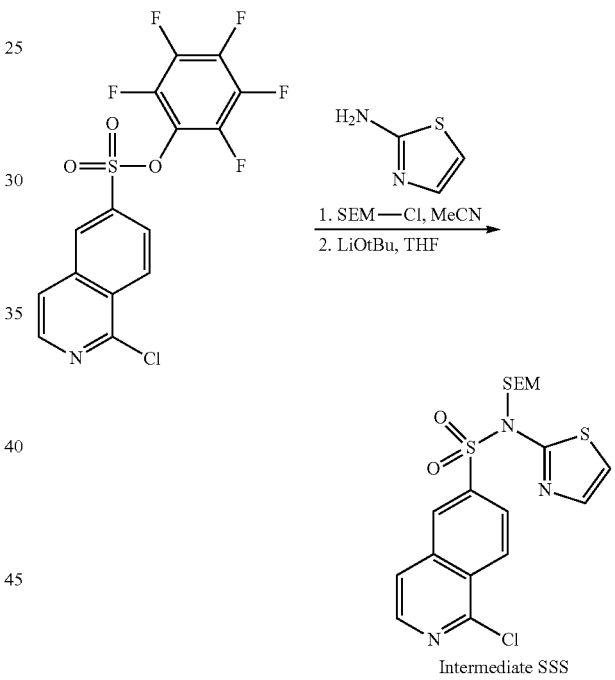

Intermediate SSS

A solution of thiazol-2-amine (0.134 g, 1.342 mmol) in 3 mL MeCN was treated with SEM-Cl (0.238 ml, 1.342 mmol) and was allowed to stir at room temperature for 30 minutes. LC/MS showed mostly product, so the reaction mixture was treated with perfluorophenyl 1-chloroisoquinoline-6-sulfonate (See, Example 73, Step 1; 0.500 g, 1.220 mmol) and was cooled to −10° C. Lithium tert-butoxide (1N in THF) (2.441 ml, 2.441 mmol) was added, and the reaction mixture was allowed to warm to room temperature overnight. The reaction mixture was poured into water and was extracted with DCM. The organics were dried over MgSO$_4$ and concentrated. Purification of the crude residue by silica gel column chromatography (0 to 100% EtOAc/heptane) gave 1-chloro-N-(thiazol-2-yl)-N-((2-(trimethylsilyl)ethoxy)methyl)isoquinoline-6-sulfonamide (0.220 g, 0.482 mmol, 39.5% yield). m/z (ESI) 456.0 (M+H)+;

Intermediate TTT

2-(4-(DIFLUOROMETHYL)-2-METHOXYPHENYL)-4,4,5,5-TETRAMETHYL-1,3,2-DIOXABOROLANE

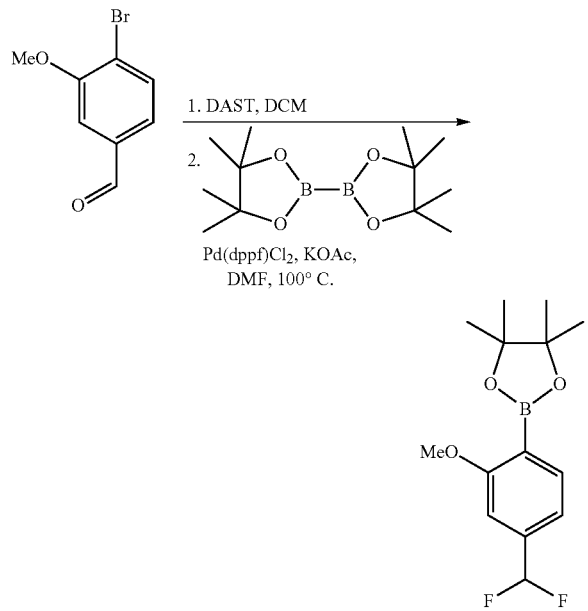

A solution of 4-bromo-3-methoxybenzaldehyde (Combi-Blocks, San Diego, Calif., 1.832 g, 8.52 mmol) in 25 mL of DCM was cooled to 0° C. and was treated with DAST (1.407 ml, 10.65 mmol) drop wise over 10 minutes. After stirring for one hour, little conversion was observed, so the reaction mixture was gently heated to reflux with a heat gun and was then allowed to stir at room temperature overnight. The reaction mixture was poured into saturated $NaHCO_3$ solution (aq) and was extracted with DCM. The organics were dried over $MgSO_4$ and concentrated. The crude residue was taken up in 20 mL of DMF, was treated with bis(pinacolato)diboron (3.25 g, 12.78 mmol), $PdCl_2$(dppf)-$CH_2Cl_2$ adduct (0.696 g, 0.852 mmol), and potassium acetate (3.34 g, 34.1 mmol) and was heated to 100° C. overnight. The reaction mixture was allowed to cool to room temperature and was diluted with DCM. The reaction mixture was filtered through a plug of diatomaceous earth and the filtrate was concentrated. Purification of the crude residue by silica gel column chromatography (0 to 50% EtOAc/heptane) gave 2-(4-(difluoromethyl)-2-methoxyphenyl)-4,4,5,5-tetramethyl-1,3,2-dioxaborolane (0.948 g, 3.34 mmol, 39.2% yield). m/z (ESI) 285.3 (M+Na)+;

Intermediate UUU

2-(2-(METHOXYMETHYL)-4-(TRIFLUOROMETHYL)PHENYL)-4,4,5,5-TETRAMETHYL-1,3,2-DIOXABOROLANE

A solution of 1-bromo-2-iodo-4-(trifluoromethyl)benzene (1.000 g, 2.85 mmol) in 3 mL of THF was treated with isopropylmagnesium chloride (1.567 ml, 3.13 mmol) and was allowed to stir for 10 minutes. MOM-Cl (0.260 ml, 3.42 mmol) was added, and the reaction mixture was heated to reflux for one hour. The reaction mixture was poured into 1N aqueous HCl and was extracted with DCM. The organics were dried over $MgSO_4$ and concentrated. The crude residue was taken up in 3 mL of DMF, treated with $PdCl_2$(dppf)-$CH_2Cl_2$ adduct (0.233 g, 0.285 mmol), bis(pinacolato)diboron (1.447 g, 5.70 mmol), and potassium acetate (1.119 g, 11.40 mmol) and was heated to 80° C. for 72 hours. The reaction mixture was diluted with DCM and was filtered through a plug of diatomaceous earth. The filtrate was concentrated then purified directly by silica gel column chromatography (0 to 50% EtOAc/heptane) yielding 2-(2-(methoxymethyl)-4-(trifluoromethyl)phenyl)-4,4,5,5-tetramethyl-1,3,2-dioxaborolane (0.741 g, 2.344 mmol, 82% yield). m/z (ESI) 317.1 (M+H)+

Intermediate VVV 6-(benzylthio)-1-chloro-4-methoxyisoquinoline

83

-continued

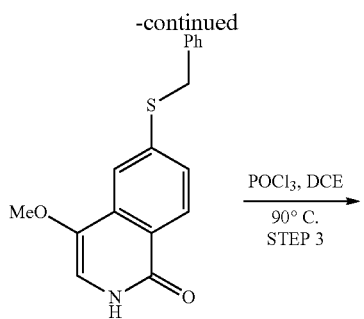

POCl₃, DCE
90° C.
STEP 3

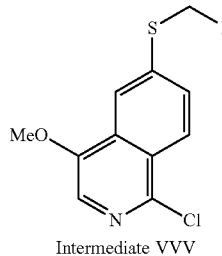

Intermediate VVV

STEP 1: 6-BROMO-4-METHOXYISOQUINOLIN-1(2H)-ONE

A round bottom flask was charged with 6-bromo-2h-isoquinolin-1-one (1.0 g, 4.46 mmol), methanol (8 mL), and methanesulfonic acid (0.290 ml, 4.46 mmol) and the flask was cooled to 0° C. In a separate flask, iodosobenzene diacetate (1.581 g, 4.91 mmol) was dissolved in methanol (8 mL) and added to the reaction. The reaction was warmed to room temperature and stirred for one hour, then heated to 50° C. and stirred overnight. The reaction was concentrated and triturated with isopropanol. The solution was stirred for 10 minutes, then filtered. The solids were washed with isopropanol and vacuum dried to afford 6-bromo-4-methoxyisoquinolin-1(2H)-one as a tan solid. (ESI) 254.1 (M+H

STEP 2: 6-(BENZYLTHIO)-4-METHOXYISOQUINOLIN-1(2H)-ONE

The title compound was prepared in an analogous manner to that of Intermediate PPP, Step 2, except that 6-bromo-4-methoxyisoquinolin-1(2H)-one was used instead of 6-bromo-4-fluoroisoquinolin-1(2H)-one to afford 6-(benzylthio)-4-methoxyisoquinolin-1(2H)-one as a brown solid. (ESI) 298.3 (M+H)⁺.

STEP 3: 6-(BENZYLTHIO)-1-CHLORO-4-METHOXYISOQUINOLINE

A vial was charged with 6-(benzylthio)-4-methoxyisoquinolin-1(2H)-one (0.933 g, 3.14 mmol) and DCE (15.69 ml). POCl₃ (0.585 ml, 6.27 mmol) was added and the reaction was stirred overnight at 90° C. The reaction was diluted with ethyl acetate and washed with water. The aqueous layer was extracted with ethyl acetate, and the combined organic layers were dried with sodium sulfate, filtered, and concentrated to afford crude 6-(benzylthio)-1-chloro-4-methoxy-isoquinoline (Intermediate VVV) as a brown solid. (ESI) 316.3 (M+H)⁺.

84

Intermediate WWW

1-CHLORO-N-(2,4-DIMETHOXYBENZYL)-4-HYDROXY-N-(THIAZOL-2-YL)ISOQUINOLINE-6-SULFONAMIDE

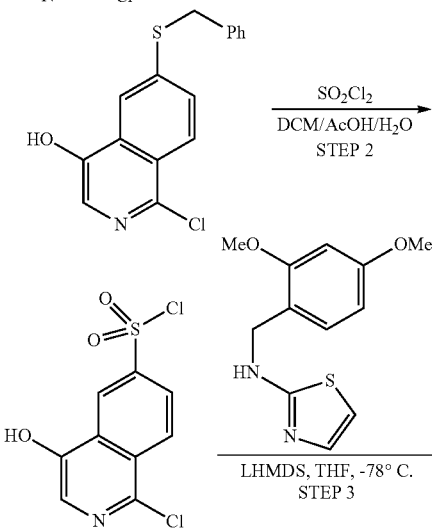

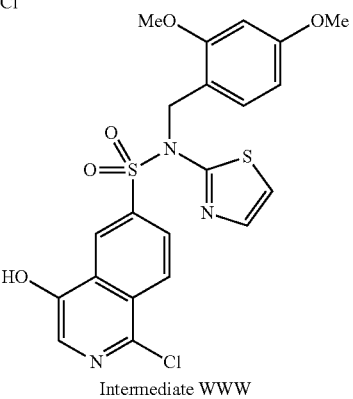

Intermediate WWW

STEP 1: 6-(BENZYLTHIO)-1-CHLOROISOQUINOLIN-4-OL 6-(benzylthio)-1-chloro-4-methoxyisoquinoline (Intermediate VVV; 0.400 g, 1.267 mmol) was dissolved in DCM (12.67 ml) and cooled to 0° C. Boron tribromide (0.487 ml, 5.06 mmol) was added and the reaction was stirred for 30 minutes, then warmed to room temperature and stirred overnight. The reaction was cooled to 0° C. and carefully quenched with saturated sodium bicarbonate solution. The reaction was diluted with ethyl acetate and the layers were separated. The aqueous layer was extracted with ethyl acetate, and the combined organic layers were dried with sodium sulfate, filtered, and concentrated to afford crude 6-(benzylthio)-1-chloroisoquinolin-4-ol as an orange solid. (ESI) 302.1 (M+H)+.

STEP 2: 1-CHLORO-4-HYDROXYISOQUINOLINE-6-SULFONYL CHLORIDE

A round-bottom flask was charged with 6-(benzylthio)-1-chloroisoquinolin-4-ol (0.280 g, 0.928 mmol), DCM (8.84 ml), acetic acid (0.221 ml), and water (0.221 ml) to give a thin suspension. The flask was cooled in an ice-bath for 10 min, then sulfuryl chloride (0.226 ml, 2.78 mmol) was added in one portion, leading to a solution. The reaction was stirred for 30 minutes, then warmed to room temperature and stirred for one hour. The reaction was concentrated and purified via column chromatography (40 g silica gel column, gradient elution 0 to 100% EtOAc:Heptane) to afford 1-chloro-4-hydroxyisoquinoline-6-sulfonyl chloride (as a light pink solid. (ESI) 280.1 (M+H)+.

STEP 3: 1-CHLORO-N-(2,4-DIMETHOXYBENZYL)-4-HYDROXY-N-(THIAZOL-2-YL)ISOQUINOLINE-6-SULFONAMIDE

The title compound was prepared in an analogous manner to that of Intermediate PPP, Step 5, except that 1-chloro-4-hydroxyisoquinoline-6-sulfonyl chloride was used instead of perfluorophenyl 1-chloro-4-fluoroisoquinoline-6-sulfonate. The final compound was purified via column chromatography (40 g silica gel column, gradient elution 0 to 50% EtOAc:Heptane) to afford 1-chloro-N-(2,4-dimethoxybenzyl)-4-hydroxy-N-(thiazol-2-yl)isoquinoline-6-sulfonamide as a yellow solid. (ESI) 492.2 (M+H)+.

Intermediate XXX perfluorophenyl 1-chloro-4-cyanoisoquinoline-6-sulfonate

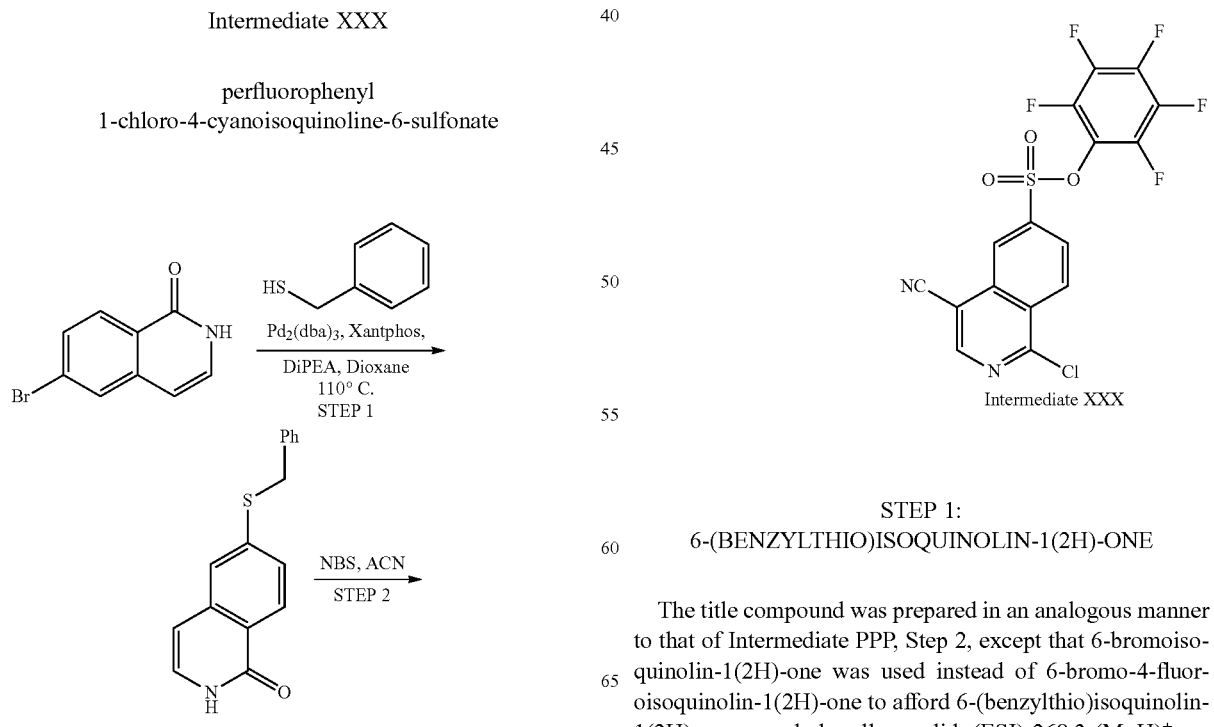

STEP 1: 6-(BENZYLTHIO)ISOQUINOLIN-1(2H)-ONE

The title compound was prepared in an analogous manner to that of Intermediate PPP, Step 2, except that 6-bromoisoquinolin-1(2H)-one was used instead of 6-bromo-4-fluoroisoquinolin-1(2H)-one to afford 6-(benzylthio)isoquinolin-1(2H)-one as a dark yellow solid. (ESI) 268.3 (M+H)+.

STEP 2: 6-(BENZYLTHIO)-4-BROMOISOQUINOLIN-1(2H)-ONE

A round bottom flask was charged with 6-(benzylthio) isoquinolin-1(2H)-one (1.1 g, 4.11 mmol), NBS (0.732 g, 4.11 mmol), and acetonitrile (20.57 ml). The reaction was stirred overnight at room temperature. The reaction was diluted with ethyl acetate and washed with water. The aqueous layer was extracted with ethyl acetate, and the combined organic layers were washed with brine, dried with sodium sulfate, filtered, and concentrated to afford a brown solid. The solid was triturated in DCM and filtered. The solids were isolated to afford 6-(benzylthio)-4-bromoisoquinolin-1(2H)-one as a silver solid. m/z (ESI) 346.1 (M+H)$^+$.

STEP 3: 6-(benzylthio)-1-oxo-1,2-dihydroisoquinoline-4-carbonitrile

A vial was charged with 6-(benzylthio)-4-bromoisoquinolin-1(2H)-one (0.583 g, 1.684 mmol), copper (i) cyanide (0.052 ml, 1.684 mmol), and NMP (8.42 ml). The reaction was heated to 200° C. and stirred for four hours. The reaction was diluted with ethyl acetate and washed with water. The aqueous layer was extracted with ethyl acetate, and the combined organic layers were dried with sodium sulfate, filtered, and concentrated. The material was purified via column chromatography (40 g silica gel column, gradient elution 0 to 10% MeOH:EtOAc) to afford 6-(benzylthio)-1-oxo-1,2-dihydroisoquinoline-4-carbonitrile as a brown solid. m/z (ESI) 293.1 (M+H)$^+$.

STEP 4: 6-(BENZYLTHIO)-1-CHLOROISOQUINOLINE-4-CARBONITRILE

A vial was charged with 6-(benzylthio)-1-oxo-1,2-dihydroisoquinoline-4-carbonitrile (0.492 g, 1.683 mmol) and DCE (8.41 ml). POCl$_3$ (0.314 ml, 3.37 mmol) was added and the reaction was stirred overnight at 90° C. The reaction was diluted with ethyl acetate and washed with water. The aqueous layer was extracted with ethyl acetate, and the combined organic layers were dried with sodium sulfate, filtered, and concentrated. The material was purified via column chromatography (40 g silica gel column, gradient elution 0 to 100% EtOAc:Heptane) to afford 6-(benzylthio)-1-chloroisoquinoline-4-carbonitrile as a brown solid. m/z (ESI) 311.1 (M+H)$^+$.

STEP 5: PERFLUOROPHENYL 1-CHLORO-4-CYANOISOQUINOLINE-6-SULFONATE

The titled compound was prepared in an analogous manner to that of Intermediate PPP, Step 4 except that 6-(benzylthio)-1-chloroisoquinoline-4-carbonitrile was used instead of 6-(benzylthio)-1-chloro-4-fluoroisoquinoline. The product was purified via column chromatography (40 g silica gel column, gradient elution 0 to 50% EtOAc:Heptane) to afford perfluorophenyl 1-chloro-4-cyanoisoquinoline-6-sulfonate as a clear oil. m/z (ESI) 436.1 (M+H)$^+$.

Intermediate YYY

1-CHLORO-4-CYANO-N-(2,4-DIMETHOXYBENZYL)-N-(THIAZOL-2-YL)ISOQUINOLINE-6-SULFONAMIDE

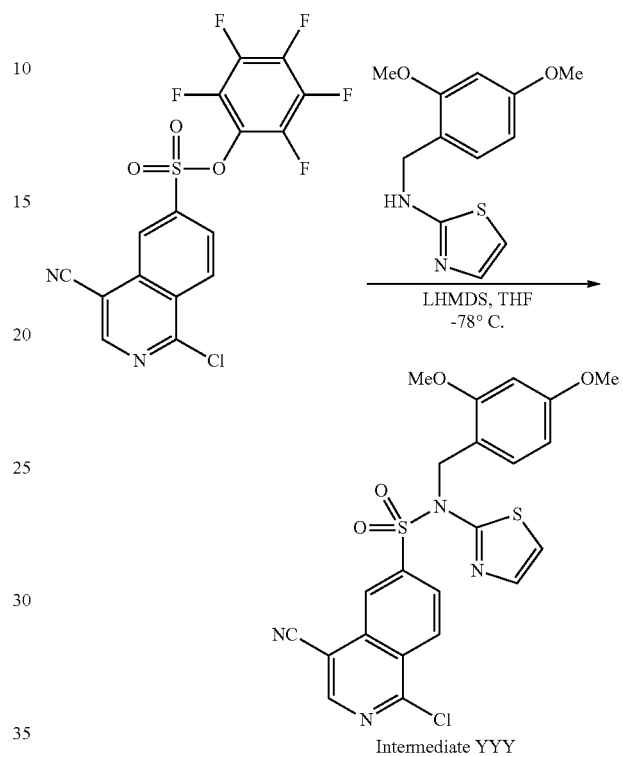

Intermediate YYY

Intermediate YYY was synthesized in a manner similar to Intermediate PPP, Step 5, except that perfluorophenyl 1-chloro-4-cyanoisoquinoline-6-sulfonate (Intermediate XXX) was used instead of perfluorophenyl 1-chloro-4-fluoroisoquinoline-6-sulfonate (from Intermediate PPP, step 4). The final compound was purified via column chromatography (40 g silica gel column, gradient elution 0 to 50% EtOAc:Heptane) to afford 1-chloro-4-cyano-N-(2,4-dimethoxybenzyl)-N-(thiazol-2-yl)isoquinoline-6-sulfonamide as a bright yellow solid. (ESI) 501.2 (M+H)$^+$.

Intermediate ZZZ

PERFLUOROPHENYL 1-(PYRROLIDIN-2-YL)ISOQUINOLINE-6-SULFONATE 2,2,2-TRIFLUOROACETATE

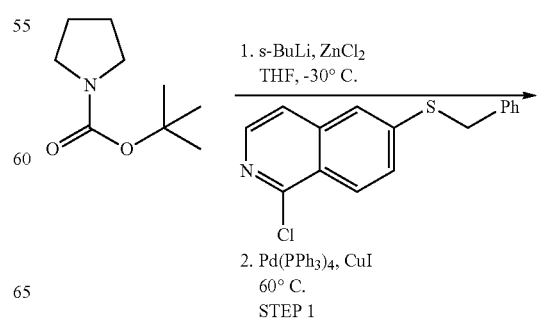

1. s-BuLi, ZnCl$_2$
THF, -30° C.

2. Pd(PPh$_3$)$_4$, CuI
60° C.
STEP 1

-continued

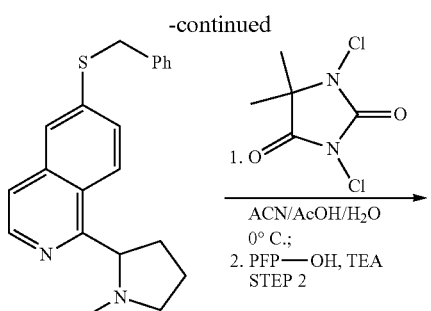

1. <image-content: 1,3-dichloro-5,5-dimethylhydantoin> ACN/AcOH/H₂O 0° C.;
2. PFP—OH, TEA
STEP 2

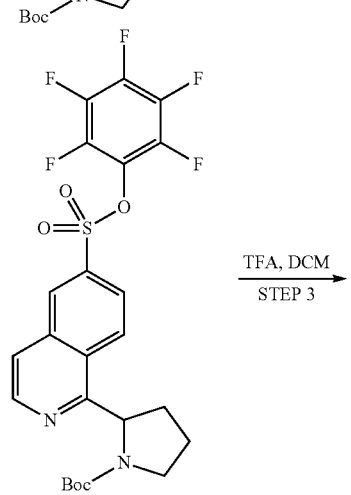

TFA, DCM
STEP 3

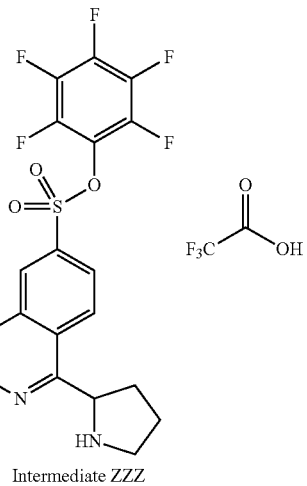

Intermediate ZZZ

STEP 1: TERT-BUTYL 2-(6-(BENZYLTHIO)ISO-QUINOLIN-1-YL)PYRROLIDINE-1-CARBOXYLATE

A 100-mL round-bottom flask was charged with tert-butyl 1-pyrrolidinecarboxylate (1.625 ml, 9.27 mmol) and THF (23.33 ml) to give a clear solution. The flask was flushed with Ar (g), then cooled in a −30° C. dry ice-acetone bath for 10 min. Sec-butyllithium (1.4 M in cyclohexane) (8.75 ml, 12.25 mmol) was added drop wise over 5 min. The resulting mixture was stirred for 10 minutes at −30° C., then zinc chloride (1.0 M in diethyl ether) (7.00 ml, 7.00 mmol) was added drop wise. The reaction was stirred for 5 minutes, then the cooling bath was removed. After 25 min, a solid mixture of 6-(benzylthio)-1-chloroisoquinoline (from Intermediate LLL, step 1; 1.0 g, 3.50 mmol), Pd(Ph₃P)₄ (0.809 g, 0.700 mmol), and copper(i) iodide (0.333 g, 1.750 mmol) was added in one portion. The reaction was capped and stirred at 60° C. for one hour. The reaction was filtered through a pad of diatomaceous earth, washing thoroughly with ethyl acetate. The filtrate was concentrated and purified via column chromatography (80 g silica gel column, gradient elution 0 to 100% EtOAc:Heptane followed by a 20% MeOH/EtOAc flush) to afford tert-butyl 2-(6-(benzylthio) isoquinolin-1-yl)pyrrolidine-1-carboxylate as a yellow solid. (ESI) 421.3 (M+H)⁺.

STEP 2: TERT-BUTYL 2-(6-((PERFLUOROPHE-NOXY)SULFONYL)ISOQUINOLIN-1-YL)PYR-ROLIDINE-1-CARBOXYLATE

A round-bottom flask was charged with tert-butyl 2-(6-(benzylthio)isoquinolin-1-yl)pyrrolidine-1-carboxylate (1.41 g, 3.35 mmol), acetonitrile (31.6 ml), acetic acid (1.183 ml), and water (0.789 ml). The flask was cooled in an ice-bath for 10 min, then 1,3-dichloro-5,5-dimethylimida-zolidine-2,4-dione (1.321 g, 6.71 mmol) was added in one portion and the reaction was stirred for 30 minutes. 2,3,4,5,6-pentafluorophenol (0.527 ml, 5.03 mmol) was added, then triethylamine (1.869 ml, 13.41 mmol) was added drop wise. The mixture was stirred for several minutes, then the cooling bath was removed and the reaction was stirred for 30 minutes. The reaction was concentrated and purified via silica gel column chromatography, 80 g, gradient elution 0 to 50% EtOAc:Heptane) to afford tert-butyl 2-(6-((perfluo-rophenoxy)sulfonyl)isoquinolin-1-yl)pyrrolidine-1-car-boxylate as a white solid. LC-MS showed a small impurity present, but the material was carried forward without further purification. (ESI) 545.1 (M+H)⁺.

STEP 3: PERFLUOROPHENYL 1-(PYRROLIDIN-2-YL)ISOQUINOLINE-6-SULFONATE 2,2,2-TRIFLUOROACETATE

A round-bottom flask was charged with tert-butyl 2-(6-((perfluorophenoxy)sulfonyl)isoquinolin-1-yl)pyrrolidine-1-carboxylate (1.02 g, 1.873 mmol) and DCM (5.0 mL) to give a light yellow solution. TFA (1.443 ml, 18.73 mmol) was added in one portion to give a yellow solution. The reaction was stirred for two hours. The reaction was concentrated, dissolved in diethyl ether, and sonicated until a fine white solid triturated out of solution. The solids were filtered, washed with diethyl ether, and vacuum dried overnight to afford perfluorophenyl 1-(pyrrolidin-2-yl)isoquino-line-6-sulfonate 2,2,2-trifluoroacetate as a white solid. (ESI) 445.3 (M+H)⁺.

Intermediate AAAA

1-CHLORO-N-(2,4-DIMETHOXYBENZYL)-N-(THIAZOL-2-YL)PHTHALAZINE-6-SULFONA-MIDE

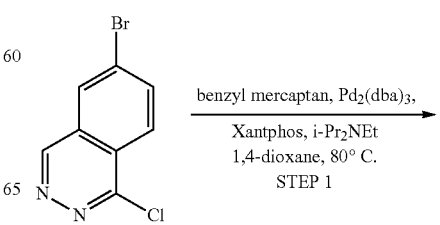

benzyl mercaptan, Pd₂(dba)₃,
Xantphos, i-Pr₂NEt
1,4-dioxane, 80° C.
STEP 1

-continued

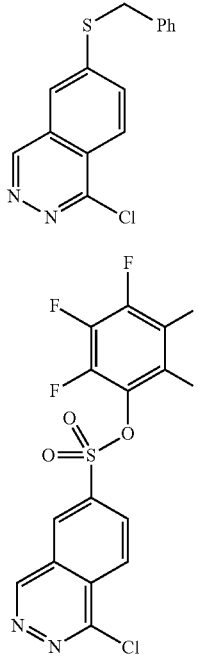

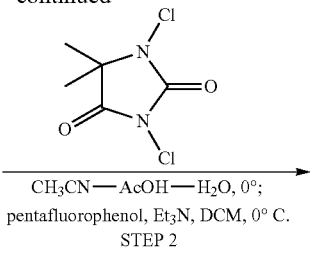

STEP 2

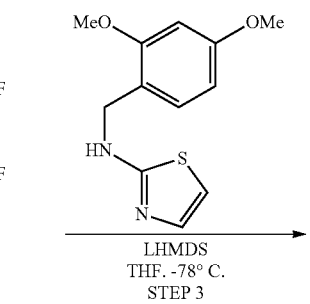

LHMDS
THF, -78° C.
STEP 3

Intermediate AAAA

STEP 1: 6-(BENZYLTHIO)-1-CHLOROPHTHALAZINE

A two-neck round-bottom flask was charged with 6-bromo-1-chlorophthalazine (Pharmablock, Nanjing Hi-Tech Zone, China, 4.44 g, 18.24 mmol), Xantphos (0.528 g, 0.912 mmol), and $Pd_2(dba)_3$ (0.417 g, 0.456 mmol). 1,4-dioxane (36.5 ml) and N,N-diisopropylethylamine (6.37 ml, 36.5 mmol) were added. The flask was fitted with a reflux condenser and placed in an 80° C. heating bath. After 5 min, benzyl mercaptan (2.265 ml, 19.15 mmol) was added drop wise. After 20 min. the mixture was cooled, then concentrated under a vacuum. EtOAc (about 25 mL) was added to the residue, and the flask was rotated on the rotovap in a 40° C. bath for 1.5 h. This removed most of the solid from the sides of the flask. The flask was sonicated for 30 s, then the mixture was concentrated under a vacuum. The residue was taken up in EtOAc to form a thick slurry. The flask was sonicated for 30 s, then the mixture was filtered. The collected solid was washed with several large volumes of EtOAc (until the filtrates were essentially colorless). The filtrate was concentrated, and the residue was purified by chromatography on silica gel (80-g column with a 25-g silica gel loading column, 0 to 50% EtOAc/Heptane, then 50 to 100% EtOAc/Heptane). The resulting solid was taken up in heptane, sonicated for 30 s, then filtered. The collected solid was washed with heptane (3×, which removed some of the yellow color), and dried under a stream of N2 (g) for 20 min to give 6-(benzylthio)-1-chlorophthalazine (3.975 g, 13.86 mmol, 76% yield) as a light-orange powder: $^1$H NMR (400 MHz, CHLOROFORM-d) δ ppm=9.28 (d, J=0.7 Hz, 1 H), 8.14 (d, J=8.8 Hz, 1 H), 7.82 (dd, J=1.9, 8.8 Hz, 1 H), 7.69 (d, J=1.8 Hz, 1 H), 7.45-7.28 (m, 5 H), 4.35 (s, 2 H); m/z (ESI) 287.2 (M+H)$^+$.

STEP 2: PERFLUOROPHENYL 1-CHLOROPHTHALAZINE-6-SULFONATE

A round-bottom flask was charged with 6-(benzylthio)-1-chlorophthalazine (2.20 g, 7.67 mmol), acetonitrile (72.2 ml), acetic acid (2.71 ml), and water (1.805 ml) to give a clear, orange solution. The flask was cooling in an ice-bath for 10 min, then 1,3-dichloro-5,5-dimethylimidazolidine-2,4-dione (3.02 g, 15.34 mmol) was added in one portion. After 30 min, 2,3,4,5,6-pentafluorophenol (2.82 g, 15.34 mmol) and triethylamine (4.28 ml, 30.7 mmol) were added in sequence. After 30 min, the mixture was diluted with EtOAc (100 mL), washed with water (50 ml), washed with 0.5 N aq. HCl (100 mL), washed with brine, and dried over sodium sulfate. The residue was dissolved in DCM and loaded onto a chilled 25-g silica gel loading column. The column was dried with a vacuum hose, then eluted onto a pre-equilibrated 80-g column with 0 to 50% EtOAc/Heptane to give perfluorophenyl 1-chlorophthalazine-6-sulfonate (2.134 g, 5.20 mmol, 67.7% yield) as a yellow solid: $^1$H NMR (400 MHz, CHLOROFORM-d) δ ppm=9.64 (d, J=0.7 Hz, 1 H), 8.72 (d, J=1.8 Hz, 1 H), 8.65-8.59 (m, 1 H), 8.56-8.50 (m, 1 H); m/z (ESI) 411.2 (M+H)$^+$.

STEP 3: 1-CHLORO-N-(2,4-DIMETHOXYBEN-ZYL)-N-(THIAZOL-2-YL)PHTHALAZINE-6-SULFONAMIDE

A round-bottom flask was charged with N-(2,4-dimethoxybenzyl)thiazol-2-amine (181 mg, 0.723 mmol) and THF (32870 to give a clear solution. The flask was cooled in a dry ice-acetone bath for 5 min, then lithium bis(trimethylsilyl)amide (1M in THF) (723 μl 0.723 mmol) was added. The flask was removed from the bath for 2 min, then resubmerged. After 5 min, a solution of perfluorophenyl 1-chlorophthalazine-6-sulfonate (270 mg, 0.657 mmol) in THF (0.7 mL with a 0.3 mL wash) was added drop wise. After 5 min, the dry ice-acetone bath was swapped out for an ice-water bath. After 1 h, the mixture was diluted with saturated aq. ammonium chloride solution and EtOAc. The layers were separated, and the aq. layer was washed with brine, dried over sodium sulfate, filtered, and concentrated. The residue was purified by chromatography on silica gel (40-g column, 20 to 70% EtOAc/Heptane) to give 1-chloro-N-(2,4-dimethoxybenzyl)-N-(thiazol-2-yl)phthalazine-6-sulfonamide (112 mg, 0.235 mmol, 35.7% yield) as a cream-colored solid: m/z (ESI) 477.2 (M+H)$^+$.

Intermediate BBBB

1-(2-METHOXY-4-(TRIFLUOROMETHYL)PHENYL)PHTHALAZINE-6-SULFONYL CHLORIDE

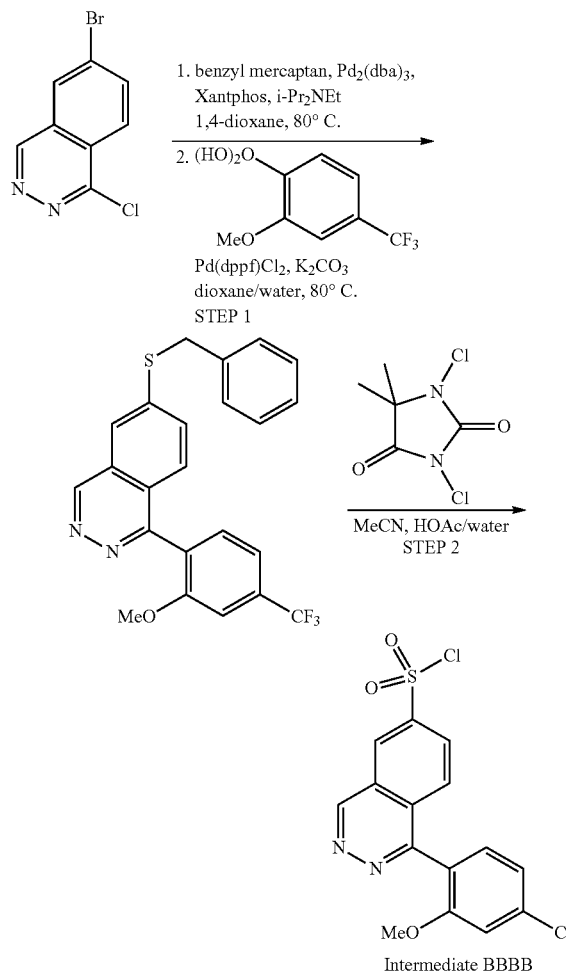

STEP 1: 6-(BENZYLTHIO)-1-(2-METHOXY-4-(TRIFLUOROMETHYL)PHENYL)PHTHALAZINE

A solution of 6-bromo-1-chlorophthalazine (0.500 g, 2.053 mmol), Pd$_2$(dba)$_3$ (0.047 g, 0.051 mmol), Xantphos (0.059 g, 0.103 mmol), and n,n-diisopropylethylamine (1.076 ml, 6.16 mmol) in 6 mL of dioxane was heated to 60° C. and was treated with benzyl mercaptan (0.243 ml, 2.053 mmol) drop wise. After stirring for one hour, LC/MS showed product and bis coupled product. (2-methoxy-4-(trifluoromethyl)phenyl)boronic acid (0.407 g, 1.848 mmol), potassium carbonate (1.135 g, 8.21 mmol), PdCl$_2$(dppf)-CH$_2$Cl$_2$ adduct (0.168 g, 0.205 mmol), and 2 mL of water were added and the reaction mixture was heated to 80° C. overnight. LC/MS showed mostly product, so the reaction mixture was allowed to cool to room temperature. The aqueous layer was removed, and the organics were concentrated. Purification of the crude residue by silica gel column chromatography (0 to 100% EtOAc/heptane) gave 6-(benzylthio)-1-(2-methoxy-4-(trifluoromethyl)phenyl)phthalazine (0.340 g, 0.797 mmol, 38.8% yield). m/z (ESI) 427.2 (M+H)+

STEP 2: 1-(2-METHOXY-4-(TRIFLUOROMETHYL)PHENYL)PHTHALAZINE-6-SULFONYL CHLORIDE

A solution of 6-(benzylthio)-1-(2-methoxy-4-(trifluoromethyl)phenyl)phthalazine 2 (0.340 g, 0.797 mmol) in 20 mL of MeCN, 0.75 mL of acetic acid, and 0.5 mL of water (20/0.75/0.5 ratio) was cooled to 0° C. and was treated with 1,3-dichloro-5,5-dimethylimidazolidine-2,4-dione (0.314 g, 1.595 mmol). After stirring for one hour, LC/MS showed mostly product, so the reaction mixture was diluted with DCM and was treated with MgSO$_4$. After stirring for 10 minutes, the reaction mixture was filtered and concentrated. Purification of the crude residue by silica gel column chromatography (0 to 40% EtOAc/heptane) gave 1-(2-methoxy-4-(trifluoromethyl)phenyl)phthalazine-6-sulfonyl chloride (0.200 g, 0.497 mmol, 62.3% yield).

Intermediate CCCC

1-CHLORO-N-(5-FLUOROTHIAZOL-2-YL)-N-(4-METHOXYBENZYL)PHTHALAZINE-6-SULFONAMIDE

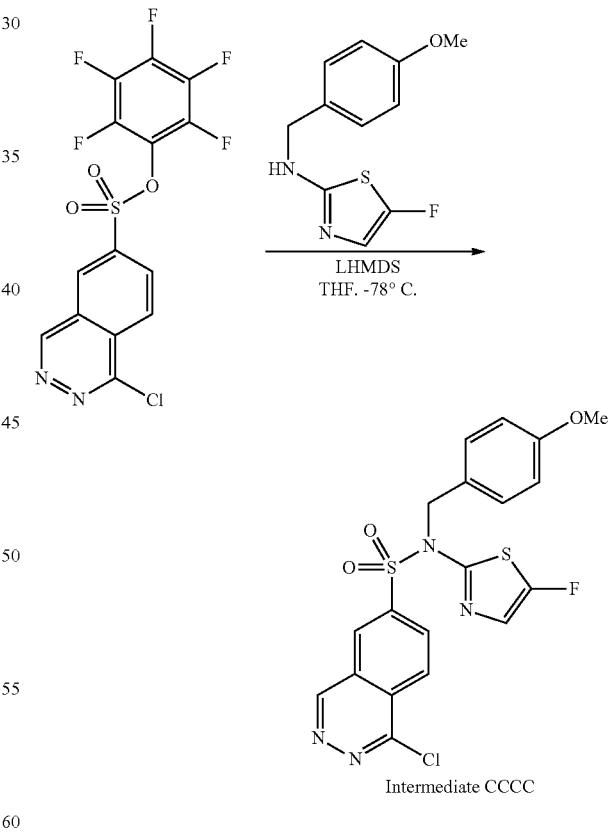

A round-bottom flask was charged with 5-fluoro-N-(4-methoxybenzyl)thiazol-2-amine (Intermediate MMM) (184 mg, 0.774 mmol) and THF (1 mL) to give a clear, light-orange solution. The flask was cooled in a dry ice-acetone bath for 5 min to give a suspension. Lithium bis(trimethylsilyl)amide (1M in THF) (774 µl, 0.774 mmol) was added drop wise to give a clay-colored suspension. The mixture was stirred for 15 min, after which time it was a solution. A solution of perfluorophenyl 1-chlorophthalazine-6-sulfonate (from Intermediate AAAA, Step 2; 265 mg, 0.645 mmol) in THF (1 mL with a 0.25 mL syringe/vial wash) was added drop wise. After 45 min, the mixture was diluted with saturated aq. ammonium chloride and extracted with EtOAc. The organic extract was dried over sodium sulfate, filtered, and concentrated. The residue was purified by chromatography on silica gel (40-g column, 20 to 70% EtOAc/Heptane) to give 1-chloro-N-(5-fluorothiazol-2-yl)-N-(4-methoxybenzyl)phthalazine-6-sulfonamide (129 mg, 0.277 mmol, 43.0% yield) as a cream-colored solid: m/z (ESI) 465.2 (M+H)$^+$.

Intermediate DDDD 4-(2-METHOXY-4-(TRIFLUOROMETHYL)PHENYL)QUINAZOLINE-7-SULFONYL CHLORIDE

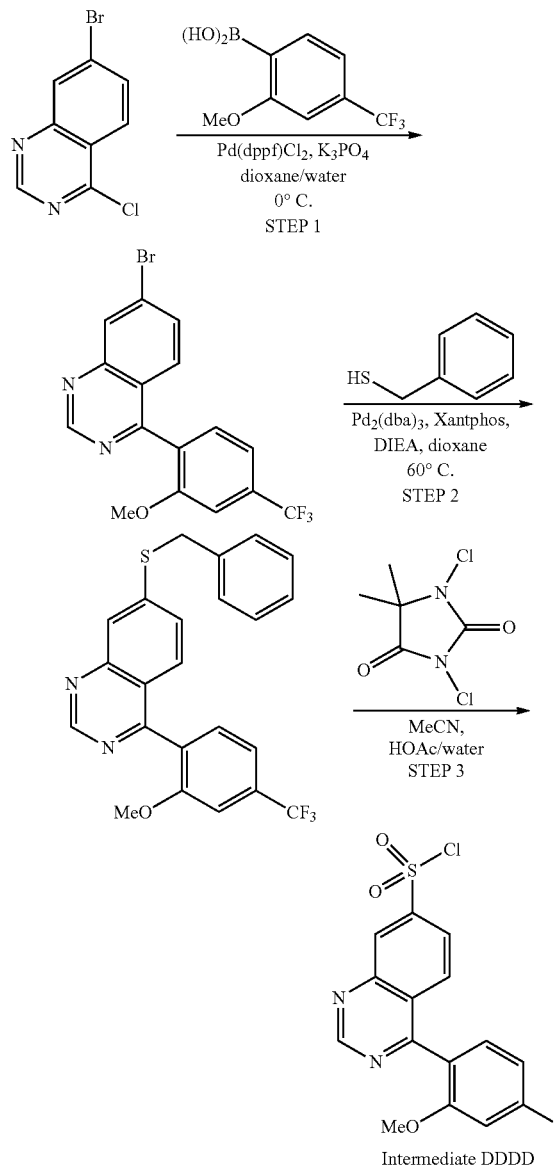

STEP 1: 7-BROMO-4-(2-METHOXY-4-(TRIFLUOROMETHYL)PHENYL)QUINAZOLINE

A solution of PdCl$_2$(dppf)-CH$_2$Cl$_2$ adduct (0.402 g, 0.493 mmol), 2-methoxy-4-(trifluoromethyl)phenyl)boronic acid (Combi-Blocks, San Diego, Calif.; 3.97 g, 18.07 mmol), 7-bromo-4-chloroquinazoline (Synnovator, Inc., Raleigh, N.C., 4.000 g, 16.43 mmol), and potassium phosphate (13.95 g, 65.7 mmol) in 33 mL of dioxane was cooled to 0° C., was treated with 11 mL of water and was allowed to stir for 30 minute then room temperature overnight. The reaction mixture was diluted with DCM and filtered through a plug of diatomaceous earth. The aqueous layer was removed and the organics concentrated to yield crude material which was carried forward without further purification. m/z (ESI) 384.9 (M+H)+

STEP 2: 7-(BENZYLTHIO)-4-(2-METHOXY-4-(TRIFLUOROMETHYL)PHENYL)QUINAZOLINE

Crude 7-bromo-4-(2-methoxy-4-(trifluoromethyl)phenyl)quinazoline was dissolved in 33 mL of dioxane, was treated with Pd$_2$(dba)$_3$ (0.376 g, 0.411 mmol), Xantphos (0.475 g, 0.821 mmol), and n,n-diisopropylethylamine (8.61 ml, 49.3 mmol), and was heated to 60° C. Benzyl mercaptan (1.943 ml, 16.43 mmol) was added, and the reaction mixture was allowed to stir for one hour at 60° C. The reaction mixture was concentrated and was purified by silica gel column chromatography (0 to 75% EtOAc/heptane) to yield 7-(benzylthio)-4-(2-methoxy-4-(trifluoromethyl)phenyl)quinazoline (4.616 g, 10.82 mmol, 65.9% yield) with minor impurities. m/z (ESI) 427.2 (M+H)$^+$.

STEP 3: 4-(2-METHOXY-4-(TRIFLUOROMETHYL)PHENYL)QUINAZOLINE-7-SULFONYL CHLORIDE

A solution of 7-(benzylthio)-4-(2-methoxy-4-(trifluoromethyl)phenyl)quinazoline (4.560 g, 10.69 mmol) in 44 mL of DCM and 0.44 mL of a 3:2 HOAc/water solution was cooled to 0° C. and was treated with 1,3-dichloro-5,5-dimethylimidazolidine-2,4-dione (4.21 g, 21.39 mmol). After stirring for 15 minutes, the reaction mixture was diluted with water. The layers were separated, and the organics were dried over MgSO$_4$ and concentrated. Purification of the crude residue by silica gel column chromatography gave 4-(2-methoxy-4-(trifluoromethyl)phenyl)quinazoline-7-sulfonyl chloride (2.475 g, 6.14 mmol, 57.5% yield) as a yellow solid. m/z (ESI) 402.9 (M+H)$^+$.

Intermediate EEEE 4-(4-(DIFLUOROMETHYL)-2-METHOXYPHENYL)QUINAZOLINE-7-SULFONYL CHLORIDE

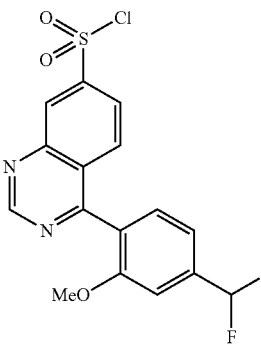

Intermediate EEEE was synthesized in a similar manner to Intermediate DDDD, using 2-(4-(difluoromethyl)-2-methoxyphenyl)-4,4,5,5-tetramethyl-1,3,2-dioxaborolane instead of 2-methoxy-4-(trifluoromethyl)phenyl)boronic acid in the first step. m/z (ESI) 385.2

Intermediate FFFF 4-(4-CHLORO-2-METHOXYPHENYL)QUINAZOLINE-7-SULFONYL CHLORIDE

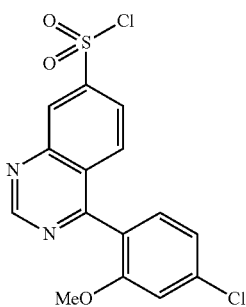 [SMILES: COc1cc(Cl)ccc1-c1ncnc2cc(S(=O)(=O)Cl)ccc12]

Intermediate FFFF was synthesized in a similar manner to Intermediate DDDD, using (4-chloro-2-methoxyphenyl)boronic acid instead of 2-methoxy-4-(trifluoromethyl)phenyl) boronic acid in the first step. m/z (ESI) 371.1

Intermediate GGGG

3-METHOXY-4-(4,4,5,5-TETRAMETHYL-1,3,2-DIOXABOROLAN-2-YL)BENZONITRILE

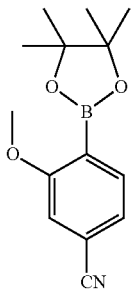

A solution of 4-bromo-3-methoxybenzonitrile (Combi-Blocks, San Diego, Calif., 2.500 g, 11.79 mmol) in 100 mL of diethyl ether was cooled to −78° C. and was treated with n-butyllithium (4.95 ml, 12.38 mmol). After stirring for 10 minutes, 2-isopropoxy-4,4,5,5-tetramethyl-1,3,2-dioxaborolane (3.07 ml, 16.51 mmol) was added, and the cooling bath was removed. After stirring for an additional 2 hours, LC/MS showed mostly product, so the reaction mixture was quenched with saturated NH₄Cl solution. After stirring for 20 minutes, the reaction mixture was poured into a separatory funnel charged with EtOAc. The organic layer was separated, dried over MgSO4 and concentrated. Purification of the crude residue by silica gel column chromatography (0 to 100% EtOAc/heptane) gave 3-methoxy-4-(4,4,5,5-tetramethyl-1,3,2-dioxaborolan-2-yl)benzonitrile (1.62 g, 6.25 mmol, 53.0% yield) with minor impurities. m/z (ESI) 260.1 (M+H)+

Intermediate HHHH 4-(4-CYANO-2-METHOXYPHENYL)QUINAZOLINE-7-SULFONYL CHLORIDE

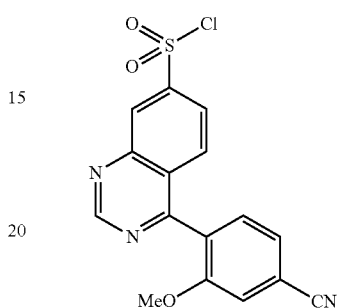

Intermediate HHHH was synthesized in a similar manner to Intermediate DDDD, using 3-methoxy-4-(4,4,5,5-tetramethyl-1,3,2-dioxaborolan-2-yl)benzonitrile (Intermediate GGGG) instead of 2-methoxy-4-(trifluoromethyl)phenyl) boronic acid in the first step. m/z (ESI) 360.0

Intermediate IIII 2-(5-CHLORO-4-(DIFLUOROMETHYL)-2-METHOXYPHENYL)-4,4,5,5-TETRAMETHYL-1,3,2-DIOXABOROLANE

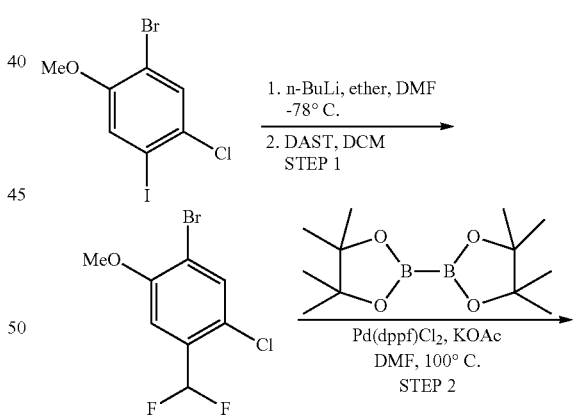

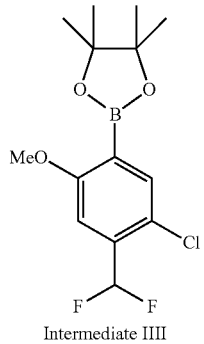

Intermediate IIII

STEP 1: 1-BROMO-5-CHLORO-4-(DIFLUOROM-ETHYL)-2-METHOXYBENZENE

A solution of 2-bromo-4-chloro-5-iodoanisole (3.50 g, 10.08 mmol) in 40 mL of diethyl ether was cooled to −78° C. and was treated with n-butyllithium (2.5M in hexanes; 4.23 ml, 10.58 mmol). After stirring for 10 minutes, the reaction mixture was quenched with DMF (1.560 ml, 20.15 mmol) and the cooling bath was removed. The reaction mixture was quenched with MeOH and saturated aqueous NH$_4$Cl solution. The reaction mixture was poured into water and extracted with DCM. The organics were dried over MgSO$_4$ and concentrated. The crude residue was dissolved in 10 mL of DCM and was treated with DAST (1.464 ml, 11.08 mmol). After stirring overnight, the reaction mixture was poured into saturated NaHCO$_3$ solution (aq) and was extracted with DCM. The organics were dried over MgSO$_4$ and concentrated. Purification of the crude residue by silica gel column chromatography (0 to 20% EtOAc/heptane) gave 1-bromo-5-chloro-4-(difluoromethyl)-2-methoxybenzene (1.55 g, 5.71 mmol, 56.7% yield).

STEP 2: 2-(5-CHLORO-4-(DIFLUOROMETHYL)-2-METHOXYPHENYL)-4,4,5,5-TETRAMETHYL-1,3,2-DIOXABOROLANE

A solution of PdCl$_2$(dppf)-CH$_2$Cl$_2$ adduct (0.466 g, 0.571 mmol), bis(pinacolato)diboron (2.175 g, 8.56 mmol), 1-bromo-5-chloro-4-(difluoromethyl)-2-methoxybenzene (1.550 g, 5.71 mmol), and potassium acetate (2.241 g, 22.84 mmol) in 6 ml of DMF was heated to 100° C. overnight. The reaction mixture was diluted with DCM, filtered through a plug of diatomaceous earth and concentrated under a vacuum. Purification of the crude residue by silica gel column chromatography (0 to 20% EtOAc/heptane) gave 2-(5-chloro-4-(difluoromethyl)-2-methoxyphenyl)-4,4,5,5-tetramethyl-1,3,2-dioxaborolane (0.630 g, 1.978 mmol, 34.6% yield). m/z (ESI) 237.0 (M+H)+

Intermediate JJJJ

4-(5-CHLORO-4-(DIFLUOROMETHYL)-2-METHOXYPHENYL)QUINAZOLINE-7-SULFONYL CHLORIDE

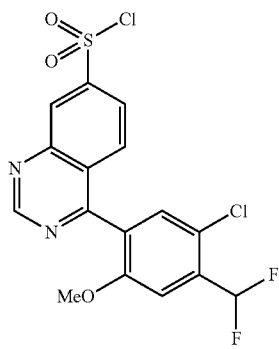 [SMILES: COc1cc(C(F)F)c(Cl)cc1-c1ncnc2cc(S(=O)(=O)Cl)ccc12]

Intermediate JJJJ was synthesized in a similar manner to Intermediate DDDD, using 2-(5-chloro-4-(difluoromethyl)-2-methoxyphenyl)-4,4,5,5-tetramethyl-1,3,2-dioxaborolane (Intermediate IIII) instead of 2-methoxy-4-(trifluoromethyl) phenyl)boronic acid in the first step. m/z (ESI) 459.0 (M+H)+

Intermediate KKKK 4-chloro-N-(2,4-dimethoxybenzyl)-N-(thiazol-2-yl) quinazoline-7-sulfonamide

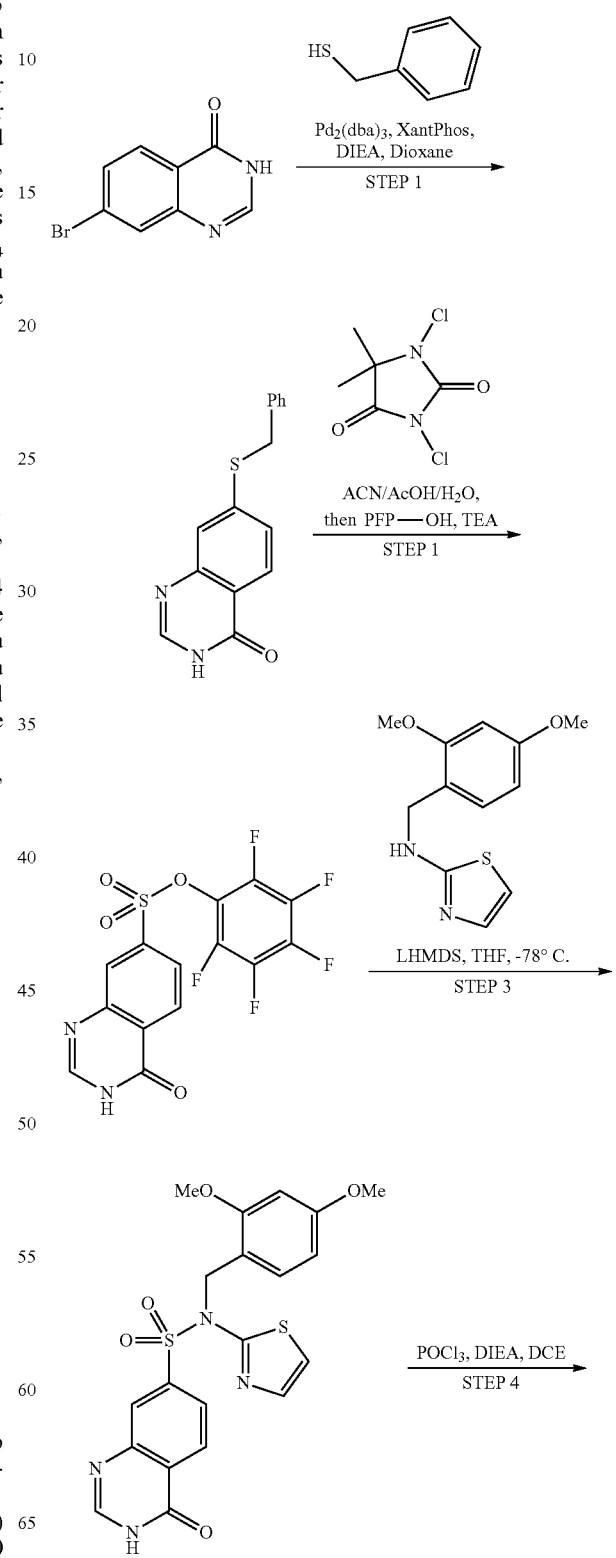

-continued

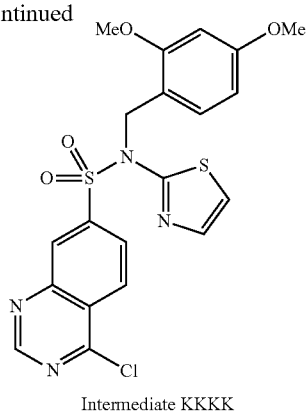

Intermediate KKKK

STEP 1: 7-(BENZYLTHIO)QUINAZOLIN-4(3H)-ONE

A round bottom flask was charged with 7-bromoquinazolin-4(3H)-one (10 g, 44.4 mmol), Xantphos (1.286 g, 2.222 mmol), and $Pd_2(dba)_3$ (1.017 g, 1.111 mmol). The flask was flushed with Ar (g), then dioxane (89 ml), benzyl mercaptan (5.52 ml, 46.7 mmol), and n,n-diisopropylethylamine (15.52 ml, 89 mmol) were added in sequence. The reaction was fitted with a reflux condenser, heated to 90° C., and stirred for one hour. The reaction was diluted with water and filtered. The solids were washed thoroughly with water, then air dried for several hours and triturated with ethyl acetate. After stirring overnight, the solids were filtered, washed with ethyl acetate, and vacuum dried over a nitrogen blanket overnight to afford 7-(benzylthio)quinazolin-4(3H)-one as a light yellow solid. (ESI) 269.1 $(M+H)^+$.

STEP 2: PERFLUOROPHENYL 4-OXO-3,4-DIHYDROQUINAZOLINE-7-SULFONATE

A round-bottom flask was charged with 7-(benzylthio) quinazolin-4(3H)-one (1.0 g, 3.73 mmol), acetonitrile (35.1 ml), acetic acid (1.315 ml), and water (0.877 ml) to give a thin suspension. The flask was cooled in an ice-bath for 10 min, then 1,3-dichloro-5,5-dimethylimidazolidine-2,4-dione (1.468 g, 7.45 mmol) was added in one portion, leading to a solution. The reaction was stirred for one hour. 2,3,4,5,6-pentafluorophenol (0.781 ml, 7.45 mmol) was added followed by drop wise addition of triethylamine (1.299 ml, 9.32 mmol). The reaction was stirred for 90 minutes. The reaction was concentrated, diluted with ethyl acetate and washed with water. The aqueous layer was extracted with ethyl acetate, and the combined organic layers were dried with sodium sulfate, filtered, and concentrated. The material was dissolved in DCM and loaded onto a silica gel cartridge, leaving a white solid on top. The solid was scraped out of the cartridge and set aside. The remaining material was purified via silica gel column chromatography (40 g, gradient elution 0 to 50% EtOAc:Heptane) and combined with the previously isolated material to afford perfluorophenyl 4-oxo-3,4-dihydroquinazoline-7-sulfonate as a white solid. (ESI) 393.0 $(M+H)^+$.

STEP 3: N-(2,4-DIMETHOXYBENZYL)-4-OXO-N-(THIAZOL-2-YL)-3,4-DIHYDROQUINAZOLINE-7-SULFONAMIDE

A solution of N-(2,4-dimethoxybenzyl)thiazol-2-amine (0.791 g, 3.16 mmol) in tetrahydrofuran (11.57 ml) was cooled in a dry ice-acetone bath for 5 min. Lithium bis (trimethylsilyl)amide (1M in THF) (3.31 ml, 3.31 mmol) was added drop wise, then the flask was removed from the cooling bath for 5 min. The flask was again cooled into a dry ice-acetone bath for 20 min, resulting in the formation of a thick slurry. A solution of perfluorophenyl 4-oxo-3,4-dihydroquinazoline-7-sulfonate (1.18, 3.01 mmol) in THF (12 mL) was added drop wise, and the reaction was stirred for 30 minutes. An additional equivalent of lithium bis(trimethylsilyl)amide (1M in THF) (3.31 ml, 3.31 mmol) was added and the reaction was stirred for 30 minutes. The reaction was warmed to room temperature and quenched with saturated ammonium chloride solution, diluted with ethyl acetate and washed with water. The aqueous layer was extracted three times with ethyl acetate, and the combined organic layers were dried with sodium sulfate, filtered, and concentrated. The material was dissolved in ethyl acetate and loaded onto a silica cartridge, leaving a tan solid on top. The solid was scraped out of the cartridge and set aside. The remaining material was purified by chromatography on a 40-g silica gel column with 0 to 100% EtOAc/Heptane followed by a 10% MeOH/DCM flush. The product containing fractions were concentrated and combined with the previously isolated material to afford N-(2,4-dimethoxybenzyl)-4-oxo-N-(thiazol-2-yl)-3,4-dihydroquinazoline-7-sulfonamide as a tan solid. (ESI) 481.1 $(M+Na)^+$.

STEP 4: 4-CHLORO-N-(2,4-DIMETHOXYBENZYL)-N-(THIAZOL-2-YL)QUINAZOLINE-7-SULFONAMIDE

N-(2,4-dimethoxybenzyl)-4-oxo-N-(thiazol-2-yl)-3,4-dihydroquinazoline-7-sulfonamide (0.990 g, 2.159 mmol) was dissolved in toluene (10.80 ml) and $POCl_3$ (0.403 ml, 4.32 mmol) was added. The reaction was stirred for 90 minutes at room temperature, then heated to 90° C. and stirred for four hours. The reaction was diluted with ethyl acetate and washed with saturated sodium bicarbonate solution. The aqueous layer was extracted twice with ethyl acetate, and the combined organic layers were dried with sodium sulfate, filtered, and concentrated to afford a brown oily solid. The solid was triturated in heptane, stirred for 30 minutes, and filtered. The resulting material was vacuum dried to afford crude 4-chloro-N-(2,4-dimethoxybenzyl)-N-(thiazol-2-yl) quinazoline-7-sulfonamide as a free flowing tan solid. (ESI) 499.1 $(M+Na)^+$.

Intermediate LLLL

4-CHLORO-N-(4-METHOXYBENZYL)-N-(THIAZOL-2-YL)QUINOLINE-7-SULFONAMIDE

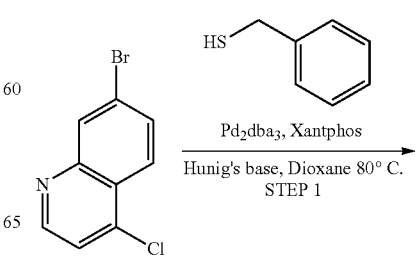

Pd$_2$dba$_3$, Xantphos
Hunig's base, Dioxane 80° C.
STEP 1

-continued

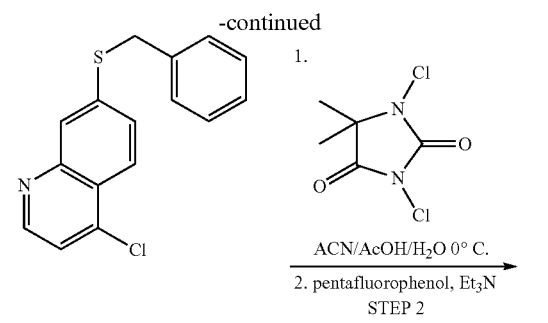

ACN/AcOH/H₂O 0° C.
2. pentafluorophenol, Et₃N
STEP 2

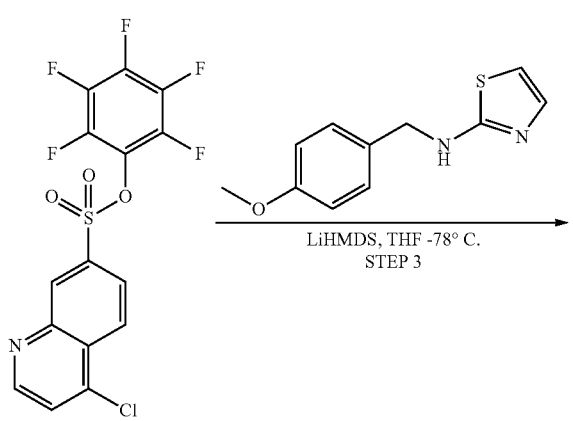

LiHMDS, THF -78° C.
STEP 3

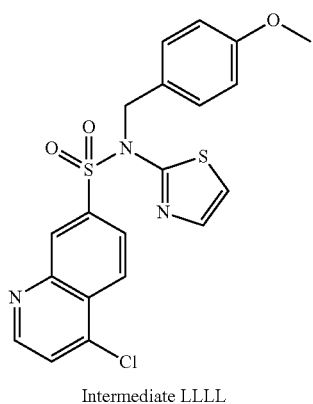

Intermediate LLLL

STEP 1: 7-(BENZYLTHIO)-4-CHLOROQUINOLINE

A 250-mL 3-neck round-bottom flask was charged with 7-bromo-4-chloroquinoline (BioBlocks, Inc., San Diego, Calif.; 7.000 g, 28.9 mmol), Xantphos (0.835 g, 1.443 mmol), and Pd₂(dba)₃ (0.661 g, 0.722 mmol), and after flushing with argon, dioxane (57.7 ml) and n,n-diisopropylethylamine (10.08 ml, 57.7 mmol) were added in sequence. The flask was fitted with a reflux condenser, and was placed in a heating bath at 80° C. for 10 minutes, after which benzyl mercaptan (3.58 ml, 30.3 mmol) was added drop wise via syringe. The reaction was stirred for 20 minutes until completion. The material was diluted with water, and washed with DCM (×3), and the combined organics were dried via phase separator (Radley's Technology) and concentrated under a vacuum. Upon dissolving the material in DCM, solids remained out of solution, and they were filtered off and washed with DCM. The corresponding filtrate was concentrated under a vacuum and purified via silica gel chromatography (120-g column) eluting with 0 to 100% ethyl acetate in heptanes to yield 7-(benzylthio)-4-chloroquinoline (7.35 g, 25.7 mmol, 89% yield) as a light yellow solid. m/z (ESI) 286.0 (M+H)⁺.

STEP 2: PERFLUOROPHENYL 4-CHLOROQUINOLINE-7-SULFONATE

A round-bottom flask was charged with 7-(benzylthio)-4-chloroquinoline (7.35 g, 25.7 mmol), acetonitrile (242 ml), acetic acid (9.08 ml), and water (6.05 ml), and after cooling the suspension in an ice bath for 10 minutes, 1,3-dichloro-5,5-dimethylimidazolidine-2,4-dione (10.13 g, 51.4 mmol) was added in one portion to form a heterogeneous solution. After 20 minutes, conversion to 4-chloroquinoline-7-sulfonyl chloride was observed, and 2,3,4,5,6-pentafluorophenol (9.47 g, 51.4 mmol) was added, followed by drop wise addition of triethylamine (8.96 ml, 64.3 mmol). After 40 minutes, the mixture was diluted with EtOAc (200 mL) and washed with water (2×200 mL) and brine, and then dried over sodium sulfate. After filtration and concentration under a vacuum, the material was purified via silica gel chromatography (120-g column) eluting with 0 to 35% ethyl acetate in heptane to yield perfluorophenyl 4-chloroquinoline-7-sulfonate (10.54 g, 25.7 mmol, 100% yield) as a light yellow oily solid. m/z (ESI) 410.1 (M+H)⁺.

STEP 3: 4-CHLORO-N-(4-METHOXYBENZYL)-N-(THIAZOL-2-YL)QUINOLINE-7-SULFONAMIDE

A solution of N-(4-methoxybenzyl)thiazol-2-amine (0.306 g, 1.389 mmol) in THF (5.29 ml) was cooled to −78° C. for 10 minutes, and lithium bis(trimethylsilyl)amide (1.0M solution in THF) (1.323 ml, 1.323 mmol) was added drop wise. The cold bath was removed for 5 minutes, and then the reaction vessel was re-cooled to −78° C. for 10 minutes. A solution of perfluorophenyl 4-chloroquinoline-7-sulfonate (0.542 g, 1.323 mmol) in THF (2.65 ml, 1.323 mmol) was added drop wise, and the reaction was stirred for 15 minutes until complete conversion to the desired product. After warming to RT, the reaction was quenched with sat. aq ammonium chloride solution, diluted with EtOAc (5 mL) and washed with water (10 mL×2). The combined organics were dried over sodium sulfate, filtered and concentrated. The material was then purified via silica gel chromatography (40-g column) eluting with 0 to 100% ethyl acetate in heptanes, to yield 4-chloro-N-(4-methoxybenzyl)-N-(thiazol-2-yl)quinoline-7-sulfonamide (0.481 g, 1.079 mmol, 82% yield) as a white solid. m/z (ESI) 446.1 (M+H)⁺.

Intermediate MMMM

4-CHLORO-N-(PYRIMIDIN-4-YL)QUINOLINE-7-SULFONAMIDE

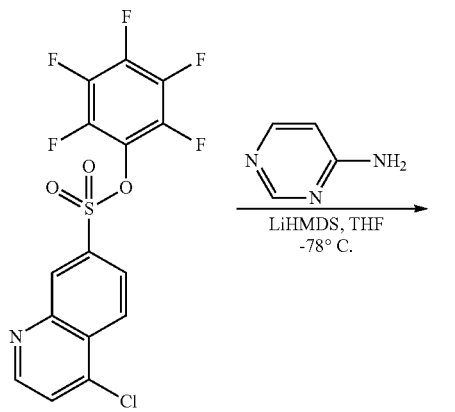

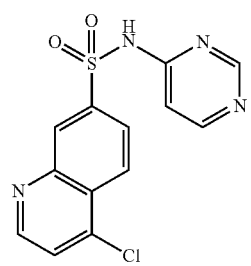

A flask containing a solution of 4-aminopyrimidine (0.026 g, 0.268 mmol) and perfluorophenyl 4-chloroquinoline-7-sulfonate (from Step 2, Intermediate LLLL; 0.100 g, 0.244 mmol) in THF (1.220 ml) was cooled to −78° C. for 10 minutes, and then lithium bis(trimethylsilyl)amide, 1.0 m solution in tetrahydrofuran (0.488 ml, 0.488 mmol) was added dropwise. After 20 minutes, the reaction had gone to completion. The reaction mixture was quenched with aq. ammonium chloride, and concentrated under a vacuum. A 2:1 mixture of DCM:H$_2$O was added, the flask sonicated, and the solids filtered to yield 4-chloro-N-(pyrimidin-4-yl) quinoline-7-sulfonamide (0.053 g, 0.165 mmol, 67.7% yield) as a light brown solid (carried forward crude). m/z (ESI) 321.0 (M+H)$^+$.

Intermediate NNNN

3-AMINO-4-(2-METHOXY-4-(TRIFLUOROMETHYL)PHENYL)-N-(4-METHOXYBENZYL)-N-(THIAZOL-2-YL)QUINOLINE-7-SULFONAMIDE

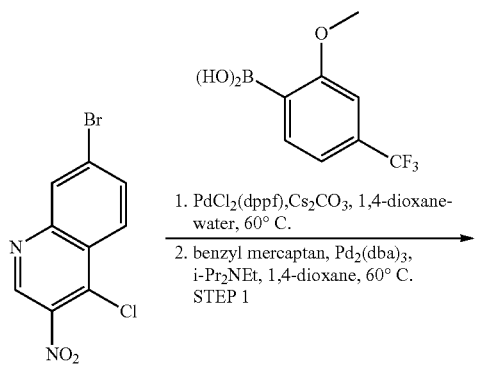

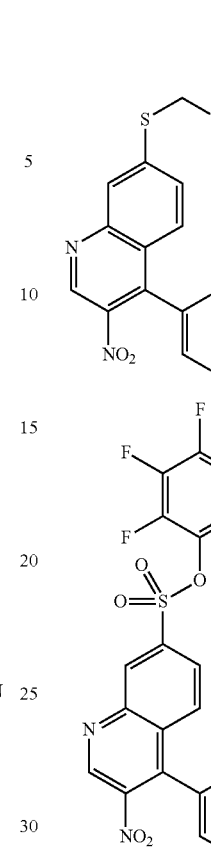

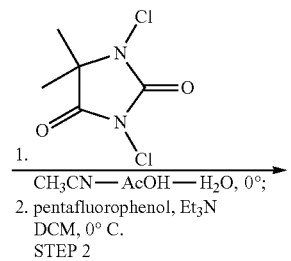

1. CH$_3$CN—AcOH—H$_2$O, 0°;
2. pentafluorophenol, Et$_3$N DCM, 0° C.
STEP 2

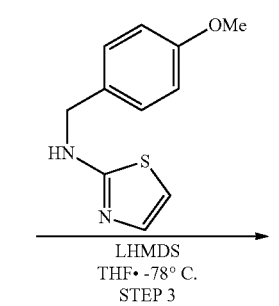

LHMDS
THF• -78° C.
STEP 3

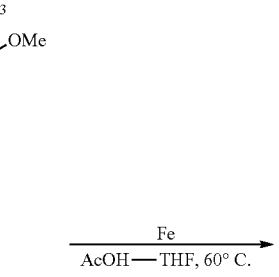

Fe
AcOH—THF, 60° C.
STEP 4

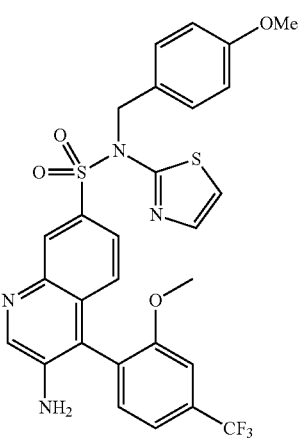

Intermediate NNNN

STEP 1: 7-(BENZYLTHIO)-4-(2-METHOXY-4-(TRIFLUOROMETHYL)PHENYL)-3-NITROQUINOLINE

A round-bottom flask was charged with 7-bromo-4-chloro-3-nitroquinoline (1.083 g, 3.77 mmol, from Capot Chemical, Zhejiang, China), (2-methoxy-4-(trifluoromethyl)phenyl)boronic acid (0.911 g, 4.14 mmol), potassium carbonate (1.562 g, 11.30 mmol), and $PdCl_2(dppf)$ (0.138 g, 0.188 mmol). The flask was flushed with Ar (g), then 1,4-dioxane (9.42 ml) and water (3.14 ml) were added. The flask was fitted with a reflux condenser and lowered into a 60° C. oil bath for 45 min. The mixture was diluted with water and extracted with EtOAc (2×). The combined organic extracts were dried over sodium sulfate, filtered, and concentrated. The residue was taken up in 1,4-dioxane (9.42 ml). Xantphos (0.109 g, 0.188 mmol), $Pd_2(dba)_3$ (0.086 g, 0.094 mmol), n,n-diisopropylethylamine (1.316 ml, 7.53 mmol), and benzyl mercaptan (0.490 ml, 4.14 mmol) were added in sequence. The reflux condenser was attached, and the flask was heated to 60° C. for 2 h. The mixture was cooled to room temperature, diluted with EtOAc, then filtered through diatomaceous earth. The filtrate was concentrated, and the residue was purified by chromatography on silica gel (40-g column, 25-g silica gel loading column, 0 to 40% EtOAc/Heptane) to give 7-(benzylthio)-4-(2-methoxy-4-(trifluoromethyl)phenyl)-3-nitroquinoline (1.4698 g, 3.12 mmol, 83% yield) as a yellow solid. NMR indicated a 70:30 mixutre of desired product to bis-coupling byproduct form the first step. m/z (ESI) 471.2 (M+H)+.

STEP 2: PERFLUOROPHENYL 4-(2-METHOXY-4-(TRIFLUOROMETHYL)PHENYL)-3-NITROQUINOLINE-7-SULFONATE

A round-bottom flask was charged with 7-(benzylthio)-4-(2-methoxy-4-(trifluoromethyl)phenyl)-3-nitroquinoline (1.4698 g, 2.343 mmol), acetonitrile (22.05 ml), acetic acid (0.827 ml), and water (0.551 ml) to give a clear, orange solution. The flask was cooled in an ice-water bath for 15 min to give a yellow suspension, then 1,3-dichloro-5,5-dimethylimidazolidine-2,4-dione (0.923 g, 4.69 mmol) was added in one portion, resulting in the formation of a clear solution within 20 s. After 25 min, 2,3,4,5,6-pentafluorophenol (0.647 g, 3.51 mmol) and triethylamine (1.306 ml, 9.37 mmol) were added in sequence. The mixture was stirred for 30 min, then diluted with EtOAc (50 mL) and washed with water (2×50 ml), washed with brine, dried over sodium sulfate, filtered, and concentrated. The residue was dissolved in DCM and purified by chromatography on silica gel (40-g column, 25-g silica gel loading column, 0 to 40% EtOAc/Heptane) to give 1.51 g of a yellow solid. NMR showed a 3:1 mix of desired product to bis-coupling byproduct from STEP 1. This equated to a product purity of 77 wt %. The material was used directly in the next step. m/z (ESI) 595.2 (M+H)+.

STEP 3: 4-(2-METHOXY-4-(TRIFLUOROMETHYL)PHENYL)-N-(4-METHOXYBENZYL)-3-NITRO-N-(THIAZOL-2-YL)QUINOLINE-7-SULFONAMIDE

A round-bottom flask was charged with N-(4-methoxybenzyl)thiazol-2-amine (0.353 g, 1.603 mmol) and THF (7.29 ml) to give an opaque solution. The flask was cooled in a dry ice-acetone bath for 5 min to give a milky suspension, then lithium bis(trimethylsilyl)amide (1M in THF) (1.603 ml, 1.603 mmol) was added. The flask was removed from the bath for 5 min to give a clear solution, then resubmerged. The mixture appeared to remain a solution. After 5 min, a solution of perfluorophenyl 4-(2-methoxy-4-(trifluoromethyl)phenyl)-3-nitroquinoline-7-sulfonate (1.125 g, 1.457 mmol) in THF (3 mL with a 2 mL wash) was added drop wise. The mixture was stirred for 45 min, then diluted with saturated aq. ammonium chloride solution and warmed to room temperature. The mixture was diluted with water and extracted with EtOAc (2×). The combined organic extracts were dried over sodium sulfate, filtered, and concentrated. The residue was purified by chromatography on silica gel (40-g column, 0 to 40% EtOAc/Heptane) to give 4-(2-methoxy-4-(trifluoromethyl)phenyl)-N-(4-methoxybenzyl)-3-nitro-N-(thiazol-2-yl)quinoline-7-sulfonamide (0.759 g, 1.204 mmol, 83% yield) as a yellow foam. m/z (ESI) 631.2 (M+H)+.

STEP 4: 3-AMINO-4-(2-METHOXY-4-(TRIFLUOROMETHYL)PHENYL)-N-(4-METHOXYBENZYL)-N-(THIAZOL-2-YL)QUINOLINE-7-SULFONAMIDE

A round-bottom flask was charged with 4-(2-methoxy-4-(trifluoromethyl)phenyl)-N-(4-methoxybenzyl)-3-nitro-N-(thiazol-2-yl)quinoline-7-sulfonamide (0.759 g, 1.204 mmol), THF (2.006 ml), and acetic acid (2.006 ml) to give a yellow solution. Iron (0.672 g, 12.04 mmol) powder was added, and the flask was fitted with a reflux condenser and placed in a 60° C. heating bath. The mixture was stirred for 50 min, then cooled to room temperature, diluted with THF, and filtered through diatomaceous earth with the aid of THF. The filtrate was concentrated. The residue was concentrated from DCM/heptane (2×), then concentrated from DCM to give 3-amino-4-(2-methoxy-4-(trifluoromethyl)phenyl)-N-(4-methoxybenzyl)-N-(thiazol-2-yl)quinoline-7-sulfonamide (0.714 g, 1.189 mmol, 99% yield) as a tan foam. m/z (ESI) 601.2 (M+H)+.

IntermediateS OOOO and PPPP

4-BROMO-N-(PYRIMIDIN-4-YL)ISOQUINOLINE-7-SULFONAMIDE and 4-BROMO-N-(4-METHOXYBENZYL)-N-(THIAZOL-2-YL)ISOQUINOLINE-7-SULFONAMIDE

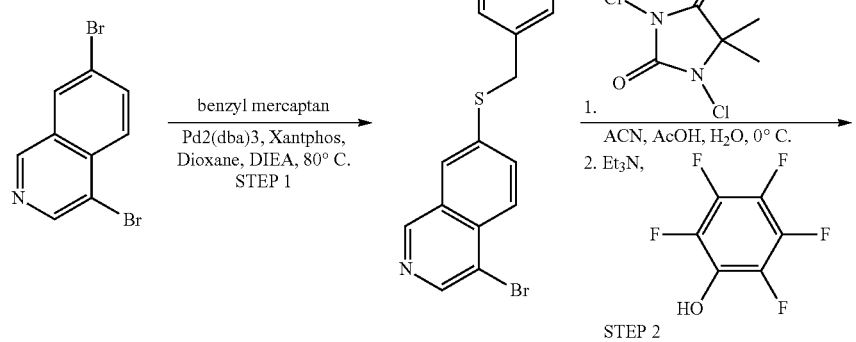

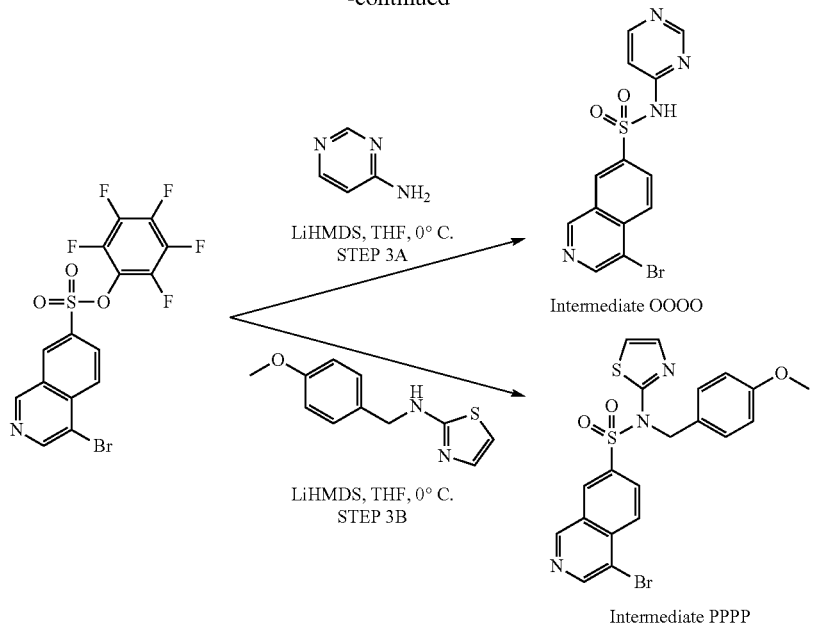

Intermediate OOOO

Intermediate PPPP

STEP 1: 7-(BENZYLTHIO)-4-BROMOISOQUINOLINE

To a vial charged with 4,7-dibromoisoquinoline (Pharmabridge, Inc., Doylestown, Pa.) (0.783 g, 2.73 mmol) was added dioxane (10.91 ml), DIEA (0.953 ml, 5.46 mmol), Xantphos (0.316 g, 0.546 mmol), $Pd_2(dba)_3$ (0.250 g, 0.273 mmol) and benzyl mercaptan (0.323 ml, 2.73 mmol). The vessel was sealed and heated to 60° C. for 4 hrs affording conversion to desired product as the primary species. The mixture was dried under reduced pressure and the crude material purified with a 40 HP silicycle column (SiliCycle, Inc. Quebec City, Canada) ramping EtOAc in heptane (0 to 25%, then isocratic at 25%, with 10% DCM isocratic throughout) providing product 7-(benzylthio)-4-bromoisoquinoline (0.573 g, 1.735 mmol, 63.6% yield), obtained as an orange solid. m/z (ESI) 330.2 $(M+H)^+$.

STEP 2: PERFLUOROPHENYL 4-BROMOISOQUINOLINE-7-SULFONATE

To a vial charged with 7-(benzylthio)-4-bromoisoquinoline (0.570 g, 1.726 mmol) was added acetonitrile (16.24 ml), acetic acid (0.609 ml), water (0.406 ml). The resulting solution was cooled in an ice water bath and 1,3-dichloro-5,5-dimethyl-2-imidazolidinedione (0.453 ml, 3.45 mmol) was added. After 1 hr LC/MS of the resulting solution indicated product, 4-bromoisoquinoline-7-sulfonyl chloride, as the primary species. m/z (ESI) 306.0 $(M+H)^+$. To the mixture was added 2,3,4,5,6-pentafluorophenol (0.361 ml, 3.45 mmol) and triethylamine (0.962 ml, 6.90 mmol) affording a yellow solution. After 45 min LC/MS indicated conversion to desired product (PFP ester). The mixture was diluted with EtOAc and extracted with $H_2O$. The aqueous phase was extracted with EtOAc. The combined organics were dried with $Na_2SO_4$, filtered, and dried under reduced pressure. The crude material was purified with a 40 g silicycle HP column (SiliCycle, Inc. Quebec City, Canada) ramping EtOAc in heptane (0-15%) providing product as a pale yellow oil, perfluorophenyl 4-bromoisoquinoline-7-sulfonate (0.618 g, 1.361 mmol, 79% yield). m/z (ESI) 454.1 $(M+H)^+$.

STEP 3A 4-BROMO-N-(PYRIMIDIN-4-YL)ISOQUINOLINE-7-SULFONAMIDE

To a flask containing ice cold suspension of pyrimidin-4-amine (0.402 g, 4.23 mmol) in THF (5.42 ml) was added lithium bis(trimethylsilyl)amide (1M in THF) (1.550 ml, 1.550 mmol) drop wise over 10 min. The mixture was stirred for 15 min providing a white suspension. A solution of perfluorophenyl 4-bromoisoquinoline-7-sulfonate (0.640 g, 1.409 mmol) in THF (5.0 ml) was added drop wise and the resulting mixture stirred for 1 hr. To the solution was added acetic acid (500 μl) and the solution dried under reduced pressure. The crude material was purified with a 40 g HP Silicycle column (SiliCycle, Inc. Quebec City, Canada) ramping EtOAc in heptane (0 to 25%) to elute starting material, then MeOH in DCM (0 to 20%) providing product which had coeluted with aminopyrimidine. The mixture was purified with a 10 g PE-AX column (Biotage AB, Uppsala, Sweden) washing with MeOH, then about 3% HCl in MeOH to provide 4-bromo-N-(pyrimidin-4-yl)isoquinoline-7-sulfonamide (Intermediate OOOO) (0.125 g, 0.342 mmol, 24.29% yield) as a white solid (possibly HCl salt). m/z (ESI) 365.1 $(M+H)^+$.

STEP 3B 4-BROMO-N-(4-METHOXYBENZYL)-N-(THIAZOL-2-YL)ISOQUINOLINE-7-SULFONAMIDE

To a flask charged with N-(4-methoxybenzyl)thiazol-2-amine (180 mg, 0.816 mmol) was added THF (3 ml) and the resulting mixture cooled in an ice water bath prior to the addition of lithium bis(trimethylsilyl)amide (1M in THF) (855 μl, 0.855 mmol). The resulting light brown solution was stirred for 15 min at 0° C. prior to the addition of a solution of perfluorophenyl 4-bromoisoquinoline-7-sulfonate (353 mg, 0.777 mmol) in THF (2 ml), followed by 1 ml THF wash. The resulting solution was allowed to stir and warm slowly to room temperature (ice melt). After 2 hr LC/MS indicated about 70% conversion fairly cleanly, with starting amine and PFP ester present (no change from 1 hr). The solution was cooled back to 0° C. and 0.5 eq LiHMDS (1 M) was added. After 1 hr LC/MS indicated complete consumption of starting material. To the mixture was added 400 μl acetic acid and the mixture was dried under reduced pressure and purified with a 40 g HP Silicycle column (SiliCycle, Inc. Quebec City, Canada) ramping EtOAc in heptane (0 to 50%, 10% DCM throughout) affording product as a white solid 4-bromo-N-(4-methoxybenzyl)-N-(thiazol-2-yl)isoquinoline-7-sulfonamide (Intermediate PPPP) (202 mg, 0.412 mmol, 53.0% yield). m/z (ESI) 490.0 (M+H)+.

Example 1 (Method 1)

1-(2-CYANO-5-METHOXY-3'-(TRIFLUOROM-ETHYL)-[1,1'-BIPHENYL]-4-YL)-N-(ISOXAZOL-3-YL)ISOQUINOLINE-6-SULFONAMIDE

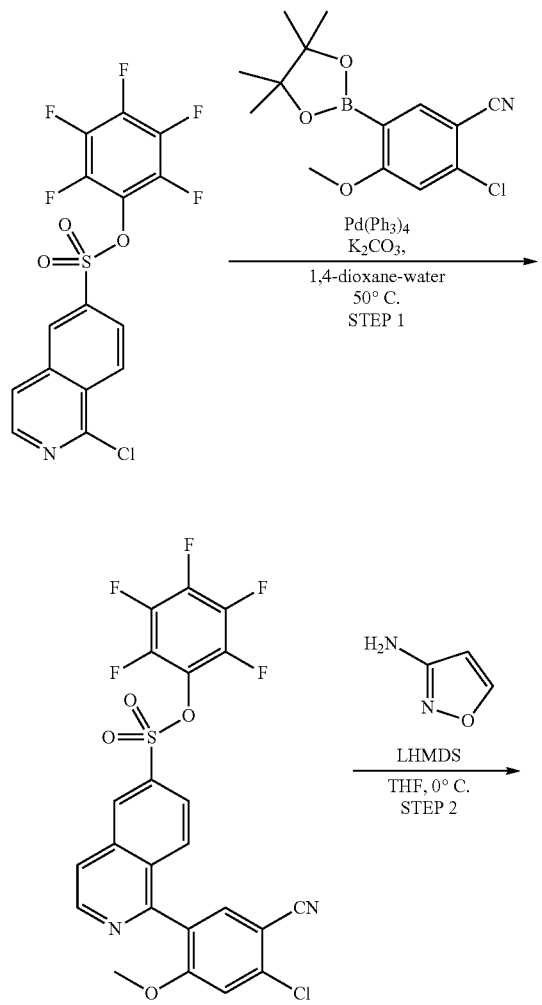

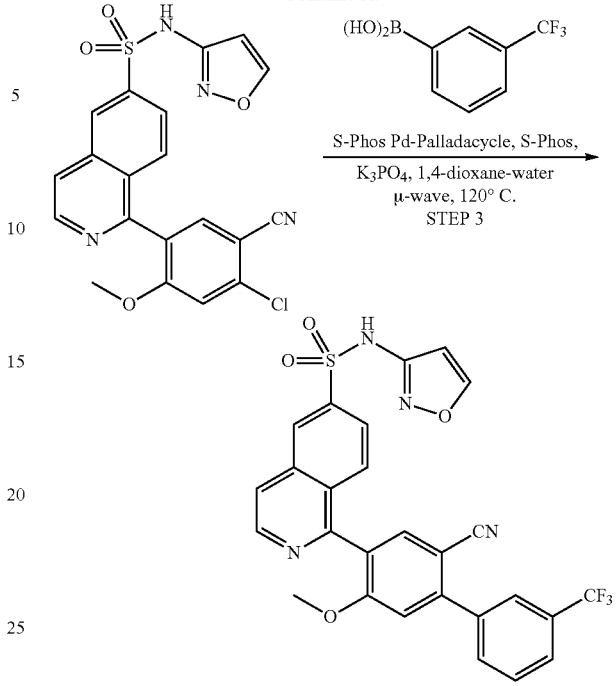

STEP 1: PERFLUOROPHENYL 1-(4-CHLORO-5-CYANO-2-METHOXYPHENYL)ISOQUINOLINE-6-SULFONATE

A RBF was charged with perfluorophenyl 1-chloroisoquinoline-6-sulfonate (7.734 g, 18.88 mmol), 2-chloro-4-methoxy-5-(4,4,5,5-tetramethyl-1,3,2-dioxaborolan-2-yl)benzonitrile (6.65 g, 22.65 mmol), potassium carbonate (7.83 g, 56.6 mmol), and tetrakistriphenylphosphinepalladium(0) (2.181 g, 1.888 mmol). The flask was flushed with Ar (g), then 1,4-dioxane (70.8 ml) and water (23.60 ml) were added. The flask was lowered into a 50° C. heating bath for 1 h. The mixture was diluted with water and EtOAc, and the organic layer was dried over sodium sulfate, filtered, and concentrated. The residue was purified by chromatography on silica gel (100-g Ultra SNAP column, with 5-50% EtOAc/Heptane) to give a light-yellow solid. The solid was taken up in heptane and filtered. The collected solid was washed with heptane (3×), dried under a stream of N₂ (g), then dried under vacuum to give perfluorophenyl 1-(4-chloro-5-cyano-2-methoxyphenyl)isoquinoline-6-sulfonate (7.0406 g, 13.02 mmol, 69.0% yield) as a light-yellow solid with an estimated purity (by LCMS) of 80%. The material was used without further purification. m/z (ESI) 541.1 (M+H)+.

STEP 2: 1-(4-CHLORO-5-CYANO-2-METHOXY-PHENYL)-N-(ISOXAZOL-3-YL)ISOQUINOLINE-6-SULFONAMIDE

A RBF was charged with perfluorophenyl 1-(4-chloro-5-cyano-2-methoxyphenyl)isoquinoline-6-sulfonate (4.0722 g, 7.53 mmol), THF (37.6 ml). isoxazol-3-amine (0.834 ml, 11.29 mmol) to give a clear solution. The flask was cooled in an ice-water bath for 10 min, then lithium bis(trimethylsilyl)amide (1M in THF) (18.82 ml, 18.82 mmol) was added. After 1 h, the mixture was diluted with 0.5 N aq. HCl (25 mL). The layers were separated, and the aq. layer was extracted with EtOAc. The organic layers were combined and washed with 0.5 N aq. HCl (100 mL). The aqueous layer was extracted with EtOAc (2×). The combined organic extracts were washed with brine, dried over sodium sulfate, filtered, and concentrated. The residue was purified by chromatography on silica gel (100-g Ultra SNAP column, 4% MeOH/DCM) to give 1-(4-chloro-5-cyano-2-methoxyphenyl)-N-(isoxazol-3-yl)isoquinoline-6-sulfonamide (2.8202 g, 6.40 mmol, 85% yield) as a light-yellow solid. m/z (ESI) 441.0 (M+H)$^+$.

STEP 3: 1-(2-CYANO-5-METHOXY-3'-(TRIFLUOROMETHYL)-[1,1'-BIPHENYL]-4-YL)-N-(ISOXAZOL-3-YL)ISOQUINOLINE-6-SULFONAMIDE

A vial was charged with 1-(4-chloro-5-cyano-2-methoxyphenyl)-N-(isoxazol-3-yl)isoquinoline-6-sulfonamide (183.3 mg, 0.416 mmol). (3-(trifluoromethyl)phenyl)boronic acid (197 mg, 1.039 mmol), chloro(2-dicyclohexylphosphino-2',6'-dimethoxy-1,1'-biphenyl)[2-(2-aminoethyl)phenyl)]palladium(ii) dichloromethane (15.75 mg, 0.021 mmol), and potassium phosphate (441 mg, 2.079 mmol). The vial was flushed with Ar (g), then 1,4-dioxane (1890 µl) and water (189 µl) were added. The vial was sealed and heated in a Biotage Initiator microwave reactor for 1 h at 120° C. The mixture was diluted with EtOAc and stirred for 1 h. The mixture was then filtered to give ca. 240 mg of an off-white solid. The solid was taken up in DMSO and filtered through a 0.2 micron filter. The filtrate was purified by reverse-phase HPLC (50-95% CH$_3$CN/H$_2$O with 0.1% TFA) over two runs. Fractions containing desired product were combined and concentrated. The material was concentrated from MeOH, then taken up in MeOH, sonicated, and filtered. The collected solid was washed with MeOH (2×), dried under a stream of N$_2$ (g), then dried under vacuum to give 1-(2-cyano-5-methoxy-3'-(trifluoromethyl)-[1,1'-biphenyl]-4-yl)-N-(isoxazol-3-yl)isoquinoline-6-sulfonamide (104 mg, 0.189 mmol, 45.4% yield) as an off-white solid. $^1$H NMR (400 MHz, DMSO-d$_6$) δ=11.95 (br. s., 1 H), 8.86-8.63 (m, 3 H), 8.20 (d, J=5.8 Hz, 1 H), 8.12-8.03 (m, 2 H), 7.99 (s, 1 H), 7.96-7.81 (m, 4 H), 7.51 (s, 1 H), 6.50 (d, J=1.6 Hz, 1 H), 3.82 (s, 3H). m/z (ESI) 551.2 (M+H)$^+$.

Example 2 (Method 2)

N-(ISOXAZOL-3-YL)-1-(2-METHOXY-[1,1'-BIPHENYL]-3-YL)ISOQUINOLINE-6-SULFONAMIDE

STEP 1: 1-CHLORO-N-(ISOXAZOL-3-YL)ISOQUINOLINE-6-SULFONAMIDE

A vial was charged with perfluorophenyl 1-chloroisoquinoline-6-sulfonate (1.29 g, 3.15 mmol), isoxazol-3-amine (0.244 ml, 3.31 mmol) and isoxazol-3-amine (0.244 ml, 3.31 mmol). The vial was flushed with Ar (g), then THF (15.74 ml) was added to give a clear solution. The flask was cooled in an ice-water bath for 10 min, then lithium bis(trimethylsilyl)amide (1M in THF) (6.61 ml, 6.61 mmol) was added. After 10 min, the mixture was quenched by the addition of 1N aq. HCl and extracted with EtOAc (3×). The combined organic extracts were dried over sodium sulfate, filtered, and concentrated. The residue was dissolved from MeOH/DCM, then taken up in DCM and filtered. The collected solid was washed with DCM (3×), then dried under a stream of N$_2$ (g) to give 1-chloro-N-(isoxazol-3-yl)isoquinoline-6-sulfonamide (730 mg, 2.357 mmol, 74.9% yield) as a light-yellow solid. m/z (ESI) 310.2 (M+H)$^+$.

STEP 2: N-(ISOXAZOL-3-YL)-1-(2-METHOXY-[1,1'-BIPHENYL]-3-YL)ISOQUINOLINE-6-SULFONAMIDE

A vial was charged with 1-chloro-N-(isoxazol-3-yl)isoquinoline-6-sulfonamide (77.91 mg, 0.252 mmol), (2-methoxy-[1,1'-biphenyl]-3-yl)boronic acid (86 mg, 0.377 mmol, Afferchem), potassium carbonate (104 mg, 0.755 mmol), and tetrakistriphenylphosphinepalladium(0) (14.53 mg, 0.013 mmol). The vial was flushed with Ar (g), then 1,4-dioxane (943 µl) and water (3140 were added. The vial was sealed and heated in a Biotage Initiator microwave reactor for 1 h at 100° C. LCMS showed clean desired product. The mixture was extracted with EtOAc (3×), then the combined organic extracts were concentrated. The residue was dissolved in DMSO, and the resulting solution was filtered through a 0.2 micron filter. The filtrate was purified (0.1% NH$_4$OH, CH$_3$CN in water, reverse-phase HPLC) to give N-(isoxazol-3-yl)-1-(2-methoxy-[1,1'-biphenyl]-3-yl) isoquinoline-6-sulfonamide (77 mg, 0.168 mmol, 66.9% yield) as an off-white solid. $^1$H NMR (500 MHz, DMSO-d$_6$) δ=8.64 (d, J=5.7 Hz, 1 H), 8.44 (s, 1 H), 8.32 (s, 1 H), 8.03 (d, J=5.7 Hz, 1 H), 7.89 (dd, J=1.5, 8.8 Hz, 1H), 7.77 (d, J=8.8 Hz, 1 H), 7.62 (d, J=7.6 Hz, 2 H), 7.53 (t, J=4.7 Hz, 1H), 7.47 (t, J=7.6 Hz, 2 H), 7.41-7.34 (m, 3 H), 2.95 (s, 3 H). m/z (ESI) 458.0 (M+H)$^+$.

Example 3 (Method 3)

1-(2-FLUORO-5-METHOXY-3'-(TRIFLUOROM-ETHYL)-[1,1'-BIPHENYL]-4-YL)-N-(ISOXAZOL-3-YL)PHTHALAZINE-6-SULFONAMIDE

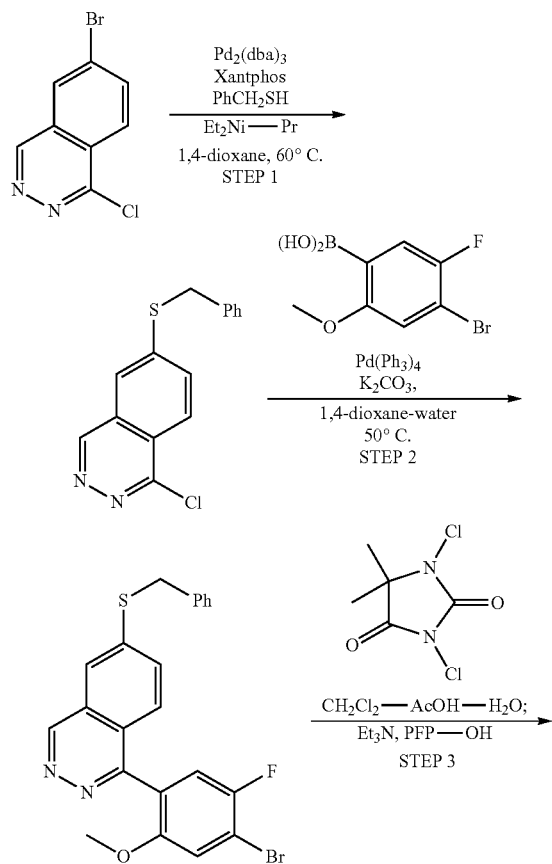

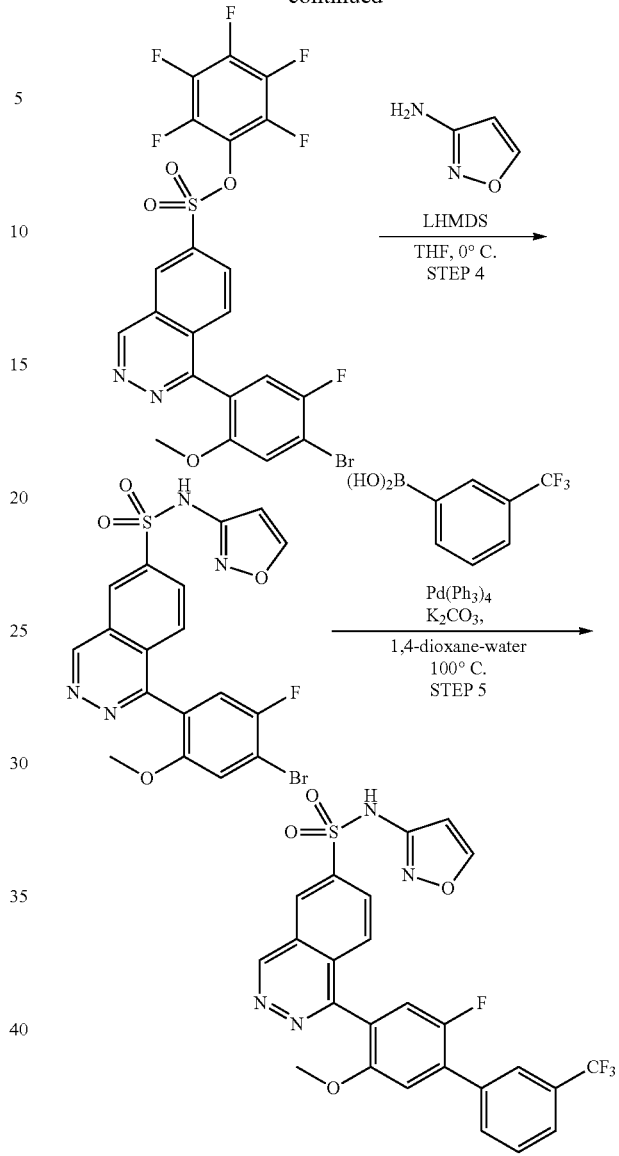

STEP 1:
6-(BENZYLTHIO)-1-CHLOROPHTHALAZINE

A two-neck RBF was charged with 6-bromo-1-chlorophthalazine (4.78 g, 19.63 mmol, Pharmablock), Xantphos (0.568 g, 0.982 mmol), and Pd$_2$(dba)$_3$ (0.449 g, 0.491 mmol). 1,4-dioxane (39.3 ml) and N,N-diisopropylethylamine (6.86 ml, 39.3 mmol) were added. The flask was fitted with a reflux condenser and placed in an 80° C. heating bath. After 5 min, benzyl mercaptan (2.438 ml, 20.61 mmol) was added over 30 s. After 30 min, the mixture was removed from the heating bath. The mixture was cooled, diluted with EtOAc, and washed with 1N aq. HCl. The aq. layer was extracted with EtOAc, and the combined organic extracts were dried over sodium sulfate, filtered, and concentrated. The residue was purified by chromatography on silica gel (100-g Ultra SNAP column, 50% EtOAc/Heptane). Fractions containing the product (including some mixed fractions) were combined and concentrated. The resulting solid was taken up in heptane and filtered. The collected solid was washed with heptane (2×), dried under a stream of N₂ (g), then dried under vacuum to give 6-(benzylthio)-1-chlorophthalazine (464 mg, 1.618 mmol, 8.24% yield) as a yellow solid. m/z (ESI) 287.1 (M+H)⁺.

STEP 2: 6-(BENZYLTHIO)-1-(4-BROMO-5-FLUORO-2-METHOXYPHENYL)PHTHALAZINE

A RBF was charged with 6-(benzylthio)-1-chlorophthalazine (808 mg, 2.82 mmol), (4-bromo-5-fluoro-2-methoxyphenyl)boronic acid (736 mg, 2.96 mmol), and tetrakistriphenylphosphinepalladium(0) (326 mg, 0.282 mmol). The flask was flushed with Ar (g), then 1,4-dioxane (1.06E+04 μl) and water (35220 were added in sequence. The flask was fitted with a reflux condenser and heated to 60° C. for 4 h. The mixture was diluted with water and extracted with EtOAc (3×). The combined organic extracts were dried over sodium sulfate, filtered, and concentrated. The residue was purified by chromatography on silica gel (40-g Redi-Sep Gold column, 25-g silica gel loading column, 20-70% EtOAc/Heptane) to give 6-(benzylthio)-1-(4-bromo-5-fluoro-2-methoxyphenyl)phthalazine (582 mg, 1.278 mmol, 45.4% yield) as a brown foam. m/z (ESI) 455.0 (M+H)⁺.

STEP 3: PERFLUOROPHENYL 1-(4-BROMO-5-FLUORO-2-METHOXYPHENYL)PHTHALAZINE-6-SULFONATE

A RBF was charged with 6-(benzylthio)-1-(4-bromo-5-fluoro-2-methoxyphenyl)phthalazine (0.587 g, 1.289 mmol), DCM (10.11 ml), acetic acid (0.379 ml), and water (0.253 ml) to give clear, yellow solution. The flask was cooled in an ice-water bath for 10 min, then 1,3-dichloro-5,5-dimethylimidazolidine-2,4-dione (0.521 g, 2.64 mmol) was added in one portion. After 15 min, an additional portion of oxidant (ca. 260 mg). After another 30 min, 2,3,4,5,6-pentafluorophenol (0.356 g, 1.934 mmol) and triethylamine (0.719 ml, 5.16 mmol) were added in sequence. The mixture was stirred for 20 min, then was diluted water, then extracted with DCM (3×). The combined organic extracts were dried over sodium sulfate, filtered, and concentrated. The residue was purified by chromatography on silica gel (40-g Redi-Sep Gold column, 25-g silica gel loading column, 0-50% EtOAc/Heptane) to give perfluorophenyl 1-(4-bromo-5-fluoro-2-methoxyphenyl)phthalazine-6-sulfonate (0.394 g, 0.680 mmol, 52.8% yield) as a yellow foam. m/z (ESI) 579.0 (M+H)+.

STEP 4: 1-(4-BROMO-5-FLUORO-2-METHOXYPHENYL)-N-(ISOXAZOL-3-YL)PHTHALAZINE-6-SULFONAMIDE

A RBF was charged with perfluorophenyl 1-(4-bromo-5-fluoro-2-methoxyphenyl)phthalazine-6-sulfonate (394 mg, 0.680 mmol), isoxazol-3-amine (57.8 μl, 0.782 mmol) and THF (6802 μl) to give a clear, orange solution. The flask was cooled in an ice-water bath for 10 min, then lithium bis(trimethylsilyl)amide (1M in THF) (1428 μl, 1.428 mmol) was added dropwise. After 20 min, the mixture was diluted with EtOAc, washed with 1N aq. HCl (2×), washed with brine, dried over sodium sulfate, filtered, and concentrated. The residue was purified by chromatography (12-g Redi-Sep Gold column, 0-5% MeOH/DCM) to give 1-(4-bromo-5-fluoro-2-methoxyphenyl)-N-(isoxazol-3-yl)phthalazine-6-sulfonamide (124 mg, 0.259 mmol, 38.0% yield) as a light-yellow solid. ¹H NMR (400 MHz, DMSO-d₆)=12.05 (br. s., 1 H), 9.97 (d, J=0.9 Hz, 1 H), 8.91-8.82 (m, 1 H), 8.76 (d, J=1.8 Hz, 1 H), 8.27 (dd, J=2.0, 8.8 Hz, 1 H), 7.93-7.87 (m, 1H), 7.61 (d, J=5.7 Hz, 1 H), 7.55 (d, J=8.6 Hz, 1 H), 6.49 (d, J=1.8 Hz, 1 H), 3.68 (s, 3 H). m/z (ESI) 579.0 (M+H)⁺.

STEP 5: 1-(2-FLUORO-5-METHOXY-3'-(TRIFLUOROMETHYL)-[1,1'-BIPHENYL]-4-YL)-N-(ISOXAZOL-3-YL)PHTHALAZINE-6-SULFONAMIDE

A vial was charged with 1-(4-bromo-5-fluoro-2-methoxyphenyl)-N-(isoxazol-3-yl)phthalazine-6-sulfonamide (70.3 mg, 0.147 mmol), potassium carbonate (60.8 mg, 0.440 mmol), 3-trifluoromethylboronic acid, (41.9 mg, 0.221 mmol) and tetrakistriphenylphosphinepalladium(0) (16.95 mg, 0.015 mmol). The vial was flushed with Ar (g), then 1,4-dioxane (550 μl) and water (183 μl) were added. The vial was heated to 100° C. in an oil bath for 5 h. LCMS showed only 5% conversion. The temperature was raised to 80° C. for 5 h. The mixture was diluted with water and brine, then extracted with EtOAc (3×). The combined organic extracts were concentrated. The residue was purified by chromatography on silica gel (12-g Redi-Sep Gold column, 0-3%, 3-6%, 6-10% MeOH/DCM) to give 1-(2-fluoro-5-methoxy-3'-(trifluoromethyl)-[1,1'-biphenyl]-4-yl)-N-(isoxazol-3-yl)phthalazine-6-sulfonamide (45.22 mg, 0.083 mmol, 56.6% yield) as an off-white solid. ¹H NMR (400 MHz, DMSO-d₆) δ=12.04 (br. s., 1 H), 9.97 (s, 1 H), 8.87 (d, J=1.5 Hz, 1H), 8.73 (d, J=1.5 Hz, 1 H), 8.30 (dd, J=1.9, 8.8 Hz, 1 H), 8.03 (br. s., 2 H), 7.93 (d, J=8.7 Hz, 1 H), 7.88-7.77 (m, 2 H), 7.52 (d, J=10.4 Hz, 1 H), 7.44 (d, J=6.3 Hz, 1 H), 6.48 (d, J=1.8 Hz, 1 H), 3.75 (s, 3 H). m/z (ESI) 545.0 (M+H)⁺.

Example 4 (Method 4)

1-(3',5'-DIFLUORO-3-(1-METHYL-1H-PYRAZOL-5-YL)-[1,1'-BIPHENYL]-4-YL)-N-(ISOXAZOL-3-YL)ISOQUINOLINE-6-SULFONAMIDE 2,2,2-TRIFLUOROACETATE

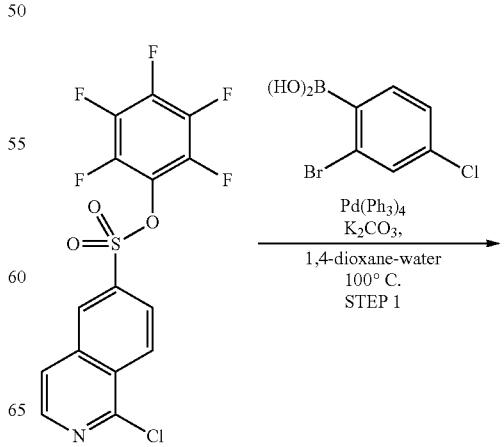

119
-continued

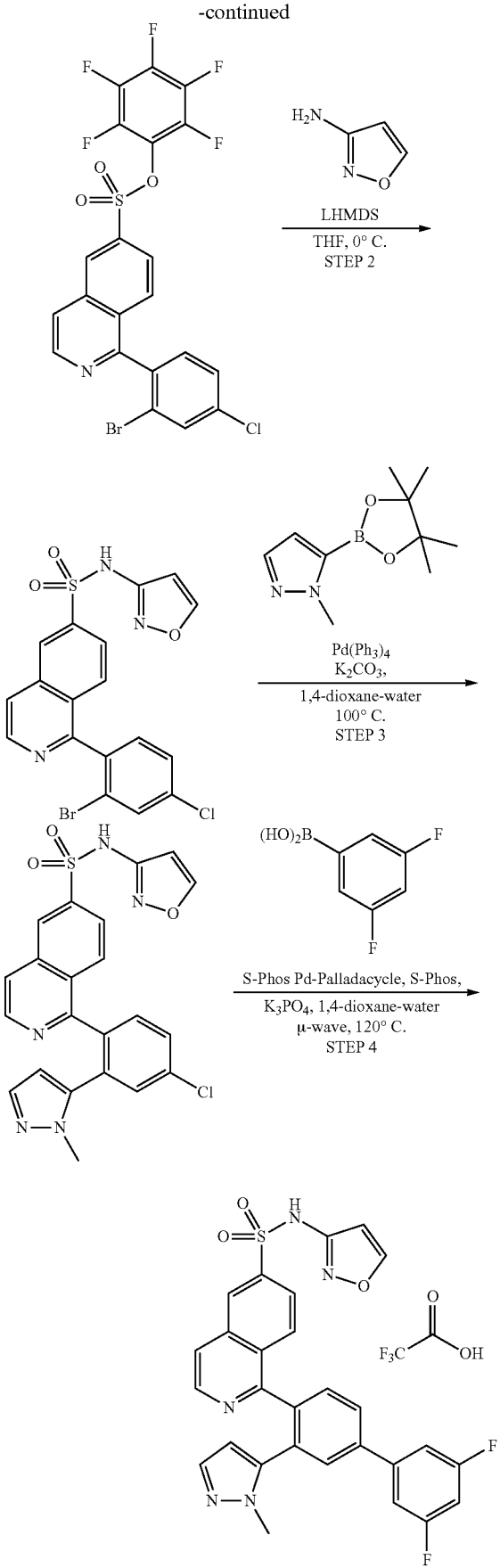

120

STEP 1: 1-(2-BROMO-4-CHLOROPHENYL)ISOQUINOLINE-6-SULFONATE

A RBF was charged with perfluorophenyl 1-chloroisoquinoline-6-sulfonate (1.57 g, 3.83 mmol), (2-bromo-4-chlorophenyl)boronic acid (1.082 g, 4.60 mmol). potassium carbonate (1.589 g, 11.50 mmol), and Pd(Ph$_3$P)$_4$ (0.443 g, 0.383 mmol). The flask was flushed with Ar (g), then 1,4-dioxane (14.37 ml) and water (4.79 ml) were added in sequence. The flask was fitted with a reflux condenser and heated to 50° C. After 1.5 h, the mixture was cooled and diluted with EtOAc. The layers were separated, and the aq. layer was extracted with EtOAc. The combined organic layers were dried over sodium sulfate, filtered, and concentrated. The residue was purified by chromatography on silica gel (40-g Redi-Sep Gold column, 25-g silica gel loading column, 10-50% EtOAc/Heptane with 10% DCM) to give perfluorophenyl 1-(2-bromo-4-chlorophenyl)isoquinoline-6-sulfonate (1.34 g, 2.373 mmol, 61.9% yield) as a white foam. Analysis of the material indicated it was 82% pure, and it was used without further purification. m/z (ESI) 563.9 (M+H)$^+$.

STEP 2: 1-(2-BROMO-4-CHLOROPHENYL)-N-(ISOXAZOL-3-YL)ISOQUINOLINE-6-SULFONAMIDE

A RBF was charged with perfluorophenyl 1-(2-bromo-4-chlorophenyl)isoquinoline-6-sulfonate (1.041 g, 1.843 mmol), isoxazol-3-amine (0.157 ml, 2.12 mmol) and THF (12.29 ml) to give a clear solution. The flask was cooled in an ice-water bath for 10 min, then lithium bis(trimethylsilyl) amide (1M in THF) (3.87 ml, 3.87 mmol) was added dropwise. After 20 min, the mixture was quenched by the addition of 1N aq. HCl, then warmed to room temperature. The mixture was extracted with EtOAc (3×), and the combined organic extracts were concentrated. The residue was purified by chromatography (40-g Redi-Sep Gold column, 25-g silica gel loading column, 0-4% MeOH/DCM) to give 1-(2-bromo-4-chlorophenyl)-N-(isoxazol-3-yl)isoquinoline-6-sulfonamide (829 mg, 1.784 mmol, 97% yield) as an off-white foam. m/z (ESI) 464.0 (M+H)+.

STEP 3: 1-(4-CHLORO-2-(1-METHYL-1H-PYRAZOL-5-YL)PHENYL)-N-(ISOXAZOL-3-YL)ISOQUINOLINE-6-SULFONAMIDE

A vial was charged with 1-(2-bromo-4-chlorophenyl)-N-(isoxazol-3-yl)isoquinoline-6-sulfonamide (308 mg, 0.663 mmol), 1-methyl-5-(4,4,5,5-tetramethyl-1,3,2-dioxaborolan-2-yl)-1H-pyrazole (207 mg, 0.994 mmol), potassium carbonate (275 mg, 1.988 mmol), and Pd(Ph$_3$P)$_4$ (0.077 g, 0.066 mmol). The vial was flushed with Ar (g), then 1,4-dioxane (1657 µl) and water (5520 were added. The vial was sealed and placed in a 100° C. heating bath overnight. In the morning, additional portions of boronic acid (ca. 300 mg), potassium carbonate (275 mg, 1.988 mmol), and Pd(Ph$_3$P)$_4$ (77 mg, 0.066 mmol) were added, and the vial was returned to the heat for 8 h. The mixture was diluted with water and extracted with EtOAc (3×). The combined organic extracts were dried over sodium sulfate, filtered, and concentrated. The reside was purified by chromatography on silica gel (40-g Redi-Sep Gold column, 25-g silica gel loading column, 10-60% of a 3:1 EtOAc/EtOH mixture in heptane, with 5% DCM as co-solvent) to give a solid. The solid was taken up in heptane and filtered. The collected solid was washed with heptane (4×), dried under a stream of N$_2$ (g) to give 1-(4-chloro-2-(1-methyl-1H-pyrazol-5-yl)phenyl)-N-(isoxazol-3-yl)isoquinoline-6-sulfonamide (72.5 mg, 0.156 mmol, 23.48% yield) as an off-white solid. m/z (ESI) 466.1 (M+H)⁺.

STEP 4: 1-(3',5'-DIFLUORO-3-(1-METHYL-1H-PYRAZOL-5-YL)-[1,1'-BIPHENYL]-4-YL)-N-(ISOXAZOL-3-YL)ISOQUINOLINE-6-SULFONAMIDE 2,2,2-TRIFLUOROACETATE

A vial was charged with 1-(4-chloro-2-(1-methyl-1H-pyrazol-5-yl)phenyl)-N-(isoxazol-3-yl)isoquinoline-6-sulfonamide (71.28 mg, 0.153 mmol), (3,5-difluorophenyl)boronic acid (48.3 mg, 0.306 mmol), chloro(2-dicyclohexylphosphino-2',6'-dimethoxy-1,1'-biphenyl)[2-(2-aminoethylphenyl)]palladium(ii) dichloromethane (5.79 mg, 7.65 µmol), and potassium phosphate (162 mg, 0.765 mmol). The vial was flushed with Ar (g), then 1,4-dioxane (695 µl) and water (69.50 were added. The vial was sealed and heated in a Biotage Initiator microwave reactor for 1 h at 120° C. The mixture was diluted with water and extracted with EtOAc (4×). The combined organic extracts were concentrated. The residue was taken up in MeOH/DMSO, then filtered through a 0.2 micron filter. The filtrate was purified by reverse-phase HPLC (35-80% CH₃CN/H₂O with 0.1% TFA). Fractions containing product were combined and concentrated, and the residue was concentrated from DCM to give 1-(3',5'-difluoro-3-(1-methyl-1H-pyrazol-5-yl)-[1,1'-biphenyl]-4-yl)-N-(isoxazol-3-yl)isoquinoline-6-sulfonamide 2,2,2-trifluoroacetate (17.76 mg, 0.027 mmol, 17.65% yield) as a light-yellow solid. ¹H NMR (400 MHz, DMSO-d₆)=11.86 (br. s., 1 H), 8.74 (d, J=1.8 Hz, 1 H), 8.66 (d, J=5.7 Hz, 1 H), 8.60 (d, J=1.5 Hz, 1 H), 8.10-7.99 (m, 3H), 7.89-7.78 (m, 2 H), 7.73-7.67 (m, 3 H), 7.31 (tt, J=2.3, 9.2 Hz, 1 H), 6.99 (d, J=1.9 Hz, 1 H), 6.44 (d, J=1.8 Hz, 1 H), 5.59 (d, J=1.9 Hz, 1 H), 3.64 (s, 3 H). m/z (ESI) 544.1 (M+H)⁺.

Example 5 (Method 5)

1-(3',5'-DIFLUORO-3-METHOXY-[1,1'-BIPHENYL]-4-YL)-N-(ISOTHIAZOL-3-YL)ISOQUINOLINE-6-SULFONAMIDE 2,2,2-TRIFLUOROACETATE

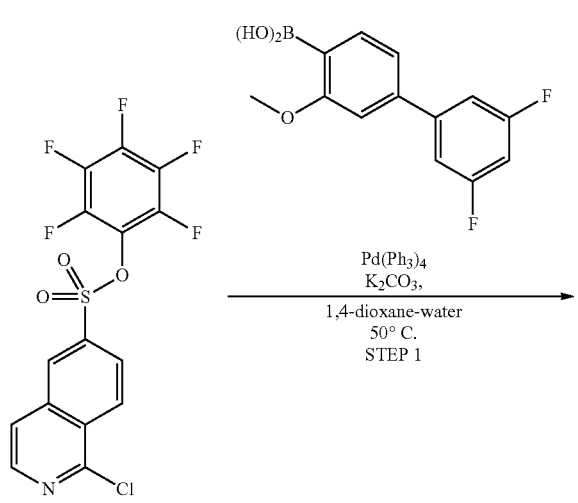

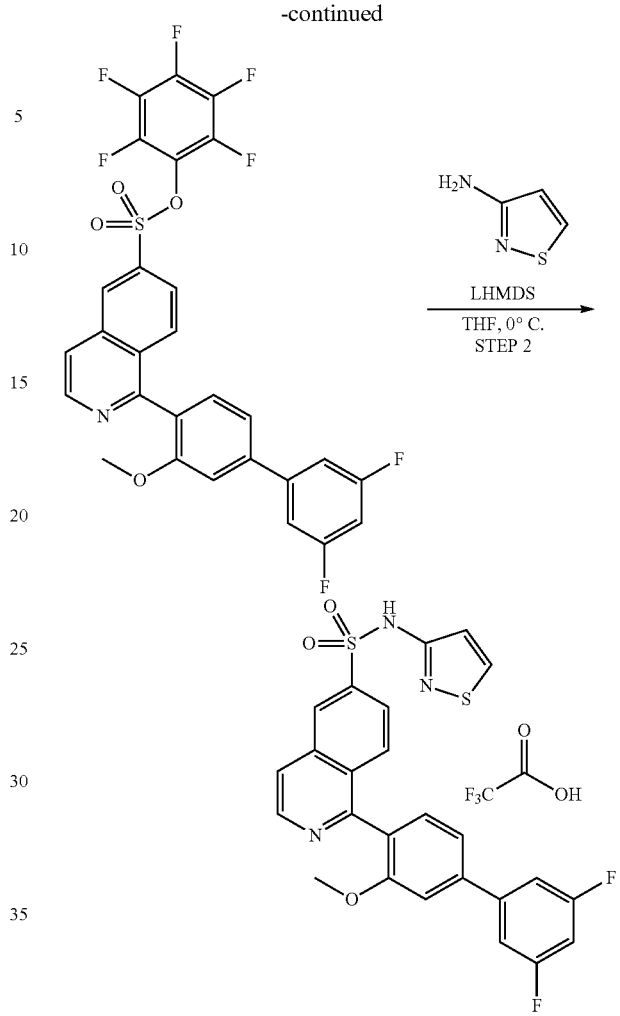

STEP 1: PERFLUOROPHENYL 1-(3',5'-DIFLUORO-3-METHOXY-[1,1'-BIPHENYL]-4-YL)ISOQUINOLINE-6-SULFONATE

A RBF was charged with perfluorophenyl 1-chloroisoquinoline-6-sulfonate (4.40 g, 10.74 mmol), (3',5'-difluoro-3-methoxy-[1,1'-biphenyl]-4-yl)boronic acid (3.40 g, 12.89 mmol), potassium carbonate (4.45 g, 32.2 mmol), and Pd(Ph₃P)₄ (1.241 g, 1.074 mmol). The flask was flushed with Ar (g), then 1,4-dioxane (40.3 ml) and water (13.42 ml) were added in sequence. The flask was fitted with a reflux condenser and lowered into a 50° C. heating bath for 1 h. The mixture was diluted with water and extracted with EtOAc (2×). The combined organic extracts were dried over sodium sulfate, filtered, and concentrated. The residue was purified by chromatography on silica gel (100-g SNAP Ultra column, 0-50% EtOAc/Heptane). Fractions containing the desired product were combined and concentrated to give perfluorophenyl 1-(3',5'-difluoro-3-methoxy-[1,1'-biphenyl]-4-yl)isoquinoline-6-sulfonate (4.179 g, 7.04 mmol, 65.6% yield) as an off-white solid. ¹H NMR (400 MHz, DMSO-d₆) δ=8.93 (d, J=1.6 Hz, 1 H), 8.84 (d, J=5.6 Hz, 1 H), 8.20 (d, J=5.7 Hz, 1 H), 8.07 (dd, J=1.9, 9.0 Hz, 1 H), 7.95 (d, J=8.9 Hz, 1 H), 7.70-7.62 (m, 2 H), 7.59-7.50 (m, 3 H), 7.36-7.27 (m, 1 H), 3.79 (s, 3 H). m/z (ESI) 594.0 (M+H)⁺.

STEP 2: 1-(3',5'-DIFLUORO-3-METHOXY-[1,1'-BIPHENYL]-4-YL)-N-(ISOTHIAZOL-3-YL)ISOQUINOLINE-6-SULFONAMIDE 2,2,2-TRIFLUOROACETATE

A vial was charged with perfluorophenyl 1-(3',5'-difluoro-3-methoxy-[1,1'-biphenyl]-4-yl)isoquinoline-6-sulfonate (98.51 mg, 0.166 mmol), isothiazol-3-amine (18.28 mg, 0.183 mmol), and THF (1.9 mL) to give a yellow mixture. The vial was cooled in an ice-water bath for 10 min, then lithium bis(trimethylsilyl)amide (1M in THF) (349 µl, 0.349 mmol) was added dropwise. After 40 min, the mixture was diluted with 1N aq. HCl and EtOAc. The layers were separated, and the organic layer was washed with water, washed with brine, dried over sodium sulfate, filtered, and concentrated. The residue was purified by chromatography on silica gel (12-g Redi-Sep Gold column, 0-4% MeOH/DCM) to give an impure oil. The oil was dissovled in MeOH, and the resulting solution was purified by reverse-phase HPLC (40-85% $CH_3CN/H_2O$ with 0.1% TFA). Fractions containing the desired product were combined and concentrated to give 1-(3',5'-difluoro-3-methoxy-[1,1'-biphenyl]-4-yl)-N-(isothiazol-3-yl)isoquinoline-6-sulfonamide 2,2,2-trifluoroacetate (61 mg, 0.098 mmol, 58.9% yield) as a yellow solid. $^1$H NMR (400 MHz, DMSO-$d_6$) δ=11.87 (s, 1 H), 8.93 (d, J=4.8 Hz, 1 H), 8.74 (d, J=5.8 Hz, 1 H), 8.71 (d, J=1.9 Hz, 1 H), 8.18 (d, J=5.3 Hz, 1 H), 7.97 (dd, J=1.9, 8.9 Hz, 1 H), 7.84 (d, J=8.9 Hz, 1 H), 7.64 (dd, J=2.2, 9.1 Hz, 2 H), 7.53 (s, 2 H), 7.48-7.44 (m, 1 H), 7.48-7.43 (m, 1 H), 7.31 (tt, J=2.2, 9.3 Hz, 1 H), 7.05 (d, J=4.8 Hz, 1 H), 3.77 (s, 3 H). m/z (ESI) 510.0 (M+H)+.

Example 6 (Method 6)

N-(ISOXAZOL-3-YL)-1-(3-METHOXY-3'-(TRIFLUOROMETHYL)-[1,1'-BIPHENYL]-4-YL)ISOQUINOLINE-6-SULFONAMIDE

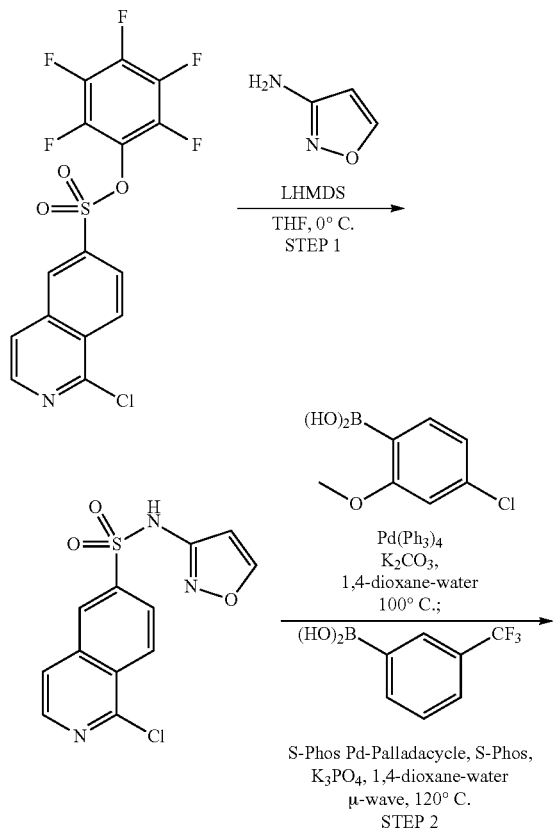

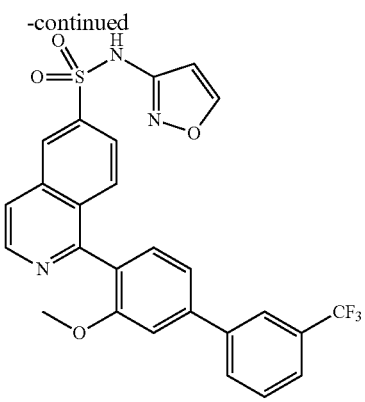

STEP 1: 1-CHLORO-N-(ISOXAZOL-3-YL)ISOQUINOLINE-6-SULFONAMIDE

A vial was charged with perfluorophenyl 1-chloroisoquinoline-6-sulfonate (1.29 g, 3.15 mmol), isoxazol-3-amine (0.244 ml, 3.31 mmol) and isoxazol-3-amine (0.244 ml, 3.31 mmol). The vial was flushed with Ar (g), then THF (15.74 ml) was added to give a clear solution. The flask was cooled in an ice-water bath for 10 min, then lithium bis(trimethylsilyl)amide (1M in THF) (6.61 ml, 6.61 mmol) was added. After 10 min, the mixture was quenched by the addition of 1N aq. HCl and extracted with EtOAc (3x). The combined organic extracts were dried over sodium sulfate, filtered, and concentrated. The residue was dissolved from MeOH/DCM, then taken up in DCM and filtered. The collected solid was washed with DCM (3x), then dried under a stream of $N_2$ (g) to give 1-chloro-N-(isoxazol-3-yl)isoquinoline-6-sulfonamide (730 mg, 2.357 mmol, 74.9% yield) as a light-yellow solid. m/z (ESI) 310.2 (M+H)$^+$.

STEP 2: N-(ISOXAZOL-3-YL)-1-(3-METHOXY-3'-(TRIFLUOROMETHYL)-[1,1'-BIPHENYL]-4-YL)ISOQUINOLINE-6-SULFONAMIDE

A vial was charged with 1-chloro-N-(isoxazol-3-yl)isoquinoline-6-sulfonamide (104.6 mg, 0.338 mmol), (4-chloro-2-methoxyphenyl)boronic acid (66.1 mg, 0.355 mmol), potassium carbonate (140 mg, 1.013 mmol), and Pd(Ph$_3$P)$_4$ (19.51 mg, 0.017 mmol). The vial was flushed with Ar (g), then 1,4-dioxane (1266 µl) and water (422 µl) were added. The vial was sealed and heated in a Biotage Initiator microwave reactor for 1 h at 100° C. (3-(trifluoromethyl)phenyl)boronic acid (141 mg, 0.743 mmol), S-Phos Precatalyst (12.79 mg, 0.017 mmol), dicyclohexyl (2',6'-dimethoxy-[1,1'-biphenyl]-2-yl)phosphine (6.93 mg, 0.017 mmol), and potassium phosphate (215 mg, 1.013 mmol) were added. The vial was heated in the microwave at 120° C. for 30 min. The mixture was diluted with EtOAc and washed with water (containing a small amount of brine), then washed with brine. This led to an emulsion, which was kept with the aq. layer. The aq. layer was extracted with EtOAc (2x), and the combined organic extracts were dried over sodium sulfate, filtered, and concentrated. The mixture was taken up in DMSO (2.5 mL) and filtered through a 0.45 micron filter (with 0.5 mL of a DMSO syringe-wash). The filtrate was purified by reverse-phase HPLC (with 0.1% NH₄OH, using CH₃CN in H₂O) to afford N-(isoxazol-3-yl)-1-(3-methoxy-3'-(trifluoromethyl)-[1,1'-biphenyl]-4-yl)isoquinoline-6-sulfonamide (66 mg, 0.126 mmol, 37.2% yield) as a light-yellow solid. $^1$H NMR (500 MHz, DMSO-d$_6$) δ=8.64 (d, J=5.7 Hz, 1 H), 8.46 (s, 1 H), 8.39 (s, 1 H), 8.17-8.09 (m, 2 H), 8.02 (d, J=5.7 Hz, 1 H), 7.86 (dd, J=1.4, 8.8 Hz, 1 H), 7.81-7.66 (m, 3 H), 7.58-7.39 (m, 3 H), 6.29 (s, 1 H), 3.78 (s, 3 H). m/z (ESI) 526.0 (M+H)+.

Example 7 (Method 7)

1-(2-CHLORO-3'-FLUORO-5-METHOXY-[1,1'-BIPHENYL]-4-YL)-N-(1,2,4-OXADIAZOL-3-YL)ISOQUINOLINE-6-SULFONAMIDE 2,2,2-TRIFLUOROACETATE

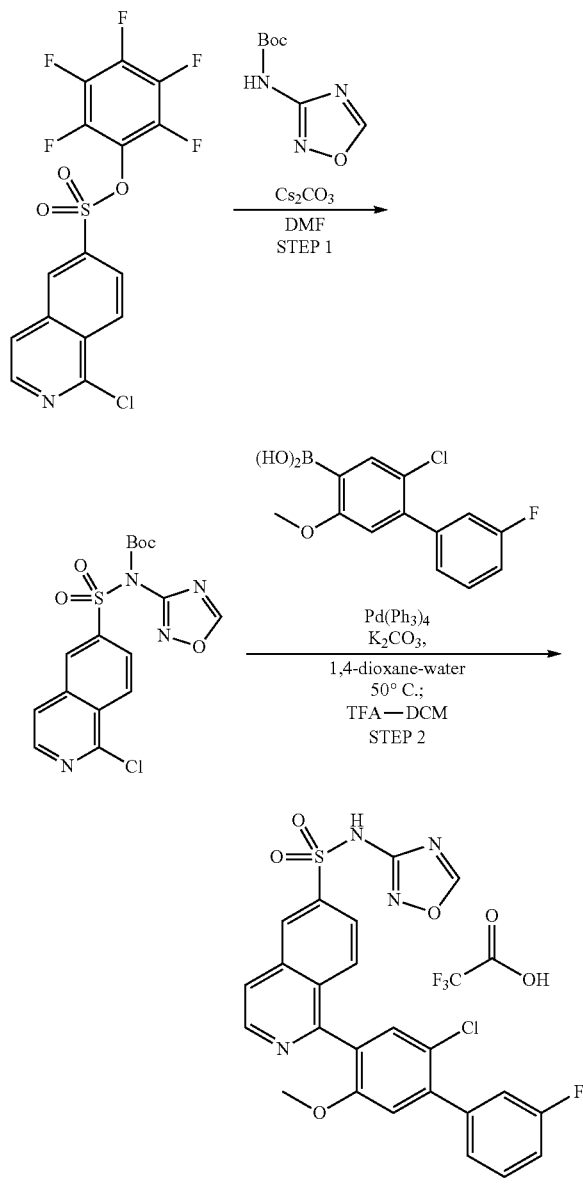

STEP 1: TERT-BUTYL (1-CHLOROISOQUINOLIN-6-YL)SULFONYL(1,2,4-OXADIAZOL-3-YL) CARBAMATE

A RBF was charged with perfluorophenyl 1-chloroisoquinoline-6-sulfonate (827.55 mg, 2.020 mmol), tert-butyl 1,2,4-oxadiazol-3-ylcarbamate (486 mg, 2.63 mmol, prepared according to J. Chem. Soc., Perkin Trans. 1. 1973, 47-51), and cesium carbonate (987 mg, 3.03 mmol). The flask was flushed with Ar (g), then DMF (1.01E+040 was added. After 2 h, the reaction mixture was diluted with EtOAc. The organic solution was washed with water (2×). The second wash required a small amount of brine to clear an emulsion. The organic layer was then dried over sodium sulfate, filtered, and concentrated. The residue was then taken up in EtOAc, sonicated, and filtered. The collected solid was washed with EtOAc (2×), dried under a stream of N$_2$ (g), then dried under vacuum to give tert-butyl chloroisoquinolin-6-yl)sulfonyl(1,2,4-oxadiazol-3-yl)carbamate (419 mg, 1.020 mmol, 50.5% yield) as a white solid. $^1$H NMR (400 MHz, DMSO-d$_6$)=9.98 (s, 1 H), 8.97 (d, J=2.0 Hz, 1 H), 8.68 (d, J=9.0 Hz, 1 H), 8.57 (d, J=5.7 Hz, 1 H), 8.34-8.27 (m, 2 H), 1.23 (s, 9H). m/z (ESI) 411.0 (M+H)⁺.

STEP 2: 1-(2-CHLORO-3'-FLUORO-5-METHOXY-[1,1'-BIPHENYL]-4-YL)-N-(1,2,4-OXADIAZOL-3-YL)ISOQUINOLINE-6-SULFONAMIDE 2,2,2-TRIFLUOROACETATE

A vial was charged with tert-butyl(1-chloroisoquinolin-6-yl)sulfonyl(1,2,4-oxadiazol-3-yl)carbamate (91.83 mg, 0.224 mmol). (2-chloro-3'-fluoro-5-methoxy-[1,1'-biphenyl]-4-yl)boronic acid (88 mg, 0.313 mmol), potassium carbonate (93 mg, 0.671 mmol), and Pd(Ph₃P)₄ (25.8 mg, 0.022 mmol). The vial was flushed with Ar (g), then 1,4-dioxane (838 µl) and water (2790 were added. The vial was heated to 50° C. in a Biotage Initiator microwave reactor for 2 h. The layers were separated (via pipette), and the aq. layer was extracted with EtOAc (3×). The combined organic extracts were concentrated. The residue was dissolved in DCM (1 mL) and TFA (0.5 mL). After 3 h of stirring, the mixture was concentrated. The residue was dissolved in MeOH, and the resulting solution was purified by reverse-phase HPLC (40-85% CH₃CN/H₂O with 0.1% TFA). The fractions containing product were combined and concentrated. The residue was concentrated from DCM (2×), then the resulting yellow solid was taken up in DCM, sonicated, and filtered. The collected solid was washed with DCM (4×), dried under a stream of N₂ (g), and dried under vacuum to give 1-(2-chloro-3'-fluoro-5-methoxy-[1,1'-biphenyl]-4-yl)-N-(1,2,4-oxadiazol-3-yl)isoquinoline-6-sulfonamide 2,2,2-trifluoroacetate (74 mg, 0.118 mmol, 53.0% yield) as a yellow solid. $^1$H NMR (400 MHz, DMSO-d$_6$) δ=9.36 (s, 1 H), 8.81-8.69 (m, 2 H), 8.23 (d, J=5.6 Hz, 1 H), 8.03 (dd, J=1.9, 8.9 Hz, 1 H), 7.92 (d, J=9.0 Hz, 1 H), 7.64-7.53 (m, 2 H), 7.49-7.40 (m, 2 H), 7.36-7.27 (m, 2 H), 3.71 (s, 3 H). m/z (ESI) 511.1 (M+H)⁺.

Example 8 (Method 8)

1-(3',5'-DIFLUORO-3-METHOXY-[1,1'-BIPHENYL]-4-YL)-N-(5-METHOXY-1,3,4-THIADIAZOL-2-YL)ISOQUINOLINE-6-SULFONAMIDE

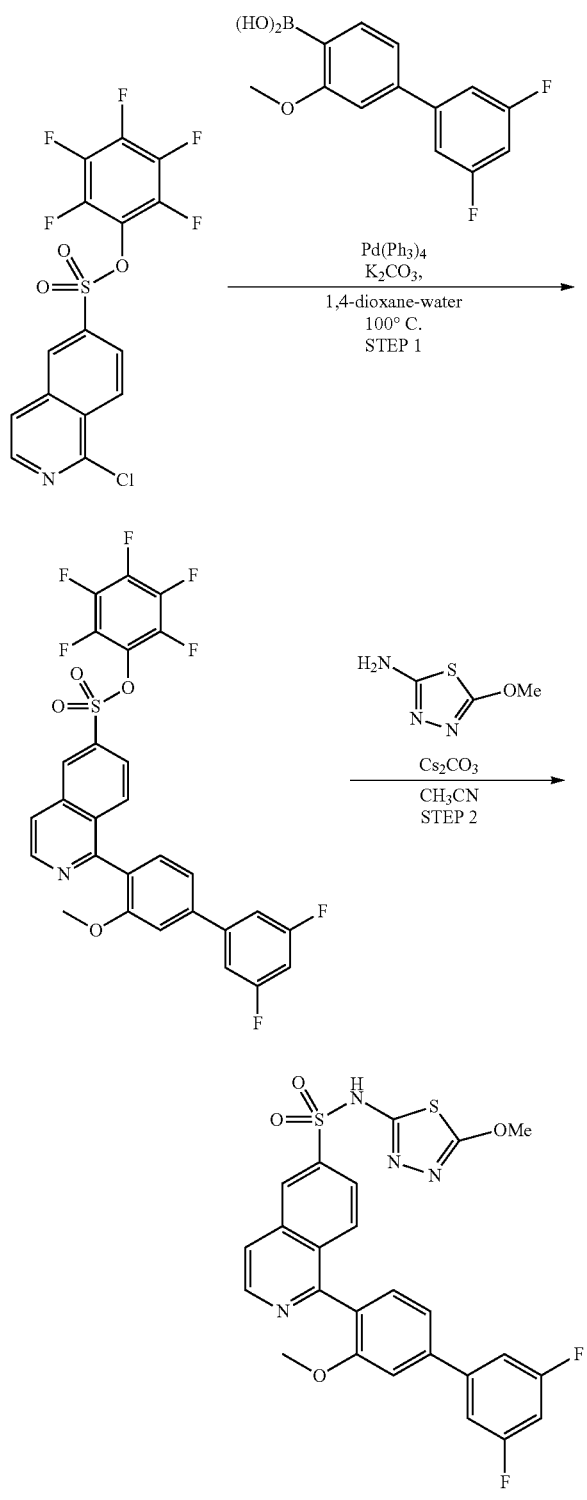 [SMILES: O=S(=O)(Oc1c(F)c(F)c(F)c(F)c1F)c1ccc2c(Cl)nccc2c1 ; COc1cc(-c2cc(F)cc(F)c2)ccc1B(O)O ; COc1cc(-c2cc(F)cc(F)c2)ccc1-c1nccc2cc(S(=O)(=O)Oc3c(F)c(F)c(F)c(F)c3F)ccc12 ; "Cs2CO3" ; COc1nnc(N)s1 ; COc1nnc(NS(=O)(=O)c2ccc3c(-c4ccc(-c5cc(F)cc(F)c5)cc4OC)nccc3c2)s1]

STEP 1: PERFLUOROPHENYL 1-(3',5'-DIFLUORO-3-METHOXY-[1,1'-BIPHENYL]-4-YL)ISOQUINOLINE-6-SULFONATE

A RBF was charged with perfluorophenyl 1-chloroisoquinoline-6-sulfonate (4.40 g, 10.74 mmol), (3',5'-difluoro-3-methoxy-[1,1'-biphenyl]-4-yl)boronic acid (3.40 g, 12.89 mmol), potassium carbonate (4.45 g, 32.2 mmol), and Pd(Ph$_3$P)$_4$ (1.241 g, 1.074 mmol). The flask was flushed with Ar (g), then 1,4-dioxane (40.3 ml) and water (13.42 ml) were added in sequence. The flask was fitted with a reflux condenser and lowered into a 50° C. heating bath for 1 h. The mixture was diluted with water and extracted with EtOAc (2×). The combined organic extracts were dried over sodium sulfate, filtered, and concentrated. The residue was purified by chromatography on silica gel (100-g SNAP Ultra column, 0-50% EtOAc/Heptane). The fractions containing the desired product were combined and concentrated to give perfluorophenyl 1-(3',5'-difluoro-3-methoxy-[1,1'-biphenyl]-4-yl)isoquinoline-6-sulfonate (4.179 g, 7.04 mmol, 65.6% yield) as an off-white solid. $^1$H NMR (400 MHz, DMSO-d$_6$)=8.93 (d, J=1.6 Hz, 1 H), 8.84 (d, J=5.6 Hz, 1 H), 8.20 (d, J=5.7 Hz, 1 H), 8.07 (dd, J=1.9, 9.0 Hz, 1 H), 7.95 (d, J=8.9 Hz, 1 H), 7.70-7.62 (m, 2 H), 7.59-7.50 (m, 3 H), 7.36-7.27 (m, 1 H), 3.79 (s, 3 H). m/z (ESI) 594.0 (M+H)$^+$.

STEP 2: 1-(3',5'-DIFLUORO-3-METHOXY-[1,1'-BIPHENYL]-4-YL)-N-(5-METHOXY-1,3,4-THIADIAZOL-2-YL)ISOQUINOLINE-6-SULFONAMIDE

A vial was charged with perfluorophenyl 1-(3',5'-difluoro-3-methoxy-[1,1'-biphenyl]-4-yl)isoquinoline-6-sulfonate (48.45 mg, 0.082 mmol). 5-methoxy-1,3,4-thiadiazol-2-amine (11.78 mg, 0.090 mmol, Chembridge), and cesium carbonate (80 mg, 0.245 mmol). The vial was flushed with Ar (g), then acetonitrile (408 μl) was added. LCMS after 2 hrs showed about 50% conversion to the desired product. LCMS after 16 hrs showed fairly clean desired product. The mixture was diluted with 0.5 N aq. HCl and water, then extracted with EtOAc (2×). The combined organic extracts were dried over sodium sulfate, filtered, and concentrated. The residue was purified by chromatography Amyon silica gel (12-g Redi-Sep Gold column, 0-10% MeOH/DCM) to give 1-(3',5'-difluoro-3-methoxy-[1,1'-biphenyl]-4-yl)-N-(5-methoxy-1,3,4-thiadiazol-2-yl)isoquinoline-6-sulfonamide (38.91 mg, 0.072 mmol, 88% yield) as a tan solid. $^1$H NMR (400 MHz, DMSO-d$_6$) δ=13.91-13.34 (m, 1 H), 8.71 (d, J=5.7 Hz, 1 H), 8.55 (d, J=1.9 Hz, 1 H), 8.11 (d, J=5.3 Hz, 1 H), 7.92-7.84 (m, 1 H), 7.78 (d, J=8.9 Hz, 1 H), 7.68-7.60 (m, 2 H), 7.57-7.49 (m, 2 H), 7.46-7.41 (m, 1 H), 7.30 (tt, J=2.3, 9.3 Hz, 1 H), 4.01 (s, 3 H), 3.78 (s, 3 H). m/z (ESI) 541.1 (M+H)$^+$.

Example 9 (Method 9)

1-(2-CHLORO-3'-FLUORO-5-METHOXY-[1,1'-BIPHENYL]-4-YL)-N-(1,3,4-THIADIAZOL-2-YL)PHTHALAZINE-6-SULFONAMIDE

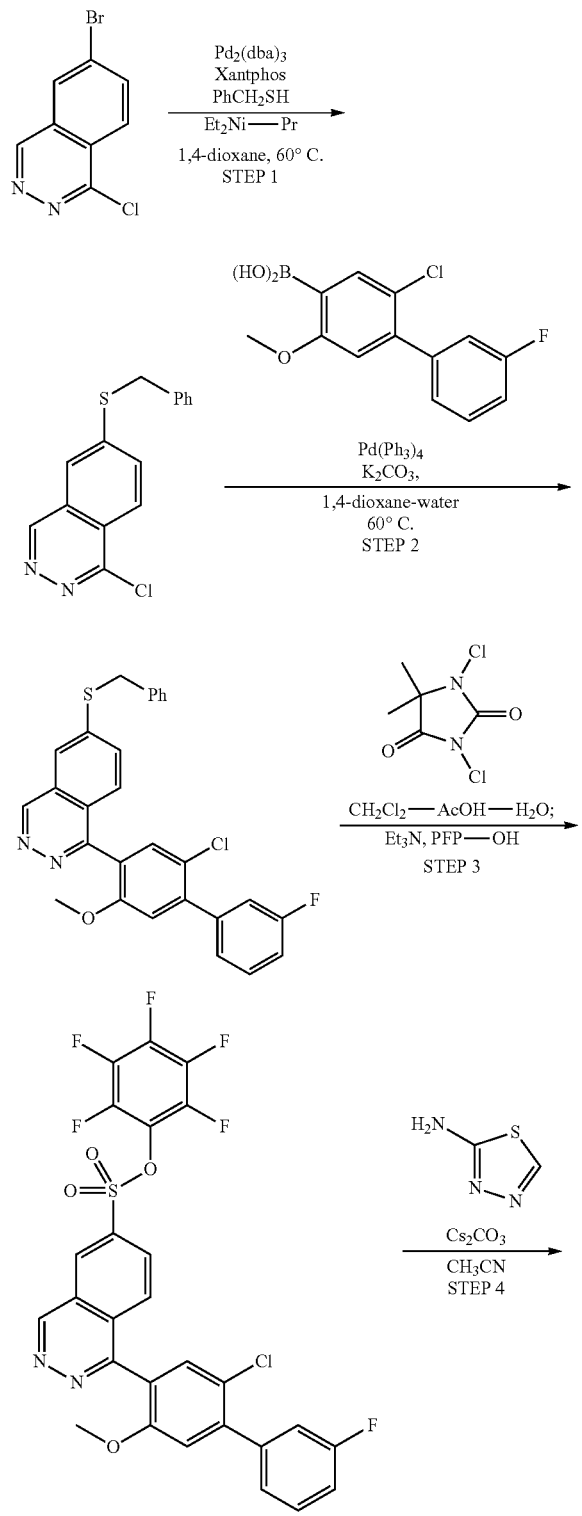

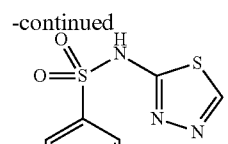

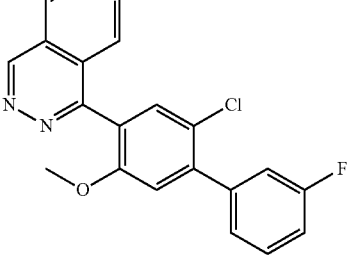

STEP 1: 6-(BENZYLTHIO)-1-CHLOROPHTHALAZINE

A two-neck RBF was charged with 6-bromo-1-chlorophthalazine (4.78 g, 19.63 mmol, Pharmablock), Xantphos (0.568 g, 0.982 mmol), and $Pd_2(dba)_3$ (0.449 g, 0.491 mmol). 1,4-dioxane (39.3 ml) and N,N-diisopropylethylamine (6.86 ml, 39.3 mmol) were added. The flask was fitted with a reflux condenser and placed in an 80° C. heating bath. After 5 min, benzyl mercaptan (2.438 ml, 20.61 mmol) was added over 30 s. After 30 min, the mixture was removed from the heating bath. The mixture was cooled, diluted with EtOAc, and washed with 1N aq. HCl. The aq. layer was extracted with EtOAc, and the combined organic extracts were dried over sodium sulfate, filtered, and concentrated. The residue was purified by chromatography on silica gel (100-g Ultra SNAP column, 50% EtOAc/Heptane). Fractions containing the product (including some mixed fractions) were combined and concentrated. The resulting solid was taken up in heptane and filtered. The collected solid was washed with heptane (2x), dried under a stream of $N_2$ (g), then dried under vacuum to give 6-(benzylthio)-1-chlorophthalazine (464 mg, 1.618 mmol, 8.24% yield) as a yellow solid. m/z (ESI) 287.1 $(M+H)^+$.

STEP 2: 6-(BENZYLTHIO)-1-(2-CHLORO-3'-FLUORO-5-METHOXY-[1,1'-BIPHENYL]-4-YL)PHTHALAZINE

A RBF was charged with 6-(benzylthio)-1-chlorophthalazine (454 mg, 1.583 mmol), (2-chloro-3'-fluoro-5-methoxy-[1,1'-biphenyl]-4-yl)boronic acid (666 mg, 2.375 mmol), potassium carbonate (656 mg, 4.75 mmol), and $Pd(Ph_3P)_4$ (183 mg, 0.158 mmol). The flask was flushed with Ar (g), then 1,4-dioxane (6332 µl) and water (1583 µl) were added. A reflux condenser was attached, and the flask was heat to 70° C. for 5 h. The mixture was cooled to room temperature, then diluted with EtOAc, washed with water, washed with brine, dried over sodium sulfate, filtered, and concentrated. The residue was purified by chromatography on silica gel (40-g Redi-Sep Gold column, 25-g silica gel loading column, 10-100% EtOAc/Heptane) to give 640 mg of a yellow solid. The material was repurified by chromatography, this time with 20-70% EtOAc/Heptane, then with 100% EtOAc to give 6-(benzylthio)-1-(2-chloro-3'-fluoro-5-methoxy-[1,1'-biphenyl]-4-yl)phthalazine (640 mg, 1.314 mmol, 83% yield) as a yellow solid that was about 80% pure as judged by LCMS. The material was used without further purification. m/z (ESI) 487.1 $(M+H)^+$.

STEP 3: PERFLUOROPHENYL 1-(2-CHLORO-3'-FLUORO-5-METHOXY-[1,1'-BIPHENYL]-4-YL)PHTHALAZINE-6-SULFONATE

A RBF was charged with 6-(benzylthio)-1-(2-chloro-3'-fluoro-5-methoxy-[1,1'-biphenyl]-4-yl)phthalazine (530 mg, 0.871 mmol), DCM (8194 µl), acetic acid (307 µl), and water (205 µl) to give clear, yellow solution. The flask was cooled in an ice-water bath for 10 min, then 1,3-dichloro-5,5-dimethylimidazolidine-2,4-dione (352 mg, 1.785 mmol) was added in one portion. After 20 min, an additional portion of oxidant (ca. 175 mg) was added. After another 10 min of stirring, 2,3,4,5,6-pentafluorophenol (240 mg, 1.306 mmol) and triethylamine (485 µl, 3.48 mmol) were added in sequence. The mixture was stirred for 20 min, then was diluted with saturated aq. sodium bicarbonate solution, and the mixture was stirred vigorously for 5 min. The mixture was then extracted with DCM (3×). The combined organic extracts were dried over sodium sulfate, filtered, and concentrated. The residue was purified by chromatography on silica gel (40-g Redi-Sep Gold column, 25-g silica gel loading column, 0-50% EtOAc/Heptane) to give perfluorophenyl 1-(2-chloro-3'-fluoro-5-methoxy-[1,1'-biphenyl]-4-yl)phthalazine-6-sulfonate (289.99 mg, 0.475 mmol, 54.5% yield) as a yellow solid. m/z 611.2 (M+H)$^+$.

STEP 4: 1-(2-CHLORO-3'-FLUORO-5-METHOXY-[1,1'-BIPHENYL]-4-YL)-N-(1,3,4-THIADIAZOL-2-YL)PHTHALAZINE-6-SULFONAMIDE

A vial was charged with perfluorophenyl 1-(2-chloro-3'-fluoro-5-methoxy-[1,1'-biphenyl]-4-yl)phthalazine-6-sulfonate (78.5 mg, 0.128 mmol) 1,3,4-thiadiazol-2-amine (15.59 mg, 0.154 mmol), and cesium carbonate (126 mg, 0.385 mmol). acetonitrile (6420 was added to give a suspension. After 5 h, the mixture was quenched by the addition of 1N aq. HCl (and a small amount of brine to help with an emulsion) and extracted with EtOAc (5×). The combined organic extracts were concentrated. The residue was purified by chromatography on silica gel (12-g Redi-Sep Gold column, 0-7.5% MeOH/DCM) to give 1-(2-chloro-3'-fluoro-5-methoxy-[1,1'-biphenyl]-4-yl)-N-(1,3,4-thiadiazol-2-yl)phthalazine-6-sulfonamide (27.28 mg, 0.052 mmol, 40.2% yield) as a light-yellow solid. $^1$H NMR (400 MHz, DMSO-d$_6$) δ=14.58 (br. s., 1 H), 9.95 (d, J=0.8 Hz, 1 H), 8.82 (s, 1 H), 8.77 (d, J=1.4 Hz, 1 H), 8.26 (dd, J=1.9, 8.8 Hz, 1 H), 7.85 (d, J=8.7 Hz, 1 H), 7.66 (s, 1 H), 7.59 (dt, J=6.3, 8.1 Hz, 1 H), 7.49-7.41 (m, 2 H), 7.38-7.25 (m, 2 H), 3.73 (s, 3 H). m/z (ESI) 528.0 (M+H)$^+$.

Example 10 (Method 10)

1-(2-CHLORO-3'-FLUORO-5-METHOXY-[1,1'-BIPHENYL]-4-YL)-N-(ISOXAZOL-3-YL)PHTHALAZINE-6-SULFONAMIDE

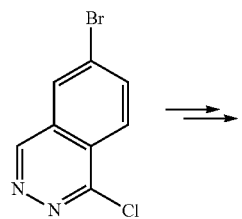

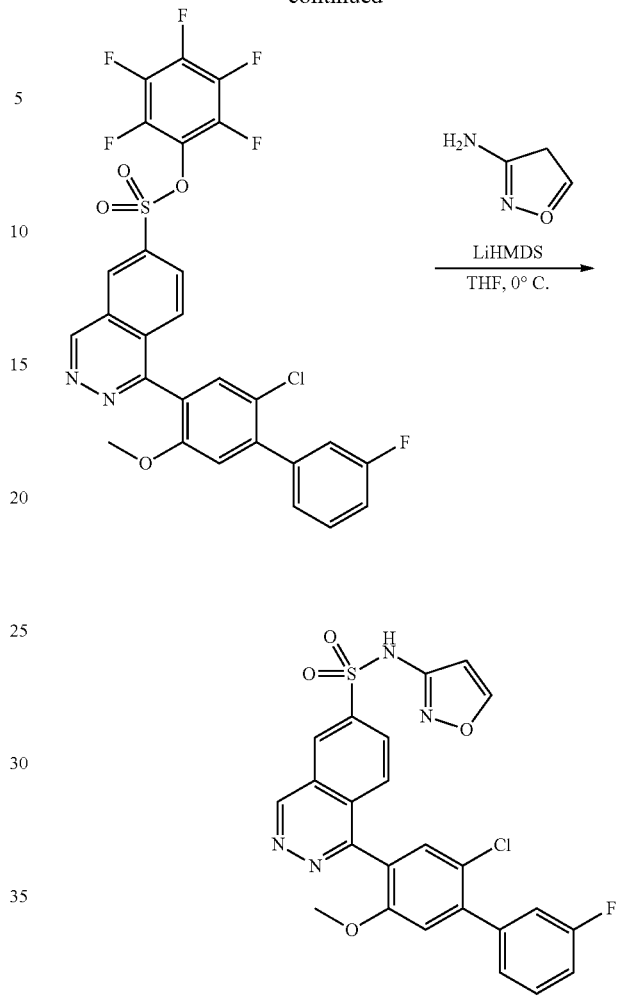

Perfluorophenyl 1-(2-chloro-3'-fluoro-5-methoxy-[1,1'-biphenyl]-4-yl)phthalazine-6-sulfonate was made using Method 9, Steps 1-3. Step 4 differed as follows: a vial was charged with perfluorophenyl 1-(2-chloro-3'-fluoro-5-methoxy-[1,1'-biphenyl]-4-yl)phthalazine-6-sulfonate (88.3 mg, 0.145 mmol), isoxazol-3-amine (12.28 µl, 0.166 mmol) and THF (1445 µl) to give a clear solution. The vial was cooled in an ice-water bath for 10 min, then lithium bis(trimethylsilyl)amide (1M in THF) (304 µl, 0.304 mmol) was added dropwise. After 20 min, the mixture was quenched by the addition of 1N aq. HCl, then warmed to room temperature. The mixture was extracted with EtOAc (3×), and the combined organic extracts were concentrated. The residue was purified by chromatography (12-g Redi-Sep Gold column, 0-4% MeOH/DCM) to give 1-(2-chloro-3'-fluoro-5-methoxy-[1,1'-biphenyl]-4-yl)-N-(isoxazol-3-yl)phthalazine-6-sulfonamide (50.2 mg, 0.098 mmol, 68.0% yield) as a light-yellow solid. $^1$H NMR (400 MHz, DMSO-d$_6$) δ=12.05 (br. s., 1 H), 9.98 (d, J=0.8 Hz, 1 H), 8.93-8.86 (m, 1 H), 8.76 (d, J=1.9 Hz, 1 H), 8.31 (dd, J=2.0, 8.8 Hz, 1 H), 8.00-7.91 (m, 1 H), 7.68 (s, 1 H), 7.63-7.53 (m, 1 H), 7.51-7.41 (m, 2 H), 7.38-7.28 (m, 2 H), 6.50 (d, J=1.9 Hz, 1 H), 3.72 (s, 3 H). m/z (ESI) 511.1 (M+H)$^+$.

Example 11 (Method 11)

1-(3'-FLUORO-3-(HYDROXYMETHYL)-[1,1'-BIPHENYL]-4-YL)-N-(1,3,4-THIADIAZOL-2-YL)ISOQUINOLINE-6-SULFONAMIDE

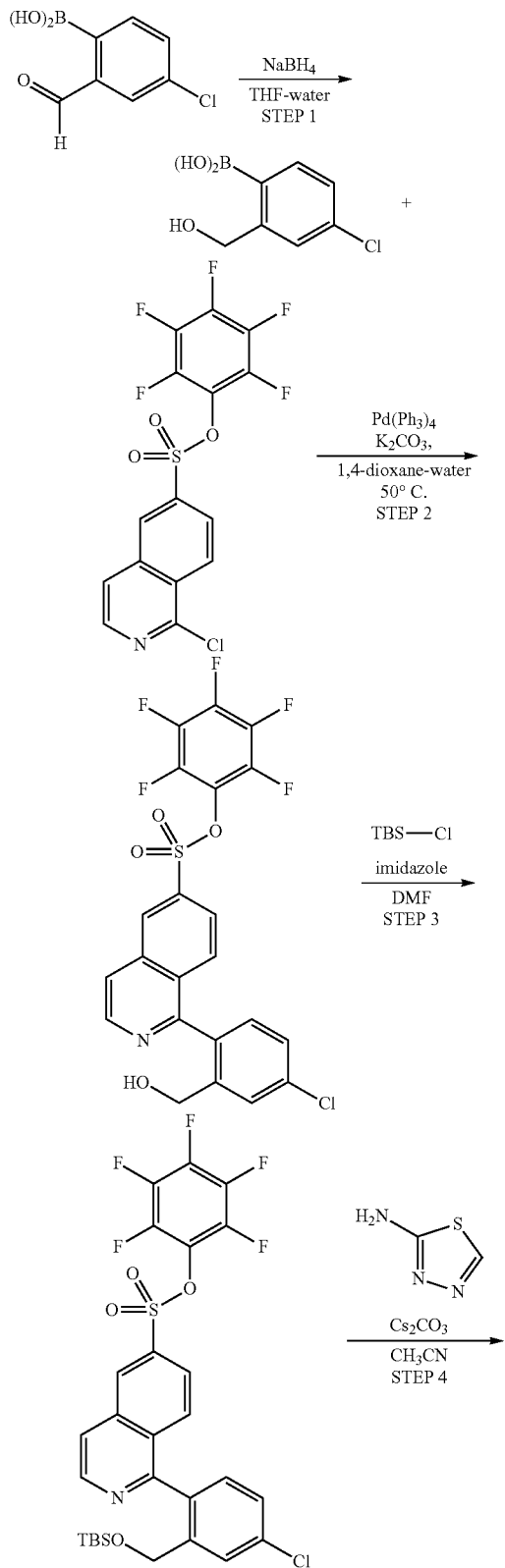

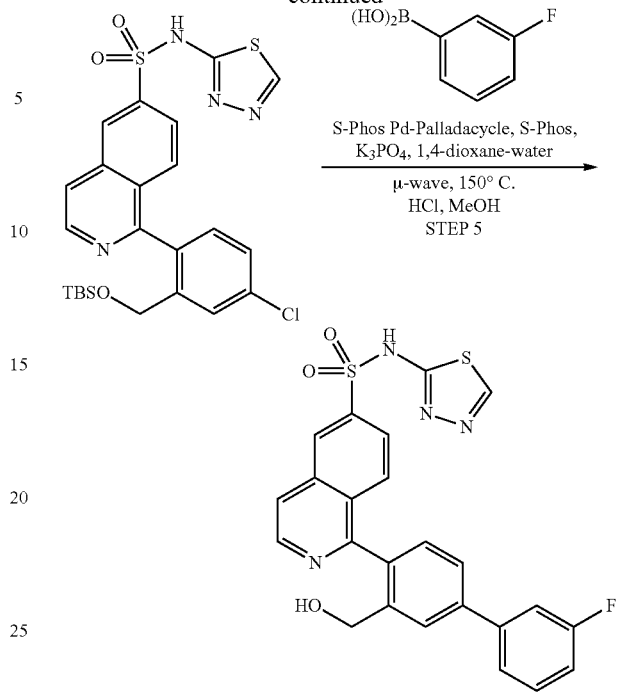

STEP 1 (4-CHLORO-2-(HYDROXYMETHYL)PHENYL)BORONIC ACID

A RBF was charged with (4-chloro-2-formylphenyl)boronic acid (1.243 g, 6.74 mmol), THF (11 mL), and water (9 mL) to give a clear, light-yellow solution. Sodium borohydride (0.638 g, 16.85 mmol) was added in one portion, resulting in a vigorous exotherm and bubbling. After 2 h, the mixture was diluted with 2N aq. HCl, then stirred for 5 min. The mixture was filtered, and the collected solid was washed with water (4×), then dried under a stream of $N_2$ (g) overnight to give (4-chloro-2-(hydroxymethyl)phenyl)boronic acid (1.085 g, 5.82 mmol, 86% yield) as a white powder.

STEP 2: PERFLUOROPHENYL 1-(4-CHLORO-2-(HYDROXYMETHYL)PHENYL)ISOQUINOLINE-6-SULFONATE

A RBF was charged with perfluorophenyl 1-chloroisoquinoline-6-sulfonate (1.65 g, 4.03 mmol), (4-chloro-2-(hydroxymethyl)phenyl)boronic acid (0.976 g, 5.24 mmol), potassium carbonate (1.670 g, 12.08 mmol), and $Pd(Ph_3P)_4$ (0.465 g, 0.403 mmol). The vial was flushed with Ar (g), then 1,4-dioxane (15.10 ml) and water (5.03 ml) were added. The flask was lowered into a 50° C. heating bath for 2 h. The mixture was diluted with water and extracted with EtOAc (2×). The combined organic extracts were dried over sodium sulfate, filtered, and concentrated. The residue was purified by chromatography on silica gel (40-g Redi-Sep Gold column, 25-g silica gel loading column, 10-60% EtOAc/Heptane) to give perfluorophenyl 1-(4-chloro-2-(hydroxymethyl)phenyl)isoquinoline-6-sulfonate (1.035 g, 2.006 mmol, 49.8% yield) as a light-yellow foam. $^1$H NMR (400 MHz, DMSO-$d_6$) δ=8.97 (d, J=2.1 Hz, 1 H), 8.83 (d, J=5.7 Hz, 1 H), 8.28-8.20 (m, 1H), 8.09 (dd, J=2.1, 9.0 Hz, 1 H), 7.90 (d, J=9.0 Hz, 1 H), 7.72 (d, J=2.2 Hz, 1 H), 7.53 (dd, J=2.2, 8.1 Hz, 1 H), 7.42-7.38 (m, 1 H), 5.23 (t, J=5.4 Hz, 1 H), 4.41-4.07 (m, 2 H). m/z (ESI) 516.0 (M+H)+.

STEP 3: PERFLUOROPHENYL 1-(2-(((TERT-BUTYLDIMETHYLSILYL)OXY)METHYL)-4-CHLOROPHENYL)ISOQUINOLINE-6-SULFONATE

A RBF was charged with perfluorophenyl 1-(4-chloro-2-(hydroxymethyl)phenyl)isoquinoline-6-sulfonate (701.5 mg, 1.360 mmol), DMF (20000, and imidazole (102 mg, 1.496 mmol). tert-Butyldimethylchlorosilane (50 wt % in toluene) (516 μl, 1.496 mmol) was added dropwise. After 30 min of stirring, the mixture was diluted with EtOAc and washed with water (2×), washed with brine, dried over sodium sulfate, filtered, and concentrated. The residue was purified by chromatography on silica gel (50-g SNAP Ultra column, 0-20% EtOAc/Heptane) to give perfluorophenyl 1-(2-(((tert-butyldimethylsily)oxy)methyl)-4-chlorophenyl)isoquinoline-6-sulfonate (563 mg, 0.894 mmol, 65.7% yield) as a light-yellow oil. m/z (ESI) 630.2 (M+H)+.

STEP 4: 1-(2-(((TERT-BUTYLDIMETHYLSILYL)OXY)METHYL)-4-CHLOROPHENYL)-N-(1,3,4-THIADIAZOL-2-YL)ISOQUINOLINE-6-SULFONAMIDE

A vial was charged with perfluorophenyl 1-(2-(((tert-butyldimethylsilyl)oxy)methyl)-4-chlorophenyl)isoquinoline-6-sulfonate (287 mg, 0.455 mmol), 1,3,4-thiadiazol-2-amine (50.7 mg, 0.501 mmol), and cesium carbonate (445 mg, 1.366 mmol). The vial was flushed with Ar (g), then acetonitrile (22770 was added. The mixture was stirred overnight, then was diluted with saturated aq. ammonium chloride and water and extracted with EtOAc (3×). The combined organic extracts were dried over sodium sulfate, filtered, and concentrated. The residue was purified by chromatography on silica gel (50-g SNAP Ultra column, 0-5% MeOH/DCM) to give 1-(2-(((tert-butyldimethylsilyl)oxy)methyl)-4-chlorophenyl)-N-(1,3,4-thiadiazol-2-yl)isoquinoline-6-sulfonamide (226.87 mg, 0.415 mmol, 91% yield) as an off-white foam. m/z (ESI) 547.1 (M+H)+.

STEP 5: 1-(3'-FLUORO-3-(HYDROXYMETHYL)-[1,1'-BIPHENYL]-4-YL)-N-(1,3,4-THIADIAZOL-2-YL)ISOQUINOLINE-6-SULFONAMIDE

A vial was charged with 1-(2-(((tert-butyldimethylsilyl)oxy)methyl)-4-chlorophenyl)-N-(1,3,4-thiadiazol-2-yl)isoquinoline-6-sulfonamide (98.8 mg, 0.181 mmol), (3-fluorophenyl)boronic acid (50.5 mg, 0.361 mmol), chloro(2-dicyclohexylphosphino-2',6'-dimethoxy-1,1'-biphenyl)[2-(2-aminoethylphenyl)]palladium(ii) dichloromethane (6.84 mg, 9.03 μmol), dicyclohexyl(2',6'-dimethoxy-[1,1'-biphenyl]-2-yl)phosphine (3.71 mg, 9.03 μmol), and potassium phosphate (115 mg, 0.542 mmol). The vial was flushed with Ar (g), then 1,4-dioxane (821 μl) and water (82 μl) were added. The vial was sealed and heated in a Biotage Initiator microwave reactor for 1 h at 150° C. mixture was extracted with EtOAc (3×), and the combined organic extracts were concentrated. The residue was taken up in MeOH (1 mL) and concentrated HCl (0.05 mL). After 1 h, the mixture was concentrated. The residue was purified by chromatography on silica gel (12-g Redi-Sep Gold column, 4% MeOH/DCM) to give 1-(3'-fluoro-3-(hydroxymethyl)-[1,1'-biphenyl]-4-yl)-N-(1,3,4-thiadiazol-2-yl)isoquinoline-6-sulfonamide (40.2 mg, 0.082 mmol, 45.2% yield) as an off-white solid. 1H NMR (400 MHz, DMSO-d6) δ=14.50 (br. s., 1 H), 8.80 (s, 1 H), 8.72 (d, J=5.7 Hz, 1 H), 8.60 (d, J=1.8 Hz, 1 H), 8.15 (d, J=5.3 Hz, 1 H), 7.99 (d, J=1.7 Hz, 1 H), 7.92-7.88 (m, 1 H), 7.81 (d, J=8.9 Hz, 1 H), 7.76 (dd, J=2.0, 7.9 Hz, 1 H), 7.66-7.62 (m, 2 H), 7.61-7.54 (m, 1 H), 7.42 (d, J=7.9 Hz, 1 H), 7.29-7.23 (m, 1 H), 5.09 (br. s., 1 H), 4.59-4.08 (m, 2 H). m/z (ESI) 493.1 (M+H)+.

Example 12 (Method 12)

1-(3'-FLUORO-3-(HYDROXYMETHYL)-[1,1'-BIPHENYL]-4-YL)-N-(ISOXAZOL-3-YL)ISOQUINOLINE-6-SULFONAMIDE 2,2,2-TRIFLUOROACETATE

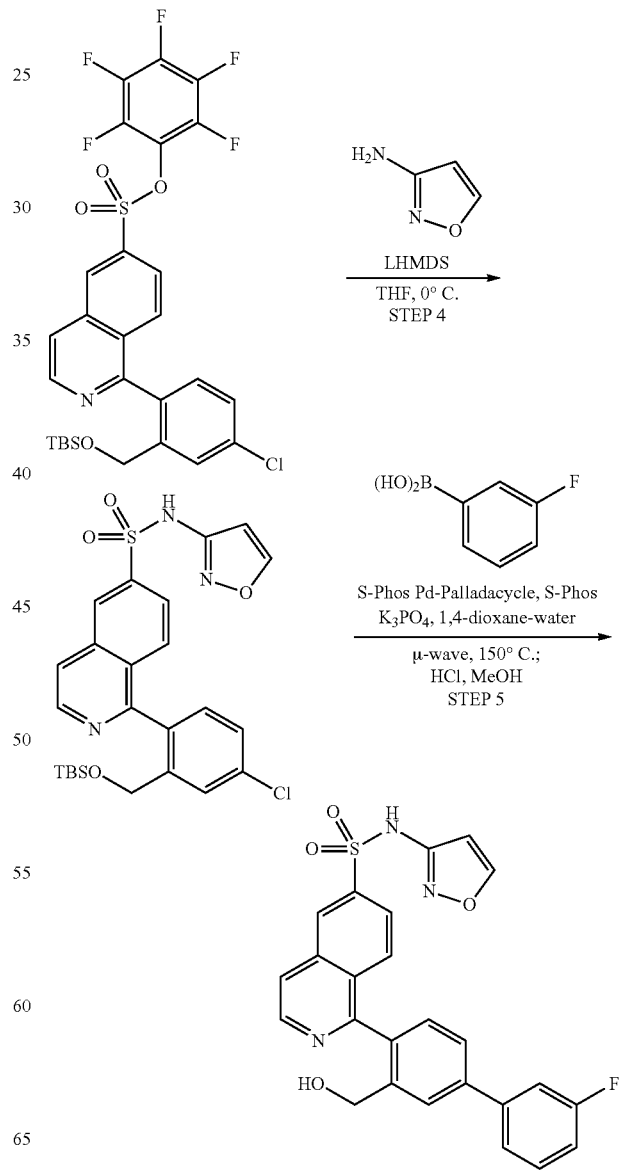

STEP 4: 1-(2-(((TERT-BUTYLDIMETHYLSILYL) OXY)METHYL)-4-CHLOROPHENYL)-N-(ISOXAZOL-3-YL)ISOQUINOLINE-6-SULFONAMIDE

The procedure described in method 10, Steps 1-3 was followed to form perfluorophenyl 1-(2-(((tert-butyldimethylsilyl)oxy)methyl)-4-chlorophenyl)isoquinoline-6-sulfonate. Then Step 4 was continued as follows: a vial was charged with perfluorophenyl 1-(2-(((tert-butyldimethylsilyl)oxy)methyl)-4-chlorophenyl)isoquinoline-6-sulfonate (276 mg, 0.438 mmol), THF (21900, and isoxazol-3-amine (35.6 µl, 0.482 mmol) to give a clear solution. The vial was cooled in an ice-water bath for 10 min, then lithium bis(trimethylsilyl)amide (1M in THF) (920 µl, 0.920 mmol) was added dropwise. After 30 min, the mixture was quenched by the addition of saturated aq. ammonium chloride and water, then extracted with EtOAc (2×). The combined organic extracts were dried over sodium sulfate, filtered, and concentrated. The residue was purified by chromatography on silica gel (50-g SNAP Ultra column, 0-5% MeOH/DCM) to give 1-(2-(((tert-butyldimethylsilyl)oxy)methyl)-4-chlorophenyl)-N-(isoxazol-3-yl)isoquinoline-6-sulfonamide (229.7 mg, 0.433 mmol, 99% yield) as a white foam. m/z (ESI) 530.2 (M+H)+.

STEP 5: 1-(3'-FLUORO-3-(HYDROXYMETHYL)-[1,1'-BIPHENYL]-4-YL)-N-(ISOXAZOL-3-YL)ISOQUINOLINE-6-SULFONAMIDE 2,2,2-TRIFLUOROACETATE

A vial was charged with 1-(2-(((tert-butyldimethylsilyl)oxy)methyl)-4-chlorophenyl)-N-(isoxazol-3-yl)isoquinoline-6-sulfonamide (88.07 mg, 0.166 mmol) (3-fluorophenyl)boronic acid (34.9 mg, 0.249 mmol), chloro(2-dicyclohexylphosphino-2',6'-dimethoxy-1,1'-biphenyl)[2-(2-aminoethylphenyl)]palladium(ii) dichloromethane (6.29 mg, 8.31 µmol), and potassium phosphate (106 mg, 0.498 mmol). The vial was flushed with Ar (g), then 1,4-dioxane (755 µl) and water (760 were added. The vial was sealed and heated in a Biotage Initiator microwave reactor for 90 min 120° C., then for 2.5 h at 150° C. Additional portions of (3-fluorophenyl)boronic acid (34.9 mg, 0.249 mmol), chloro(2-dicyclohexylphosphino-2',6'-dimethoxy-1,1'-biphenyl)[2-(2-aminoethylphenyl)]palladium(ii) dichloromethane (6.29 mg, 8.31 µmol), and potassium phosphate (106 mg, 0.498 mmol) were added. The vial was heated for an additional 1 h at 150° C. The mixture was extracted with EtOAc (5×), and the combined organic extracts were concentrated. The residue was taken up in MeOH (1 mL). Concentrated HCl (0.025 mL) was added. After 30 min, an additional portion of concentrated HCl (0.05 mL) was added. After another 30 min, the mixture was concentrated, and the residue was dissolved in MeOH. The solution was filtered through a 0.2 micron filter. The filtrate was purified by reverse-phase HPLC (25-70% $CH_3CN/H_2O$ with 0.1% TFA). Fractions containing clean desired product were combined and concentrated to give 1-(3'-fluoro-3-(hydroxymethyl)-[1,1'-biphenyl]-4-yl)-N-(isoxazol-3-yl)isoquinoline-6-sulfonamide 2,2,2-trifluoroacetate (22.9 mg, 0.039 mmol, 23.38% yield) as a light-yellow solid. $^1$H NMR (400 MHz, DMSO-$d_6$) δ=11.98 (br. s., 1 H), 8.80-8.72 (m, 3 H), 8.24 (d, J=5.6 Hz, 1 H), 8.04-7.87 (m, 3 H), 7.78 (dd, J=2.0, 7.9 Hz, 1 H), 7.67-7.54 (m, 3 H), 7.46 (d, J=7.9 Hz, 1 H), 7.30-7.24 (m, 1 H), 6.51 (d, J=1.9 Hz, 1 H), 4.62-4.05 (m, 2 H). m/z (ESI) 476.1 (M+H)+.

Example 13 (Method 13)

4-(3',5'-DIFLUORO-3-METHOXY-[1,1'-BIPHENYL]-4-YL)-N-(1,3,4-THIADIAZOL-2-YL)QUINOLINE-7-SULFONAMIDE

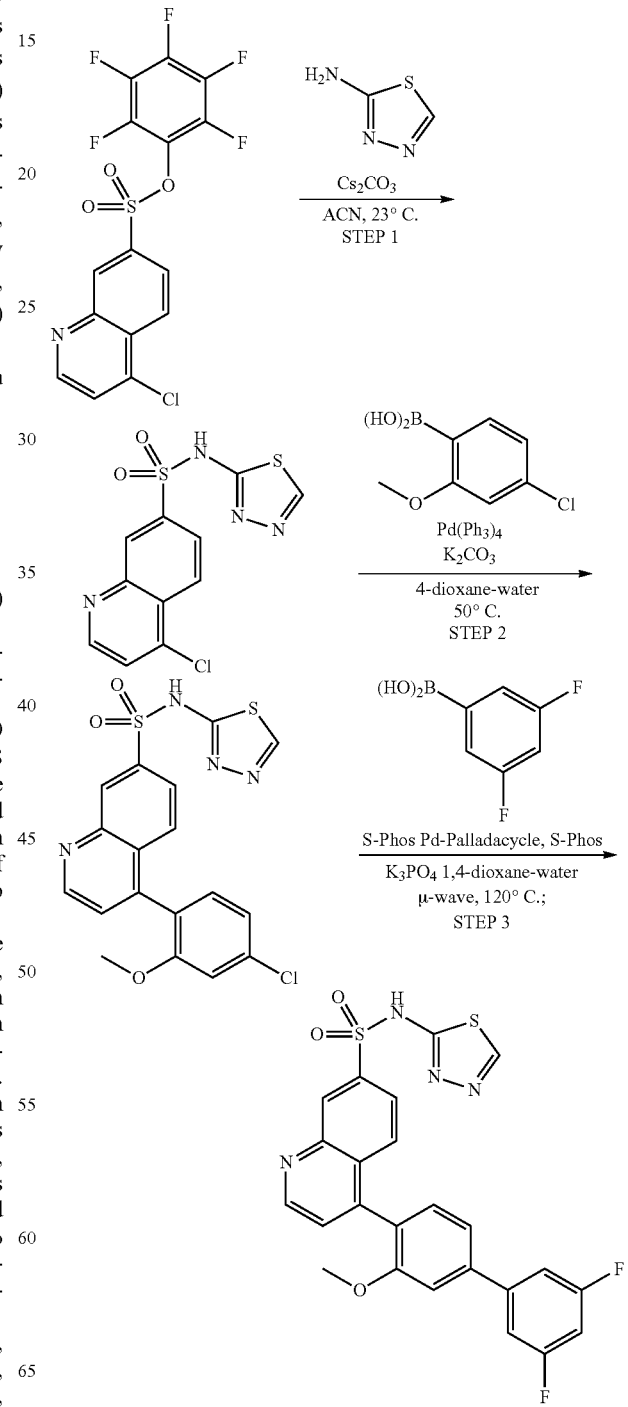

STEP 1: 4-CHLORO-N-(1,3,4-THIADIAZOL-2-YL)QUINOLINE-7-SULFONAMIDE

A vial was charged with perfluorophenyl 4-chloroquinoline-7-sulfonate (1.0 g, 2.441 mmol), 1,3,4-thiadiazol-2-amine (0.272 g, 2.68 mmol), and cesium carbonate (2.386 g, 7.32 mmol). The vial was flushed with Ar (g), then acetonitrile (12.20 ml) was added. The reaction was stirred for four hours at room temperature. The mixture was diluted with EtOAc and 1 N aq. HCl. The layers were separated, and the aq. layer was extracted with EtOAc (2×). The combined organic extracts were dried over sodium sulfate, filtered, and concentrated to afford crude 4-chloro-N-(1,3,4-thiadiazol-2-yl)quinoline-7-sulfonamide (0.325 g, 0.995 mmol, 40.7% yield) as a yellow solid. m/z (ESI) 327.0 (M+H)$^+$.

STEP 2: 4-(4-CHLORO-2-METHOXYPHENYL)-N-(1,3,4-THIADIAZOL-2-YL)QUINOLINE-7-SULFONAMIDE

A microwave vial was charged with 4-chloro-N-(1,3,4-thiadiazol-2-yl)quinoline-7-sulfonamide (0.314 g, 0.961 mmol), (4-chloro-2-methoxyphenyl)boronic acid (0.269 g, 1.441 mmol), potassium carbonate (0.398 g, 2.88 mmol), and Pd(Ph3P)4 (0.111 g, 0.096 mmol). The vial was flushed with Ar (g), then Dioxane (2.88 ml) and Water (0.961 ml) were added. The reaction was microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-10% MeOH:DCM) to afford 4-(4-chloro-2-methoxyphenyl)-N-(1,3,4-thiadiazol-2-yl)quinoline-7-sulfonamide (0.166, 0.383 mmol, 39.9% yield) as a tan solid. m/z (ESI) 433.0 (M+H)$^+$.

STEP 3: 4-(3',5'-DIFLUORO-3-METHOXY-[1,1'-BIPHENYL]-4-YL)-N-(1,3,4-THIADIAZOL-2-YL)QUINOLINE-7-SULFONAMIDE

A vial was charged with 4-(4-chloro-2-methoxyphenyl)-N-(1,3,4-thiadiazol-2-yl)quinoline-7-sulfonamide (0.055 g, 0.127 mmol), (3,5-difluorophenyl)boronic acid (0.040 g, 0.254 mmol), dicyclohexyl(2',6'-dimethoxy-[1,1'-biphenyl]-2-yl)phosphine (2.61 mg, 6.35 µmol), chloro(2-dicyclohexylphosphino-2',6'-dimethoxy-1,1'-biphenyl)[2-(2-aminoethylphenyl)]palladium(ii) dichloromethane (4.81 mg, 6.35 µmol), and potassium phosphate (0.081 g, 0.381 mmol). The vial was flushed with Ar (g), then 1,4-dioxane (0.577 ml) and Water (0.058 ml) were added in sequence. The vial was sealed and microwaved at 100° C. for one hour. The reaction was diluted with ethyl acetate and washed with water. The aqueous layer was extracted with ethyl acetate, and the combined organic layers were dried with sodium sulfate, filtered, and concentrated. The material was purified via Gilson HPLC (25-70% MeCN:H2O w/0.1% TFA modifier). The product fractions were partitioned between ethyl acetate and water. The aqueous layer was extracted with ethyl acetate, and the combined organic layers were dried with sodium sulfate, filtered, and concentrated to afford 4-(3',5'-difluoro-3-methoxy-[1,1'-biphenyl]-4-yl)-N-(1,3,4-thiadiazol-2-yl)quinoline-7-sulfonamide (0.029 g, 0.057 mmol, 44.7% yield) as a yellow solid. $^1$H NMR (400 MHz, DMSO-d$_6$) δ=9.09 (d, J=4.4 Hz, 1 H), 8.79 (s, 1 H), 8.46 (d, J=1.7 Hz, 1 H), 7.87 (dd, J=1.9, 8.9 Hz, 1 H), 7.74 (d, J=8.9 Hz, 1 H), 7.63 (dd, J=2.2, 9.0 Hz, 2 H), 7.60 (d, J=4.4 Hz, 1 H), 7.56 (d, J=1.6 Hz, 1 H), 7.54-7.51 (m, 1 H), 7.41 (d, J=7.7 Hz, 1 H), 7.30 (tt, J=2.2, 9.3 Hz, 1 H), 3.79 (s, 3 H). m/z (ESI) 511.1 (M+H)$^+$.

Example 14 (Method 14)

1-(2-CHLORO-3'-FLUORO-5-METHOXY-[1,1'-BIPHENYL]-4-YL)-4-OXO-N-(1,3,4-THIADIAZOL-2-YL)-3,4-DIHYDROPHTHALAZINE-6-SULFONAMIDE

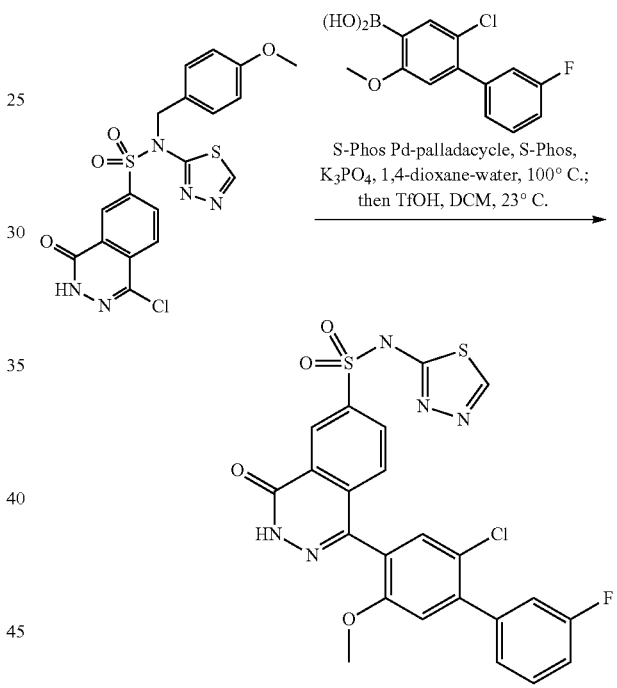

A microwave vial was charged with 1-chloro-N-(4-methoxybenzyl)-4-oxo-N-(1,3,4-thiadiazol-2-yl)-3,4-dihydrophthalazine-6-sulfonamide (0.220 g, 0.474 mmol), (2-chloro-3'-fluoro-5-methoxy-[1,1'-biphenyl]-4-yl)boronic acid (0.146 g, 0.522 mmol), SPhos Precatalyst (0.018 g, 0.024 mmol), dicyclohexyl(2',6'-dimethoxy-[1,1'-biphenyl]-2-yl)phosphine (9.73 mg, 0.024 mmol), and potassium phosphate (0.302 g, 1.423 mmol). The vial was flushed with Ar (g), then Dioxane (3.95 ml) and Water (0.790 ml) were added. The reaction was microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(2-chloro-3'-fluoro-5-methoxy-[1,1'-biphenyl]-4-yl)-N-(4- methoxybenzyl)-4-oxo-N-(1,3,4-thiadiazol-2-yl)-3,4-dihydrophthalazine-6-sulfonamide. The material was dissolved in DCM and TFOH (0.15 ml, 1.689 mmol) was added. The reaction was stirred for 30 minutes at room temperature. The reaction was concentrated and purified via column chromatography (RediSep Gold 12 g, gradient elution 0-10% MeOH:DCM) to afford 1-(2-chloro-3'-fluoro-5-methoxy-[1,1'-biphenyl]-4-yl)-4-oxo-N-(1,3,4-thiadiazol-2-yl)-3,4-dihydrophthalazine-6-sulfonamide (0.026 g, 0.048 mmol, 10.08% yield) as a white solid. $^1$H NMR (400 MHz, DMSO-d$_6$) δ=13.16 (s, 1 H), 8.83-8.79 (m, 1 H), 8.62 (d, J=2.0 Hz, 1H), 8.21 (dd, J=2.1, 8.4 Hz, 1 H), 7.60-7.53 (m, 3 H), 7.41 (d, J=7.8 Hz, 2 H), 7.32 (t, J=8.9 Hz, 1 H), 7.27 (s, 1 H), 3.75 (s, 3 H). m/z (ESI) 544.1 (M+H)$^+$.

Example 15 (Method 15)

4-(2-CHLORO-3'-FLUORO-5-METHOXY-[1,1'-BIPHENYL]-4-YL)-N-(PYRIDAZIN-3-YL)QUINAZOLINE-7-SULFONAMIDE

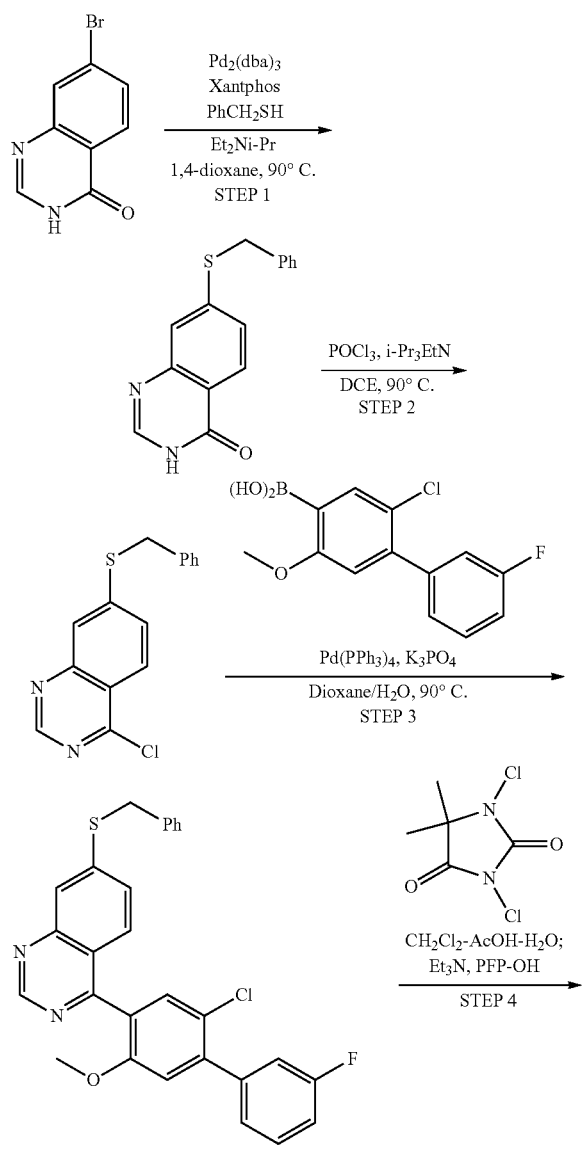

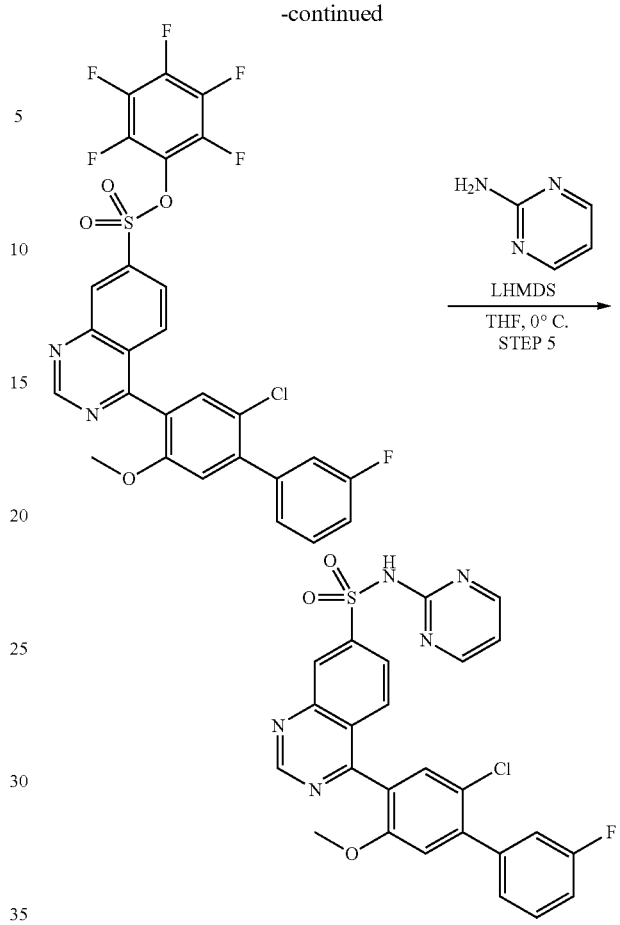

STEP 1: 7-(BENZYLTHIMUINAZOLIN-4(3H)-ONE

A RBF was charged with 7-bromoquinazolin-4(3H)-one (10 g, 44.4 mmol, Milestone Pharmatech), xantphos (1.286 g, 2.222 mmol), and pd2(dba)3 (1.017 g, 1.111 mmol). The flask was flushed with Ar (g), then Dioxane (89 ml), benzyl mercaptan (5.52 ml, 46.7 mmol), and n,n-diisopropylethylamine (15.52 ml, 89 mmol) were added in sequence. The flask was fitted with a reflux condenser and reaction was heated to 90° C. and stirred for one hour. The reaction was diluted with water and filtered. The solids were washed thoroughly with water, then air dried for several hours and triturated with ethyl acetate. After stirring overnight, the solids were filtered, washed with ethyl acetate, and vacuum dried over a nitrogen blanket overnight to afford 7-(benzylthio)quinazolin-4(3H)-one (10.51 g, 39.2 mmol, 88% yield) as a light yellow solid. m/z (ESI) 269.1 (M+H)$^+$.

STEP 2: 7-(BENZYLTHIO)-4-CHLOROQUINAZOLINE

A flask was charged with 7-(benzylthio)quinazolin-4 (3H)-one (5.0 g, 18.63 mmol) and DCE (93 ml). POCl$_3$ (5.21 ml, 55.9 mmol) was added, followed by hunig's base (16.27 ml, 93 mmol). The flask was fitted with a reflux condenser, and the reaction was stirred for two hours at 90° C. The reaction was washed with water and the layers were separated. The aqueous layer was extracted with ethyl acetate, and the combined organic layers were washed with brine, dried over sodium sulfate, filtered, and concentrated. The material was purified via column chromatography (RediSep Gold 80 g, gradient elution 0-75% EtOAc:Heptane) to afford 7-(benzylthio)-4-chloroquinazoline (4.08 g, 14.23 mmol, 76% yield) as a light yellow solid. m/z (ESI) 287.0 (M+H)$^+$.

STEP 3: 7-(BENZYLTHIO)-4-(2-CHLORO-3'-FLUORO-5-METHOXY-[1,1'-BIPHENYL]-4-YL)QUINAZOLINE

A microwave vial was charged with 7-(benzylthio)-4-chloroquinazoline (0.372 g, 1.298 mmol), (2-chloro-3'-fluoro-5-methoxy-[1,1'-biphenyl]-4-yl)boronic acid (0.364 g, 1.298 mmol), tetrakis(triphenylphosphine)palladium(0) (0.150 g, 0.130 mmol), and potassium carbonate (0.897 g, 6.49 mmol). Dioxane (3.24 ml) and Water (1.081 ml) were added, the vial was flushed with argon and sealed, and heated in a microwave initiator at 90° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-75% EtOAc:Heptane) to afford 7-(benzylthio)-4-(2-chloro-3'-fluoro-5-methoxy-[1,1'-biphenyl]-4-yl)quinazoline (0.490 g, 1.006 mmol, 78% yield) as a yellow solid. m/z (ESI) 487.1 (M+H)$^+$.

STEP 4 PERFLUOROPHENYL 4-(2-CHLORO-3'-FLUORO-5-METHOXY-[1,1'-BIPHENYL]-4-YL)QUINAZOLINE-7-SULFONATE

A RBF was charged with 7-(benzylthio)-4-(2-chloro-3'-fluoro-5-methoxy-[1,1'-biphenyl]-4-yl)quinazoline (0.490 g, 1.006 mmol), DCM (9.47 ml), acetic acid (0.355 ml), and water (0.237 ml) to give a thin suspension. The flask was cooled in an ice-bath for 10 min, then 1,3-dichloro-5,5-dimethylimidazolidine-2,4-dione (0.496 g, 2.52 mmol) was added in one portion, leading to a solution. The reaction was stirred for 15 minutes. 2,3,4,5,6-pentafluorophenol (0.211 ml, 2.012 mmol) was added followed by dropwise addition of triethylamine (0.351 ml, 2.52 mmol). The reaction was stirred for 30 minutes. The reaction was concentrated and purified via column chromatography (RediSep Gold 40 g, gradient elution 0-50% EtOAc:Heptane) to afford perfluorophenyl 4-(2-chloro-3'-fluoro-5-methoxy-[1,1'-biphenyl]-4-yl)quinazoline-7-sulfonate (0.538 g, 0.881 mmol, 88% yield) as a light yellow solid. m/z (ESI) 611.2 (M+H)$^+$.

STEP 5: 4-(2-CHLORO-3'-FLUORO-5-METHOXY-[1,1'-BIPHENYL]-4-YL)-N-(PYRIDAZIN-3-YL)QUINAZOLINE-7-SULFONAMIDE

A RBF was charged with perfluorophenyl 4-(2-chloro-3'-fluoro-5-methoxy-[1,1'-biphenyl]-4-yl)quinazoline-7-sulfonate (0.045 g, 0.074 mmol), pyridazin-3-amine (7.71 mg, 0.081 mmol), and THF (0.368 ml) to give a clear solution. The flask was cooled in an ice-water bath for 10 min, then lithium bis(trimethylsilyl)amide (1M in THF) (0.162 ml, 0.162 mmol) was added dropwise. The reaction was stirred for 30 minutes. The reaction was diluted with 1N aq. HCl and EtOAc. The aqueous layer was extracted with ethyl acetate, and the combined organic layers were dried with sodium sulfate, filtered, and concentrated. The material was purified via column chromatography (RediSep Gold 12 g, gradient elution 25-75% Heptane:[3:1 EtOAc:EtOH]) to afford 4-(2-chloro-3'-fluoro-5-methoxy-[1,1'-biphenyl]-4-yl)-N-(pyridazin-3-yl)quinazoline-7-sulfonamide (0.020 g, 0.038 mmol, 52.0% yield) as a white solid. $^1$H NMR (400 MHz, DMSO-d$_6$) δ=9.49 (br. s., 1 H), 8.49 (br. s., 1 H), 8.37 (br. s., 1 H), 8.13-7.97 (m, 2 H), 7.92 (d, J=8.6 Hz, 1 H), 7.75 (d, J=6.5 Hz, 1 H), 7.67 (br. s., 1 H), 7.59 (d, J=6.3 Hz, 1 H), 7.44 (br. s., 2 H), 7.32 (br. s., 2 H), 3.74 (br. s., 3 H). m/z (ESI) 522.2 (M+H)$^+$.

Example 16 (Method 16)

1-(2-FLUORO-5-METHOXY-3'-(TRIFLUOROMETHYL)-[1,1'-BIPHENYL]-4-YL)-4-HYDROXY-N-(ISOXAZOL-3-YL)ISOQUINOLINE-6-SULFONAMIDE

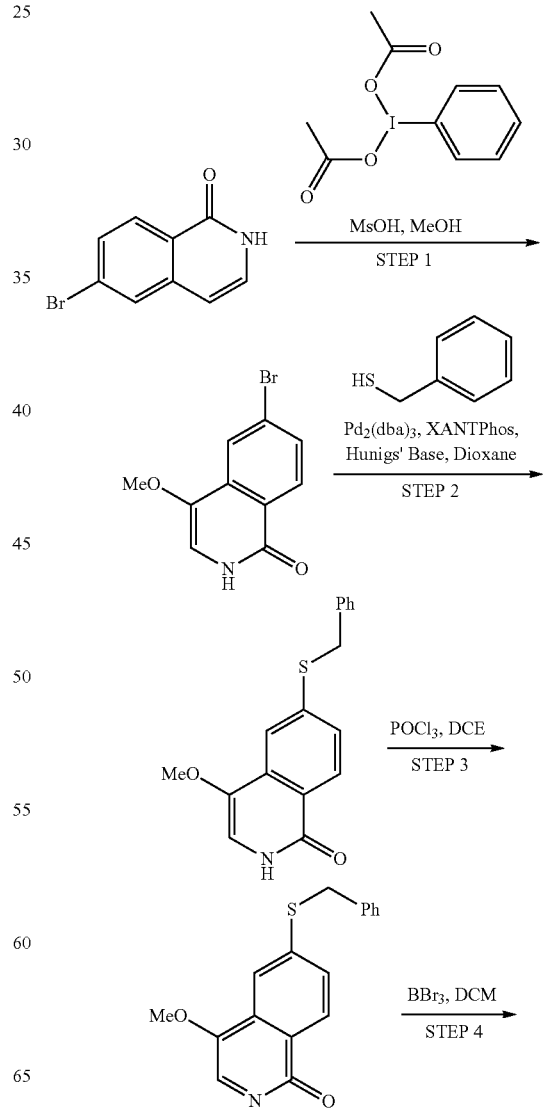

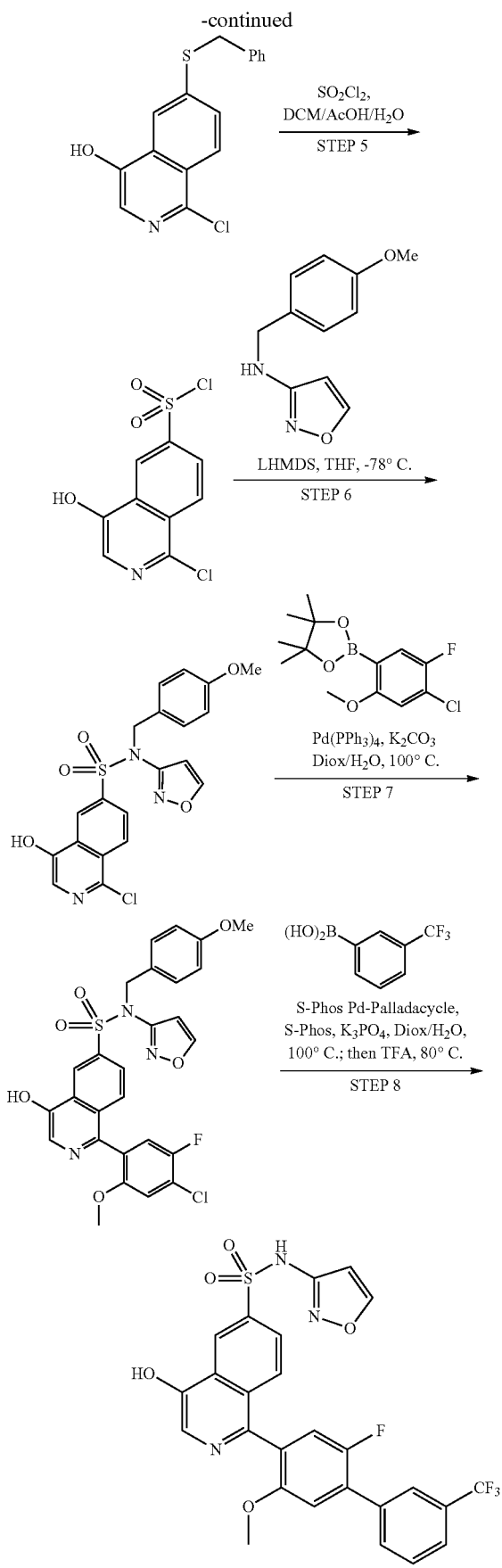

STEP 1:
6-BROMO-4-METHOXYISOQUINOLIN-1(2H)-ONE

A RBF was charged with 6-bromo-2h-isoquinolin-1-one (1.0 g, 4.46 mmol), methanol (8 mL), and methanesulfonic acid (0.290 ml, 4.46 mmol) and cooled to 0° C. In a separate flask, iodosobenzene diacetate (1.581 g, 4.91 mmol) was dissolved in methanol (8 mL) and added to the reaction. The reaction was warmed to room temperature and stirred for one hour, then heated to 50° C. and stirred overnight. The reaction was concentrated and triturated with isopropanol. The solution was stirred for 10 minutes, then filtered. The solids were washed with isopropanol and vacuum dried to afford 6-bromo-4-methoxyisoquinolin-1(2H)-one as a tan solid. (ESI) 254.1 (M+H)$^+$.

STEP 2: 6-(BENZYLTHIO)-4-METHOXYISOQUINOLIN-1(2H)-ONE

The title compound was prepared in an analogous manner to that of Intermediate 1-chloro-N-(4-methoxybenzyl)-4-oxo-N-(1,3,4-thiadiazol-2-yl)-3,4-dihydrophthalazine-6-sulfonamide, Step 2, except that 6-bromo-4-methoxyisoquinolin-1(2H)-one was used instead of 6-bromo-4-fluoroisoquinolin-1(2H)-one to afford 6-(benzylthio)-4-methoxyisoquinolin-1(2H)-one as a brown solid. (ESI) 298.3 (M+H)$^+$.

STEP 3: 6-(BENZYLTHIO)-1-CHLORO-4-METHOXYISOQUINOLINE

A vial was charged with 6-(benzylthio)-4-methoxyisoquinolin-1(2H)-one (0.933 g, 3.14 mmol) and DCE (15.69 ml). POCl3 (0.585 ml, 6.27 mmol) was added and the reaction was stirred overnight at 90° C. The reaction was diluted with ethyl acetate and washed with water. The aqueous layer was extracted with ethyl acetate, and the combined organic layers were dried with sodium sulfate, filtered, and concentrated to afford crude 6-(benzylthio)-1-chloro-4-methoxyisoquinoline as a brown solid. (ESI) 316.3 (M+H)$^+$.

STEP 4:
6-(BENZYLTHIO)-1-CHLOROISOQUINOLIN-4-OL 6-(Benzylthio)-1-chloro-4-methoxyisoquinoline (0.400 g, 1.267 mmol) was dissolved in DCM (12.67 ml) and cooled to 0° C. Boron tribromide (0.487 ml, 5.06 mmol) was added and the reaction was stirred for 30 minutes, then warmed to room temperature and stirred overnight. The reaction was cooled to 0° C. and carefully quenched with saturated sodium bicarbonate solution. The reaction diluted with ethyl acetate and the layers were separated. The aqueous layer was extracted with ethyl acetate, and the combined organic layers were dried with sodium sulfate, filtered, and concentrated to afford crude 6-(benzylthio)-1-chloroisoquinolin-4-ol as an orange solid. (ESI) 302.1 (M+H)$^+$.

STEP 5:
1-CHLORO-4-HYDROXYISOQUINOLINE-6-SULFONYL CHLORIDE

A RBF was charged with 6-(benzylthio)-1-chloroisoquinolin-4-ol (0.280 g, 0.928 mmol), DCM (8.84 ml), acetic acid (0.221 ml), and water (0.221 ml) to give a thin suspension. The flask was cooled in an ice-bath for 10 min, then sulfuryl chloride (0.226 ml, 2.78 mmol) was added in one portion, leading to a solution. The reaction was stirred for 30 minutes, then warmed to RT and stirred for one hour. The reaction was concentrated and purified via column chromatography (RediSep Gold 40 g silica gel column, gradient elution 0-100% EtOAc:Heptane) to afford 1-chloro-4-hydroxyisoquinoline-6-sulfonyl chloride as a light pink solid. (ESI) 280.1 (M+H)⁺.

STEP 6: 1-CHLORO-4-HYDROXY-N-(ISOXAZOL-3-YL)-N-(4-METHOXYBENZYL)ISOQUINOLINE-6-SULFONAMIDE

A flask was charged with 1-chloro-4-hydroxyisoquinoline-6-sulfonyl chloride (1.3 g, 4.67 mmol), N-(4-methoxybenzyl)isoxazol-3-amine (1.002 g, 4.91 mmol), and THF (31.2 ml) and cooled to −78° C. in a dry ice/acetone bath for 10 minutes. LHMDS (1.0M in THF) (9.82 ml, 9.82 mmol) was added dropwise and the reaction was stirred for 30 minutes. The reaction was warmed to room temperature and quenched with saturated ammonium chloride solution, diluted with ethyl acetate and washed with water. The aqueous layer was extracted three times with ethyl acetate, and the combined organic layers were dried with sodium sulfate, filtered, and concentrated. The material was dissolved in ethyl acetate and loaded onto an silica cartridge, affording a yellow solid on top. The solid was collected and set aside. The remaining material was purified by chromatography on a 40-g Redi-Sep Gold column with 0-100% EtOAc/Heptane and combined with the previously isolated material to afford 1-chloro-4-hydroxy-N-(isoxazol-3-yl)-N-(4-methoxybenzyl)isoquinoline-6-sulfonamide (1.24 g, 2.78 mmol, 59.5% yield) as a light yellow solid. m/z (ESI) 446.1 (M+H)⁺.

STEP 7: 1-(4-CHLORO-5-FLUORO-2-METHOXYPHENYL)-4-HYDROXY-N-(ISOXAZOL-3-YL)-N-(4-METHOXYBENZYL)ISOQUINOLINE-6-SULFONAMIDE

A microwave vial was charged with 1-chloro-4-hydroxy-N-(isoxazol-3-yl)-N-(4-methoxybenzyl)isoquinoline-6-sulfonamide (0.250 g, 0.561 mmol), 2-(4-chloro-5-fluoro-2-methoxyphenyl)-4,4,5,5-tetramethyl-1,3,2-dioxaborolane (0.241 g, 0.841 mmol, HDH Pharma), tetrakis(triphenylphosphine)palladium(0) (0.065 g, 0.056 mmol), and potassium carbonate (0.387 g, 2.80 mmol). Dioxane (2.80 ml) and Water (0.934 ml) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 0-100% EtOAc:Heptane) to afford 1-(4-chloro-5-fluoro-2-methoxyphenyl)-4-hydroxy-N-(isoxazol-3-yl)-N-(4-methoxybenzyl)isoquinoline-6-sulfonamide (0.319 g, 0.560 mmol, 100% yield) as a yellow solid. m/z (ESI) 570.2 (M+H)⁺.

STEP 8: 1-(2-FLUORO-5-METHOXY-3'-(TRIFLUOROMETHYL)-[1,1'-BIPHENYL]-4-YL)-4-HYDROXY-N-(ISOXAZOL-3-YL)ISOQUINOLINE-6-SULFONAMIDE

A microwave vial was charged with 1-(4-chloro-5-fluoro-2-methoxyphenyl)-4-hydroxy-N-(isoxazol-3-yl)-N-(4-methoxybenzyl)isoquinoline-6-sulfonamide (0.075 g, 0.132 mmol), (3-(trifluoromethyl)phenyl)boronic acid (0.037 g, 0.197 mmol), SPhos Precatalyst (4.98 mg, 6.58 µmol), dicyclohexyl(2',6'-dimethoxy-[1,1'-biphenyl]-2-yl)phosphine (2.70 mg, 6.58 µmol), and potassium phosphate (0.084 g, 0.395 mmol). The vial was flushed with Ar (g), then Dioxane (1.097 mL) and Water (0.219 mL) were added. The reaction was microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(2-fluoro-5-methoxy-3'-(trifluoromethyl)-[1,1'-biphenyl]-4-yl)-4-hydroxy-N-(isoxazol-3-yl)-N-(4-methoxybenzyl)isoquinoline-6-sulfonamide. The material was dissolved in neat TFA (1 mL, 12.98 mmol) and stirred at 80° C. for one hour. The reaction was concentrated and purified via column chromatography (RediSep Gold 12 g, gradient elution 0-75% [3:1 EtOAc/EtOH]:Heptane) to afford 1-(2-fluoro-5-methoxy-3'-(trifluoromethyl)-[1,1'-biphenyl]-4-yl)-4-hydroxy-N-(isoxazol-3-yl)isoquinoline-6-sulfonamide (0.046 g, 0.082 mmol, 62.5% yield) as a yellow solid. ¹H NMR (400 MHz, DMSO-d₆) δ=11.85 (br. s., 1 H), 11.20 (br. s., 1 H), 8.74 (t, J=1.3 Hz, 1 H), 8.71 (s, 1 H), 8.29 (s, 1 H), 8.04-7.98 (m, 2 H), 7.95-7.90 (m, 1 H), 7.87-7.75 (m, 3 H), 7.39-7.30 (m, 2H), 6.47 (t, J=1.3 Hz, 1 H), 3.71 (s, 3 H). m/z (ESI) 560.2 (M+H)⁺.

Example 17 (Method 17)

1-(2-CHLORO-3'-FLUORO-5-METHOXY-[1,1'-BIPHENYL]-4-YL)-4-HYDROXY-N-(ISOXAZOL-3-YL)ISOQUINOLINE-6-SULFONAMIDE

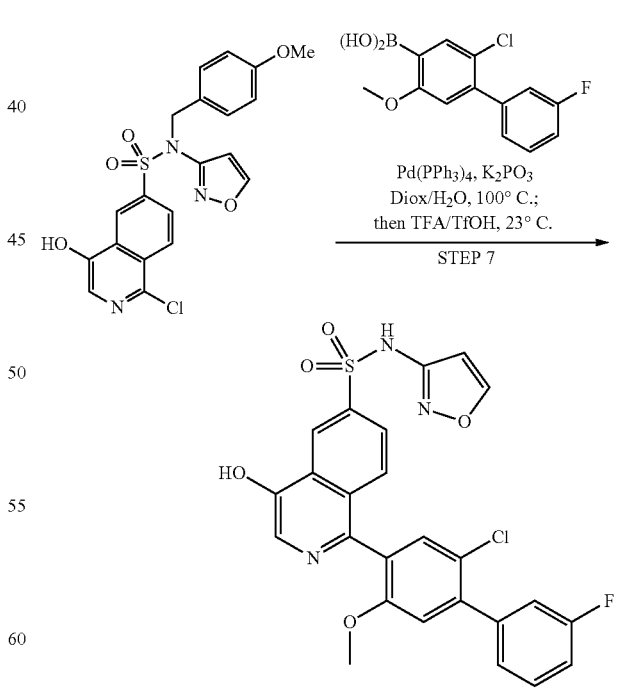

1-chloro-4-hydroxy-N-(isoxazol-3-yl)-N-(4-methoxybenzyl)isoquinoline-6-sulfonamide was made via Method 16, Steps 1-6. Step 7 continued as follows: a microwave vial was charged with 1-chloro-4-hydroxy-N-(isoxazol-3-yl)-N-

(4-methoxybenzyl)isoquinoline-6-sulfonamide (0.200 g, 0.449 mmol), (2-chloro-3'-fluoro-5-methoxy-[1,1'-biphenyl]-4-yl)boronic acid (0.138 g, 0.493 mmol), tetrakis(triphenylphosphine)palladium(0) (0.052 g, 0.045 mmol), and potassium carbonate (0.310 g, 2.243 mmol). Dioxane (2.243 ml) and Water (0.748 ml) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(2-chloro-3'-fluoro-5-methoxy-[1,1'-biphenyl]-4-yl)-4-hydroxy-N-(isoxazol-3-yl)-N-(4-methoxybenzyl)isoquinoline-6-sulfonamide The material was dissolved in DCM and TFA (0.1 ml, 1.298 mmol) was added, followed by triflic acid (0.1 ml, 1.126 mmol). The reaction was stirred for 30 minutes at room temperature. The reaction was concentrated and purified via column chromatography (RediSep Gold 12 g, gradient elution 0-10% MeOH:DCM) to afford 1-(2-chloro-3'-fluoro-5-methoxy-[1,1'-biphenyl]-4-yl)-4-hydroxy-N-(isoxazol-3-yl)isoquinoline-6-sulfonamide (0.049 g, 0.093 mmol, 20.77% yield) as a yellow solid. $^1$H NMR (400 MHz, DMSO-d$_6$) δ=11.86 (br. s., 1 H), 11.19 (s, 1 H), 8.73 (dd, J=1.7, 13.5 Hz, 2 H), 8.29 (s, 1 H), 7.93 (dd, J=2.0, 8.9 Hz, 1 H), 7.79 (d, J=8.8 Hz, 1 H), 7.63-7.54 (m, 1 H), 7.49 (s, 1 H), 7.46-7.40 (m, 2H), 7.35-7.28 (m, 1 H), 7.23 (s, 1 H), 6.47 (d, J=1.8 Hz, 1 H), 3.70 (s, 3 H). m/z (ESI) 526.1 (M+H)+.

Example 18 (Method 18)

1-(3'-FLUORO-3-METHOXY-[1,1'-BIPHENYL]-4-YL)-4-OXO-N-(1,3,4-THIADIAZOL-2-YL)-3,4-DIHYDROPHTHALAZINE-6-SULFONAMIDE

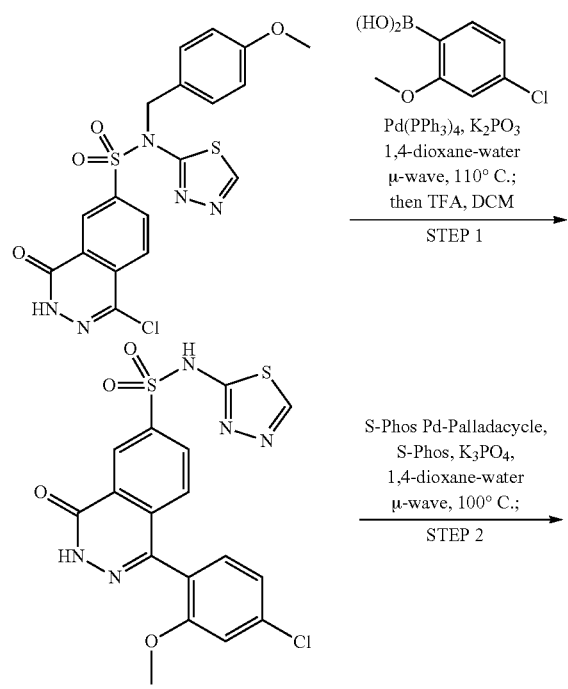

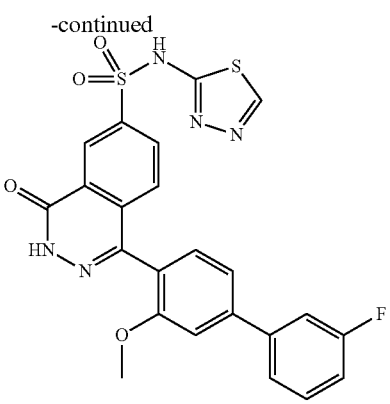

STEP 1: 1-(4-CHLORO-2-METHOXYPHENYL)-4-OXO-N-(1,3,4-THIADIAZOL-2-YL)-3,4-DIHYDROPHTHALAZINE-6-SULFONAMIDE

A microwave vial was charged with 1-chloro-N-(4-methoxybenzyl)-4-oxo-N-(1,3,4-thiadiazol-2-yl)-3,4-dihydrophthalazine-6-sulfonamide (0.072 g, 0.155 mmol), (4-chloro-2-methoxyphenyl)boronic acid (0.032 g, 0.171 mmol), potassium carbonate (0.064 g, 0.466 mmol), and Pd(Ph3P)4 (0.018 g, 0.016 mmol). The vial was flushed with Ar (g), then Dioxane (1.164 ml) and Water (0.388 ml) were added. The reaction was microwaved at 110° C. for three hours. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(4-chloro-2-methoxyphenyl)-N-(4-methoxybenzyl)-4-oxo-N-(1,3,4-thiadiazol-2-yl)-3,4-dihydrophthalazine-6-sulfonamide. The material was dissolved in DCM and TFA (0.15 ml, 1.947 mmol) was added. The reaction was stirred overnight at room temperature. The reaction was concentrated and purified via column chromatography (RediSep Gold 12 g, gradient elution 0-10% MeOH:DCM) to afford 1-(4-chloro-2-methoxyphenyl)-4-oxo-N-(1,3,4-thiadiazol-2-yl)-3,4-dihydrophthalazine-6-sulfonamide (0.019 g, 0.042 mmol, 27.2% yield) as a white solid. m/z (ESI) 450.0 (M+H)$^+$.

STEP 2: 1-(3'-FLUORO-3-METHOXY-[1,1'-BIPHENYL]-4-YL)-4-OXO-N-(1,3,4-THIADIAZOL-2-YL)-3,4-DIHYDROPHTHALAZINE-6-SULFONAMIDE

A vial was charged with 1-(4-chloro-2-methoxyphenyl)-4-oxo-N-(1,3,4-thiadiazol-2-yl)-3,4-dihydrophthalazine-6-sulfonamide (0.019 g, 0.042 mmol), (3-fluorophenyl)boronic acid (0.012 g, 0.084 mmol), dicyclohexyl(2',6'-dimethoxy-[1,1'-biphenyl]-2-yl)phosphine (0.867 mg, 2.112 µmol), chloro(2-dicyclohexylphosphino-2',6'-dimethoxy-1,1'-biphenyl)[2-(2-aminoethylphenyl)]palladium(ii) dichloromethane (1.600 mg, 2.112 µmol), and potassium phosphate (0.027 g, 0.127 mmol). The vial was flushed with Ar (g), then 1,4-dioxane (0.256 ml) and Water (0.026 ml) were added in sequence. The vial was sealed and microwaved at 100° C. for two hours. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-10% MeOH:DCM) to afford 1-(3'-fluoro-3-methoxy-[1,1'-biphenyl]-4- yl)-4-oxo-N-(1,3,4-thiadiazol-2-yl)-3,4-dihydrophthalazine-6-sulfonamide (0.013 g, 0.026 mmol, 60.4% yield) as a white solid. $^1$H NMR (400 MHz, DMSO-$d_6$) δ=13.09 (br. s., 1 H), 8.79 (br. s., 1 H), 8.61 (br. s., 1 H), 8.18 (d, J=9.3 Hz, 1 H), 7.68 (br. s., 2 H), 7.60-7.39 (m, 5 H), 7.32-7.20 (m, J=7.9 Hz, 1 H), 3.81 (br. s., 3 H). m/z (ESI) 510.1 (M+H)$^+$.

Example 19 (Method 19)

4-(2,3'-DICHLORO-4'-FLUORO-5-METHOXY-[1,1'-BIPHENYL]-4-YL)-N-(ISOXAZOL-3-YL)QUINAZOLINE-7-SULFONAMIDE

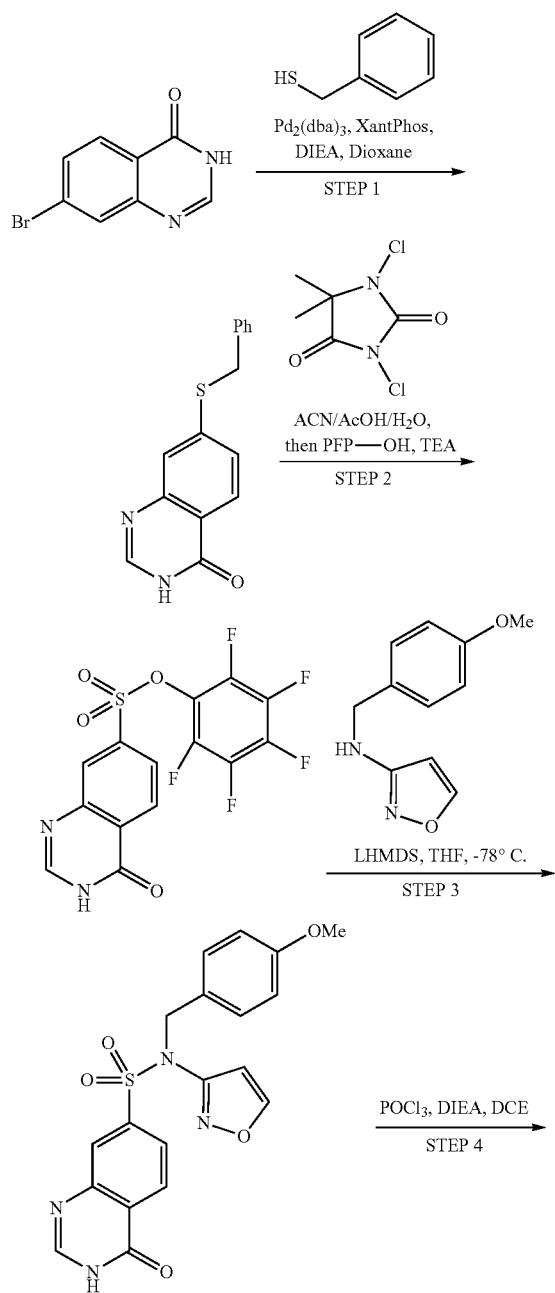

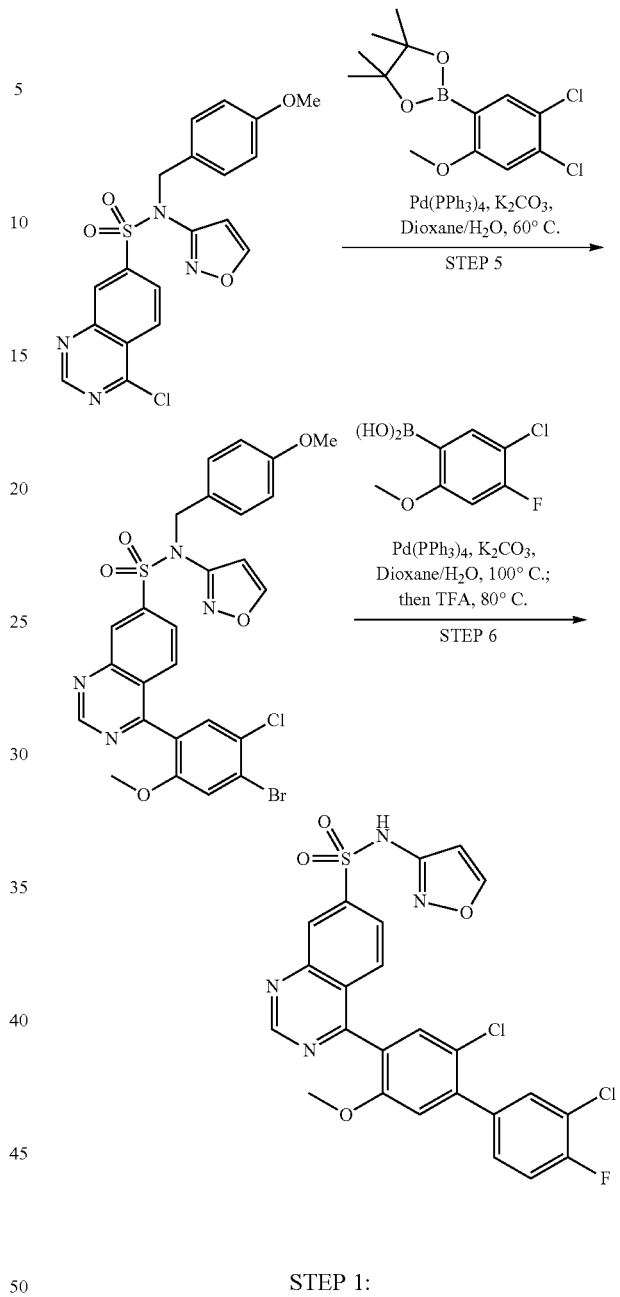

STEP 1:
7-(BENZYLTHIO)QUINAZOLIN-4(3H)-ONE

A RBF was charged with 7-bromoquinazolin-4(3H)-one (10 g, 44.4 mmol, Milestone Pharmatech), xantphos (1.286 g, 2.222 mmol), and pd2(dba)3 (1.017 g, 1.111 mmol). The flask was flushed with Ar (g), then dioxane (89 ml), benzyl mercaptan (5.52 ml, 46.7 mmol), and n,n-diisopropylethylamine (15.52 ml, 89 mmol) were added in sequence. The reaction was fitted with a reflux condenser, heated to 90° C., and stirred for one hour. The reaction was diluted with water and filtered. The solids were washed thoroughly with water, then air dried for several hours and triturated with ethyl acetate. After stirring overnight, the solids were filtered, washed with ethyl acetate, and vacuum dried over a nitrogen blanket overnight to afford 7-(benzylthio)quinazolin-4(3H)-one as a light yellow solid. m/z (ESI) 269.1 (M+H)$^+$.

STEP 2: PERFLUOROPHENYL 4-OXO-3,4-DIHYDROQUINAZOLINE-7-SULFONATE

A RBF was charged with 7-(benzylthio)quinazolin-4 (3H)-one (1.0 g, 3.73 mmol), acetonitrile (35.1 ml), acetic acid (1.315 ml), and water (0.877 ml) to give a thin suspension. The flask was cooled in an ice-bath for 10 min, then 1,3-dichloro-5,5-dimethylimidazolidine-2,4-dione (1.468 g, 7.45 mmol) was added in one portion, leading to a solution. The reaction was stirred for one hour. 2,3,4,5,6-Pentafluorophenol (0.781 ml, 7.45 mmol) was added followed by dropwise addition of TEA (1.299 ml, 9.32 mmol). The reaction was stirred for 90 minutes. The reaction was concentrated, diluted with ethyl acetate and washed with water. The aqueous layer was extracted with ethyl acetate, and the combined organic layers were dried with sodium sulfate, filtered, and concentrated. The material was dissolved in DCM and loaded onto a silica gel cartridge, leaving a white solid on top. The solid was scraped out of the cartridge and set aside. The remaining material was purified via column chromatography (RediSep Gold 40 g, gradient elution 0-50% EtOAc:Heptane) and combined with the previously isolated material to afford perfluorophenyl 4-oxo-3,4-dihydroquinazoline-7-sulfonate as a white solid. m/z (ESI) 393.0 (M+H)$^+$.

STEP 3: N-(ISOXAZOL-3-YL)-N-(4-METHOXYBENZYL)-4-OXO-3,4-DIHYDROQUINAZOLINE-7-SULFONAMIDE

A solution of N-(4-methoxybenzyl)isoxazol-3-amine (1.093 g, 5.35 mmol) in THF (19.61 ml) was cooled in a dry ice-acetone bath for 5 min. Lithium bis(trimethylsilyl)amide (1M in THF) (5.61 ml, 5.61 mmol) was added dropwise, then the flask was removed from the cooling bath for 5 min. The flask was again cooled into a dry ice-acetone bath for 20 min, resulting in the formation of a thick slurry. A solution of perfluorophenyl 4-oxo-3,4-dihydroquinazoline-7-sulfonate (2.0 g, 5.10 mmol) in THF (20 mL) was added dropwise, and the reaction was stirred for 30 minutes. An additional equivalent of lithium bis(trimethylsilyl)amide (1M in THF) (5.61 ml, 5.61 mmol) was added and the reaction was stirred for 30 minutes. The reaction was warmed to room temperature and quenched with saturated ammonium chloride solution, diluted with ethyl acetate and washed with water. The aqueous layer was extracted three times with ethyl acetate, and the combined organic layers were dried with sodium sulfate, filtered, and concentrated. The material was triturated in DCM and filtered. The solids were washed with DCM and vacuum dried to afford N-(isoxazol-3-yl)-N-(4-methoxybenzyl)-4-oxo-3,4-dihydroquinazoline-7-sulfonamide (1.89 g, 4.58 mmol, 90% yield) as a light yellow solid. m/z (ESI) 413.1 (M+H)$^+$.

STEP 4: 4-CHLORO-N-(ISOXAZOL-3-YL)-N-(4-METHOXYBENZYL)QUINAZOLINE-7-SULFONAMIDE

N-(isoxazol-3-yl)-N-(4-methoxybenzyl)-4-oxo-3,4-dihydroquinazoline-7-sulfonamide (0.920 g, 2.231 mmol) was dissolved in DCE (5 mL). Hunig's base (1.169 ml, 6.69 mmol) was added, followed by phosphoryl trichloride (0.417 ml, 4.46 mmol). The reaction was stirred at 80° C. overnight. 2 mL of Hunig's base was added followed by a catalytic amount of pyridine. Water was added and the biphasic solution was stirred for five minutes. The layers were separated and the aqueous layer was extracted with ethyl acetate. The combined organic layers were washed with brine, dried with sodium sulfate, filtered, and concentrated. The material was purified via column chromatography (RediSep Gold 40 g, gradient elution 0-50% EtOAc:Heptane w/1% TEA modifier) to afford 4-chloro-N-(isoxazol-3-yl)-N-(4-methoxybenzyl)quinazoline-7-sulfonamide (0.235 g, 0.545 mmol, 24.45% yield) as a light yellow solid. m/z (ESI) 431.1 (M+H)$^+$.

STEP 5: 4-(4-BROMO-5-CHLORO-2-METHOXYPHENYL)-N-(ISOXAZOL-3-YL)-N-(4-METHOXYBENZYL)QUINAZOLINE-7-SULFONAMIDE

A vial was charged with 4-chloro-N-(isoxazol-3-yl)-N-(4-methoxybenzyl)quinazoline-7-sulfonamide (0.284 g, 0.659 mmol), (4-bromo-5-chloro-2-methoxyphenyl)boronic acid (0.175 g, 0.659 mmol), tetrakis(triphenylphosphine)palladium (0) (0.076 g, 0.066 mmol), and potassium carbonate (0.455 g, 3.30 mmol). Dioxane (3.30 ml) and Water (1.099 ml) were added and the reaction was stirred at 60° C. for two hours. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 4-(4-bromo-5-chloro-2-methoxyphenyl)-N-(isoxazol-3-yl)-N-(4-methoxybenzyl)quinazoline-7-sulfonamide (0.264 g, 0.429 mmol, 65.0% yield) as a white solid. m/z (ESI) 615.0 (M+H)$^+$.

STEP 6: 4-(2,3'-DICHLORO-4'-FLUORO-5-METHOXY-[1,1'-BIPHENYL]-4-YL)-N-(ISOXAZOL-3-YL)QUINAZOLINE-7-SULFONAMIDE

A vial was charged with 4-(4-bromo-5-chloro-2-methoxyphenyl)-N-(isoxazol-3-yl)-N-(4-methoxybenzyl)quinazoline-7-sulfonamide (0.065 g, 0.106 mmol), (3-chloro-4-fluorophenyl)boronic acid (0.018 g, 0.106 mmol), tetrakis(triphenylphosphine)palladium(0) (0.012 g, 10.55 µmol), and potassium carbonate (0.073 g, 0.528 mmol). Dioxane (0.528 mL) and Water (0.176 mL) were added and the reaction was stirred at 100° C. for 30 minutes. The reaction was diluted with ethyl acetate and washed with water. The aqueous layer was extracted with ethyl acetate, and the combined organic layers were dried with sodium sulfate, filtered, and concentrated. The material was dissolved in neat TFA (1 mL, 12.98 mmol) and stirred at 80° C. for one hour. The reaction was concentrated and purified via column chromatography (RediSep Gold 12 g, gradient elution 0-100% EtOAc:Heptane) to afford 4-(2,3'-dichloro-4'-fluoro-5-methoxy-[1,1'-biphenyl]-4-yl)-N-(isoxazol-3-yl) quinazoline-7-sulfonamide (0.016 g, 0.029 mmol, 27.8% yield) as a light yellow solid. $^1$H NMR (400 MHz, DMSO-d$_6$) δ=12.15-11.90 (m, 1 H), 9.53 (s, 1 H), 8.75 (br. s., 1 H), 8.51 (br. s., 1 H), 8.16-7.91 (m, 2 H), 7.83 (d, J=5.5 Hz, 1 H), 7.72-7.51 (m, 3 H), 7.35 (s, 1 H), 6.53 (br. s., 1 H), 3.74 (s, 3 H). m/z (ESI) 545.0 (M+H)$^+$.

Example 20 (Method 20)

4-(5-CYANO-4-(5-FLUORO-2-METHOXYPYRIDIN-3-YL)-2-METHOXYPHENYL)-N-(1,3,4-THIADIAZOL-2-YL)QUINAZOLINE-7-SULFONAMIDE

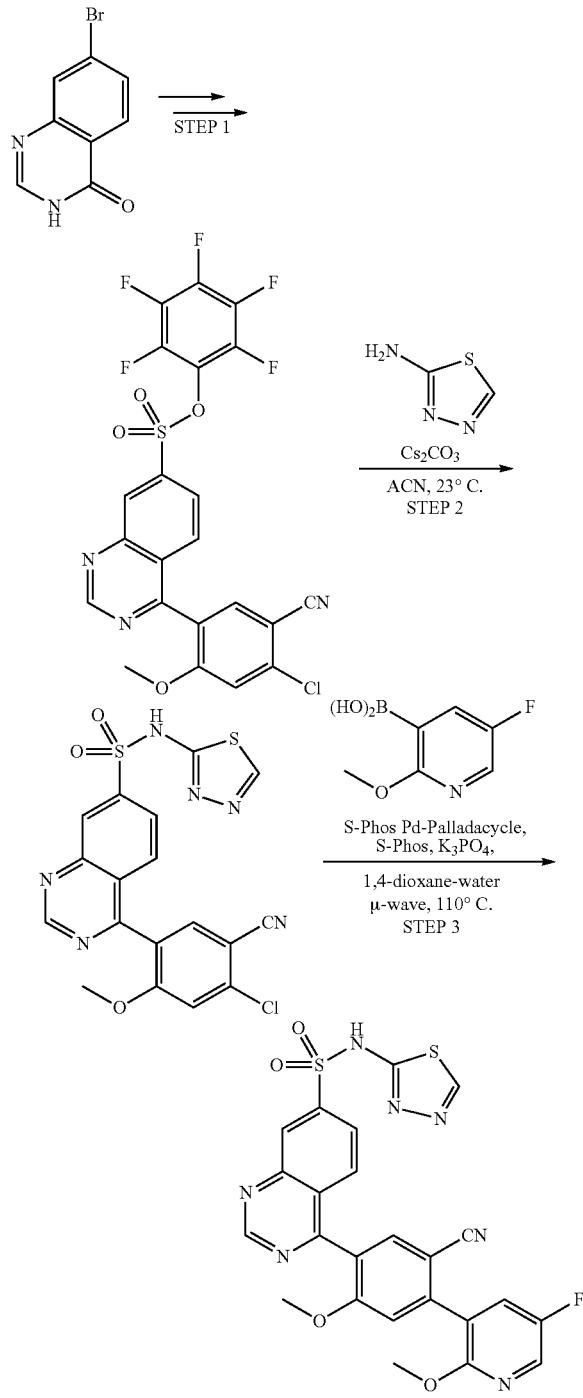

STEP 1: PERFLUOROPHENYL 4-(4-CHLORO-5-CYANO-2-METHOXYPHENYL)QUINAZOLINE-7-SULFONATE

The title compound was prepared in an analogous manner to that of Method 15, Steps 1-4, except that 2-chloro-4-methoxy-5-(4,4,5,5-tetramethyl-1,3,2-dioxaborolan-2-yl) benzonitrile was used instead of (2-chloro-3'-fluoro-5-methoxy-[1,1'-biphenyl]-4-yl)boronic acid in Step 4 to afford perfluorophenyl 4-(4-chloro-5-cyano-2-methoxyphenyl)quinazoline-7-sulfonate as a yellow oily foam. m/z (ESI) 542.0 (M+H)$^+$.

STEP 2: 4-(4-CHLORO-5-CYANO-2-METHOXYPHENYL)-N-(1,3,4-THIADIAZOL-2-YL)QUINAZOLINE-7-SULFONAMIDE

A vial was charged with perfluorophenyl 4-(4-chloro-5-cyano-2-methoxyphenyl)quinazoline-7-sulfonate (1.00 g, 1.846 mmol), 1,3,4-thiadiazol-2-amine (0.205 g, 2.030 mmol), and cesium carbonate (1.804 g, 5.54 mmol). The vial was flushed with Ar (g), then acetonitrile (9.23 ml) was added. The reaction was stirred overnight at room temperature. The mixture was diluted with EtOAc and 1 N aq. HCl. The layers were separated, and the aq. layer was extracted with EtOAc (2x). The combined organic extracts were dried over sodium sulfate, filtered, and concentrated. The material was purified via column chromatography (RediSep Gold 12 g, gradient elution 0-5% MeOH:DCM) to afford 4-(4-chloro-5-cyano-2-methoxyphenyl)-N-(1,3,4-thiadiazol-2-yl)quinazoline-7-sulfonamide (0.404 g, 0.880 mmol, 47.7% yield) as an light yellow solid. m/z (ESI) 459.0 (M+H)$^+$.

STEP 3: 4-(5-CYANO-4-(5-FLUORO-2-METHOXYPYRIDIN-3-YL)-2-METHOXYPHENYL)-N-(1,3,4-THIADIAZOL-2-YL)QUINAZOLINE-7-SULFONAMIDE

A vial was charged with 4-(4-chloro-5-cyano-2-methoxyphenyl)-N-(1,3,4-thiadiazol-2-yl)quinazoline-7-sulfonamide (0.060 g, 0.131 mmol), (5-fluoro-2-methoxypyridin-3-yl)boronic acid (0.045 g, 0.261 mmol, Combi-Blocks), dicyclohexyl(2',6'-dimethoxy-[1,1'-biphenyl]-2-yl)phosphine (2.68 mg, 6.54 μmol), chloro(2-dicyclohexylphosphino-2',6'-dimethoxy-1,1'-biphenyl)[2-(2-aminoethylphenyl)]palladium(ii) dichloromethane (4.95 mg, 6.54 μmol), and potassium phosphate (0.083 g, 0.392 mmol). The vial was flushed with Ar (g), then 1,4-dioxane (0.594 ml) and Water (0.059 ml) were added in sequence. The vial was sealed and microwaved at 110° C. for one hour. The reaction was diluted with DCM and washed with water. The aqueous layer was extracted with DCM, and the combined organic layers were dried with sodium sulfate, filtered, and concentrated. The material was purified via column chromatography (RediSep Gold 12 g, gradient elution 0-5% MeOH: DCM) to afford 4-(5-cyano-4-(5-fluoro-2-methoxypyridin-3-yl)-2-methoxyphenyl)-N-(1,3,4-thiadiazol-2-yl) quinazoline-7-sulfonamide (0.038 g, 0.069 mmol, 52.9% yield) as a light yellow solid. $^1$H NMR (400 MHz, DMSO-$d_6$) δ=9.52 (s, 1 H), 8.80 (s, 1 H), 8.42 (d, J=1.7 Hz, 1 H), 8.37 (d, J=3.0 Hz, 1 H), 8.05 (s, 1 H), 8.03 (d, J=2.7 Hz, 1 H), 8.02-8.00 (m, 1 H), 7.91 (d, J=8.8 Hz, 1 H), 7.54 (s, 1 H), 3.93 (s, 3 H), 3.82 (s, 3 H). m/z (ESI) 550.1 (M+H)$^+$.

Example 21 (Method 21)

1-(2-CHLORO-3'-FLUORO-5-METHOXY-[1,1'-BIPHENYL]-4-YL)-N-(ISOXAZOL-3-YL)-3-METHYL-4-OXO-3,4-DIHYDROPHTHALAZINE-6-SULFONAMIDE

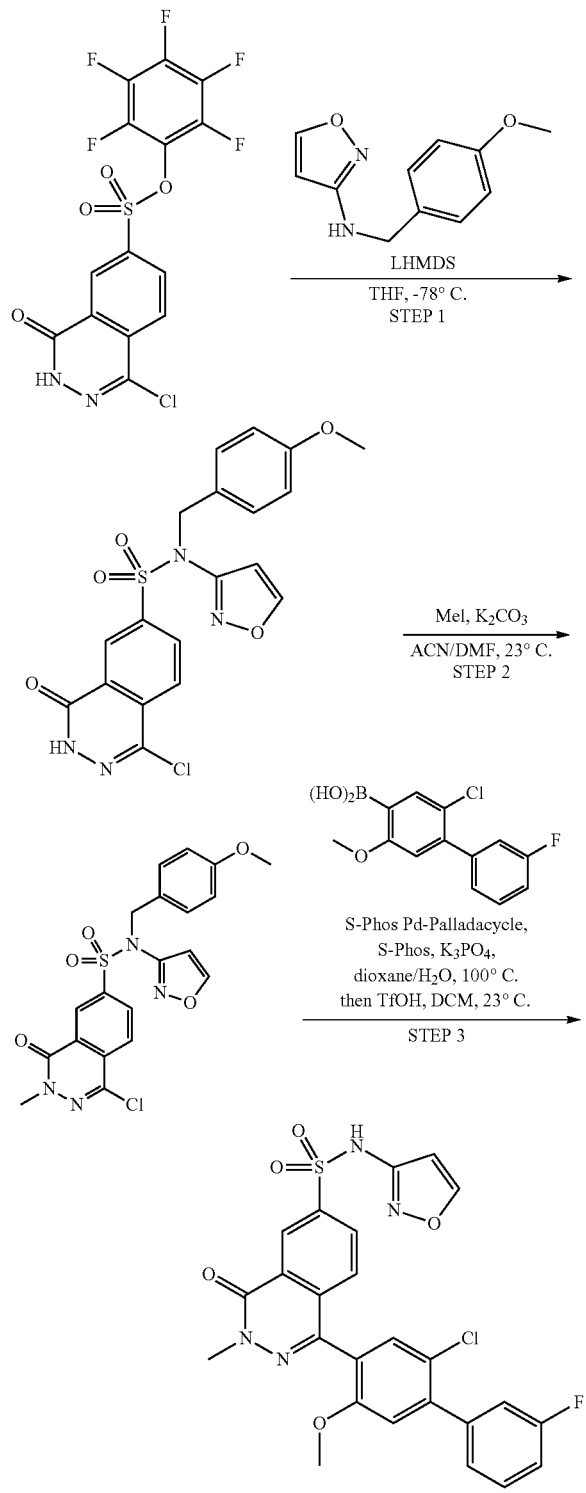

STEP 1: 1-CHLORO-N-(ISOXAZOL-3-YL)-N-(4-METHOXYBENZYL)-4-OXO-3,4-DIHYDROPHTHALAZINE-6-SULFONAMIDE

The title compound was prepared in an analogous manner to that of Intermediate 1-chloro-N-(4-methoxybenzyl)-4-oxo-N-(1,3,4-thiadiazol-2-yl)-3,4-dihydrophthalazine-6-sulfonamide, except that N-(4-methoxybenzyl)isoxazol-3-amine was used instead of N-(4-methoxybenzyl)-1,3,4-thiadiazol-2-amine to afford 1-chloro-N-(isoxazol-3-yl)-N-(4-methoxybenzyl)-4-oxo-3,4-dihydrophthalazine-6-sulfonamide as an off-white solid. m/z (ESI) 447.0 (M+H)$^+$.

STEP 2: 1-CHLORO-N-(ISOXAZOL-3-YL)-N-(4-METHOXYBENZYL)-3-METHYL-4-OXO-3,4-DIHYDROPHTHALAZINE-6-SULFONAMIDE

A vial was charged with 1-chloro-N-(isoxazol-3-yl)-N-(4-methoxybenzyl)-4-oxo-3,4-dihydrophthalazine-6-sulfonamide (2.3 g, 5.15 mmol), potassium carbonate (2.134 g, 15.44 mmol), DMF (2.340 ml), and Acetonitrile (23.40 ml). Iodomethane (0.644 ml, 10.29 mmol) was added and the reaction was stirred overnight at room temperature. The reaction was concentrated and partitioned between ethyl acetate and water. The aqueous layer was extracted twice with ethyl acetate, and the combined organic layers were washed three times with water, washed with brine, dried with sodium sulfate, filtered, and concentrated to afford crude 1-chloro-N-(isoxazol-3-yl)-N-(4-methoxybenzyl)-3-methyl-4-oxo-3,4-dihydrophthalazine-6-sulfonamide (1.96 g, 4.25 mmol, 83% yield) as an orange solid. m/z (ESI) 483.0 (M+Na)$^+$.

STEP 3: 1-(2-CHLORO-3'-FLUORO-5-METHOXY-[1,1'-BIPHENYL]-4-YL)-N-(ISOXAZOL-3-YL)-3-METHYL-4-OXO-3,4-DIHYDROPHTHALAZINE-6-SULFONAMIDE

A microwave vial was charged with 1-chloro-N-(isoxazol-3-yl)-N-(4-methoxybenzyl)-3-methyl-4-oxo-3,4-dihydrophthalazine-6-sulfonamide (0.450 g, 0.976 mmol), (2-chloro-3'-fluoro-5-methoxy-[1,1'-biphenyl]-4-yl)boronic acid (0.301 g, 1.074 mmol), SPhos Precatalyst (0.037 g, 0.049 mmol), dicyclohexyl(2',6'-dimethoxy-[1,1'-biphenyl]-2-yl)phosphine (0.020 g, 0.049 mmol), and potassium phosphate (0.622 g, 2.93 mmol). The vial was flushed with Ar (g), then Dioxane (3.25 ml) and Water (0.651 ml) were added. The reaction was microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(2-chloro-3'-fluoro-5-methoxy-[1,1'-biphenyl]-4-yl)-N-(isoxazol-3-yl)-N-(4-methoxybenzyl)-3-methyl-4-oxo-3,4-dihydrophthalazine-6-sulfonamide. The material was dissolved in DCM and triflic acid (0.30 ml, 3.38 mmol) was added. The reaction was stirred for one hour at room temperature. The reaction was concentrated and purified via column chromatography (RediSep Gold 40 g, gradient elution 25-75% [3:1 EtOAc/EtOH]:Heptane followed by a 10% MeOH:DCM flush). The isolated material was triturated in ethyl acetate and filtered. The solids were washed with ethyl acetate and vacuum dried under a nitrogen blanket overnight to afford 1-(2-chloro-3'-fluoro-5-methoxy-[1,1'-biphenyl]-4-yl)-N-(isoxazol-3-yl)-3-methyl-4-oxo-3,4-dihydrophthalazine-6-sulfonamide (0.246 g, 0.455 mmol, 46.6% yield) as a white solid. $^1$H NMR (400 MHz, DMSO-d$_6$) δ=11.98 (br. s., 1 H), 8.77 (d, J=1.9 Hz, 1 H), 8.75 (dd, J=0.5, 2.0 Hz, 1 H), 8.26 (dd, J=2.0, 8.6 Hz, 1 H), 7.64 (dd, J=0.5, 8.5 Hz, 1 H), 7.62-7.55 (m, 2 H), 7.44-7.39 (m, 2 H), 7.35-7.29 (m, 1 H), 7.27 (s, 1 H), 6.47 (d, J=1.9 Hz, 1 H), 3.79 (s, 3 H), 3.75 (s, 3 H). m/z (ESI) 541.1 (M+H)$^+$.

Example 22 (Method 22)

1-(2-CYANO-5-METHOXY-3'-(TRIFLUOROMETHYL)-[1,1'-BIPHENYL]-4-YL)-N-(ISOXAZOL-3-YL)ISOQUINOLINE-6-SULFONAMIDE

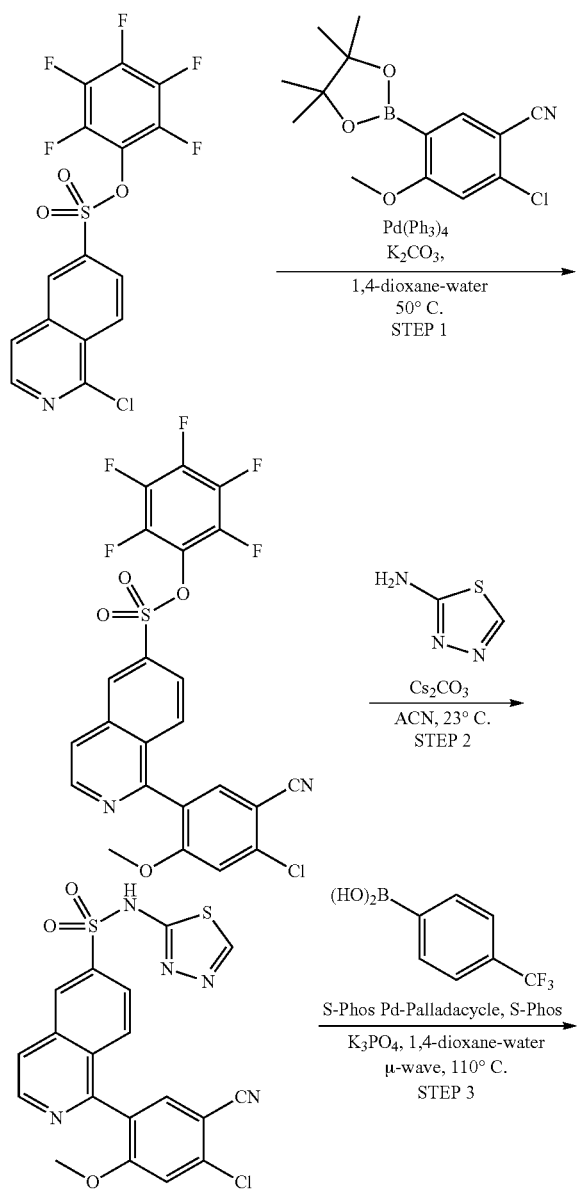

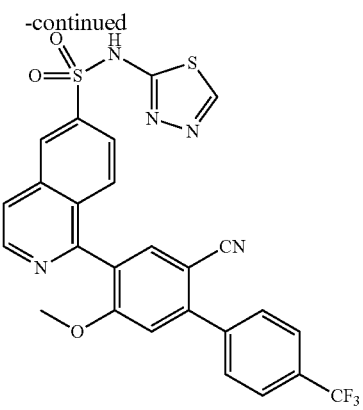

STEP 1: PERFLUOROPHENYL 1-(4-CHLORO-5-CYANO-2-METHOXYPHENYL)ISOQUINOLINE-6-SULFONATE

A RBF was charged with perfluorophenyl 1-chloroisoquinoline-6-sulfonate (7.734 g, 18.88 mmol), 2-chloro-4-methoxy-5-(4,4,5,5-tetramethyl-1,3,2-dioxaborolan-2-yl)benzonitrile (6.65 g, 22.65 mmol), potassium carbonate (7.83 g, 56.6 mmol), and tetrakistriphenylphosphinepalladium(0) (2.181 g, 1.888 mmol). The flask was flushed with Ar (g), then 1,4-dioxane (70.8 ml) and water (23.60 ml) were added. The flask was lowered into a 50° C. heating bath for 1 h. The mixture was diluted with water and EtOAc, and the organic layer was dried over sodium sulfate, filtered, and concentrated. The residue was purified by chromatography on silica gel (100-g Ultra SNAP column, with 5-50% EtOAc/Heptane) to give a light-yellow solid. The solid was taken up in heptane and filtered. The collected solid was washed with heptane (3×), dried under a stream of N$_2$ (g), then dried under vacuum to give perfluorophenyl 1-(4-chloro-5-cyano-2-methoxyphenyl)isoquinoline-6-sulfonate (7.0406 g, 13.02 mmol, 69.0% yield) as a light-yellow solid. m/z (ESI) 541.1 (M+H)$^+$.

STEP 2: 1-(4-CHLORO-5-CYANO-2-METHOXYPHENYL)-N-(1,3,4-THIADIAZOL-2-YL)ISOQUINOLINE-6-SULFONAMIDE

A flask was charged with perfluorophenyl 1-(4-chloro-5-cyano-2-methoxyphenyl)isoquinoline-6-sulfonate (2.58 g, 4.77 mmol), 1,3,4-thiadiazol-2-amine (4 ml, 5.72 mmol), and cesium carbonate (4.66 g, 14.31 mmol). Acetonitrile (47.7 ml) was added and the reaction was stirred for two hours at room temperature. The reaction was diluted with ethyl acetate and washed with 1N HCl solution. The aqueous layer was extracted with ethyl acetate, and the combined organic layers were dried with sodium sulfate, filtered, and concentrated. The material was dissolved in DCM and loaded onto a silica cartridge, leaving a solid on top. The solid was scraped out and set aside. The remaining material was purified via column chromatography (RediSep Gold 80 g, gradient elution 0-100% [3:1 EtOAc:EtOH]:Heptanes) and combined with the previously isolated material to afford 1-(4-chloro-5-cyano-2-methoxyphenyl)-N-(1,3,4-thiadiazol-2-yl)isoquinoline-6-sulfonamide (1.74 g, 3.80 mmol, 80% yield) as an off-white solid. m/z (ESI) 458.1 (M+H)+.

STEP 3: 1-(2-CYANO-5-METHOXY-4'-(TRIF-LUOROMETHYL)-[1,1'-BIPHENYL]-4-YL)-N-(1,3,4-THIADIAZOL-2-YL)ISOQUINOLINE-6-SULFONAMIDE

A vial was charged with 1-(2-cyano-5-methoxy-4'-(trifluoromethyl)-[1,1'-biphenyl]-4-yl)-N-(1,3,4-thiadiazol-2-yl)isoquinoline-6-sulfonamide (125 mg, 0.273 mmol), (4-(trifluoromethyl)phenyl)boronic acid (62 mg, 0.328 mmol), chloro(2-dicyclohexylphosphino-2',6'-dimethoxy-1,1'-biphenyl) [2-(2-aminoethylphenyl)]palladium(ii) dichloromethane (12 mg, 0.016 mmol), and potassium phosphate (209 mg, 0.983 mmol). The vial was flushed with Ar (g), then 1,4-dioxane (1.2 mL) and water (0.25 ml) were added. The vial was sealed and heated in a Biotage Initiator microwave reactor for 1 h at 120° C. The mixture was diluted with EtOAc and stirred for 1 h. The mixture was then filtered to give ca. 240 mg of an off-white solid. The solid was taken up in DMSO and filtered through a 0.2 micron filter. The filtrate was purified by reverse-phase HPLC (50-95% CH$_3$CN/H$_2$O with 0.1% TFA) The product fractions were partitioned between EtOAc and water. The aqueous layer was extracted with ethyl acetate, and the combined organic layers were dried with sodium sulfate, filtered, and concentrated to afford 1-(2-cyano-5-methoxy-4'-(trifluoromethyl)-[1,1'-biphenyl]-4-yl)-N-(1,3,4-thiadiazol-2-yl)isoquinoline-6-sulfonamide (0.096 g, 0.169 mmol, 51.6% yield) as a yellow solid. 1H NMR (500 MHz, DMSO-d6) δ ppm 3.17 (s, 1 H) 3.75 (s, 1 H) 3.80 (s, 3 H) 7.20 (br. s., 1 H) 7.34-7.41 (m, 2 H) 7.42-7.59 (m, 3 H) 7.72 (d, J=8.82 Hz, 1 H) 7.84-7.98 (m, 2 H) 8.09 (d, J=5.66 Hz, 1 H) 8.47 (s, 1 H) 8.61 (s, 1 H) 8.66 (d, J=5.66 Hz, 1 H). m/z (ESI) 551.2 (M+H)+

Example 23 (Method 23)

1-(5-CYANO-4-(3,3-DIFLUOROAZETIDIN-1-YL)-2-METHOXYPHENYL)-N-(ISOXAZOL-3-YL)ISOQUINOLINE-6-SULFONAMIDE

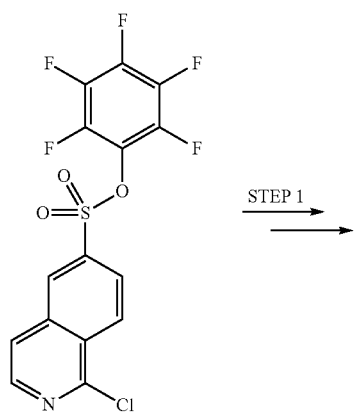

STEP 1

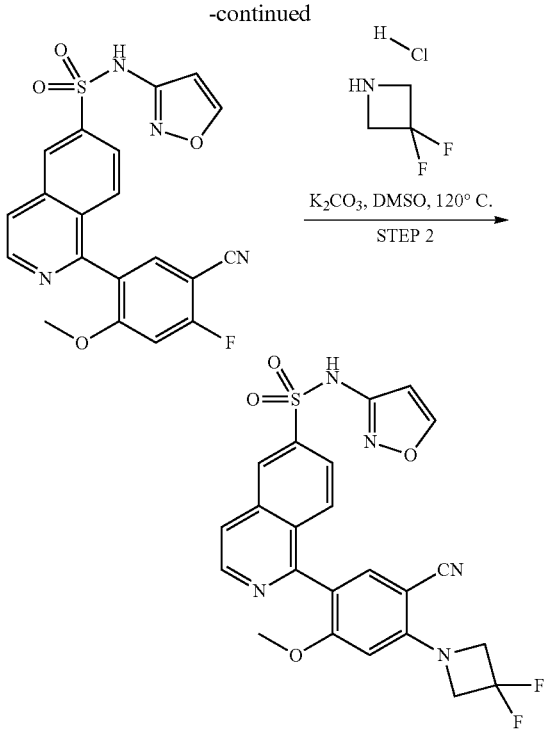

STEP 1: 1-(5-CYANO-4-FLUORO-2-METHOXYPHENYL)-N-(1,3,4-THIADIAZOL-2-YL)ISOQUINOLINE-6-SULFONAMIDE

The title compound was prepared in an analogous manner to that of Method 1, Step 1-2 except that 2-fluoro-4-methoxy-5-(4,4,5,5-tetramethyl-1,3,2-dioxaborolan-2-yl)benzonitrile was used instead of 2-chloro-4-methoxy-5-(4,4,5,5-tetramethyl-1,3,2-dioxaborolan-2-yl)benzonitrile to afford as an off-white solid. m/z (ESI) 425.1 (M+H)+.

STEP 2: 1-(5-CYANO-4-(3,3-DIFLUOROAZETIDIN-1-YL)-2-METHOXYPHENYL)-N-(ISOXAZOL-3-YL)ISOQUINOLINE-6-SULFONAMIDE

A vial was charged with 1-(5,6-dichloro-2-methoxypyridin-3-yl)-N-(1,3,4-thiadiazol-2-yl)isoquinoline-6-sulfonamide (0.060 g, 0.128 mmol), 3,3-difluoroazetidin hydrochloride (0.056 ml, 0.429 mmol), and potassium carbonate (0.053 g, 0.384 mmol). DMSO (0.641 ml) was added and the reaction was stirred at 120° C. for 24 hours. The reaction was diluted with ethyl acetate and washed with water. The aqueous layer was extracted with ethyl acetate, and the combined organic layers were dried with sodium sulfate, filtered, and concentrated. The material was purified via Gilson HPLC (25-70% MeCN:H2O w/0.1% TFA modifier). The product fractions were partitioned between ethyl acetate and water. The aqueous layer was extracted with ethyl acetate, and the combined organic layers were dried with sodium sulfate, filtered, and concentrated to afford 1-(5-cyano-4-(3,3-difluoroazetidin-1-yl)-2-methoxyphenyl)-N-(isoxazol-3-yl)isoquinoline-6-sulfonamide (0.089 g, 0.179 mmol, 83% yield) as a bright yellow solid. $^1$H NMR (400

MHz, DMSO-d$_6$) δ=11.92 (br. s., 1 H), 8.74 (d, J=1.9 Hz, 1 H), 8.70 (d, J=5.8 Hz, 1 H), 8.68 (d, J=2.0 Hz, 1 H), 8.16 (d, J=5.6 Hz, 1 H), 7.96-7.92 (m, 1 H), 7.87-7.83 (m, 1 H), 7.60 (s, 1 H), 6.49 (d, J=1.9 Hz, 1 H), 6.40 (s, 1 H), 4.71 (t, J=12.4 Hz, 4 H), 3.72 (s, 3 H). m/z (ESI) 498.2 (M+H)+.

Example 24 (Method 24)

1-(5-CYANO-4-(3,3-DIFLUOROAZETIDIN-1-YL)-2-METHOXYPHENYL)-N-(1,3,4-THIADIAZOL-2-YL)ISOQUINOLINE-6-SULFONAMIDE

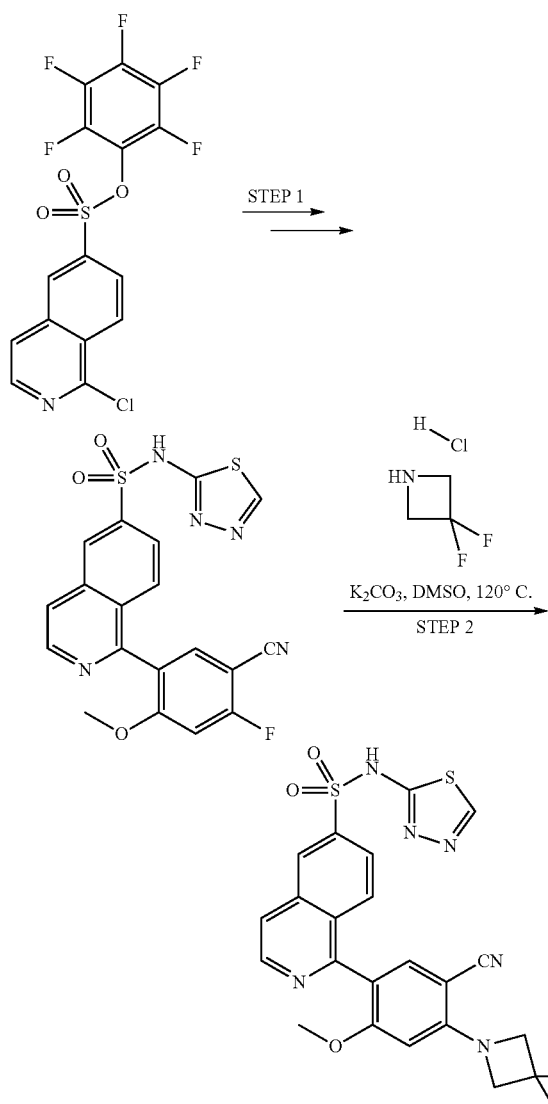

STEP 1: 1-(5-CYANO-4-FLUORO-2-METHOXYPHENYL)-N-(ISOXAZOL-3-YL)ISOQUINOLINE-6-SULFONAMIDE

The title compound was prepared in an analogous manner to that of Method 22, Step 1-2, where 2-fluoro-4-methoxy-5-(4,4,5,5-tetramethyl-1,3,2-dioxaborolan-2-yl)benzonitrile was used instead of 2-chloro-4-methoxy-5-(4,4,5,5-tetramethyl-1,3,2-dioxaborolan-2-yl)benzonitrile to afford 1-(5-cyano-4-fluoro-2-methoxyphenyl)-N-(1,3,4-thiadiazol-2-yl)isoquinoline-6-sulfonamide as an off-white solid. m/z (ESI) 442.1 (M+H)+.

STEP 2: 1-(5-CYANO-4-(3,3-DIFLUOROAZETIDIN-1-YL)-2-METHOXYPHENYL)-N-(1,3,4-THIADIAZOL-2-YL)ISOQUINOLINE-6-SULFONAMIDE

The title compound was prepared in an analogous manner to that of Method 23, Step 2 except that 1-(5-cyano-4-fluoro-2-methoxyphenyl)-N-(1,3,4-thiadiazol-2-yl)isoquinoline-6-sulfonamide was used instead of 1-(5-cyano-4-fluoro-2-methoxyphenyl)-N-(isoxazol-3-yl)isoquinoline-6-sulfonamide to afford 1-(5-cyano-4-(3,3-difluoroazetidin-1-yl)-2-methoxyphenyl)-N-(1,3,4-thiadiazol-2-yl)isoquinoline-6-sulfonamide as an off-white solid. $^1$H NMR (400 MHz, DMSO-d$_6$) δ=8.81 (s, 1 H), 8.69 (d, J=5.9 Hz, 1 H), 8.59 (d, J=1.5 Hz, 1 H), 8.19 (d, J=5.8 Hz, 1 H), 7.91 (dd, J=1.8, 8.9 Hz, 1 H), 7.81 (d, J=8.9 Hz, 1 H), 7.62 (s, 1 H), 6.41 (s, 1 H), 4.72 (t, J=12.3 Hz, 4 H), 3.74 (s, 10 H). m/z (ESI) 515.2 (M+H)+.

Example 25 (Method 25)

1-(2-FLUORO-5-METHOXY-3'-(TRIFLUOROMETHYL)-[1,1'-BIPHENYL]-4-YL)-N-(ISOXAZOL-3-YL)-3-METHYL-4-OXO-3,4-DIHYDROPHTHALAZINE-6-SULFONAMIDE

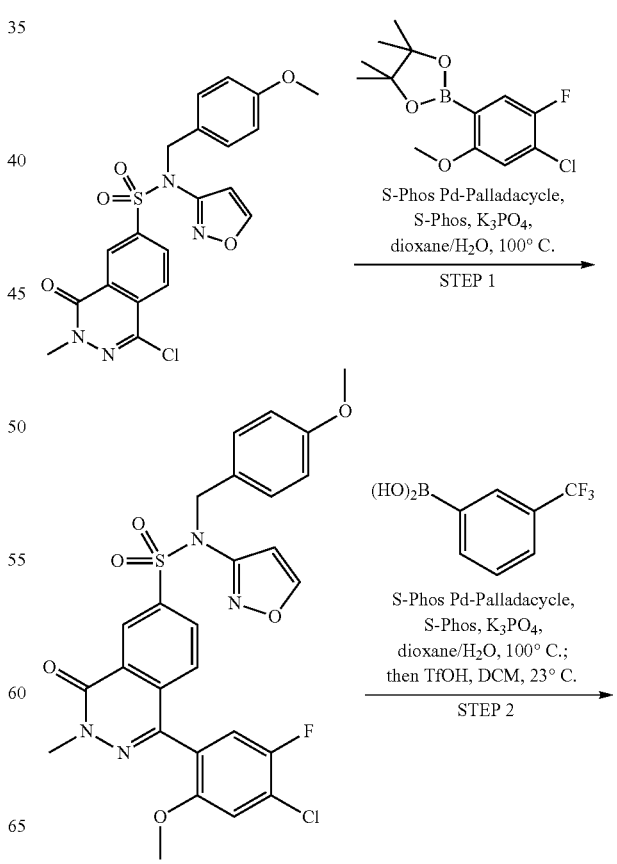

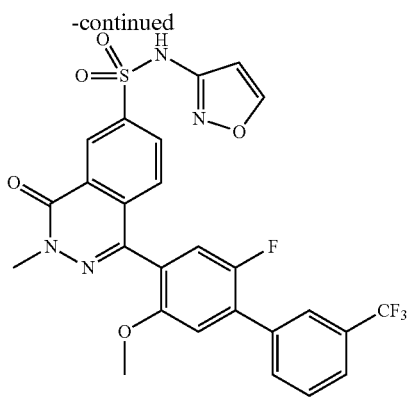

STEP 1: 1-(4-CHLORO-5-FLUORO-2-METHOXYPHENYL)-N-(ISOXAZOL-3-YL)-N-(4-METHOXYBENZYL)-3-METHYL-4-OXO-3,4-DIHYDROPHTHALAZINE-6-SULFONAMIDE

A microwave vial was charged with 1-chloro-N-(isoxazol-3-yl)-N-(4-methoxybenzyl)-3-methyl-4-oxo-3,4-dihydrophthalazine-6-sulfonamide (0.100 g, 0.217 mmol), 2-(4-chloro-5-fluoro-2-methoxyphenyl)-4,4,5,5-tetramethyl-1,3,2-dioxaborolane (0.075 g, 0.260 mmol), SPhos Precatalyst (8.22 mg, 10.85 µmol), dicyclohexyl(2',6'-dimethoxy-[1,1'-biphenyl]-2-yl)phosphine (4.45 mg, 10.85 µmol), and potassium phosphate (0.138 g, 0.651 mmol). The vial was flushed with Ar (g), then Dioxane (1.808 ml) and Water (0.362 ml) were added. The reaction was microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(4-chloro-5-fluoro-2-methoxyphenyl)-N-(isoxazol-3-yl)-N-(4-methoxybenzyl)-3-methyl-4-oxo-3,4-dihydrophthalazine-6-sulfonamide (0.089 g, 0.152 mmol, 70.1% yield) as a white solid. m/z (ESI) 585.2 (M+H)+.

STEP 2: 1-(2-FLUORO-5-METHOXY-3'-(TRIFLUOROMETHYL)-[1,1'-BIPHENYL]-4-YL)-N-(ISOXAZOL-3-YL)-3-METHYL-4-OXO-3,4-DIHYDROPHTHALAZINE-6-SULFONAMIDE

A microwave vial was charged with 1-(4-chloro-5-fluoro-2-methoxyphenyl)-N-(isoxazol-3-yl)-N-(4-methoxybenzyl)-3-methyl-4-oxo-3,4-dihydrophthalazine-6-sulfonamide (0.089 g, 0.152 mmol), (3-(trifluoromethyl)phenyl)boronic acid (0.029 g, 0.152 mmol), SPhos Precatalyst (5.76 mg, 7.61 µmol), dicyclohexyl(2',6'-dimethoxy-[1,1'-biphenyl]-2-yl)phosphine (3.12 mg, 7.61 µmol), and potassium phosphate (0.097 g, 0.456 mmol). The vial was flushed with Ar (g), then Dioxane (1.268 ml) and Water (0.254 ml) were added. The reaction was microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was dissolved in DCM and triflic acid (0.1 ml, 1.126 mmol) was added. The reaction was stirred for one hour at room temperature. The reaction was concentrated, dissolved in DMSO, filtered through a syringe filter, and purified via Gilson HPLC (50-95% MeCN:H2O w/0.1% TFA modifier). The product fractions were partitioned between ethyl acetate and water. The aqueous layer was extracted with ethyl acetate, and the combined organic layers were dried with sodium sulfate, filtered, and concentrated to afford 1-(2-fluoro-5-methoxy-3'-(trifluoromethyl)-[1,1'-biphenyl]-4-yl)-N-(isoxazol-3-yl)-3-methyl-4-oxo-3,4-dihydrophthalazine-6-sulfonamide (0.034 g, 0.059 mmol, 38.9% yield) as a white solid. $^1$H NMR (400 MHz, DMSO-d$_6$) δ=11.97 (br. s., 1 H), 8.76 (dd, J=1.7, 6.5 Hz, 2 H), 8.25 (dd, J=2.0, 8.6 Hz, 1 H), 8.00 (s, 2 H), 7.89-7.75 (m, 2 H), 7.65 (d, J=8.6 Hz, 1 H), 7.45 (d, J=10.3 Hz, 1 H), 7.40 (d, J=6.4 Hz, 1 H), 6.47 (d, J=1.8 Hz, 1 H), 3.80 (s, 3 H), 3.77 (s, 3 H). m/z (ESI) 575.2 (M+H)+.

Example 26 (Method 26)

4-(2-CHLORO-3'-FLUORO-5-METHOXY-[1,1'-BIPHENYL]-4-YL)-N-(1,2,4-OXADIAZOL-3-YL)QUINAZOLINE-7-SULFONAMIDE

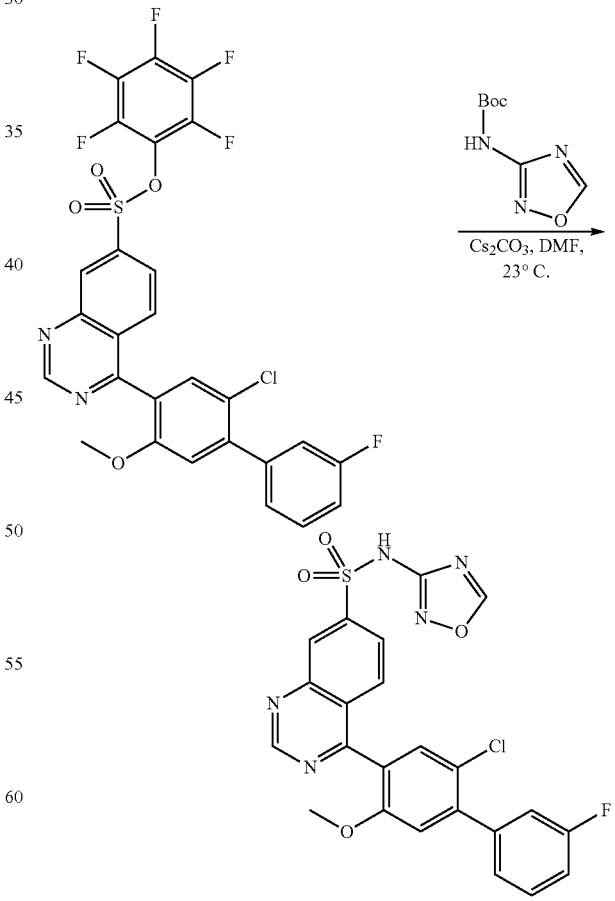

A vial was charged with perfluorophenyl 4-(2-chloro-3'-fluoro-5-methoxy-[1,1'-biphenyl]-4-yl)quinazoline-7-sulfonate (0.075 g, 0.123 mmol, prepared via Method 15, Step 4), tert-butyl 1,2,4-oxadiazol-3-ylcarbamate (0.027 g, 0.147 mmol), and cesium carbonate (0.060 g, 0.184 mmol). The flask was flushed with Ar (g), then DMF (0.614 ml) was added. The reaction was stirred overnight at room temperature. The reaction was diluted with EtOAc and washed with water (2×). The organic layer was then dried over sodium sulfate, filtered, and concentrated. The material was purified via column chromatography (RediSep Gold 12 g, gradient elution 0-100% EtOAc:Heptane followed by a 10% MeOH:DCM flush) to afford 4-(2-chloro-3'-fluoro-5-methoxy-[1,1'-biphenyl]-4-yl)-N-(1,2,4-oxadiazol-3-yl)quinazoline-7-sulfonamide (0.031 g, 0.061 mmol, 49.3% yield) as a white solid. $^1$H NMR (400 MHz, DMSO-d$_6$) δ=9.44 (s, 1 H), 8.88 (br. s., 1 H), 8.45 (s, 1 H), 8.08-8.00 (m, 1 H), 7.82 (d, J=8.7 Hz, 1 H), 7.66 (s, 1 H), 7.62-7.53 (m, 1 H), 7.50-7.40 (m, 2 H), 7.37-7.26 (m, 2 H), 3.75 (s, 3 H). m/z (ESI) 512.2 (M+H)+.

Example 27 (Method 27)

1-(2-CHLORO-3'-FLUORO-5-METHOXY-[1,1'-BIPHENYL]-4-YL)-4-CYANO-N-(ISOXAZOL-3-YL)ISOQUINOLINE-6-SULFONAMIDE

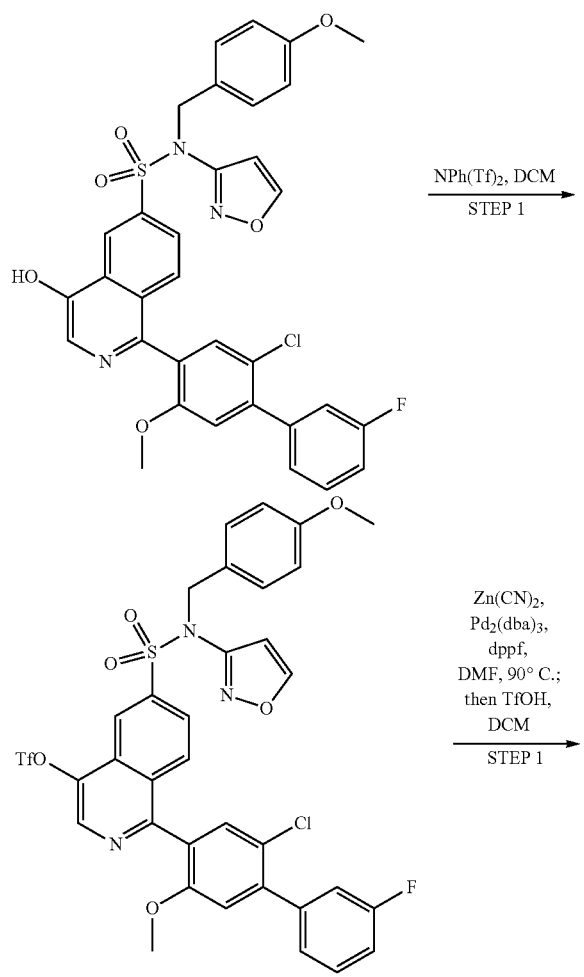

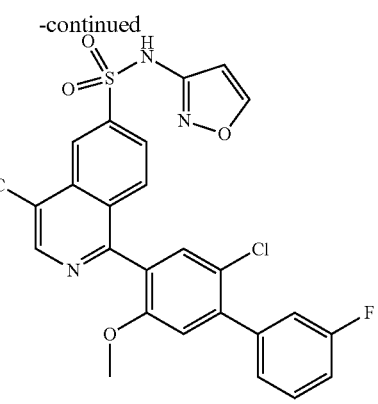

STEP 1: 1-(2-CHLORO-3'-FLUORO-5-METHOXY-[1,1'-BIPHENYL]-4-YL)-6-(N-(ISOXAZOL-3-YL)-N-(4-METHOXYBENZYL)SULFAMOYL)ISOQUINOLIN-4-YL TRIFLUOROMETHANESULFONATE 1-(2-Chloro-3'-fluoro-5-methoxy-[1,1'-biphenyl]-4-yl)-4-hydroxy-N-(isoxazol-3-yl)-N-(4-methoxybenzyl)isoquinoline-6-sulfonamide (0.178 g, 0.276 mmol, prepared via Method 17) and 1,1,1-trifluoro-N-phenyl-N-((trifluoromethyl)sulfonyl)methanesulfonamide (0.118 g, 0.331 mmol) were combined in DCM (5.51 ml). Triethylamine (0.115 ml, 0.827 mmol) was added, and the solution was stirred at RT for two hours. The solution was loaded on a silica cartridge and purified via column chromatography (RediSep 80 g, gradient elution 0-50% EtOAc:Heptane) to afford 1-(2-chloro-3'-fluoro-5-methoxy-[1,1'-biphenyl]-4-yl)-6-(N-(isoxazol-3-yl)-N-(4-methoxybenzyl)sulfamoyl)isoquinolin-4-yl trifluoromethanesulfonate (0.182 g, 0.234 mmol, 85% yield) as a light yellow solid. m/z (ESI) 778.1 (M+H)+.

STEP 2: 1-(2-CHLORO-3'-FLUORO-5-METHOXY-[1,1'-BIPHENYL]-4-YL)-4-CYANO-N-(ISOXAZOL-3-YL)ISOQUINOLINE-6-SULFONAMIDE

A vial was charged with 1-(2-chloro-3'-fluoro-5-methoxy-[1,1'-biphenyl]-4-yl)-6-(N-(isoxazol-3-yl)-N-(4-methoxybenzyl)sulfamoyl)isoquinolin-4-yl trifluoromethanesulfonate (0.090 g, 0.116 mmol), Pd$_2$(dba)$_3$ (10.59 mg, 0.012 mmol), 1,1'-bis(diphenylphosphino)ferrocene (0.013 g, 0.023 mmol), and zinc cyanide (0.015 mL, 0.231 mmol). DMF (1.157 mL) was added, and the reaction was stirred at 90° C. for one hour. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 12 g, gradient elution 0-50% EtOAc:Heptane) to afford 1-(2-chloro-3'-fluoro-5-methoxy-[1,1'-biphenyl]-4-yl)-4-cyano-N-(isoxazol-3-yl)-N-(4-methoxybenzyl)isoquinoline-6-sulfonamide as a light yellow solid. The material was dissolved in DCM and triflic acid (0.1 mL, 1.126 mmol) was added. The reaction was stirred at room temperature for 30 minutes. The reaction was concentrated and purified via column chromatography (RediSep Gold 12 g, gradient elution 0-10% MeOH:DCM) to afford 1-(2-chloro-3'-fluoro-5-methoxy-[1,1'-biphenyl]-4-yl)-4-cyano-N-(isoxazol-3-yl)isoquinoline-6-sulfonamide (0.053 g, 0.099 mmol, 86% yield) as a tan solid. $^1$H NMR (400 MHz, DMSO-$d_6$) δ=9.33 (s, 1 H), 8.77 (d, J=1.8 Hz, 1 H), 8.66-8.58 (m, 1 H), 8.21-8.07 (m, 2 H), 7.63 (s, 1 H), 7.59 (dt, J=6.4, 8.0 Hz, 1 H), 7.47-7.41 (m, 2 H), 7.36-7.30 (m, 2 H), 6.50 (d, J=1.9 Hz, 1 H), 3.71 (s, 3 H). m/z (ESI) 535.1 (M+H)+.

Example 28 (Method 28)

1-(2-CYANO-3',5'-DIFLUORO-5-METHOXY-[1,1'-BIPHENYL]-4-YL)-N-(PYRIMIDIN-4-YL)ISOQUINOLINE-6-SULFONAMIDE

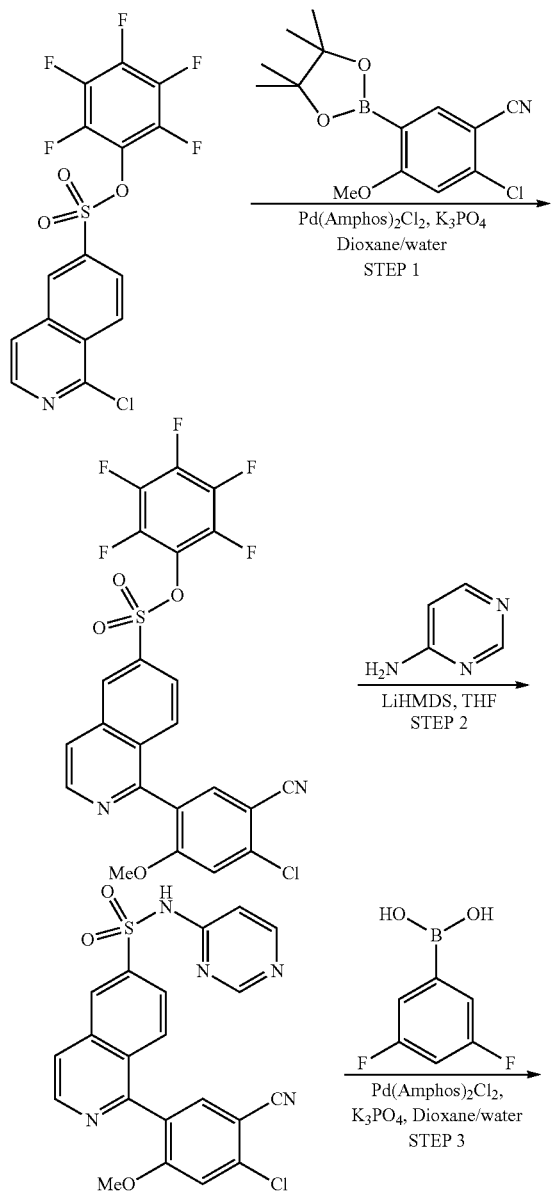

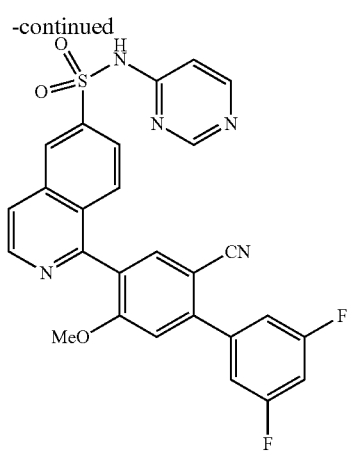

STEP 1: PERFLUOROPHENYL 1-(4-CHLORO-5-CYANO-2-METHOXYPHENYL)ISOQUINOLINE-6-SULFONATE

A solution of 1,1-bis[(di-t-butyl-p-methylaminophenyl]palladium(ii) chloride (1.187 g, 1.676 mmol), perfluorophenyl 1-chloroisoquinoline-6-sulfonate (13.73 g, 33.5 mmol), 2-chloro-4-methoxy-5-(4,4,5,5-tetramethyl-1,3,2-dioxaborolan-2-yl)benzonitrile (HDH Pharma, 9.840 g, 33.5 mmol), and potassium phosphate (28.5 g, 134 mmol) in 110 mL of dioxane and 35 mL water was heated to 50° C. for 20 minutes. The reaction mixture was poured into water and was extracted with DCM. The organics were dried over MgSO4 and concentrated. Purification of the crude residue by silica gel column chromatography (0-60% EtOAc/heptane) gave perfluorophenyl 1-(4-chloro-5-cyano-2-methoxyphenyl)isoquinoline-6-sulfonate (7.771 g, 14.37 mmol, 42.9% yield). m/z (ESI) 540.9 (M+H)$^+$.

STEP 2: 1-(4-CHLORO-5-CYANO-2-METHOXYPHENYL)-N-(PYRIMIDIN-4-YL)ISOQUINOLINE-6-SULFONAMIDE

A solution of pyrimidin-4-amine (0.547 g, 5.75 mmol) and perfluorophenyl 1-(4-chloro-5-cyano-2-methoxyphenyl)isoquinoline-6-sulfonate (2.590 g, 4.79 mmol) in 20 ml THF was cooled to 0° C. and was treated with LHMDS 1N in THF (4.79 ml, 4.79 mmol). After stirring for 2 hours, the reaction mixture was treated with HCl 4N in dioxane (4.79 ml, 19.16 mmol). After stirring for an additional hour, the reaction mixture was concentrated. Purification of the crude residue by reverse phase column chromatography [Puriflash C18, 10-100% (0.1% NH4OH in MeOH)/(0.1% NH4OH in water)] gave 1-(4-chloro-5-cyano-2-methoxyphenyl)-N-(pyrimidin-4-yl)isoquinoline-6-sulfonamide (2.050 g, 4.54 mmol, 95% yield) with ~30% sulfonic acid impurity. m/z (ESI) 452.1 (M+H)$^+$.

STEP 3: 1-(2-CYANO-3',5'-DIFLUORO-5-METHOXY-[1,1'-BIPHENYL]-4-YL)-N-(PYRIMIDIN-4-YL)ISOQUINOLINE-6-SULFONAMIDE

A microwave vial charged with 1,1-bis[(di-t-butyl-p-methylaminophenyl]palladium(ii) chloride (0.017 g, 0.024 mmol), (3,5-difluorophenyl)boronic acid (0.077 g, 0.487 mmol), 1-(4-chloro-5-cyano-2-methoxyphenyl)-N-(pyrimidin-4-yl)isoquinoline-6-sulfonamide (110 mg, 0.243 mmol), potassium phosphate (0.221 g, 0.974 mmol), and 1.5 mL dioxane 0.5 mL water was heated to 150° C. in a Biotage Initiator microwave reactor for 30 minutes. The organic layer was removed and treated with HCl 4N in dioxane (1 mL, 1.0 mmol). The reaction mixture was then concentrated. Purification of the crude residue was performed by using YMC-ODS-packed C18, 100 mm×30 mm ID column, 20%-70% B gradient over 16 min, water with 0.1% TFA/acetonitrile with 0.1% TFA mobile phase. $^1$H NMR (DMSO-d$_6$) δ: 8.65-8.76 (m, 2 H), 8.58 (s, 1 H), 8.25 (br. s., 1 H), 8.18 (d, J=5.7 Hz, 1 H), 7.94-8.01 (m, 2 H), 7.77 (d, J=8.9 Hz, 1 H), 7.55 (d, J=6.0 Hz, 2 H), 7.43-7.51 (m, 2 H), 6.96-7.10 (m, 1 H), 3.82 (s, 3 H). m/z (ESI) 530.2 (M+H)$^+$.

Example 29 (Method 29)

1-(4-(4-FLUORO-3-METHYLPHENOXY)-2-METHOXYPHENYL)-N-(PYRIMIDIN-4-YL)ISO-QUINOLINE-6-SULFONAMIDE

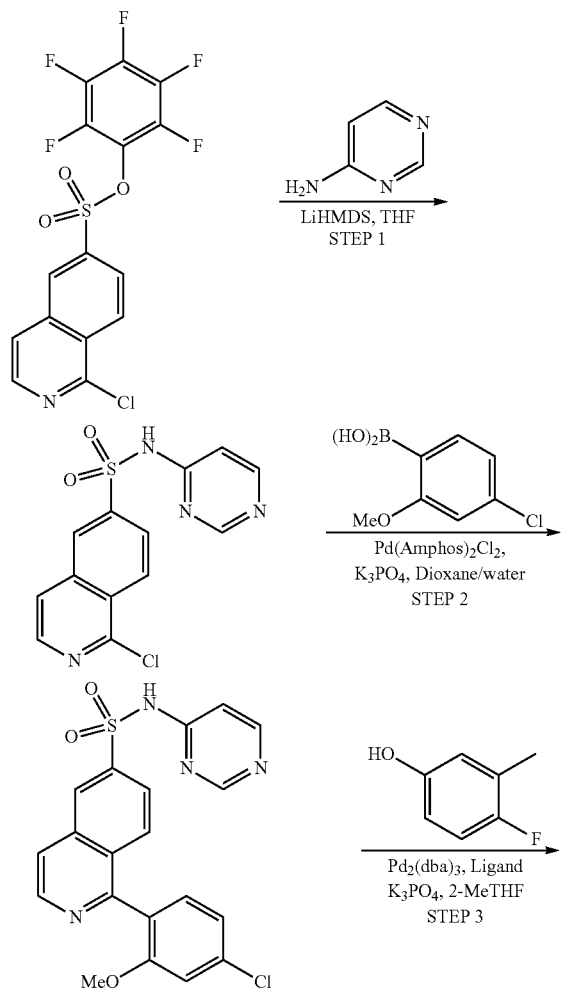

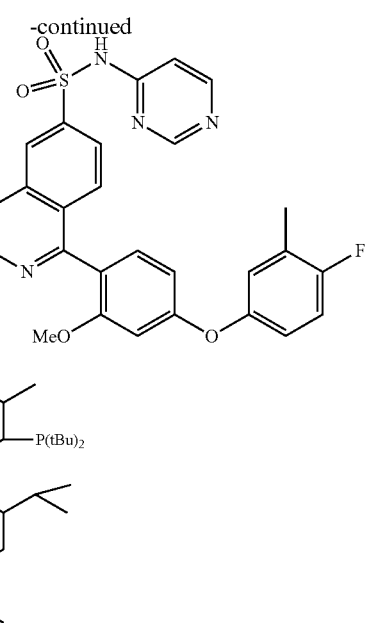

Ligand =

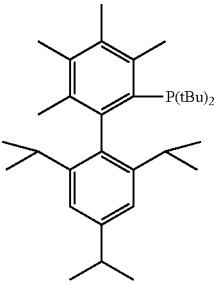

STEP 1: 1-CHLORO-N-(PYRIMIDIN-4-YL)ISO-QUINOLINE-6-SULFONAMIDE

A solution of perfluorophenyl 1-chloroisoquinoline-6-sulfonate (7.000 g, 17.09 mmol) and pyrimidin-4-amine (1.625 g, 17.09 mmol) in 17 mL THF was cooled to 0° C. and was treated with LiHMDS 1N in THF (17.09 ml, 17.09 mmol). After stirring for one hour, the reaction mixture was concentrated. The crude residue was used in the next step without purification. m/z (ESI) 321.0 (M+H)$^+$.

STEP 2: 1-(4-CHLORO-2-METHOXYPHENYL)-N-(PYRIMIDIN-4-YL)ISOQUINOLINE-6-SULFONAMIDE

The crude residue from step one was dissolved in 50 mL dioxane 17 mL water, was treated with Pd(Amphos)$_2$Cl$_2$ (0.605 g, 0.854 mmol), (4-chloro-2-methoxyphenyl)boronic acid (3.18 g, 17.09 mmol), and potassium phosphate (14.51 g, 68.3 mmol) and was heated to 110° C. for 2 hours. The reaction mixture was allowed to cool to room temperature. The aqueous layer was removed, and the organics were treated with HCl 4N in dioxane (17.09 ml, 68.3 mmol). After stirring for 10 minutes, the reaction mixture was concentrated. The crude residue was triturated with hot MeCN yielding 1-(4-chloro-2-methoxyphenyl)-N-(pyrimidin-4-yl) isoquinoline-6-sulfonamide (5.25 g, 12.30 mmol, 72.0% yield) as the HCl salt with minor impurities. m/z (ESI) 427.0 (M+H)$^+$.

STEP 3: 1-(4-(4-FLUORO-3-METHYLPHENOXY)-2-METHOXYPHENYL)-N-(PYRIMIDIN-4-YL)ISOQUINOLINE-6-SULFONAMIDE

A microwave vial charged with Pd$_2$(dba)$_3$ (0.016 g, 0.018 mmol), di-tert-butyl(2',4',6'-triisopropyl-3,4,5,6-tetramethyl-[1,1'-biphenyl]-2-yl)phosphine (0.034 g, 0.070 mmol), 4-fluoro-3-methylphenol (0.089 g, 0.703 mmol), 1-(4- chloro-2-methoxyphenyl)-N-(pyrimidin-4-yl)isoquinoline-6-sulfonamide (0.150 g, 0.351 mmol), potassium phosphate (0.298 mg, 1.406 µmol) and 2 mL 2-MeTHF was heated to 165° C. in a Biotage Initiator microwave reactor for 45 minutes. The crude reaction mixture was filtered through a 0.45 µM syringe filter then was treated with HCl 4N in dioxane. After stirring for an additional 30 minutes, the reaction mixture was concentrated. The crude residue was purified by PREP LC/MS-2 System Column: XBridge 19×100 mm 12230326114 03 Mobile phase: 0.1% NH4OH in water/acetonitrile Flow rate: 40 ml/min Inj: 2000 uL. Samples were filtered before injection for the first purification Gradient: 10 min 10-40%_LV_NH3; 10 min 10-60%_LV_NH3. Samples were purified twice to achieve maximum purity of 1-(4-(4-fluoro-3-methylphenoxy)-2-methoxyphenyl)-n-(pyrimidin-4-yl)isoquinoline-6-sulfonamide (0.0046 g, 0.009 mmol, 2.5% yield). $^1$H NMR (DMSO-d$_6$) δ: 8.60-8.69 (m, 2 H), 8.56 (s, 1 H), 8.24 (br. s., 1 H), 8.06 (d, J=5.1 Hz, 1 H), 7.95 (d, J=9.0 Hz, 1 H), 7.77 (d, J=8.5 Hz, 1 H), 7.30 (d, J=8.3 Hz, 1 H), 7.22 (t, J=8.9 Hz, 1 H), 7.14 (br. s., 1 H), 7.02 (br. s., 2 H), 6.90 (s, 1 H), 6.59 (d, J=8.3 Hz, 1 H), 3.61 (s, 3 H), 2.26 (s, 3 H). m/z (ESI) 517.0 (M+H)$^+$.

Example 30 (Method 30)

1-(4-(5-FLUORO-2-METHOXYPYRIDIN-3-YL)-2-METHOXYPHENYL)-N-(1,3,4-THIADIAZOL-2-YL)ISOQUINOLINE-6-SULFONAMIDE

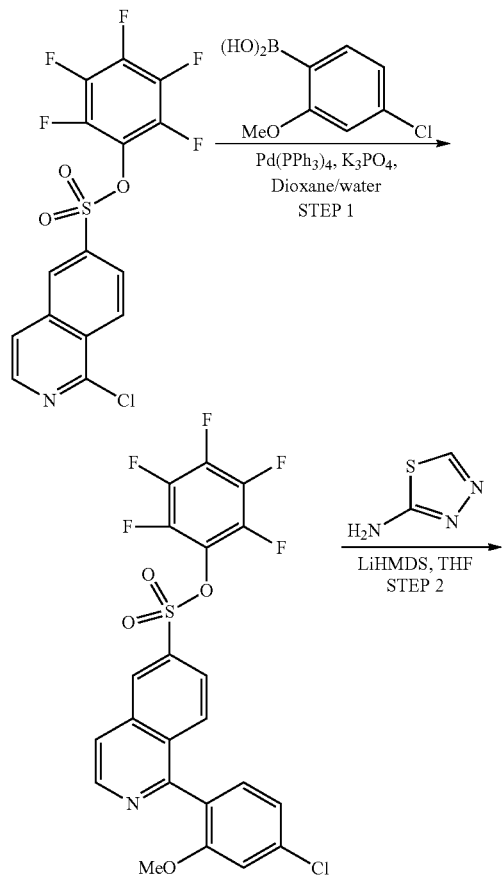

STEP 1: PERFLUOROPHENYL 1-(4-CHLORO-2-METHOXYPHENYL)ISOQUINOLINE-6-SULFONATE

A solution of Pd(Ph3p)4 (1.974 g, 1.709 mmol), (4-chloro-2-methoxyphenyl)boronic acid (3.82 g, 20.50 mmol), perfluorophenyl 1-chloroisoquinoline-6-sulfonate (7.000 g, 17.09 mmol), and potassium phosphate (14.51 g, 68.3 mmol) in 40 mL dioxane 10 mL water was heated to 50° C. for one hour. The reaction mixture was filtered through a plug of celite and the aqueous layer was removed. The organics were then concentrated. The crude residue was used in the next step without purification. m/z (ESI) 516.0 (M+H)$^+$.

STEP 2: 1-(4-CHLORO-2-METHOXYPHENYL)-N-(1,3,4-THIADIAZOL-2-YL)ISOQUINOLINE-6-SULFONAMIDE

The crude residue from step one was dissolved in 40 mL dioxane, was treated with 1,3,4-thiadiazol-2-amine (1.728 g, 17.09 mmol) and potassium phosphate (14.51 g, 68.3 mmol) and was heated to 80° C. overnight. The reaction mixture was diluted with EtOAc and washed with water. The organics were treated with HCl 4N in dioxane (12.81 ml, 51.3 mmol), allowed to stir for 10 minutes, then concentrated. Purification of the crude residue by reverse phase column chromatography [Redisep Gold C18, 10-100% (0.1% NH4OH in MeOH)/(0.1% NH4OH in water)] gave 1-(4-chloro-2-methoxyphenyl)-N-(1,3,4-thiadiazol-2-yl)isoquinoline-6-sulfonamide (3.44 g, 7.95 mmol, 46.5% yield) with minor impurities. m/z (ESI) 432.9 (M+H)+.

STEP 3: 1-(4-(5-FLUORO-2-METHOXYPYRIDIN-3-YL)-2-METHOXYPHENYL)-N-(1,3,4-THIADIAZOL-2-YL)ISOQUINOLINE-6-SULFONAMIDE

A microwave vial charged with Pd(Amphos)₂Cl₂ (0.011 g, 0.016 mmol), 5-fluoro-2-methoxy-3-(4,4,5,5-tetramethyl-1,3,2-dioxaborolan-2-yl)pyridine (0.082 g, 0.323 mmol, Combi-Blocks), 1-(4-chloro-2-methoxyphenyl)-N-(1,3,4-thiadiazol-2-yl)isoquinoline-6-sulfonamide (0.070 g, 0.162 mmol), potassium phosphate (0.137 g, 0.647 mmol), 1.5 mL dioxane and 0.25 mL water was heated to 150° C. in a Biotage Initiator microwave reactor for 30 minutes. The aqueous layer was removed, and the reaction mixture was treated with HCl 4N in dioxane (0.162 ml, 0.647 mmol). After stirring for 10 minutes, the reaction mixture was concentrated. Purification of the crude residue by reverse phase column chromatography [RediSep Gold C18, 10-100% (0.1% NH4OH in MeOH)/(0.1% NH4OH in water)] gave 1-(4-(5-fluoro-2-methoxypyridin-3-yl)-2-methoxyphenyl)-N-(1,3,4-thiadiazol-2-yl)isoquinoline-6-sulfonamide (0.052 g, 0.099 mmol, 61.4% yield). ¹H NMR (ACETONITRILE-d3) δ: 8.64 (d, J=5.7 Hz, 1H), 8.47 (d, J=1.8 Hz, 1H), 8.37 (s, 1H), 8.08 (d, J=3.0 Hz, 1H), 7.84-7.91 (m, 2H), 7.66-7.76 (m, 2H), 7.30-7.42 (m, 3H), 3.96 (s, 3H), 3.68 (s, 3H). m/z (ESI) 524.0 (M+H)+.

Example 31 (Method 31)

1-(4-(5-FLUORO-2-METHOXYPYRIDIN-3-YL)-2-METHOXYPHENYL)-N-(ISOXAZOL-3-YL)ISOQUINOLINE-6-SULFONAMIDE

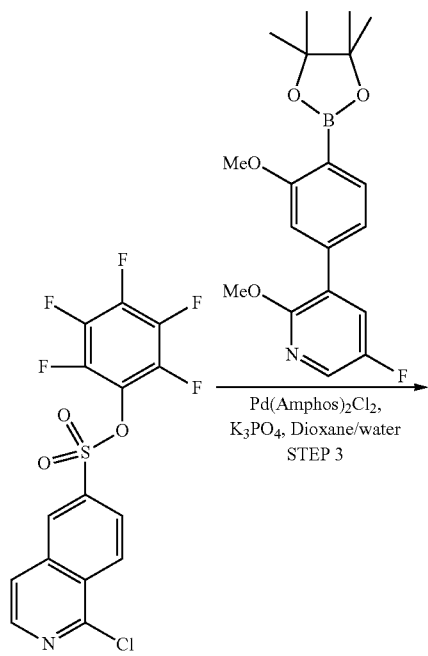

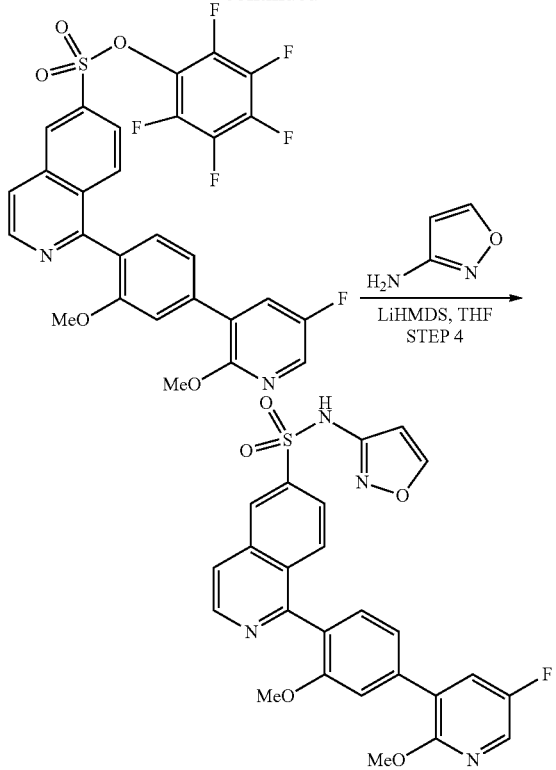

STEP 1: PERFLUOROPHENYL 1-(4-(5-FLUORO-2-METHOXYPYRIDIN-3-YL)-2-METHOXYPHENYL)ISOQUINOLINE-6-SULFONATE

A solution of 1,1-bis[(di-t-butyl-p-methylaminophenyl] palladium(ii) chloride (0.083 g, 0.117 mmol), perfluorophenyl 1-chloroisoquinoline-6-sulfonate (0.958 g, 2.339 mmol), 5-fluoro-2-methoxy-3-(3-methoxy-4-(4,4,5,5-tetramethyl-1,3,2-dioxaborolan-2-yl)phenyl)pyridine (0.840 g, 2.339 mmol), and potassium phosphate (1.986 g, 9.35 mmol) in 10 mL dioxane 4 mL water was heated to 50° C. for 20 minutes. The reaction mixture was poured into water and was extracted with DCM. The organics were dried over MgSO4 and concentrated. Purification of the crude residue by silica gel column chromatography (0-30% EtOAc/heptane) gave perfluorophenyl 1-(4-(5-fluoro-2-methoxypyridin-3-yl)-2-methoxyphenyl)isoquinoline-6-sulfonate (0.885 g, 1.459 mmol, 62.4% yield). m/z (ESI) 606.9 (M+H)+.

STEP 2: 1-(4-(5-FLUORO-2-METHOXYPYRIDIN-3-YL)-2-METHOXYPHENYL)-N-(ISOXAZOL-3-YL)ISOQUINOLINE-6-SULFONAMIDE

A solution of isoxazol-3-amine (0.152 ml, 2.061 mmol) and perfluorophenyl 14445-fluoro-2-methoxypyridin-3-yl)-2-methoxyphenyl)isoquinoline-6-sulfonate (0.250 g, 0.412 mmol) in 2 ml THF was cooled to 0° C. and was treated with LHMDS 1N in THF (0.412 ml, 0.412 mmol). After stirring for 3 hours, the reaction mixture was treated with hcl 4N in dioxane (0.824 ml, 3.30 mmol). After stirring for an additional hour, the reaction mixture was concentrated. Purification of the crude residue by reverse phase column chromatography [Puriflash C18, 10-100% (0.1% NH4OH in MeOH)/(0.1% NH4OH in water)] gave 14445-fluoro-2- methoxypyridin-3-yl)-2-methoxyphenyl)-N-(isoxazol-3-yl)isoquinoline-6-sulfonamide (0.055 g, 0.109 mmol, 26.3% yield). $^1$H NMR (ACETONITRILE-d3) δ: 8.70 (d, J=5.7 Hz, 1H), 8.55 (d, J=1.9 Hz, 1H), 8.30 (d, J=1.8 Hz, 1H), 8.08 (d, J=2.9 Hz, 1H), 7.88-7.94 (m, 2H), 7.78-7.84 (m, 1H), 7.72 (dd, J=8.7, 2.9 Hz, 1H), 7.33-7.44 (m, 3H), 6.43 (d, J=1.8 Hz, 1H), 3.96 (s, 3H), 3.69 (s, 3H). m/z (ESI) 507.0 (M+H)$^+$.

Example 32 (Method 32)

1-(4-(3-FLUORO-5-METHYLPHENOXY)-2-METHOXYPHENYL)-N-(1,3,4-THIADIAZOL-2-YL)ISOQUINOLINE-6-SULFONAMIDE

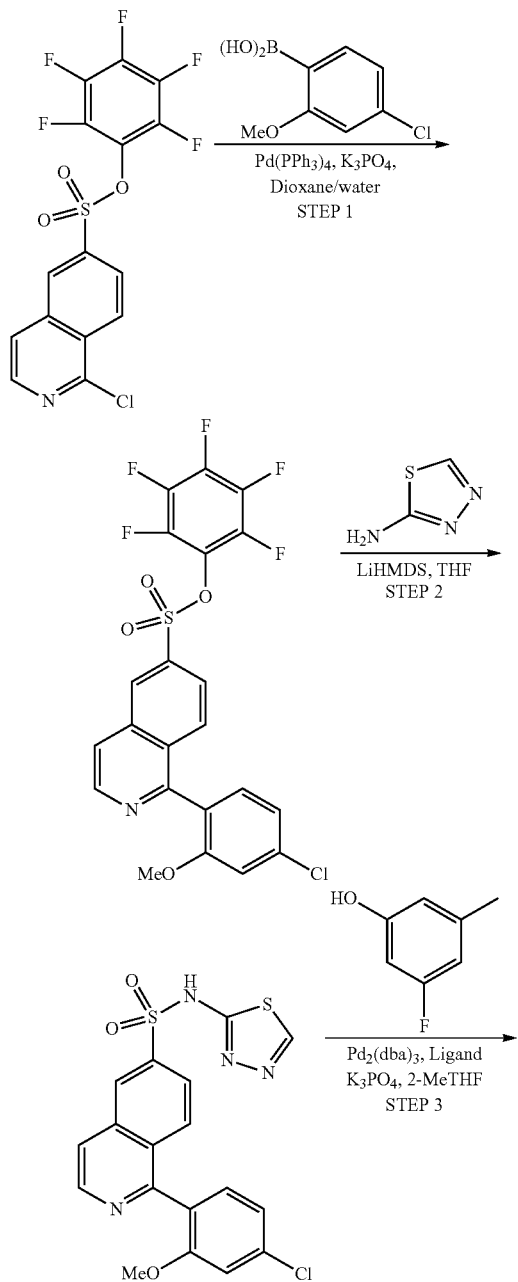

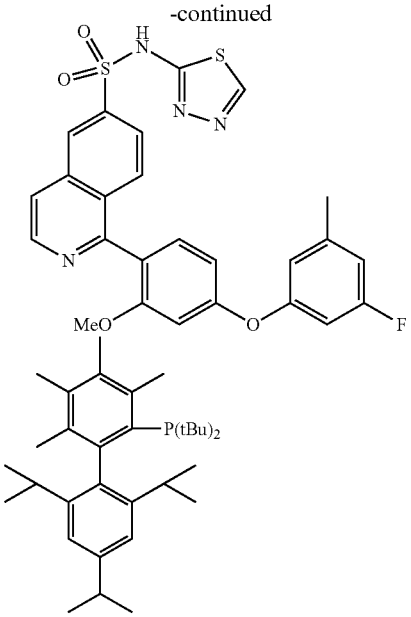

STEP 1: PERFLUOROPHENYL 1-(4-CHLORO-2-METHOXYPHENYL)ISOQUINOLINE-6-SULFONATE

A solution of Pd(Ph$_3$P)$_4$ (1.974 g, 1.709 mmol), (4-chloro-2-methoxyphenyl)boronic acid (3.82 g, 20.50 mmol), perfluorophenyl 1-chloroisoquinoline-6-sulfonate (7.000 g, 17.09 mmol), and potassium phosphate (14.51 g, 68.3 mmol) in 40 mL dioxane 10 mL water was heated to 50° C. for one hour. The reaction mixture was filtered through a plug of celite and the aqueous layer was removed. The organics were then concentrated. The crude residue was used in the next step without purification. m/z (ESI) 516.0 (M+H)$^+$.

STEP 2: 1-(4-CHLORO-2-METHOXYPHENYL)-N-(1,3,4-THIADIAZOL-2-YL)ISOQUINOLINE-6-SULFONAMIDE

The crude residue from Step 1 was dissolved in 40 mL dioxane, was treated with 1,3,4-thiadiazol-2-amine (1.728 g, 17.09 mmol) and potassium phosphate (14.51 g, 68.3 mmol) and was heated to 80° C. overnight. The reaction mixture was diluted with EtOAc and washed with water. The organics were treated with hcl 4N in dioxane (12.81 ml, 51.3 mmol), allowed to stir for 10 minutes, then concentrated. Purification of the crude residue by reverse phase column chromatography [Redisep Gold C18, 10-100% (0.1% NH4OH in MeOH)/(0.1% NH4OH in water)] gave 1-(4-chloro-2-methoxyphenyl)-N-(1,3,4-thiadiazol-2-yl)isoquinoline-6-sulfonamide (3.44 g, 7.95 mmol, 46.5% yield) with minor impurities. m/z (ESI) 432.9 (M+H)$^+$.

STEP 3: 1-(4-(3-FLUORO-5-METHYLPHENOXY)-2-METHOXYPHENYL)-N-(1,3,4-THIADIAZOL-2-YL)ISOQUINOLINE-6-SULFONAMIDE

A microwave vial charged with Pd$_2$(dba)$_3$ (0.052 g, 0.057 mmol), di-tert-butyl(2',4',6'-triisopropyl-3,4,5,6-tetramethyl-[1,1'-biphenyl]-2-yl)phosphine (0.111 g, 0.231 mmol), 3-fluoro-5-methylphenol (0.175 g, 1.386 mmol), 1-(4-chloro-2-methoxyphenyl)-N-(1,3,4-thiadiazol-2-yl)isoquinoline-6-sulfonamide (0.200 g, 0.462 mmol), potassium phosphate (0.392 g, 1.848 mmol), and 1.5 mL 2-MeTHF was heated to 165° C. in a Biotage Initiator microwave reactor for 30 minutes. The reaction mixture was filtered through a 0.45 m syringe filter and was treated with hcl 4N in dioxane (0.462 ml, 1.848 mmol). After stirring for 10 minutes, the reaction mixture was concentrated. Purification of the crude residue by reverse phase column chromatography [RediSep Gold C18, 10-100% (0.1% NH4OH in MeOH)/(0.1% NH4OH in water)] gave 1-(4-(3-fluoro-5-methylphenoxy)-2-methoxyphenyl)-N-(1,3,4-thiadiazol-2-yl)isoquinoline-6-sulfonamide (0.012 g, 0.023 mmol, 4.97% yield). $^1$H NMR (ACETONITRILE-d3) δ: 8.66 (d, J=5.8 Hz, 1H), 8.48 (d, J=1.4 Hz, 1H), 8.39 (s, 1H), 7.78-7.91 (m, 3H), 7.34 (d, J=8.2 Hz, 1H), 6.87 (d, J=2.2 Hz, 1H), 6.67-6.81 (m, 4H), 3.59-3.64 (m, 3H), 2.35 (d, J=0.6 Hz, 3H). m/z (ESI) 523.0 (M+H)$^+$.

Example 33 (Method 33)

1-(4-(5-FLUORO-6-METHYLPYRIDIN-2-YL)-2-METHOXY-5-METHYLPHENYL)-N-(ISOXAZOL-3-YL)ISOQUINOLINE-6-SULFONAMIDE

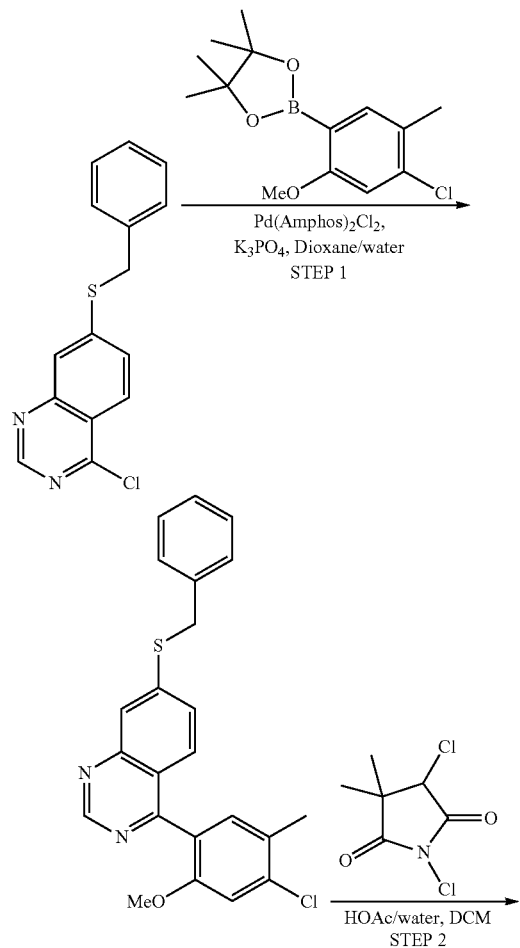

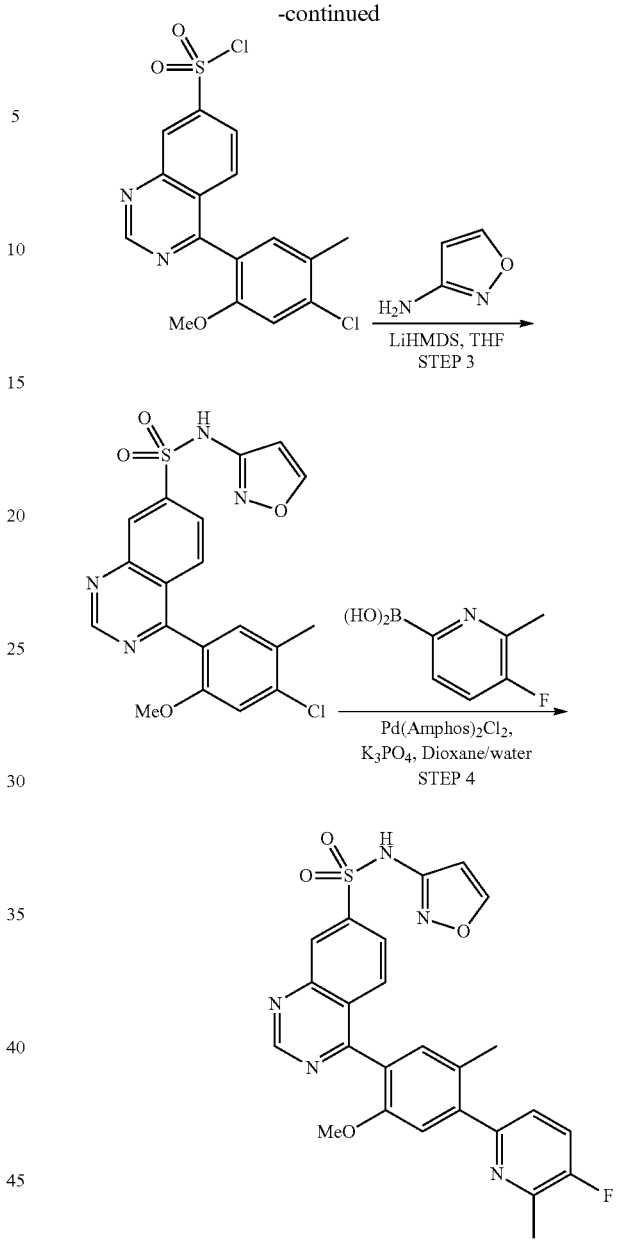

STEP 1: 6-(BENZYLTHIO)-1-(4-CHLORO-2-METHOXY-5-METHYLPHENYL)ISOQUINOLINE

A solution of 1,1-bis[(di-t-butyl-p-methylaminophenyl] palladium(ii) chloride (0.313 g, 0.442 mmol), 7-(benzylthio)-4-chloroquinazoline (2.54 g, 8.85 mmol), 2-(4-chloro-2-methoxy-5-methylphenyl)-4,4,5,5-tetramethyl-1,3,2-dioxaborolane (2.50 g, 8.85 mmol), and potassium phosphate (7.51 g, 35.4 mmol) in 20 mL dioxane 8 mL water was heated to 100° C. for 20 minutes. The reaction mixture was then poured into water and was extracted with DCM. The organics were dried over MgSO$_4$ and concentrated. The crude residue was used in the next step without purification. m/z (ESI) 407.1 (M+H)$^+$.

STEP 2: 1-(4-CHLORO-2-METHOXY-5-METHYLPHENYL)ISOQUINOLINE-6-SULFONYL CHLORIDE

The crude residue from step one was dissolved in 20 mL DCM and was treated with 0.4 mL (1.5:1 HOAc/water) followed by 1,3-dichloro-5,5-dimethylimidazolidine-2,4-dione (3.49 g, 17.69 mmol). After stirring for 30 minutes at room temperature the reaction mixture was diluted with DCM, dried over MgSO₄ and concentrated. Purification of the crude residue by silica gel column chromatography (0-100% EtOAc/heptane) gave 4-(4-chloro-2-methoxy-5-methylphenyl)quinazoline-7-sulfonyl chloride (1.470 g, 3.84 mmol, 43.4% yield). m/z (ESI) 383.1 (M+H)⁺.

STEP 3: 1-(4-CHLORO-2-METHOXY-5-METHYLPHENYL)-N-(ISOXAZOL-3-YL)ISOQUINOLINE-6-SULFONAMIDE

A solution of isoxazol-3-amine (1.417 ml, 19.18 mmol) and 4-(4-chloro-2-methoxy-5-methylphenyl)quinazoline-7-sulfonyl chloride (1.470 g, 3.84 mmol) in 20 mL THF was cooled to 0° C. LHMDS 1N in THF (3.84 ml, 3.84 mmol) was added, and the reaction mixture was allowed to slowly warm to RT overnight. The reaction mixture was treated with HCl 4N in dioxane (7.67 ml, 30.7 mmol) and was allowed to stir for 30 minutes. The reaction mixture was then concentrated. Purification of the crude residue by reverse phase column chromatography [Redisep Gold C18, 10-100% (0.1% NH₄OH in MeOH)/(0.1% NH₄OH in water)] gave 4-(4-chloro-2-methoxy-5-methylphenyl)-N-(isoxazol-3-yl)quinazoline-7-sulfonamide (0.423 g, 0.982 mmol, 25.6% yield). m/z (ESI) 431.11 (M+H)⁺.

STEP 4: 1-(4-(5-FLUORO-6-METHYLPYRIDIN-2-YL)-2-METHOXY-5-METHYLPHENYL)-N-(ISOXAZOL-3-YL)ISOQUINOLINE-6-SULFONAMIDE

A microwave vial charged with Pd(Amphos)₂Cl₂ (0.018 g, 0.026 mmol), (5-fluoro-6-methylpyridin-2-yl)boronic acid (0.119 g, 0.766 mmol, Small Molecules), 4-(4-chloro-2-methoxy-5-methylphenyl)-N-(isoxazol-3-yl)quinazoline-7-sulfonamide (0.110 g, 0.255 mmol), potassium phosphate (0.217 g, 1.021 mmol), 2 mL dioxane and 0.5 mL water was heated to 150° C. in a Biotage Initiator microwave reactor for 30 minutes. The aqueous layer was removed, and the reaction mixture was treated with HCl 4N in dioxane (0.255 ml, 1.021 mmol). After stirring for 10 minutes, the reaction mixture was concentrated. Purification of the crude residue by reverse phase column chromatography [RediSep Gold C18, 10-100% (0.1% NH4OH in MeOH)/(0.1% NH4OH in water)] gave 4-(4-(5-fluoro-6-methylpyridin-2-yl)-2-methoxy-5-methylphenyl)-N-(isoxazol-3-yl)quinazoline-7-sulfonamide (0.003 g, 5.93 μmol, 2.325% yield). ¹H NMR (ACETONITRILE-d3) δ: 9.44 (s, 1H), 8.55 (t, J=1.1 Hz, 1H), 8.34-8.39 (m, 1H), 7.97 (d, J=1.3 Hz, 2H), 7.53-7.59 (m, 1H), 7.42-7.48 (m, 1H), 7.33 (s, 1H), 7.20 (s, 1H), 6.47-6.53 (m, 1H), 3.69 (s, 3H), 2.57 (d, J=3.0 Hz, 3H), 2.32 (s, 3H). m/z (ESI) 506.0 (M+H)⁺.

Example 34 (Method 34)

4-(4'-CHLORO-2-METHOXY-3',5-DIMETHYL-[1,1'-BIPHENYL]-4-YL)-N-(ISOXAZOL-3-YL)QUINAZOLINE-7-SULFONAMIDE

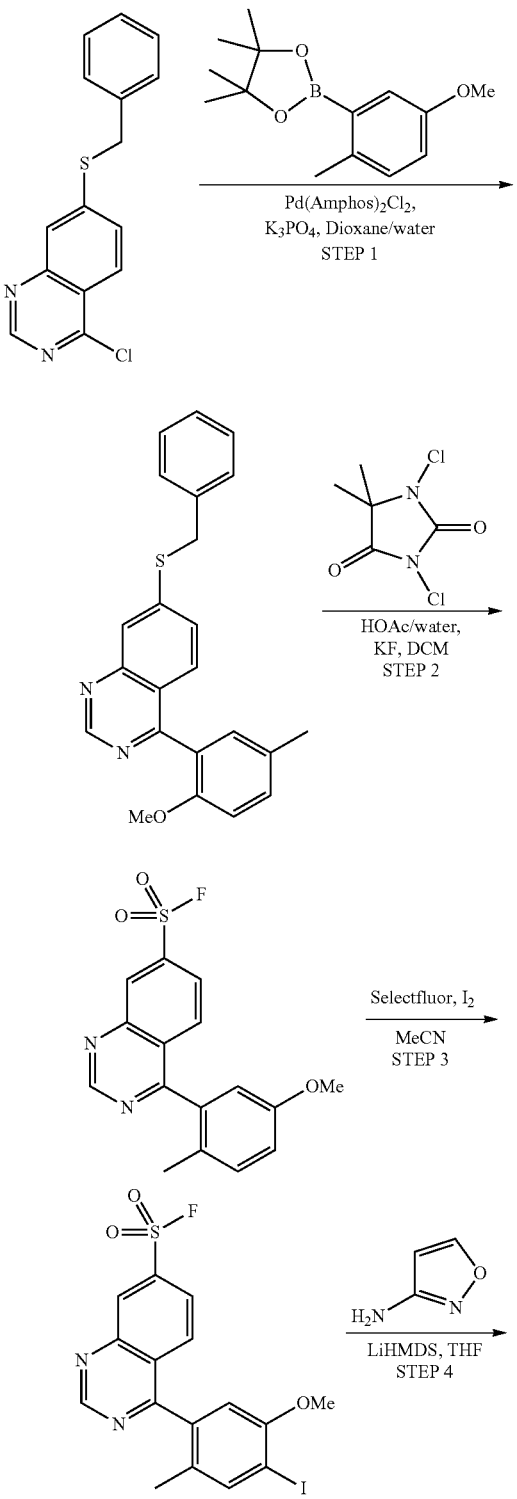

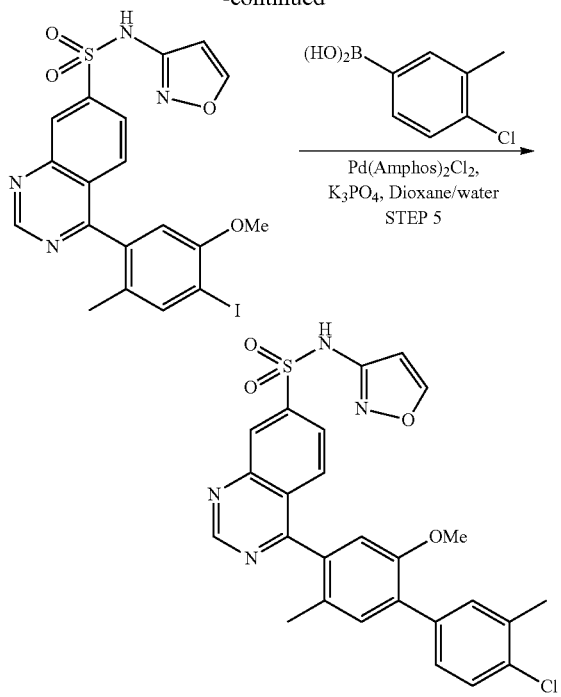

STEP 1: 7-(BENZYLTHIO)-4-(4-CHLORO-2-METHOXY-5-METHYLPHENYL)QUINAZOLINE

A solution of PdCl$_2$(Amphos)$_2$ (0.185 g, 0.262 mmol), 2-(5-methoxy-2-methylphenyl)-4,4,5,5-tetramethyl-1,3,2-dioxaborolane (1.428 g, 5.75 mmol), 7-(benzylthio)-4-chloroquinazoline (1.500 g, 5.23 mmol), and potassium phosphate (4.44 g, 20.92 mmol) in 18 mL dioxane 6 mL water was heated to 50° C. for 30 minutes. The organic layer was then separated and concentrated. The crude residue was used in the next step without purification. m/z (ESI) 373.2 (M+H)$^+$.

STEP 2: 4-(5-METHOXY-2-METHYLPHENYL)QUINAZOLINE-7-SULFONYL FLUORIDE

The crude residue from step one was dissolved in 20 mL DCM, was treated with 3 mL (1.5:1 HOAc/water) followed by 1,3-dichloro-5,5-dimethylhydantoin (2.061 ml, 15.69 mmol). After stirring for 30 minutes, potassium fluoride (3.04 g, 52.3 mmol) was added. After stirring for an additional 30 minutes, the reaction mixture was diluted with DCM and was washed with saturated NaHCO3 solution. The organics were dried over MgSO4 and concentrated. The crude residue was used in the next step without purification. m/z (ESI) 333.0 (M+H)$^+$.

STEP 3: 4-(4-IODO-5-METHOXY-2-METHYLPHENYL)QUINAZOLINE-7-SULFONYL FLUORIDE

The crude residue from step two was dissolved in 30 mL MeCN, was treated with selectfluor (3.71 g, 10.46 mmol) and was heated to 60° C. Iodine (2.66 g, 10.46 mmol) was added, and the reaction mixture was allowed to stir for 3 hours. The reaction mixture was then diluted with ether and was filtered through a plug of celite. The filtrate was then concentrated. Purification of the crude residue by silica gel column chromatography (0-70% EtOAc/heptane) gave 4-(4-iodo-5-methoxy-2-methylphenyl)quinazoline-7-sulfonyl fluoride (0.483 g, 1.054 mmol, 20.15% yield). m/z (ESI) 459.0 (M+H)$^+$.

STEP 4: 4-(4-IODO-5-METHOXY-2-METHYLPHENYL)-N-(ISOXAZOL-3-YL)QUINAZOLINE-7-SULFONAMIDE

A solution of 3-aminoisoxazole (0.389 ml, 5.27 mmol) and 4-(4-iodo-5-methoxy-2-methylphenyl)quinazoline-7-sulfonyl fluoride (0.483 g, 1.054 mmol) in 5 mL THF was cooled to 0° C. and was treated with LHMDS 1N in THF (5.27 ml, 5.27 mmol). After stirring for one hour, the reaction mixture was concentrated. Purification of the crude residue by reverse phase column chromatography [Redisep Gold C18, 10-100% (0.1% NH4OH in MeOH)/(0.1% NH4OH in water)] gave 4-(4-iodo-5-methoxy-2-methylphenyl)-N-(isoxazol-3-yl)quinazoline-7-sulfonamide (0.311 g, 0.595 mmol, 56.5% yield). m/z (ESI) 522.9 (M+H)$^+$.

STEP 5: 4-(4'-CHLORO-2-METHOXY-3',5-DIMETHYL-[1,1'-BIPHENYL]-4-YL)-N-(ISOXAZOL-3-YL)QUINAZOLINE-7-SULFONAMIDE

A microwave vial charged with PdCl$_2$(Amphos)$_2$ (0.014 g, 0.020 mmol), (4-chloro-3-methylphenyl)boronic acid (0.067 g, 0.394 mmol), 4-(4-iodo-5-methoxy-2-methylphenyl)-N-(isoxazol-3-yl)quinazoline-7-sulfonamide (0.103 g, 0.197 mmol), potassium phosphate (0.167 g, 0.789 mmol), and 3 mL dioxane 1 mL water was heated to 150° C. in a Biotage Initiator microwave reactor for 30 minutes. The organic layer was treated with hcl 4N in dioxane (0.197 ml, 0.789 mmol) and was concentrated. Purification of the crude residue by reverse phase column chromatography [Redisep Gold C18, 10-100% (0.1% NH4OH in MeOH)/(0.1% NH4OH in water)] gave 4-(4'-chloro-2-methoxy-3',5-dimethyl-[1,1'-biphenyl]-4-yl)-N-(isoxazol-3-yl)quinazoline-7-sulfonamide (0.047 g, 0.090 mmol, 45.7% yield). $^1$H NMR (ACETONITRILE-d3) δ: 9.46 (s, 1H), 8.59 (d, J=1.7 Hz, 1H), 8.35 (d, J=1.9 Hz, 1H), 7.98-8.04 (m, 1H), 7.89-7.96 (m, 1H), 7.52-7.57 (m, 1H), 7.41-7.45 (m, 2H), 7.35 (s, 1H), 7.03 (s, 1H), 6.49 (d, J=1.9 Hz, 1H), 3.71-3.75 (m, 3H), 2.44 (s, 3H), 2.05 (s, 3H). m/z (ESI) 521.0 (M+H)$^+$.

Example 35 (Method 35)

1-(4'-CHLORO-2-METHOXY-3',5-DIMETHYL-[1,1'-BIPHENYL]-4-YL)-N-(ISOXAZOL-3-YL)ISOQUINOLINE-6-SULFONAMIDE

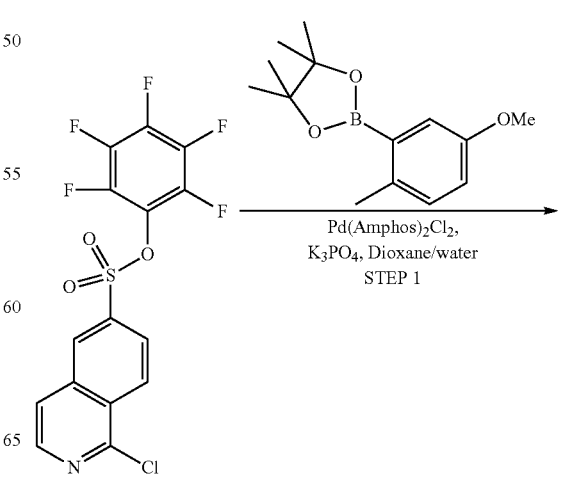

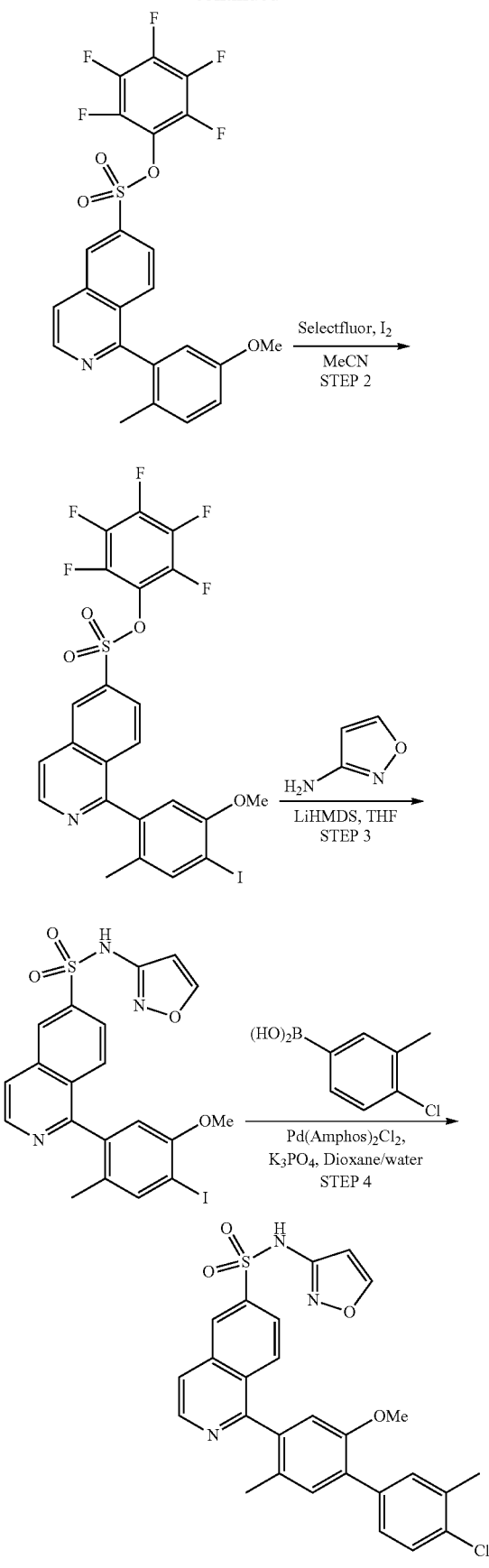

STEP 1: PERFLUOROPHENYL 1-(5-METHOXY-2-METHYLPHENYL)ISOQUINOLINE-6-SULFONATE

A solution of PdCl$_2$(Amphos)$_2$ (0.173 g, 0.244 mmol), 2-(5-methoxy-2-methylphenyl)-4,4,5,5-tetramethyl-1,3,2-dioxaborolane (1.332 g, 5.37 mmol), perfluorophenyl 1-chloroisoquinoline-6-sulfonate (2.000 g, 4.88 mmol), and potassium phosphate (4.14 g, 19.53 mmol) in 15 mL dioxane 5 mL water was heated to 50° C. for 30 minutes. The reaction mixture was then diluted with DCM and was washed with saturated NaHCO3 solution. The organics were dried over MgSO4 and concentrated. The crude residue was used in the next step without purification. m/z (ESI) 496.2 (M+H)$^+$.

STEP 2: PERFLUOROPHENYL 1-(4-IODO-5-METHOXY-2-METHYLPHENYL)ISOQUINOLINE-6-SULFONATE

The crude residue from step one was dissolved in 30 mL MeCN, was treated with selectfluor (3.46 g, 9.76 mmol) and was heated to 60° C. Iodine (2.478 g, 9.76 mmol) was added, and the reaction mixture was allowed to stir for 3 hours. The reaction mixture was then diluted with ether and was filtered through a plug of celite. The filtrate was then concentrated. Purification of the crude residue by silica gel column chromatography (0-70% EtOAc/heptane) gave perfluorophenyl 1-(4-iodo-5-methoxy-2-methylphenyl)isoquinoline-6-sulfonate (0.413 g, 0.665 mmol, 13.62% yield). m/z (ESI) 621.9 (M+H)$^+$.

STEP 3: 1-(4-IODO-5-METHOXY-2-METHYLPHENYL)-N-(ISOXAZOL-3-YL)ISOQUINOLINE-6-SULFONAMIDE

A solution of 3-aminoisoxazole (0.246 ml, 3.32 mmol) and perfluorophenyl 1-(4-iodo-5-methoxy-2-methylphenyl)isoquinoline-6-sulfonate (0.413 g, 0.665 mmol) in 5 mL THF was cooled to 0° C. and was treated with LHMDS 1N in THF (3.32 ml, 3.32 mmol). After stirring for one hour, LC/MS showed mostly product, so the reaction mixture was concentrated. Purification of the crude residue by reverse phase column chromatography [Redisep Gold C18, 10-100% (0.1% NH4OH in MeOH)/(0.1% NH4OH in water)] gave 1-(4-iodo-5-methoxy-2-methylphenyl)-N-(isoxazol-3-yl)isoquinoline-6-sulfonamide (0.156 g, 0.299 mmol, 45.0% yield). m/z (ESI) 522.0 (M+H)$^+$.

STEP 4: 1-(4'-CHLORO-2-METHOXY-3',5-DIMETHYL-[1,1'-BIPHENYL]-4-YL)-N-(ISOXAZOL-3-YL)ISOQUINOLINE-6-SULFONAMIDE

A microwave vial charged with PdCl$_2$(Amphos)$_2$ (10.59 mg, 0.015 mmol), (4-chloro-3-methylphenyl)boronic acid (0.051 g, 0.299 mmol), 1-(4-iodo-5-methoxy-2-methylphenyl)-N-(isoxazol-3-yl)isoquinoline-6-sulfonamide (0.078 g, 0.150 mmol), potassium phosphate (0.127 g, 0.598 mmol), and 3 mL dioxane 1 mL water was heated to 150° C. in a Biotage Initiator microwave reactor for 30 minutes. The organic layer was treated with HCl 4N in dioxane (0.150 ml, 0.598 mmol) and was concentrated. Purification of the crude residue by reverse phase column chromatography [Redisep Gold C18, 10-100% (0.1% NH4OH in MeOH)/(0.1% NH4OH in water)] gave 1-(4'-chloro-2-methoxy-3',5-dimethyl-[1,1'-biphenyl]-4-yl)-N-(isoxazol-3-yl)isoquinoline-6-sulfonamide (0.050 g, 0.096 mmol, 64.3% yield). $^1$H NMR (ACETONITRILE-d3) δ: 8.73 (d, J=5.7 Hz, 1H), 8.60 (d, J=1.8 Hz, 1H), 8.33 (d, J=1.9 Hz, 1H), 7.89-7.97 (m, 2H), 7.82-7.88 (m, 1H), 7.51-7.56 (m, 1H), 7.40-7.44 (m, 2H), 7.32 (s, 1H), 7.00 (s, 1H), 6.46 (d, J=1.8 Hz, 1H), 3.70-3.74 (m, 3H), 2.41-2.45 (m, 3H), 1.95 (s, 3H). m/z (ESI) 520.0 (M+H)+.

Example 36 (Method 36)

4-(2-CYCLOPROPYL-4-(TRIFLUOROMETHYL)-PHENYL)-N-(PYRIMIDIN-4-YL)QUINAZOLINE-7-SULFONAMIDE

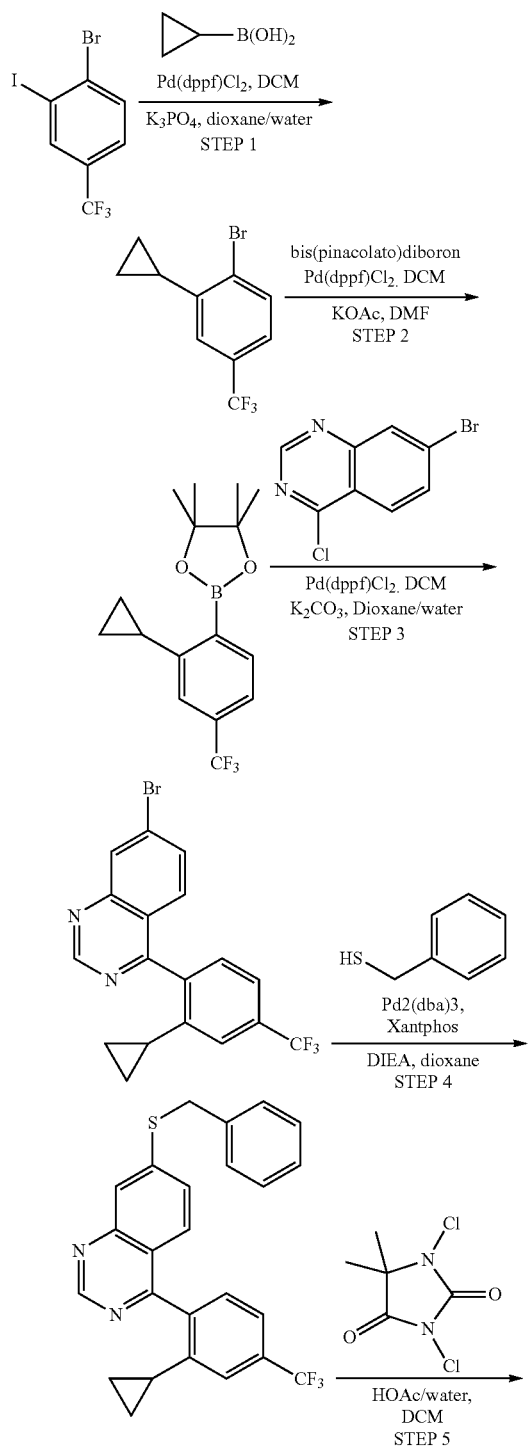

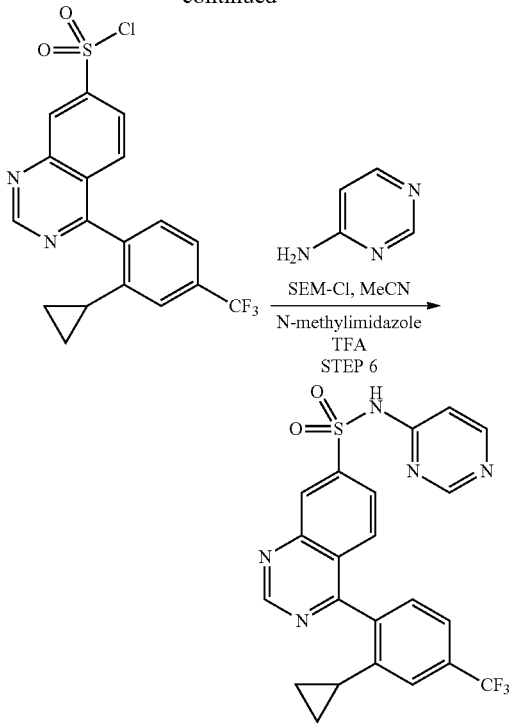

STEP 1: 1-BROMO-2-CYCLOPROPYL-4-(TRIFLUOROMETHYL)BENZENE

A solution of PdCl$_2$(dppf)-CH$_2$Cl$_2$adduct (0.407 g, 0.499 mmol), cyclopropylboronic acid (1.028 g, 11.97 mmol), 1-bromo-2-iodo-4-(trifluoromethyl)benzene (3.500 g, 9.97 mmol, Oakwood), and potassium phosphate (6.35 g, 29.9 mmol) in 20 mL dioxane 10 mL water was heated to 100° C. overnight. The reaction mixture was allowed to cool to room temperature.

The aqueous layer was removed, and the organics were filtered through a 0.45 M syringe filter and concentrated. The crude residue was used in the next step without purification.

STEP 2: 2-(2-CYCLOPROPYL-4-(TRIFLUOROMETHYL)PHENYL)-4,4,5,5-TETRAMETHYL-1,3,2-DIOXABOROLANE

The crude residue from Step 1 was dissolved in 20 ml DMF, was treated with bis(pinacolato)diboron (3.80 g, 14.96 mmol), PdCl$_2$(dppf)-CH$_2$Cl$_2$adduct (0.407 g, 0.499 mmol), and KOAc (3.92 g, 39.9 mmol) and was heated to 100° C. overnight. The reaction mixture was then diluted with heptane/ether (1:1) and was washed with water. The organics were then concentrated. Purification of the crude residue by silica gel column chromatography (0-20% EtOAc/heptane) gave 2-(2-cyclopropyl-4-(trifluoromethyl)phenyl)-4,4,5,5-tetramethyl-1,3,2-dioxaborolane (1.19 g, 3.81 mmol, 38.2% yield). m/z (ESI) 313.2 (M+H)+.

STEP 3: 7-BROMO-4-(2-CYCLOPROPYL-4-(TRIFLUOROMETHYL)PHENYL)-QUINAZOLINE

A solution of PdCl$_2$(dppf)-CH$_2$Cl$_2$adduct (0.117 g, 0.144 mmol), 2-(2-cyclopropyl-4-(trifluoromethyl)phenyl)-4,4,5,5-tetramethyl-1,3,2-dioxaborolane (1.077 g, 3.45 mmol), 7-bromo-4-chloroquinazoline (0.700 g, 2.87 mmol, Synnovator), and potassium carbonate (1.589 g, 11.50 mmol) in 15 mL dioxane was treated with 6 mL water and was allowed to stir at RT overnight. The reaction mixture was diluted with ether and washed with water. The organics were dried over MgSO$_4$ and concentrated. Purification of the crude residue by silica gel column chromatography (0-100% EtOAc/heptane) gave 7-bromo-4-(2-cyclopropyl-4-(trifluoromethyl)phenyl)quinazoline (0.363 g, 0.923 mmol, 32.1% yield). m/z (ESI) 394.2 (M+H)$^+$.

STEP 4: 7-(BENZYLTHIO)-4-(2-CYCLOPROPYL-4-(TRIFLUOROMETHYL)-PHENYL)QUINAZOLINE

A solution of 7-bromo-4-(2-cyclopropyl-4-(trifluoromethyl)phenyl)quinazoline (0.360 g, 0.916 mmol), Pd$_2$(dba)$_3$ (0.021 g, 0.023 mmol), xantphos (0.040 g, 0.069 mmol), and n,n-diisopropylethylamine (0.480 ml, 2.75 mmol) in 6 mL dioxane was heated to 60° C. and was treated with benzyl mercaptan (0.108 ml, 0.916 mmol). After stirring for one hour, the reaction mixture was concentrated. The crude residue was used in the next step without purification. m/z (ESI) 437.1 (M+H)$^+$.

STEP 5: 4-(2-CYCLOPROPYL-4-(TRIFLUOROMETHYL)PHENYL)QUINAZOLINE-7-SULFONYL CHLORIDE

The crude residue from step four was dissolved in 3 mL DCM and 0.3 mL (3:2 HOAc/water) and was cooled to 0° C. 1,3-dichloro-5,5-dimethylimidazolidine-2,4-dione (0.541 g, 2.75 mmol) was added, and the reaction mixture was allowed to stir for one hour. The reaction mixture was then diluted with DCM, dried over MgSO4 and was concentrated. Purification of the crude residue by silica gel column chromatography (0-100% EtOAc/heptane) gave 4-(2-cyclopropyl-4-(trifluoromethyl)phenyl)quinazoline-7-sulfonyl chloride (0.205 g, 0.497 mmol, 54.2% yield). m/z (ESI) 413.1 (M+H)$^+$.

STEP 6: 4-(2-CYCLOPROPYL-4-(TRIFLUOROMETHYL)PHENYL)-N-(PYRIMIDIN-4-YL)QUINAZOLINE-7-SULFONAMIDE

A solution of pyrimidin-4-amine (0.035 g, 0.363 mmol) in 1 mL MeCN was treated with SEM-Cl (0.064 ml, 0.363 mmol) and was allowed to stir for one hour at room temperature. 4-(2-cyclopropyl-4-(trifluoromethyl)phenyl)quinazoline-7-sulfonyl chloride (0.100 g, 0.242 mmol) was added as a solution in 3 mL MeCN. The reaction mixture was placed under argon, and 1-methylimidazole (0.058 ml, 0.727 mmol) was added. After stirring for two hours, the reaction mixture was concentrated. The crude residue was dissolved in 1 mL TFA and was allowed to stir at RT for 2 hours. The reaction mixture was then concentrated. Purification of the crude residue by reverse phase column chromatography [RediSep Gold C18, 10-100% (0.1% NH4OH in MeOH)/(0.1% NH4OH in water)] gave 4-(2-cyclopropyl-4-(trifluoromethyl)phenyl)-N-(pyrimidin-4-yl)quinazoline-7-sulfonamide (0.039 g, 0.083 mmol, 34.1% yield). $^1$H NMR (ACETONITRILE-d3) δ: 9.44 (s, 1H), 8.63 (s, 1H), 8.45 (br. s., 1H), 8.14 (br. s., 1H), 8.05 (d, J=8.6 Hz, 1H), 7.74 (d, J=8.7 Hz, 1H), 7.65 (dd, J=8.0, 1.0 Hz, 1H), 7.48 (d, J=8.0 Hz, 1H), 7.39 (s, 1H), 7.01 (br. s., 1H), 1.54 (tt, J=8.2, 5.4 Hz, 1H), 0.66-0.83 (m, 2H), 0.53-0.66 (m, 2H). m/z (ESI) 472.0 (M+H)$^+$.

Example 37 (Method 37)

1-(4-(1H-INDOL-1-YL)-2-METHOXYPHENYL)-N-(1,3,4-THIADIAZOL-2-YL)ISOQUINOLINE-6-SULFONAMIDE

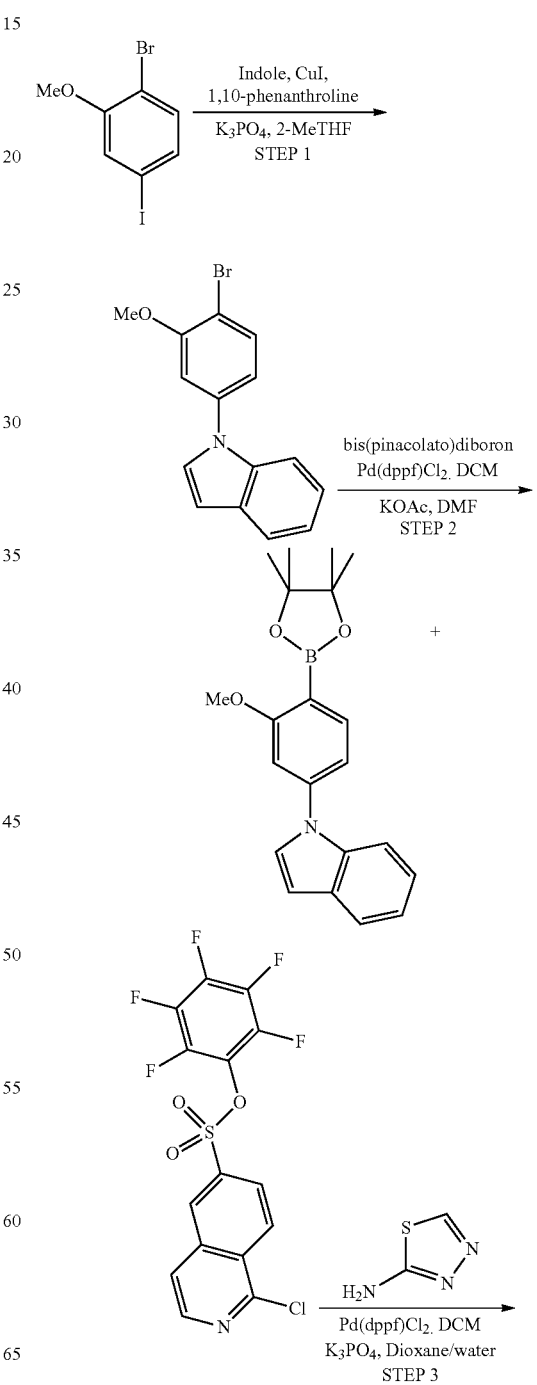

-continued

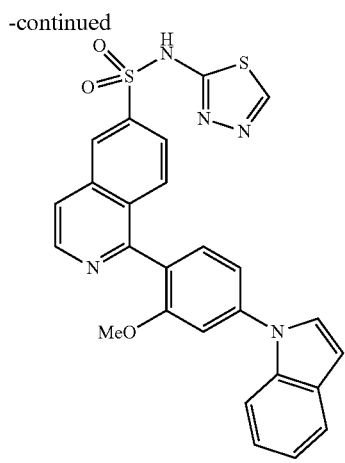

STEP 1:
1-(4-BROMO-3-METHOXYPHENYL)-1H-INDOLE

A microwave vial charged with copper(I) iodide (0.122 g, 0.639 mmol), 1,10-phenanthroline (0.115 g, 0.639 mmol), 1H-indole (0.749 g, 6.39 mmol), 1-bromo-4-iodo-2-methoxybenzene (2.000 g, 6.39 mmol, Combi-Blocks), potassium phosphate (4.07 g, 19.17 mmol), and 12 mL 2-MeTHF was heated to 140° C. in a Biotage Initiator microwave reactor for 120 minutes. The reaction mixture was then poured into water and was extracted with DCM. The organics were dried over MgSO4 and concentrated. Purification of the crude residue by silica gel column chromatography (0-20% EtOAc/heptane) gave 1-(4-bromo-3-methoxyphenyl)-1H-indole (1.96 g, 6.49 mmol, 101% yield). m/z (ESI) 302.1 (M+H)$^+$.

STEP 2: 1-(3-METHOXY-4-(4,4,5,5-TETRAMETHYL-1,3,2-DIOXABOROLAN-2-YL)PHENYL)-1H-INDOLE

A solution of PdCl$_2$(dppf)-CH$_2$Cl$_2$adduct (0.530 g, 0.649 mmol), bis(pinacolato)diboron (1.977 g, 7.78 mmol), 1-(4-bromo-3-methoxyphenyl)-1H-indole (1.960 g, 6.49 mmol), and potassium acetate (2.55 g, 25.9 mmol) in 13 mL DMF was heated to 110° C. overnight. The reaction mixture was diluted with ether and filtered through a plug of celite. The filtrate was then concentrated. Purification of the crude residue by silica gel column chromatography (0-20% EtOAc/heptane) gave 1-(3-methoxy-4-(4,4,5,5-tetramethyl-1,3,2-dioxaborolan-2-yl)phenyl)-1H-indole (0.910 g, 2.61 mmol, 40.2% yield). m/z (ESI) 350.1 (M+H)$^+$.

STEP 3: 1-(4-(1H-INDOL-1-YL)-2-METHOXYPHENYL)-N-(1,3,4-THIADIAZOL-2-YL)ISOQUINOLINE-6-SULFONAMIDE

A solution of perfluorophenyl 1-chloroisoquinoline-6-sulfonate (0.500 g, 1.220 mmol), 1,3,4-thiadiazol-2-amine (0.123 g, 1.220 mmol), and potassium phosphate (1.295 g, 6.10 mmol) in 3 mL MeCN was heated to 80° C. overnight. The reaction mixture was then concentrated. The crude residue was dissolved in 5 mL dioxane 2 mL water, was treated with PdCl$_2$(dppf)-CH$_2$Cl$_2$adduct (0.100 g, 0.122 mmol) and 1-(3-methoxy-4-(4,4,5,5-tetramethyl-1,3,2-dioxaborolan-2-yl)phenyl)-1H-indole (0.384 g, 1.098 mmol) and was heated to 110° C. overnight. The aqueous layer was then removed, and the reaction mixture was treated with HCl 4N in dioxane (1.525 ml, 6.10 mmol). After stirring for an additional 20 minutes, the reaction mixture was concentrated. Purification of the crude residue by reverse phase column chromatography [Redisep Gold C18, 10-100% (0.1% NH4OH in MeOH)/(0.1% NH4OH in water)] gave 1-(4-(1H-indol-1-yl)-2-methoxyphenyl)-N-(1,3,4-thiadiazol-2-yl)isoquinoline-6-sulfonamide (0.031 g, 0.060 mmol, 4.95% yield). $^1$H NMR (ACETONITRILE-d3) δ: 8.71 (d, J=5.8 Hz, 1H), 8.52 (s, 1H), 8.32-8.41 (m, 3H), 8.08 (dd, J=8.0, 1.6 Hz, 1H), 7.94 (d, J=5.6 Hz, 1H), 7.87-7.90 (m, 2H), 7.85 (d, J=3.7 Hz, 1H), 7.80 (d, J=2.1 Hz, 1H), 7.65 (dd, J=8.1, 2.1 Hz, 1H), 7.51 (d, J=8.2 Hz, 1H), 7.23 (dd, J=7.8, 4.6 Hz, 1H), 6.76 (d, J=3.7 Hz, 1H), 3.76 (s, 3H). m/z (ESI) 515.0 (M+H)$^+$.

Example 38 (Method 38)

N-(ISOXAZOL-3-YL)-4-(2-METHOXY-4-(TRIFLUOROMETHYL)PHENYL)QUINAZOLINE-7-SULFONAMIDE

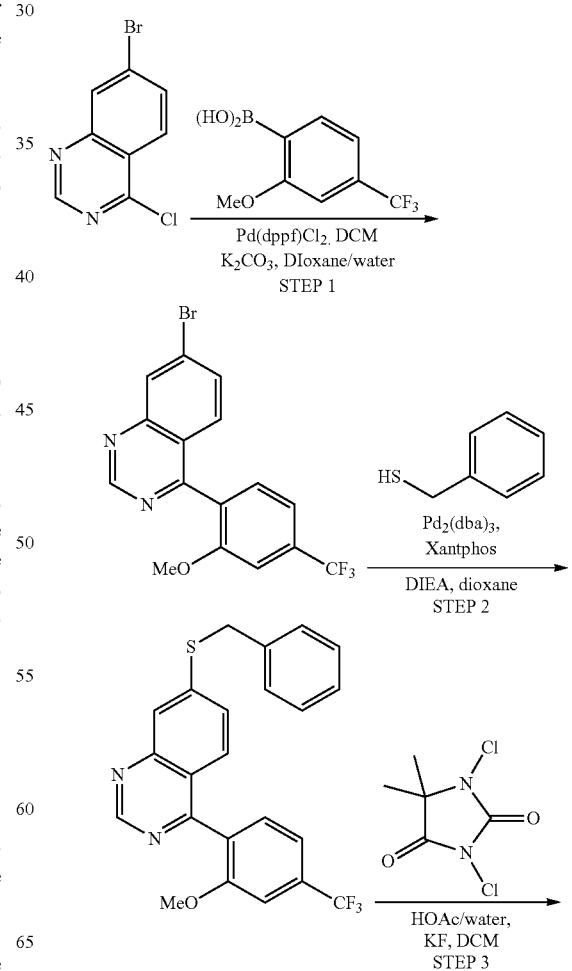

-continued

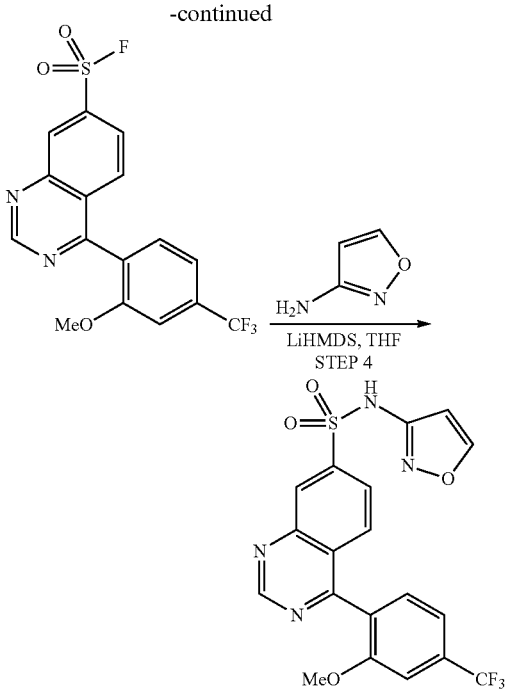

STEP 1: 7-BROMO-4-(2-METHOXY-4-(TRIF-LUOROMETHYL)PHENYL)-QUINAZOLINE

A solution of PdCl$_2$(dppf)-CH$_2$Cl$_2$adduct (0.503 g, 0.616 mmol),(2-methoxy-4-(trifluoromethyl)phenyl)boronic acid (2.98 g, 13.55 mmol), 7-bromo-4-chloroquinazoline (3.000 g, 12.32 mmol, Synnovator), and potassium carbonate (6.81 g, 49.3 mmol) in 37 mL dioxane was treated with 12 mL water and was allowed to stir at RT overnight. The reaction mixture was diluted with ether and washed with water. The organics were dried over MgSO$_4$ and concentrated. The crude residue was used in the next step without purification. m/z (ESI) 384.9 (M+H)$^+$.

STEP 2: 7-(BENZYLTHIO)-4-(2-METHOXY-4-(TRIFLUOROMETHYL)PHENYL)-QUINAZOLINE

The crude residue from step one was dissolved in 25 mL dioxane, was treated with Pd$_2$(dba)$_3$ (0.282 g, 0.308 mmol), xantphos (0.535 g, 0.924 mmol), and DIEA (6.46 ml, 37.0 mmol) and was heated to 60° C. Benzyl mercaptan (1.457 ml, 12.32 mmol) was added, and the reaction mixture was allowed to stir for one hour. The reaction mixture was then concentrated. Purification of the crude residue by silica gel column chromatography (0-100% EtOAc/heptane) gave 7-(benzylthio)-4-(2-methoxy-4-(trifluoromethyl)phenyl) quinazoline (4.43 g, 10.39 mmol, 84% yield). m/z (ESI) 427.2 (M+H)$^+$.

STEP 3: 4-(2-METHOXY-4-(TRIFLUOROMETHYL)PHENYL)QUINAZOLINE-7-SULFONYL FLUORIDE

A solution of 7-(benzylthio)-4-(2-methoxy-4-(trifluoromethyl)phenyl)quinazoline (4.43 g, 10.39 mmol) in 40 mL MeCN and 8 mL (1.5:1 HOAc/water) solution was treated with 1,3-dichloro-5,5-dimethylimidazolidine-2,4-dione (8.19 g, 41.6 mmol) and was allowed to stir at RT for one hour. Potassium fluoride (3.02 g, 51.9 mmol) was added, and the reaction mixture was allowed to stir for an additional hour. The reaction mixture was then diluted with DCM and dried over MgSO4. The organics were then concentrated. Purification of the crude residue by silica gel column chromatography (0-100% EtOAc/heptane) gave 4-(2-methoxy-4-(trifluoromethyl)phenyl)quinazoline-7-sulfonyl fluoride (0.630 g, 1.631 mmol, 15.70% yield). m/z (ESI) 387.1 (M+H)$^+$.

STEP 4: N-(ISOXAZOL-3-YL)-4-(2-METHOXY-4-(TRIFLUOROMETHYL)-PHENYL)QUINAZOLINE-7-SULFONAMIDE

A solution of isoxazol-3-amine (0.096 ml, 1.294 mmol) and 4-(2-methoxy-4-(trifluoromethyl)phenyl)quinazoline-7-sulfonyl fluoride (0.100 g, 0.259 mmol) in 2 ml THF was cooled to 0° C. and was treated with LHMDS 1N in THF (0.259 ml, 0.259 mmol). After stirring for 3 hours, the reaction mixture was treated with HCl 4N in dioxane (0.518 ml, 2.071 mmol). After stirring for an additional hour, the reaction mixture was concentrated. Purification of the crude residue by reverse phase column chromatography [Puriflash C18, 10-100% (0.1% NH4OH in MeOH)/(0.1% NH4OH in water)] gave N-(isoxazol-3-yl)-4-(2-methoxy-4-(trifluoromethyl)phenyl)quinazoline-7-sulfonamide (0.014 g, 0.031 mmol, 12.01% yield). $^1$H NMR (ACETONITRILE-d3) δ: 9.41-9.46 (m, 1H), 8.55 (d, J=1.7 Hz, 1H), 8.27-8.31 (m, 1H), 7.97 (dd, J=8.8, 1.8 Hz, 1H), 7.80 (dd, J=8.9, 0.5 Hz, 1H), 7.54-7.60 (m, 1H), 7.44-7.50 (m, 2H), 6.41-6.44 (m, 1H), 3.75 (s, 3H). m/z (ESI) 451.0 (M+H)$^+$.

Example 39 (Method 39)

1-(2-METHYL-5-PHENOXYPHENYL)-N-(PYRIMIDIN-4-YL)ISOQUINOLINE-6-SULFONAMIDE

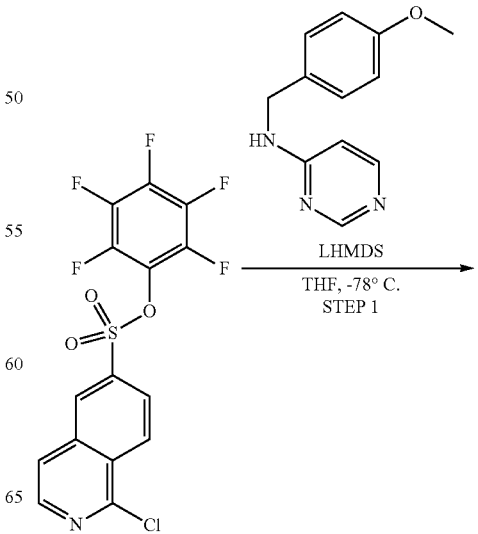

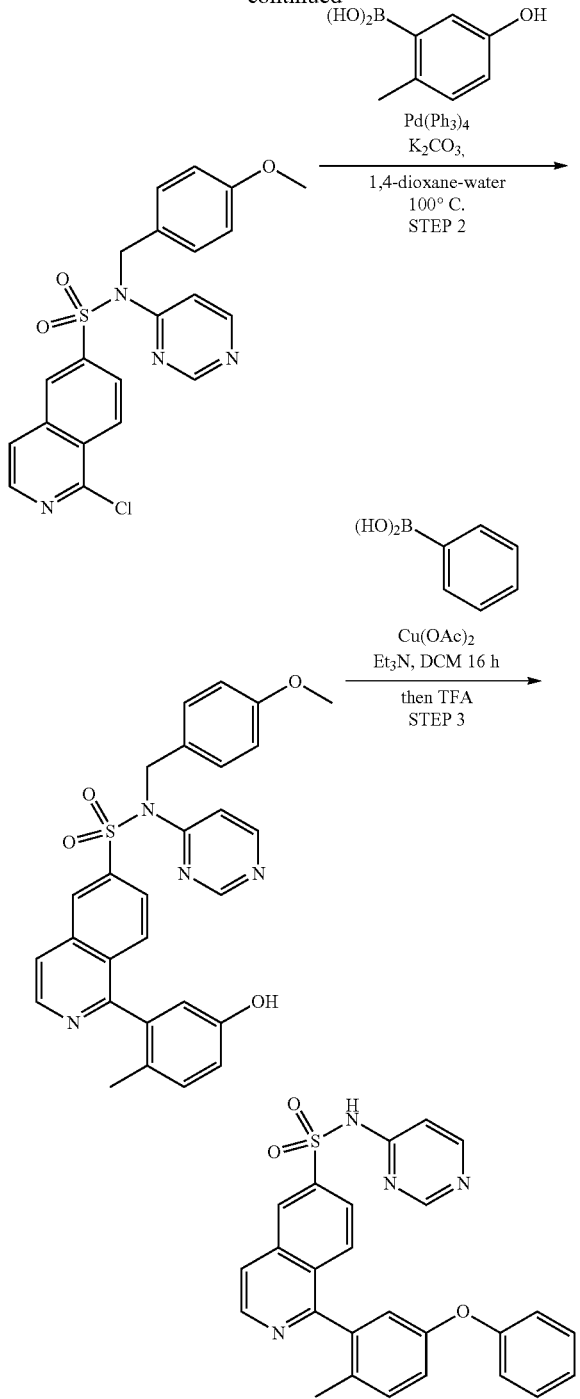

STEP 1: 1-CHLORO-N-(4-METHOXYBENZYL)-N-(PYRIMIDIN-4-YL)ISOQUINOLINE-6-SULFONAMIDE

A vial was charged with N-(4-methoxybenzyl)pyrimidin-4-amine (1.051 g, 4.88 mmol) and THF (9.76 ml), The vial was flushed with Ar (g), then cooled in an dry ice-acetone bath for 10 min, then lithium bis(trimethylsilyl)amide (1M in THF) (4.88 mL, 4.88 mmol) was added. After 10 min, solution of perfluorophenyl 1-chloroisoquinoline-6-sulfonate (2.00 g, 4.88 mmol) in THF (5.0 mL) was added dropwise. The ice bath was removed and the reaction was stirred for an additional 45 minutes. The mixture was quenched by the addition of saturated NH$_4$Cl and extracted with EtOAc (3×). The combined organic extracts were dried over sodium sulfate, filtered, and concentrated. The residue was purified by chromatography on silica gel (100-g Ultra SNAP column, 50% EtOAc/Heptane). Fractions containing the product were combined and concentrated to give 1-chloro-N-(4-methoxybenzyl)-N-(pyrimidin-4-yl)isoquinoline-6-sulfonamide (0.826 g, 1.873 mmol, 38.4% yield) as an off white solid. m/z (ESI) 441.0 (M+H)$^+$.

STEP 2: 1-(5-HYDROXY-2-METHYLPHENYL)-N-(4-METHOXYBENZYL)-N-(PYRIMIDIN-4-YL)ISOQUINOLINE-6-SULFONAMIDE

A vial was charged with 1-chloro-N-(4-methoxybenzyl)-N-(pyrimidin-4-yl)isoquinoline-6-sulfonamide (300 mg, 0.680 mmol), (5-hydroxy-2-methylphenyl)boronic acid (0.155 g, 1.021 mmol), potassium carbonate (0.282 g, 2.041 mmol), and tetrakistriphenylphosphinepalladium(0) (79 mg, 0.068 mmol). The vial was flushed with Ar (g), then 1,4-dioxane (2.55 ml) and water (0.86 ml) were added. The vial was sealed and heated in a Biotage Initiator microwave reactor for 1 h at 100° C. LCMS showed clean desired product. The mixture was extracted with EtOAc (3×), then the combined organic extracts were concentrated. The residue was purified by chromatography on silica gel (12-g Redi-Sep Gold column, 0-50%, then 50-100% EtOAc/Heptane) to give 1-(5-hydroxy-2-methylphenyl)-N-(4-methoxybenzyl)-N-(pyrimidin-4-yl)isoquinoline-6-sulfonamide (0.274 g, 0.535 mmol, 79% yield) as a cream-colored foam. m/z (ESI) 513.3 (M+H)$^+$.

STEP 3: 1-(2-METHYL-5-PHENOXYPHENYL)-N-(PYRIMIDIN-4-YL)ISOQUINOLINE-6-SULFONAMIDE

To a microwave vial was added, phenylboronic acid (0.024 g, 0.195 mmol), 1-(5-hydroxy-2-methylphenyl)-N-(4-methoxybenzyl)-N-(pyrimidin-4-yl)isoquinoline-6-sulfonamide (0.050 g, 0.098 mmol), triethylamine (0.041 ml, 0.293 mmol), and copper (ii) acetate (0.019 ml, 0.195 mmol). DCM (0.488 ml) was added and the reaction was sealed and stirred at room temperature for 16 hours. The reaction was quenched with water, extracted with DCM (3×), dried over sodium sulfate, filtered, and concentrated. The residue was dissolved in 2 mL DCM and TFA (1 mL) was added. The reaction was stirred at RT for 3 hours. The solvent was removed and added NaHCO3 (sat) and extracted with DCM (3×), dried over MgSO4 and filtered. Removed solvent in vaccuo and the residue was purified by chromatography on silica gel (100-g Ultra SNAP column, 0-10% MeOH/DCM). Fractions containing the product were combined and concentrated to give 1-(5-hydroxy-2-methylphenyl)-N-(4-methoxybenzyl)-N-(pyrimidin-4-yl)isoquinoline-6-sulfonamide (0.015 g, 0.032 mmol, 33% yield). $^1$H NMR (400 MHz, DMSO-d$_6$) δ ppm 8.67-8.77 (m, 3H) 8.18 (d, J=5.48 Hz, 2H) 8.01 (dd, J=8.90, 1.86 Hz, 2H) 7.76 (d, J=8.80 Hz, 2H) 7.32-7.48 (m, 3H) 7.04-7.17 (m, 3H) 6.95 (d, J=2.54 Hz, 1H) 1.94 (s, 3H). m/z (ESI) 469.2 (M+H)$^+$.

Example 40 (Method 40)

1-(2-METHYL-5-(PYRIDIN-2-YLOXY)PHENYL)-N-(PYRIMIDIN-4-YL)ISOQUINOLINE-6-SULFONAMIDE

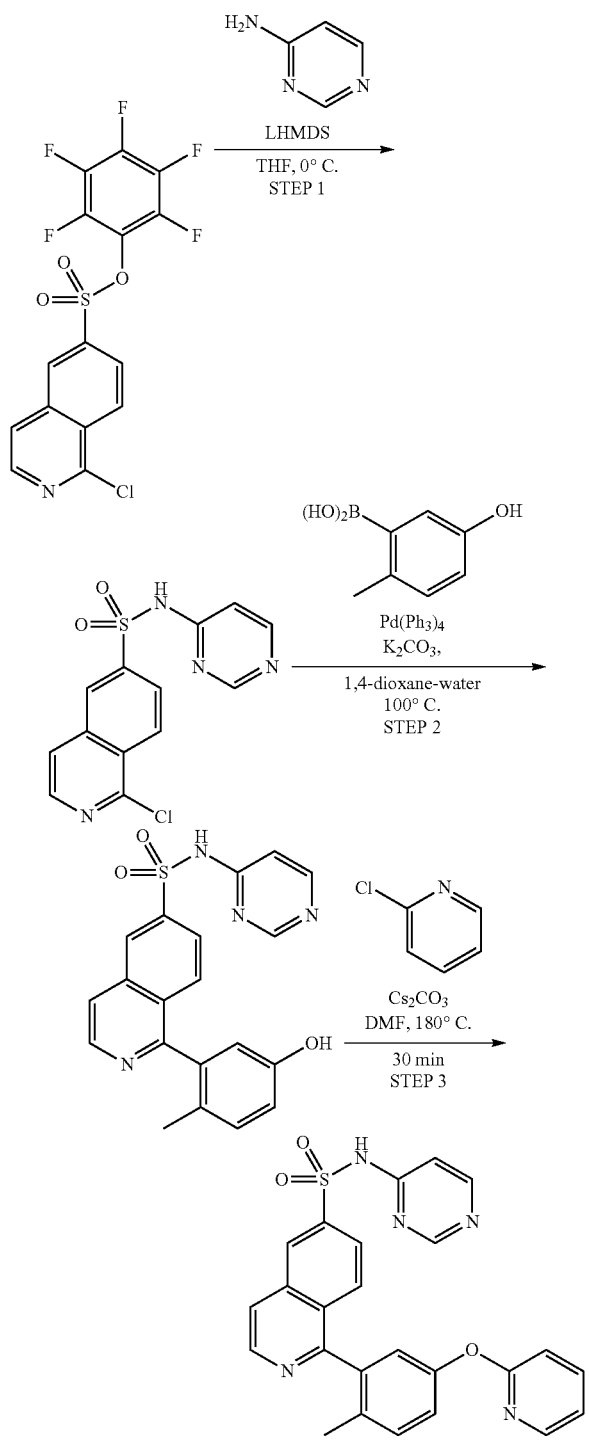

STEP 1: 1-CHLORO-N-(PYRIMIDIN-4-YL)ISOQUINOLINE-6-SULFONAMIDE

1-Chloro-N-(pyrimidin-4-yl)isoquinoline-6-sulfonamide was prepared in an analogous manner to that of Method 2, Step 1, except that pyrimidin-4-amine was used in place of isoxazol-3-amine m/z (ESI) 321.1 (M+H)$^+$.

STEP 2: 1-(5-HYDROXY-2-METHYLPHENYL)-N-(PYRIMIDIN-4-YL)ISOQUINOLINE-6-SULFONAMIDE 1-(5-Hydroxy-2-methylphenyl)-N-(pyrimidin-4-yl)isoquinoline-6-sulfonamide was prepared in an analogous manner to that of Method 39, Step 2, except that 1-chloro-N-(pyrimidin-4-yl)isoquinoline-6-sulfonamide was used in place of -chloro-N-(4-methoxybenzyl)-N-(pyrimidin-4-yl)isoquinoline-6-sulfonamide. m/z (ESI) 393.0 (M+H)$^+$.

STEP 3: 1-(2-METHYL-5-(PYRIDIN-2-YLOXY)PHENYL)-N-(PYRIMIDIN-4-YL)ISOQUINOLINE-6-SULFONAMIDE

To a microwave vial was added, 1-(5-hydroxy-2-methylphenyl)-N-(pyrimidin-4-yl)isoquinoline-6-sulfonamide (0.050 g, 0.127 mmol), 2-chloropyridine (0.012 ml, 0.127 mmol), and cesium carbonate (0.125 g, 0.382 mmol). DMF (0.637 ml) was added and the vial was capped. The reaction was heated in a Biotage Initiator microwave reactor for 30 minutes at 180° C. The reaction was cooled to room temperature, filtered through pad of celite and washed with DMSO (2 mL). The filtrate was purified by reverse-phase HPLC (35-80% CH$_3$CN/H$_2$O with 0.1% TFA). Fractions containing product were combined, washed with saturated NaHCO$_3$ and extracted with DCM (3×). The organic layer was dried over MgSO4, filtered and concentrated to give 1-(2-methyl-5-(pyridin-2-yloxy)phenyl)-N-(pyrimidin-4-yl)isoquinoline-6-sulfonamide (0.022 g, 0.047 mmol, 37% yield). $^1$H NMR (400 MHz, DMSO-d$_6$) δ ppm 8.64-8.74 (m, 2H) 8.54 (s, 1H) 8.15-8.26 (m, 2H) 8.12 (d, J=5.67 Hz, 1H) 7.98 (s, 1H) 7.84 (s, 1H) 7.76 (d, J=8.90 Hz, 1H) 7.44 (d, J=8.41 Hz, 1H) 7.20 (dd, J=8.22, 2.54 Hz, 1H) 7.09-7.15 (m, 1H) 7.05 (d, J=2.25 Hz, 2H) 6.99 (d, J=6.26 Hz, 1H) 1.94-2.03 (m, 15H). m/z (ESI) 470.1 (M+H)$^+$.

Example 41 (Method 41)

1-(2-METHOXY-5-PHENYLPYRIDIN-3-YL)-N-(PYRIMIDIN-4-YL)ISOQUINOLINE-6-SULFONAMIDE

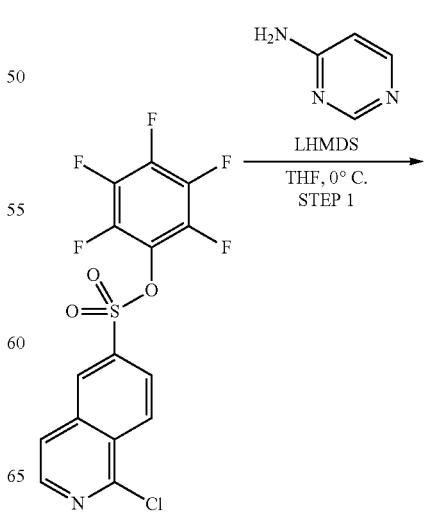

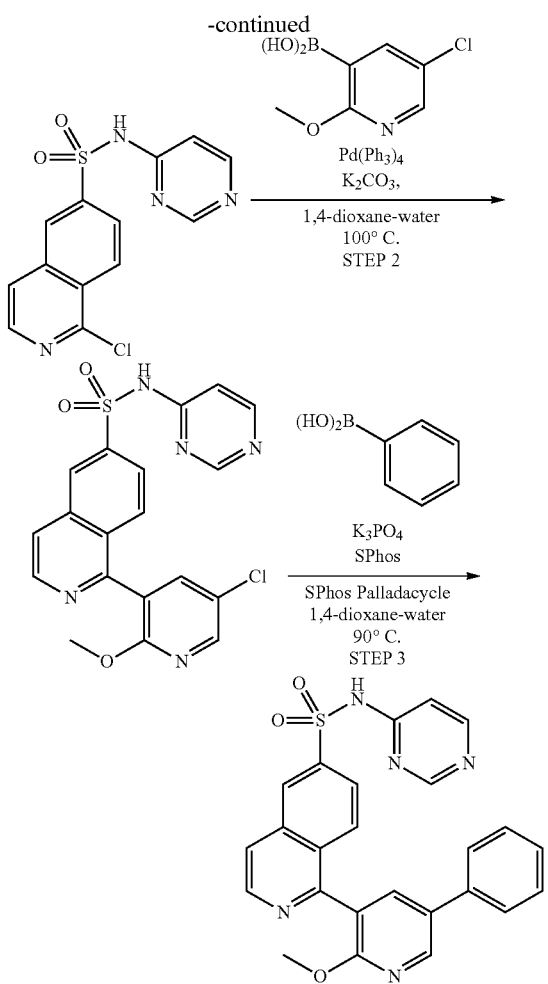

STEP 1: 1-CHLORO-N-(PYRIMIDIN-4-YL)ISO-QUINOLINE-6-SULFONAMIDE 1-chloro-N-(pyrimidin-4-yl)isoquinoline-6-sulfonamide was prepared in an analogous manner to that of Method 2, Step 1, except that pyrimidin-4-amine was used in place of isoxazol-3-amine. m/z (ESI) 321.1 (M+H)⁺.

STEP 2: 1-(5-CHLORO-2-METHOXYPYRIDIN-3-YL)-N-(PYRIMIDIN-4-YL)ISOQUINOLINE-6-SULFONAMIDE 1-(5-Chloro-2-methoxypyridin-3-yl)-N-(pyrimidin-4-yl)isoquinoline-6-sulfonamide was prepared in an analogous manner to that of Method 39, Step 2, except that (5-chloro-2-methoxypyridin-3-yl)boronic acid (Combi-Blocks) was used in place of 5-hydroxy-2-methylphenyl)boronic acid. m/z (ESI) 428.1 (M+H)⁺.

STEP 3: 1-(2-METHOXY-5-PHENYLPYRIDIN-3-YL)-N-(PYRIMIDIN-4-YL)ISOQUINOLINE-6-SULFONAMIDE

To a vial was added, 1-(5-chloro-2-methoxypyridin-3-yl)-N-(pyrimidin-4-yl)isoquinoline-6-sulfonamide (0.075 g, 0.175 mmol), chloro(2-dicyclohexylphosphino-2',6'-dimethoxy-1,1'-biphenyl)[2-(2-aminoethylphenyl)]palladium(ii) dichloromethane adduct (0.066 g, 0.088 mmol), 2-dicyclohexylphosphino-2',6'-dimethoxy-1'1'-biphenyl (1.799 mg, 4.38 μmol), phenylboronic acid (0.043 g, 0.351 mmol), potassium phosphate, tribasic (0.092 g, 0.526 mmol), water (0.080 ml) and 1,4-dioxane (0.797 ml). The vial was capped and heated to 90° C. After 2 hours, reaction was cooled, quenched with water, extracted with DCM (3×), dried over sodium sulfate, filtered, and concentrated. The filtrate was purified by reverse-phase HPLC (35-80% CH₃CN/H₂O with 0.1% TFA). Fractions containing product were combined, washed with saturated NaHCO₃ and extracted with DCM (3×). The organic layer was dried over MgSO4, filtered and concentrated to give 1-(2-methoxy-5-phenylpyridin-3-yl)-N-(pyrimidin-4-yl)isoquinoline-6-sulfonamide (0.044 g, 0.094 mmol, 54% yield). ¹H NMR (400 MHz, DMSO-d₆) δ ppm 8.69-8.76 (m, 1 H) 8.73 (d, J=15.55 Hz, 1H) 8.11-8.20 (m, 1 H) 8.01 (s, 1 H) 7.95-7.98 (m, 1 H) 7.72-7.81 (m, 2 H) 7.52-7.68 (m, 5 H) 7.44-7.51 (m, 1 H) 7.29-7.43 (m, 2 H) 3.80-3.86 (m, 3 H). m/z (ESI) 470.1 (M+H)⁺.

Example 43 (Method 43)

1-(2-CHLORO-3'-FLUORO-5-METHOXY-[1,1'-BIPHENYL]-4-YL)-7-FLUORO-N-(ISOXAZOL-3-YL)ISOQUINOLINE-6-SULFONAMIDE

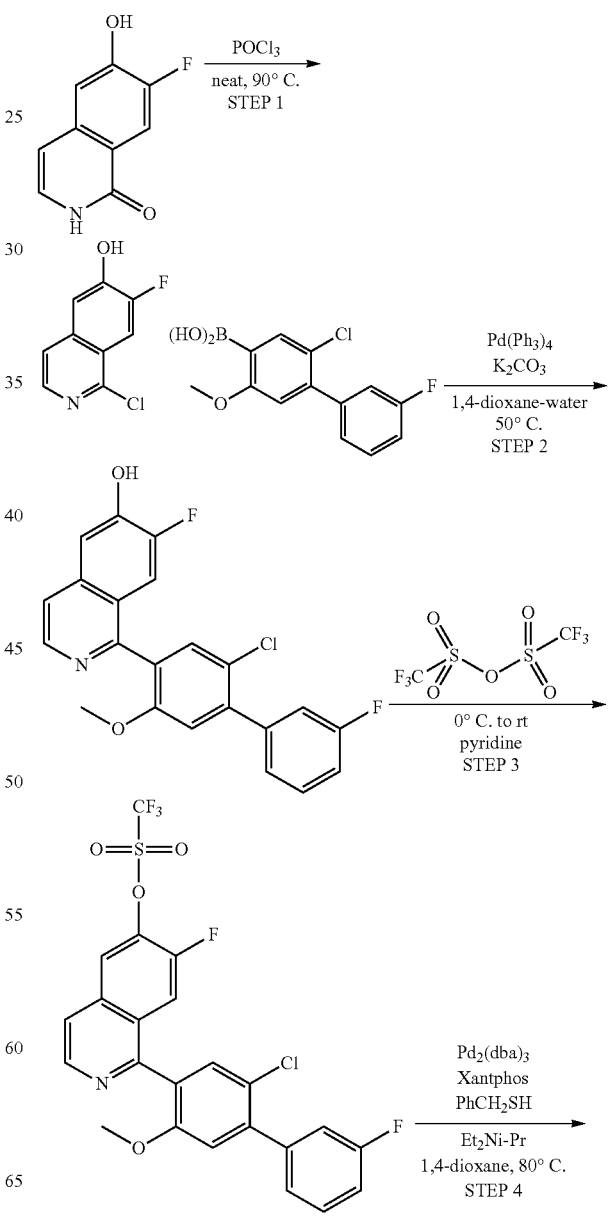

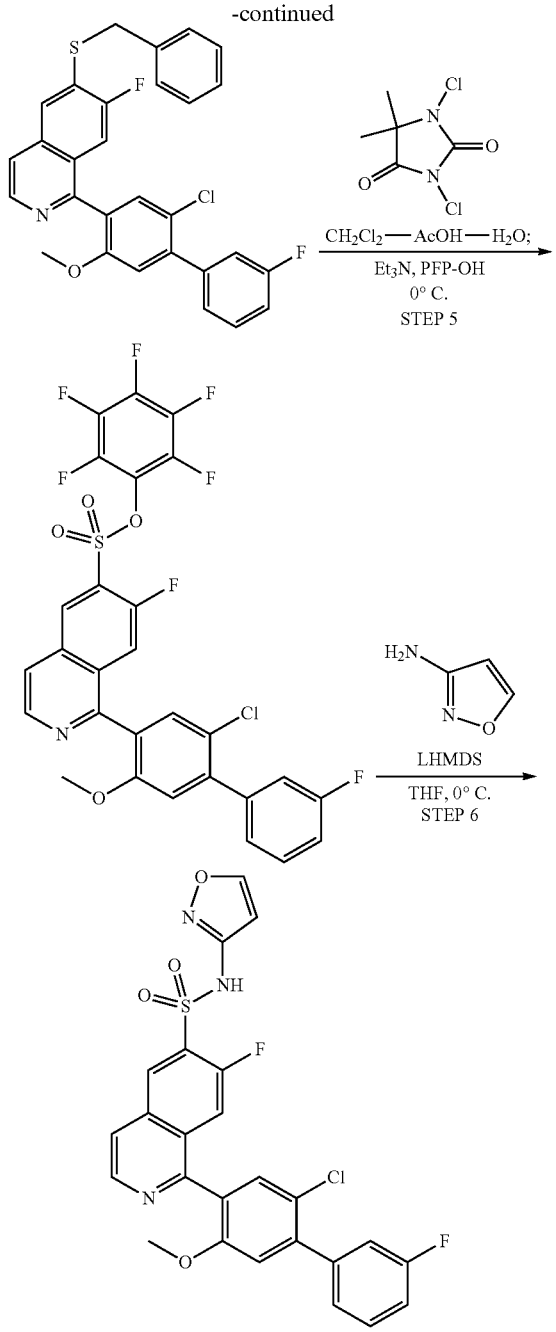

STEP 1: 1-CHLORO-7-FLUOROISOQUINOLIN-6-OL

A sealed tube was charged with 7-fluoro-6-hydroxyisoquinolin-1(2H)-one (3.15 g, 17.58 mmol, FCH Group) and phosphorus oxychloride (6.56 ml, 70.3 mmol) was added and the reaction was stirred for 16 hrs at 90° C. (neat) until reaction was complete by LCMS. The mixture was cooled 0° C. in an ice bath, then of ice was added. The reaction was then quenched with 2M HCl and allowed to warm to RT. A precipitate formed and was filtered and rinsed copiously with water. The crude 1-chloro-7-fluoroisoquinolin-6-ol (3.28 g, 16.60 mmol, 94% yield) was carried forward without further purification. m/z (ESI) 198.1 (M+H)+.

STEP 2: 1-(2-CHLORO-3'-FLUORO-5-METHOXY-[1,1'-BIPHENYL]-4-YL)-7-FLUOROISOQUINOLIN-6-OL

A sealed tube was charged with 1-chloro-7-fluoroisoquinolin-6-ol (1.5 g, 7.59 mmol), (2-chloro-3'-fluoro-5-methoxy-[1,1'-biphenyl]-4-yl)boronic acid (2.56 g, 9.11 mmol), potassium carbonate (3.15 g, 22.77 mmol), and tetrakistriphenylphosphinepalladium(0) (1.754 g, 1.518 mmol). The vial was flushed with Ar (g), then Dioxane (28.5 ml) and Water (9.49 ml) were added. The tube was heated at 50° C. for 3 hrs until the reaction was complete by LCMS. The mixture was cooled to RT and partitioned between ammonium chloride solution and EtOAc. The layers were separated, extracted 3 times with EtOAc, and the organic extracts were dried over sodium sulfate, filtered, and concentrated. The residue was purified by chromatography on silica gel (40-g Redi-Sep Gold column, 100-g silica gel loading column, 0-100% EtOAc/Heptane) to give 1-(2-chloro-3'-fluoro-5-methoxy-[1,1'-biphenyl]-4-yl)-7-fluoroisoquinolin-6-ol (2.2 g, 5.53 mmol, 72.9% yield) as a white solid. m/z (ESI) 398.1 (M+H)+.

STEP 3: 1-(2-CHLORO-3'-FLUORO-5-METHOXY-[1,1'-BIPHENYL]-4-YL)-7-FLUOROISOQUINOLIN-6-YL TRIFLUOROMETHANESULFONATE

Dissolved 1-(2-chloro-3'-fluoro-5-methoxy-[1,1'-biphenyl]-4-yl)-7-fluoroisoquinolin-6-ol (2.2 g, 5.53 mmol) in pyridine (11.06 ml) and cooled to 0° C. in an ice bath. Added trifluoromethanesulfonic anhydride (2.326 ml, 13.83 mmol) dropwise (smokes) and let warm to rt and stirred at RT for 1 hr until reaction was complete by LCMS. Water and DCM were added to the reaction mixture, then the phases were separated. Extracted aqueous 3× with DCM, dried over Na2SO4, filtered and concentrated via rotary evaporation. Crude 1-(2-chloro-3'-fluoro-5-methoxy-[1,1'-biphenyl]-4-yl)-7-fluoroisoquinolin-6-yl trifluoromethanesulfonate (3.5 g, 6.61 mmol, 119% yield) was brought on to the next reaction without further purification. m/z (ESI) 530.0 (M+H)+.

STEP 4: 6-(BENZYLTHIO)-1-(2-CHLORO-3'-FLUORO-5-METHOXY-[1,1'-BIPHENYL]-4-YL)-7-FLUOROISOQUINOLINE

Dissolved Pd2(dba)3 (0.127 g, 0.138 mmol), xantphos (0.160 g, 0.276 mmol), and 1-(2-chloro-3'-fluoro-5-methoxy-[1,1'-biphenyl]-4-yl)-7-fluoroisoquinolin-6-yl trifluoromethanesulfonate (2.93 g, 5.53 mmol) in 1,4-dioxane (11.06 ml) in a sealed tube and added n,n-diisopropylethylamine (1.932 ml, 11.06 mmol). Heated to 80° C. for 5 min then added benzyl mercaptan (0.654 ml, 5.53 mmol) dropwise. The reaction was maintained at 80° C. for 1 hr until the reaction was complete by LCMS. The mixture was cooled to RT, diluted with EtOAc, and washed with 1N aq. HCl. The aqueous layer was extracted 3 times with EtOAc, and the combined organic extracts were dried over sodium sulfate, filtered, and concentrated. The residue was purified by chromatography on silica gel (100-g column, 25-g silica gel loading column, gradient 0-100% EtOAc/Heptane). 6-(benzylthio)-1-(2-chloro-3'-fluoro-5-methoxy-[1,1'-biphenyl]-4-yl)-7-fluoroisoquinoline (2.57 g, 5.10 mmol, 92% yield) was isolated as an offwhite solid. m/z (ESI) 504.2 (M+H)+.

STEP 5: PERFLUOROPHENYL 1-(2-CHLORO-3'-FLUORO-5-METHOXY-[1,1'-BIPHENYL]-4-YL)-7-FLUOROISOQUINOLINE-6-SULFONATE

A RBF was charged with 6-(benzylthio)-1-(2-chloro-3'-fluoro-5-methoxy-[1,1'-biphenyl]-4-yl)-7-fluoroisoquinoline (2.57 g, 5.10 mmol), DCM (48.0 ml), Acetic Acid (1.800 ml), and Water (1.200 ml). The flask was cooled in an ice-bath for 10 min, then 1,3-dichloro-5,5-dimethylimidazolidine-2,4-dione (2.51 g, 12.75 mmol) was added in one portion. The reaction mixture was stirred at 0° C. for 15 minutes until LCMS showed complete conversion to sulfonyl chloride, so 2,3,4,5,6-pentafluorophenol (1.068 ml, 10.20 mmol) was added followed by dropwise addition of triethylamine (1.777 ml, 12.75 mmol). The reaction was stirred for 30 minutes at 0° C. until reaction was complete by LCMS. The reaction mixture was concentrated directly and purified via column chromatography (100 g column, gradient elution 0-50% EtOAc:Heptane) to afford perfluorophenyl 1-(2-chloro-3'-fluoro-5-methoxy-[1,1'-biphenyl]-4-yl)-7-fluoroisoquinoline-6-sulfonate (2.0 g, 3.19 mmol, 62.5% yield). m/z (ESI) 628.1 (M+H)$^+$.

STEP 6: 1-(2-CHLORO-3'-FLUORO-5-METHOXY-[1,1'-BIPHENYL]-4-YL)-7-FLUORO-N-(ISOXAZOL-3-YL)ISOQUINOLINE-6-SULFONAMIDE

A RBF was charged with perfluorophenyl 1-(2-chloro-3'-fluoro-5-methoxy-[1,1'-biphenyl]-4-yl)-7-fluoroisoquinoline-6-sulfonate (780 mg, 1.242 mmol), THF (6211 µl), and isoxazol-3-amine (101 µl, 1.366 mmol). The flask was cooled in an ice-water bath for 10 min, then lithium bis(trimethylsilyl)amide (1M in THF) (2733 µl, 2.73 mmol) was added dropwise. The reaction was stirred at 0° C. for 30 min until reaction was complete by LCMS. The reaction mixture was quenched with 1 N HCl, and extracted 3× with EtOAc. Dried organics over Na2SO4 and concentrated via rotary evaporation. The residue was purified by chromatography on silica gel (50-g column, gradient DCM:DCM:MeOH (10%) 0-100%). The foamy orange oil from the evaporated fractions was then further purified via tritration (2 times) with iPrOH to yield 1-(2-chloro-3'-fluoro-5-methoxy-[1,1'-biphenyl]-4-yl)-7-fluoro-N-(isoxazol-3-yl)isoquinoline-6-sulfonamide (365 mg, 0.691 mmol, 55.7% yield) as an offwhite solid. $^1$H NMR (400 MHz, DMSO-d$_6$) δ ppm 12.24 (br. s., 1 H) 8.84 (d, J=7.14 Hz, 1 H) 8.69-8.77 (m, 2 H) 8.21 (d, J=5.18 Hz, 1 H) 7.50-7.62 (m, 3 H) 7.40-7.47 (m, 2 H) 7.28-7.35 (m, 1 H) 7.25 (s, 1 H) 6.43 (d, J=1.76 Hz, 1 H) 3.72 (s, 3 H). m/z (ESI) 528.1 (M+H)$^+$.

Example 44 (Method 44)

(7-FLUORO-1-(3'-FLUORO-3-METHOXY-[1,1'-BIPHENYL]-4-YL)-N-(1,2,4-THIADIAZOL-5-YL)ISOQUINOLINE-6-SULFONAMIDE

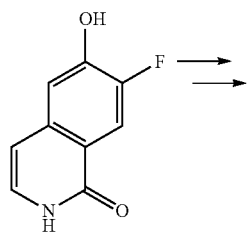

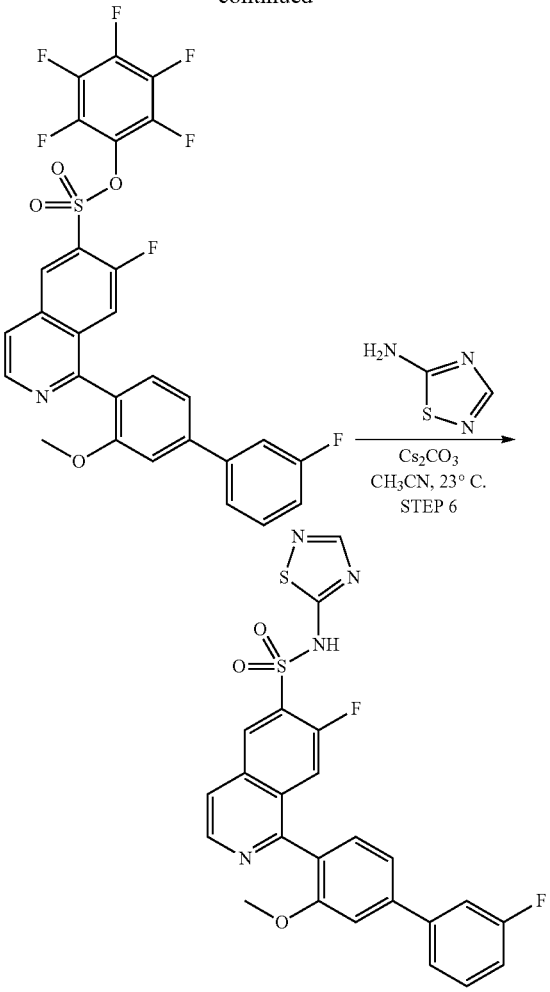

STEP 6

7-FLUORO-1-(3'-FLUORO-3-METHOXY-[1,1'-BIPHENYL]-4-YL)-N-(1,2,4-THIADIAZOL-5-YL)ISOQUINOLINE-6-SULFONAMIDE 7-fluoro-1-(3'-fluoro-3-methoxy-[1,1'-biphenyl]-4-yl)-N-(1,2,4-thiadiazol-5-yl)isoquinoline-6-sulfonamide was made via Method 43, Steps 1-5, using (3'-fluoro-3-methoxy-[1,1'-biphenyl]-4-yl)boronic acid for Step 2. Step 6 continued as follows: a vial was charged with perfluorophenyl 7-fluoro-1-(3'-fluoro-3-methoxy-[1,1'-biphenyl]-4-yl)isoquinoline-6-sulfonate (55 mg, 0.093 mmol), 1,2,4-thiadiazol-5-amine (10.31 mg, 0.102 mmol), and cesium carbonate (91 mg, 0.278 mmol). The vial was flushed with Ar (g), then acetonitrile (4630 was added. The reaction was stirred overnight at room temperature until reaction was complete by LCMS. The mixture was diluted with EtOAc and 1 N aq. HCl. The layers were separated, and the aqueous layer was extracted with EtOAc (2×). The combined organic extracts were dried over sodium sulfate, filtered, and concentrated. The residue was purified by chromatography on silica gel (12-g column, gradient DCM:DCM:MeOH (10%) 0-100%) to give 7-fluoro-1-(3'-fluoro-3-methoxy-[1,1'-biphenyl]-4-yl)-N-(1,2,4-thiadiazol-5-yl)isoquinoline-6-sulfonamide (30 mg, 0.059 mmol, 63.4% yield) as an off-white solid. $^1$H NMR (400 MHz, DMSO-d$_6$) δ ppm 8.62-8.74 (m, 2 H) 8.42 (s, 1 H) 8.17 (d, J=5.18 Hz, 1H) 7.66-7.80 (m, 2 H)

7.53-7.64 (m, 1 H) 7.43-7.52 (m, 3 H) 7.40 (d, J=11.25 Hz, 1 H) 7.27 (td, J=8.53, 2.40 Hz, 1 H) 3.80 (s, 3 H). m/z (ESI) 511.1 (M+H)+.

Example 45 (Method 45)

1-(6-(4-FLUOROPHENOXY)-2-METHOXYPYRIDIN-3-YL)-N-(PYRIMIDIN-4-YL)ISOQUINOLINE-6-SULFONAMIDE

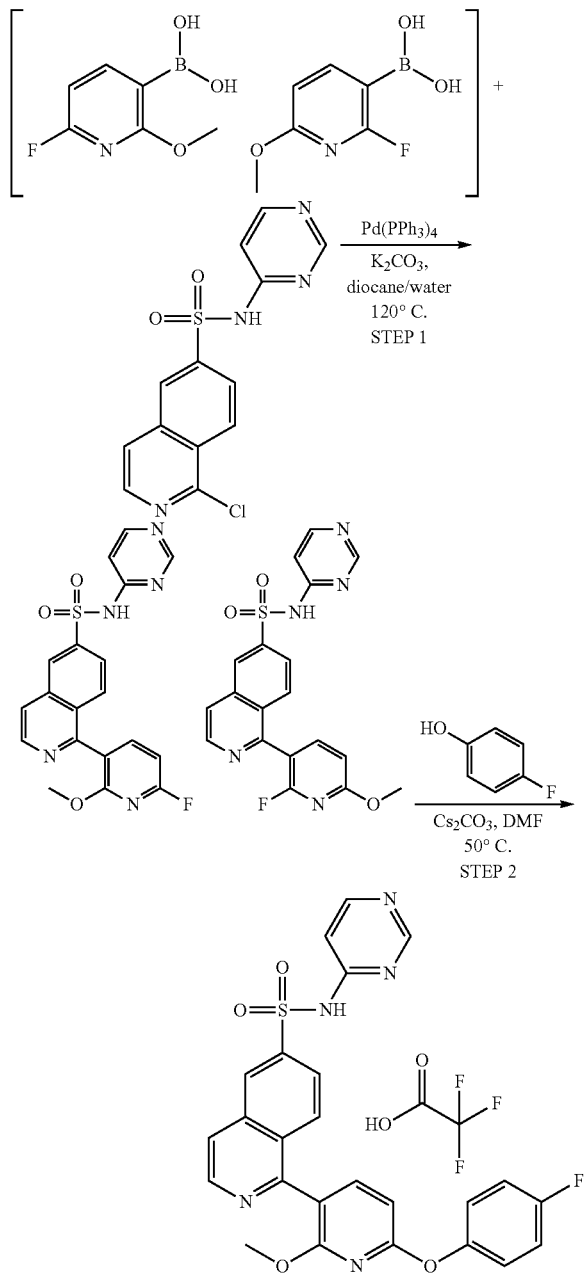

STEP 1: 1-(6-FLUORO-2-METHOXYPYRIDIN-3-YL)-N-(PYRIMIDIN-4-YL)ISOQUINOLINE-6-SULFONAMIDE AND 1-(2-FLUORO-6-METHOXYPYRIDIN-3-YL)-N-(PYRIMIDIN-4-YL)ISOQUINOLINE-6-SULFONAMIDE

To a microwave vial was added 1-chloro-N-(pyrimidin-4-yl)isoquinoline-6-sulfonamide, made via Method 29, Step 1 (~50% salts by weight, 6.0 g, 9.4 mmol), a 1:1 mixture of (6-fluoro-2-methoxypyridin-3-yl)boronic acid and its regioisomer (2-fluoro-6-methoxypyridin-3-yl)boronic acid) (2.078 g, 12.16 mmol, HDH Pharma), K$_2$CO$_3$ (6.5 g, 47 mmol), Pd(Ph$_3$P)$_4$ (1.08 g, 0.935 mmol), 1,4-dioxane (47 mL) and water (16 mL). The vial was sealed and the mixture was heated at 120° C. overnight. The reaction mixture was adsorbed onto silica gel and purified by silica gel chromatography (methanol/DCM: 0-50%) affording a light yellow solid. Some material remained on the dry pack, which was slurried and (in two parts) loaded directly onto a KP-C18-HS 60 g biotage column using reverse phase MPLC [IPA in H$_2$O (with 1% NH$_4$OH) (0-100%)]. Material from the two purifications was combined to provide a 1:1 mixture of 1-(6-fluoro-2-methoxypyridin-3-yl)-N-(pyrimidin-4-yl)isoquinoline-6-sulfonamide and 1-(2-fluoro-6-methoxypyridin-3-yl)-N-(pyrimidin-4-yl)isoquinoline-6-sulfonamide (1.9 g, 4.6 mmol, 49% yield). m/z (ESI) 412.1 (M+H)+.

STEP 2: 1-(6-(4-FLUOROPHENOXY)-2-METHOXYPYRIDIN-3-YL)-N-(PYRIMIDIN-4-YL)ISOQUINOLINE-6-SULFONAMIDE

A 1:1 mixture of 1-(6-fluoro-2-methoxypyridin-3-yl)-N-(pyrimidin-4-yl)isoquinoline-6-sulfonamide and 1-(2-fluoro-6-methoxypyridin-3-yl)-N-(pyrimidin-4-yl)isoquinoline-6-sulfonamide (10 mg, 0.024 mmol), Cs$_2$CO$_3$ (40 mg, 0.12 mmol), 4-fluorophenol (14 mg, 0.12 mmol), and DMF (120 uL) were combined in a resealable tube and heated to 50° C. The resulting material was combined with crude products from several other test reactions in which various bases were employed. Purification by reverse phase HPLC using a Waters Xbridge C18 19×100 mm 10 micron column with gradient conditions using a mobile phase of 0.1% TFA in water/CH$_3$CN provided 1-(6-(4-fluorophenoxy)-2-methoxypyridin-3-yl)-N-(pyrimidin-4-yl)isoquinoline-6-sulfonamide 2,2,2-trifluoroacetate, 75% purity by UV215. $^1$H NMR (500 MHz, DMSO-d$_6$) δ ppm 8.65-8.73 (m, 2 H) 8.57 (s, 1 H) 8.21-8.28 (m, 1 H) 8.17 (d, J=5.77 Hz, 1H) 7.94-8.01 (m, 1 H) 7.85-7.93 (m, 2 H) 7.28-7.39 (m, 4 H) 7.03 (br. s., 1 H) 6.69 (d, J=8.01 Hz, 1 H) 3.58 (s, 3 H). m/z (ESI) 504.0 (M+H)+.

Example 46 (Method 46)

1-(6-(DIISOBUTYLAMINO)-2-METHOXYPYRIDIN-3-YL)-N-(PYRIMIDIN-4-YL)ISOQUINOLINE-6-SULFONAMIDE

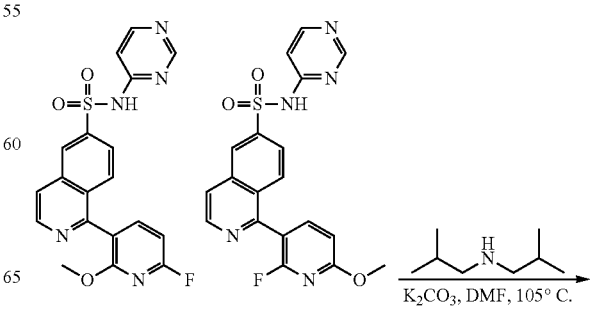

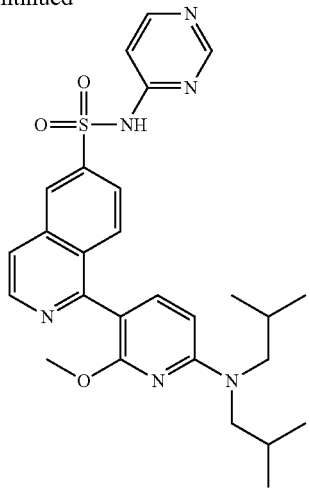
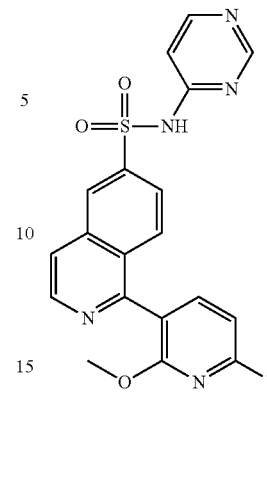

A 1:1 mixture of 1-(6-fluoro-2-methoxypyridin-3-yl)-N-(pyrimidin-4-yl)isoquinoline-6-sulfonamide and 1-(2-fluoro-6-methoxypyridin-3-yl)-N-(pyrimidin-4-yl)isoquinoline-6-sulfonamide (12 mg, 0.028 mmol) (from Method 46, Step 1), K₂CO₃ (19 mg, 0.14 mmol), diisobutylamine (18 mg, 0.14 mmol), and DMF (140 μL) were combined in a resealable tube and heated to 105° C. overnight. The product was purified by reverse phase mass-directed HPLC ([(LC/MS-2 System, column: XBridge 19×100 mm, mobile phase: 0.1% NH₄OH in water/acetonitrile, gradient: 10 min 10-40% LV NH3; 10 min 5-30% LV NH3)] to provide 1-(6-(diisobutylamino)-2-methoxypyridin-3-yl)-N-(pyrimidin-4-yl)isoquinoline-6-sulfonamide (5.4 mg, 0.010 mmol, 36% yield, 77% achiral purity by UV215). H NMR (400 MHz, CD3OD) δ ppm 8.67 (d, J=1.66 Hz, 1 H) 8.61 (d, J=5.77 Hz, 1 H) 8.47 (s, 1 H) 8.17-8.20 (m, 1 H) 7.96-8.04 (m, 2 H) 7.84 (d, J=8.90 Hz, 1 H) 7.43 (d, J=8.12 Hz, 1 H) 7.02 (dd, J=6.36, 1.08 Hz, 1 H) 6.27 (d, J=8.02 Hz, 1 H) 3.95 (s, 3 H) 2.96-3.05 (m, 2 H) 2.35-2.45 (m, 2 H) 1.75-1.85 (m, 2 H) 0.58 (d, J=16.63 Hz, 12 H). m/z (ESI) 521.2 (M+H)⁺.

Example 47 (Method 47)

1-(2-METHOXY-6-(NEOPENTYLAMINO)PYRIDIN-3-YL)-N-(PYRIMIDIN-4-YL)ISOQUINOLINE-6-SULFONAMIDE AND EXAMPLE 2942466 1-(6-METHOXY-2-(NEOPENTYLAMINO)PYRIDIN-3-YL)-N-(PYRIMIDIN-4-YL)ISOQUINOLINE-6-SULFONAMIDE

Title compounds were prepared according to Method 47, except with 2,2-dimethylpropan-1-amine in place of diisobutylamine as reagent and with an additional purification step to isolate both regioisomeric products: Supercritical fluid chromatography (SFC) using a 5 micron column (OJ-H, 2×25 CM) was performed under isocratic conditions with a mobile phase of CO₂ and 19% MeOH co-solvent containing 0.1% diethylamine modifier to provide 1-(2-methoxy-6-(neopentylamino)pyridin-3-yl)-N-(pyrimidin-4-yl)isoquinoline-6-sulfonamide (5.8 mg, 12 mol, 15% yield) ¹H NMR (600 MHz, Acetonitrile-d₃) δ ppm 8.55 (d, J=5.57 Hz, 1 H) 8.34-8.46 (m, 2 H) 8.00 (br. s., 1 H) 7.87 (d, J=8.09 Hz, 1 H) 7.78 (d, J=8.70 Hz, 1 H) 7.74 (d, J=5.57 Hz, 1 H) 7.43 (d, J=8.01 Hz, 1 H) 6.84 (br. s., 1 H) 6.21 (d, J=8.01 Hz, 1 H) 5.37-5.48 (m, 1 H) 3.70 (s, 3 H) 3.23-3.30 (m, 2 H) 0.98 (s, 9 H) m/z (ESI) 479.2 (M+H)⁺ and 1-(6-methoxy-2-(neopentylamino)pyridin-3-yl)-N-(pyrimidin-4-yl)isoquinoline-6-sulfonamide (3.4 mg, 7.1 μmol, 8.3% yield)¹H NMR (600 MHz, Acetonitrile-d₃) δ ppm 8.56 (d, J=5.65 Hz, 1 H) 8.47 (s, 1 H) 8.36 (br. s., 1 H) 8.02 (d, J=8.93 Hz, 1 H) 7.98 (d, J=4.50 Hz, 1 H) 7.93 (dd, J=8.85, 1.30 Hz, 1 H) 7.77 (d, J=5.57 Hz, 1 H) 7.48 (d, J=8.01 Hz, 1 H) 6.76-6.82 (m, 2 H) 6.04 (d, J=8.09 Hz, 1 H) 3.92 (s, 3 H) 3.30 (d, J=6.10 Hz, 2 H) 0.86 (s, 9 H) m/z (ESI) 479.2 (M+H)⁺.

Example 48 (Method 48)

1-(2-METHOXY-6-((3-METHYL-1,2,4-OXADIAZOL-5-YL)METHOXY)PYRIDIN-3-YL)-N-(PYRIMIDIN-4-YL)ISOQUINOLINE-6-SULFONAMIDE 2,2,2-TRIFLUOROACETATE

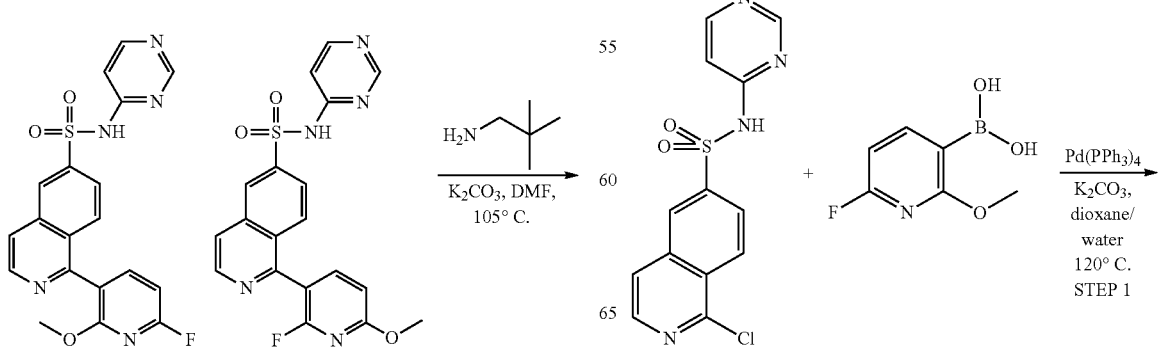

-continued

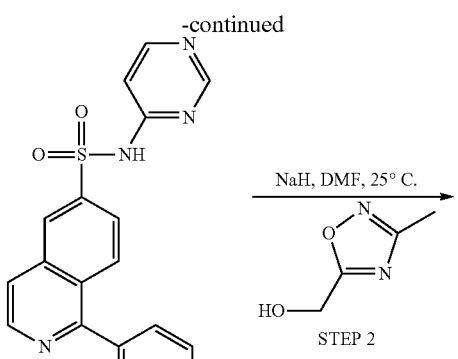

NaH, DMF, 25° C.

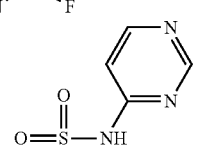

STEP 2

(3-methyl-1,2,4-oxadiazol-5-yl)methanol (110 mg, 0.97 mmol, ASDI), sodium hydride (60 wt %, 39 mg, 0.97 mmol), and DMF (0.28 mL) were combined in a reaction vial and stirred at room temperature overnight. The reaction mixture was purified by reverse phase HPLC using a Waters Xbridge C18 19×100 mm 10 micron column with gradient conditions using a mobile phase of 0.1% TFA in water/CH$_3$CN to provide 1-(2-methoxy-6-((3-methyl-1,2,4-oxadiazol-5-yl)methoxy)pyridin-3-yl)-N-(pyrimidin-4-yl)isoquinoline-6-sulfonamide 2,2,2-trifluoroacetate (13.9 mg, 0.022 mmol, 23% yield). $^1$H NMR (500 MHz, DMSO-d$_6$) δ ppm 8.67-8.71 (m, 2 H) 8.57 (s, 1 H) 8.24 (d, J=6.25 Hz, 1H) 8.18 (d, J=5.61 Hz, 1 H) 8.00 (d, J=8.76 Hz, 1 H) 7.86 (d, J=8.01 Hz, 1 H) 7.82 (d, J=8.92 Hz, 1 H) 7.03 (br. s., 1 H) 6.77 (d, J=8.01 Hz, 1 H) 5.73 (s, 2 H) 3.63 (s, 3 H) 2.36 (s, 3 H). m/z (ESI) 506.0 (M+H)$^+$.

Example 49 (Method 49)

N-(ISOXAZOL-3-YL)-1-(3-METHOXY-[1,1'-BI-PHENYL]-4-YL)ISOQUINOLINE-6-SULFONA-MIDE

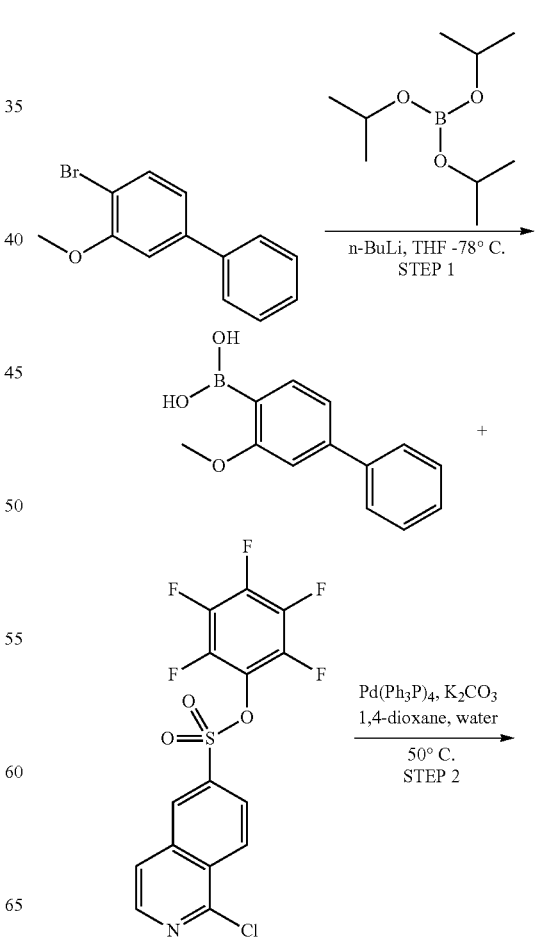

STEP 1: 1-(6-FLUORO-2-METHOXYPYRIDIN-3-YL)-N-(PYRIMIDIN-4-YL)ISOQUINOLINE-6-SULFONAMIDE

To a microwave vial was added 1-chloro-N-(pyrimidin-4-yl)isoquinoline-6-sulfonamide made via Method 29, Step 1 (~50% salts by weight, 5.0 g, 7.8 mmol), (6-fluoro-2-methoxypyridin-3-yl)boronic acid [(1.73 g, 10.1 mmol, HDH Pharma), K$_2$CO$_3$ (5.39 g, 39.0 mmol), Pd(Ph$_3$P)$_4$ (0.900 g, 0.780 mmol), 1,4-dioxane (39 mL), and water (13 mL). The vial was sealed and the reaction mixture was heated in an oil bath at 120° C. overnight. The crude reaction mixture was filtered through a 0.45 μm syringe filter and purified by reverse phase MPLC with NH$_4$OH as a modifier to provide 1-(6-fluoro-2-methoxypyridin-3-yl)-N-(pyrimidin-4-yl)isoquinoline-6-sulfonamide (678 mg, 1.65 mmol, 21.1% yield). m/z (ESI) 412.2 (M+H)$^+$.

STEP 2: 1-(2-METHOXY-6-((3-METHYL-1,2,4-OXADIAZOL-5-YL)METHOXY)-PYRIDIN-3-YL)-N-(PYRIMIDIN-4-YL)ISOQUINOLINE-6-SULFONAMIDE 2,2,2-TRIFLUOROACETATE 1-(6-fluoro-2-methoxypyridin-3-yl)-N-(pyrimidin-4-yl) isoquinoline-6-sulfonamide (40 mg, 0.097 mmol),

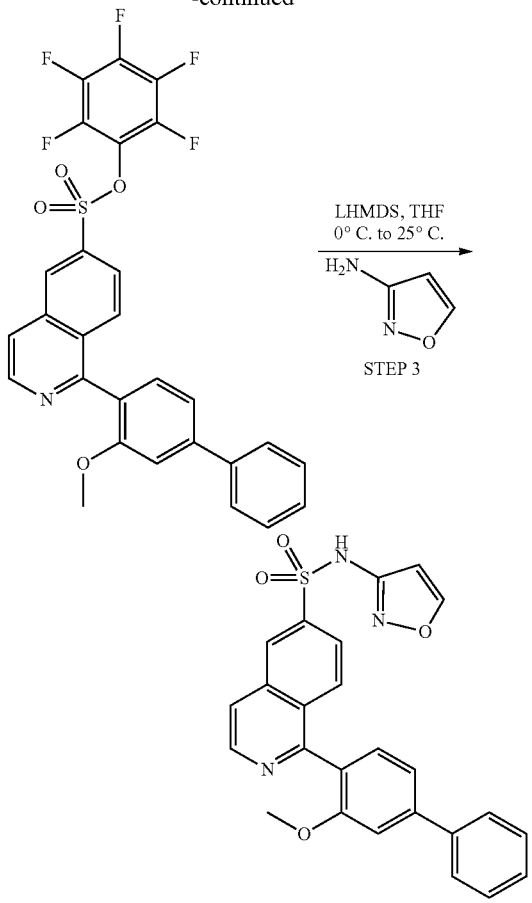

STEP 1:
(3-METHOXY-[1,1'-BIPHENYL]-4-YL)BORONIC ACID

A RBF was charged with 4-bromo-3-methoxy-1,1'-biphenyl (800 mg, 3.1 mmol, Combi-Blocks), triisopropyl borate (0.850 mL, 3.7 mmol), and THF (10 mL) and cooled in a dry ice-acetone bath for 10 min, then n-butyllithium (2.5 M in hexane, 1.470 ml, 3.68 mmol) was added dropwise over 1 min. After 20 min stirring, the flask was placed into an ice-water bath. After 10 min the mixture was diluted with 2N aq. NaOH solution. The cooling bath was removed and the mixture was stirred vigorously for 20 min and then diluted with water and ether. The layers were separated and the ethereal layer was extracted with water. The combined aq. layers were then acidified with 6N aq. HCl (50 mL). The mixture was filtered and the collected solid was dried under a stream of $N_2$ for 2 h to give a white solid. The filtrate was extracted with $CH_2Cl_2$ (3×), and the combined organic extracts were dried over $Na_2SO_4$, filtered, and concentrated to give an additional 260 mg material that was combined with the above to provide (3-methoxy-[1,1'-biphenyl]-4-yl)boronic acid as a white solid. The material was used without further purification. m/z (ESI) 229.2 $(M+H)^+$.

STEP 2: PERFLUOROPHENYL 1-(3-METHOXY-[1,1'-BIPHENYL]-4-YL)ISOQUINOLINE-6-SULFONATE

A resealable flask was charged with perfluorophenyl 1-chloroisoquinoline-6-sulfonate (172 mg, 0.421 mmol), (3-methoxy-[1,1'-biphenyl]-4-yl)boronic acid (96 mg, 0.42 mmol), $K_2CO_3$ (175 mg, 1.263 mmol), and $Pd(Ph_3P)_4$ (48.6 mg, 0.042 mmol). The flask was flushed with argon, then dioxane (1.6 mL) and water (0.53 mL) were added in sequence. The mixture was stirred at 50° C. for one hour, diluted with water and extracted with EtOAc (2×). The combined organic extracts were dried over $Na_2SO_4$, filtered, and concentrated. The residue was purified by chromatography on silica gel (100-g SNAP Ultra column, 0-50% EtOAc/Heptane) to provide perfluorophenyl 1-(3-methoxy-[1,1'-biphenyl]-4-yl)isoquinoline-6-sulfonate (98 mg, 0.18 mmol, 42% yield) as an off-white solid. m/z (ESI) 558.0 $(M+H)^+$.

STEP 3: N-(ISOXAZOL-3-YL)-1-(3-METHOXY-[1,1'-BIPHENYL]-4-YL)ISOQUINOLINE-6-SULFONAMIDE

A RBF was charged with perfluorophenyl 1-(3-methoxy-[1,1'-biphenyl]-4-yl)isoquinoline-6-sulfonate (43.4 mg, 0.078 mmol), THF (0.39 mL), and isoxazol-3-amine (7.2 mg, 0.086 mmol) to give a clear, light-yellow solution. The flask was cooled in an ice-water bath for 10 min, then lithium bis(trimethylsilyl)amide (1M in THF, 0.17 mL, 0.17 mmol) was added dropwise and the mixture was stirred for 20 minutes. The crude material was purified by reverse phase HPLC using a Waters Xbridge C18 19×100 mm 10 micron column with gradient conditions using a mobile phase of 0.1% $NH_4OH$ in water/$CH_3CN$ to provide N-(isoxazol-3-yl)-1-(3-methoxy-[1,1'-biphenyl]-4-yl)isoquinoline-6-sulfonamide (5.0 mg, 0.011 mmol, 14% yield) as a yellow solid. 1H NMR (500 MHz, DMSO-d6) δ ppm 8.70 (d, J=5.66 Hz, 1 H) 8.59 (s, 1 H) 8.61 (s, 1 H) 8.08 (d, J=5.72 Hz, 1 H) 7.90 (dd, J=8.95, 1.63 Hz, 1 H) 7.78-7.86 (m, 3 H) 7.53 (app t, J=7.64 Hz, 2 H) 7.34-7.48 (m, 4 H) 6.42 (s, 1 H) 3.75 (s, 3 H). m/z (ESI) 458.0 $(M+H)^+$.

Example 50 (Method 50)

1-(3-METHOXY-[1,1'-BIPHENYL]-4-YL)-N-(1,3,4-THIADIAZOL-2-YL)ISOQUINOLINE-6-SULFONAMIDE

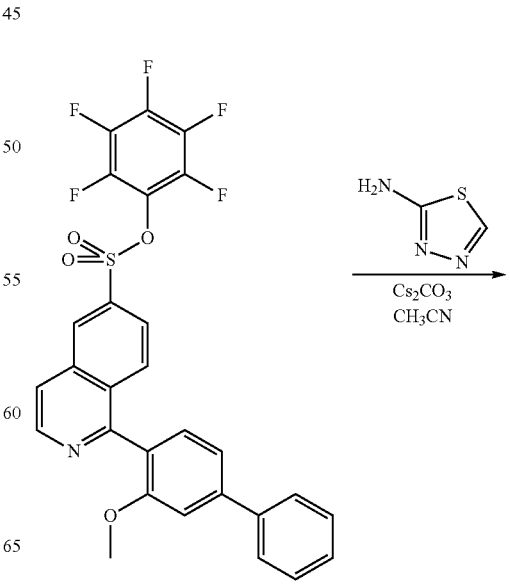

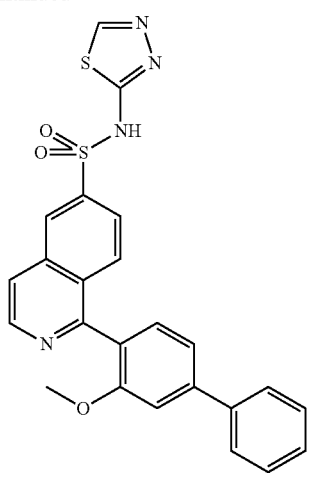

A vial was charged with perfluorophenyl 1-(3-methoxy-[1,1'-biphenyl]-4-yl)isoquinoline-6-sulfonate (51.4 mg, 0.092 mmol) from Method 50, Step 2,1,3,4-thiadiazol-2-amine (10 mg, 0.10 mmol), and Cs$_2$CO$_3$ (90 mg, 0.28 mmol). The vial was flushed with Ar (g), then CH$_3$CN (0.46 mL) was added and the mixture was stirred at RT overnight. The crude material was purified by reverse phase HPLC using a Waters Xbridge C18 19×100 mm 10 micron column with gradient conditions using a mobile phase of 0.1% NH$_4$OH in water/CH$_3$CN to provide 1-(3-methoxy-[1,1'-biphenyl]-4-yl)-N-(1,3,4-thiadiazol-2-yl)isoquinoline-6-sulfonamide (10 mg, 23% yield). $^1$H NMR (500 MHz, DMSO-d$_6$) δ ppm 8.61-8.69 (m, 2 H) 8.47 (s, 1 H) 8.05 (d, J=5.66 Hz, 1 H) 7.78-7.90 (m, 3 H) 7.75 (d, J=8.87 Hz, 1 H) 7.52 (t, J=7.61 Hz, 2 H) 7.37-7.48 (m, 4 H) 3.75 (s, 3 H). m/z (ESI) 475.0 (M+H)$^+$.

Example 51 (Method 51)

2-ACETYL-1-(2-METHOXY-4-(TRIFLUOROM-ETHYL)PHENYL)-N-(1,2,4-THIADIAZOL-5-YL)-1,2,3,4-TETRAHYDROISOQUINOLINE-6-SULFONAMIDE

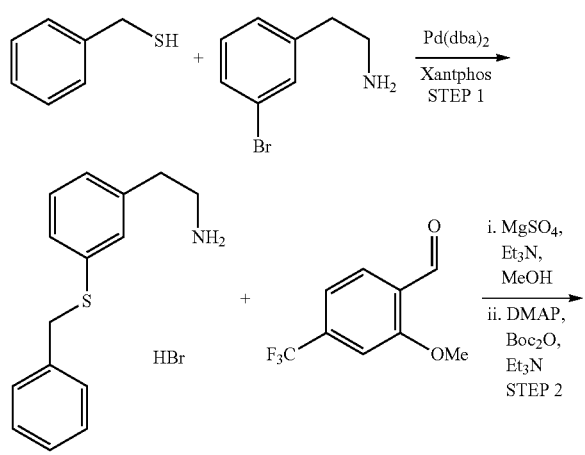

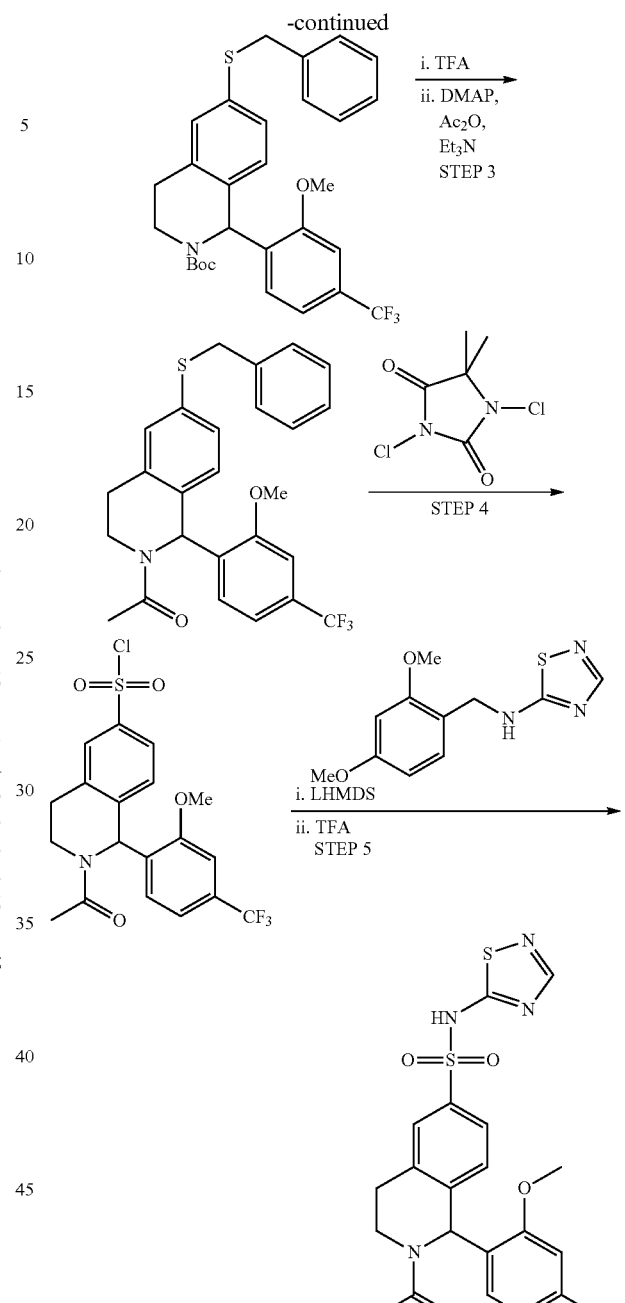

STEP 1:
2-(3-(BENZYLTHIO)PHENYL)ETHANAMINE HYDROBROMIDE

A sealable vial was charged with Pd(dba)$_2$ (1.437 g, 2.499 mmol), Xantphos (1.446 g, 2.499 mmol) and sealed with a septum cap. The vial was flushed with N$_2$ and dioxane (0.3 mL) was added via syringe. The resulting mixture was heated at 90° C. for 10 min to generate pre-activated catalyst solution. A separate sealable vial was charged with 2-(3-bromophenyl)ethanamine (10.0 g, 50.0 mmol), dioxane (50.0 ml), diisopropylethylamine (17.46 ml, 100 mmol) and phenylmethanethiol (6.45 ml, 55.0 mmol). The pre-activated catalyst solution prepared above was then transferred into the vial containing reagents and the reaction was heated at 90° C. in an oil bath for 30 min. After cooling, the resulting slurry was then diluted with iPrOH and the suspended solid was collected by vacuum filtration to yield 2-(3-(benzylthio) phenyl)ethanamine hydrobromide (13.015 g, 40.1 mmol, 80% yield) as a greenish solid. m/z (ESI) 244.2 (M+H)$^+$.

STEP 2: 6-(BENZYLTHIO)-1-(2-METHOXY-4-(TRIFLUOROMETHYL)PHENYL)-1,2,3,4-TETRAHYDROISOQUINOLINE

A microwave vial was charged with 2-methoxy-4-(trifluoromethyl)benzaldehyde (0.645 g, 3.16 mmol, Alfa Aesar), MgSO$_4$ (0.951 g, 7.90 mmol), 2-(3-(benzylthio) phenyl)ethanamine hydrobromide (0.769 g, 2.36 mmol). The vial was sealed with a septum cap and anhydrous MeOH (15.80 ml) was added followed by triethylamine (1.321 ml, 9.48 mmol). The resulting mixture was heated in the microwave (Biotage Initiator) at 100° C. for 1.5 h. After cooling, the reaction mixture was filtered through Celite, rinsing with EtOAc, the mother liquor was concentrated, re-suspended in EtOAc (suspension) and filtered again to remove white solid. The remaining mother liquor was concentrated and the residue was taken up in trifluoroacetic acid (9 mL) and transferred to a new microwave vial. The resulting yellow solution was heated in the microwave at 112° C. for 1.5 h. After cooling, the reaction mixture was concentrated and partitioned between saturated aqueous NaHCO$_3$ (20 mL) and EtOAc (30 mL). The layers were separated and the aqueous layer was extracted with EtOAc (20 mL). The combined organic layers were washed with brine (10 mL), dried (Na$_2$SO$_4$) and concentrated to provide 6-(benzylthio)-1-(2-methoxy-4-(trifluoromethyl)phenyl)-1,2,3,4-tetrahydroisoquinoline. The crude residue was used directly without further purification. m/z (ESI) 430.3 (M+H)$^+$.

Crude 6-(benzylthio)-1-(2-methoxy-4-(trifluoromethyl) phenyl)-1,2,3,4-tetrahydroisoquinoline was taken up in 2-MeTHF (15.80 ml), to the solution was added di-tert-butyl dicarbonate (1.724 g, 7.90 mmol), followed by triethylamine (1.321 ml, 9.48 mmol) and dimethylaminopyridine (0.039 g, 0.316 mmol). The solution was maintained at rt for 1 h, at which time the reaction solution was concentrated for purification by MPLC (Biotage Isolera). The crude residue was taken up in minimal CH$_2$Cl$_2$ and absorbed onto a 25 g loading cartridge and passed through a Redi-Sep® Gold pre-packed silica gel column (80 g) using a gradient of 98:2 Heptane:EtOAc to 100% EtOAc to afford tert-butyl 6-(benzylthio)-1-(2-methoxy-4-(trifluoromethyl)phenyl)-3,4-dihydroisoquinoline-2(1H)-carboxylate (0.880 g, 1.662 mmol, 52.6% yield) as a yellow film. m/z (ESI) 552.3 (M+Na).

STEP 3: 1-(6-(BENZYLTHIO)-1-(2-METHOXY-4-(TRIFLUOROMETHYL)-PHENYL)-3,4-DIHYDROISOQUINOLIN-2(1H)-YL)ETHANONE

A RBF was charged with tert-butyl 6-(benzylthio)-1-(2-methoxy-4-(trifluoromethyl)phenyl)-3,4-dihydroisoquinoline-2(1H)-carboxylate (0.245 g, 0.463 mmol), dichloromethane (1 ml), followed by trifluoroacetic acid (0.713 ml, 9.25 mmol). The solution was maintained at rt for 10 min at which time it was concentrated to provide 6-(benzylthio)-1-(2-methoxy-4-(trifluoromethyl)phenyl)-1,2,3,4-tetrahydroisoquinoline. The crude residue was used without further purification.

A RBF was charged with 6-(benzylthio)-1-(2-methoxy-4-(trifluoromethyl)phenyl)-1,2,3,4-tetrahydroisoquinoline (0.199 g, 0.463 mmol) and N,N-dimethylpyridin-4-amine (5.66 mg, 0.046 mmol). A septum was attached and triethylamine (0.194 ml, 1.390 mmol) was added, followed by acetic anhydride (0.175 ml, 1.853 mmol). The solution was maintained at rt for 20 min then concentrated for purification by MPLC (Biotage Isolera). The crude residue was taken up in minimal CH$_2$Cl$_2$ and absorbed onto a Biotage 25 g SNAP column and eluted using a gradient of 95:5 Heptane:EtOAc to 100% EtOAc affording 1-(6-(benzylthio)-1-(2-methoxy-4-(trifluoromethyl)phenyl)-3,4-dihydroisoquinolin-2(1H)-yl)ethanone (0.113 g, 0.240 mmol, 51.7% yield) as a light-yellow film. m/z (ESI) 472.2 (M+H)$^+$.

STEP 4: 2-ACETYL-1-(2-METHOXY-4-(TRIFLUOROMETHYL)PHENYL)-1,2,3,4-TETRAHYDROISOQUINOLINE-6-SULFONYL CHLORIDE

A RBF was charged with 1-(6-(benzylthio)-1-(2-methoxy-4-(trifluoromethyl)phenyl)-3,4-dihydroisoquinolin-2(1H)-yl)ethanone (0.113 g, 0.240 mmol), and acetonitrile (1.127 ml) was added followed by acetic acid (0.043 ml), and water (0.028 ml). The solution was cooled to 0° C. and 1,3-dichloro-5,5-dimethylimidazolidine-2,4-dione (0.052 g, 0.264 mmol) was added as a solid in a single portion. The solution was maintained at 0° C. for 30 min, at which time it was concentrated. The resulting residue was partitioned between ice water (10 mL) and EtOAc (10 mL). The layers were separated and the aqueous layer was extracted with EtOAc (1×10 mL). The combined organic extracts were washed with brine (5 mL) and dried over Na$_2$SO$_4$ and concentrated in vacuo to give 2-acetyl-1-(2-methoxy-4-(trifluoromethyl)phenyl)-1,2,3,4-tetrahydroisoquinoline-6-sulfonyl chloride (0.110 g, 0.246 mmol, 102% yield), which was contaminated with a small amount of residual solvent. m/z (ESI) 448.3 (M+H)$^+$.

STEP 5: 2-ACETYL-1-(2-METHOXY-4-(TRIFLUOROMETHYL)PHENYL)-N-(1,2,4-THIADIAZOL-5-YL)-1,2,3,4-TETRAHYDROISOQUINOLINE-6-SULFONAMIDE

A RBF was charged with N-(2,4-dimethoxybenzyl)-1,2,4-thiadiazol-5-amine (0.056 g, 0.221 mmol), a septum was attached, and the flask flushed with N$_2$ line. THF (2.456 ml) was added and the solution was cooled to −78° C. A THF solution of 2-acetyl-1-(2-methoxy-4-(trifluoromethyl)phenyl)-1,2,3,4-tetrahydroisoquinoline-6-sulfonyl chloride (0.110 g, 0.246 mmol), was added, followed by a 1 M THF solution of lithium hexamethyldisilylazide (LHMDS) (0.491 ml, 0.491 mmol). Following the addition of LHMDS, the reaction was quenched at −78° C. by the addition of saturated aqueous NH$_4$Cl. The reaction mixture was partitioned between water (5 mL) and EtOAc (10 mL). The layers were separated and the aqueous layer was extracted with EtOAc (1×10 mL). The combined organic extracts were dried over Na$_2$SO$_4$ and concentrated in vacuo. The solution was concentrated for purification by MPLC (Biotage Isolera). The crude residue was taken up in minimal CH$_2$Cl$_2$ and absorbed onto a 5 g loading cartridge and passed through a Redi-Sep® Gold pre-packed silica gel column (12 g) using a gradient of 98:2 Heptane:EtOAc to 100% EtOAc to afford 2-acetyl-N-(2,4-dimethoxybenzyl)-1-(2-methoxy-4-(trifluoromethyl) phenyl)-N-(1,2,4-thiadiazol-5-yl)-1,2,3,4-tetrahydroisoquinoline-6-sulfonamide (0.046 g, 0.069 mmol, 28.3% yield) as a colorless film. m/z (ESI) 661.2 (M−H)$^−$.

The product described above (2-acetyl-N-(2,4-dimethoxybenzyl)-1-(2-methoxy-4-(trifluoromethyl)phenyl)-N-(1,2,4-thiadiazol-5-yl)-1,2,3,4-tetrahydroisoquinoline-6-sulfonamide) was taken up in 1 mL of CH$_2$Cl$_2$ and 0.5 mL of trifluoroacetic acid was added at rt. The solution was maintained at rt for 30 min at which time it was diluted with MeOH and concentrated. The crude reaction mixture was taken up in minimal MeOH/DMSO and purified by preparative HPLC (Gilson: 25-85% CH$_3$CN:H$_2$O (1% TFA modifier) over 15 min) Clean fractions were combined and concentrated to afford 2-acetyl-1-(2-methoxy-4-(trifluoromethyl)phenyl)-N-(1,2,4-thiadiazol-5-yl)-1,2,3,4-tetrahydroisoquinoline-6-sulfonamide (0.020 g, 0.039 mmol, 15.89% yield) as a white amorphous solid. 1 H NMR (500 MHz, DMSO-d$_6$) δ ppm 2.09 (s, 3 H) 2.91 (br. s., 1 H) 3.00-3.11 (m, 2 H) 3.79 (br. s., 1 H) 3.85 (s, 3 H) 3.98 (s, 1 H) 7.15-7.42 (m, 4 H) 7.58 (d, J=7.21 Hz, 1 H) 7.67 (br. s., 1 H) 8.40-8.51 (m, 1 H); m/z (ESI) 513.0 (M+H)$^+$.

Example 52 (Method 52)

2-ACETYL-1-(3'-FLUORO-3-METHOXY-[1,1'-BIPHENYL]-4-YL)-N-(1,3,4-THIADIAZOL-2-YL)-1,2,3,4-TETRAHYDROISOQUINOLINE-6-SULFONAMIDE

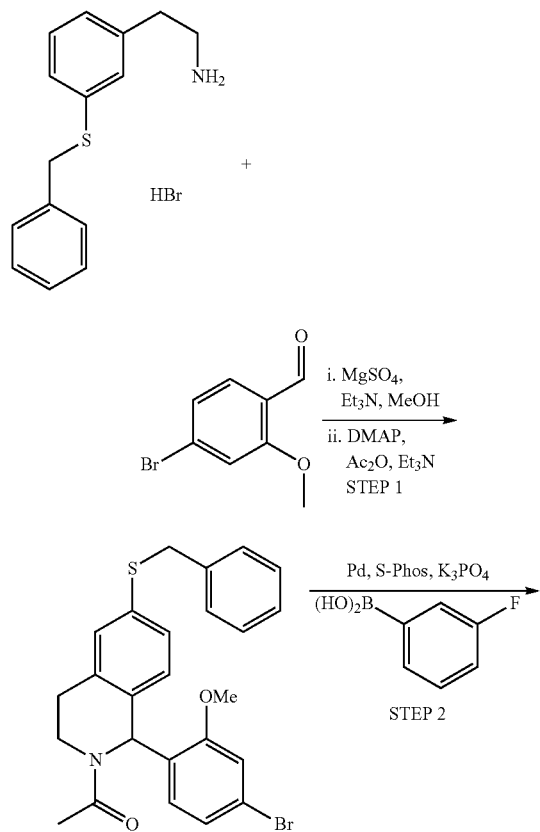

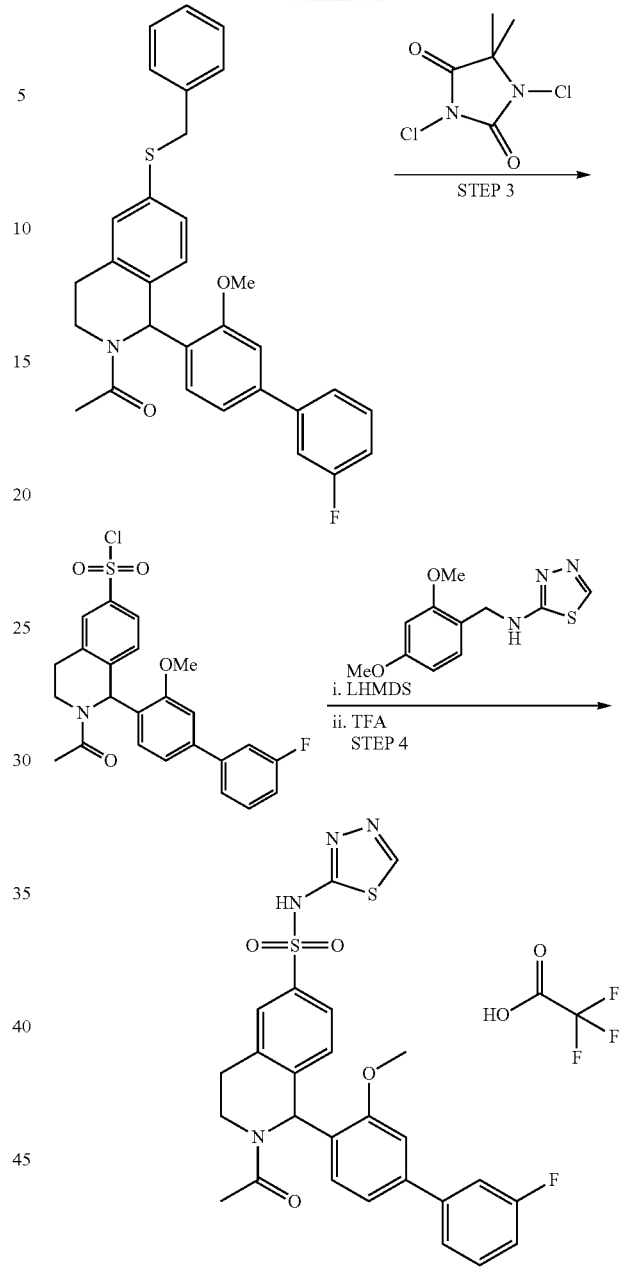

STEP 1: 1-(6-(BENZYLTHIO)-1-(4-BROMO-2-METHOXYPHENYL)-3,4-DIHYDROISOQUINOLIN-2(1H)-YL)ETHANONE

A microwave vial was charged with 4-bromo-2-methoxybenzaldehyde (1.00 g, 4.65 mmol), MgSO$_4$ (1.399 g, 11.63 mmol 2-(3-(benzylthio)phenyl)ethanamine hydrobromide (1.132 g, 3.48 mmol, from Method 51, Step 1). The vial was sealed with a septum cap and anhydrous MeOH (23.25 mL) was added, followed by triethylamine (1.944 ml, 13.95 mmol). The mixture was heated in the MW at 100° C. for 1.5 h. After cooling, the reaction mixture was filtered through Celite, rinsing with EtOAc (20 mL). The solution was concentrated, then re-suspended in EtOAc (suspension) and filtered again to remove white solid. The remaining yellow solution was concentrated and the residue was taken up in trifluoroacetic acid (9 mL) and transferred to a new microwave vial. The resulting yellow solution was heated in the microwave at 112° C. for 2 h, then and additional 2 h at 115° C. After cooling, the reaction mixture was concentrated and partitioned between saturated aqueous NaHCO$_3$ (20 mL) and EtOAc (30 mL). The layers were separated and the aqueous layer was extracted with CH$_2$Cl$_2$ (2×20 mL). The combined organic layers were dried (Na2SO4) and concentrated to provide 6-(benzylthio)-1-(4-bromo-2-methoxyphenyl)-1,2,3,4-tetrahydroisoquinoline (1.902 g, 4.32 mmol, 93% yield) as a brown foam, which was used directly without further purification.

Crude 6-(benzylthio)-1-(4-bromo-2-methoxyphenyl)-1,2,3,4-tetrahydroisoquinoline was taken up in 2-MeTHF (23.25 ml) and acetic anhydride (1.099 ml, 11.63 mmol) was added, followed by triethylamine (1.944 ml, 13.95 mmol) and dimethylaminopyridine (0.057 g, 0.465 mmol). The solution was maintained at rt for 1 h. The solution was concentrated for purification by MPLC (Biotage Isolera). The crude residue absorbed onto a Biotage SNAP pre-packed silica gel column (50 g) and eluted using a gradient of 98:2 Heptane:EtOAc to 100% EtOAc to afford 1-(6-(benzylthio)-1-(4-bromo-2-methoxyphenyl)-3,4-dihydroisoquinolin-2(1H)-yl)ethanone (0.840 g, 1.741 mmol, 37.4% yield) as a yellow film. m/z (ESI) 482.1 (M+H)$^+$.

STEP 2: 1-(6-(BENZYLTHIO)-1-(3'-FLUORO-3-METHOXY-[1,1'-BIPHENYL]-4-YL)-3,4-DIHYDROISOQUINOLIN-2(1H)-YL)ETHANONE

A microwave vial was charged with 1-(6-(benzylthio)-1-(4-bromo-2-methoxyphenyl)-3,4-dihydroisoquinolin-2(1H)-yl)ethanone (0.771 g, 1.598 mmol), S-Phos Precatalyst (0.121 g, 0.160 mmol), potassium phosphate (1.696 g, 7.99 mmol), dicyclohexyl(2',6'-dimethoxy-[1,1'-biphenyl]-2-yl)phosphine (0.033 g, 0.080 mmol), and (3-fluorophenyl)boronic acid (0.447 g, 3.20 mmol). The vial was sealed with a septum cap and flushed with N$_2$, then 1,4-dioxane (552 µl) and water (55.2 µl) were added. The vial was heated in a Biotage Initiator microwave reactor for 1 h at 120° C. The crude reaction mixture was purified by MPLC (Biotage Isolera) as described: Loose silica gel was added to the crude reaction mixture, along with a small amount of CH$_2$Cl$_2$. The mixture was concentrated until silica gel was free flowing and the resulting mixture was packed into a 25 g custom loading cartridge. The mixture was eluted through a Redi-Sep® Gold pre-packed silica gel column (40 g) using a gradient of 95:5 CH$_2$Cl$_2$: 90/10 CH$_2$Cl$_2$/MeOH to 100% 90/10 CH$_2$Cl$_2$/MeOH to afford 1-(6-(benzylthio)-1-(3'-fluoro-3-methoxy-[1,1'-biphenyl]-4-yl)-3,4-dihydroisoquinolin-2(1H)-yl)ethanone (0.886 g, 1.8 mmol) as a tan amorphous solid that contained some unidentified impurities. m/z (ESI) 498.3 (M+H)$^+$.

STEP 3: 2-ACETYL-1-(3'-FLUORO-3-METHOXY-[1,1'-BIPHENYL]-4-YL)-1,2,3,4-TETRAHYDROISOQUINOLINE-6-SULFONYL CHLORIDE

A RBF was charged with 1-(6-(benzylthio)-1-(3'-fluoro-3-methoxy-[1,1'-biphenyl]-4-yl)-3,4-dihydroisoquinolin-2(1H)-yl)ethanone (0.355 g, 0.713 mmol), followed by acetonitrile (3.36 ml), acetic acid (0.128 ml), and water (0.084 ml). The solution was cooled to 0° C. and 1,3-dichloro-5,5-dimethylimidazolidine-2,4-dione (0.155 g, 0.785 mmol) was added as a solid in a single portion. The solution was maintained solution at 0° C. for 30 min. The reaction mixture was concentrated and the residue was partitioned between ice water (20 mL) and EtOAc (20 mL). The layers were separated and the aqueous layer was extracted with EtOAc (1×10 mL). The combined organic extracts were washed with brine (10 mL) and dried over Na$_2$SO$_4$ and concentrated in vacuo to give 2-acetyl-1-(3'-fluoro-3-methoxy-[1,1'-biphenyl]-4-yl)-1,2,3,4-tetrahydroisoquinoline-6-sulfonyl chloride (0.491 g, 1.036 mmol, 145% yield). The product contaminated with residual solvent but was of sufficient purity for the next step. m/z (ESI) 474.0 (M+H)$^+$.

STEP 4: 2-ACETYL-1-(3'-FLUORO-3-METHOXY-[1,1'-BIPHENYL]-4-YL)-N-(1,3,4-THIADIAZOL-2-YL)-1,2,3,4-TETRAHYDROISOQUINOLINE-6-SULFONAMIDE 2,2,2-TRIFLUOROACETATE

A RBF was charged with N-(4-methoxybenzyl)-1,3,4-thiadiazol-2-amine (0.126 g, 0.568 mmol). A septum was attached and the flask was flushed with N$_2$. THF (6.31 ml) was added and the solution was cooled to −78° C. A THF solution of LHMDS (1.262 ml, 1.262 mmol) was added, followed by a THF solution of 2-acetyl-1-(3'-fluoro-3-methoxy-[1,1'-biphenyl]-4-yl)-1,2,3,4-tetrahydroisoquinoline-6-sulfonyl chloride (0.299 g, 0.631 mmol, 0.4 M). The reaction mixture was maintained at −78° C. for 30 min, then warmed to 0° C. The reaction was quenched by the addition of saturated aqueous NH$_4$Cl (5 mL). The resulting mixture was extracted with EtOAc (3×20 mL). The combined organic layers were dried (Na$_2$SO$_4$), concentrated in vacuo and purified by MPLC silica gel chromatography (Biotage Isolera). The crude residue was taken up in minimal CH$_2$Cl$_2$ and absorbed directly onto a a Biotage SNAP pre-packed silica gel column (25 g) and eluted using a gradient of 95:5 Heptane:EtOAc to 100% EtOAc with 2% EtOH as an additive to afford 2-acetyl-1-(3'-fluoro-3-methoxy-[1,1'-biphenyl]-4-yl)-N-(4-methoxybenzyl)-N-(1,3,4-thiadiazol-2-yl)-1,2,3,4-tetrahydroisoquinoline-6-sulfonamide (0.173 g, 0.263 mmol, 41.6% yield) as a light-yellow film.

To a RBF charged with 2-acetyl-1-(3'-fluoro-3-methoxy-[1,1'-biphenyl]-4-yl)-N-(4-methoxybenzyl)-N-(1,3,4-thiadiazol-2-yl)-1,2,3,4-tetrahydroisoquinoline-6-sulfonamide (0.173 g, 0.263 mmol, 41.6% yield) in DCM (2 mL) was added TFA (1 mL) at rt. After 1 h, solution was concentrated. The crude residue was taken up in minimal MeOH/DMSO and purified by preparative HPLC (Gilson, 20-90% CH$_3$CN:H2O (1% TFA modifier) over 15 min) Clean fractions were combined and concentrated to afford 2-acetyl-1-(3'-fluoro-3-methoxy-[1,1'-biphenyl]-4-yl)-N-(1,3,4-thiadiazol-2-yl)-1,2,3,4-tetrahydroisoquinoline-6-sulfonamide 2,2,2-trifluoroacetate (0.019 g, 0.029 mmol, 4.61% yield) as a white amorphous solid. 1H NMR (400 MHz, DMSO-d$_6$) (Rotamers present, integrals reported as observed at 25° C.) δ ppm 2.10 (s, 1.8 H) 2.19 (s, 1.6 H) 2.85-3.21 (m, 3 H) 3.80 (t, J=5.77 Hz, 2 H) 3.86 (s, 2 H) 4.01 (s, 1.8 H) 4.29 (br d, J=13.50 Hz, 0.6 H) 6.45 (s, 0.5 H) 6.73-6.89 (m, 1.2 H) 7.05-7.41 (m, 5.3 H) 7.45-7.62 (m, 4.6 H) 7.67 (d, J=4.30 Hz, 1.2 H) 8.76 (d, J=4.30 Hz, 1 H); m/z (ESI) 539.1 (M+H)$^+$ Examples 53-A & 53-B (Method 53)

(S)-2-ACETYL-1-(3'-FLUORO-3-METHOXY-[1,1'-BIPHENYL]-4-YL)-N-(ISOXAZOL-3-YL)-1,2,3,4-TETRAHYDROISOQUINOLINE-6-SULFONA-MIDE (53-A)

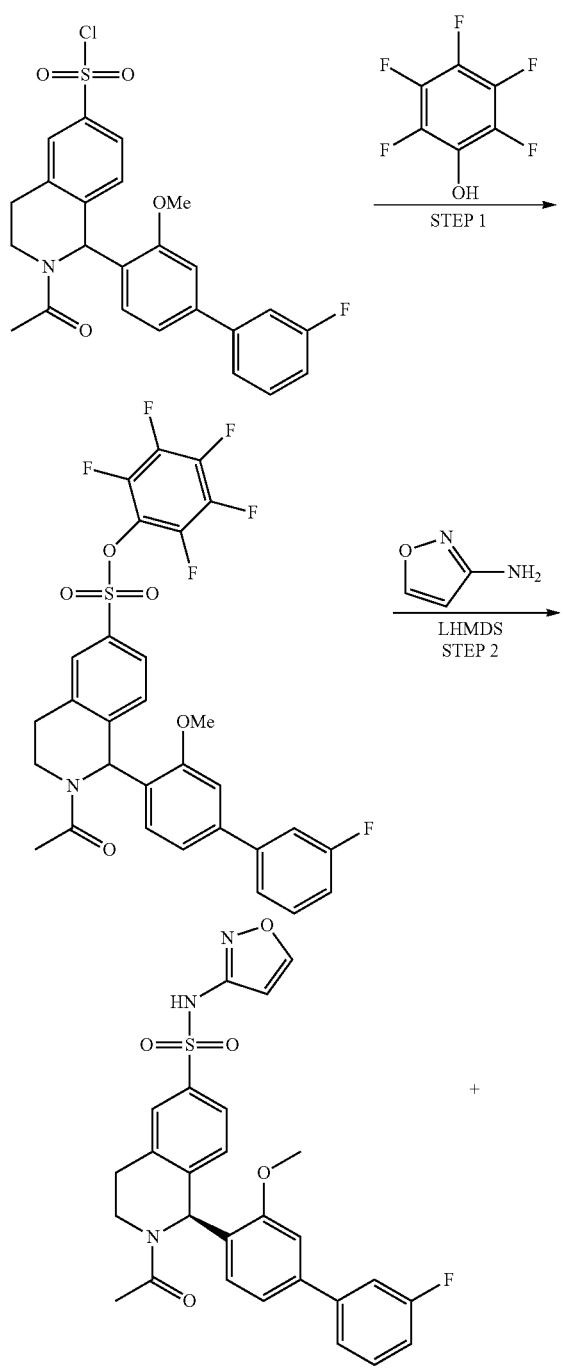

-continued

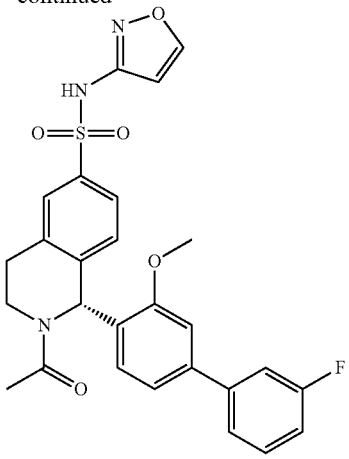

STEP 1: PERFLUOROPHENYL 2-ACETYL-1-(3'-FLUORO-3-METHOXY-[1,1'-BIPHENYL]-4-YL)-1,2,3,4-TETRAHYDROISOQUINOLINE-6-SUL-FONATE

A RBF was charged with 2-acetyl-1-(3'-fluoro-3-methoxy-[1,1'-biphenyl]-4-yl)-1,2,3,4-tetrahydroisoquino-line-6-sulfonyl chloride (0.192 g, 0.405 mmol, made via Method 52, Step 3), and 2,3,4,5,6-pentafluorophenol (0.089 g, 0.486 mmol). A septum was attached and the flask was flushed with N$_2$. THF (2 mL) was added and the solution was submerged in an ice bath to control exotherm. To this mixture was added TEA (0.169 ml, 1.215 mmol), drop-wise over 1 min. The ice bath was removed and the solution allowed to warm to rt and stir for 30 min. The solution was concentrated for purification by MPLC (Biotage Isolera). The crude residue was taken up in minimal CH$_2$Cl$_2$ and absorbed onto a Biotage SNAP column (50 g) (used as a loading cartridge) and passed through a Redi-Sep® Gold pre-packed silica gel column (120 g) using a gradient of 98:2 Heptane:EtOAc to 100% EtOAc with a 1% DCM additive to afford perfluorophenyl 2-acetyl-1-(3'-fluoro-3-methoxy-[1, 1'-biphenyl]-4-yl)-1,2,3,4-tetrahydro-isoquinoline-6-sul-fonate (0.121 g, 48% yield) as a colorless foam. m/z (ESI) 622.2 (M+H)$^+$.

STEP 2: (S)-2-ACETYL-1-(3'-FLUORO-3-METHOXY-[1,1'-BIPHENYL]-4-YL)-N-(ISOX-AZOL-3-YL)-1,2,3,4-TETRAHYDROISOQUINO-LINE-6-SULFONAMIDE

A RBF was charged with perfluorophenyl 2-acetyl-1-(3'-fluoro-3-methoxy-[1,1'-biphenyl]-4-yl)-1,2,3,4-tetrahy-droisoquinoline-6-sulfonate (0.121 g, 0.195 mmol), and isoxazol-3-amine (0.020 g, 0.234 mmol). The flask was sealed with a septum, and flushed with N$_2$. Tetrahydrofuran (1.947 ml) was added and the solution was cooled to −78° C. A THF solution of LHMDS (0.389 ml, 0.389 mmol) was added and the solution was maintained at −78° C. for 10 min, then allowed to warm to rt. The reaction mixture was partitioned between saturated aqueous NH$_4$Cl (10 mL) and EtOAc (10 mL). The layers were separated and the aqueous layer was extracted with EtOAc (1×10 mL). The combined organic extracts were dried over Na$_2$SO$_4$ and concentrated in vacuo for purification. The crude reaction mixture was taken up in minimal MeOH and purified by preparative HPLC (Gilson, Phenomenex Luna column, 5 micron, C18(2), 100 Å, 150×30 mm 20-90% CH3CN:H2O (1% TFA modifier) over 15 min) Clean fractions were combined and concentrated to afford (S)-2-acetyl-1-(3'-fluoro-3-methoxy-[1,1'-biphenyl]-4-yl)-N-(isoxazol-3-yl)-1,2,3,4-tetrahydroisoquinoline-6-sulfonamide (0.033 g, 0.063 mmol, 32.5% yield) as a white amorphous solid. Separation of enantiomers was performed using supercritical fluid chromatography (SFC). The column used was AS-H 4.6×100 mm. The mobile phase was run under isocratic conditions; $CO_2$ with (35)% methanol co-solvent at 5 mL/min flowrate to obtain (S)-2-acetyl-1-(3'-fluoro-3-methoxy-[1,1'-biphenyl]-4-yl)-N-(isoxazol-3-yl)-1,2,3,4-tetrahydroisoquinoline-6-sulfonamide (0.033 g, >98% ee) as the first eluting peak. $^1$H NMR (400 MHz, MeOH-$d_4$)) (Rotamers present, integrals reported as observed at 25° C.) δ ppm 2.20 (s, 1.5 H) 2.32 (s, 1.8 H) 2.96-3.13 (m, 2 H) 3.21-3.31 (m, 0.6 H) 3.79 (s, 1.4 H) 3.82-3.89 (m, 0.6 H) 3.93-4.00 (m, 0.6 H) 4.03 (s, 1.6 H) 4.46 (d, J=13.30 Hz, 0.5 H) 6.49 (br. s., 1 H) 6.53-6.60 (m, 0.6 H) 6.81 (d, J=7.92 Hz, 0.5 H) 6.91 (s, 0.5 H) 7.02-7.22 (m, 2.5 H) 7.24-7.52 (m, 4.8 H) 7.71 (d, J=8.31 Hz, 1 H) 7.81 (d, J=9.19 Hz, 1 H) 8.46 (br. s., 1 H); m/z (ESI) 522.3 (M+H)$^+$. (R)-2-acetyl-1-(3'-fluoro-3-methoxy-[1,1'-biphenyl]-4-yl)-N-(isoxazol-3-yl)-1,2,3,4-tetrahydroisoquinoline-6-sulfonamide was obtained as the second eluting peak in the enantiomeric separation. The analytical data (NMR, ESI m/z) are identical to that described for obtain (S)-2-acetyl-1-(3'-fluoro-3-methoxy-[1,1'-biphenyl]-4-yl)-N-(isoxazol-3-yl)-1,2,3,4-tetrahydroisoquinoline-6-sulfonamide.

Example 54 (Method 54)

1-(2-CHLORO-3'-FLUORO-5-METHOXY-[1,1'-BIPHENYL]-4-YL)-N-(THIAZOL-4-YL)ISOQUINOLINE-6-SULFONAMIDE

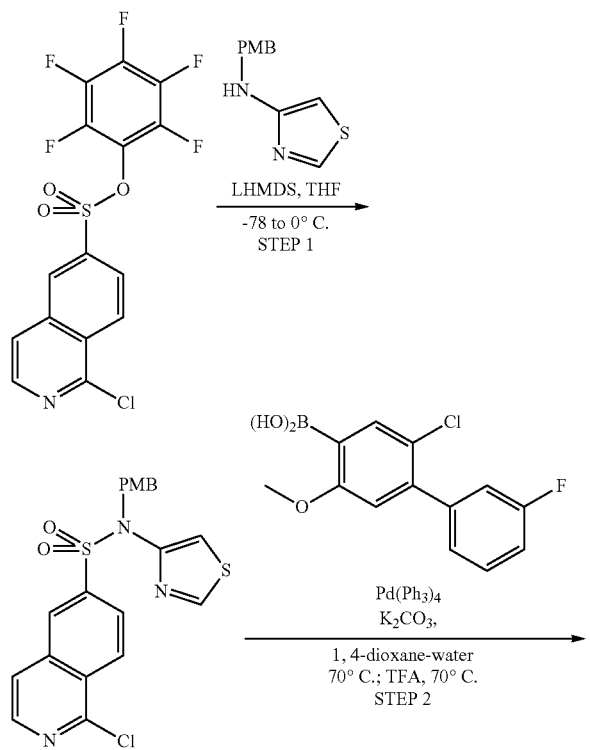

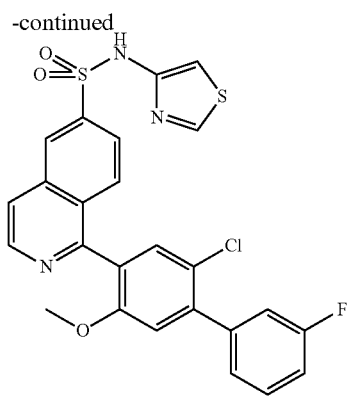

STEP 1: 1-CHLORO-N-(4-METHOXYBENZYL)-N-(THIAZOL-4-YL)ISOQUINOLINE-6-SULFONAMIDE

A RBF was charged with N-(4-methoxybenzyl)thiazol-4-amine (0.574 g, 2.60 mmol) and THF (11.84 ml) to give a brown mixture. The flask was cooled in a dry ice-acetone bath for 10 min, then lithium bis(trimethylsilyl)amide (1M in THF) (2.60 ml, 2.60 mmol) was added dropwise. The bath was removed for 5 min, then the flask was recooled in the bath. After 5 min, a solution of perfluorophenyl 1-chloroisoquinoline-6-sulfonate (0.9702 g, 2.368 mmol) in THF (4 mL with a 2 mL syringe-wash) was added dropwise. The flask was then placed in an ice-water bath for 20 min. The mixture was quenched by the addition of saturated aq. ammonium chloride and water, then extracted with EtOAc (2×). The combined organic extracts were dried over sodium sulfate, filtered, and concentrated. The residue was purified by chromatography on silica gel (40-g Redi-Sep Gold column, 25-g silica gel loading column, 0-50% EtOAc/Heptane). The resulting solid was taken up in heptane, filtered, washed with heptane (2×), and dried under a stream of $N_2$ (g) to give 1-chloro-N-(4-methoxybenzyl)-N-(thiazol-4-yl)isoquinoline-6-sulfonamide (0.709 g, 1.590 mmol, 67.1% yield) as a cream-colored solid. m/z (ESI) 446.0 (M+H)$^+$.

STEP 2: 1-(2-CHLORO-3'-FLUORO-5-METHOXY-[1,1'-BIPHENYL]-4-YL)-N-(THIAZOL-4-YL)ISOQUINOLINE-6-SULFONAMIDE

A vial was charged with 1-chloro-N-(4-methoxybenzyl)-N-(thiazol-4-yl)isoquinoline-6-sulfonamide (77.23 mg, 0.173 mmol), (2-chloro-3'-fluoro-5-methoxy-[1,1'-biphenyl]-4-yl)boronic acid (63.1 mg, 0.225 mmol) potassium carbonate (71.8 mg, 0.520 mmol), and pd(ph3p)4 (20.01 mg, 0.017 mmol). The vial was flushed with Ar (g), then 1,4-dioxane (649 µl) and water (216 µl) were added. The vial was heated to 70° C. in an oil bath for 1.5 h. The mixture was diluted with water and extracted with EtOAc (3×). The combined organic extracts were concentrated. The residue was taken up in TFA (1 mL) to give a yellow solution. The flask was stoppered and placed in an 70° C. heating bath for 15 min, then the mixture was concentrated. The residue was dissolved in DMSO, and the resulting solution was filtered through a 0.2 micron filter. The filtrate was purified by reverse-phase HPLC (40-85% CH₃CN/H₂O with 0.1% TFA). Fractions containing product were combined and concentrated from DCM to give 1-(2-chloro-3'-fluoro-5-methoxy-[1,1'-biphenyl]-4-yl)-N-(thiazol-4-yl)isoquinoline-6-sulfonamide 2,2,2-trifluoroacetate (74.5 mg, 0.116 mmol, 67.2% yield) as a light-yellow solid. $^1$H NMR (400 MHz, DMSO-d₆) δ=11.39 (s, 1 H), 8.87 (d, J=2.2 Hz, 1 H), 8.73 (d, J=5.8 Hz, 1 H), 8.63 (d, J=1.8 Hz, 1 H), 8.14 (d, J=5.5 Hz, 1 H), 7.98-7.93 (m, 1 H), 7.90-7.83 (m, 1 H), 7.64-7.54 (m, 2 H), 7.50-7.42 (m, 2 H), 7.37-7.30 (m, 1 H), 7.28 (s, 1 H), 7.15 (d, J=2.2 Hz, 1 H), 3.71 (s, 3 H). m/z (ESI) 526.1 (M+H)⁺.

Example 55 (Method 55)

1-(2-CHLORO-3'-FLUORO-5-METHOXY-[1,1'-BIPHENYL]-4-YL)-N-(ISOXAZOL-3-YL)-4-METHOXYPHTHALAZINE-6-SULFONAMIDE

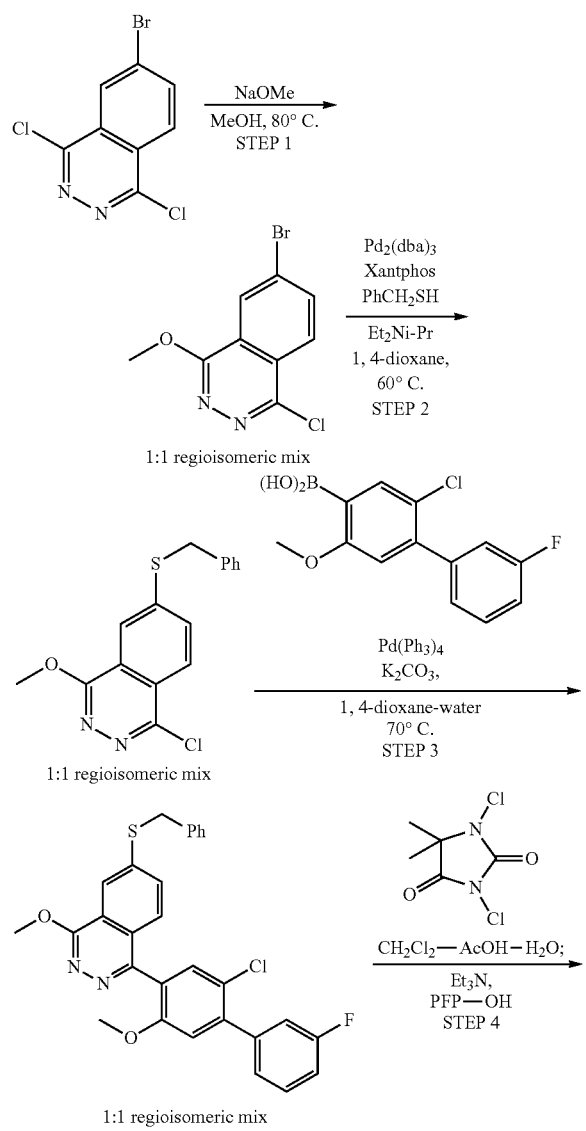

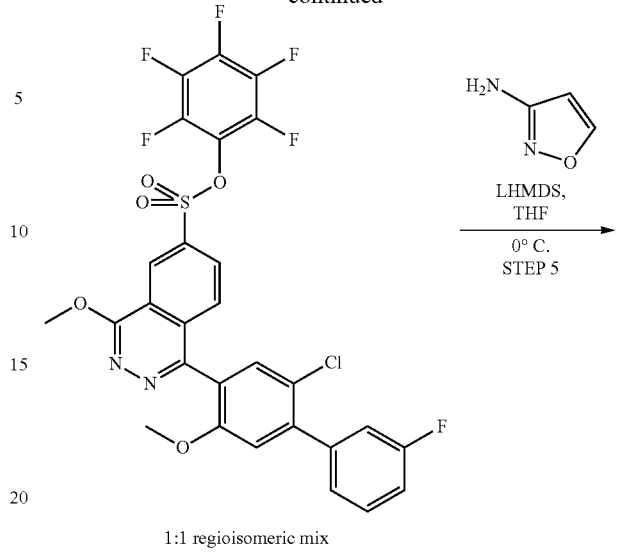

STEP 1: 6-BROMO-1-CHLORO-4-METHOXYPHTHALAZINE

A RBF was charged with 6-bromo-1,4-dichlorophthalazine (Synthonix, Inc., Wake Forest, N.C., 3.11 g, 11.19 mmol), MeOH (44.8 ml), and sodium methoxide (1.088 g, 20.14 mmol) to give a suspension. The flask was fitted with a reflux condenser then placed in an 80° C. heating bath. After 3 h, an additional portion of sodium methoxide (350 mg) was added. Following another 1.5 h of stirring, the mixture was cooled to RT, then paritioned between DCM and 1N aq. HCl. The layers were separated, and the aq. layer was extracted with DCM (2×). The combined organic extracts were dried over sodium sulfate, filtered, and concentrated. The residue was concentrated from DCM/heptane, then taken up in heptane and filtered. The filtered solid was washed with heptane (3×), then dried under a stream of N₂ (g) to give 2.72 g of a white solid, which was a ca. 1:1 mixture of 6-bromo-1-chloro-4-methoxyphthalazine and 6-bromo-4-chloro-1-methoxyphthalazine. The regioisomeric mixture was used directly in the next step. m/z (ESI) 272.9 (M+H)⁺.

STEP 2: 6-(BENZYLTHIO)-1-CHLORO-4-METHOXYPHTHALAZINE

A RBF was charged with 6-bromo-1-chloro-4-methoxyphthalazine (1.62 g, 5.92 mmol), Xantphos (0.171 g, 0.296 mmol), and Pd$_2$(dba)$_3$ (0.136 g, 0.148 mmol). 1,4-Dioxane (11.85 ml), n,n-diisopropylethylamine (2.069 ml, 11.85 mmol), and benzyl mercaptan (0.736 ml, 6.22 mmol) were added. The flask was placed in a 60° C. heating bath. After 25 min, the mixture was cooled to RT and diluted with EtOAc and water. A solid persisted, so the mixture was filtered. The collected solid was washed with EtOAc (2×), then dried under a stream of N$_2$ (g) to give 6-(benzylthio)-1-chloro-4-methoxyphthalazine (916 mg, 2.89 mmol, 48.8% yield) as a light-green solid as an assumed 1:1 mixture of regioisomers that was used directly in the next step. m/z (ESI) 317.1 (M+H)+.

STEP 3: 6-(BENZYLTHIO)-1-(2-CHLORO-3'-FLUORO-5-METHOXY-[1,1'-BIPHENYL]-4-YL)-4-METHOXYPHTHALAZINE

A RBF was charged with 6-(benzylthio)-1-chloro-4-methoxyphthalazine (904 mg, 2.85 mmol), (2-chloro-3'-fluoro-5-methoxy-[1,1'-biphenyl]-4-yl)boronic acid (880 mg, 3.14 mmol), potassium carbonate (1183 mg, 8.56 mmol), and pd(ph3p)4 (330 mg, 0.285 mmol). The flask was flushed with Ar (g), then 1,4-dioxane (1.14E+04 µl) and water (2853 µl) were added. A reflux condenser was attached, and the flask was lowered into a 70° C. heating bath. After 3 h, the mixture was cooled to RT, then diluted with water and EtOAc. A significant solid persisted in the organic layer. The layers were separated, and the organic layer was concentrated. The residue was concentrated from MeOH/DCM, then taken up in boiling MeOH. The mixture was cooled and sonicated for 1 min, then filtered. The collected solid was washed with MeOH (3×), then dried under a stream of N$_2$ (g) to give 6-(benzylthio)-1-(2-chloro-3'-fluoro-5-methoxy-[1,1'-biphenyl]-4-yl)-4-methoxyphthalazine (1.06 g, 2.050 mmol, 71.9% yield) as an off-white solid and as an assumed mixture of regioisomers. This material was used directly in the next step. m/z (ESI) 517.2 (M+H)+.

STEP 4: PERFLUOROPHENYL 1-(2-CHLORO-3'-FLUORO-5-METHOXY-[1,1'-BIPHENYL]-4-YL)-4-METHOXYPHTHALAZINE-6-SULFONATE

A RBF was charged with 6-(benzylthio)-1-(2-chloro-3'-fluoro-5-methoxy-[1,1'-biphenyl]-4-yl)-4-methoxyphthalazine (1.056 g, 2.042 mmol), DCM (19.22 ml), acetic acid (0.721 ml), and water (0.481 ml) to give clear, yellow solution. The flask was cooled in an ice-water bath for 10 min, then 1,3-dichloro-5,5-dimethylimidazolidine-2,4-dione (0.825 g, 4.19 mmol) was added in one portion. After 20 min, an additional portion of oxidant (ca. 500 mg) was added. After another 10 min, 2,3,4,5,6-pentafluorophenol (0.564 g, 3.06 mmol) and triethylamine (1.139 ml, 8.17 mmol) were added in sequence. After 20 min, the mixture was diluted with saturated aq. sodium bicarbonate solution, and the mixture was stirred vigorously for 5 min. The mixture was then extracted with DCM (3×). The combined organic extracts were dried over sodium sulfate, filtered, and concentrated. The residue was purified by chromatography on silica gel (40-g Redi-Sep Gold column, 25-g silica gel loading column, 0-50% EtOAc/Heptane with 10% DCM) to give a white solid. The solid was taken up in heptane and filtered. The collected solid was washed with heptane (2×), then dried under a stream of N$_2$ (g) to give perfluorophenyl 1-(2-chloro-3'-fluoro-5-methoxy-[1,1'-biphenyl]-4-yl)-4-methoxyphthalazine-6-sulfonate (936 mg, 1.460 mmol, 71.5% yield) as white solid that was 85% pure by LCMS analysis and assumed to be a 1:1 mixture of regioisomers. This material was used directly in the next step.

STEP 5: 1-(2-CHLORO-3'-FLUORO-5-METHOXY-[1,1'-BIPHENYL]-4-YL)-N-(ISOXAZOL-3-YL)-4-METHOXYPHTHALAZINE-6-SULFONAMIDE

A vial was charged with perfluorophenyl 1-(2-chloro-3'-fluoro-5-methoxy-[1,1'-biphenyl]-4-yl)-4-methoxyphthalazine-6-sulfonate (152 mg, 0.237 mmol), isoxazol-3-amine (20.15 µl, 0.273 mmol) and THF (23720 to give a clear solution. The vial was cooled in an ice-water bath for 10 min, then lithium bis(trimethylsilyl)amide (1M in THF) (498 µl, 0.498 mmol) was added dropwise. After 20 min showed conversion to the desired product. The mixture was quenched by the addition of 1N aq. HCl, then warmed to room temperature. The mixture was extracted with EtOAc (3×), and the combined organic extracts were concentrated. The material was then separated using the following conditions: Column: AS-H Solvent: 25% methanol w/0.2% diethylamine. The first eluting peak was concentrated from DCM to give a cream-colored solid and was assigned as 1-(2-chloro-3'-fluoro-5-methoxy-[1,1'-biphenyl]-4-yl)-N-(isoxazol-3-yl)-4-methoxy-phthalazine-6-sulfonamide compound with diethylamine (1:1) (79.65 mg, 0.130 mmol, 54.7% yield) as an off-white solid. $^1$H NMR (400 MHz, DMSO-d$_6$) δ=8.50 (dd, J=0.6, 1.7 Hz, 1 H), 8.25-8.12 (m, 4 H), 7.64-7.54 (m, 3 H), 7.50-7.42 (m, 2 H), 7.35-7.29 (m, 1 H), 7.27 (s, 1 H), 6.10 (d, J=1.8 Hz, 1 H), 4.26 (s, 3 H), 3.72 (s, 3 H), 2.93 (q, J=7.3 Hz, 4 H), 1.16 (t, J=7.2 Hz, 6 H). m/z (ESI) 541.1 (M+H)+.

Example 56 (Method 56)

1-(1-(3,5-DIFLUOROPHENYL)-5-METHOXY-2-OXO-1,2-DIHYDROPYRIDIN-4-YL)-N-(ISOXAZOL-3-YL)ISOQUINOLINE-6-SULFONAMIDE

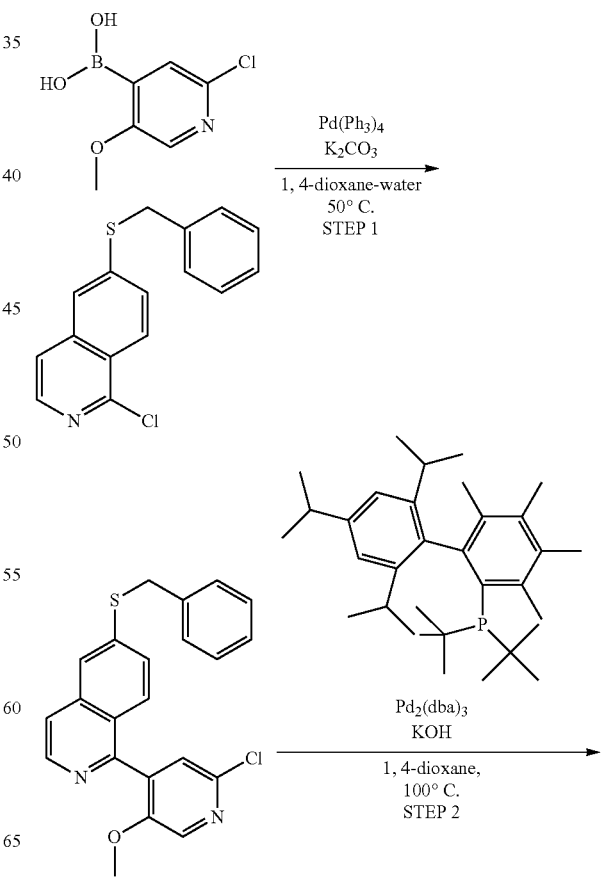

229
-continued

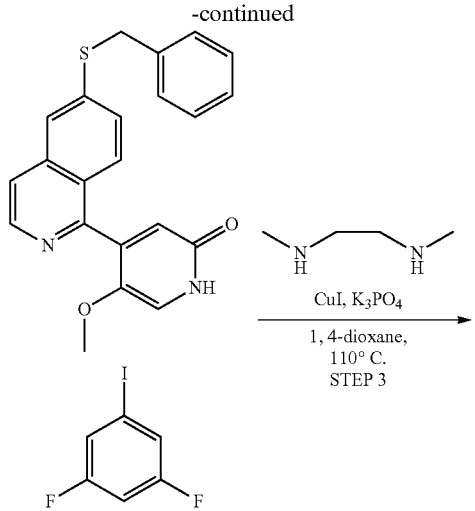

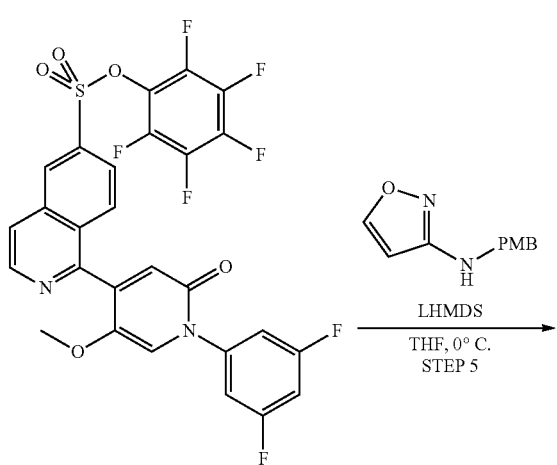

230
-continued

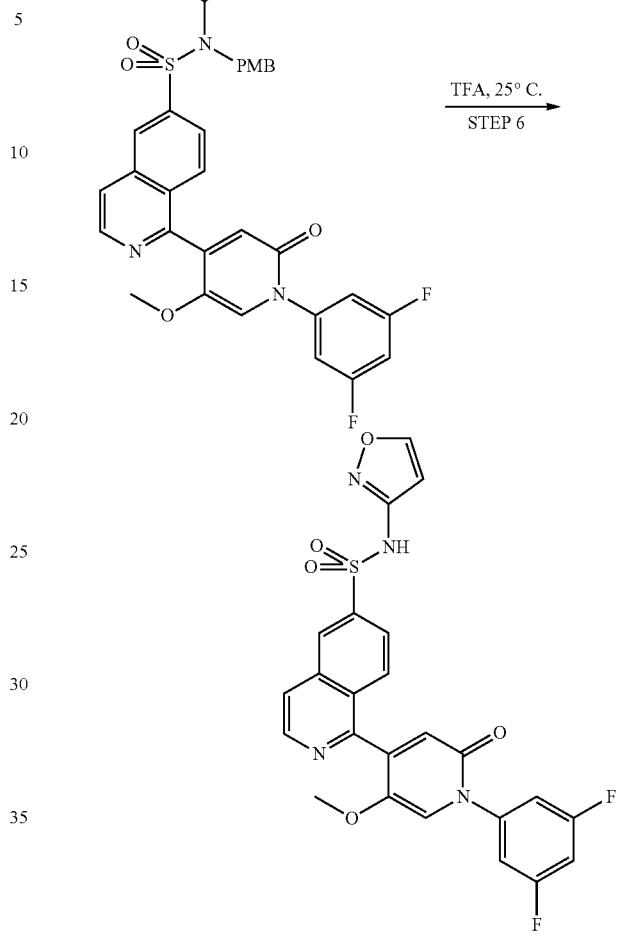

STEP 1: 6-(BENZYLTHIO)-1-(2-CHLORO-5-METHOXYPYRIDIN-4-YL)ISOQUINOLINE

A round-bottom flask was charged with (2-chloro-5-methoxypyridin-4-yl)boronic acid (472 mg, 2.52 mmol), 6-(benzylthio)-1-chloroisoquinoline (600 mg, 2.099 mmol), made via Step 1 of Intermediate Y), potassium carbonate (870 mg, 6.30 mmol), and pd(ph3p)4 (243 mg, 0.210 mmol). The vial was flushed with Ar (g), then Dioxane (7873 µl) and Water (2624 µl) were added. The flask was fitted with a reflux condenser and heated in a 50° C. heating bath for 3 hrs until reaction was complete by LCMS. The mixture was partitioned between ammonium chloride solution and EtOAc. The layers were separated, extracted 3 times with EtOAc, and the organic extracts were dried over sodium sulfate, filtered, and concentrated. The residue was purified by chromatography on silica gel (40-g Redi-Sep Gold column, 25-g silica gel loading column, 0-100% EtOAc/Heptane) to give 6-(benzylthio)-1-(2-chloro-5-methoxypyridin-4-yl)isoquinoline (755 mg, 1.922 mmol, 92% yield) as a white solid. m/z (ESI) 393.2 (M+H)$^+$.

STEP 2: 4-(6-(BENZYLTHIO)ISOQUINOLIN-1-YL)-5-METHOXYPYRIDIN-2(1H)-ONE

Dissolved Pd$_2$dba$_3$ (53.6 mg, 0.059 mmol), 2-di-i-butyl-phosphino-3,4,5,6-tetramethyl-2',4',6'-tri-i-propylbiphenyl (56.3 mg, 0.117 mmol) and 6-(benzylthio)-1-(2-chloro-5-methoxypyridin-4-yl)isoquinoline (460 mg, 1.171 mmol) in dioxane (23420 and water (23420 at 110° C. for 3 hrs until reaction was complete by LCMS. The reaction was quenched with ammonium chloride and extracted with EtOAc. Organics were dried over Na₂SO₄, concentrated, and purified via column chromatography with a gradient Hep:EtOAc (0-100%), which did not elute compound, so was further eluted and purified with a gradient DCM/DCM:MeOH (90:10) 0-100% to give 4-(6-(benzylthio)-isoquinolin-1-yl)-5-methoxypyridin-2(1H)-one (344 mg, 0.919 mmol, 78% yield). m/z (ESI) 375.2 (M+H)+.

STEP 3: 4-(6-(BENZYLTHIO)ISOQUINOLIN-1-YL)-1-(3,5-DIFLUOROPHENYL)-5-METHOXY-PYRIDIN-2(1H)-ONE

Dissolved 1,3-difluoro-5-iodobenzene (265 mg, 1.102 mmol) and 4-(6-(benzylthio)isoquinolin-1-yl)-5-methoxypyridin-2(1H)-one (344 mg, 0.919 mmol) in 1,4-dioxane (1837 µl) and added potassium phosphate (390 mg, 1.837 mmol), copper(i) iodide (35.0 mg, 0.184 mmol), and N1,N2-dimethylethane-1,2-diamine (39.6 µl, 0.367 mmol) in a sealed tube. Flushed with argon and heated to 110° C. for 16 hrs until reaction was complete by LCMS. Cooled the reaction to rt and quenched reaction with water and extracted with EtOAc (3×), dried organics over Na2 SO4, filtered and concentrated via rotary evaporation. Purified residue via column chromatography with a gradient DCM/DCM:MeOH(90:10) 0-100% to yield 4-(6-(benzylthio)isoquinolin-1-yl)-1-(3,5-difluorophenyl)-5-methoxypyridin-2(1H)-one (304 mg, 0.625 mmol, 68.0% yield). m/z (ESI) 487.3 (M+H)⁺.

STEP 4: PERFLUOROPHENYL 1-(1-(3,5-DIFLUOROPHENYL)-5-METHOXY-2-OXO-1,2-DIHYDROPYRIDIN-4-YL)ISOQUINOLINE-6-SULFONATE

A RBF was charged with 4-(6-(benzylthio)isoquinolin-1-yl)-1-(3,5-difluorophenyl)-5-methoxypyridin-2(1H)-one (300 mg, 0.617 mmol), DCM (58030, Acetic Acid (2180, and Water (145 µl) to give a thin suspension. The flask was cooled in an ice-bath for 10 min, then 1,3-dichloro-5,5-dimethylimidazolidine-2,4-dione (304 mg, 1.542 mmol) was added in one portion, leading to a solution. The reaction was stirred for 15 minutes until LCMS showed complete conversion to sulfonyl chloride, so 2,3,4,5,6-pentafluorophenol (129 µl 1.233 mmol) was added followed by dropwise addition of triethylamine (215 µl, 1.542 mmol). The reaction was stirred for 30 minutes at 0° C. until reaction was complete by LCMS. The reaction was concentrated and purified via column chromatography with a gradient elution 0-100% Hep:EtOAc to afford perfluorophenyl 1-(1-(3,5-difluorophenyl)-5-methoxy-2-oxo-1,2-dihydropyridin-4-yl) isoquinoline-6-sulfonate (100 mg, 0.164 mmol, 26.6% yield). m/z (ESI) 611.1 (M+H)⁺.

STEP 5: 1-(1-(3,5-DIFLUOROPHENYL)-5-METHOXY-2-OXO-1,2-DIHYDROPYRIDIN-4-YL)-N-(ISOXAZOL-3-YL)-N-(4-METHOXYBENZYL)ISOQUINOLINE-6-SULFONAMIDE

A RBF was charged with perfluorophenyl 1-(1-(3,5-difluorophenyl)-5-methoxy-2-oxo-1,2-dihydropyridin-4-yl) isoquinoline-6-sulfonate (100 mg, 0.164 mmol), THF (819 µl and isoxazol-3-amine (134 µl, 1.818 mmol) to give a clear, light-yellow solution. The flask was cooled in an ice-water bath for 10 min, then lithium bis(trimethylsilyl) amide (1M in THF) (197 µl, 0.197 mmol) was added dropwise. The reaction was stirred at 0 C for 30 min until reaction was complete by LCMS. The reaction mixture was quenched with saturated ammonium chloride solution and extract with EtOAc (3 times). The combined organics were dried over Na2SO4, filtered and concentrated. The residue was then purified via column chromatography with a gradient Hep:EtOAc column (0-100%) to yield 1-(1-(3,5-difluorophenyl)-5-methoxy-2-oxo-1,2-dihydropyridin-4-yl)-N-(isoxazol-3-yl)-N-(4-methoxybenzyl)isoquinoline-6-sulfonamide (60 mg, 0.095 mmol, 58.1% yield). m/z (ESI) 631.3 (M+H)⁺.

STEP 6: 1-(1-(3,5-DIFLUOROPHENYL)-5-METHOXY-2-OXO-1,2-DIHYDROPYRIDIN-4-YL)-N-(ISOXAZOL-3-YL)ISOQUINOLINE-6-SULFONAMIDE 1-(1-(3,5-difluorophenyl)-5-methoxy-2-oxo-1,2-dihydropyridin-4-yl)-N-(isoxazol-3-yl)-N-(4-methoxybenzyl)isoquinoline-6-sulfonamide (60 mg, 0.095 mmol, 58.1% yield) was dissolved in 0.5 mL of TFA and stirred at 50° C. for 2 hrs until reaction was complete by LCMS. The reaction was concentrated and purified directly via column chromatography with a gradient DCM:DCM:MeOH (10%) 0-100% to yield 1-(1-(3,5-difluorophenyl)-5-methoxy-2-oxo-1,2-dihydropyridin-4-yl)-N-(isoxazol-3-yl)isoquinoline-6-sulfonamide as a yellow solid. m/z (ESI) 511.1 (M+H)+. ¹H NMR (400 MHz, DMSO-d₆) δ ppm 11.86-12.00 (m, 1 H) 8.72-8.78 (m, 2 H) 8.68-8.71 (m, 1 H) 8.17-8.24 (m, 1 H) 8.01-8.07 (m, 1 H) 7.99 (d, J=1.96 Hz, 1 H) 7.38-7.50 (m, 4 H) 6.57 (d, J=0.39 Hz, 1 H) 6.50 (d, J=1.86 Hz, 1 H) 3.51 (s, 3 H).

Example 57 (Method 57)

3-(2-CHLORO-3'-FLUORO-5-METHOXY-[1,1'-BIPHENYL]-4-YL)-N-(ISOXAZOL-3-YL)-1-METHYL-1H-INDOLE-6-SULFONAMIDE

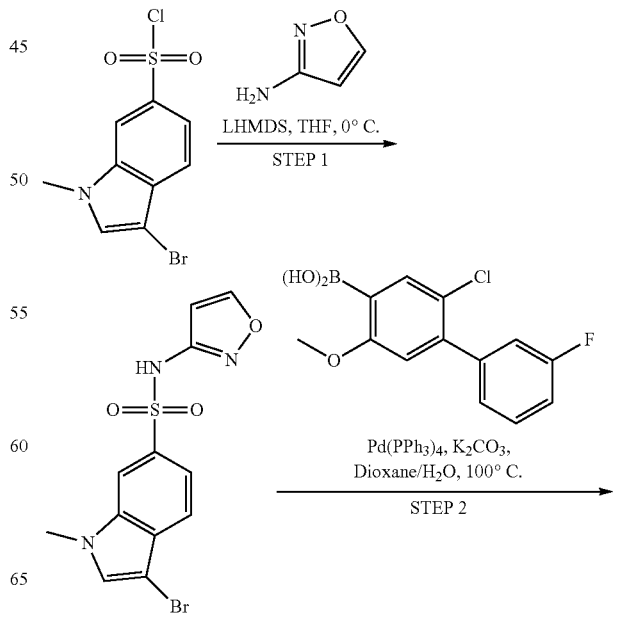

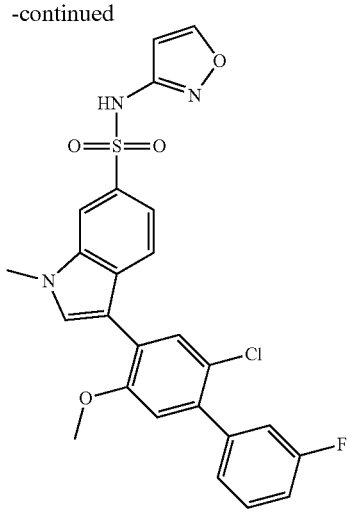

STEP 1: 3-BROMO-N-(ISOXAZOL-3-YL)-1-METHYL-1H-INDOLE-6-SULFONAMIDE

A RBF was charged with 3-bromo-1-methyl-1H-indole-6-sulfonyl chloride (0.100 g, 0.324 mmol), isoxazol-3-amine (0.026 ml, 0.356 mmol), and THF (1.620 ml) to give a clear solution. The flask was cooled in an ice-water bath for 10 minutes, then lithium bis(trimethylsilyl)amide (1M in THF) (0.713 ml, 0.713 mmol) was added dropwise. The reaction was stirred for 30 minutes. The reaction was diluted with 1N aq. HCl and EtOAc. The aqueous layer was extracted with ethyl acetate, and the combined organic layers were dried with sodium sulfate, filtered, and concentrated to afford 3-bromo-N-(isoxazol-3-yl)-1-methyl-1H-indole-6-sulfonamide (0.120 g, 0.337 mmol, 104% yield) as a light yellow solid. m/z (ESI) 356.0 (M+H)+.

STEP 2: 3-(2-CHLORO-3'-FLUORO-5-METHOXY-[1,1'-BIPHENYL]-4-YL)-N-(ISOXAZOL-3-YL)-1-METHYL-1H-INDOLE-6-SULFONAMIDE

A microwave vial was charged with 3-bromo-N-(isoxazol-3-yl)-1-methyl-1H-indole-6-sulfonamide (0.060 g, 0.168 mmol), (2-chloro-3'-fluoro-5-methoxy-[1,1'-biphenyl]-4-yl)boronic acid (0.071 g, 0.253 mmol), Pd(Ph$_3$P)$_4$ (0.019 g, 0.017 mmol), and potassium carbonate (0.070 g, 0.505 mmol). The vial was flushed with Ar (g), then dioxane (0.632 ml) and water (0.211 ml) were added in sequence. The vial was sealed and microwaved at 100° C. for 30 minutes. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 12 g, gradient elution 0-100% EtOAc:Heptane). The resulting solid was triturated in ethyl acetate, filtered, and washed with ethyl acetate. The solid was dried under a nitrogen blanket to afford 3-(2-chloro-3'-fluoro-5-methoxy-[1,1'-biphenyl]-4-yl)-N-(isoxazol-3-yl)-1-methyl-1H-indole-6-sulfonamide (0.026 g, 0.051 mmol, 30.1% yield) as a white solid. $^1$H NMR (400 MHz, DMSO-d$_6$) δ=11.49 (s, 1 H), 8.69 (d, J=1.8 Hz, 1 H), 8.07 (d, J=1.4 Hz, 1 H), 7.96 (s, 1 H), 7.78 (d, J=8.5 Hz, 1 H), 7.61-7.51 (m, 3 H), 7.42-7.37 (m, 2 H), 7.32-7.24 (m, 1 H), 7.16 (s, 1 H), 6.52 (d, J=1.9 Hz, 1 H), 3.95 (s, 3 H), 3.85 (s, 3 H). m/z (ESI) 512.2 (M+H)+.

Example 58 (Method 58)

3-CYANO-1-(2,3'-DIFLUORO-5-METHOXY-[1,1'-BIPHENYL]-4-YL)-N-(ISOXAZOL-3-YL)ISO-QUINOLINE-6-SULFONAMIDE

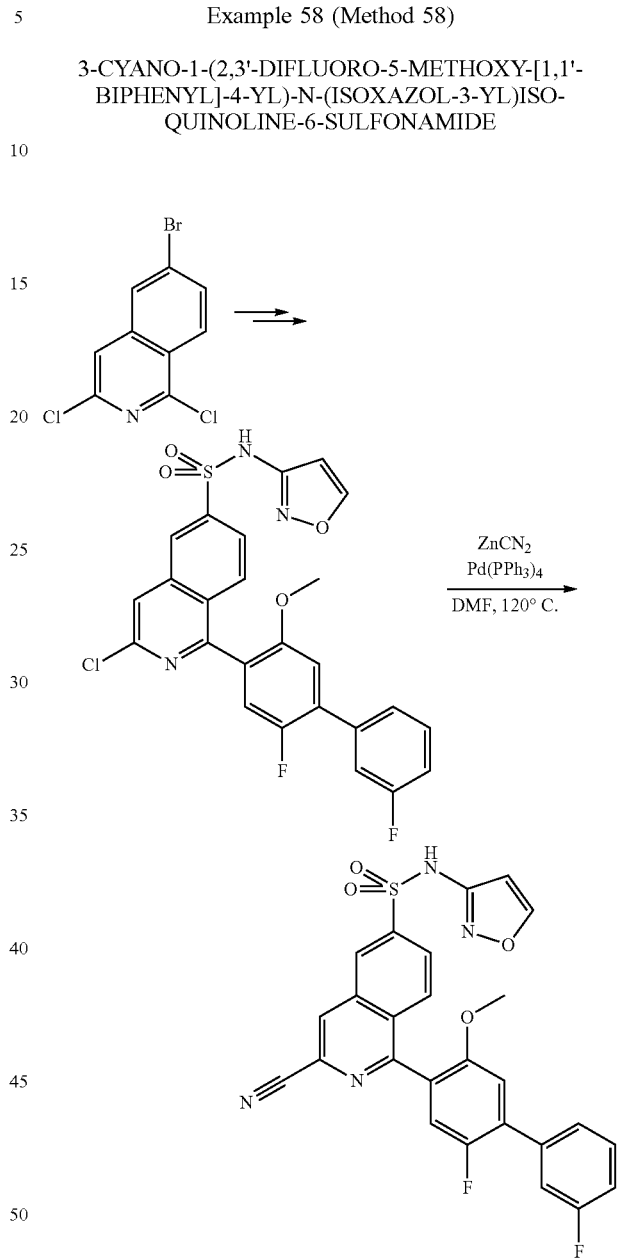

3-Chloro-1-(2,3'-difluoro-5-methoxy-[1,1'-biphenyl]-4-yl)-N-(isoxazol-3-yl)isoquinoline-6-sulfonamide was prepared via Method 3, utilizing 6-bromo-1,3-dichloroisoquinoline (Bellen Chemistry Co) as the starting material in the first step. The synthesis continued as follows: in a 2-mL sealed tube, added 3-chloro-1-(2,3'-difluoro-5-methoxy-[1,1'-biphenyl]-4-yl)-N-(isoxazol-3-yl)isoquinoline-6-sulfonamide (0.106 g, 0.200 mmol), dicyanozinc (0.023 g, 0.200 mmol) and (Ph$_3$P)$_4$Pd (0.023 g, 0.020 mmol) in DMF (Solvent Volume: 0.667 ml), purged solvent with nitrogen for 5 minutes, and sealed. The vessel was heated to 120° C. in a heating block for 2 days. LCMS indicated conversion to desired product. After cooling to rt, the crude mixture was subject to HPLC purification using 0.1% TFA in ACN and water as mobile phase to provide 3-cyano-1-(2,3'-difluoro-5-methoxy-[1,1'-biphenyl]-4-yl)-N-(isoxazol-3-yl)isoquinoline-6-sulfonamide (4.88 mg, 10% yield). m/z (ESI) 519.0 [M+1]. $^1$H NMR (500 MHz, DMSO-d6) δ ppm 3.73 (s, 3 H) 6.47 (d, J=1.50 Hz, 1 H) 7.30-7.41 (m, 1 H) 7.46 (d, J=10.37 Hz, 1 H) 7.51-7.70 (m, 9 H) 8.02 (d, J=8.92 Hz, 1H) 8.16 (dd, J=8.95, 1.58 Hz, 1 H) 8.80 (s, 1 H) 8.95 (s, 1 H).

Example 59 (Method 59)

4-(5-CHLORO-2-METHOXY-4-(TRIFLUOROMETHYL)PHENYL)-N-(ISOXAZOL-3-YL)QUINAZOLINE-7-SULFONAMIDE

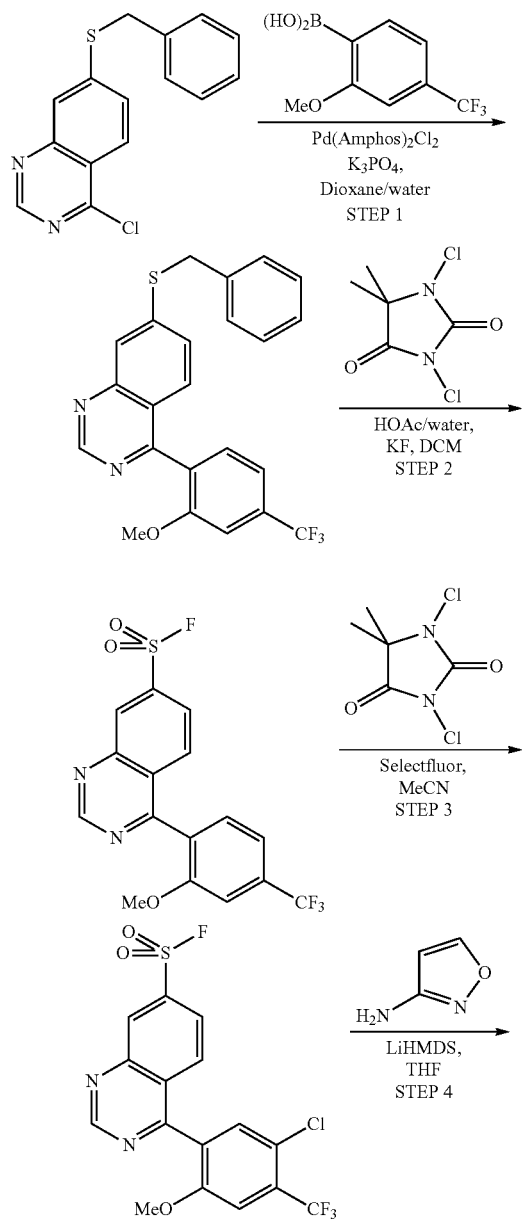

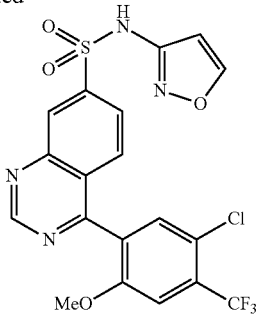

STEP 1: 7-(BENZYLTHIO)-4-(2-METHOXY-4-(TRIFLUOROMETHYL)PHENYL)-QUINAZOLINE

A solution of PdCl$_2$(Amphos)$_2$ (0.247 g, 0.349 mmol), (2-methoxy-4-(trifluoromethyl)phenyl)boronic acid (1.687 g, 7.67 mmol), 7-(benzylthio)-4-chloroquinazoline (2.000 g, 6.97 mmol, made via Method 15 Steps 1-2), and potassium phosphate (5.92 g, 27.9 mmol) in 15 mL dioxane and 5 mL water was heated to 70° C. for 30 minutes. The reaction mixture was diluted with DCM and washed with water. The organics were dried over MgSO$_4$ and concentrated. The crude residue was used in the next step without purification. m/z (ESI) 427.2 (M+H)$^+$.

STEP 2: 4-(2-METHOXY-4-(TRIFLUOROMETHYL)PHENYL)QUINAZOLINE-7-SULFONYL FLUORIDE

The crude residue from step one was dissolved in 20 mL DCM and was treated with 4 mL (1.5:1 HOAc/water) followed by 1,3-dichloro-5,5-dimethylimidazolidine-2,4-dione (2.75 g, 13.95 mmol). After stirring for one hour at room temperature, potassium fluoride (2.026 g, 34.9 mmol) was added, and the reaction mixture was allowed to stir for an additional hour. The reaction mixture was diluted with DCM and washed with water. The organics were dried over MgSO$_4$ and concentrated. The crude residue was used in the next step without purification. m/z (ESI) 387.0 (M+H)$^+$.

STEP 3: 4-(5-CHLORO-2-METHOXY-4-(TRIFLUOROMETHYL)PHENYL)-QUINAZOLINE-7-SULFONYL FLUORIDE

The crude residue from step two was dissolved in 20 mL MeCN, was treated with selectfluor (2.471 g, 6.97 mmol) and 1,3-dichloro-5,5-dimethylimidazolidine-2,4-dione (2.75 g, 13.95 mmol) and was heated to reflux for 4 hours. The reaction mixture was then diluted with DCM and washed with water. The organics were dried over MgSO4 and concentrated. Purification of the crude residue by silica gel column chromatography (0-30% EtOAc/heptane) gave 4-(5-chloro-2-methoxy-4-(trifluoromethyl)phenyl)quinazoline-7-sulfonyl fluoride (1.150 g, 2.73 mmol, 39.2% yield) as well as 4-(3-chloro-2-methoxy-4-(trifluoromethyl)phenyl)quinazoline-7-sulfonyl fluoride (0.323 g, 0.768 mmol, 11.01% yield). m/z (ESI) 420.9 (M+H)$^+$.

STEP 4: 4-(5-CHLORO-2-METHOXY-4-(TRIF-LUOROMETHYL)PHENYL)-N-(ISOXAZOL-3-YL)QUINAZOLINE-7-SULFONAMIDE

A solution of 4-(5-chloro-2-methoxy-4-(trifluoromethyl) phenyl)quinazoline-7-sulfonyl fluoride (0.650 g, 1.545 mmol) in 12 mL THF and was treated with 3-aminoisoxazole (0.571 ml, 7.72 mmol) followed by slow addition of LHMDS 1N in THF (7.72 ml, 7.72 mmol). After stirring for one hour, the reaction mixture was treated with hcl 4N in dioxane (4.63 ml, 18.54 mmol) and was concentrated. Purification of the crude residue by reverse phase column chromatography [Redisep Gold C18, 10-100% (0.1% NH4OH in MeOH)/(0.1% NH4OH in water)] gave 4-(5-chloro-2-methoxy-4-(trifluoromethyl)phenyl)-N-(isoxazol-3-yl)quinazoline-7-sulfonamide (0.521 g, 1.075 mmol, 69.6% yield). $^1$H NMR (ACETONITRILE-d3) δ: 9.44 (s, 1H), 8.55 (d, J=1.9 Hz, 1H), 8.30 (d, J=1.8 Hz, 1H), 7.98 (dd, J=8.8, 1.9 Hz, 1H), 7.83 (dd, J=8.9, 0.5 Hz, 1H), 7.62 (s, 1H), 7.54 (s, 1H), 6.44 (d, J=1.8 Hz, 1H), 3.75 (s, 3H). m/z (ESI) 485.0 (M+H)$^+$.

Example 60 (Method 60)

N-(ISOXAZOL-3-YL)-1-(2-METHOXY-5-METHYL-4-(TRIFLUOROMETHYL)PHENYL)ISOQUINOLINE-6-SULFONAMIDE

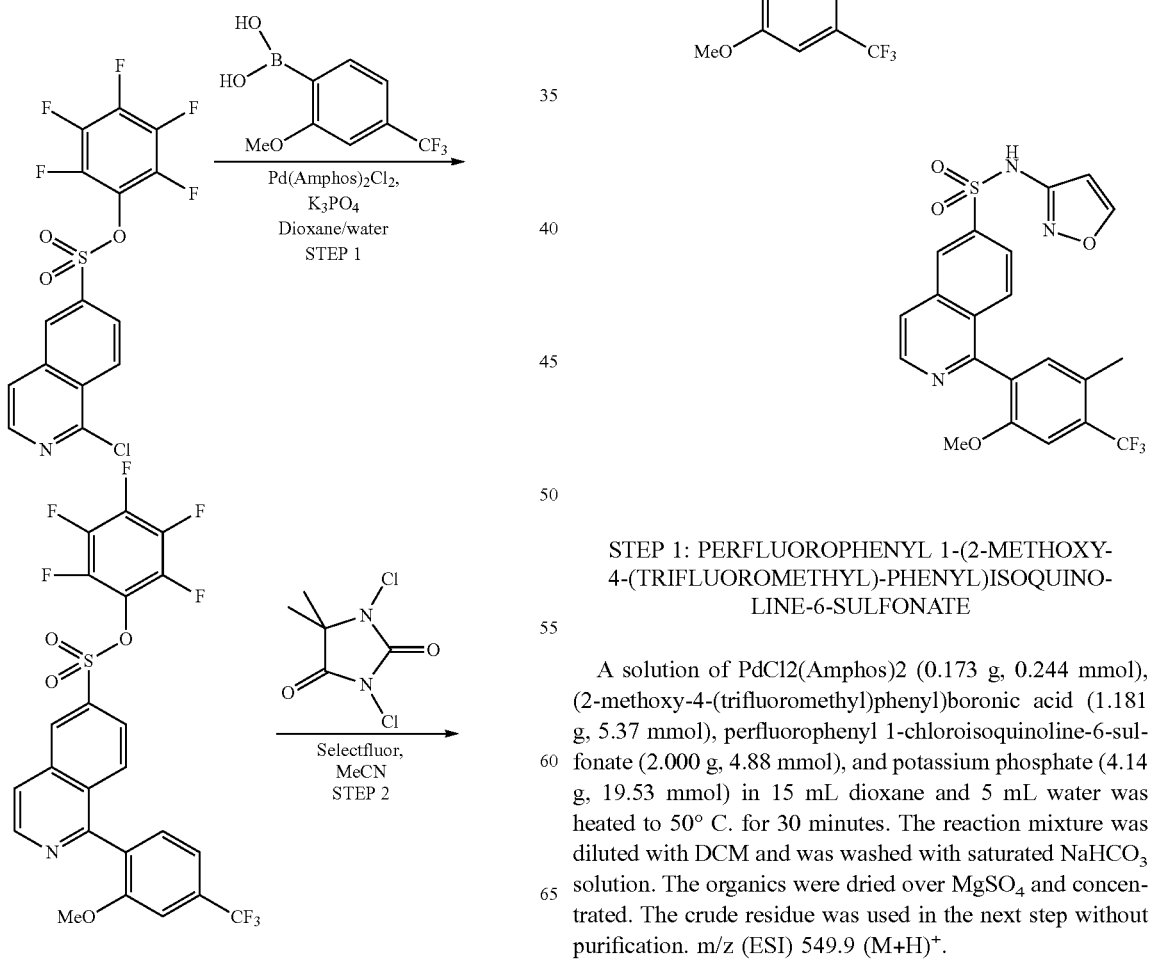

STEP 1: PERFLUOROPHENYL 1-(2-METHOXY-4-(TRIFLUOROMETHYL)-PHENYL)ISOQUINOLINE-6-SULFONATE

A solution of PdCl2(Amphos)2 (0.173 g, 0.244 mmol), (2-methoxy-4-(trifluoromethyl)phenyl)boronic acid (1.181 g, 5.37 mmol), perfluorophenyl 1-chloroisoquinoline-6-sulfonate (2.000 g, 4.88 mmol), and potassium phosphate (4.14 g, 19.53 mmol) in 15 mL dioxane and 5 mL water was heated to 50° C. for 30 minutes. The reaction mixture was diluted with DCM and was washed with saturated NaHCO3 solution. The organics were dried over MgSO4 and concentrated. The crude residue was used in the next step without purification. m/z (ESI) 549.9 (M+H)$^+$.

STEP 2: PERFLUOROPHENYL 1-(5-CHLORO-2-METHOXY-4-(TRIFLUOROMETHYL)PHENYL) ISOQUINOLINE-6-SULFONATE

The crude residue from step one was dissolved in 30 mL MeCN, was treated with selectfluor (3.46 g, 9.76 mmol) and 1,3-dichloro-5,5-dimethylimidazolidine-2,4-dione (1.923 g, 9.76 mmol), and was heated to 85° C. overnight. The reaction mixture was diluted with DCM and washed with saturated NaHCO$_3$ solution. The organics were dried over MgSO$_4$ and concentrated. The crude residue was used in the next step without purification. m/z (ESI) 584.1 (M+H)$^+$.

STEP 3: 1-(5-CHLORO-2-METHOXY-4-(TRIFLUOROMETHYL)PHENYL)-N-(ISOXAZOL-3-YL)ISOQUINOLINE-6-SULFONAMIDE

The crude residue from step two was dissolved in 30 mL THF, was treated with 3-aminoisoxazole (1.803 ml, 24.41 mmol), and was cooled to 0° C. LHMDS 1N in THF (24.41 ml, 24.41 mmol) was added, and the reaction mixture was allowed to stir for one hour. LC/MS showed mostly product so HCl 4N in dioxane (14.64 ml, 58.6 mmol) was added, and the reaction mixture was concentrated. Purification of the crude residue by reverse phase column chromatography [Redisep Gold C18, 10-100% (0.1% NH4OH in MeOH)/(0.1% NH$_4$OH in water)] gave 1-(5-chloro-2-methoxy-4-(trifluoromethyl)phenyl)-N-(isoxazol-3-yl)isoquinoline-6-sulfonamide (0.338 g, 0.699 mmol, 14.31% yield). $^1$H NMR (ACETONITRILE-d3) δ: 8.75 (d, J=5.7 Hz, 1H), 8.61 (d, J=1.9 Hz, 1H), 8.38 (d, J=1.8 Hz, 1H), 8.00 (dd, J=5.7, 0.6 Hz, 1H), 7.87-7.93 (m, 1H), 7.79-7.86 (m, 1H), 7.60 (s, 1H), 7.52 (s, 1H), 6.50 (d, J=1.8 Hz, 1H), 3.73 (s, 3H). m/z (ESI) 484.0 (M+H)$^+$.

STEP 4: N-(ISOXAZOL-3-YL)-1-(2-METHOXY-5-METHYL-4-(TRIFLUOROMETHYL)PHENYL) ISOQUINOLINE-6-SULFONAMIDE

A microwave vial charged with PdCl2(Amphos)2 (0.015 g, 0.021 mmol), methylboronic acid (0.025 g, 0.413 mmol), 1-(5-chloro-2-methoxy-4-(trifluoromethyl)phenyl)-N-(isoxazol-3-yl)isoquinoline-6-sulfonamide (0.100 g, 0.207 mmol), potassium phosphate (0.175 g, 0.827 mmol), 1.5 mL dioxane, and 0.5 mL water was heated to 150° C. in a Biotage Initiator microwave reactor for 30 minutes. The organic layer was separated, treated with hcl 4N in dioxane (0.207 ml, 0.827 mmol), and concentrated. Purification of the crude residue by reverse phase column chromatography [Puriflash C18, 10-100% (0.1% NH4OH in MeOH)/(0.1% NH$_4$OH in water)] gave N-(isoxazol-3-yl)-1-(2-methoxy-5-methyl-4-(trifluoromethyl)phenyl)isoquinoline-6-sulfonamide (0.044 g, 0.095 mmol, 45.9% yield). $^1$H NMR (ACETONITRILE-d3) δ: 8.72 (d, J=5.8 Hz, 1H), 8.58 (d, J=1.9 Hz, 1H), 8.37 (d, J=1.9 Hz, 1H), 7.95 (d, J=5.7 Hz, 1H), 7.88 (dd, J=8.9, 1.9 Hz, 1H), 7.73-7.81 (m, 1H), 7.37-7.42 (m, 1H), 7.32-7.37 (m, 1H), 6.48 (d, J=1.9 Hz, 1H), 3.69 (s, 3H), 2.47 (d, J=1.9 Hz, 3H). m/z (ESI) 464.0 (M+H)$^+$.

EXAMPLE 61 (Method 61)

4-(3',5'-DIFLUORO-5-METHOXY-2-METHYL-[1,1'-BIPHENYL]-4-YL)-N-(ISOXAZOL-3-YL)QUINAZOLINE-7-SULFONAMIDE

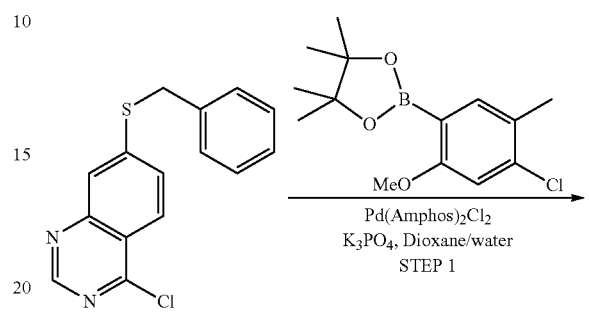

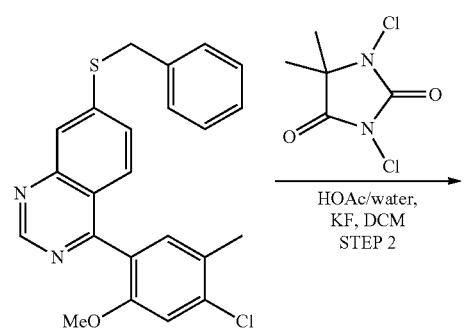

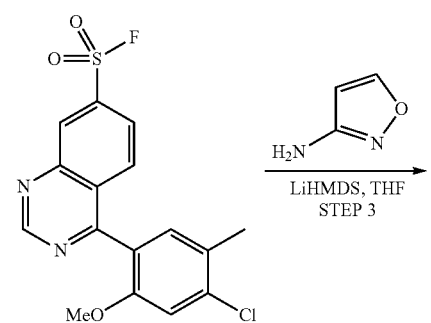

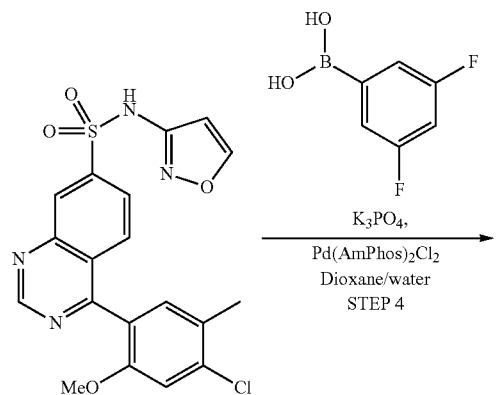

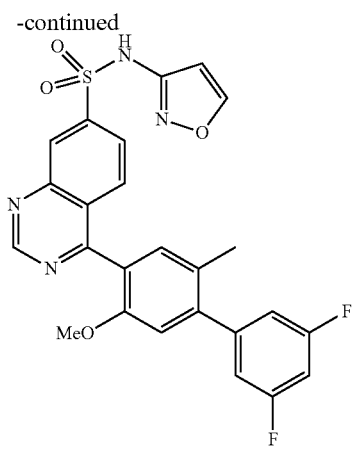

STEP 1: 7-(BENZYLTHIO)-4-(4-CHLORO-2-METHOXY-5-METHYLPHENYL)QUINAZOLINE

A solution of PdCl$_2$(Amphos)2 (0.185 g, 0.262 mmol), 2-(4-chloro-2-methoxy-5-methylphenyl)-4,4,5,5-tetramethyl-1,3,2-dioxaborolane (1.626 g, 5.75 mmol), 7-(benzylthio)-4-chloroquinazoline (1.500 g, 5.23 mmol, made via Method 15 Steps 1-2), and potassium phosphate (4.44 g, 20.92 mmol) in 18 mL dioxane 6 mL water was heated to 50° C. for 30 minutes. The organics were separated and concentrated. The crude residue was used in the next step without purification. m/z (ESI) 407.1 (M+H)$^+$.

STEP 2: 4-(4-CHLORO-2-METHOXY-5-METHYLPHENYL)QUINAZOLINE-7-SULFONYL FLUORIDE

The crude residue from step one was dissolved in 20 mL DCM, was treated with 3 mL (1.5:1 HOAc/water) followed by 1,3-dichloro-5,5-dimethylhydantoin (1.374 ml, 10.46 mmol). After stirring for 30 minutes, potassium fluoride (3.04 g, 52.3 mmol) was added. After stirring for an additional 30 minutes, the reaction mixture was diluted with DCM and was washed with saturated NaHCO$_3$ solution. The organics were dried over MgSO$_4$ and concentrated. The crude residue was used in the next step without purification. m/z (ESI) 366.9 (M+H)$^+$.

STEP 3: 4-(4-CHLORO-2-METHOXY-5-METHYLPHENYL)-N-(ISOXAZOL-3-YL)QUINAZOLINE-7-SULFONAMIDE

The crude residue from step two was dissolved in 20 mL THF and was treated with 3-aminoisoxazole (1.932 ml, 26.2 mmol) followed by slow addition of LHMDS 1N in THF (26.2 ml, 26.2 mmol). After stirring for one hour, the reaction mixture was treated with hcl 4N in dioxane (15.69 ml, 62.8 mmol) and was concentrated. Purification of the crude residue by reverse phase column chromatography [Redisep Gold C18, 10-100% (0.1% NH$_4$OH in MeOH)/ (0.1% NH$_4$OH in water)] gave 4-(4-chloro-2-methoxy-5-methylphenyl)-N-(isoxazol-3-yl)quinazoline-7-sulfonamide (2.473 g, 5.74 mmol, 110% yield) with minor impurities. $^1$H NMR (ACETONITRILE-d3) δ: 9.41 (s, 1H), 8.53 (s, 1H), 8.34 (s, 1H), 7.95 (d, J=9.4 Hz, 1H), 7.83-7.90 (m, 1H), 7.33 (s, 1H), 7.24 (s, 1H), 6.47 (s, 1H), 3.67 (s, 3H), 2.37 (s, 3H). m/z (ESI) 431.0 (M+H)$^+$.

STEP 4: 4-(3',5'-DIFLUORO-5-METHOXY-2-METHYL-[1,1'-BIPHENYL]-4-YL)-N-(ISOXAZOL-3-YL)QUINAZOLINE-7-SULFONAMIDE

A microwave vial charged with PdCl2(Amphos)2 (0.025 g, 0.035 mmol), Potassium phosphate (0.296 g, 1.393 mmol), (3,5-difluorophenyl)boronic acid (0.165 g, 1.044 mmol), 4-(4-chloro-2-methoxy-5-methylphenyl)-N-(isoxazol-3-yl)quinazoline-7-sulfonamide (0.150 g, 0.348 mmol), 1 mL dioxane 0.5 mL water was heated to 150° C. in a Biotage Initiator microwave reactor for 45 minutes. The reaction mixture was then separated and the organic layer was treated with HCl 4N in dioxane (0.35 mL, 1.393 mmol). The reaction mixture was then filtered through a 0.4 uM syringe filter and was concentrated. Purification of the crude residue was performed using the following conditions: PREP LC/MS-2 System Column: XBridge 19×100 mm 12230326114 03 Mobile phase: 0.1% NH4OH in water/ acetonitrile Flow rate: 40 ml/min Inj: 2000 uL. Gradient: 10 min 10-40%_LV_NH3; 10 min 20-50%_LV_NH3 yielding 4-(3',5'-difluoro-5-methoxy-2-methyl-[1,1'-biphenyl]-4-yl)-n-(isoxazol-3-yl)quinazoline-7-sulfonamide (0.020 g, 0.039 mmol, 11.3% yield). 1H NMR (500 MHz, DMSO-d6) δ: ppm 2.25 (s, 3 H) 3.70 (s, 3 H) 6.47 (s, 1 H) 7.13 (s, 1 H) 7.23-7.35 (m, 4 H) 7.39 (s, 1 H) 7.93 (d, J=8.82 Hz, 1 H) 8.03 (dd, J=8.76, 1.60 Hz, 1H) 8.47 (s, 1H) 8.67 (s, 1 H) 9.48 (s, 1 H). m/z (ESI) 509.0 (M+H)$^+$.

EXAMPLE 62 (Method 62)

1-(3',4'-DIFLUORO-5-METHOXY-2-METHYL-[1,1'-BIPHENYL]-4-YL)-N-(ISOXAZOL-3-YL)ISOQUINOLINE-6-SULFONAMIDE

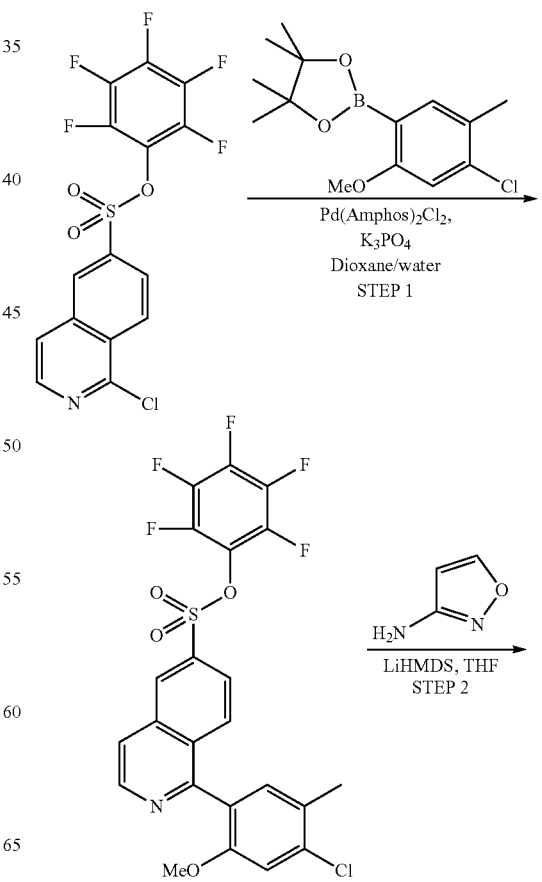

243

-continued

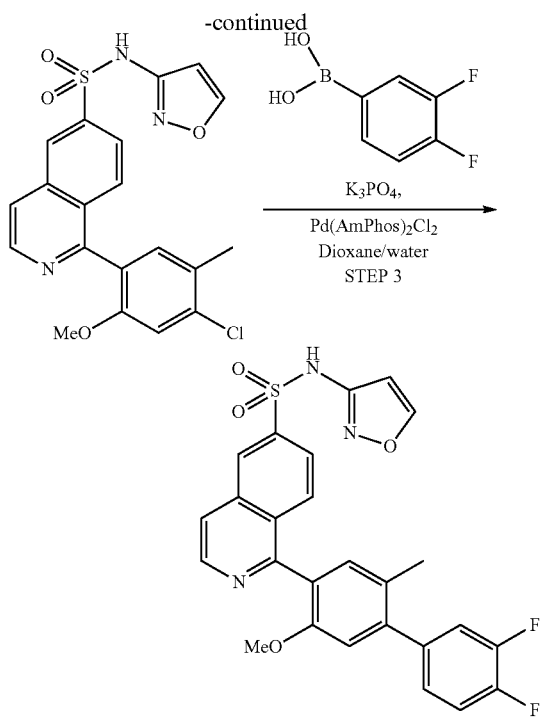

STEP 1: PERFLUOROPHENYL 1-(4-CHLORO-2-METHOXY-5-METHYLPHENYL)ISOQUINO-LINE-6-SULFONATE

A solution of PdCl₂(Amphos)2 (0.173 g, 0.244 mmol), 2-(4-chloro-2-methoxy-5-methylphenyl)-4,4,5,5-tetramethyl-1,3,2-dioxaborolane (1.517 g, 5.37 mmol), perfluorophenyl 1-chloroisoquinoline-6-sulfonate (2.000 g, 4.88 mmol), and potassium phosphate (4.14 g, 19.53 mmol) in 15 mL dioxane 5 mL water was heated to 50° C. for 30 minutes. The reaction mixture was diluted with DCM and was washed with saturated NaHCO₃ solution. The organics were dried over MgSO₄ and concentrated. The crude residue was used in the next step without purification. m/z (ESI) 530.1 (M+H)⁺.

STEP 2: 1-(4-CHLORO-2-METHOXY-5-METHYLPHENYL)-N-(ISOXAZOL-3-YL)ISOQUINO-LINE-6-SULFONAMIDE

The crude residue from step one was dissolved in 20 mL THF and was treated with 3-aminoisoxazole (1.803 ml, 24.41 mmol) followed by slow addition of LiHMDS 1N in THF (24.41 ml, 24.41 mmol). After stirring for one hour, the reaction mixture was treated with HCl 4N in dioxane (14.64 ml, 58.6 mmol) and was concentrated. Purification of the crude residue by reverse phase column chromatography [Redisep Gold C18, 10-100% (0.1% NH₄OH in MeOH)/(0.1% NH4OH in water)] gave 1-(4-chloro-2-methoxy-5-methylphenyl)-N-(isoxazol-3-yl)isoquinoline-6-sulfonamide (2.079 g, 4.84 mmol, 99% yield). ¹H NMR (ACETONITRILE-d3): 8.69 (d, J=5.8 Hz, 1H), 8.55 (d, J=1.9 Hz, 1H), 8.34 (d, J=1.9 Hz, 1H), 7.89-7.93 (m, 1H), 7.84-7.89 (m, 1H), 7.77-7.83 (m, 1H), 7.27 (d, J=0.6 Hz, 1H), 7.20 (s, 1H), 6.46 (d, J=1.8 Hz, 1H), 3.64 (s, 3H), 2.36 (s, 3H). m/z (ESI) 430.0 (M+H)⁺.

244

STEP 3: 1-(3',4'-DIFLUORO-5-METHOXY-2-METHYL-[1,1'-BIPHENYL]-4-YL)-N-(ISOX-AZOL-3-YL)ISOQUINOLINE-6-SULFONAMIDE

A microwave vial charged with PdCl₂(Amphos)2 (0.025 g, 0.035 mmol), (3,4-difluorophenyl)boronic acid (0.165 g, 1.044 mmol), 1-(4-chloro-2-methoxy-5-methylphenyl)-N-(isoxazol-3-yl)isoquinoline-6-sulfonamide (0.110 g, 0.256 mmol), potassium phosphate (0.295 g, 1.392 mmol), 1.5 mL dioxane, and 0.5 mL water was heated to 150° C. in a Biotage Initiator microwave reactor for 45 minutes. The reaction mixture was then separated and the organic layer was treated with HCl 4N in dioxane (0.35 mL, 1.393 mmol). The reaction mixture was then filtered through a 0.4 uM syringe filter and was concentrated. Purification of the crude residue was performed using the following conditions: PREP LC/MS-2 System Column: XBridge 19×100 mm 12230326114 03 Mobile phase: 0.1% NH₄OH in water/acetonitrile Flow rate: 40 ml/min Inj: 2000 uL. Gradient: 10 min 10-40%_LV_NH3 yielding 1-(3',4'-difluoro-5-methoxy-2-methyl-[1,1'-biphenyl]-4-yl)-n-(isoxazol-3-yl) isoquinoline-6-sulfonamide (0.014 g, 0.0276 mmol, 7.7% yield). ¹H NMR (DMSO-d₆) δ: 8.67-8.73 (m, 2H), 8.63 (s, 1H), 8.10 (d, J=5.7 Hz, 1H), 7.93 (dd, J=8.9, 1.7 Hz, 1H), 7.84 (d, J=8.9 Hz, 1H), 7.52-7.63 (m, 2H), 7.34 (br. s., 1H), 7.27 (s, 1H), 7.03-7.08 (m, 1H), 6.44-6.48 (m, 1H), 3.53-3.75 (m, 3H), 2.23 (s, 3H). m/z (ESI) 508.0 (M+H)⁺.

EXAMPLE 63 (Method 63)

4-(3'-CYCLOPROPYL-4'-FLUORO-5-METHOXY-2-METHYL-[1,1'-BIPHENYL]-4-YL)-N-(ISOX-AZOL-3-YL)QUINAZOLINE-7-SULFONAMIDE

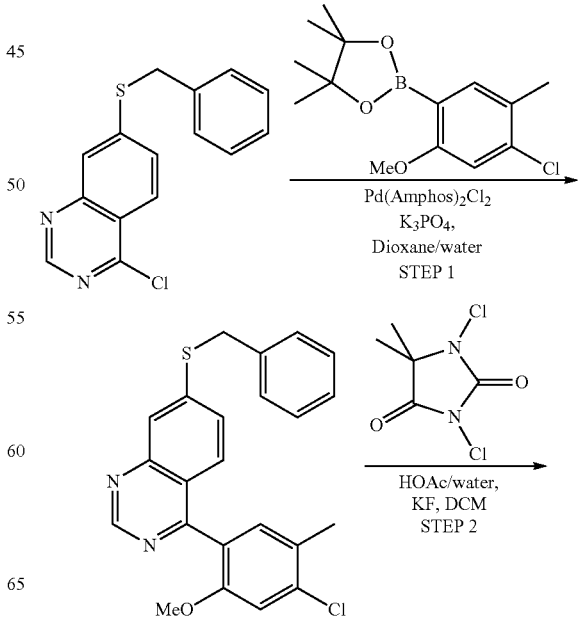

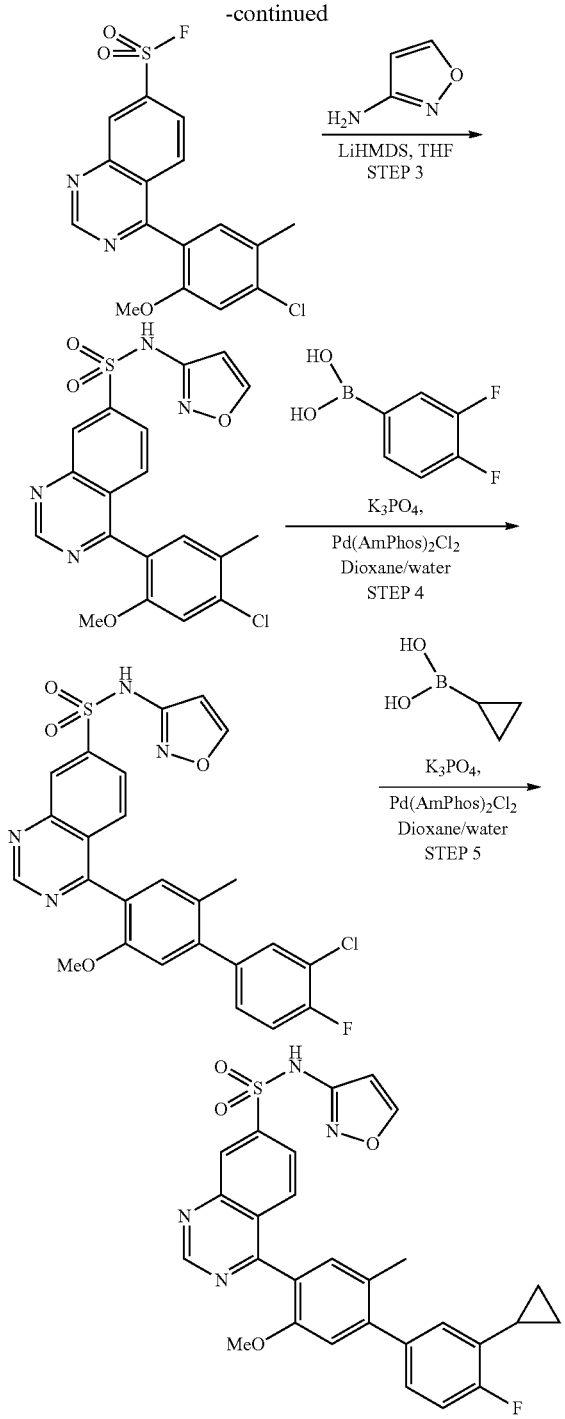

STEP 1: 7-(BENZYLTHIO)-4-(4-CHLORO-2-METHOXY-5-METHYLPHENYL)QUINAZOLINE

A solution of PdCl2(Amphos)2 (0.185 g, 0.262 mmol), 2-(4-chloro-2-methoxy-5-methylphenyl)-4,4,5,5-tetramethyl-1,3,2-dioxaborolane (1.626 g, 5.75 mmol), 7-(benzylthio)-4-chloroquinazoline (1.500 g, 5.23 mmol), and potassium phosphate (4.44 g, 20.92 mmol) in 18 mL dioxane 6 mL water was heated to 50° C. for 30 minutes. The organics were separated and concentrated. The crude residue was used in the next step without purification. m/z (ESI) 407.1 (M+H)$^+$.

STEP 2: 4-(4-CHLORO-2-METHOXY-5-METHYLPHENYL)QUINAZOLINE-7-SULFONYL FLUORIDE

The crude residue from step one was dissolved in 20 mL DCM, was treated with 3 mL (1.5:1 HOAc/water) followed by 1,3-dichloro-5,5-dimethylhydantoin (1.374 ml, 10.46 mmol). After stirring for 30 minutes, potassium fluoride (3.04 g, 52.3 mmol) was added. After stirring for an additional 30 minutes, the reaction mixture was diluted with DCM and was washed with saturated NaHCO$_3$ solution. The organics were dried over MgSO$_4$ and concentrated. The crude residue was used in the next step without purification. m/z (ESI) 366.9 (M+H)$^+$.

STEP 3: 4-(4-CHLORO-2-METHOXY-5-METHYLPHENYL)-N-(ISOXAZOL-3-YL)QUINAZOLINE-7-SULFONAMIDE

The crude residue from step two was dissolved in 20 mL THF and was treated with 3-aminoisoxazole (1.932 ml, 26.2 mmol) followed by slow addition of LiHMDS 1N in THF (26.2 ml, 26.2 mmol). After stirring for one hour, the reaction mixture was treated with HCl 4N in dioxane (15.69 ml, 62.8 mmol) and was concentrated. Purification of the crude residue by reverse phase column chromatography [Redisep Gold C18, 10-100% (0.1% NH$_4$OH in MeOH)/(0.1% NH4OH in water)] gave 4-(4-chloro-2-methoxy-5-methylphenyl)-N-(isoxazol-3-yl)quinazoline-7-sulfonamide (2.473 g, 5.74 mmol, 110% yield) with minor impurities. m/z (ESI) 431.0 (M+H)$^+$.

STEP 4: 4-(3'-CHLORO-4'-FLUORO-5-METHOXY-2-METHYL-[1,1'-BIPHENYL]-4-YL)-N-(ISOXAZOL-3-YL)QUINAZOLINE-7-SULFONAMIDE

A microwave vial charged with PdCl2(Amphos)2 (0.025 g, 0.035 mmol), (3-chloro-4-fluorophenyl)boronic acid (0.182 g, 1.044 mmol), 4-(4-chloro-2-methoxy-5-methylphenyl)-N-(isoxazol-3-yl)quinazoline-7-sulfonamide (0.150 g, 0.348 mmol), potassium phosphate (0.443 g, 2.089 mmol), and 1.5 mL dioxane and 0.5 mL water was heated to 165° C. in a Biotage Initiator microwave reactor for 90 minutes. The reaction mixture was then poured into water and extracted with 2-MeTHF. The organics were then concentrated. The crude residue was used in the next step without purification. m/z (ESI) 525.0 (M+H)$^+$.

STEP 5: 4-(3'-CYCLOPROPYL-4'-FLUORO-5-METHOXY-2-METHYL-[1,1'-BIPHENYL]-4-YL)-N-(ISOXAZOL-3-YL)QUINAZOLINE-7-SULFONAMIDE

The crude residue from step four, was dissolved in 2 mL dioxane and was transferred to a microwave vial charged with PdCl$_2$(Amphos)2 (0.025 g, 0.035 mmol), cyclopropylboronic acid (0.120 g, 1.393 mmol), potassium phosphate (0.443 g, 2.089 mmol), and 1 mL water. The reaction mixture was then heated to 165° C. in a Biotage Initiator microwave reactor for 30 minutes. The organic layer was then removed, treated with hcl 4N in dioxane (0.870 ml, 3.48 mmol), and was concentrated. Purification of the crude residue by reverse phase column chromatography [Puriflash C18, 10-100% (0.1% NH$_4$OH in MeOH)/(0.1% NH$_4$OH in water)] 4-(3'-cyclopropyl-4'-fluoro-5-methoxy-2-methyl-[1,1'-biphenyl]-4-yl)-N-(isoxazol-3-yl)quinazoline-7-sulfonamide (0.025 g, 0.047 mmol, 13.53% yield) with minor impurities. $^1$H NMR (ACETONITRILE-d3) δ: 9.39-9.43 (m, 1H), 8.53 (d, J=1.6 Hz, 1H), 8.32 (d, J=1.8 Hz, 1H), 7.96-8.01 (m, 1H), 7.88-7.93 (m, 1H), 7.31 (d, J=0.3 Hz, 1H), 7.20-7.27 (m, 1H), 7.12-7.20 (m, 1H), 6.98-7.07 (m, 2H), 6.46 (d, J=1.8 Hz, 1H), 3.65-3.69 (m, 3H), 2.21 (s, 3H), 2.10-2.19 (m, 1H), 0.97-1.07 (m, 2H), 0.77-0.84 (m, 2H). m/z (ESI) 531.0 (M+H)$^+$.

EXAMPLE 64 (Method 64)

5-(5-CYANO-6-(3,5-DIFLUOROPHENYL)-2-METHOXYPYRIDIN-3-YL)-N-(PYRIMIDIN-4-YL)NAPHTHALENE-2-SULFONAMIDE

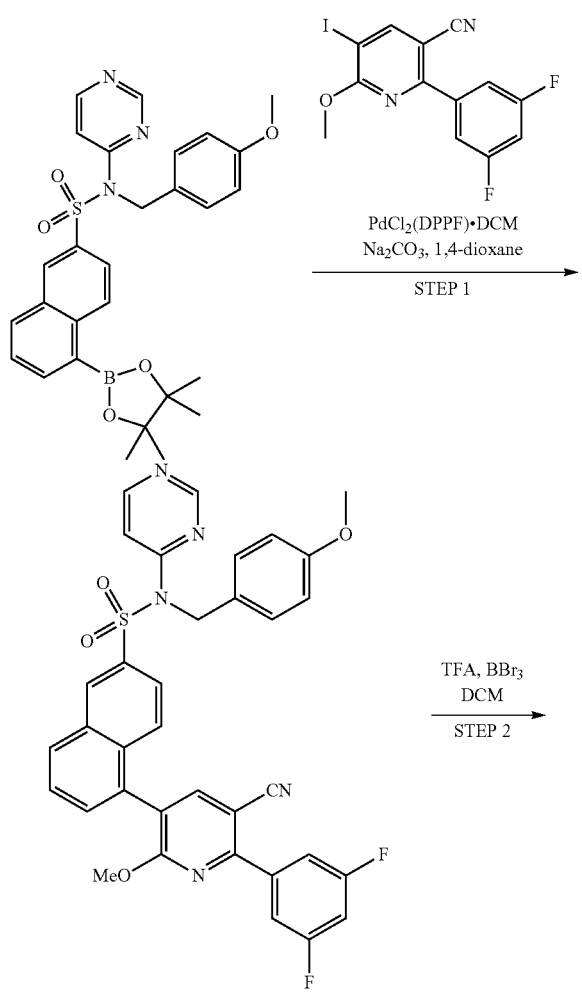

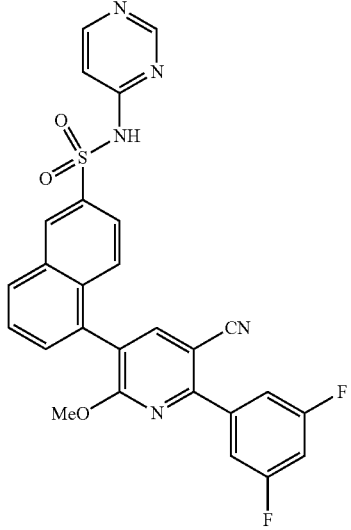

STEP-1: 5-(5-CYANO-6-(3,5-DIFLUOROPHE-NYL)-2-METHOXYPYRIDIN-3-YL)-N-(4-METHOXYBENZYL)-N-(PYRIMIDIN-4-YL) NAPHTHALENE-2-SULFONAMIDE

A vial was charged with N-(4-methoxybenzyl)-N-(pyrimidin-4-yl)-5-(4,4,5,5-tetramethyl-1,3,2-dioxaborolan-2-yl)naphthalene-2-sulfonamide (241 mg, 0.453 mmol), 2-(3,5-difluorophenyl)-5-iodo-6-methoxynicotinonitrile (202 mg, 0.544 mmol) and PdCl$_2$(DPPF)-DCM adduct (74.1 mg, 0.091 mmol). 1,4-Dioxane (2.27 mL) and t-butanol (2.27 mL) were added to the reaction vial followed by sodium carbonate in water (1.9 M) (716 μl, 1.36 mmol). The reaction vial was then swept with nitrogen and sealed with a screw cap. The whole was stirred and sonicated for 5 min. The resulting light red mixture was then heated to 50° C. After 1 h, LCMS showed a complete conversion of SM to product. The reaction was cooled to rt, filtered through a frit with an aid of DCM. The filtrate was dried over MgSO$_4$, filtered, and concentrated. The crude product was absorbed onto a plug of silica gel and purified by chromatography through a Redi-Sep pre-packed silica gel column (40 g), eluting with a gradient of 0% to 50% EtOAc in heptane, to provide 5-(5-cyano-6-(3,5-difluorophenyl)-2-methoxypyridin-3-yl)-N-(4-methoxybenzyl)-N-(pyrimidin-4-yl)naphthalene-2-sulfonamide (247 mg, 84% yield) as black solid. MS (ESI, positive ion) m/z; 650.2 (M+1). $^1$H NMR (500 MHz, DMSO-d$_6$) δ ppm 3.61-3.76 (m, 3H) 3.89-4.01 (m, 3 H) 5.30 (s, 2 H) 6.88 (m, J=8.76 Hz, 2 H) 7.29 (m, J=8.44 Hz, 2 H) 7.50-7.58 (m, 2 H) 7.64-7.87 (m, 6 H) 8.29 (d, J=8.87 Hz, 1 H) 8.40 (s, 1 H) 8.59 (d, J=5.88 Hz, 1 H) 8.75 (s, 1 H) 8.83 (s, 1 H).

STEP-2: 5-(5-CYANO-6-(3,5-DIFLUOROPHE-NYL)-2-METHOXYPYRIDIN-3-YL)-N-(PYRIMI-DIN-4-YL)NAPHTHALENE-2-SULFONAMIDE

To a solution of 5-(5-cyano-6-(3,5-difluorophenyl)-2-methoxypyridin-3-yl)-N-(4-methoxybenzyl)-N-(pyrimidin-4-yl)naphthalene-2-sulfonamide (230 mg, 0.354 mmol) in DCM (3.54 mL) was added TFA (136 μl, 1.770 mmol). The whole was stirred at rt. After 1 h, LCMS showed mainly starting material and a very small amount of product. 136 uL of TFA was added. After 1 h, LCMS showed mainly SM and a very small amount of product. Thus boron tribromide (1.0 M in DCM) (1.77 mL, 1.77 mmol) was added. The solution turned red immediately. After 5 min, LCMS showed mainly debenzylated product. The whole was diluted with 30 mL of DCM and cooled to 0° C. The reaction was quenched slowly with 15 mL of MeOH. After warming to rt, the whole was concentrated to afford an orange solid. The solid was triturated w a mixture of i-PrOH and heptane. Pink precipitates were collected with an aid of heptane. HPLC showed 88% pure. $^1$H NMR confirmed the product, 5-(5-cyano-6-(3,5-difluorophenyl)-2-methoxypyridin-3-yl)-N-(pyrimidin-4-yl)naphthalene-2-sulfonamide (161 mg, 0.304 mmol, 86% yield) and showed some impurities. A small amount of impure product was purified further by RPLC on the acidic Gilson. Fractions containing the product were combined and concentrated. White precipitate was collected with an aid of water and dried. MS (ESI, positive ion) m/z; 530.1 (M+1). $^1$H NMR (500 MHz, DMSO-$d_6$) δ ppm 3.92 (s, 3 H) 7.08 (br. s., 1 H) 7.54 (t, J=9.40 Hz, 1 H) 7.64-7.71 (m, 2 H) 7.71-7.82 (m, 3 H) 7.87 (d, J=7.43 Hz, 1 H) 8.30 (d, J=8.01 Hz, 2 H) 8.38 (s, 1 H) 8.59 (s, 1 H) 8.70 (s, 1 H).

Intermediates

Boronic Acids:

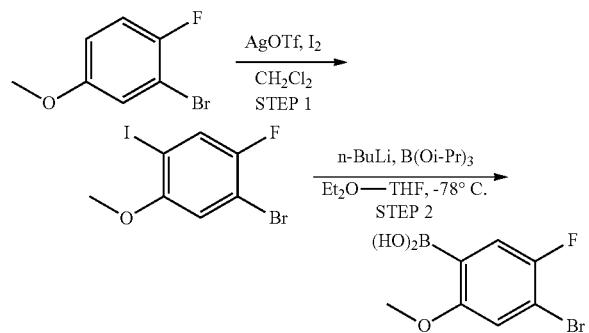

Intermediate A (4-BROMO-5-FLUORO-2-METHOXYPHENYL)BORONIC ACID

STEP 1: 1-BROMO-2-FLUORO-4-IODO-5-METHOXYBENZENE

A RBF was charged with 2-bromo-1-fluoro-4-methoxybenzene (4 g, 19.51 mmol) and DCM (78 ml) to give a clear solution. Silver trifluoromethanesulfonate (5.51 g, 21.46 mmol) and iodine (5.45 g, 21.46 mmol) were added in sequence. After 1.5 h, the mixture was filtered through celite with the aid of DCM. The filtrate was diluted with saturated aq. sodium bicarbonate solution leading to a messy mixture with solids. The aq. layer was extracted with DCM. The combined organic extracts were washed with saturated aq. sodium thiosulfate, which cleared up the mixture. The mixture was diluted with water to aid phase separation. The aq. layer was was extracted with DCM (1×), and the combined organic extracts were dried over sodium sulfate, filtered, and concentrated to give 6.40 g of a brown, crystalline solid. The crude product was purified by chromatography on silica gel (80-g Redi-Sep Gold column, 25-g silica gel loading column, 5-30% EtOAc/Heptane) to give 1-bromo-2-fluoro-4-iodo-5-methoxybenzene (5.767 g, 17.43 mmol, 89% yield) as an off-white solid. $^1$H NMR (400 MHz, DMSO-$d_6$) δ=7.83 (d, J=7.8 Hz, 1 H), 7.29 (d, J=6.0 Hz, 1 H), 3.83 (s, 3 H).

STEP 2: (4-BROMO-5-FLUORO-2-METHOXYPHENYL)BORONIC ACID

A RBF was charged with 1-bromo-2-fluoro-4-iodo-5-methoxybenzene (3.00 g, 9.07 mmol) and ether (21 mL) to give a clear solution. The flask was cooled in a dry ice-acetone bath for 10 min to give a suspension, then n-butyllithium (2.5M in hexanes) (4.35 ml, 10.88 mmol) was added dropwise. After 15 min, THF (10 mL) was added dropwise over 3 min, which resulted in a solution. An additional portion of n-BuL isolation (1 mL) was added. After 20 min, a 2N aq. sodium hydroxide solution (50 mL) was added, and the mixture was warmed to room temperature. The mixture was extracted with water (3×), and the combined aq. extracts were washed with ether (1×), then acidified with 6N aq. HCl (20 mL). The mixture was aged (with occasionally agitation) for 20 min, then filtered. The collected solid was washed with water (2×), the dried overnight under a stream of $N_2$ (g) to give (4-bromo-5-fluoro-2-methoxyphenyl)boronic acid (1.407 g, 5.65 mmol, 62.4% yield) as an off-white solid. The material appeared to be around 90% pure by NMR and was used without further purification. $^1$H NMR (400 MHz, DMSO-$d_6$) δ=7.93 (s, 2 H), 7.49-7.41 (m, 1 H), 7.35 (d, J=8.9 Hz, 1 H), 7.25 (d, J=5.3 Hz, 1 H), 3.79 (s, 3 H). m/z (ESI) 249.1 (M+H)$^+$.

Intermediate AM 2-(4-BROMO-5-CHLORO-2-METHOXYPHENYL)-4,4,5,5-TETRAMETHYL-1,3,2-DIOXABOROLANE

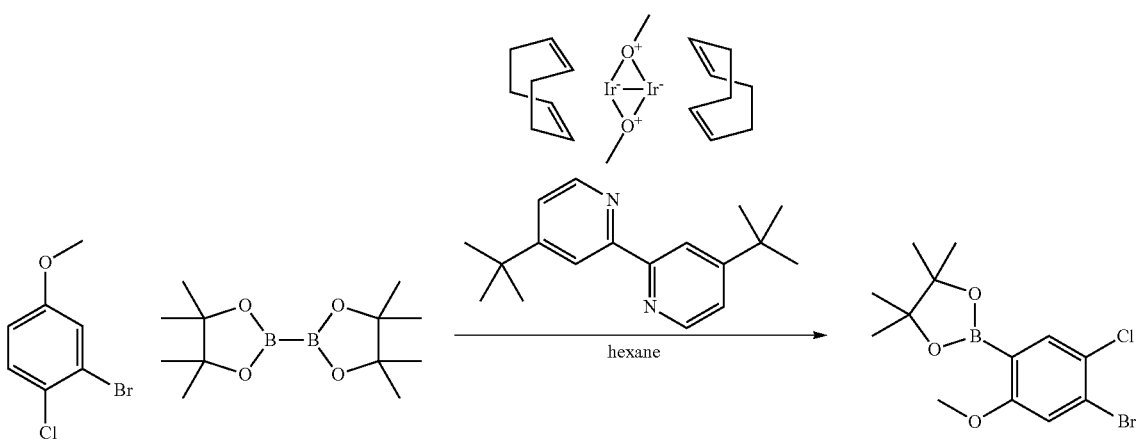

A RBF was charged with (1,5-cyclooctadiene)(methoxy)-iridium(i) dimer (0.056 g, 0.085 mmol), 4,4'-di-tert-butyl-2,2'-dipyridyl (0.045 g, 0.169 mmol), and bispinocolatodiboron (1.519 g, 5.98 mmol). The flask was flushed with Ar (g), then hexane (17.37 ml) was added. A reflux condenser was attached to the flask, and the flask was heated to 50° C. f for 20 min. 3-Bromo-4-chloroanisole (1.534 ml, 11.29 mmol) was added. After 1 hour of heating, an additional portion of bispinocolatodiboron (1.519 g, 5.98 mmol) was added. After another 20 min, additional portions of (1,5-cyclooctadiene)(methoxy)-iridium(i) dimer (0.056 g, 0.085 mmol) and 4,4'-di-tert-butyl-2,2'-dipyridyl (0.045 g, 0.169 mmol) were added. After 30 min, the heating was turned off and the mixture was allowed to cool to room temperature overnight with the bath. In the morning the mixture was diluted with water and EtOAc and stirred until bubbling had ceased. The layers were separated, and the aq. layer was extracted with EtOAc. The combined organic extracts were dried over sodium sulfate, filtered, and concentrated. The residue was purified by chromatography on silica gel (80-g Redi-Sep Gold column, 25-g silica gel column, 0-30% EtOAc/Heptane) to give 2-(4-bromo-5-chloro-2-methoxyphenyl)-4,4,5,5-tetramethyl-1,3,2-dioxaborolane (2.42 g) as a light-yellow, gummy solid. m/z (ESI) 347.0 (M+H)$^+$.

Intermediate AN

3',5'-DIFLUORO-4-METHOXY-5-(4,4,5,5-TETRAMETHYL-1,3,2-DIOXABOROLAN-2-YL)-[1,1'-BIPHENYL]-2-CARBONITRILE

STEP 1: 3',5'-DIFLUORO-4-METHOXY-[1,1'-BIPHENYL]-2-CARBONITRILE

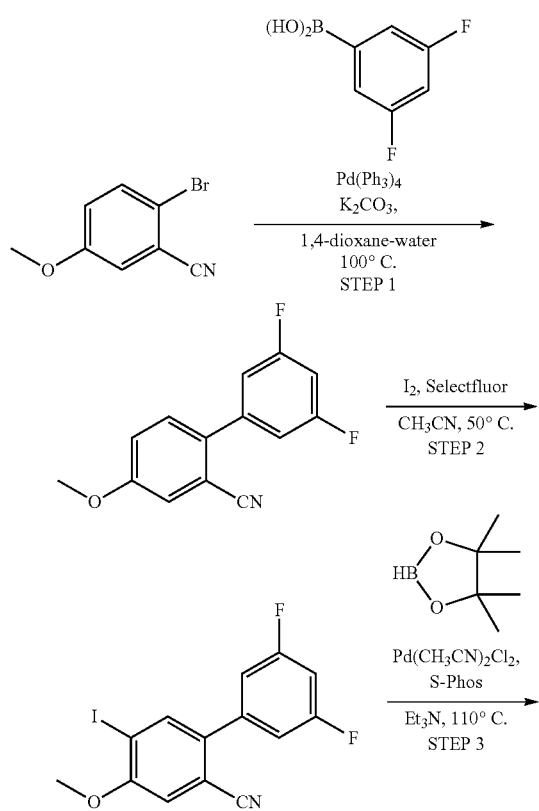

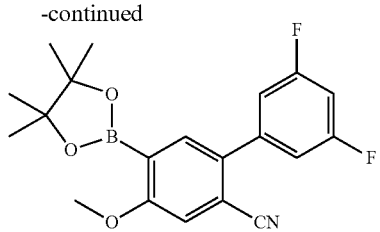

A RBF was charged with 2-bromo-5-methoxybenzonitrile (2.968 g, 14.00 mmol), (3,5-difluorophenyl)boronic acid (2.431 g, 15.40 mmol), potassium carbonate (5.80 g, 42.0 mmol), and Pd(Ph$_3$P)$_4$ (0.809 g, 0.700 mmol). The flask was flushed with Ar (g), then 1,4-dioxane (22.40 ml) and water (5.60 ml) were added in sequence. A reflux condenser was attached, and the flask was heated to 90° C. overnight. An additional portion of boronic acid (ca. 1 g) was added, and the heat was raised to 110° C. by for 6 h. The mixture was cooled, then diluted with water and EtOAc. A solid persisted in the organic layer. The layers were separated, and the aq. layer was extracted with EtOAc (1×), and the combined organic extracts were dried over sodium sulfate, filtered, and concentrated. The residue was taken up in DCM and filtered. The filter pad was washed with DCM (3×). The residue was concentrated. The residue was dissolved in warm DCM, and the resulting solution was purified by chromatography on silica gel (100-g SNAP Ultra column, 25-g silica gel loading column, 0-50% EtOAc/Heptane containing 10% DCM). Fractions containing product were combined and concentrated. The residue was taken up in heptane and filtered. The collected solid was washed with heptane (2×) and dried under a stream of N$_2$ (g) to give 3',5'-difluoro-4-methoxy-[1,1'-biphenyl]-2-carbonitrile (2.745 g, 11.19 mmol, 80% yield) as a flaky, white solid. $^1$H NMR (400 MHz, DMSO-d$_6$)=7.64-7.53 (m, 2 H), 7.42-7.22 (m, 4 H), 3.87 (s, 3 H). m/z (ESI) 246.1 (M+H)$^+$.

STEP 2: 3',5'-DIFLUORO-5-IODO-4-METHOXY-[1,1'-BIPHENYL]-2-CARBONITRILE

A RBF was charged with 3',5'-difluoro-4-methoxy-[1,1'-biphenyl]-2-carbonitrile (2.7422 g, 11.18 mmol), acetonitrile (74.5 ml), iodine (1.561 g, 6.15 mmol), and SelectFluor (3.96 g, 11.18 mmol) to give a thick suspension. The flask was fitted with a reflux condenser and heated in a 50° C. for 4 h. The mixture was cooled to room temperature, then was filtered though celite with the aid of EtOAc. The filtrate was washed with saturated aq. sodium bicarbonate solution, washed with saturated aq. sodium thiosulfate solution, dried over sodium sulfate, filtered, and concentrated. The mixture was taken up in boiling THF-MeOH, then cooled to give a fine suspension. The mixture was loaded onto a 100-g Ultra SNAP column with the aid of THF. The column was dried under vacuum. The column was then eluted with 0-40% EtOAc/Heptane with 10% DCM to give a solid. The solid was dissolved in boiling EtOAc to give an amber colored solution. This solution was cooled and aged overnight resulting in the formation of small, white crystals. The mixture was filtered, and the collected solid was washed with ice-cold EtOAc (1×) and dried under a stream of N$_2$ (g) to give 3',5'-difluoro-5-iodo-4-methoxy-[1,1'-biphenyl]-2-carbonitrile as an off-white crystalline solid. $^1$H NMR (400 MHz, DMSO-d$_6$)=7.62 (d, J=8.6 Hz, 1 H), 7.43-7.26 (m, 4 H), 3.95 (br. s., 3 H). m/z (ESI) 394.0 (M+Na)$^+$.

STEP 3: 3',5'-DIFLUORO-4-METHOXY-5-(4,4,5, 5-TETRAMETHYL-1,3,2-DIOXABOROLAN-2-YL)-[1,1'-BIPHENYL]-2-CARBONITRILE

A vial was charged with 3',5'-difluoro-5-iodo-4-methoxy-[1,1'-biphenyl]-2-carbonitrile (456 mg, 1.229 mmol), dicyclohexyl(2',6'-dimethoxy-[1,1'-biphenyl]-2-yl)phosphine (40.4 mg, 0.098 mmol), and bis(acetonitrile)dichloropalladium(ii) (6.38 mg, 0.025 mmol). The vial was flushed with Ar (g), then 1,4-dioxane (30720, triethylamine (514 µl, 3.69 mmol), and 4,4,5,5-tetramethyl-1,3,2-dioxaborolane (1M in THF) (1843 µl, 1.843 mmol). The vial was sealed and placed in a 110° C. heating bath for 30 min. The mixture was cooled to room temperature, diluted with EtOAc, combined with the reaction above, and filtered through celite. The filtrate was concentrated, and the residue was purified by chromatography on silica gel (50-g Ultra SNAP column, 0-40% EtOAc/Heptane with 10% DCM) to give 3',5'-difluoro-4-methoxy-5-(4,4,5,5-tetramethyl-1,3,2-dioxaborolan-2-yl)-[1,1'-biphenyl]-2-carbonitrile (356.4 mg, 0.960 mmol, 78% yield) as an off-white solid. $^1$H NMR (400 MHz, DMSO-$d_6$) δ=7.66 (d, J=8.7 Hz, 1 H), 7.42 (d, J=8.8 Hz, 1 H), 7.39-7.25 (m, 3 H), 3.85 (s, 3 H), 1.34 (s, 12 H).

Intermediate AO

(6-CHLORO-3'-FLUORO-4-METHOXY-[1,1'-BIPHENYL]-3-YL)BORONIC ACID

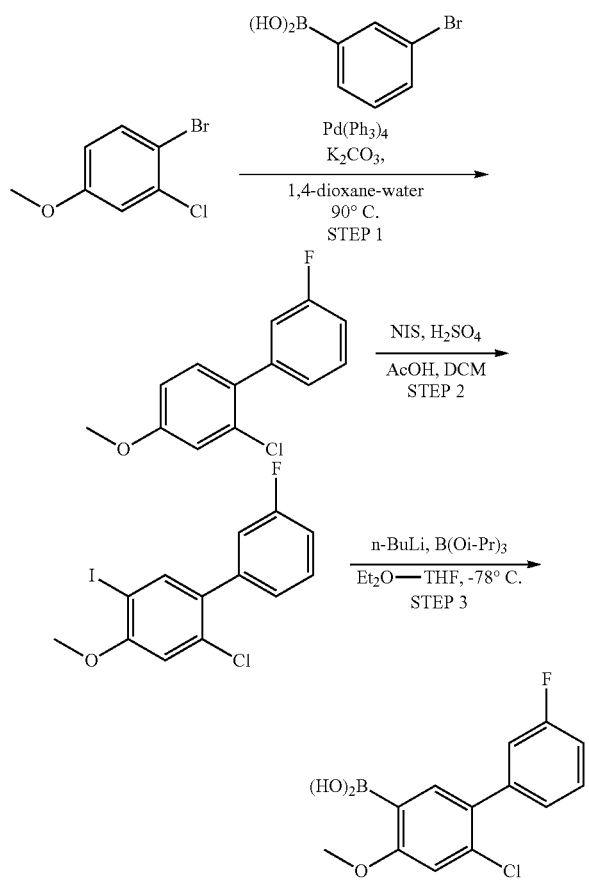

STEP 1: 2-CHLORO-3'-FLUORO-4-METHOXY-1,1'-BIPHENYL

A RBF was charged with 1-bromo-2-chloro-4-methoxybenzene (2.623 g, 11.84 mmol, Oakwood), (3-fluorophenyl)boronic acid (1.989 g, 14.21 mmol), potassium carbonate (4.91 g, 35.5 mmol), and tetrakis (0.684 g, 0.592 mmol). The flask was flushed with Ar (g), then 1,4-dioxane (31.6 ml) and water (7.90 ml) were added. A reflux condenser was attached, and the flask was lowered into a 90° C. heating bath. After 2 hrs, the LCMS showed about 85-90% conversion to another material, although there were a few other peaks present. TLC appeared similar. The mixture was cooled, then extracted with EtOAc. The organic layer was dried over sodium sulfate, filtered, and concentrated. The residue was purified by chromatography on silica gel (100-g Ultra SNAP column, 25-g silica gel loading column, 0-5% MeOH/DCM). Fractions containing product were combined and concentrated to give 2.83 g of a clear oil. By NMR, this material was a 4:1 mixture of the title compound to the starting material. The material was used in the next step without further purification.

STEP 2: 2-CHLORO-3'-FLUORO-5-IODO-4-METHOXY-1,1'-BIPHENYL

A RBF was charged with 2-chloro-3'-fluoro-4-methoxy-1,1'-biphenyl (2.83 g, 10.76 mmol) DCM (15.83 ml), AcOH (15.83 ml), and sulfuric acid (0.316 ml, 5.92 mmol) to give a clear solution. N-Iodosuccinimide (2.421 g, 10.76 mmol) was added in one portion to give a maroon-colored solution. After 5 hr of stirring, the mixture was diluted with DCM and some saturated aq. sodium bicarbonate solution, then washed with water, washed with saturated aq. sodium thiosulfate, dried over sodium sulfate, filtered, and concentrated. The residue was purified by chromatography on silica gel (100-g Ultra SNAP column, 25-g silica gel column, 0-10% EtOAc/Heptane with 5% DCM) to give 2-chloro-3'-fluoro-5-iodo-4-methoxy-1,1'-biphenyl (2.474 g, 6.82 mmol, 63.4% yield) as a clear oil. $^1$H NMR (400 MHz, DMSO-$d_6$)=7.79 (s, 1 H), 7.54-7.39 (m, 1 H), 7.31-7.14 (m, 4 H), 3.90 (s, 3 H). m/z (ESI) 362.9 (M+H)$^+$.

STEP 3: (6-CHLORO-3'-FLUORO-4-METHOXY-[1,1'-BIPHENYL]-3-YL)BORONIC ACID

A RBF was charged with 2-chloro-3'-fluoro-5-iodo-4-methoxy-1,1'-biphenyl (2.474 g, 6.82 mmol), triisopropyl borate (2.060 ml, 8.87 mmol), and THF (34.1 ml). The flask was cooled in a dry ice-acetone bath for 10 min, then n-butyllithium (2.5 M in hexane) (3.55 ml, 8.87 mmol) was added dropwise over 1 min. Following 40 min of stirring, the cooling bath was removed. After 15 min, a solution of 2N aq. NaOH (30 mL) was added. The resulting biphasic mixture was stirred for 20 min, then partitioned between water and ether. The layers were separated, and the ethereal layer was extracted with water (2x). The combined aq. extracts were washed with ether. The combined aq. layers were acidified with 3N aq. HCl (60 mL) to give a slurry. After 5 min, the slurry was filtered, and the collected solid was washed with water (2x), then dried under a stream of N$_2$ (g) for 1 h to give (6-chloro-3'-fluoro-4-methoxy-[1,1'-biphenyl]-3-yl)boronic acid (1.23 g, 4.39 mmol, 64.3% yield) as a white solid. m/z (ESI) 281.1 (M+H)$^+$.

Intermediate AP

(3',5'-DIFLUORO-3-METHOXY-[1,1'-BIPHENYL]-4-YL)BORONIC ACID

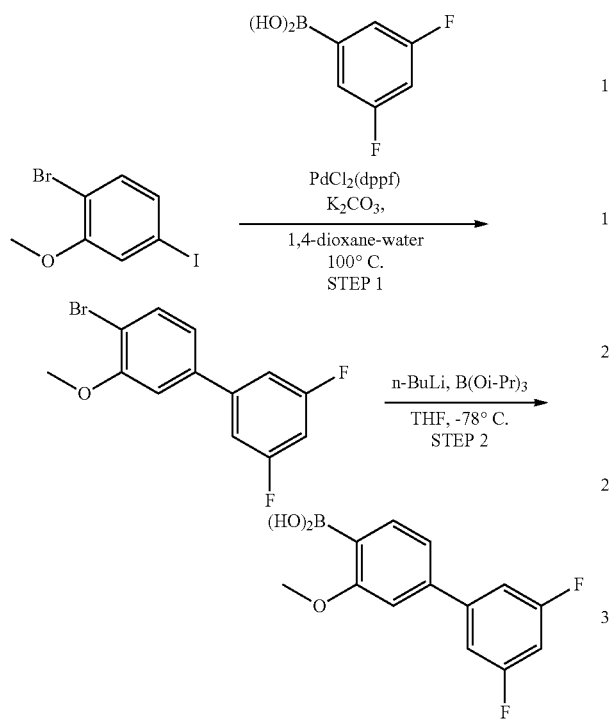

STEP 1: 4-BROMO-3',5'-DIFLUORO-3-METHOXY-1,1'-BIPHENYL

A RBF was charged with 1-bromo-4-iodo-2-methoxybenzene (6.25 g, 19.97 mmol, Combi-Blocks), (3,5-difluorophenyl)boronic acid (3.47 g, 21.97 mmol), potassium carbonate (8.28 g, 59.9 mmol), and PdCl$_2$(dppf)-CH$_2$Cl$_2$ (0.816 g, 0.999 mmol). The flask was flushed with Ar (g), then 1,4-dioxane (30.0 ml) and water (9.99 ml) were added in sequence. The mixture was stirred for 4 h, then diluted with water. The diluted mixture was extracted with EtOAc (3×), and the combined organic extracts were dried over sodium sulfate, filtered, and concentrated. The residue was taken up in DCM and loaded onto a pre-equilibrated 340-g SNAP Ultra column. The column was eluted with 0-10% EtOAc/Heptane containing 5% DCM. Fractions containing the desired product were combined and concentrated. The residue was taken up in heptane and filtered. The collected solid was washed with heptane (3×), then dried under a stream of N$_2$ (g). The process was repeated with the filtrate to give a second crop of material. The two crops were dried under vacuum to give 4-bromo-3',5'-difluoro-3-methoxy-1,1'-biphenyl (5.18 g) as a white solid. $^1$H NMR (400 MHz, DMSO-d$_6$) δ=7.66 (d, J=8.2 Hz, 1 H), 7.58-7.49 (m, 2 H), 7.40 (d, J=1.9 Hz, 1 H), 7.33-7.20 (m, 2 H), 3.96 (s, 3H). m/z (ESI) 301.1.

STEP 2: (3',5'-DIFLUORO-3-METHOXY-[1,1'-BIPHENYL]-4-YL)BORONIC ACID

A RBF was charged with 4-bromo-3',5'-difluoro-3-methoxy-1,1'-biphenyl (5.147 g, 17.21 mmol), triisopropyl borate (4.79 ml, 20.65 mmol), and THF (57.4 ml). The flask was cooled in a dry ice-acetone bath for 10 min, then n-butyllithium (2.5 M in hexane) (8.26 ml, 20.65 mmol) was added dropwise over 1 min. After 20 min, the flask was lowered into an ice-water bath. After another 10 min, a 2N aq. NaOH solution was added, the cooling bath was removed, and the mixture was stirred vigorously for 20 min. The mixture was diluted with water and ether. The layers were separated, and the ethereal layer was extracted with water. The combined aq. layers were then acidified with 6N aq. HCl (50 mL). The mixture was filtered, and the collected solid was dried under a stream of N$_2$ (g), for 2 h to give ca. 3.14 g of a white solid. The filtrate was extracted with DCM (3×), and the combined organic extracts were dried over sodium sulfate, filtered, and concentrated to give an additional 260 mg of a white solid. The solids were combined to give (3',5'-difluoro-3-methoxy-[1,1'-biphenyl]-4-yl)boronic acid (3.40 g, 12.88 mmol, 74.8% yield) as a white solid. m/z (ESI) 265.1 (M+H)$^+$.

Intermediate AQ

2-((3'-FLUORO-4-(4,4,5,5-TETRAMETHYL-1,3,2-DIOXABOROLAN-2-YL)-[1,1'-BIPHENYL]-3-YL)OXY)ACETONITRILE

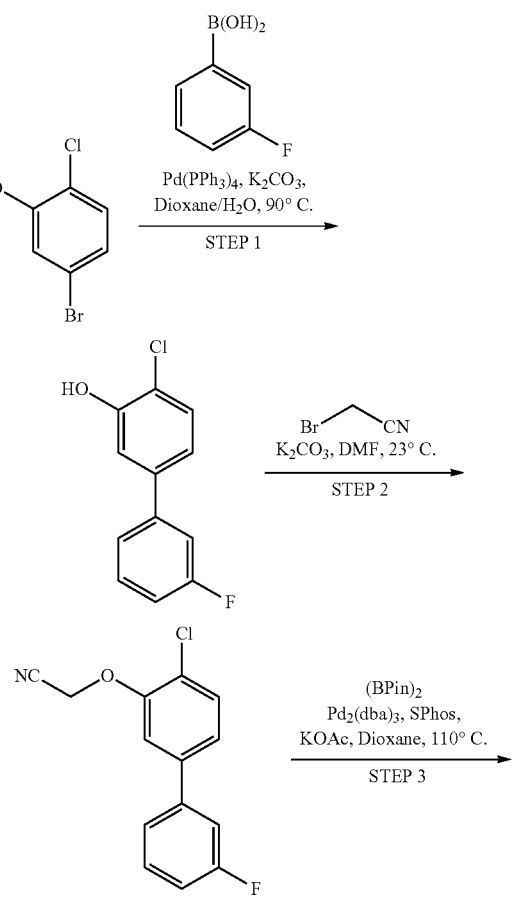

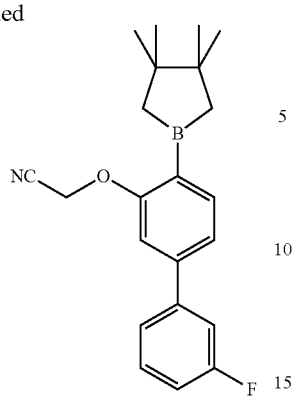

STEP 1: 4-CHLORO-3'-FLUORO-[1,1'-BIPHENYL]-3-OL

A microwave vial was charged with 5-bromo-2-chlorophenol (1 g, 4.82 mmol), (3-fluorophenyl)boronic acid (0.742 g, 5.30 mmol), tetrakis(triphenylphosphine)palladium(0) (0.279 g, 0.241 mmol), and potassium carbonate (1.999 g, 14.46 mmol). Dioxane (18.08 ml) and Water (6.03 ml) were added, the vial was flushed with argon and sealed, and heated in a microwave initiator at 90° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 0-50% EtOAc:Heptane) to afford 4-chloro-3'-fluoro-[1,1'-biphenyl]-3-ol (0.873 g, 3.92 mmol, 81% yield) as a clear colorless oil. m/z (ESI) 223.1 (M+H)$^+$.

STEP 2: 2-((4-CHLORO-3'-FLUORO-[1,1'-BIPHENYL]-3-YL)OXY)ACETONITRILE

4-Chloro-3'-fluoro-[1,1'-biphenyl]-3-ol (0.873 g, 3.92 mmol) was dissolved in DMF (7.84 ml) and potassium carbonate (0.542 g, 3.92 mmol) was added, followed by bromoacetonitrile (0.300 ml, 4.31 mmol). The reaction was stirred overnight at room temperature. The reaction was diluted with ethyl acetate and washed with water. The aqueous layer was extracted with ethyl acetate, and the combined organic layers were dried with sodium sulfate, filtered, and concentrated to afford 2-((4-chloro-3'-fluoro-[1,1'-biphenyl]-3-yl)oxy)acetonitrile (0.990 g, 3.78 mmol, 96% yield) as a white solid. m/z (ESI) 263.0 (M+H)$^+$.

STEP 3: 2-((3'-FLUORO-4-(4,4,5,5-TETRAMETHYL-1,3,2-DIOXABOROLAN-2-YL)-[1,1'-BIPHENYL]-3-YL)OXY)ACETONITRILE

A RBF was charged with 2-((4-chloro-3'-fluoro-[1,1'-biphenyl]-3-yl)oxy)acetonitrile (0.905 g, 3.46 mmol), Pd$_2$(dba)$_3$ (0.317 g, 0.346 mmol), SPhos (0.568 g, 1.383 mmol), bis(pinacolato)diboron (1.756 g, 6.92 mmol), and potassium acetate (1.358 g, 13.83 mmol). 1,4-dioxane (17.29 ml) was added, the flask was fitted with a reflux condenser, and the reaction was heated at 110° C. for four hours. The reaction was filtered through a pad of Celite and washed thoroughly with ethyl acetate. The filtrate was concentrated and the material was purified via column chromatography (RediSep Gold 40 g, gradient elution 0-25% EtOAc:Heptane) to afford 2-((3'-fluoro-4-(4,4,5,5-tetramethyl-1,3,2-dioxaborolan-2-yl)-[1,1'-biphenyl]-3-yl)oxy)acetonitrile (0.889 g, 2.52 mmol, 72.8% yield) as an orange oil. m/z (ESI) 354.2 (M+H)$^+$.

Intermediate AR

POTASSIUM TRIFLUORO(6-FLUOROPYRIDIN-2-YL)BORATE

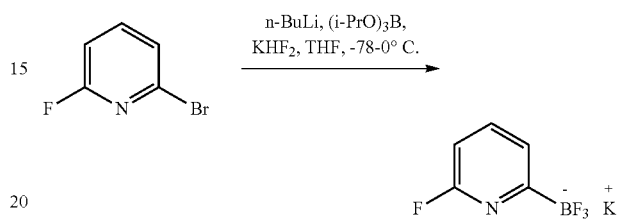

A 250 mL three-necked RBF was charged with 2-bromo-6-fluoropyridine (2.0 g, 11.36 mmol) and fitted with an addition funnel. The flask was evacuated and backfilled with nitrogen three times, then THF (56.8 ml) was added and the reaction was cooled to −78° C. Triisopropyl borate (2.90 ml, 12.50 mmol) was added, then the addition funnel was charged with n-butyllithium (2.5M in hexanes) (5.45 ml, 13.64 mmol). The solution of butyllithium was added slowly dropwise over 2 hours. The reaction was stirred for 3 hours at −78° C. then allowed to warm to room temperature overnight. The reaction was cooled to 0° C. Potassium hydrogen fluoride (2.66 g, 34.1 mmol) was dissolved in 10 mL of water and added dropwise to the reaction, which was stirred overnight. The reaction was concentrated, dissolved in methanol, and filtered. The solids were washed with methanol, and the filtrate was concentrated and put on high vacuum to remove as much residual water as possible. The solids were washed with acetone, filtered, and vacuum dried to afford potassium trifluoro(6-fluoropyridin-2-yl)borate (2.06 g, 10.15 mmol, 89% yield) as a white solid. 1 H NMR (400 MHz, DMSO-d6) δ=7.61-7.53 (m, 4 H), 7.23 (dd, J=3.8, 7.2 Hz, 1 H), 6.63 (dd, J=2.8, 8.0 Hz, 1 H).

Intermediate H

(2-CHLORO-3',5'-DIFLUORO-5-METHOXY-[1,1'-BIPHENYL]-4-YL)BORONIC ACID

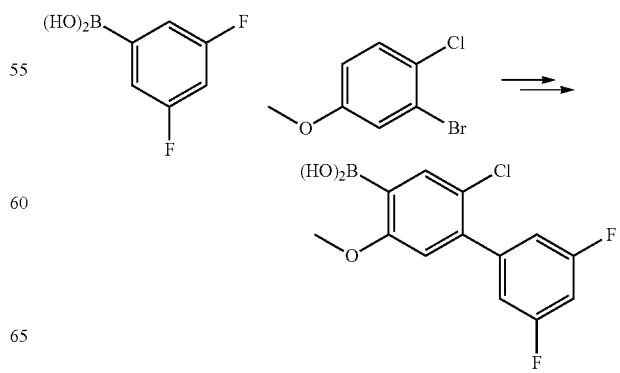

The title compound was prepared in an analogous manner to that of 6-chloro-3'-fluoro-4-methoxy-[1,1'-biphenyl]-3-yl)boronic acid except that 2(3,5-difluorophenyl)boronic acid and 3-bromo-4-chloroanisole were used as the coupling partners in Step 1 to afford (2-chloro-3',5'-difluoro-5-methoxy-[1,1'-biphenyl]-4-yl)boronic acid as a white solid. m/z (ESI) 298.1 (M+H)⁺.

Intermediate I (5,6-DICHLORO-2-METHOXYPYRIDIN-3-YL)BORONIC ACID

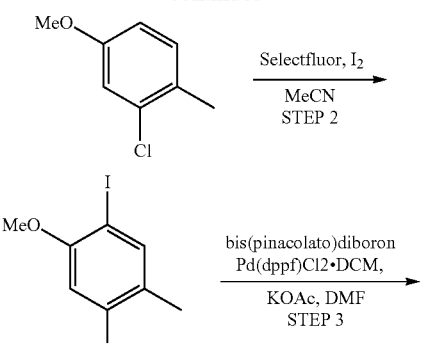

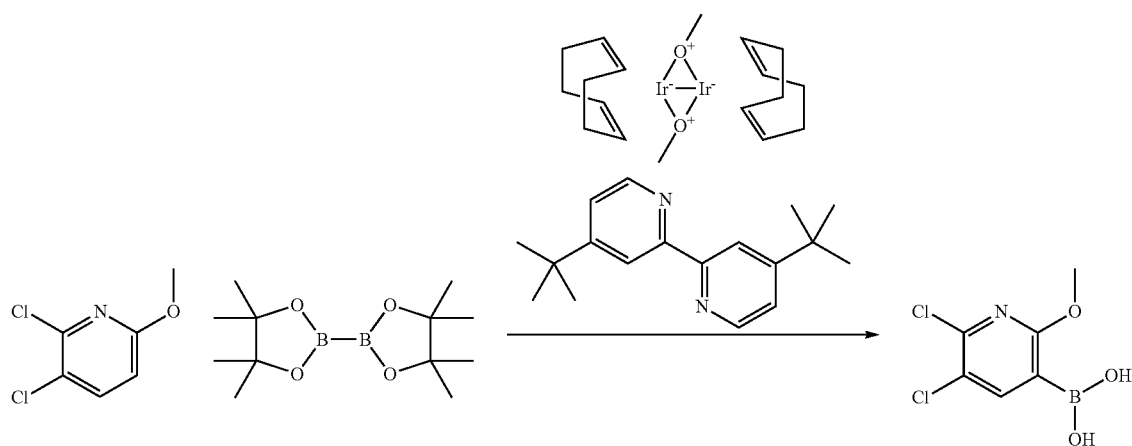

To a RBF was added (1,5-cyclooctadiene)(methoxy)-iridium(i) dimer (0.223 g, 0.337 mmol), 4,4-di-tert-butyl-2,2-dipyridyl (0.181 g, 0.674 mmol) and bis(pinacolato)diboron (2.85 g, 11.23 mmol) in heptane (112 ml). The reaction mixture was vacuumed and refilled with dry nitrogen. After stirring for 10 min, 2,3-dichloro-6-methoxypyridine (2.0 g, 11.23 mmol) was added. The resulting reaction mixture was stirred at room temperature overnight. The reaction was diluted with ethyl acetate and washed twice with 1N HCl solution. The organic layer was extracted twice with 1N sodium hydroxide solution, and the combined aqueous layers were acidified with concentrated HCl solution and extracted twice with ethyl acetate. The combined organic layers were dried over sodium sulfate, filtered, and concentrated to afford (5,6-dichloro-2-methoxypyridin-3-yl)boronic acid (1.75 g, 7.89 mmol, 70.2% yield) as an oily light yellow solid. m/z (ESI) 222.1 (M+H)⁺.

Intermediate J 2-(4-CHLORO-2-METHOXY-5-METHYLPHENYL)-4,4,5,5-TETRAMETHYL-1,3,2-DIOXABOROLANE

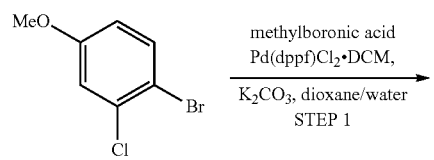

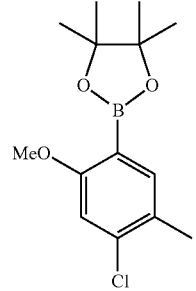

STEP 1:
2-CHLORO-4-METHOXY-1-METHYLBENZENE

A solution of Pd(amphos)₂Cl₂ (0.799 g, 1.129 mmol), methylboronic acid (7.43 g, 124 mmol), 1-bromo-2-chloro-4-methoxybenzene (25.000 g, 113 mmol, Oakwood), and potassium phosphate (71.9 g, 339 mmol) in 200 mL dioxane 60 mL water was heated to 70° C. overnight. The reaction mixture was then diluted with heptane. The organics were separated and concentrated. The crude residue was used in the next step without purification.

STEP 2: 1-CHLORO-4-IODO-5-METHOXY-2-METHYLBENZENE

The crude residue from step one was dissolved in 200 mL MeCN, was treated with selectfluor (40.0 g, 113 mmol) then was heated to 60° C. Iodine (28.6 g, 113 mmol) was added, and the reaction mixture was allowed to stir for 2 hours. The reaction mixture was then diluted with heptane/ether and quenched with saturated NaHCO3 solution. The organics were washed with water, dried over MgSO4 solution and concentrated. The crude residue was used in the next step without purification.

STEP 3: 2-(4-CHLORO-2-METHOXY-5-METHYLPHENYL)-4,4,5,5-TETRAMETHYL-1,3,2-DIOXABOROLANE

The crude residue from step two was dissolved in 100 mL DMF, was treated with bis(pinacolato)diboron (28.7 g, 113 mmol), PdCl$_2$(dppf)-CH$_2$Cl$_2$adduct (4.61 g, 5.64 mmol), and potassium acetate (44.3 g, 452 mmol) and was heated to 120° C. overnight. The reaction mixture was cooled to RT, was diluted with DCM and filtered through a plug of celite. The filtrate was then concentrated and purified by silica gel column chromatography (0-20% EtOAc/heptane) yielding 2-(4-chloro-2-methoxy-5-methylphenyl)-4,4,5,5-tetramethyl-1,3,2-dioxaborolane (6.16 g, 21.80 mmol, 19.31% yield) with a minor impurity. m/z (ESI) 283.0 (M+H)$^+$.

Intermediate K 2-(5-METHOXY-2-METHYLPHENYL)-4,4,5,5-TETRAMETHYL-1,3,2-DIOXABOROLANE 3-chloroanisole (6.39 ml, 45.2 mmol), and potassium phosphate (28.8 g, 135 mmol) in 150 mL dioxane 50 mL water was heated to 110° C. for 2 hours. The reaction mixture was then diluted with heptane, the organics dried over MgSO4 and concentrated. The crude residue was used in the next reaction without purification.

STEP 2: 2-(5-METHOXY-2-METHYLPHENYL)-4,4,5,5-TETRAMETHYL-1,3,2-DIOXABOROLANE

The crude residue from step one was dissolved in 100 mL dioxane, was treated with bis(pinacolato)diboron (11.47 g, 45.2 mmol), potassium phosphate (28.8 g, 135 mmol), XPhos (0.215 g, 0.452 mmol) and (xphos) palladium(ii) phenethylamine chloride (0.334 g, 0.452 mmol) and was heated to 100° c. overnight. The reaction mixture was then concentrated. Purification of the crude residue by silica gel column chromatography (0-20% EtOAc/heptane) gave 2-(5-methoxy-2-methylphenyl)-4,4,5,5-tetramethyl-1,3,2-dioxaborolane (7.80 g, 31.4 mmol, 69.6% yield). m/z (ESI) 249.3 (M+H)$^+$.

Intermediate L

5-FLUORO-2-METHOXY-3-(3-METHOXY-4-(4,4,5,5-TETRAMETHYL-1,3,2-DIOXABOROLAN-2-YL)PHENYL)PYRIDINE

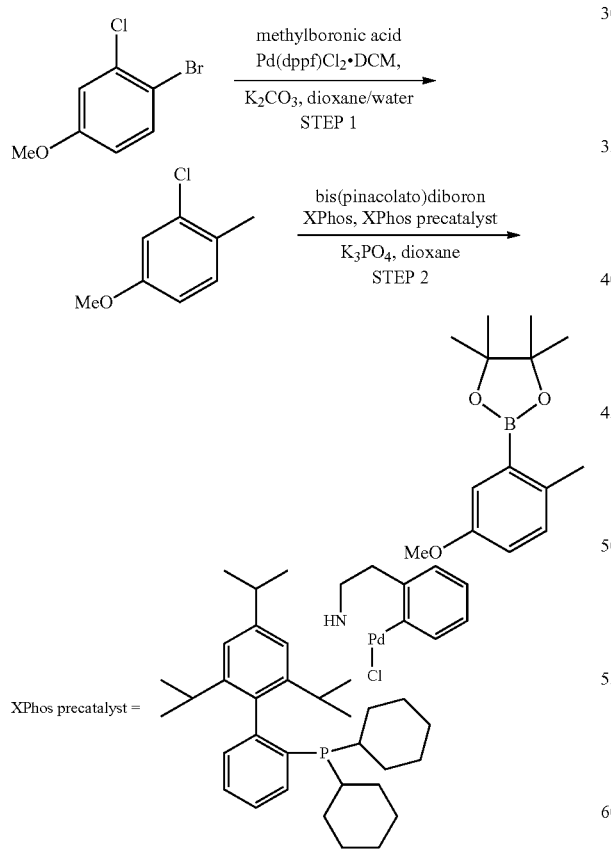

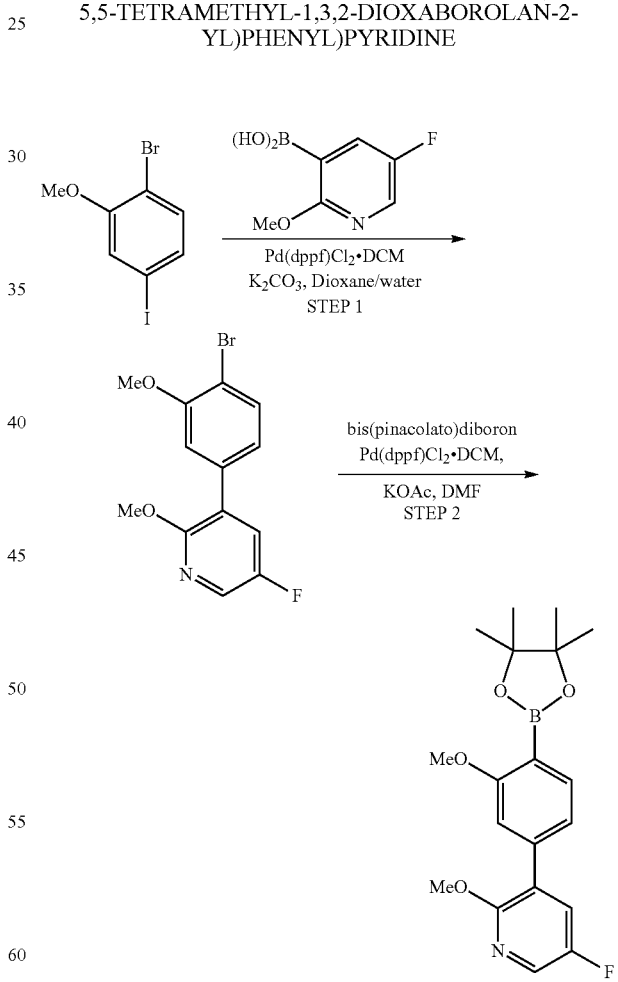

STEP 1:
2-CHLORO-4-METHOXY-1-METHYLBENZENE

A solution of PdCl$_2$(dppf)-CH$_2$Cl$_2$adduct (0.922 g, 1.129 mmol), methylboronic acid (2.70 g, 45.2 mmol), 4-bromo-

STEP 1: 3-(4-BROMO-3-METHOXYPHENYL)-5-FLUORO-2-METHOXYPYRIDINE

A solution of PdCl$_2$(dppf)-CH$_2$Cl$_2$ adduct (0.261 g, 0.320 mmol), (5-fluoro-2-methoxypyridin-3-yl)boronic acid (1.202 g, 7.03 mmol, Combi-Blocks), 1-bromo-4-iodo-2-methoxybenzene (2.000 g, 6.39 mmol, Combi-Blocks), and potassium carbonate (3.53 g, 25.6 mmol) in 20 mL dioxane 7 mL water was heated to 100° C. overnight. The reaction mixture was then allowed to cool to room temperature. The organics were separated and concentrated. Purification of the crude residue by silica gel column chromatography (0-70% EtOAc/heptane) gave 3-(4-bromo-3-methoxyphenyl)-5-fluoro-2-methoxypyridine (1.395 g, 4.47 mmol, 69.9% yield) with minor impurities. m/z (ESI) 313.2 $(M+H)^+$.

STEP 2: 5-FLUORO-2-METHOXY-3-(3-METHOXY-4-(4,4,5,5-TETRAMETHYL-1,3,2-DIOXABOROLAN-2-YL)PHENYL)PYRIDINE

A solution of $PdCl_2$(dppf)-$CH_2Cl_2$ adduct (0.365 g, 0.447 mmol), bis(pinacolato)diboron (1.419 g, 5.59 mmol), 3-(4-bromo-3-methoxyphenyl)-5-fluoro-2-methoxypyridine (1.395 g, 4.47 mmol), and potassium acetate (1.754 g, 17.88 mmol) in 10 mL DMF was heated to 110° C. overnight. The reaction mixture was poured into water and was extracted with DCM. The organics were dried over $MgSO_4$ and concentrated. Purification of the crude residue by silica gel column chromatography (0-20% EtOAc/heptane) gave 5-fluoro-2-methoxy-3-(3-methoxy-4-(4,4,5,5-tetramethyl-1,3,2-dioxaborolan-2-yl)phenyl)pyridine (0.840 g, 2.339 mmol, 52.3% yield) as a light yellow oil. m/z (ESI) 360.3 $(M+H)^+$.

Intermediate M

5-FLUORO-2-(3-METHOXY-4-(4,4,5,5-TETRAMETHYL-1,3,2-DIOXABOROLAN-2-YL)PHENOXY)PYRIDINE

STEP 1: 2-(4-BROMO-3-METHOXYPHENOXY)-5-FLUOROPYRIDINE

A microwave vial charged with 5-fluoro-2-hydroxypyridine (0.795 g, 7.03 mmol, Combi-Blocks), 1-bromo-4-iodo-2-methoxybenzene (2.000 g, 6.39 mmol, Combi-Blocks), copper(i) iodide (0.122 g, 0.639 mmol), 1-(-)-proline (0.110 g, 0.959 mmol), potassium fluoride (2.228 g, 38.3 mmol) and 10 mL DMSO was heated to 180° C. in a Biotage Initiator microwave reactor for 45 minutes. The reaction mixture was poured into water and was extracted with DCM. The organics were then concentrated. Purification of the crude residue by silica gel column chromatography (0-70% EtOAc/heptane) gave 2-(4-bromo-3-methoxyphenoxy)-5-fluoropyridine (0.840 g, 2.82 mmol, 44.1% yield). m/z (ESI) 297.9 $(M+H)^+$.

STEP 2: 5-FLUORO-2-(3-METHOXY-4-(4,4,5,5-TETRAMETHYL-1,3,2-DIOXABOROLAN-2-YL)PHENOXY)PYRIDINE

A solution of PdCl2(dppf)-$CH_2Cl_2$adduct (0.093 g, 0.114 mmol), bis(pinacolato)diboron (0.362 g, 1.426 mmol), 2-(4-bromo-3-methoxyphenoxy)-5-fluoropyridine (0.340 g, 1.141 mmol), and potassium acetate (0.448 g, 4.56 mmol) in 2.5 mL DMF was heated to 100° C. overnight. The reaction mixture was then diluted with DCM and washed with water. The organics were dried over MgSO4 and concentrated. Purification of the crude residue by silica gel column chromatography (0-40% EtOAc/heptane) gave 5-fluoro-2-(3-methoxy-4-(4,4,5,5-tetramethyl-1,3,2-dioxaborolan-2-yl)phenoxy)pyridine (0.134 g, 0.388 mmol, 34.0% yield). m/z (ESI) 346.2 $(M+H)^+$.

Intermediate N (5-(BENZYLOXY)-2-METHYLPHENYL)BORONIC ACID

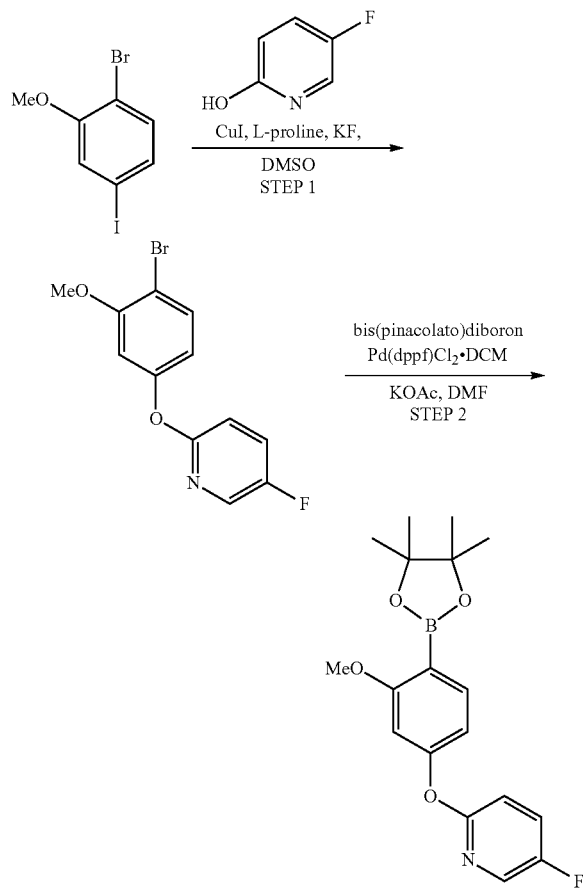

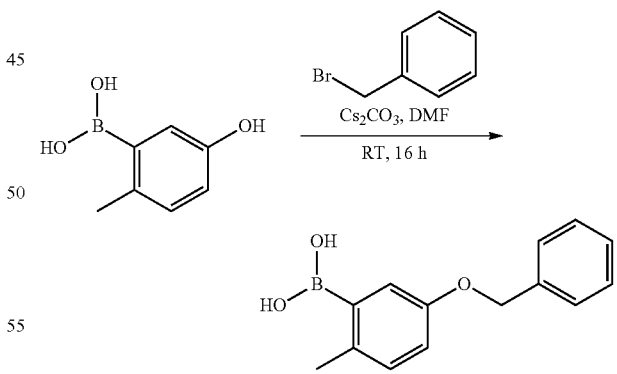

To a RBF was added (bromomethyl)benzene (0.169 g, 0.987 mmol), (5-hydroxy-2-methylphenyl)boronic acid (0.050 g, 0.329 mmol) (aldrich), cesium carbonate (0.322 g, 0.987 mmol), and DMF (1.645 ml). The reaction was stirred at RT overnight. Reaction complete as determined by MS. Water was added and the reaction was stirred for 30 minutes. Filtered solid and dried in vaccuo to yield (5-(benzyloxy)-2-methylphenyl)boronic acid (0.065 g, 0.269 mmol, 82% yield). m/z (ESI) 243.1 $(M+H)^+$.

Intermediate O

(5-(CYCLOPROPYLMETHOXY)-2-METHYLPHENYL)-BORONIC ACID

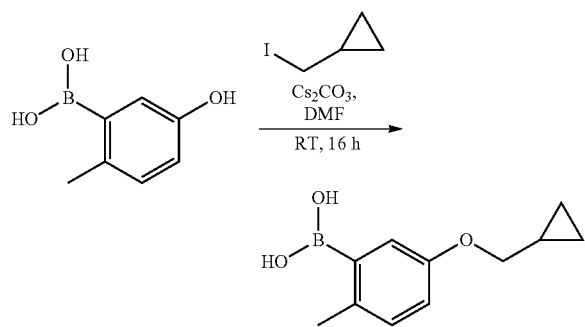

This was prepared in the same manner as (5-(benzyloxy)-2-methylphenyl)boronic acid, with the exception that (iodomethyl)cyclopropane was used instead of (bromomethyl)benzene. (ESI) 207.3 (M+H)$^+$.

Intermediate P

(2-CHLORO-3'-FLUORO-5-METHOXY-[1,1'-BIPHENYL]-4-YL)BORONIC ACID

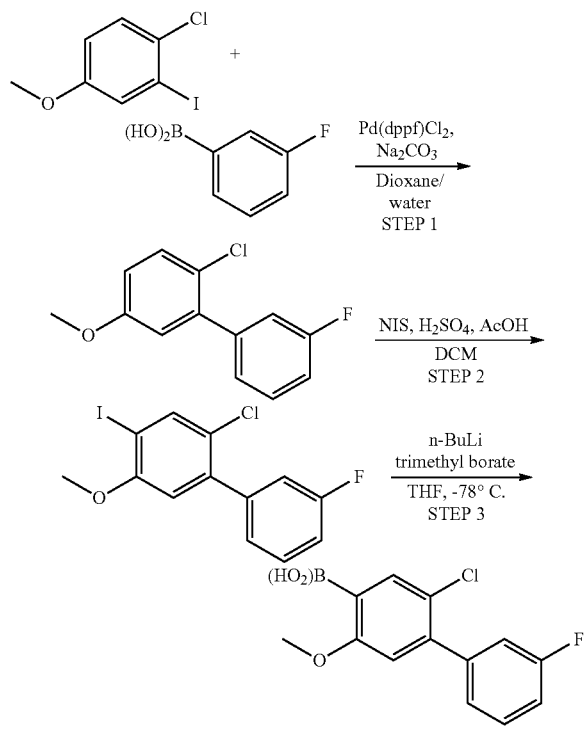

STEP 1: (3-FLUOROPHENYL)BORONIC ACID

To a solution of 1-chloro-2-iodo-4-methoxybenzene (40.0 g, 149 mmol, Combi Block), (3-fluorophenyl)boronic acid (27.2 g, 194 mmol, Combi Block), 2M aqueous sodium carbonate (186 mL, 373 mmol) in dioxane (800 mL) was added PdCl$_2$(dppf)-DCM complex (12.2 g, 14.9 mmol). The reaction mixture was degassed with nitrogen for 10 minutes and then heated at 90° C. for 16 h. After completion, the reaction mixture was diluted with water (600 mL) and extracted with ethyl acetate (2×1000 mL). The organic layer was dried over sodium sulfate and concentrated under reduced pressure to obtain the crude material which was purified by column chromatography (silica: 100-200; elution: 5% ethyl acetate in hexanes) to get 2-chloro-3'-fluoro-5-methoxy-1,1'-biphenyl (27.0 g, 76.7%) as clear liquid. TLC solvent system: 100% hexanes, Product's R$_f$: 0.7. MS (ESI, positive ion) m/z; No ionization peak was detectable. $^1$H NMR (400 MHz, CDCl$_3$) δ 7.43-7.33 (m, 2H), 7.21 (d, J=7.7 Hz, 1H), 7.16 (d, J=9.8 Hz, 1H), 7.08 (td, J=8.6, 2.7 Hz, 1H), 6.89-6.82 (m, 2H), 3.82 (s, 3H).

STEP-2: 2-CHLORO-3'-FLUORO-5-METHOXY-1,1'-BIPHENYL

To a solution of 2-chloro-3'-fluoro-5-methoxy-1,1'-biphenyl (27.0 g, 114 mmol) in DCM (165 mL) and acetic acid (165 mL) was added sulfuric acid (3.35 mL, 62.9 mmol). N-iodosuccinimide (25.7 g, 114 mmol) was added and the reaction mixture was stirred at ambient temperature for 16 h. After completion, the reaction mixture was diluted with water (500 mL) and extracted with ethyl acetate (2×750 mL). The organic layer was dried over sodium sulfate and concentrated to obtain crude material which was purified by column chromatography (silica: 100-200; elution: 1% ethyl acetate in hexanes) to get 2-chloro-3'-fluoro-4-iodo-5-methoxy-1,1'-biphenyl (28.0 g, 67.6%) as light pink solid. TLC solvent system: 100% hexanes, Product's R$_f$: 0.6. MS (ESI, positive ion) m/z; No ionization. $^1$H NMR (400 MHz, CDCl$_3$) δ 7.86 (s, 1H), 7.41 (td, J=8.1, 5.9 Hz, 1H), 7.20 (d, J=7.7 Hz, 1H), 7.17-7.07 (m, 2H), 6.73 (s, 1H), 3.88 (s, 3H).

STEP-3: 2-CHLORO-3'-FLUORO-4-IODO-5-METHOXY-1,1'-BIPHENYL

To a solution of 2-chloro-3'-fluoro-4-iodo-5-methoxy-1,1'-biphenyl (26.6 g, 73.4 mmol) in THF (250 mL) was added n-BuLi (1.6 M in hexanes) (55.1 mL, 88.1 mmol) at −78° C. The reaction mixture was stirred at same temperature for 30 minutes. Trimethyl borate (12.3 mL, 110 mmol) was added at −78° C. and the reaction mixture was stirred at same temperature for another 1 h. After completion, the reaction mixture was quenched with 1N HCl (200 mL) at −78° C. and was stirred at RT for 10 minutes. The aqueous layer was extracted with ethyl acetate (2×250 mL), organic layer was dried over sodium sulfate and concentrated to obtain crude material which was purified by column chromatography (silica:100-200; elution: 12.5% ethyl acetate in hexanes) to get (2-chloro-3'-fluoro-5-methoxy-[1,1'-biphenyl]-4-yl)boronic acid as white solid (5.35 g, 26.0%). TLC solvent system: 30% ethyl acetate in hexanes, Product's R$_f$: 0.5. MS (ESI, positive ion) m/z; No ionization. $^1$H NMR (400 MHz, CDCl$_3$) δ 7.91 (s, 1H), 7.42 (td, J=8.0, 5.8 Hz, 1H), 7.24 (d, J=7.7 Hz, 1H), 7.18 (dt, J=9.8, 2.0 Hz, 1H), 7.11 (td, J=8.4, 2.6 Hz, 1H), 6.85 (s, 1H), 5.75 (s, 2H), 3.93 (s, 3H).

Intermediate Q

(3'-FLUORO-3-METHOXY-[1,1'-BIPHENYL]-4-YL)BORONIC ACID

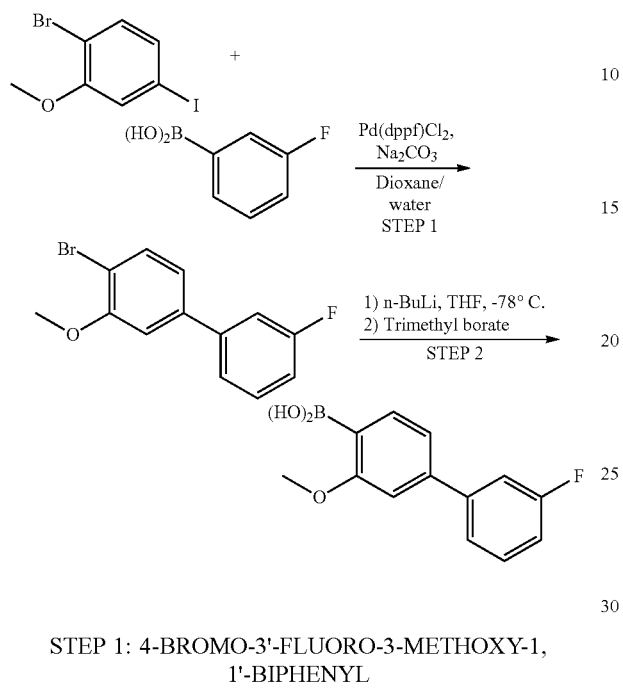

STEP 1: 4-BROMO-3'-FLUORO-3-METHOXY-1,1'-BIPHENYL

To a solution of 1-bromo-4-iodo-2-methoxybenzene (20.0 g, 63.9 mmol, Oakwood), (3-fluorophenyl)boronic acid (11.6 g, 83.0 mmol, Combi Block), 2M aqueous sodium carbonate (79.8 mL, 160 mmol) in dioxane (200 mL) was added $PdCl_2$(dppf).DCM complex (5.21 g, 6.39 mmol). The reaction mixture was degassed with nitrogen for 10 minutes and then heated at 90° C. for 16 h. After completion, the reaction mixture was diluted with water (300 mL) and extracted with ethyl acetate (2×500 mL). The organic layer was dried over sodium sulfate and concentrated under reduced pressure to obtain the crude material which was purified by column chromatography (silica: 100-200; elution: 5% ethyl acetate in hexanes) to get 4-bromo-3'-fluoro-3-methoxy-1,1'-biphenyl (16.5 g, 92.6%) as yellow liquid. TLC solvent system: 10% ethyl acetate in hexanes, Product's $R_f$: 0.7. MS (ESI, positive ion) m/z; No ionization. $^1$H NMR (400 MHz, $CDCl_3$) δ 7.60 (d, J=8.0 Hz, 1H), 7.40 (tt, J=8.7, 4.6 Hz, 1H), 7.36-7.31 (m, 1H), 7.26-7.22 (m, 1H), 7.08-7.01 (m, 3H), 3.97 (s, 3H).

STEP 2: (3'-FLUORO-3-METHOXY-[1,1'-BIPHENYL]-4-YL)BORONIC ACID

To a solution of 4-bromo-3'-fluoro-3-methoxy-1,1'-biphenyl (14.4 g, 51.6 mmol) in THF (150 mL) was added n-BuLi (1.6 M in hexanes) (38.7 mL, 61.9 mmol) at −78° C. The reaction mixture was stirred at same temperature for 30 minutes. Trimethyl borate (8.63 mL, 77.4 mmol) was added at −78° C. and the reaction mixture was stirred at same temperature for another 1 h. After completion, the reaction mixture was quenched with 1N HCl (150 mL) at −78° C. and was stirred at room temperature for 10 minutes. The aqueous layer was extracted with ethyl acetate (2×200 mL), organic layer was dried over sodium sulfate and concentrated to obtain crude material which was purified by column chromatography (silica: 100-200; elution: 10% ethyl acetate in hexanes) to get (3'-fluoro-3-methoxy-[1,1'-biphenyl]-4-yl) boronic acid as white solid (5.35 g, 20.4%). TLC solvent system: 10% ethyl acetate in hexanes, Product's $R_f$: 0.3. MS (ESI, positive ion) m/z; No ionization pek was detectable. $^1$H NMR (400 MHz, DMSO) δ 7.75 (s, 2H), 7.69-7.46 (m, 4H), 7.33-7.15 (m, 3H), 3.91 (s, 3H).

Intermediate R

2-CHLORO-4-METHOXY-5-(4,4,5,5-TETRAMETHYL-1,3,2-DIOXABOROLAN-2-YL)BENZONITRILE

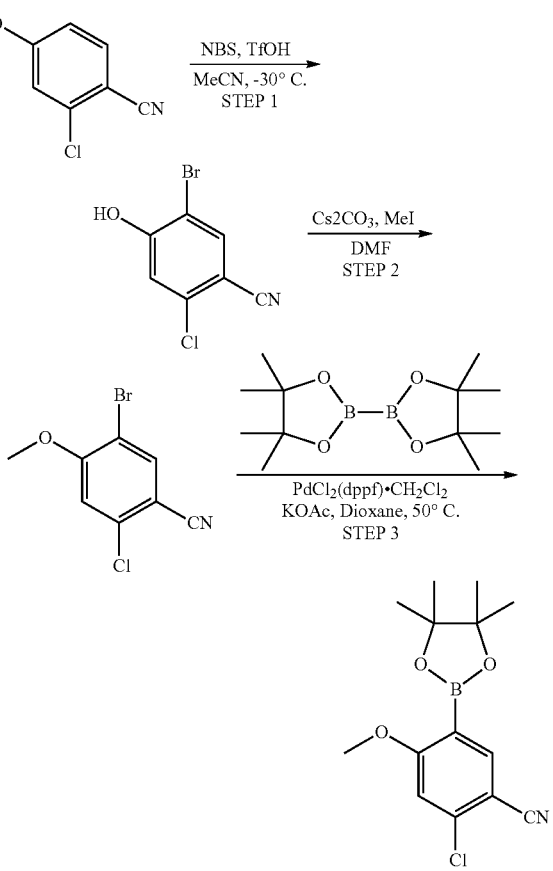

STEP 1: SYNTHESIS OF 5-BROMO-2-CHLORO-4-HYDROXYBENZONITRILE

To a solution of 2-chloro-4-hydroxybenzonitrile (20.0 g, 130 mmol, Apollo) in acetonitrile (400 mL) was added triflic acid (12.7 mL, 156 mmol, Spectrochem) and NBS (27.8 g, 156 mmol, Spectrochem) at −30° C. The reaction mixture was allowed to warm to room temperature and stirred for 15 h. The reaction mixture was quenched with saturated aqueous $NaHSO_3$ solution (1.00 L) and extracted with ethyl acetate (2×3.00 L). The combined organic layer was washed with water (1.00 L), dried over sodium sulfate, filtered and concentrated under reduced pressure to obtain the crude compound which was purified by column chromatography (silica gel: 60-120 mesh; elution: 0-6% ethyl acetate in hexanes) to obtain 5-bromo-2-chloro-4-hydroxybenzonitrile (16.0 g, 52.9%) as white solid. TLC solvent system: 20% ethyl acetate in hexanes. Product's $R_f$: 0.6. MS (ESI, positive ion) m/z; 230 (M−1). $^1$H NMR (400 MHz, MeOD) δ 7.93 (s, 1H), 7.06 (s, 1H). Note: OH proton not observed.

STEP 2: SYNTHESIS OF 5-BROMO-2-CHLORO-4-METHOXYBENZONITRILE

To a solution of 5-bromo-2-chloro-4-hydroxybenzonitrile (90.0 g, 387 mmol) in DMF (900 mL) was added cesium carbonate (252 g, 774 mmol, GLR Scientific) and methyl iodide (60 mL, 968 mmol, Spectrochem). The reaction mixture was stirred at room temperature for 16 h. The reaction mixture was quenched with ice cold water (2.00 L) and extracted with ethyl acetate (2×3.00 L). The combined organic layer was washed with water, dried over sodium sulfate, filtered and concentrated under reduced pressure to obtain the crude compound which was purified by column chromatography (silica gel: 100-200 mesh; elution: 0-4% ethyl acetate in hexanes) to obtain 5-bromo-2-chloro-4-methoxybenzonitrile (50 g, 52.4%) as white solid. TLC solvent system: 20% ethyl acetate in hexanes. Product's $R_f$: 0.7. MS (ESI, positive ion) m/z; No ionization. $^1$H NMR (400 MHz, MeOD) δ 7.80 (s, 1H), 6.98 (s, 1H), 3.96 (s, 3H).

STEP 3: SYNTHESIS OF 2-CHLORO-4-METHOXY-5-(4,4,5,5-TETRAMETHYL-1,3,2-DIOXABOROLAN-2-YL)

To a solution 5-bromo-2-chloro-4-methoxybenzonitrile (20.0 g, 81.4 mmol) and 4,4,4',4',5,5,5',5'-octamethyl-2,2'-bi(1,3,2-dioxaborolane) (20.6 g, 81.4 mmol, RCP) in 1,4-dioxan (360 mL) was added KOAc (19.9 g, 203 mmol, Spectrochem) and the reaction mixture was degassed with nitrogen for 20 minutes. PdCl$_2$(dppf).DCM complex (6.60 g, 8.10 mmol, GLR) was added and the reaction mixture allowed to stir at 60° C. for 15 h. The reaction mixture was diluted with ethyl acetate (300 mL) and filtered through celite bed. The filtrate was concentrated under reduced pressure to obtain the crude which was further purified by column chromatography (neutral alumina, 100% hexanes) to obtain 2-chloro-4-methoxy-5-(4,4,5,5-tetramethyl-1,3,2-dioxaborolan-2-yl) (11 g, 46.2%) as off white solid. TLC solvent system: 20% ethyl acetate in hexanes, Product's $R_f$: 0.2. MS (ESI, positive ion) m/z; 294 (M+1). $^1$H NMR (400 MHz, CDCl$_3$) δ 7.96 (s, 1H), 6.94 (s, 1H), 3.89 (s, 3H), 1.35 (s, 12H).

Intermediate S

N-(4-METHOXYBENZYL)ISOXAZOL-3-AMINE

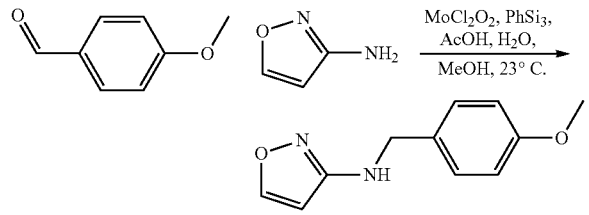

A flask was charged with 4-methoxybenzaldehyde (3.62 ml, 29.8 mmol), 3-aminoisoxazole (2 ml, 27.1 mmol), MeOH (135 ml), water (2.438 ml, 135 mmol), and acetic acid (1.705 ml, 29.8 mmol). The reaction was stirred for 15 minutes, after which molybdenum dichloride dioxide (0.269 g, 1.354 mmol) and phenylsilane (5.01 ml, 40.6 mmol) were added. The reaction was stirred overnight at room temperature. The reaction was filtered through a pad of Celite, which was washed with ethyl acetate. The filtrate was concentrated, diluted with ethyl acetate and washed with saturated sodium bicarbonate solution. The aqueous layer was extracted with ethyl acetate, and the combined organic layers were washed with water, washed with brine, dried with sodium sulfate, filtered, and concentrated. The material was purified via column chromatography (RediSep Gold 80 g, gradient elution 0-50% EtOAc:Heptane) to afford N-(4-methoxybenzyl)isoxazol-3-amine (4.10, 20.08 mmol, 74.2% yield) as a light yellow solid. m/z (ESI) 205.1 (M+H)$^+$.

Intermediate T

N-(4-METHOXYBENZYL)-1,3,4-THIADIAZOL-2-AMINE

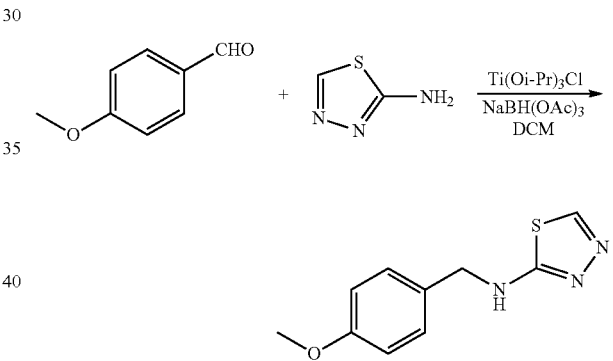

To a solution of 4-methoxybenzaldehyde (30.0 g, 220 mmol, Spectrochem) and 1,3,4-thiadiazol-2-amine (22.2 g, 220 mmol, Combi Block) in dichloromethane (650 mL) was added Ti(O$^i$Pr)$_3$Cl (115 g, 441 mmol, Aldrich) and the mixture was stirred at room temperature for 3 h. The reaction mixture was cooled to 0° C. and NaBH(OAc)$_3$ (187 g, 882 mmol, RCP) was added in portions and stirred at RT for 16 h. The reaction mixture (in portions of 100 mL) was quenched with saturated NaHCO$_3$ solution and extracted with dichloromethane (2×500 mL). The combined organic layer was dried over sodium sulfate, filtered and concentrated under reduced pressure to obtain the crude material which was further purified by column chromatography (silica gel 100-200 mesh and 0-1% methanol in DCM) to obtain N-(4-methoxybenzyl)-1,3,4-thiadiazol-2-amine (26.5 g, 55%) as off white solid. TLC solvent system: 5% methanol in dichloromethane. Product's $R_f$: 0.3. MS (ESI, positive ion) m/z; 222 (M+1). $^1$H NMR (400 MHz, DMSO) δ 8.61 (s, 1H), 8.18 (s, 1H), 7.28 (d, J=8.5 Hz, 2H), 6.90 (d, J=8.6 Hz, 2H), 4.40 (d, J=5.7 Hz, 2H), 3.73 (s, 3H).

Intermediate U

N-(4-METHOXYBENZYL)PYRIMIDIN-4-AMINE

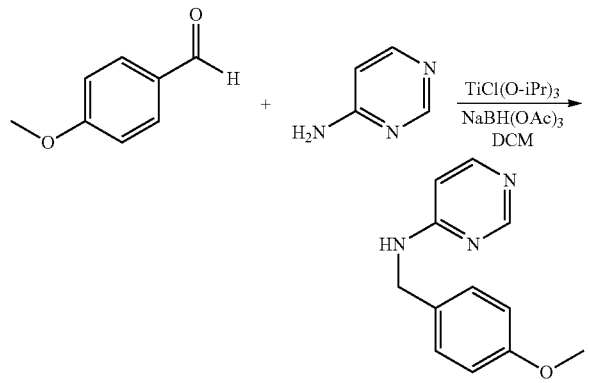

p-Anisaldehyde (320 g, 2.35 mol, 1.0 equiv; Aldrich, St. Louis, Mo.) and 4-aminopyrimidine (246 g, 2.58 mol, 1.1 equiv; AK Scientific, Inc., Union City, Calif.) were dissolved in anhydrous DCM (8.0 L). To this solution under $N_2$ atmosphere at room temperature was added a solution of Ti(Oi-Pr)$_3$Cl (1348 g, 5.17 mol, 2.2 equiv; Aldrich) in anhydrous DCM (1 L) in one portion and the reaction mixture was stirred at RT for 30 minutes. The reaction mixture was then cooled to 10° C. and NaBH(OAc)$_3$ (1495 g, 7.05 mol, 3.0 equiv; Aldrich) was added in portions over 30 min followed by the addition of acetic acid (10 mL). (Note: A mild exotherm of 10-19° C. was observed). Upon completion of the addition, the reaction mixture was allowed to warm up to RT and stirred overnight. The reaction was monitored using LC/MS. Product formation was observed along with many other peaks. Upon completion the reaction mixture was quenched slowly and carefully pouring over a well-stirred saturated aqueous NaHCO$_3$ (30 L). The crude product was then extracted with dichloromethane (3×12 L) and the organic extracts were combined, washed with brine (5 L), dried over Na$_2$SO$_4$, and concentrated under reduced pressure. The crude residue was initially triturated with hexanes to obtain a solid. The crude solid was further triturated with MTBE to remove most of the impurities. The crude product was purified using column chromatography eluting with MeOH/ethyl acetate (2:98 to 5:95) to afford N-(4-methoxybenzyl)pyrimidin-4-amine as a white solid with >99% purity (129 g, 26% yield). $^1$H NMR (400 MHz, DMSO) δ ppm 8.40 (s, 1H), 8.02 (d, J=6.1 Hz, 1H), 7.82 (t, J=6.0 Hz, 1H), 7.24 (d, J=8.0 Hz, 2H), 6.98-6.77 (m, 2H), 6.48 (s, 1H), 4.43 (s, 2H), 3.72 (s, 3H). m/z (ESI) 216.0 (M+H)$^+$.

Intermediate V

N-(4-METHOXYBENZYL)-1,2,4-THIADIAZOL-5-AMINE

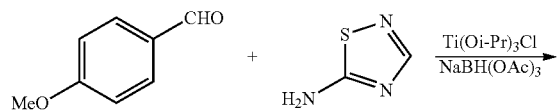

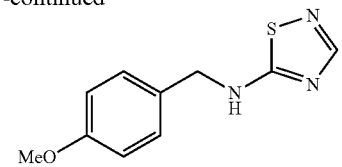

To a suspension of 4-methoxybenzaldehyde (10.0 g, 73.4 mmol) and 1,2,4-thiadiazol-5-amine (7.40 g, 73.4 mmol) in dichloromethane (200 mL) was added chlorotitanium triisopropoxide (28.6 g, 110 mmol) portionwise over 5 min. After stirring for 3 hours, sodium triacetoxyborohydride (38.9 g, 184 mmol) was added portion wise at 0° C. and allowed to stir for additional 1 hour. The reaction was cooled in ice/water mixture quenched with saturated NaHCO$_3$ solution (300 mL) and extracted with dichloromethane (2×300 mL). The organic layer was separated, dried over Na$_2$SO$_4$, filtered and concentrated to obtain the crude which was purified by column chromatography using silica gel (100-200 mesh) and 0-30% ethyl acetate in hexane to give 5.5 g (34%) of (4-methoxybenzyl)-1,2,4-thiadiazol-5-amine as an off-white solid. MS (ESI, positive) m/z: 222.1; $^1$H NMR (400 MHz, DMSO-d$_6$) δ 8.89 (s, 1H), 7.92 (s, 1 H), 7.27 (d, J=8.5 Hz, 2 H), 6.91 (d, J=8.5 Hz, 2H), 4.42 (d, J=5.4 Hz, 2 H), 3.73 (s, 3 H).

Intermediate W

N-(2,4-DIMETHOXYBENZYL)-1,2,4-THIADIAZOL-5-AMINE

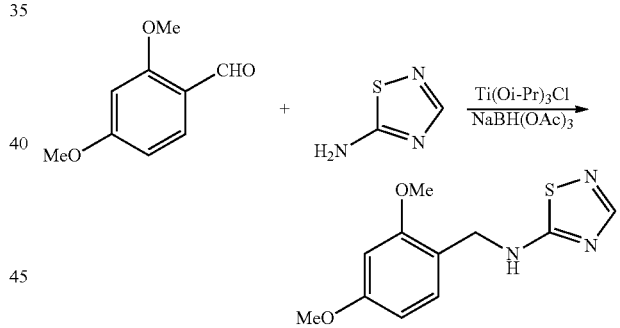

To a solution of 1,2,4-thiadiazol-5-amine (150 g, 1.48 mol, 1.1 eq) and 2,4-dimethoxybenzaldehyde (224.1 g, 1.35 mol, 1 eq) in anhydrous DCM (6 L) was added chlorotitanium triisopropoxide (771.3 g, 2.96 mol, 2.2 eq) slowly over 15 minutes. The resulting yellow solution was stirred for 30 minutes and then treated with sodium triacetoxyborohydride (715.3 g, 3.38 mol, 2.5 eq) portionwise (Note: the reaction temperature increased from RT to 34° C.). After 2 hours, LC-MS analysis showed formation of the product. The reaction mixture was cooled using an ice-water bath and neutralized with saturated aqueous NaHCO$_3$ to pH-7. The resulting thick slurry was passed through a short celite pad and washed with DCM. The white solid left on the pad was collected, put into flask, charged with DCM and water, and then stirred well. The resulting slurry was again passed through a short celite pad and washed with DCM. All the filtrates were combined. The organic layer was separated, dried, filtered, and concentrated. The oily residue was purified by column chromatography, affording N-(2,4-Dimethoxybenzyl)-1,2,4-thiadiazol-5-amine (160 g, >95% purity) as a white solid in 47% yield. MS (ESI, positive) m/z: 252.3. ¹HNMR (400 MHz, DMSO-d₆): δ ppm ¹H NMR (400 MHz, DMSO-d₆) δ 8.68 (s, 1 H), 7.89 (s, 1 H), 7.17 (d, J=8.2 Hz, 1 H), 6.57 (s, 1 H), 6.49 (d, J=8.3 Hz, 1 H), 4.37 (d, J=5.2 Hz, 2 H), 3.80 (s, 3 H), 3.75 (s, 3 H).

Intermediate X

N-(2,4-DIMETHOXYBENZYL)-1,3,4-THIADIAZOL-2-AMINE

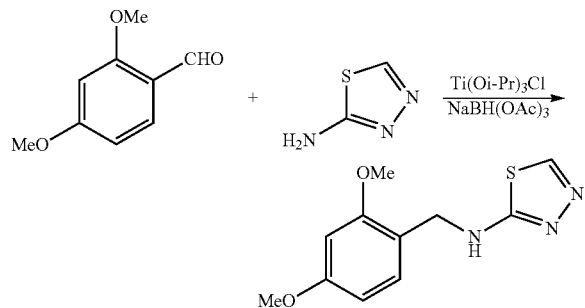

N-(2,4-dimethoxybenzyl)-1,3,4-thiadiazol-2-amine was prepared in a manner analogous to N-(2,4-Dimethoxybenzyl)-1,2,4-thiadiazol-5-amine wherein 1,2,4-thiadiazol-5-amine was replaced with 1,3,4-thiadiazol-2-amine MS (ESI, positive) m/z: 252.0.

Intermediate Y

PERFLUOROPHENYL 1-CHLOROISOQUINOLINE-6-SULFONATE

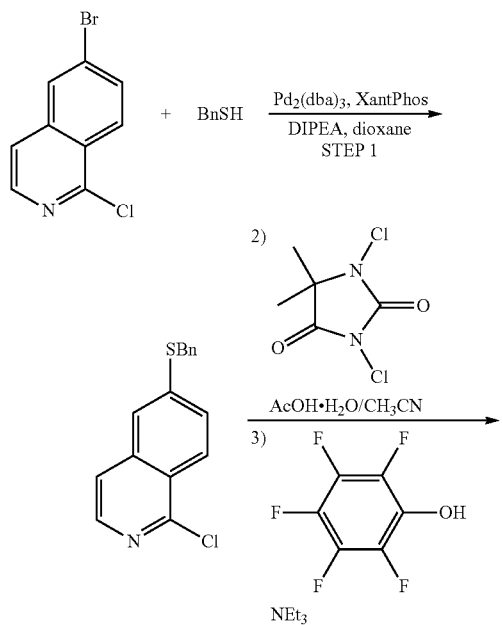

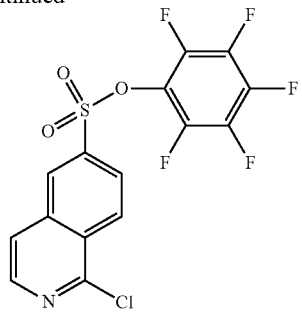

STEP 1: SYNTHESIS OF 6-(BENZYLTHIO)-1-CHLOROISOQUINOLINE

To a 12 L three-neck flask were charged with 6-bromo-1-chloroisoquinoline (Bellen and Activate; 396 g, 1.63 mol), Pd₂(dba)₃ (37.4 g, 40.8 mmol), XantPhos (47.2 g, 81.7 mmol) and dioxane (3.60 L), followed by DIPEA (427 mL, 2.45 mol) and the resulting mixture was degassed with nitrogen three times. Then the mixture was heated to 63° C. and a degassed solution of BnSH (202 mL, 1.71 mol) in dioxane (1.20 L) was added slowly over 4 hours. After addition was over, LC-MS showed full conversion and the mixture was cooled to room temperature. The mixture was filtered through a pad of Celite. The solid was washed with ethyl acetate. The volume of the filtrate was reduced under reduced pressure and it was poured into isopropanol (3.30 L) slowly with stirring. The resulting mixture was stirred at room temperature for 2 hours and then cooled to 0° C. The solid was filtered, washed with cold mixture of isopropanol and heptane (1:1, 500 mL×2) and dried to give 351 g of 6-(benzylthio)-1-chloroisoquinoline which was still contaminated with some bis-coupled byproduct This was taken forward as such for the next step. The mother liquor was concentrated and purified by column chromatography (eluting with DCM/hexanes=1:2 to 1:1) to give 48.0 g of pure 6-(benzylthio)-1-chloroisoquinoline. Total: 399 g was obtained.

STEP 2 AND 3: PERFLUOROPHENYL 1-CHLOROISOQUINOLINE-6-SULFONATE

To a 12 L three-neck flask were charged with 6-(benzylthio)-1-chloroisoquinoline (394 g, 1.38 mol), CH₃CN (4.00 L), AcOH (489 mL) and water (323 mL) and the resulting mixture was cooled to 0-5° C. under nitrogen. 1,3-Dichloro-5,5-dimethylimidazolidine-2,4-dione (543 g, 2.76 mol) was added portion-wise over 70 min keeping the internal temperature below 10° C. The resulting suspension was stirred at 0-5° C. under nitrogen for 30 min and LC-MS showed full conversion. Then a solution of 2,3,4,5,6-pentafluorophenol (507 g, 2.76 mol) in CH₃CN (400 mL) was added over 5 min, following by NEt₃ (480 mL, 3.45 mol) over 25 min keeping the internal temperature below 10° C. The mixture was continued to be stirred at 0-5° C. for 30 min. LC-MS showed complete reaction and water (2.80 L) was added slowly over 30 min keeping the internal temperature below 5° C. The resulting yellow suspension was stirred at 0-5° C. for 2 hours. Then the mixture was filtered and the solid was combined with 48.0 g of product from previous batches. This material was stirred in water, filtered and dried to give 489 g of yellow solid. ¹H NMR of the crude showed some impurities. The yellow solid was suspended in DCM and filtered through a plug of silica gel eluting with 100% DCM to give 461 g of perfluorophenyl 1-chloroisoquinoline-6-sulfonate with >99% purity. Yield: 62% for two steps. ¹H NMR (300 MHz, d₆-DMSO) δ ppm 8.96 (dd, J=1.5 Hz, 1H), 8.60-8.53 (m, 2H), 7.45 (d, J=11.7 Hz, 1H), 8.27 (dd, J=9.0, 2.1 Hz, 1H), 8.20 (d, J=5.4 Hz, 1H). HPLC purity: >99% (215 nm and 254 nm). LCMS: m/z: 410.0/412.0 (M+1).

Intermediate Z

PERFLUOROPHENYL 4-CHLOROQUINOLINE-7-SULFONATE

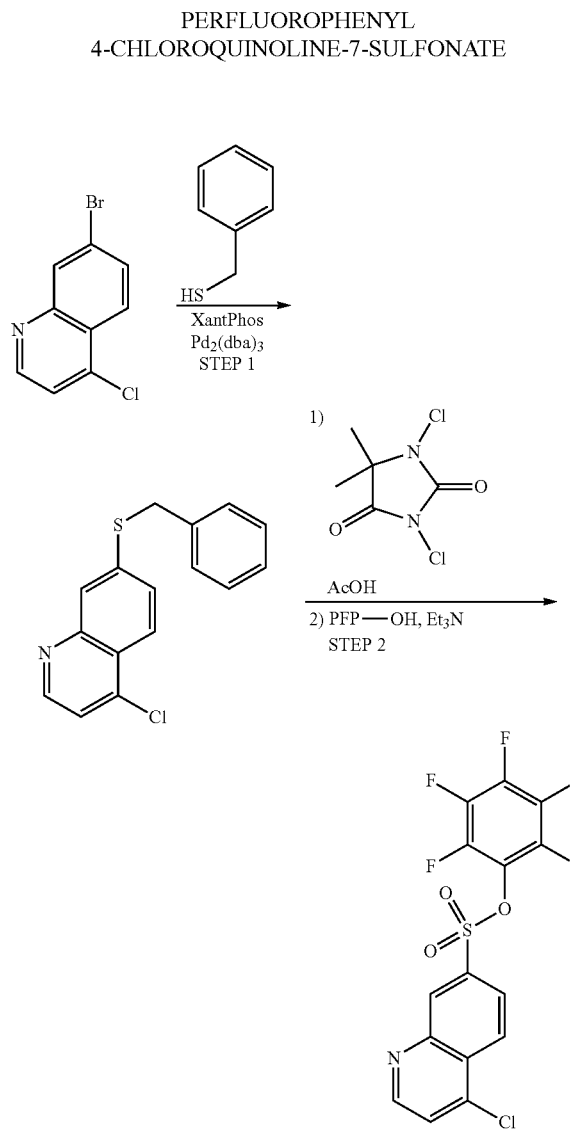

STEP 1: 7-(BENZYLTHIO)-4-CHLOROQUINOLINE

Tris(dibenzylidene acetone)-dipalladium (0) (3.80 g, 4.15 mmol, Hindustan Platinum), and xantphos (6.00 g, 10.4 mmol, GLR) were taken in 1,4-dioxane (50.0 mL) and degassed with N₂ for 15 mins. The mixture was heated at 90° C. for 10 min to pre-generate the active catalyst. 7-Bromo-4-chloroquinoline (50.0 g, 208 mmol, Silica Heterocycles), DIPEA (72.5 mL, 415 mmol, Spectrochem) and benzyl mercaptan (25.7 g, 207.5 mmol, Alfa Aesar) were taken in 1,4-dioxane (200 mL) in a separate RBF and degassed with N₂ for 10 min. The pre-activated catalyst solution prepared above was cooled to room temperature and transferred into the RBF containing the reactants via syringe. The reaction mixture was heated at 100° C. for 6 h. The reaction mixture was allowed to cool to room temperature. Water (1.0 L) was added and the aqueous layer was extracted with ethyl acetate (2×500 mL). The combined organic extract was dried over sodium sulfate, filtered and concentrated under reduced pressure to obtain the crude material which was further purified by column chromatography (silica gel 100-200 mesh, elution 0-20% ethyl acetate in hexanes) to obtain 7-(benzylthio)-4-chloroquinoline (50.0 g, 85%) as yellowish solid. TLC solvent system: 20% ethyl acetate in hexanes. Product's R$_f$: 0.4. MS (ESI, positive ion) m/z; 286(M+1). ¹H NMR (400 MHz, CDCl₃) δ 8.71 (d, J=4.7 Hz, 1H), 8.08 (d, J=8.8 Hz, 1H), 7.93 (d, J=1.7 Hz, 1H), 7.49 (dd, J=8.8, 1.8 Hz, 1H), 7.46-7.38 (m, 3H), 7.32 (t, J=7.3 Hz, 2H), 7.29-7.22 (m, 1H), 4.31 (s, 1H).

STEP 2: PERFLUOROPHENYL 4-CHLOROQUINOLINE-7-SULFONATE

To a solution of 7-(benzylthio)-4-chloroquinoline (15.0 g, 52.4 mmol) in acetonitrile (200 mL) was added acetic acid (20 mL) and water (10 mL) and the resulting solution was cooled to 0° C. To this solution 1,3-dichloro-5,5-dimethyl-imidazolidine-2,4-dione (20.6 g, 105 mmol, Aldrich) was added in a single lot. The resulting reaction mixture was maintained at 0° C. for 20 mins. Pentafluorophenol (14.4 g, 78.9 mmol) was added followed by the addition of triethyl amine (29.0 mL, 210 mmol) in a dropwise manner. The resulting reaction mixture was stirred at 0° C. for 20 min. The reaction mixture was diluted with water (500 mL) and extracted with ethyl acetate (2×500 mL). The combined organic layer was dried over sodium sulfate, filtered and concentrated under reduced pressure to obtain the crude material which was purified by column chromatography (silica gel 100-200 mesh, elution 0-10% ethyl acetate in hexanes) to obtain perfluorophenyl 4-chloroquinoline-7-sulfonate (12.0 g, 57%) as white solid. TLC solvent system: 30% ethyl acetate in hexanes. Product's R$_F$: 0.6. MS (ESI, positive ion) m/z; 409.9 (M+1). ¹H NMR (400 MHz, CDCl₃) δ 8.98 (d, J=4.7 Hz, 1H), 8.79 (d, J=1.5 Hz, 1H), 8.51 (d, J=8.9 Hz, 1H), 8.15 (dd, J=9.0, 1.7 Hz, 1H), 7.73 (d, J=4.7 Hz, 1H).

Intermediate AK

1-CHLORO-N-(4-METHOXYBENZYL)-4-OXO-N-(1,3,4-THIADIAZOL-2-YL)-3,4-DIHYDROPHTHALAZINE-6-SULFONAMIDE

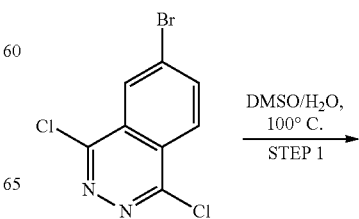

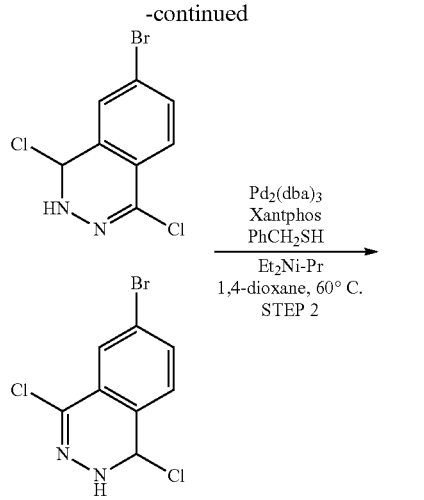

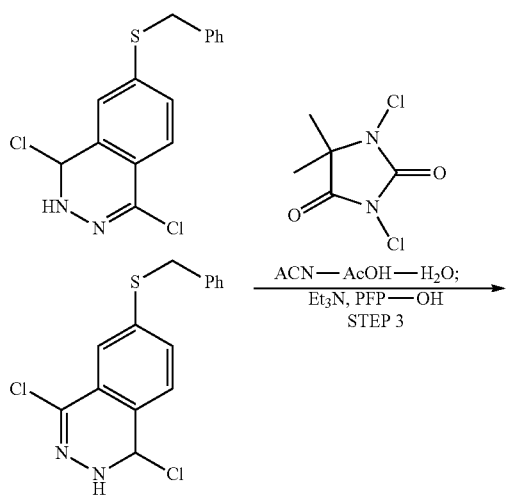

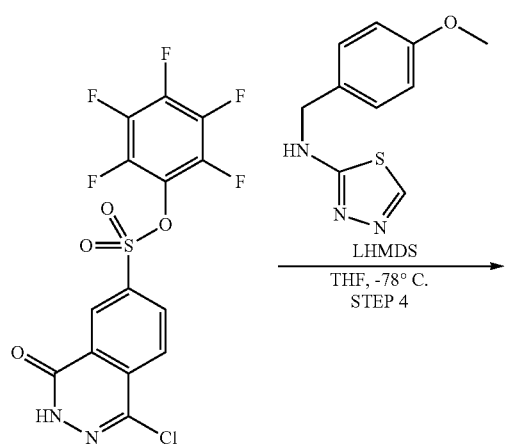

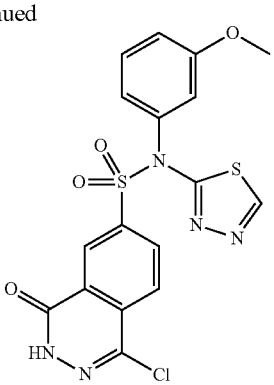

STEP 1: 7-BROMO-4-CHLOROPHTHALAZIN-1(2H)-ONE

A vial was charged with 6-bromo-1,4-dichlorophthalazine (5.0 g, 17.99 mmol, Synthonix), DMSO (19.99 ml), and water (4.00 ml). The reaction was heated to 100° C. and stirred for one hour. The reaction was diluted with water, cooled to 0° C. and stirred for 5 minutes. The solids were filtered, thoroughly washed with water, and dried under a nitrogen blanket overnight to afford a mixture of 7-bromo-4-chlorophthalazin-1(2H)-one and 6-bromo-4-chlorophthalazin-1(2H)-one (4.62 g, 17.80 mmol, 99% yield) as a white solid. m/z (ESI) 259.0 (M+H)$^+$.

STEP 2: 7-(BENZYLTHIO)-4-CHLOROPHTHALAZIN-1(2H)-ONE

A vial was charged with 7-bromo-4-chlorophthalazin-1 (2H)-one (mixture of isomers) (4.62 g, 17.80 mmol), xantphos (0.515 g, 0.890 mmol), and Pd$_2$(dba)$_3$ (0.408 g, 0.445 mmol). The flask was flushed with Ar (g), then dioxane (35.6 ml), benzyl mercaptan (2.211 ml, 18.69 mmol), and n,n-diisopropylethylamine (6.22 ml, 35.6 mmol) were added in sequence. The reaction was heated to 60° C. and stirred for one hour. The reaction was diluted with water and filtered. The solids were washed with water and dried overnight under a nitrogen blanket. The resulting solid was triturated with ethyl acetate and stirred until a uniform heterogenous mixture was obtained, about 1 hour. The solids were filtered, washed with ethyl acetate, and dried overnight under a nitrogen blanket to afford a mixture of 7-(benzylthio)-4-chlorophthalazin-1(2H)-one and 6-(benzylthio)-4-chlorophthalazin-1(2H)-one (4.55 g, 15.03 mmol, 84% yield) as a yellow solid. m/z (ESI) 303.0 (M+H)$^+$.

STEP 3: PERFLUOROPHENYL 1-CHLORO-4-OXO-4,4A-DIHYDROPHTHALAZINE-6-SULFONATE

A RBF was charged with 7-(benzylthio)-4-chlorophthalazin-1(8aH)-one (mixture of isomers) (4.55 g, 15.03 mmol), ACN (141 ml), acetic acid (5.30 ml), and water (3.54 ml) to give a thin suspension. The flask was cooled in an ice-bath for 10 min, then 1,3-dichloro-5,5-dimethylimidazolidine-2,4-dione (7.40 g, 37.6 mmol) was added in one portion, leading to a solution. The reaction was stirred for 15 minutes. 2,3,4,5,6-pentafluorophenol (3.15 ml, 30.1 mmol) was added followed by dropwise addition of triethylamine (5.24 ml, 37.6 mmol). The reaction was stirred for 30 minutes. The reaction was concentrated and purified via column chromatography (RediSep Gold 40 g, gradient elution 0-25% EtOAc:Heptane) to afford perfluorophenyl 1-chloro-4-oxo-4,4a-dihydrophthalazine-6-sulfonate (3.16 g, 7.41 mmol, 49.3% yield) as a white solid. m/z (ESI) 427.0 (M+H)+.

STEP 4: 1-CHLORO-N-(4-METHOXYBENZYL)-4-OXO-N-(1,3,4-THIADIAZOL-2-YL)-3,4-DIHYDROPHTHALAZINE-6-SULFONAMIDE

A solution of N-(4-methoxybenzyl)-1,3,4-thiadiazol-2-amine (0.856 g, 3.87 mmol) in tetrahydrofuran (14.06 ml) was cooled in a dry ice-acetone bath for 5 min. Lithium bis(trimethylsilyl)amide (1M in THF) (7.38 ml, 7.38 mmol) was added dropwise, then the flask was removed from the cooling bath for 5 min. The flask was again cooled into a dry ice-acetone bath for 20 min, resulting in the formation of a thick slurry. A solution of perfluorophenyl 1-chloro-4-oxo-3,4-dihydrophthalazine-6-sulfonate (1.5 g, 3.52 mmol) in THF (14 mL) was added dropwise, and the reaction was stirred for one hour. The reaction was quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by chromatography on an 80-g Redi-Sep Gold column with 0-100% EtOAc/Heptane to afford 1-chloro-N-(4-methoxybenzyl)-4-oxo-N-(1,3,4-thiadiazol-2-yl)-3,4-dihydrophthalazine-6-sulfonamide (0.649 g, 1.399 mmol, 39.8% yield) as a white solid. m/z (ESI) 486.0 (M+H)+.

Intermediate AB

CA. 1:1 MIXTURE OF 2-(4-CHLORO-3-FLUORO-5-METHYLPHENYL)-4,4,5,5-TETRAMETHYL-1,3,2-DIOXABOROLANE AND 2-(3-CHLORO-2-FLUORO-4-METHYLPHENYL)-4,4,5,5-TETRAMETHYL-1,3,2-DIOXABOROLANE

A RBF was charged with (1,5-cyclooctadiene)(methoxy)-iridium(i) dimer (0.069 g, 0.104 mmol), 4,4'-di-tert-butyl-2,2'-dipyridyl (0.056 g, 0.208 mmol), and bispin (1.862 g, 7.33 mmol). The flask was flushed with Ar (g), then hexanes (21.28 ml) was added. A reflux condenser was attached to the flask, and the flask was heated to 50° C. The flask was heated to 50° C. for 2 h. The mixture was diluted with water and stirred until bubbling had ceased, then extracted with EtOAc (2×). The combined organic extracts were dried over sodium sulfate, filtered, and concentrated. The residue was purified by chromatography on silica gel (50-g Redi-Sep Gold column, 25-g silica gel column, 0-20% EtOAc/Heptane) to give an 2.2 g of a clear oil that appeared to be a ca. 1:1 mixture of 2-(4-chloro-3-fluoro-5-methylphenyl)-4,4,5, 5-tetramethyl-1,3,2-dioxaborolane and 2-(3-chloro-2-fluoro-4-methylphenyl)-4,4,5,5-tetramethyl-1,3,2-dioxaborolane. This material was used directly in a Sukuzi reaction.

Intermediate AC

N-(4-METHOXYBENZYL)THIAZOL-4-AMINE

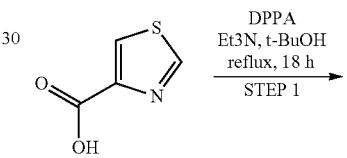

DPPA
Et3N, t-BuOH
reflux, 18 h
STEP 1

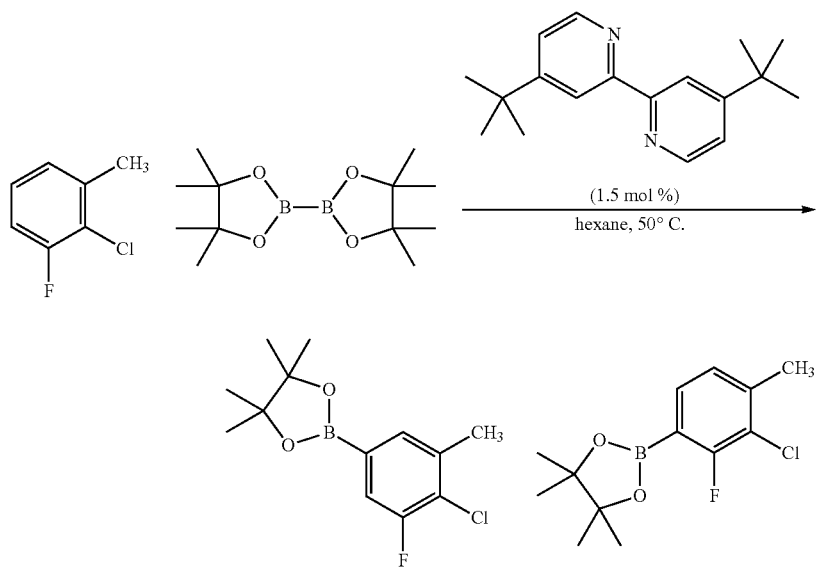

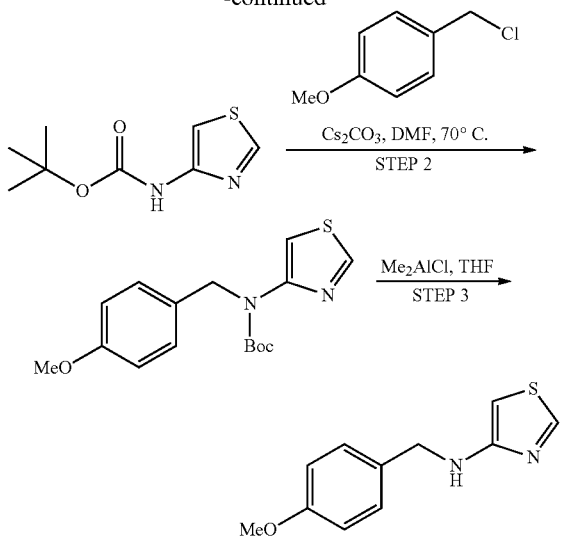

STEP 1: TERT-BUTYL THIAZOL-4-YLCARBAMATE

To a suspension of thiazole-4-carboxylic acid (19.6 g, 151 mmol, GLR) in tert-butyl alcohol (400 mL) was added triethyl amine (24.8 mL, 181 mmol, Finar) and diphenyl-phosphoryl azide (41.7 mL, 182 mmol, Aldrich) and the reaction mixture was heated at reflux for 18 h. The reaction mixture was cooled to room temperature and concentrated under reduced pressure. The residue was taken in ethyl acetate (500 mL), washed with water (500 mL) and then with saturated aqueous NaHCO$_3$ solution (500 mL). The organic layer was dried over sodium sulfate, filtered and concentrated under reduced pressure to obtain the crude material which was further purified by column chromatography (silica gel 100-200 mesh and 0-20% ethyl acetate in hexanes) to obtain tert-butyl thiazol-4-ylcarbamate (20.0 g, 66.6%) as off-white solid. TLC solvent system: 20% ethyl acetate in hexane. Product's R$_f$: 0.5. MS (ESI, positive ion) m/z=201 (M+1)$^+$. $^1$H NMR (400 MHz, DMSO) δ 10.21 (s, 1H), 8.89 (d, J=2.3 Hz, 1H), 7.23 (s, 1H), 1.46 (s, 9H).

STEP 2: TERT-BUTYL 4-METHOXYBENZYL (THIAZOL-4-YL)CARBAMATE

To a solution of tert-butyl thiazol-4-ylcarbamate (13.0 g, 64.9 mmol) in DMF (150 mL) was added Cs$_2$CO$_3$ (42.3 g, 130 mmol) and 1-(chloromethyl)-4-methoxybenzene (12.1 g, 78.0 mmol, Spectrochem). The reaction mixture was stirred at 80° C. for 6 h. The reaction mixture was allowed to cool to RT and water (500 mL) was added. The aqueous layer was extracted with diethyl ether (2×500 mL). The combined organic layer was dried over sodium sulfate, filtered and concentrated under reduced pressure to obtain the crude material which was further purified by column chromatography (silica gel 100-200 mesh and 0-20% ethyl acetate in hexanes) to obtain tert-butyl 4-methoxybenzyl (thiazol-4-yl)carbamate (15.0 g, 80%) as off-white solid. TLC solvent system: 20% ethyl acetate in hexanes. Product's R$_f$: 0.7. MS (ESI, positive ion) m/z=321 (M+1)$^+$. $^1$H NMR (400 MHz, DMSO) δ 8.95 (d, J=2.3 Hz, 1H), 7.42 (s, 1H), 7.14 (d, J=8.4 Hz, 2H), 6.90-6.75 (m, 2H), 5.02 (s, 2H), 3.70 (s, 3H), 1.42 (s, 9H).

STEP 3: N-(4-METHOXYBENZYL)THIAZOL-4-AMINE

To a solution of tert-butyl 4-methoxybenzyl(thiazol-4-yl) carbamate (20.0 g, 62.4 mmol) in THF (100 mL) was added Me$_2$AlCl (1M in THF, Aldrich) (93.6 mL, 93.6 mmol) at 0° C. The reaction was allowed to stir at room temperature for 5 h. The reaction mixture was poured into ice-cold water and extracted with ethyl acetate (2×500 mL). The combined organic layer was dried over sodium sulfate, filtered and concentrated under reduced pressure to obtain the crude material which was further purified by column chromatography (silica gel 100-200 mesh and 0-50% ethyl acetate in hexanes) to obtain N-(4-methoxybenzyl)thiazol-4-amine (9.8 g, 73%) as off-white solid. TLC solvent system: 30% ethyl acetate in hexanes. Product's R$_f$: 0.3. MS (ESI, positive ion) m/z=220.9 (M+1)$^+$. $^1$H NMR (400 MHz, DMSO) δ 8.73 (d, J=2.2 Hz, 1H), 7.28 (d, J=8.5 Hz, 2H), 6.96-6.76 (m, 2H), 6.54 (t, J=6.3 Hz, 1H), 5.76 (d, J=2.2 Hz, 1H), 4.18 (d, J=6.2 Hz, 2H), 3.71 (s, 3H).

Intermediate AD

(2-CHLORO-5-METHOXYPYRIDIN-4-YL)BORONIC ACID

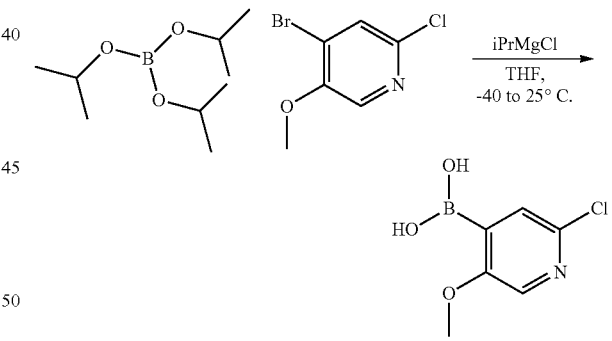

Dissolved 4-bromo-2-chloro-5-methoxypyridine (2 g, 8.99 mmol, Combi Blocks) in THF (30.0 ml) and cooled to −40 C in an acetonitrile/dry ice bath. Added iPrMgCl (8.99 ml, 17.98 mmol) and let stir for 30 min then added triisopropyl borate (4.17 ml, 17.98 mmol) and let warm to rt over 1 hr until reaction was complete by LCMS. Quenched reaction with 2 N HCl, and extracted 3 times with EtOAc and 2 times with DCM. The combined organic extracts were dried over sodium sulfate, filtered, and concentrated. Crude (2-chloro-5-methoxypyridin-4-yl)boronic acid (1.7 g, 9.07 mmol, 101% yield) was brought on to the next reaction as a tan solid without further purification. m/z (ESI) 188.1 (M+H)+.

Intermediate AE

3-BROMO-1-METHYL-1H-INDOLE-6-SULFONYL CHLORIDE

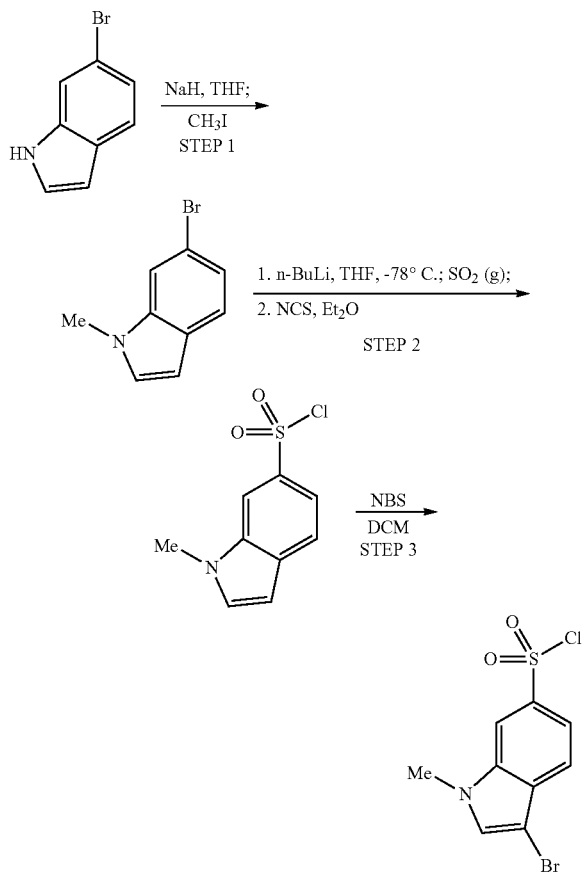

STEP 1: 6-BROMO-1-METHYL-1H-INDOLE

A 1-liter RBF was charged with 6-bromo-1H-indole (14.9 g, 76.0 mmol) and THF (150 ml) to give a dark maroon solution. The flask was put under a $N_2$ sweep, and sodium hydride (60 wt %) (3.64 g, 91.0 mmol) was added in several portions over 15 min. The resulting mixture was stirred for 20 min, then iodomethane (5.94 ml, 95.0 mmol) was added via syringe. Within a few minutes, an exotherm was observed. After stirring for 20 min, the mixture was concentrated in vacuo, and the residue was taken up in saturated aq. sodium bicarbonate solution and extracted with DCM (3×). The combined organic extracts were dried over sodium sulfate, filtered, and concentrated. The crude product was purified by chromatography on silica gel (0 to 40% EtOAc/heptane) to afford 6-bromo-1-methyl-1H-indole (14.4 g, 91% yield) as lightly colored oil. $^1$H NMR (400 MHz, CDCl$_3$) δ=7.51-7.46 (m, 2 H), 7.24-7.19 (m, 1 H), 7.03 (d, J=3.1 Hz, 1 H), 6.47 (dd, J=0.9, 3.1 Hz, 1 H), 3.77 (s, 3 H).

STEP 2: 1-METHYL-1H-INDOLE-6-SULFONYL CHLORIDE

A 1-L RBF was charged 6-bromo-1-methyl-1H-indole (14.4 g, 68.7 mmol). The flask was flushed with Ar, then THF (300 mL) was added to give a clear solution. The flask was cooled in a dry ice-acetone bath for 20 min, then n-butyl lithium (36.0 ml, 76.0 mmol) was added dropwise over 10 min to give a white slurry. The mixture was stirred for 20 min, then sulfur dioxide was added to the mixture via syringe for 15 min. The mixture was then warmed to 0° C. and concentrated in vacuo. The residue was suspended in diethyl ether (400 mL). The flask was rotated in a 50° C. oil bath (on the rotovap) for a couple of minutes, leading to a finer solid. The mixture was cooled to 0° C., then n-chlorosuccinimide (9.18 g, 68.7 mmol) was added in one portion. The mixture was stirred for 15 min, then silica gel (20 g) was added, and the mixture was stirred for another 5 min at 0° C. before being filtered through a pad of Celite® (diatomaceous earth). The filter pad was washed twice with diethyl ether, and the filtrates were combined. The combined solution was concentrated, then taken up in diethyl ether. The suspension was placed in a 5° C. refrigerator overnight. In the morning, the mixture was filtered, and the collected solid was washed with ice-cold diethyl ether (3×) then air-dried for 5 min to give about 3.8 g of a yellow solid. The filtrate was concentrated, and the residue was purified by chromatography on silica gel (0 to 40% EtOAc/heptane). The fractions containing product were combined with the solid described above, dissolved in DCM, and concentrated to give 1-methyl-1H-indole-6-sulfonyl chloride (9.59 g, 60.7% yield) as a yellow solid. $^1$H NMR (400 MHz, CDCl$_3$) δ=8.08 (td, J=0.8, 1.6 Hz, 1 H), 7.82-7.72 (m, 2 H), 7.39 (d, J=3.0 Hz, 1 H), 3.93 (s, 3 H).

STEP 3: 3-BROMO-1-METHYL-1H-INDOLE-6-SULFONYL CHLORIDE

A solution of 1-methyl-1H-indole-6-sulfonyl chloride (8.76 g, 38.2 mmol) in DCM (190 ml) was treated with n-bromosuccinimide (7.47 g, 42.0 mmol). The resulting mixture was stirred in the dark for 2.5 h, then filtered through a silica gel pad. The filter pad was washed with DCM (2×), and the filtrates were combined. The combined solution was concentrated to give 3-bromo-1-methyl-1H-indole-6-sulfonyl chloride (11.6 g, 98% yield) as an orange solid. $^1$H NMR (400 MHz, CDCl$_3$) δ=8.08 (dd, J=0.4, 1.7 Hz, 1 H), 7.87-7.80 (m, 1 H), 7.79-7.70 (m, 1 H), 7.42 (s, 1 H), 3.93 (s, 3 H).

Intermediate AF

(2,3'-DIFLUORO-5-METHOXY-[1,1'-BIPHENYL]-4-YL)BORONIC ACID

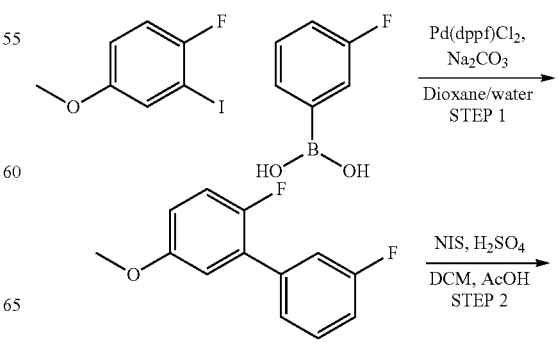

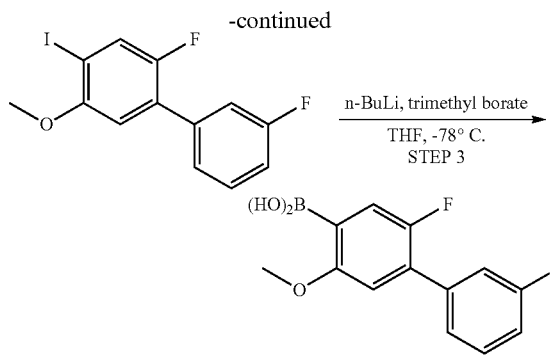

STEP-1: SYNTHESIS OF 2,3'-DIFLUORO-5-METHOXY-1,1'-BIPHENYL

To a solution of 1-fluoro-2-iodo-4-methoxybenzene (10.0 g, 39.7 mmol), (3-fluorophenyl)boronic acid (7.22 g, 51.5 mmol), 2M aqueous sodium carbonate (49.6 mL, 99.2 mmol) in dioxane (200 mL) was added $PdCl_2(dppf)$-DCM complex (3.24 g, 3.69 mmol). The reaction mixture was degassed with nitrogen for 10 minutes and then heated at 90° C. for 16 h. After completion, the reaction mixture was diluted with water (150 mL) and extracted with ethyl acetate (2×300 mL). The organic layer was dried over sodium sulfate and concentrated under reduced pressure to obtain the crude material which was purified by column chromatography (silica gel: 100-200; elution: 0-20% ethyl acetate in hexanes) to get 2,3'-difluoro-5-methoxy-1,1'-biphenyl (8.5 g, 97%) as off-white solid. TLC solvent system: 100% hexanes, Product's $R_f$: 0.7; MS (ESI, positive ion) m/z; No ionization was detected.

STEP-2: SYNTHESIS OF 2,3'-DIFLUORO-4-IODO-5-METHOXY-1,1'-BIPHENYL

To a solution of 2,3'-difluoro-5-methoxy-1,1'-biphenyl (8.50 g, 38.6 mmol) in DCM (100 mL) and acetic acid (100 mL) was added sulfuric acid (1.12 mL, 21.2 mmol). N-Iodosuccinimide (10.5 g, 38.6 mmol) was added and the reaction mixture was stirred at ambient temperature for 16 h. After completion, the reaction mixture was diluted with water (200 mL) and extracted with ethyl acetate (2×250 mL). The organic layer was dried over sodium sulfate and concentrated to obtain crude material which was purified by column chromatography (silica gel: 100-200; elution: 1% ethyl acetate in hexanes) to get 2,3'-difluoro-4-iodo-5-methoxy-1,1'-biphenyl (9.0 g, 68%) as oil. TLC solvent system: 100% hexanes, Product's $R_f$: 0.6 MS (ESI, positive ion) m/z; No ionization.

STEP-3: SYNTHESIS OF (2,3'-DIFLUORO-5-METHOXY-[1,1'-BIPHENYL]-4-YL)BORONIC ACID

To a solution of 2,3'-difluoro-4-iodo-5-methoxy-1,1'-biphenyl (9.00 g, 26.1 mmol) in THF (90 mL) was added n-BuLi (1.6 M in hexanes) (25.0 mL, 39.1 mmol) at −78° C. The reaction mixture was stirred at same temperature for 30 minutes. Trimethyl borate (3.23 g, 31.3 mmol) was added at −78° C. and the reaction mixture was stirred at same temperature for another 1 h. After completion, the reaction mixture was quenched with 1N HCl (100 mL) at −78° C. and was stirred at room temperature for 10 minutes. The aqueous layer was extracted with ethyl acetate (2×150 mL), organic layer was dried over sodium sulfate and concentrated to obtain crude material which was purified by column chromatography (silica:100-200; elution: 0-10% ethyl acetate in hexanes) to get (2,3'-difluoro-5-methoxy-[1,1'-biphenyl]-4-yl)boronic acid as light yellow solid (3.8 g, 48%). TLC solvent system: 20% ethyl acetate in hexanes, Product's $R_f$: 0.4. MS (ESI, positive ion) m/z; No ionization. $^1H$ NMR (400 MHz, DMSO) δ 7.92 (s, 2H), 7.54 (q, J=7.4 Hz, 1H), 7.46 (d, J=8.5 Hz, 2H), 7.35 (d, J=10.8 Hz, 1H), 7.27 (td, J=9.0, 2.5 Hz, 1H), 7.08 (d, J=5.9 Hz, 1H), 3.86 (s, 3H).

Intermediate AG

2-(5-CHLORO-4-(DIFLUOROMETHYL)-2-METHOXYPHENYL)-4,4,5,5-TETRAMETHYL-1,3,2-DIOXABOROLANE

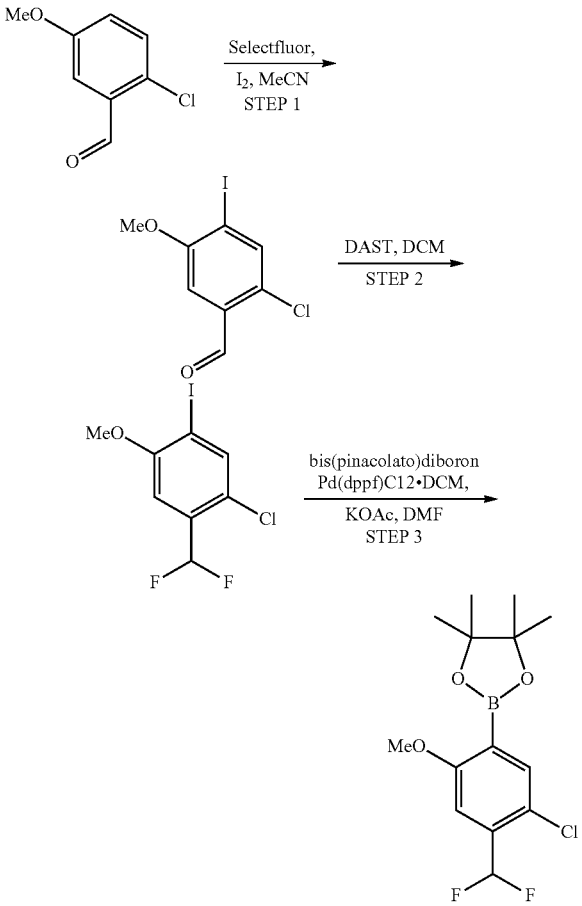

STEP 1: 2-CHLORO-4-IODO-5-METHOXYBENZALDEHYDE

A solution of 2-chloro-5-methoxybenzaldehyde (10.00 g, 58.6 mmol) and selectfluor (21.80 g, 61.6 mmol) in 100 mL acetonitrile was treated with iodine (16.37 g, 64.5 mmol) and was heated to 60° C. for 2 hours. The reaction mixture was then treated with saturated NaHCO3 solution, and was allowed to stir at room temperature for one hour. The reaction mixture was extracted with DCM, the organics dried over MgSO4 and concentrated. Purification of the crude residue by silica gel column chromatography (0-20% EtOAc/heptane) gave 2-chloro-4-iodo-5-methoxybenzaldehyde (7.750 g, 26.1 mmol, 44.6% yield). m/z (ESI) 298.8 (M+H)+.

STEP 2: 1-CHLORO-2-(DIFLUOROMETHYL)-5-IODO-4-METHOXYBENZENE

A solution of 2-chloro-4-iodo-5-methoxybenzaldehyde (7.75 g, 26.1 mmol) in 100 mL DCM was cooled to 0° C. and was treated with DAST (4.14 ml, 31.4 mmol). After stirring for 30 minutes, the cooling bath was removed, and the reaction mixture was allowed to stir at room temperature overnight. The reaction mixture was then quenched with saturated NaHCO3 solution. The layers were separated, and the organics were dried over MgSO4 and concentrated. The crude residue was used in the next step without purification. m/z (ESI) no ion observed.

STEP 3: 2-(5-CHLORO-4-(DIFLUOROMETHYL)-2-METHOXYPHENYL)-4,4,5,5-TETRAMETHYL-1,3,2-DIOXABOROLANE

The crude residue from step one was dissovled in 30 mL DMF and was treated with bis(pinacolato)diboron (9.96 g, 39.2 mmol), PdCl2(dppf)-CH2Cl2adduct (1.067 g, 1.307 mmol), and potassium acetate (10.26 g, 105 mmol) and the reaction mixture was heated to 100° C. overnight. The reaction mixture was then allowed to cool to room temperature and was diluted with ether. The reaction mixture was filtered through a plug of celite and the filtrate was concentrated. Purification of the crude residue by silica gel column chromatography (0-20% EtOAc/heptane) gave 2-(5-chloro-4-(difluoromethyl)-2-methoxyphenyl)-4,4,5,5-tetramethyl-1,3,2-dioxaborolane (9.90 g, 31.1 mmol, 119% yield) with minor impurities. m/z (ESI) 319.2 (M+H)+.

Intermediate AH

5-BROMONAPHTHALENE-2-SULFONYL CHLORIDE

STEP-1: 5-BROMONAPHTHALENE-2-SULFONIC ACID

To an ice cooled solution of 5-aminonaphthalene-2-sulfonic acid (200 g, 897 mmol, Alfa Aesar) in aqueous NaOH (0.850 M, 1262 mL) was added aqueous HBr (48%, 272 mL) dropwise. The resulting suspension was cooled to −5° C. and a solution of NaNO2 (68.0 g, 986 mmol, Spectrochem) in water (200 mL) was added drop wise with stirring, keeping the internal temperature below 0° C. The reaction mixture was stirred at −5° C. to 0° C. for 30 min. Urea (6.40 g, 108 mmol, Spectrochem) was added to decompose excess nitrite. The diazonium salt was added dropwise (over 30 min) with stirring to a heated (70° C.) solution of CuBr (129 g, 897 mmol, Spectrochem) in aqueous HBr (48%, 546 mL). The mixture was then stirred at 80° C. for 30 mins. The mixture was cooled to room temperature and stirred for 12 h. The precipitate thus formed were filtered, washed with water, and dried under vacuum to get 5-bromonaphthalene-2-sulfonic acid (180 g, 70%) as a grey solid. MS (ESI, negative ion) m/z; 286.1 (M−1). 1H NMR (400 MHz, DMSO) δ 8.22 (d, J=1.7 Hz, 1H), 8.08 (t, J=8.8 Hz, 2H), 7.94-7.81 (m, 2H), 7.45 (t, J=7.8 Hz, 1H).

STEP-2: 5-BROMONAPHTHALENE-2-SULFONYL CHLORIDE

To a suspension of 5-bromonaphthalene-2-sulfonic acid (25.0 g, 87 mmol) in anhydrous DMF (250 mL) was added SOCl2 (20.7 g, 174.1 mmol, Spectrochem) dropwise keeping the temperature below 30° C. The resulting yellow solution was stirred at room temperature for 1.5 h. The reaction mixture was diluted with diethyl ether (1 L) and washed with ice-water (500 mL). The combined organic layer was dried over sodium sulfate, filtered and concentrated under reduced pressure to obtain crude 5-bromonaphthalene-2-sulfonyl chloride (25.0 g, crude) as orange solid which was immediately used for next reaction. TLC solvent system: 20% ethyl acetate in hexanes. Product's Rf: 0.5. Note: The compound is not very stable at room temperature and should be used immediately in next step.

Intermediate AI

N-(4-METHOXYBENZYL)-N-(PYRIMIDIN-4-YL)-5-(4,4,5,5-TETRAMETHYL-1,3,2-DIOXABOROLAN-2-YL)NAPHTHALENE-2-SULFONAMIDE

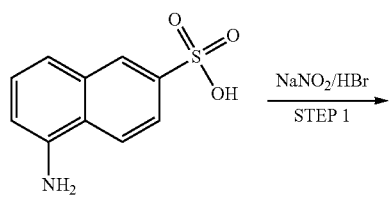

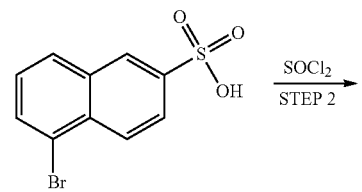

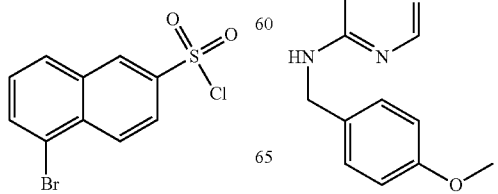

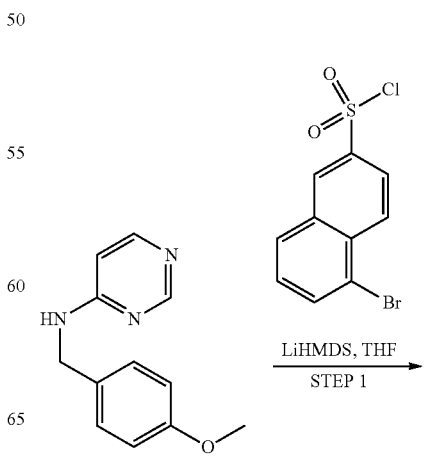

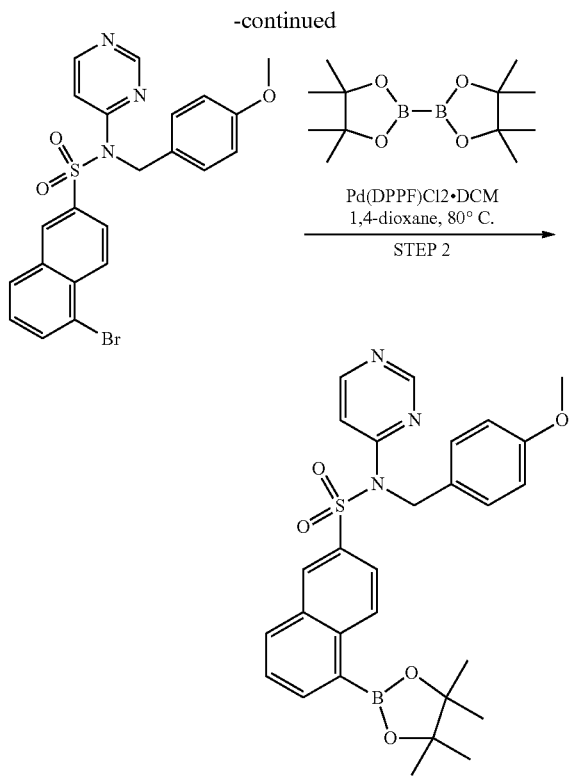

STEP-1: 5-BROMO-N-(4-METHOXYBENZYL)-N-(PYRIMIDIN-4-YL)NAPHTHALENE-2-SULFONAMIDE

To a solution of N-(4-methoxybenzyl)pyrimidin-4-amine (20.0 g, 92.9 mmol) (Intermediate U) in THF (200 mL) was added LiHMDS (1M in THF, 185.9 mL, mmol, Aldrich) at −78° C. The reaction mixture was stirred at 0° C. for 20 min. The reaction mixture was recooled to −78° C. and a solution of 5-bromonaphthalene-2-sulfonyl chloride (42.5 g, 139 mmol, Intermediate AH) in THF (100 mL) was added. The reaction mixture was allowed to stir at RT for 1 h. The reaction was quenched with ice cold water (500 mL) and extracted with ethyl acetate (2×500 mL). The combined organic layer was dried over sodium sulfate, filtered and concentrated under reduced pressure to obtain the crude material which was purified by column chromatography (neutral alumina, elution 0-10% ethyl acetate in hexanes) to obtain 5-bromo-N-(4-methoxybenzyl)-N-(pyrimidin-4-yl)naphthalene-2-sulfonamide (4.0 g, 9.0%) as off white solid. TLC solvent system: 30% ethyl acetate in hexanes. Product's $R_f$: 0.4. MS (ESI, positive ion) m/z; 484.1 (M+1). $^1$H NMR (400 MHz, DMSO) δ 8.83 (s, 1H), 8.75 (d, J=1.8 Hz, 1H), 8.59 (d, J=5.9 Hz, 1H), 8.27 (dd, J=15.1, 8.6 Hz, 2H), 8.12 (d, J=7.4 Hz, 1H), 8.01 (dd, J=9.0, 1.9 Hz, 1H), 7.63 (t, J=7.9 Hz, 1H), 7.50 (d, J=5.9 Hz, 1H), 7.29 (d, J=8.7 Hz, 2H), 6.88 (d, J=8.7 Hz, 2H), 5.31 (s, 2H), 3.71 (s, 3H).

STEP-2: N-(2,4-DIMETHOXYBENZYL)-N-(PYRIMIDIN-4-YL)-5-(4,4,5,5-TETRAMETHYL-1,3,2-DIOXABOROLAN-2-YL) NAPHTHALENE-2-SULFONAMIDE

A mixture of 5-bromo-N-(4-methoxybenzyl)-N-(pyrimidin-4-yl)naphthalene-2-sulfonamide (3.0 g, 6.19 mmol), bis(pinacolato)diboron (2.35 g, 9.28 mmol, RCP) and KOAc (1.8 g, 18.6 mmol, Qualigens) in 1,4-dioxane (20 mL) was degassed with N$_2$ for 10 min. PdCl$_2$(DPPF)-DCM (252 mg, 0.309 mmol, GLR) was added and the reaction mixture was heated at 80° C. for 5 h. The reaction mixture was cooled to RT, diluted with ethyl acetate (100 mL) and passed through a celite bed. The filtrate was washed with water (50 mL). The organic layer was dried over sodium sulfate, filtered and concentrated under reduced pressure to obtain the crude material which was purified by column chromatography (silica gel: 100-200 mesh, elution 0-20% ethyl acetate in hexanes) to obtain N-(4-methoxybenzyl)-N-(pyrimidin-4-yl)-5-(4,4,5,5-tetramethyl-1,3,2-dioxaborolan-2-yl)naphthalene-2-sulfonamide (1.9 g, 56%) as off white solid. TLC solvent system: 50% ethyl acetate in hexanes. Product's $R_f$: 0.5. MS (ESI, positive ion) m/z; 532.1 (M+1). $^1$H NMR (400 MHz, DMSO) δ 8.82 (s, 1H), 8.80-8.73 (m, 1H), 8.66 (d, J=2.2 Hz, 1H), 8.57 (d, J=5.9 Hz, 1H), 8.30 (d, J=8.4 Hz, 1H), 8.16 (dd, J=7.1, 1.3 Hz, 1H), 7.96-7.86 (m, 1H), 7.70 (t, J=7.6 Hz, 1H), 7.57-7.51 (m, 1H), 7.35-7.27 (m, 2H), 6.93-6.84 (m, 2H), 5.32 (s, 2H), 3.71 (s, 3H), 1.37 (s, 12H).

Intermediate AJ

2-(3,5-DIFLUOROPHENYL)-5-IODO-6-METHOXYNICOTINONITRILE

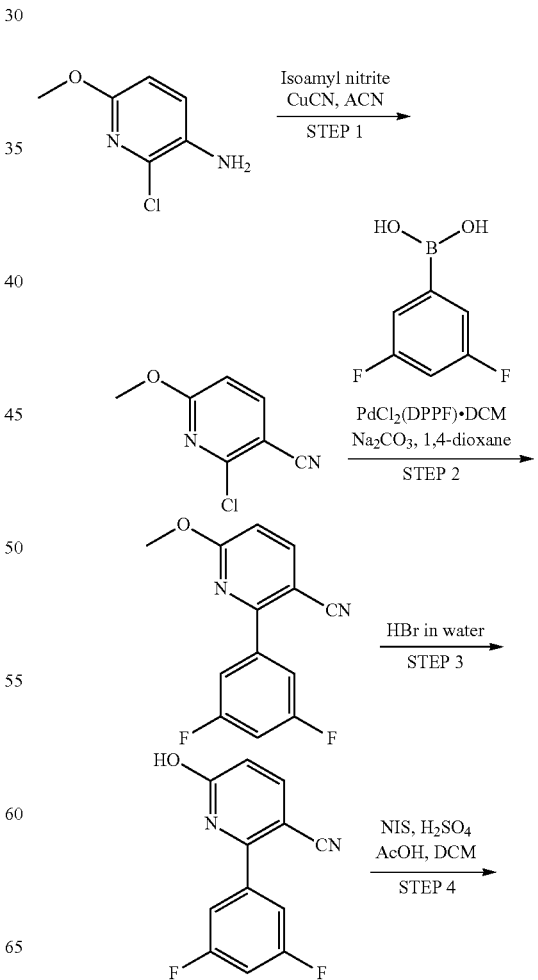

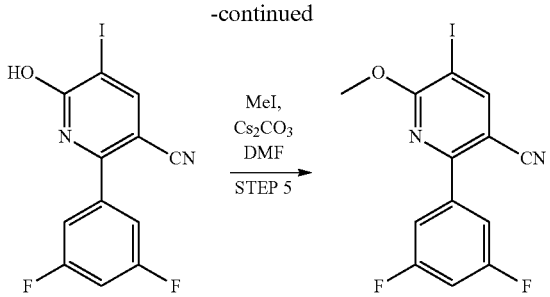

STEP-1: 2-CHLORO-6-METHOXYNICOTINONITRILE

To a suspension of copper cyanide (13.6 g, 152 mmol, Spectrochem) in acetonitrile (500 mL) was added isoamyl nitrite (25.4 mL, 190 mmol). A solution of 2-chloro-6-methoxypyridin-3-amine (20.0 g, 127 mmol, Vyas Bio) in acetonitrile (100 mL) was added to the above suspension dropwise. The reaction mixture was heated at 65° C. for 4 h. After completion, the reaction mixture was diluted with water (500 mL) and extracted with ethyl acetate (2×500 mL). The organic layer was dried over sodium sulfate and concentrated to obtain crude material which was purified by column chromatography (silica: 100-200; elution: 5% ethyl acetate in hexanes) to get 2-chloro-6-methoxynicotinonitrile (5.0 g, 23.4%) as brown solid. TLC solvent system: 20% ethyl acetate in hexanes, Product's $R_f$: 0.4. MS (ESI, positive ion) m/z; No ionization. $^1$H NMR (400 MHz, DMSO) δ 8.28 (d, J=8.5 Hz, 1H), 7.05 (d, J=8.5 Hz, 1H), 3.94 (s, 3H).

STEP-2: 2-(3,5-DIFLUOROPHENYL)-6-METHOXYNICOTINONITRILE

To a solution of 2-chloro-6-methoxynicotinonitrile (5.00 g, 29.6 mmol), (3,5-difluorophenyl)boronic acid (6.05 g, 38.5 mmol, Combi Block) 2M aqueous sodium carbonate (37.0 mL, 74.1 mmol) in 1,4-dioxane (75 mL) was added $PdCl_2$ (DPPF).DCM complex (2.42 g, 2.96 mmol). The reaction mixture was degassed with nitrogen for 10 minutes and then heated at 90° C. for 16 h. After completion, the reaction mixture was diluted with water (100 mL) and extracted with ethyl acetate (2×150 mL). The organic layer was dried over sodium sulfate and concentrated under reduced pressure to obtain the crude material which was purified by column chromatography (silica: 100-200; elution: 5% ethyl acetate in hexanes) to get 2-(3,5-difluorophenyl)-6-methoxynicotinonitrile (3.5 g, 48%) as yellow solid. TLC solvent system: 20% ethyl acetate in hexanes, Product's $R_f$: 0.3. MS (ESI, positive ion) m/z; No ionization. $^1$H NMR (400 MHz, DMSO) δ 8.29 (d, J=8.6 Hz, 1H), 7.65 (d, J=7.5 Hz, 2H), 7.50 (t, J=9.4 Hz, 1H), 7.09 (d, J=8.6 Hz, 1H), 4.01 (s, 3H).

STEP-3: 2-(3,5-DIFLUOROPHENYL)-6-HYDROXYNICOTINONITRILE

A solution of 2-(3,5-difluorophenyl)-6-methoxynicotinonitrile (3.50 g, 14.2 mmol) in hydrobromic acid (~47% in water) (70 mL) was heated at 100° C. for 16 h. After completion, the reaction mixture was diluted with water (100 mL) and quenched with solid sodium bicarbonate until the effervescence subsides. The aqueous layer was extracted with ethyl acetate (2×200 mL). The organic layer was dried over sodium sulfate and concentrated to get 2-(3,5-difluorophenyl)-6-hydroxynicotinonitrile (3.00 g, 91%) as crude orange solid. TLC solvent system: 40% ethyl acetate in hexanes, Product's $R_f$: 0.3. MS (ESI, positive ion) m/z; No ionization. $^1$H NMR (400 MHz, DMSO) δ 12.55 (s, 1H), 7.88 (d, J=9.2 Hz, 1H), 7.68-7.37 (m, 3H), 6.60 (d, J=9.4 Hz, 1H).

STEP-4: 2-(3,5-DIFLUOROPHENYL)-5-IODO-6-METHOXYNICOTINONITRILE

To a solution of 2-(3,5-difluorophenyl)-6-hydroxynicotinonitrile (3.00 g, 12.9 mmol) in DCM (40 mL) and acetic acid (40 mL) was added sulfuric acid (0.370 mL, 7.11 mmol). N-iodosuccinimide (2.90 g, 12.9 mmol) was added and the reaction mixture was stirred at ambient temperature for 16 h. After completion, the reaction mixture was diluted with water (150 mL) and extracted with ethyl acetate (2×100 mL). The organic layer was dried over sodium sulfate and concentrated to obtain crude 2-(3,5-difluorophenyl)-6-hydroxy-5-iodonicotinonitrile (4.5 g, crude) as white solid. TLC solvent system: 40% ethyl acetate in hexanes, Product's $R_f$: 0.4. MS (ESI, positive ion) m/z; No ionization.

STEP-5: 2-(3,5-DIFLUOROPHENYL)-5-IODO-6-METHOXYNICOTINONITRILE

To a solution of 2-(3,5-difluorophenyl)-6-hydroxy-5-iodonicotinonitrile (4.50 g, 12.5 mmol) in DMF (50 mL) was added cesium carbonate (10.2 g, 31.4 mmol). Methyl iodide (1.56 mL, 25.1 mmol) was added and the reaction mixture was stirred at ambient temperature for 16 h. After completion, the reaction mixture was diluted with water (200 mL) and extracted with ethyl acetate (2×100 mL). The organic layer was dried over sodium sulfate and concentrated to obtain crude material which was purified by column chromatography (silica: 100-200; elution: pure hexanes) to get 2-(3,5-difluorophenyl)-5-iodo-6-methoxynicotinonitrile (370 mg, 8% over two steps) as white solid. TLC solvent system: 20% ethyl acetate in hexanes, Product's $R_f$: 0.6. MS (ESI, positive ion) m/z; No ionization. $^1$H NMR (400 MHz, DMSO) δ 8.81 (s, 1H), 7.66 (td, J=7.2, 4.9 Hz, 2H), 7.51 (tt, J=9.4, 2.5 Hz, 1H), 4.05 (s, 3H).

Intermediate QQQQ

4-CHLORO-N-(2,4-DIMETHOXYBENZYL)-N-(1,2,4-THIADIAZOL-5-YL)QUINOLINE-7-SULFONAMIDE

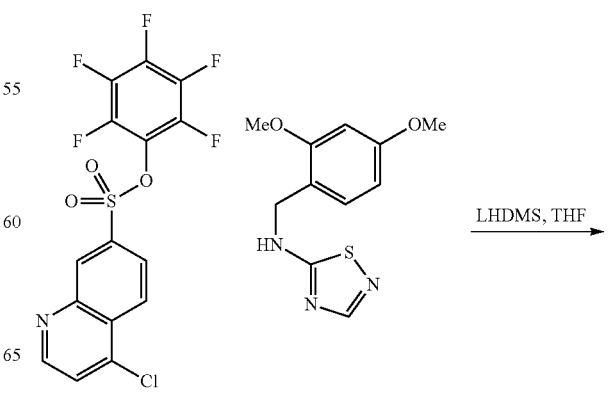

293
-continued

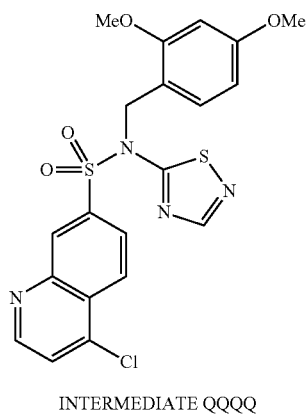

INTERMEDIATE QQQQ

A flask was charged with N-(2,4-dimethoxybenzyl)-1,2,4-thiadiazol-5-amine (302 mg, 1.204 mmol) and THF (5471 µl to give a clear solution. The flask was cooled in a dry ice-acetone bath for 5 min, and then a solution of perfluorophenyl 4-chloroquinoline-7-sulfonate (448.3 mg, 1.094 mmol) in THF (1 mL with a 0.5 mL syringe wash) was added drop wise. After 1 h, the mixture was diluted with saturated aq ammonium chloride, water, and EtOAc, and the layers were separated. The organic layer was dried over sodium sulfate, filtered, and concentrated. The residue was purified by chromatography on silica gel (40-g Redi-Sep Gold column, 20-70% EtOAc/Heptane) to give an off-white solid. The solid was taken up in heptane and filtered. The collected solid was washed with heptane (2×), then dried under a stream of $N_2$ (g) for 2 h to give 4-chloro-N-(2,4-dimethoxybenzyl)-N-(1,2,4-thiadiazol-5-yl)quinoline-7-sulfonamide (426 mg, 0.893 mmol, 82% yield) as a white solid. m/z (ESI) 477.0 (M+H)+.

Intermediate SSSS (2-CHLORO-3'-FLUORO-5-METHOXY-[1,1'-BI-PHENYL]-4-YL)BORONIC ACID

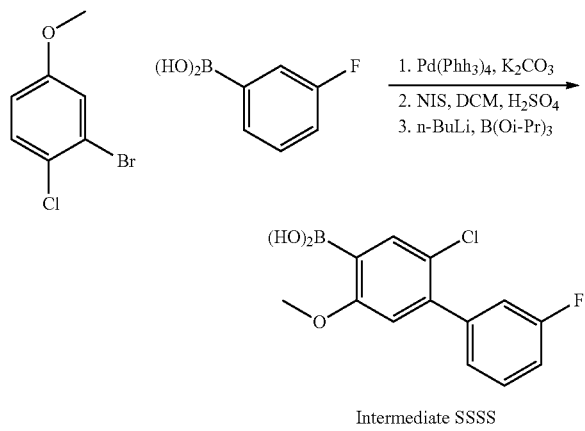

Intermediate SSSS

294
STEP 1: 2-CHLORO-3'-FLUORO-5-METHOXY-1,1'-BIPHENYL

A round-bottom flask was charged with 3-bromo-4-chloroanisole (1.625 ml, 7.34 mmol), (3-fluorophenyl)boronic acid (1.129 g, 8.07 mmol), potassium carbonate (3.04 g, 22.01 mmol), and tetrakistriphenylphosphine palladium (0) (0.424 g, 0.367 mmol). The flask was flushed with Ar (g), then 1,4-dioxane (19.57 ml) and water (4.89 ml) were added. A reflux condenser was attached, and the flask was lowered into a 90° C. heating bath. After 2 h, the mixture was cooled, diluted with ethyl acetate, and washed with brine. The organic layer was dried over sodium sulfate, filtered, and concentrated. The residue was purified by chromatography on silica gel (80-g Redi-Sep Gold column, 0-10% EtOAc/Heptane) to give an oily solid as product that was used directly in the next step. m/z (ESI) 281.1 (M+H)+.

STEP 2: 2-CHLORO-3'-FLUORO-4-IODO-5-METHOXY-1,1'-BIPHENYL

A round-bottom flask was charged with 2-chloro-3'-fluoro-5-methoxy-1,1'-biphenyl (1.288 g, 5.44 mmol), DCM (8.00 ml), AcOH (8.00 ml), and sulfuric acid (0.160 ml, 2.99 mmol) to give a clear solution. n-Iodosuccinimide (1.224 g, 5.44 mmol) was added in one portion to give a maroon-colored solution. After 7 h, the mixture was diluted with DCM, washed with water, washed with saturated aq. sodium thiosulfate, dried over sodium sulfate, filtered, and concentrated. The residue was purified by chromatography on silica gel (40-g Redi-Sep Gold column, 25-g silica gel column, 0-5% EtOAc/Heptane) give 2-chloro-3'-fluoro-4-iodo-5-methoxy-1,1'-biphenyl (1.68 g, 4.63 mmol, 85% yield) as a clear oil. m/z (ESI) 362.0 (M+H)+.

STEP 3: (2-CHLORO-3'-FLUORO-5-METHOXY-[1,1'-BIPHENYL]-4-YL)BORONIC ACID

A round-bottom flask was charged with 2-chloro-3'-fluoro-4-iodo-5-methoxy-1,1'-biphenyl (1.68 g, 4.63 mmol), triisopropyl borate (1.399 ml, 6.02 mmol), and THF (23.17 ml). The flask was cooled in a dry ice-acetone bath for 10 min, then n-butyllithium (2.5 M in hexane) (2.409 ml, 6.02 mmol) was added drop wise over 1 min. After 40 min, a solution of 2 N aq. NaOH (25 mL) was added. The resulting biphasic mixture was stirred for 10 min, and then partitioned between water and ether. The layers were separated, and the ethereal layer was extracted with water (2×). The combined aq. extracts were washed with ether, and the ethereal layer was back-extracted with water. The combined aq. layers were acidified with 3N aq. HCl (50 mL), and the aq. mixture was extracted with DCM (3×). The combined DCM-layers were dried over sodium sulfate, filtered, and concentrated to give (2-chloro-3'-fluoro-5-methoxy-[1,1'-biphenyl]-4-yl)boronic acid (0.859 g, 3.06 mmol, 66.1% yield) as an oily solid. m/z (ESI) 281.1 (M+H)+.

295
Intermediate TTTT

PERFLUOROPHENYL 1-(2-CHLORO-3'-FLUORO-5-METHOXY-[1,1'-BIPHENYL]-4-YL)ISOQUINOLINE-6-SULFONATE

296
Intermediate WWWW 1-(4-CHLORO-5-CYANO-2-METHOXYPHENYL)-N-(ISOXAZOL-3-YL)ISOQUINOLINE-6-SULFONAMIDE

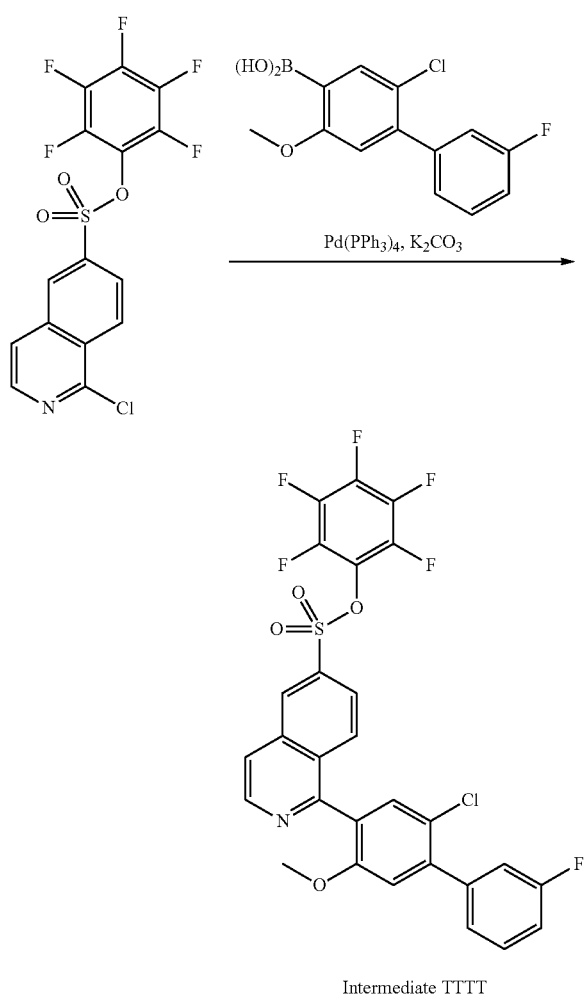

Intermediate TTTT

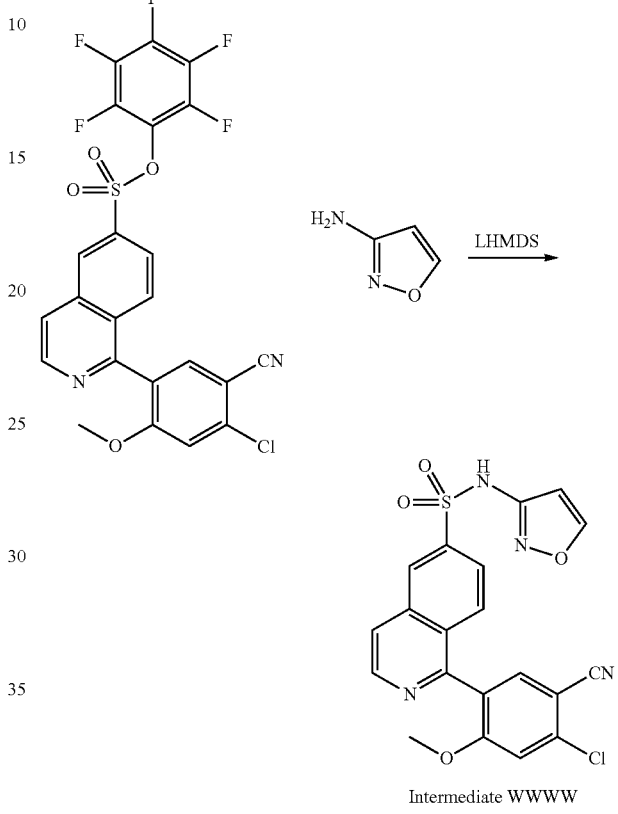

Intermediate WWWW

A round-bottom flask was charged with perfluorophenyl 1-chloroisoquinoline-6-sulfonate (from Step 1 of Example 73, 500 mg, 1.220 mmol), (2-chloro-3'-fluoro-5-methoxy-[1,1'-biphenyl]-4-yl)boronic acid (Intermediate SSSS; 479 mg, 1.709 mmol) potassium carbonate (506 mg, 3.66 mmol), and Pd(Ph₃P)₄ (141 mg, 0.122 mmol). The vial was flushed with Ar (g), then 1,4-dioxane (4576 µl) and water (1525 µl) were added. The flask was fitted with a reflux condenser and heated in a 50° C. heating bath for 40 min. The mixture was partitioned between water and EtOAc. The layers were separated, and the organic layer was washed with brine, dried over sodium sulfate, filtered, and concentrated. The residue was purified by chromatography on silica gel (40-g Redi-Sep Gold column, 25-g silica gel loading column, 0-50% EtOAc/Heptane) to give perfluorophenyl 1-(2-chloro-3'-fluoro-5-methoxy-[1,1'-biphenyl]-4-yl)isoquinoline-6-sulfonate (593.7 mg, 0.973 mmol, 80% yield) as a white foam. m/z (ESI) 609.9 (M+H)$^+$.

A round-bottom flask was charged with perfluorophenyl 1-(4-chloro-5-cyano-2-methoxyphenyl)isoquinoline-6-sulfonate (INTERMEDIATE VVVV, 257 mg, 0.475 mmol), isoxazol-3-amine (77 µl, 1.045 mmol), and THF (3 mL) to give a clear solution. The flask was cooled in an ice-water bath for 10 min, then lithium bis(trimethylsilyl)amide (1M in THF) (608 µl, 0.608 mmol) was added. After 40 min, additional portions of isoxazol-3-amine (77 µl, 1.045 mmol) and lithium bis(trimethylsilyl)amide (1M in THF) (608 µl, 0.608 mmol) were added. Following an additional 10 min of stirring, the reaction mixture was loaded directly onto a 25-g silica gel loading column with the aid of DCM. The column was dried under vacuum for 5 min, then eluted onto a pre-equilibrated 25-g SNAP Ultra column with 0-10% MeOH/DCM to give an orange oil. The oil was further by chromatography on silica gel (40-g Redi-Sep Gold column, 4% MeOH/DCM) to give ca. 320 mg of an amber oil. The oil was dissolved in EtOAc, and the organic solution was washed with 0.5 N aq. HCl, dried over sodium sulfate, filtered, and concentrated to give 1-(4-chloro-5-cyano-2-methoxyphenyl)-N-(isoxazol-3-yl)isoquinoline-6-sulfonamide (182 mg, 0.413 mmol, 87% yield) as a clear oil. m/z (ESI) 441.3 (M+H)$^+$.

Intermediate XXXX

PERFLUOROPHENYL 1-(5-CHLORO-2-METHOXYPHENYL)ISOQUINOLINE-6-SULFONATE

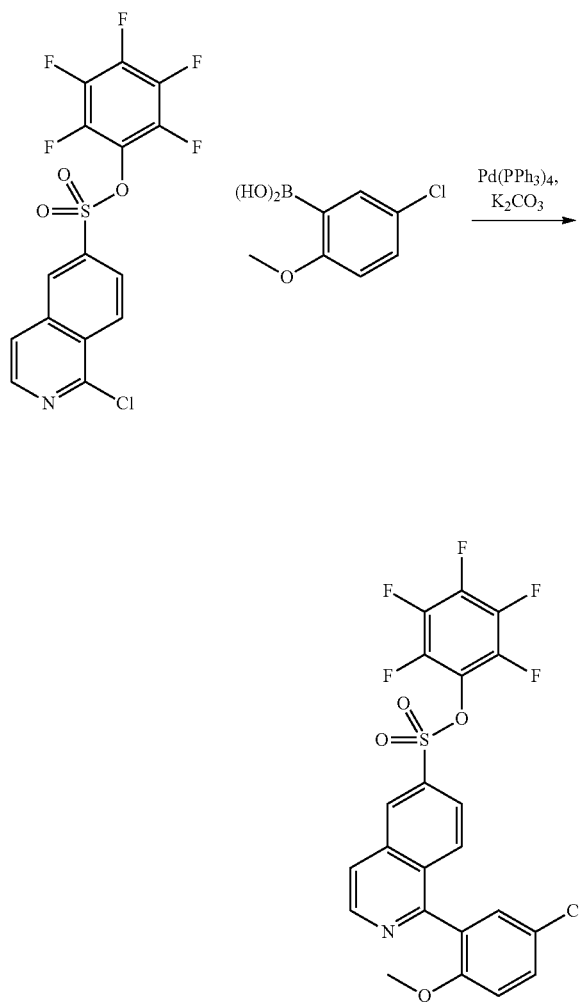

Intermediate XXXX

Intermediate YYYY 1-(5-CHLORO-2-METHOXYPHENYL)-N-(1,3,4-THIADIAZOL-2-YL)ISOQUINOLINE-6-SULFONAMIDE

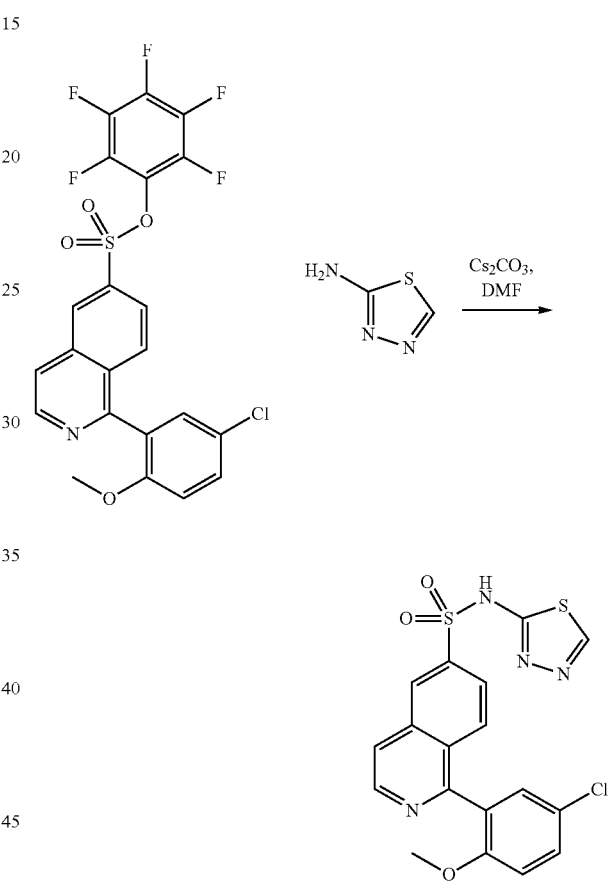

Intermediate YYYY

A round-bottom flask was charged with perfluorophenyl 1-chloroisoquinoline-6-sulfonate (see Example 73, Step 1, 1.12 g, 2.73 mmol), 5-chloro-2-methoxyphenyl)boronic acid (0.764 g, 4.10 mmol), potassium carbonate (1.133 g, 8.20 mmol), and Pd(Ph$_3$P)$_4$ (0.316 g, 0.273 mmol). The vial was flushed with Ar (g), then 1,4-dioxane (10.25 ml) and water (3.42 ml) were added. The flask was fitted with a reflux condenser and heated in a 50° C. heating bath for 2 h. The mixture was diluted with water and extracted with EtOAc (1×). The combined organic extracts were dried over sodium sulfate, filtered, and concentrated. The residue was purified by chromatography on silica gel (40-g Redi-Sep Gold column, 0-50% EtOAc/Heptane) to give perfluorophenyl 1-(5-chloro-2-methoxyphenyl)isoquinoline-6-sulfonate (1.073 g, 2.080 mmol, 76% yield) as a white foam. m/z (ESI) 516.0 (M+H)$^+$.

A round-bottom flask was charged with perfluorophenyl 1-(5-chloro-2-methoxyphenyl)isoquinoline-6-sulfonate (INTERMEDIATE XXXX, 464.57 mg, 0.901 mmol), 1,3,4-thiadiazol-2-amine (182 mg, 1.801 mmol), and cesium carbonate (880 mg, 2.70 mmol). DMF (4503 µl) was added, and the mixture was stirred overnight. The mixture was diluted with EtOAc and 0.5 N aq. HCl. The layers were separated, and the organic extract was washed with brine, dried over sodium sulfate, filtered, and concentrated. The residue was purified by chromatography on silica gel (25-g SNAP Ultra column, 0-7% MeOH/DCM) to give 1-(5-chloro-2-methoxyphenyl)-N-(1,3,4-thiadiazol-2-yl)isoquinoline-6-sulfonamide (378 mg, 0.873 mmol, 97% yield) as a light-yellow foam. m/z (ESI) 433.2 (M+H)$^+$.

Intermediate ZZZZ

1-CHLORO-N-(4-METHOXYBENZYL)-N-(PYRIMIDIN-4-YL)ISOQUINOLINE-6-SULFONAMIDE

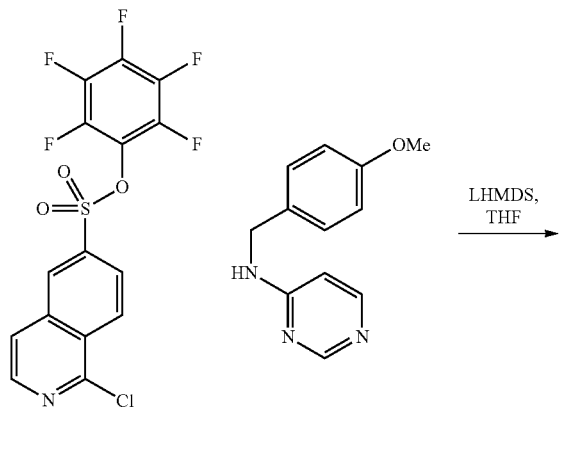

Intermediate AAAAA

1-(5-CHLORO-2-METHOXYPHENYL)-N-(4-METHOXYBENZYL)-N-(PYRIMIDIN-4-YL)ISOQUINOLINE-6-SULFONAMIDE

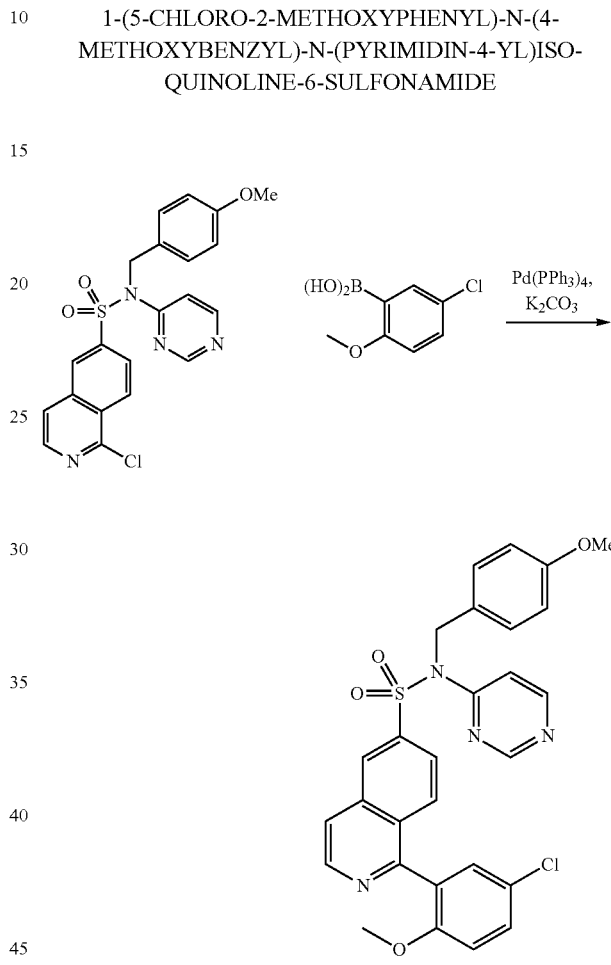

A 100-mL round-bottom flask was charged with N-(4-methoxybenzyl)pyrimidin-4-amine (Intermediate OO; 0.796 g, 3.70 mmol) and THF (16.08 ml). The flask was cooled in a dry ice-acetone bath for 10 min, then lithium bis(trimethylsilyl)amide (1M in THF) (3.70 ml, 3.70 mmol) was added drop wise. The flask was removed from the cooling bath for 5 min, then recooled for 5 min. A solution of perfluorophenyl 1-chloroisoquinoline-6-sulfonate (see EXAMPLE 73, STEP 1, 1.515 g, 3.70 mmol) in THF (4 mL with a 1-mL flask wash) was added drop wise. After 20 min, the flask was switched to an ice-water bath. The mixture was stirred for 20 min, then an additional portion of LHMDS solution (1 mL) was added drop wise. The mixture was warmed to room temperature and quenched by the addition of saturated aq. ammonium chloride. The mixture was extracted with EtOAc (2×), and the combined organic extracts were dried over sodium sulfate, filtered, and concentrated. The residue was purified by chromatography on silica gel (40-g Redi-Sep Gold column, 25-g silica gel loading column, 0-50% EtOAc/Heptane) to give 1-chloro-N-(4-methoxybenzyl)-N-(pyrimidin-4-yl)isoquinoline-6-sulfonamide (648 mg, 1.470 mmol, 39.7% yield) as a tan foam. m/z (ESI) 441.2 (M+H)$^+$.

A vial was charged with 1-chloro-N-(4-methoxybenzyl)-N-(pyrimidin-4-yl)isoquinoline-6-sulfonamide (INTERMEDIATE ZZZZ; 100 mg, 0.227 mmol), (5-chloro-2-methoxyphenyl)boronic acid (63.4 mg, 0.340 mmol), potassium carbonate (94 mg, 0.680 mmol), and pd(ph3p)4 (26.2 mg, 0.023 mmol). The vial was flushed with Ar (g), then 1,4-dioxane (851 µl) and water (284 µl were added. The vial was sealed and heated to 100° C. for 30 min in a Biotage Initiator microwave reactor. The mixture was extracted with EtOAc (3×), and the combined organic extracts were concentrated. The residue was purified by chromatography on silica gel (40-g Redi-Sep Gold column, 0-40% EtOAc/Heptane, then 70% EtOAc/Heptane) to give 1-(5-chloro-2-methoxyphenyl)-N-(4-methoxybenzyl)-N-(pyrimidin-4-yl)isoquinoline-6-sulfonamide (91.2 mg, 0.167 mmol, 73.5% yield) as an off-white foam. m/z (ESI) 547.2 (M+H)$^+$.

Intermediate BBBBB

1-(4-CHLORO-2-METHOXYPHENYL)-N-(4-METHOXYBENZYL)-N-(PYRIMIDIN-4-YL)ISOQUINOLINE-6-SULFONAMIDE

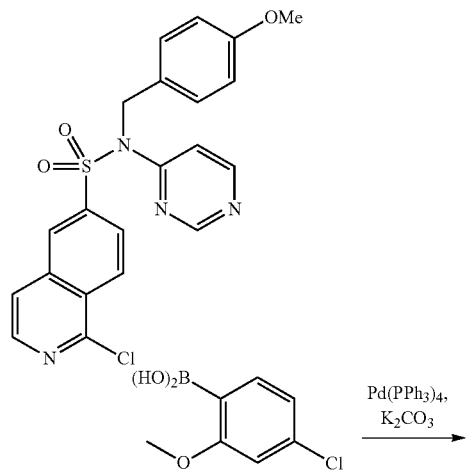

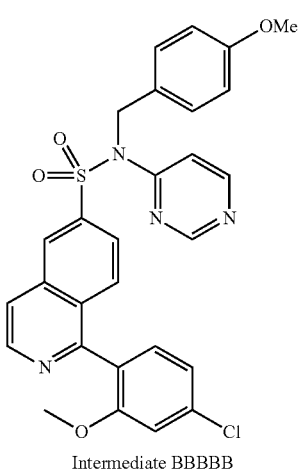

Intermediate BBBBB

A vial was charged with 1-chloro-N-(4-methoxybenzyl)-N-(pyrimidin-4-yl)isoquinoline-6-sulfonamide (INTERMEDIATE ZZZZ, 310.8 mg, 0.705 mmol), (4-chloro-2-methoxyphenyl)boronic acid (197 mg, 1.057 mmol), potassium carbonate (292 mg, 2.115 mmol), and Pd(PPh$_3$)$_4$ (81 mg, 0.070 mmol). The vial was flushed with Ar (g), then 1,4-dioxane (2643 µl) and water (881 µl were added. The vial was sealed and heated to 100° C. for 30 min in a Biotage Initiator microwave reactor. The mixture was extracted with EtOAc (3×), and the combined organic extracts were concentrated. The residue was purified by chromatography on silica gel (40-g Redi-Sep Gold column, 0-40% EtOAc/Heptane) to give 1-(4-chloro-2-methoxyphenyl)-N-(4-methoxybenzyl)-N-(pyrimidin-4-yl)isoquinoline-6-sulfonamide (352 mg, 0.643 mmol, 91% yield) as a cream-colored foam. m/z (ESI) 547.2 (M+H)$^+$.

Intermediate DDDDD

PERFLUOROPHENYL 1-(4-CHLORO-2-METHYLPHENYL)ISOQUINOLINE-6-SULFONATE

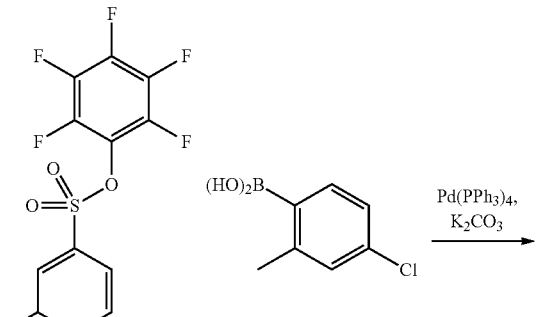

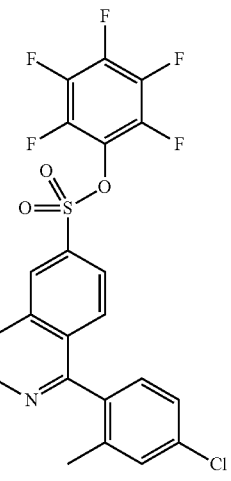

Intermediate DDDDD

A round-bottom flask was charged with perfluorophenyl 1-chloroisoquinoline-6-sulfonate (see EXAMPLE 73, Step 1, 518.97 mg, 1.267 mmol), (4-chloro-2-methylphenyl)boronic acid (324 mg, 1.900 mmol), potassium carbonate (525 mg, 3.80 mmol), and Pd(PPh$_3$)$_4$ (146 mg, 0.127 mmol). The flask was flushed with Ar (g), then 1,4-dioxane (4750 µl) and water (1583 µl) were added. The flask was sealed and heated in a 50° C. heating bath overnight. The mixture was diluted with water and extracted with EtOAc (2×). The combined organic extracts were dried over sodium sulfate, filtered, and concentrated. The residue was purified by chromatography on silica gel (40-g Redi-Sep Gold column, 0-30% EtOAc/Heptane) to give perfluorophenyl 1-(4-chloro-2-methylphenyl)isoquinoline-6-sulfonate (249 mg, 0.498 mmol, 39.3% yield) as a clear oil. m/z (ESI) 500.0 (M+H)+.

303
Intermediate EEEEE 1-(6-CHLORO-2-METHOXYPYRIDIN-3-YL)-N-(4-METHOXYBENZYL)-N-(PYRIMIDIN-4-YL)ISOQUINOLINE-6-SULFONAMIDE

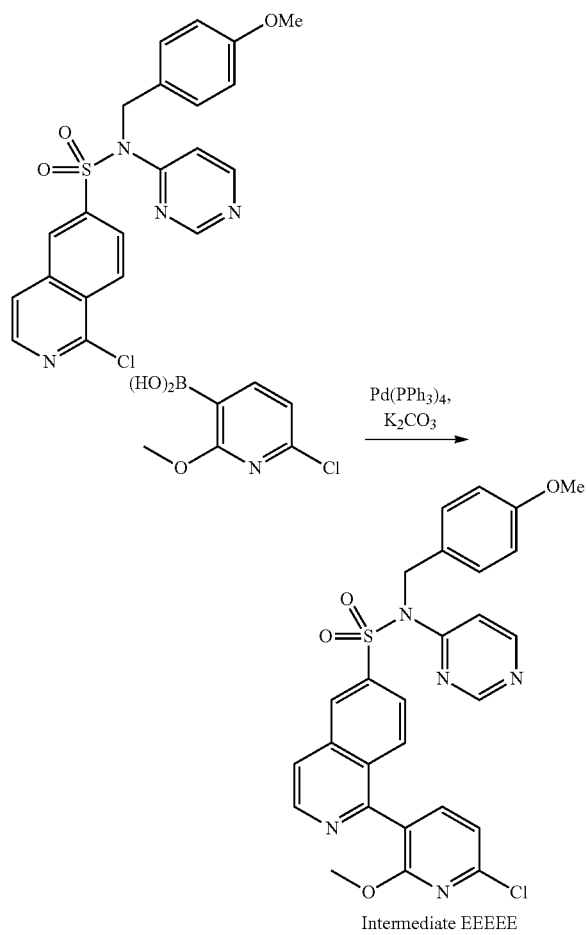

Intermediate EEEEE

A vial was charged with 1-chloro-N-(4-methoxybenzyl)-N-(pyrimidin-4-yl)isoquinoline-6-sulfonamide (INTERMEDIATE ZZZZ, 97 mg, 0.220 mmol), (6-chloro-2-methoxypyridin-3-yl)boronic acid (45.3 mg, 0.242 mmol), potassium carbonate (91 mg, 0.660 mmol), and pd(ph3p)4 (12.71 mg, 0.011 mmol). The vial was flushed with Ar (g), then 1,4-dioxane (825 µl) and water (2750 were added. The vial was sealed and heated to 80° C. for 45 min in a Biotage Initiator microwave reactor. LCMS showed primarily the desired product. The mixture was extracted with EtOAc (3×), and the combined organic extracts were concentrated. The residue was purified by chromatography on silica gel (12-g Redi-Sep Gold column, 0-50% EtOAc/Heptane, then 50-100% EtOAc/Heptane) to give 1-(6-chloro-2-methoxypyridin-3-yl)-N-(4-methoxybenzyl)-N-(pyrimidin-4-yl)isoquinoline-6-sulfonamide (117 mg, 0.213 mmol, 97% yield) as a cream-colored foam. m/z (ESI) 548.2 (M+H)+.

304
Intermediate FFFFF (4-CHLORO-5-FLUORO-2-METHOXYPHENYL)BORONIC ACID

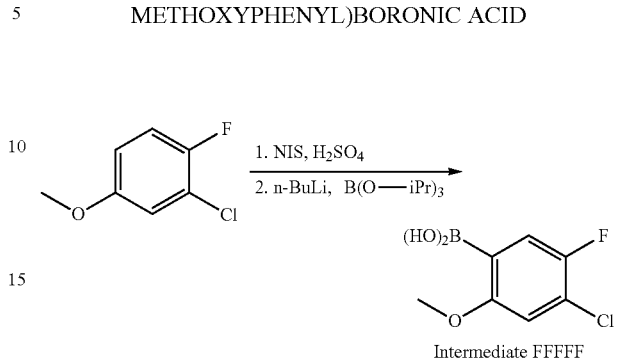

Intermediate FFFFF

STEP 1: 1-CHLORO-2-FLUORO-4-IODO-5-METHOXYBENZENE

A round-bottom flask was charged with 2-chloro-1-fluoro-4-methoxybenzene (Alfa Aesar, Ward Hill, Mass., 2.714 g, 16.90 mmol), DCM (24.86 ml), AcOH (24.86 ml), and sulfuric acid (0.496 ml, 9.30 mmol) to give a solution. n-iodosuccinimide (3.80 g, 16.90 mmol) was added in a single portion. TLC showed what appeared to be conversion of the starting material to a slightly higher, move UV-active spot. The mixture was diluted with DCM, washed with water (2×), washed with saturated aq. sodium thiosulfate, dried over sodium sulfate, filtered, and concentrated. The residue was purified by chromatography on silica gel (50-g SNAP Ultra column, 0-10% EtOAc/Heptane) to give 3.409 g of a clear oil. This oil was used directly in the next reaction without further purification.

STEP 2: (4-CHLORO-5-FLUORO-2-METHOXYPHENYL)BORONIC ACID

A round-bottom flask was charged with 1-chloro-2-fluoro-4-iodo-5-methoxybenzene (3.40 g, 11.87 mmol), triisopropyl borate (3.58 ml, 15.43 mmol), and THF (29.7 ml). The flask was cooled in a dry ice-acetone bath for 10 min, then n-butyllithium (2.5 M in hexane) (6.17 ml, 15.43 mmol) was added drop wise over 1 min. After 1 h, a 2N aq. NaOH solution (25 mL) was added, and the mixture was warmed to room temperature. After another 20 min, the mixture was diluted with water then acidified with 6N aq. HCl (40 mL). The mixture was extracted with ether (2×), and the combined organic extracts were dried over magnesium sulfate, filtered, and concentrated. The residue was taken up in DCM and filtered to give 708 mg of a white solid. The filtrate was purified by chromatography on silica gel (50-g SNAP Ultra column, 0-40% EtOAc/Heptane) to give an additional portion of white solid. The two solids were combined to give (4-chloro-5-fluoro-2-methoxyphenyl)boronic acid (1.273 g, 6.23 mmol, 52.5% yield) as a white solid. m/z (ESI) 205.2 (M+H)+.

Intermediate GGGGG

PERFLUOROPHENYL 1-(4-CHLORO-5-FLUORO-2-METHOXYPHENYL)ISOQUINO-LINE-6-SULFONATE

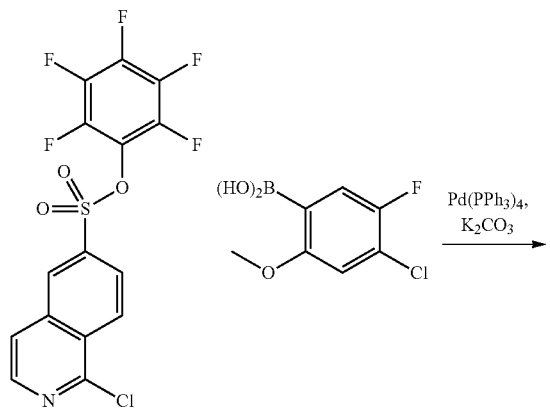

Intermediate GGGGG

A round-bottom flask was charged with perfluorophenyl 1-chloroisoquinoline-6-sulfonate (see EXAMPLE 73, STEP 1, 1.7 g, 4.15 mmol), (4-chloro-5-fluoro-2-methoxyphenyl) boronic acid (INTERMEDIATE FFFFF; 1.272 g, 6.22 mmol), potassium carbonate (1.720 g, 12.45 mmol), and Pd(PPh$_3$)$_4$ (0.479 g, 0.415 mmol). The vial was flushed with Ar (g), then 1,4-dioxane (15.56 ml) and water (5.19 ml) were added. The flask was fitted with a reflux condenser and heated in a 50° C. heating bath for 1 h. The mixture was diluted with water and extracted with EtOAc (2×). The combined organic extracts were dried over sodium sulfate, filtered, and concentrated. The residue was purified by chromatography on silica gel (40-g Redi-Sep Gold column, 0-50% EtOAc/Heptane) to give perfluorophenyl 1-(4-chloro-5-fluoro-2-methoxyphenyl)isoquinoline-6-sulfonate (1.89 g, 3.54 mmol, 85% yield) as a white foam. m/z (ESI) 534.0 (M+H)+.

Intermediate HHHHH 1-(4-CHLORO-5-FLUORO-2-METHOXYPHE-NYL)-N-(1,3,4-THIADIAZOL-2-YL)ISOQUINO-LINE-6-SULFONAMIDE

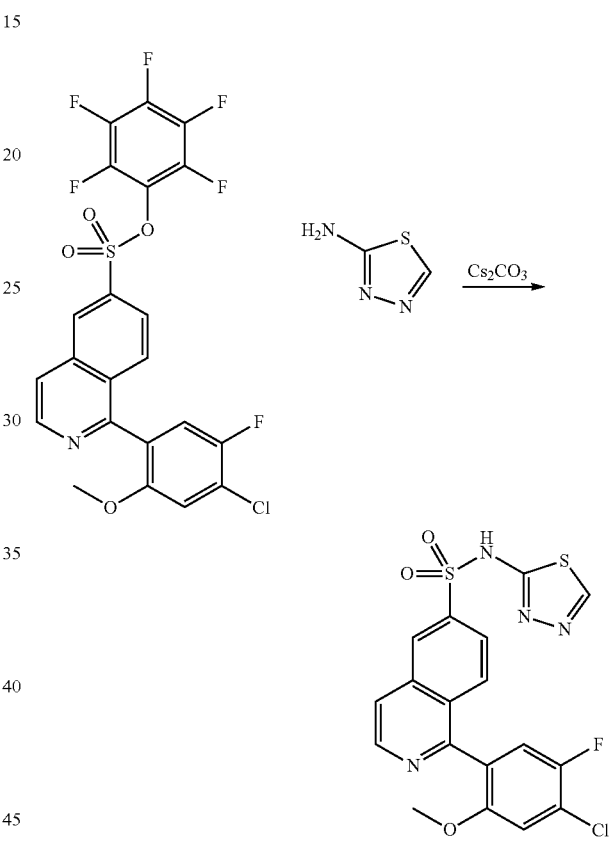

Intermediate HHHHH

A vial was charged with perfluorophenyl 1-(4-chloro-5-fluoro-2-methoxyphenyl)isoquinoline-6-sulfonate (INTERMEDIATE GGGGG, 1.233 g, 2.310 mmol). 1,3,4-thiadiazol-2-amine (0.280 g, 2.77 mmol), and cesium carbonate (2.258 g, 6.93 mmol). Acetonitrile (11.55 ml) was added, and the mixture was stirred overnight. The mixture was diluted with EtOAc and 0.5 N aq. HCl. The layers were separated, and the aq. layer was extracted with EtOAc (2×). The combined organic extracts were dried over sodium sulfate, filtered, and concentrated. The residue was purified by chromatography on silica gel (25-g SNAP Ultra column, 0-5% MeOH/DCM) to give 1-(4-chloro-5-fluoro-2-methoxyphenyl)-N-(1,3,4-thiadiazol-2-yl)isoquinoline-6-sulfonamide (632 mg, 1.402 mmol, 60.7% yield) as an off-white solid. m/z (ESI) 451.0 (M+H)+.

Intermediate JJJJJ

(3',5'-DIFLUORO-3-METHOXY-[1,1'-BIPHENYL]-4-YL)BORONIC ACID

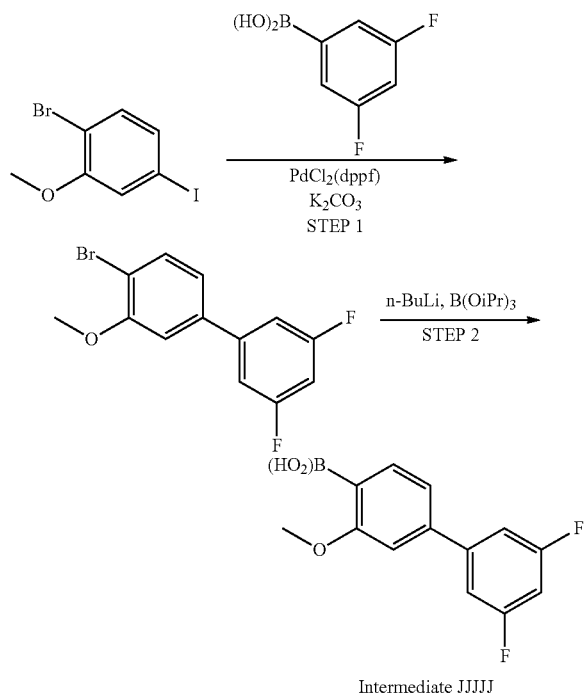

Intermediate JJJJJ

STEP 1: 4-BROMO-3',5'-DIFLUORO-3-METHOXY-1,1'-BIPHENYL

A round-bottom flask was charged with 1-bromo-4-iodo-2-methoxybenzene (Combi-Blocks, Inc., San Diego, Calif., 6.25 g, 19.97 mmol), (3,5-difluorophenyl)boronic acid (3.47 g, 21.97 mmol), potassium carbonate (8.28 g, 59.9 mmol), and PdCl$_2$(dppf)-CH$_2$Cl$_2$ (0.816 g, 0.999 mmol). The flask was flushed with Ar (g), then 1,4-dioxane (30.0 ml) and water (9.99 ml) were added in sequence. The mixture was stirred at room temperature for 4 h. The reaction mixture was diluted with water and extracted with EtOAc (3×). The combined organic extracts were dried over sodium sulfate, filtered, and concentrated. The residue was taken up in DCM and loaded onto a pre-equilibrated 340-g SNAP Ultra column. The column was eluted with 0-10% EtOAc/Heptane containing 5% DCM. Fractions containing the desired product were combined and concentrated. The residue was taken up in heptane and filtered. The collected solid was washed with heptane (3×), then dried under a stream of N$_2$ (g). The process was repeated with the filtrate to give a second crop of material. The two crops were dried under vacuum to give 4-bromo-3',5'-difluoro-3-methoxy-1,1'-biphenyl as a white solid. $^1$H NMR (400 MHz, DMSO-d$_6$)=7.66 (d, J=8.2 Hz, 1 H), 7.58-7.49 (m, 2 H), 7.40 (d, J=1.9 Hz, 1 H), 7.33-7.20 (m, 2 H), 3.96 (s, 3 H). m/z (ESI) 301.1.

STEP 2: (3',5'-DIFLUORO-3-METHOXY-[1,1'-BIPHENYL]-4-YL)BORONIC ACID

A round-bottom flask was charged with 4-bromo-3',5'-difluoro-3-methoxy-1,1'-biphenyl (5.147 g, 17.21 mmol), triisopropyl borate (4.79 ml, 20.65 mmol), and THF (57.4 ml). The flask was cooled in a dry ice-acetone bath for 10 min, then n-butyllithium (2.5 M in hexane) (8.26 ml, 20.65 mmol) was added drop wise over 1 min. The mixture was stirred for 20 min, then the flask was lowered into an ice-water bath. After 10 min, a 2N aq. NaOH solution was added, the cooling bath was removed, and the mixture was stirred vigorously for 20 min. The mixture was diluted with water and ether. The layers were separated, and the ethereal layer was extracted with water. The combined aq. layers were then acidified with 6N aq. HCl (50 mL). The mixture was filtered, and the collected solid was dried under a stream of N$_2$ (g), for 2 h to give ca. 3.14 g of a white solid. The filtrate was extracted with DCM (3×), and the combined organic extracts were dried over sodium sulfate, filtered, and concentrated to give an additional 260 mg of a white solid. The solids were combined to give (3',5'-difluoro-3-methoxy-[1,1'-biphenyl]-4-yl)boronic acid (3.40 g, 12.88 mmol, 74.8% yield) as a white solid. m/z (ESI) 265.1 (M+H)$^+$.

Intermediate KKKKK

PERFLUOROPHENYL 1-(3',5'-DIFLUORO-3-METHOXY-[1,1'-BIPHENYL]-4-YL)ISOQUINOLINE-6-SULFONATE

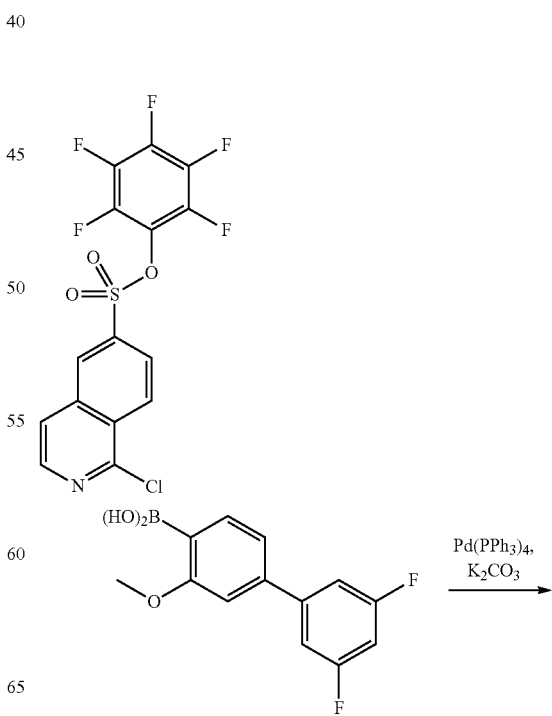

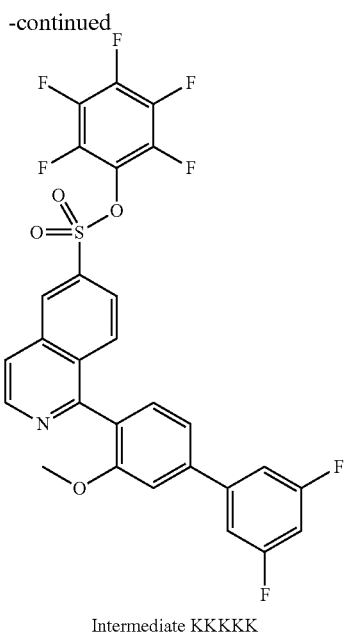

Intermediate KKKKK

A round-bottom flask was charged with perfluorophenyl 1-chloroisoquinoline-6-sulfonate (see EXAMPLE 73, STEP 1, 4.40 g, 10.74 mmol), (3',5'-difluoro-3-methoxy-[1,1'-biphenyl]-4-yl)boronic acid (INTERMEDIATE JJJJJ; 3.40 g, 12.89 mmol), potassium carbonate (4.45 g, 32.2 mmol), and Pd(Ph$_3$P)$_4$ (1.241 g, 1.074 mmol). The flask was flushed with Ar (g), then 1,4-dioxane (40.3 ml) and water (13.42 ml) were added in sequence. The flask was fitted with a reflux condenser and lowered into a 50° C. heating bath for 1 h. The mixture was diluted with water and extracted with EtOAc (2×). The combined organic extracts were dried over sodium sulfate, filtered, and concentrated. TLC showed two major spots. The residue was purified by chromatography on silica gel (100-g SNAP Ultra column, 0-50% EtOAc/Heptane). Fractions containing the desired product were combined and concentrated to give perfluorophenyl 1-(3',5'-difluoro-3-methoxy-[1,1'-biphenyl]-4-yl)isoquinoline-6-sulfonate (4.179 g, 7.04 mmol, 65.6% yield) as an off-white solid. $^1$H NMR (400 MHz, DMSO-d$_6$)=8.93 (d, J=1.6 Hz, 1 H), 8.84 (d, J=5.6 Hz, 1 H), 8.20 (d, J=5.7 Hz, 1 H), 8.07 (dd, J=1.9, 9.0 Hz, 1 H), 7.95 (d, J=8.9 Hz, 1 H), 7.70-7.62 (m, 2 H), 7.59-7.50 (m, 3 H), 7.36-7.27 (m, 1 H), 3.79 (s, 3 H). m/z (ESI) 594.0 (M+H)$^+$.

Intermediate MMMMM

1-CHLORO-N-(2,4-DIMETHOXYBENZYL)-4-FLUORO-N-(1,2,4-THIADIAZOL-5-YL)ISOQUINOLINE-6-SULFONAMIDE

Intermediate MMMMM

The title compound was prepared in an analogous manner to that of INTERMEDIATE PPP, except that N-(2,4-dimethoxybenzyl)-1,2,4-thiadiazol-5-amine was used instead of N-(2,4-dimethoxybenzyl)thiazol-2-amine in Step 5. The final compound was purified via column chromatography (RediSep Gold 12 g silica gel column, gradient elution 25-100% EtOAc:Heptane) to afford 1-chloro-N-(2,4-dimethoxybenzyl)-4-fluoro-N-(1,2,4-thiadiazol-5-yl)isoquinoline-6-sulfonamide as an off-white solid. (ESI) 517.1 (M+Na)$^+$.

Table I provides data for the examples, as representative compounds of the present invention, as follows: compound name (as named by ACD software, version 12; while the compound names in the written examples presented herein were named using ChemDraw Ultra version 12); molecular weight measured (MW); the method by which the compound was made; the NMR of the representative example; and biological data including in-vitro Nav 1.7 PX data (IC$_{50}$ in uM) and Nav 1.5 PX data (IC$_{50}$ in uM), where available.

TABLE I

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 43 | 1-(2-chloro-3'-fluoro-5-methoxy-4-biphenylyl)-7-fluoro-N-3-isoxazolyl-6-isoquinolinesulfonamide | 528.1 | 43 | 1H NMR (400 MHz, DMSO-d6) d ppm 12.24 (br. s., 1 H) 8.84 (d, J = 7.14 Hz, 1 H) 8.69-8.77 (m, 2 H) 8.21 (d, J = 5.18 Hz, 1 H) 7.50-7.62 (m, 3 H) 7.40-7.47 (m, 2 H) 7.28-7.35 (m, 1 H) 7.25 (s, 1 H) 6.43 (d, J = 1.76 Hz, 1 H) 3.72 (s, 3 H). | 0.0456 | >10.0 |
| 44 | 7-fluoro-1-(3'-fluoro-3-methoxy-4-biphenylyl)-N-1,2,4-thiadiazol-5-yl-6-isoquinolinesulfonamide | 511.1 | 44 | $^1$H NMR (400 MHz, DMSO-d$_6$) d ppm 8.62-8.74 (m, 2 H) 8.42 (s, 1 H) 8.17 (d, J = 5.18 Hz, 1 H) 7.66-7.80 (m, 2 H) 7.53-7.64 (m, 1 H) 7.43-7.52 (m, 3 H) 7.40 (d, J = 11.25 Hz, 1 H) 7.27 (td, J = 8.53, 2.40 Hz, 1 H) 3.80 (s, 3 H). | 0.0488 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 45 | 1-(6-(4-fluorophenoxy)-2-methoxy-3-pyridinyl)-N-4-pyrimidinyl-6-isoquinolinesulfonamide | 504.0 | 45 | $^1$H NMR (500 MHz, DMSO-d$_6$) d ppm 8.65-8.73 (m, 2 H) 8.57 (s, 1 H) 8.21-8.28 (m, 1 H) 8.17 (d, J = 5.77 Hz, 1 H) 7.94-8.01 (m, 1 H) 7.85-7.93 (m, 2 H) 7.28-7.39 (m, 4 H) 7.03 (br. s., 1 H) 6.69 (d, J = 8.01 Hz, 1 H) 3.58 (s, 3 H) | 1.51 | |
| 46 | 1-(6-(bis(2-methylpropyl)amino)-2-methoxy-3-pyridinyl)-N-4-pyrimidinyl-6-isoquinolinesulfonamide | 521.2 | 46 | $^1$H NMR (400 MHz, CD$_3$OD) d ppm 8.67 (d, J = 1.66 Hz, 1 H) 8.61 (d, J = 5.77 Hz, 1 H) 8.47 (s, 1 H) 8.17-8.20 (m, 1 H) 7.96-8.04 (m, 2 H) 7.84 (d, J = 8.90 Hz, 1 H) 7.43 (d, J = 8.12 Hz, 1 H) 7.02 (dd, J = 6.36, 1.08 Hz, 1 H) 6.27 (d, J = 8.02 Hz, 1 H) 3.95 (s, 3 H) 2.96-3.05 (m, 2 H) 2.35-2.45 (m, 2 H) 1.75-1.85 (m, 2 H) 0.58 (d, J = 16.63 Hz, 12 H) | 13.6 | |
| 48 | 1-(2-methoxy-6-((3-methyl-1,2,4-oxadiazol-5-yl)methoxy)-3-pyridinyl)-N-4-pyrimidinyl-6-isoquinolinesulfonamide | 506.0 | 48 | $^1$H NMR (500 MHz, DMSO-d$_6$) d ppm 8.67-8.71 (m, 2 H) 8.57 (s, 1 H) 8.24 (d, J = 6.25 Hz, 1 H) 8.18 (d, J = 5.61 Hz, 1 H) 8.00 (d, J = 8.76 Hz, 1 H) 7.86 (d, J = 8.01 Hz, 1 H) 7.82 (d, J = 8.92 Hz, 1 H) 7.03 (br. s., 1 H) 6.77 (d, J = 8.01 Hz, 1 H) 5.73 (s, 2 H) 3.63 (s, 3 H) 2.36 (s, 3 H) | | |
| 49 | N-3-isoxazolyl-1-(3-methoxy-4-biphenylyl)-6-isoquinolinesulfonamide | 458.0 | 49 | $^1$H NMR (500 MHz, DMSO-d$_6$) d ppm 8.70 (d, J = 5.66 Hz, 1 H) 8.59 (s, 1 H) 8.61 (s, 1 H) 8.08 (d, J = 5.72 Hz, 1 H) 7.90 (dd, J = 8.95, 1.63 Hz, 1 H) 7.78-7.86 (m, 3 H) 7.53 (t, J = 7.64 Hz, 2 H) 7.34-7.48 (m, 4 H) 6.42 (s, 1 H) 3.75 (s, 3 H) | 0.311 | >10.0 |
| 65 | 1-(6-(cyclohexyloxy)-2-methoxy-3-pyridinyl)-N-4-pyrimidinyl-6-isoquinolinesulfonamide | 492.0 | 48 | $^1$H NMR (500 MHz, DMSO-d$_6$) d ppm 8.68-8.72 (m, 2 H) 8.58 (s, 1 H) 8.23 (app dd, J = 12.26, 6.12 Hz, 2 H) 8.01 (d, J = 7.91 Hz, 1 H) 7.92 (d, J = 8.87 Hz, 1 H) 7.78 (d, J = 7.96 Hz, 1 H) 7.02 (br. s., 1 H) 6.56 (d, J = 8.07 Hz, 1 H) 5.00-5.09 (m, 1 H) 3.77 (s, 3 H) 2.03-2.10 (m, 2 H) 1.74-1.81 (m, 2 H) 1.51-1.62 (m, 3 H) 1.39-1.48 (m, 2 H) 1.27-1.36 (m, 1 H) | 1.73 | |
| 50 | 1-(3-methoxy-4-biphenylyl)-N-1,3,4-thiadiazol-2-yl-6-isoquinolinesulfonamide | 475.0 | 50 | $^1$H NMR (500 MHz, DMSO-d$_6$) d ppm 8.61-8.69 (m, 2 H) 8.47 (s, 1 H) 8.05 (d, J = 5.66 Hz, 1 H) 7.78-7.90 (m, 3 H) 7.75 (d, J = 8.87 Hz, 1 H) 7.52 (t, J = 7.61 Hz, 2 H) 7.37-7.48 (m, 4 H) 3.75 (s, 3 H) | 0.174 | >10.0 |
| 66 | 1-(6-(cyclohexylmethoxy)-2-methoxy-3-pyridinyl)-N-4-pyrimidinyl-6-isoquinolinesulfonamide | 506.2 | 48 | $^1$H NMR (500 MHz, DMSO-d$_6$) d ppm 8.67-8.72 (m, 2 H) 8.58 (s, 1 H) 8.25 (d, J = 5.98 Hz, 1 H) 8.20 (d, J = 5.72 Hz, 1 H) 8.01 (d, J = 8.66 Hz, 1 H) 7.90 (d, J = 8.82 Hz, 1 H) 7.79 (d, J = 7.96 Hz, 1 H) 7.02 (br. s., 1 H) 6.59 (d, J = 8.01 Hz, 1 H) 4.20 (d, J = 5.93 Hz, 2 H) 3.78 (s, 3 H) 1.78-1.88 (m, 3 H) 1.70-1.78 (m, 2 H) 1.62-1.70 (m, 1 H) 1.15-1.32 (m, 3 H) 1.04-1.13 (m, 2 H) | 0.349 | >10.0 |
| 67 | 1-(6-(2,2-dimethylpropoxy)-2-methoxy-3-pyridinyl)-N-4-pyrimidinyl-6-isoquinolinesulfonamide | 480.2 | 48 | $^1$H NMR (500 MHz, DMSO-d$_6$) d ppm 8.69-8.72 (m, 2 H) 8.58 (s, 1 H) 8.21-8.26 (m, 2 H) 8.01 (d, J = 9.14 Hz, 1 H) 7.91 (d, J = 8.82 Hz, 1 H) 7.80 (d, J = 8.07 Hz, 1 H) 7.03 (br. s., 1 H) 6.62 (d, J = 8.01 Hz, 1 H) 4.08 (s, 2 H) 3.78 (s, 3 H) 1.05 (s, 9 H) | 1.01 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 68 | 1-(2-methoxy-6-(methyl(2-methylpropyl)amino)-3-pyridinyl)-N-4-pyrimidinyl-6-isoquinolinesulfonamide | 479.2 | 47 | $^1$H NMR (600 MHz, Acetonitrile-d$_3$) d ppm 8.55 (d, J = 5.65 Hz, 1 H) 8.43 (d, J = 1.37 Hz, 1 H) 8.37 (br. s., 1 H) 7.99 (d, J = 5.19 Hz, 1 H) 7.89 (dd, J = 8.81, 1.72 Hz, 1 H) 7.73-7.82 (m, 2 H) 7.53 (d, J = 8.24 Hz, 1 H) 6.80 (d, J = 5.87 Hz, 1 H) 6.25 (d, J = 8.16 Hz, 1 H) 3.73 (s, 3 H) 3.45 (d, J = 7.40 Hz, 2 H) 3.10 (s, 3 H) 2.11-2.20 (m, 1 H) 0.95 (d, J = 6.71 Hz, 6 H) | 2.88 | |
| 69 | 1-(6-((4,4-difluorocyclohexyl)methoxy)-2-methoxy-3-pyridinyl)-N-4-pyrimidinyl-6-isoquinolinesulfonamide | 542.2 | 48 | 1H NMR (500 MHz, DMSO-d6) d ppm 8.68-8.72 (m, 2 H) 8.58 (s, 1 H) 8.23 (app dd, J = 13.36, 6.14 Hz, 2 H) 8.01 (d, J = 9.99 Hz, 1 H) 7.90 (d, J = 8.87 Hz, 1 H) 7.80 (d, J = 8.01 Hz, 1 H) 7.03 (br. s., 1 H) 6.61 (d, J = 7.96 Hz, 1 H) 4.28 (d, J = 6.09 Hz, 2 H) 3.79 (s, 3 H) 2.20-1.81 (m, 7 H) 1.33-1.42 (m, 2 H) | 0.459 | >30.0 |
| 70 | 1-(2-((2,2-dimethylpropyl)amino)-6-methoxy-3-pyridinyl)-N-4-pyrimidinyl-6-isoquinolinesulfonamide | 479.2 | 47 | 1H NMR (600 MHz, Acetonitrile-d3) d ppm 8.56 (d, J = 5.65 Hz, 1 H) 8.47 (s, 1 H) 8.36 (br. s., 1 H) 8.02 (d, J = 8.93 Hz, 1 H) 7.98 (d, J = 4.50 Hz, 1 H) 7.93 (dd, J = 8.85, 1.30 Hz, 1 H) 7.77 (d, J = 5.57 Hz, 1 H) 7.48 (d, J = 8.01 Hz, 1 H) 6.76-6.82 (m, 2 H) 6.04 (d, J = 8.09 Hz, 1 H) 3.92 (s, 3 H) 3.30 (d, J = 6.10 Hz, 2 H) 0.86 (s, 9 H) | 2.51 | |
| 71 | 1-(6-(4,4-difluoro-1-piperidinyl)-2-methoxy-3-pyridinyl)-N-4-pyrimidinyl-6-isoquinolinesulfonamide | 513.1 | 47 | $^1$H NMR (600 MHz, Acetonitrile-d$_3$) d ppm 8.62 (d, J = 5.65 Hz, 1 H) 8.56 (d, J = 1.68 Hz, 1 H) 8.47 (s, 1 H) 8.18 (d, J = 6.26 Hz, 1 H) 7.93 (dd, J = 8.89, 1.87 Hz, 1 H) 7.85-7.88 (m, 1 H) 7.83 (d, J = 5.72 Hz, 1 H) 7.60 (d, J = 8.24 Hz, 1 H) 7.02 (dd, J = 6.33, 1.14 Hz, 1 H) 6.52 (d, J = 8.24 Hz, 1 H) 3.79-3.85 (m, 4 H) 3.73 (s, 3 H) 2.01-2.11 (m, 4 H) | 0.834 | |
| 72 | 1-(2-methoxy-6-(1-pyrrolidinyl)-3-pyridinyl)-N-4-pyrimidinyl-6-isoquinolinesulfonamide | 463.3 | 47 | $^1$H NMR (600 MHz, Acetonitrile-d$_3$) d ppm 8.63 (d, J = 5.65 Hz, 1 H) 8.57 (d, J = 1.07 Hz, 1 H) 8.48 (s, 1 H) 8.23 (d, J = 6.26 Hz, 1 H) 7.88-7.96 (m, 2 H) 7.82 (d, J = 5.72 Hz, 1 H) 7.55 (d, J = 8.16 Hz, 1 H) 7.06 (d, J = 6.33 Hz, 1 H) 6.13 (d, J = 8.16 Hz, 1 H) 3.75 (s, 3 H) 3.51 (br. s., 4 H) 2.02 (t, J = 6.60 Hz, 4 H) | 7.71 | |
| 73 | 1-(6-(cyclohexylamino)-2-methoxy-3-pyridinyl)-N-4-pyrimidinyl-6-isoquinolinesulfonamide | 491.3 | 47 | $^1$H NMR (600 MHz, Acetonitrile-d$_3$) d ppm 8.61 (d, J = 5.72 Hz, 1 H) 8.55 (s, 1 H) 8.48 (s, 1 H) 8.20 (d, J = 6.26 Hz, 1 H) 7.88-7.93 (m, 2 H) 7.81 (d, J = 5.72 Hz, 1 H) 7.46 (d, J = 8.09 Hz, 1 H) 7.04 (dd, J = 6.29, 1.11 Hz, 1 H) 6.17 (d, J = 8.09 Hz, 1 H) 5.29 (br. s., 1 H) 3.73-3.79 (m, 1 H) 3.70 (s, 3 H) 2.03-2.11 (m, 2 H) 1.74-1.81 (m, 2 H) 1.62-1.69 (m, 1 H) 1.37-1.47 (m, 2 H) 1.21-1.33 (m, 3 H) | 0.436 | >10.0 |
| 74 | 1-(6-((4,4-difluorocyclohexyl)amino)-2-methoxy-3-pyridinyl)-N-4-pyrimidinyl-6-isoquinolinesulfonamide | 527.1 | 47 | $^1$H NMR (600 MHz, Acetonitrile-d$_3$) d ppm 8.63 (d, J = 5.72 Hz, 1 H) 8.57 (d, J = 1.22 Hz, 1 H) 8.49 (s, 1 H) 8.22 (d, J = 6.33 Hz, 1 H) 7.88-7.96 (m, 2 H) 7.83 (d, J = 5.72 Hz, 1 H) 7.48 (d, J = 8.01 Hz, 1 H) 7.06 (dd, J = 6.29, 0.80 Hz, 1 H) 6.21 (d, J = 8.09 Hz, 1 H) 5.41 (d, J = 7.48 Hz, 1 H) 3.99 (s, 1 H) 3.73 (s, 3 H) 2.07-2.17 (m, 4 H) 1.95-2.04 (m, 2 H) 1.59-1.70 (m, 2 H) | 0.811 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 47 | 1-(6-((2,2-dimethylpropyl)amino)-2-methoxy-3-pyridinyl)-N-4-pyrimidinyl-6-isoquinolinesulfonamide | 479.2 | 47 | $^1$H NMR (600 MHz, Acetonitrile-d$_3$) d ppm 8.55 (d, J = 5.57 Hz, 1 H) 8.34-8.46 (m, 2 H) 8.00 (br. s., 1 H) 7.87 (d, J = 8.09 Hz, 1 H) 7.78 (d, J = 8.70 Hz, 1 H) 7.74 (d, J = 5.57 Hz, 1 H) 7.43 (d, J = 8.01 Hz, 1 H) 6.84 (br. s., 1 H) 6.21 (d, J = 8.01 Hz, 1 H) 5.37-5.48 (m, 1 H) 3.70 (s, 3 H) 3.23-3.30 (m, 2 H) 0.98 (s, 9 H) | 0.899 | |
| 75 | 1-(6-((4,4-difluorocyclohexyl)oxy)-2-methoxy-3-pyridinyl)-N-4-pyrimidinyl-6-isoquinolinesulfonamide | 528.0 | 48 | 1H NMR (500 MHz, DMSO-d6) d ppm 8.69-8.74 (m, 2 H) 8.58 (s, 1 H) 8.22-8.28 (m, 2 H) 8.03 (d, J = 8.92 Hz, 1 H) 7.94 (d, J = 8.92 Hz, 1 H) 7.82 (d, J = 8.01 Hz, 1 H) 7.02 (d, J = 5.56 Hz, 1 H) 6.63 (d, J = 8.07 Hz, 1 H) 5.28 (br. s., 1 H) 3.79 (s, 3 H) 2.3-2.0 (m, 6 H) 2.0-1.9 (m, 2 H | 0.727 | |
| 76 | 1-(4'-chloro-2-cyano-3'-fluoro-5-methoxy-4-biphenylyl)-N-3-isoxazolyl-6-isoquinolinesulfonamide | 535.0 | 1 | 1H NMR (500 MHz, DMSO-d6) d ppm 3.81 (s, 4 H) 6.40 (s, 1 H) 7.47 (s, 1 H) 7.64 (d, J = 8.23 Hz, 1 H) 7.78 (d, J = 8.87 Hz, 1 H) 7.82-7.93 (m, 3 H) 7.96 (s, 1 H) 8.14 (d, J = 5.56 Hz, 1 H) 8.53-8.63 (m, 2 H) 8.71 (d, J = 5.66 Hz, 1 H) | 0.0585 | >10.0 |
| 77 | 1-(2-cyano-3'-fluoro-5-methoxy-5'-methyl-4-biphenylyl)-N-3-isoxazolyl-6-isoquinolinesulfonamide | 515.2 | 1 | 1H NMR (500 MHz, DMSO-d6) d ppm 3.81 (s, 4 H) 6.39 (s, 1 H) 7.24 (d, J = 9.72 Hz, 1 H) 7.38-7.44 (m, 4 H) 7.77 (d, J = 8.87 Hz, 1 H) 7.89-7.95 (m, 2 H) 8.13 (d, J = 5.66 Hz, 1 H) 8.59 (s, 1 H) 8.56 (s, 1 H) 8.71 (d, J = 5.66 Hz, 1 H) | 0.0725 | >10.0 |
| 78 | 1-(3'-chloro-2-cyano-5-methoxy-4'-methyl-4-biphenylyl)-N-3-isoxazolyl-6-isoquinolinesulfonamide | 531.0 | 1 | 1H NMR (500 MHz, DMSO-d6) d ppm 2.44 (s, 3 H) 3.81 (s, 4 H) 6.47-6.49 (m, 1 H) 7.43 (s, 1 H) 7.57-7.59 (m, 1 H) 7.61-7.64 (m, 1 H) 7.81 (d, J = 1.39 Hz, 1 H) 7.84-7.87 (m, 1 H) 7.92-7.95 (m, 2 H) 8.18 (d, J = 5.66 Hz, 1 H) 8.70 (s, 1 H) 8.68 (s, 1 H) 8.75 (d, J = 5.66 Hz, 1 H) | 0.033 | >10.0 |
| 79 | 1-(2-cyano-5-methoxy-2'-methyl-4-biphenylyl)-N-3-isoxazolyl-6-isoquinolinesulfonamide | 497.0 | 1 | 1H NMR (500 MHz, DMSO-d6) d ppm 2.28 (br. s., 3 H) 3.75 (s, 4 H) 6.41-6.45 (m, 1 H) 7.29 (s, 1 H) 7.37 (br. s., 2 H) 7.40-7.45 (m, 2 H) 7.85 (d, J = 8.87 Hz, 1 H) 7.90-7.99 (m, 2 H) 8.15 (d, J = 5.66 Hz, 1 H) 8.63 (br. s., 2 H) 8.73 (d, J = 5.66 Hz, 1 H) | 0.088 | >10.0 |
| 80 | 1-(2-cyano-3',4'-difluoro-5-methoxy-4-biphenylyl)-N-3-isoxazolyl-6-isoquinolinesulfonamide | 519.0 | 1 | 1H NMR (500 MHz, DMSO-d6) d ppm 3.17 (s, 1 H) 3.81 (s, 4 H) 6.38 (s, 1 H) 7.44 (s, 1 H) 7.60-7.73 (m, 2 H) 7.77 (d, J = 8.87 Hz, 1 H) 7.86-7.97 (m, 3 H) 8.13 (d, J = 5.66 Hz, 1 H) 8.58 (s, 1 H) 8.54 (s, 1 H) 8.70 (d, J = 5.66 Hz, 1 H) | 0.0282 | >10.0 |
| 81 | 1-(2-cyano-3'-fluoro-5-methoxy-4'-methyl-4-biphenylyl)-N-3-isoxazolyl-6-isoquinolinesulfonamide | 515.1 | 1 | 1H NMR (500 MHz, DMSO-d6) d ppm 2.35 (s, 3 H) 3.81 (s, 4 H) 6.42 (s, 1 H) 7.41 (s, 1 H) 7.48-7.60 (m, 3 H) 7.81 (d, J = 8.87 Hz, 1 H) 7.89-7.97 (m, 2 H) 8.15 (d, J = 5.66 Hz, 1 H) 8.62 (br. s., 2 H) 8.72 (d, J = 5.72 Hz, 1 H) | 0.0903 | >10.0 |
| 82 | 1-(4'-chloro-2-cyano-5-methoxy-3'-methyl-4-biphenylyl)-N-3-isoxazolyl-6-isoquinolinesulfonamide | 531.0 | 1 | 1H NMR (500 MHz, DMSO-d6) d ppm 2.44-2.47 (m, 3 H) 3.80 (s, 4 H) 6.48 (d, J = 1.60 Hz, 1 H) 7.40-7.43 (m, 1 H) 7.58 (dd, J = 8.15, 1.95 Hz, 1 H) 7.64 (d, J = 8.23 Hz, 1 H) 7.73 (s, 1 H) 7.84-7.87 (m, 1 H) 7.92-7.95 (m, 2 H) 8.18 (d, J = 5.61 Hz, 1 H) 8.67-8.76 (m, 3 H) | 0.0261 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 83 | 1-(5-cyano-4-(5-fluoro-2-methoxy-3-pyridinyl)-2-methoxyphenyl)-N-3-isoxazolyl-6-isoquinolinesulfonamide | 532.0 | 1 | 1H NMR (500 MHz, DMSO-d6) d ppm 3.77 (s, 4 H) 3.93 (s, 3 H) 6.29 (s, 1 H) 7.09 (br. s., 1 H) 7.45 (s, 1 H) 7.69 (d, J = 8.82 Hz, 1 H) 7.87-7.95 (m, 2 H) 8.02 (dd, J = 8.25, 2.97 Hz, 1 H) 8.08 (d, J = 5.66 Hz, 1 H) 8.36 (d, J = 2.94 Hz, 1 H) 8.40 (br. s., 1 H) 8.49 (s, 1 H) 8.66 (d, J = 5.66 Hz, 1 H) | 0.236 | >10.0 |
| 84 | 1-(3'-chloro-2-cyano-4'-fluoro-5-methoxy-4-biphenylyl)-N-3-isoxazolyl-6-isoquinolinesulfonamide | 535.0 | 1 | 1H NMR (500 MHz, DMSO-d6) d ppm 3.81 (s, 4 H) 6.41-6.44 (m, 1 H) 7.46 (s, 1 H) 7.64-7.69 (m, 1 H) 7.76-7.83 (m, 2 H) 7.90-7.97 (m, 2 H) 8.02 (dd, J = 7.08, 2.11 Hz, 1 H) 8.15 (d, J = 5.66 Hz, 1 H) 8.63 (br. s., 2 H) 8.72 (d, J = 5.66 Hz, 1 H) | 0.0147 | >10.0 |
| 85 | 1-(2-cyano-4'-fluoro-5-methoxy-3'-methyl-4-biphenylyl)-N-3-isoxazolyl-6-isoquinolinesulfonamide | 515.1 | 1 | 1H NMR (500 MHz, DMSO-d6) d ppm 2.22 (s, 2 H) 2.36 (s, 2 H) 3.80 (s, 2 H) 6.48 (d, J = 1.60 Hz, 1 H) 7.07 (dd, J = 10.12, 8.31 Hz, 1 H) 7.35-7.41 (m, 2 H) 7.58-7.71 (m, 3 H) 7.85 (d, J = 8.98 Hz, 1 H) 7.91-7.98 (m, 1 H) 8.02 (s, 1 H) 8.17 (d, J = 5.66 Hz, 1 H) 8.66-8.77 (m, 2 H) | 0.0288 | >10.0 |
| 86 | 1-(3'-chloro-2-cyano-5'-fluoro-5-methoxy-4-biphenylyl)-N-3-isoxazolyl-6-isoquinolinesulfonamide | 535.1 | 1 | 1H NMR (500 MHz, DMSO-d6) d ppm 3.82 (s, 4 H) 6.43 (s, 1 H) 7.49 (s, 1 H) 7.67 (dd, J = 9.08, 1.28 Hz, 2 H) 7.72 (s, 1 H) 7.79 (d, J = 8.87 Hz, 1 H) 7.92 (dd, J = 8.90, 1.63 Hz, 1 H) 7.97 (s, 1 H) 8.16 (d, J = 5.61 Hz, 1 H) 8.63 (br. s., 2 H) 8.73 (d, J = 5.66 Hz, 1 H) | 0.0244 | >10.0 |
| 87 | 1-(4'-chloro-2-fluoro-5-methoxy-3'-methyl-4-biphenylyl)-N-3-pyridazinyl-6-isoquinolinesulfonamide | 535.1 | 1 | 1H NMR (400 MHz, DMSO-d6) d = 8.74 (d, J = 5.9 Hz, 1 H), 8.70 (d, J = 1.6 Hz, 1 H), 8.36 (d, J = 3.0 Hz, 1 H), 8.25 (d, J = 5.8 Hz, 1 H), 8.02-7.97 (m, 2 H), 7.88 (d, J = 8.8 Hz, 1 H), 7.75-7.70 (m, 2 H), 7.60-7.53 (m, 2 H), 7.43 (d, J = 10.5 Hz, 1 H), 7.34 (d, J = 6.4 Hz, 1 H), 3.73 (s, 3 H), 2.44 (s, 3 H). | 0.178 | |
| 88 | 1-(4'-chloro-2-fluoro-5-methoxy-3'-methyl-4-biphenylyl)-N-2-pyrimidinyl-6-isoquinolinesulfonamide | 535.1 | 1 | 1H NMR (400 MHz, DMSO-d6) d = 12.18 (br. s., 1 H), 8.76 (d, J = 1.3 Hz, 1 H), 8.72 (d, J = 5.7 Hz, 1 H), 8.50 (d, J = 4.9 Hz, 2 H), 8.18 (d, J = 5.5 Hz, 1 H), 8.05 (dd, J = 1.9, 8.9 Hz, 1 H), 7.83 (d, J = 8.9 Hz, 1 H), 7.70 (s, 1 H), 7.60-7.52 (m, 2 H), 7.36 (d, J = 10.5 Hz, 1 H), 7.30 (d, J = 6.5 Hz, 1 H), 7.04 (t, J = 4.9 Hz, 1 H), 3.70 (s, 3 H), 2.44 (s, 3 H). | 0.227 | |
| 89 | 1-(2,4'-difluoro-5-methoxy-3'-methyl-4-biphenylyl)-N-3-isoxazolyl-6-isoquinolinesulfonamide | 508.0 | 1 | 1H NMR (500 MHz, DMSO-d6) d = 8.69 (d, J = 5.7 Hz, 1 H), 8.57 (s, 1 H), 8.10 (d, J = 5.7 Hz, 1 H), 7.91 (dd, J = 1.6, 8.9 Hz, 1 H), 7.81 (d, J = 8.9 Hz, 1 H), 7.63 (d, J = 7.0 Hz, 1 H), 7.59-7.51 (m, J = 6.8 Hz, 1 H), 7.37-7.25 (m, 3 H), 6.40 (s, 1 H), 3.70 (s, 3 H), 2.35 (s, 3 H). | 0.0964 | |
| 90 | 1-(4'-chloro-2-fluoro-5-methoxy-3'-methyl-4-biphenylyl)-N-3-isoxazolyl-6-isoquinolinesulfonamide | 524.0 | 1 | 1H NMR (500 MHz, DMSO-d6) d = 11.90 (br. s., 1 H), 8.77-8.69 (m, 2 H), 8.66 (s, 1 H), 8.14 (d, J = 5.7 Hz, 1 H), 7.94 (dd, J = 1.7, 8.9 Hz, 1 H), 7.89-7.83 (m, 1 H), 7.70 (s, 1 H), 7.60-7.51 (m, 2 H), 7.36 (d, J = 10.4 Hz, 1 H), 7.30 (d, J = 6.4 Hz, 1 H), 6.48 (d, J = 1.7 Hz, 1 H), 3.71 (s, 3 H), 2.44 (s, 3 H). | 0.0595 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 91 | 1-(3'-chloro-2-fluoro-5-methoxy-4'-methyl-4-biphenylyl)-N-3-isoxazolyl-6-isoquinolinesulfonamide | 524.0 | 1 | 1H NMR (500 MHz, DMSO-d6) d = 12.08-11.54 (m, 1 H), 8.75-8.69 (m, 2 H), 8.66 (s, 1 H), 8.14 (d, J = 5.7 Hz, 1 H), 7.94 (dd, J = 1.7, 8.9 Hz, 1 H), 7.89-7.84 (m, 1 H), 7.76 (s, 1 H), 7.59 (d, J = 7.9 Hz, 1 H), 7.54-7.49 (m, 1 H), 7.38-7.29 (m, 2 H), 6.48 (d, J = 1.6 Hz, 1 H), 3.71 (s, 3 H), 2.42 (s, 3 H). | 0.101 | |
| 2 | N-3-isoxazolyl-1-(2-methoxy-3-biphenylyl)-6-isoquinolinesulfonamide | 458.0 | 2 | 1H NMR (500 MHz, DMSO-d6) d = 8.64 (d, J = 5.7 Hz, 1 H), 8.44 (s, 1 H), 8.32 (s, 1 H), 8.03 (d, J = 5.7 Hz, 1 H), 7.89 (dd, J = 1.5, 8.8 Hz, 1 H), 7.77 (d, J = 8.8 Hz, 1 H), 7.62 (d, J = 7.6 Hz, 2 H), 7.53 (t, J = 4.7 Hz, 1 H), 7.47 (t, J = 7.6 Hz, 2 H), 7.41-7.34 (m, 3 H), 2.95 (s, 3 H). | | |
| 92 | 1-(5-fluoro-4-(5-fluoro-2-methoxy-3-pyridinyl)-2-methoxyphenyl)-N-2-pyrimidinyl-6-isoquinolinesulfonamide | 536.2 | 1 | 1H NMR (400 MHz, DMSO-d6) d = 8.58 (d, J = 5.7 Hz, 1 H), 8.44 (d, J = 1.4 Hz, 1 H), 8.28 (d, J = 3.0 Hz, 1 H), 8.11 (s, 2 H), 8.00 (d, J = 5.4 Hz, 1 H), 7.98-7.92 (m, 2 H), 7.61 (d, J = 8.8 Hz, 1 H), 7.30 (d, J = 9.7 Hz, 1 H), 7.26 (d, J = 6.0 Hz, 1 H), 6.42 (t, J = 4.6 Hz, 1 H), 3.91 (s, 3 H), 3.66 (s, 3 H). | 0.278 | |
| 93 | 1-(5-fluoro-4-(5-fluoro-2-methoxy-3-pyridinyl)-2-methoxyphenyl)-N-3-isoxazolyl-6-isoquinolinesulfonamide | 525.2 | 1 | 1H NMR (400 MHz, DMSO-d6) d = 11.93 (br. s., 1 H), 8.77-8.73 (m, 2 H), 8.70 (d, J = 1.9 Hz, 1 H), 8.30 (d, J = 2.9 Hz, 1 H), 8.18 (d, J = 5.4 Hz, 1 H), 7.99-7.96 (m, 1 H), 7.92 (dd, J = 3.0, 8.4 Hz, 1 H), 7.90-7.87 (m, 1 H), 7.35 (d, J = 9.7 Hz, 1 H), 7.30 (d, J = 5.9 Hz, 1 H), 6.51 (d, J = 1.9 Hz, 1 H), 3.91 (s, 3 H), 3.66 (s, 3 H). | 0.0677 | |
| 94 | 1-(2-chloro-4'-fluoro-5-methoxy-3'-methyl-4-biphenylyl)-N-3-isoxazolyl-6-isoquinolinesulfonamide | 524.0 | 1 | 1H NMR (500 MHz, DMSO-d6) d = 11.85 (br. s, 1 H), 8.73 (d, J = 5.7 Hz, 1 H), 8.71-8.63 (m, 1 H), 8.14 (d, J = 5.7 Hz, 1 H), 7.95 (dd, J = 1.7, 8.9 Hz, 1 H), 7.90-7.85 (m, 1 H), 7.54-7.48 (m, 2 H), 7.43 (t, J = 5.5 Hz, 1 H), 7.29 (t, J = 9.1 Hz, 1 H), 7.21 (s, 1 H), 6.48 (d, J = 1.6 Hz, 1 H), 3.69 (s, 3 H), 2.34 (s, 3 H). | 0.0506 | |
| 95 | 1-(4'-chloro-2,3'-difluoro-5-methoxy-4-biphenylyl)-N-3-isoxazolyl-6-isoquinolinesulfonamide | 528.0 | 1 | 1H NMR (500 MHz, DMSO-d6) d = 12.11-11.52 (m, 1 H), 8.71 (d, J = 5.7 Hz, 1 H), 8.63 (d, J = 7.8 Hz, 2 H), 8.13 (d, J = 5.7 Hz, 1 H), 7.93 (dd, J = 1.6, 8.9 Hz, 1 H), 7.86-7.72 (m, 3 H), 7.60 (d, J = 8.3 Hz, 1 H), 7.41-7.33 (m, 2 H), 6.44-6.44 (m, 0 H), 6.48-6.40 (m, 1 H), 3.72 (s, 3 H). | 0.069 | |
| 96 | 1-(2,3'-dichloro-5-methoxy-4'-methyl-4-biphenylyl)-N-3-isoxazolyl-6-isoquinolinesulfonamide | 540.0 | 1 | 1H NMR (500 MHz, DMSO-d6) d = 12.10-11.60 (m, 1 H), 8.77-8.71 (m, 2 H), 8.67 (d, J = 1.1 Hz, 1 H), 8.15 (d, J = 5.7 Hz, 1 H), 7.99-7.93 (m, 1 H), 7.91-7.85 (m, 1 H), 7.62 (s, 1 H), 7.55-7.42 (m, 3 H), 7.24 (s, 1 H), 6.49 (d, J = 1.7 Hz, 1 H), 3.70 (s, 3 H), 2.42 (s, 3 H). | 0.0738 | |
| 97 | 1-(3'-chloro-2-fluoro-5-methoxy-4-biphenylyl)-N-2-pyrimidinyl-6-isoquinolinesulfonamide | 521.1 | 1 | 1H NMR (400 MHz, DMSO-d6) d = 12.22 (br. s., 1 H), 8.76 (d, J = 1.5 Hz, 1 H), 8.72 (d, J = 5.7 Hz, 1 H), 8.50 (d, J = 5.0 Hz, 2 H), 8.18 (d, J = 5.4 Hz, 1 H), 8.05 (dd, J = 1.9, 8.9 Hz, 1 H), 7.84 (d, J = 8.9 Hz, 1 H), 7.78 (d, J = 1.1 Hz, 1 H), 7.68 (qd, J = 1.6, 7.3 Hz, 1 H), 7.60-7.52 (m, 2 H), 7.40-7.32 (m, 2 H), 7.04 (t, J = 4.9 Hz, 1 H), 3.71 (s, 3 H). | 0.111 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 98 | N-3-isoxazolyl-1-(2,3',5'-trifluoro-5-methoxy-4-biphenylyl)-6-isoquinolinesulfonamide | 512.2 | 1 | 1H NMR (400 MHz, DMSO-d6) d = 11.92 (br. s., 1 H), 8.78-8.73 (m, 2 H), 8.70 (d, J = 1.9 Hz, 1 H), 8.18 (d, J = 5.3 Hz, 1 H), 8.00-7.93 (m, 1 H), 7.91-7.85 (m, 1 H), 7.49 (dd, J = 1.1, 6.4 Hz, 2 H), 7.45-7.33 (m, 3 H), 6.50 (d, J = 1.9 Hz, 1 H), 3.72 (s, 3 H). | 0.0345 | |
| 99 | 1-(5-fluoro-4-(5-fluoro-2-methoxy-3-pyridinyl)-2-methoxyphenyl)-N-3-isothiazolyl-6-isoquinolinesulfonamide | 541.1 | 1 | 1H NMR (400 MHz, DMSO-d6) d = 11.87 (s, 1 H), 8.92 (d, J = 4.8 Hz, 1 H), 8.73 (d, J = 5.7 Hz, 1 H), 8.70 (d, J = 1.7 Hz, 1 H), 8.29 (d, J = 3.0 Hz, 1 H), 8.16 (d, J = 5.9 Hz, 1 H), 7.99 (dd, J = 1.9, 8.9 Hz, 1 H), 7.92 (dd, J = 3.0, 8.4 Hz, 1 H), 7.85 (d, J = 8.9 Hz, 1 H), 7.34 (d, J = 9.7 Hz, 1 H), 7.29 (d, J = 5.9 Hz, 1 H), 7.04 (d, J = 4.8 Hz, 1 H), 3.91 (s, 3 H), 3.65 (s, 3 H). | 0.0663 | |
| 3 | 1-(2-fluoro-5-methoxy-3'-(trifluoromethyl)-4-biphenylyl)-N-3-isoxazolyl-6-phthalazinesulfonamide | 545.0 | 3 | $^1$H NMR (400 MHz, DMSO-d$_6$) d = 12.04 (br. s., 1 H), 9.97 (s, 1 H), 8.87 (d, J = 1.5 Hz, 1 H), 8.73 (d, J = 1.5 Hz, 1 H), 8.30 (dd, J = 1.9, 8.8 Hz, 1 H), 8.03 (br. s., 2 H), 7.93 (d, J = 8.7 Hz, 1 H), 7.88-7.77 (m, 2 H), 7.52 (d, J = 10.4 Hz, 1 H), 7.44 (d, J = 6.3 Hz, 1 H), 6.48 (d, J = 1.8 Hz, 1 H), 3.75 (s, 3 H). | 0.0305 | |
| 100 | 1-(4-bromo-5-fluoro-2-methoxyphenyl)-N-3-isoxazolyl-6-phthalazinesulfonamide | 479.0 | 3 | 1H NMR (400 MHz, DMSO-d6) d = 12.05 (br. s., 1 H), 9.97 (d, J = 0.9 Hz, 1 H), 8.91-8.82 (m, 1 H), 8.76 (d, J = 1.8 Hz, 1 H), 8.27 (dd, J = 2.0, 8.8 Hz, 1 H), 7.93-7.87 (m, 1 H), 7.61 (d, J = 5.7 Hz, 1 H), 7.55 (d, J = 8.6 Hz, 1 H), 6.49 (d, J = 1.8 Hz, 1 H), 3.68 (s, 3 H). | | |
| 101 | 1-(2,4'-dichloro-3'-fluoro-5-methoxy-4-biphenylyl)-N-3-isoxazolyl-6-isoquinolinesulfonamide | 544.1 | 3 | 1H NMR (400 MHz, DMSO-d6) d = 11.92 (br. s., 1 H), 8.73 (d, J = 5.7 Hz, 1 H), 8.68 (dd, J = 1.6, 15.0 Hz, 2 H), 8.15 (d, J = 5.4 Hz, 1 H), 7.97-7.92 (m, 1 H), 7.88-7.84 (m, 1 H), 7.76 (t, J = 8.1 Hz, 1 H), 7.69 (dd, J = 2.0, 10.3 Hz, 1 H), 7.56 (s, 1 H), 7.48 (dd, J = 1.4, 8.3 Hz, 1 H), 7.29 (s, 1 H), 6.47 (d, J = 1.8 Hz, 1 H), 3.70 (s, 3 H). | 0.0739 | |
| 102 | 4-(2-fluoro-5-methoxy-3'-(trifluoromethyl)-4-biphenylyl)-N-3-isoxazolyl-7-quinazolinesulfonamide | 545.2 | 19 | 1H NMR (400 MHz, DMSO-d6) d = 12.05 (br. s., 1 H), 9.54 (s, 1 H), 8.76 (d, J = 1.8 Hz, 1 H), 8.53 (d, J = 1.4 Hz, 1 H), 8.09-7.96 (m, 4 H), 7.89-7.77 (m, 2 H), 7.53 (d, J = 10.4 Hz, 1 H), 7.45 (d, J = 6.4 Hz, 1 H), 6.54 (d, J = 1.9 Hz, 1 H), 3.77 (s, 3 H). | 0.0229 | |
| 4 | 1-(3',5'-difluoro-3-(1-methyl-1H-pyrazol-5-yl)-4-biphenylyl)-N-3-isoxazolyl-6-isoquinolinesulfonamide | 544.1 | 4 | $^1$H NMR (400 MHz, DMSO-d$_6$) d = 11.86 (br. s., 1 H), 8.74 (d, J = 1.8 Hz, 1 H), 8.66 (d, J = 5.7 Hz, 1 H), 8.60 (d, J = 1.5 Hz, 1 H), 8.10-7.99 (m, 3 H), 7.89-7.78 (m, 2 H), 7.73-7.67 (m, 3 H), 7.31 (tt, J = 2.3, 9.2 Hz, 1 H), 6.99 (d, J = 1.9 Hz, 1 H), 6.44 (d, J = 1.8 Hz, 1 H), 5.59 (d, J = 1.9 Hz, 1 H), 3.64 (s, 3 H) | 0.148 | |
| 103 | 4-(4'-chloro-2-fluoro-5-methoxy-3'-methyl-4-biphenylyl)-N-3-isoxazolyl-7-quinazolinesulfonamide | 525.2 | 19 | 1H NMR (400 MHz, DMSO-d6) Shift = 12.05 (br. s., 1 H), 9.53 (s, 1 H), 8.76 (d, J = 1.9 Hz, 1 H), 8.52 (d, J = 1.6 Hz, 1 H), 8.09-7.98 (m, 2 H), 7.71 (s, 1 H), 7.61-7.53 (m, 2 H), 7.49 (d, J = 10.4 Hz, 1 H), 7.36 (d, J = 6.3 Hz, 1 H), 6.53 (d, J = 1.8 Hz, 1 H), 3.75 (s, 3 H), 2.44 (s, 3 H) | 0.024 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 104 | 4-(3'-chloro-2-fluoro-5-methoxy-4-biphenylyl)-N-3-isoxazolyl-7-quinazolinesulfonamide | 511.1 | 19 | 1H NMR (400 MHz, DMSO-d6) d = 12.06 (br. s., 1 H), 9.54 (s, 1 H), 8.76 (d, J = 1.8 Hz, 1 H), 8.52 (d, J = 1.5 Hz, 1 H), 8.11-7.97 (m, 2 H), 7.78 (d, J = 1.0 Hz, 1 H), 7.69 (qd, J = 1.7, 7.1 Hz, 1 H), 7.62-7.53 (m, 2 H), 7.51 (d, J = 10.4 Hz, 1 H), 7.41 (d, J = 6.4 Hz, 1 H), 6.54 (d, J = 1.8 Hz, 1 H), 3.76 (s, 3 H). | 0.0084 | |
| 105 | 1-(5-chloro-4-(5-fluoro-2-methoxy-3-pyridinyl)-2-methoxyphenyl)-N-3-isoxazolyl-6-isoquinolinesulfonamide | 541.0 | 1 | 1H NMR (500 MHz, DMSO-d6) d = 8.69 (d, J = 5.7 Hz, 1 H), 8.56 (d, J = 11.4 Hz, 2 H), 8.29 (d, J = 2.9 Hz, 1 H), 8.10 (d, J = 5.7 Hz, 1 H), 7.94 (dd, J = 1.5, 8.9 Hz, 1 H), 7.84 (dd, J = 3.0, 8.3 Hz, 1 H), 7.79 (d, J = 8.8 Hz, 1 H), 7.51 (s, 1 H), 7.28 (s, 1 H), 7.07 (br. s, 1 H), 6.39 (s, 1 H), 3.90 (s, 3 H), 3.67 (s, 3 H). | 0.0293 | |
| 106 | 1-(2-cyano-4'-fluoro-5-methoxy-4-biphenylyl)-N-3-isoxazolyl-6-isoquinolinesulfonamide | 501.1 | 1 | 1H NMR (500 MHz, DMSO-d6) d ppm 3.17 (s, 1 H) 3.81 (s, 4 H) 6.41-6.45 (m, 1 H) 7.39-7.48 (m, 3 H) 7.77-7.85 (m, 3 H) 7.88-7.98 (m, 2 H) 8.15 (d, J = 5.66 Hz, 1 H) 8.62 (br. s., 2 H) 8.72 (d, J = 5.66 Hz, 1 H) | 0.0625 | >10.0 |
| 107 | 1-(2-cyano-3',5'-difluoro-5-methoxy-4-biphenylyl)-N-2-pyrimidinyl-6-isoquinolinesulfonamide | 530.2 | 1 | 1H NMR (400 MHz, DMSO-d6) d = 12.19 (br. s., 1 H), 8.78 (s, 1 H), 8.74 (d, J = 5.7 Hz, 1 H), 8.50 (d, J = 4.9 Hz, 2 H), 8.22 (d, J = 5.7 Hz, 1 H), 8.05 (dd, J = 1.8, 8.9 Hz, 1 H), 7.98 (s, 1 H), 7.80 (d, J = 8.8 Hz, 1 H), 7.59-7.42 (m, 5 H), 7.04 (t, J = 4.8 Hz, 1 H), 3.81 (s, 3 H). | 0.255 | >10.0 |
| 5 | 1-(3',5'-difluoro-3-methoxy-4-biphenylyl)-N-3-isothiazolyl-6-isoquinolinesulfonamide | 510.0 | 5 | 1H NMR (400 MHz, DMSO-d6) d = 11.87 (s, 1 H), 8.93 (d, J = 4.8 Hz, 1 H), 8.74 (d, J = 5.8 Hz, 1 H), 8.71 (d, J = 1.9 Hz, 1 H), 8.18 (d, J = 5.3 Hz, 1 H), 7.97 (dd, J = 1.9, 8.9 Hz, 1 H), 7.84 (d, J = 8.9 Hz, 1 H), 7.64 (dd, J = 2.2, 9.1 Hz, 2 H), 7.53 (s, 2 H), 7.48-7.44 (m, 1 H), 7.48-7.43 (m, 1 H), 7.31 (tt, J = 2.2, 9.3 Hz, 1 H), 7.05 (d, J = 4.8 Hz, 1 H), 3.77 (s, 3 H). | 0.337 | >10.0 |
| 6 | N-3-isoxazolyl-1-(3-methoxy-3'-(trifluoromethyl)-4-biphenylyl)-6-isoquinolinesulfonamide | 526.0 | 6 | ¹H NMR (500 MHz, DMSO-d₆) d = 8.64 (d, J = 5.7 Hz, 1 H), 8.46 (s, 1 H), 8.39 (s, 1 H), 8.17-8.09 (m, 2 H), 8.02 (d, J = 5.7 Hz, 1 H), 7.86 (dd, J = 1.4, 8.8 Hz, 1 H), 7.81-7.66 (m, 3 H), 7.58-7.39 (m, 3 H), 6.29 (s, 1 H), 3.78 (s, 3 H). | 0.0789 | >10.0 |
| 108 | 1-(2-chloro-3'-fluoro-5-methoxy-4-biphenylyl)-N-2-pyrimidinyl-6-isoquinolinesulfonamide | 544.1 | 10 | 1H NMR (400 MHz, DMSO-d6) d = 11.92 (br. s., 1 H), 8.73 (d, J = 5.7 Hz, 1 H), 8.68 (dd, J = 1.6, 15.0 Hz, 2 H), 8.15 (d, J = 5.4 Hz, 1 H), 7.97-7.92 (m, 1 H), 7.88-7.84 (m, 1 H), 7.76 (t, J = 8.1 Hz, 1 H), 7.69 (dd, J = 2.0, 10.3 Hz, 1 H), 7.56 (s, 1 H), 7.48 (dd, J = 1.4, 8.3 Hz, 1 H), 7.29 (s, 1 H), 6.47 (d, J = 1.8 Hz, 1 H), 3.70 (s, 3 H). | 0.0862 | >10.0 |
| 10 | 1-(2-chloro-3'-fluoro-5-methoxy-4-biphenylyl)-N-3-isoxazolyl-6-phthalazinesulfonamide | 511.1 | 10 | 1H NMR (400 MHz, DMSO-d6) d = 12.05 (br. s., 1 H), 9.98 (d, J = 0.8 Hz, 1 H), 8.93-8.86 (m, 1 H), 8.76 (d, J = 1.9 Hz, 1 H), 8.31 (dd, J = 2.0, 8.8 Hz, 1 H), 8.00-7.91 (m, 1 H), 7.68 (s, 1 H), 7.63-7.53 (m, 1 H), 7.51-7.41 (m, 2 H), 7.38-7.28 (m, 2 H), 6.50 (d, J = 1.9 Hz, 1 H), 3.72 (s, 3 H). | 0.0841 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 109 | 1-(2-cyano-3'-fluoro-5-methoxy-4-biphenylyl)-N-2-pyrimidinyl-6-isoquinolinesulfonamide | 512.2 | 1 | 1H NMR (400 MHz, DMSO-d6) d = 12.10 (br. s, 1 H), 8.78 (s, 1 H), 8.74 (d, J = 5.7 Hz, 1 H), 8.50 (d, J = 5.0 Hz, 2 H), 8.21 (d, J = 5.5 Hz, 1 H), 8.05 (dd, J = 1.7, 8.9 Hz, 1 H), 7.96 (s, 1 H), 7.82 (d, J = 8.8 Hz, 1 H), 7.69-7.56 (m, 3 H), 7.45 (s, 1 H), 7.44-7.37 (m, 1 H), 7.04 (t, J = 5.0 Hz, 1 H), 3.81 (s, 3 H). | 0.241 | |
| 110 | 1-(6-chloro-3'-fluoro-4-methoxy-3-biphenylyl)-N-1,3,4-thiadiazol-2-yl-6-isoquinolinesulfonamide | 527.0 | 8 | 1H NMR (500 MHz, DMSO-d6) d = 8.76 (s, 1 H), 8.67 (s, 1 H), 8.58-8.49 (m, 1 H), 8.11 (d, J = 5.7 Hz, 1 H), 7.91-7.73 (m, 1 H), 7.55-7.42 (m, 2 H), 7.40 (s, 1 H), 7.31 (d, J = 7.6 Hz, 2 H), 7.26-7.17 (m, 1 H), 3.75 (br. s., 3 H. | 0.109 | >10.0 |
| 111 | 1-(3'-chloro-2-cyano-5-methoxy-4-biphenylyl)-N-3-isoxazolyl-6-isoquinolinesulfonamide | 517.0 | 1 | 1H NMR (500 MHz, DMSO-d6) d ppm 3.17 (s, 1 H) 3.82 (s, 4 H) 6.42-6.46 (m, 1 H) 7.46 (s, 1 H) 7.61-7.67 (m, 2 H) 7.69-7.75 (m, 1 H) 7.79-7.86 (m, 2 H) 7.89-8.00 (m, 2 H) 8.16 (d, J = 5.66 Hz, 1 H) 8.64 (s, 2 H) 8.73 (d, J = 5.66 Hz, 1 H) | 0.0218 | >10.0 |
| 112 | 1-(2-cyano-5-methoxy-3'-methyl-4-biphenylyl)-N-3-isoxazolyl-6-isoquinolinesulfonamide | 497.1 | 1 | 1H NMR (500 MHz, DMSO-d6) d ppm 3.80 (s, 4 H) 6.45 (d, J = 1.50 Hz, 1 H) 7.33-7.41 (m, 3 H) 7.45-7.59 (m, 4 H) 7.84 (d, J = 8.87 Hz, 1 H) 7.90-7.97 (m, 2 H) 8.16 (d, J = 5.66 Hz, 1 H) 8.65 (br. s., 2 H) 8.73 (d, J = 5.66 Hz, 1 H) | 0.0395 | >10.0 |
| 113 | 1-(2-chloro-3'-fluoro-5-methoxy-4-biphenylyl)-N-2-pyrimidinyl-6-phthalazinesulfonamide | 522.2 | 3 | 1H NMR (400 MHz, DMSO-d6) d = 12.76-12.17 (m, 1 H), 9.99 (d, J = 0.8 Hz, 1 H), 8.95 (d, J = 1.5 Hz, 1 H), 8.50 (d, J = 5.0 Hz, 2 H), 8.42 (dd, J = 1.9, 8.8 Hz, 1 H), 7.87 (d, J = 8.8 Hz, 1 H), 7.67 (s, 1 H), 7.59 (dt, J = 6.4, 8.1 Hz, 1 H), 7.49-7.41 (m, 2 H), 7.37-7.28 (m, 2 H), 7.04 (t, J = 5.0 Hz, 1 H), 3.72 (s, 3 H). | 0.095 | >10.0 |
| 114 | 1-(3'-chloro-2-cyano-5-methoxy-5'-methyl-4-biphenylyl)-N-3-isoxazolyl-6-isoquinolinesulfonamide | 531.0 | 1 | 1H NMR (500 MHz, DMSO-d6) d ppm 2.44 (s, 3 H) 3.81 (s, 4 H) 6.48 (d, J = 1.50 Hz, 1 H) 7.43 (s, 1 H) 7.47 (s, 1 H) 7.52 (s, 1 H) 7.60 (s, 1 H) 7.84 (d, J = 8.98 Hz, 1 H) 7.92-7.96 (m, 2 H) 8.18 (d, J = 5.66 Hz, 1 H) 8.70 (s, 1 H) 8.68 (s, 1 H) 8.75 (d, J = 5.72 Hz, 1 H) | 0.0288 | >10.0 |
| 9 | 1-(2-chloro-3'-fluoro-5-methoxy-4-biphenylyl)-N-1,3,4-thiadiazol-2-yl-6-phthalazinesulfonamide | 528.0 | 9 | 1H NMR (400 MHz, DMSO-d6) d = 14.58 (br. s., 1 H), 9.95 (d, J = 0.8 Hz, 1 H), 8.82 (s, 1 H), 8.77 (d, J = 1.4 Hz, 1 H), 8.26 (dd, J = 1.9, 8.8 Hz, 1 H), 7.85 (d, J = 8.7 Hz, 1 H), 7.66 (s, 1 H), 7.59 (dt, J = 6.3, 8.1 Hz, 1 H), 7.49-7.41 (m, 2 H), 7.38-7.25 (m, 2 H), 3.73 (s, 3 H). | 0.112 | >10.0 |
| 115 | 1-(2-fluoro-5-methoxy-3'-(trifluoromethyl)-4-biphenylyl)-N-3-isoxazolyl-6-isoquinolinesulfonamide | 544.0 | 1 | 1H NMR (500 MHz, DMSO-d6) d = 8.72 (d, J = 5.7 Hz, 1 H), 8.63 (d, J = 4.5 Hz, 2 H), 8.13 (d, J = 5.6 Hz, 1 H), 8.06-7.98 (m, 2 H), 7.93 (dd, J = 1.6, 8.9 Hz, 1 H), 7.89-7.77 (m, 3 H), 7.44-7.34 (m, 2 H), 6.47-6.42 (m, 1 H), 3.73 (s, 3 H). | 0.0135 | >10.0 |
| 116 | 1-(3'-chloro-2-fluoro-5-methoxy-4-biphenylyl)-N-3-isoxazolyl-6-isoquinolinesulfonamide | 510.2 | 1 | 1H NMR (400 MHz, DMSO-d6) d = 11.92 (br. s., 1 H), 8.75 (dd, J = 2.0, 3.7 Hz, 2 H), 8.69 (d, J = 1.8 Hz, 1 H), 8.17 (d, J = 5.4 Hz, 1 H), 8.00-7.86 (m, 2 H), 7.78 (s, 1 H), 7.72-7.66 (m, 1 H), 7.62-7.50 (m, 2 H), 7.39 (d, J = 10.5 Hz, 1 H), 7.35 (d, J = 6.5 Hz, 1 H), 6.50 (d, J = 1.8 Hz, 1 H), 3.72 (s, 3 H). | 0.0163 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 117 | 1-(4-bromo-5-chloro-2-methoxyphenyl)-N-3-isoxazolyl-6-isoquinolinesulfonamide | 494.0 | 1 | 1H NMR (400 MHz, DMSO-d6) d = 12.08-11.64 (m, 1 H), 8.74 (d, J = 1.8 Hz, 1 H), 8.72 (d, J = 5.7 Hz, 1 H), 8.67 (d, J = 1.9 Hz, 1 H), 8.16 (dd, J = 0.6, 5.8 Hz, 1 H), 7.94-7.89 (m, 1 H), 7.87-7.83 (m, 1 H), 7.63 (s, 1 H), 7.61 (s, 1 H), 6.49 (d, J = 1.8 Hz, 1 H), 3.68 (s, 3 H). | 0.108 | |
| 118 | 1-(2-cyano-5-methoxy-3'-(trifluoromethyl)-4-biphenylyl)-N-1,2,4-oxadiazol-3-yl-6-isoquinolinesulfonamide | 552.2 | 1 | 1H NMR (400 MHz, DMSO-d6) d = 9.26 (br. s., 1 H), 8.75 (d, J = 5.8 Hz, 1 H), 8.72 (s, 1 H), 8.22 (d, J = 5.6 Hz, 1 H), 8.12-8.04 (m, 2 H), 8.02-7.97 (m, 2 H), 7.95-7.91 (m, 1 H), 7.88-7.82 (m, 2 H), 7.51 (s, 1 H), 3.83 (s, 3 H). | 0.021 | >10.0 |
| 119 | 1-(2,4'-dichloro-5-methoxy-3'-methyl-4-biphenylyl)-N-3-isoxazolyl-6-isoquinolinesulfonamide | 540.0 | 1 | 1H NMR (400 MHz, DMSO-d6) d = 11.92 (br. s., 1 H), 8.77-8.72 (m, 2 H), 8.68 (d, J = 1.8 Hz, 1 H), 8.16 (d, J = 5.4 Hz, 1 H), 7.98-7.92 (m, 1 H), 7.90-7.85 (m, 1 H), 7.59-7.55 (m, 2 H), 7.54 (s, 1 H), 7.43 (dd, J = 1.8, 8.2 Hz, 1 H), 7.23 (s, 1 H), 6.50 (d, J = 1.8 Hz, 1 H), 3.69 (s, 3 H), 2.44 (s, 3 H). | 0.0736 | |
| 120 | 1-(2-chloro-3'-fluoro-5-methoxy-4-biphenylyl)-N-3-pyridazinyl-6-isoquinolinesulfonamide | 521.2 | 5 | 1H NMR (400 MHz, DMSO-d6) d = 8.72 (d, J = 5.8 Hz, 1 H), 8.67 (d, J = 1.8 Hz, 1 H), 8.36 (d, J = 3.4 Hz, 1 H), 8.18 (d, J = 5.7 Hz, 1 H), 8.02-7.96 (m, 2 H), 7.84 (d, J = 8.9 Hz, 1 H), 7.73 (dd, J = 4.2, 9.6 Hz, 1 H), 7.63-7.55 (m, 2 H), 7.49-7.43 (m, 2 H), 7.36-7.30 (m, 1 H), 7.29 (s, 1 H), 3.72 (s, 3 H). | 0.141 | >10.0 |
| 121 | 1-(6-chloro-3'-fluoro-4-methoxy-3-biphenylyl)-N-3-isoxazolyl-6-isoquinolinesulfonamide | 510.0 | 5 | 1H NMR (500 MHz, DMSO-d6) d = 8.69 (d, J = 5.7 Hz, 1 H), 8.62 (d, J = 13.2 Hz, 2 H), 8.11 (d, J = 5.7 Hz, 1 H), 7.95-7.81 (m, 2 H), 7.51-7.44 (m, 2 H), 7.40 (s, 1 H), 7.31 (d, J = 7.5 Hz, 2 H), 7.22 (t, J = 9.0 Hz, 1 H), 6.44 (s, 1 H), 3.74 (s, 3 H). | 0.0917 | >10.0 |
| 7 | 1-(2-chloro-3'-fluoro-5-methoxy-4-biphenylyl)-N-1,2,4-oxadiazol-3-yl-6-isoquinolinesulfonamide | 511.1 | 7 | ¹H NMR (400 MHz, DMSO-d$_6$) d = 9.36 (s, 1 H), 8.81-8.69 (m, 2 H), 8.23 (d, J = 5.6 Hz, 1 H), 8.03 (dd, J = 1.9, 8.9 Hz, 1 H), 7.92 (d, 7 = 9.0 Hz, 1 H), 7.64-7.53 (m, 2 H), 7.49-7.40 (m, 2 H), 7.36-7.27 (m, 2 H), 3.71 (s, 3 H). | 0.0477 | >10.0 |
| 122 | 1-(6-chloro-3'-fluoro-4-methoxy-3-biphenylyl)-N-2-pyrimidinyl-6-isoquinolinesulfonamide | 521.0 | 5 | 1H NMR (500 MHz, DMSO-d6) d = 12.24 (br s, 1 H), 8.74 (s, 1 H), 8.69 (d, J = 5.7 Hz, 1 H), 8.49 (d, J = 4.9 Hz, 1 H), 8.16 (d, J = 5.7 Hz, 1 H), 8.03 (dd, J = 1.7, 8.9 Hz, 1 H), 7.86 (d, J = 8.9 Hz, 1 H), 7.51-7.43 (m, 2 H), 7.40 (s, 1 H), 7.30 (d, J = 8.0 Hz, 2 H), 7.21 (t, J = 8.9 Hz, 1 H), 7.02 (t, J = 4.9 Hz, 1 H), 3.73 (s, 3 H). | 0.112 | >10.0 |
| 123 | 1-(3',5'-difluoro-3-methoxy-4-biphenylyl)-N-2-pyrimidinyl-6-isoquinolinesulfonamide | 505.1 | 5 | 1H NMR (400 MHz, DMSO-d6) d = 12.27 (s, 1 H), 8.81 (s, 1 H), 8.78 (d, J = 5.7 Hz, 1 H), 8.56 (d, J = 4.9 Hz, 2 H), 8.22 (d, J = 5.6 Hz, 1 H), 8.09 (dd, J = 1.9, 8.9 Hz, 1 H), 7.85 (d, J = 9.0 Hz, 1 H), 7.74-7.67 (m, 2 H), 7.62-7.55 (m, 2 H), 7.52-7.47 (m, 1 H), 7.36 (tt, J = 2.3, 9.2 Hz, 1 H), 7.10 (t, J = 4.8 Hz, 1 H), 3.82 (s, 3 H). | 0.171 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 124 | 1-(4'-chloro-2-fluoro-5-methoxy-3'-methyl-4-biphenylyl)-N-3-isoxazolyl-6-phthalazinesulfonamide | 525.0 | 3 | 1H NMR (400 MHz, DMSO-d6) d = 12.05 (br. s., 1 H), 9.97 (s, 1 H), 8.87 (d, J = 1.4 Hz, 1 H), 8.74 (d, J = 1.5 Hz, 1 H), 8.30 (dd, J = 1.9, 8.8 Hz, 1 H), 7.93 (d, J = 8.6 Hz, 1 H), 7.72 (s, 1 H), 7.62-7.54 (m, 2 H), 7.49 (d, J = 10.4 Hz, 1 H), 7.36 (d, J = 6.5 Hz, 1 H), 6.49 (d, J = 1.7 Hz, 1 H), 3.73 (s, 3 H), 2.46 (s, 3 H). | | |
| 125 | 1-(3',5'-difluoro-3-methoxy-4-biphenylyl)-N-(6-methoxy-4-pyrimidinyl)-6-isoquinolinesulfonamide | 535.0 | 5 | 1H NMR (500 MHz, DMSO-d6) d ppm 3.76 (s, 4 H) 3.73 (s, 3 H) 6.11 (s, 1 H) 7.28 (br. s., 1 H) 7.40-7.45 (m, 1 H) 7.46-7.58 (m, 2 H) 7.66 (d, J = 8.76 Hz, 1 H) 7.63 (d, J = 8.33 Hz, 2 H) 7.89 (d, J = 8.71 Hz, 1 H) 8.04 (d, J = 5.82 Hz, 1 H) 8.15 (s, 1 H) 8.49 (br. s., 1 H) 8.63 (d, J = 5.82 Hz, 1 H) | 0.497 | >10.0 |
| 126 | 1-(3',5'-difluoro-3-methoxy-4-biphenylyl)-N-(5-methyl-3-isoxazolyl)-6-isoquinolinesulfonamide | 508.1 | 5 | 1H NMR (500 MHz, DMSO-d6) d ppm 2.16 (s, 3 H) 3.77 (s, 4 H) 5.97 (s, 1 H) 7.28 (t, J = 9.46 Hz, 1 H) 7.41 (d, J = 7.75 Hz, 1 H) 7.46-7.57 (m, 2 H) 7.57-7.71 (m, 3 H) 7.84 (d, J = 8.60 Hz, 1 H) 8.01 (d, J = 5.61 Hz, 1 H) 8.42 (s, 1 H) 8.63 (d, J = 5.66 Hz, 1 H) | 4.19 | |
| 127 | 1-(3',5'-difluoro-3-methoxy-4-biphenylyl)-N-1,2,4-oxadiazol-3-yl-6-isoquinolinesulfonamide | 495.2 | 8 | 1H NMR (400 MHz, DMSO-d6) d = 9.35 (s, 1 H), 8.80-8.68 (m, 2 H), 8.22 (d, J = 5.5 Hz, 1 H), 8.01 (dd, J = 1.9, 8.9 Hz, 1 H), 7.88 (d, J = 8.9 Hz, 1 H), 7.70-7.50 (m, 5 H), 7.49-7.42 (m, 1 H), 7.30 (tt, J = 2.3, 9.3 Hz, 1 H), 3.78 (s, 3 H). | 0.106 | >10.0 |
| 128 | 1-(3',5'-difluoro-3-methoxy-4-biphenylyl)-N-5-isoxazolyl-6-isoquinolinesulfonamide | 494.0 | 5 | 1H NMR (500 MHz, DMSO-d6) d ppm 3.42 (br. s., 5 H) 3.68-3.85 (m, 3 H) 7.29 (br. s., 1 H) 7.43 (d, J = 7.75 Hz, 1 H) 7.47-7.58 (m, 2 H) 7.58-7.71 (m, 2 H) 7.88 (d, J = 9.08 Hz, 1 H) 8.04 (d, J = 5.50 Hz, 1 H) 8.47 (s, 1 H) 8.65 (d, J = 5.88 Hz, 1 H) | 3.51 | |
| 8 | 1-(3',5'-difluoro-3-methoxy-4-biphenylyl)-N-(5-methoxy-1,3,4-thiadiazol-2-yl)-6-isoquinolinesulfonamide | 541.1 | 8 | $^1$H NMR (400 MHz, DMSO-d$_6$) d = 13.91-13.34 (m, 1 H), 8.71 (d, J = 5.7 Hz, 1 H), 8.55 (d, J = 1.9 Hz, 1 H), 8.11 (d, J = 5.3 Hz, 1 H), 7.92-7.84 (m, 1 H), 7.78 (d, J = 8.9 Hz, 1 H), 7.68-7.60 (m, 2 H), 7.57-7.49 (m, 2 H), 7.46-7.41 (m, 1 H), 7.30 (tt, J = 2.3, 9.3 Hz, 1 H), 4.01 (s, 3 H), 3.78 (s, 3 H). | 3.29 | |
| 129 | 1-(3',5'-difluoro-3-methoxy-4-biphenylyl)-N-1,2,5-thiadiazol-3-yl-6-isoquinolinesulfonamide | 511.1 | 5 | 1H NMR (500 MHz, DMSO-d6) d ppm 3.70-3.82 (m, 4 H) 7.28 (t, J = 8.82 Hz, 1 H) 7.38-7.57 (m, 3 H) 7.58-7.68 (m, 3 H) 7.91 (d, J = 8.92 Hz, 1 H) 8.02 (d, J = 5.50 Hz, 1 H) 8.15 (s, 1 H) 8.52 (s, 1 H) 8.62 (d, J = 5.56 Hz, 1 H) | 0.428 | >10.0 |
| 130 | 1-(3',5'-difluoro-3-methoxy-4-biphenylyl)-N-(3-methyl-1,2,4-thiadiazol-5-yl)-6-isoquinolinesulfonamide | 525.2 | 8 | 1H NMR (400 MHz, DMSO-d6) d = 8.73 (d, J = 5.8 Hz, 1 H), 8.61 (d, J = 1.7 Hz, 1 H), 8.20 (d, J = 5.7 Hz, 1 H), 7.96-7.90 (m, 1 H), 7.83 (d, J = 8.9 Hz, 1 H), 7.65 (dd, J = 2.2, 9.0 Hz, 2 H), 7.58-7.51 (m, 2 H), 7.50-7.45 (m, 1 H), 7.30 (tt, J = 2.3, 9.3 Hz, 1 H), 3.78 (s, 3 H), 2.29 (s, 3 H). | 1.04 | >30.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 131 | 1-(3',5'-difluoro-3-methoxy-4-biphenylyl)-N-(6-methyl-2-pyrazinyl)-6-isoquinolinesulfonamide | 519.1 | 5 | 1H NMR (500 MHz, DMSO-d6) d ppm 2.18 (s, 3 H) 3.76 (s, 4 H) 7.24-7.35 (m, 1 H) 7.42 (d, J = 7.64 Hz, 1 H) 7.46-7.56 (m, 2 H) 7.57-7.73 (m, 4 H) 7.86 (br. s., 1H) 7.98 (d, J = 8.39 Hz, 1 H) 8.03 (d, J = 5.88 Hz, 1 H) 8.56-8.65 (m, 2 H) | 1.63 | |
| 132 | N-(5-cyano-1,3-thiazol-2-yl)-1-(3',5'-difluoro-3-methoxy-4-biphenylyl)-6-isoquinolinesulfonamide | 535.1 | 8 | 1H NMR (400 MHz, DMSO-d6) d = 8.68 (d, J = 5.7 Hz, 1 H), 8.53 (d, J = 1.8 Hz, 1 H), 8.15-8.06 (m, 2 H), 7.89 (dd, J = 1.9, 8.9 Hz, 1 H), 7.74 (d, J = 8.9 Hz, 1 H), 7.67-7.60 (m, 2 H), 7.55-7.49 (m, 2 H), 7.45-7.42 (m, 1 H), 7.29 (tt, J = 2.3, 9.3 Hz, 1 H), 3.77 (s, 3 H). | 0.695 | |
| 133 | 1-(3',5'-difluoro-3-methoxy-4-biphenylyl)-N-(5-methyl-1,3,4-thiadiazol-2-yl)-6-isoquinolinesulfonamide | 525.2 | 8 | 1H NMR (400 MHz, DMSO-d6) d = 14.11 (br. s., 1 H), 8.70 (d, J = 5.7 Hz, 1 H), 8.54 (d, J = 1.9 Hz, 1 H), 8.10 (d, J = 5.6 Hz, 1 H), 7.91-7.85 (m, 1 H), 7.77 (d, J = 8.9 Hz, 1 H), 7.68-7.59 (m, 2 H), 7.56-7.48 (m, 2 H), 7.46-7.40 (m, 1 H), 7.30 (tt, J = 2.3, 9.3 Hz, 1 H), 3.77 (s, 3 H), 2.47 (s, 3 H). | 1.56 | |
| 134 | 1-(3',5'-difluoro-3-methoxy-4-biphenylyl)-N-(3-methoxy-1,2,4-thiadiazol-5-yl)-6-isoquinolinesulfonamide | 541.1 | 8 | 1H NMR (400 MHz, DMSO-d6) d = 8.72 (d, J = 5.8 Hz, 1 H), 8.58 (d, J = 1.8 Hz, 1 H), 8.20 (d, J = 5.9 Hz, 1 H), 7.95-7.90 (m, 1 H), 7.81 (d, J = 8.9 Hz, 1 H), 7.65 (dd, J = 2.2, 9.1 Hz, 2 H), 7.58-7.44 (m, 3 H), 7.30 (tt, J = 2.3, 9.2 Hz, 1 H), 3.89 (s, 3 H), 3.79 (s, 3 H). | 1.28 | |
| 135 | 1-(3',5'-difluoro-3-methoxy-4-biphenylyl)-N-(5-fluoro-2-pyrimidinyl)-6-isoquinolinesulfonamide | 523.1 | 5 | 1H NMR (500 MHz, DMSO-d6) d ppm 3.65-3.82 (m, 4 H) 7.27 (d, J = 9.67 Hz, 1 H) 7.42 (d, J = 7.59 Hz, 1 H) 7.46-7.56 (m, 2 H) 7.58-7.68 (m, 3 H) 7.94 (d, J = 8.17 Hz, 1 H) 8.03 (d, J = 4.92 Hz, 1 H) 8.30 (br. s., 1 H) 8.53 (br. s., 1 H) 8.63 (d, J = 5.29 Hz, 1 H) | 0.378 | >10.0 |
| 136 | N-((1-(3',5'-difluoro-3-methoxy-4-biphenylyl)-6-isoquinolinyl)sulfonyl)acetamide | 469.1 | 5 | 1H NMR (500 MHz, DMSO-d6) d ppm 1.70 (s, 2 H) 3.78 (s, 4 H) 7.28 (br. s., 1 H) 7.41 (d, J = 7.75 Hz, 1 H) 7.46-7.55 (m, 3 H) 7.56-7.66 (m, 3 H) 7.85 (d, J = 8.01 Hz, 1 H) 8.00 (d, J = 5.56 Hz, 1 H) 8.40 (s, 1 H) 8.61 (d, J = 5.82 Hz, 1 H) | 11.2 | |
| 137 | 1-(3',5'-difluoro-3-methoxy-4-biphenylyl)-N-1,3-oxazol-2-yl-6-isoquinolinesulfonamide | 494.1 | 5 | 1H NMR (500 MHz, DMSO-d6) d ppm 3.77 (s, 4 H) 7.29 (br. s., 1 H) 7.41-7.47 (m, 1 H) 7.49-7.60 (m, 3 H) 7.64 (t, J = 8.87 Hz, 3 H) 7.77 (d, J = 8.71 Hz, 1 H) 7.92 (d, J = 9.19 Hz, 1 H) 8.01 (d, J = 5.98 Hz, 1 H) 8.22 (s, 1 H) 8.49 (s, 1 H) 8.63 (d, J = 5.93 Hz, 1 H) | 0.36 | >10.0 |
| 138 | 1-(3',5'-difluoro-3-methoxy-4-biphenylyl)-N-3-pyridazinyl-6-isoquinolinesulfonamide | 505.0 | 5 | 1H NMR (500 MHz, DMSO-d6) d ppm 3.76 (s, 4 H) 7.28 (t, J = 9.14 Hz, 2 H) 7.34 (br. s., 2 H) 7.41 (d, J = 7.75 Hz, 1 H) 7.45-7.56 (m, 2 H) 7.57-7.67 (m, 3 H) 7.91 (d, J = 9.14 Hz, 1 H) 8.01 (d, J = 5.61 Hz, 1 H) 8.30 (br. s., 1 H) 8.50 (s, 1 H) 8.62 (d, J = 5.66 Hz, 1 H) | 0.251 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 139 | 1-(6-cyano-3',5'-difluoro-4-methoxy-3-biphenylyl)-N-3-isoxazolyl-6-isoquinolinesulfonamide | 519.2 | 1 | 1H NMR (400 MHz, DMSO-d6) d = 11.95 (br. s., 1 H), 8.81 (d, J = 5.7 Hz, 1 H), 8.74 (dd, J = 1.8, 3.6 Hz, 2 H), 8.25 (d, J = 5.3 Hz, 1 H), 7.96 (dd, J = 1.9, 8.9 Hz, 1 H), 7.88-7.79 (m, 2 H), 7.70 (d, J = 9.0 Hz, 1 H), 7.66-7.51 (m, 3 H), 7.43-7.31 (m, 3 H), 6.50 (d, J = 1.9 Hz, 1 H), 3.74 (s, 3 H). | 15.3 | |
| 140 | 1-(3',5'-difluoro-3-methoxy-4-biphenylyl)-N-2-pyrazinyl-6-isoquinolinesulfonamide | 505.0 | 5 | 1H NMR (500 MHz, DMSO-d6) d ppm 3.76 (s, 4 H) 7.28 (t, J = 9.06 Hz, 1 H) 7.41 (d, J = 7.69 Hz, 1 H) 7.45-7.56 (m, 2 H) 7.58-7.67 (m, 3 H) 7.70 (br. s., 1 H) 7.86 (br. s., 1 H) 7.93 (d, J = 8.76 Hz, 1 H) 7.97-8.04 (m, 2 H) 8.51 (s, 1 H) 8.61 (d, J = 5.61 Hz, 1 H) | 0.652 | |
| 141 | 1-(3',5'-difluoro-3-methoxy-4-biphenylyl)-N-2-pyridinyl-6-isoquinolinesulfonamide | 504.1 | 5 | 1H NMR (500 MHz, DMSO-d6) d ppm 3.76 (s, 4 H) 6.63 (br. s., 1 H) 7.00 (d, J = 8.17 Hz, 1 H) 7.26-7.32 (m, 1 H) 7.41 (d, J = 7.59 Hz, 1 H) 7.47-7.57 (m, 3 H) 7.57-7.73 (m, 3 H) 7.92 (s, 1 H) 7.90 (s, 1 H) 8.02 (d, J = 5.93 Hz, 1 H) 8.51 (s, 1 H) 8.63 (d, J = 5.61 Hz, 1 H) | 1.01 | |
| 142 | 1-(3',5'-difluoro-3-methoxy-4-biphenylyl)-N-3-isoxazolyl-6-isoquinolinesulfonamide | 494.1 | 5 | 1H NMR (400 MHz, DMSO-d6) d = 11.90 (br. s., 1 H), 8.77-8.72 (m, 2 H), 8.67 (d, J = 1.8 Hz, 1 H), 8.13 (d, J = 5.3 Hz, 1 H), 7.95-7.91 (m, 1 H), 7.84 (d, J = 9.0 Hz, 1 H), 7.67-7.60 (m, 2 H), 7.55-7.49 (m, 2 H), 7.47-7.41 (m, 1 H), 7.30 (tt, J = 2.3, 9.3 Hz, 1 H), 6.50 (d, J = 1.8 Hz, 1 H), 3.77 (s, 3 H). | 0.168 | >30.0 |
| 143 | 1-(3',5'-difluoro-3-methoxy-4-biphenylyl)-N-(5-(trifluoromethyl)-1,3-oxazol-2-yl)-6-isoquinolinesulfonamide | 562.1 | 5 | 1H NMR (500 MHz, DMSO-d6) d ppm 3.77 (s, 4 H) 3.88 (s, 1 H) 7.28 (br. s., 1 H) 7.43 (d, J = 7.48 Hz, 1 H) 7.46-7.55 (m, 2 H) 7.62 (t, J = 8.47 Hz, 3 H) 7.82 (br. s., 1 H) 7.90-7.98 (m, 2 H) 8.47 (s, 1 H) 8.60 (d, J = 5.61 Hz, 1 H) | 3.22 | |
| 11 | 1-(3'-fluoro-3-(hydroxymethyl)-4-biphenylyl)-N-1,3,4-thiadiazol-2-yl-6-isoquinolinesulfonamide | 493.1 | 11 | 1H NMR (400 MHz, DMSO-d6) d = 14.50 (br. s., 1 H), 8.80 (s, 1 H), 8.72 (d, J = 5.7 Hz, 1 H), 8.60 (d, J = 1.8 Hz, 1 H), 8.15 (d, J = 5.3 Hz, 1 H), 7.99 (d, J = 1.7 Hz, 1 H), 7.92-7.88 (m, 1 H), 7.81 (d, J = 8.9 Hz, 1 H), 7.76 (dd, J = 2.0, 7.9 Hz, 1 H), 7.66-7.62 (m, 2 H), 7.61-7.54 (m, 1 H), 7.42 (d, J = 7.9 Hz, 1 H), 7.29-7.23 (m, 1 H), 5.09 (br. s., 1 H), 4.59-4.08 (m, 2 H). | 1.6 | |
| 144 | 1-(2-cyano-3'-fluoro-5-methoxy-4-biphenylyl)-N-4-pyrimidinyl-6-isoquinolinesulfonamide | 512.2 | 1 | 1H NMR (400 MHz, DMSO-d6) d = 8.80-8.67 (m, 2 H), 8.59 (s, 1 H), 8.25 (d, J = 6.4 Hz, 1 H), 8.19 (d, J = 5.3 Hz, 1 H), 8.01-7.95 (m, 2 H), 7.80 (d, J = 8.9 Hz, 1 H), 7.69-7.57 (m, 3 H), 7.46 (s, 1 H), 7.44-7.37 (m, 1 H), 7.03 (d, J = 6.2 Hz, 1 H), 3.82 (s, 3 H). | 0.106 | >10.0 |
| 12 | 1-(3'-fluoro-3-(hydroxymethyl)-4-biphenylyl)-N-3-isoxazolyl-6-isoquinolinesulfonamide | 476.1 | 12 | $^1$H NMR (400 MHz, DMSO-d$_6$) d = 11.98 (br. s., 1 H), 8.80-8.72 (m, 3 H), 8.24 (d, J = 5.6 Hz, 1 H), 8.04-7.87 (m, 3 H), 7.78 (dd, J = 2.0, 7.9 Hz, 1 H), 7.67-7.54 (m, 3 H), 7.46 (d, J = 7.9 Hz, 1 H), 7.30-7.24 (m, 1 H), 6.51 (d, J = 1.9 Hz, 1 H), 4.62-4.05 (m, 2 H). | 2.21 | |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 145 | 1-(6-cyano-3',5'-difluoro-4-methoxy-3-biphenylyl)-N-4-pyrimidinyl-6-isoquinolinesulfonamide | 530.2 | 5 | 1H NMR (400 MHz, DMSO-d6) d = 13.14 (d, J = 3.9 Hz, 1 H), 8.77 (d, J = 5.7 Hz, 1 H), 8.71 (d, J = 1.5 Hz, 1 H), 8.56 (s, 1 H), 8.26-8.18 (m, 2 H), 7.99 (dd, J = 1.9, 8.8 Hz, 1 H), 7.88-7.80 (m, 1 H), 7.76-7.65 (m, 2 H), 7.44-7.36 (m, 3 H), 7.02 (d, J = 6.3 Hz, 1 H), 3.74 (s, 3 H). | 9.11 | |
| 146 | 1-(3-(hydroxymethyl)-3'-(trifluoromethyl)-4-biphenylyl)-N-3-isoxazolyl-6-isoquinolinesulfonamide | 526.1 | 12 | 1H NMR (400 MHz, DMSO-d6) d = 11.93 (br. s., 1 H), 8.79-8.64 (m, 3 H), 8.18 (d, J = 5.4 Hz, 1 H), 8.13-8.01 (m, 3 H), 7.97-7.85 (m, 2 H), 7.84-7.75 (m, 3 H), 7.46 (d, J = 7.9 Hz, 1 H), 6.50 (d, J = 1.8 Hz, 1 H), 5.10 (br. s., 1 H), 4.46-4.18 (m, 2 H). | 0.12 | >10.0 |
| 1 | 1-(2-cyano-5-methoxy-4'-(trifluoromethyl)-4-biphenylyl)-N-3-isoxazolyl-6-isoquinolinesulfonamide | 551.2 | 1 | 1H NMR (400 MHz, DMSO-d6) d = 11.93 (br. s., 1 H), 8.90-8.61 (m, 3 H), 8.20 (d, J = 5.4 Hz, 1 H), 8.05-7.81 (m, 7 H), 7.50 (s, 1 H), 6.50 (d, J = 1.8 Hz, 1 H), 3.82 (s, 3 H). | 0.0547 | >10.0 |
| 147 | 1-(4-methoxy-4'-(trifluoromethyl)-3-biphenylyl)-N-4-pyrimidinyl-6-isoquinolinesulfonamide | 537.2 | 1 | 1H NMR (400 MHz, DMSO-d6) d = 13.04 (br. s., 1 H), 8.71 (d, J = 5.7 Hz, 1 H), 8.67 (s, 1 H), 8.58 (s, 1 H), 8.25 (br. s., 1 H), 8.12 (d, J = 5.8 Hz, 1 H), 7.98-7.88 (m, 4 H), 7.81-7.72 (m, 4 H), 7.37 (d, J = 8.7 Hz, 1 H), 7.03 (br. s., 1 H), 3.71 (s, 3 H). | 0.0719 | >10.0 |
| 148 | 1-(2-cyano-5-methoxy-3'-(trifluoromethyl)-4-biphenylyl)-N-3-isoxazolyl-6-isoquinolinesulfonamide | 551.2 | 1 | $^1$H NMR (400 MHz, DMSO-d$_6$) d = 11.95 (br. s., 1 H), 8.86-8.63 (m, 3 H), 8.20 (d, J = 5.8 Hz, 1 H), 8.12-8.03 (m, 2 H), 7.99 (s, 1 H), 7.96-7.81 (m, 4 H), 7.51 (s, 1 H), 6.50 (d, J = 1.6 Hz, 1 H), 3.82 (s, 3 H). | 0.0286 | >10.0 [2] |
| 149 | 1-(3',5'-difluoro-3-methoxy-4-biphenylyl)-N-(5-methoxy-3-isoxazolyl)-6-isoquinolinesulfonamide | 524.1 | 5 | 1H NMR (500 MHz, DMSO-d6) d ppm 3.69 (br. s., 1 H) 3.77 (s, 3 H) 3.84 (s, 3 H) 5.37 (s, 1 H) 7.29 (t, J = 9.00 Hz, 1 H) 7.42 (d, J = 7.80 Hz, 1 H) 7.46-7.57 (m, 2 H) 7.63 (d, J = 6.46 Hz, 2 H) 7.69 (d, J = 8.82 Hz, 1 H) 7.86 (d, J = 8.65 Hz, 1 H) 8.02 (d, J = 5.61 Hz, 1 H) 8.46 (s, 1 H) 8.64 (d, J = 5.56 Hz, 1 H) | 1.46 | |
| 150 | 1-(6-cyano-3',5'-difluoro-4-methoxy-3-biphenylyl)-N-1,3,4-thiadiazol-2-yl-6-isoquinolinesulfonamide | 536.2 | 8 | 1H NMR (400 MHz, DMSO-d6) d = 14.52 (br. s., 1 H), 8.80-8.73 (m, 2 H), 8.61 (d, J = 1.7 Hz, 1 H), 8.22 (d, J = 5.6 Hz, 1 H), 7.90 (dd, J = 1.8, 8.9 Hz, 1 H), 7.85 (d, J = 8.8 Hz, 1 H), 7.76-7.67 (m, 2 H), 7.42-7.36 (m, 3 H), 3.74 (s, 3 H). | 6 | |
| 151 | 1-(5-(benzyloxy)-2-methylphenyl)-N-4-pyrimidinyl-6-isoquinolinesulfonamide | 483.0 | 2 | 1H NMR (400 MHz, DMSO-d6) d ppm 8.64-8.80 (m, 2 H) 8.58 (s, 1 H) 8.12 (d, J = 5.58 Hz, 1 H) 7.87-8.00 (m, 1 H) 7.65 (d, J = 8.90 Hz, 2 H) 7.24-7.51 (m, 7 H) 7.07-7.13 (m, 1 H) 6.94 (d, J = 2.74 Hz, 1 H) 5.11 (s, 2 H) 1.88 (s, 3 H) m/z (ESI) 483.0 (M + H)+. | 0.424 | >30.0 |
| 42 | 1-(2,3'-difluoro-5-methoxy-4-biphenylyl)-N-3-isoxazolyl-2-oxo-1,2-dihydro-6-quinolinesulfonamide | 510.0 | 42 | $^1$H NMR (400 MHz, CHLOROFORM-d) d ppm 8.27 (d, J = 1.76 Hz, 1 H) 8.15 (d, J = 2.05 Hz, 1 H) 7.97 (br. s., 1 H) 7.74-7.84 (m, 2 H) 7.43-7.53 (m, 1 H) 7.37-7.42 (m, 1 H) 7.33 (d, J = 9.98 Hz, 1 H) 7.11-7.18 (m, 2 H) 7.09 (d, J = 9.49 Hz, 1 H) 6.86 (dd, J = 14.67, 9.29 Hz, 2 H) 6.61 (d, J = 1.76 Hz, 1 H) 3.72-3.81 (m, 3 H). m/z (ESI) 510.0 (M + H)$^+$. | 0.027 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 39 | 1-(2-methyl-5-phenoxyphenyl)-N-4-pyrimidinyl-6-isoquinolinesulfonamide | 469.2 | 39 | $^1$H NMR (400 MHz, DMSO-d$_6$) d ppm 8.67-8.77 (m, 3 H) 8.18 (d, J = 5.48 Hz, 2 H) 8.01 (dd, J = 8.90, 1.86 Hz, 2 H) 7.76 (d, J = 8.80 Hz, 2 H) 7.32-7.48 (m, 3 H) 7.04-7.17 (m, 3 H) 6.95 (d, J = 2.54 Hz, 1 H) 1.94 (s, 3 H). m/z (ESI) 469.2 (M + H)+. | 0.488 | >10.0 |
| 152 | 1-(2-methoxy-5-phenyl-3-pyridinyl)-N-4-pyrimidinyl-6-isoquinolinesulfonamide | 470.1 | 41 | $^1$H NMR (400 MHz, DMSO-d$_6$) d ppm 8.69-8.76 (m, 1 H) 8.73 (d, J = 15.55 Hz, 1 H) 8.11-8.20 (m, 1 H) 8.01 (s, 1 H) 7.95-7.98 (m, 1 H) 7.72-7.81 (m, 2 H) 7.52-7.68 (m, 5 H) 7.44-7.51 (m, 1 H) 7.29-7.43 (m, 2 H) 3.80-3.86 (m, 3 H). m/z (ESI) 470.1 (M + H)+. | 2.44 | |
| 40 | 1-(2-methyl-5-(2-pyridinyloxy)phenyl)-N-4-pyrimidinyl-6-isoquinolinesulfonamide | 470.1 | 40 | $^1$H NMR (400 MHz, DMSO-d$_6$) d ppm 8.64-8.74 (m, 2 H) 8.54 (s, 1 H) 8.15-8.26 (m, 2 H) 8.12 (d, J = 5.67 Hz, 2 H) 7.98 (s, 1 H) 7.84 (s, 1 H) 7.76 (d, J = 8.90 Hz, 1 H) 7.44 (d, J = 8.41 Hz, 1 H) 7.20 (dd, J = 8.22, 2.54 Hz, 1 H) 7.09-7.15 (m, 1 H) 7.05 (d, J = 2.25 Hz, 2 H) 6.99 (d, J = 6.26 Hz, 1 H) 1.94-2.03 (m, 15 H). m/z (ESI) 470.1 (M + H)+. | 5.69 | |
| 153 | 1-(5-(cyclopropylmethoxy)-2-methylphenyl)-N-4-pyrimidinyl-6-isoquinolinesulfonamide | 447.0 | 2 | 1H NMR (400 MHz, DMSO-d6) d ppm 8.70 (d, J = 5.67 Hz, 2 H) 8.58 (s, 1 H) 8.12 (d, J = 5.87 Hz, 2 H) 7.91-8.03 (m, 2 H) 7.70 (d, J = 8.51 Hz, 1 H) 7.29 (d, J = 8.51 Hz, 1 H) 7.00 (dd, J = 8.51, 2.64 Hz, 1 H) 6.82 (d, J = 2.74 Hz, 1 H) 3.80 (d, J = 6.94 Hz, 3 H) 1.20 (s, 1 H) 0.46-0.61 (m, 2 H) 0.23-0.36 (m, 2 H). m/z (ESI) 447.0 (M + H)+. | 7.68 | |
| 154 | 1-(4'-chloro-2-cyano-3'-fluoro-5-methoxy-4-biphenylyl)-N-4-pyrimidinyl-6-isoquinolinesulfonamide | 545.8 | 28 | $^1$H NMR (DMSO-d$_6$) δ: 8.67-8.75 (m, 2H), 8.58 (s, 1H), 8.25 (br. s., 1H), 8.18 (d, J = 5.8 Hz, 1H), 7.94-8.00 (m, 2H), 7.81-7.91 (m, 2H), 7.78 (d, J = 8.8 Hz, 1H), 7.64 (d, J = 8.4 Hz, 1H), 7.48 (s, 1H), 6.97-7.09 (m, 1H), 3.82 (s, 3H) | 0.0435 | >30.0 |
| 155 | 1-(2-cyano-4'-fluoro-5-methoxy-3'-methyl-4-biphenylyl)-N-4-pyrimidinyl-6-isoquinolinesulfonamide | 526.0 | 28 | $^1$H NMR (DMSO-d$_6$) δ: 8.65-8.75 (m, 2H), 8.58 (s, 1H), 8.25 (d, J = 5.6 Hz, 1H), 8.18 (d, J = 5.7 Hz, 1H), 7.98 (dd, J = 8.8, 1.5 Hz, 1H), 7.93 (s, 1H), 7.79 (d, J = 8.9 Hz, 1H), 7.67 (d, J = 7.2 Hz, 1H), 7.60 (br. s., 1H), 7.33-7.41 (m, 2H), 6.98-7.07 (m, 1H), 3.81 (s, 3H), 2.37 (s, 3H) | 0.0455 | 23.4 |
| 156 | 1-(2-cyano-5-methoxy-3'-methyl-4-biphenylyl)-N-4-pyrimidinyl-6-isoquinolinesulfonamide | 508.0 | 28 | $^1$H NMR (DMSO-d$_6$) δ: 8.66-8.76 (m, 2H), 8.59 (s, 1H), 8.25 (d, J = 6.0 Hz, 1H), 8.19 (d, J = 5.7 Hz, 1H), 7.99 (dd, J = 8.9, 1.5 Hz, 1H), 7.93 (s, 1H), 7.81 (d, J = 8.9 Hz, 1H), 7.45-7.56 (m, 3H), 7.35-7.40 (m, 2H), 6.98-7.08 (m, 1H), 3.81 (s, 3H), 2.44 (s, 3H) | 0.0473 | 30.8 |
| 157 | 1-(2-cyano-5-methoxy-2'-methyl-4-biphenylyl)-N-4-pyrimidinyl-6-isoquinolinesulfonamide | 508.3 | 28 | $^1$H NMR (DMSO-d$_6$) δ: 8.68-8.77 (m, 2H), 8.59 (s, 1H), 8.23-8.28 (m, 1H), 8.20 (d, J = 5.6 Hz, 1H), 8.00 (s, 1H), 7.94 (s, 1H), 7.84 (d, J = 8.8 Hz, 1H), 7.34-7.46 (m, 4H), 7.30 (s, 1H), 6.98-7.07 (m, 1H), 3.75 (s, 3H), 2.28 (br. s., 3H) | 0.206 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 158 | 1-(3'-chloro-2-cyano-4'-fluoro-5-methoxy-4-biphenylyl)-N-4-pyrimidinyl-6-isoquinolinesulfonamide | 546.1 | 28 | $^1$H NMR (DMSO-d$_6$) δ: 8.67-8.75 (m, 2H), 8.58 (s, 1H), 8.25 (d, J = 5.6 Hz, 1H), 8.18 (d, J = 5.6 Hz, 1H), 7.95-8.04 (m, 3H), 7.78 (d, J = 8.8 Hz, 2H), 7.67 (t, J = 8.9 Hz, 1H), 7.47 (s, 1H), 6.98-7.06 (m, 1H), 3.82 (s, 3H) | 0.0194 | 5.85 |
| 159 | 1-(3'-chloro-2-cyano-5-methoxy-4'-methyl-4-biphenylyl)-N-4-pyrimidinyl-6-isoquinolinesulfonamide | 541.9 | 28 | $^1$H NMR (DMSO-d$_6$) δ: 8.68-8.76 (m, 2H), 8.58 (s, 1H), 8.25 (d, J = 5.9 Hz, 1H), 8.19 (d, J = 5.8 Hz, 1H), 7.92-8.01 (m, 2H), 7.76-7.83 (m, 2H), 7.63 (dd, J = 7.8, 1.6 Hz, 1H), 7.55-7.60 (m, 1H), 7.43 (s, 1H), 6.99-7.08 (m, 1H), 3.81 (s, 3H), 2.44 (s, 3H) | 0.0387 | >30.0 |
| 160 | 1-(3'-chloro-2-cyano-5-methoxy-5'-methyl-4-biphenylyl)-N-4-pyrimidinyl-6-isoquinolinesulfonamide | 541.9 | 28 | $^1$H NMR (DMSO-d$_6$) δ: 8.65-8.75 (m, 2H), 8.58 (s, 1H), 8.25 (br. s., 1H), 8.18 (d, J = 5.7 Hz, 1H), 7.92-8.01 (m, 2H), 7.78 (d, J = 8.9 Hz, 1H), 7.61 (s, 1H), 7.52 (s, 1H), 7.47 (s, 1H), 7.43 (s, 1H), 6.98-7.09 (m, 1H), 3.81 (s, 3H), 2.44 (s, 3H) | 0.0138 | 18.3 |
| 29 | 1-(4-(4-fluoro-3-methylphenoxy)-2-methoxyphenyl)-N-4-pyrimidinyl-6-isoquinolinesulfonamide | 517.0 | 29 | $^1$H NMR (DMSO-d$_6$) δ: 8.60-8.69 (m, 2H), 8.56 (s, 1H), 8.24 (br. s., 1H), 8.06 (d, J = 5.1 Hz, 1H), 7.95 (d, J = 9.0 Hz, 1H), 7.77 (d, J = 8.5 Hz, 1H), 7.30 (d, J = 8.3 Hz, 1H), 7.22 (t, J = 8.9 Hz, 1H), 7.14 (br. s., 1H), 7.02 (br. s., 2H), 6.90 (s, 1H), 6.59 (d, J = 8.3 Hz, 1H), 3.61 (s, 3H), 2.26 (s, 3H) | 1.58 | |
| 161 | 1-(4'-chloro-2-cyano-5-methoxy-3'-methyl-4-biphenylyl)-N-4-pyrimidinyl-6-isoquinolinesulfonamide | 542.2 | 28 | $^1$H NMR (DMSO-d$_6$) δ: 8.68-8.76 (m, 2H), 8.59 (s, 1H), 8.25 (d, J = 6.0 Hz, 1H), 8.19 (d, J = 5.7 Hz, 1H), 7.93-8.01 (m, 2H), 7.71-7.82 (m, 2H), 7.56-7.67 (m, 2H), 7.42 (s, 1H), 6.98-7.07 (m, 1H), 3.81 (s, 3H), 2.46 (s, 3H) | 0.0174 | >30.0 |
| 162 | 1-(2-cyano-5'-fluoro-2',5-dimethoxy-4-biphenylyl)-N-4-pyrimidinyl-6-isoquinolinesulfonamide | 541.9 | 28 | $^1$H NMR (DMSO-d$_6$) δ: 8.67-8.76 (m, 2H), 8.59 (s, 1H), 8.25 (d, J = 6.3 Hz, 1H), 8.19 (d, J = 5.7 Hz, 1H), 8.01 (d, J = 8.9 Hz, 1H), 7.89 (s, 1H), 7.80 (d, J = 8.9 Hz, 1H), 7.32-7.40 (m, 3H), 7.21-7.28 (m, 1H), 6.97-7.09 (m, 1H), 3.83 (s, 3H), 3.77 (s, 3H) | 0.47 | >10.0 |
| 163 | 1-(2-cyano-3'-fluoro-5-methoxy-4'-methyl-4-biphenylyl)-N-4-pyrimidinyl-6-isoquinolinesulfonamide | 526.3 | 28 | $^1$H NMR (DMSO-d$_6$) δ: 8.66-8.76 (m, 2H), 8.58 (s, 1H), 8.25 (d, J = 6.0 Hz, 1H), 8.19 (d, J = 5.7 Hz, 1H), 7.92-8.01 (m, 2H), 7.80 (d, J = 8.9 Hz, 1H), 7.57 (d, J = 10.2 Hz, 1H), 7.47-7.54 (m, 2H), 7.42 (s, 1H), 6.97-7.07 (m, 1H), 3.81 (s, 3H), 2.35 (s, 3H) | 0.0921 | >10.0 |
| 164 | 1-(2-cyano-3'-fluoro-5-methoxy-5'-methyl-4-biphenylyl)-N-4-pyrimidinyl-6-isoquinolinesulfonamide | 526.0 | 28 | $^1$H NMR (DMSO-d$_6$) δ: 8.66-8.75 (m, 2H), 8.58 (s, 1H), 8.25 (br. s., 1H), 8.18 (d, J = 5.7 Hz, 1H), 7.92-8.01 (m, 2H), 7.78 (d, J = 8.9 Hz, 1H), 7.42 (d, J = 11.4 Hz, 3H), 7.24 (d, J = 9.7 Hz, 1H), 6.97-7.10 (m, 1H), 3.81 (s, 3H), 2.45 (s, 3H) | 0.0924 | >30.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 165 | 1-(2-cyano-5-methoxy-2',4',5'-trimethyl-4-biphenylyl)-N-4-pyrimidinyl-6-isoquinolinesulfonamide | 536.2 | 28 | $^1$H NMR (DMSO-d$_6$) δ: 8.68-8.75 (m, 2H), 8.59 (s, 1H), 8.25 (d, J = 5.4 Hz, 1H), 8.19 (d, J = 5.7 Hz, 1H), 7.96-8.03 (m, 1H), 7.90 (s, 1H), 7.81 (d, J = 8.8 Hz, 1H), 7.24 (s, 1H), 7.18 (s, 1H), 7.13 (s, 1H), 6.98-7.08 (m, 1H), 3.74 (s, 3H), 2.28 (d, J = 5.5 Hz, 6H), 2.20 (br. s., 3H) | 0.0306 | >30.0 |
| 28 | 1-(2-cyano-3',5'-difluoro-5-methoxy-4-biphenylyl)-N-4-pyrimidinyl-6-isoquinolinesulfonamide | 530.2 | 28 | $^1$H NMR (DMSO-d$_6$) δ: 8.65-8.76 (m, 2H), 8.58 (s, 1H), 8.25 (br. s., 1H), 8.18 (d, J = 5.7 Hz, 1H), 7.94-8.01 (m, 2H), 7.77 (d, J = 8.9 Hz, 1H), 7.55 (d, J = 6.0 Hz, 2H), 7.43-7.51 (m, 2H), 6.96-7.10 (m, 1H), 3.82 (s, 3H) | 0.144 | >10.0 |
| 30 | 1-(4-(5-fluoro-2-methoxy-3-pyridinyl)-2-methoxyphenyl)-N-1,3,4-thiadiazol-2-yl-6-isoquinolinesulfonamide | 524.0 | 30 | $^1$H NMR (ACETONITRILE-d3) δ: 8.64 (d, J = 5.7 Hz, 1H), 8.47 (d, J = 1.8 Hz, 1H), 8.37 (s, 1H), 8.08 (d, J = 3.0 Hz, 1H), 7.84-7.91 (m, 2H), 7.66-7.76 (m, 2H), 7.30-7.42 (m, 3H), 3.96 (s, 3H), 3.68 (s, 3H). | 0.0801 | >30.0 |
| 166 | 1-(2-methoxy-4-(2-methoxy-3-pyridinyl)phenyl)-N-1,3,4-thiadiazol-2-yl-6-isoquinolinesulfonamide | 506.0 | 30 | $^1$H NMR (ACETONITRILE-d3) δ: 8.66 (d, J = 5.8 Hz, 1H), 8.48 (d, J = 1.7 Hz, 1H), 8.37 (s, 1H), 8.20 (dd, J = 4.9, 1.9 Hz, 1H), 7.85-7.91 (m, 2H), 7.83 (dd, J = 7.3, 1.9 Hz, 1H), 7.77 (d, J = 8.9 Hz, 1H), 7.35-7.41 (m, 2H), 7.28-7.33 (m, 1H), 7.08 (dd, J = 7.3, 5.0 Hz, 1H), 3.97 (s, 3H), 3.69 (s, 3H) | 0.794 | |
| 167 | 1-(3'-fluoro-2-methoxy-5-methyl-4-biphenylyl)-N-3-isoxazolyl-6-isoquinolinesulfonamide | 490.0 | 35 | $^1$H NMR (ACETONITRILE-d3) δ: 8.72 (d, J = 5.8 Hz, 1H), 8.59 (d, J = 1.8 Hz, 1H), 8.29 (d, J = 1.9 Hz, 1H), 7.90-7.96 (m, 2H), 7.81-7.86 (m, 1H), 7.37-7.51 (m, 3H), 7.35 (d, J = 0.4 Hz, 1H), 7.07-7.16 (m, 1H), 7.02 (s, 1H), 6.44 (d, J = 1.8 Hz, 1H), 3.74 (s, 3H), 1.95 (s, 3H) | 2.72 | |
| 35 | 1-(4'-chloro-2-methoxy-3',5-dimethyl-4-biphenylyl)-N-3-isoxazolyl-6-isoquinolinesulfonamide | 520.0 | 35 | $^1$H NMR (ACETONITRILE-d3) δ: 8.73 (d, J = 5.7 Hz, 1H), 8.60 (d, J = 1.8 Hz, 1H), 8.33 (d, J = 1.9 Hz, 1H), 7.89-7.97 (m, 2H), 7.82-7.88 (m, 1H), 7.51-7.56 (m, 1H), 7.40-7.44 (m, 2H), 7.32 (s, 1H), 7.00 (s, 1H), 6.46 (d, J = 1.8 Hz, 1H), 3.70-3.74 (m, 3H), 2.41-2.45 (m, 3H), 1.95 (s, 3H). | 3.3 | |
| 168 | 4-(5'-fluoro-2,2'-dimethoxy-5-methyl-4-biphenylyl)-N-3-isoxazolyl-7-quinazolinesulfonamide | 521.1 | 34 | $^1$H NMR (ACETONITRILE-d3) δ: 9.44 (s, 1H), 8.56 (d, J = 1.7 Hz, 1H), 8.28 (d, J = 1.8 Hz, 1H), 8.03 (dd, J = 8.8, 1.8 Hz, 1H), 7.91 (dd, J = 8.8, 0.5 Hz, 1H), 7.23 (s, 1H), 7.03-7.16 (m, 3H), 7.01 (s, 1H), 6.45 (d, J = 1.9 Hz, 1H), 3.78 (s, 3H), 3.66-3.71 (m, 3H) | 8.54 | |
| 169 | 1-(5-chloro-4-(difluoromethyl)-2-methoxyphenyl)-N-3-isoxazolyl-6-isoquinolinesulfonamide | 466.0 | 28 | $^1$H NMR (ACETONITRILE-d3) δ: 8.61 (d, J = 5.7 Hz, 1H), 8.45 (d, J = 1.8 Hz, 1H), 8.10 (d, J = 1.8 Hz, 1H), 7.90 (dd, J = 8.9, 1.8 Hz, 1H), 7.80-7.86 (m, 1H), 7.65 (d, J = 8.9 Hz, 1H), 7.47 (t, J = 1.1 Hz, 1H), 7.41 (s, 1H), 6.91-7.28 (m, 1H), 3.70 (s, 3H) | 0.104 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 170 | 1-(2-methoxy-4-(2-methylphenoxy)phenyl)-N-4-pyrimidinyl-6-isoquinolinesulfonamide | 499.0 | 29 | $^1$H NMR (DMSO-d$_6$) δ: 8.60-8.69 (m, 2H), 8.56 (s, 1H), 8.25 (br. s., 1H), 8.06 (d, J = 5.9 Hz, 1H), 7.95 (d, J = 9.0 Hz, 1H), 7.78 (d, J = 8.8 Hz, 1H), 7.37 (d, J = 8.1 Hz, 1H), 7.27 (d, J = 8.3 Hz, 2H), 7.12-7.20 (m, 1H), 7.08 (d, J = 8.2 Hz, 1H), 7.03 (br. s., 1H), 6.87 (d, J = 2.0 Hz, 1H), 6.45 (d, J = 8.1 Hz, 1H), 3.61 (s, 3H), 2.25 (s, 3H) | 0.171 | >10.0 |
| 171 | 1-(3',4'-difluoro-5-methoxy-2-methyl-4-biphenylyl)-N-1,3,4-thiadiazol-2-yl-6-isoquinolinesulfonamide | 525.0 | 30 | $^1$H NMR (ACETONITRILE-d$_3$) δ: 8.68 (d, J = 5.7 Hz, 1H), 8.50 (d, J = 1.7 Hz, 1H), 8.39 (s, 1H), 7.91 (d, J = 5.8 Hz, 1H), 7.84-7.89 (m, 1H), 7.78-7.84 (m, 1H), 7.33-7.44 (m, 2H), 7.23-7.29 (m, 2H), 7.00 (s, 1H), 3.62-3.67 (m, 3H), 2.24 (s, 3H) | 0.0334 | >10.0 |
| 172 | 1-(3',5'-difluoro-5-methoxy-2-methyl-4-biphenylyl)-N-1,3,4-thiadiazol-2-yl-6-isoquinolinesulfonamide | 525.0 | 30 | $^1$H NMR (ACETONITRILE-d$_3$) δ: 8.71 (d, J = 5.8 Hz, 1H), 8.51-8.55 (m, 1H), 8.42 (s, 1H), 7.87-7.96 (m, 2H), 7.79-7.85 (m, 1H), 7.31 (s, 1H), 7.13 (s, 2H), 7.05 (s, 2H), 3.68 (s, 3H), 2.29 (s, 3H) | 0.0349 | >10.0 |
| 173 | 4-(2,5'-dimethoxy-2',5-dimethyl-4-biphenylyl)-N-3-isoxazolyl-7-quinazolinesulfonamide | 517.2 | 34 | $^1$H NMR (ACETONITRILE-d3) δ: 9.45 (s, 1H), 8.57 (d, J = 1.5 Hz, 1H), 8.27-8.34 (m, 1H), 7.98-8.05 (m, 1H), 7.90-7.95 (m, 1H), 7.13-7.23 (m, 2H), 7.01 (s, 1H), 6.86 (dd, J = 8.4, 2.9 Hz, 1H), 6.80 (d, J = 2.7 Hz, 1H), 6.43-6.50 (m, 1H), 3.79 (s, 3H), 3.68 (s, 3H), 2.04 (s, 3H) | 3.84 | |
| 174 | 1-(4-(4-fluorophenoxy)-2-methoxyphenyl)-N-1,3,4-thiadiazol-2-yl-6-isoquinolinesulfonamide | 509.0 | 32 | $^1$H NMR (ACETONITRILE-d$_3$) δ: 8.66 (d, J = 5.8 Hz, 1H), 8.49 (d, J = 1.5 Hz, 1H), 8.39 (s, 1H), 7.89 (d, J = 5.7 Hz, 1H), 7.78-7.87 (m, 2H), 7.31 (d, J = 8.3 Hz, 1H), 7.13-7.21 (m, 4H), 6.83 (d, J = 2.2 Hz, 1H), 6.66 (dd, J = 8.3, 2.2 Hz, 1H), 3.61 (s, 3H) | 0.141 | >10.0 |
| 34 | 4-(4'-chloro-2-methoxy-3',5-dimethyl-4-biphenylyl)-N-3-isoxazolyl-7-quinazolinesulfonamide | 521.0 | 34 | $^1$H NMR (ACETONITRILE-d3) δ: 9.46 (s, 1H), 8.59 (d, J = 1.7 Hz, 1H), 8.35 (d, J = 1.9 Hz, 1H), 7.98-8.04 (m, 1H), 7.89-7.96 (m, 1H), 7.52-7.57 (m, 1H), 7.41-7.45 (m, 2H), 7.35 (s, 1H), 7.03 (s, 1H), 6.49 (d, J = 1.9 Hz, 1H), 3.71-3.75 (m, 3H), 2.44 (s, 3H), 2.05 (s, 3H) | 2.61 | |
| 175 | 1-(4-(3,4-difluorophenoxy)-2-methoxyphenyl)-N-4-pyrimidinyl-6-isoquinolinesulfonamide | 521.0 | 29 | $^1$H NMR (DMSO-d$_6$) δ: 8.59-8.70 (m, 2H), 8.55 (s, 1H), 8.23 (br. s., 1H), 8.07 (d, J = 5.5 Hz, 1H), 7.94 (d, J = 7.1 Hz, 1H), 7.78 (d, J = 9.2 Hz, 1H), 7.51 (d, J = 9.3 Hz, 1H), 7.34 (d, J = 8.2 Hz, 2H), 6.91-7.05 (m, 3H), 6.70 (d, J = 5.9 Hz, 1H), 3.62 (s, 3H) | 0.197 | >10.0 |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 176 | 1-(4-(3,4-dimethylphenoxy)-2-methoxyphenyl)-N-4-pyrimidinyl-6-isoquinolinesulfonamide | 513.0 | 29 | $^1$H NMR (DMSO-d$_6$) δ: 8.58-8.68 (m, 2H), 8.54 (s, 1H), 8.21 (br. s., 1H), 8.05 (d, J = 5.5 Hz, 1H), 7.94 (d, J = 9.2 Hz, 1H), 7.76 (d, J = 8.5 Hz, 1H), 7.28 (d, J = 8.3 Hz, 1H), 7.20 (d, J = 7.8 Hz, 1H), 6.98 (br. s., 2H), 6.88 (d, J = 2.2 Hz, 2H), 6.56 (d, J = 8.2 Hz, 1H), 3.60 (s, 3H), 2.23 (d, J = 10.3 Hz, 6H) | 0.204 | >10.0 |
| 177 | 1-(4-(3-fluoro-4-methylphenoxy)-2-methoxyphenyl)-N-4-pyrimidinyl-6-isoquinolinesulfonamide | 517.0 | 29 | $^1$H NMR (DMSO-d$_6$) δ: 8.59-8.68 (m, 2H), 8.55 (s, 1H), 8.23 (br. s., 1H), 8.06 (d, J = 5.9 Hz, 1H), 7.94 (d, J = 9.2 Hz, 1H), 7.77 (d, J = 9.0 Hz, 1H), 7.28-7.36 (m, 2H), 7.00 (d, J = 8.4 Hz, 2H), 6.88-6.96 (m, 2H), 6.67 (d, J = 6.1 Hz, 1H), 3.61 (s, 3H), 2.23 (s, 3H) | 0.0993 | >10.0 |
| 178 | 1-(4-(3,5-difluorophenoxy)-2-methoxyphenyl)-N-4-pyrimidinyl-6-isoquinolinesulfonamide | 521.0 | 29 | $^1$H NMR (DMSO-d$_6$) δ: 8.61 (br. s., 2H), 8.53 (br. s., 1H), 8.20 (br. s., 1H), 8.04-8.12 (m, 1H), 7.89-7.96 (m, 1H), 7.74-7.81 (m, 1H), 7.65-7.72 (m, 1H), 7.46-7.57 (m, 1H), 7.27-7.34 (m, 1H), 7.17-7.25 (m, 1H), 7.12 (br. s., 1H), 6.98 (br. s., 1H), 6.60-6.66 (m, 1H), 3.64 (d, J = 6.5 Hz, 3H) | 18.7 | |
| 179 | 1-(4-(3-fluoro-5-methylphenoxy)-2-methoxyphenyl)-N-4-pyrimidinyl-6-isoquinolinesulfonamide | 517.0 | 29 | $^1$H NMR (DMSO-d$_6$) δ: 8.61-8.69 (m, 2H), 8.56 (s, 1H), 8.25 (br. s., 1H), 8.08 (d, J = 5.8 Hz, 1H), 7.95 (d, J = 8.9 Hz, 1H), 7.79 (d, J = 8.6 Hz, 1H), 7.34 (d, J = 8.2 Hz, 1H), 6.93-7.06 (m, 2H), 6.78-6.90 (m, 3H), 6.72 (d, J = 8.2 Hz, 1H), 3.63 (s, 3H), 2.34 (s, 3H) | 0.077 | >10.0 |
| 180 | 1-(4-(3,5-dimethylphenoxy)-2-methoxyphenyl)-N-4-pyrimidinyl-6-isoquinolinesulfonamide | 513.2 | 29 | $^1$H NMR (DMSO-d$_6$) δ: 8.57-8.66 (m, 2H), 8.52 (s, 1H), 8.19 (br. s., 1H), 8.05 (d, J = 5.5 Hz, 1H), 7.94 (d, J = 8.6 Hz, 1H), 7.76 (d, J = 8.7 Hz, 1H), 7.29 (d, J = 8.3 Hz, 1H), 6.98 (br. s., 1H), 6.89 (s, 1H), 6.84 (s, 1H), 6.77 (s, 2H), 6.60 (d, J = 8.1 Hz, 1H), 3.61 (s, 3H), 2.29 (s, 6H) | 0.52 | >10.0 |
| 181 | 1-(2-methoxy-4-(3-methylphenoxy)phenyl)-N-4-pyrimidinyl-6-isoquinolinesulfonamide | 499.0 | 29 | $^1$H NMR (DMSO-d$_6$) δ: 8.61-8.69 (m, 2H), 8.56 (s, 1H), 8.24 (br. s., 1H), 8.07 (d, J = 5.9 Hz, 1H), 7.95 (d, J = 7.4 Hz, 1H), 7.78 (d, J = 8.5 Hz, 1H), 7.29-7.36 (m, 2H), 6.89-7.05 (m, 4H), 6.63 (d, J = 8.4 Hz, 1H), 3.61 (s, 3H), 2.34 (s, 3H) | 0.126 | >10.0 |
| 182 | 1-(2-methoxy-4-(4-methoxyphenoxy)phenyl)-N-4-pyrimidinyl-6-isoquinolinesulfonamide | 515.0 | 29 | $^1$H NMR (DMSO-d$_6$) δ: 8.57-8.66 (m, 2H), 8.52 (s, 1H), 8.20 (d, J = 6.0 Hz, 1H), 8.04 (d, J = 5.6 Hz, 1H), 7.93 (d, J = 8.6 Hz, 1H), 7.75 (d, J = 8.4 Hz, 1H), 7.27 (d, J = 8.3 Hz, 1H), 7.14 (d, J = 8.8 Hz, 2H), 6.93-7.04 (m, 3H), 6.85 (d, J = 2.0 Hz, 1H), 6.53 (d, J = 6.5 Hz, 1H), 3.77 (s, 3H), 3.60 (s, 3H) | 0.305 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 183 | 1-(2-methoxy-4-(3-methoxyphenoxy)phenyl)-N-4-pyrimidinyl-6-isoquinolinesulfonamide | 515.0 | 29 | $^1$H NMR (DMSO-d$_6$) δ: 8.58-8.69 (m, 2H), 8.54 (s, 1H), 8.22 (br. s., 1H), 8.06 (d, J = 5.4 Hz, 1H), 7.95 (d, J = 10.2 Hz, 1H), 7.77 (d, J = 8.6 Hz, 1H), 7.29-7.38 (m, 2H), 6.99 (br. s., 1H), 6.93 (s, 1H), 6.64-6.80 (m, 3H), 3.78 (s, 3H), 3.61 (s, 3H) | 0.203 | >10.0 |
| 184 | 1-(2-cyano-5-methoxy-3'-(trifluoromethyl)-4-biphenylyl)-N-4-pyrimidinyl-6-isoquinolinesulfonamide | 562.0 | 28 | $^1$H NMR (DMSO-d$_6$) δ: 8.66-8.76 (m, 2H), 8.59 (s, 1H), 8.25 (br. s., 1H), 8.19 (d, J = 5.7 Hz, 1H), 8.04-8.12 (m, 2H), 7.91-8.01 (m, 3H), 7.77-7.88 (m, 2H), 7.51 (s, 1H), 6.97-7.09 (m, 1H), 3.83 (s, 3H) | 0.0363 | >30.0 |
| 185 | 1-(2-cyano-5-methoxy-4'-(trifluoromethyl)-4-biphenylyl)-N-4-pyrimidinyl-6-isoquinolinesulfonamide | 562.0 | 28 | $^1$H NMR (DMSO-d$_6$) δ: 8.68-8.77 (m, 2H), 8.59 (s, 1H), 8.25 (d, J = 6.3 Hz, 1H), 8.19 (d, J = 5.7 Hz, 1H), 7.94-8.02 (m, 6H), 7.82 (d, J = 8.9 Hz, 1H), 7.50 (s, 1H), 6.98-7.08 (m, 1H), 3.82 (s, 3H) | 0.056 | 20.7 |
| 186 | 1-(2-cyano-4'-fluoro-5-methoxy-4-biphenylyl)-N-4-pyrimidinyl-6-isoquinolinesulfonamide | 512.2 | 28 | $^1$H NMR (DMSO-d$_6$) δ: 8.67-8.75 (m, 2H), 8.59 (s, 1H), 8.22-8.28 (m, 1H), 8.19 (d, J = 5.8 Hz, 1H), 7.93-8.01 (m, 2H), 7.81 (dd, J = 8.3, 4.8 Hz, 3H), 7.39-7.49 (m, 3H), 6.98-7.08 (m, 1H), 3.81 (s, 3H) | 0.15 | >10.0 |
| 187 | 1-(4-(2,5-difluorophenoxy)-2-methoxyphenyl)-N-1,3,4-thiadiazol-2-yl-6-isoquinolinesulfonamide | 527.0 | 32 | $^1$H NMR (ACETONITRILE-d$_3$) δ: 8.66 (d, J = 5.7 Hz, 1H), 8.48 (d, J = 1.7 Hz, 1H), 8.39 (s, 1H), 7.89 (d, J = 5.3 Hz, 1H), 7.78-7.88 (m, 2H), 7.27-7.37 (m, 2H), 6.94-7.08 (m, 2H), 6.89 (d, J = 2.3 Hz, 1H), 6.72 (dd, J = 8.3, 2.2 Hz, 1H), 3.60-3.65 (m, 3H) | 0.0994 | >10.0 |
| 36 | 4-(2-cyclopropyl-4-(trifluoromethyl)phenyl)-N-4-pyrimidinyl-7-quinazolinesulfonamide | 472.0 | 36 | $^1$H NMR (ACETONITRILE-d3) δ: 9.44 (s, 1H), 8.63 (s, 1H), 8.45 (br. s., 1H), 8.14 (br. s., 1H), 8.05 (d, J = 8.6 Hz, 1H), 7.74 (d, J = 8.7 Hz, 1H), 7.65 (dd, J = 8.0, 1.0 Hz, 1H), 7.48 (d, J = 8.0 Hz, 1H), 7.39 (s, 1H), 7.01 (br. s., 1H), 1.54 (tt, J = 8.2, 5.4 Hz, 1H), 0.66-0.83 (m, 2H), 0.53-0.66 (m, 2H) | 0.744 | |
| 188 | 1-(2-methoxy-4-(2-methoxy-5-methyl-3-pyridinyl)phenyl)-N-1,3,4-thiadiazol-2-yl-6-isoquinolinesulfonamide | 520.0 | 30 | $^1$H NMR (ACETONITRILE-d3) δ: 8.70 (d, J = 5.8 Hz, 1H), 8.51 (d, J = 1.8 Hz, 1H), 8.40 (s, 1H), 8.02 (dd, J = 2.3, 0.8 Hz, 1H), 7.92 (d, J = 5.2 Hz, 1H), 7.79-7.90 (m, 2H), 7.69 (dd, J = 2.3, 0.6 Hz, 1H), 7.36-7.43 (m, 2H), 7.31-7.35 (m, 1H), 3.92-3.96 (m, 3H), 3.70 (s, 3H), 2.33 (t, J = 0.7 Hz, 3H) | 0.215 | >30.0 |
| 38 | N-3-isoxazolyl-4-(2-methoxy-4-(trifluoromethyl)phenyl)-7-quinazolinesulfonamide | 451.0 | 38 | $^1$H NMR (ACETONITRILE-d3) δ: 9.41-9.46 (m, 1H), 8.55 (d, J = 1.7 Hz, 1H), 8.27-8.31 (m, 1H), 7.97 (dd, J = 8.8, 1.8 Hz, 1H), 7.80 (dd, J = 8.9, 0.5 Hz, 1H), 7.54-7.60 (m, 1H), 7.44-7.50 (m, 2H), 6.41-6.44 (m, 1H), 3.75 (s, 3H). | 2.57 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 37 | 1-(4-(1H-indol-1-yl)-2-methoxyphenyl)-N-1,3,4-thiadiazol-2-yl-6-isoquinolinesulfonamide | 515.0 | 37 | $^{1}$H NMR (ACETONITRILE-d3) δ: 8.71 (d, J = 5.8 Hz, 1H), 8.52 (s, 1H), 8.32-8.41 (m, 3H), 8.08 (dd, J = 8.0, 1.6 Hz, 1H), 7.94 (d, J = 5.6 Hz, 1H), 7.87-7.90 (m, 2H), 7.85 (d, J = 3.7 Hz, 1H), 7.80 (d, J = 2.1 Hz, 1H), 7.65 (dd, J = 8.1, 2.1 Hz, 1H), 7.51 (d, J = 8.2 Hz, 1H), 7.23 (dd, J = 7.8, 4.6 Hz, 1H), 6.76 (d, J = 3.7 Hz, 1H), 3.76 (s, 3H). | 0.12 | >30.0 |
| 189 | 1-(4-(5-fluoro-2-methoxy-4-pyridinyl)-2-methoxyphenyl)-N-1,3,4-thiadiazol-2-yl-6-isoquinolinesulfonamide | 524.0 | 30 | $^{1}$H NMR (ACETONITRILE-d3) δ: 8.67-8.71 (m, 1H), 8.50 (d, J = 1.9 Hz, 1H), 8.36-8.41 (m, 1H), 8.16 (d, J = 2.4 Hz, 1H), 7.90-7.95 (m, 1H), 7.84-7.89 (m, 1H), 7.74-7.80 (m, 1H), 7.45-7.49 (m, 1H), 7.39 (dq, J = 4.8, 1.7 Hz, 2H), 7.04 (d, J = 5.4 Hz, 1H), 3.94 (s, 3H), 3.71-3.75 (m, 3H) | 0.394 | >30.0 |
| 190 | 1-(4-(2-fluoro-5-methylphenoxy)-2-methoxyphenyl)-N-1,3,4-thiadiazol-2-yl-6-isoquinolinesulfonamide | 523.0 | 32 | $^{1}$H NMR (ACETONITRILE-d$_{3}$) δ: 8.65 (d, J = 5.8 Hz, 1H), 8.46-8.50 (m, 1H), 8.38 (s, 1H), 7.83-7.90 (m, 2H), 7.80 (s, 1H), 7.30 (d, J = 8.3 Hz, 1H), 7.13-7.22 (m, 1H), 7.00-7.11 (m, 2H), 6.84 (d, J = 2.3 Hz, 1H), 6.60-6.64 (m, 1H), 6.49-6.56 (m, 1H), 3.62 (s, 3H), 2.33 (s, 3H) | 0.243 | >10.0 |
| 191 | 4-(5'-fluoro-2',5-dimethoxy-2-methyl-4-biphenylyl)-N-3-isoxazolyl-7-quinazolinesulfonamide | 521.0 | 33 | $^{1}$H NMR (ACETONITRILE-d3) δ: 9.41-9.45 (m, 1H), 8.53-8.58 (m, 1H), 8.36-8.40 (m, 1H), 7.93-8.01 (m, 2H), 7.31 (s, 1H), 7.12-7.21 (m, 1H), 7.06 (s, 2H), 6.99 (s, 1H), 6.49-6.54 (m, 1H), 3.76-3.82 (m, 3H), 3.62-3.67 (m, 3H), 2.08-2.13 (m, 3H) | 0.0447 | >10.0 |
| 192 | 4-(2-cyclopropyl-4-(trifluoromethyl)phenyl)-N-1,3,4-thiadiazol-2-yl-7-quinazolinesulfonamide | 478.0 | 36 | $^{1}$H NMR (ACETONITRILE-d3) δ: 9.47 (s, 1H), 8.55 (d, J = 1.8 Hz, 1H), 8.41 (s, 1H), 7.95 (dd, J = 8.8, 1.8 Hz, 1H), 7.78 (dd, J = 8.8, 0.6 Hz, 1H), 7.66 (dd, J = 7.9, 1.0 Hz, 1H), 7.50 (d, J = 7.9 Hz, 1H), 7.41 (d, J = 0.5 Hz, 1H), 1.50-1.60 (m, 1H), 0.67-0.82 (m, 2H), 0.57-0.67 (m, 2H) | 4.94 | |
| 193 | 1-(4-(2-(difluoromethoxy)-3-pyridinyl)-2-methoxyphenyl)-N-1,3,4-thiadiazol-2-yl-6-isoquinolinesulfonamide | 542.0 | 30 | $^{1}$H NMR (ACETONITRILE-d3) δ: 8.70 (d, J = 5.7 Hz, 1H), 8.52 (d, J = 1.7 Hz, 1H), 8.40 (s, 1H), 8.26 (dd, J = 4.9, 1.9 Hz, 1H), 8.03 (dd, J = 7.5, 1.9 Hz, 1H), 7.94 (d, J = 5.3 Hz, 1H), 7.86-7.91 (m, 1H), 7.83 (d, J = 8.8 Hz, 1H), 7.63 (s, 1H), 7.44-7.48 (m, 1H), 7.30-7.38 (m, 3H), 3.71 (s, 3H) | 0.871 | |
| 31 | 1-(4-(5-fluoro-2-methoxy-3-pyridinyl)-2-methoxyphenyl)-N-3-isoxazolyl-6-isoquinolinesulfonamide | 507.0 | 31 | $^{1}$H NMR (ACETONITRILE-d3) δ: 8.70 (d, J = 5.7 Hz, 1H), 8.55 (d, J = 1.9 Hz, 1H), 8.30 (d, J = 1.8 Hz, 1H), 8.08 (d, J = 2.9 Hz, 1H), 7.88-7.94 (m, 2H), 7.78-7.84 (m, 1H), 7.72 (dd, J = 8.7, 2.9 Hz, 1H), 7.33-7.44 (m, 3H), 6.43 (d, J = 1.8 Hz, 1H), 3.96 (s, 3H), 3.69 (s, 3H). | 0.169 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 33 | 4-(4-(5-fluoro-6-methyl-2-pyridinyl)-2-methoxy-5-methylphenyl)-N-3-isoxazolyl-7-quinazolinesulfonamide | 506.0 | 33 | $^1$H NMR (ACETONITRILE-d3) δ: 9.44 (s, 1H), 8.55 (t, J = 1.1 Hz, 1H), 8.34-8.39 (m, 1H), 7.97 (d, J = 1.3 Hz, 2H), 7.53-7.59 (m, 1H), 7.42-7.48 (m, 1H), 7.33 (s, 1H), 7.20 (s, 1H), 6.47-6.53 (m, 1H), 3.69 (s, 3H), 2.57 (d, J = 3.0 Hz, 3H), 2.32 (s, 3H) | 0.445 | >10.0 |
| 194 | 1-(4-(3-fluoro-4-methylphenoxy)-2-methoxyphenyl)-N-1,3,4-thiadiazol-2-yl-6-isoquinolinesulfonamide | 523.0 | 32 | $^1$H NMR (ACETONITRILE-d$_3$) δ: 8.63 (d, J = 5.7 Hz, 1H), 8.43-8.47 (m, 1H), 8.36 (s, 1H), 7.87 (s, 2H), 7.73-7.79 (m, 1H), 7.32 (d, J = 8.2 Hz, 1H), 6.84 (s, 3H), 6.68-6.73 (m, 1H), 6.49-6.56 (m, 2H), 3.60 (s, 3H), 2.26 (d, J = 2.0 Hz, 3H) | 0.133 | >10.0 |
| 195 | 1-(4-((5-fluoro-2-pyridinyl)oxy)-2-methoxyphenyl)-N-3-isoxazolyl-6-isoquinolinesulfonamide | 493.0 | 31 | $^1$H NMR (ACETONITRILE-d3) δ: 8.71 (d, J = 5.8 Hz, 1H), 8.53-8.58 (m, 1H), 8.36 (d, J = 1.8 Hz, 1H), 8.11 (d, J = 3.1 Hz, 1H), 7.83-7.94 (m, 3H), 7.65 (ddd, J = 8.9, 7.8, 3.1 Hz, 1H), 7.37 (d, J = 8.2 Hz, 1H), 7.10 (ddd, J = 9.0, 3.6, 0.5 Hz, 1H), 6.94 (d, J = 2.2 Hz, 1H), 6.84 (dd, J = 8.3, 2.2 Hz, 1H), 6.48 (d, J = 1.9 Hz, 1H), 3.62 (s, 3H) | 1.61 | |
| 32 | 1-(4-(3-fluoro-5-methylphenoxy)-2-methoxyphenyl)-N-1,3,4-thiadiazol-2-yl-6-isoquinolinesulfonamide | 523.0 | 32 | $^1$H NMR (ACETONITRILE-d3) δ: 8.66 (d, J = 5.8 Hz, 1H), 8.48 (d, J = 1.4 Hz, 1H), 8.39 (s, 1H), 7.78-7.91 (m, 3H), 7.34 (d, J = 8.2 Hz, 1H), 6.87 (d, J = 2.2 Hz, 1H), 6.67-6.81 (m, 4H), 3.59-3.64 (m, 3H), 2.35 (d, J = 0.6 Hz, 3H). | 0.129 | |
| 196 | 1-(4-(2-fluoro-6-methoxy-3-pyridinyl)-2-methoxyphenyl)-N-1,3,4-thiadiazol-2-yl-6-isoquinolinesulfonamide | 524.0 | 30 | $^1$H NMR (ACETONITRILE-d3) δ: 8.68 (d, J = 5.8 Hz, 1H), 8.49 (d, J = 1.7 Hz, 1H), 8.38 (s, 1H), 8.04 (dd, J = 10.2, 8.2 Hz, 1H), 7.84-7.93 (m, 2H), 7.75-7.81 (m, 1H), 7.43 (d, J = 7.5 Hz, 1H), 7.27-7.34 (m, 2H), 6.84 (dd, J = 8.2, 1.2 Hz, 1H), 3.95 (s, 3H), 3.70 (s, 3H) | 1.05 | |
| 197 | 1-(2-cyano-3',4'-difluoro-5-methoxy-4-biphenylyl)-N-4-pyrimidinyl-6-isoquinolinesulfonamide | 530.0 | 28 | $^1$H NMR (ACETONITRILE-d$_3$) δ: 8.70-8.75 (m, 1H), 8.63-8.68 (m, 1H), 8.43-8.50 (m, 1H), 7.95-8.02 (m, 2H), 7.76-7.83 (m, 2H), 7.62-7.70 (m, 1H), 7.43-7.58 (m, 3H), 7.25-7.30 (m, 1H), 7.02-7.15 (m, 1H), 3.76-3.79 (m, 3H) | 0.076 | >10.0 |
| 198 | 4-(4-(5-fluoro-2-methoxy-3-pyridinyl)-2-methoxy-5-methylphenyl)-N-3-isoxazolyl-7-quinazolinesulfonamide | 522.0 | 33 | $^1$H NMR (ACETONITRILE-d3) δ: 9.42 (s, 1H), 8.54 (d, J = 1.6 Hz, 1H), 8.28-8.34 (m, 1H), 8.13 (d, J = 2.9 Hz, 1H), 7.97-8.02 (m, 1H), 7.89-7.95 (m, 1H), 7.52 (dd, J = 8.3, 3.0 Hz, 1H), 7.33 (s, 1H), 7.03 (s, 1H), 6.42-6.49 (m, 1H), 3.90-3.92 (m, 3H), 3.63-3.67 (m, 3H), 2.13 (s, 3H) | 0.183 | >10.0 |
| 199 | 4-(3',4'-difluoro-5-methoxy-2-methyl-4-biphenylyl)-N-3-isoxazolyl-7-quinazolinesulfonamide | 509.0 | 33 | $^1$H NMR (ACETONITRILE-d3) δ: 9.42 (s, 1H), 8.53 (d, J = 1.6 Hz, 1H), 8.30-8.35 (m, 1H), 7.95-8.01 (m, 1H), 7.88-7.94 (m, 1H), 7.22-7.45 (m, 4H), 7.04 (s, 1H), 6.44-6.49 (m, 1H), 3.68 (s, 3H), 2.24-2.28 (m, 3H) | 0.036 | >10.0 |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 200 | 1-(2-methoxy-4-(2-methoxy-5-pyrimidinyl(phenyl)-N-1,3,4-thiadiazol-2-yl-6-isoquinolinesulfonamide | 507.0 | 30 | $^1$H NMR (ACETONITRILE-d3) δ: 8.92 (s, 2H), 8.68 (d, J = 5.8 Hz, 1H), 8.50 (d, J = 1.8 Hz, 1H), 8.39 (s, 1H), 7.91 (dd, J = 5.8, 0.6 Hz, 1H), 7.84-7.88 (m, 1H), 7.75-7.79 (m, 1H), 7.46 (dd, J = 7.6, 0.4 Hz, 1H), 7.35-7.40 (m, 2H), 4.03 (s, 3H), 3.74 (s, 3H) | | |
| 201 | 4-(5-cyano-4-(5-fluoro-2-methoxy-3-pyridinyl)-2-methoxyphenyl)-N-3-isoxazolyl-7-quinazolinesulfonamide | 533.2 | 3 | 1H NMR (400 MHz, DMSO-d6) δ = 12.07 (br. s., 1 H), 9.56 (s, 1 H), 8.77 (d, J = 1.8 Hz, 1 H), 8.54 (d, J = 1.7 Hz, 1 H), 8.38 (d, J = 3.0 Hz, 1 H), 8.13-7.92 (m, 4 H), 7.54 (s, 1 H), 6.54 (d, J = 1.8 Hz, 2 H), 3.93 (s, 3 H), 3.81 (s, 3 H) | 0.424 | >10.0 |
| 13 | 4-(3',5'-difluoro-3-methoxy-4-biphenylyl)-N-1,3,4-thiadiazol-2-yl-7-quinolinesulfonamide | 511.1 | 13 | 1H NMR (400 MHz, DMSO-d6) δ = 9.09 (d, J = 4.4 Hz, 1 H), 8.79 (s, 1 H), 8.46 (d, J = 1.7 Hz, 1 H), 7.87 (dd, J = 1.9, 8.9 Hz, 1 H), 7.74 (d, J = 8.9 Hz, 1 H), 7.63 (dd, J = 2.2, 9.0 Hz, 2 H), 7.60 (d, J = 4.4 Hz, 1 H), 7.56 (d, J = 1.6 Hz, 1 H), 7.54-7.51 (m, 1 H), 7.41 (d, J = 7.7 Hz, 1 H), 7.30 (tt, J = 2.2, 9.3 Hz, 1 H), 3.79 (s, 3 H) | 0.453 | |
| 14 | 1-(2-chloro-3'-fluoro-5-methoxy-4-biphenylyl)-4-oxo-N-1,3,4-thiadiazol-2-yl-3,4-dihydro-6-phthalazinesulfonamide | 544.1 | 14 | 1H NMR (400 MHz, DMSO-d6) δ = 13.16 (s, 1 H), 8.83-8.79 (m, 1 H), 8.62 (d, J = 2.0 Hz, 1 H), 8.21 (dd, J = 2.1, 8.4 Hz, 1 H), 7.60-7.53 (m, 3 H), 7.41 (d, J = 7.8 Hz, 2 H), 7.32 (t, J = 8.9 Hz, 1 H), 7.27 (s, 1 H), 3.75 (s, 3 H) | 0.131 | >10.0 |
| 15 | 4-(2-chloro-3'-fluoro-5-methoxy-4-biphenylyl)-N-3-pyridazinyl-7-quinazolinesulfonamide | 522.2 | 15 | 1H NMR (400 MHz, DMSO-d6) δ = 9.49 (br. s., 1 H), 8.49 (br. s., 1 H), 8.37 (br. s., 1 H), 8.13-7.97 (m, 2 H), 7.92 (d, J = 8.6 Hz, 1 H), 7.75 (d, J = 6.5 Hz, 1 H), 7.67 (br. s., 1 H), 7.59 (d, J = 6.3 Hz, 1 H), 7.44 (br. s., 2 H), 7.32 (br. s., 2 H), 3.74 (br. s., 3 H) | 0.11 | |
| 202 | 4-(2-cyano-3',5'-difluoro-5-methoxy-4-biphenylyl)-N-3-isoxazolyl-7-quinazolinesulfonamide | 520.1 | 3 | 1H NMR (400 MHz, DMSO-d6) δ = 12.08 (d, J = 4.2 Hz, 1 H), 9.55 (s, 1 H), 8.76 (s, 1 H), 8.54 (s, 1 H), 8.10 (s, 1 H), 8.08-7.95 (m, 2 H), 7.55 (br. s., 3 H), 7.53-7.45 (m, 1 H), 6.53 (d, J = 1.7 Hz, 1 H), 3.86 (s, 3 H) | 0.046 | >10.0 |
| 203 | 4-(2-cyano-3'-fluoro-5-methoxy-4-biphenylyl)-N-3-isoxazolyl-7-quinazolinesulfonamide | 502.1 | 3 | 1H NMR (400 MHz, DMSO-d6) δ = 12.07 (br. s., 1 H), 9.56 (s, 1 H), 8.76 (d, J = 1.9 Hz, 1 H), 8.54 (d, J = 1.6 Hz, 1 H), 8.08 (s, 1 H), 8.08-8.04 (m, 1 H), 8.03-7.99 (m, 1 H), 7.70-7.58 (m, 3 H), 7.51 (s, 1 H), 7.46-7.39 (m, 1 H), 6.54 (d, J = 1.8 Hz, 1 H), 3.85 (s, 3 H) | 0.0288 | >10.0 |
| 16 | 1-(2-fluoro-5-methoxy-3'-(trifluoromethyl)-4-biphenylyl)-4-hydroxy-N-3-isoxazolyl-6-isoquinolinesulfonamide | 560.2 | 16 | 1H NMR (400 MHz, DMSO-d6) δ = 11.85 (br. s., 1 H), 11.20 (br. s., 1 H), 8.74 (t, J = 1.3 Hz, 1 H), 8.71 (s, 1 H), 8.29 (s, 1 H), 8.04-7.98 (m, 2 H), 7.95-7.90 (m, 1 H), 7.87-7.75 (m, 3 H), 7.39-7.30 (m, 2 H), 6.47 (t, J = 1.3 Hz, 1 H), 3.71 (s, 3 H) | | |
| 18 | 1-(3'-fluoro-3-methoxy-4-biphenylyl)-4-oxo-N-1,3,4-thiadiazol-2-yl-3,4-dihydro-6-phthalazinesulfonamide | 510.1 | 18 | 1H NMR (400 MHz, DMSO-d6) δ = 13.09 (br. s., 1 H), 8.79 (br. s., 1 H), 8.61 (br. s., 1 H), 8.18 (d, J = 9.3 Hz, 1 H), 7.68 (br. s., 2 H), 7.60-7.39 (m, 5 H), 7.32-7.20 (m, J = 7.9 Hz, 1 H), 3.81 (br. s., 3 H) | 1.42 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 19 | 4-(2,3'-dichloro-4'-fluoro-5-methoxy-4-biphenylyl)-N-3-isoxazolyl-7-quinazolinesulfonamide | 545.0 | 19 | 1H NMR (400 MHz, DMSO-d6) δ = 12.15-11.90 (m, 1 H), 9.53 (s, 1 H), 8.75 (br. s., 1 H), 8.51 (br. s., 1 H), 8.16-7.91 (m, 2 H), 7.83 (d, J = 5.5 Hz, 1 H), 7.72-7.51 (m, 3 H), 7.35 (s, 1 H), 6.53 (br. s., 1 H), 3.74 (s, 3 H) | 0.0078 | |
| 20 | 4-(5-cyano-4-(5-fluoro-2-methoxy-3-pyridinyl)-2-methoxyphenyl)-N-1,3,4-thiadiazol-2-yl-7-quinazolinesulfonamide | 550.1 | 20 | 1H NMR (400 MHz, DMSO-d6) δ = 9.52 (s, 1 H), 8.80 (s, 1 H), 8.42 (d, J = 1.7 Hz, 1 H), 8.37 (d, J = 3.0 Hz, 1 H), 8.05 (s, 1 H), 8.03 (d, J = 2.7 Hz, 1 H), 8.02-8.00 (m, 1 H), 7.91 (d, J = 8.8 Hz, 1 H), 7.54 (s, 1 H), 3.93 (s, 3 H), 3.82 (s, 3 H) | 0.182 | >10.0 |
| 204 | 4-(2,4'-dichloro-5-methoxy-3'-methyl-4-biphenylyl)-N-3-isoxazolyl-7-quinazolinesulfonamide | 543.1 | 19 | 1H NMR (400 MHz, DMSO-d6) δ = 12.05 (br. s., 1 H), 9.59-9.48 (m, 1 H), 8.76 (d, J = 1.8 Hz, 1 H), 8.52 (br. s., 1 H), 8.12-7.96 (m, 2 H), 7.72-7.63 (m, 1 H), 7.61-7.52 (m, 2 H), 7.43 (d, J = 7.8 Hz, 1 H), 7.32-7.23 (m, 1 H), 6.53 (d, J = 1.8 Hz, 1 H), 3.76-3.69 (m, 3 H), 2.46-2.41 (m, 3 H) | 0.0218 | |
| 205 | 1-(3'-chloro-2-fluoro-5-methoxy-4-biphenylyl)-4-hydroxy-N-3-isoxazolyl-6-isoquinolinesulfonamide | 526.1 | 16 | 1H NMR (400 MHz, DMSO-d6) δ = 11.86 (br. s., 1 H), 11.23 (br. s., 1 H), 8.75 (d, J = 1.8 Hz, 1 H), 8.71 (d, J = 1.7 Hz, 1 H), 8.28 (s, 1 H), 7.93 (dd, J = 1.9, 8.9 Hz, 1 H), 7.82-7.74 (m, 2 H), 7.67 (dd, J = 1.6, 7.3 Hz, 1 H), 7.61-7.51 (m, 2 H), 7.36-7.27 (m, 1 H), 6.47 (d, J = 1.8 Hz, 1 H), 3.71 (s, 3 H) | | |
| 206 | 4-(2-chloro-3',5'-difluoro-5-methoxy-4-biphenylyl)-N-3-isoxazolyl-7-quinazolinesulfonamide | 529.1 | 19 | 1H NMR (400 MHz, DMSO-d6) δ = 12.05 (br. s., 1 H), 9.54 (s, 1 H), 8.77 (d, J = 1.9 Hz, 1 H), 8.53 (d, J = 1.7 Hz, 1 H), 8.09-8.05 (m, 1 H), 8.02-7.97 (m, 1 H), 7.70 (s, 1 H), 7.44-7.32 (m, 4 H), 6.54 (d, J = 1.8 Hz, 1 H), 3.75 (s, 3 H) | 0.0145 | |
| 207 | 4-(2-chloro-3'-fluoro-5-methoxy-4-biphenylyl)-N-1,2,5-thiadiazol-3-yl-7-quinazolinesulfonamide | 528.2 | 15 | 1H NMR (400 MHz, DMSO-d6) δ = 9.49 (br. s., 1 H), 8.49 (br. s., 1 H), 8.37 (br. s., 1 H), 8.13-7.97 (m, 2 H), 7.92 (d, J = 8.6 Hz, 1 H), 7.75 (d, J = 6.5 Hz, 1 H), 7.67 (br. s., 1 H), 7.59 (d, J = 6.3 Hz, 1 H), 7.44 (br. s., 2 H), 7.32 (br. s., 2 H), 3.74 (br. s., 3 H) | 0.0515 | |
| 208 | 1-(3-(cyanomethoxy)-3'-fluoro-4-biphenylyl)-N-4-pyrimidinyl-6-isoquinolinesulfonamide | 512.2 | 5 | 1H NMR (400 MHz, DMSO-d6) δ = 8.73 (d, J = 5.8 Hz, 1 H), 8.68 (s, 1 H), 8.57 (s, 1 H), 8.23 (br. s., 1 H), 8.15 (d, J = 5.7 Hz, 1 H), 7.97 (dd, J = 1.8, 8.9 Hz, 1 H), 7.78 (d, J = 9.0 Hz, 1 H), 7.75-7.69 (m, 3 H), 7.65-7.57 (m, 2 H), 7.53 (d, J = 7.9 Hz, 1 H), 7.30 (dt, J = 2.2, 8.7 Hz, 1 H), 7.02 (br. s., 1 H), 5.25 (d, J = 3.1 Hz, 2 H) | 0.23 | >30.0 |
| 209 | 4-(4-(5-fluoro-2-methoxy-3-pyridinyl)-2-methoxyphenyl)-N-1,3,4-thiadiazol-2-yl-7-quinolinesulfonamide | 524.2 | 13 | 1H NMR (400 MHz, DMSO-d6) δ = 9.09 (d, J = 4.4 Hz, 1 H), 8.79 (s, 1 H), 8.46 (d, J = 1.8 Hz, 1 H), 8.23 (d, J = 2.9 Hz, 1 H), 7.98 (dd, J = 3.0, 8.9 Hz, 1 H), 7.89 (dd, J = 1.9, 8.9 Hz, 1 H), 7.76 (d, J = 8.8 Hz, 1 H), 7.61 (d, J = 4.4 Hz, 1 H), 7.47-7.37 (m, 3 H), 3.94 (s, 3 H), 3.73 (s, 3 H) | 0.328 | >10.0 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 210 | 4-(3'-fluoro-3-methoxy-4-biphenylyl)-N-1,3,4-thiadiazol-2-yl-7-quinolinesulfonamide | 493.1 | 13 | 1H NMR (400 MHz, DMSO-d6) δ = 9.09 (d, J = 4.4 Hz, 1 H), 8.79 (s, 1 H), 8.46 (d, J = 1.8 Hz, 1 H), 7.87 (dd, J = 1.9, 8.9 Hz, 1 H), 7.76 (d, J = 8.9 Hz, 1 H), 7.73-7.66 (m, 2 H), 7.61 (d, J = 4.4 Hz, 1 H), 7.56 (dt, J = 6.4, 8.1 Hz, 1 H), 7.52 (d, J = 1.5 Hz, 1 H), 7.50-7.46 (m, 1 H), 7.43-7.38 (m, 1 H), 7.27 (dt, J = 1.8, 8.6 Hz, 1 H), 3.79 (s, 3 H) | 1.05 | |
| 211 | 4-(2-cyano-5-methoxy-3'-(trifluoromethyl)-4-biphenylyl)-N-3-isoxazolyl-7-quinazolinesulfonamide | 552.2 | 3 | 1H NMR (400 MHz, DMSO-d6) δ = 12.07 (br. s., 1 H), 9.56 (s, 1 H), 8.77 (d, J = 1.8 Hz, 1 H), 8.54 (d, J = 1.5 Hz, 1 H), 8.12-8.00 (m, 5 H), 7.97-7.92 (m, 1 H), 7.89-7.83 (m, 1 H), 7.57 (s, 1 H), 6.54 (d, J = 1.8 Hz, 1 H), 3.86 (s, 3 H) | 0.0169 | >10.0 |
| 212 | 1-(5-fluoro-4-(6-fluoro-2-pyridinyl)-2-methoxyphenyl)-N-1,3,4-thiadiazol-2-yl-6-isoquinolinesulfonamide | 512.2 | 13 | 1H NMR (400 MHz, DMSO-d6) δ = 8.80 (s, 1 H), 8.72 (d, J = 5.7 Hz, 1 H), 8.58 (s, 1 H), 8.23-8.12 (m, 2 H), 7.89 (dd, J = 1.9, 8.9 Hz, 2 H), 7.85-7.79 (m, 1 H), 7.66 (d, J = 6.2 Hz, 1 H), 7.43 (d, J = 11.1 Hz, 1 H), 7.29 (dd, J = 2.4, 8.0 Hz, 1 H), 3.72 (s, 3 H) | 1.37 | |
| 213 | 4-(2-chloro-4'-fluoro-5-methoxy-3'-methyl-4-biphenylyl)-N-3-isoxazolyl-7-quinazolinesulfonamide | 525.2 | 19 | 1H NMR (400 MHz, DMSO-d6) δ = 12.06 (br. s., 1 H), 9.53 (s, 1 H), 8.76 (d, J = 1.8 Hz, 1 H), 8.52 (d, J = 1.6 Hz, 1 H), 8.09-7.98 (m, 2 H), 7.66 (s, 1 H), 7.50 (dd, J = 1.7, 7.4 Hz, 1 H), 7.47-7.40 (m, 1 H), 7.33-7.26 (m, 2 H), 6.54 (d, J = 1.8 Hz, 1 H), 3.73 (s, 3 H), 2.34 (d, J = 1.7 Hz, 3 H) | 0.0382 | |
| 214 | 4-(5-chloro-4-(5-fluoro-2-methoxy-3-pyridinyl)-2-methoxyphenyl)-N-3-isoxazolyl-7-quinazolinesulfonamide | 542.2 | 19 | 1H NMR (400 MHz, DMSO-d6) δ = 12.06 (br. s., 1 H), 9.53 (d, J = 3.7 Hz, 1 H), 8.77 (br. s., 1 H), 8.53 (br. s., 1 H), 8.31 (br. s., 1 H), 8.09 (d, J = 7.1 Hz, 1 H), 8.01 (br. s., 1 H), 7.85 (d, J = 4.5 Hz, 1 H), 7.65 (d, J = 3.8 Hz, 1 H), 7.36 (d, J = 3.5 Hz, 1 H), 6.54 (d, J = 1.7 Hz, 1 H), 3.89 (d, J = 3.8 Hz, 3 H), 3.70 (d, J = 3.7 Hz, 3 H) | 0.0198 | |
| 215 | 1-(2-chloro-3'-fluoro-5-methoxy-4-biphenylyl)-3-methyl-4-oxo-N-1,3,4-thiadiazol-2-yl-3,4-dihydro-6-phthalazinesulfonamide | 558.0 | 21 | 1H NMR (400 MHz, DMSO-d6) δ = 8.81 (s, 1 H), 8.65 (d, J = 1.5 Hz, 1 H), 8.20 (dd, J = 2.0, 8.5 Hz, 1 H), 7.62-7.54 (m, 3 H), 7.45-7.39 (m, 2 H), 7.32 (dt, J = 2.1, 8.5 Hz, 1 H), 7.28 (s, 1 H), 3.79 (s, 3 H), 3.75 (s, 3 H) | 0.0823 | >10.0 |
| 21 | 1-(2-chloro-3'-fluoro-5-methoxy-4-biphenylyl)-N-3-isoxazolyl-3-methyl-4-oxo-3,4-dihydro-6-phthalazinesulfonamide | 541.1 | 21 | 1H NMR (400 MHz, DMSO-d6) δ = 11.98 (br. s., 1 H), 8.77 (d, J = 1.9 Hz, 1 H), 8.75 (dd, J = 0.5, 2.0 Hz, 1 H), 8.26 (dd, J = 2.0, 8.6 Hz, 1 H), 7.64 (dd, J = 0.5, 8.5 Hz, 1 H), 7.62-7.55 (m, 2 H), 7.44-7.39 (m, 2 H), 7.35-7.29 (m, 1 H), 7.27 (s, 1 H), 6.47 (d, J = 1.9 Hz, 1 H), 3.79 (s, 3 H), 3.75 (s, 3 H) | 0.0424 | >10.0 |
| 216 | 4-(2-cyano-3',5'-difluoro-5-methoxy-4-biphenylyl)-N-1,3,4-thiadiazol-2-yl-7-quinazolinesulfonamide | 537.0 | 20 | 1H NMR (400 MHz, DMSO-d6) δ = 9.53 (s, 1 H), 8.81 (s, 1 H), 8.42 (d, J = 1.7 Hz, 1 H), 8.09 (s, 1 H), 8.04-7.98 (m, 1 H), 7.90 (d, J = 8.7 Hz, 1 H), 7.57-7.53 (m, 3 H), 7.52-7.45 (m, 1 H), 3.86 (s, 3 H) | 0.0456 | >10.0 |
| 217 | 1-(2-cyano-5-methoxy-3'-methyl-4-biphenylyl)-N-1,3,4-thiadiazol-2-yl-6-isoquinolinesulfonamide | 514.0 | 22 | 1H NMR (500 MHz, DMSO-d6) δ ppm 3.17 (s, 1 H) 3.75 (s, 1 H) 3.80 (s, 3 H) 7.20 (br. s., 1 H) 7.34-7.41 (m, 2 H) 7.42-7.59 (m, 3 H) 7.72 (d, J = 8.82 Hz, 1 H) 7.84-7.98 (m, 2 H) 8.09 (d, J = 5.66 Hz, 1 H) 8.47 (s, 1 H) 8.61 (s, 1 H) 8.66 (d, J = 5.66 Hz, 1 H) | 0.0223 | >10.0 |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 218 | 1-(2-cyano-3'-fluoro-5-methoxy-4'-methyl-4-biphenylyl)-N-1,3,4-thiadiazol-2-yl-6-isoquinolinesulfonamide | 532.0 | 22 | 1H NMR (500 MHz, DMSO-d6) δ ppm 2.35 (s, 3 H) 3.81 (s, 4 H) 7.41 (s, 1 H) 7.46-7.60 (m, 3 H) 7.73 (d, J = 8.87 Hz, 1 H) 7.83-7.94 (m, 2 H) 8.11 (d, J = 5.66 Hz, 1 H) 8.50 (s, 1 H) 8.63-8.70 (m, 2 H) | 0.0229 | >10.0 |
| 22 | 1-(2-cyano-5-methoxy-4'-(trifluoromethyl)-4-biphenylyl)-N-1,3,4-thiadiazol-2-yl-6-isoquinolinesulfonamide | 568.0 | 22 | 1H NMR (500 MHz, DMSO-d6) δ ppm 3.17 (s, 1 H) 3.75 (s, 1 H) 3.80 (s, 3 H) 7.20 (br. s., 1 H) 7.34-7.41 (m, 2 H) 7.42-7.59 (m, 3 H) 7.72 (d, J = 8.82 Hz, 1 H) 7.84-7.98 (m, 2 H) 8.09 (d, J = 5.66 Hz, 1 H) 8.47 (s, 1 H) 8.61 (s, 1 H) 8.66 (d, J = 5.66 Hz, 1 H) | 0.0258 | >10.0 |
| 219 | 1-(2-cyano-4'-fluoro-5-methoxy-4-biphenylyl)-N-1,3,4-thiadiazol-2-yl-6-isoquinolinesulfonamide | 518.0 | 22 | 1H NMR (500 MHz, DMSO-d6) δ ppm 3.81 (s, 4 H) 7.37-7.48 (m, 3 H) 7.72-7.84 (m, 3 H) 7.84-7.94 (m, 2 H) 8.12 (d, J = 5.66 Hz, 1 H) 8.51 (s, 1 H) 8.65-8.71 (m, 2 H) | 0.0338 | >10.0 |
| 220 | 1-(2-cyano-5-methoxy-2'-methyl-4-biphenylyl)-N-1,3,4-thiadiazol-2-yl-6-isoquinolinesulfonamide | 515.0 | 22 | 1H NMR (500 MHz, DMSO-d6) δ ppm 2.28 (br. s., 3 H) 3.75 (s, 4 H) 7.28 (s, 1 H) 7.37 (br. s., 2 H) 7.40-7.53 (m, 2 H) 7.75 (d, J = 8.87 Hz, 1 H) 7.84-7.93 (m, 2 H) 8.11 (d, J = 5.66 Hz, 1 H) 8.49 (s, 1 H) 8.61-8.70 (m, 2 H) | 0.0401 | >10.0 |
| 221 | 1-(3'-chloro-2-cyano-4'-fluoro-5-methoxy-4-biphenylyl)-N-1,3,4-thiadiazol-2-yl-6-isoquinolinesulfonamide | 553.0 | 22 | 1H NMR (500 MHz, DMSO-d6) δ ppm 3.81 (s, 4 H) 7.45 (s, 1 H) 7.62-7.72 (m, 2 H) 7.74-7.82 (m, 1 H) 7.85 (dd, J = 8.84, 1.58 Hz, 1 H) 7.92 (s, 1 H) 7.97-8.13 (m, 2 H) 8.42 (s, 1 H) 8.54 (s, 1 H) 8.64 (d, J = 5.66 Hz, 1 H) | 0.0092 | >10.0 |
| 17 | 1-(2-chloro-3'-fluoro-5-methoxy-4-biphenylyl)-4-hydroxy-N-3-isoxazolyl-6-isoquinolinesulfonamide | 526.1 | 17 | 1H NMR (400 MHz, DMSO-d6) δ = 11.86 (br. s., 1 H), 11.19 (s, 1 H), 8.73 (dd, J = 1.7, 13.5 Hz, 2 H), 8.29 (s, 1 H), 7.93 (dd, J = 2.0, 8.9 Hz, 1 H), 7.79 (d, J = 8.8 Hz, 1 H), 7.63-7.54 (m, 1 H), 7.49 (s, 1 H), 7.46-7.40 (m, 2 H), 7.35-7.28 (m, 1 H), 7.23 (s, 1 H), 6.47 (d, J = 1.8 Hz, 1 H), 3.70 (s, 3 H) | 0.0851 | >10.0 |
| 222 | 1-(2-cyano-3'-fluoro-5-methoxy-5'-methyl-4-biphenylyl)-N-1,3,4-thiadiazol-2-yl-6-isoquinolinesulfonamide | 532.0 | 22 | 1H NMR (500 MHz, DMSO-d6) δ ppm 3.17 (s, 1 H) 3.81 (s, 4 H) 7.24 (d, J = 9.62 Hz, 1 H) 7.37-7.45 (m, 4 H) 7.74 (d, J = 8.87 Hz, 1 H) 7.85-7.97 (m, 2 H) 8.12 (d, J = 5.72 Hz, 1 H) 8.52 (s, 1 H) 8.66-8.71 (m, 2 H) | 0.0218 | >10.0 |
| 223 | 1-(5-cyano-4-(5-fluoro-2-methoxy-3-pyridinyl)-2-methoxyphenyl)-N-1,3,4-thiadiazol-2-yl-6-isoquinolinesulfonamide | 548.1 | 22 | 1H NMR (500 MHz, DMSO-d6) δ ppm 3.77 (s, 4 H) 3.93 (s, 4 H) 7.46 (s, 1 H) 7.71 (d, J = 8.76 Hz, 1 H) 7.84-7.96 (m, 2 H) 8.02 (dd, J = 8.31, 2.91 Hz, 1 H) 8.11 (d, J = 5.56 Hz, 1 H) 8.36 (d, J = 2.94 Hz, 1 H) 8.50 (s, 1 H) 8.63-8.70 (m, 2 H) | 0.0723 | >10.0 |
| 224 | 1-(4'-chloro-2-cyano-3'-fluoro-5-methoxy-4-biphenylyl)-N-1,3,4-thiadiazol-2-yl-6-isoquinolinesulfonamide | 553.0 | 22 | 1H NMR (500 MHz, DMSO-d6) δ ppm 3.81 (s, 4 H) 7.45 (s, 1 H) 7.60-7.72 (m, 2 H) 7.81-7.92 (m, 3 H) 7.94 (s, 1 H) 8.08 (d, J = 5.72 Hz, 1 H) 8.44 (s, 1 H) 8.56 (s, 1 H) 8.65 (d, J = 5.66 Hz, 1 H) | 0.0186 | >10.0 |
| 23 | 1-(5-cyano-4-(3,3-difluoro-1-azetidinyl)-2-methoxyphenyl)-N-3-isoxazolyl-6-isoquinolinesulfonamide | 498.2 | 23 | 1H NMR (400 MHz, DMSO-d6) δ = 11.92 (br. s., 1 H), 8.74 (d, J = 1.9 Hz, 1 H), 8.70 (d, J = 5.8 Hz, 1 H), 8.68 (d, J = 2.0 Hz, 1 H), 8.16 (d, J = 5.6 Hz, 1 H), 7.96-7.92 (m, 1 H), 7.87-7.83 (m, 1 H), 7.60 (s, 1 H), 6.49 (d, J = 1.9 Hz, 1 H), 6.40 (s, 1 H), 4.71 (t, J = 12.4 Hz, 4 H), 3.72 (s, 3 H) | 0.988 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 225 | 1-(3'-chloro-2-cyano-5-methoxy-5'-methyl-4-biphenylyl)-N-1,3,4-thiadiazol-2-yl-6-isoquinolinesulfonamide | 549.0 | 22 | 1H NMR (500 MHz, DMSO-d6) δ ppm 3.81 (s, 5 H) 7.41 (s, 1 H) 7.46 (s, 1 H) 7.52 (s, 1 H) 7.61 (s, 1 H) 7.69 (d, J = 8.82 Hz, 1 H) 7.84-7.94 (m, 2 H) 8.09 (d, J = 5.72 Hz, 1 H) 8.46 (s, 1 H) 8.60 (s, 1 H) 8.66 (d, J = 5.66 Hz, 1 H) | 0.0111 | >10.0 |
| 226 | 4-(2-cyano-5-methoxy-3'-(trifluoromethyl)-4-biphenylyl)-N-1,3,4-thiadiazol-2-yl-7-quinazolinesulfonamide | 569.2 | 22 | 1H NMR (400 MHz, DMSO-d6) δ = 9.53 (s, 1 H), 8.81 (s, 1 H), 8.42 (d, J = 1.4 Hz, 1 H), 8.10 (s, 2 H), 8.08 (d, J = 7.9 Hz, 1 H), 8.03-7.98 (m, 1 H), 7.97-7.92 (m, 2 H), 7.89-7.83 (m, 1 H), 7.57 (s, 1 H), 3.87 (s, 3 H) | 0.0116 | >10.0 |
| 227 | 4-(2-chloro-3'-fluoro-5-methoxy-4-biphenylyl)-N-3-isoxazolyl-7-quinazolinesulfonamide | 511.1 | 15 | 1H NMR (400 MHz, DMSO-d6) δ = 12.06 (br. s., 1 H), 9.53 (s, 1 H), 8.77 (d, J = 1.9 Hz, 1 H), 8.52 (d, J = 1.6 Hz, 1 H), 8.08-8.05 (m, 1 H), 8.04-8.00 (m, 1 H), 7.68 (s, 1 H), 7.59 (dt, J = 6.3, 8.1 Hz, 1 H), 7.47-7.42 (m, 2 H), 7.37-7.30 (m, 2 H), 6.54 (d, J = 1.9 Hz, 1 H), 3.74 (s, 3 H) | 0.0369 | >10.0 |
| 24 | 1-(5-cyano-4-(3,3-difluoro-1-azetidinyl)-2-methoxyphenyl)-N-1,3,4-thiadiazol-2-yl-6-isoquinolinesulfonamide | 515.2 | 24 | 1H NMR (400 MHz, DMSO-d6) δ = 8.81 (s, 1 H), 8.69 (d, J = 5.9 Hz, 1 H), 8.59 (d, J = 1.5 Hz, 1 H), 8.19 (d, J = 5.8 Hz, 1 H), 7.91 (dd, J = 1.8, 8.9 Hz, 1 H), 7.81 (d, J = 8.9 Hz, 1 H), 7.62 (s, 1 H), 6.41 (s, 1 H), 4.72 (t, J = 12.3 Hz, 4 H), 3.74 (s, 10 H) | 1.36 | |
| 228 | 1-(4'-chloro-2-cyano-5-methoxy-3'-methyl-4-biphenylyl)-N-1,3,4-thiadiazol-2-yl-6-isoquinolinesulfonamide | 550.0 | 22 | 1H NMR (500 MHz, DMSO-d6) δ ppm 3.81 (s, 5 H) 7.35-7.44 (m, 1 H) 7.55-7.67 (m, 3 H) 7.67-7.76 (m, 3 H) 7.87 (dd, J = 8.84, 1.58 Hz, 1 H) 7.92 (s, 1 H) 8.10 (d, J = 5.72 Hz, 1 H) 8.48 (s, 1 H) 8.61-8.69 (m, 2 H) | 0.0133 | >10.0 |
| 229 | 1-(3'-chloro-2-cyano-5-methoxy-4'-methyl-4-biphenylyl)-N-1,3,4-thiadiazol-2-yl-6-isoquinolinesulfonamide | 548.0 | 22 | 1H NMR (500 MHz, DMSO-d6) δ ppm 3.81 (s, 5 H) 7.41 (s, 1 H) 7.57 (d, J = 7.91 Hz, 1 H) 7.63 (dd, J = 7.83, 1.52 Hz, 1 H) 7.69 (d, J = 8.87 Hz, 1 H) 7.78-7.89 (m, 2 H) 7.91 (s, 1 H) 8.08 (d, J = 5.66 Hz, 1 H) 8.45 (s, 1 H) 8.58 (s, 1 H) 8.65 (d, J = 5.66 Hz, 1 H) | 0.0205 | >10.0 |
| 230 | 1-(2-cyano-4'-fluoro-5-methoxy-3'-methyl-4-biphenylyl)-N-1,3,4-thiadiazol-2-yl-6-isoquinolinesulfonamide | 532.0 | 22 | 1H NMR (500 MHz, DMSO-d6) δ ppm 2.22 (s, 1 H) 2.36 (s, 2 H) 3.17 (br. s., 1 H) 3.35 (br. s., 3 H) 3.80 (s, 2 H) 7.07 (dd, J = 10.15, 8.33 Hz, 1 H) 7.22-7.41 (m, 1 H) 7.57-7.75 (m, 3 H) 7.82-7.94 (m, 1 H) 8.03 (s, 1 H) 8.10 (d, J = 5.66 Hz, 1 H) 8.48 (s, 1 H) 8.61-8.70 (m, 1 H) | 0.0127 | >10.0 |
| 231 | 1-(3-(cyanomethoxy)-3'-fluoro-4-biphenylyl)-N-3-isoxazolyl-6-isoquinolinesulfonamide | 501.1 | 5 | 1H NMR (400 MHz, DMSO-d6) δ = 11.90 (br. s., 1 H), 8.75 (d, J = 5.7 Hz, 1 H), 8.72 (d, J = 1.8 Hz, 1 H), 8.69 (d, J = 1.8 Hz, 1 H), 8.16 (d, J = 5.5 Hz, 1 H), 7.97-7.91 (m, 1 H), 7.87-7.82 (m, 1 H), 7.76-7.67 (m, 3 H), 7.65-7.56 (m, 2 H), 7.52 (d, J = 7.9 Hz, 1 H), 7.29 (dt, J = 2.2, 8.8 Hz, 1 H), 6.48 (d, J = 1.8 Hz, 1 H), 5.24 (d, J = 1.9 Hz, 2 H) | 0.14 | >30.0 |
| 232 | 1-(2-chloro-3'-fluoro-5-methoxy-4-biphenylyl)-N-3-isoxazolyl-4-oxo-3,4-dihydro-6-phthalazinesulfonamide | 527.2 | 14 | 1H NMR (400 MHz, DMSO-d6) δ = 13.22 (s, 1 H), 11.96 (br. s., 1 H), 8.77 (d, J = 1.8 Hz, 1 H), 8.72 (d, J = 1.8 Hz, 1 H), 8.26 (dd, J = 2.0, 8.5 Hz, 1 H), 7.65-7.54 (m, 3 H), 7.45-7.39 (m, 2 H), 7.36-7.29 (m, 1 H), 7.27 (s, 1 H), 6.47 (d, J = 1.8 Hz, 1 H), 3.75 (s, 3 H) | 0.126 | |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 233 | 1-(2-chloro-3',5'-difluoro-5-methoxy-4-biphenylyl)-N-3-isoxazolyl-3-methyl-4-oxo-3,4-dihydro-6-phthalazinesulfonamide | 559.1 | 21 | 1H NMR (400 MHz, DMSO-d6) δ = 11.98 (br. s., 1 H), 8.76 (dd, J = 1.8, 7.2 Hz, 2 H), 8.26 (dd, J = 2.0, 8.5 Hz, 1 H), 7.65-7.60 (m, 2 H), 7.46-7.25 (m, 4 H), 6.47 (d, J = 1.8 Hz, 1 H), 3.80 (s, 3 H), 3.76 (s, 3 H) | 0.138 | >30.0 |
| 234 | 1-(2-fluoro-5-methoxy-3'-(trifluoromethyl)-4-biphenylyl)-3-methyl-4-oxo-N-1,3,4-thiadiazol-2-yl-3,4-dihydro-6-phthalazinesulfonamide | 592.1 | 25 | 1H NMR (400 MHz, DMSO-d6) δ = 8.82 (s, 1 H), 8.66 (d, J = 1.5 Hz, 1 H), 8.20 (dd, J = 2.0, 8.5 Hz, 1 H), 8.01 (br. s., 2 H), 7.91-7.75 (m, 2 H), 7.59 (d, J = 8.5 Hz, 1 H), 7.45 (d, J = 10.3 Hz, 1 H), 7.41 (d, J = 6.4 Hz, 1 H), 3.80 (s, 3 H), 3.78 (s, 3 H) | 0.0784 | >10.0 |
| 26 | 4-(2-chloro-3'-fluoro-5-methoxy-4-biphenylyl)-N-1,2,4-oxadiazol-3-yl-7-quinazolinesulfonamide | 512.2 | 26 | 1H NMR (400 MHz, DMSO-d6) δ = 9.44 (s, 1 H), 8.88 (br. s., 1 H), 8.45 (s, 1 H), 8.08-8.00 (m, 1 H), 7.82 (d, J = 8.7 Hz, 1 H), 7.66 (s, 1 H), 7.62-7.53 (m, 1 H), 7.50-7.40 (m, 2 H), 7.37-7.26 (m, 2 H), 3.75 (s, 3 H) | 0.085 | >10.0 |
| 235 | 1-(2-chloro-3',5'-difluoro-5-methoxy-4-biphenylyl)-3-methyl-4-oxo-N-1,3,4-thiadiazol-2-yl-3,4-dihydro-6-phthalazinesulfonamide | 576.0 | 21 | 1H NMR (400 MHz, DMSO-d6) δ = 8.70-8.60 (m, 2 H), 8.16 (dd, J = 1.9, 8.4 Hz, 1 H), 7.60 (s, 1 H), 7.49 (d, J = 8.3 Hz, 1 H), 7.42-7.27 (m, 5 H), 3.78 (s, 3 H), 3.75 (s, 3 H) | 0.0471 | >10.0 |
| 236 | 1-(5-chloro-6-(3,3-difluoro-1-azetidinyl)-2-methoxy-3-pyridinyl)-N-1,3,4-thiadiazol-2-yl-6-isoquinolinesulfonamide | 525.0 | 24 | 1H NMR (400 MHz, DMSO-d6) δ = 8.80 (d, J = 2.8 Hz, 1 H), 8.68 (dd, J = 2.6, 5.7 Hz, 1 H), 8.56 (s, 1 H), 8.12 (d, J = 5.5 Hz, 1 H), 7.88 (s, 2 H), 7.79 (d, J = 2.6 Hz, 1 H), 4.68 (t, J = 12.7 Hz, 4 H), 3.76 (d, J = 2.4 Hz, 3 H) | 0.382 | >30.0 |
| 237 | 1-(5-chloro-6-(3,3-difluoro-1-pyrrolidinyl)-2-methoxy-3-pyridinyl)-N-1,3,4-thiadiazol-2-yl-6-isoquinolinesulfonamide | 539.2 | 24 | 1H NMR (400 MHz, DMSO-d6) δ = 8.80 (d, J = 1.7 Hz, 1 H), 8.67 (d, J = 5.8 Hz, 1 H), 8.55 (s, 1 H), 8.11 (d, J = 5.3 Hz, 1 H), 7.89 (s, 2 H), 7.76 (d, J = 1.6 Hz, 1 H), 4.16 (t, J = 13.6 Hz, 2 H), 3.99 (t, J = 7.2 Hz, 2 H), 3.76 (s, 3 H), 2.55 (br. s., 2 H) | 0.336 | >30.0 |
| 25 | 1-(2-fluoro-5-methoxy-3'-(trifluoromethyl)-4-biphenylyl)-N-3-isoxazolyl-3-methyl-4-oxo-3,4-dihydro-6-phthalazinesulfonamide | 575.2 | 25 | 1H NMR (400 MHz, DMSO-d6) δ = 11.97 (br. s., 1 H), 8.76 (dd, J = 1.7, 6.5 Hz, 2 H), 8.25 (dd, J = 2.0, 8.6 Hz, 1 H), 8.00 (s, 2 H), 7.89-7.75 (m, 2 H), 7.65 (d, J = 8.6 Hz, 1 H), 7.45 (d, J = 10.3 Hz, 1 H), 7.40 (d, J = 6.4 Hz, 1 H), 6.47 (d, J = 1.8 Hz, 1 H), 3.80 (s, 3 H), 3.77 (s, 3 H) | 0.0941 | >10.0 |
| 238 | 1-(3-(cyanomethoxy)-3'-fluoro-4-biphenylyl)-N-1,3,4-thiadiazol-2-yl-6-isoquinolinesulfonamide | 518.2 | 8 | 1H NMR (400 MHz, DMSO-d6) δ = 8.79 (s, 1 H), 8.73 (d, J = 5.7 Hz, 1 H), 8.58 (d, J = 1.8 Hz, 1 H), 8.15 (d, J = 5.4 Hz, 1 H), 7.91-7.85 (m, 1 H), 7.79 (d, J = 9.0 Hz, 1 H), 7.75-7.68 (m, 3 H), 7.65-7.57 (m, 2 H), 7.52 (d, J = 7.8 Hz, 1 H), 7.30 (dt, J = 1.8, 8.6 Hz, 1 H), 5.25 (d, J = 2.2 Hz, 2 H) | 0.144 | >10.0 |
| 239 | 4-(2-chloro-3'-fluoro-5-methoxy-4-biphenylyl)-N-3-isoxazolyl-7-quinolinesulfonamide | 510.0 | 2 | 1H NMR (400 MHz, DMSO-d6) δ = 11.89 (br. s., 1 H), 9.12 (d, J = 4.3 Hz, 1 H), 8.75 (d, J = 1.8 Hz, 1 H), 8.56 (d, J = 1.7 Hz, 1 H), 7.96 (dd, J = 1.9, 8.8 Hz, 1 H), 7.82 (d, J = 8.9 Hz, 1 H), 7.68 (d, J = 4.4 Hz, 1 H), 7.63-7.54 (m, 2 H), 7.44 (d, J = 7.4 Hz, 2 H), 7.37-7.26 (m, 2 H), 6.52 (d, J = 1.7 Hz, 1 H), 3.72 (s, 3 H) | 0.115 | 11.2 |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 27 | 1-(2-chloro-3'-fluoro-5-methoxy-4-biphenylyl)-4-cyano-N-3-isoxazolyl-6-isoquinolinesulfonamide | 535.1 | 27 | 1H NMR (400 MHz, DMSO-d6) δ = 9.33 (s, 1 H), 8.77 (d, J = 1.8 Hz, 1 H), 8.66-8.58 (m, 1 H), 8.21-8.07 (m, 2 H), 7.63 (s, 1 H), 7.59 (dt, J = 6.4, 8.0 Hz, 1 H), 7.47-7.41 (m, 2 H), 7.36-7.30 (m, 2 H), 6.50 (d, J = 1.9 Hz, 1 H), 3.71 (s, 3 H) | 0.282 | >10.0 |
| 240 | 1-(5,6-dichloro-2-methoxy-3-pyridinyl)-N-1,3,4-thiadiazol-2-yl-6-isoquinolinesulfonamide | 470.0 | 8 | 1H NMR (400 MHz, DMSO-d6) δ = 8.80 (s, 1 H), 8.72 (d, J = 5.7 Hz, 1 H), 8.59 (d, J = 1.7 Hz, 1 H), 8.20 (s, 1 H), 8.19 (d, J = 5.3 Hz, 1 H), 7.92-7.89 (m, 1 H), 7.88-7.85 (m, 1 H), 3.79 (s, 3 H) | 1.87 | |
| 241 | 4-(2-cyano-3'-fluoro-5-methoxy-4-biphenylyl)-N-1,3,4-thiadiazol-2-yl-7-quinazolinesulfonamide | 519.1 | 20 | 1H NMR (400 MHz, DMSO-d6) δ = 9.51 (s, 1 H), 8.79 (s, 1 H), 8.40 (d, J = 1.6 Hz, 1 H), 8.06 (s, 1 H), 8.02-7.97 (m, 1 H), 7.94-7.88 (m, 1 H), 7.71-7.57 (m, 3 H), 7.50 (s, 1 H), 7.45-7.35 (m, 1 H), 3.85 (s, 3 H) | 0.0691 | >10.0 |
| 242 | 1-(5-chloro-6-(dimethylamino)-2-methoxy-3-pyridinyl)-N-1,3,4-thiadiazol-2-yl-6-isoquinolinesulfonamide | 477.0 | 24 | 1H NMR (400 MHz, DMSO-d6) δ = 8.80 (s, 1 H), 8.67 (d, J = 5.5 Hz, 1 H), 8.56 (s, 1 H), 8.13 (d, J = 6.0 Hz, 1 H), 7.96-7.87 (m, J = 3.8 Hz, 2 H), 7.76 (s, 1 H), 3.77 (s, 3 H), 3.12 (s, 6 H) | 1.87 | |
| 243 | 4-(2-chloro-3'-fluoro-5-methoxy-4-biphenylyl)-N-2-pyrimidinyl-7-quinazolinesulfonamide | 522.1 | 15 | 1H NMR (400 MHz, DMSO-d6) δ = 9.51 (s, 1 H), 8.61 (d, J = 1.5 Hz, 1 H), 8.52 (d, J = 4.9 Hz, 2 H), 8.16 (dd, J = 1.8, 8.9 Hz, 1 H), 7.96 (d, J = 8.8 Hz, 1 H), 7.68 (s, 1 H), 7.59 (dt, J = 6.3, 8.0 Hz, 1 H), 7.48-7.41 (m, 2 H), 7.37-7.29 (m, 2 H), 7.05 (t, J = 4.6 Hz, 1 H), 3.74 (s, 3 H) | 0.0803 | >10.0 |
| 244 | 1-(5-chloro-6-(4,4-difluoro-1-piperidinyl)-2-methoxy-3-pyridinyl)-N-1,3,4-thiadiazol-2-yl-6-isoquinolinesulfonamide | 553.1 | 24 | 1H NMR (400 MHz, DMSO-d6) δ = 8.80 (s, 1 H), 8.69 (d, J = 5.8 Hz, 1 H), 8.57 (s, 1 H), 8.13 (d, J = 5.9 Hz, 1 H), 7.90 (s, 2 H), 7.85 (s, 1 H), 3.77 (s, 3H), 3.62 (br. s., 4 H), 2.27-2.10 (m, 4 H) | 0.424 | >30.0 |
| 52 | (1R)-2-acetyl-1-(3'-fluoro-3-methoxy-4-biphenylyl)-N-1,3,4-thiadiazol-2-yl-1,2,3,4-tetrahydro-6-isoquinolinesulfonamide, (1S)-2-acetyl-1-(3'-fluoro-3-methoxy-4-biphenylyl)-N-1,3,4-thiadiazol-2-yl-1,2,3,4-tetrahydro-6-isoquinolinesulfonamide | 539.1 | 52 | 1H NMR (400 MHz, DMSO-d$_6$) (Rotamers present, integrals reported as observed at 25° C.) d ppm 2.10 (s, 1.8 H) 2.19 (s, 1.6 H) 2.85-3.21 (m, 3 H) 3.80 (t, J = 5.77 Hz, 2 H) 3.86 (s, 2 H) 4.01 (s, 1.8 H) 4.29 (br d, J = 13.50 Hz, 0.6 H) 6.45 (s, 0.5 H) 6.73-6.89 (m, 1.2 H) 7.05-7.41 (m, 5.3 H) 7.45-7.62 (m, 4.6 H) 7.67 (d, J = 4.30 Hz, 1.2 H) 8.76 (d, J = 4.30 Hz, 1 H) | 1.69 | |
| 53-A | (1S)-2-acetyl-1-(3'-fluoro-3-methoxy-4-biphenylyl)-N-3-isoxazolyl-1,2,3,4-tetrahydro-6-isoquinolinesulfonamide | 522.3 | 53 | $^1$H NMR (400 MHz, MeOH-d$_4$)) (Rotamers present, integrals reported as observed at 25° C.) d ppm 2.20 (s, 1.5 H) 2.32 (s, 1.8 H) 2.96-3.13 (m, 2 H) 3.21-3.31 (m, 0.6 H) 3.79 (s, 1.4 H) 3.82-3.89 (m, 0.6 H) 3.93-4.00 (m, 0.6 H) 4.03 (s, 1.6 H) 4.46 (d, J = 13.30 Hz, 0.5 H) 6.49 (br. s., 1 H) 6.53-6.60 (m, 0.6 H) 6.81 (d, J = 7.92 Hz, 0.5 H) 6.91 (s, 0.5 H) 7.02-7.22 (m, 2.5 H) 7.24-7.52 (m, 4.8 H) 7.71 (d, J = 8.31 Hz, 1 H) 7.81 (d, J = 9.19 Hz, 1 H) 8.46 (br. s., 1 H) | 1.09 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 51 | (1R)-2-acetyl-1-(2-methoxy-4-(trifluoromethyl)phenyl)-N-1,2,4-thiadiazol-5-yl-1,2,3,4-tetrahydro-6-isoquinolinesulfonamide, (1S)-2-acetyl-1-(2-methoxy-4-(trifluoromethyl)phenyl)-N-1,2,4-thiadiazol-5-yl-1,2,3,4-tetrahydro-6-isoquinolinesulfonamide | 513.0 | 51 | 1H NMR (500 MHz, DMSO-d$_6$) d ppm 2.09 (s, 3 H) 2.91 (br. s., 1 H) 3.00-3.11 (m, 2 H) 3.79 (br. s., 1 H) 3.85 (s, 3 H) 3.98 (s, 1 H) 7.15-7.42 (m, 4 H) 7.58 (d, J = 7.21 Hz, 1 H) 7.67 (br. s., 1 H) 8.40-8.51 (m, 1 H); | 0.225 | 51 |
| 53-B | (1R)-2-acetyl-1-(3'-fluoro-3-methoxy-4-biphenylyl)-N-3-isoxazolyl-1,2,3,4-tetrahydro-6-isoquinolinesulfonamide | 522.3 | 53 | $^1$H NMR (400 MHz, MeOH-d$_4$)) (Rotamers present, integrals reported as observed at 25° C.) d ppm 2.20 (s, 1.5 H) 2.32 (s, 1.8 H) 2.96-3.13 (m, 2 H) 3.21-3.31 (m, 0.6 H) 3.79 (s, 1.4 H) 3.82-3.89 (m, 0.6 H) 3.93-4.00 (m, 0.6 H) 4.03 (s, 1.6 H) 4.46 (d, J = 13.30 Hz, 0.5 H) 6.49 (br. s., 1 H) 6.53-6.60 (m, 0.6 H) 6.81 (d, J = 7.92 Hz, 0.5 H) 6.91 (s, 0.5 H) 7.02-7.22 (m, 2.5 H) 7.24-7.52 (m, 4.8 H) 7.71 (d, J = 8.31 Hz, 1 H) 7.81 (d, J = 9.19 Hz, 1 H) 8.46 (br. s., 1 H) | | 53-B |
| 245 | 1-(2,4'-dichloro-5-methoxy-3'-methyl-4-biphenylyl)-N-3-isoxazolyl-6-phthalazinesulfonamide | 541.1 | 3 | $^1$H NMR (400 MHz, DMSO-d$_6$) δ = 12.05 (br. s., 1 H), 9.98 (s, 1 H), 8.88 (d, J = 1.9 Hz, 1 H), 8.76 (d, J = 1.9 Hz, 1 H), 8.30 (dd, J = 1.9, 8.8 Hz, 1 H), 7.93 (d, J = 8.8 Hz, 1 H), 7.66 (s, 1 H), 7.61-7.54 (m, 2 H), 7.44 (dd, J = 2.2, 8.2 Hz, 1 H), 7.28 (s, 1 H), 6.50 (d, J = 1.9 Hz, 1 H), 3.71 (s, 3 H), 2.44 (s, 3 H). | 0.0154 | |
| 246 | 1-(2,3'-dichloro-5-methoxy-4'-methyl-4-biphenylyl)-N-3-isoxazolyl-6-phthalazinesulfonamide | 541.1 | 3 | $^1$H NMR (400 MHz, DMSO-d$_6$) δ = 12.05 (br. s., 1 H), 9.98 (d, J = 0.7 Hz, 1 H), 8.90-8.73 (m, 2 H), 8.30 (dd, J = 1.9, 8.8 Hz, 1 H), 7.94 (d, J = 8.8 Hz, 1 H), 7.68-7.61 (m, 2 H), 7.56-7.45 (m, 2 H), 7.30 (s, 1 H), 6.50 (d, J = 1.8 Hz, 1 H), 3.72 (s, 3 H), 2.43 (s, 3 H). | 0.0172 | |
| 247 | 4-(4-chloro-2-methoxy-5-methylphenyl)-N-3-isoxazolyl-7-quinazolinesulfonamide | 431.0 | 61 | $^1$H NMR (ACETONITRILE-d$_3$) δ: 9.41 (s, 1H), 8.53 (s, 1H), 8.34 (s, 1H), 7.95 (d, J = 9.4 Hz, 1H), 7.83-7.90 (m, 1H), 7.33 (s, 1H), 7.24 (s, 1H), 6.47 (s, 1H), 3.67 (s, 3H), 2.37 (s, 3H) | 0.243 | |
| 248 | 1-(4-chloro-2-methoxy-5-methylphenyl)-N-3-isoxazolyl-6-isoquinolinesulfonamide | 430.0 | 62 | $^1$H NMR (ACETONITRILE-d3) δ: 8.69 (d, J = 5.8 Hz, 1H), 8.55 (d, J = 1.9 Hz, 1H), 8.34 (d, J = 1.9 Hz, 1H), 7.89-7.93 (m, 1H), 7.84-7.89 (m, 1H), 7.77-7.83 (m, 1H), 7.27 (d, J = 0.6 Hz, 1H), 7.20 (s, 1H), 6.46 (d, J = 1.8 Hz, 1H), 3.64 (s, 3H), 2.36 (s, 3H). | 0.187 | |
| 249 | 1-(5-chloro-2-methoxy-4-(trifluoromethyl)phenyl)-N-3-isoxazolyl-6-isoquinolinesulfonamide | 484.0 | 60 | $^1$H NMR (ACETONITRILE-d3) δ: 8.75 (d, J = 5.7 Hz, 1H), 8.61 (d, J = 1.9 Hz, 1H), 8.38 (d, J = 1.8 Hz, 1H), 8.00 (dd, J = 5.7, 0.6 Hz, 1H), 7.87-7.93 (m, 1H), 7.79-7.86 (m, 1H), 7.60 (s, 1H), 7.52 (s, 1H), 6.50 (d, J = 1.8 Hz, 1H), 3.73 (s, 3H). | 0.224 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 250 | 1-(4-(difluoromethyl)-2-methoxy-5-methylphenyl)-N-3-isoxazolyl-6-isoquinolinesulfonamide | 446.0 | 62 | $^{1}$H NMR (ACETONITRILE-d3) δ: 8.70 (d, J = 5.7 Hz, 1H), 8.55 (d, J = 1.9 Hz, 1H), 8.33 (d, J = 1.8 Hz, 1H), 7.93 (d, J = 5.1 Hz, 1H), 7.87 (dd, J = 8.9, 2.0 Hz, 1H), 7.77 (d, J = 8.9 Hz, 1H), 7.29-7.33 (m, 1H), 7.25-7.29 (m, 1H), 6.84-7.17 (m, 1H), 6.45 (d, J = 1.9 Hz, 1H), 3.65-3.69 (m, 3H), 2.41 (s, 3H) | 0.728 | |
| 251 | 1-(5-cyclopropyl-4-(difluoromethyl)-2-methoxyphenyl)-N-3-isoxazolyl-6-isoquinolinesulfonamide | 472.0 | 62 | $^{1}$H NMR (ACETONITRILE-d3) δ: 8.70 (d, J = 5.8 Hz, 1H), 8.56 (d, J = 1.9 Hz, 1H), 8.35 (d, J = 1.9 Hz, 1H), 7.93 (dd, J = 5.8, 0.6 Hz, 1H), 7.87 (dd, J = 8.9, 2.0 Hz, 1H), 7.73-7.78 (m, 1H), 7.15-7.45 (m, 2H), 7.13 (s, 1H), 6.47 (d, J = 1.9 Hz, 1H), 3.64-3.70 (m, 3H), 2.02-2.14 (m, 1H), 0.90-1.00 (m, 2H), 0.60-0.71 (m, 2H). | 0.431 | |
| 252 | 4-(4'-chloro-5-methoxy-2,3'-dimethyl-4-biphenylyl)-N-3-isoxazolyl-7-quinazolinesulfonamide | 521.0 | 61 | 1H NMR (ACETONITRILE-d3) d: 9.44 (s, 1H), 8.54-8.58 (m, 1H), 8.38 (d, J = 1.9 Hz, 1H), 7.97 (dd, J = 3.8, 1.3 Hz, 2H), 7.46-7.52 (m, 1H), 7.39-7.43 (m, 1H), 7.33 (s, 1H), 7.24-7.31 (m, 1H), 7.04 (s, 1H), 6.51 (d, J = 1.8 Hz, 1H), 3.67 (s, 3H), 2.46 (s, 3H), 2.25 (s, 3H) | 0.032 | |
| 253 | 1-(4'-chloro-5-methoxy-2,3'-dimethyl-4-biphenylyl)-N-3-isoxazolyl-6-isoquinolinesulfonamide | 520.0 | 62 | $^{1}$H NMR (ACETONITRILE-d3) δ: 8.71 (d, J = 5.8 Hz, 1H), 8.56 (s, 1H), 8.35 (d, J = 1.9 Hz, 1H), 7.84-7.94 (m, 3H), 7.48 (d, J = 8.2 Hz, 1H), 7.41 (s, 1H), 7.23-7.30 (m, 2H), 7.00 (s, 1H), 6.47 (d, J = 1.8 Hz, 1H), 3.64 (s, 3H), 2.46 (s, 3H), 2.24 (s, 3H) | 0.118 | |
| 54 | 1-(2-chloro-3'-fluoro-5-methoxy-4-biphenylyl)-N-1,3-thiazol-4-yl-6-isoquinolinesulfonamide | 526.1 | 54 | $^{1}$H NMR (400 MHz, DMSO-d$_{6}$) δ = 11.39 (s, 1 H), 8.87 (d, J = 2.2 Hz, 1 H), 8.73 (d, J = 5.8 Hz, 1 H), 8.63 (d, J = 1.8 Hz, 1 H), 8.14 (d, J = 5.5 Hz, 1 H), 7.98-7.93 (m, 1 H), 7.90-7.83 (m, 1 H), 7.64-7.54 (m, 2 H), 7.50-7.42 (m, 2 H), 7.37-7.30 (m, 1 H), 7.28 (s, 1 H), 7.15 (d, J = 2.2 Hz, 1 H), 3.71 (s, 3 H). | 0.493 | |
| 55 | 1-(2-chloro-3'-fluoro-5-methoxy-4-biphenylyl)-N-3-isoxazolyl-4-methoxy-6-phthalazinesulfonamide | 541.1 | 55 | $^{1}$H NMR (400 MHz, DMSO-d$_{6}$) δ = 8.50 (dd, J = 0.6, 1.7 Hz, 1 H), 8.25-8.12 (m, 4 H), 7.64-7.54 (m, 3 H), 7.50-7.42 (m, 2 H), 7.35-7.29 (m, 1 H), 7.27 (s, 1 H), 6.10 (d, J = 1.8 Hz, 1 H), 4.26 (s, 3 H), 3.72 (s, 3 H), 2.93 (q, J = 7.3 Hz, 4 H), 1.16 (t, J = 7.2 Hz, 6 H). | 0.0326 | |
| 254 | 1-(2-chloro-3'-fluoro-5-methoxy-4-biphenylyl)-N-3-isothiazolyl-6-isoquinolinesulfonamide | 526.1 | 5 | $^{1}$H NMR (400 MHz, DMSO-d$_{6}$) δ = 11.87 (s, 1 H), 8.92 (d, J = 4.8 Hz, 1 H), 8.73 (d, J = 5.8 Hz, 1 H), 8.70 (d, J = 1.9 Hz, 1 H), 8.16 (d, J = 5.2 Hz, 1 H), 8.02-7.94 (m, 1 H), 7.86 (d, J = 8.9 Hz, 1 H), 7.62-7.53 (m, 2 H), 7.48-7.40 (m, 2 H), 7.36-7.29 (m, 1 H), 7.27 (s, 1 H), 7.05 (d, J = 4.7 Hz, 1 H), 3.70 (s, 3 H). | 0.289 | |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 255 | 1-(2,4'-dichloro-5-methoxy-3'-methyl-4-biphenylyl)-N-3-isothiazolyl-6-phthalazinesulfonamide | 557.0 | 3 | $^1$H NMR (500 MHz, DMSO-d$_6$) δ ppm 2.44 (s, 3 H) 3.70 (s, 3 H) 7.01 (d, J = 4.76 Hz, 1 H) 7.27 (s, 1 H) 7.44 (dd, J = 8.20, 1.74 Hz, 1 H) 7.52-7.68 (m, 5 H) 7.89 (d, J = 8.76 Hz, 1 H) 8.33 (dd, J = 8.76, 1.71 Hz, 1 H) 8.86-8.92 (m, 2 H) 9.96 (s, 1 H). | 0.32 | |
| 256 | 1-(2-chloro-3',5'-difluoro-5-methoxy-4-biphenylyl)-N-3-isothiazolyl-6-phthalazinesulfonamide | 545.0 | 3 | $^1$H NMR (500 MHz, DMSO-d$_6$) δ = 9.94 (s, 1 H), 8.86-8.73 (m, 2 H), 8.32 (dd, J = 1.6, 8.7 Hz, 1 H), 7.82 (d, J = 8.8 Hz, 1 H), 7.67 (s, 1 H), 7.47-7.23 (m, 4 H), 6.95 (d, J = 4.7 Hz, 1 H), 3.72 (s, 3 H) | 0.0852 | |
| 257 | 1-(2-chloro-3'-fluoro-5-methoxy-4-biphenylyl)-N-1,3-oxazol-2-yl-6-isoquinolinesulfonamide | 510.1 | 5 | $^1$H NMR (500 MHz, DMSO-d$_6$) δ = 12.23 (br. s, 1 H), 8.70 (d, J = 5.7 Hz, 1 H), 8.60 (d, J = 1.2 Hz, 1 H), 8.10 (d, J = 5.7 Hz, 1 H), 7.96 (dd, J = 1.7, 8.9 Hz, 1 H), 7.80 (d, J = 8.9 Hz, 1 H), 7.64-7.52 (m, 3 H), 7.44 (d, J = 8.2 Hz, 2 H), 7.36-7.24 (m, 3 H), 3.71 (s, 3 H). | 0.222 | |
| 60 | N-3-isoxazolyl-1-(2-methoxy-5-methyl-4-(trifluoromethyl)phenyl)-6-isoquinolinesulfonamide | 464.0 | 60 | $^1$H NMR (ACETONITRILE-d3) δ: 8.72 (d, J = 5.8 Hz, 1H), 8.58 (d, J = 1.9 Hz, 1H), 8.37 (d, J = 1.9 Hz, 1H), 7.95 (d, J = 5.7 Hz, 1H), 7.88 (dd, J = 8.9, 1.9 Hz, 1H), 7.73-7.81 (m, 1H), 7.37-7.42 (m, 1H), 7.32-7.37 (m, 1H), 6.48 (d, J = 1.9 Hz, 1H), 3.69 (s, 3H), 2.47 (d, J = 1.9 Hz, 3H) | 0.189 | |
| 258 | 1-(5-cyclopropyl-2-methoxy-4-(trifluoromethyl)phenyl)-N-3-isoxazolyl-6-isoquinolinesulfonamide | 490.0 | 60 | $^1$H NMR (ACETONITRILE-d3) δ: 8.71 (d, J = 5.8 Hz, 1H), 8.57 (d, J = 1.9 Hz, 1H), 8.36 (d, J = 1.9 Hz, 1H), 7.95 (dd, J = 5.8, 0.6 Hz, 1H), 7.87 (dd, J = 8.9, 1.9 Hz, 1H), 7.70-7.77 (m, 1H), 7.40 (s, 1H), 7.12 (s, 1H), 6.48 (d, J = 1.8 Hz, 1H), 3.69 (s, 3H), 2.15-2.25 (m, 1H), 0.98 (d, J = 8.4 Hz, 2H), 0.67-0.74 (m, 2H). | 0.543 | |
| 59 | 4-(5-chloro-2-methoxy-4-(trifluoromethyl)phenyl)-N-3-isoxazolyl-7-quinazolinesulfonamide | 485.0 | 59 | $^1$H NMR (ACETONITRILE-d3) δ: 9.44 (s, 1H), 8.55 (d, J = 1.9 Hz, 1H), 8.30 (d, J = 1.8 Hz, 1H), 7.98 (dd, J = 8.8, 1.9 Hz, 1H), 7.83 (dd, J = 8.9, 0.5 Hz, 1H), 7.62 (s, 1H), 7.54 (s, 1H), 6.44 (d, J = 1.8 Hz, 1H), 3.75 (s, 3H) | 0.182 | |
| 259 | 4-(3-chloro-2-methoxy-4-(trifluoromethyl)phenyl)-N-3-isoxazolyl-7-quinazolinesulfonamide | 485.0 | 59 | $^1$H NMR (ACETONITRILE-d3) δ: 9.43 (s, 1H), 8.54 (d, J = 1.7 Hz, 1H), 8.16 (d, J = 1.7 Hz, 1H), 7.99 (dd, J = 8.8, 1.8 Hz, 1H), 7.70-7.80 (m, 2H), 7.53 (dd, J = 8.1, 0.8 Hz, 1H), 6.17 (s, 1H), 3.50 (s, 3H) | | |
| 56 | 1-(1-(3,5-difluorophenyl)-5-methoxy-2-oxo-1,2-dihydro-4-pyridinyl)-N-3-isoxazolyl-6-isoquinolinesulfonamide | 511.1 | 56 | $^1$H NMR (400 MHz, DMSO-d$_6$) δ ppm 11.86-12.00 (m, 1 H) 8.72-8.78 (m, 2 H) 8.68-8.71 (m, 1 H) 8.17-8.24 (m, 1 H) 8.01-8.07 (m, 1 H) 7.99 (d, J = 1.96 Hz, 1 H) 7.38-7.50 (m, 4 H) 6.57 (d, J = 0.39 Hz, 1 H) 6.50 (d, J = 1.86 Hz, 1 H) 3.51 (s, 3 H). | 11.8 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 61 | 4-(3',5'-difluoro-5-methoxy-2-methyl-4-biphenylyl)-N-3-isoxazolyl-7-quinazolinesulfonamide | 509.0 | 61 | $^1$H NMR (DMSO-d$_6$) δ: 9.48 (s, 1H), 8.67 (s, 1H), 8.47 (s, 1H), 8.03 (dd, J = 8.8, 1.6 Hz, 1H), 7.93 (d, J = 8.8 Hz, 1H), 7.39 (s, 1H), 7.22-7.35 (m, 3H), 7.13 (s, 1H), 6.47 (s, 1H), 3.70 (s, 3H), 2.25 (s, 3H) | 0.0504 | |
| 260 | 4-(3'-fluoro-5-methoxy-2,5'-dimethyl-4-biphenylyl)-N-3-isoxazolyl-7-quinazolinesulfonamide | 505.0 | 61 | $^1$H NMR (DMSO-d$_6$) δ: 9.49 (s, 1H), 8.69 (s, 1H), 8.47 (s, 1H), 8.03 (dd, J = 8.8, 1.6 Hz, 1H), 7.91-7.98 (m, 1H), 7.37 (s, 1H), 7.05-7.17 (m, 4H), 6.48 (d, J = 1.3 Hz, 1H), 3.69 (s, 3H), 2.42 (s, 3H), 2.23 (s, 3H) | 0.0367 | |
| 261 | 4-(4'-fluoro-5-methoxy-2,3'-dimethyl-4-biphenylyl)-N-3-isoxazolyl-7-quinazolinesulfonamide | 505.0 | 61 | $^1$H NMR (DMSO-d$_6$) δ: 9.47 (s, 1H), 8.64 (s, 1H), 8.45 (s, 1H), 8.02 (dd, J = 8.8, 1.5 Hz, 1H), 7.93 (d, J = 8.8 Hz, 1H), 7.40 (d, J = 8.3 Hz, 1H), 7.21-7.37 (m, 3H), 7.01-7.08 (m, 1H), 6.45 (s, 1H), 3.66-3.70 (m, 3H), 2.33 (s, 3H), 2.20-2.23 (m, 3H) | 0.0381 | |
| 262 | N-3-isoxazolyl-4-(5-methoxy-2,2',4',5'-tetramethyl-4-biphenylyl)-7-quinazolinesulfonamide | 515.2 | 61 | $^1$H NMR (DMSO-d$_6$) δ: 9.43 (s, 1H), 8.50 (br. s., 1H), 8.38 (s, 1H), 7.97-8.02 (m, 1H), 7.87 (d, J = 8.7 Hz, 1H), 7.77 (s, 1H), 7.33 (s, 1H), 7.11 (s, 1H), 6.90 (s, 1H), 6.36 (s, 1H), 3.63 (s, 3H), 2.24 (d, J = 6.6 Hz, 6H), 2.15 (d, J = 2.7 Hz, 3H), 1.99 (s, 3H) | 0.0625 | |
| 263 | N-3-isoxazolyl-4-(5-methoxy-2,3'-dimethyl-4-biphenylyl)-7-quinazolinesulfonamide | 487.0 | 61 | $^1$H NMR (DMSO-d$_6$) δ: 9.49 (s, 1H), 8.73 (d, J = 1.3 Hz, 1H), 8.49 (d, J = 1.2 Hz, 1H), 8.01-8.07 (m, 1H), 7.93-8.01 (m, 1H), 7.33-7.41 (m, 2H), 7.20-7.31 (m, 3H), 7.03-7.07 (m, 1H), 6.51 (d, J = 1.5 Hz, 1H), 3.67-3.70 (m, 3H), 2.40 (s, 3H), 2.20-2.24 (m, 3H) | 0.102 | |
| 264 | 4-(3'-chloro-5-methoxy-2-methyl-4-biphenylyl)-N-3-isoxazolyl-7-quinazolinesulfonamide | 507.0 | 61 | 1H NMR (DMSO-d6) d: 9.48 (s, 1H), 8.65 (s, 1H), 8.45 (s, 1H), 8.02 (dd, J = 8.8, 1.5 Hz, 1H), 7.94 (d, J = 8.8 Hz, 1H), 7.43-7.57 (m, 4H), 7.38 (s, 1H), 7.10 (s, 1H), 6.45 (d, J = 1.2 Hz, 1H), 3.69 (s, 3H), 2.23 (s, 3H) | 0.0121 | |
| 265 | N-3-isoxazolyl-4-(5-methoxy-2-methyl-3'-(trifluoromethyl)-4-biphenylyl)-7-quinazolinesulfonamide | 541.0 | 61 | $^1$H NMR (DMSO-d$_6$) δ: 9.50 (s, 1H), 8.71 (s, 1H), 8.49 (s, 1H), 8.01-8.07 (m, 1H), 7.93-8.01 (m, 1H), 7.72-7.86 (m, 4H), 7.41 (s, 1H), 7.15 (s, 1H), 6.49 (d, J = 1.5 Hz, 1H), 3.70 (s, 3H), 2.22 (s, 3H) | 0.0184 | |
| 266 | 4-(5'-chloro-2',5-dimethoxy-2-methyl-4-biphenylyl)-N-3-isoxazolyl-7-quinazolinesulfonamide | 537.0 | 61 | $^1$H NMR (DMSO-d$_6$) δ: 9.43 (s, 1H), 8.50 (br. s., 1H), 8.38 (s, 1H), 7.99 (dd, J = 8.7, 1.4 Hz, 1H), 7.87 (d, J = 8.8 Hz, 1H), 7.46 (dd, J = 8.8, 2.6 Hz, 1H), 7.25-7.33 (m, 2H), 7.12-7.20 (m, 1H), 7.01 (s, 1H), 6.36 (s, 1H), 3.79 (s, 3H), 3.63-3.68 (m, 3H), 2.05 (s, 3H) | 0.0181 | |
| 267 | 4-(3'-chloro-5-methoxy-2,4'-dimethyl-4-biphenylyl)-N-3-isoxazolyl-7-quinazolinesulfonamide | 521.0 | 61 | $^1$H NMR (DMSO-d$_6$) δ: 9.49 (s, 1H), 8.70 (s, 1H), 8.48 (s, 1H), 8.00-8.06 (m, 1H), 7.93-8.00 (m, 1H), 7.45-7.54 (m, 2H), 7.37 (s, 2H), 7.08 (s, 1H), 6.49 (d, J = 1.4 Hz, 1H), 3.69 (s, 3H), 2.41 (s, 3H), 2.23 (s, 3H) | 0.0287 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 268 | 4-(3'-chloro-5-methoxy-2,5'-dimethyl-4-biphenylyl)-N-3-isoxazolyl-7-quinazolinesulfonamide | 521.0 | 61 | $^1$H NMR (DMSO-d$_6$) δ: 9.48 (s, 1H), 8.68 (s, 1H), 8.47 (s, 1H), 8.03 (dd, J = 8.8, 1.6 Hz, 1H), 7.94 (d, J = 8.8 Hz, 1H), 7.35 (d, J = 18.8 Hz, 3H), 7.26 (s, 1H), 7.08 (s, 1H), 6.48 (s, 1H), 3.69 (s, 3H), 2.41 (s, 3H), 2.22 (s, 3H) | 0.0239 | |
| 269 | 4-(3'-chloro-4'-fluoro-5-methoxy-2-methyl-4-biphenylyl)-N-3-isoxazolyl-7-quinazolinesulfonamide | 525.0 | 61 | $^1$H NMR (DMSO-d$_6$) δ: 9.49 (s, 1H), 8.70 (s, 1H), 8.48 (s, 1H), 8.03 (dd, J = 8.9, 1.7 Hz, 1H), 7.95 (d, J = 8.8 Hz, 1H), 7.72 (dd, J = 7.2, 1.9 Hz, 1H), 7.47-7.58 (m, 2H), 7.38 (s, 1H), 7.12 (s, 1H), 6.49 (d, J = 1.4 Hz, 1H), 3.69 (s, 3H), 2.23 (s, 3H) | 0.0252 | |
| 270 | 4-(3'-chloro-5'-fluoro-5-methoxy-2-methyl-4-biphenylyl)-N-3-isoxazolyl-7-quinazolinesulfonamide | 525.0 | 61 | $^1$H NMR (DMSO-d$_6$) δ: 9.48 (s, 1H), 8.67 (s, 1H), 8.47 (s, 1H), 8.03 (dd, J = 8.8, 1.5 Hz, 1H), 7.93 (d, J = 8.9 Hz, 1H), 7.51 (d, J = 8.8 Hz, 1H), 7.35-7.46 (m, 3H), 7.14 (s, 1H), 6.47 (s, 1H), 3.68-3.72 (m, 3H), 2.24 (s, 3H) | 0.0299 | |
| 271 | 4-(4'-chloro-3'-fluoro-5-methoxy-2-methyl-4-biphenylyl)-N-3-isoxazolyl-7-quinazolinesulfonamide | 525.0 | 61 | $^1$H NMR (DMSO-d$_6$) δ: 9.44 (s, 1H), 8.54 (br. s., 1H), 8.40 (s, 1H), 8.30 (s, 1H), 8.00 (dd, J = 8.8, 1.4 Hz, 1H), 7.87 (d, J = 8.8 Hz, 1H), 7.67-7.74 (m, 1H), 7.57-7.66 (m, 1H), 7.34-7.40 (m, 1H), 7.12 (s, 1H), 6.38 (s, 1H), 3.69 (s, 3H), 2.24 (s, 3H) | 0.0472 | |
| 272 | 1-(3',5'-difluoro-5-methoxy-2-methyl-4-biphenylyl)-N-3-isoxazolyl-6-isoquinolinesulfonamide | 508.0 | 62 | $^1$H NMR (DMSO-d$_6$) δ: 8.69-8.88 (m, 2H), 8.63-8.69 (m, 1H), 8.12 (d, J = 5.7 Hz, 1H), 7.94 (dd, J = 8.9, 1.7 Hz, 1H), 7.85 (d, J = 8.9 Hz, 1H), 7.18-7.34 (m, 4H), 7.05-7.13 (m, 1H), 6.50 (d, J = 1.7 Hz, 1H), 3.53-3.72 (m, 3H), 2.10-2.28 (m, 3H) | 0.0319 | |
| 62 | 1-(3',4'-difluoro-5-methoxy-2-methyl-4-biphenylyl)-N-3-isoxazolyl-6-isoquinolinesulfonamide | 508.0 | 62 | $^1$H NMR (DMSO-d$_6$) δ: 8.67-8.73 (m, 2H), 8.63 (s, 1H), 8.10 (d, J = 5.7 Hz, 1H), 7.93 (dd, J = 8.9, 1.7 Hz, 1H), 7.84 (d, J = 8.9 Hz, 1H), 7.52-7.63 (m, 2H), 7.34 (br. s., 1H), 7.27 (s, 1H), 7.03-7.08 (m, 1H), 6.44-6.48 (m, 1H), 3.53-3.75 (m, 3H), 2.23 (s, 3H) | 0.0376 | |
| 273 | 1-(3'-fluoro-5-methoxy-2,5'-dimethyl-4-biphenylyl)-N-3-isoxazolyl-6-isoquinolinesulfonamide | 504.0 | 62 | $^1$H NMR (DMSO-d$_6$) δ: 8.69-8.79 (m, 2H), 8.63-8.69 (m, 1H), 8.11 (d, J = 5.7 Hz, 1H), 7.94 (dd, J = 8.9, 1.7 Hz, 1H), 7.86 (d, J = 8.9 Hz, 1H), 7.26 (s, 1H), 7.06-7.16 (m, 3H), 7.03 (s, 1H), 6.50 (d, J = 1.7 Hz, 1H), 3.53-3.71 (m, 3H), 2.42 (s, 3H), 2.10-2.29 (m, 3H) | 0.0733 | |
| 274 | 1-(4'-fluoro-5-methoxy-2,3'-dimethyl-4-biphenylyl)-N-3-isoxazolyl-6-isoquinolinesulfonamide | 504.0 | 62 | $^1$H NMR (DMSO-d$_6$) δ: 8.69-8.79 (m, 2H), 8.64-8.69 (m, 1H), 8.11 (d, J = 5.7 Hz, 1H), 7.93 (dd, J = 8.9, 1.7 Hz, 1H), 7.86 (d, J = 8.9 Hz, 1H), 7.39 (d, J = 7.1 Hz, 1H), 7.28-7.35 (m, 1H), 7.22-7.28 (m, 2H), 7.00 (s, 1H), 6.50 (d, J = 1.7 Hz, 1H), 3.53-3.73 (m, 3H), 2.33 (s, 3H), 2.13-2.26 (m, 3H) | 0.0632 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 275 | N-3-isoxazolyl-1-(5-methoxy-2,2',4',5'-tetramethyl-4-biphenylyl)-6-isoquinolinesulfonamide | 514.6 | 62 | $^1$H NMR (DMSO-d$_6$) δ: 8.69 (d, J = 5.4 Hz, 1H), 8.59 (s, 1H), 8.63 (s, 1H), 8.07 (d, J = 5.7 Hz, 1H), 7.92 (d, J = 9.0 Hz, 1H), 7.82 (br. s., 1H), 7.23 (s, 1H), 7.10 (s, 1H), 6.96 (d, J = 16.2 Hz, 1H), 6.85 (s, 1H), 6.41-6.45 (m, 1H), 3.59 (s, 3H), 2.25 (s, 6H), 2.04 (br. s., 3H), 1.98 (s, 3H) | 0.242 | |
| 276 | N-3-isoxazolyl-1-(5-methoxy-2,3'-dimethyl-4-biphenylyl)-6-isoquinolinesulfonamide | 486.0 | 62 | $^1$H NMR (DMSO-d$_6$) δ: 8.68-8.74 (m, 2H), 8.64 (s, 1H), 8.10 (d, J = 5.7 Hz, 1H), 7.76-7.98 (m, 2H), 7.33-7.46 (m, 1H), 7.21-7.32 (m, 4H), 6.97-7.15 (m, 1H), 6.44-6.51 (m, 1H), 3.61-3.77 (m, 3H), 2.40 (s, 3H), 2.08-2.28 (m, 3H) | 0.169 | |
| 277 | 1-(3'-chloro-5-methoxy-2-methyl-4-biphenylyl)-N-3-isoxazolyl-6-isoquinolinesulfonamide | 506.0 | 62 | $^1$H NMR (DMSO-d$_6$) δ: 8.72 (dd, J = 3.6, 1.8 Hz, 2H), 8.65 (s, 1H), 8.11 (d, J = 5.6 Hz, 1H), 7.75-7.96 (m, 2H), 7.39-7.56 (m, 4H), 7.17-7.36 (m, 1H), 7.05 (s, 1H), 6.49 (d, J = 1.6 Hz, 1H), 3.56-3.73 (m, 3H), 2.22 (s, 3H) | 0.04 | |
| 278 | N-3-isoxazolyl-1-(5-methoxy-2-methyl-3'-(trifluoromethyl)-4-biphenylyl)-6-isoquinolinesulfonamide | 541.0 | 62 | $^1$H NMR (DMSO-d$_6$) δ: 8.67-8.74 (m, 2H), 8.63 (s, 1H), 8.11 (d, J = 5.7 Hz, 1H), 7.89-8.00 (m, 1H), 7.73-7.88 (m, 5H), 7.30 (s, 1H), 7.06-7.12 (m, 1H), 6.44-6.50 (m, 1H), 3.53-3.73 (m, 3H), 2.21 (s, 3H) | 0.0609 | |
| 279 | 1-(4-(5-fluoro-2-methoxy-3-pyridinyl)-2-methoxy-5-methylphenyl)-N-3-isoxazolyl-6-isoquinolinesulfonamide | 521.0 | 62 | $^1$H NMR (DMSO-d$_6$) δ: 8.64-8.72 (m, 2H), 8.62 (s, 1H), 8.24 (d, J = 2.9 Hz, 1H), 8.09 (d, J = 5.7 Hz, 1H), 7.94 (dd, J = 8.9, 1.7 Hz, 1H), 7.83 (d, J = 8.9 Hz, 1H), 7.75 (dd, J = 8.3, 2.9 Hz, 1H), 7.25 (s, 1H), 6.96-7.13 (m, 1H), 6.45 (d, J = 1.4 Hz, 1H), 3.88 (s, 3H), 3.53-3.72 (m, 3H), 2.07 (s, 3H) | 0.063 | |
| 280 | 1-(5'-fluoro-2',5-dimethoxy-2-methyl-4-biphenylyl)-N-3-isoxazolyl-6-isoquinolinesulfonamide | 520.0 | 62 | $^1$H NMR (DMSO-d$_6$) δ: 8.65-8.78 (m, 2H), 8.62 (s, 1H), 8.09 (d, J = 5.7 Hz, 1H), 7.93 (dd, J = 8.9, 1.6 Hz, 1H), 7.85 (d, J = 8.9 Hz, 1H), 7.18-7.32 (m, 2H), 7.10-7.18 (m, 2H), 6.93-6.98 (m, 1H), 6.46 (d, J = 1.5 Hz, 1H), 3.77 (s, 3H), 3.61 (s, 3H), 2.05 (s, 3H) | 0.0603 | |
| 281 | 1-(5'-chloro-2',5-dimethoxy-2-methyl-4-biphenylyl)-N-3-isoxazolyl-6-isoquinolinesulfonamide | 536.0 | 62 | $^1$H NMR (DMSO-d$_6$) δ: 8.71 (d, J = 5.9 Hz, 2H), 8.64 (s, 1H), 8.10 (d, J = 5.7 Hz, 1H), 7.94 (d, J = 8.9 Hz, 1H), 7.86 (d, J = 8.9 Hz, 1H), 7.46 (dd, J = 8.8, 2.6 Hz, 1H), 7.28 (d, J = 2.6 Hz, 1H), 7.11-7.24 (m, 2H), 6.96 (s, 1H), 6.48 (d, J = 1.5 Hz, 1H), 3.79 (s, 3H), 3.54-3.66 (m, 3H), 2.04 (s, 3H) | 0.0164 | |
| 282 | 1-(3'-chloro-5-methoxy-2,4'-dimethyl-4-biphenylyl)-N-3-isoxazolyl-6-isoquinolinesulfonamide | 520.0 | 62 | $^1$H NMR (DMSO-d$_6$) δ: 8.68-8.85 (m, 2H), 8.65 (s, 1H), 8.11 (d, J = 5.7 Hz, 1H), 7.93 (dd, J = 8.9, 1.7 Hz, 1H), 7.86 (d, J = 9.0 Hz, 1H), 7.44-7.62 (m, 2H), 7.31-7.41 (m, 1H), 7.26 (s, 1H), 7.03 (s, 1H), 6.48 (d, J = 1.7 Hz, 1H), 3.53-3.72 (m, 3H), 2.32-2.44 (m, 3H), 2.11-2.28 (m, 3H) | 0.0986 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 283 | 1-(3'-chloro-5-methoxy-2,5'-dimethyl-4-biphenylyl)-N-3-isoxazolyl-6-isoquinolinesulfonamide | 520.0 | 62 | $^1$H NMR (DMSO-d$_6$) δ: 8.67-8.77 (m, 2H), 8.49-8.67 (m, 1H), 8.11 (d, J = 5.7 Hz, 1H), 7.77-7.97 (m, 2H), 7.21-7.38 (m, 4H), 6.98-7.14 (m, 1H), 6.45-6.59 (m, 1H), 3.56-3.69 (m, 3H), 2.41 (s, 3H), 2.21 (s, 3H) | 0.0375 | |
| 284 | 1-(3'-chloro-4'-fluoro-5-methoxy-2-methyl-4-biphenylyl)-N-3-isoxazolyl-6-isoquinolinesulfonamide | 524.0 | 62 | $^1$H NMR (DMSO-d$_6$) δ: 8.67-8.82 (m, 2H), 8.49-8.67 (m, 1H), 8.11 (d, J = 5.6 Hz, 1H), 7.77-7.98 (m, 2H), 7.71 (dd, J = 7.2, 1.8 Hz, 1H), 7.44-7.63 (m, 2H), 7.23-7.40 (m, 1H), 7.02-7.19 (m, 1H), 6.45-6.52 (m, 1H), 3.55-3.76 (m, 3H), 2.22 (s, 3H) | 0.0228 | |
| 285 | 1-(3'-chloro-5'-fluoro-5-methoxy-2-methyl-4-biphenylyl)-N-3-isoxazolyl-6-isoquinolinesulfonamide | 524.0 | 62 | $^1$H NMR (DMSO-d$_6$) δ: 8.69-8.75 (m, 2H), 8.66 (s, 1H), 8.12 (d, J = 5.6 Hz, 1H), 7.94 (dd, J = 8.9, 1.7 Hz, 1H), 7.81-7.87 (m, 1H), 7.50 (d, J = 8.7 Hz, 1H), 7.43 (s, 1H), 7.38 (d, J = 9.0 Hz, 1H), 7.29 (s, 1H), 7.09 (s, 1H), 6.49 (d, J = 1.7 Hz, 1H), 3.63-3.68 (m, 3H), 2.24 (s, 3H) | 0.058 | |
| 286 | 1-(4'-chloro-3'-fluoro-5-methoxy-2-methyl-4-biphenylyl)-N-3-isoxazolyl-6-isoquinolinesulfonamide | 524.0 | 62 | $^1$H NMR (DMSO-d$_6$) δ: 8.67 (d, J = 5.4 Hz, 1H), 8.54 (br. s., 2H), 8.05 (d, J = 5.3 Hz, 1H), 7.89 (s, 1H), 7.78 (s, 1H), 7.70 (s, 1H), 7.38 (s, 1H), 7.25-7.31 (m, 2H), 7.06 (s, 1H), 6.38 (br. s., 1H), 3.62-3.68 (m, 3H), 2.24 (s, 3H) | 0.188 | |
| 287 | 1-(3'-chloro-3-methoxy-4'-methyl-4-biphenylyl)-N-3-isoxazolyl-6-isoquinolinesulfonamide | 506.1 | 1 | $^1$H NMR (400 MHz, DMSO-d$_6$) δ = 11.91 (br. s., 1 H), 8.78-8.73 (m, 2 H), 8.69 (d, J = 1.8 Hz, 1 H), 8.16 (d, J = 5.5 Hz, 1 H), 7.98-7.92 (m, 1 H), 7.90-7.82 (m, 2 H), 7.68 (dd, J = 2.1, 8.3 Hz, 1 H), 7.55 (d, J = 8.3 Hz, 1 H), 7.47 (s, 1 H), 7.44 (s, 2 H), 6.50 (d, J = 1.8 Hz, 1 H), 3.76 (s, 3 H), 2.45 (s, 3 H). | 0.111 | |
| 288 | 1-(4'-chloro-3-methoxy-3'-methyl-4-biphenylyl)-N-3-isoxazolyl-6-isoquinolinesulfonamide | 506.1 | 1 | $^1$H NMR (400 MHz, DMSO-d$_6$) δ = 11.91 (br. s., 1 H), 8.77-8.72 (m, 2 H), 8.69 (d, J = 1.8 Hz, 1 H), 8.16 (d, J = 5.5 Hz, 1 H), 7.97-7.91 (m, 1 H), 7.90-7.86 (m, 1 H), 7.84 (d, J = 2.0 Hz, 1 H), 7.68 (dd, J = 2.1, 8.3 Hz, 1 H), 7.55 (d, J = 8.3 Hz, 1 H), 7.47 (s, 1 H), 7.44 (s, 2 H), 6.50 (d, J = 1.8 Hz, 1 H), 3.76 (s, 3 H), 2.45 (s, 3 H). | 0.0775 | |
| 289 | 4-(2-chloro-3'-fluoro-5-methoxy-4-biphenylyl)-N-(5-fluoro-2-pyrimidinyl)-7-quinazolinesulfonamide | 540.1 | 15 | $^1$H NMR (500 MHz, DMSO-d$_6$) δ = 3.74 (s, 3H) 7.28-7.38 (m, 2H), 7.44 (d, J = 7.43 Hz, 2 H), 7.50-7.82 (m, 1H), 7.88 (s, 1 H), 7.99 (d, J = 8.22 Hz, 1H), 8.17 (dd, J = 8.84, 1.58 Hz, 1H), 8.58-8.89 (m, 3H), 9.58 (s., 1 H), 12.32 (br. S, 1H) | 0.0895 | |
| 290 | 1-(4'-chloro-3'-fluoro-3-methoxy-4-biphenylyl)-N-3-isoxazolyl-6-isoquinolinesulfonamide | 510.1 | 1 | $^1$H NMR (400 MHz, DMSO-d$_6$) δ = 11.90 (br. s., 1 H), 8.77-8.71 (m, 2 H), 8.67 (d, J = 1.8 Hz, 1 H), 8.13 (d, J = 5.6 Hz, 1 H), 7.99-7.90 (m, 2 H), 7.88-7.80 (m, 1 H), 7.77-7.68 (m, 2 H), 7.55-7.40 (m, 3 H), 6.50 (d, J = 1.8 Hz, 1 H), 3.76 (s, 3 H). | 0.137 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 291 | 5-(2-chloro-3'-fluoro-5-methoxy-4-biphenylyl)-N-3-isoxazolyl-2-naphthalenesulfonamide | 509.1 | 2 | 1H NMR (500 MHz, DMSO-d6) δ ppm 3.69 (s, 3 H) 6.49 (d, J = 1.66 Hz, 1 H) 7.23 (s, 1 H) 7.26-7.37 (m, 1 H) 7.38-7.46 (m, 3 H) 7.52-7.66 (m, 2 H) 7.67-7.76 (m, 2 H) 7.82 (dd, J = 9.00, 1.79 Hz, 1 H) 8.24 (d, J = 8.17 Hz, 1 H) 8.60-8.64 (m, 1 H) 8.71 (d, J = 1.66 Hz, 1 H) 11.72 (br. s., 1 H) | 1.16 | |
| 292 | 5-(2-cyano-3'-fluoro-5-methoxy-4-biphenylyl)-N-3-isoxazolyl-2-naphthalenesulfonamide | 500.1 | 6 | 1H NMR (400 MHz, MeOH) Shift 8.52 (d, J = 1.76 Hz, 1H), 8.24 (d, J = 1.76 Hz, 1H), 8.05 (d, J = 8.31 Hz, 1H), 7.81-7.87 (m, 1H), 7.71 (s, 1H), 7.63-7.69 (m, 1H), 7.43-7.62 (m, 5H), 7.20-7.33 (m, 2H), 6.33 (d, J = 1.76 Hz, 1H), 3.79 (s, 3H) | 0.256 | |
| 293 | 1-(4'-chloro-3'-fluoro-3-methoxy-4-biphenylyl)-N-2-pyrimidinyl-6-isoquinolinesulfonamide | 521.2 | 1 | $^1$H NMR (400 MHz, DMSO-d$_6$) δ = 12.20 (br. s., 1 H), 8.77-8.66 (m, 2 H), 8.50 (d, J = 4.9 Hz, 2 H), 8.15 (d, J = 5.3 Hz, 1 H), 8.07-8.00 (m, 1 H), 7.98-7.92 (m, 1 H), 7.80 (d, J = 8.9 Hz, 1 H), 7.75-7.69 (m, 2 H), 7.65-7.58 (m, 1 H), 7.57-7.51 (m, 2 H), 7.50-7.39 (m, 2 H), 7.04 (t, J = 4.9 Hz, 1 H), 3.75 (s, 3 H). | 0.407 | |
| 294 | 1-(2-chloro-3'-fluoro-5-methoxy-4-biphenylyl)-N-(5-fluoro-2-pyrimidinyl)-6-isoquinolinesulfonamide | 539.2 | 5 | $^1$H NMR (400 MHz, DMSO-d$_6$) δ = 12.21 (s, 1 H), 8.77 (d, J = 1.9 Hz, 1 H), 8.74 (d, J = 5.7 Hz, 1 H), 8.62 (d, J = 0.7 Hz, 2 H), 8.19 (d, J = 5.3 Hz, 1 H), 8.05 (dd, J = 1.9, 8.9 Hz, 1 H), 7.86 (d, J = 9.0 Hz, 1 H), 7.63-7.52 (m, 2 H), 7.50-7.39 (m, 2 H), 7.35-7.29 (m, 1 H), 7.27 (s, 1 H), 3.70 (s, 3 H). | 0.256 | |
| 295 | 4-(4'-chloro-2,3'-difluoro-5-methoxy-5'-methyl-4-biphenylyl)-N-3-isoxazolyl-7-quinazolinesulfonamide | 543.0 | 19 | $^1$H NMR (400 MHz, DMSO-d$_6$) δ = 12.06 (br. s., 1 H), 9.57-9.49 (m, 1 H), 8.77 (d, J = 1.9 Hz, 1 H), 8.53 (d, J = 1.7 Hz, 1 H), 8.11-7.90 (m, 2 H), 7.68-7.57 (m, 2 H), 7.55-7.47 (m, 1 H), 7.41 (d, J = 6.3 Hz, 1 H), 6.54 (d, J = 1.8 Hz, 1 H), 3.74 (s, 3 H), 2.49 (s, 3 H). | 0.059 | |
| 296 | 4-(3'-chloro-2,2'-difluoro-5-methoxy-4'-methyl-4-biphenylyl)-N-3-isoxazolyl-7-quinazolinesulfonamide | 543.0 | 19 | $^1$H NMR (400 MHz, DMSO-d$_6$) δ = 12.06 (br. s., 1 H), 9.54 (s, 1 H), 8.77 (d, J = 1.9 Hz, 1 H), 8.53 (d, J = 1.5 Hz, 1 H), 8.10-7.99 (m, 2 H), 7.55-7.47 (m, 2 H), 7.40 (d, J = 7.8 Hz, 1 H), 7.34 (d, J = 5.8 Hz, 1 H), 6.54 (d, J = 1.8 Hz, 1 H), 3.72 (s, 3 H), 2.47 (s, 3 H). | 0.105 | |
| 297 | 4-(3'-chloro-2-fluoro-5-methoxy-5'-methyl-4-biphenylyl)-N-3-isoxazolyl-7-quinazolinesulfonamide | 525.1 | 19 | $^1$H NMR (400 MHz, DMSO-d$_6$) δ = 12.05 (br. s., 1 H), 9.53 (s, 1 H), 8.76 (d, J = 1.8 Hz, 1 H), 8.52 (d, J = 1.8 Hz, 1 H), 8.11-7.91 (m, 3 H), 7.56 (s, 1 H), 7.52-7.46 (m, 2 H), 7.43-7.35 (m, 2 H), 6.53 (d, J = 1.8 Hz, 1 H), 3.75 (s, 3 H), 2.43 (s, 3 H). | 0.074 | |
| 57 | 3-(2-chloro-3'-fluoro-5-methoxy-4-biphenylyl)-N-3-isoxazolyl-1-methyl-1H-indole-6-sulfonamide | 512.2 | 57 | $^1$H NMR (400 MHz, DMSO-d$_6$) δ = 11.49 (s, 1 H), 8.69 (d, J = 1.8 Hz, 1 H), 8.07 (d, J = 1.4 Hz, 1 H), 7.96 (s, 1 H), 7.78 (d, J = 8.5 Hz, 1 H), 7.61-7.51 (m, 3 H), 7.42-7.37 (m, 2 H), 7.32-7.24 (m, 1 H), 7.16 (s, 1 H), 6.52 (d, J = 1.9 Hz, 1 H), 3.95 (s, 3 H), 3.85 (s, 3 H) | 12.9 | |

TABLE I-continued

| Example No. | Compound name | LC MS | Method Use To Make | NMR | Nav 1.7 PX IC$_{50}$ (µM) | Nav 1.5 PX IC$_{50}$ (µM) |
|---|---|---|---|---|---|---|
| 298 | 1-(2,3'-difluoro-5-methoxy-4-biphenylyl)-N-3-isoxazolyl-2-oxo-1,2-dihydro-6-quinolinesulfonamide | 510.0 | 42 | 1H NMR (400 MHz, DMSO-d6) d ppm 8.64 (d, J = 1.17 Hz, 1 H) 8.34 (d, J = 2.05 Hz, 1 H) 8.23 (d, J = 9.59 Hz, 1 H) 7.85 (dd, J = 8.90, 2.15 Hz, 1 H) 7.66-7.75 (m, 2 H) 7.56-7.62 (m, 3 H) 7.43 (d, J = 6.85 Hz, 1 H) 7.29-7.38 (m, 1 H) 6.83 (dd, J = 17.46, 9.24 Hz, 2 H) 6.40 (d, J = 1.76 Hz, 1 H) 3.75 (s, 3 H) | 0.055 | |
| 299 | 1-(2,3'-difluoro-5-methoxy-4-biphenylyl)-N-3-isoxazolyl-2-oxo-1,2-dihydro-6-quinolinesulfonamide | 510.0 | 42 | 1H NMR (400 MHz, DMSO-d6) ppm 8.63 (d, J = 1.37 Hz, 1 H) 8.34 (d, J = 2.15 Hz, 1 H) 8.22 (d, J = 9.68 Hz, 1 H) 7.85 (dd, J = 8.95, 2.20 Hz, 1 H) 7.66-7.75 (m, 2 H) 7.54-7.62 (m, 3 H) 7.43 (d, J = 6.94 Hz, 1 H) 7.33 (d, J = 1.56 Hz, 1 H) 6.80-6.89 (m, 2 H) 6.39 (d, J = 1.66 Hz, 1 H) 3.75 (s, 3 H) | | 6.19 |
| 300 | 4-(3',5'-dichloro-2-fluoro-5-methoxy-4-biphenylyl)-N-3-isoxazolyl-7-quinazolinesulfonamide | 545.0 | 19 | $^1$H NMR (400 MHz, DMSO-d$_6$) δ = 12.05 (br. s., 1 H), 9.54 (s, 1 H), 8.76 (d, J = 1.8 Hz, 1 H), 8.53 (d, J = 1.7 Hz, 1 H), 8.12-8.03 (m, 1 H), 8.01-7.96 (m, 1 H), 7.84-7.77 (m, 2 H), 7.76-7.70 (m, 1 H), 7.67-7.59 (m, 1 H), 7.58-7.50 (m, 2 H), 7.45 (d, J = 6.3 Hz, 1 H), 6.53 (d, J = 1.9 Hz, 1 H), 3.76 (s, 3 H). | 0.026 | |
| 301 | 4-(2,3'-difluoro-5-methoxy-5'-methyl-4-biphenylyl)-N-3-isoxazolyl-7-quinazolinesulfonamide | 509.1 | 19 | $^1$H NMR (400 MHz, DMSO-d$_6$) δ = 12.06 (br. s., 1 H), 9.53 (s, 1 H), 8.77 (d, J = 1.9 Hz, 1 H), 8.53 (d, J = 1.7 Hz, 1 H), 8.14-7.95 (m, 2 H), 7.49 (d, J = 10.5 Hz, 1 H), 7.40-7.28 (m, 3 H), 7.16 (d, J = 9.8 Hz, 1 H), 6.54 (d, J = 1.8 Hz, 1 H), 3.75 (s, 3 H), 2.43 (s, 3 H). | 0.032 | |
| 302 | 4-(3'-chloro-2,5'-difluoro-5-methoxy-4-biphenylyl)-N-3-isoxazolyl-7-quinazolinesulfonamide | 529.1 | 19 | $^1$H NMR (400 MHz, DMSO-d$_6$) δ = 12.05 (br. s., 1 H), 9.54 (s, 1 H), 8.76 (d, J = 1.8 Hz, 1 H), 8.52 (d, J = 1.8 Hz, 1 H), 8.08-8.03 (m, 1 H), 8.01-7.95 (m, 1 H), 7.67 (d, J = 1.4 Hz, 1 H), 7.64-7.56 (m, 2 H), 7.52 (d, J = 10.5 Hz, 1 H), 7.45 (d, J = 6.3 Hz, 1 H), 6.53 (d, J = 1.8 Hz, 1 H), 3.76 (s, 3 H). | 0.022 | |
| 303 | N-3-isoxazolyl-1-(2-methoxy-4-(6-(2,2,2-trifluoroethoxy)-3-pyridinyl)phenyl)-6-isoquinolinesulfonamide | 557.2 | 1 | $^1$H NMR (400 MHz, DMSO-d$_6$) δ = 11.92 (br. s., 1 H), 8.75 (q, J = 1.9 Hz, 2 H), 8.70 (d, J = 1.9 Hz, 2 H), 8.29 (dd, J = 2.5, 8.6 Hz, 1 H), 8.18 (d, J = 5.7 Hz, 1 H), 7.98-7.93 (m, 1 H), 7.91-7.85 (m, 1 H), 7.52 (s, 1 H), 7.46 (s, 2 H), 7.15 (dd, J = 0.6, 8.6 Hz, 1 H), 6.50 (d, J = 1.9 Hz, 1 H), 5.09 (q, J = 9.1 Hz, 2 H), 3.76 (s, 3 H). | 0.48 | |
| 64 | 5-(5-cyano-6-(3,5-difluorophenyl)-2-methoxy-3-pyridinyl)-N-4-pyrimidinyl-2-naphthalenesulfonamide | 530.1 | 64 | 1H NMR (500 MHz, DMSO-d6) δ ppm 3.92 (s, 3 H) 7.08 (br. s., 1 H) 7.54 (t, J = 9.40 Hz, 1 H) 7.64-7.71 (m, 2 H) 7.71-7.82 (m, 3 H) 7.87 (d, J = 7.43 Hz, 1 H) 8.30 (d, J = 8.01 Hz, 2 H) 8.38 (s, 1 H) 8.59 (s, 1 H) 8.70 (s, 1 H). | 0.091 | |
| 58 | 3-cyano-1-(2,3'-difluoro-5-methoxy-4-biphenylyl)-N-3-isoxazolyl-6-isoquinolinesulfonamide | 519.0 | 58 | 1H NMR (500 MHz, DMSO-d6) δ ppm 3.73 (s, 3 H) 6.47 (d, J = 1.50 Hz, 1 H) 7.30-7.41 (m, 1 H) 7.46 (d, J = 10.37 Hz, 1 H) 7.51-7.70 (m, 9 H) 8.02 (d, J = 8.92 Hz, 1 H) 8.16 (dd, J = 8.95, 1.58 Hz, 1 H) 8.80 (s, 1 H) 8.95 (s, 1 H) | | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 304 | 4-(4'-ethoxy-2-fluoro-5-methoxy-3'-methyl-4-biphenylyl)-N-3-isoxazolyl-7-quinazolinesulfonamide | 535.3 | 19 | $^1$H NMR (400 MHz, DMSO-d$_6$) δ = 12.07 (br. s., 1 H), 9.53 (s, 1 H), 8.74 (d, J = 1.8 Hz, 1 H), 8.51 (d, J = 1.5 Hz, 1 H), 8.12-7.94 (m, 2 H), 7.54-7.48 (m, 2 H), 7.43 (d, J = 10.6 Hz, 1 H), 7.30 (d, J = 6.5 Hz, 1 H), 7.11-7.06 (m, 1 H), 6.52 (d, J = 1.9 Hz, 1 H), 4.13 (q, J = 6.9 Hz, 2 H), 3.75 (s, 3 H), 2.26 (s, 3 H), 1.40 (t, J = 6.9 Hz, 3 H). | 0.61 | |
| 305 | 1-(2,3'-difluoro-5,5'-dimethoxy-4-biphenylyl)-N-3-isoxazolyl-6-isoquinolinesulfonamide | 524.2 | 19 | $^1$H NMR (400 MHz, DMSO-d$_6$) δ = 11.92 (br. s., 1 H), 8.79-8.72 (m, 2 H), 8.69 (d, J = 1.9 Hz, 1 H), 8.17 (d, J = 5.4 Hz, 1 H), 7.98-7.93 (m, 1 H), 7.91-7.84 (m, 1 H), 7.38 (d, J = 10.5 Hz, 1 H), 7.34 (d, J = 6.4 Hz, 1 H), 7.17-7.08 (m, 2 H), 6.96 (td, J = 2.3, 11.1 Hz, 1 H), 6.50 (d, J = 1.9 Hz, 1 H), 3.87 (s, 3 H), 3.71 (s, 3 H). | 0.04 | |
| 63 | 4-(3'-cyclopropyl-4'-fluoro-5-methoxy-2-methyl-4-biphenylyl)-N-3-isoxazolyl-7-quinazolinesulfonamide | 531.0 | 63 | $^1$H NMR (ACETONITRILE-d3) δ: 9.39-9.43 (m, 1H), 8.53 (d, J = 1.6 Hz, 1H), 8.32 (d, J = 1.8 Hz, 1H), 7.96-8.01 (m, 1H), 7.88-7.93 (m, 1H), 7.31 (d, J = 0.3 Hz, 1H), 7.20-7.27 (m, 1H), 7.12-7.20 (m, 1H), 6.98-7.07 (m, 2H), 6.46 (d, J = 1.8 Hz, 1H), 3.65-3.69 (m, 3H), 2.21 (s, 3H), 2.10-2.19 (m, 1H), 0.97-1.07 (m, 2H), 0.77-0.84 (m, 2H) | 0.034 | |
| 306 | 4-(3'-cyclopropyl-5'-fluoro-5-methoxy-2-methyl-4-biphenylyl)-N-3-isoxazolyl-7-quinazolinesulfonamide | 531.0 | 63 | $^1$H NMR (ACETONITRILE-d3) δ: 9.40-9.43 (m, 1H), 8.52 (d, J = 1.9 Hz, 1H), 8.30 (d, J = 1.8 Hz, 1H), 7.96-8.01 (m, 1H), 7.85-7.92 (m, 1H), 7.32 (s, 1H), 6.96-7.05 (m, 3H), 6.86 (dt, J = 10.5, 2.0 Hz, 1H), 6.45 (d, J = 1.8 Hz, 1H), 3.66-3.69 (m, 3H), 2.25 (s, 3H), 1.97-2.06 (m, 1H), 1.01-1.09 (m, 2H), 0.75-0.82 (m, 2H) | 0.061 | |
| 307 | 4-(2'-fluoro-5-methoxy-2,5'-dimethyl-4-biphenylyl)-N-3-isoxazolyl-7-quinazolinesulfonamide | 505.2 | 61 | $^1$H NMR (ACETONITRILE-d3) δ: 9.42 (s, 1H), 8.52 (d, J = 1.9 Hz, 1H), 8.30 (d, J = 1.9 Hz, 1H), 7.96-8.01 (m, 1H), 7.88-7.93 (m, 1H), 7.34 (s, 1H), 7.19-7.30 (m, 2H), 7.14 (dd, J = 9.8, 8.4 Hz, 1H), 7.04 (s, 1H), 6.45 (d, J = 1.8 Hz, 1H), 3.66 (s, 3H), 2.40 (s, 3H), 2.17 (s, 3H) | 0.113 | |
| 308 | 4-(5'-chloro-2'-fluoro-5-methoxy-2-methyl-4-biphenylyl)-N-3-isoxazolyl-7-quinazolinesulfonamide | 525.0 | 61 | $^1$H NMR (ACETONITRILE-d3) δ: 9.45 (s, 1H), 8.55-8.59 (m, 1H), 8.38 (d, J = 1.8 Hz, 1H), 7.90-8.01 (m, 2H), 7.43-7.51 (m, 2H), 7.36 (s, 1H), 7.27 (ddd, J = 9.3, 8.6, 0.5 Hz, 1H), 7.07 (s, 1H), 6.52 (d, J = 1.9 Hz, 1H), 3.64-3.68 (m, 3H), 2.18 (s, 3H) | 0.056 | |
| 309 | 4-(2-chloro-3'-fluoro-5-methoxy-5'-methyl-4-biphenylyl)-N-3-isoxazolyl-7-quinazolinesulfonamide | 525.2 | 20 | $^1$H NMR (400 MHz, DMSO-d$_6$) δ = 12.05 (br. s., 1 H), 9.53 (s, 1 H), 8.76 (s, 1 H), 8.52 (s, 1 H), 8.15-7.93 (m, 2 H), 7.67 (s, 1 H), 7.30 (s, 1 H), 7.26-7.13 (m, 3 H), 6.53 (d, J = 1.6 Hz, 1 H), 3.74 (s, 3 H), 2.43 (s, 3 H) | 0.04 | |

TABLE I-continued

| Example No. | Compound name | LC MS | Method Use To Make | NMR | Nav 1.7 PX IC$_{50}$ (μM) | Nav 1.5 PX IC$_{50}$ (μM) |
|---|---|---|---|---|---|---|
| 310 | 4-(2,3'-dichloro-5'-fluoro-5-methoxy-4-biphenylyl)-N-3-isoxazolyl-7-quinazolinesulfonamide | 545.0 | 20 | $^1$H NMR (400 MHz, DMSO-d$_6$) δ = 12.07 (br. s., 1 H), 9.54 (s, 1 H), 8.77 (d, J = 1.9 Hz, 1 H), 8.53 (d, J = 1.6 Hz, 1 H), 8.11-8.04 (m, 1 H), 8.02-7.96 (m, 1 H), 7.69 (s, 1 H), 7.59 (td, J = 2.2, 8.8 Hz, 1 H), 7.55-7.51 (m, 1 H), 7.48 (td, J = 1.8, 9.4 Hz, 1 H), 7.37 (s, 1 H), 6.54 (d, J = 1.9 Hz, 1 H), 3.75 (s, 3 H) | 0.045 | |
| 311 | 4-(2,3'-dichloro-5-methoxy-5'-methyl-4-biphenylyl)-N-3-isoxazolyl-7-quinazolinesulfonamide | 541.1 | 20 | $^1$H NMR (400 MHz, DMSO-d$_6$) δ = 12.06 (br. s., 1 H), 9.53 (s, 1 H), 8.77 (d, J = 1.8 Hz, 1 H), 8.52 (d, J = 1.6 Hz, 1 H), 8.10-8.04 (m, 1 H), 8.03-7.98 (m, 1 H), 7.67 (s, 1 H), 7.41 (d, J = 11.8 Hz, 2 H), 7.36 (s, 1 H), 7.30 (s, 1 H), 6.54 (d, J = 1.8 Hz, 1 H), 3.74 (s, 3 H), 2.42 (s, 3 H) | 0.04 | |

Example 314 (Method 66)

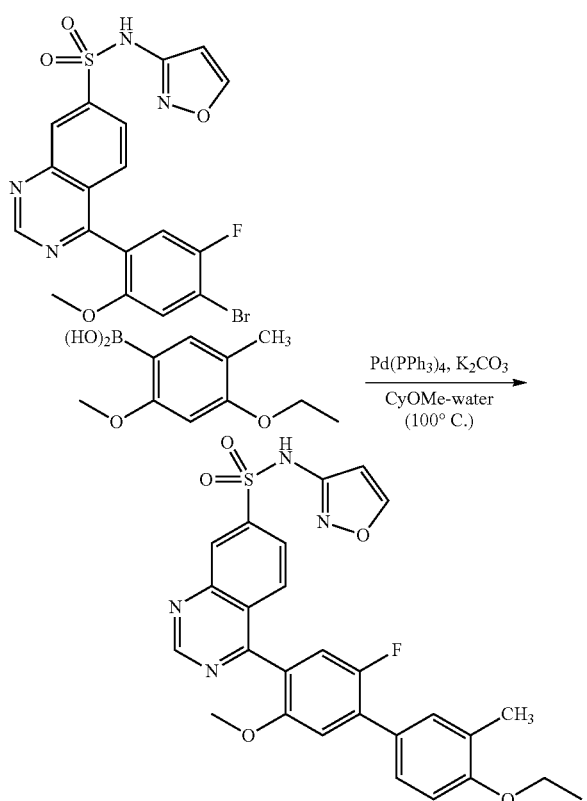

SYNTHESIS OF 4-(4'-ETHOXY-2-FLUORO-5-METHOXY-3'-METHYL-4-BIPHENYLYL)-N-3-ISOXAZOLYL-7-QUINAZOLINESULFONAMIDE

A vial was charged with 4-(4-bromo-5-fluoro-2-methoxyphenyl)-N-(isoxazol-3-yl)quinazoline-7-sulfonamide (72.45 mg, 0.151 mmol), (4-ethoxy-3-methylphenyl)boronic acid (32.7 mg, 0.181 mmol), potassium carbonate (62.7 mg, 0.453 mmol), and Pd(Ph$_3$P)$_4$ (17.47 mg, 0.015 mmol). The vial was flushed with Ar (g), then CyOMe (567 μl) and water (189 μl) were added. The vial was sealed and heated to 100° C. for 40 min. The mixture was diluted with water and brine, then extracted with EtOAc (3x). The combined organic extracts were concentrated. The residue was dissolved in DMSO, and the resulting solution was filtered through a 0.2 micron filter. The filtrate was purified by reverse-phase HPLC (50-95% CH$_3$CN/H$_2$O with 0.1% TFA). Fractions containing desired product were combined and concentrated. The residue was taken up in 2-PrOH. The resulting solution was diluted with water and filtered. The collected solid was washed with water (1x), dried under a stream of N$_2$ (g), and dried under vacuum to give 40 mg of the title compound as a yellow solid. $^1$H NMR (400 MHz, DMSO-d$_6$) δ=12.07 (br. s., 1 H), 9.53 (s, 1 H), 8.74 (d, J=1.8 Hz, 1 H), 8.51 (d, J=1.5 Hz, 1 H), 8.12-7.94 (m, 2 H), 7.54-7.48 (m, 2 H), 7.43 (d, J=10.6 Hz, 1 H), 7.30 (d, J=6.5 Hz, 1 H), 7.11-7.06 (m, 1 H), 6.52 (d, J=1.9 Hz, 1 H), 4.13 (q, J=6.9 Hz, 2 H), 3.75 (s, 3 H), 2.26 (s, 3 H), 1.40 (t, J=6.9 Hz, 3 H). m/z (ESI) 535.3 (M+H)$^+$.

Example 315 (Method 67)

4-(3'-CHLORO-2-FLUORO-5-METHOXY-4-BIPHENYLYL)-N-2-PYRIMIDINYL-7-QUINAZOLINESULFONAMIDE

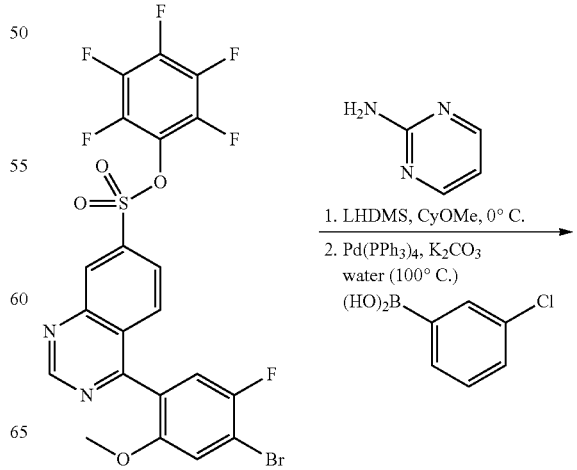

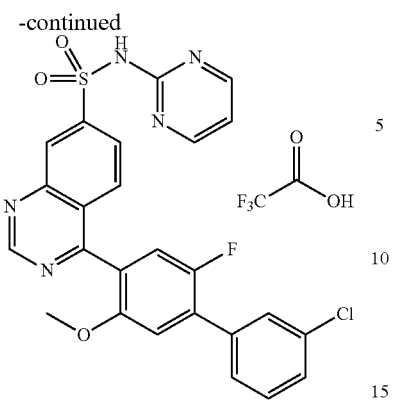

A vial was charged with perfluorophenyl 4-(4-bromo-5-fluoro-2-methoxyphenyl)quinazoline-7-sulfonate (83.16 mg, 0.144 mmol), pyrimidin-2-amine (15.02 mg, 0.158 mmol), and CyOMe (538 μl) to give a clear, yellow solution. The flask was cooled in an ice-bath for 10 min. Lithium bis(trimethylsilyl)amide (1M in THF) (301 μl, 0.301 mmol) was added dropwise, resulting in a cloudy orange mixture. The mixture was warmed to room temperature, then (3-chlorophenyl)boronic acid (33.7 mg, 0.215 mmol), potassium carbonate (59.5 mg, 0.431 mmol), and Pd(Ph₃P)₄ (16.59 mg, 0.014 mmol) were added. The vial was flushed with Ar (g), then water (179 μl) was added. The vial was sealed and heated to 100° C. for 30 min. The mixture was cooled, diluted with water and brine, and extracted with EtOAc (3×). The combined organic extracts were combined. The residue was dissolved in DMSO, and the resulting solution was filtered through a 0.2 micron filter. The filtrate was purified by reverse-phase HPLC (45-90% $CH_3CN/H_2O$ with 0.1% TFA). Fractions containing product were combined and concentrated to give 4-(3'-chloro-2-fluoro-5-methoxy-4-biphenylyl)-N-2-pyrimidinyl-7-quinazolinesulfonamide (52 mg, 50% yield) as an off-white solid. ¹H NMR (400 MHz, DMSO-d₆) δ=9.51 (s, 1 H), 8.61 (d, J=1.5 Hz, 1 H), 8.52 (d, J=5.0 Hz, 2 H), 8.16 (dd, J=1.8, 8.8 Hz, 1 H), 7.96 (d, J=8.8 Hz, 1 H), 7.78 (s, 1 H), 7.72-7.65 (m, 1 H), 7.62-7.53 (m, 2 H), 7.51 (d, J=10.4 Hz, 1 H), 7.40 (d, J=6.4 Hz, 1 H), 7.05 (t, J=5.1 Hz, 1 H), 3.75 (s, 3 H). m/z (ESI) 522.1 (M+H)⁺.

Example 316 (Method 68)

1-(2,3'-DIFLUORO-5,5'-DIMETHOXY-4-BIPHENYLYL)-N-3-ISOXAZOLYL-6-ISOQUINOLINE-SULFONAMIDE

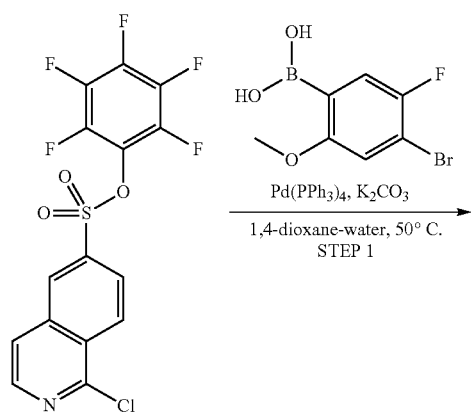

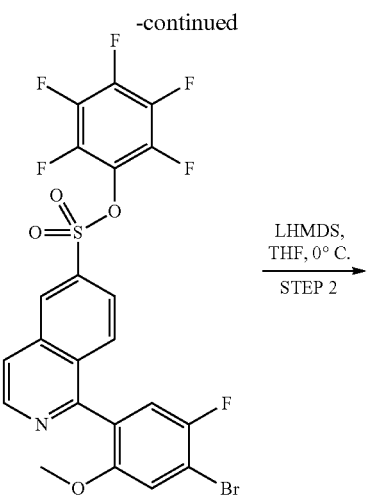

STEP 1: PERFLUOROPHENYL 1-(4-BROMO-5-FLUORO-2-METHOXYPHENYL)ISOQUINO-LINE-6-SULFONATE

A RBF was charged with perfluorophenyl 1-chloroisoquinoline-6-sulfonate (1.429 g, 3.49 mmol), (4-bromo-5-fluoro-2-methoxyphenyl)boronic acid (0.963 g, 3.87 mmol), and Pd(Ph₃P)₄ (0.403 g, 0.349 mmol). The flask was flushed with Ar (g), then 1,4-dioxane (13.08 ml) and water (4.36 ml) were added in sequence. The flask was fitted with a reflux condenser and lowered into to 50° C. for 1 h. The mixture was cooled and diluted with EtOAc. The layers were separated, and the organic layer was washed with brine, dried over sodium sulfate, filtered, and concentrated. The residue was purified by chromatography on silica gel (40-g Redi- Sep Gold column, 25-g silica gel loading column, 0-30% EtOAc/Heptane) to give perfluorophenyl 1-(4-bromo-5-fluoro-2-methoxyphenyl)isoquinoline-6-sulfonate (1.459 g, 2.52 mmol, 72.3% yield) as an light-orange foam. $^1$H NMR (400 MHz, DMSO-d$_6$)=8.93 (d, J=2.1 Hz, 1 H), 8.82 (d, J=5.7 Hz, 1 H), 8.24-8.19 (m, 1 H), 8.05 (dd, J=2.1, 9.0 Hz, 1 H), 7.95 (d, J=9.0 Hz, 1 H), 7.59 (d, J=5.7 Hz, 1 H), 7.53 (d, J=8.7 Hz, 1 H), 3.68 (s, 3 H). m/z (ESI) 578.0 (M+H)$^+$.

STEP 2: 1-(4-BROMO-5-FLUORO-2-METHOXY-PHENYL)-N-(ISOXAZOL-3-YL)ISOQUINOLINE-6-SULFONAMIDE

A RBF was charged with perfluorophenyl 1-(4-bromo-5-fluoro-2-methoxyphenyl)isoquinoline-6-sulfonate (864 mg, 1.494 mmol), isoxazol-3-amine (127 µl, 1.718 mmol) and THF (9961 µl) to give a clear solution. The flask was cooled in an ice-water bath for 10 min, then lithium bis(trimethylsilyl)amide (1M in THF) (3138 µl, 3.14 mmol) was added dropwise. After 15 min, the mixture was diluted with EtOAc and washed with 1N aq. HCl (2×), washed with brine, dried over sodium sulfate, filtered, and concentrated. The residue was purified by chromatography (40-g Redi-Sep Gold column, 25-g silica gel loading column, 0-4% MeOH/DCM) to give 1-(4-bromo-5-fluoro-2-methoxyphenyl)-N-(isoxazol-3-yl)isoquinoline-6-sulfonamide (698.3 mg, 1.460 mmol, 98% yield) as an off-white foam. $^1$H NMR (400 MHz, DMSO-d$_6$) δ=11.91 (br. s., 1 H), 8.76-8.71 (m, 2 H), 8.67 (d, J=1.9 Hz, 1 H), 8.15 (d, J=5.2 Hz, 1 H), 7.94-7.81 (m, 2 H), 7.55 (d, J=5.8 Hz, 1 H), 7.44 (d, J=8.7 Hz, 1 H), 6.49 (d, J=1.8 Hz, 1 H), 3.66 (s, 3 H). m/z (ESI) 478.0 (M+H)$^+$.

STEP 3: 1-(2,3'-DIFLUORO-5,5'-DIMETHOXY-[1,1'-BIPHENYL]-4-YL)-N-(ISOXAZOL-3-YL)ISOQUINOLINE-6-SULFONAMIDE

A vial was charged with 1-(4-bromo-5-fluoro-2-methoxyphenyl)-N-(isoxazol-3-yl)isoquinoline-6-sulfonamide (78.83 mg, 0.165 mmol), (3-fluoro-5-methoxyphenyl)boronic acid (33.6 mg, 0.198 mmol), potassium carbonate (68.3 mg, 0.494 mmol), and Pd(Ph$_3$P)$_4$ (19.05 mg, 0.016 mmol). The vial was flushed with Ar (g), then CyOMe (618 µl) and water (206 µl) were added. The vial was sealed and heated to 100° C. for 2 h. The mixture was diluted with water, then extracted with EtOAc (3×). The combined organic extracts were concentrated. The residue was purified by chromatography on silica gel (12-g Redi-Sep Gold column, 0-5% MeOH/DCM) to give 72 mg of a yellow solid. The material was dissolved in DMSO, and the resulting solution was filtered through a 0.2 micron filter. The filtrate was purified by reverse-phase HPLC (40-85% CH$_3$CN/H$_2$O with 0.1% TFA). Fractions containing the desired product were combined and concentrated from DCM to give 1-(2,3'-difluoro-5,5'-dimethoxy-4-biphenylyl)-n-3-isoxazolyl-6-isoquinolinesulfonamide as the trifluoroacetate salt (53 mg, 0.083 mmol, 50.4% yield) as a light-yellow solid. $^1$H NMR (400 MHz, DMSO-d$_6$) δ=11.92 (br. s., 1 H), 8.79-8.72 (m, 2 H), 8.69 (d, J=1.9 Hz, 1 H), 8.17 (d, J=5.4 Hz, 1 H), 7.98-7.93 (m, 1 H), 7.91-7.84 (m, 1 H), 7.38 (d, J=10.5 Hz, 1 H), 7.34 (d, J=6.4 Hz, 1 H), 7.17-7.08 (m, 2 H), 6.96 (td, J=2.3, 11.1 Hz, 1 H), 6.50 (d, J=1.9 Hz, 1 H), 3.87 (s, 3 H), 3.71 (s, 3 H). m/z (ESI) 524.2 (M+H)$^+$.

Examples 317 & 318 (Method 69)

(M)-4-(2-CHLORO-3'-FLUORO-5-METHOXY-4-BIPHENYLYL)-N-3-ISOXAZOLYL-3-METHYL-7-ISOQUINOLINE SULFONAMIDE (ex 317) AND (P)-4-(2-CHLORO-3'-FLUORO-5-METHOXY-4-BIPHENYLYL)-N-3-ISOXAZOLYL-3-METHYL-7-ISOQUINOLINESULFONAMIDE (ex. 318)

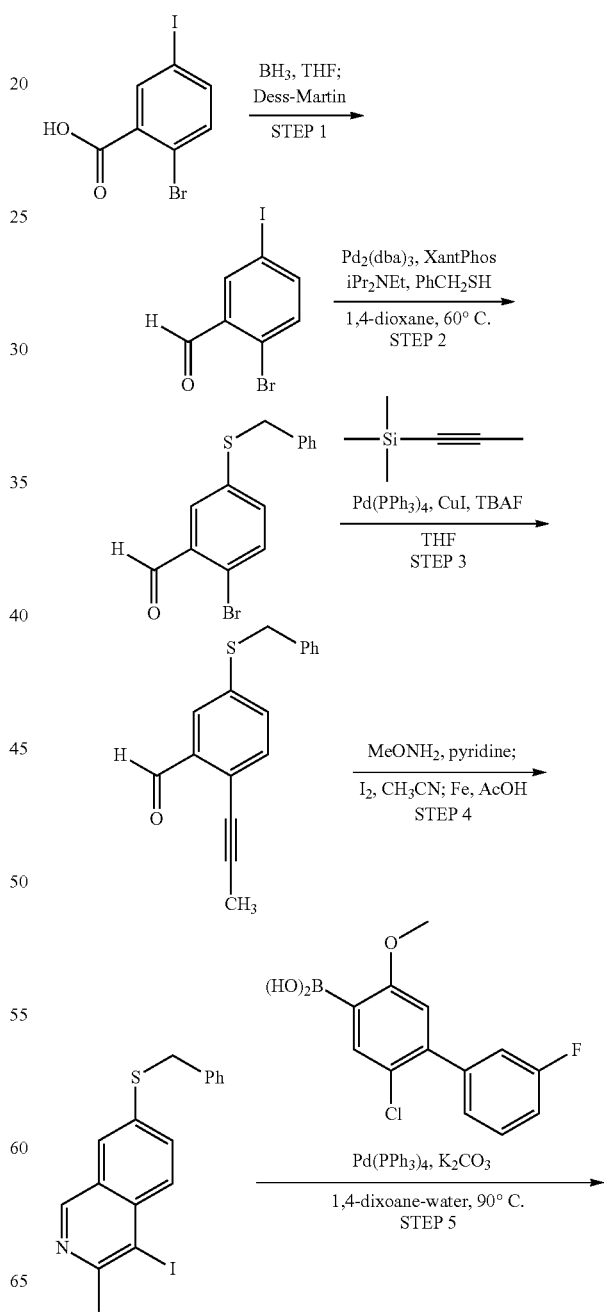

393
-continued

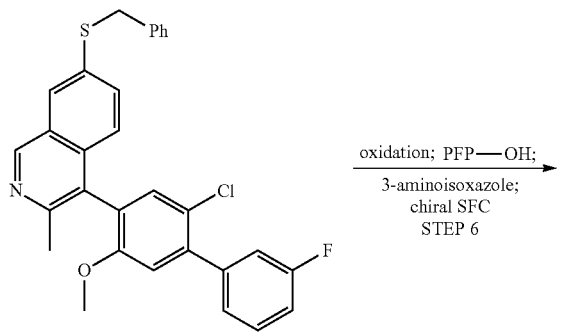

oxidation; PFP—OH;
3-aminoisoxazole;
chiral SFC
STEP 6

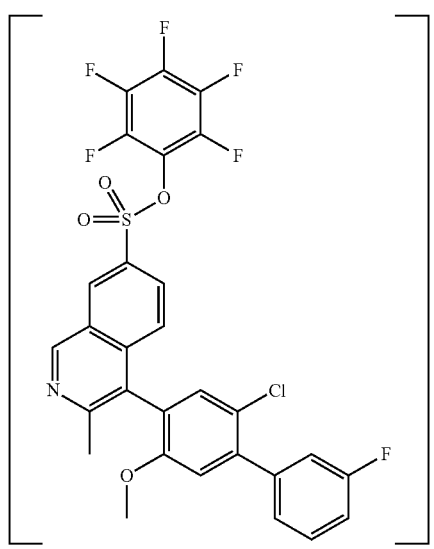

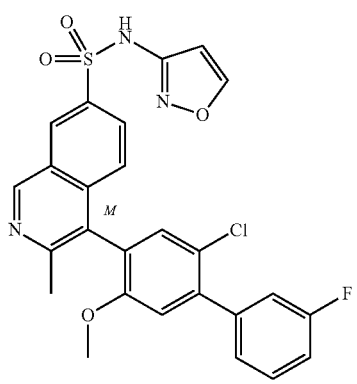

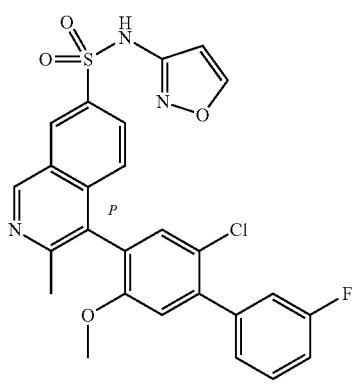

394

STEP 1: 2-BROMO-5-IODOBENZYLADEHYDE

A RBF was charged with 2-bromo-5-iodobenzoic acid (9.673 g, 29.6 mmol) and THF (99 ml) to give a clear solution. The flask was cooled in an ice-water bath for 15 min, then borane tetrahydrofuran complex, 1.0 m in tetrahydrofuran (29.6 ml, 29.6 mmol) was carefully added in portions over 20 min. The mixture was stirred overnight. In the morning, an additional portion of borane solution (5 mL) was added, and the mixture was briefly heated to reflux. The flask was lowered into an ice-water bath, then methanol was carefully added. The mixture was stirred at room temperature for 20 min then concentrated. The residue was concentrated from MeOH, then concentrated from DCM to give a white solid. The solid was dried further under vacuum for 2 h, then taken up in DCM (125 mL) to give a cloudy suspension. The flask was lowered into an ice-water bath for 20 min, then Dess-Martin periodinane (13.80 g, 32.5 mmol) was added in one portion. After 1 h, the mixture was quenched by the addition of saturated aq. sodium thiosulfate solution (100 mL) and saturated aq. sodium bicarbonate (130 mL). The mixture was stirred for 20 min at room temperature then the layers were separated. The aq. layer was diluted with water (80 mL) and extracted with DCM (2×). The combined organic extracts were dried over sodium sulfate, filtered, and concentrated to give ca. 9.3 g of 2-bromo-5-iodobenzaldehyde as an off-white solid. $^1$H NMR (400 MHz, DMSO-$d_6$)=10.09 (s, 1 H), 8.07 (d, J=2.2 Hz, 1 H), 7.93 (dd, J=2.3, 8.4 Hz, 1 H), 7.59 (d, J=8.3 Hz, 1 H).

STEP 2: 5-(BENZYLTHIO)-2-BROMOBENZALDEHYDE

A EBF was charged with 2-bromo-5-iodobenzaldehyde (3.007 g, 9.67 mmol), Xantphos (0.280 g, 0.484 mmol), and Pd$_2$(dba)$_3$ (0.221 g, 0.242 mmol). The flask was flushed with 1,4-dioxane (19.34 ml), N,N-diisopropylethylamine (3.38 ml, 19.34 mmol), and benzyl mercaptan (1.087 ml, 9.19 mmol). The flask was fitted with a reflux condenser and placed in a 60° C. heating bath for 20 min. The mixture was cooled to room temperature and partitioned between 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (100-g SNAP Ultra column, 25-g silica gel loading column, 0-30% EtOAc/Heptane) to give 5-(benzylthio)-2-bromobenzaldehyde (2.49 g, 8.11 mmol, 84% yield) as a clear oil which slowly solidified into crystals. m/z (ESI) 307.0 (M+H)$^+$.

STEP 3: 5-(BENZYLTHIO)-2-(PROP-1-YN-1-YL)BENZALDEHYDE

A RBF was charged with 5-(benzylthio)-2-bromobenzaldehyde (2.49 g, 8.11 mmol), tetrakis (0.937 g, 0.811 mmol), copper(i) iodide (0.154 g, 0.811 mmol), and tetrabutylammonium fluoride trihydrate (3.84 g, 12.16 mmol). The flask was flushed with Ar (g), then THF (40.5 ml) and 1-(trimethylsilyl)-1-propyne (1.815 ml, 12.16 mmol) were added in sequence. The flask was lowered into a 50° C. heating bath for 30 min. The aq. layer was extracted with EtOAc, and the combined organic extracts were washed with brine, dried over sodium sulfate, filtered, and concentrated. The residue was purified by chromatography on silica gel (50-g SNAP Ultra column, 25-g silica loading column, 0-15%, then 15-25% EtOAc/Heptane) to afford 5-(benzylthio)-2-(prop-1-yn-1-yl)benzaldehyde (1.915 g, 7.19 mmol, 89% yield) as a light-orange oil. m/z (ESI) 267.1 (M+H)$^+$.

STEP 4: 7-(BENZYLTHIO)-4-IODO-3-METHYLISOQUINOLINE

A RBF was charged with 5-(benzylthio)-2-(prop-1-yn-1-yl)benzaldehyde (1.457 g, 5.47 mmol), ethanol (15.63 ml), O-methylhydroxylamine hydrochloride (0.548 g, 6.56 mmol), and pyridine (1.770 ml, 21.88 mmol) (9:30 am). After 1 h, the mixture was concentrated in vacou. The residue was purified by chromatography on silica gel (50-g SNAP Ultra column, 0-50% EtOAc/Heptane) to give (E)-5-(benzylthio)-2-(prop-1-yn-1-yl)benzaldehyde O-methyl oxime as a lightly-colored oil. A RBF was charged with (E)-5-(benzylthio)-2-(prop-1-yn-1-yl)benzaldehyde O-methyl oxime (1.75 g, 5.92 mmol), sodium bicarbonate (2.99 g, 35.5 mmol), acetonitrile (100 mL) and iodine (1.955 g, 7.70 mmol) (4:40 pm). The mixture was stirred overnight. The mixture was filtered, and the collected solid was washed with EtOAc (2×) and dried under a stream of $N_2$ (g) briefly to give 3.66 g of an orange solid. The solid was added to a flask containing iron (3.31 g, 59.2 mmol), MeOH (20 mL), and acetic acid (20 mL). The flask was fitted with a reflux condenser, then placed in a 70° C. heating bath for 45 min. The mixture was cooled, diluted with MeOH, and concentrated. The residue was concentrated from MeOH, then taken up in MeOH. The resulting solution was loaded onto a 25-g silica gel loading column. A white solid persisted on the filter. The column was then partially dried under vacuum before being eluted onto a pre-equilibrated 50-g SNAP Ultra column with 0-40% EtOAc/Heptane, and was then flushed with 40% EtOAc/Heptane, then 10% MeOH/DCM to give 7-(benzylthio)-4-iodo-3-methylisoquinoline (370 mg, 0.946 mmol, 15.96% yield) as a yellow solid. m/z (ESI) 392.0 (M+H)$^+$.

STEP 5: 7-(BENZYLTHIO)-4-(2-CHLORO-3'-FLUORO-5-METHOXY-[1,1'-BIPHENYL]-4-YL)-3-METHYLISOQUINOLINE

A RBF was charged with 7-(benzylthio)-4-iodo-3-methylisoquinoline (394 mg, 1.007 mmol), (2-chloro-3'-fluoro-5-methoxy-[1,1'-biphenyl]-4-yl)boronic acid (424 mg, 1.510 mmol), potassium carbonate (418 mg, 3.02 mmol), and Pd(Ph$_3$P)$_4$ (116 mg, 0.101 mmol). The flask was flushed with Ar (g), then 1,4-dioxane (3776 µl) and water (1259 µl) were added. A reflux condenser was attached, and the flask was lowered into a 90° C. heating bath for 1 h. mixture was cooled, diluted with water, and extracted with EtOAc (2×). The combined organic extracts were dried over sodium sulfate, filtered, and concentrated. The residue was purified by chromatography on silica gel (50-g SNAP Ultra column, 25-g silica gel loading column, 0-50% EtOAc/Heptane) to give 7-(benzylthio)-4-(2-chloro-3'-fluoro-5-methoxy-[1,1'-biphenyl]-4-yl)-3-methylisoquinoline (431.5 mg, 0.863 mmol, 86% yield) as a light-yellow foam. $^1$H NMR (400 MHz, DMSO-d$_6$) δ=9.17 (s, 1 H), 8.08 (d, J=1.9 Hz, 1 H), 7.65-7.53 (m, 2 H), 7.50-7.38 (m, 5 H), 7.34-7.28 (m, 3 H), 7.27-7.18 (m, 3 H), 4.40 (s, 2 H), 3.71 (s, 3 H), 2.37 (s, 3 H). m/z (ESI) 500.1 (M+H)$^+$.

STEP 6: (M)-4-(2-CHLORO-3'-FLUORO-5-METHOXY-4-BIPHENYLYL)-N-3-ISOXAZOLYL-3-METHYL-7-ISOQUINOLINESULFONAMIDE AND (P)-4-(2-CHLORO-3'-FLUORO-5-METHOXY-4-BIPHENYLYL)-N-3-ISOXAZOLYL-3-METHYL-7-ISOQUINOLINESULFONAMIDE

A RBF was charged with 7-(benzylthio)-4-(2-chloro-3'-fluoro-5-methoxy-[1,1'-biphenyl]-4-yl)-3-methylisoquinoline (429 mg, 0.858 mmol). DCM (6729 µl), acetic acid (252 µl), and water (168 µl) to give clear solution. The flask was cooled in an ice-water bath for 10 min, then 1,3-dichloro-5,5-dimethylimidazolidine-2,4-dione (347 mg, 1.759 mmol) was added in one portion. After 30 min, an additional portion of oxidant (ca. 170 mg) was added. After another 5 min, 2,3,4,5,6-pentafluorophenol (237 mg, 1.287 mmol) was added in one portion, then triethylamine (478 µl, 3.43 mmol) was added dropwise. The mixture was stirred for 45 min then warmed to room temperature and loaded onto a 25-g silica gel loading column. The column was dried by attaching a vacuum hose to one end for 5 min. The column was then eluted onto a pre-equilibrated 25-g Ultra SNAP column with 0-50% EtOAc/Heptane. Two spots were collected together to give 630 mg of a white foam. A portion of this material was carried on directly in the next step. A solution containing the white foam prepared above (321.69 mg, 0.412 mmol), isoxazol-3-amine (45.7 µl, 0.619 mmol) and THF (4125 µl) was cooled in an ice-bath for 15 min, then lithium bis(trimethylsilyl)amide (1M in THF) (1444 µl, 1.444 mmol) was added dropwise. After 20 min, additional portions of amine (1.5 equiv) and LHMDS solution (0.75 mL) were added. After another 20 min of stirring, the mixture was warmed to room temperature and diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (25-g silica gel column, 0-5% MeOH/DCM). The product was collected with some of a slightly higher spot to give 182 mg of an amber oil. This material was dissolved in 1:1 DCM/MeOH, and the resulting solution was purified by chiral SFC Chiralpak OZ-H column with 40% MeOH/60% CO$_2$ to give (M)-4-(2-chloro-3'-fluoro-5-methoxy-4-biphenylyl)-N-3-isoxazolyl-3-methyl-7-isoquinolinesulfonamide as peak 1 and (P)-4-(2-chloro-3'-fluoro-5-methoxy-4-biphenylyl)-N-3-isoxazolyl-3-methyl-7-isoquinolinesulfonamide as peak 2. Both materials were obtained as tan solids. Data for peak 1: $^1$H NMR (400 MHz, DMF) δ=11.83 (br. s., 1 H), 9.51 (s, 1 H), 8.75 (d, J=1.6 Hz, 1 H), 8.65 (d, J=1.2 Hz, 1 H), 7.99 (dd, J=2.0, 9.0 Hz, 1 H), 7.58 (dt, J=6.4, 7.9 Hz, 1 H), 7.52-7.41 (m, 4 H), 7.36-7.22 (m, 2 H), 6.44 (d, J=1.8 Hz, 1 H), 3.71 (s, 3 H), 2.42 (s, 3 H). m/z (ESI) 524.2 (M+H)$^+$. Data for peak 2: $^1$H NMR (400 MHz, DMF)=11.83 (br. s., 1 H), 9.51 (s, 1 H), 8.75 (d, J=1.6 Hz, 1 H), 8.65 (d, J=1.2 Hz, 1 H), 7.99 (dd, J=2.0, 9.0 Hz, 1 H), 7.58 (dt, J=6.4, 7.9 Hz, 1 H), 7.52-7.41 (m, 4 H), 7.36-7.22 (m, 2 H), 6.44 (d, J=1.8 Hz, 1 H), 3.71 (s, 3 H), 2.42 (s, 3 H). m/z (ESI) 524.2 (M+H)$^+$.

Example 328 (Method 77)

4-(2-CHLORO-3'-FLUORO-5-METHOXY-[1,1'-BIPHENYL]-4-YL)-N-(ISOXAZOL-3-YL)-2-METHYL-1-OXO-1,2-DIHYDROISOQUINO-LINE-7-SULFONAMIDE TRIFLUOROMETHANESULFONATE

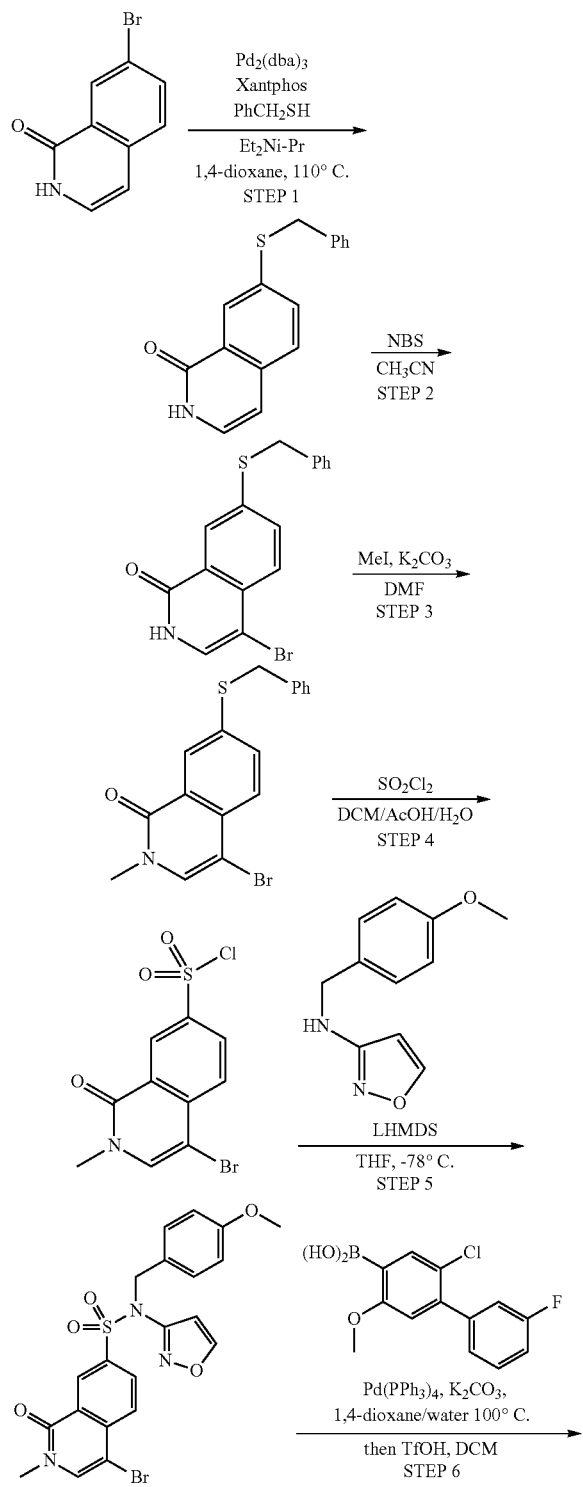

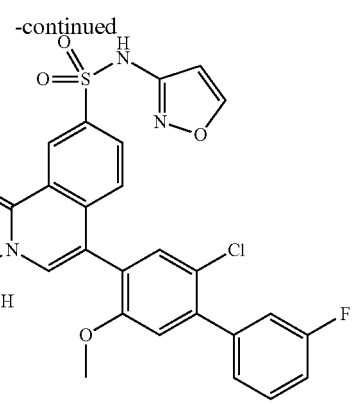

STEP 1: 7-(BENZYLTHIO)ISOQUINOLIN-1(2M-ONE

A vial was charged with 7-bromoisoquinolin-1(2H)-one (1.704 g, 7.61 mmol), xantphos (0.220 g, 0.380 mmol), and $Pd_2(dba)_3$ (0.174 g, 0.190 mmol). The flask was flushed with Ar (g), then dioxane (15.21 ml), benzyl mercaptan (1 ml, 8.45 mmol), and n,n-diisopropylethylamine (2.66 ml, 15.21 mmol) were added in sequence. The reaction was heated to 110° C. and stirred for 30 minutes. The reaction was diluted with water and stirred for one hour. The solids were filtered, washed thoroughly with water, and dried overnight under a nitrogen blanket. The solids were taken up in minimal ethyl acetate and stirred for one hour. The solids were filtered, washed with ethyl acetate, and dried overnight under a nitrogen blanket to afford 7-(benzylthio)isoquinolin-1(2H)-one (2.06 g, 7.71 mmol, 100% yield) as an olive yellow solid. m/z (ESI) 268.1 (M+H)⁺.

STEP 2: 7-(BENZYLTHIO)-4-BROMOISOQUINOLIN-1(2H)-ONE

A vial was charged with 7-(benzylthio)isoquinolin-1(2H)-one (0.200 g, 0.748 mmol), NBS (0.146 g, 0.823 mmol), and acetonitrile (3.74 ml). The reaction was stirred overnight at room temperature. The reaction was diluted with water and stirred vigorously for 15 minutes. The solution was filtered and the solids were washed with water and vacuum dried under a nitrogen blanket to afford 7-(benzylthio)-4-bromoisoquinolin-1(2H)-one (0.223 g, 0.644 mmol, 86% yield) as a yellow solid. m/z (ESI) 348.0 (M+H)⁺.

STEP 3: 7-(BENZYLTHIO)-4-BROMO-2-METHYLISOQUINOLIN-1(2H)-ONE

To a solution of 7-(benzylthio)-4-bromoisoquinolin-1(2H)-one (0.223 g, 0.644 mmol) and potassium carbonate (0.223 g, 1.610 mmol) in DMF (3.22 ml) was added iodomethane (0.060 ml, 0.966 mmol). The reaction was stirred overnight at room temperature. The reaction was diluted with water and stirred for one hour. The solution was filtered, and the solids were washed thoroughly with water and dried under a nitrogen blanket to afford 7-(benzylthio)-4-bromo-2-methylisoquinolin-1(2H)-one (0.181 g, 0.502 mmol, 78% yield) as a brown solid. m/z (ESI) 363.0 (M+H)⁺.

STEP 4: 4-BROMO-2-METHYL-1-OXO-1,2-DI-HYDROISOQUINOLINE-7-SULFONYL CHLORIDE

A RBF was charged with 7-(benzylthio)-4-bromo-2-methylisoquinolin-1(2H)-one (0.181 g, 0.502 mmol), DCM (4.78 ml), acetic acid (0.120 ml), and water (0.120 ml). The flask was cooled in an ice-bath for 10 minutes, then sulfuryl chloride (0.122 ml, 1.507 mmol) was added in one portion, leading to a solution. The reaction was stirred for 30 minutes, then warmed to room temperature and stirred for one hour. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 40 g, gradient elution 0-50% EtOAc:Heptane) to afford 4-bromo-2-methyl-1-oxo-1,2-dihydroisoquinoline-7-sulfonyl chloride (0.086 g, 0.256 mmol, 50.9% yield) as a light yellow solid. m/z (ESI) 335.9 (M+H)+.

STEP 5: 4-BROMO-N-(ISOXAZOL-3-YL)-N-(4-METHOXYBENZYL)-2-METHYL-1-OXO-1,2-DIHYDROISOQUINOLINE-7-SULFONAMIDE

A flask was charged with 4-bromo-2-methyl-1-oxo-1,2-dihydroisoquinoline-7-sulfonyl chloride (0.085 g, 0.253 mmol), N-(4-methoxybenzyl)isoxazol-3-amine (0.054 g, 0.265 mmol), and THF (1.684 ml) and cooled to −78° C. in a dry ice/acetone bath for 10 minutes. LHMDS (1.0 M in THF) (0.303 ml, 0.303 mmol) was added dropwise and the reaction was stirred for 30 minutes. The reaction was warmed to RT and quenched with saturated ammonium chloride solution, diluted with ethyl acetate and washed with water. The aqueous layer was extracted 3× with ethyl acetate, and the combined organic layers were dried with sodium sulfate, filtered, and concentrated. The material was purified via column chromatography (RediSep Gold 12 g, gradient elution 0-75% EtOAc:Heptane) to afford 4-bromo-N-(isoxazol-3-yl)-N-(4-methoxybenzyl)-2-methyl-1-oxo-1,2-dihydroisoquinoline-7-sulfonamide (0.070 g, 0.139 mmol, 55.0% yield) as a white solid. m/z (ESI) 504.0 (M+H)+.

STEP 6: 4-(2-CHLORO-3'-FLUORO-5-METHOXY-[1,1'-BIPHENYL]-4-YL)-N-(ISOXAZOL-3-YL)-2-METHYL-1-OXO-1,2-DIHYDROISOQUINOLINE-7-SULFONAMIDE TRIFLUOROMETHANESULFONATE

A microwave vial was charged with 4-bromo-N-(isoxazol-3-yl)-N-(4-methoxybenzyl)-2-methyl-1-oxo-1,2-dihydroisoquinoline-7-sulfonamide (0.070 g, 0.139 mmol), (2-chloro-3'-fluoro-5-methoxy-[1,1'-biphenyl]-4-yl)boronic acid (0.058 g, 0.208 mmol), Pd(Ph3P)4 (0.016 g, 0.014 mmol), and potassium carbonate (0.058 g, 0.416 mmol). The vial was flushed with Ar (g), then dioxane (0.520 mL) and water (0.173 mL) were added. The reaction was microwaved at 100° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 4-(2-chloro-3'-fluoro-5-methoxy-[1,1'-biphenyl]-4-yl)-N-(isoxazol-3-yl)-N-(4-methoxybenzyl)-2-methyl-1-oxo-1,2-dihydroisoquinoline-7-sulfonamide. The material was dissolved in DCM and trifluoromethanesulfonic acid (0.1 mL, 0.666 mmol) was added. The reaction was stirred for 30 minutes at RT. The reaction was concentrated, triturated with methanol, and filtered. The resulting solids were dried overnight under a nitrogen blanket to afford 4-(2-chloro-3'-fluoro-5-methoxy-[1,1'-biphenyl]-4-yl)-N-(isoxazol-3-yl)-2-methyl-1-oxo-1,2-dihydroisoquinoline-7-sulfonamide trifluoromethanesulfonate (0.041 g, 0.059 mmol, 42.8% yield) as an off-white solid. 1H NMR (400 MHz, DMSO-d6) δ=11.75 (s, 1 H), 8.78-8.66 (m, 2 H), 8.05 (dd, J=2.2, 8.7 Hz, 1 H), 7.76 (s, 1 H), 7.62-7.53 (m, 1 H), 7.51 (s, 1 H), 7.44-7.35 (m, 3 H), 7.34-7.27 (m, 1 H), 7.21 (s, 1 H), 6.44 (d, J=1.9 Hz, 1 H), 3.73 (s, 3 H), 3.58 (s, 3 H). m/z (ESI): 540.2 (M+H)+.

Example 329 (Method 78)

4-(2,3'-DICHLORO-4'-FLUORO-5-METHOXY-[1,1'-BIPHENYL]-4-YL)-N-(PYRIMIDIN-2-YL)QUINAZOLINE-7-SULFONAMIDE

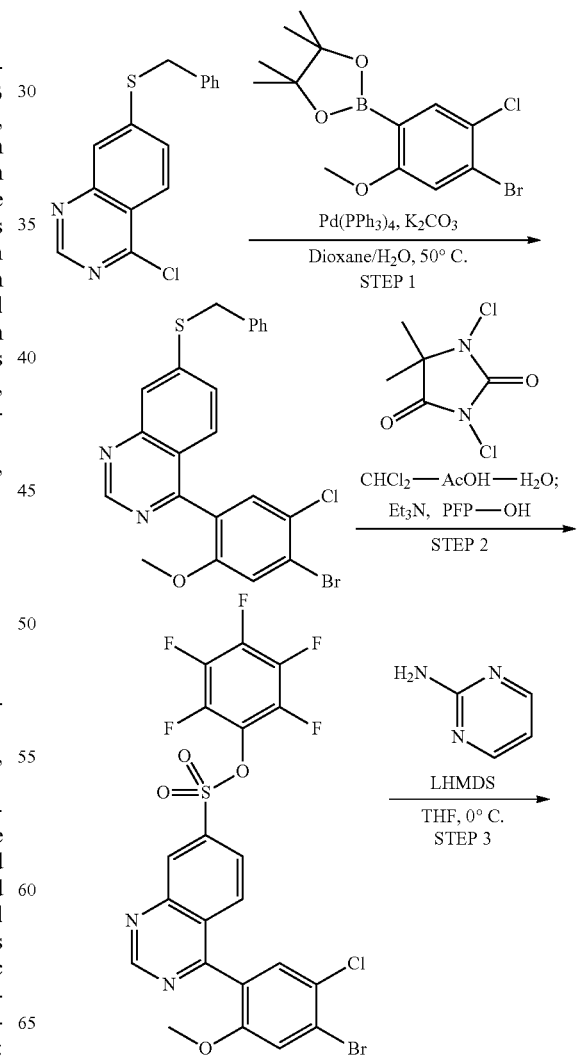

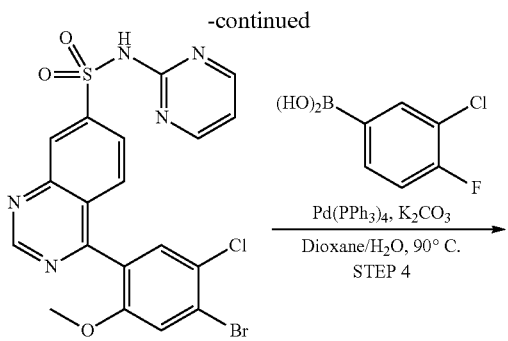

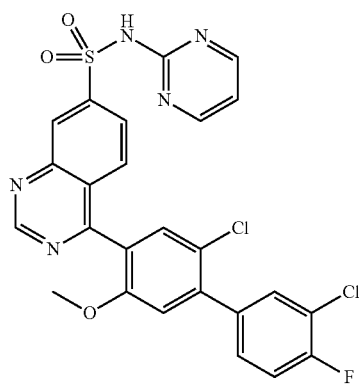

STEP 1: 7-(BENZYLTHIO)-4-(4-BROMO-5-CHLORO-2-METHOXYPHENYL)QUINAZOLINE

A RBF was charged with 7-(benzylthio)-4-chloroquinazoline (3.0 g, 10.46 mmol), 2-(4-bromo-5-chloro-2-methoxyphenyl)-4,4,5,5-tetramethyl-1,3,2-dioxaborolane (3.82 g, 10.98 mmol), tetrakis(triphenylphosphine)palladium(0) (1.0 g, 0.865 mmol), and potassium carbonate (7.23 g, 52.3 mmol). Dioxane (39.2 ml) and water (13.08 ml) were added, the flask was flushed with argon and sealed, and heated at 50° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-50% EtOAc:Heptane) to afford 7-(benzylthio)-4-(4-bromo-5-chloro-2-methoxyphenyl)quinazoline (4.35 g, 9.22 mmol, 88% yield) as a yellow solid. m/z (ESI) 471.0 (M+H)$^+$.

STEP 2: PERFLUOROPHENYL 4-(4-BROMO-5-CHLORO-2-METHOXYPHENYL)QUINAZOLINE-7-SULFONATE

A RBF was charged with 7-(benzylthio)-4-(4-bromo-5-chloro-2-methoxyphenyl)quinazoline (4.94 g, 10.47 mmol), DCM (99 ml), acetic acid (3.70 ml), and water (2.464 ml) to give a thin suspension. The flask was cooled in an ice-bath for 10 min, then 1,3-dichloro-5,5-dimethylimidazolidine-2,4-dione (5.16 g, 26.2 mmol) was added in one portion, leading to a solution. The reaction was stirred for 15 minutes. 2,3,4,5,6-pentafluorophenol (2.194 ml, 20.94 mmol) was added followed by dropwise addition of triethylamine (3.65 ml, 26.2 mmol). The reaction was stirred for 30 minutes. The reaction was concentrated and purified via column chromatography (RediSep Gold 40 g, gradient elution 0-50% EtOAc:Heptane) to afford perfluorophenyl 4-(4-bromo-5-chloro-2-methoxyphenyl)quinazoline-7-sulfonate (4.24 g, 7.12 mmol, 68.0% yield) as a light yellow solid. m/z (ESI) 595.0 (M+H)$^+$.

STEP 3: 4-(4-BROMO-5-CHLORO-2-METHOXYPHENYL)-N-(PYRIMIDIN-2-YL)QUINAZOLINE-7-SULFONAMIDE

A RBF was charged with perfluorophenyl 4-(4-bromo-5-chloro-2-methoxyphenyl)quinazoline-7-sulfonate (1.5 g, 2.52 mmol), pyrimidin-2-amine (0.263 g, 2.77 mmol), and THF (12.59 ml) to give a clear solution. The flask was cooled in a dry ice/acetone bath for 10 min, then lithium bis(trimethylsilyl)amide (1M in THF) (5.54 ml, 5.54 mmol) was added dropwise. The reaction was stirred for 30 minutes. The reaction was diluted with 1N aq. HCl and EtOAc. The aqueous layer was extracted with ethyl acetate, and the combined organic layers were washed with brine and concentrated. The resulting solid was triturated in ethyl acetate and filtered, and the resulting solids were washed with ethyl acetate and dried under a nitrogen blanket to afford 4-(4-bromo-5-chloro-2-methoxyphenyl)-N-(pyrimidin-2-yl)quinazoline-7-sulfonamide (0.918 g, 1.812 mmol, 71.9% yield) as a light yellow solid. m/z (ESI) 506.0 (M+H)$^+$.

STEP 4: 4-(2,3'-DICHLORO-4'-FLUORO-5-METHOXY-[1,1'-BIPHENYL]-4-YL)-N-(PYRIMIDIN-2-YL)QUINAZOLINE-7-SULFONAMIDE

A vial was charged with 4-(4-bromo-5-chloro-2-methoxyphenyl)-N-(pyrimidin-2-yl)quinazoline-7-sulfonamide (0.100 g, 0.197 mmol), (3-chloro-4-fluorophenyl)boronic acid (0.052 g, 0.296 mmol), tetrakis(triphenylphosphine)palladium(0) (0.023 g, 0.020 mmol), and potassium carbonate (0.136 g, 0.987 mmol). Dioxane (0.987 ml) and water (0.329 ml) were added and the reaction was stirred at 90° C. for 30 minutes. The reaction was diluted with ethyl acetate and washed with 1 N aqueous HCl solution. The aqueous layer was extracted with ethyl acetate, and the combined organic layers were dried with sodium sulfate, filtered, and concentrated. The material was purified via column chromatography (RediSep Gold 12 g, gradient elution 25-75% [3:1 EtOAc/EtOH]:Heptane to afford 4-(2,3'-dichloro-4'-fluoro-5-methoxy-[1,1'-biphenyl]-4-yl)-N-(pyrimidin-2-yl)quinazoline-7-sulfonamide (0.103 g, 0.185 mmol, 94% yield) as a light yellow solid. $^1$H NMR (400 MHz, DMSO-d$_6$) δ=9.51 (s, 1 H), 8.61 (s, 1 H), 8.52 (d, J=4.8 Hz, 2 H), 8.16 (dd, J=1.8, 8.8 Hz, 1 H), 7.95 (d, J=9.0 Hz, 1 H), 7.83 (dd, J=1.8, 7.1 Hz, 1 H), 7.68 (s, 1 H), 7.64-7.58 (m, 3 H), 7.35 (s, 1 H), 7.05 (br. s., 1 H), 3.74 (s, 3 H). m/z (ESI) 558.0 (M+H)$^+$.

Example 330 & 331 (Method 79)

(M)-4-(2-CHLORO-3'-FLUORO-5-METHOXY-[1,1'-BIPHENYL]-4-YL)-N-(ISOXAZOL-3-YL)-3-METHYLQUINOLINE-7-SULFONAMIDE (330) AND (P)-4-(2-CHLORO-3'-FLUORO-5-METHOXY-[1,1'-BIPHENYL]-4-YL)-N-(ISOXAZOL-3-YL)-3-METHYLQUINOLINE-7-SULFONAMIDE (313)

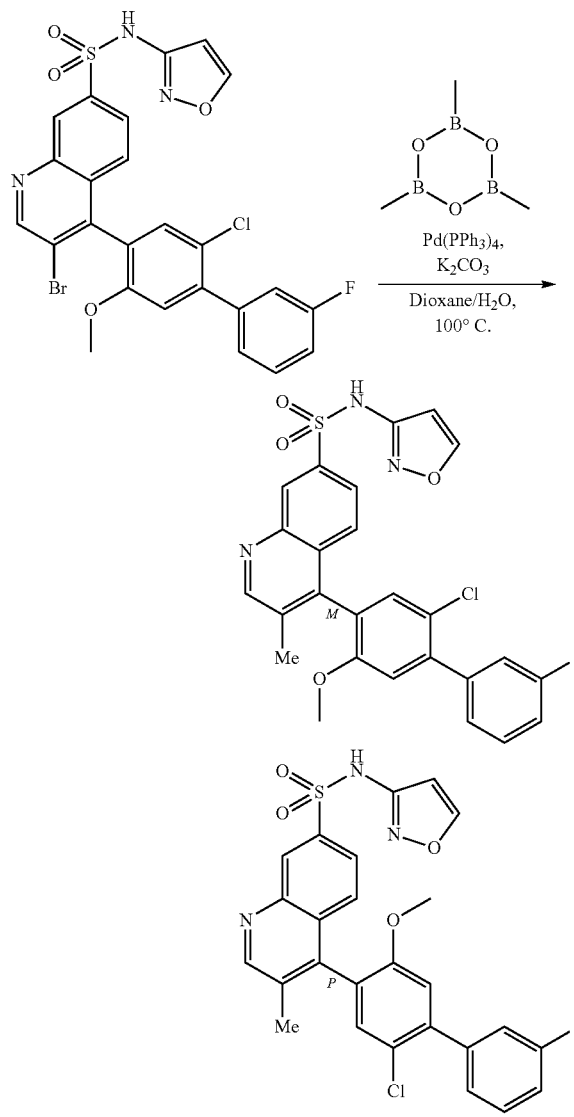

A vial was charged with 3-bromo-4-(2-chloro-3'-fluoro-5-methoxy-[1,1'-biphenyl]-4-yl)-N-(isoxazol-3-yl)quinoline-7-sulfonamide (0.125 g, 0.212 mmol), tetrakis(triphenylphosphine)palladium(0) (0.025 g, 0.021 mmol), and potassium carbonate (0.147 g, 1.061 mmol). Dioxane (1.061 ml) and water (0.354 ml) were added followed by trimethylboroxine (0.044 ml, 0.318 mmol) and the reaction was stirred at 90° C. overnight. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 10-75% [3:1 EtOAc/EtOH]:Heptane) to afford 4-(2-chloro-3'-fluoro-5-methoxy-[1,1'-biphenyl]-4-yl)-N-(isoxazol-3-yl)-3-methylquinoline-7-sulfonamide (0.054 g, 0.103 mmol, 48.5% yield) as a white solid. This material was purified by chiral SFC on Chiralpak AD-H column (25% MeOH/75% CO$_2$) to afford (M)-4-(2-chloro-3'-fluoro-5-methoxy-[1,1'-biphenyl]-4-yl)-N-(isoxazol-3-yl)-3-methylquinoline-7-sulfonamide as Peak 1 and (P)-4-(2-chloro-3'-fluoro-5-methoxy-[1,1'-biphenyl]-4-yl)-N-(isoxazol-3-yl)-3-methylquinoline-7-sulfonamide as Peak 2, both as off-white solids. Peak 1: $^1$H NMR (400 MHz, DMSO-d$_6$) δ=11.84 (br. s., 1 H), 9.03 (br. s., 1 H), 8.62 (br. s., 1 H), 8.47 (br. s., 1 H), 7.87 (d, J=8.7 Hz, 1 H), 7.64-7.52 (m, 2 H), 7.46 (br. s., 3 H), 7.36-7.26 (m, 2 H), 6.43 (br. s., 1 H), 3.71 (s, 3 H), 2.26 (s, 3 H). m/z (ESI) 524.0 (M+H)$^+$. Peak 2: $^1$H NMR (400 MHz, DMSO-d$_6$) δ=11.84 (br. s., 1 H), 9.03 (br. s., 1 H), 8.62 (br. s., 1 H), 8.47 (br. s., 1 H), 7.87 (d, J=8.7 Hz, 1 H), 7.64-7.52 (m, 2 H), 7.46 (br. s., 3 H), 7.36-7.26 (m, 2 H), 6.43 (br. s., 1 H), 3.71 (s, 3 H), 2.26 (s, 3 H). m/z (ESI) 524.0 (M+H)$^+$.

Example 332 & 333 (Method 80)

(M)-4-(2-CHLORO-3'-FLUORO-5-METHOXY-[1,1'-BIPHENYL]-4-YL)-3-ETHYL-N-(ISOXAZOL-3-YL)QUINOLINE-7-SULFONAMIDE (332) AND (P)-4-(2-CHLORO-3'-FLUORO-5-METHOXY-[1,1'-BIPHENYL]-4-YL)-3-ETHYL-N-(ISOXAZOL-3-YL)QUINOLINE-7-SULFONAMIDE (333)

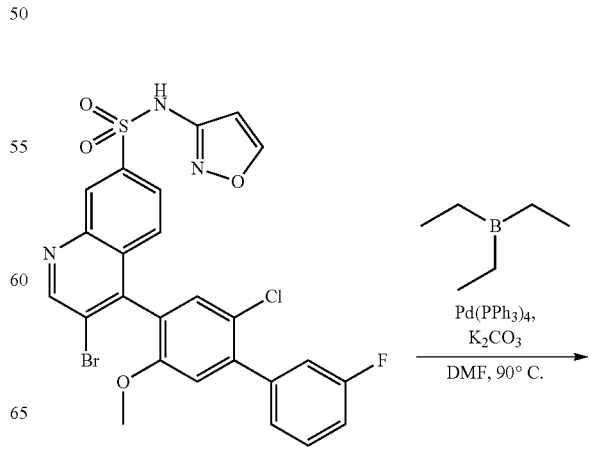

-continued

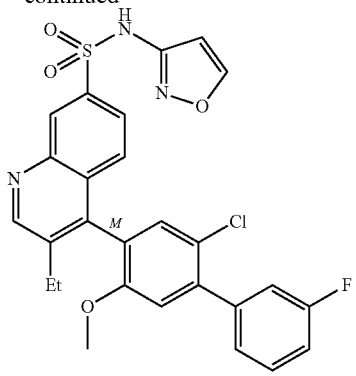

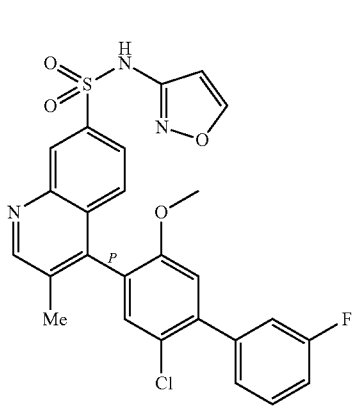

A vial was charged with 3-bromo-4-(2-chloro-3'-fluoro-5-methoxy-[1,1'-biphenyl]-4-yl)-N-(isoxazol-3-yl)quinoline-7-sulfonamide (0.125 g, 0.212 mmol), tetrakis(triphenylphosphine)palladium(0) (0.025 g, 0.021 mmol), and potassium carbonate (0.147 g, 1.061 mmol). DMF (1.415 ml) was added followed by triethylborane (1.0M in hexanes) (0.318 ml, 0.318 mmol) and the reaction was stirred at 90° C. overnight. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 10-75% [3:1 EtOAc/EtOH]:Heptane) to afford 4-(2-chloro-3'-fluoro-5-methoxy-[1,1'-biphenyl]-4-yl)-3-ethyl-N-(isoxazol-3-yl)quinoline-7-sulfonamide (0.089 g, 0.165 mmol, 78% yield) as a white solid. This material was purified by chiral SFC on Chiralpak AD-H column (30% MeOH/70% CO$_2$) to afford (M)-4-(2-chloro-3'-fluoro-5-methoxy-[1,1'-biphenyl]-4-yl)-3-ethyl-N-(isoxazol-3-yl)quinoline-7-sulfonamide as Peak 1 and (P)-4-(2-chloro-3'-fluoro-5-methoxy-[1,1'-biphenyl]-4-yl)-3-ethyl-N-(isoxazol-3-yl)quinoline-7-sulfonamide as Peak 2, both as off-white solids. Peak 1: $^1$H NMR (400 MHz, DMSO-d$_6$) δ=11.84 (br. s., 1 H), 9.09 (s, 1 H), 8.68 (br. s., 1 H), 8.50 (br. s., 1 H), 7.88 (d, J=8.6 Hz, 1 H), 7.63-7.50 (m, 2 H), 7.50-7.42 (m, 3 H), 7.37-7.24 (m, 2 H), 6.47 (s, 1 H), 3.70 (s, 3 H), 3.56-3.37 (m, 2 H), 2.58 (dd, J=8.0, 16.5 Hz, 2 H), 1.12 (t, J=7.3 Hz, 3 H). m/z (ESI) 538.1 (M+H)$^+$. Peak 2: $^1$H NMR (400 MHz, DMSO-d$_6$) δ=11.84 (br. s., 1 H), 9.09 (s, 1 H), 8.68 (br. s., 1 H), 8.50 (br. s., 1 H), 7.88 (d, J=8.6 Hz, 1 H), 7.63-7.50 (m, 2 H), 7.50-7.42 (m, 3 H), 7.37-7.24 (m, 2 H), 6.47 (s, 1 H), 3.70 (s, 3 H), 3.56-3.37 (m, 2 H), 2.58 (dd, J=8.0, 16.5 Hz, 2 H), 1.12 (t, J=7.3 Hz, 3 H). m/z (ESI) 538.1 (M+H)$^+$.

Example 334 & 335 (Method 81)

(M)-4-(2-CHLORO-3'-FLUORO-5-METHOXY-[1,1'-BIPHENYL]-4-YL)-3-CYANO-N-(ISOXAZOL-3-YL)QUINOLINE-7-SULFONAMIDE (334) AND (P)-4-(2-CHLORO-3'-FLUORO-5-METHOXY-[1,1'-BIPHENYL]-4-YL)-3-CYANO-N-(ISOXAZOL-3-YL)QUINOLINE-7-SULFONAMIDE (335)

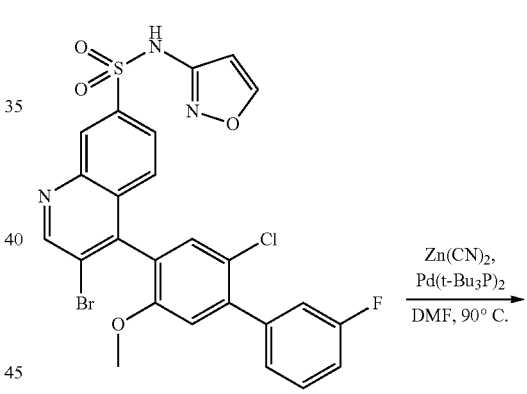

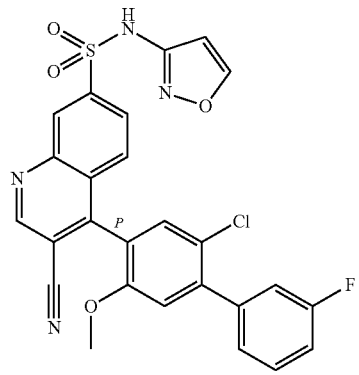

-continued

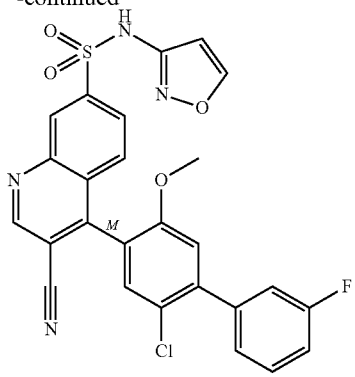

A vial was charged with 3-bromo-4-(2-chloro-3'-fluoro-5-methoxy-[1,1'-biphenyl]-4-yl)-N-(isoxazol-3-yl)quinoline-7-sulfonamide (0.125 g, 0.212 mmol), dicyanozinc (0.050 g, 0.425 mmol), and bis(tri-t-butylphosphine)palladium(0) (0.016 g, 0.032 mmol). The vial was flushed with Ar (g), then DMAC (1.061 ml) was added. The reaction was heated to 90° C. and stirred for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 0-35% [3:1 EtOAc/EtOH]:Heptane) to afford 4-(2-chloro-3'-fluoro-5-methoxy-[1,1'-biphenyl]-4-yl)-3-cyano-N-(isoxazol-3-yl)quinoline-7-sulfonamide (0.076 g, 0.142 mmol, 66.9% yield) as an off-white solid. This material was purified by chiral SFC on Chiralpak AD-H column (30% MeOH/70% CO₂) to afford (P)-4-(2-chloro-3'-fluoro-5-methoxy-[1,1'-biphenyl]-4-yl)-3-cyano-N-(isoxazol-3-yl)quinoline-7-sulfonamide as Peak 1 and (M)-4-(2-chloro-3'-fluoro-5-methoxy-[1,1'-biphenyl]-4-yl)-3-cyano-N-(isoxazol-3-yl)quinoline-7-sulfonamide as Peak 2, both as off-white solids. Peak 1: ¹H NMR (400 MHz, DMSO-d₆) δ=12.04 (br. s., 1 H), 9.43 (s, 1 H), 8.72 (d, J=1.8 Hz, 1 H), 8.62 (d, J=1.9 Hz, 1 H), 8.07 (dd, J=1.9, 8.9 Hz, 1 H), 7.89 (d, J=8.9 Hz, 1 H), 7.75 (s, 1 H), 7.60 (dt, J=6.2, 8.1 Hz, 1 H), 7.51-7.44 (m, 2 H), 7.39 (s, 1 H), 7.37-7.30 (m, 1 H), 6.51 (d, J=1.8 Hz, 1 H), 3.77 (s, 3 H). m/z (ESI) 535.0 (M+H)⁺. ee=88%. Peak 2: ¹H NMR (400 MHz, DMSO-d₆) δ=12.04 (br. s., 1 H), 9.43 (s, 1 H), 8.72 (d, J=1.8 Hz, 1 H), 8.62 (d, J=1.9 Hz, 1 H), 8.07 (dd, J=1.9, 8.9 Hz, 1 H), 7.89 (d, J=8.9 Hz, 1 H), 7.75 (s, 1 H), 7.60 (dt, J=6.2, 8.1 Hz, 1 H), 7.51-7.44 (m, 2 H), 7.39 (s, 1 H), 7.37-7.30 (m, 1 H), 6.51 (d, J=1.8 Hz, 1 H), 3.77 (s, 3 H). m/z (ESI) 535.0 (M+H)⁺. ee=86%.

Example 336 (Method 82)

3-AMINO-4-(2-CHLORO-3'-FLUORO-5-METHOXY-[1,1'-BIPHENYL]-4-YL)-N-(ISOXAZOL-3-YL)QUINOLINE-7-SULFONAMIDE

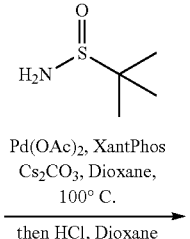

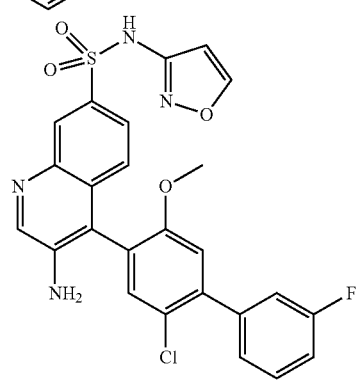

A vial was charged with 3-bromo-4-(2-chloro-3'-fluoro-5-methoxy-[1,1'-biphenyl]-4-yl)-N-(isoxazol-3-yl)quinoline-7-sulfonamide (0.145 g, 0.246 mmol), tert-butylsulfinamide (0.045 g, 0.369 mmol), palladium (ii) acetate (5.53 mg, 0.025 mmol), xantphos (0.028 g, 0.049 mmol), and cesium carbonate (0.160 g, 0.492 mmol). The vial was capped and was evacuated and backfilled with N2 (2×). Dioxane (1.642 ml) was added. The reaction mixture was stirred and heated at 100° C. for 3 hours. The reaction was cooled to RT. HCl (4.0M in dioxane) (0.985 ml, 3.94 mmol) was added and the reaction was stirred for 15 minutes. The reaction was diluted with ethyl acetate and washed with water and 1N HCl. The aqueous layer was extracted with ethyl acetate, and the combined organic layers were dried with sodium sulfate, filtered, and concentrated. The material was purified via column chromatography (RediSep Gold 40 g, gradient elution 10-75% [3:1 EtOAc/EtOH]:Heptane) to afford 3-amino-4-(2-chloro-3'-fluoro-5-methoxy-[1,1'-biphenyl]-4-yl)-N-(isoxazol-3-yl)quinoline-7-sulfonamide (0.041 g, 0.078 mmol, 31.7% yield) as a yellow solid. ¹H NMR (400 MHz, DMSO-d₆) δ=11.60 (br. s., 1 H), 8.78-8.61 (m, 2 H), 8.28 (d, J=1.9 Hz, 1 H), 7.68 (dd, J=2.0, 8.9 Hz, 1 H), 7.63-7.54 (m, 1 H), 7.47-7.20 (m, 6 H), 6.47 (d, J=1.8 Hz, 1 H), 5.83 (s, 2 H), 3.71 (s, 3 H). m/z (ESI) 525.0 (M+H)⁺.

Example 337, 338, 339, & 340 (Method 83)

(M)-4-(2-CHLORO-3'-FLUORO-5-METHOXY-[1,1'-BIPHENYL]-4-YL)-3-HYDROXY-N-(ISOXAZOL-3-YL)QUINOLINE-7-SULFONAMIDE AND (P)-4-(2-CHLORO-3'-FLUORO-5-METHOXY-[1,1'-BIPHENYL]-4-YL)-3-HYDROXY-N-(ISOXAZOL-3-YL)QUINOLINE-7-SULFONAMIDE AND (M)-4-(2-CHLORO-3'-FLUORO-5-METHOXY-[1,1'-BIPHENYL]-4-YL)-N-(ISOXAZOL-3-YL)-3-METHOXYQUINOLINE-7-SULFONAMIDE AND (P)-4-(2-CHLORO-3'-FLUORO-5-METHOXY-[1,1'-BIPHENYL]-4-YL)-N-(ISOXAZOL-3-YL)-3-METHOXYQUINOLINE-7-SULFONAMIDE

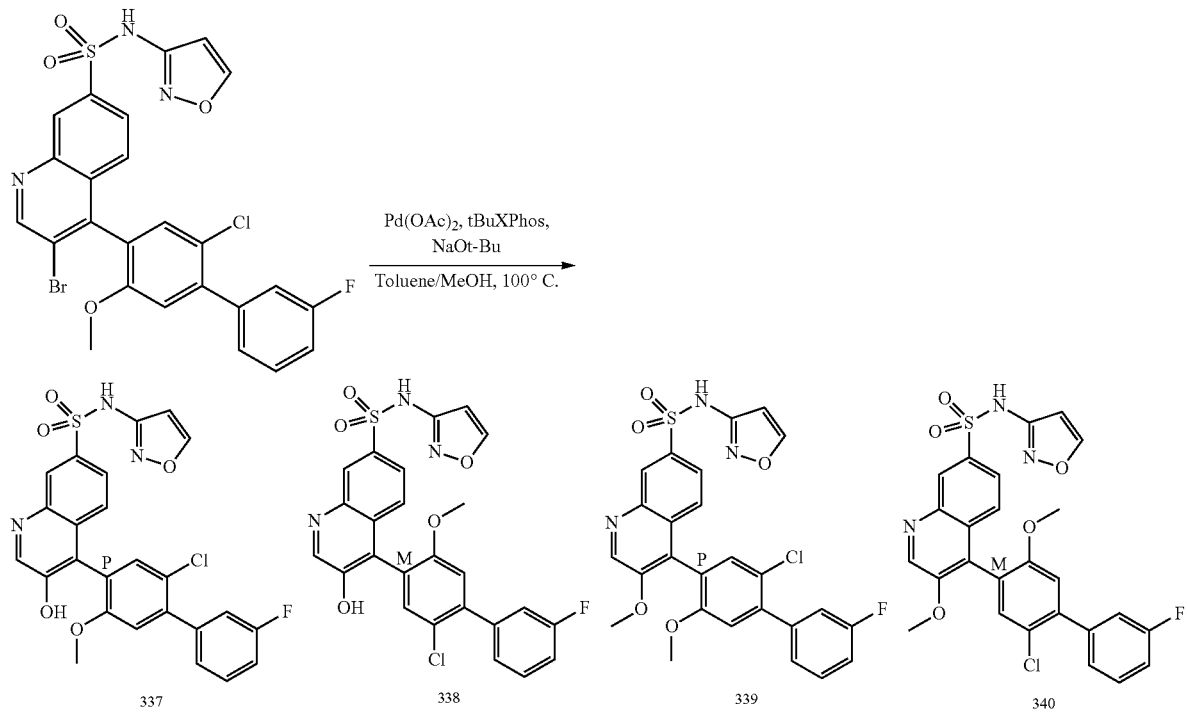

A vial was charged with 3-bromo-4-(2-chloro-3'-fluoro-5-methoxy-[1,1'-biphenyl]-4-yl)-N-(isoxazol-3-yl)quinoline-7-sulfonamide (0.300 g, 0.509 mmol), palladium (ii) acetate (0.011 g, 0.051 mmol), sodium tert-butoxide (0.073 g, 0.764 mmol), and 2-di-tert-butylphosphino-2',4',6'-triisopropylbiphenyl (0.043 g, 0.102 mmol). The vial was capped and was evacuated and backfilled with N$_2$ gas (2×). The solvents methanol (0.749 ml) and toluene (0.749 ml) were added. The reaction mixture was stirred and heated in a heating block at 100° C. for 3 hours. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 10-75% [3:1 EtOAc/EtOH]:Heptane) to afford 4-(2-chloro-3'-fluoro-5-methoxy-[1,1'-biphenyl]-4-yl)-3-hydroxy-N-(isoxazol-3-yl)quinoline-7-sulfonamide (0.068 g, 0.129 mmol, 25.4% yield) as a light yellow solid. This material was purified by chiral SFC on Chiralpak AD-H column (35% MeOH/65% CO$_2$) to afford (P)-4-(2-chloro-3'-fluoro-5-methoxy-[1,1'-biphenyl]-4-yl)-3-hydroxy-N-(isoxazol-3-yl)quinoline-7-sulfonamide as Peak 1 and (M)-4-(2-chloro-3'-fluoro-5-methoxy-[1,1'-biphenyl]-4-yl)-3-hydroxy-N-(isoxazol-3-yl)quinoline-7-sulfonamide as Peak 2, both as off-white solids. Peak 1: $^1$H NMR (400 MHz, DMSO-d$_6$) δ=11.74 (s, 1H), 10.79 (s, 1H), 8.88 (s, 1H), 8.73 (d, J=1.7 Hz, 1H), 8.43 (d, J=1.8 Hz, 1H), 7.82 (dd, J=1.9, 8.9 Hz, 1H), 7.63-7.54 (m, 1H), 7.49 (d, J=8.9 Hz, 1H), 7.44 (t, J=3.7 Hz, 3H), 7.35-7.28 (m, 1H), 7.25 (s, 1H), 6.49 (d, J=1.7 Hz, 1H), 3.70 (s, 3H). m/z (ESI) 526.1 (M+H)$^+$. ee=50%. Peak 2: $^1$H NMR (400 MHz, DMSO-d$_6$) δ=11.74 (s, 1H), 10.79 (s, 1H), 8.88 (s, 1H), 8.73 (d, J=1.7 Hz, 1H), 8.43 (d, J=1.8 Hz, 1H), 7.82 (dd, J=1.9, 8.9 Hz, 1H), 7.63-7.54 (m, 1H), 7.49 (d, J=8.9 Hz, 1H), 7.44 (t, J=3.7 Hz, 3H), 7.35-7.28 (m, 1H), 7.25 (s, 1H), 6.49 (d, J=1.7 Hz, 1H), 3.70 (s, 3H). m/z (ESI) 526.1 (M+H)$^+$. ee=30%.

Also isolated 4-(2-chloro-3'-fluoro-5-methoxy-[1,1'-biphenyl]-4-yl)-N-(isoxazol-3-yl)-3-methoxyquinoline-7-sulfonamide. This material was purified by chiral SFC on Chiralpak AD-H column (45% MeOH/55% CO$_2$) to afford (P)-4-(2-chloro-3'-fluoro-5-methoxy-[1,1'-biphenyl]-4-yl)-N-(isoxazol-3-yl)-3-methoxyquinoline-7-sulfonamide as Peak 1 and (M)-4-(2-chloro-3'-fluoro-5-methoxy-[1,1'-biphenyl]-4-yl)-N-(isoxazol-3-yl)-3-methoxyquinoline-7-sulfonamide as Peak 2, both as off-white solids. Peak 1: $^1$H NMR (400 MHz, DMSO-d$_6$) δ=11.80 (s, 1H), 9.21 (s, 1H), 8.73 (d, J=1.8 Hz, 1H), 8.50 (d, J=1.8 Hz, 1H), 7.86 (dd, J=2.0, 8.9 Hz, 1H), 7.62-7.53 (m, 2H), 7.49-7.43 (m, 3H), 7.35-7.28 (m, 1H), 7.26 (s, 1H), 6.50 (d, J=1.8 Hz, 1H), 4.04 (s, 3H), 3.69 (s, 3H). m/z (ESI) 540.2 (M+H)$^+$. ee=80%. Peak 2: $^1$H NMR (400 MHz, DMSO-d$_6$) δ=11.80 (s, 1H), 9.21 (s, 1H), 8.73 (d, J=1.8 Hz, 1H), 8.50 (d, J=1.8 Hz, 1H), 7.86 (dd, J=2.0, 8.9 Hz, 1H), 7.62-7.53 (m, 2H), 7.49-7.43 (m, 3H), 7.35-7.28 (m, 1H), 7.26 (s, 1H), 6.50 (d, J=1.8 Hz, 1H), 4.04 (s, 3H), 3.69 (s, 3H). m/z (ESI) 540.2 (M+H)$^+$. ee=82%.

Example 343 (Method 87)

4-(3'-CHLORO-2-FLUORO-5-METHOXY-[1,1'-BIPHENYL]-4-YL)-N-(ISOXAZOL-3-YL)-1-OXO-1,2-DIHYDROISOQUINOLINE-7-SULFONAMIDE

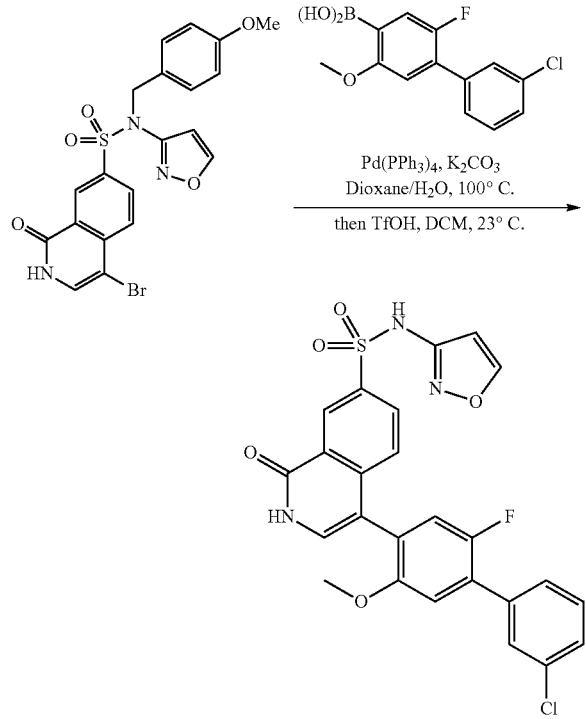

A microwave vial was charged with 4-bromo-N-(isoxazol-3-yl)-N-(4-methoxybenzyl)-1-oxo-1,2-dihydroisoquinoline-7-sulfonamide (0.200 g, 0.408 mmol), (3'-chloro-2-fluoro-5-methoxy-[1,1'-biphenyl]-4-yl)boronic acid (0.172 g, 0.612 mmol), Pd(Ph3P)4 (0.047 g, 0.041 mmol), and potassium carbonate (0.169 g, 1.224 mmol). The vial was flushed with Ar (g), then dioxane (1.530 mL) and water (0.510 mL) were added. The reaction was microwaved at 100° C. for 90 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 4-(3'-chloro-2-fluoro-5-methoxy-[1,1'-biphenyl]-4-yl)-N-(isoxazol-3-yl)-N-(4-methoxybenzyl)-1-oxo-1,2-dihydroisoquinoline-7-sulfonamide (0.183 g, 0.283 mmol, 69.4% yield). The material was dissolved in DCM and trifluoromethanesulfonic acid (0.1 mL, 0.666 mmol) was added. The reaction was stirred for 30 minutes at RT. The reaction was concentrated and purified via column chromatography (RediSep Gold 12 g, gradient elution 10-75% [3:1 EtOAc/EtOH]:Heptane) to afford 4-(3'-chloro-2-fluoro-5-methoxy-[1,1'-biphenyl]-4-yl)-N-(isoxazol-3-yl)-1-oxo-1,2-dihydroisoquinoline-7-sulfonamide (0.058 g, 0.110 mmol, 27.0% yield) as a white solid. $^1$H NMR (400 MHz, DMSO-$d_6$) δ=11.89 (d, J=6.0 Hz, 1 H), 11.75 (s, 1 H), 8.73 (dd, J=1.9, 10.4 Hz, 2 H), 8.04 (dd, J=2.2, 8.7 Hz, 1 H), 7.73 (d, J=1.3 Hz, 1 H), 7.67-7.61 (m, 1 H), 7.60-7.49 (m, 2 H), 7.39-7.30 (m, 3 H), 7.27 (d, J=6.7 Hz, 1 H), 6.44 (d, J=1.8 Hz, 1 H), 3.74 (s, 3 H). m/z (ESI) 526.1 (M+H)$^+$.

Example 344 (Method 88)

4-(3'-CHLORO-2-FLUORO-5-METHOXY-[1,1'-BIPHENYL]-4-YL)-N-(ISOXAZOL-3-YL)-2-METHYL-1-OXO-1,2-DIHYDROISOQUINOLINE-7-SULFONAMIDE

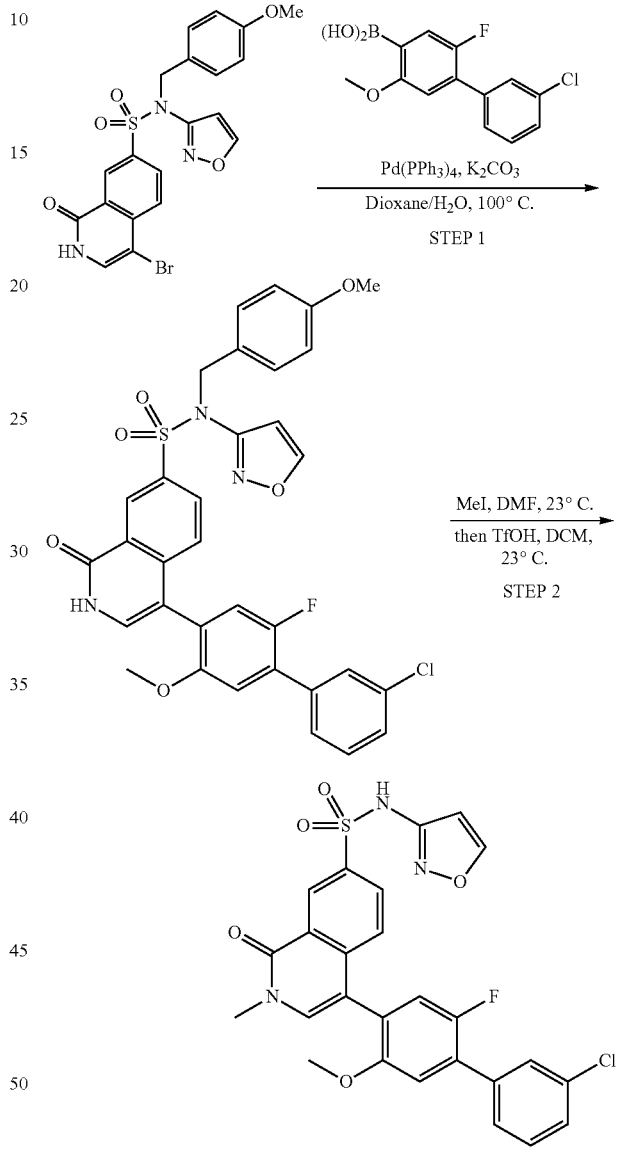

STEP 1: 4-(3'-CHLORO-2-FLUORO-5-METHOXY-[1,1'-BIPHENYL]-4-YL)-N-(ISOXAZOL-3-YL)-N-(4-METHOXYBENZYL)-1-OXO-1,2-DIHYDROISOQUINOLINE-7-SULFONAMIDE

A microwave vial was charged with 4-bromo-N-(isoxazol-3-yl)-N-(4-methoxybenzyl)-1-oxo-1,2-dihydroisoquinoline-7-sulfonamide (0.200 g, 0.408 mmol), (3'-chloro-2-fluoro-5-methoxy-[1,1'-biphenyl]-4-yl)boronic acid (0.172 g, 0.612 mmol), Pd(Ph$_3$P)$_4$ (0.047 g, 0.041 mmol), and potassium carbonate (0.169 g, 1.224 mmol). The vial was flushed with Ar (g), then dioxane (1.530 mL) and water (0.510 mL) were added. The reaction was microwaved at 100° C. for 90 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 4-(3'-chloro-2-fluoro-5-methoxy-[1,1'-biphenyl]-4-yl)-N-(isoxazol-3-yl)-N-(4-methoxybenzyl)-1-oxo-1,2-dihydroisoquinoline-7-sulfonamide (0.183 g, 0.283 mmol, 69.4% yield). m/z (ESI) 646.1 (M+H)$^+$.

STEP 2: 4-(3'-CHLORO-2-FLUORO-5-METHOXY-[1,1'-BIPHENYL]-4-YL)-N-(ISOXAZOL-3-YL)-2-METHYL-1-OXO-1,2-DIHYDROISOQUINOLINE-7-SULFONAMIDE

A vial was charged with 4-(3'-chloro-2-fluoro-5-methoxy-[1,1'-biphenyl]-4-yl)-N-(isoxazol-3-yl)-N-(4-methoxybenzyl)-1-oxo-1,2-dihydroisoquinoline-7-sulfonamide (0.100 g, 0.155 mmol), potassium carbonate (0.043 g, 0.310 mmol), and DMF (1.548 ml). Iodomethane (0.015 ml, 0.232 mmol) was added and the reaction was stirred for three hours at room temperature. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 4-(3'-chloro-2-fluoro-5-methoxy-[1,1'-biphenyl]-4-yl)-N-(isoxazol-3-yl)-N-(4-methoxybenzyl)-2-methyl-1-oxo-1,2-dihydroisoquinoline-7-sulfonamide. The material was dissolved in DCM and triflic acid (0.1 ml, 1.126 mmol) was added. The reaction was stirred for one hour at room temperature. The material was concentrated and the material was purified via column chromatography (RediSep Gold 12 g, gradient elution 10-75% [3:1 EtOAc/EtOH]:Heptane) to afford a brown oil. The material was triturated in methanol, filtered, and vacuum dried to afford 4-(3'-chloro-2-fluoro-5-methoxy-[1,1'-biphenyl]-4-yl)-N-(isoxazol-3-yl)-2-methyl-1-oxo-1,2-dihydroisoquinoline-7-sulfonamide (0.050 g, 0.093 mmol, 59.8% yield) as an off-white solid. $^1$H NMR (400 MHz, DMSO-d$_6$) δ=11.75 (s, 1 H), 8.75 (dd, J=2.0, 3.5 Hz, 2 H), 8.05 (dd, J=2.1, 8.7 Hz, 1 H), 7.78-7.71 (m, 2 H), 7.65 (dd, J=1.6, 7.4 Hz, 1 H), 7.60-7.51 (m, 2 H), 7.39 (d, J=8.8 Hz, 1 H), 7.33 (d, J=10.7 Hz, 1 H), 7.29 (d, J=6.7 Hz, 1 H), 6.45 (d, J=1.9 Hz, 1 H), 3.75 (s, 3 H), 3.58 (s, 3 H). m/z (ESI) 540.1 (M+H)$^+$.

Example 345 (Method 89)

4-(3'-CHLORO-4'-FLUORO-5-METHOXY-2-METHYL-[1,1'-BIPHENYL]-4-YL)-N-(PYRIMIDIN-2-YL)QUINAZOLINE-7-SULFONAMIDE

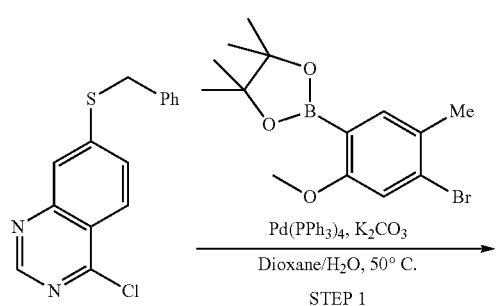

STEP 1: 7-(BENZYLTHIO)-4-(4-BROMO-2-METHOXY-5-METHYLPHENYL)QUINAZOLINE

A vial was charged with 7-(benzylthio)-4-chloroquinazoline (0.606 g, 2.113 mmol), 2-(4-bromo-2-methoxy-5-methylphenyl)-4,4,5,5-tetramethyl-1,3,2-dioxaborolane (0.691 g, 2.113 mmol), tetrakis(triphenylphosphine)palladium(0)

(0.244 g, 0.211 mmol), and potassium carbonate (1.460 g, 10.57 mmol). Dioxane (7.92 ml) and water (2.64 ml) were added, the vial was flushed with argon and sealed, and heated at 50° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-50% EtOAc: Heptane) to afford 7-(benzylthio)-4-(4-bromo-2-methoxy-5-methylphenyl)quinazoline (0.699 g, 1.549 mmol, 73.3% yield) as a yellow solid. m/z (ESI) 453.0 (M+H)+.

STEP 2: PERFLUOROPHENYL 4-(4-BROMO-2-METHOXY-5-METHYLPHENYL)QUINAZO-LINE-7-SULFONATE

A RBF was charged with 7-(benzylthio)-4-(4-bromo-2-methoxy-5-methylphenyl)quinazoline (0.699 g, 1.549 mmol), DCM (14.57 ml), acetic acid (0.547 ml), and water (0.364 ml) to give a thin suspension. The flask was cooled in an ice-bath for 10 min, then 1,3-dichloro-5,5-dimethyl-imidazolidine-2,4-dione (0.763 g, 3.87 mmol) was added in one portion, leading to a solution. The reaction was stirred for 15 minutes. 2,3,4,5,6-Pentafluorophenol (0.324 ml, 3.10 mmol) was added followed by dropwise addition of triethylamine (0.540 ml, 3.87 mmol). The reaction was stirred for 30 minutes. The reaction was concentrated and purified via column chromatography (RediSep Gold 40 g, gradient elution 0-50% EtOAc:Heptane) to afford perfluorophenyl 4-(4-bromo-2-methoxy-5-methylphenyl)quinazoline-7-sulfonate (0.783 g, 1.361 mmol, 88% yield) as an off-white solid. m/z (ESI) 575.0 (M+H)+.

STEP 3: 4-(4-BROMO-2-METHOXY-5-METHYL-PHENYL)-N-(PYRIMIDIN-2-YL)QUINAZOLINE-7-SULFONAMIDE

A RBF was charged with perfluorophenyl 4-(4-bromo-2-methoxy-5-methylphenyl)quinazoline-7-sulfonate (0.783 g, 1.361 mmol), pyrimidin-2-amine (0.142 g, 1.497 mmol), and THF (6.81 ml) to give a clear solution. The flask was cooled to 0° C. for 10 min, then lithium bis(trimethylsilyl) amide (1M in THF) (2.99 ml, 2.99 mmol) was added dropwise. The reaction was stirred for 30 minutes. The reaction was diluted with 1N aq. HCl and EtOAc. The aqueous layer was extracted with ethyl acetate, and the combined organic layers were washed with 1N aq. HCl, washed with brine, dried with sodium sulfate, filtered, and concentrated to afford crude 4-(4-bromo-2-methoxy-5-methylphenyl)-N-(pyrimidin-2-yl)quinazoline-7-sulfonamide (0.680 g, 1.398 mmol, 100% yield) as a yellow solid. m/z (ESI) 488.0 (M+H)+.

STEP 4: 4-(3'-CHLORO-4'-FLUORO-5-METHOXY-2-METHYL-[1,1'-BIPHENYL]-4-YL)-N-(PYRIMIDIN-2-YL)QUINAZOLINE-7-SULFO-NAMIDE

A vial was charged with 4-(4-bromo-2-methoxy-5-methylphenyl)-N-(pyrimidin-2-yl)quinazoline-7-sulfonamide (0.100 g, 0.206 mmol), (3-chloro-4-fluorophenyl)boronic acid (0.054 g, 0.308 mmol), tetrakis(triphenylphosphine)palladium(0) (0.024 g, 0.021 mmol), and potassium carbonate (0.142 g, 1.028 mmol). Dioxane (1.028 ml) and water (0.343 ml) were added and the reaction was stirred at 90° C. for 30 minutes. The reaction was diluted with DMSO, filtered through a syringe filter. The resulting solution was purified via reverse phase HPLC (Xbridge 19×100 mm, 10 um, 40 ml/min, 25-85% 0.1% TFA in Acetonitrile) to afford 4-(3'-chloro-4'-fluoro-5-methoxy-2-methyl-[1,1'-biphenyl]-4-yl)-N-(pyrimidin-2-yl)quinazoline-7-sulfonamide (0.044 g, 0.082 mmol, 39.9% yield) as a white solid. $^1$H NMR (500 MHz, DMSO-$d_6$) δ=2.23 (s, 3 H) 3.54 (br. s., 1 H) 3.69 (s, 4 H) 6.88 (br. s., 1 H) 7.11 (s, 1 H) 7.37 (s, 1 H) 7.47-7.57 (m, 2 H) 7.73 (dd, J=7.15, 1.78 Hz, 1 H) 7.86 (d, J=8.76 Hz, 1 H) 8.11 (dd, J=8.76, 1.53 Hz, 1 H) 8.41 (d, J=4.75 Hz, 2 H) 8.53 (s, 1 H) 9.45 (s, 1 H). m/z (ESI) 536.1 (M+H)+.

Example 352 (Method 93)

1-(2-CHLORO-3'-FLUORO-5-METHOXY-[1,1'-BIPHENYL]-4-YL)-2-IMINO-N-(ISOXAZOL-3-YL)-1,2-DIHYDROQUINOLINE-6-SULFONA-MIDE

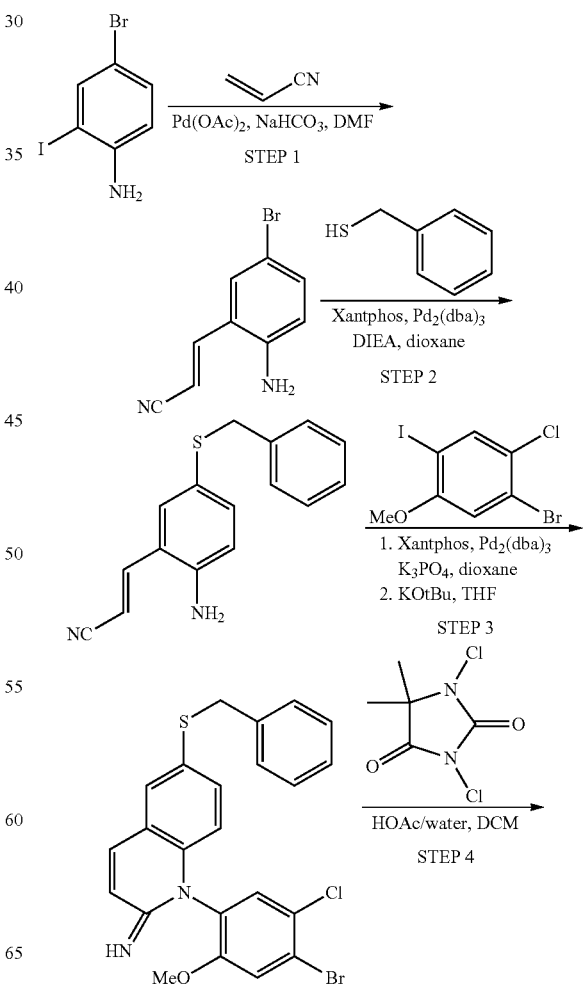

-continued

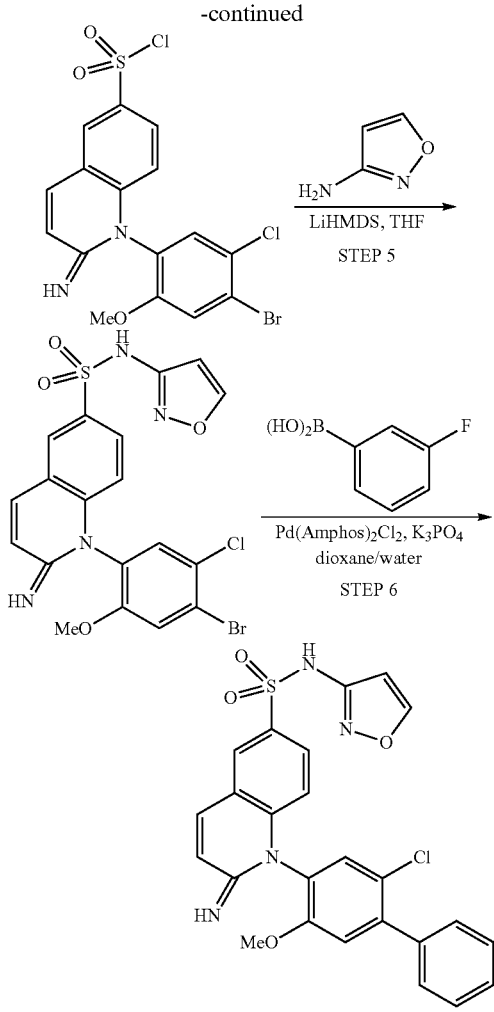

STEP 1: (E)-3-(2-AMINO-5-BROMOPHENYL)ACRYLONITRILE

A solution of acrylonitrile (1.11 mL, 16.8 mmol), Pd(OAc)$_2$ (0.188 g, 0.84 mmol), 4-bromo-2-iodoaniline (5.000 g, 16.78 mmol), and NaHCO$_3$ (2.82 g, 33.6 mmol) in 8 mL DMF was heated to 90° C. for 6 hours. The reaction mixture was poured into water and extracted with DCM. The organics were dried over MgSO$_4$ and concentrated. Purification of the crude residue by silica gel column chromatography gave (E)-3-(2-amino-5-bromophenyl)acrylonitrile (2.26 g, 10.13 mmol, 60.4% yield) as a yellow solid with minor impurities. m/z (ESI) 223.2 (M+H)$^+$.

STEP 2: (E)-3-(2-AMINO-5-(BENZYLTHIO)PHENYL)ACRYLONITRILE

A solution of (E)-3-(2-amino-5-bromophenyl)acrylonitrile (2.26 g, 10.13 mmol), xantphos (0.879 g, 1.520 mmol), Pd$_2$(dba)$_3$ (0.464 g, 0.507 mmol), and n,n-diisopropylethylamine (5.31 ml, 30.4 mmol) in 20 mL dioxane was heated to 90° C. then was treated with benzyl mercaptan (1.917 ml, 16.21 mmol). After stirring for 6 hours, the reaction mixture was poured into water and was extracted with DCM. The organics were dried over MgSO$_4$ and concentrated. Purification of the crude residue by silica gel column chromatography (0-100% EtOAc/heptane) gave (E)-3-(2-amino-5-(benzylthio)phenyl)acrylonitrile (2.20 g, 8.26 mmol, 82% yield) as a yellow solid. m/z (ESI) 267.1 (M+H)$^+$.

STEP 3: 6-(BENZYLTHIO)-1-(4-BROMO-5-CHLORO-2-METHOXYPHENYL) QUINOLIN-2(1H)-IMINE

A solution of xantphos (0.391 g, 0.676 mmol), 1-bromo-2-chloro-4-iodo-5-methoxybenzene (1.721 g, 4.96 mmol), (E)-3-(2-amino-5-(benzylthio)phenyl)acrylonitrile (1.200 g, 4.51 mmol), Pd$_2$(dba)$_3$ (0.206 g, 0.225 mmol), and potassium phosphate (2.87 g, 13.52 mmol) in 10 mL dioxane was heated to 90° C. for 3 hours. Potassium tert-butoxide 1N in THF (4.51 ml, 4.51 mmol) was added, and the reaction mixture was heated to 100° C. overnight. The reaction mixture was filtered through a plug of celite and was concentrated. The crude residue was used in the next step without purification. m/z (ESI) 487.0 (M+H)$^+$.

STEP 4: 1-(4-BROMO-5-CHLORO-2-METHOXYPHENYL)-2-IMINO-1,2-DIHYDROQUINOLINE-6-SULFONYL CHLORIDE

The crude residue from step 3 was dissolved in 20 mL DCM 4 mL (1.5:1 HOAc/water) and was treated with 1,3-dichloro-5,5-dimethylimidazolidine-2,4-dione (1.775 g, 9.01 mmol). After stirring for 30 minutes, the reaction mixture was diluted with DCM, dried over MgSO4 and concentrated. Purification of the crude residue by silica gel column chromatography (0-90% EtOAc/heptane 10% MeOH) gave 1-(4-bromo-5-chloro-2-methoxyphenyl)-2-imino-1,2-dihydroquinoline-6-sulfonyl chloride (0.450 g, 0.974 mmol, 21.61% yield) with minor impurities. m/z (ESI) 462.9 (M+H)$^+$.

STEP 5: 1-(4-BROMO-5-CHLORO-2-METHOXYPHENYL)-2-IMINO-N-(ISOXAZOL-3-YL)-1,2-DIHYDROQUINOLINE-6-SULFONAMIDE

A solution of 3-aminoisoxazole (0.360 ml, 4.87 mmol) and 1-(4-bromo-5-chloro-2-methoxyphenyl)-2-imino-1,2-dihydroquinoline-6-sulfonyl chloride (0.450 g, 0.974 mmol) in 10 mL THF, was cooled to 0° C. LHMDS 1N in THF (4.87 ml, 4.87 mmol) was added, and the cooling bath was removed. After stirring for an additional hour, the reaction mixture was treated with TFA (0.375 mL, 4.87 mmol) and was concentrated. Purification of the crude residue by reverse phase column chromatography [Redisep Gold C18, 10-100% (0.1% NH4OH in MeOH)/(0.1% NH4OH in water)] gave 1-(4-bromo-5-chloro-2-methoxyphenyl)-2-imino-N-(isoxazol-3-yl)-1,2-dihydroquinoline-6-sulfonamide (0.100 g, 0.196 mmol, 20.15% yield) with impurities. m/z (ESI) 511.0 (M+H)$^+$.

STEP 6: 1-(2-CHLORO-3'-FLUORO-5-METHOXY-[1,1'-BIPHENYL]-4-YL)-2-IMINO-N-(ISOXAZOL-3-YL)-1,2-DIHYDROQUINOLINE-6-SULFONAMIDE

A microwave vial charged with Amphos (0.014 g, 0.020 mmol), (3-fluorophenyl)boronic acid (0.034 g, 0.245 mmol), 1-(4-bromo-5-chloro-2-methoxyphenyl)-2-imino-N-(isoxazol-3-yl)-1,2-dihydroquinoline-6-sulfonamide (0.100 g, 0.196 mmol), potassium phosphate (0.167 g, 0.785 mmol), 1.5 ml dioxane and 0.5 ml water was heated to 150° C. in a Biotage initiator microwave reactor for 45 minutes. The organics were separated, treated with TFA (0.060 ml, 0.785 mmol), and were concentrated. Purification of the crude residue by reverse phase column chromatography [Puriflash C18, 10-100% (0.1% NH4OH in MeOH)/(0.1% NH4OH in water)] gave 1-(2-chloro-3'-fluoro-5-methoxy-[1,1'-biphenyl]-4-yl)-2-imino-N-(isoxazol-3-yl)-1,2-dihydroquinoline-6-sulfonamide (0.004 g, 7.62 µmol, 3.88% yield). m/z (ESI) 525.1 (M+H)+. 1H NMR (ACETONITRILE-d3) δ: 8.30-8.36 (m, 1H), 8.19-8.26 (m, 1H), 7.95-8.02 (m, 2H), 7.51-7.62 (m, 2H), 7.31-7.45 (m, 3H), 7.21-7.30 (m, 1H), 7.10-7.17 (m, 1H), 6.88-6.96 (m, 1H), 6.11-6.18 (m, 1H), 3.73-3.78 (m, 3H).

Example 361 (Method 100)

4-(2-CHLORO-3'-FLUORO-5-METHOXY-4-BIPHENYLYL)-N-3-ISOTHIAZOLYL-7-QUINAZOLINE SULFONAMIDE

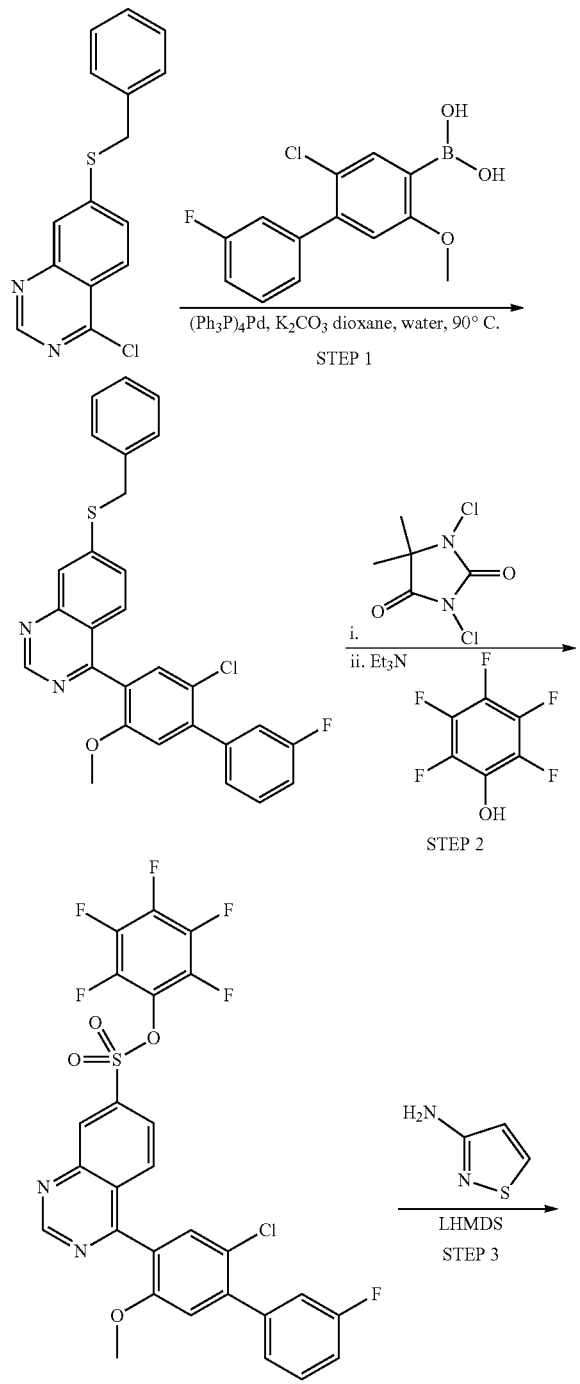

-continued

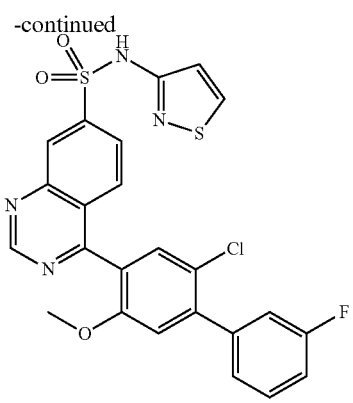

STEP 1: 7-(BENZYLTHIO)-4-(2-CHLORO-3'-FLUORO-5-METHOXY-[1,1'-BIPHENYL]-4-YL)QUINAZOLINE

A microwave vial was charged with 7-(benzylthio)-4-chloroquinazoline (0.372 g, 1.298 mmol), (2-chloro-3'-fluoro-5-methoxy-[1,1'-biphenyl]-4-yl)boronic acid (0.364 g, 1.298 mmol), tetrakis(triphenylphosphine)palladium (0.150 g, 0.130 mmol), and potassium carbonate (0.897 g, 6.49 mmol). The vial was sealed with a septum cap and dioxane (3.24 ml) and water (1.081 ml) were added via syringe and the vial was flushed with argon. The mixture was microwaved at 90° C. for 30 minutes. The mixture was diluted with ethyl acetate (20 mL) and washed with water (20 mL). The aqueous layer was extracted with ethyl acetate (10 mL), and the combined organic layers were dried with sodium sulfate, filtered, and concentrated. The material was purified via column chromatography (RediSep Gold 12 g, gradient elution 0-75% EtOAc: Heptane) to afford 7-(benzylthio)-4-(2-chloro-3'-fluoro-5-methoxy-[1,1'-biphenyl]-4-yl)quinazoline (522.4 mg, 83 yield) as a yellow solid.

STEP 2: PERFLUOROPHENYL 4-(2-CHLORO-3'-FLUORO-5-METHOXY-[1,1'-BIPHENYL]-4-YL)QUINAZOLINE-7-SULFONATE

A flask was charged with 7-(benzylthio)-4-(2-chloro-3'-fluoro-5-methoxy-[1,1'-biphenyl]-4-yl)quinazoline (0.52 g, 1.133 mmol), DCM (10.8 ml), Acetic Acid (0.355 ml), and Water (0.27 ml) to give yellow solution. The flask was cooled in an ice-bath for 10 min, then 1,3-dichloro-5,5-dimethylimidazolidine-2,4-dione (0.558 g, 2.83 mmol) was added in one portion, yielding an orange solution, which was maintained at 0° C. for 20 minutes. To the solution was added 2,3,4,5,6-pentafluorophenol (0.417 ml, 2.267 mmol), followed by dropwise addition of triethylamine (0.287 mg, 2.83 mmol). The resulting solution was maintained at 0° C. for 20 min at which time the solution was concentrated and purified via column chromatography (RediSep Gold 40 g, gradient elution 0-50% EtOAc:Heptane) to afford perfluorophenyl 4-(2-chloro-3'-fluoro-5-methoxy-[1,1'-biphenyl]-4-yl)quinazoline-7-sulfonate (0.418 g, 60.4% yield) as a light yellow solid.

STEP 3: 4-(2-CHLORO-3'-FLUORO-5-METHOXY-4-BIPHENYLYL)-N-3-ISOTHIAZ-OLYL-7-QUINAZOLINESULFONAMIDE

A flask was charged with perfluorophenyl 4-(2-chloro-3'-fluoro-5-methoxy-[1,1'-biphenyl]-4-yl)quinazoline-7-sulfonate (79.1 mg, 0.129 mmol), isothiazol-3-amine (16.86 mg, 0.168 mmol, Small Molecules) and THF (1.295 mL) to give a cloudy mixture. The flask was cooled in an ice-water bath for 10 min, then lithium bis(trimethylsilyl)amide (1M in THF) (0.272 mL, 0.272 mmol) was added dropwise to generate a yellow homogeneous solution, which then became cloudy. The mixture was diluted with EtOAc (20 mL), washed with 1N aq. HCl(3×10 mL), dried over sodium sulfate, filtered, and concentrated. The residue was purified by HPLC purification with 0.1% 1220H in ACN and water as mobile phase to give 4-(2-chloro-3'-fluoro-5-methoxy-[1,1'-biphenyl]-4-yl)-N-(isothiazol-3-yl)quinazoline-7-sulfonamide as a white solid. 1H NMR (500 MHz, DMSO-d6) δ 11.55 (br. s., 1H), 9.51 (s, 1H), 8.55 (d, J=1.23 Hz, 1H), 8.18 (d, J=2.94 Hz, 1H), 8.09 (dd, J=1.58, 8.79 Hz, 1H), 7.97 (d, J=8.82 Hz, 1H), 7.64-7.76 (m, 1H), 7.55-7.63 (m, 1H), 7.43 (d, J=7.75 Hz, 2H), 7.28-7.37 (m, 2H), 7.19 (dd, J=3.55, 9.00 Hz, 1H), 3.73 (s, 3H). m/z (ESI) 527.0 (M+H)+.

Example 362 (Method 101)

1-(3'-(DIFLUOROMETHYL)-2,5'-DIFLUORO-5-METHOXY-4-BIPHENYLYL)-N-3-ISOX-AZOLYL-6-ISOQUINOLINESULFONAMIDE

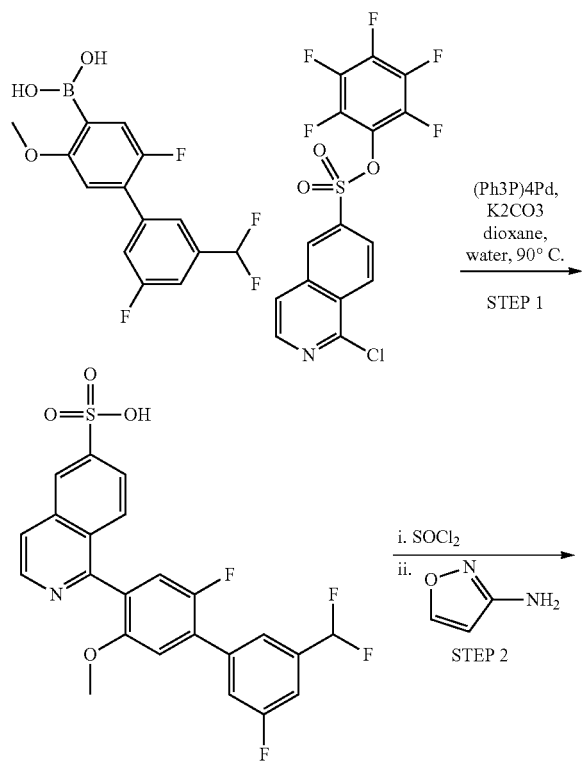

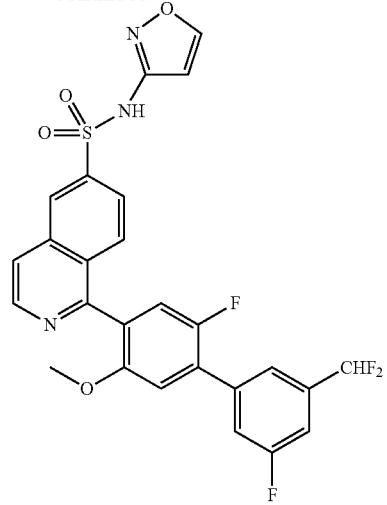

STEP 1: 1-(3'-(DIFLUOROMETHYL)-2,5'-DIFLUORO-5-METHOXY-[1,1'-BIPHENYL]-4-YL)ISOQUINOLINE-6-SULFONIC ACID

A RBF was charged with (3'-(difluoromethyl)-2,5'-difluoro-5-methoxy-[1,1'-biphenyl]-4-yl)boronic acid (111 mg, 0.353 mmol), perfluorophenyl 1-chloroisoquinoline-6-sulfonate (145 mg, 0.353 mmol), potassium carbonate (195 mg, 1.414 mmol) and Pd(Ph3P)4 (40.8 mg, 0.035 mmol). The flask was flushed with Ar (g), then Dioxane (1325 µl) and Water (442 µl) were added in sequence. The flask was fitted with a reflux condenser and heated at 60° C. for 2 h, then at 75° C. for 2 h. The mixture was cooled and diluted with EtOAc (10 mL). The layers were separated, and the organic layer was dried over sodium sulfate, filtered, and concentrated. The residue was purified by chromatography on silica gel (12-g Redi-Sep Gold column, 76/24/2 EtOAc/EtOH/AcOH gave 1-(3'-(difluoromethyl)-2,5'-difluoro-5-methoxy-[1,1'-biphenyl]-4-yl)isoquinoline-6-sulfonic acid (56 mg, 0.117 mmol, 33.2% yield). m/z (ESI) 478.1 (M+H)+.

STEP 2: 1-(3'-(DIFLUOROMETHYL)-2,5'-DIFLUORO-5-METHOXY-4-BIPHENYLYL)-N-3-ISOXAZOLYL-6-ISOQUINOLINESULFONA-MIDE

To a RBF was added 1-(3'-(difluoromethyl)-2,5'-difluoro-5-methoxy-[1,1'-biphenyl]-4-yl)isoquinoline-6-sulfonic acid (56 mg, 0.117 mmol) and thionyl chloride (0.856 mL, 11.73 mmol). To the solution was added dimethylformamide (1.816 µl, 0.023 mmol) to give a yellow solution and stirred for 5 min until formation of sulfonyl chloride (1-(3'-(difluoromethyl)-2,5'-difluoro-5-methoxy-[1,1'-biphenyl]-4-yl)isoquinoline-6-sulfonyl chloride). m/z (ESI) 495.9 (M+H)+. The solvent was evaporated in vacuo, azeotroping with toluene (2×1 ml) to yield a yellow solid. To the solid was added DCM (1.173 mL). The cloudy mixture was cooled to 0° C. To the mixture was added 3-aminoisoxazole (0.01733 mL, 0.235 mmol) and triethylamine (0.049 mL, 0.352 mmol) after 20 min, additional 3-aminoisoxazole (0.05 mL) and pyridine (0.2 mL) were added. The mixture was stirred at rt for 18 h. HCl (1M, aq. 4 mL) was added and the mixture was extracted with EtOAc (10 mL) and DCM (10 mL). The combined organic phases were concentrated and the residue was taken up in minimal MeOH/DMSO and purified by preparative HPLC (Gilson, Phenomenex Luna column, 5 micron, C18(2), 100 Å, 150×30 mm 20-90% $CH_3CN:H_2O$ (1% TFA modifier) over 15 min) The clean fractions were combined and concentrated to afford 1-(3'-(difluoromethyl)-2,5'-difluoro-5-methoxy-[1,1'-biphenyl]-4-yl)-N-(isoxazol-3-yl)isoquinoline-6-sulfonamide (18 mg, 0.033 mmol, 28.2% yield) as a yellow amorphous solid. $^1$H NMR (500 MHz, DMSO-$d_6$) δ 11.90 (br. s., 1H), 8.63-8.85 (m, 2H), 8.13-8.24 (m, 1H), 7.85-8.02 (m, 2H), 7.74-8.05 (m, 3H), 7.56 (d, J=8.92 Hz, 1H), 7.37-7.48 (m, 1H), 7.01-7.33 (m, 1H), 6.50 (d, J=1.71 Hz, 1H), 6.38-6.61 (m, 1H), 3.73 (s, 3H). m/z (ESI) 544.2 (M+H)$^+$.

Example 373 (Method 107)

1-(2-CYANO-5-METHOXY-3'-(TRIFLUOROM-ETHYL)-4-BIPHENYLYL)-N-2-PYRIMIDINYL-6-ISOQUINOLINESULFONAMIDE

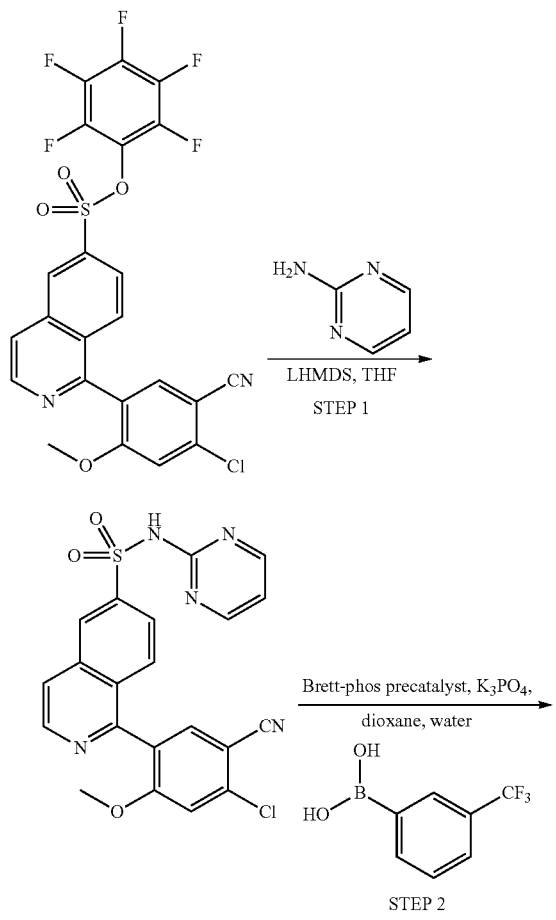

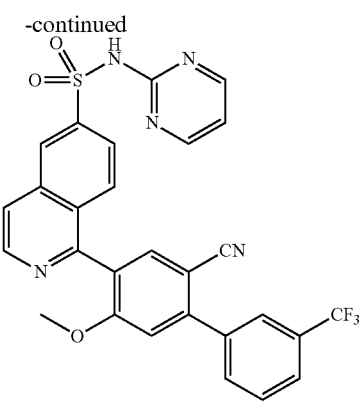

STEP 1: 1-(4-CHLORO-5-CYANO-2-METHOXY-PHENYL)-N-(PYRIMIDIN-2-YL)ISOQUINO-LINE-6-SULFONAMIDE

A RBF was charged with perfluorophenyl 1-(4-chloro-5-cyano-2-methoxyphenyl)isoquinoline-6-sulfonate (144 mg, 0.266 mmol), pyrimidin-2-amine (27.9 mg, 0.293 mmol), and THF (1.414 mL) to give a clear, yellow solution. The flask was cooled to −78° C. for 10 min, then a THF solution of lithium bis(trimethylsilyl)amide (0.559 mL, 0.559 mmol, 1M) was added dropwise to give a clear yellow solution. The solution was warmed to 0° C. and maintained for 30 min. The mixture was diluted with 1 N aq. HCl (5 mL) and EtOAc (10 mL). The layers were separated, and the aq. layer was diluted with brine (10 mL) and extracted with EtOAc (3×10 mL) and DCM (1×10 mL). The combined organic extracts were concentrated and triturated with MeOH (3×5 mL) to give 1-(4-chloro-5-cyano-2-methoxyphenyl)-N-(pyrimidin-2-yl)isoquinoline-6-sulfonamide (92.1 mg, 0.204 mmol) as a white solid. m/z (ESI) 452.1 (M+H)$^+$.

STEP 2: 1-(2-CYANO-5-METHOXY-3'-(TRIF-LUOROMETHYL)-[1,1'-BIPHENYL]-4-YL)-N-(PYRIMIDIN-2-YL)ISOQUINOLINE-6-SULFO-NAMIDE

A vial was charged with 3-(trifluoromethyl)phenylboronic acid (97 mg, 0.510 mmol), chloro(2-dicyclohexylphos-phino-2',6'-dimethoxy-1,1'-biphenyl)[2-(2-aminoethylphe-nyl)]palladium(ii) dichloromethane (7.72 mg, 10.19 μmol), potassium phosphate (216 mg, 1.019 mmol), dicyclohexyl (2',6'-dimethoxy-[1,1'-biphenyl]-2-yl)phosphine (4.18 mg, 10.19 μmol), 1-(4-chloro-5-cyano-2-methoxyphenyl)-N-(pyrimidin-2-yl)isoquinoline-6-sulfonamide (92.1 mg, 0.204 mmol), 1,4-dioxane (0.926 mL), water (0.093 mL). The vial was flushed with $N_2$ (g), then sealed and heated in a Biotage Initiator microwave reactor for 1 h at 120° C. The mixture was extracted with EtOAc (3×), and the combined organic extracts were concentrated. The residue was purified by reverse phase HPLC using acetonitrile and water with 0.1% NH4OH additive to provide 1-(2-cyano-5-methoxy-3'-(trifluoromethyl)-[1,1'-biphenyl]-4-yl)-N-(pyrimidin-2-yl)isoquinoline-6-sulfonamide (41.7 mg, 0.074 mmol, 36.4% yield). $^1$H NMR (500 MHz, DMSO-$d_6$) δ 12.21 (br. s., 1H), 8.68-8.81 (m, 2H), 8.49 (d, J=4.86 Hz, 2H), 8.21 (d, J=5.66 Hz, 1H), 8.02-8.13 (m, 3H), 7.98 (s, 1H), 7.93 (d, J=8.12 Hz, 1H), 7.79-7.88 (m, 2H), 7.51 (s, 1H), 7.03 (t, J=4.81 Hz, 1H), 3.82 (s, 3H). m/z (ESI) 562.2 (M+H)$^+$.

Example 374 (Method 108)

1-(2-CYANO-5-METHOXY-3'-(TRIFLUOROM-ETHYL)-4-BIPHENYLYL)-N-(5-FLUORO-2-PYRIMIDINYL)-6-ISOQUINOLINESULFONAMIDE

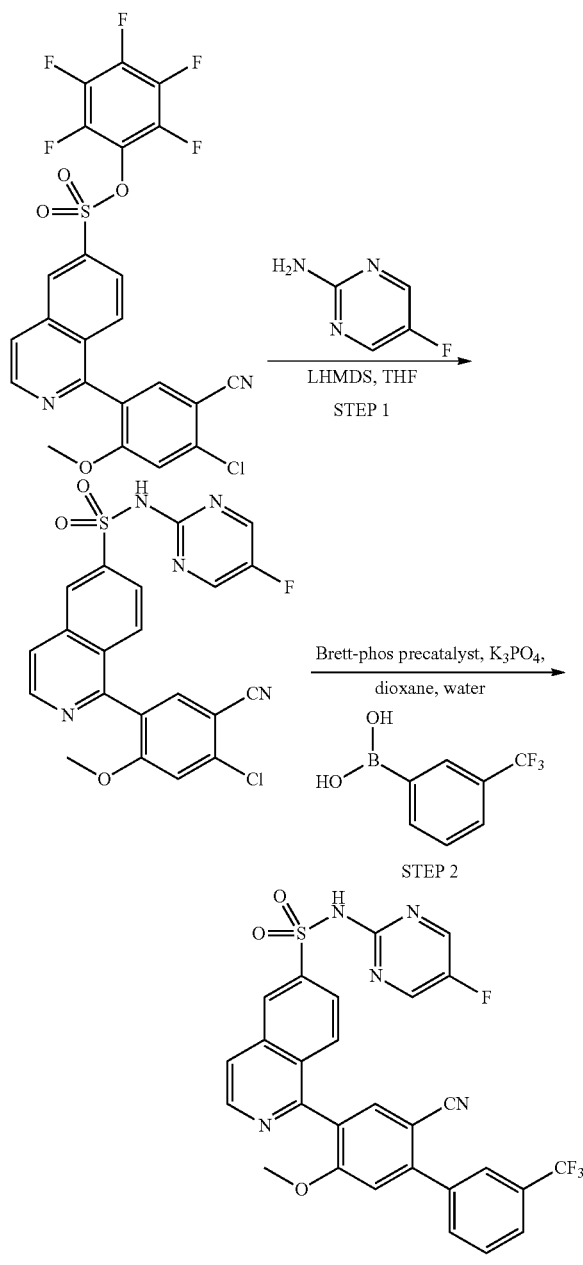

STEP 1: 1-(4-CHLORO-5-CYANO-2-METHOXYPHENYL)-N-(5-FLUOROPYRIMIDIN-2-YL)ISOQUINOLINE-6-SULFONAMIDE

A RBF was charged with perfluorophenyl 1-(4-chloro-5-cyano-2-methoxyphenyl)isoquinoline-6-sulfonate (150 mg, 0.277 mmol), 2-amino-5-fluoropyrimidine (34.5 mg, 0.305 mmol, Oakwood), and THF (1.414 mL) to give a clear, yellow solution. The flask was cooled to 0° C. 10 min, then a THF solution of lithium bis(trimethylsilyl)amide (0.582 mL, 0.582 mmol, 1 M) was added dropwise to give a clear yellow solution. After 30 min, the mixture was diluted with 1 N aq. HCl (5 mL) and EtOAc (20 mL). The layers were separated, and the aq. layer was diluted with brine (10 mL) and extracted with EtOAc (3×10 mL) The combined organic extracts were concentrated to yield 1-(4-chloro-5-cyano-2-methoxyphenyl)-N-(5-fluoropyrimidin-2-yl)isoquinoline-6-sulfonamide (130 mg, 0.277 mmol) which was of sufficient purity for further use. m/z (ESI) 470.1 (M+H)$^+$.

Step 2: 1-(2-CYANO-5-METHOXY-3'-(TRIFLUOROMETHYL)-4-BIPHENYLYL)-N-(5-FLUORO-2-PYRIMIDINYL)-6-ISOQUINOLINESULFONAMIDE 1-(2-Cyano-5-methoxy-3'-(trifluoromethyl)-[1,1'-biphenyl]-4-yl)-N-(5-fluoropyrimidin-2-yl)isoquinoline-6-sulfonamide was prepared from 1-(4-chloro-5-cyano-2-methoxyphenyl)-N-(5-fluoropyrimidin-2-yl)isoquinoline-6-sulfonamide as described in step 2 of method 107. $^1$H NMR (500 MHz, DMSO-d$_6$) δ 8.68 (d, J=5.66 Hz, 1H), 8.60 (s, 1H), 8.35 (s, 2H), 8.04-8.16 (m, 3H), 7.89-8.02 (m, 3H), 7.81-7.88 (m, 1H), 7.72 (d, J=8.87 Hz, 1H), 7.50 (s, 1H), 3.82 (s, 3H). m/z (ESI) 580.2 (M+H)$^+$.

Example 375 (Method 109)

4-(3'-CHLORO-2-FLUORO-5-METHOXY-[1,1'-BIPHENYL]-4-YL)-N-(5-FLUOROPYRIMIDIN-2-YL)QUINAZOLINE-7-SULFONAMIDE

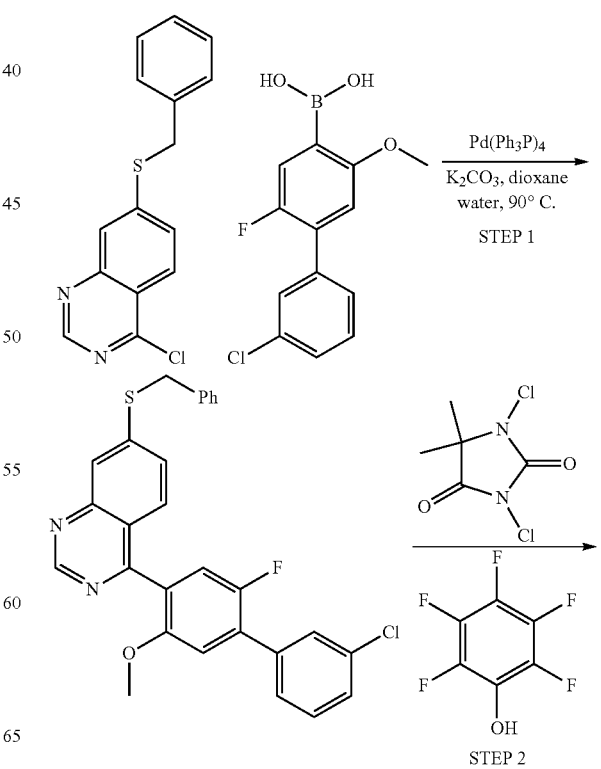

427
-continued

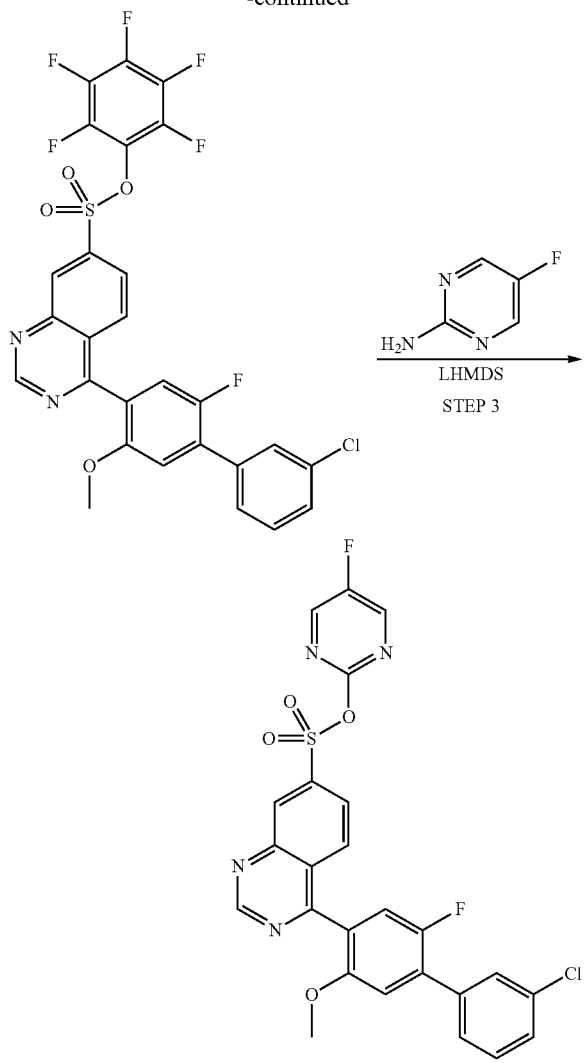

STEP 1: 7-(BENZYLTHIO)-4-(3'-CHLORO-2-FLUORO-5-METHOXY-[1,1'-BIPHENYL]-4-YL) QUINAZOLINE

A microwave vial was charged with 7-(benzylthio)-4-chloroquinazoline (481 mg, 1.676 mmol), (3'-chloro-2-fluoro-5-methoxy-[1,1'-biphenyl]-4-yl)boronic acid (470 mg, 1.676 mmol), tetrakis(triphenylphosphine)palladium (194 mg, 0.168 mmol) and potassium carbonate (1158 mg, 8.38 mmol). The vial was sealed with a septum cap and 1,4-dioxane (4189 µl) and water (1396 µl) were added via syringe. The vial was flushed with $N_2$ and sealed, and microwaved at 90° C. for 40 min. The reaction was diluted with ethyl acetate (10 mL) and washed with water (5 mL) and brine (5 mL) and concentrated. The residue was purified via column chromatography (25 g, gradient elution 5-75% EtOAc in Heptane to afford 7-(benzylthio)-4-(3'-chloro-2-fluoro-5-methoxy-[1,1'-biphenyl]-4-yl)quinazoline (650 mg, 1.335 mmol, 80% yield) as a yellow solid. m/z (ESI) 487.2 (M+H)⁺.

428

STEP 2: PERFLUOROPHENYL 4-(3'-CHLORO-2-FLUORO-5-METHOXY-[1,1'-BIPHENYL]-4-YL) QUINAZOLINE-7-SULFONATE

A RBF was charged with 7-(benzylthio)-4-(3'-chloro-2-fluoro-5-methoxy-[1,1'-biphenyl]-4-yl)quinazoline (650 mg, 1.335 mmol), DCM (12.72 mL), AcOH (0.318 mL), and water (0.318 mL) to give yellow solution. The flask was cooled to 0° C. for 10 min, then 1,3-dichloro-5,5-dimethyl-imidazolidine-2,4-dione (657 mg, 3.34 mmol) was added as a solid in a single portion. The reaction was maintained at 0° C. for 20 minutes at which time 2,3,4,5,6-pentafluorophenol (491 mg, 2.67 mmol) was added followed by dropwise addition of triethylamine (0.465 mL, 3.34 mmol) to give a clear solution. The reaction was maintained at 0° C. for 30 minutes. The solution was concentrated and purified via column chromatography (RediSep Gold 40 g, gradient elution 0-50% EtOAc in Heptane) to afford perfluorophenyl 4-(3'-chloro-2-fluoro-5-methoxy-[1,1'-biphenyl]-4-yl)quinazoline-7-sulfonate (727 mg, 1.190 mmol, 89% yield) as a light yellow solid. m/z (ESI) 611.1 (M+H)⁺.

STEP 3: 4-(3'-CHLORO-2-FLUORO-5-METHOXY-[1,1'-BIPHENYL]-4-YL)-N-(5-FLUOROPYRIMIDIN-2-YL)QUINAZOLINE-7-SULFONAMIDE 4-(3'-Chloro-2-fluoro-5-methoxy-[1,1'-biphenyl]-4-yl)-N-(5-fluoropyrimidin-2-yl)quinazoline-7-sulfonamide was prepared from perfluorophenyl 4-(3'-chloro-2-fluoro-5-methoxy-[1,1'-biphenyl]-4-yl)quinazoline-7-sulfonate in a manner similar to that described for step 1 of method 108. ¹H NMR (500 MHz, DMSO-$d_6$) δ 9.48 (s, 1H), 8.54 (s, 1H), 8.46 (s, 2H), 8.10 (dd, J=1.36, 8.79 Hz, 1H), 7.89 (d, J=8.76 Hz, 1H), 7.78 (s, 1H), 7.68 (d, J=6.57 Hz, 1H), 7.52-7.62 (m, 3H), 7.49 (d, J=10.31 Hz, 1H), 7.39 (d, J=6.25 Hz, 1H), 3.76 (s, 3H), sulfonamide NH absent due to exchange with water. m/z (ESI) 540.1 (M+H)⁺.

Example 376 (Method 110)

4-(3'-CHLORO-2-FLUORO-5-METHOXY-4-BIPHENYLYL)-N-1,2,4-OXADIAZOL-3-YL-7-QUINAZOLINESULFONAMIDE

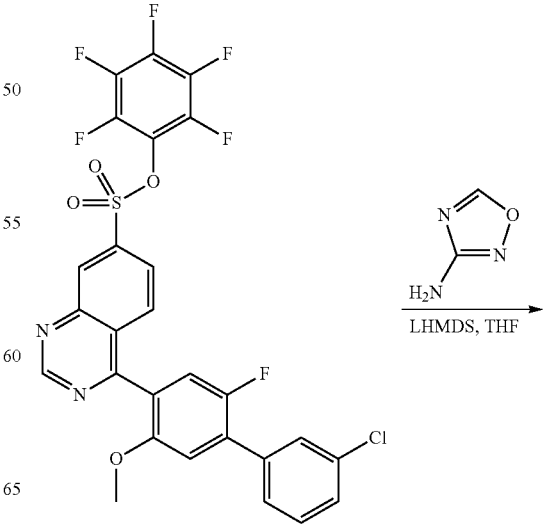

429

-continued

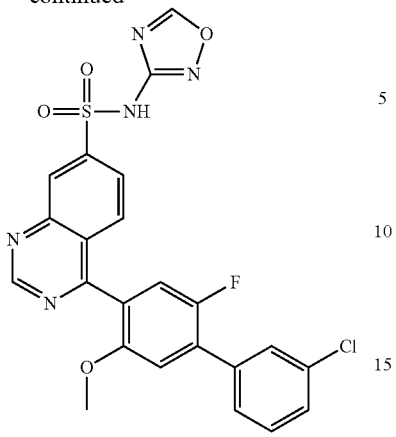

To a tube was added perfluorophenyl 4-(3'-chloro-2-fluoro-5-methoxy-[1,1'-biphenyl]-4-yl)quinazoline-7-sulfonate (96 mg, 0.157 mmol) and 1,2,4-oxadiazol-3-amine in THF (1571 μl). The reaction mixture was cooled to 0° C. A THF solution of lithium bis(trimethylsilyl)amide (55.2 mg, 0.330 mmol, 1M) was added dropwise. The reaction was allowed to warm to RT and maintained for 18 h. Methanol (5 mL) was added to the mixture and it was concentrated. The residue was purified by reverse phase HPLC using 0.1% NH$_4$OH modifier in acetonitrile and water as a mobile phase to provide 4-(3'-chloro-2-fluoro-5-methoxy-[1,1'-biphenyl]-4-yl)-N-(1,2,4-oxadiazol-3-yl)quinazoline-7-sulfonamide. $^1$H NMR (500 MHz, DMSO-d$_6$) δ 9.40 (s, 1H), 8.72 (s, 1H), 8.40 (s, 1H), 8.00 (d, J=8.87 Hz, 1H), 7.79 (s, 1H), 7.75 (d, J=8.60 Hz, 1H), 7.69 (d, J=6.68 Hz, 1H), 7.52-7.61 (m, 2H), 7.47 (d, J=10.36 Hz, 1H), 7.37 (d, J=6.20 Hz, 1H), 3.77 (s, 3H), sulfonamide peak is absent due to exchange in water. m/z (ESI) 512.0 (M+H)$^+$.

Example 377 (Method 111)

4-(3'-CHLORO-2-FLUORO-5-METHOXY-4-BIPHENYLYL)-N-3-ISOTHIAZOLYL-7-QUINAZOLINESULFONAMIDE

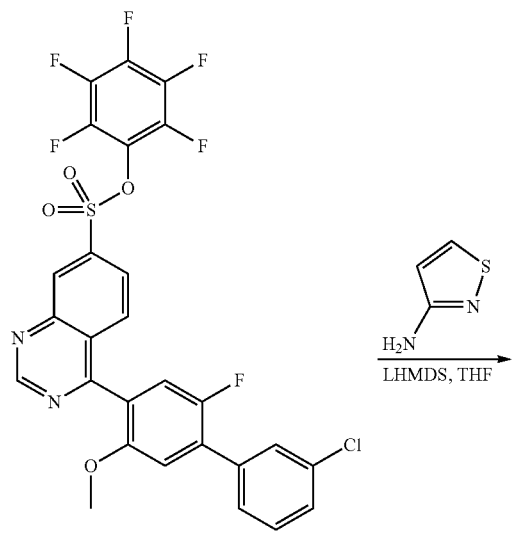

430

-continued

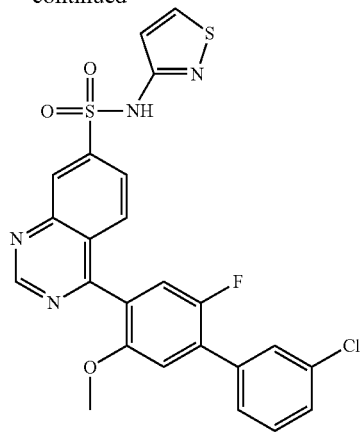

4-(3'-Chloro-2-fluoro-5-methoxy-4-biphenylyl)-N-3-isothiazolyl-7-quinazolinesulfonamide was synthesized from perfluorophenyl 4-(3'-chloro-2-fluoro-5-methoxy-[1,1'-biphenyl]-4-yl)quinazoline-7-sulfonate in a manner similar to that described in step 1 of method 108 using isothiazol-3-amine (Small Molecules) instead of 2-amino-5-fluoropyrimidine. $^1$H NMR (500 MHz, DMSO-d$_6$) δ 9.49 (s, 1H), 8.83 (d, J=4.54 Hz, 1H), 8.50 (s, 1H), 8.06 (dd, J=1.55, 8.76 Hz, 1H), 7.93 (d, J=8.82 Hz, 1H), 7.78 (s, 1H), 7.68 (d, J=6.20 Hz, 1H), 7.52-7.62 (m, 2H), 7.49 (d, J=10.36 Hz, 1H), 7.39 (d, J=6.25 Hz, 1H), 6.99 (d, J=4.65 Hz, 1H), 3.75 (s, 3H), sulfonamide NH absent due to exchange with water. m/z (ESI) 527.0 (M+H)$^+$.

Example 378 (Method 112)

4-(2-CHLORO-3'-FLUORO-5-METHOXY-4-BIPHENYLYL)-N-1,3-THIAZOL-4-YL-7-QUINAZOLINESULFONAMIDE

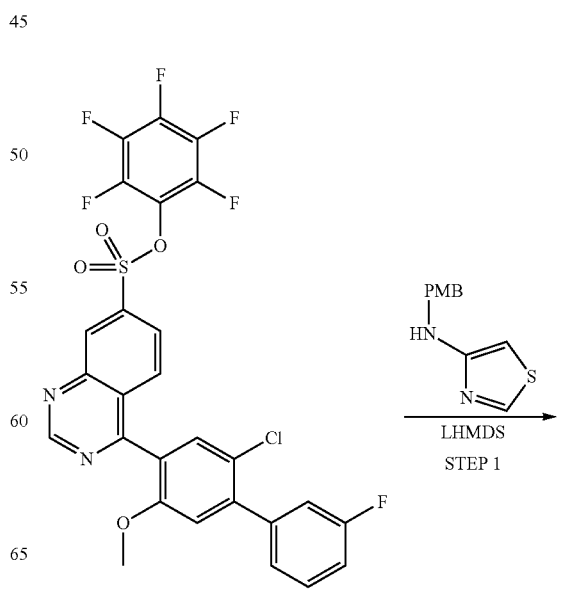

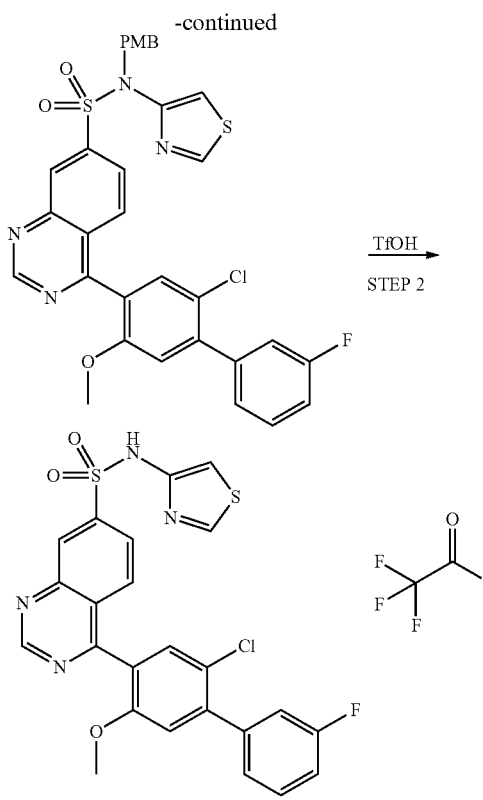

STEP 1: 4-(2-CHLORO-3'-FLUORO-5-METHOXY-[1,1'-BIPHENYL]-4-YL)-N-(4-METHOXYBENZYL)-N-(THIAZOL-4-YL)QUINAZOLINE-7-SULFONAMIDE

A RBF was charged with perfluorophenyl 4-(2-chloro-3'-fluoro-5-methoxy-[1,1'-biphenyl]-4-yl)quinazoline-7-sulfonate (103 mg, 0.169 mmol), N-(4-methoxybenzyl)thiazol-4-amine (40.9 mg, 0.185 mmol) and THF (843 µl) to give a brown mixture. The flask was cooled to −78° C. for 10 min, then a THF solution of lithium bis(trimethylsilyl)amide (185 µl, 0.185 mmol, 1 M) was added dropwise. The mixture was quenched by the addition of saturated aq. ammonium chloride (5 mL) and water (5 mL), and extracted with EtOAc (2×20 mL). The combined organic extracts were dried over sodium sulfate, filtered, and concentrated. The residue was purified by chromatography on silica gel (25-g Redi-Sep Gold column, 12-g silica gel loading column, 0-50% EtOAc in heptanes). The resulting solid was triturated with heptane (2×5 mL), and dried under a stream of N$_2$ (g) to give 4-(2-chloro-3'-fluoro-5-methoxy-[1,1'-biphenyl]-4-yl)-N-(4-methoxybenzyl)-N-(thiazol-4-yl)quinazoline-7-sulfonamide (63 mg, 0.097 mmol, 57.7% yield) as a cream-colored solid. m/z (ESI) 647.1 (M+H)$^+$.

STEP 2: 4-(2-CHLORO-3'-FLUORO-5-METHOXY-4-BIPHENYLYL)-N-1,3-THIAZOL-4-YL-7-QUINAZOLINESULFONAMIDE

To a RBF was added 4-(2-chloro-3'-fluoro-5-methoxy-[1,1'-biphenyl]-4-yl)-N-(4-methoxybenzyl)-N-(thiazol-4-yl)quinazoline-7-sulfonamide (63 mg, 0.097 mmol) in DCM (2 mL). To the yellow solution was added triflic acid (0.104 mL, 1.168 mmol) dropwise. The reaction turned black. After 10 min, the mixture was diluted with water and extracted with EtOAc (10 mL). The layers were separated and the organic phase was concentrated. The residue was purified by reverse phase HPLC with AcCN/H$_2$O to give 4-(2-chloro-3'-fluoro-5-methoxy-[1,1'-biphenyl]-4-yl)-N-(thiazol-4-yl)quinazoline-7-sulfonamide 2,2,2-trifluoroacetate (21 mg, 0.033 mmol, 33.7% yield). $^1$H NMR (400 MHz, DMSO-d$_6$) δ 11.50 (s, 1H), 9.52 (s, 1H), 8.89 (d, J=2.15 Hz, 1H), 8.45-8.54 (m, 1H), 8.02-8.10 (m, 1H), 7.96-8.01 (m, 1H), 7.66-7.72 (m, 1H), 7.60 (dt, J=6.36, 8.07 Hz, 1H), 7.42-7.50 (m, 2H), 7.29-7.38 (m, 2H), 7.22 (d, J=2.15 Hz, 1H), 3.75 (s, 3H). m/z (ESI) 527.2 (M+H)$^+$.

Example 379 (Method 113)

1-(2,4'-DICHLORO-5-METHOXY-3'-METHYL-4-BIPHENYLYL)-N-1,3,4-THIADIAZOL-2-YL-6-ISOQUINOLINESULFONAMIDE

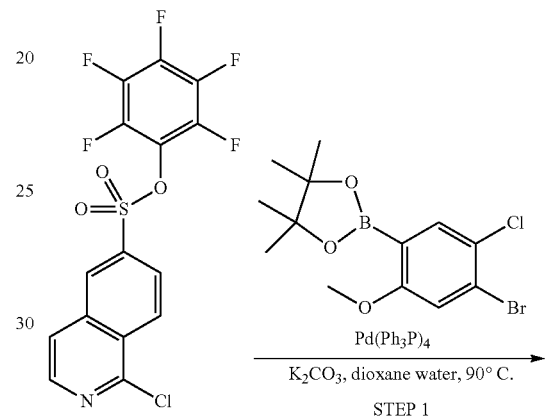

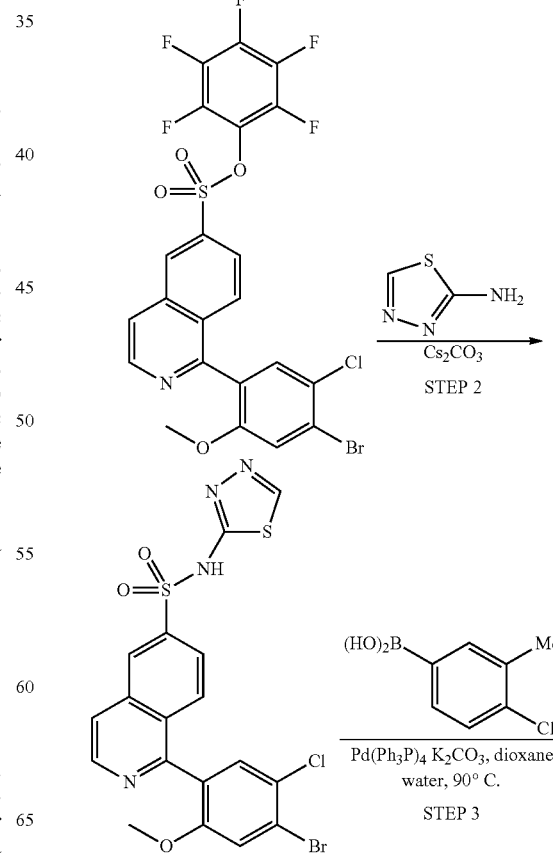

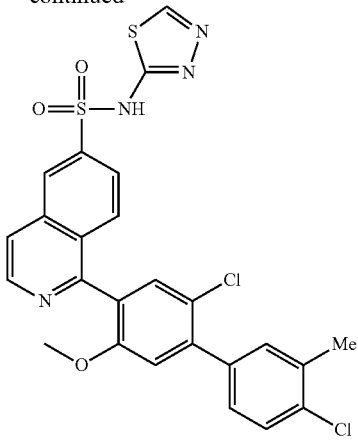

STEP 1: PERFLUOROPHENYL 1-(4-BROMO-5-CHLORO-2-METHOXYPHENYL)ISOQUINO-LINE-6-SULFONATE

A RBF was charged with perfluorophenyl 1-chloroisoquinoline-6-sulfonate (1.54 g, 3.76 mmol), 2-(4-bromo-5-chloro-2-methoxyphenyl)-4,4,5,5-tetramethyl-1,3,2-dioxaborolane (1.450 g, 4.17 mmol), and Pd(Ph$_3$P)$_4$ (0.434 g, 0.376 mmol). The flask was flushed with Ar (g), then dioxane (14.10 ml) and water (4.70 ml) were added in sequence. The flask was fitted with a reflux condenser and heated at 50° C. heating bath for 1 h. The mixture was cooled and diluted with EtOAc (50 mL). The layers were separated, and the organic layer was dried over sodium sulfate, filtered, and concentrated. The residue was purified by chromatography on silica gel (50-g Redi-Sep Gold column, 25-g silica gel loading column, 0-30% EtOAc in heptanes to give perfluorophenyl 1-(4-bromo-5-chloro-2-methoxyphenyl)isoquinoline-6-sulfonate (1.555 g, 2.61 mmol, 69.6% yield) as a yellow foam. m/z (ESI) 594.0 (M+H)$^+$.

STEP 2: 1-(4-BROMO-5-CHLORO-2-METHOXY-PHENYL)-N-(1,3,4-THIADIAZOL-2-YL)ISOQUI-NOLINE-6-SULFONAMIDE

A RBF was charged with perfluorophenyl 1-(4-bromo-5-chloro-2-methoxyphenyl)isoquinoline-6-sulfonate (519 mg, 0.873 mmol), 2-amino-1,3,4-thiadiazole (106 mg, 1.047 mmol), cesium carbonate (0.209 mL, 2.62 mmol) in MeCN (4.363 mL) to give a suspension. The mixture was stirred at rt for 18 h. The mixture was concentrated and taken up in HCl (1N, 10 mL) and a yellow solid precipitated. The yellow solid was collected by vacuum filtration and purified by chromatography through a Redi-Sep pre-packed silica gel column (12 g), eluting with a gradient of 0%-10% MeOH/DCM, to provide 1-(4-bromo-5-chloro-2-methoxyphenyl)-N-(1,3,4-thiadiazol-2-yl)isoquinoline-6-sulfonamide (0.285 g, 0.60 mmol). m/z (ESI) 510.9 (M+H)$^+$.

STEP 3: 1-(2,4'-DICHLORO-5-METHOXY-3'-METHYL-4-BIPHENYLYL)-N-1,3,4-THIADI-AZOL-2-YL-6-ISOQUINOLINESULFONAMIDE

A microwave vial was charged with 1-(4-bromo-5-chloro-2-methoxyphenyl)-N-(1,3,4-thiadiazol-2-yl)isoquinoline-6-sulfonamide (58.4 mg, 0.114 mmol), (4-chloro-3-methylphenyl)boronic acid (29.2 mg, 0.171 mmol), potassium carbonate (47.3 mg, 0.342 mmol), and Pd(Ph$_3$P)$_4$ (13.19 mg, 0.011 mmol). The vial was sealed with a septum cap and the vial flushed with N2 (g), then dioxane (428 µl) and water (143 µl) were added via syringe. The mixture was heated at 90° C. in an oil bath, then heated at 120° C. for 1 h in the microwave. Water (5 mL) was added to the mixture. The mixture was extracted with EtOAc (2×10 mL). The combined organic phases were concentrated. The residue was purified by reverse-phase HPLC using 0.1% NH$_4$OH in acetonitrile and water to provide 1-(2,4'-dichloro-5-methoxy-3'-methyl-4-biphenylyl)-N-1,3,4-thiadiazol-2-yl-6-isoquinolinesulfonamide. $^1$H NMR (500 MHz, DMSO-d$_6$) δ 8.62-8.69 (m, 2H), 8.48 (s, 1H), 8.08 (d, J=5.71 Hz, 1H), 7.88 (dd, J=1.50, 8.91 Hz, 1H), 7.75 (d, J=8.88 Hz, 1H), 7.53-7.63 (m, 2H), 7.50 (s, 1H), 7.43 (dd, J=1.72, 8.23 Hz, 1H), 7.21 (s, 1H), 3.69 (s, 3H), 2.43 (s, 3H), sulfonamide NH not observed due to exchange with water. m/z (ESI) 557.0 (M+H)$^+$.

Example 380 (Method 114)

1-(2-CHLORO-3',5'-DIFLUORO-5-METHOXY-4-BIPHENYLYL)-N-1,3,4-THIADIAZOL-2-YL-6-ISOQUINOLINESULFONAMIDE

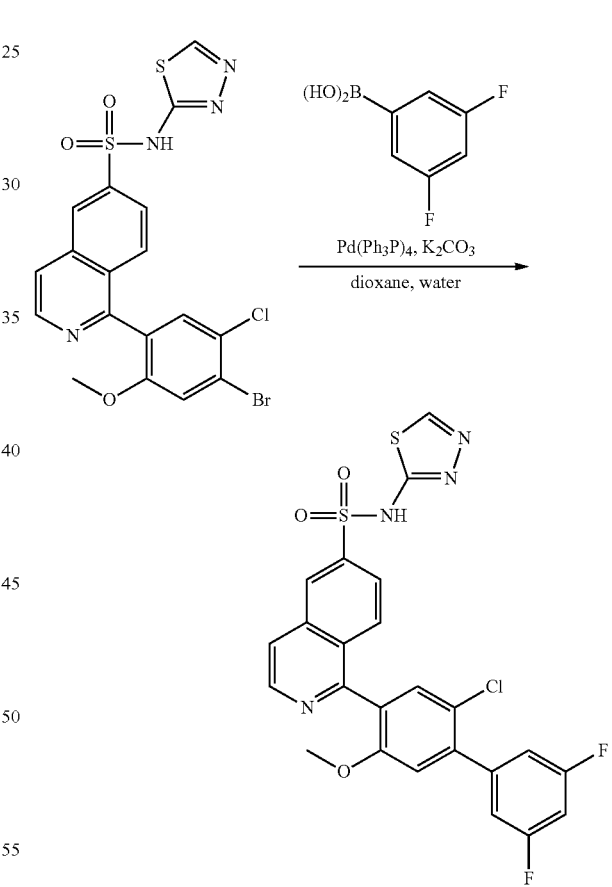

A microwave vial was charged with 1-(4-bromo-5-chloro-2-methoxyphenyl)-N-(1,3,4-thiadiazol-2-yl)isoquinoline-6-sulfonamide (91.2 mg, 0.178 mmol), (3,5-difluorophenyl)boronic acid (42.2 mg, 0.267 mmol), potassium carbonate (73.9 mg, 0.535 mmol), and Pd(Ph$_3$P)$_4$ (20.59 mg, 0.018 mmol). The vial sealed with a septum cap and the vial was flushed with N$_2$ (g), then dioxane (668 µl) and Water (223 µl) were added via syringe. The mixture was sealed and heated to 100° C., after 1 h, the mixture was heated to 120° C. for 1 h in microwave. Water (5 mL) was added to the mixture and the mixture was extracted with EtOAc (2×10 mL). The combined organic phases were concentrated. The residue was purified by reverse-phase HPLC using 0.1% NH₄OH in acetonitrile and water to provide 1-(2-chloro-3',5'-difluoro-5-methoxy-4-biphenylyl)-N-1,3,4-thiadiazol-2-yl-6-isoquinolinesulfonamide. ¹H NMR (500 MHz, DMSO-d₆) δ 8.65 (d, J=5.65 Hz, 1H), 8.62 (s, 1H), 8.46 (s, 1H), 8.07 (d, J=5.65 Hz, 1H), 7.88 (dd, J=1.50, 8.85 Hz, 1H), 7.72 (d, J=8.88 Hz, 1H), 7.53 (s, 1H), 7.32-7.41 (m, 3H), 7.28 (s, 1H), 3.71 (s, 3H), sulfonamide NH was not observed due to exchange with water. m/z (ESI) 545.0 (M+H)⁺.

Example 386 (Method 119)

5-(5-CYANO-6-(3,5-DIFLUOROPHENYL)-2-OXO-1,2-DIHYDROPYRIDIN-3-YL)-N-(PYRIMIDIN-4-YL)NAPHTHALENE-2-SULFONAMIDE

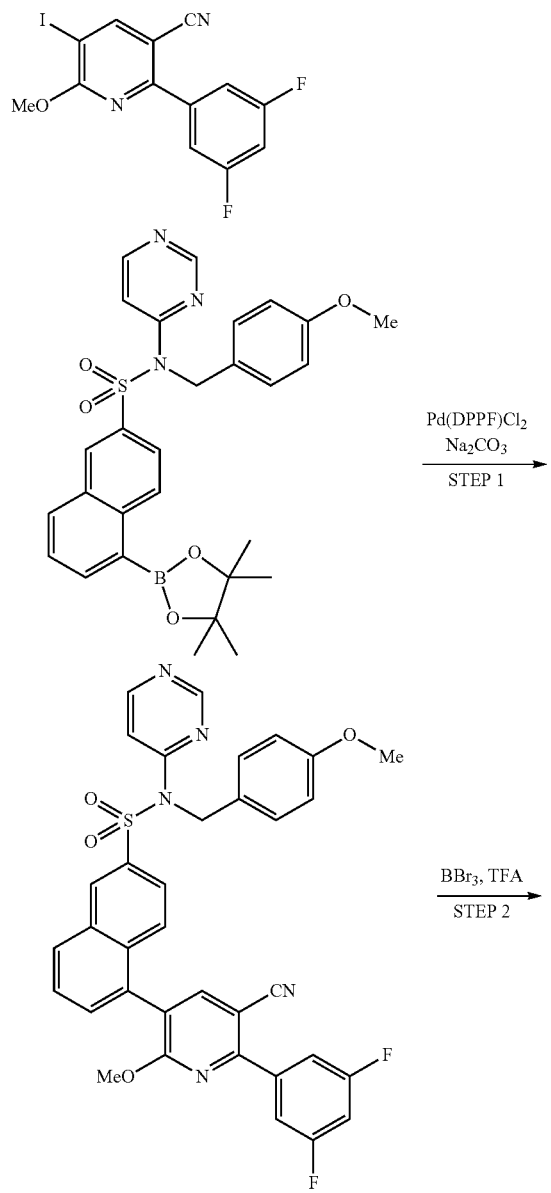

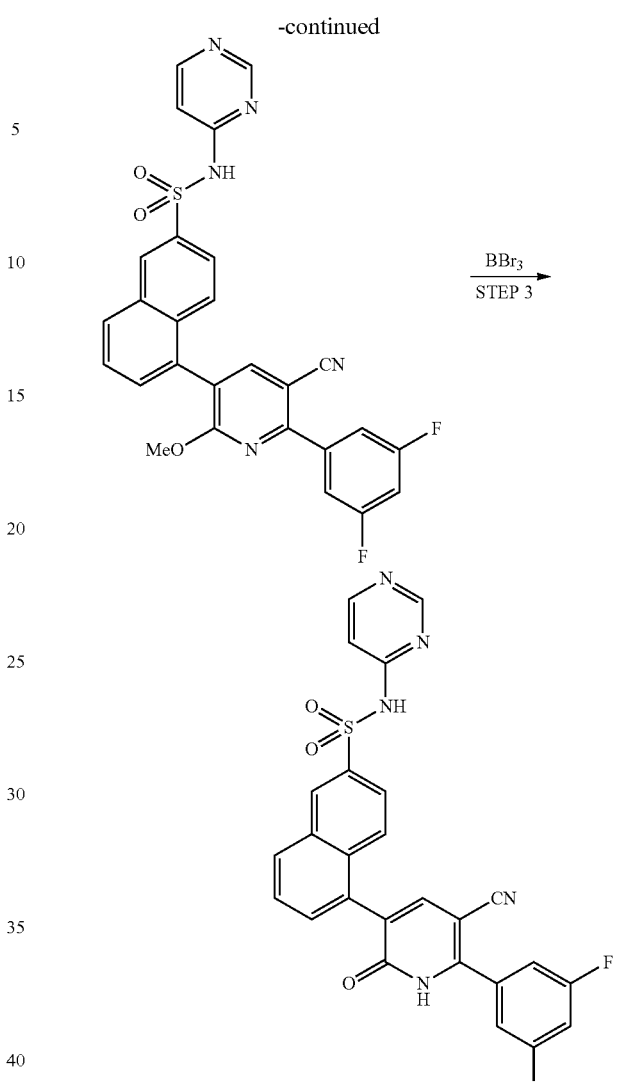

STEP 1: 5-(5-CYANO-6-(3,5-DIFLUOROPHENYL)-2-METHOXYPYRIDIN-3-YL)-N-(4-METHOXYBENZYL)-N-(PYRIMIDIN-4-YL)NAPHTHALENE-2-SULFONAMIDE

A pressure vessel was charged with N-(4-methoxybenzyl)-N-(pyrimidin-4-yl)-5-(4,4,5,5-tetramethyl-1,3,2-dioxaborolan-2-yl)naphthalene-2-sulfonamide (241 mg, 0.453 mmol), 2-(3,5-difluorophenyl)-5-iodo-6-methoxynicotinonitrile (202 mg, 0.544 mmol) and PdCl₂(DPPF)DCM adduct (74.1 mg, 0.091 mmol). Dioxane (2267 μl) and t-butanol (2267 μl) were added to the reaction vial followed by sodium carbonate in water (1.9 M, 716 μl, 1.360 mmol). The reaction was then swept with nitrogen and sealed with a screw cap. The whole was stirred and sonicated for 5 min. The resulting light red mixture was then heated to 50° C. After 1 h, LCMS showed a complete conversion of SM to product. The whole was cooled to rt and filtered through a frit with an aid of DCM. The filtrate was dried over MgSO₄, filtered, and concentrated. The crude material was absorbed onto a plug of silica gel and purified by chromatography through a Redi-Sep pre-packed silica gel column (40 g), eluting with a gradient of 0% to 50% EtOAc in heptane, to provide 5-(5-cyano-6-(3,5-difluorophenyl)-2-methoxypyridin-3-yl)-N-(4-methoxybenzyl)-N-(pyrimidin-4-yl)naphthalene-2-sulfonamide (247 mg, 84% yield) as black solid. m/z (ESI) [M+H]$^+$=651.2. $^1$H NMR (500 MHz, DMSO-d$_6$) δ ppm 3.61-3.76 (m, 3 H) 3.89-4.01 (m, 3 H) 5.30 (s, 2 H) 6.88 (m, J=8.76 Hz, 2 H) 7.29 (m, J=8.44 Hz, 2 H) 7.50-7.58 (m, 2 H) 7.64-7.87 (m, 6 H) 8.29 (d, J=8.87 Hz, 1 H) 8.40 (s, 1 H) 8.59 (d, J=5.88 Hz, 1 H) 8.75 (s, 1 H) 8.83 (s, 1 H).

STEP 2: SYNTHESIS OF 5-(5-CYANO-6-(3,5-DIFLUOROPHENYL)-2-METHOXYPYRIDIN-3-YL)-N-(PYRIMIDIN-4-YL)NAPHTHALENE-2-SULFONAMIDE

To a solution of 5-(5-cyano-6-(3,5-difluorophenyl)-2-methoxypyridin-3-yl)-N-(4-methoxybenzyl)-N-(pyrimidin-4-yl)naphthalene-2-sulfonamide (230 mg, 0.354 mmol) in DCM (3540 μl) was added TFA (136 μl, 1.770 mmol). The whole was stirred at rt. After 1 h an additional 136 L of TFA was added and stirred for 1 more hr. Boron tribromide (1.0 M in DCM) (1770 μl, 1.770 mmol) was added and the solution turned red immediately. After 5 min, LCMS showed mainly debenzylated product. The whole was diluted with 30 mL of DCM, cooled to 0° C., and quenched with 15 mL of MeOH slowly. Then the whole was warmed to rt and concentrated to afford an orange solid. The solid was triturated with a mixture of i-PrOH and heptane. Pink precipitates were collected with an aid of heptane and dried to afford 5-(5-cyano-6-(3,5-difluorophenyl)-2-methoxypyridin-3-yl)-N-(pyrimidin-4-yl)naphthalene-2-sulfonamide (161 mg, 86% yield). m/z (ESI): [M+H]$^+$:=530. $^1$H NMR (500 MHz, DMSO-d$_6$) δ ppm 3.92 (s, 3 H) 7.08 (br. s., 1 H) 7.54 (t, J=9.40 Hz, 1 H) 7.64-7.71 (m, 2 H) 7.71-7.82 (m, 3 H) 7.87 (d, J=7.43 Hz, 1 H) 8.30 (d, J=8.01 Hz, 2 H) 8.38 (s, 1 H) 8.59 (s, 1 H) 8.70 (s, 1 H).

STEP 3: SYNTHESIS OF 5-(5-CYANO-6-(3,5-DIFLUOROPHENYL)-2-OXO-1,2-DIHYDROPYRIDIN-3-YL)-N-(PYRIMIDIN-4-YL)NAPHTHALENE-2-SULFONAMIDE

To a solution of 5-(5-cyano-6-(3,5-difluorophenyl)-2-methoxypyridin-3-yl)-N-(pyrimidin-4-yl)naphthalene-2-sulfonamide (30 mg, 0.057 mmol) in DCM (567 μl) was added boron tribromide (1.0 M in DCM) (283 μl, 0.283 mmol). The whole was heated to 50° C. for 1 h. An additional 0.3 mL of BBr$_3$ (1M in DCM) was added and the whole was heated to 50° C. and stirred for 2 d. After cooling to rt, the whole was diluted with 30 mL of DCM. The whole was further cooled to 0° C., and quenched with 15 mL of MeOH slowly. After warming to rt, the whole was concentrated. The residue was dissolved in DMSO, filtered, and purified by RPLC on the acidic Gilson. Fractions containing the product were combined and concentrated. Water was lypholized off to afford 5-(5-cyano-6-(3,5-difluorophenyl)-2-oxo-1,2-dihydropyridin-3-yl)-N-(pyrimidin-4-yl)naphthalene-2-sulfonamide (4.3 mg, 15% yield) as white solid. m/z (ESI): [M+H]$^+$=516. $^1$H NMR (500 MHz, DMSO-d$_6$) δ ppm 7.08 (br. s., 1 H) 7.51-7.65 (m, 4 H) 7.73 (t, J=7.67 Hz, 1 H) 7.79-7.91 (m, 2 H) 7.99 (br. s., 1 H) 8.22-8.38 (m, 2 H) 8.60 (br. s., 1 H) 8.67 (br. s., 1 H) 12.98 (s, 1 H).

Example 392 (Method 123)

1-(4-FLUORO-5-(5-FLUORO-3-PYRIDINYL)-2-METHOXYPHENYL)-N-3-ISOXAZOLYL-6-ISOQUINOLINESULFONAMIDE

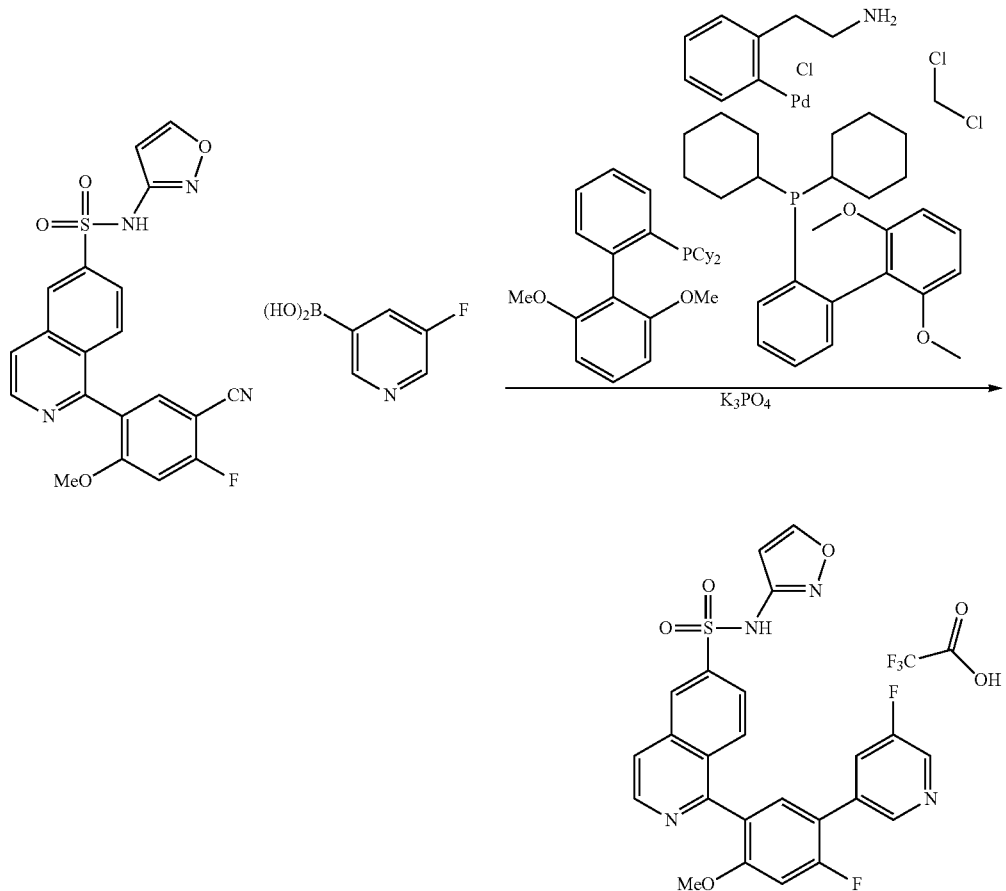

A vial was charged with 1-(5-chloro-4-fluoro-2-methoxyphenyl)-N-(isoxazol-3-yl)isoquinoline-6-sulfonamide (100 mg, 0.230 mmol), (5-fluoropyridin-3-yl)boronic acid (65.0 mg, 0.461 mmol), chloro(2-dicyclohexylphosphino-2',6'-dimethoxy-1,1'-biphenyl)[2-(2-aminoethylphenyl)]-palladium (ii) dichloromethane (8.73 mg, 0.012 mmol), dicyclohexyl(2',6'-dimethoxy-[1,1'-biphenyl]-2-yl)phosphine (4.73 mg, 0.012 mmol) and potassium phosphate (245 mg, 1.152 mmol). The vial was flushed with Ar (g), then 1,4-dioxane (1 mL) and water (0.1 mL) were added. The vial was sealed and heated in a Biotage Initiator microwave reactor for 4 h at 120° C. After cooling to rt, the reaction mixture was filtered. The crude material was purified by reverse-phase preparative HPLC using 0.1% TFA in $CH_3CN/H_2O$, gradient 10% to 90% over 20 min to provide 1-(4-fluoro-5-(5-fluoropyridin-3-yl)-2-methoxyphenyl)-N-(isoxazol-3-yl)isoquinoline-6-sulfonamide 2,2,2-trifluoroacetate as a yellow solid (7 mg, 5% yield). $^1$H NMR (400 MHz, MeOH) δ 8.77 (t, J=1.17 Hz, 1H), 8.73 (d, J=6.06 Hz, 1H), 8.68 (d, J=1.56 Hz, 1H), 8.51 (d, J=2.74 Hz, 1H), 8.48 (d, J=1.86 Hz, 1H), 8.33 (d, J=6.06 Hz, 1H), 8.13 (d, J=1.47 Hz, 2H), 7.94 (d, J=9.68 Hz, 1H), 7.78 (d, J=8.51 Hz, 1H), 7.33 (d, J=12.72 Hz, 1H), 6.55 (d, J=1.76 Hz, 1H), 3.84 (s, 3H). m/z (ESI) 495.0 [M+1].

Example 393 (Method 124)

3-CHLORO-1-(2,3'-DIFLUORO-5-METHOXY-4-BIPHENYLYL)-N-3-ISOXAZOLYL-6-ISOQUINOLINESULFONAMIDE

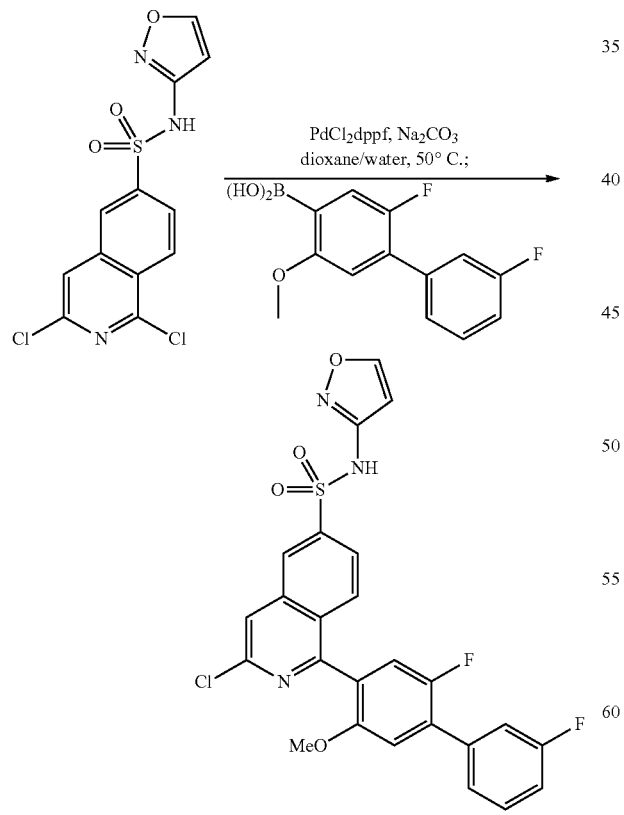

A solution of $PdCl_2dppf$ (0.142 g, 0.174 mmol), 1,3-dichloro-N-(isoxazol-3-yl)-N-(4-methoxybenzyl)isoquinoline-6-sulfonamide (0.6 g, 1.743 mmol), (2-chloro-3'-fluoro-5-methoxy-[1,1'-biphenyl]-4-yl)boronic acid (0.732 g, 2.61 mmol), and 2M aqueous sodium carbonate (1.74 ml, 3.48 mmol) in dioxanes (4.36 ml) was heated to 50° C. in a heating block for 1 h. After cooling to rt, the crude material was absorbed onto a plug of silica gel and purified by chromatography through a Redi-Sep pre-packed silica gel column (120 g), eluting with a gradient of 0% to 60% EtOAc in hexane, to provide 3-chloro-1-(2-chloro-3'-fluoro-5-methoxy-[1,1'-biphenyl]-4-yl)-N-(isoxazol-3-yl)-N-(4-methoxybenzyl)isoquinoline-6-sulfonamide (0.55 g, 60% yield). One portion of the material was further purified by reverse phase preparative HPLC using 0.1% TFA in $CH_3CN/H_2O$, gradient 10% to 90% to provide 3-chloro-1-(2-chloro-3'-fluoro-5-methoxy-[1,1'-biphenyl]-4-yl)-N-(isoxazol-3-yl)-N-(4-methoxybenzyl)isoquinoline-6-sulfonamide. 1H NMR (400 MHz, CHLOROFORM-d) δ 8.42 (d, J=1.76 Hz, 1H), 8.30 (d, J=1.76 Hz, 1H), 7.89-7.96 (m, 1H), 7.87 (s, 1H), 7.82-7.86 (m, 1H), 7.44-7.53 (m, 1H), 7.39-7.43 (m, 1H), 7.35 (td, J=1.19, 9.85 Hz, 1H), 7.24-7.30 (m, 2H), 7.16 (ddt, J=1.03, 2.59, 8.36 Hz, 1H), 7.06 (d, J=6.06 Hz, 1H), 6.68 (d, J=1.76 Hz, 1H), 3.73 (s, 3H). m/z (ESI) 528.0 [M].

Example 394 (Method 125)

1-(2-CHLORO-3'-FLUORO-5-METHOXY-[1,1'-BIPHENYL]-4-YL)-N-(ISOXAZOL-3-YL)-3-OXO-2,3-DIHYDROISOQUINOLINE-6-SULFONAMIDE

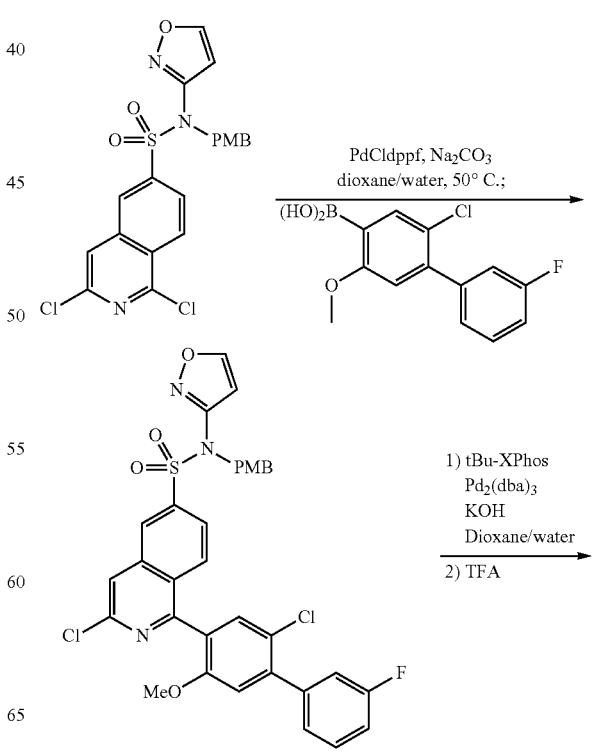

-continued

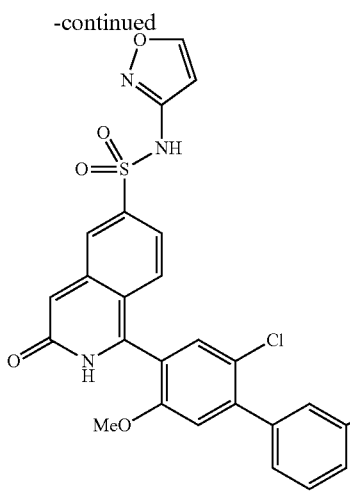

STEP 1: 3-CHLORO-1-(2-CHLORO-3'-FLUORO-5-METHOXY-[1,1'-BIPHENYL]-4-YL)-N-(ISOXAZOL-3-YL)-N-(4-METHOXYBENZYL)ISOQUINOLINE-6-SULFONAMIDE

A solution of $PdCl_2dppf$ (0.088 g, 0.108 mmol), 1,3-dichloro-N-(isoxazol-3-yl)-N-(4-methoxybenzyl)isoquinoline-6-sulfonamide (1 g, 2.154 mmol), (2-chloro-3'-fluoro-5-methoxy-[1,1'-biphenyl]-4-yl)boronic acid (0.604 g, 2.154 mmol), and 2M aqueous sodium carbonate (2.154 ml, 4.31 mmol) in dioxane (4.31 ml) was heated to 50° C. in a heating block for 1 h. After cooling to rt, the crude material was absorbed onto a plug of silica gel and purified by chromatography through a Redi-Sep pre-packed silica gel column (120 g), eluting with a gradient of 0% to 60% EtOAc in hexane, to provide 3-chloro-1-(2-chloro-3'-fluoro-5-methoxy-[1,1'-biphenyl]-4-yl)-N-(isoxazol-3-yl)-N-(4-methoxybenzyl)isoquinoline-6-sulfonamide (1.2 g, 1.806 mmol, 84% yield). m/z (ESI) 565.1 [M+1].

STEP 2: 1-(2-CHLORO-3'-FLUORO-5-METHOXY-[1,1'-BIPHENYL]-4-YL)-3-HYDROXY-N-(ISOXAZOL-3-YL)-N-(4-METHOXYBENZYL)ISOQUINOLINE-6-SULFONAMIDE

A glass microwave reaction vessel was charged with 3-chloro-1-(2-chloro-3'-fluoro-5-methoxy-[1,1'-biphenyl]-4-yl)-N-(isoxazol-3-yl)-N-(4-methoxybenzyl)isoquinoline-6-sulfonamide (100 mg, 0.150 mmol), potassium hydroxide (16.89 mg, 0.301 mmol), tris(dibenzylideneacetone) dipalladium (0) (13.78 mg, 0.015 mmol), and 2-di-tert-butylphosphino-2',4',6'-triisopropylbiphenyl (12.78 mg, 0.030 mmol). The vial was capped and was evacuated and backfilled with $N_2$ (2×). The solvents were added under vacuum followed by backfilling of $N_2$ gas. The reaction mixture was stirred and heated in a heating block at 100° C. overnight. After cooling to rt, the crude material was absorbed onto a plug of silica gel and purified by chromatography through a Redi-Sep pre-packed silica gel column (12 g), eluting with a gradient of 0% to 10% MeOH in $CH_2CL_2$, to provide 1-(2-chloro-3'-fluoro-5-methoxy-[1,1'-biphenyl]-4-yl)-3-hydroxy-N-(isoxazol-3-yl)-N-(4-methoxybenzyl)isoquinoline-6-sulfonamide (100 mg, 0.155 mmol, 103% yield). m/z (ESI) 646.2 [M].

STEP 3: 1-(2-CHLORO-3'-FLUORO-5-METHOXY-[1,1'-BIPHENYL]-4-YL)-N-(ISOXAZOL-3-YL)-3-OXO-2,3-DIHYDROISOQUINOLINE-6-SULFONAMIDE

To a 1 mL vial was added 1-(2-chloro-3'-fluoro-5-methoxy-[1,1'-biphenyl]-4-yl)-3-hydroxy-N-(isoxazol-3-yl)-N-(4-methoxybenzyl)isoquinoline-6-sulfonamide (95 mg, 0.147 mmol) in TFA (3676 µl). The reaction mixture was warmed to 80° C. and stirred for 1 h. After cooling to rt, the reaction mixture was concentrated in vacuo. The crude material was purified by reverse-phase preparative HPLC using 0.1% TFA in $CH_3CN/H_2O$, gradient 10% to 90% over 20 min to provide 1-(2-chloro-3'-fluoro-5-methoxy-[1,1'-biphenyl]-4-yl)-N-(isoxazol-3-yl)-3-oxo-2,3-dihydroisoquinoline-6-sulfonamide 2,2,2-trifluoroacetate as a yellow solid (9 mg, 10% yield). $^1H$ NMR (500 MHz, DMSO-$d_6$) δ 11.82 (br. s., 1H), 8.74 (d, J=1.71 Hz, 1H), 8.43 (s, 1H), 7.71 (d, J=8.98 Hz, 1H), 7.51-7.62 (m, 4H), 7.43 (d, J=7.37 Hz, 3H), 7.27-7.36 (m, 2H), 7.25 (d, J=1.82 Hz, 2H), 6.49 (d, J=1.76 Hz, 1H). m/z (ESI) 526.1 [M].

Example 395, 396 & 397 (Method 126)

1-(2-CHLORO-3'-FLUORO-5-METHOXY-[1,1'-BIPHENYL]-4-YL)-N-(ISOXAZOL-3-YL)-2-METHYL-3-OXO-2,3-DIHYDROISOQUINOLINE-6-SULFONAMIDE(395), (P)-1-(2-CHLORO-3'-FLUORO-5-METHOXY-[1,1'-BIPHENYL]-4-YL)-N-(ISOXAZOL-3-YL)-2-METHYL-3-OXO-2,3-DIHYDROISOQUINOLINE-6-SULFONAMIDE (396) AND (M)-1-(2-CHLORO-3'-FLUORO-5-METHOXY-[1,1'-BIPHENYL]-4-YL)-N-(ISOXAZOL-3-YL)-2-METHYL-3-OXO-2,3-DIHYDROISOQUINOLINE-6-SULFONAMIDE (397)

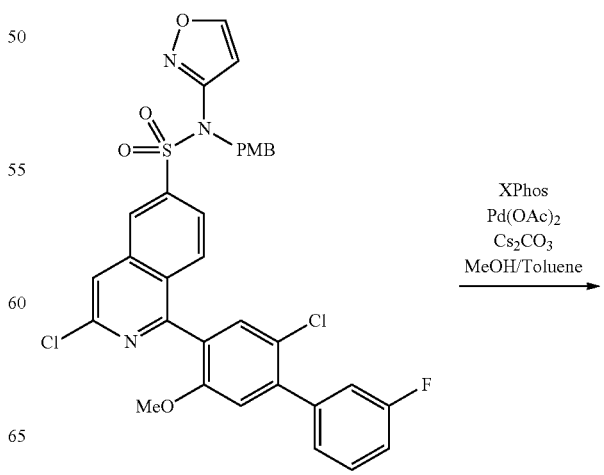

443

-continued

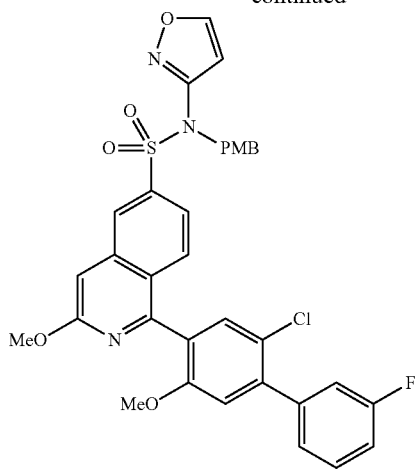

1) MeI, NaI MeCN, 80° C.
2) TFA

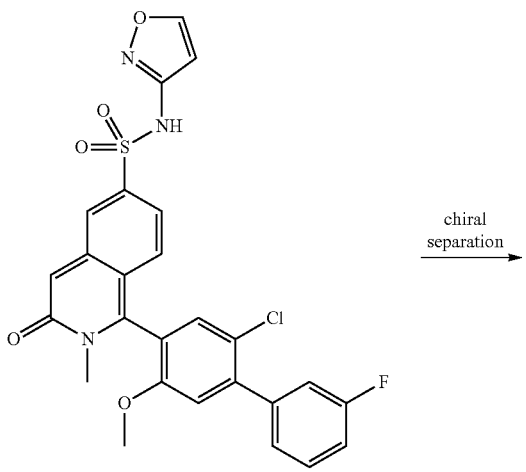

chiral separation

444

-continued

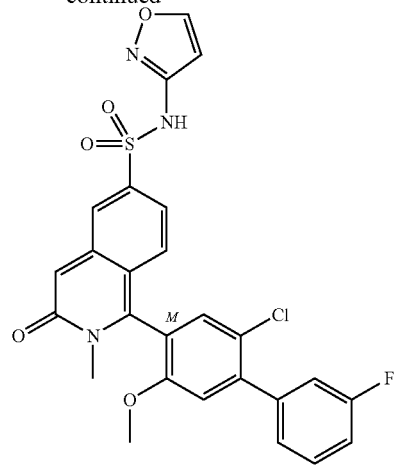

STEP 1: 1-(2-CHLORO-3'-FLUORO-5-METHOXY-[1,1'-BIPHENYL]-4-YL)-N-(ISOXAZOL-3-YL)-3-METHOXY-N-(4-METHOXYBENZYL)ISOQUINOLINE-6-SULFONAMIDE

A glass microwave reaction vessel was charged with 3-chloro-1-(2-chloro-3'-fluoro-5-methoxy-[1,1'-biphenyl]-4-yl)-N-(isoxazol-3-yl)-N-(4-methoxybenzyl)isoquinoline-6-sulfonamide (436 mg, 0.656 mmol, made via method 125, step 1), palladium (ii) acetate (14.73 mg, 0.066 mmol), cesium carbonate (321 mg, 0.984 mmol), and 2-di-tert-butylphosphino-2',4',6'-triisopropylbiphenyl (55.7 mg, 0.131 mmol). The vial was capped and was evacuated and backfilled with $N_2$ (2×). The solvents MeOH (656 µl) and toluene (656 µl) were added under vacuum followed by backfilling of $N_2$. The reaction mixture was stirred and heated in a heating block at 100° C. for 3 h. After cooling to rt, the crude material was absorbed onto a plug of silica gel and purified by chromatography through a Redi-Sep pre-packed silica gel column (12 g), eluting with a gradient of 0% to 10% MeOH in $CH_2Cl_2$, to provide 1-(2-chloro-3'-fluoro-5-methoxy-[1,1'-biphenyl]-4-yl)-N-(isoxazol-3-yl)-3-methoxy-N-(4-methoxybenzyl)isoquinoline-6-sulfonamide (210 mg, 0.318 mmol, 48.5% yield). m/z (ESI) 660.2 [M].

STEP 2: 1-(2-CHLORO-3'-FLUORO-5-METHOXY-[1,1'-BIPHENYL]-4-YL)-N-(ISOXAZOL-3-YL)-N-(4-METHOXYBENZYL)-2-METHYL-3-OXO-2,3-DIHYDROISOQUINOLINE-6-SULFONAMIDE

To a 2 ml microwave vial, was added 1-(2-chloro-3'-fluoro-5-methoxy-[1,1'-biphenyl]-4-yl)-N-(isoxazol-3-yl)-3-methoxy-N-(4-methoxybenzyl)isoquinoline-6-sulfonamide (210 mg, 0.318 mmol) in MeCN (1591 µl sodium iodide (191 mg, 1.273 mmol) and iodomethane (395 µl, 6.36 mmol) at rt. The reaction mixture was heated at 80° C. for 2 days. After cooling to rt, the crude material was absorbed onto a plug of silica gel and purified by chromatography through a Redi-Sep pre-packed silica gel column (12 g), eluting with a gradient of 0% to 10% MeOH in $CH_2Cl_2$, to provide 1-(2-chloro-3'-fluoro-5-methoxy-[1,1'-biphenyl]-4-yl)-N-(isoxazol-3-yl)-N-(4-methoxybenzyl)-2-methyl-3-oxo-2,3-dihydroisoquinoline-6-sulfonamide (190 mg, 0.288 mmol, 90% yield). m/z (ESI) 660.0 [M].

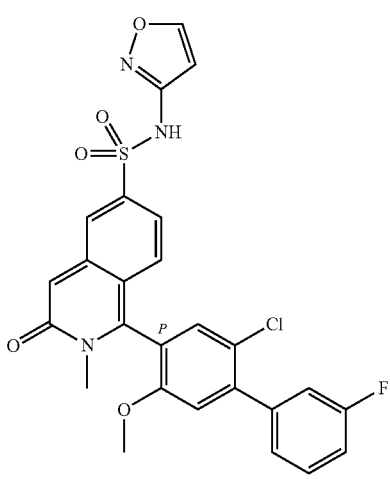

STEP 3: 1-(2-CHLORO-3'-FLUORO-5-METHOXY-[1,1'-BIPHENYL]-4-YL)-N-(ISOX-AZOL-3-YL)-2-METHYL-3-OXO-2,3-DIHYDROISOQUINOLINE-6-SULFONAMIDE

To a 1 mL vial was added 1-(2-chloro-3'-fluoro-5-methoxy-[1,1'-biphenyl]-4-yl)-N-(isoxazol-3-yl)-N-(4-methoxybenzyl)-2-methyl-3-oxo-2,3-dihydroisoquinoline-6-sulfonamide (190 mg, 0.288 mmol) in TFA (3598 µl). The reaction mixture was warmed to 80° C. for 1 h. After cooling to rt, the reaction mixture was concentrated in vacuo. The crude material was purified by reverse-phase preparative HPLC using 0.1% TFA in $CH_3CN/H_2O$, gradient 10% to 90% over 20 min to provide 1-(2-chloro-3'-fluoro-5-methoxy-[1,1'-biphenyl]-4-yl)-N-(isoxazol-3-yl)-2-methyl-3-oxo-2,3-dihydroisoquinoline-6-sulfonamide 2,2,2-trifluoroacetate as a yellow solid (120 mg, 64% yield). $^1$H NMR (400 MHz, DMSO-$d_6$) δ 11.79-11.93 (brs, 1H), 8.77 (d, J=1.76 Hz, 1H), 8.08 (d, J=1.76 Hz, 1H), 7.71 (s, 1H), 7.60 (dt, J=6.41, 8.04 Hz, 1H), 7.41-7.50 (m, 2H), 7.28-7.39 (m, 2H), 7.08-7.14 (m, 1H), 6.97-7.07 (m, 2H), 6.48 (d, J=1.76 Hz, 1H), 3.80 (s, 3H), 3.39-3.44 (m, 3H). m/z (ESI) 540.0 [M].

The racemic product was separated via Chiralpak AD-H column (45% MeOH/55% CO2) to give (P)-1-(2-chloro-3'-fluoro-5-methoxy-[1,1'-biphenyl]-4-yl)-N-(isoxazol-3-yl)-2-methyl-3-oxo-2,3-dihydroisoquinoline-6-sulfonamide and (M)-1-(2-chloro-3'-fluoro-5-methoxy-[1,1'-biphenyl]-4-yl)-N-(isoxazol-3-yl)-2-methyl-3-oxo-2,3-dihydroisoquinoline-6-sulfonamide. Data for peak 1: $^1$H NMR (400 MHz, DMSO-$d_6$) δ 11.79-11.93 (brs, 1H), 8.77 (d, J=1.76 Hz, 1H), 8.08 (d, J=1.76 Hz, 1H), 7.71 (s, 1H), 7.60 (dt, J=6.41, 8.04 Hz, 1H), 7.41-7.50 (m, 2H), 7.28-7.39 (m, 2H), 7.08-7.14 (m, 1H), 6.97-7.07 (m, 2H), 6.48 (d, J=1.76 Hz, 1H), 3.80 (s, 3H), 3.39-3.44 (m, 3H). m/z (ESI) 540.0 [M]. Data for peak 2: $^1$H NMR (400 MHz, DMSO-$d_6$) δ 11.79-11.93 (brs, 1H), 8.77 (d, J=1.76 Hz, 1H), 8.08 (d, J=1.76 Hz, 1H), 7.71 (s, 1H), 7.60 (dt, J=6.41, 8.04 Hz, 1H), 7.41-7.50 (m, 2H), 7.28-7.39 (m, 2H), 7.08-7.14 (m, 1H), 6.97-7.07 (m, 2H), 6.48 (d, J=1.76 Hz, 1H), 3.80 (s, 3H), 3.39-3.44 (m, 3H). m/z (ESI) 540.0 [M].

Example 398 (Method 127)

4-(2-CHLORO-3'-FLUORO-5-METHOXY-[1,1'-BIPHENYL]-4-YL)-N-(ISOXAZOL-3-YL)-3-OXO-2,3-DIHYDROISOQUINOLINE-7-SULFONAMIDE

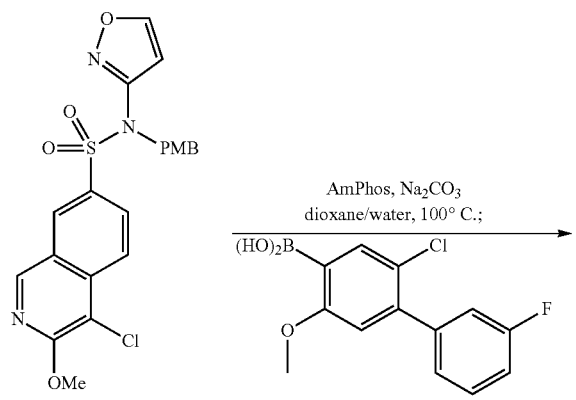

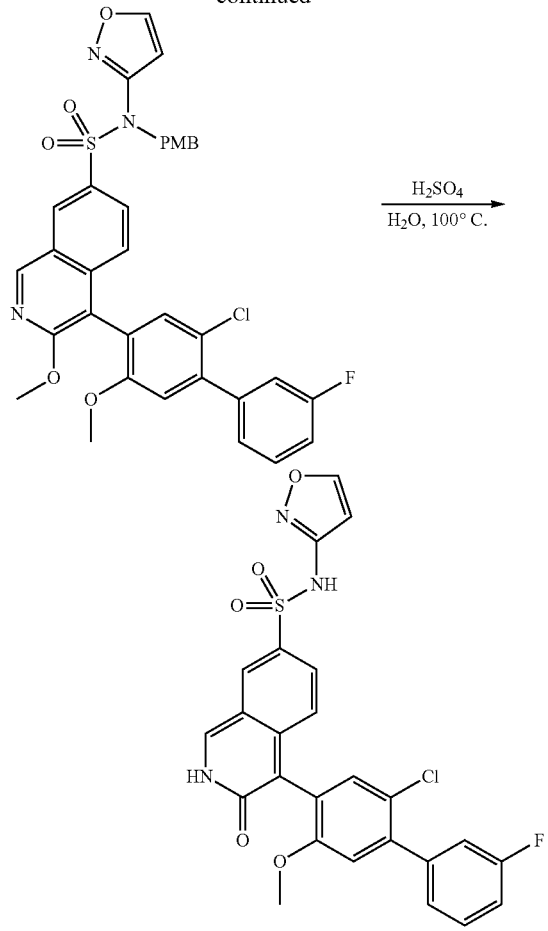

STEP 1: 4-(2-CHLORO-3'-FLUORO-5-METHOXY-[1,1'-BIPHENYL]-4-YL)-N-(ISOX-AZOL-3-YL)-3-METHOXY-N-(4-METHOXY-BENZYL)ISOQUINOLINE-7-SULFONAMIDE

A vial was charged with 4-chloro-N-(isoxazol-3-yl)-3-methoxy-N-(4-methoxybenzyl)isoquinoline-7-sulfonamide (282 mg, 0.613 mmol), (2-chloro-3'-fluoro-5-methoxy-[1,1'-biphenyl]-4-yl)boronic acid (172 mg, 0.613 mmol). Pd(AmPhos)2Cl2 (43.4 mg, 0.061 mmol), potassium phosphate (390 mg, 1.840 mmol), Dioxane (3066 µl), and Water (1022 µl). The vial was sealed and heated in a heating block at 100° C. for 2 h. After cooling to rt, the crude material was absorbed onto a plug of silica gel and purified by chromatography through a Redi-Sep pre-packed silica gel column (12 g), eluting with a gradient of 0% to 100% EtOAc in hexane, to provide 4-(2-chloro-3'-fluoro-5-methoxy-[1,1'-biphenyl]-4-yl)-N-(isoxazol-3-yl)-3-methoxy-N-(4-methoxybenzyl)isoquinoline-7-sulfonamide (200 mg, 0.303 mmol, 49.4% yield) as white solid. m/z (ESI) 660.2 [M].

STEP 2: 4-(2-CHLORO-3'-FLUORO-5-METHOXY-[1,1'-BIPHENYL]-4-YL)-N-(ISOX-AZOL-3-YL)-3-OXO-2,3-DIHYDROISOQUINO-LINE-7-SULFONAMIDE

To a solution of 4-(2-chloro-3'-fluoro-5-methoxy-[1,1'-biphenyl]-4-yl)-N-(isoxazol-3-yl)-3-methoxyisoquinoline- 7-sulfonamide (10 mg, 0.019 mmol) in water (617 µl) was added sulfuric acid (296 µl, 5.56 mmol) at rt. The reaction mixture was heated to 100° C. in a heating block for 16 h. The reaction mixture was concentrated in vacuo. The residue was extracted with EtOAc (3×). The combined organic layers were concentrated in vacuo. The crude material was purified by reverse-phase preparative HPLC using 0.1% TFA in $CH_3CN/H_2O$, gradient 15% to 90% over 20 min to provide 4-(2-chloro-3'-fluoro-5-methoxy-[1,1'-biphenyl]-4-yl)-N-(isoxazol-3-yl)-3-oxo-2,3-dihydroisoquinoline-7-sulfonamide 2,2,2-trifluoroacetate as a yellow solid (8 mg, 81% yield). $^1$H NMR (500 MHz, DMSO-d6) δ 11.67 (s, 1H), 9.12-9.21 (m, 1H), 8.73 (s, 1H), 8.62 (br. s., 1H), 7.75 (br. s., 1H), 7.54-7.63 (m, 1H), 7.38-7.47 (m, 3H), 7.27-7.37 (m, J=8.60 Hz, 2H), 7.20 (s, 1H), 6.46 (s, 1H), 3.69 (s, 4H). m/z (ESI) 526.0 [M].

Example 399 (Method 128)

1-(4-FLUORO-2-METHOXY-5-(2-PYRIDINYL)PHENYL)-N-3-ISOXAZOLYL-6-ISOQUINOLINE-SULFONAMIDE

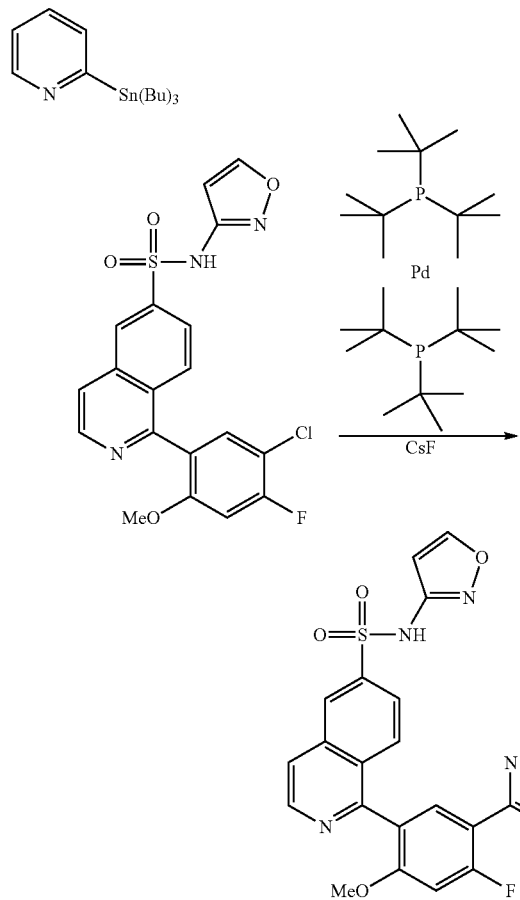

A pressure flask was charged with 1-(5-chloro-4-fluoro-2-methoxyphenyl)-N-(isoxazol-3-yl)isoquinoline-6-sulfonamide (100 mg, 0.230 mmol), cesium fluoride (18.72 µl, 0.507 mmol), bis(tri-t-butylphosphine)palladium (0) (11.78 mg, 0.023 mmol), 2-(tributylstannyl)pyridine (110 mg, 0.300 mmol), and 1,4-dioxane (Solvent Volume: 1.1 mL). The mixture was purged with argon and the flask was sealed. The reaction was heated to 100° C. for 18 hr. After cooling to rt, the reaction mixture was filtered. The crude material was purified by reverse-phase preparative HPLC using 0.1% TFA in $CH_3CN/H_2O$, gradient 10% to 90% over 20 min to provide a material that was contaminated with possibly $tBu_3P$ ligand. The material was further purified by chromatography on silica gel (4-g Redi-Sep Gold column, 0-10% MeOH/EtOAc) to give 1-(4-fluoro-2-methoxy-5-(pyridin-2-yl)phenyl)-N-(isoxazol-3-yl)isoquinoline-6-sulfonamide 2,2,2-trifluoroacetate as a pale yellow solid (5 mg, 4% yield). $^1$H NMR (400 MHz, MeOH) δ 8.52-8.71 (m, 3H), 8.43 (d, J=1.76 Hz, 1H), 7.79-8.11 (m, 6H), 7.34 (ddd, J=1.32, 4.92, 7.36 Hz, 1H), 7.15 (d, J=13.11 Hz, 1H), 6.51 (d, J=1.86 Hz, 1H), 3.76 (s, 3H). m/z (ESI) 477.0 [M+1].

Example 400 (Method 129)

1-(2-CHLORO-3'-FLUORO-5-METHOXY-4-BIPHENYLYL)-3-CYANO-N-3-ISOXAZOLYL-6-ISOQUINOLINESULFONAMIDE

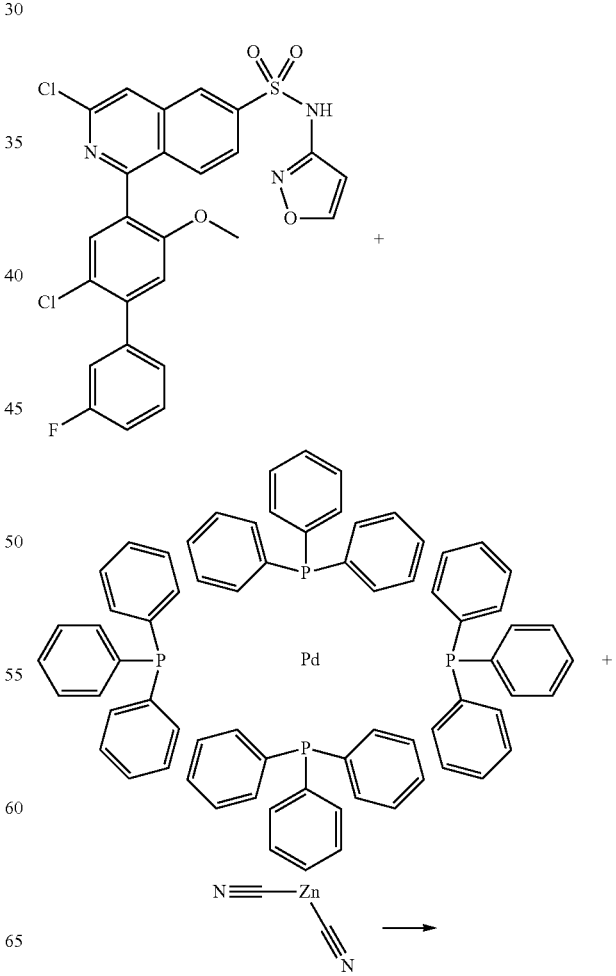

449

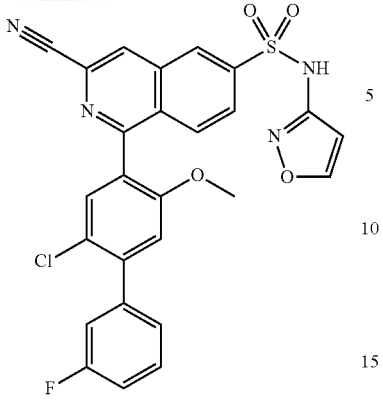

450

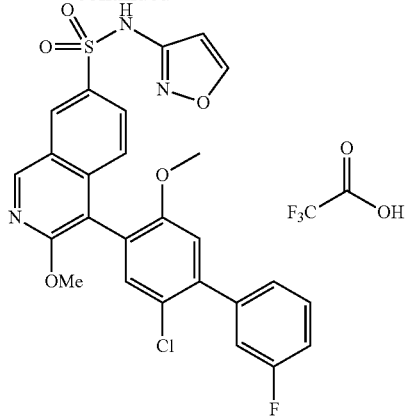

In a 2 mL sealed tube, added 3-chloro-1-(2-chloro-3'-fluoro-5-methoxy-[1,1'-biphenyl]-4-yl)-N-(isoxazol-3-yl)isoquinoline-6-sulfonamide (0.109 g, 0.200 mmol, prepared via method 125), dicyanozinc (0.023 g, 0.200 mmol) and $(Ph_3P)_4Pd$ (0.023 g, 0.020 mmol) in DMF (Solvent Volume: 0.667 ml), purged solvent with nitrogen for 5 minutes, sealed. The vessel was heated to 120° C. in a heating block for 2 days. After cooling to rt, the crude mixture was subject to HPLC purification using 0.1% TFA in ACN and water as mobile phase to provide 1-(2-chloro-3'-fluoro-5-methoxy-[1,1'-biphenyl]-4-yl)-3-cyano-N-(isoxazol-3-yl)isoquinoline-6-sulfonamide 2,2,2-trifluoroacetate (5 mg, 4% yield). $^1$H NMR (400 MHz, MeOH) δ 8.76 (d, J=1.86 Hz, 1H), 8.64 (s, 1H), 8.48 (d, J=1.86 Hz, 1H), 8.18 (dd, J=1.86, 8.90 Hz, 1H), 7.99-8.05 (m, 1H), 7.66-7.77 (m, 1H), 7.48-7.60 (m, 3H), 7.40 (td, J=1.28, 7.70 Hz, 1H), 7.34 (ddd, J=1.47, 2.47, 9.85 Hz, 1H), 7.14-7.26 (m, 3H), 6.55 (d, J=1.86 Hz, 1H), 3.74 (s, 3H). m/z (ESI) 534.9 [M].

Example 401 (Method 130)

4-(2-CHLORO-3'-FLUORO-5-METHOXY-[1,1'-BIPHENYL]-4-YL)-N-(ISOXAZOL-3-YL)-3-METHOXYISOQUINOLINE-7-SULFONAMIDE

To a 1 mL vial was added 4-(2-chloro-3'-fluoro-5-methoxy-[1,1'-biphenyl]-4-yl)-N-(isoxazol-3-yl)-3-methoxy-N-(4-methoxybenzyl)isoquinoline-7-sulfonamide (90 mg, 0.136 mmol) in TFA (1704 μl). The reaction mixture was warmed to 80° C. and stirred for 1 h. After cooling to rt, the reactin mixture was concentrated in vacuo. The crude material was absorbed onto a plug of silica gel and purified by chromatography through a Redi-Sep pre-packed silica gel column (12 g), eluting with a gradient of 0% to 10% MeOH in $CH_2Cl_2$, to provide 4-(2-chloro-3'-fluoro-5-methoxy-[1,1'-biphenyl]-4-yl)-N-(isoxazol-3-yl)-3-methoxyisoquinoline-7-sulfonamide 2,2,2-trifluoroacetate (87 mg, 0.133 mmol, 98% yield) as tan solid. $^1$H NMR (500 MHz, DMSO-$d_6$) δ 11.74 (br. s., 1H), 9.42 (s, 1H), 8.75 (dd, J=1.60, 19.88 Hz, 2H), 7.90 (dd, J=1.82, 9.08 Hz, 1H), 7.53-7.61 (m, 1H), 7.41-7.51 (m, 4H), 7.27-7.34 (m, 1H), 7.23 (s, 1H), 6.48 (d, J=1.66 Hz, 1H), 3.97 (s, 3H), 3.69 (s, 3H). m/z (ESI) 540.0 [M].

Example 402 (Method 131)

4-(2-CHLORO-3'-FLUORO-5-METHOXY-[1,1'-BIPHENYL]-4-YL)-N-(ISOXAZOL-3-YL)-2-METHYL-3-OXO-2,3-DIHYDROISOQUINOLINE-7-SULFONAMIDE

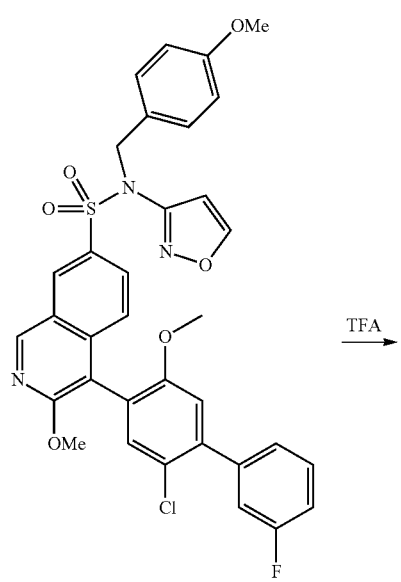

TFA →

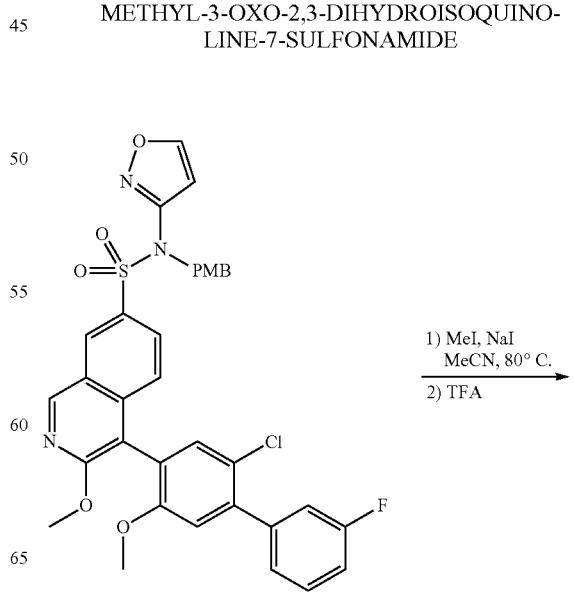

1) MeI, NaI
MeCN, 80° C.
2) TFA →

-continued

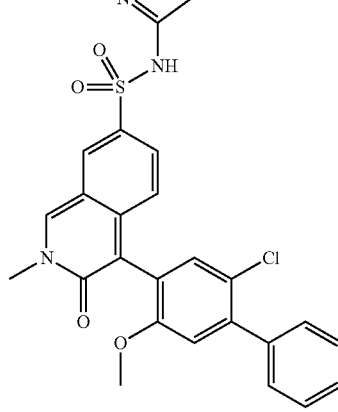

STEP 1: 4-(2-CHLORO-3'-FLUORO-5-METHOXY-[1,1'-BIPHENYL]-4-YL)-N-(ISOXAZOL-3-YL)-N-(4-METHOXYBENZYL)-2-METHYL-3-OXO-2,3-DIHYDROISOQUINOLINE-7-SULFONAMIDE

To a 2 ml microwave vial, was added 4-(2-chloro-3'-fluoro-5-methoxy-[1,1'-biphenyl]-4-yl)-N-(isoxazol-3-yl)-3-methoxy-N-(4-methoxybenzyl)isoquinoline-7-sulfonamide (180 mg, 0.273 mmol) in MeCN (1363 µl), sodium iodide (163 mg, 1.091 mmol) and iodomethane (339 µl, 5.45 mmol) at rt. The reaction mixture was heated at 80° C. for 4 d. After cooling to rt, the crude material was absorbed onto a plug of silica gel and purified by chromatography through a Redi-Sep pre-packed silica gel column (12 g), eluting with a gradient of 0% to 10% MeOH in CH2CL2, to provide 4-(2-chloro-3'-fluoro-5-methoxy-[1,1'-biphenyl]-4-yl)-N-(isoxazol-3-yl)-N-(4-methoxybenzyl)-2-methyl-3-oxo-2,3-dihydroisoquinoline-7-sulfonamide as yellow solid. m/z (ESI) 560.0 [M].

STEP 2: 4-(2-CHLORO-3'-FLUORO-5-METHOXY-[1,1'-BIPHENYL]-4-YL)-N-(ISOXAZOL-3-YL)-2-METHYL-3-OXO-2,3-DIHYDROISOQUINOLINE-7-SULFONAMIDE

To a 1 mL vial was added 4-(2-chloro-3'-fluoro-5-methoxy-[1,1'-biphenyl]-4-yl)-N-(isoxazol-3-yl)-N-(4-methoxybenzyl)-2-methyl-3-oxo-2,3-dihydroisoquinoline-7-sulfonamide (70 mg, 0.106 mmol) in TFA (1326 µl). The reaction mixture was warmed to 80° C. and stirred for 45 min. After cooling to rt, the reaction mixture was concentrated in vacuo. The crude material was absorbed onto a plug of silica gel and purified by chromatography through a Redi-Sep pre-packed silica gel column (12 g), eluting with a gradient of 0% to 10% MeOH in $CH_2Cl_2$, to provide 4-(2-chloro-3'-fluoro-5-methoxy-[1,1'-biphenyl]-4-yl)-N-(isoxazol-3-yl)-2-methyl-3-oxo-2,3-dihydroisoquinoline-7-sulfonamide 2,2,2-trifluoroacetate as yellow solid (57 mg, 83% yield). $^1$H NMR (500 MHz, DMSO-$d_6$) δ 11.61 (br. s., 1H), 9.22 (s, 1H), 8.73 (d, J=1.66 Hz, 1H), 8.30 (s, 1H), 7.52-7.60 (m, 1H), 7.46 (dd, J=1.82, 9.51 Hz, 1H), 7.37-7.43 (m, 2H), 7.32 (s, 1H), 7.26-7.31 (m, 1H), 7.17 (s, 1H), 6.98 (d, J=9.51 Hz, 1H), 6.43 (d, J=1.60 Hz, 1H). m/z (ESI) 540.2 [M].

Example 403 (Method 132)

1-(2,3'-DIFLUORO-5-METHOXY-[1,1'-BIPHENYL]-4-YL)-N-(ISOXAZOL-3-YL)-N,2-DIMETHYL-3-OXO-2,3-DIHYDROISOQUINOLINE-6-SULFONAMIDE

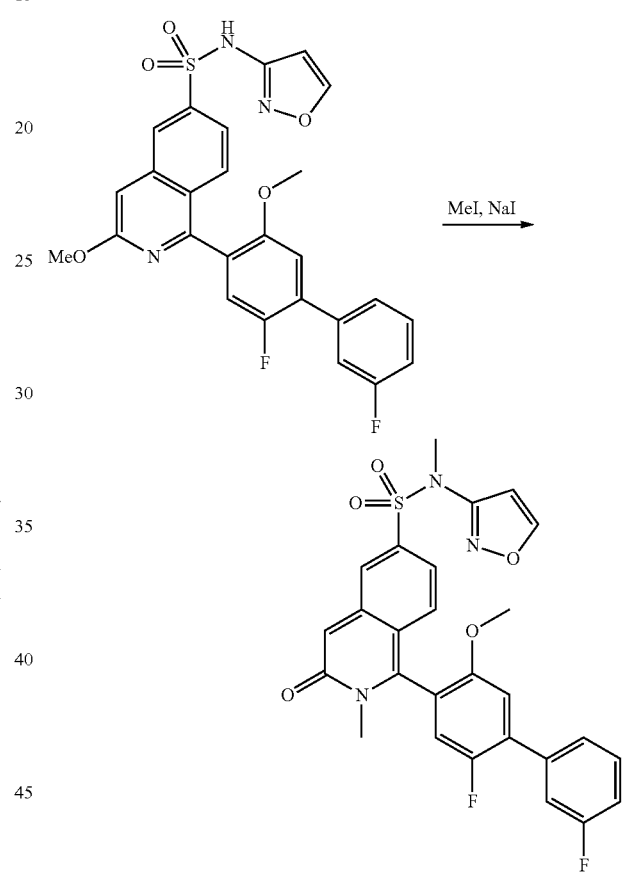

To a 2 mL microwave vial, was added 1-(2,3'-difluoro-5-methoxy-[1,1'-biphenyl]-4-yl)-N-(isoxazol-3-yl)-3-methoxyisoquinoline-6-sulfonamide (20 mg, 0.038 mmol) in MeCN (191 µl), sodium iodide (17.18 mg, 0.115 mmol) and iodomethane (14.24 µl, 0.229 mmol) at rt. The reaction mixture was heated at 45° C. in a heating block for 5 d. After cooling to rt, the reaction mixture was filtered. The crude material was purified by reverse phase HPLC using 0.1% NH4OH in ACN and water as mobile phase (4 mg, 21% yield). $^1$H NMR (400 MHz, CHLOROFORM-d) δ 8.29 (d, J=1.76 Hz, 1H), 7.84-7.88 (m, 1H), 7.47-7.57 (m, 1H), 7.40-7.45 (m, 1H), 7.33-7.38 (m, 1H), 7.28 (s, 4H), 7.19 (ddt, J=0.98, 2.54, 8.36 Hz, 1H), 7.09-7.14 (m, 2H), 7.07 (d, J=9.29 Hz, 2H), 6.98 (s, 1H), 6.88 (d, J=1.86 Hz, 1H), 6.82 (dd, J=1.76, 9.29 Hz, 1H), 3.82 (s, 3H), 3.63 (s, 3H). m/z (ESI) 538.2 [M+1].

Example 435

4-(2-CHLORO-3',5'-DIFLUORO-5-METHOXY-[1,1'-BIPHENYL]-4-YL)-N-(PYRIMIDIN-2-YL)QUINAZOLINE-7-SULFONAMIDE

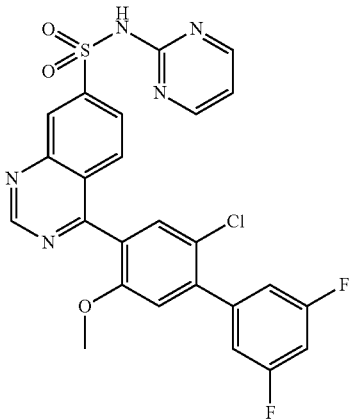 [SMILES: COc1cc(-c2cc(F)cc(F)c2)c(Cl)cc1-c1ncnc2cc(S(=O)(=O)Nc3ncccn3)ccc12]

The title compound was prepared via method 78 except that (3,5-difluorophenyl)boronic acid was used instead of (3-chloro-4-fluorophenyl)boronic acid in Step 4 to afford 4-(2-chloro-3',5'-difluoro-5-methoxy-[1,1'-biphenyl]-4-yl)-N-(pyrimidin-2-yl)quinazoline-7-sulfonamide (0.097 g, 0.180 mmol, 91% yield) as a light yellow solid. $^1$H NMR (400 MHz, DMSO-$d_6$) δ=9.52 (s, 1 H), 8.62 (s, 1 H), 8.53 (d, J=4.9 Hz, 2 H), 8.40 (s, 1 H), 8.17 (dd, J=1.8, 8.9 Hz, 1 H), 7.94 (d, J=8.8 Hz, 1 H), 7.70 (s, 1 H), 7.45-7.32 (m, 5 H), 7.06 (t, J=4.7 Hz, 1 H), 5.76 (s, 1 H), 3.75 (s, 3 H). m/z (ESI) 540.1 (M+H)$^+$.

Example 436

4-(2,4'-DICHLORO-5-METHOXY-3'-METHYL-[1,1'-BIPHENYL]-4-YL)-N-(PYRIMIDIN-2-YL)QUINAZOLINE-7-SULFONAMIDE

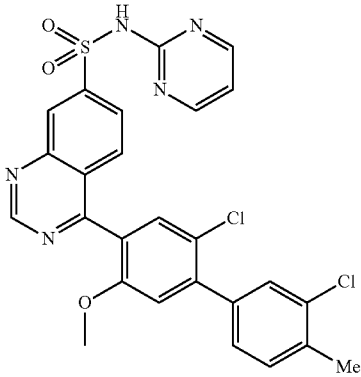 [SMILES: COc1cc(-c2ccc(C)c(Cl)c2)c(Cl)cc1-c1ncnc2cc(S(=O)(=O)Nc3ncccn3)ccc12]

The title compound was prepared via method 78 except that (4-chloro-3-methylphenyl)boronic acid was used instead of (3-chloro-4-fluorophenyl)boronic acid in Step 4 to afford 4-(2,4'-dichloro-5-methoxy-3'-methyl-[1,1'-biphenyl]-4-yl)-N-(pyrimidin-2-yl)quinazoline-7-sulfonamide (0.101 g, 0.183 mmol, 93% yield) as a light yellow solid. $^1$H NMR (400 MHz, DMSO-$d_6$) δ=9.51 (s, 1 H), 8.61 (s, 1 H), 8.52 (d, J=4.9 Hz, 2 H), 8.16 (dd, J=1.8, 8.8 Hz, 1 H), 7.95 (d, J=8.9 Hz, 1 H), 7.67 (s, 1 H), 7.60-7.55 (m, 2 H), 7.43 (td, J=1.1, 8.3 Hz, 1 H), 7.29 (s, 1 H), 7.05 (br. s., 1 H), 3.73 (s, 3 H), 2.44 (s, 3 H). m/z (ESI) 554.2 (M+H)$^+$.

Example 437

4-(2,3'-DICHLORO-5-METHOXY-[1,1'-BIPHENYL]-4-YL)-N-(PYRIMIDIN-2-YL)QUINAZOLINE-7-SULFONAMIDE

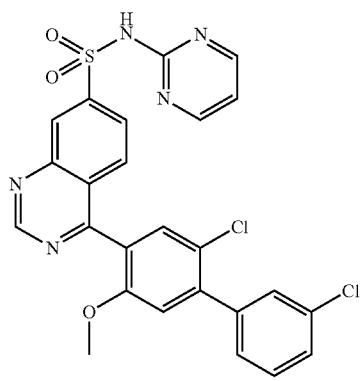 [SMILES: COc1cc(-c2cccc(Cl)c2)c(Cl)cc1-c1ncnc2cc(S(=O)(=O)Nc3ncccn3)ccc12]

The title compound was prepared via method 78 except that (3-chlorophenyl)boronic acid was used instead of (3-chloro-4-fluorophenyl)boronic acid in Step 4 to afford 4-(2,3'-dichloro-5-methoxy-[1,1'-biphenyl]-4-yl)-N-(pyrimidin-2-yl)quinazoline-7-sulfonamide (0.100 g, 0.186 mmol, 94% yield) as a light yellow solid. $^1$H NMR (400 MHz, DMSO-$d_6$) δ=9.52 (s, 1 H), 8.61 (d, J=1.2 Hz, 1 H), 8.53 (d, J=5.0 Hz, 2 H), 8.17 (dd, J=1.8, 8.8 Hz, 1 H), 7.96 (d, J=8.8 Hz, 1 H), 7.68 (s, 1 H), 7.67-7.64 (m, 1 H), 7.59-7.55 (m, 3 H), 7.33 (s, 1 H), 7.06 (t, J=4.8 Hz, 1 H), 3.74 (s, 3 H). m/z (ESI) 540.1 (M+H)$^+$.

Example 438

4-(3',5'-DIFLUORO-5-METHOXY-2-METHYL-[1,1'-BIPHENYL]-4-YL)-N-(PYRIMIDIN-2-YL)QUINAZOLINE-7-SULFONAMIDE

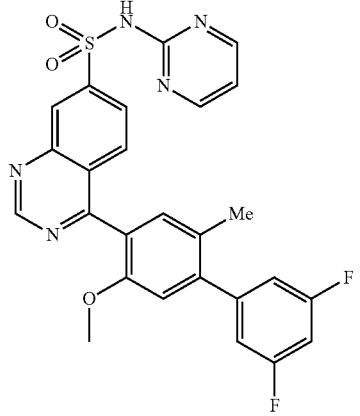 [SMILES: COc1cc(-c2cc(F)cc(F)c2)c(C)cc1-c1ncnc2cc(S(=O)(=O)Nc3ncccn3)ccc12]

The title compound was prepared via method 89 except that (3,5-difluorophenyl)boronic acid was used instead of (3-chloro-4-fluorophenyl)boronic acid in Step 4 to afford 4-(3',5'-difluoro-5-methoxy-2-methyl-[1,1'-biphenyl]-4-yl)-N-(pyrimidin-2-yl)quinazoline-7-sulfonamide (0.053 g, 0.102 mmol, 75% yield) as an off-white solid. $^1$H NMR (400 MHz, DMSO-d$_6$) δ=9.49 (s, 1 H), 8.59 (s, 1 H), 8.51 (d, J=4.9 Hz, 2 H), 8.15 (dd, J=1.8, 8.9 Hz, 1 H), 7.92 (d, J=8.8 Hz, 1 H), 7.40 (s, 1 H), 7.36-7.24 (m, 3 H), 7.14 (s, 1 H), 7.04 (br. s., 1 H), 3.70 (s, 3 H), 2.26 (s, 3 H). m/z (ESI) 520.1 (M+H)$^+$.

Example 439

4-(4'-CHLORO-5-METHOXY-2,3'-DIMETHYL-[1,1'-BIPHENYL]-4-YL)-N-(PYRIMIDIN-2-YL)QUINAZOLINE-7-SULFONAMIDE

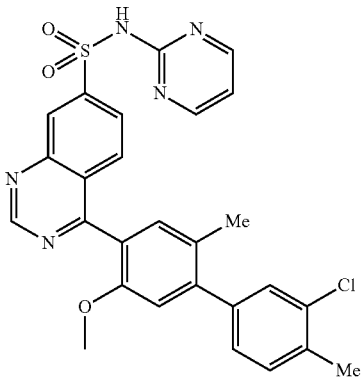 [SMILES: COc1cc(-c2ccc(C)c(Cl)c2)c(C)cc1-c1ncnc2cc(S(=O)(=O)Nc3ncccn3)ccc12]

The title compound was prepared via method 89 except that (4-chloro-3-methylphenyl)boronic acid was used instead of (3-chloro-4-fluorophenyl)boronic acid in Step 4 to afford 4-(4'-chloro-5-methoxy-2,3'-dimethyl-[1,1'-biphenyl]-4-yl)-N-(pyrimidin-2-yl)quinazoline-7-sulfonamide (0.056 g, 0.105 mmol, 51.2% yield) as a white solid. $^1$H NMR (500 MHz, DMSO-d$_6$) δ=2.22 (s, 4 H) 2.49 (br. s., 2 H) 3.68 (s, 4 H) 6.98 (t, J=4.81 Hz, 1 H) 7.07 (s, 1 H) 7.26-7.41 (m, 2 H) 7.47 (s, 1 H) 7.52 (d, J=8.14 Hz, 1 H) 7.91 (d, J=8.82 Hz, 1 H) 8.13 (dd, J=8.82, 1.58 Hz, 1 H) 8.47 (d, J=4.86 Hz, 2 H) 8.53-8.59 (m, 1 H) 9.47 (s, 1 H). m/z (ESI) 532.2 (M+H)$^+$.

Example 440

4-(3'-CHLORO-5-METHOXY-2-METHYL-[1,1'-BIPHENYL]-4-YL)-N-(PYRIMIDIN-2-YL)QUINAZOLINE-7-SULFONAMIDE

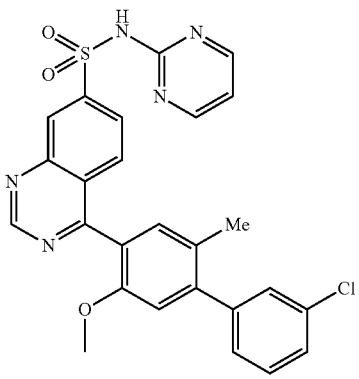 [SMILES: COc1cc(-c2cccc(Cl)c2)c(C)cc1-c1ncnc2cc(S(=O)(=O)Nc3ncccn3)ccc12]

The title compound was prepared via method 89 except that (3-chlorophenyl)boronic acid was used instead of (3-chloro-4-fluorophenyl)boronic acid in Step 4 to afford 4-(3'-chloro-5-methoxy-2-methyl-[1,1'-biphenyl]-4-yl)-N-(pyrimidin-2-yl)quinazoline-7-sulfonamide (0.018 g, 0.035 mmol, 17.06% yield) as a light yellow solid. $^1$H NMR (400 MHz, DMSO-d$_6$) δ=9.49 (s, 1 H), 8.60 (s, 1 H), 8.52 (d, J=4.6 Hz, 2 H), 8.15 (d, J=8.8 Hz, 1 H), 7.94 (d, J=8.9 Hz, 1 H), 7.61-7.44 (m, 4 H), 7.39 (s, 1 H), 7.11 (s, 1 H), 7.05 (br. s., 1 H), 3.69 (s, 3 H), 2.23 (s, 3 H). m/z (ESI) 518.2 (M+H)$^+$.

Examples 441 & 442

(M)-4 4-(2-CHLORO-3'-FLUORO-5-METHOXY-[1,1'-BIPHENYL]-4-YL)-N-(ISOXAZOL-3-YL)-3-METHYLCINNOLINE-7-SULFONAMIDE (441) AND (P)-4-(2-CHLORO-3'-FLUORO-5-METHOXY-[1,1'-BIPHENYL]-4-YL)-N-(ISOXAZOL-3-YL)-3-METHYLCINNOLINE-7-SULFONAMIDE (442)

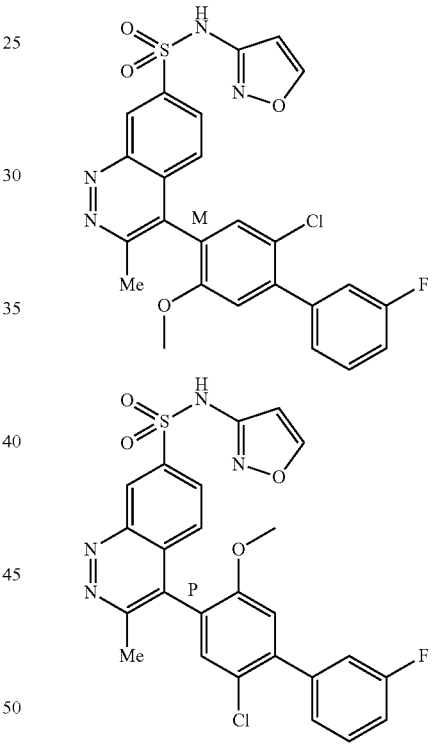

The title compound was prepared via method 79 except that 3-bromo-4-(2-chloro-3'-fluoro-5-methoxy-[1,1'-biphenyl]-4-yl)-N-(isoxazol-3-yl)cinnoline-7-sulfonamide was used instead of 3-bromo-4-(2-chloro-3'-fluoro-5-methoxy-[1,1'-biphenyl]-4-yl)-N-(isoxazol-3-yl)quinoline-7-sulfonamide. This material was purified by chiral SFC on Chiralpak AD-H column (35% MeOH/65% CO$_2$) to afford (M)-4-(2-chloro-3'-fluoro-5-methoxy-[1,1'-biphenyl]-4-yl)-N-(isoxazol-3-yl)-3-methylcinnoline-7-sulfonamide as Peak 1 and (P)-4-(2-chloro-3'-fluoro-5-methoxy-[1,1'-biphenyl]-4-yl)-N-(isoxazol-3-yl)-3-methylcinnoline-7-sulfonamide as Peak 2, both as off-white solids. Peak 1: $^1$H NMR (400 MHz, DMSO-d$_6$) δ=12.03 (br. s., 1 H), 8.94 (s, 1 H), 8.72 (s, 1 H), 8.10 (dd, J=1.9, 9.0 Hz, 1 H), 7.72 (d, J=9.0 Hz, 1 H), 7.62 (s, 1 H), 7.61-7.55 (m, 1 H), 7.49-7.43 (m, 2 H), 7.37-7.29 (m, 2 H), 6.52 (d, J=1.5 Hz, 1 H), 3.74 (s, 3 H), 2.71 (s, 3

H). m/z (ESI) 525.0 (M+H)⁺. Peak 2: ¹H NMR (400 MHz, DMSO-d₆) δ=12.03 (br. s., 1 H), 8.94 (s, 1 H), 8.72 (s, 1 H), 8.10 (dd, J=1.9, 9.0 Hz, 1 H), 7.72 (d, J=9.0 Hz, 1 H), 7.62 (s, 1 H), 7.61-7.55 (m, 1 H), 7.49-7.43 (m, 2 H), 7.37-7.29 (m, 2 H), 6.52 (d, J=1.5 Hz, 1 H), 3.74 (s, 3 H), 2.71 (s, 3 H). m/z (ESI) 525.0 (M+H)⁺.

Examples 443 & 444

(M)-4-(2-CHLORO-3'-FLUORO-5-METHOXY-[1,1'-BIPHENYL]-4-YL)-3-ETHYL-N-(ISOXAZOL-3-YL)CINNOLINE-7-SULFONAMIDE (443) AND (P)-4-(2-CHLORO-3'-FLUORO-5-METHOXY-[1,1'-BIPHENYL]-4-YL)-3-ETHYL-N-(ISOXAZOL-3-YL)CINNOLINE-7-SULFONAMIDE (444)

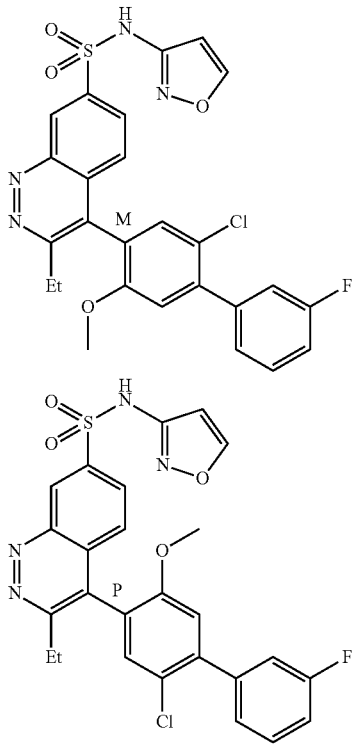

The title compound was prepared via method 80 except that 3-bromo-4-(2-chloro-3'-fluoro-5-methoxy-[1,1'-biphenyl]-4-yl)-N-(isoxazol-3-yl)cinnoline-7-sulfonamide was used instead of 3-bromo-4-(2-chloro-3'-fluoro-5-methoxy-[1,1'-biphenyl]-4-yl)-N-(isoxazol-3-yl)quinoline-7-sulfonamide. This material was purified by chiral SFC on Chiralpak AD-H column (35% MeOH/65% CO₂) to afford (M)-4-(2-chloro-3'-fluoro-5-methoxy-[1,1'-biphenyl]-4-yl)-3-ethyl-N-(isoxazol-3-yl)cinnoline-7-sulfonamide as Peak 1 and (P)-4-(2-chloro-3'-fluoro-5-methoxy-[1,1'-biphenyl]-4-yl)-3-ethyl-N-(isoxazol-3-yl)cinnoline-7-sulfonamide as Peak 2, both as off-white solids. Peak 1: ¹H NMR (400 MHz, DMSO-d₆)δ=12.03 (br. s., 1 H), 8.93 (br. s., 1 H), 8.69 (br. s., 1 H), 8.10 (d, J=8.3 Hz, 1 H), 7.72-7.54 (m, 3 H), 7.46 (d, J=7.9 Hz, 2 H), 7.33 (s, 2 H), 6.50 (br. s., 1 H), 3.72 (s, 3 H), 2.96 (d, J=8.2 Hz, 2 H), 1.29 (t, J=7.5 Hz, 3 H). m/z (ESI) 539.0 (M+H)⁺. Peak 2: ¹H NMR (400 MHz, DMSO-d₆) δ=12.03 (br. s., 1 H), 8.93 (br. s., 1 H), 8.69 (br. s., 1 H), 8.10 (d, J=8.3 Hz, 1 H), 7.72-7.54 (m, 3 H), 7.46 (d, J=7.9 Hz, 2 H), 7.33 (s, 2 H), 6.50 (br. s., 1 H), 3.72 (s, 3 H), 2.96 (d, J=8.2 Hz, 2 H), 1.29 (t, J=7.5 Hz, 3 H). m/z (ESI) 539.0 (M+H)⁺.

Example 445

4-(2-CHLORO-3'-FLUORO-5-METHOXY-[1,1'-BIPHENYL]-4-YL)-N-(ISOXAZOL-3-YL)-3-METHOXYCINNOLINE-7-SULFONAMIDE

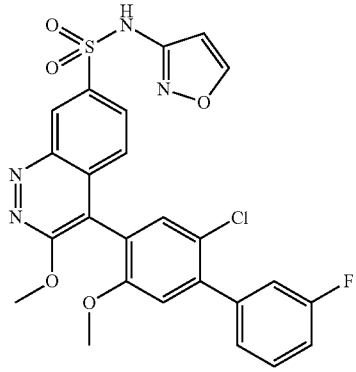 [SMILES: COc1cc(-c2cccc(F)c2)c(Cl)cc1-c1c(OC)nnc2cc(S(=O)(=O)Nc3ccon3)ccc12]

The title compound was prepared via method 83 except that 3-bromo-4-(2-chloro-3'-fluoro-5-methoxy-[1,1'-biphenyl]-4-yl)-N-(isoxazol-3-yl)cinnoline-7-sulfonamide was used instead of 3-bromo-4-(2-chloro-3'-fluoro-5-methoxy-[1,1'-biphenyl]-4-yl)-N-(isoxazol-3-yl)quinoline-7-sulfonamide. The material was purified via Gilson HPLC (50-95% MeCN:H2O w/0.1% TFA modifier). The product fractions were partitioned between ethyl acetate and water. The aqueous layer was extracted with ethyl acetate, and the combined organic layers were dried with sodium sulfate, filtered, and concentrated to afford 4-(2-chloro-3'-fluoro-5-methoxy-[1,1'-biphenyl]-4-yl)-N-(isoxazol-3-yl)-3-methoxycinnoline-7-sulfonamide (0.012 g, 0.022 mmol, 10.47% yield) as an orange solid. ¹H NMR (400 MHz, DMSO-d₆) δ=11.99 (br. s., 1 H), 8.86 (s, 1 H), 8.76 (s, 1 H), 7.99 (d, J=9.0 Hz, 1 H), 7.69 (d, J=8.9 Hz, 1 H), 7.64-7.54 (m, 2 H), 7.44 (d, J=6.3 Hz, 2 H), 7.38-7.25 (m, 2 H), 6.55 (s, 1 H), 4.24 (s, 3 H), 3.72 (s, 3 H). m/z (ESI) 541.1 (M+H)⁺.

Example 446

3-AMINO-4-(2-CHLORO-3'-FLUORO-5-METHOXY-[1,1'-BIPHENYL]-4-YL)-N-(ISOXAZOL-3-YL)CINNOLINE-7-SULFONAMIDE

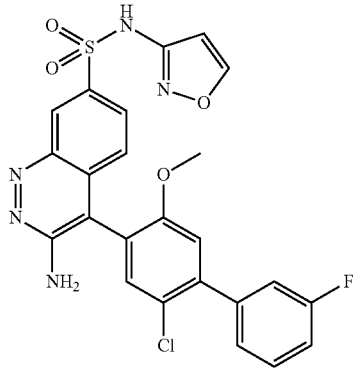 [SMILES: COc1cc(-c2cccc(F)c2)c(Cl)cc1-c1c(N)nnc2cc(S(=O)(=O)Nc3ccon3)ccc12]

The title compound was prepared via method 82 except that -bromo-4-(2-chloro-3'-fluoro-5-methoxy-[1,1'-biphenyl]-4-yl)-N-(isoxazol-3-yl)cinnoline-7-sulfonamide was used instead of 3-bromo-4-(2-chloro-3'-fluoro-5-methoxy-[1,1'-biphenyl]-4-yl)-N-(isoxazol-3-yl)quinoline-7-sulfonamide to afford 3-amino-4-(2-chloro-3'-fluoro-5-methoxy-[1,1'-biphenyl]-4-yl)-N-(isoxazol-3-yl)cinnoline-7-sulfonamide (0.031 g, 0.059 mmol, 27.8% yield) as a yellow solid. ¹H NMR (400 MHz, DMSO-d₆) δ=11.79 (s, 1 H), 8.74 (d, J=1.8 Hz, 1 H), 8.64 (d, J=1.8 Hz, 1 H), 7.79 (dd, J=2.0, 9.1 Hz, 1 H), 7.64-7.54 (m, 1 H), 7.48 (s, 1 H), 7.45-7.26 (m, 5 H), 6.52 (d, J=1.8 Hz, 1 H), 3.73 (s, 3 H), 1.10 (s, 2 H). m/z (ESI) 526.1 (M+H)⁺.

Example 451

4-(3'-CHLORO-2,5'-DIFLUORO-5-METHOXY-[1,1'-BIPHENYL]-4-YL)-N-(ISOXAZOL-3-YL)-1-OXO-1,2-DIHYDROISOQUINOLINE-7-SULFONAMIDE

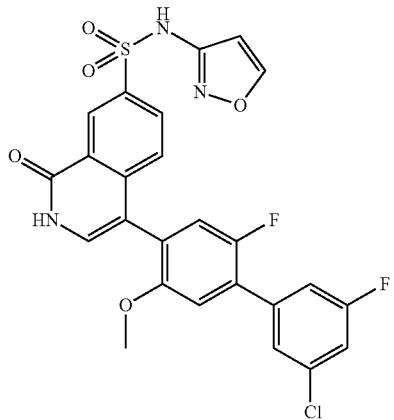 [SMILES: COc1cc(-c2cc(F)cc(Cl)c2)c(F)cc1-c1c[nH]c(=O)c2cc(S(=O)(=O)Nc3ccon3)ccc12]

The title compound was prepared via method 87 except that (3'-chloro-2,5'-difluoro-5-methoxy-[1,1'-biphenyl]-4-yl)boronic acid was used instead of (3'-chloro-2-fluoro-5-methoxy-[1,1'-biphenyl]-4-yl)boronic acid to afford 4-(3'-chloro-2,5'-difluoro-5-methoxy-[1,1'-biphenyl]-4-yl)-N-(isoxazol-3-yl)-1-oxo-1,2-dihydroisoquinoline-7-sulfonamide (0.046 g, 0.085 mmol, 20.73% yield) as an off-white solid. ¹H NMR (400 MHz, DMSO-d₆) δ=11.90 (d, J=6.1 Hz, 1 H), 11.75 (s, 1 H), 8.73 (dd, J=2.0, 12.2 Hz, 2 H), 8.04 (dd, J=2.2, 8.7 Hz, 1 H), 7.62 (d, J=1.3 Hz, 1 H), 7.59-7.51 (m, 2 H), 7.39-7.28 (m, 4 H), 6.45 (d, J=1.8 Hz, 1 H), 3.75 (s, 3 H). m/z (ESI) 544.1 (M+H)⁺.

Example 452

4-(4'-CHLORO-2-FLUORO-5-METHOXY-3'-METHYL-[1,1'-BIPHENYL]-4-YL)-N-(ISOXAZOL-3-YL)-1-OXO-1,2-DIHYDROISOQUINOLINE-7-SULFONAMIDE

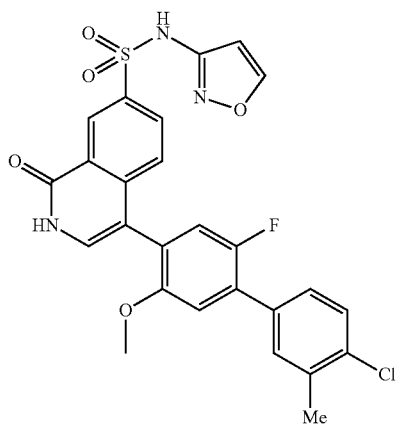 [SMILES: COc1cc(-c2ccc(Cl)c(C)c2)c(F)cc1-c1c[nH]c(=O)c2cc(S(=O)(=O)Nc3ccon3)ccc12]

The title compound was prepared via method 87 except that (4'-chloro-2-fluoro-5-methoxy-3'-methyl-[1,1'-biphenyl]-4-yl)boronic acid was used instead of (3'-chloro-2-fluoro-5-methoxy-[1,1'-biphenyl]-4-yl)boronic acid to afford 4-(4'-chloro-2-fluoro-5-methoxy-3'-methyl-[1,1'-biphenyl]-4-yl)-N-(isoxazol-3-yl)-1-oxo-1,2-dihydroisoquinoline-7-sulfonamide (0.056 g, 0.104 mmol, 25.4% yield) as a white solid. ¹H NMR (400 MHz, DMSO-d₆) δ=11.88 (d, J=6.0 Hz, 1H), 11.74 (s, 1H), 8.73 (dd, J=1.9, 12.4 Hz, 2H), 8.04 (dd, J=2.1, 8.7 Hz, 1H), 7.66 (s, 1H), 7.59-7.54 (m, 1H), 7.53-7.48 (m, 1H), 7.40-7.27 (m, 3H), 7.23 (d, J=6.7 Hz, 1H), 6.45 (d, J=1.8 Hz, 1H), 3.73 (s, 3H), 2.43 (s, 3H). m/z (ESI) 540.0 (M+H)⁺.

Example 453

4-(3'-CHLORO-2,5'-DIFLUORO-5-METHOXY-[1,1'-BIPHENYL]-4-YL)-N-(ISOXAZOL-3-YL)-2-METHYL-1-OXO-1,2-DIHYDROISOQUINOLINE-7-SULFONAMIDE

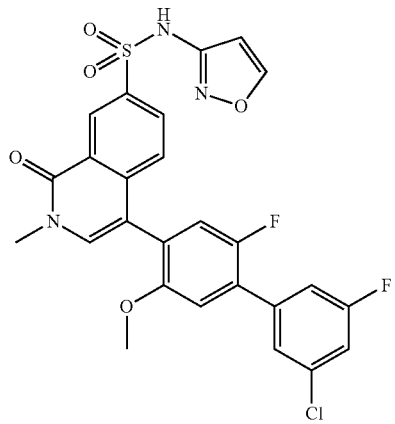 [SMILES: COc1cc(-c2cc(F)cc(Cl)c2)c(F)cc1-c1cn(C)c(=O)c2cc(S(=O)(=O)Nc3ccon3)ccc12]

The title compound was prepared via method 88 except that (3'-chloro-2,5'-difluoro-5-methoxy-[1,1'-biphenyl]-4-yl)boronic acid was used instead of (3'-chloro-2-fluoro-5-methoxy-[1,1'-biphenyl]-4-yl)boronic acid in Step 1 to afford 4-(3'-chloro-2,5'-difluoro-5-methoxy-[1,1'-biphenyl]-4-yl)-N-(isoxazol-3-yl)-2-methyl-1-oxo-1,2-dihydroisoquinoline-7-sulfonamide (0.045 g, 0.081 mmol, 53.6% yield) as an off-white solid. ¹H NMR (400 MHz, DMSO-d₆) δ=11.75 (s, 1 H), 8.77-8.74 (m, 2 H), 8.05 (dd, J=2.1, 8.7 Hz, 1 H), 7.75 (s, 1 H), 7.63 (d, J=1.2 Hz, 1 H), 7.56 (dd, J=1.8, 8.8 Hz, 2 H), 7.39-7.32 (m, 3 H), 6.45 (d, J=1.8 Hz, 1 H), 3.76 (s, 3 H), 3.58 (s, 3 H). m/z (ESI) 558.0 (M+H)⁺.

Example 454

4-(4'-CHLORO-2-FLUORO-5-METHOXY-3'-METHYL-[1,1'-BIPHENYL]-4-YL)-N-(ISOXAZOL-3-YL)-2-METHYL-1-OXO-1,2-DIHYDROISOQUINOLINE-7-SULFONAMIDE

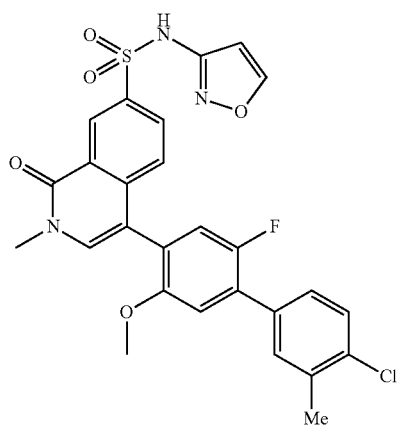 [SMILES: COc1cc(-c2ccc(Cl)c(C)c2)c(F)cc1-c1cn(C)c(=O)c2cc(S(=O)(=O)Nc3ccon3)ccc12]

The title compound was prepared via method 88 except that (4'-chloro-2-fluoro-5-methoxy-3'-methyl-[1,1'-biphenyl]-4-yl)boronic acid was used instead of (3'-chloro-2-fluoro-5-methoxy-[1,1'-biphenyl]-4-yl)boronic acid in Step 1 to afford 4-(4'-chloro-2-fluoro-5-methoxy-3'-methyl-[1,1'-biphenyl]-4-yl)-N-(isoxazol-3-yl)-2-methyl-1-oxo-1,2-dihydroisoquinoline-7-sulfonamide (0.064 g, 0.116 mmol, 76% yield) as a white solid. $^1$H NMR (400 MHz, DMSO-$d_6$) δ=11.75 (s, 1H), 8.74 (d, J=1.7 Hz, 2H), 8.09-7.99 (m, 1H), 7.74 (s, 1H), 7.66 (s, 1H), 7.60-7.48 (m, 2H), 7.38 (d, J=8.6 Hz, 1H), 7.31 (d, J=10.6 Hz, 1H), 7.24 (d, J=6.6 Hz, 1H), 6.44 (d, J=1.6 Hz, 1H), 3.73 (s, 3H), 3.58 (s, 3H), 2.43 (s, 3H). m/z (ESI) 554.1 (M+H)$^+$.

Examples 455 & 456

(P)-1-(2-CHLORO-3'-FLUORO-5-METHOXY-[1,1'-BIPHENYL]-4-YL)-N-(ISOXAZOL-3-YL)-2-OXO-1,2-DIHYDROQUINOLINE-6-SULFONAMIDE (455) and (M)-1-(2-CHLORO-3'-FLUORO-5-METHOXY-[1,1'-BIPHENYL]-4-YL)-N-(ISOXAZOL-3-YL)-2-OXO-1,2-DIHYDROQUINOLINE-6-SULFONAMIDE (456)

These compounds were prepared via method 65 using 3-fluorophenyl boronic acid as the boronic acid. The racemic product was separated via chiral SFC on a Chiralpak AS-H column (30% MeOH/70% $CO_2$) to give (P)-1-(2-chloro-3'-fluoro-5-methoxy-[1,1'-biphenyl]-4-yl)-N-(isoxazol-3-yl)-2-oxo-1,2-dihydroquinoline-6-sulfonamide as peak 1 and (M)-1-(2-chloro-3'-fluoro-5-methoxy-[1,1'-biphenyl]-4-yl)-N-(isoxazol-3-yl)-2-oxo-1,2-dihydroquinoline-6-sulfonamide as peak 2. Both materials were obtained as white solids. Data for peak 1: $^1$H NMR (400 MHz, DMSO-$d_6$) δ=11.68 (s, 1 H), 8.74 (d, J=1.76 Hz, 1 H), 8.39 (d, J=2.25 Hz, 1 H), 8.24 (d, J=9.49 Hz, 1 H), 7.88 (dd, J=8.95, 2.20 Hz, 1 H), 7.70 (s, 1 H), 7.56-7.63 (m, 1 H), 7.42-7.47 (m, 2 H), 7.30-7.38 (m, 2 H), 6.88 (d, J=9.00 Hz, 1 H), 6.83 (d, J=9.68 Hz, 1 H) 6.46 (d, J=1.86 Hz, 1 H), 3.74 (s, 3 H). m/z (ESI) 526.0 (M+H)$^+$. Data for peak 2: $^1$H NMR (400 MHz, DMSO-$d_6$) δ=11.68 (s, 1 H), 8.73 (d, J=1.76 Hz, 1 H), 8.38 (d, J=2.15 Hz, 1 H), 8.24 (d, J=9.49 Hz, 1 H), 7.88 (dd, J=8.95, 2.20 Hz, 1 H), 7.70 (s, 1 H), 7.60 (td, J=8.09, 6.41 Hz, 1 H), 7.43-7.48 (m, 2 H), 7.30-7.37 (m, 2 H), 6.88 (d, J=9.00 Hz, 1 H), 6.83 (d, J=9.68 Hz, 1 H), 6.45 (d, J=1.76 Hz, 1 H), 3.74 (s, 3 H). m/z (ESI) 526.0 (M+H)$^+$.

Example 479

4-(2-CHLORO-3'-FLUORO-5-METHOXY-4-BIPHENYLYL)-N-(5-FLUORO-2-PYRIDINYL)-7-QUINAZOLINESULFONAMIDE

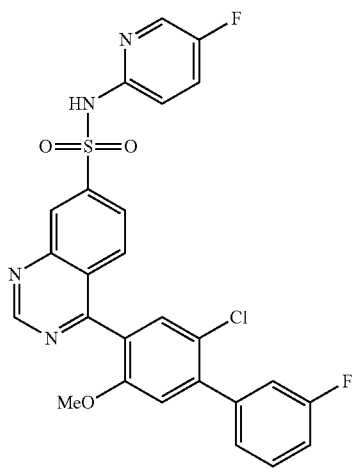 [SMILES: COc1cc(-c2cccc(F)c2)c(Cl)cc1-c1ncnc2cc(S(=O)(=O)Nc3ccc(F)cn3)ccc12]

4-(2-Chloro-3'-fluoro-5-methoxy-4-biphenylyl)-N-(5-fluoro-2-pyridinyl)-7-quinazolinesulfonamide was prepared from perfluorophenyl 4-(2-chloro-3'-fluoro-5-methoxy-[1,1'-biphenyl]-4-yl)quinazoline-7-sulfonate via method 100 using 2-amino-5-fluoropyridine instead of), isothiazol-3-amine $^1$H NMR (500 MHz, DMSO-$d_6$) δ 11.55 (br. s., 1H), 9.51 (s, 1H), 8.55 (d, J=1.23 Hz, 1H), 8.18 (d, J=2.94 Hz, 1H), 8.09 (dd, J=1.58, 8.79 Hz, 1H), 7.97 (d, J=8.82 Hz, 1H), 7.64-7.76 (m, 2H), 7.55-7.63 (m, 1H), 7.43 (d, J=7.75 Hz, 2H), 7.28-7.37 (m, 2H), 7.19 (dd, J=3.55, 9.00 Hz, 1H), 3.73 (s, 3H). m/z (ESI) 539.2 (M+H)$^+$.

Intermediate AM 4-(4-BROMO-5-FLUORO-2-METHOXYPHENYL)-N-(ISOXAZOL-3-YL)QUINAZOLINE-7-SULFONAMIDE

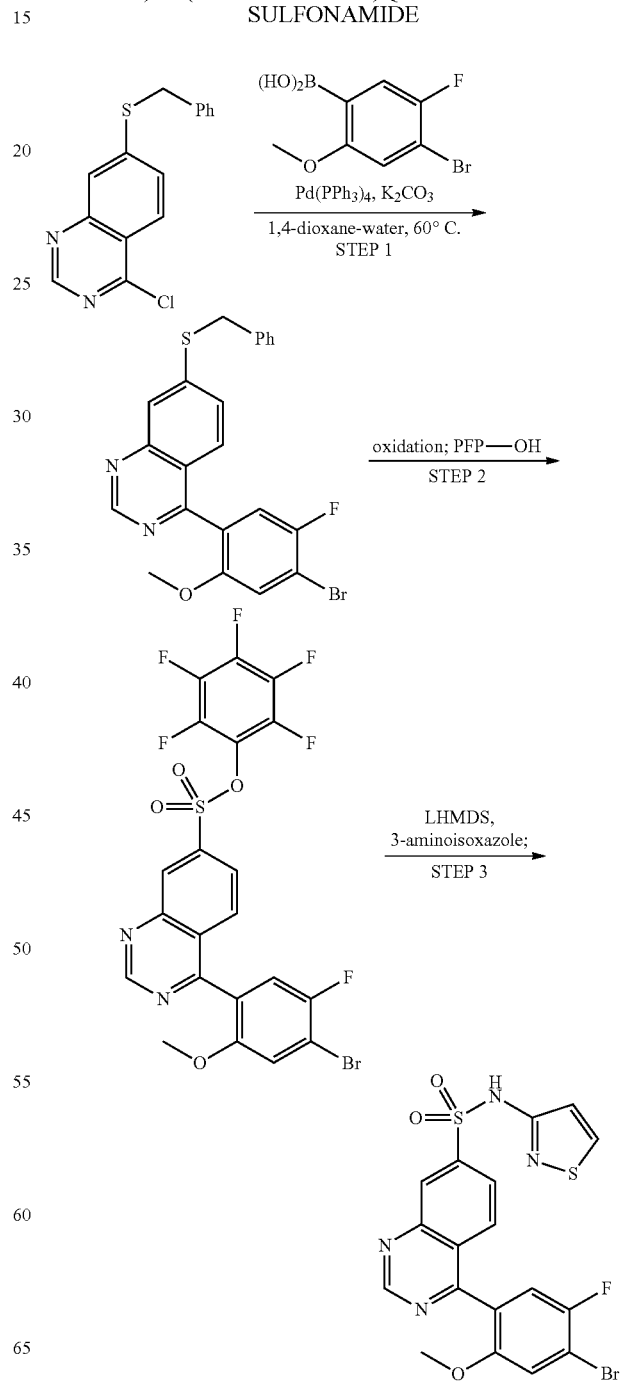

STEP 1: 7-(BENZYLTHIO)-4-(4-BROMO-5-FLUORO-2-METHOXYPHENYL)QUINAZOLINE

A RBF was charged with 7-(benzylthio)-4-chloroquinazoline (4.50 g, 12.55 mmol), (4-bromo-5-fluoro-2-methoxyphenyl)boronic acid (3.64 g, 13.18 mmol), and Pd(Ph₃P)₄ (1.451 g, 1.255 mmol). The flask was flushed with Ar (g), then 1,4-dioxane (47.1 ml) and water (15.69 ml) were added in sequence. The flask was fitted with a reflux condenser and heated to 60° C. overnight. The mixture was diluted with water and extracted with EtOAc (3×). The combined organic extracts were dried over sodium sulfate, filtered, and concentrated. The residue was purified by chromatography on silica gel (100-g Ultra SNAP column, 25-g silica gel loading column, 10-50% EtOAc/Heptane) to give 7-(benzylthio)-4-(4-bromo-5-fluoro-2-methoxyphenyl)quinazoline (2.7 g, 5.93 mmol, 47.2% yield) as a cream-colored solid. m/z (ESI) 455.0 (M+H)⁺.

STEP 2: PERFLUOROPHENYL 4-(4-BROMO-5-FLUORO-2-METHOXYPHENYL)QUINAZOLINE-7-SULFONATE

A RBF was charged with 7-(benzylthio)-4-(4-bromo-5-fluoro-2-methoxyphenyl)quinazoline (2.70 g, 5.93 mmol), DCM (46.5 ml), acetic acid (1.744 ml), and water (1.163 ml) to give clear, orange solution. The flask was cooled in an ice-water bath for 10 min, then 1,3-dichloro-5,5-dimethylimidazolidine-2,4-dione (3.50 g, 17.79 mmol) was added in one portion. After 20 min, 2,3,4,5,6-pentafluorophenol (1.637 g, 8.89 mmol) and triethylamine (3.31 ml, 23.72 mmol) (dropwise) were added in sequence. After another 20 min, the mixture was diluted water, then extracted with DCM (2×). The combined organic extracts were dried over sodium sulfate, filtered, and concentrated. The residue was purified by chromatography on silica gel (50-g Redi-Sep Gold column, 25-g silica gel loading column, 0-40% EtOAc/Heptane) to give perfluorophenyl 4-(4-bromo-5-fluoro-2-methoxyphenyl)quinazoline-7-sulfonate as an off-white solid. m/z (ESI) 579.0 (M+H)⁺.

STEP 3: 4-(4-BROMO-5-FLUORO-2-METHOXYPHENYL)-N-(ISOXAZOL-3-YL)QUINAZOLINE-7-SULFONAMIDE

A RBF was charged with perfluorophenyl 4-(4-bromo-5-fluoro-2-methoxyphenyl)quinazoline-7-sulfonate (1.109 g, 1.914 mmol), THF (9.57 ml), and isoxazol-3-amine (0.156 ml, 2.106 mmol) to give a clear, yellow solution. The flask was cooled in an ice-water bath for 10 min, then lithium bis(trimethylsilyl)amide (1M in THF) (4.02 ml, 4.02 mmol) was added dropwise. After another 10 min of stirring, the mixture was diluted with 1N aq. HCl and extracted with EtOAc (2×). The combined organic extracts were dried over sodium sulfate, filtered, and concentrated. The residue was purified by chromatography on silica gel (50-g SNAP Ultra column, 25-g silica gel loading column, 0-5% MeOH/DCM) to give 4-(4-bromo-5-fluoro-2-methoxyphenyl)-N-(isoxazol-3-yl)quinazoline-7-sulfonamide (0.815 g, 1.700 mmol, 89% yield) as a light-yellow foam. m/z (ESI) 479.0 (M+H)⁺.

Intermediate AN

(3'-CHLORO-3-FLUORO-5-METHOXY-[1,1'-BIPHENYL]-4-YL)BORONIC ACID

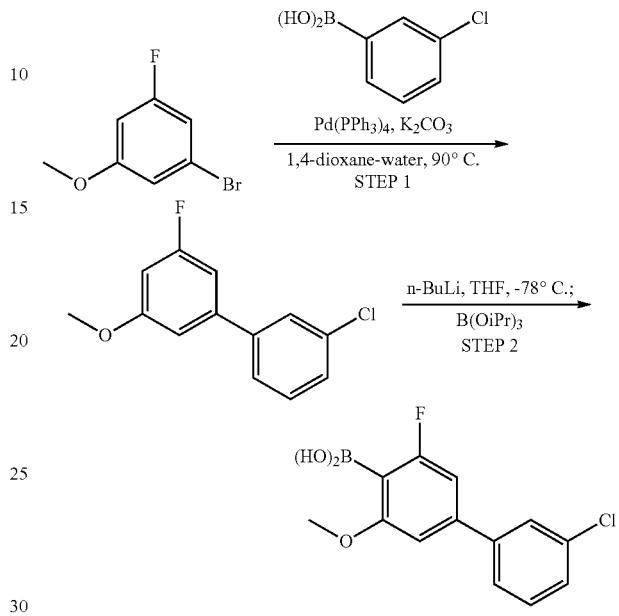

STEP 1: 3'-CHLORO-3-FLUORO-5-METHOXY-1,1'-BIPHENYL

A RBF was charged with 1-bromo-3-fluoro-5-methoxybenzene (2.104 g, 10.26 mmol). (3-chlorophenyl)boronic acid (1.765 g, 11.29 mmol) potassium carbonate (4.25 g, 30.8 mmol), and Pd(Ph₃P)₄ (0.593 g, 0.513 mmol). The flask was flushed with Ar (g), then 1,4-dioxane (25.7 ml) and water (8.55 ml) were added. A reflux condenser was attached, and the flask was lowered into a 90° C. heating bath for 45 min. The mixture was cooled to room temperature, diluted with water, and extracted with EtOAc (2×). The combined organic extracts were dried over sodium sulfate, filtered, and concentrated. The residue was purified by chromatography on silica gel (50-g SNAP Ultra column, 25-g silica gel column, 0-5% EtOAc/Heptane) to give 3'-chloro-3-fluoro-5-methoxy-1,1'-biphenyl (2.47 g, 10.44 mmol, 102% yield) as a clear oil containing about 10 wt % impurities.

STEP 2: (3'-CHLORO-3-FLUORO-5-METHOXY-[1,1'-BIPHENYL]-4-YL)BORONIC ACID

A RBF was charged with 3'-chloro-3-fluoro-5-methoxy-1,1'-biphenyl (513 mg, 2.168 mmol) and THF (7225 µl) to give a clear solution. The flask was cooled in a dry ice-acetone bath for 10 min, then n-butyllithium (1.8M in hexanes) (1445 µl, 2.60 mmol) was added dropwise. After 30 min, triisopropyl borate (597 µl, 2.60 mmol) was added dropwise, and the cooling bath was removed. After 10 min, the mixture was diluted with 2N aq. NaOH, and the resulting biphasic mixture was stirred for 40 min. The mixture was diluted with water and ether. The layers were separated, and the organic layer was extracted with water (1×). The combined aq. extracts were acidified with 2N aq. HCl (30 mL).

The resulting suspension was stirred for 20 min then filtered. The collected solid was washed with water (3×), then dried under a stream of N₂ (g) for 1 h to give (3'-chloro-3-fluoro-5-methoxy-[1,1'-biphenyl]-4-yl)boronic acid (147 mg, 0.524 mmol, 24.18% yield) as an off-white solid. m/z (ESI) 281.0 (M+H)⁺.

Intermediate AO

3'-CHLORO-3-FLUORO-4-IODO-5-METHOXY-1,1'-BIPHENYL

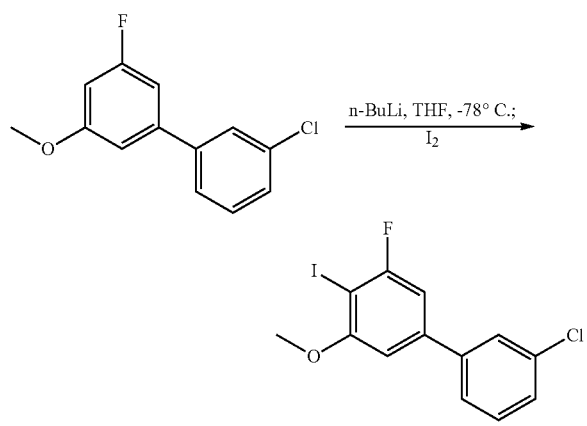

A RBF was charged with 3'-chloro-3-fluoro-5-methoxy-1,1'-biphenyl (577.6 mg, 2.441 mmol) and THF (8135 µl) to give a clear solution. The flask was cooled in a dry ice-acetone bath for 10 min, then n-butyllithium (1.8M in hexanes) (1627 µl, 2.93 mmol) was added dropwise. After 30 min, a solution of iodine (929 mg, 3.66 mmol) in THF (3 mL) was added dropwise. TLC after 5 min showed conversion to a slightly lower spot. The mixture was diluted with saturated aq. sodium thiosulfate solution and warmed to room temperature. The mixture was diluted with water and extracted with EtOAc (2×), and the combined organic extracts were dried over sodium sulfate, filtered, and concentrated. The residue was purified by chromatography on silica gel (25-g Ultra SNAP column, 0-5% EtOAc/Heptane) to give 3'-chloro-3-fluoro-4-iodo-5-methoxy-1,1'-biphenyl (687 mg, 1.895 mmol, 78% yield) as an off-white solid. ¹H NMR (400 MHz, DMSO-d₆)=7.87 (td, J=1.0, 1.8 Hz, 1 H), 7.74 (td, J=1.8, 7.0 Hz, 1 H), 7.55-7.43 (m, 2 H), 7.25 (dd, J=1.8, 9.1 Hz, 1 H), 7.14-7.07 (m, 1 H), 3.97 (s, 3 H).

Intermediate AQ

2-BROMO-5-IODO-4-METHOXYBENZONITRILE

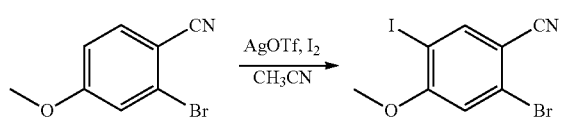

A RBF was charged with 2-bromo-4-methoxybenzonitrile (891 mg, 4.20 mmol, Matrix Scientific) and DCM (1.68E+04 µl) to give a clear solution. silver trifluoromethanesulfonate (1188 mg, 4.62 mmol) and iodine (1173 mg, 4.62 mmol) were added in sequence. The resulting mixture was stirred for 2 d. Additional portions of silver trifluoromethanesulfonate (1188 mg, 4.62 mmol) and iodine (1173 mg, 4.62 mmol) were added, and the mixture was stirred for another 5 h. The reaction mixture was then filtered through celite with the aid of DCM. The filtrate was shaken with saturated aq. sodium thiosulfate until the color disappeared. The biphasic mixture was diluted with water then the layers were separated. The aq. layer was extracted with DCM (2×). The combined organic extracts were dried over sodium sulfate, filtered, and concentrated. The residue was purified by chromatography on silica gel (40-g Redi-Sep Gold column, 25-g silica gel column, 5-30% EtOAc/Heptane) give 2-bromo-5-iodo-4-methoxybenzonitrile (811 mg, 2.400 mmol, 57.1% yield) as an off-white solid. m/z (ESI) 337.8 (M+H)⁺.

Intermediate AU

3-BROMO-4-(2-CHLORO-3'-FLUORO-5-METHOXY-[1,1'-BIPHENYL]-4-YL)-N-(ISOXAZOL-3-YL)QUINOLINE-7-SULFONAMIDE

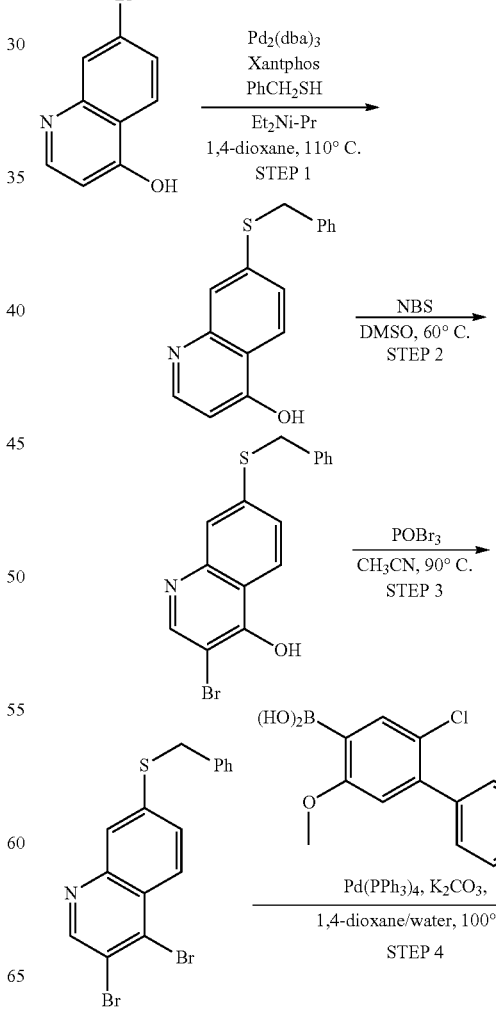

-continued

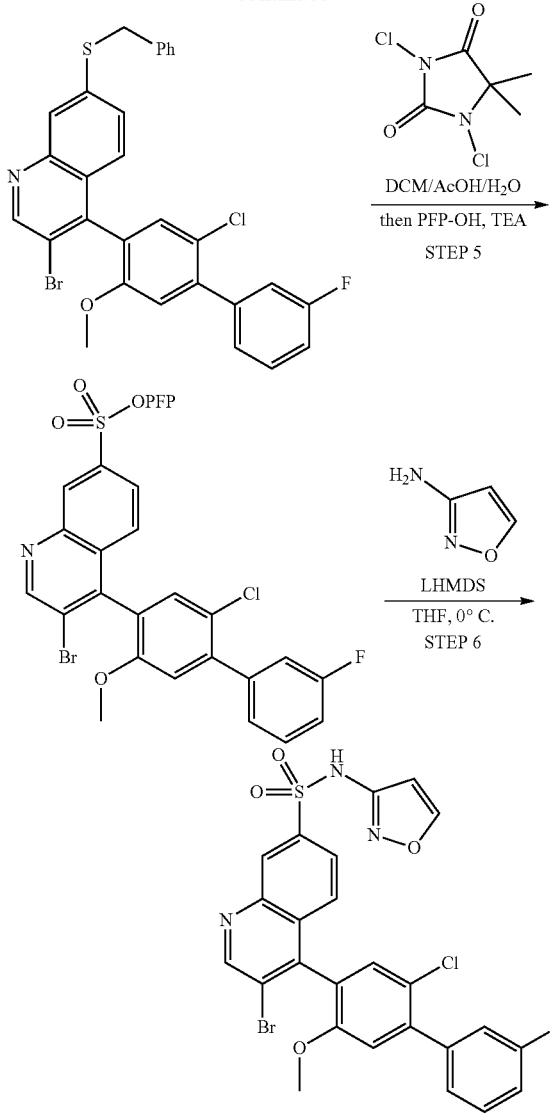

STEP 1: 7-(BENZYLTHIO)QUINOLIN-4-OL

A vial was charged with 7-bromoquinolin-4-ol (5.0 g, 22.32 mmol), xantphos (0.646 g, 1.116 mmol), and Pd$_2$(dba)$_3$ (0.511 g, 0.558 mmol). The flask was flushed with Ar (g), then dioxane (44.6 ml), benzyl mercaptan (2.90 ml, 24.55 mmol), and n,n-diisopropylethylamine (7.80 ml, 44.6 mmol) were added in sequence. The reaction was heated to 110° C. and stirred for 30 minutes. The reaction was diluted with water and filtered. The solids were washed with water and dried under a nitrogen blanket overnight. The solid was triturated with ethyl acetate and stirred for one hour. The solids were filtered, washed with ethyl acetate, and dried under a nitrogen blanket to afford 7-(benzylthio)quinolin-4-ol (6.09 g, 22.78 mmol, 100% yield) as a light yellow solid. m/z (ESI) 268.1 (M+H)$^+$.

STEP 2: 7-(BENZYLTHIO)-3-BROMOQUINOLIN-4-OL 7-(Benzylthio)quinolin-4-ol (1.0 g, 3.74 mmol) was dissolved in DMSO (17.00 ml) and water (1.700 ml). NBS (0.732 g, 4.11 mmol) was added and the reaction was heated to 60° C. and stirred for two hours. The reaction was diluted with water, stirred for 15 minutes, and filtered. The solids were washed with water and dried under a nitrogen blanket overnight to afford 7-(benzylthio)-3-bromoquinolin-4-ol (1.67 g, 4.82 mmol, 100% yield) as a tan solid. m/z (ESI) 348.0 (M+H)$^+$.

STEP 3: 7-(BENZYLTHIO)-3,4-DIBROMOQUINOLINE

A vial was charged with 7-(benzylthio)-3-bromoquinolin-4(1H)-one (5.23 g, 15.11 mmol), Acetonitrile (60.4 ml), and hunig's base (7.91 ml, 45.3 mmol). Phosphorus oxybromide (6.06 g, 21.15 mmol) was added and the reaction was stirred at 90° C. for four hours. The reaction was diluted with ethyl acetate and washed with water. The aqueous layer was extracted with ethyl acetate, and the combined organic layers were dried with sodium sulfate, filtered, and concentrated. The material was triturated in i-PrOH, filtered, and washed with i-PrOH. The solids were dried overnight under a nitrogen blanket to afford 7-(benzylthio)-3,4-dibromoquinoline (4.79 g, 11.71 mmol, 78% yield) as a yellow solid. m/z (ESI) 407.9 (M+H)$^+$.

STEP 4: 7-(BENZYLTHIO)-3-BROMO-4-(2-CHLORO-3'-FLUORO-5-METHOXY-[1,1'-BIPHENYL]-4-YL)QUINOLINE

A vial was charged with 7-(benzylthio)-3,4-dibromoquinoline (2.0 g, 4.89 mmol), (2-chloro-3'-fluoro-5-methoxy-[1,1'-biphenyl]-4-yl)boronic acid (2.057 g, 7.33 mmol), and tetrakis(triphenylphosphine)palladium(0) (0.282 g, 0.244 mmol). Dioxane (40.7 ml) and potassium hydroxide (1.5M aqueous solution) (6.52 ml, 9.78 mmol) were added, the vial was flushed with argon and sealed, and stirred at 90° C. overnight. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-50% EtOAc:Heptane) to afford 7-(benzylthio)-3-bromo-4-(2-chloro-3'-fluoro-5-methoxy-[1,1'-biphenyl]-4-yl)quinoline (2.08 g, 3.68 mmol, 75% yield) as an off-white solid. m/z (ESI) 564.0 (M+H)$^+$.

STEP 5: PERFLUOROPHENYL 3-BROMO-4-(2-CHLORO-3'-FLUORO-5-METHOXY-[1,1'-BIPHENYL]-4-YL)QUINOLINE-7-SULFONATE

A RBF was charged with 7-(benzylthio)-3-bromo-4-(2-chloro-3'-fluoro-5-methoxy-[1,1'-biphenyl]-4-yl)quinoline (2.08 g, 3.68 mmol), DCM (34.7 ml), acetic acid (1.300 ml), and water (0.866 ml) to give a thin suspension. The flask was cooled in an ice-bath for 10 min, then 1,3-dichloro-5,5-dimethylimidazolidine-2,4-dione (1.814 g, 9.21 mmol) was added in one portion, leading to a solution. The reaction was stirred for 15 minutes. 2,3,4,5,6-pentafluorophenol (0.771 ml, 7.36 mmol) was added followed by dropwise addition of triethylamine (1.283 ml, 9.21 mmol). The reaction was stirred for 30 minutes. The reaction was concentrated and purified via column chromatography (RediSep Gold 40 g, gradient elution 0-50% EtOAc:Heptane) to afford perfluorophenyl 3-bromo-4-(2-chloro-3'-fluoro-5-methoxy-[1,1'-biphenyl]-4-yl)quinoline-7-sulfonate (2.01 g, 2.92 mmol, 79% yield) as a white solid. m/z (ESI) 687.8 (M+H)$^+$.

STEP 6: 3-BROMO-4-(2-CHLORO-3'-FLUORO-5-METHOXY-[1,1'-BIPHENYL]-4-YL)-N-(ISOXAZOL-3-YL)QUINOLINE-7-SULFONAMIDE

A RBF was charged with perfluorophenyl 3-bromo-4-(2-chloro-3'-fluoro-5-methoxy-[1,1'-biphenyl]-4-yl)quinoline-7-sulfonate (1.15 g, 1.670 mmol), isoxazol-3-amine (0.136 ml, 1.836 mmol), and THF (8.35 ml) to give a clear solution. The flask was cooled to 0° C. for 10 min, then lithium bis(trimethylsilyl)amide (1M in THF) (3.67 ml, 3.67 mmol) was added dropwise. The reaction was stirred for 30 minutes. The reaction was diluted with 1N aq. HCl and EtOAc. The aqueous layer was extracted with ethyl acetate, and the combined organic layers were washed with 1N aq. HCl, washed with brine, dried with sodium sulfate, filtered, and concentrated to afford crude 3-bromo-4-(2-chloro-3'-fluoro-5-methoxy-[1,1'-biphenyl]-4-yl)-N-(isoxazol-3-yl)quinoline-7-sulfonamide (1.27 g, 2.157 mmol, 100% yield) as a light yellow solid. m/z (ESI) 587.9 (M+H)$^+$.

Intermediate AV

3-BROMO-4-(2-CHLORO-3'-FLUORO-5-METHOXY-[1,1'-BIPHENYL]-4-YL)-N-(ISOXAZOL-3-YL)CINNOLINE-7-SULFONAMIDE

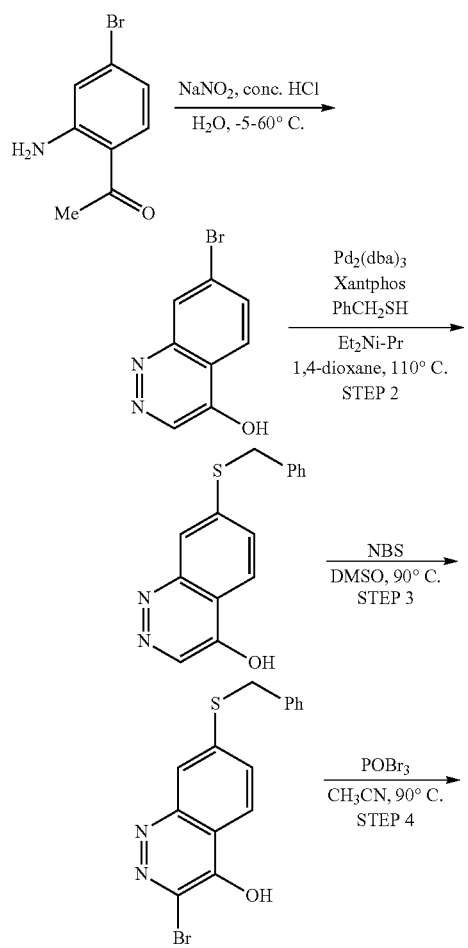

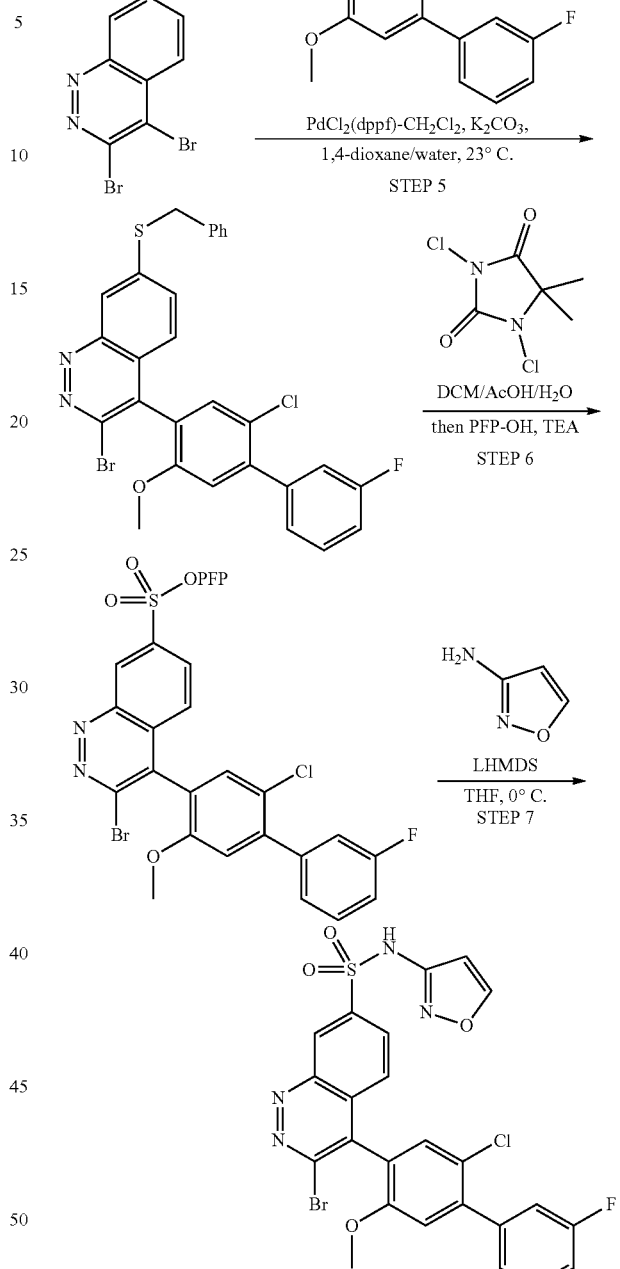

STEP 1: 7-BROMOCINNOLIN-4-OL 1-(2-amino-4-bromophenyl)ethanone (10.0 g, 46.7 mmol, Ark Pharm) was dissolved in concentrated HCl (270 ml, 3240 mmol) and water (46.7 ml) and cooled to −5° C. in an ice/brine bath. A solution of sodium nitrite (3.38 g, 49.1 mmol) in water (20 mL) was added slowly dropwise. The reaction was stirred for one hour, then the temperature was raised to 60° C. and the reaction was stirred overnight. The reaction was cooled to RT and filtered. The solids were suspended in water and solid sodium hydroxide was added until the pH~12. The solution was neutralized to pH~7 with concentrated HCl, resulting in a white precipitate. The solids were filtered, washed with water, and dried overnight under a nitrogen blanket to afford 7-bromocinnolin-4-ol (9.10 g, 40.4 mmol, 87% yield) as an off-white solid. m/z (ESI) 227.0 (M+H)+.

STEP 2: 7-(BENZYLTHIO)CINNOLIN-4(1H)-ONE

A flask was charged with 7-bromocinnolin-4(1H)-one (9.10 g, 40.4 mmol), xantphos (1.170 g, 2.022 mmol), and $Pd_2(dba)_3$ (0.926 g, 1.011 mmol). The flask was flushed with Ar (g), then dioxane (81 ml), benzyl mercaptan (5.26 ml, 44.5 mmol), and n,n-diisopropylethylamine (14.12 ml, 81 mmol) were added in sequence. The reaction was heated to 110° C. and stirred for 30 minutes. The reaction was diluted with water and filtered. The solids were washed with water and dried under a nitrogen blanket overnight. The solid was triturated with ethyl acetate and stirred for one hour. The solids were filtered, washed with ethyl acetate, and dried under a nitrogen blanket to afford 7-(benzylthio)cinnolin-4(1H)-one (10.63 g, 39.6 mmol, 98% yield) as a light yellow solid. m/z (ESI) 269.1 (M+H)+.

STEP 3: 7-(BENZYLTHIO)-3-BROMOCINNOLIN-4(1H)-ONE

A round bottom flask was charged with 7-(benzylthio) cinnolin-4(1H)-one (8.42 g, 31.4 mmol), NBS (8.38 g, 47.1 mmol) and DMSO (209 ml) and heated to 90° C. for one hour. The reaction was cooled to RT, submerged in an ice bath, and water was added. The resulting suspension was stirred for 30 minutes and filtered. The solids were washed with water and dried overnight under a nitrogen blanket to afford 7-(benzylthio)-3-bromocinnolin-4(1H)-one (8.0 g, 23.04 mmol, 73.4% yield) as a light yellow solid. m/z (ESI) 349.0 (M+H)+.

STEP 4: 7-(BENZYLTHIO)-3,4-DIBROMOCINNOLINE

A flask was charged with 7-(benzylthio)-3-bromocinnolin-4(1H)-one (4.00 g, 11.52 mmol), acetonitrile (46.1 ml), and Hunig's base (6.04 ml, 34.6 mmol). Phosphorus oxybromide (4.62 g, 16.13 mmol) was added and the reaction was stirred at 90° C. for four hours. The reaction was poured into ice water and stirred for 15 minutes. The heterogenous solution was neutralized to pH~7 with concentrated HCl solution and stirred overnight. The solids were filtered, washed with water, and dried overnight under a nitrogen blanket to afford 7-(benzylthio)-3,4-dibromocinnoline (3.89 g, 9.48 mmol, 82% yield) as a brown solid. m/z (ESI) 409.0 (M+H)+.

STEP 5: 7-(BENZYLTHIO)-3-BROMO-4-(2-CHLORO-3'-FLUORO-5-METHOXY-[1,1'-BIPHENYL]-4-YL)CINNOLINE

A vial was charged with 7-(benzylthio)-3,4-dibromocinnoline (2.0 g, 4.88 mmol), (2-chloro-3'-fluoro-5-methoxy-[1,1'-biphenyl]-4-yl)boronic acid (1.505 g, 5.36 mmol), $PdCl_2(dppf)$-$CH_2Cl_2$ adduct (0.398 g, 0.488 mmol), and potassium carbonate (3.37 g, 24.38 mmol). Dioxane (18.29 ml) and Water (6.10 ml) were added, the vial was flushed with argon and sealed, and stirred overnight at room temperature. The reaction was diluted with DCM and washed with water. The aqueous layer was extracted with DCM, and the combined organic layers were dried with sodium sulfate, filtered, and concentrated. The material was purified via column chromatography (RediSep Gold 80 g, gradient elution 0-100% EtOAc:Heptane) to afford 7-(benzylthio)-3-bromo-4-(2-chloro-3'-fluoro-5-methoxy-[1,1'-biphenyl]-4-yl)cinnoline (1.46 g, 2.58 mmol, 52.9% yield) as a yellow solid. (TFA). m/z (ESI) 565.0 (M+H)+.

STEP 6: PERFLUOROPHENYL 3-BROMO-4-(2-CHLORO-3'-FLUORO-5-METHOXY-[1,1'-BIPHENYL]-4-YL)CINNOLINE-7-SULFONATE

A RBF was charged with 7-(benzylthio)-3-bromo-4-(2-chloro-3'-fluoro-5-methoxy-[1,1'-biphenyl]-4-yl)cinnoline (1.46 g, 2.58 mmol), DCM (24.28 ml), acetic acid (0.911 ml), and water (0.607 ml) to give a thin suspension. The flask was cooled in an ice-bath for 10 min, then 1,3-dichloro-5,5-dimethylimidazolidine-2,4-dione (1.271 g, 6.45 mmol) was added in one portion, leading to a solution. The reaction was stirred for 15 minutes. 2,3,4,5,6-pentafluorophenol (0.541 ml, 5.16 mmol) was added followed by dropwise addition of triethylamine (0.899 ml, 6.45 mmol). The reaction was stirred for 30 minutes. The reaction was concentrated and purified via column chromatography (RediSep Gold 40 g, gradient elution 0-50% EtOAc:Heptane) to afford perfluorophenyl 3-bromo-4-(2-chloro-3'-fluoro-5-methoxy-[1,1'-biphenyl]-4-yl)cinnoline-7-sulfonate (1.57 g, 2.276 mmol, 88% yield) as a yellow solid. m/z (ESI) 688.8 (M+H)+.

STEP 7: 3-BROMO-4-(2-CHLORO-3'-FLUORO-5-METHOXY-[1,1'-BIPHENYL]-4-YL)-N-(ISOXAZOL-3-YL)CINNOLINE-7-SULFONAMIDE

A RBF was charged with perfluorophenyl 3-bromo-4-(2-chloro-3'-fluoro-5-methoxy-[1,1'-biphenyl]-4-yl)cinnoline-7-sulfonate (1.57 g, 2.276 mmol), isoxazol-3-amine (0.185 ml, 2.504 mmol), and THF (11.38 ml) to give a clear solution. The flask was cooled to 0° C. for 10 min, then lithium bis(trimethylsilyl)amide (1M in THF) (5.01 ml, 5.01 mmol) was added dropwise. The reaction was stirred for 30 minutes. The reaction was diluted with 1N aq. HCl and EtOAc. The aqueous layer was extracted with ethyl acetate, and the combined organic layers were washed with 1N aq. HCl, washed with brine, dried with sodium sulfate, filtered, and concentrated to afford crude 3-bromo-4-(2-chloro-3'-fluoro-5-methoxy-[1,1'-biphenyl]-4-yl)-N-(isoxazol-3-yl) cinnoline-7-sulfonamide (1.72 g, 2.92 mmol, 100% yield) as an orange solid. m/z (ESI) 589.0 (M+H)+.

Intermediate AX

4-(2-CHLORO-3'-FLUORO-5-METHOXY-[1,1'-BIPHENYL]-4-YL)-N-(ISOXAZOL-3-YL)-2-METHYL-1-OXO-1,2-DIHYDROISOQUINOLINE-7-SULFONAMIDE TRIFLUOROMETHANESULFONATE

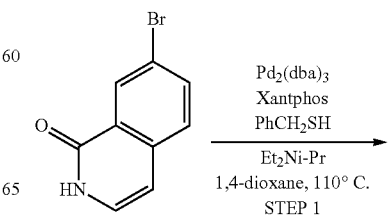

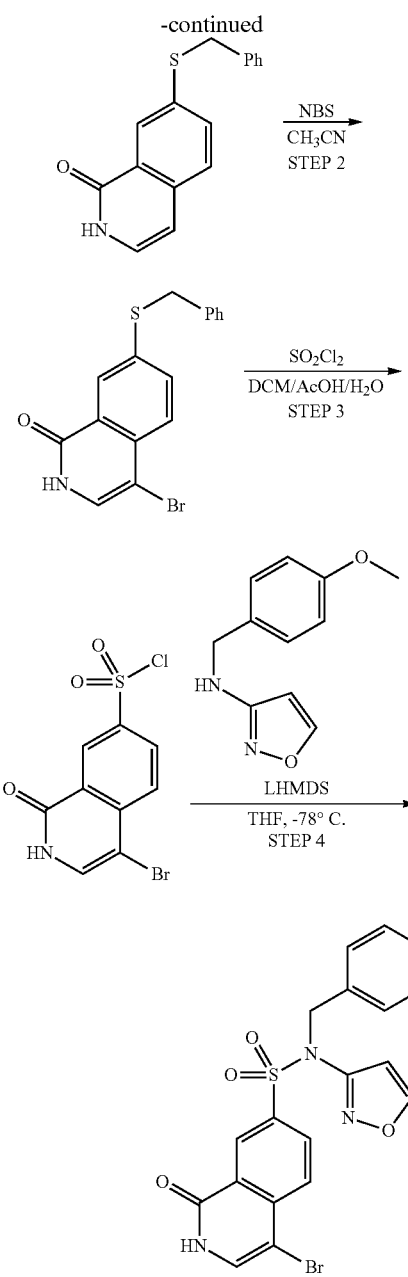

STEP 1: 7-(BENZYLTHIO)ISOQUINOLIN-1(2H)-ONE

A vial was charged with 7-bromoisoquinolin-1(2H)-one (1.704 g, 7.61 mmol), xantphos (0.220 g, 0.380 mmol), and Pd2(dba)3 (0.174 g, 0.190 mmol). The flask was flushed with Ar (g), then dioxane (15.21 ml), benzyl mercaptan (1 ml, 8.45 mmol), and n,n-diisopropylethylamine (2.66 ml, 15.21 mmol) were added in sequence. The reaction was diluted with water and stirred for one hour. The solids were filtered, washed thoroughly with water, and dried overnight under a nitrogen blanket. The solids were taken up in minimal ethyl acetate and stirred for one hour. The solids were filtered, washed with ethyl acetate, and dried overnight under a nitrogen blanket to afford 7-(benzylthio)isoquinolin-1(2H)-one (2.06 g, 7.71 mmol, 101% yield) as an olive yellow solid. m/z (ESI) 268.1 (M+H)$^+$.

STEP 2: 7-(BENZYLTHIO)-4-BROMOISOQUINOLIN-1(2H)-ONE

A RBF was charged with 7-(benzylthio)isoquinolin-1 (2H)-one (1.75 g, 6.55 mmol), NBS (1.282 g, 7.20 mmol), and acetonitrile (32.7 ml). The reaction was stirred overnight at RT. The reaction was diluted with water and stirred vigorously for 15 minutes. The solution was filtered and the solids were washed with water and vacuum dried under a nitrogen blanket to afford 7-(benzylthio)-4-bromoisoquinolin-1(2H)-one (2.20 g, 6.35 mmol, 97% yield) as a yellow solid. m/z (ESI) 346.0 (M+H)$^+$.

STEP 3: 4-BROMO-1-OXO-1,2-DIHYDROISOQUINOLINE-7-SULFONYL CHLORIDE

A RBF was charged with 7-(benzylthio)-4-bromoisoquinolin-1(2H)-one (2.20 g, 6.35 mmol), DCM (60.5 ml), acetic acid (1.513 ml), and water (1.513 ml). The flask was cooled in an ice-bath for 10 min, then sulfuryl chloride (1.545 ml, 19.06 mmol) was added dropwise. The reaction was stirred for 30 minutes, then warmed to RT and stirred for one hour. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 40 g, gradient elution 0-50% EtOAc:Heptane) to afford 4-bromo-1-oxo-1,2-dihydroisoquinoline-7-sulfonyl chloride (1.33 g, 4.12 mmol, 64.9% yield) as a light yellow solid. m/z (ESI) 321.9 (M+H)$^+$.

STEP 4: 4-BROMO-N-(ISOXAZOL-3-YL)-N-(4-METHOXYBENZYL)-1-OXO-1,2-DIHYDROISOQUINOLINE-7-SULFONAMIDE

A flask was charged with 4-bromo-1-oxo-1,2-dihydroisoquinoline-7-sulfonyl chloride (0.700 g, 2.170 mmol), N-(4-methoxybenzyl)isoxazol-3-amine (0.465 g, 2.279 mmol), and THF (14.47 ml) and cooled to −78° C. in a dry ice/acetone bath for 10 minutes. LHMDS (1.0M in THF) (4.77 ml, 4.77 mmol) was added dropwise and the reaction was stirred for 30 minutes. The reaction was warmed to room temperature and quenched with saturated ammonium chloride solution, diluted with ethyl acetate and washed with water. The aqueous layer was extracted three times with ethyl acetate, and the combined organic layers were dried with sodium sulfate, filtered, and concentrated. The material was purified via column chromatography (RediSep Gold 12 g, gradient elution 0-75% EtOAc:Heptane) to afford 4-bromo-N-(isoxazol-3-yl)-N-(4-methoxybenzyl)-1-oxo-1, 2-dihydroisoquinoline-7-sulfonamide (0.658 g, 1.342 mmol, 61.8% yield) as a white solid. m/z (ESI) 490.0 (M+H)$^+$.

Intermediate AY

2-(4-BROMO-2-METHOXY-5-METHYLPHE-NYL)-4,4,5,5-TETRAMETHYL-1,3,2-DIOXA-BOROLANE

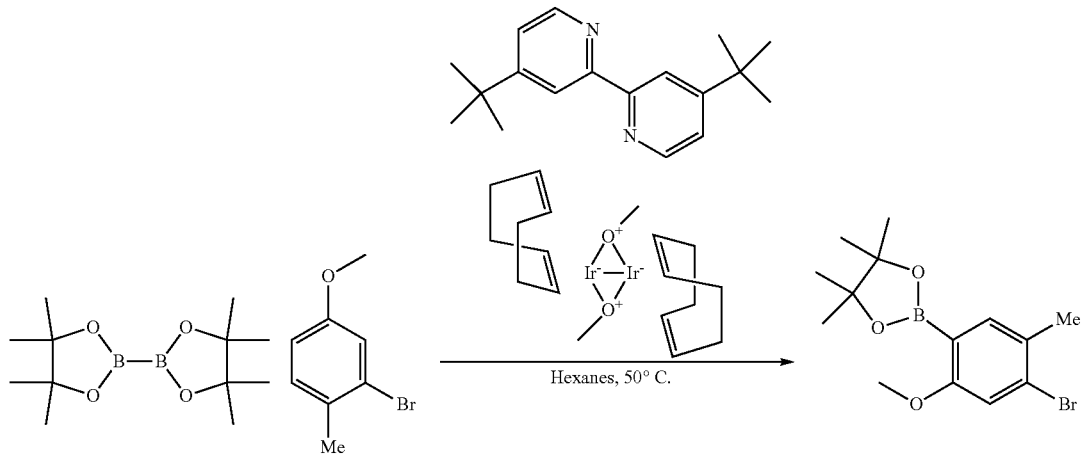

A RBF was charged with (1,5-cyclooctadiene)(methoxy)-iridium(i) dimer (0.049 g, 0.075 mmol), 4,4'-di-tert-butyl-2,2'-dipyridyl (0.040 g, 0.149 mmol), and bis(pinacolato) diboron (1.339 g, 5.27 mmol). The flask was flushed with Ar (g), then hexane (15.30 ml) was added. A reflux condenser was attached to the flask, and the flask was heated to 50° C. for 10 minutes. 2-bromo-4-methoxy-1-methylbenzene (2.0 g, 9.95 mmol) was added and the reaction was stirred overnight at 50° C. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 80 g, gradient elution 0-50% EtOAc: Heptane) to afford 2-(4-bromo-2-methoxy-5-methylphenyl)-4,4,5,5-tetramethyl-1,3,2-dioxaborolane (0.694 g, 2.122 mmol, 21.33% yield) as an off-white oily solid. m/z (ESI) 329.1 (M+H)$^+$.

Intermediate AZ

2-BROMO-3-METHOXYNAPHTHALENE

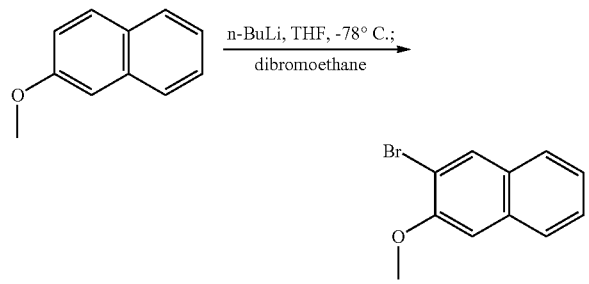

A RBF was charged 2-methoxynaphthalene (2.00 g, 12.64 mmol) and THF (30 mL) to give a clear solution. n-butyl-lithium (2.5M in hexanes) (5.66 mL, 14.16 mmol) was added dropwise. The flask was cooled in a dry ice-acetone bath for 10 min and 1,2-dibromoethane (1.634 mL, 18.96 mmol) was added dropwise. The reaction was warmed to room temperature and stirred for 16 hours. NaOH (1 M, 10 mL, 10 mmol0 was added and the reaction was heated to reflux for 1 hour. The mixture was cooled to room temperature and extracted with DCM (2×), and the combined organic extracts were dried over magnesium sulfate, filtered, and concentrated. The crude solid was recrystallized from heptane to give 2-bromo-3-methoxynaphthalene (1.75 g, 7.38 mmol, 58.4% yield) as an off-white solid. m/z (ESI) 237.1 (M+H)$^+$.

Intermediate BA

4-BROMO-5-FLUORO-2-IODOANILINE

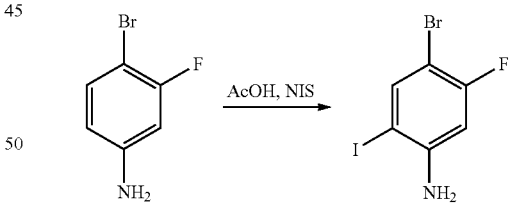

N-iodosuccinimide (2.90 ml, 28.9 mmol) was added to a solution of 4-bromo-3-fluoroaniline (5.00 g, 26.3 mmol) in AcOH (52.6 ml). The reaction was maintained at ambient temperature for 1.5 h, then diluted with 20 mL toluene and concentrated. The residue was dissolved in EtOAc and washed with 2 N aqueous NaOH. The organic phase was washed with brine, dried over sodium sulfate, filtered, and concentrated. The residue was purified by chromatography on silica gel (40-g Ultra SNAP column, 25-g silica gel loading column, 2-10% EtOAc/Heptane) to give 4-bromo-5-fluoro-2-iodoaniline (7.23 g, 22.89 mmol, 87% yield). $^1$H NMR (400 MHz, CHLOROFORM-d) δ 7.74-7.78 (m, 1H), 6.53-6.57 (m, 1H). m/z (ESI) 315.9 (M+H)$^+$.

Intermediate BB

4-(1-BROMOETHYL)-1,2-DICHLOROBENZENE

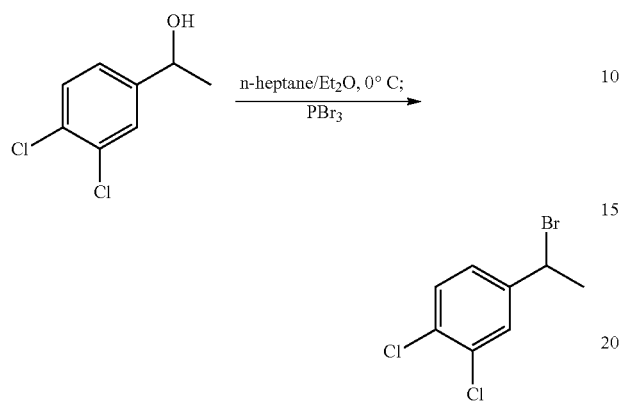

To a solution of 1-(3,4-dichlorophenyl)ethanol (0.87 g, 4.55 mmol) in n-heptane (5.00 mL) and Et$_2$O (0.500 mL) at 0° C. was added pyridine (1 drop) and phosphorous tribromide (0.214 mL, 2.277 mmol). The reaction mixture was warmed to RT and stirred for 2 h. The reaction was diluted with ether, washed with water (1×), saturated NaHCO$_3$ (1×), and brine (1×). The organic layer was dried over magnesium sulfate, filtered, and concentrated to give 4-(1-bromoethyl)-1,2-dichlorobenzene (0.985 g, 3.88 mmol, 85% yield). m/z (ESI) 249.0 (M+H)$^+$.

Intermediate BE

(3'-(DIFLUOROMETHYL)-2,5'-DIFLUORO-5-METHOXY-[1,1'-BIPHENYL]-4-YL)BORONIC ACID

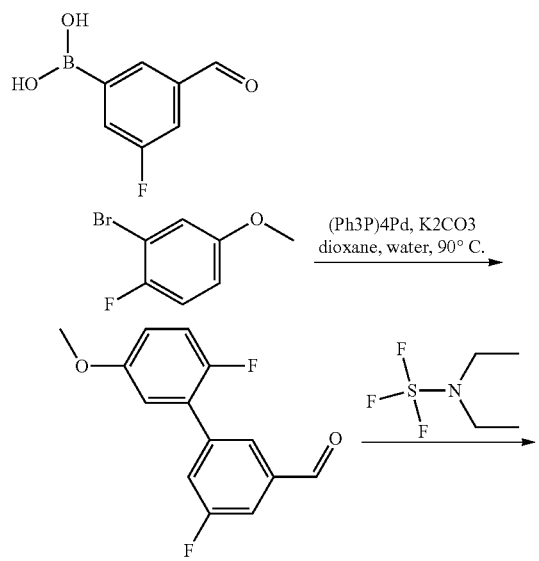

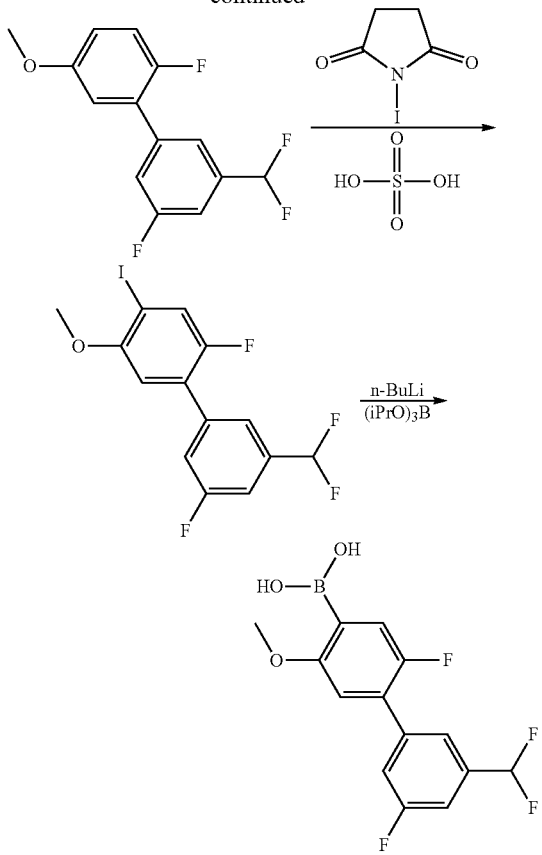

STEP 1

2',5-DIFLUORO-5'-METHOXY-[1,1'-BIPHENYL]-3-CARBALDEHYDE

To a RBF was added 2-bromo-1-fluoro-4-methoxybenzene (1.850 mL, 9.02 mmol, Oakwood), 3-fluoro-5-formylphenylboronic acid (1667 mg, 9.93 mmol, Combi-blocks), tetrakis(triphenylphosphine)palladium (521 mg, 0.451 mmol) and potassium carbonate (3741 mg, 27.1 mmol). A condenser and septum was attached and 1,4-dioxane (24.100 mL) and water (6.03 mL) were added. The mixture was heated at 90° C. for 2 h, at which time the reaction mixture was diluted with water (50 mL) and extracted with EtOAc (2×50 mL). The organic extract was washed with brine (20 mL) and dried over MgSO$_4$. The solution was filtered and concentrated. The residue was absorbed onto a plug of silica gel and purified by chromatography through a 50 g silica column, eluting with a gradient of 0% to 30% EtOAc in Heptane, to provide 2',5-difluoro-5'-methoxy-[1,1'-biphenyl]-3-carbaldehyde (640 mg, 2.58 mmol, 28.6% yield) as white solid. $^1$H NMR (400 MHz, DMSO-d$_6$) δ 10.01-10.14 (m, 1H), 8.01 (q, J=1.56 Hz, 1H), 7.82 (tdd, J=1.41, 2.59, 9.76 Hz, 1H), 7.67-7.78 (m, 1H), 7.32 (dd, J=9.05, 10.42 Hz, 1H), 7.18 (dd, J=3.23, 6.46 Hz, 1H), 7.05 (td, J=3.57, 9.00 Hz, 1H), 3.83 (s, 3H).

STEP 2: 3'-(DIFLUOROMETHYL)-2,5'-DIFLUORO-5-METHOXY-1,1'-BIPHENYL

To a 250-mL RBF was added 2',5-difluoro-5'-methoxy-[1,1'-biphenyl]-3-carbaldehyde (640 mg, 2.58 mmol) followed by DCM (8.594 mL). The clear solution was cooled to −78° C., then (diethylamino)sulfur trifluoride (1.022 mL, 7.73 mmol) was added dropwise. After 3 min, the reaction flask was put in an ice-water bath. After 4 h, sat aqueous NaHCO$_3$ was carefully added to quench the reaction. The reaction mixture was extracted with EtOAc (2×20 mL). The organic layers were combined, dried (MgSO$_4$) and concentrated. The residue was absorbed onto a plug of silica gel and purified by silica gel chromatography through a Redi-Sep pre-packed silica gel column (12 g), eluting with a gradient of 0% to 40% EtOAc in hexane, to provide 3'-(difluoromethyl)-2,5'-difluoro-5-methoxy-1,1'-biphenyl (642 mg, 2.376 mmol, 92% yield) as colorless clear oil. $^1$H NMR (400 MHz, DMSO-d$_6$) δ 7.61-7.69 (m, 2H), 7.47-7.55 (m, 1H), 7.23-7.35 (m, 1H), 6.96-7.16 (m, 3H), 3.82 (s, 3H).

STEP 3: 3'-(DIFLUOROMETHYL)-2,5'-DIFLUORO-4-IODO-5-METHOXY-1,1'-BIPHENYL

To a 250-mL RBF was added 3'-(difluoromethyl)-2,5'-difluoro-5-methoxy-1,1'-biphenyl (642 mg, 2.376 mmol) and sulfuric acid (69.7 μl, 1.307 mmol). DCM (3960 μl) and AcOH (3960 μl) were added to give a colorless clear solution. To this solution was added n-iodosuccinimide (238 μl, 2.376 mmol) as a solid in a single portion to give a maroon-colored solution. After 3 h at rt, the mixture was diluted with DCM (30 mL), washed with water (10 mL), washed with saturated aq. sodium thiosulfate (10 mL, DCM was upper layer for separation), dried over sodium sulfate, filtered, and concentrated. The residue was purified by chromatography on silica gel (50-g silica gel column, 0-5% EtOAc/Heptane) to provide 3'-(difluoromethyl)-2,5'-difluoro-4-iodo-5-methoxy-1,1'-biphenyl (771 mg, 1.946 mmol, 82% yield) as a white solid. $^1$H NMR (400 MHz, DMSO-d$_6$) δ 7.80-7.87 (m, 1H), 7.67-7.73 (m, 1H), 7.63-7.67 (m, 1H), 7.48-7.57 (m, 1H), 7.08-7.18 (m, 2H), 3.91 (d, J=2.54 Hz, 3H)

STEP 4: (3'-(DIFLUOROMETHYL)-2,5'-DIFLUORO-5-METHOXY-[1,1'-BIPHENYL]-4-YL) BORONIC ACID

A RBF was charged with 3'-(difluoromethyl)-2,5'-difluoro-4-iodo-5-methoxy-1,1'-biphenyl (770 mg, 1.944 mmol), triisopropyl borate (0.580 mL, 2.53 mmol) and THF (9.719 mL). The flask was cooled to −78° C. for 10 min, then n-butyllithium solution, 2.5 m in hexanes (1.011 mL, 2.53 mmol) was added dropwise over 1 min. The colorless solution turned green then yellow. After 30 min at −78° C., 2N aq. NaOH (10 mL) was added. The resulting biphasic mixture was stirred for 10 min, and partitioned between water (20 mL) and ether (50 mL). The layers were separated, and the ethereal layer was extracted with water (2×10 mL). The combined aqueous extracts were washed with ether (10 mL), and then were acidified with 6N aq. HCl (10 mL). The resulting aq. mixture was extracted with DCM (3×20 mL). The combined DCM layers were dried over sodium sulfate, filtered, and concentrated to give (3'-(difluoromethyl)-2,5'-difluoro-5-methoxy-[1,1'-biphenyl]-4-yl)boronic acid (111 mg, 0.353 mmol, 18.18% yield) as white solid. m/z (ESI) 315.0 (M+H)$^+$.

Intermediate BF

2-(3,5-DIFLUOROPHENYL)-5-IODO-6-METHOXYNICOTINONITRILE

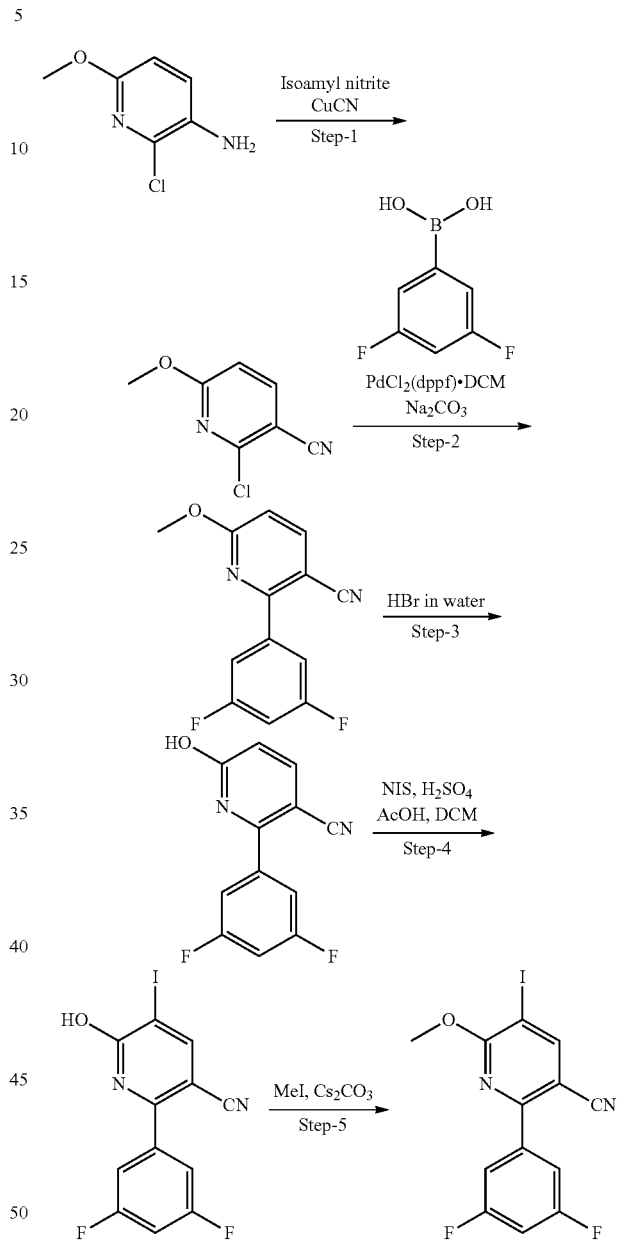

STEP 1: SYNTHESIS OF 2-CHLORO-6-METHOXYNICOTINONITRILE

To a suspension of copper cyanide (13.6 g, 151.8 mmol, Spectrochem) in acetonitrile (500 mL) was added isoamyl nitrite (25.4 mL, 189.8 mmol). A solution of 2-chloro-6-methoxypyridin-3-amine (20.0 g, 126.5 mmol, Vyas Bio) in acetonitrile (100 mL) was added to the above suspension dropwise. The reaction mixture was heated at 65° C. for 4 h. After completion, the reaction mixture was diluted with water (500 mL) and extracted with ethyl acetate (2×500 mL). The organic layer was dried over sodium sulfate and concentrated to obtain crude material which was purified by column chromatography (silica: 100-200; elution: 5% ethyl acetate in hexanes) to get 2-chloro-6-methoxynicotinonitrile (5.0 g, 23.4%) as brown solid. TLC solvent system: 20% ethyl acetate in hexanes, Product's R$_f$: 0.4. MS (ESI, positive ion) m/z; No ionization. $^1$H NMR (400 MHz, DMSO) δ 8.28 (d, J=8.5 Hz, 1H), 7.05 (d, J=8.5 Hz, 1H), 3.94 (s, 3H).

STEP 2: SYNTHESIS OF 2-(3,5-DIFLUOROPHENYL)-6-METHOXYNICOTINONITRILE

To a solution of 2-chloro-6-methoxynicotinonitrile (5.0 g, 29.6 mmol), (3,5-difluorophenyl)boronic acid (6.05 g, 38.5 mmol, Combi Block) 2M aqueous sodium carbonate (37.0 mL, 74.1 mmol) in 1,4-dioxane (75 mL) was added PdCl$_2$(dppf).DCM complex (2.42 g, 2.96 mmol). The reaction mixture was degassed with nitrogen for 10 minutes and then heated at 90° C. for 16 h. After completion, the reaction mixture was diluted with water (100 mL) and extracted with ethyl acetate (2×150 mL). The organic layer was dried over sodium sulfate and concentrated under reduced pressure to obtain the crude material which was purified by column chromatography (silica: 100-200; elution: 5% ethyl acetate in hexanes) to get 2-(3,5-difluorophenyl)-6-methoxynicotinonitrile (3.5 g, 48%) as yellow solid. TLC solvent system: 20% ethyl acetate in hexanes, Product's R$_f$: 0.3. MS (ESI, positive ion) m/z; No ionization. $^1$H NMR (400 MHz, DMSO) δ 8.29 (d, J=8.6 Hz, 1H), 7.65 (d, J=7.5 Hz, 2H), 7.50 (t, J=9.4 Hz, 1H), 7.09 (d, J=8.6 Hz, 1H), 4.01 (s, 3H).

STEP 3: SYNTHESIS OF 2-(3,5-DIFLUOROPHENYL)-6-HYDROXYNICOTINONITRILE

A solution of 2-(3,5-difluorophenyl)-6-methoxynicotinonitrile (3.5 g, 14.2 mmol) in hydrobromic acid (~47% in water) (70 mL) was heated at 100° C. for 16 h. After completion, the reaction mixture was diluted with water (100 mL) and quenched with solid sodium bicarbonate until the effervescence subsided. The aqueous layer was extracted with ethyl acetate (2×200 mL). The organic layer was dried over sodium sulfate and concentrated to get 2-(3,5-difluorophenyl)-6-hydroxynicotinonitrile (3.0 g, 91%) as crude orange solid. TLC solvent system: 40% ethyl acetate in hexanes, Product's R$_f$: 0.3. MS (ESI, positive ion) m/z; No ionization. $^1$H NMR (400 MHz, DMSO) δ 12.55 (s, 1H), 7.88 (d, J=9.2 Hz, 1H), 7.68-7.37 (m, 3H), 6.60 (d, J=9.4 Hz, 1H).

STEP 4: SYNTHESIS OF 2-(3,5-DIFLUOROPHENYL)-6-HYDROXY-5-IODONICOTINONITRILE

To a solution of 2-(3,5-difluorophenyl)-6-hydroxynicotinonitrile (3.0 g, 12.9 mmol) in DCM (40 mL) and acetic acid (40 mL) was added sulfuric acid (0.37 mL, 7.11 mmol). N-Iodosuccinimide (2.9 g, 12.9 mmol) was added and the reaction mixture was stirred at ambient temperature for 16 h. After completion, the reaction mixture was diluted with water (150 mL) and extracted with ethyl acetate (2×100 mL). The organic layer was dried over sodium sulfate and concentrated to obtain crude 2-(3,5-difluorophenyl)-6-hydroxy-5-iodonicotinonitrile (4.5 g, crude) as white solid. TLC solvent system: 40% ethyl acetate in hexanes, Product's R$_f$: 0.4. MS (ESI, positive ion) m/z; No ionization.

STEP 5: SYNTHESIS OF 2-(3,5-DIFLUOROPHENYL)-5-IODO-6-METHOXYNICOTINONITRILE

To a solution of 2-(3,5-difluorophenyl)-6-hydroxy-5-iodonicotinonitrile (4.5 g, 12.5 mmol) in DMF (50 mL) was added cesium carbonate (10.2 g, 31.4 mmol). Methyl iodide (1.56 mL, 25.1 mmol) was added and the reaction mixture was stirred at ambient temperature for 16 h. After completion, the reaction mixture was diluted with water (200 mL) and extracted with ethyl acetate (2×100 mL). The organic layer was dried over sodium sulfate and concentrated to obtain crude material which was purified by column chromatography (silica: 100-200; elution: hexanes) to get 2-(3,5-difluorophenyl)-5-iodo-6-methoxynicotinonitrile (370 mg, 8% over two steps) as white solid. TLC solvent system: 20% ethyl acetate in hexanes, Product's R$_f$: 0.6. MS (ESI, positive ion) m/z; No ionization. $^1$H NMR (400 MHz, DMSO) δ 8.81 (s, 1H), 7.66 (td, J=7.2, 4.9 Hz, 2H), 7.51 (tt, J=9.4, 2.5 Hz, 1H), 4.05 (s, 3H).

Intermediate BG

N-(4-METHOXYBENZYL)-N-(PYRIMIDIN-4-YL)-5-(4,4,5,5-TETRAMETHYL-1,3,2-DIOXABOROLAN-2-YL)NAPHTHALENE-2-SULFONAMIDE

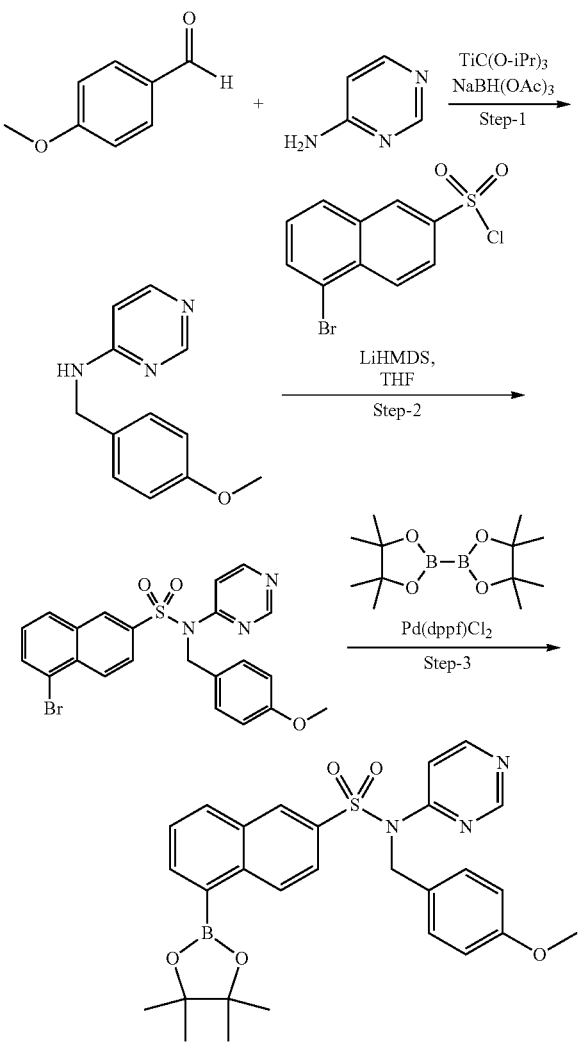

STEP 1: N-(4-METHOXYBENZYL)PYRIMIDIN-4-AMINE

To a solution of 4-methoxybenzaldehyde (30.0 g, 220.4 mmol, Spectrochem) and pyrimidin-4-amine (20.9 g, 220.4 mmol, Reallochem) in dichloromethane (660 mL) was added Ti(O$^i$Pr)$_3$Cl (114.8 g, 440.8 mmol, Aldrich) and the mixture was stirred at RT for 6 h. The reaction mixture was cooled to 0° C. and NaBH(OAc)$_3$ (186.9 g, 881.7 mmol, Aldrich) was added in portions and stirred at RT for 16 h. The reaction mixture (in portions of 100 mL) was quenched with saturated NaHCO$_3$ solution (200 mL) and extracted with DCM (2×500 mL). The combined organic layer was dried over sodium sulfate, filtered and concentrated under reduced pressure to obtain the crude material which was purified by column chromatography (silica gel 100-200 mesh, elution 0-2% methanol in DCM) to obtain N-(4-methoxybenzyl)pyrimidin-4-amine (13.0 g, 29%) as off white solid. TLC solvent system: 10% methanol in dichloromethane. Product's R$_f$: 0.3. MS (ESI, positive ion) m/z; 216 (M+1). $^1$H NMR (400 MHz, DMSO) δ 8.40 (s, 1H), 8.02 (d, J=6.1 Hz, 1H), 7.82 (t, J=6.0 Hz, 1H), 7.24 (d, J=8.0 Hz, 2H), 6.98-6.77 (m, 2H), 6.48 (s, 1H), 4.43 (s, 2H), 3.72 (s, 3H).

STEP 2: 5-BROMO-N-(4-METHOXYBENZYL)-N-(PYRIMIDIN-4-YL)NAPHTHALENE-2-SULFONAMIDE

To a solution of N-(4-methoxybenzyl)pyrimidin-4-amine (20.0 g, 92.9 mmol) in THF (200 mL) was added LiHMDS (1M in THF, 185.9 mL, mmol, Aldrich) at −78° C. The reaction mixture was stirred at 0° C. for 20 min. The reaction mixture was cooled to −78° C. and a solution of 5-bromonaphthalene-2-sulfonyl chloride (42.5 g, 139.4 mmol) in THF (100 mL) was added. The reaction mixture was allowed to stir at RT for 1 h. The reaction was quenched with ice cold water (500 mL) and extracted with ethyl acetate (2×500 mL). The combined organic layer was dried over sodium sulfate, filtered and concentrated under reduced pressure to obtain the crude material which was purified by column chromatography (neutral alumina, elution 0-10% ethyl acetate in hexanes) to obtain 5-bromo-N-(4-methoxybenzyl)-N-(pyrimidin-4-yl)naphthalene-2-sulfonamide (4.0 g, 9.0%) as off white solid. TLC solvent system: 30% ethyl acetate in hexanes. Product's R$_f$: 0.4. MS (ESI, positive ion) m/z; 484.1 (M+1). $^1$H NMR (400 MHz, DMSO) δ 8.83 (s, 1H), 8.75 (d, J=1.8 Hz, 1H), 8.59 (d, J=5.9 Hz, 1H), 8.27 (dd, J=15.1, 8.6 Hz, 2H), 8.12 (d, J=7.4 Hz, 1H), 8.01 (dd, J=9.0, 1.9 Hz, 1H), 7.63 (t, J=7.9 Hz, 1H), 7.50 (d, J=5.9 Hz, 1H), 7.29 (d, J=8.7 Hz, 2H), 6.88 (d, J=8.7 Hz, 2H), 5.31 (s, 2H), 3.71 (s, 3H).

STEP 3: N-(2,4-DIMETHOXYBENZYL)-N-(PYRIMIDIN-4-YL)-5-(4,4,5,5-TETRAMETHYL-1,3,2-DIOXABOROLAN-2-YL) NAPHTHALENE-2-SULFONAMIDE

A mixture of 5-bromo-N-(4-methoxybenzyl)-N-(pyrimidin-4-yl)naphthalene-2-sulfonamide (3.0 g, 6.19 mmol), bis(pinacolato)diboron (2.35 g, 9.28 mmol, RCP) and KOAc (1.8 g, 18.57 mmol, Qualigens) in dioxane (20 mL) was degassed with N$_2$ for 10 min. PdCl$_2$(dppf).DCM (252 mg, 0.309 mmol, GLR) was added and the reaction mixture was heated at 80° C. for 5 h. The reaction mixture was cooled to RT, diluted with ethyl acetate (100 mL) and passed through a celite bed. The filtrate was washed with water (50 mL). The organic layer was dried over sodium sulfate, filtered and concentrated under reduced pressure to obtain the crude material which was purified by column chromatography (silica gel: 100-200 mesh, elution 0-20% ethyl acetate in hexanes) to obtain N-(4-methoxybenzyl)-N-(pyrimidin-4-yl)-5-(4,4,5,5-tetramethyl-1,3,2-dioxaborolan-2-yl)naphthalene-2-sulfonamide (1.9 g, 56%) as off white solid. TLC solvent system: 50% ethyl acetate in hexanes. Product's R$_f$: 0.5. MS (ESI, positive ion) m/z; 532.1 (M+1). $^1$H NMR (400 MHz, DMSO) δ 8.82 (s, 1H), 8.80-8.73 (m, 1H), 8.66 (d, J=2.2 Hz, 1H), 8.57 (d, J=5.9 Hz, 1H), 8.30 (d, J=8.4 Hz, 1H), 8.16 (dd, J=7.1, 1.3 Hz, 1H), 7.96-7.86 (m, 1H), 7.70 (t, J=7.6 Hz, 1H), 7.57-7.51 (m, 1H), 7.35-7.27 (m, 2H), 6.93-6.84 (m, 2H), 5.32 (s, 2H), 3.71 (s, 3H), 1.37 (s, 12H).

Intermediate BI

1-(5-CHLORO-4-FLUORO-2-METHOXYPHENYL)-N-(ISOXAZOL-3-YL)ISOQUINOLINE-6-SULFONAMIDE

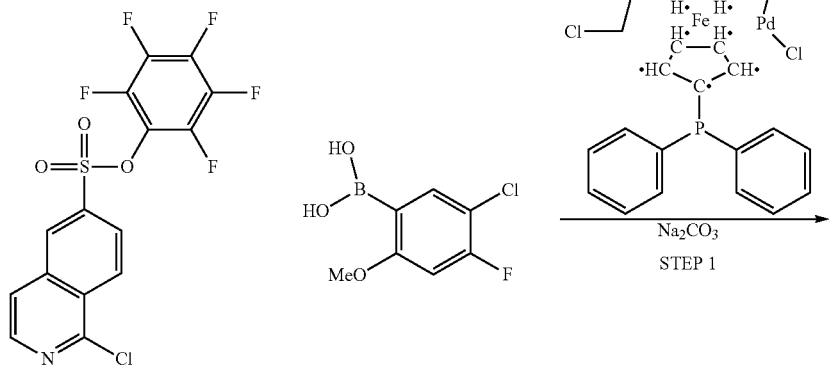

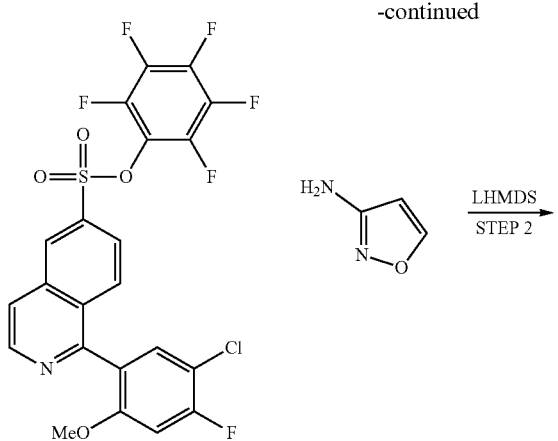
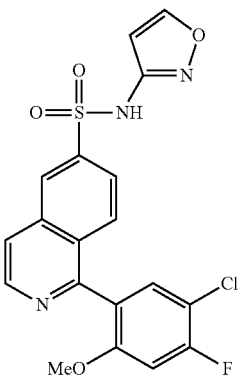

STEP 1: 1-(5-CHLORO-4-FLUORO-2-METHOXYPHENYL)ISOQUINOLINE-6-SULFONATE

A solution of PdCl$_2$dppf (0.498 g, 0.610 mmol), perfluorophenyl 1-chloroisoquinoline-6-sulfonate (5 g, 12.20 mmol), (5-chloro-4-fluoro-2-methoxyphenyl)boronic acid (2.494 g, 12.20 mmol), and 2M aqueous sodium carbonate solution (12.20 ml, 24.41 mmol) in Dioxane (24.41 ml) was heated to 50° C. in a heating block for 1 h. After cooling to rt, the crude material was absorbed onto a plug of silica gel and purified by chromatography through a Redi-Sep prepacked silica gel column (120 g), eluting with a gradient of 0% to 60% EtOAc in hexane, to provide perfluorophenyl 1-(5-chloro-4-fluoro-2-methoxyphenyl)isoquinoline-6-sulfonate (4.09 g, 7.66 mmol, 62.8% yield) as off-white solid. m/z (ESI) 534.0 [M+1].

STEP 2: 1-(5-CHLORO-4-FLUORO-2-METHOXYPHENYL)-N-(ISOXAZOL-3-YL)ISOQUINOLINE-6-SULFONAMIDE

A RBF was charged with perfluorophenyl 1-(5-chloro-4-fluoro-2-methoxyphenyl)isoquinoline-6-sulfonate (4.09 g, 7.66 mmol), THF (77 ml), and isoxazol-3-amine (0.623 ml, 8.43 mmol). The flask was cooled in an ice-bath for 10 min, then lithium bis(trimethylsilyl)amide (1M in THF) (16.09 ml, 16.09 mmol) was added dropwise and the solution was stirred for 15 min. The mixture was diluted with 1 N aq. HCl and extracted with EtOAc (2×). The combined organic extracts were dried over sodium sulfate, filtered, and concentrated. The residue was purified by chromatography on silica gel (80-g Redi-Sep Gold column, 0-5% MeOH/DCM) to give 1-(5-chloro-4-fluoro-2-methoxyphenyl)-N-(isoxazol-3-yl)isoquinoline-6-sulfonamide (2.38 g, 5.49 mmol, 71.6% yield) as a yellow solid. m/z (ESI) 434.1 [M+1].

Intermediate BJ

1,3-DICHLORO-N-(ISOXAZOL-3-YL)-N-(4-METHOXYBENZYL)ISOQUINOLINE-6-SULFONAMIDE

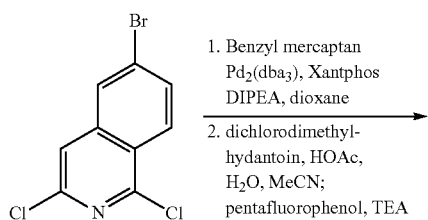

1. Benzyl mercaptan
   Pd$_2$(dba)$_3$, Xantphos
   DIPEA, dioxane
2. dichlorodimethylhydantoin, HOAc,
   H$_2$O, MeCN;
   pentafluorophenol, TEA

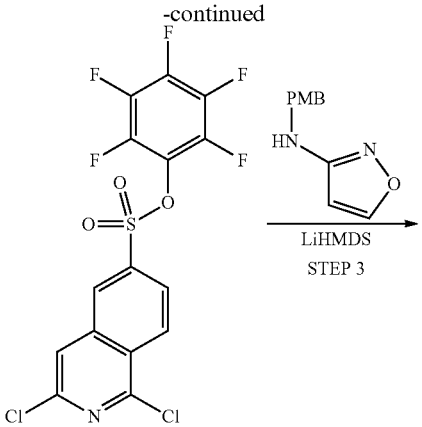
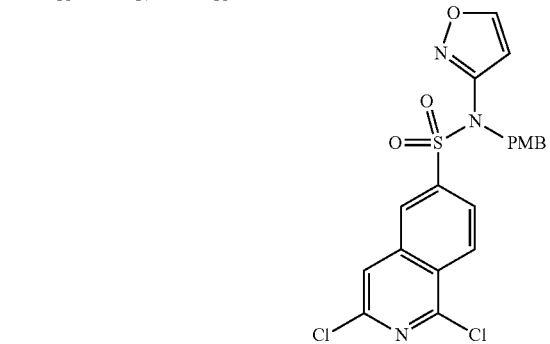

STEP 1: 6-(BENZYLTHIO)-1,3-DICHLOROISOQUINOLINE

A RBF was charged with 6-bromo-1,3-dichloroisoquinoline (5 g, 18.05 mmol, Bellen Chemistry Co.), xantphos (0.522 g, 0.903 mmol), and Pd$_2$(dba)$_3$ (0.413 g, 0.451 mmol). 1,4-dioxane (36.1 ml), n,n-diisopropylethylamine (6.31 ml, 36.1 mmol), and benzyl mercaptan (2.242 ml, 18.96 mmol) were added. The flask was placed in a 60° C. heating bath and stirred for 25 min. The mixture was cooled to RT, and the reaction mixture was concentrated in vacuo. The crude material was absorbed onto a plug of silica gel and purified by chromatography through a Redi-Sep prepacked silica gel column (40 g), eluting with a gradient of 0% to 40% EtOAc in hexane, to provide 6-(benzylthio)-1,3-dichloroisoquinoline (5.5 g, 17.17 mmol, 95% yield) as yellow solid. m/z (ESI) 321.9 [M+1].

STEP 2: 1,3-DICHLOROISOQUINOLINE-6-SULFONATE

A RBF was charged with 6-(benzylthio)-1,3-dichloroisoquinoline (5.5 g, 17.17 mmol), Acetonitrile (162 ml), Acetic Acid (6.06 ml), and Water (4.04 ml) to give a yellow suspension. The flask was cooling in an ice-bath for 10 min, then 1,3-dichloro-5,5-dimethylimidazolidine-2,4-dione (6.77 g, 34.3 mmol) was added in one portion, leading to an orange red solution. After stirring for 20 min, 2,3,4,5,6-pentafluorophenol (6.32 g, 34.3 mmol) was added. Then triethylamine (5.98 ml, 42.9 mmol) was added dropwise. Within a few minutes, the mixture became a light yellow solution and was stirred for 10 more minutes. The mixture was diluted with EtOAc (50 mL) and washed with water (2×100 ml) and brine. The organic layers were combined and concentrated. The crude material was purified by chromatography on silica gel (40-g Redi-Sep Gold column, 0-20% EtOAc/Heptane) to give perfluorophenyl 1,3-dichloroisoquinoline-6-sulfonate (6 g, 13.51 mmol, 79% yield) as yellow solid. m/z (ESI) 443.9 [M+1].

STEP 3: 1,3-DICHLORO-N-(ISOXAZOL-3-YL)-N-(4-METHOXYBENZYL)ISOQUINOLINE-6-SULFONAMIDE

A RBF was charged with perfluorophenyl 1,3-dichloroisoquinoline-6-sulfonate (4 g, 9.01 mmol), THF (90 ml), and N-(4-methoxybenzyl)isoxazol-3-amine (1.839 g, 9.01 mmol) clear, light-yellow solution. The flask was cooled in an ice-bath for 10 min, then lithium bis(trimethylsilyl)amide (18.91 ml, 18.91 mmol) was added dropwise and the reaction was stirred for 15 min. The mixture was diluted with 1 N aq. HCl and extracted with EtOAc (2×). The combined organic extracts were dried over sodium sulfate, filtered, and concentrated. The residue was purified by chromatography on silica gel (40-g Redi-Sep Gold column, 0-5% MeOH/DCM) to give 1,3-dichloro-N-(isoxazol-3-yl)-N-(4-methoxybenzyl)isoquinoline-6-sulfonamide (4.8 g, 10.34 mmol, 115% yield) as a white foam. m/z (ESI) 463.9 [M].

Intermediate BK

4-CHLORO-N-(ISOXAZOL-3-YL)-3-METHOXY-N-(4-METHOXYBENZYL)ISOQUINOLINE-7-SULFONAMIDE

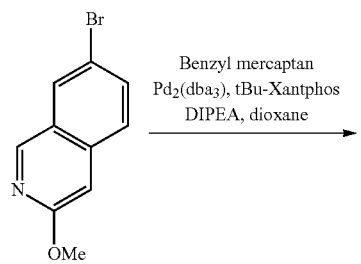

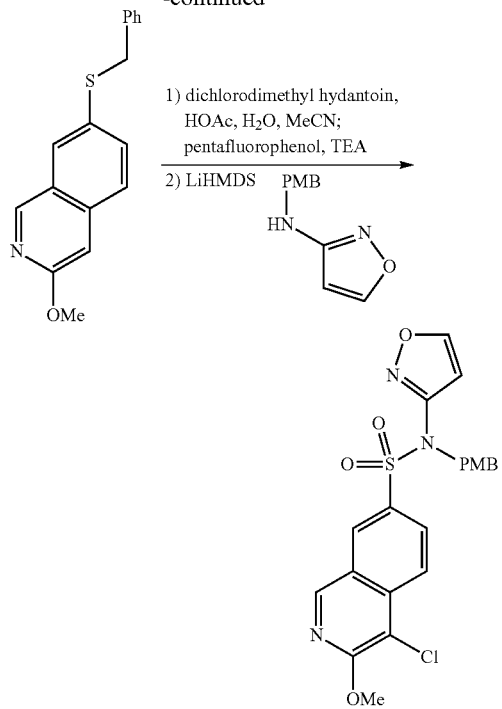

STEP 1: 7-(BENZYLTHIO)-3-METHOXYISOQUINOLINE

A RBF was charged with 7-bromo-3-methoxyisoquinoline (3.0 g, 12.60 mmol, Frontiers), xantphos (0.365 g, 0.630 mmol), and Pd$_2$(dba)$_3$ (0.288 g, 0.315 mmol). 1,4-dioxane (25.2 ml), n,n-diisopropylethylamine (4.40 ml, 25.2 mmol), and benzyl mercaptan (1.565 ml, 13.23 mmol) were added. The flask was placed in a 60° C. heating bath and the reaction was stirred for 16 hrs. The mixture was cooled to RT, and the reaction mixture was concentrated in vacuo. The crude material was absorbed onto a plug of silica gel and purified by chromatography through a Redi-Sep pre-packed silica gel column (40 g), eluting with a gradient of 0% to 40% EtOAc in hexane, to provide 7-(benzylthio)-3-methoxyisoquinoline (3.94 g, 14.00 mmol, 111% yield) as yellow solid. m/z (ESI) 282.3 [M+1].

STEP 2: PERFLUOROPHENYL 4-CHLORO-3-METHOXYISOQUINOLINE-7-SULFONATE

A RBF was charged with 7-(benzylthio)-3-methoxyisoquinoline (587 mg, 2.086 mmol), acetonitrile (19.600 ml), acetic acid (0.735 ml), and water (0.490 ml) to give a yellow suspension. The flask was cooling in an ice-bath for 10 min, then 1,3-dichloro-5,5-dimethylimidazolidine-2,4-dione (822 mg, 4.17 mmol) was added in one portion, leading to a yellow solution. After stirring for 15 min, LCMS showed mostly desired sulfonyl chloride. 2,3,4,5,6-pentafluorophenol (768 mg, 4.17 mmol) was added. Then triethylamine (0.727 ml, 5.22 mmol) was added dropwise. Within a few minutes, the mixture became a light yellow solution and was stirred for 10 min. The mixture was diluted with EtOAc (20 mL) and washed with water (2×20 ml), washed with brine. The organic layers were combined and concentrated. The crude material was purified by chromatography on silica gel (40-g Redi-Sep Gold column, 0-20% EtOAc/Heptane) to give perfluorophenyl 4-chloro-3-methoxyisoquinoline-7-sulfonate (520 mg, 1.183 mmol, 56.7% yield) as white solid. m/z (ESI) 440.0 [M+1].

STEP 3: 4-CHLORO-N-(ISOXAZOL-3-YL)-3-METHOXY-N-(4-METHOXYBENZYL)ISOQUINOLINE-7-SULFONAMIDE

A RBF was charged with perfluorophenyl 4-chloro-3-methoxyisoquinoline-7-sulfonate (520 mg, 1.183 mmol), THF (11.800 ml), and N-(4-methoxybenzyl)isoxazol-3-amine (241 mg, 1.183 mmol). The flask was cooled in an ice-bath for 10 min, then lithium bis(trimethylsilyl)amide (2.483 ml, 2.483 mmol) was added dropwise and stirred for 15 min. The mixture was diluted with 1 N aq. HCl and extracted with EtOAc (2×). The combined organic extracts were dried over sodium sulfate, filtered, and concentrated. The residue was purified by chromatography on silica gel (40-g Redi-Sep Gold column, 0-20% EtOAc/Heptane) to give 4-chloro-N-(isoxazol-3-yl)-3-methoxy-N-(4-methoxybenzyl)isoquinoline-7-sulfonamide (282 mg, 0.613 mmol, 51.9% yield) as a white foam. m/z (ESI) 440.0 [M+4].

Intermediate BL

1,3-DICHLORO-N-(ISOXAZOL-3-YL)ISOQUINOLINE-6-SULFONAMIDE

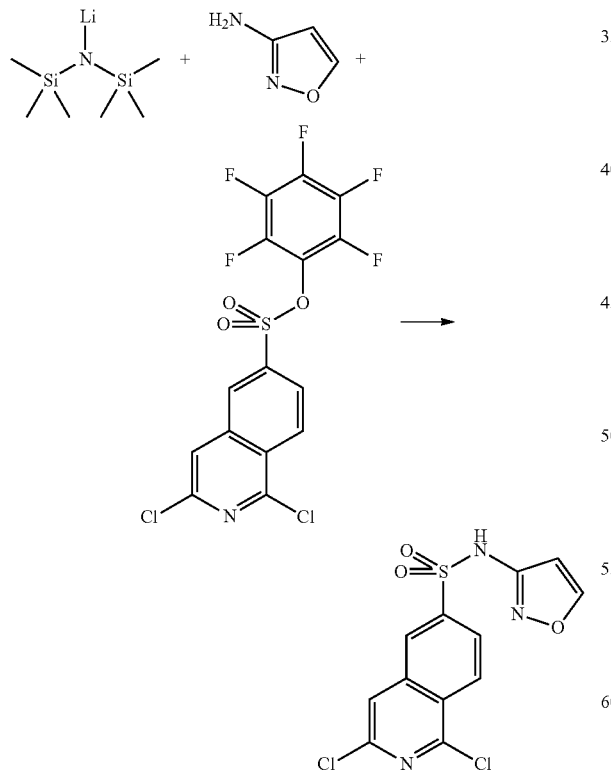

A RBF was charged with perfluorophenyl 1,3-dichloroisoquinoline-6-sulfonate (3.12 g, 7.02 mmol) THF (70.2 ml), and isoxazol-3-amine (0.571 ml, 7.73 mmol) clear, light-yellow solution. The flask was cooled in an ice-bath for 10 min, then lithium bis(trimethylsilyl)amide (1M in THF) (14.75 ml, 14.75 mmol) was added dropwise and the reaction was stirred for 15 min. The mixture was diluted with 1 N aq. HCl and extracted with EtOAc (2×). The combined organic extracts were dried over sodium sulfate, filtered, and concentrated. The residue was purified by chromatography on silica gel (40-g Redi-Sep Gold column, 0-5% MeOH/DCM) to give 1,3-dichloro-N-(isoxazol-3-yl)isoquinoline-6-sulfonamide (2.57 g, 7.47 mmol, 106% yield) as a white foam. m/z (ESI) 344.1 [M].

Intermediate BO

3-CHLORO-2-METHYL-5-(4,4,5,5-TETRAMETHYL-1,3,2-DIOXABOROLAN-2-YL)PYRIDINE

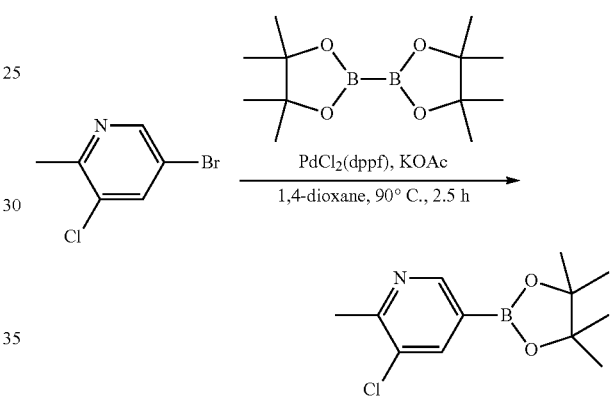

A 40-mL vial containing 5-bromo-3-chloro-2-methylpyridine (185 mg, 0.896 mmol, purchased from Synthonix Inc.), potassium acetate (264 mg, 2.69 mmol), bis(pinacolato)diboron (250 mg, 0.986 mmol), and 1,1'-bis(diphenylphosphino)ferrocene palladium(II)dichloride dichloromethane adduct (36.6 mg, 0.045 mmol) was flushed with $N_2$. Dioxane (4.5 mL) was added, and the orange slurry was stirred at 90° C. After 2.5 h, the resulting black slurry was cooled to rt, washed twice with brine, dried over $Na_2SO_4$, filtered, and concentrated in vacuo to afford 3-chloro-2-methyl-5-(4,4,5,5-tetramethyl-1,3,2-dioxaborolan-2-yl)pyridine as a black oil that was used with further purification. m/z (ESI) 254.1 $(M+H)^+$.

Intermediate BP

N-(4-METHOXYBENZYL)PYRIDAZIN-3-AMINE

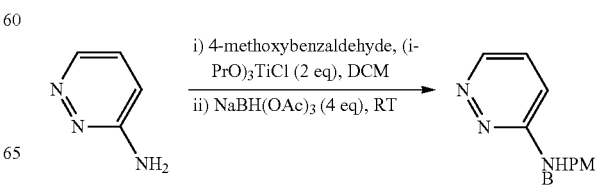

To a solution of pyridazin-3-ylamine (105 g, 1.1 mol, 1 eq) and 4-methoxybenzaldehyde (150 g, 1.1 mol, 1 eq) in DCM (3 L), was added titanium(IV) chloride triisopropoxide (572 g, 2.2 mol, 2 eq). The reaction mixture was stirred at RT for 8 h. The reaction mixture was cooled to 0° C. and sodium triacetoxyborohydride (933 g, 4.4 mol, 4 eq) was added. The reaction mixture was allowed to stir at RT 5 h. After completion of the reaction, the reaction mixture was cooled to 0° C., quenched with ice water and the solid was filtered through celite pad. The layers were separated and the aqueous layer extracted with DCM (1 L). The combined organic layer was dried over sodium sulfate, filtered and concentrated under reduced pressure. The crude mass was dissolved in minimum amount of DCM and the product was extracted in 1.5 N HCl thrice. The aqueous layer was basified with saturated NaHCO$_3$ solution; the precipitated product was filtered and dried. Then the solid obtained was washed with minimum amount of diethyl ether and dried to get 60 g of the title compound as pale pink solid (0.27 mol, 25% yield). MS (ESI pos. ion) m/z: (M+2)$^+$=216.7. $^1$H NMR (400 MHz, Chloroform-d) δ 8.56 (dd, J=1.20, 4.60 Hz, 1H), 7.31 (dd, J=2.80, 11.60 Hz, 2H), 7.15 (dd, J=4.40, 9.00 Hz, 1H), 6.89 (dd, J=2.80, 5.80 Hz, 2H), 6.63 (dd, J=1.20, 9.20 Hz, 1H), 5.15 (br. s, 1H), 4.55 (d, J=5.60 Hz, 2H), 3.81 (s, 3H).

Intermediate BQ

N-(4-METHOXYBENZYL)PYRIMIDIN-2-AMINE

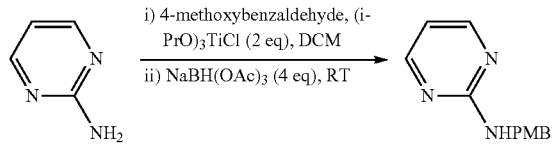

To a mixture of 2-aminopyrimidine (104.7 g, 1.1 mol, 1 eq) and 4-methoxybenzaldehyde (150 g, 1.1 mol, 1 eq) in DCM (3 L), was added titanium(IV) chloride triisopropoxide (572 g, 2.2 mol, 2 eq). The reaction mixture was stirred at room temperature for 8 h. The reaction mixture was cooled to 0° C. and sodium triacetoxyborohydride (933 g, 4.4 mol, 4 eq) was added portionwise and stirred overnight at RT. After completion of reaction, the reaction mixture was cooled to 0° C., quenched with ice water and the solid was filtered through celite pad. The layers were separated and the aqueous layer extracted in DCM (1 L). The organic layer was dried over sodium sulfate and concentrated under reduced pressure to get the crude material which was purified by column chromatography (Silica [60-120 mesh]; eluted with 20-35% EtOAc in hexane) to yield 125 g (0.58 mol, 52% yield) of the title compound as a white solid. MS (ESI pos. ion) m/z: (M+2)$^+$=216.2. $^1$H-NMR (400 MHz, DMSO-d$_6$) δ 8.26 (d, J=3.68 Hz, 2H), 7.63 (t, J=6.16 Hz, 1H), 7.23 (d, J=8.48 Hz, 2H), 6.86 (d, J=8.56 Hz, 2H), 6.56-6.54 (m, 1H), 4.42 (d, J=6.32 Hz, 2H), 3.71 (s, 3H).

Intermediate BR (3'-CHLORO-2-FLUORO-5-METHOXY-[1,1'-BI-PHENYL]-4-YL)BORONIC ACID

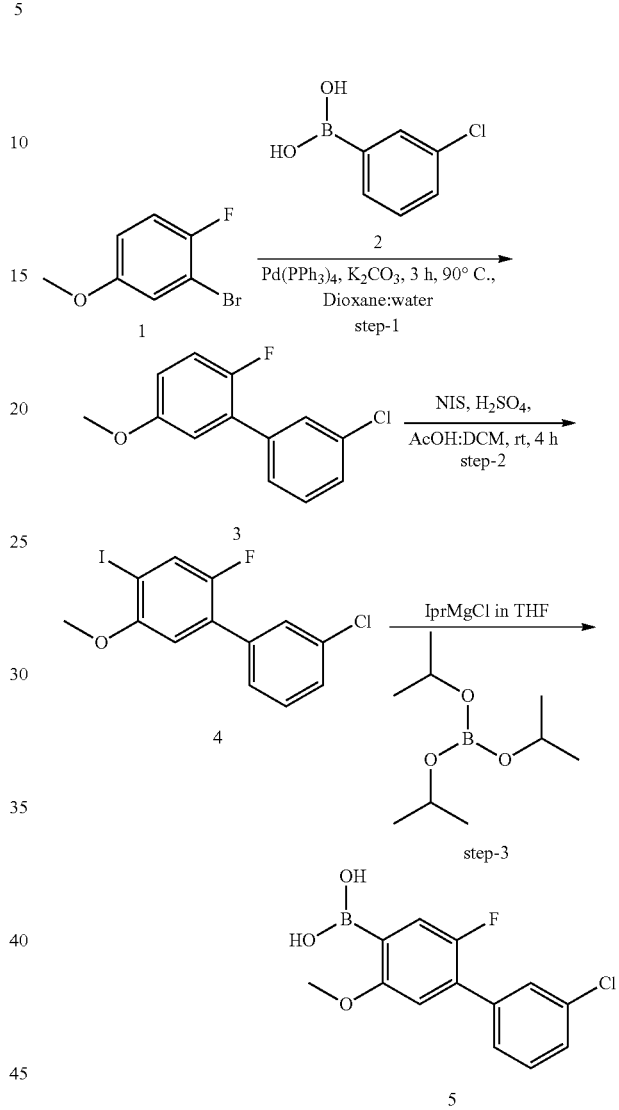

STEP 1: 3'-CHLORO-2-FLUORO-5-METHOXY-1,1'-BIPHENYL

A solution of compound-1 (100 g, 487.73 mmol, 1.0 equiv, Suzhousibian), compound-2 (83.89 g, 536.48 mmol, 1.1 equiv, Suzhousibian) and potassium carbonate (83.89 g, 536.48 mmol, 1.1 equiv) in 1,4-dioxane (2.0 L) and H$_2$O (500 mL) was degassed with nitrogen for 15 min. Pd(PPh$_3$)$_4$ (28.18 g, 24.38 mmol, 0.05 equiv) was added and the mixture was again degassed with nitrogen for 5 min. The reaction mixture was heated at 90° C. for 3 h. The reaction mass was cooled to RT, diluted with ethyl acetate (1.0 L) and washed with brine (200 mL). The organic layer was dried over sodium sulfate, filtered and concentrated under reduced pressure to get the crude material which was purified by column chromatography (silica gel 60-120 mesh, elution 100% Hexane) to get the pure compound-3 (100 g, 86%). TLC solvent system: Hexane, Product R$_f$: 0.5. $^1$H NMR (400

MHz, Chloroform-d) δ 7.54-7.50 (m, 1H), 7.42 (dq, J=4.9, 1.6 Hz, 1H), 7.39-7.31 (m, 2H), 7.10-7.04 (m, 1H), 6.90 (dd, J=6.2, 3.2 Hz, 1H), 6.84 (dt, J=8.9, 3.5 Hz, 1H), 3.82 (s, 3H).

STEP 2: 3'-CHLORO-2-FLUORO-4-IODO-5-METHOXY-1,1'-BIPHENYL

To a solution of compound-3 (100 g, 422.53 mmol, 1.0 equiv) in DCM (500 mL), AcOH (500 mL) and sulphuric acid (22.82 g, 232.46 mmol, 0.55 equiv) was added N-iodosuccinimide (95.06 g, 422.53 mmol, 1.0 equiv) in one portion. The reaction mass was stirred at room temperature for 16 h. The reaction mass was diluted with DCM (2.4 L) and the organic layer was washed with water (4×500 mL) and saturated aqueous sodium thiosulfate (1000 mL). The organic layer was dried over sodium sulphate, filtered, and concentrated under reduced pressure to get the crude material which was purified by column chromatography (silica gel 230-400 mesh, elution Hexane) to get compound-4 (110 g, 71%). TLC solvent system: Heptane, Product's $R_f$: 0.6. $^1$H NMR (400 MHz, DMSO-$d_6$) δ 7.78 (d, J=9.7 Hz, 1H), 7.66 (s, 1H), 7.60-7.45 (m, 3H), 7.09 (d, J=6.7 Hz, 1H), 3.88 (s, 3H).

STEP 3: (3'-CHLORO-2-FLUORO-5-METHOXY-[1,1'-BIPHENYL]-4-YL)BORONIC ACID

A solution of compound-4 (80 g, 220.64 mmol, 1.0 equiv) in THF (800 mL) was cooled to −78° C. under nitrogen atmosphere. Isopropyl magnesium chloride (1.3 M in THF, 339.4 mL, 2.0 equiv) was added drop-wise for 30 mins. After addition the reaction mass was allowed to warm to −55° C. and stirred for 1 h. Triisopropylborate (82.99 g, 441.2 mmol, 2.0 equiv) was added at −55° C. The reaction mass was allowed to warm to RT and stirred for 3 h. Saturated aqueous ammonium chloride solution (1000 mL) was added slowly and the mixture was extracted with EtOAc (2.0 L). The combined organic extract was washed with brine (500 mL), dried over sodium sulfate, filtered and concentrated under reduced pressure to get the crude material which was purified by stirring with n-Hexane and filtered to get compound-5 (28.0 g, 45%) as an off-white solid. TLC solvent system: 10% Ethylacetate/Hexane Product's $R_f$: 0.3. $^1$H NMR (400 MHz, DMSO-$d_6$) δ 7.93 (s, 2H), 7.67 (s, 1H), 7.62-7.46 (m, 3H), 7.36 (d, J=10.8 Hz, 1H), 7.08 (d, J=6.0 Hz, 1H), 3.87 (s, 3H).

Intermediate BS (2(2-CHLORO-3'-FLUORO-5-METHOXY-[1,1'-BIPHENYL]-4-YL)BORONIC ACID

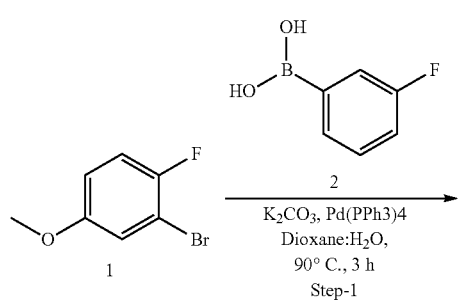

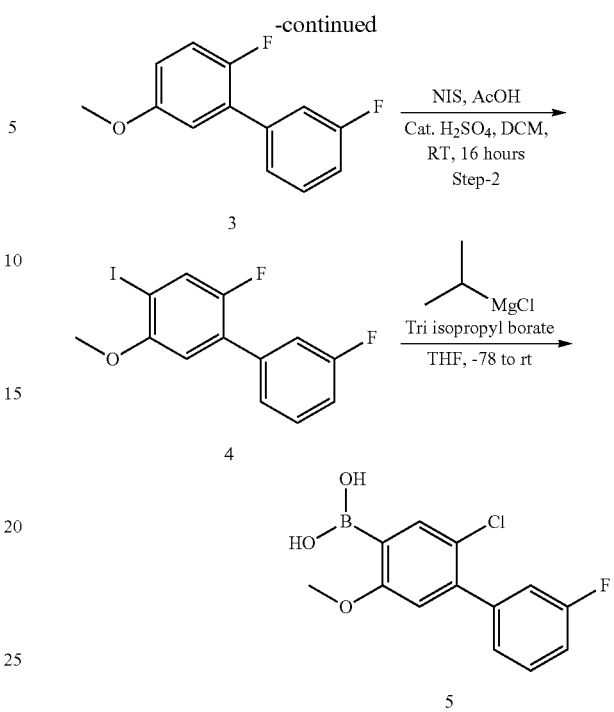

STEP 1: 2-CHLORO-3'-FLUORO-5-METHOXY-1,1'-BIPHENYL

A solution of compound-1 (50.0 g, 0.226 mol, 1.0 equiv, F-Chemical), compound-2 (34.8 g, 0.248 mol, 1.1 equiv, Combi-block) and potassium carbonate (93.66 g, 0.678 mol, 3.0 equiv) in 1,4-dioxane (500 mL) and H$_2$O (500 mL) was degassed with nitrogen for 15 min. Pd(PPh$_3$)$_4$ (13.06 g, 0.0113 mol, 0.05 equiv) was added and the mixture was again degassed with nitrogen for 5 min. The reaction mixture was heated at 90° C. for 3 h. The reaction mass was cooled to room temperature, diluted with ethyl acetate (1.0 L) and washed with brine (500 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (50.0 g, 94.8%). TLC solvent system: Heptane, Product $R_f$: 0.5. $^1$H NMR (300 MHz, Chloroform-d) δ 7.46-7.31 (m, 2H), 7.25-7.13 (m, 2H), 7.09 (tdd, J=8.6, 2.6, 1.0 Hz, 1H), 6.91-6.81 (m, 2H), 3.83 (s, 3H).

STEP 2: 2-CHLORO-3'-FLUORO-4-IODO-5-METHOXY-1,1'-BIPHENYL

To a solution of compound-3 (75.0 g, 0.321 mol, 1.0 equiv) in DCM (500 mL), AcOH (500 mL) and sulphuric acid (9.8 mL) was added N-iodosuccinimide (72.4 g, 0.321 mol, 1.0 equiv) in one portion. The reaction mass was stirred at room temperature for 16 h. The reaction mass was diluted with DCM (1.0 L) and the organic layer was washed with water (1.0 L) and saturated aqueous sodium thiosulfate (500 mL). The organic layer was dried over sodium sulphate, filtered, and concentrated under reduced pressure to get the crude material which was purified by column chromatography (silica gel 60-120 mesh, elution 1% EtOAc/Hexane) to get compound-4 (48 g, 42.0%) TLC solvent system: Heptane, Product's $R_f$: 0.6. $^1$H NMR (400 MHz, Chloroform-d)

δ 7.89 (s, 1H), 7.43 (td, J=8.0, 6.0 Hz, 1H), 7.26-7.19 (m, 1H), 7.21-7.07 (m, 2H), 6.76 (s, 1H), 3.91 (s, 3H).

STEP-3: (2(2-CHLORO-3'-FLUORO-5-METHOXY-[1,1'-BIPHENYL]-4-YL)BORONIC ACID

A solution of compound-4 (40.0 g, 0.11 mol, 1.0 equiv) in THF (400 mL) was cooled to −78° C. under nitrogen atmosphere. Isopropyl magnesium chloride (2.0 M in THF, 83 mL, 0.165 mol, 1.5 equiv) was added drop-wise over 30 min. After addition, the reaction mass was allowed warm to −55° C. and stirred for 1 h. Triisopropylborate (38.2 mL, 0.165 mol, 1.5 equiv) was added at −55° C. The reaction mass was allowed to warm to room temperature and stirred for 3 h. Saturated aqueous ammonium chloride solution (300 mL) was added slowly and the mixture was extracted with EtOAc (2×200 mL). The combined organic extract was washed with brine (300 mL), dried over sodium sulfate filtered and concentrated under reduced pressure to get the crude material which was purified by stirring with EtOAc: Hexane (1:9, 100 mL) for 30 min and filtered to get compound-5 (23.2 g, 77%) as white solid. TLC solvent system: 20% Ethylacetate/Hexane Product's $R_f$: 0.5. $^1$H NMR (400 MHz, Chloroform-d) δ 7.93 (s, 1H), 7.43 (td, J=8.0, 5.9 Hz, 1H), 7.27-7.23 (m, 1H), 7.19 (dt, J=9.7, 2.0 Hz, 1H), 7.12 (tdd, J=8.5, 2.6, 0.9 Hz, 1H), 6.87 (s, 1H), 5.92 (s, 2H), 3.94 (s, 3H).

Intermediate BT

(2-CHLORO-3',5'-DIFLUORO-5-METHOXY-[1,1'-BIPHENYL]-4-YL)BORONIC ACID

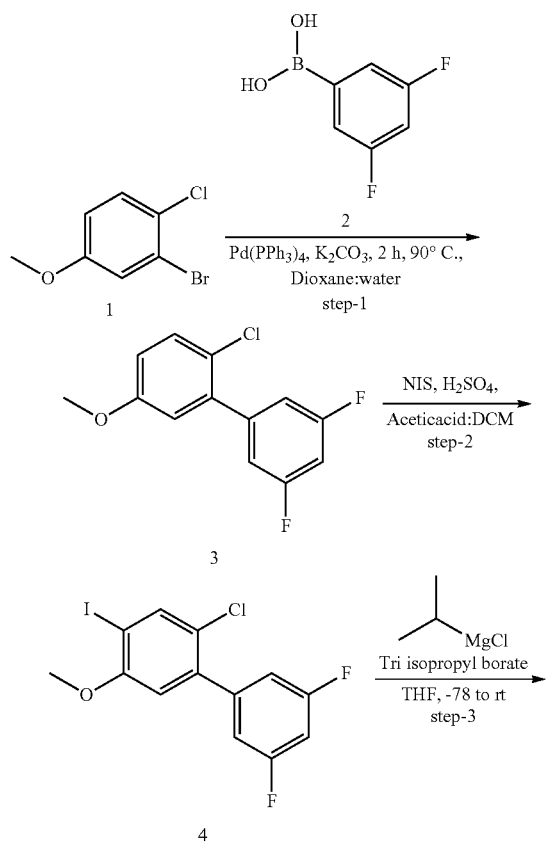

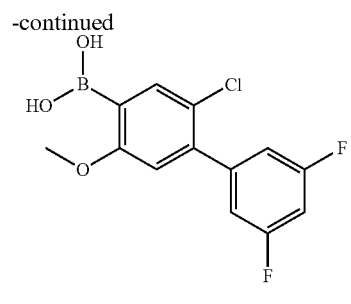

5

STEP 1: 2-CHLORO-3',5'-DIFLUORO-5-METHOXY-1,1'-BIPHENYL

A solution of compound-1 (75.0 g, 0.34 mol, 1.0 equiv, F-Chemicals), compound-2 (59.0 g, 0.37 mol, 1.1 equiv, Combi-Blocks) and potassium carbonate (141.0 g, 1.02 mol, 3.0 equiv) in 1,4-dioxane (1.3 L) and $H_2O$ (350 mL) was degassed with nitrogen for 15 min. Pd(PPh$_3$)$_4$ (19.27 g, 0.017 mol, 0.05 equiv) was added and the mixture was again degassed with nitrogen for 5 min. The reaction mixture was heated at 90° C. for 3 h. The reaction mass was cooled to room temperature, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (78 g, 89%). TLC solvent system: Heptane, Product $R_f$: 0.5. $^1$H NMR (400 MHz, Chloroform-d) δ 7.39 (d, J=8.7 Hz, 1H), 7.05-6.95 (m, 2H), 6.95-6.80 (m, 3H), 3.84 (d, J=1.3 Hz, 3H).

STEP 2: 2-CHLORO-3',5'-DIFLUORO-4-IODO-5-METHOXY-1,1'-BIPHENYL

To a solution of compound-3 (70 g, 0.27 mol, 1.0 equiv) in DCM (465 mL), AcOH (465 mL) and sulphuric acid (8.2 mL) was added N-iodosuccinimide (62.65 g, 0.27 mol, 1.0 equiv) in one portion. The reaction mass was stirred at room temperature for 16 h. The reaction mass was diluted with DCM (1.0 L) and the organic layer was washed with water (1.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (51 g, 50%). TLC solvent system: Heptane, Product's $R_f$: 0.6. $^1$H NMR (400 MHz, Chloroform-d) δ 7.87 (s, 1H), 6.97-6.82 (m, 2H), 6.71-6.69 (m, 1H), 6.67 (s, 1H), 3.89 (s, 3H)

STEP 3: (2-CHLORO-3',5'-DIFLUORO-5-METHOXY-[1,1'-BIPHENYL]-4-YL)BORONIC ACID

A solution of compound-4 (40 g, 0.105 mol, 1.0 equiv) in THF (750 mL) was cooled to −78° C. under nitrogen atmosphere. Isopropyl magnesium chloride (2.0 M in THF 79.0 mL, 0.15 mol, 1.5 equiv) was added drop-wise for 30 mins. After addition the reaction mass was allowed warm to −55° C. and stirred for 1 h. Triisopropylborate (37 mL, 0.15 mol, 1.5 equiv) was added at −55° C. The reaction mass was allowed to warm to RT and stirred for 3 h. Saturated aqueous ammonium chloride solution (500 mL) was added slowly and the mixture was extracted with EtOAc (2×750 mL). The combined organic extract was washed with brine (500 mL), dried over sodium sulfate, filtered and concentrated under reduced pressure to get the crude material which was purified by stirring with EtOAc:Hexane (1:9, 200 mL) for 30 min and filtered to get compound-5 (19.0 g, 31.3%) as white solid. TLC solvent system: 20% Ethylacetate/Hexane Product's $R_f$: 0.5. $^1$H NMR (400 MHz, DMSO-$d_6$) δ 7.97 (s, 2H), 7.58 (s, 1H), 7.36-7.31 (m, 1H), 7.26-7.21 (m, 2H), 7.02 (s, 1H), 3.84 (s, 3H).

Intermediate BU 2,3'-DICHLORO-4-IODO-5-METHOXY-1,1'-BI-PHENYL

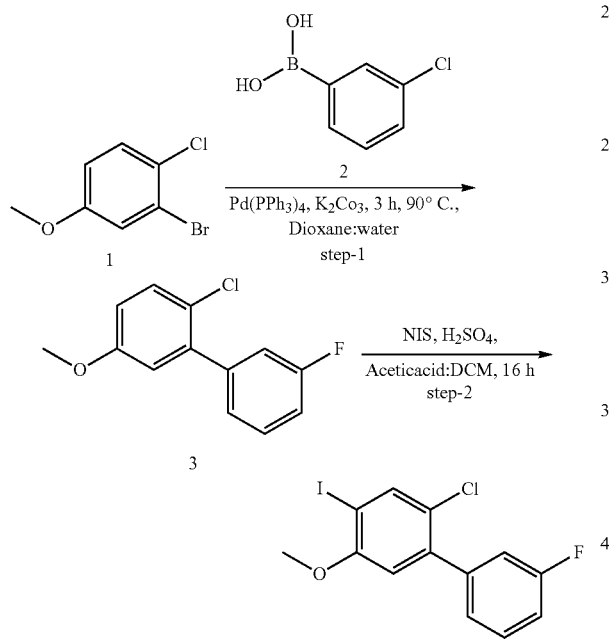

STEP 1:
2,3'-DICHLORO-5-METHOXY-1,1'-BIPHENYL

A solution of compound-1 (100 g, 0.45 mol, 1.0 equiv, F-Chemicals), compound-2 (84.72 g, 0.541 mol, 1.2 equiv, Combi-Blocks) and potassium carbonate (186.92 g, 1.35 mol, 3.0 equiv) in 1,4-dioxane (660 mL) and H$_2$O (180 mL) was degassed with nitrogen for 15 min. Pd(PPh$_3$)$_4$ (26.08 g, 0.0226 mol, 0.05 equiv) was added and the mixture was again degassed with nitrogen for 5 min. The reaction mixture was heated at 90° C. for 3 h. The reaction mass was cooled to RT, diluted with ethyl acetate (1.0 L) and washed with brine (750 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (106 g, 93%). TLC solvent system: Heptane, Product $R_f$: 0.5. $^1$H NMR (400 MHz, DMSO-$d_6$) δ 7.51-7.37 (m, 5H), 7.00-6.96 (m, 2H), 3.78 (s, 3H).

STEP 2: 2,3'-DICHLORO-4-IODO-5-METHOXY-1,1'-BIPHENYL

To a solution of compound-3 (106 g, 0.418 mol, 1.0 equiv), in DCM (208 mL), AcOH (208 mL), and sulphuric acid (39 mL) was added N-iodosuccinimide (94.26 g, 0.418 mol, 1.0 equiv) in one portion. The reaction mass was stirred at RT for 16 h. The reaction mass was diluted with DCM (800 mL) and the organic layer was washed with water (800 mL) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get liquid compound-4 (89.0 g, 56%). TLC solvent system: Heptane, Product's $R_f$: 0.6. $^1$H NMR (400 MHz, DMSO-$d_6$) δ 7.94 (s, 1H), 7.54-7.50 (m, 3H), 7.45-7.43 (m, 1H), 7.01 (s, 1H), 3.87 (s, 3H).

Intermediate BU 2,3'-DIFLUORO-4-IODO-5-METHOXY-1,1'-BIPHENYL

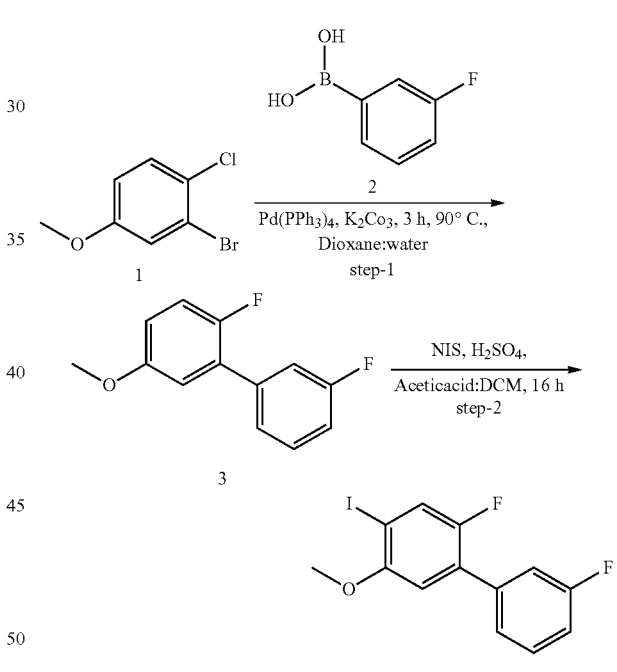

STEP 1:
2,3'-DIFLUORO-5-METHOXY-1,1'-BIPHENYL

A solution of compound-1 (50 g, 0.24 mol, 1.0 equiv, F-Chemicals), compound-2 (101 g, 0.26 mol, 1.1 equiv, Combi-Blocks) and potassium carbonate (101 g, 0.73 mol, 2.0 equiv) in 1,4-dioxane (1.0 L) and H$_2$O (250 mL) was degassed with nitrogen for 15 min. Pd(PPh$_3$)$_4$ (15.2 g, 0.013 mol, 0.05 equiv) was added and the mixture was again degassed with nitrogen for 5 min. The reaction mixture was heated at 90° C. for 3 h. The reaction mass was cooled to room temperature, diluted with ethyl acetate (1.0 L) and washed with brine (750 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (50 g, 93%). TLC solvent system: Heptane, Product R$_f$: 0.5. $^1$H NMR (400 MHz, Chloroform-d) δ 7.42 (td, J=7.9, 6.0 Hz, 1H), 7.36-7.31 (m, 1H), 7.29 (dd, J=2.5, 1.4 Hz, 1H), 7.12-7.05 (m, 2H), 6.94 (dd, J=6.2, 3.1 Hz, 1H), 6.87 (dt, J=8.9, 3.5 Hz, 1H), 3.84 (s, 3H).

STEP 2: 2,3'-DIFLUORO-4-IODO-5-METHOXY-1,1'-BIPHENYL

To a solution of compound-3 (50 g, 0.23 mol, 1.0 equiv) in DCM (90 mL), AcOH (90 mL), and sulphuric acid (16.7 mL) was added N-iodosuccinimide (51.11 g, 0.227 mol, 1.0 equiv) in one portion. The reaction mass was stirred at room temperature for 16 h. The reaction mass was diluted with DCM (500 mL) and the organic layer was washed with water (500 mL) and saturated aqueous sodium thiosulfate (300 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (45 g, 57.28%). TLC solvent system: Heptane, Product's R$_f$: 0.6. $^1$H NMR (400 MHz, Chloroform-d) δ 7.80 (d, J=9.7 Hz, 1H), 7.55-7.46 (m, 3H), 7.31-7.26 (m, 1H), 7.11 (d, J=6.6 Hz, 1H), 3.89 (s, 3H).

Intermediate BV (3'-CHLORO-5-METHOXY-2-METHYL-[1,1'-BIPHENYL]-4-YL)BORONIC ACID

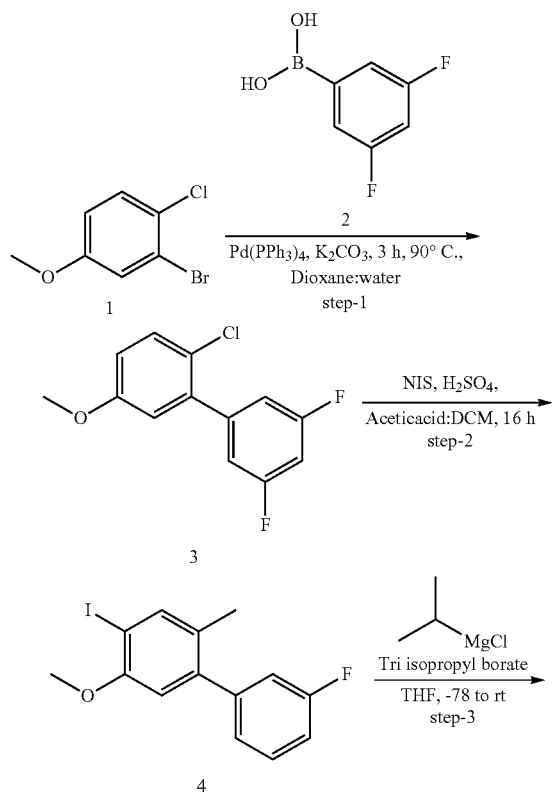

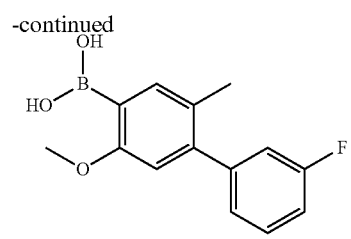

STEP 1: 2-CHLORO-3',5'-DIFLUORO-5-METHOXY-1,1'-BIPHENYL

A solution of compound-1 (120 g, 0.59 mol, 1.0 equiv, F-chemicals), compound-2 (101.4 g, 0.65 mol, 1.1 equiv, combi blocks) and potassium carbonate (247.1 g, 1.79 mol, 3.0 equiv) in 1,4-dioxane (2.0 L) and H$_2$O (500 mL) was degassed with N$_2$ for 15 min. Pd(PPh$_3$)$_4$ (34.4 g, 0.029 mol, 0.05 equiv) was added and the mixture was again degassed with N$_2$ gas for 5 min. The reaction mixture was heated at 90° C. for 3 h. The reaction mass was cooled to RT, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (110 g, 79%). TLC solvent system: heptane, Product R$_f$: 0.5. $^1$H NMR (300 MHz, Chloroform-d) δ 7.40-7.29 (m, 3H), 7.26-7.14 (m, 2H), 6.85 (dd, J=8.4, 2.7 Hz, 1H), 6.77 (d, J=2.6 Hz, 1H), 3.81 (s, 3H), 2.19 (s, 3H).

STEP 2: 3'-CHLORO-4-IODO-5-METHOXY-2-METHYL-1,1'-BIPHENYL

To a solution of compound-3 (110 g, 0.47 mol, 1.0 equiv) in DCM (750 mL), AcOH (750 mL), and sulphuric acid (15 mL) was added N-iodosuccinimide (106 g, 0.47 mol, 1.0 equiv) in one portion. The reaction mass was stirred at room temperature for 16 h. The reaction mass was diluted with DCM (1.0 L) and the organic layer was washed with water (1.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (110 g, 65%). TLC solvent system: Heptane, Product's R$_f$: 0.6. $^1$H NMR (400 MHz, Chloroform-d) δ 7.70 (s, 1H), 7.39-7.34 (m, 2H), 7.30 (d, J=12.4 Hz, 1H), 7.21 (dd, J=5.1, 2.1 Hz, 1H), 6.66 (d, J=3.0 Hz, 1H), 3.88 (d, J=3.1 Hz, 3H), 2.17 (d, J=2.9 Hz, 3H).

STEP 3: (3'-CHLORO-5-METHOXY-2-METHYL-[1,1'-BIPHENYL]-4-YL)BORONIC ACID

A solution of compound-4 (60 g, 0.167 mol, 1.0 equiv) in THF (600 mL) was cooled to −78° C. under nitrogen atmosphere. Isopropyl magnesium chloride (2.0 M in THF, 126 mL, 0.251 mol, 1.5 equiv) was added dropwise for 30 mins. After addition the reaction mass was allowed warm to −55° C. and stirred for 1 h. Triisopropylborate (58.8 mL, 0.25 mol, 1.5 equiv) was added at −55° C. The reaction mass was allowed to warm to room temperature and stirred for 3 h. Saturated aqueous ammonium chloride solution (500 mL) was added slowly and the mixture was extracted with EtOAc (2×750 mL). The combined organic extract was washed with brine (500 mL), dried over sodium sulfate, filtered and concentrated under reduced pressure to get the crude material which was purified by stirring with EtOAc:Hexane (1:9, 200 mL) for 30 min and filtered to get compound-5 (25 g, 54%) as white solid. TLC solvent system: 20% Ethylacetate/Hexane Product's $R_f$: 0.5. $^1$H NMR (400 MHz, Chloroform-d) δ 7.72 (s, 2H), 7.49-7.44 (m, 3H), 7.43 (dd, J=5.2, 1.9 Hz, 1H), 7.33 (dt, J=7.2, 1.5 Hz, 1H), 6.79 (s, 1H), 3.81 (s, 3H), 2.14 (s, 3H).

Intermediate BW

3'-CHLORO-2-FLUORO-4-IODO-5-METHOXY-1,1'-BIPHENYL

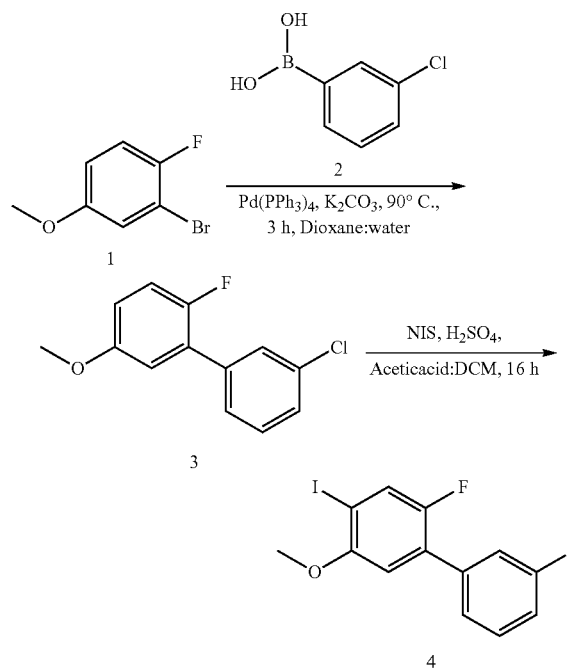

STEP 1: 3'-CHLORO-2-FLUORO-5-METHOXY-1,1'-BIPHENYL

A solution of compound-1 (100 g, 0.487 mol, 1.0 equiv, F-Chemical), compound-2 (91.52 g, 0.585 mol, 1.2 equiv, combi-block) and potassium carbonate (201.92 g, 1.46 mol, 3.0 equiv) in 1,4-dioxane (660 mL) and H$_2$O (180 mL) was degassed with nitrogen for 15 min. Pd(PPh$_3$)$_4$ (28.17.0 g, 0.024 mol, 0.05 equiv) was added and the mixture was again degassed with nitrogen for 5 min. The reaction mixture was heated at 90° C. for 3 h. The reaction mass was cooled to RT, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (92.5 g, 80%). TLC solvent system: Heptane, Product R$_f$: 0.5. $^1$H NMR (400 MHz, DMSO-d$_6$) δ 7.60-7.47 (m, 4H), 7.27-7.21 (m, 1H), 7.06-6.94 (m, 2H), 3.78 (s, 3H).

STEP 2: 3'-CHLORO-2-FLUORO-4-IODO-5-METHOXY-1,1'-BIPHENYL

To a solution of compound-3 (92.5 g, 0.39 mol, 1.0 equiv) in DCM (167 mL), AcOH (167 mL) and sulphuric acid (31 mL) was added N-iodosuccinimide (87.93 g, 0.39 mol, 1.0 equiv) in one portion. The reaction mass was stirred at RT for 16 h. The reaction mass was diluted with DCM (1.0 L) and the organic layer was washed with water (1.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (53.0 g, 38.0%). TLC solvent system: Heptane, Product's R$_f$: 0.6. $^1$H NMR (400 MHz, DMSO-d$_6$) δ 8.06 (d, J=8.0 Hz, 1H), 7.80 (s, 1H), 7.57-7.49 (m, 3H), 7.10 (d, J=8.0 Hz, 1H), 3.89 (s, 3H).

Intermediate BX (2-FLUORO-5-METHOXY-3'-(TRIFLUOROMETHYL)-[1,1'-BIPHENYL]-4-YL)BORONIC ACID

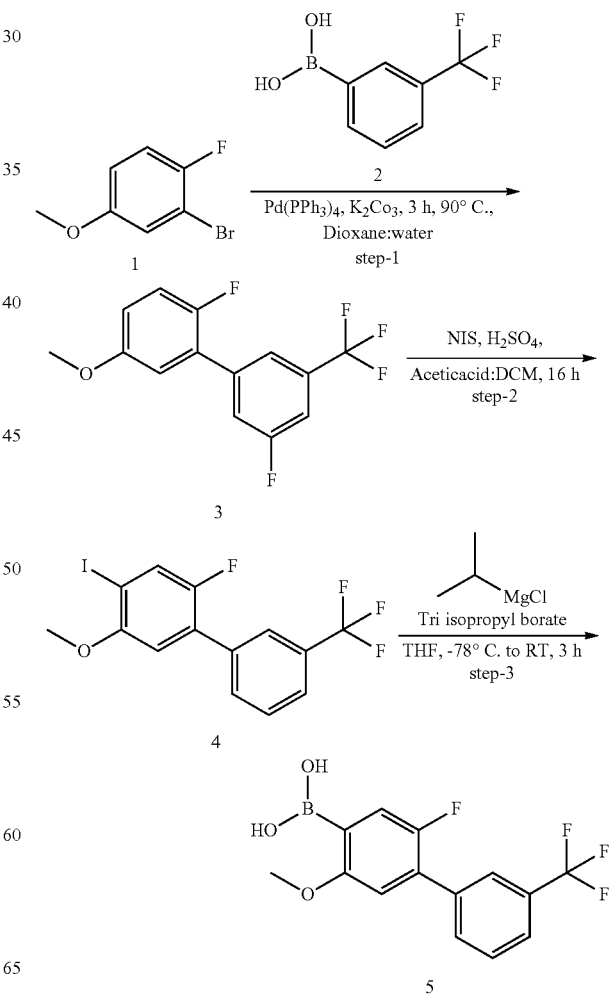

503

STEP 1: 2-Fluoro-5-methoxy-3'-(trifluoromethyl)-1,1'-biphenyl

A solution of compound-1 (70 g, 0.348 mol, 1.0 equiv, F-chemicals), compound-2 (72 g, 0.372 mol, 1.09 equiv, combi-blocks) and potassium carbonate (140 g, 1.044 mol, 3.0 quiv) in 1,4-dioxane (1.3 L) and H$_2$O (500 mL) was degassed with nitrogen for 15 min. Pd(PPh$_3$)$_4$ (21 g, 0.017 mol, 0.05 equiv) was added and the mixture was again degassed with nitrogen for 5 min. The reaction mixture was heated at 90° C. for 3 h. The reaction mass was cooled to room temperature, diluted with ethyl acetate (1.5 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (76 g, 91%). TLC solvent system: Heptane, Product R$_f$: 0.5. $^1$H NMR (400 MHz, Chloroform-d) δ 7.82 (s, 1H), 7.75 (d, J=7.6 Hz, 1H), 7.66 (d, J=7.8 Hz, 1H), 7.59 (t, J=7.8 Hz, 1H), 7.12 (t, J=9.4 Hz, 1H), 6.96 (dd, J=6.2, 3.1 Hz, 1H), 6.90 (dt, J=8.9, 3.4 Hz, 1H), 3.86 (s, 3H).

STEP 2: 2-FLUORO-4-IODO-5-METHOXY-3'-(TRIFLUOROMETHYL)-1,1'-BIPHENYL

To a solution of compound-3 (75 g, 0.28 mol, 1.0 equiv) in DCM (450 mL), AcOH (450 mL) and sulphuric acid (8.0 mL) was added N-iodosuccinimide (63 g, 0.0.28 mol, 1.0 equiv) in one portion. The reaction mass was stirred at room temperature for 16 h. The reaction mass was diluted with DCM (1.0 L) and the organic layer was washed with water (1.0 L) and saturated aqueous sodium thiosulfate (1 L). The organic layer was dried over sodium sulphate, filtered and concentrated under reduced pressure to get the crude material which was purified by column chromatography (silica gel 60-120 mesh, elution 1% EtOAc/Hexane) to get compound-4 (70 g, 63%). TLC solvent system: Heptane, Product's R$_f$: 0.6. $^1$H NMR (400 MHz, Chloroform-d) δ 7.79 (s, 1H), 7.74 (d, J=7.7 Hz, 1H), 7.68 (d, J=7.8 Hz, 1H), 7.62 (dd, J=11.1, 8.5 Hz, 2H), 6.83 (d, J=6.4 Hz, 1H), 3.94 (s, 3H).

STEP 3: (2-FLUORO-5-METHOXY-3'-(TRIFLUOROMETHYL)-[1,1'-BIPHENYL]-4-YL)BORONIC ACID

A solution of compound-4 (70 g, 0.177 mol, 1.0 equiv) in THF (700 mL) was cooled to −78° C. under nitrogen atmosphere. Isopropyl magnesium chloride (2.0 M in THF, 140 mL, 0.265 mol, 1.5 equiv) was added drop-wise for 30 min. After addition the reaction mass was allowed warm to −55° C. and stirred for 1 h. Triisopropylborate (63.1 ml, 0.265 mol, 1.5 equiv) was added at −55° C. The reaction mass was allowed to warm to room temperature and stirred for 3 h. Saturated aqueous ammonium chloride solution (700 mL) was added slowly and the mixture was extracted with EtOAc (1.5 L). The combined organic extract was washed with brine (1.0 L), dried over sodium sulfate, filtered and concentrated under reduced pressure to get the crude material which was purified by stirring with EtOAc:Hexane (1:9, 200 mL) for 30 min and filtered to get compound-5 (34 g, 60%) as white solid. TLC solvent system: 20% Ethylacetate/Hexane Product's R$_f$: 0.5. $^1$H NMR (400 MHz, DMSO-d$_6$) δ 7.95 (s, 2H), 7.92 (d, J=6.5 Hz, 2H), 7.83-7.71 (m, 2H), 7.39 (d, J=10.8 Hz, 1H), 7.13 (d, J=6.0 Hz, 1H), 3.88 (s, 3H).

504

Intermediate BY

(5-METHOXY-2-METHYL-3'-(TRIFLUOROMETHYL)-[1,1'-BIPHENYL]-4-YL)BORONIC ACID

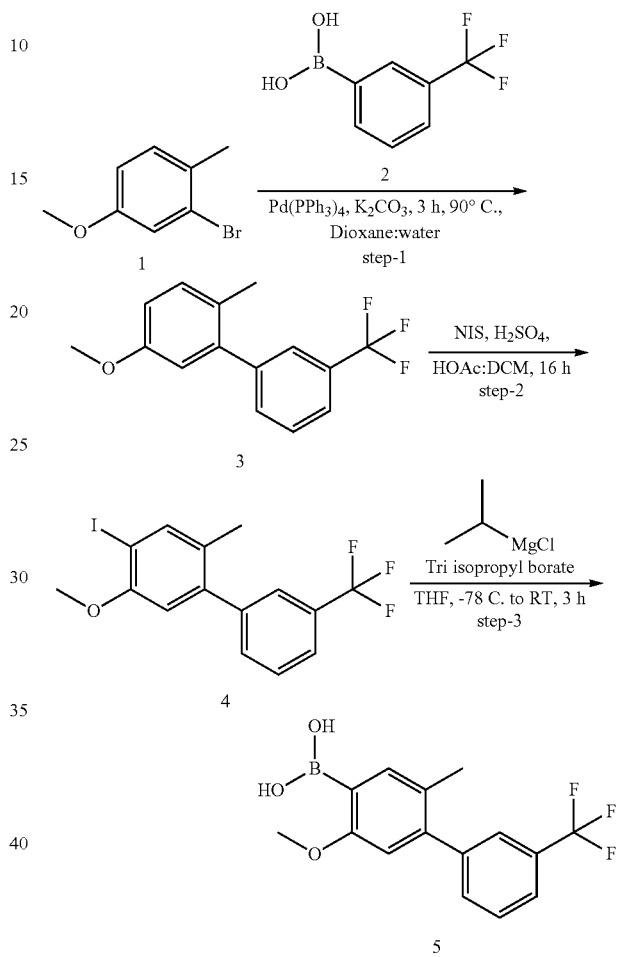

STEP 1: 5-METHOXY-2-METHYL-3'-(TRIFLUOROMETHYL)-1,1'-BIPHENYL

A solution of compound-1 (50.0 g, 0.248 mol, 1.0 equiv, F-chemicals), compound-2 (51.49 g, 0.265 mol, 1.1 equiv, combi-blocks) and potassium carbonate (100 g, 0.725 mol, 3.0 equiv) in 1,4-dioxane (1.0 L) and H$_2$O (250 mL) was degassed with nitrogen for 15 min. Pd(PPh$_3$)$_4$ (14.0 g, 0.0294 mol, 0.05 equiv) was added and the mixture was again degassed with nitrogen for 5 min. The reaction mixture was heated at 90° C. for 3 h. The reaction mass was cooled to RT, diluted with ethyl acetate (1.0 L) and washed with brine (500 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (55 g, 89%). TLC solvent system: Heptane, Product R$_f$: 0.5. $^1$H NMR (300 MHz, Chloroform-d) δ 7.62-7.53 (m, 4H), 7.27-7.19 (m, 1H), 6.88-6.78 (m, 2H), 3.82 (s, 3H), 2.19 (s, 3H).

STEP 2: 4-IODO-5-METHOXY-2-METHYL-3'-(TRIFLUOROMETHYL)-1,1'-BIPHENYL

To a solution of compound-3 (50.0 g, 0.188 mol, 1.0 equiv) in DCM (300 mL), AcOH (300 mL) and sulphuric acid (17 mL) was added N-iodosuccinimide (42.25 g, 0.188 mol, 1.0 equiv) in one portion. The reaction mass was stirred at RT for 16 h. The reaction mass was diluted with DCM (1.0 L) and the organic layer was washed with water (500 mL) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (32 g, 43.83%). TLC solvent system: Heptane, Product's $R_f$: 0.6. $^1$H NMR (400 MHz, DMSO-$d_6$) δ 7.73-7.67 (m, 5H), 6.83 (s, 1H), 3.82 (s, 3H), 2.09 (s, 3H)

STEP 3: (5-METHOXY-2-METHYL-3'-(TRIFLUOROMETHYL)-[1,1'-BIPHENYL]-4-YL)BORONIC ACID

A solution of compound-4 (36 g, 0.0918 mol, 1.0 equiv) in THF (700 mL) was cooled to −78° C. under nitrogen atmosphere. Isopropyl magnesium chloride (2.0 M in THF, 69 mL, 0.137 mol, 1.5 equiv) was added drop-wise for 30 min. After addition the reaction mass was allowed warm to −55° C. and stirred for 1 h. Triisopropylborate (32 ml, 0.137 mol, 1.5 equiv) was added at −55° C. The reaction mass was allowed to warm to RT and stirred for 3 h. Saturated aqueous ammonium chloride solution (400 mL) was added slowly and the mixture was extracted with EtOAc (800 mL). The combined organic extract was washed with brine (500 mL), dried over sodium sulfate, filtered and concentrated under reduced pressure to get the crude material which was purified by stirring with EtOAc:Hexane (1:9, 200 mL) for 30 min and filtered to get compound-5 (25 g, 89%) as white solid. TLC solvent system: 20% Ethylacetate/Hexane Product's $R_f$: 0.5. $^1$H NMR (400 MHz, DMSO-$d_6$) δ 7.76-7.69 (m, 6H), 7.49 (s, 1H), 6.84 (s, 1H), 3.82 (s, 3H), 2.149 (s, 3H)

Intermediate BX

(3'-CHLORO-2,5'-DIFLUORO-5-METHOXY-[1,1'-BIPHENYL]-4-YL)BORONIC ACID

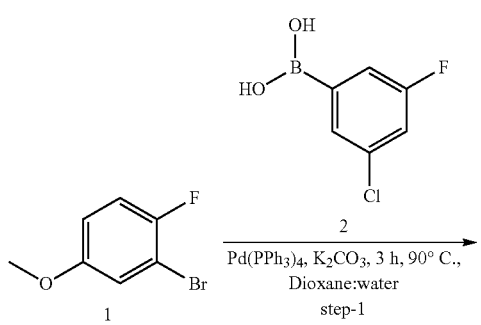

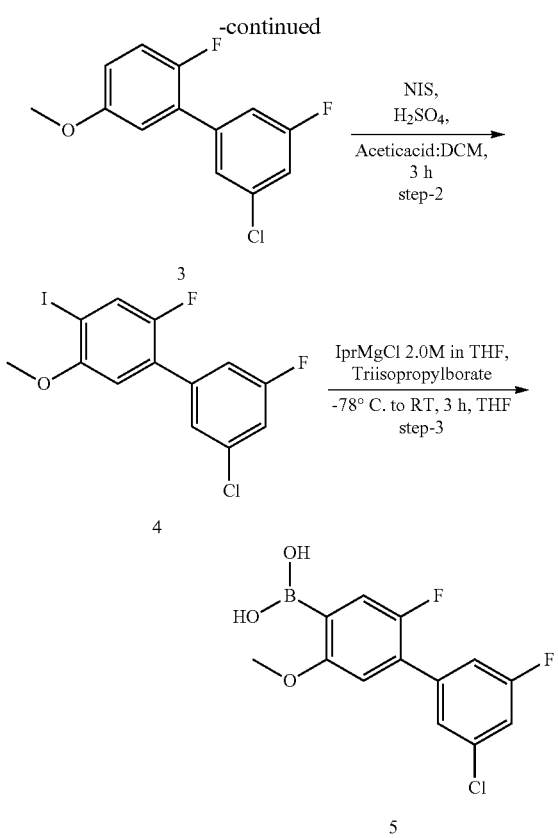

STEP 1: 3'-CHLORO-2,5'-DIFLUORO-5-METHOXY-1,1'-BIPHENYL

A solution of compound-1 (50.0 g, 0.243 mol, 1.0 equiv, F-Chemical), compound-2 (46.2 g, 0.265 mol, 1.1 equiv, combi-blocks) and potassium carbonate (100 g, 0.729 mol, 3.0 equiv) in 1,4-dioxane (1.0 L) and $H_2O$ (250 mL) was degassed with nitrogen for 15 min. Pd(PPh$_3$)$_4$ (14.0 g, 0.0294 mol, 0.05 equiv) was added and the mixture was again degassed with nitrogen for 5 min. The reaction mixture was heated at 90° C. for 3 h. The reaction mass was cooled to room temperature, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-2 (60 g, 96%). TLC solvent system: Heptane, Product $R_f$: 0.5. $^1$H NMR (300 MHz, Chloroform-d) δ 7.34 (s, 1H), 7.22-7.14 (m, 1H), 7.09 (t, J=9.6 Hz, 2H), 6.88 (dd, J=11.2, 3.9 Hz, 2H), 3.83 (s, 3H).

STEP 2: 3'-CHLORO-2,5'-DIFLUORO-4-IODO-5-METHOXY-1,1'-BIPHENYL

To a solution of compound-2 (76.0 g, 0.299 mol, 1.0 equiv) in DCM (750 mL), AcOH (750 mL) and sulphuric acid (15 mL) was added N-iodosuccinimide (113.4 g, 0.504 mol, 1.0 equiv) in one portion. The reaction mass was stirred at RT for 16 h. The reaction mass was diluted with DCM (1.0 L) and the organic layer was washed with water (1.0 L) and saturated aqueous sodium thiosulfate (1.0 L). The organic layer was dried over sodium sulphate, filtered and concentrated under reduced pressure to get the crude material which was purified by column chromatography (silica gel 60-120 mesh, elution 1% EtOAc/Hexane) to get compound-3 (80 g, 72%). TLC solvent system: Heptane, Product's $R_f$: 0.6. $^1$H NMR (400 MHz, Chloroform-d) δ 7.63 (d, J=9.3 Hz, 1H), 7.33 (s, 1H), 7.23-7.11 (m, 2H), 6.79 (d, J=6.4 Hz, 1H), 3.93 (s, 3H).

STEP 3: (3'-CHLORO-2,5'-DIFLUORO-5-METHOXY-[1,1'-BIPHENYL]-4-YL)BORONIC ACID

A solution of compound-3 (30 g, 0.078 mol, 1.0 equiv) in THF (300 mL) was cooled to −78° C. under nitrogen atmosphere. Isopropyl magnesium chloride (2.0 M in THF, 59.1 mL, 1.5 equiv) was added drop-wise for 30 mins. After addition, the reaction mass was allowed warm to −55° C. and stirred for 1 h. Triisopropylborate (27.1 mL, 0.118 mol, 1.5 equiv) was added at −55° C. The reaction mass was allowed to warm to RT and stirred for 3 h. Saturated aqueous ammonium chloride solution (200 mL) was added slowly and the mixture was extracted with EtOAc (2×200 mL). The combined organic extract was washed with brine (200 mL), dried over sodium sulfate, filtered and concentrated under reduced pressure to get the crude material which was purified by stirring with EtOAc:Hexane (1:9, 200 mL) for 30 min and filtered to get compound-4 (13.2 g, 52.8%) as white solid. TLC solvent system: 20% Ethyl acetate/Hexane Product's $R_f$: 0.5. $^1$H NMR (400 MHz, Chloroform-d) δ 7.69 (d, J=10.4 Hz, 1H), 7.36 (d, J=1.2 Hz, 1H), 7.27-7.23 (m, 1H), 7.21-7.13 (m, 1H), 6.89 (d, J=5.6 Hz, 1H), 5.78 (s, 2H), 3.97 (s, 3H).

Intermediate BY

(4'-CHLORO-2-FLUORO-5-METHOXY-3'-METHYL-[1,1'-BIPHENYL]-4-YL)BORONIC ACID

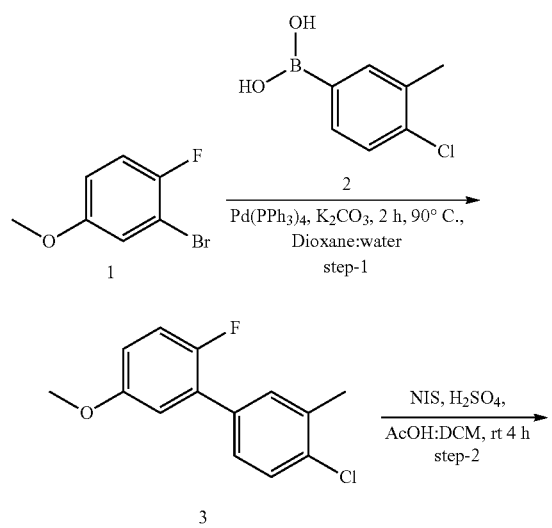

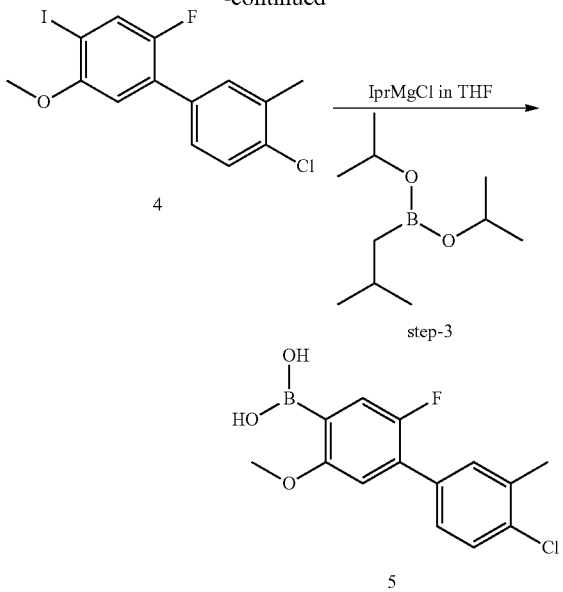

STEP 1: 4'-CHLORO-2-FLUORO-5-METHOXY-3'-METHYL-1,1'-BIPHENYL

A solution of compound-1 (100 g, 487.73 mmol, 1.0 equiv, F-chemicals), compound-2 (91.42 g, 536.50 mmol, 1.1 equiv, F-chemicals) and potassium carbonate (202.2 g, 1463.09 mmol, 3.0 equiv) in 1,4-dioxane (2.0 L) and H$_2$O (500 mL) was degassed with nitrogen for 15 min. Pd(PPh$_3$)$_4$ (28.18 g, 24.38 mmol, 0.05 equiv) was added and the mixture was again degassed with nitrogen for 5 min. The reaction mixture was heated at 90° C. for 3 h. The reaction mass was cooled to room temperature, diluted with ethyl acetate (1.0 L) and washed with brine (200 mL). The organic layer was dried over sodium sulfate, filtered and concentrated under reduced pressure to get the crude material which was purified by column chromatography (silica gel 60-120 mesh, elution Hexane) to get the pure compound-3 (105 g, 86%). TLC solvent system: Heptane, Product $R_f$: 0.5. $^1$H NMR (400 MHz, Chloroform-d) δ 7.45-7.40 (m, 2H), 7.35-7.31 (m, 1H), 7.12-7.06 (m, 1H), 6.92 (dd, J=6.3, 3.1 Hz, 1H), 6.85 (dt, J=8.9, 3.5 Hz, 1H), 3.85 (s, 3H), 2.45 (s, 3H).

STEP 2: 4'-CHLORO-2-FLUORO-4-IODO-5-METHOXY-3'-METHYL-1,1'-BIPHENYL

To a solution of compound-3 (105 g, 418.82 mmol, 1.0 equiv) in DCM (500 mL), AcOH (500 mL) and sulphuric acid (22.59 g) was added N-iodosuccinimide (94.23 g, 418.82 mmol, 1.0 equiv) in one portion. The reaction mass was stirred at room temperature for 16 h. The reaction mass was diluted with DCM (4×600 mL) and the organic layer was washed with water (3×500 mL) and saturated aqueous sodium thiosulfate (1.0 L). The organic layer was dried over sodium sulphate, filtered and concentrated under reduced pressure to get the crude material which was purified by column chromatography (silica gel 230-400 mesh; elution Hexane) to get compound-4 (110 g, 70%). TLC solvent system: Heptane, Product's $R_f$: 0.6. $^1$H NMR (400 MHz, DMSO-d$_6$) δ 7.77 (d, J=9.7 Hz, 1H), 7.59 (s, 1H), 7.52 (d, J=8.3 Hz, 1H), 7.44 (t, J=10.0 Hz, 1H), 7.06 (t, J=6.6 Hz, 1H), 3.88 (s, 3H), 2.40 (s, 3H).

STEP 3: (4'-CHLORO-2-FLUORO-5-METHOXY-3'-METHYL-[1,1'-BIPHENYL]-4-YL)BORONIC ACID

A solution of compound-4 (60 g, 159.32 mmol, 1.0 equiv) in THF (600 mL) was cooled to −78° C. under nitrogen atmosphere. Isopropyl magnesium chloride (1.3 M in THF, 245.1 mL, 2.0 equiv) was added dropwise for 30 mins. After addition the reaction mass was allowed warm to −55° C. and stirred for 1 h. Triisopropylborate (59.93 g, 318.65 mmol, 2.0 equiv) was added at −55° C. The reaction mass was allowed to warm to RT and stirred for 3 h. Saturated aqueous ammonium chloride solution (700 mL) was added slowly and the mixture was extracted with EtOAc (2×750 mL). The combined organic extract was washed with brine (400 mL), dried over sodium sulfate, filtered and concentrated under reduced pressure to get the crude material which was purified by stirring with Hexane and filtered to get compound-5 (36 g, 76%) as an off-white solid. TLC solvent system: 10% Ethylacetate/Hexane Product's $R_f$: 0.2. $^1$H NMR (400 MHz, DMSO-$d_6$) δ 7.90 (s, 2H), 7.59 (s, 1H), 7.51 (d, J=8.3 Hz, 1H), 7.43 (d, J=8.3 Hz, 1H), 7.35 (d, J=10.8 Hz, 1H), 7.03 (d, J=6.0 Hz, 1H), 3.85 (s, 3H), 2.39 (s, 3H).

Intermediate BZ

(2,3',5'-TRIFLUORO-5-METHOXY-[1,1'-BIPHENYL]-4-YL)BORONIC ACID

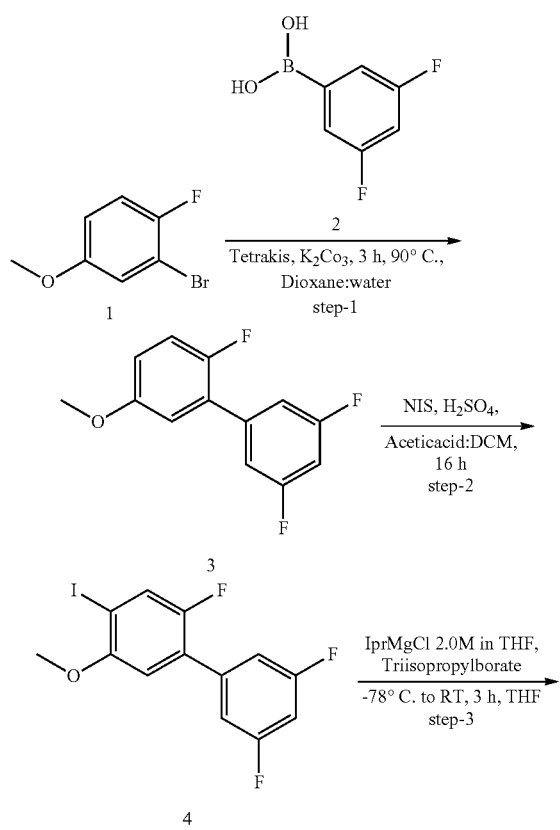

STEP 1: 2,3',5'-TRIFLUORO-5-METHOXY-1,1'-BIPHENYL

A solution of compound-1 (120 g, 0.588 mol, 1.0 equiv, F-chemicals), compound-2 (101 g, 0.641 mol, 1.1 equiv, combi-blocks) and potassium carbonate (244 g, 1.164 mol, 2.0 equiv) in 1,4-dioxane (2.0 L) and $H_2O$ (500 mL) was degassed with nitrogen for 15 min. Pd(PPh$_3$)$_4$ (34.0 g, 0.0294 mol, 0.05 equiv) was added and the mixture was again degassed with nitrogen for 5 min. The reaction mixture was heated at 90° C. for 3 h. The reaction mass was cooled to room temperature, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (125 g, 89%). TLC solvent system: Heptane, Product $R_f$: 0.5. $^1$H NMR (400 MHz, Chloroform-d) δ 7.35-7.27 (m, 1H), 7.12-7.02 (m, 2H), 6.92-6.79 (m, 3H), 3.84 (s, 3H).

STEP 2: 2,3',5'-TRIFLUORO-4-IODO-5-METHOXY-1,1'-BIPHENYL

To a solution of compound-3 (120 g, 0.504 mol, 1.0 equiv) in DCM (750 mL), AcOH (750 mL), and sulphuric acid (15 mL) was added N-iodosuccinimide (113.4 g, 0.504 mol, 1.0 equiv) in one portion. The reaction mass was stirred at room temperature for 16 h. The reaction mass was diluted with DCM (2.0 L) and the organic layer was washed with water (2.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (142 g, 76%). TLC solvent system: Heptane, Product's $R_f$: 0.6. $^1$H NMR (400 MHz, Chloroform-d) δ 7.63 (dd, J=9.3, 1.0 Hz, 1H), 7.13-7.04 (m, 2H), 6.87 (tdd, J=8.8, 2.8, 1.7 Hz, 1H), 6.80 (d, J=6.4 Hz, 1H), 3.93 (d, J=0.9 Hz, 3H).

STEP 3: (2,3',5'-TRIFLUORO-5-METHOXY-[1,1'-BIPHENYL]-4-YL)BORONIC ACID

A solution of compound-4 (75.0 g, 0.21 mol, 1.0 equiv) in THF (750 mL) was cooled to −78° C. under nitrogen atmosphere. Isopropyl magnesium chloride (2.0 M in THF, 241 mL, 0.31 mol, 1.5 equiv) was added drop-wise for 30 mins. After addition the reaction mass was allowed warm to −55° C. and stirred for 1 h. Triisopropylborate (73 mL, 0.31 mol, 1.5 equiv) was added at −55° C. The reaction mass was allowed to warm to RT and stirred for 3 h. Saturated aqueous ammonium chloride solution (700 mL) was added slowly and the mixture was extracted with EtOAc (2×1.0 L). The combined organic extract was washed with brine (1.0 L), dried over sodium sulfate filtered and concentrated under reduced pressure to get the crude material which was purified by stirring with EtOAc:Hexane (1:9, 200 mL) for 30 min and filtered to get compound-5 (30 g, 50%) as white solid. TLC solvent system: 20% Ethylacetate/Hexane Product's $R_f$: 0.5. $^1$H NMR (400 MHz, DMSO-$d_6$) δ 7.97 (s, 2H), 7.58 (s, 1H), 7.36-7.31 (m, 1H), 7.25 (d, J=7.1 Hz, 2H), 7.02 (s, J=6.0 Hz, 1H), 3.83 (s, 3H).

Intermediate CA

2-FLUORO-4-IODO-5-METHOXY-3'-(TRIFLUO-ROMETHYL)-1,1'-BIPHENYL

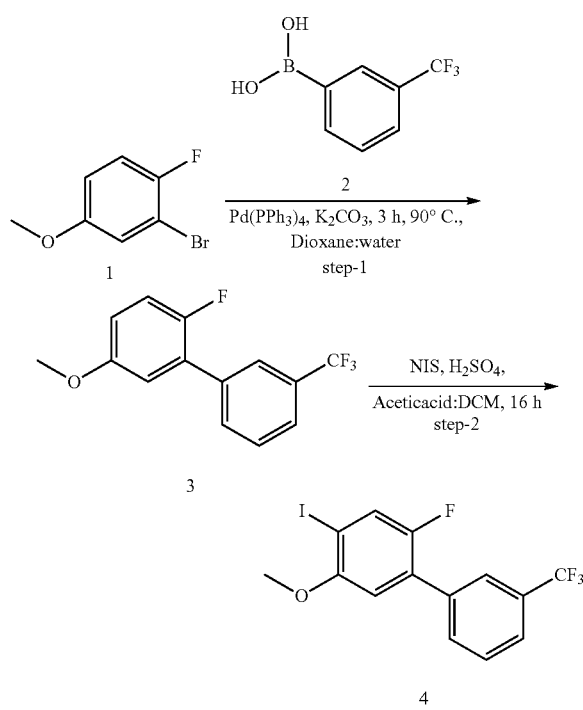

STEP 1: 2-FLUORO-5-METHOXY-3'-(TRIFLUO-ROMETHYL)-1,1'-BIPHENYL

A solution of compound-1 (50.0 g, 0.2438 mol, 1.0 equiv, Sozhoin sibica chemical), compound-2 (55.5 g, 0.29 mol, 1.2 equiv, F-chemicals) and potassium carbonate (100 g, 0.73 mol, 3.0 equiv) in 1,4-dioxane (380.0 mL) and H$_2$O (90 mL) was degassed with nitrogen for 15 min. Pd(PPh$_3$)$_4$ (14.5 g, 0.121 mol, 0.05 equiv) was added and the mixture was again degassed with nitrogen for 5 min. The reaction mixture was heated at 90° C. for 3 h. The reaction mass was cooled to RT, diluted with ethyl acetate (300 mL) and washed with brine (200 mL). The organic layer was dried over sodium sulfate, filtered and concentrated under reduced pressure to get the crude material which was purified by column chromatography (silica gel 60-120 mesh, elution 0.5% EtOAc/Hexane) to get the pure compound-3 (55 g, 83.7%) as white solid. TLC solvent system: Heptane, Product $R_f$: 0.5. $^1$H NMR (300 MHz, Chloroform-d) δ 7.80 (s, 1H), 7.74 (d, J=6.6 Hz, 1H), 7.60 (dt, J=14.9, 7.7 Hz, 2H), 7.15-7.03 (m, 1H), 6.96-6.85 (m, 2H), 3.84 (s, 3H).

STEP 2: 2-FLUORO-4-IODO-5-METHOXY-3'-(TRIFLUOROMETHYL)-1,1'-BIPHENYL

To a solution of compound-2 (55.0 g, 0.2037 mol, 1.0 equiv) in DCM (330 mL), AcOH (330 mL) and sulphuric acid (6.0 mL) was added N-iodosuccinimide (45.8 g, 0.203 mol, 1.0 equiv) in one portion. The reaction mass was stirred at room temperature for 16 h. The reaction mass was diluted with DCM (200 mL) and the organic layer was washed with water (500 mL) and saturated aqueous sodium thiosulfate (500 mL). The organic layer was dried over sodium sulphate, filtered and concentrated under reduced pressure to get the crude material which was purified by column chromatography (silica gel 60-120 mesh, elution 100% Hexane) to get compound-4 (45 g, 55.8%) as colourless liquid. TLC solvent system: Heptane, Product's $R_f$: 0.5. $^1$H NMR (400 MHz, Chloroform-d) δ 7.78 (s, 1H), 7.73 (d, J=7.7 Hz, 1H), 7.67 (d, J=7.8 Hz, 1H), 7.63 (d, J=9.2 Hz, 1H), 7.60 (d, J=7.7 Hz, 1H), 6.82 (d, J=6.4 Hz, 1H), 3.93 (s, 3H).

Intermediate CB 2,3',5'-TRIFLUORO-4-IODO-5-METHOXY-1,1'-BIPHENYL

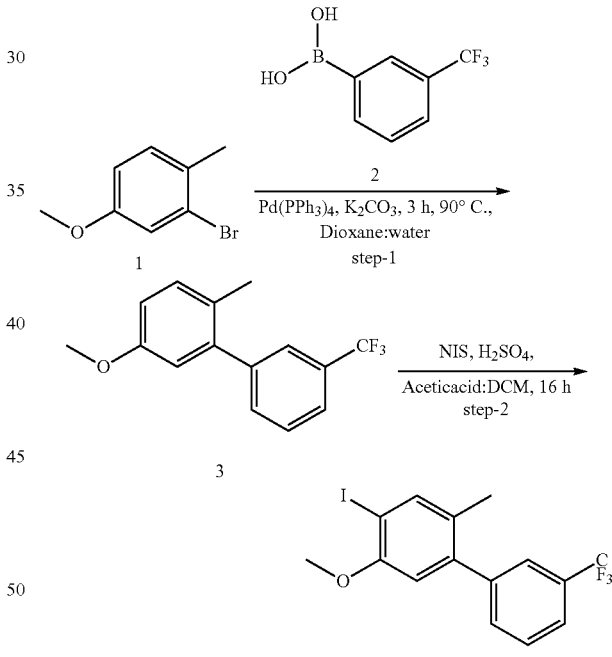

STEP 1: 5-METHOXY-2-METHYL-3'-(TRIFLUO-ROMETHYL)-1,1'-BIPHENYL

A solution of compound-1 (100 g, 0.49 mol, 1.0 equiv, Fchemicals), compound-2 (103 g, 0.54 mol, 1.1 equiv, combiblock) and potassium carbonate (206 g, 1.492 mol, 3.0 equiv) in 1,4-dioxane (2.0 L) and H$_2$O (500 mL) was degassed with nitrogen for 15 min. Pd(PPh$_3$)$_4$ (29 g, 0.029 mol, 0.05 equiv) was added and the mixture was again degassed with nitrogen for 5 min. The reaction mixture was heated at 90° C. for 3 h. The reaction mass was cooled to RT, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (100 g, 75%). TLC solvent system: Heptane, Product R$_f$: 0.5. $^1$H NMR (400 MHz, Chloroform-d) δ 7.66-7.59 (m, 2H), 7.59-7.47 (m, 2H), 7.21 (d, J=8.4 Hz, 1H), 6.87 (dd, J=8.4, 2.8 Hz, 1H), 6.79 (d, J=2.8 Hz, 1H), 3.83 (s, 3H), 2.19 (s, 3H).

STEP 2: 2,3',5'-TRIFLUORO-4-IODO-5-METHOXY-1,1'-BIPHENYL

To a solution of compound-3 (75 g, 0.28 mol, 1.0 equiv) in DCM (475 mL), AcOH (475 mL) and sulphuric acid (8 mL) was added N-iodosuccinimide (63 g, 0.281 mol, 1.0 equiv) in one portion. The reaction mass was stirred at RT for 16 h. The reaction mass was diluted with DCM (1.0 L) and the organic layer was washed with water (1.0 L) and saturated aqueous sodium thiosulfate (1 L). The organic layer was dried over sodium sulphate, filtered and concentrated under reduced pressure to get the crude material which was purified by column chromatography (silica gel 60-120 mesh, elution 2% EtOAc/Hexane) to get compound-4 (66 g, 61%). TLC solvent system: Heptane, Product's R$_f$: 0.6. $^1$H NMR (400 MHz, Chloroform-d) δ 7.72 (s, 1H), 7.66-7.65 (m, 1H), 7.59-7.50 (m, 3H), 6.67 (s, 1H), 3.89 (s, 3H), 2.16 (s, 3H).

Table 2 provides analytical characterization and biological data for the examples 312-588, as representative compounds of the present invention. The compounds in the table are name by ACD software, version 12; while the compound names in the written examples presented herein were named using ChemDraw Ultra version 12; molecular weight measured (MW); the method by which the compound was made; the NMR of the representative example (for those compounds having no detailed written procedure above); and biological data including in-vitro Nav 1.7 PX data (IC$_{50}$ in uM) and Nav 1.5 PX data (IC$_{50}$ in uM), where available.

TABLE 2

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 535 | 4-(4'-ethoxy-2-fluoro-5-methoxy-3'-methyl-4-biphenylyl)-N-3-isoxazolyl-7-quinazolinesulfonamide | 535.3 | 66 | 0.61 | | $^1$H NMR (400 MHz, DMSO-d$_6$) d = 12.07 (br. s., 1 H), 9.53 (s, 1 H), 8.74 (d, J = 1.8 Hz, 1 H), 8.51 (d, J = 1.5 Hz, 1 H), 8.12-7.94 (m, 2 H), 7.54-7.48 (m, 2 H), 7.43 (d, J = 10.6 Hz, 1 H), 7.30 (d, J = 6.5 Hz, 1 H), 7.11-7.06 (m, 1 H), 6.52 (d, J = 1.9 Hz, 1 H), 4.13 (q, J = 6.9 Hz, 2 H), 3.75 (s, 3 H), 2.26 (s, 3 H), 1.40 (t, J = 6.9 Hz, 3 H). |
| 316 | 1-(2,3'-difluoro-5,5'-dimethoxy-4-biphenylyl)-N-3-isoxazolyl-6-isoquinolinesulfonamide | 524.2 | 68 | 0.04 | | |
| 315 | 4-(3'-chloro-2-fluoro-5-methoxy-4-biphenylyl)-N-2-pyrimidinyl-7-quinazolinesulfonamide | 522.1 | 67 | 0.048 | | |
| 536 | 4-(2-fluoro-5-methoxy-3',5'-dimethyl-4-biphenylyl)-N-3-isoxazolyl-7-quinazolinesulfonamide | 505.3 | 66 | 0.051 | | 1H NMR (400 MHz, DMSO-d6) d = 12.05 (br. s., 1 H), 9.53 (s, 1 H), 8.76 (d, J = 1.9 Hz, 1 H), 8.52 (d, J = 1.5 Hz, 1 H), 8.04 (dq, J = 1.2, 8.7 Hz, 2 H), 7.45 (d, J = 10.4 Hz, 1 H), 7.35-7.25 (m, 3 H), 7.11 (s, 1 H), 6.53 (d, J = 1.9 Hz, 1 H), 3.74 (s, 3 H), 2.38 (s, 6 H). |
| 537 | 4-(3'-chloro-2-fluoro-5,5'-dimethoxy-4-biphenylyl)-N-3-isoxazolyl-7-quinazolinesulfonamide | 541.1 | 66 | 0.036 | | 1H NMR (400 MHz, DMSO-d6) d = 12.05 (br. s., 1 H), 9.53 (s, 1 H), 8.76 (d, J = 1.9 Hz, 1 H), 8.52 (d, J = 1.6 Hz, 1 H), 8.07-7.91 (m, 2 H), 7.50 (d, J = 10.4 Hz, 1 H), 7.39 (d, J = 6.3 Hz, 1 H), 7.34 (q, J = 1.6 Hz, 1 H), 7.22 (td, J = 1.3, 2.4 Hz, 1 H), 7.19-7.14 (m, 1 H), 6.53 (d, J = 1.8 Hz, 1 H), 3.87 (s, 3 H), 3.75 (s, 3 H). |
| 538 | 1-(3'-chloro-3-fluoro-5-methoxy-4-biphenylyl)-N-3-isoxazolyl-6-isoquinolinesulfonamide | 510.2 | 2 | 0.298 | | 1H NMR (400 MHz, DMSO-d6) d = 11.93 (br. s., 1 H), 8.78 (d, J = 5.7 Hz, 1 H), 8.74 (d, J = 1.8 Hz, 1 H), 8.71 (d, J = 2.0 Hz, 1 H), 8.19 (d, J = 5.2 Hz, 1 H), 7.98-7.93 (m, 2 H), 7.87-7.82 (m, 2 H), 7.59-7.51 (m, 2 H), 7.44-7.36 (m, 2 H), 6.50 (d, J = 1.9 Hz, 1 H), 3.77 (s, 3 H). |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 317 | (M)-4-(2-chloro-3'-fluoro-5-methoxy-4-biphenylyl)-N-3-isoxazolyl-3-methyl-7-isoquinolinesulfonamide | 524.2 | 69 | 0.072 | | |
| 318 | (P)-4-(2-chloro-3'-fluoro-5-methoxy-4-biphenylyl)-N-3-isoxazolyl-3-methyl-7-isoquinolinesulfonamide | 524.2 | 69 | 1.392 | | |
| 539 | 1-(2-fluoro-5-methoxy-4'-(trifluoromethyl)-4-biphenylyl)-N-3-isoxazolyl-6-isoquinolinesulfonamide | 544.1 | 6 | 0.237 | | 1H NMR (400 MHz, DMSO-d6) d = 11.93 (br. s., 1 H), 8.78 (d, J = 5.7 Hz, 1 H), 8.74 (d, J = 1.8 Hz, 1 H), 8.71 (d, J = 2.0 Hz, 1 H), 8.19 (d, J = 5.2 Hz, 1 H), 7.98-7.93 (m, 2 H), 7.87-7.82 (m, 2 H), 7.59-7.51 (m, 2 H), 7.44-7.36 (m, 2 H), 6.50 (d, J = 1.9 Hz, 1 H), 3.77 (s, 3 H). |
| 392 | 1-(4-fluoro-5-(5-fluoro-3-pyridinyl)-2-methoxyphenyl)-N-3-isoxazolyl-6-isoquinolinesulfonamide | 495.0 | 123 | 0.491 | | |
| 497 | 1-(4-fluoro-5-(6-fluoro-3-pyridinyl)-2-methoxyphenyl)-N-3-isoxazolyl-6-isoquinolinesulfonamide | 495.0 | 123 | 0.479 | | |
| 399 | 1-(4-fluoro-2-methoxy-5-(2-pyridinyl)phenyl)-N-3-isoxazolyl-6-isoquinolinesulfonamide | 477.0 | 128 | 28.45 | | |
| 400 | 1-(2-chloro-3'-fluoro-5-methoxy-4-biphenylyl)-3-cyano-N-3-isoxazolyl-6-isoquinolinesulfonamide | 534.9 | 129 | 0.128 | | |
| 394 | 1-(2-chloro-3'-fluoro-5-methoxy-4-biphenylyl)-N-3-isoxazolyl-3-oxo-2,3-dihydro-6-isoquinolinesulfonamide | 526.1 | 125 | 0.041 | | |
| 395 | 1-(2-chloro-3'-fluoro-5-methoxy-4-biphenylyl)-N-3-isoxazolyl-2-methyl-3-oxo-2,3-dihydro-6-isoquinolinesulfonamide | 540.0 | 126 | 0.125 | | |
| 403 | 1-(2,3'-difluoro-5-methoxy-4-biphenylyl)-N-3-isoxazolyl-N,2-dimethyl-3-oxo-2,3-dihydro-6-isoquinolinesulfonamide | 538.2 | 132 | | | |
| 393 | 3-chloro-1-(2,3'-difluoro-5-methoxy-4-biphenylyl)-N-3-isoxazolyl-6-isoquinolinesulfonamide | 528.0 | 124 | 0.157 | | |
| 396 | (P)-1-(2-chloro-3'-fluoro-5-methoxy-4-biphenylyl)-N-3-isoxazolyl-2-methyl-3-oxo-2,3-dihydro-6-isoquinolinesulfonamide | 540.0 | 126 | 0.036 | | |
| 397 | (M)-1-(2-chloro-3'-fluoro-5-methoxy-4-biphenylyl)-N-3-isoxazolyl-2-methyl-3-oxo-2,3-dihydro-6-isoquinolinesulfonamide | 540.0 | 126 | 12.65 | | |
| 401 | 4-(2-chloro-3'-fluoro-5-methoxy-4-biphenylyl)-N-3-isoxazolyl-3-methoxy-7-isoquinolinesulfonamide | 540.0 | 130 | 0.613 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 402 | 4-(2-chloro-3'-fluoro-5-methoxy-4-biphenylyl)-N-3-isoxazolyl-2-methyl-3-oxo-2,3-dihydro-7-isoquinolinesulfonamide | 540.2 | 131 | 0.039 | | |
| 589 | 4-(3'-fluoro-3-methoxy-4-biphenylyl)-N-3-isoxazolyl-2-methyl-3-oxo-2,3-dihydro-7-isoquinolinesulfonamide | 506.1 | 131 | 0.533 | | 1H NMR (500 MHz, DMSO-d6) ä 9.17 (s, 1H), 8.72 (s, 1H), 8.27 (s, 1H), 7.64 (d, J = 8.55 Hz, 2H), 7.49-7.57 (m, 2H), 7.33-7.43 (m, 3H), 7.16-7.26 (m, 2H), 6.94 (d, J = 9.62 Hz, 1H), 6.42 (d, J = 1.66 Hz, 1H), 3.75 (br. s., 3H), 3.74 (s, 3H) |
| 398 | 4-(2-chloro-3'-fluoro-5-methoxy-4-biphenylyl)-N-3-isoxazolyl-3-oxo-2,3-dihydro-7-isoquinolinesulfonamide | 526.0 | 127 | 0.027 | | |
| 546 | 1-(2-fluoro-5-methoxy-3'-(trifluoromethyl)-4-biphenylyl)-N-3-isoxazolyl-2-methyl-3-oxo-2,3-dihydro-6-isoquinolinesulfonamide | 574.1 | 126 | 0.029 | | 1H NMR (400 MHz, MeOH) ä 8.48 (d, J = 1.87 Hz, 1H), 8.13 (d, J = 0.62 Hz, 1H), 7.95-8.03 (m, 2H), 7.71-7.83 (m, 2H), 7.41 (d, J = 6.22 Hz, 1H), 7.36 (d, J = 9.85 Hz, 1H), 7.19-7.29 (m, 2H), 7.07 (s, 1H), 6.54 (d, J = 1.76 Hz, 1H), 3.87 (s, 3H), 3.66 (s, 3H) |
| 547 | 1-(3'-chloro-2,5'-difluoro-5-methoxy-4-biphenylyl)-N-3-isoxazolyl-3-oxo-2,3-dihydro-6-isoquinolinesulfonamide | 544.1 | 125 | 0.02 | | 1H NMR (400 MHz, DMSO-d6) ä 11.83 (s, 1H), 11.25 (br. s., 1H), 8.75 (d, J = 1.87 Hz, 1H), 8.44 (s, 1H), 7.65-7.76 (m, 2H), 7.52-7.64 (m, 3H), 7.33-7.46 (m, 2H), 7.26 (s, 1H), 6.50 (d, J = 1.76 Hz, 1H), 3.74 (s, 3H) |
| 548 | 1-(4'-chloro-2-fluoro-5-methoxy-3'-methyl-4-biphenylyl)-N-3-isoxazolyl-3-oxo-2,3-dihydro-6-isoquinolinesulfonamide | 540.0 | 125 | 0.016 | | 1H NMR (400 MHz, MeOH) ä 8.47 (d, J = 1.76 Hz, 1H), 8.36 (s, 1H), 7.73 (d, J = 8.91 Hz, 1H), 7.56-7.65 (m, 2H), 7.50 (s, 2H), 7.30 (d, J = 10.26 Hz, 1H), 7.25 (d, J = 6.32 Hz, 1H), 7.18 (s, 1H), 6.54 (d, J = 1.87 Hz, 1H), 3.79 (s, 3H), 2.49 (s, 3H) |
| 549 | 4-(4'-chloro-2-fluoro-5-methoxy-3'-methyl-4-biphenylyl)-N-3-isoxazolyl-3-oxo-2,3-dihydro-7-isoquinolinesulfonamide | 540.1 | 127 | 0.008 | | 1H NMR (400 MHz, MeOH) ä 8.91 (s, 1H), 8.52 (d, J = 1.97 Hz, 1H), 8.46 (d, J = 1.76 Hz, 1H), 7.72 (dd, J = 1.92, 9.28 Hz, 1H), 7.60 (s, 1H), 7.48 (s, 2H), 7.32 (d, J = 9.64 Hz, 1H), 7.18 (d, J = 6.63 Hz, 1H), 7.11 (d, J = 10.57 Hz, 1H), 6.51 (d, J = 1.87 Hz, 1H), 3.75 (s, 4H), 2.48 (s, 3H) |
| 550 | 4-(3'-chloro-2,5'-difluoro-5-methoxy-4-biphenylyl)-N-3-isoxazolyl-3-oxo-2,3-dihydro-7-isoquinolinesulfonamide | 544.1 | 127 | 0.006 | | 1H NMR (400 MHz, MeOH) ä 8.92 (s, 1H), 8.52 (s, 1H), 8.46 (d, J = 1.87 Hz, 1H), 7.72 (d, J = 7.77 Hz, 1H), 7.55 (s, 1H), 7.42 (d, J = 9.64 Hz, 1H), 7.27-7.35 (m, 2H), 7.22 (d, J = 6.53 Hz, 1H), 7.16 (d, J = 10.68 Hz, 1H), 6.51 (d, J = 1.87 Hz, 1H), 3.76 (s, 3H) |
| 551 | (P)-1-(2-fluoro-5-methoxy-3'-(trifluoromethyl)-4-biphenylyl)-N-3-isoxazolyl-2-methyl-3-oxo-2,3-dihydro-6-isoquinolinesulfonamide | 574.1 | 126 | 0.028 | | 1H NMR (400 MHz, MeOH) ä 8.48 (d, J = 1.87 Hz, 1H), 8.13 (d, J = 0.62 Hz, 1H), 7.95-8.03 (m, 2H), 7.71-7.83 (m, 2H), 7.41 (d, J = 6.22 Hz, 1H), 7.36 (d, J = 9.85 Hz, 1H), 7.19-7.29 (m, 2H), 7.07 (s, 1H), 6.54 (d, J = 1.76 Hz, 1H), 3.87 (s, 3H), 3.66 (s, 3H) |
| 552 | (M)-1-(2-fluoro-5-methoxy-3'-(trifluoromethyl)-4-biphenylyl)-N-3-isoxazolyl-2-methyl-3-oxo-2,3-dihydro-6-isoquinolinesulfonamide | 574.1 | 126 | 1.251 | | 1H NMR (400 MHz, MeOH) ä 8.48 (d, J = 1.87 Hz, 1H), 8.13 (d, J = 0.62 Hz, 1H), 7.95-8.03 (m, 2H), 7.71-7.83 (m, 2H), 7.41 (d, J = 6.22 Hz, 1H), 7.36 (d, J = 9.85 Hz, 1H), 7.19-7.29 (m, 2H), 7.07 (s, 1H), 6.54 (d, J = 1.76 Hz, 1H), 3.87 (s, 3H), 3.66 (s, 3H) |

TABLE 2-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 553 | 1-(2-chloro-3'-fluoro-5-methoxy-4-biphenylyl)-3-oxo-N-2-pyrimidinyl-2,3-dihydro-6-isoquinolinesulfonamide | 537.0 | 125 | 0.045 | | 1H NMR (500 MHz, DMSO-d6) ä 8.47-8.56 (m, 3H), 7.63-7.75 (m, 2H), 7.52-7.61 (m, 2H), 7.43 (d, J = 7.20 Hz, 2H), 7.28-7.35 (m, 1H), 7.26 (d, J = 9.47 Hz, 2H), 7.05 (br. s., 1H), 3.71 (s, 3H) |
| 554 | 4-(3'-cyclopropyl-4'-fluoro-5-methoxy-2-methyl-4-biphenylyl)-N-3-isoxazolyl-7-quinazolinesulfonamide | 531.0 | 33 | 0.034 | | 1H NMR (ACETONITRILE-d3) d: 9.39-9.43 (m, 1H), 8.53 (d, J = 1.6 Hz, 1H), 8.32 (d, J = 1.8 Hz, 1H), 7.96-8.01 (m, 1H), 7.88-7.93 (m, 1H), 7.31 (d, J = 0.3 Hz, 1H), 7.20-7.27 (m, 1H), 7.12-7.20 (m, 1H), 6.98-7.07 (m, 2H), 6.46 (d, J = 1.8 Hz, 1H), 3.65-3.69 (m, 3H), 2.21 (s, 3H), 2.10-2.19 (m, 1H), 0.97-1.07 (m, 2H), 0.77-0.84 (m, 2H) |
| 555 | 4-(3'-cyclopropyl-5'-fluoro-5-methoxy-2-methyl-4-biphenylyl)-N-3-isoxazolyl-7-quinazolinesulfonamide | 531.0 | 33 | 0.061 | | 1H NMR (ACETONITRILE-d3) d: 9.40-9.43 (m, 1H), 8.52 (d, J = 1.9 Hz, 1H), 8.30 (d, J = 1.8 Hz, 1H), 7.96-8.01 (m, 1H), 7.85-7.92 (m, 1H), 7.32 (s, 1H), 6.96-7.05 (m, 3H), 6.86 (dt, J = 10.5, 2.0 Hz, 1H), 6.45 (d, J = 1.8 Hz, 1H), 3.66-3.69 (m, 3H), 2.25 (s, 3H), 1.97-2.06 (m, 1H), 1.01-1.09 (m, 2H), 0.75-0.82 (m, 2H) |
| 556 | 4-(2'-fluoro-5-methoxy-2,5'-dimethyl-4-biphenylyl)-N-3-isoxazolyl-7-quinazolinesulfonamide | 505.2 | 33 | 0.113 | | 1H NMR (ACETONITRILE-d3) d: 9.42 (s, 1H), 8.52 (d, J = 1.9 Hz, 1H), 8.30 (d, J = 1.9 Hz, 1H), 7.96-8.01 (m, 1H), 7.88-7.93 (m, 1H), 7.34 (s, 1H), 7.19-7.30 (m, 2H), 7.14 (dd, J = 9.8, 8.4 Hz, 1H), 7.04 (s, 1H), 6.45 (d, J = 1.8 Hz, 1H), 3.66 (s, 3H), 2.40 (s, 3H), 2.17 (s, 3H) |
| 557 | 4-(5'-chloro-2'-fluoro-5-methoxy-2-methyl-4-biphenylyl)-N-3-isoxazolyl-7-quinazolinesulfonamide | 525.0 | 33 | 0.056 | | 1H NMR (ACETONITRILE-d3) d: 9.45 (s, 1H), 8.55-8.59 (m, 1H), 8.38 (d, J = 1.8 Hz, 1H), 7.90-8.01 (m, 2H), 7.43-7.51 (m, 2H), 7.36 (s, 1H), 7.27 (ddd, J = 9.3, 8.6, 0.5 Hz, 1H), 7.07 (s, 1H), 6.52 (d, J = 1.9 Hz, 1H), 3.64-3.68 (m, 3H), 2.18 (s, 3H) |
| 558 | 4-(5'-chloro-5-methoxy-2,2'-dimethyl-4-biphenylyl)-N-3-isoxazolyl-7-quinazolinesulfonamide | 521.0 | 33 | 0.041 | | 1H NMR (ACETONITRILE-d3) d: 9.45 (s, 1H), 8.57 (t, J = 1.1 Hz, 1H), 8.39 (d, J = 1.9 Hz, 1H), 7.96-8.00 (m, 2H), 7.32-7.36 (m, 3H), 7.25 (s, 1H), 6.93 (s, 1H), 6.52 (d, J = 1.8 Hz, 1H), 3.64 (s, 3H), 2.11-2.15 (m, 3H), 2.04 (s, 3H) |
| 559 | 4-(4'-fluoro-3',5-dimethoxy-2-methyl-4-biphenylyl)-N-3-isoxazolyl-7-quinazolinesulfonamide | 521.2 | 33 | 0.057 | | 1H NMR (ACETONITRILE-d3) d: 9.40-9.46 (m, 1H), 8.54-8.58 (m, 1H), 8.37-8.41 (m, 1H), 7.95-8.01 (m, 2H), 7.30-7.40 (m, 1H), 7.14-7.27 (m, 1H), 7.04-7.09 (m, 2H), 6.49-6.54 (m, 1H), 3.90-3.95 (m, 3H), 3.66-3.71 (m, 3H), 2.25-2.30 (m, 3H) |
| 560 | 4-(3'-fluoro-5,5'-dimethoxy-2-methyl-4-biphenylyl)-N-3-isoxazolyl-7-quinazolinesulfonamide | 521.2 | 33 | 0.035 | | 1H NMR (ACETONITRILE-d3) d: 9.44 (s, 1H), 8.56 (d, J = 1.4 Hz, 1H), 8.38 (d, J = 1.8 Hz, 1H), 7.96 (qd, J = 8.6, 1.2 Hz, 2H), 7.33 (s, 1H), 7.06 (s, 1H), 6.70-6.88 (m, 2H), 6.51 (d, J = 1.8 Hz, 1H), 3.83-3.89 (m, 3H), 3.62-3.70 (m, 3H), 2.27 (s, 3H) |
| 561 | 4-(2'-fluoro-5,5'-dimethoxy-2-methyl-4-biphenylyl)-N-3-isoxazolyl-7-quinazolinesulfonamide | 521.2 | 33 | 0.089 | | 1H NMR (ACETONITRILE-d3) d: 9.44 (s, 1H), 8.56 (d, J = 1.5 Hz, 1H), 8.36 (d, J = 1.8 Hz, 1H), 7.97 (dd, J = 11.1, 1.2 Hz, 2H), 7.34 (s, 1H), 7.18 (s, 1H), 7.07 (s, 1H), 6.91-7.06 (m, 2H), 6.50 (d, J = 1.9 Hz, 1H), 3.83 (s, 3H), 3.67 (s, 3H), 2.18 (s, 3H) |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 562 | 4-(2',3'-difluoro-5-methoxy-2-methyl-4-biphenylyl)-N-3-isoxazolyl-7-quinazolinesulfonamide | 509.1 | 33 | 0.09 | | 1H NMR (ACETONITRILE-d3) d: 9.43-9.46 (m, 1H), 8.57 (d, J = 1.4 Hz, 1H), 8.38 (d, J = 1.9 Hz, 1H), 7.93-8.02 (m, 2H), 7.17-7.41 (m, 4H), 7.08 (s, 1H), 6.51 (d, J = 1.8 Hz, 1H), 3.65-3.68 (m, 3H), 2.18 (s, 3H) |
| 563 | 4-(2',4'-difluoro-5-methoxy-2-methyl-4-biphenylyl)-N-3-isoxazolyl-7-quinazolinesulfonamide | 509.1 | 33 | 0.105 | | 1H NMR (ACETONITRILE-d3) d: 9.44 (s, 1H), 8.52-8.58 (m, 1H), 8.36 (d, J = 1.9 Hz, 1H), 7.97 (dd, J = 11.1, 1.2 Hz, 2H), 7.40-7.48 (m, 1H), 7.35 (s, 1H), 7.08-7.17 (m, 2H), 7.04 (s, 1H), 6.50 (d, J = 1.8 Hz, 1H), 3.66 (s, 3H), 2.16 (s, 3H) |
| 564 | 4-(2',5'-difluoro-5-methoxy-2-methyl-4-biphenylyl)-N-3-isoxazolyl-7-quinazolinesulfonamide | 509.1 | 33 | 0.094 | | 1H NMR (ACETONITRILE-d3) d: 9.42 (s, 1H), 8.51-8.56 (m, 1H), 8.32 (d, J = 1.8 Hz, 1H), 7.96-8.03 (m, 1H), 7.92 (d, J = 0.6 Hz, 1H), 7.35 (s, 1H), 7.16-7.32 (m, 3H), 7.07 (s, 1H), 6.46 (d, J = 1.9 Hz, 1H), 3.66 (s, 3H), 2.18 (s, 3H) |
| 565 | 4-(2',6'-difluoro-5-methoxy-2-methyl-4-biphenylyl)-N-3-isoxazolyl-7-quinazolinesulfonamide | 509.1 | 33 | 0.199 | | 1H NMR (ACETONITRILE-d3) d: 9.42-9.47 (m, 1H), 8.54-8.59 (m, 1H), 8.36-8.41 (m, 1H), 7.93-8.02 (m, 2H), 7.46-7.55 (m, 1H), 7.38-7.42 (m, 1H), 7.09-7.20 (m, 3H), 6.49-6.53 (m, 1H), 3.65 (s, 3H), 2.15 (br. s., 3H) |
| 566 | 4-(4-(2,3-dihydro-1H-inden-5-yl)-2-methoxy-5-methylphenyl)-N-3-isoxazolyl-7-quinazolinesulfonamide | 513.0 | 33 | 0.169 | | 1H NMR (ACETONITRILE-d3) d: 9.40 (s, 1H), 8.54 (d, J = 1.6 Hz, 1H), 8.30 (d, J = 1.8 Hz, 1H), 7.98 (d, J = 1.9 Hz, 1H), 7.88-7.95 (m, 1H), 7.26-7.37 (m, 3H), 7.17-7.24 (m, 1H), 7.01 (s, 1H), 6.46 (d, J = 1.8 Hz, 1H), 3.66 (s, 3H), 2.94-3.01 (m, 4H), 2.24 (s, 3H), 2.12 (t, J = 7.4 Hz, 2H) |
| 328 | 4-(2-chloro-3'-fluoro-5-methoxy-4-biphenylyl)-N-3-isoxazolyl-2-methyl-1-oxo-1,2-dihydro-7-isoquinolinesulfonamide | 540.2 | 77 | 0.068 | | |
| 329 | 4-(2,3'-dichloro-4'-fluoro-5-methoxy-4-biphenylyl)-N-2-pyrimidinyl-7-quinazolinesulfonamide | 558.0 | 78 | 0.043 | | |
| 435 | 4-(2-chloro-3',5'-difluoro-5-methoxy-4-biphenylyl)-N-2-pyrimidinyl-7-quinazolinesulfonamide | 540.1 | 78 | 0.086 | | |
| 436 | 4-(2,4'-dichloro-5-methoxy-3'-methyl-4-biphenylyl)-N-2-pyrimidinyl-7-quinazolinesulfonamide | 554.2 | 78 | 0.087 | | |
| 437 | 4-(2,3'-dichloro-5-methoxy-4-biphenylyl)-N-2-pyrimidinyl-7-quinazolinesulfonamide | 540.1 | 78 | 0.072 | | |
| 438 | 4-(3',5'-difluoro-5-methoxy-2-methyl-4-biphenylyl)-N-2-pyrimidinyl-7-quinazolinesulfonamide | 520.1 | 89 | 0.094 | | |
| 440 | 4-(3'-chloro-5-methoxy-2-methyl-4-biphenylyl)-N-2-pyrimidinyl-7-quinazolinesulfonamide | 518.2 | 89 | 0.065 | | |
| 345 | 4-(3'-chloro-4'-fluoro-5-methoxy-2-methyl-4-biphenylyl)-N-2-pyrimidinyl-7-quinazolinesulfonamide | 536.1 | 89 | 0.078 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 439 | 4-(4'-chloro-5-methoxy-2,3'-dimethyl-4-biphenylyl)-N-2-pyrimidinyl-7-quinazolinesulfonamide | 532.2 | 89 | 0.104 | | |
| 330 | (M)-4-(2-chloro-3'-fluoro-5-methoxy-4-biphenylyl)-N-3-isoxazolyl-3-methyl-7-quinolinesulfonamide | 524.0 | 79 | 0.496 | | |
| 331 | (P)-4-(2-chloro-3'-fluoro-5-methoxy-4-biphenylyl)-N-3-isoxazolyl-3-methyl-7-quinolinesulfonamide | 524.0 | 79 | 10.53 | | |
| 332 | (P)-4-(2-chloro-3'-fluoro-5-methoxy-4-biphenylyl)-3-ethyl-N-3-isoxazolyl-7-quinolinesulfonamide | 538.1 | 80 | 33.69 | | |
| 333 | (M)-4-(2-chloro-3'-fluoro-5-methoxy-4-biphenylyl)-3-ethyl-N-3-isoxazolyl-7-quinolinesulfonamide | 538.1 | 80 | 0.591 | | |
| 334 | (P)-4-(2-chloro-3'-fluoro-5-methoxy-4-biphenylyl)-3-cyano-N-3-isoxazolyl-7-quinolinesulfonamide | 535.0 | 81 | 0.101 | | |
| 335 | (M)-4-(2-chloro-3'-fluoro-5-methoxy-4-biphenylyl)-3-cyano-N-3-isoxazolyl-7-quinolinesulfonamide | 535.0 | 81 | 0.112 | | |
| 443 | (M)-4-(2-chloro-3'-fluoro-5-methoxy-4-biphenylyl)-3-ethyl-N-3-isoxazolyl-7-cinnolinesulfonamide | 539.0 | 80 | 0.087 | | |
| 444 | (M)-4-(2-chloro-3'-fluoro-5-methoxy-4-biphenylyl)-3-ethyl-N-3-isoxazolyl-7-cinnolinesulfonamide | 539.0 | 80 | 1.162 | | |
| 441 | (M)-4-(2-chloro-3'-fluoro-5-methoxy-4-biphenylyl)-N-3-isoxazolyl-3-methyl-7-cinnolinesulfonamide | 525.0 | 79 | 0.052 | | |
| 442 | (P)-4-(2-chloro-3'-fluoro-5-methoxy-4-biphenylyl)-N-3-isoxazolyl-3-methyl-7-cinnolinesulfonamide | 525.0 | 79 | 0.251 | | |
| 336 | 3-amino-4-(2-chloro-3'-fluoro-5-methoxy-4-biphenylyl)-N-3-isoxazolyl-7-quinolinesulfonamide | 525.0 | 82 | 0.035 | | |
| 445 | 4-(2-chloro-3'-fluoro-5-methoxy-4-biphenylyl)-N-3-isoxazolyl-3-methoxy-7-cinnolinesulfonamide | 541.1 | 83 | 0.107 | | |
| 446 | 3-amino-4-(2-chloro-3'-fluoro-5-methoxy-4-biphenylyl)-N-3-isoxazolyl-7-cinnolinesulfonamide | 526.1 | 82 | 0.028 | | |
| 343 | 4-(3'-chloro-2-fluoro-5-methoxy-4-biphenylyl)-N-3-isoxazolyl-1-oxo-1,2-dihydro-7-isoquinolinesulfonamide | 526.1 | 87 | 0.163 | | |
| 451 | 4-(3'-chloro-2,5'-difluoro-5-methoxy-4-biphenylyl)-N-3-isoxazolyl-1-oxo-1,2-dihydro-7-isoquinolinesulfonamide | 544.1 | 87 | 0.077 | | |
| 452 | 4-(4'-chloro-2-fluoro-5-methoxy-3'-methyl-4-biphenylyl)-N-3-isoxazolyl-1-oxo-1,2-dihydro-7-isoquinolinesulfonamide | 540.0 | 87 | 0.184 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 337 | (M)-4-(2-chloro-3'-fluoro-5-methoxy-4-biphenylyl)-3-hydroxy-N-3-isoxazolyl-7-quinolinesulfonamide | 526.1 | 83 | 0.071 | | |
| 338 | (P)-4-(2-chloro-3'-fluoro-5-methoxy-4-biphenylyl)-3-hydroxy-N-3-isoxazolyl-7-quinolinesulfonamide | 526.1 | 83 | 0.041 | | |
| 339 | (M)-4-(2-chloro-3'-fluoro-5-methoxy-4-biphenylyl)-N-3-isoxazolyl-3-methoxy-7-quinolinesulfonamide | 540.2 | 83 | 0.63 | | |
| 340 | (P)-4-(2-chloro-3'-fluoro-5-methoxy-4-biphenylyl)-N-3-isoxazolyl-3-methoxy-7-quinolinesulfonamide | 540.2 | 83 | 0.084 | | |
| 344 | 4-(3'-chloro-2-fluoro-5-methoxy-4-biphenylyl)-N-3-isoxazolyl-2-methyl-1-oxo-1,2-dihydro-7-isoquinolinesulfonamide | 540.1 | 88 | 0.049 | | |
| 453 | 4-(3'-chloro-2,5'-difluoro-5-methoxy-4-biphenylyl)-N-3-isoxazolyl-2-methyl-1-oxo-1,2-dihydro-7-isoquinolinesulfonamide | 558.0 | 88 | 0.048 | | |
| 454 | 4-(4'-chloro-2-fluoro-5-methoxy-3'-methyl-4-biphenylyl)-N-3-isoxazolyl-2-methyl-1-oxo-1,2-dihydro-7-isoquinolinesulfonamide | 554.1 | 88 | 0.051 | | |
| 386 | 5-(5-cyano-6-(3,5-difluorophenyl)-2-oxo-1,2-dihydro-3-pyridinyl)-N-4-pyrimidinyl-2-naphthalenesulfonamide | 516.0 | 119 | | | |
| 361 | 4-(2-chloro-3'-fluoro-5-methoxy-4-biphenylyl)-N-3-isothiazolyl-7-quinazolinesulfonamide | 527.0 | 100 | 0.369 | | |
| 479 | 4-(2-chloro-3'-fluoro-5-methoxy-4-biphenylyl)-N-(5-fluoro-2-pyridinyl)-7-quinazolinesulfonamide | 539.2 | 100 | 0.221 | | |
| 362 | 1-(3'-(difluoromethyl)-2,5'-difluoro-5-methoxy-4-biphenylyl)-N-3-isoxazolyl-6-isoquinolinesulfonamide | 544.2 | 101 | 0.052 | | |
| 373 | 1-(2-cyano-5-methoxy-3'-(trifluoromethyl)-4-biphenylyl)-N-2-pyrimidinyl-6-isoquinolinesulfonamide | 562.2 | 107 | 0.057 | | |
| 374 | 1-(2-cyano-5-methoxy-3'-(trifluoromethyl)-4-biphenylyl)-N-(5-fluoro-2-pyrimidinyl)-6-isoquinolinesulfonamide | 580.2 | 108 | 0.094 | | |
| 375 | 4-(3'-chloro-2-fluoro-5-methoxy-4-biphenylyl)-N-(5-fluoro-2-pyrimidinyl)-7-quinazolinesulfonamide | 540.1 | 109 | 0.107 | | |
| 376 | 4-(3'-chloro-2-fluoro-5-methoxy-4-biphenylyl)-N-1,2,4-oxadiazol-3-yl-7-quinazolinesulfonamide | 512.0 | 110 | 0.028 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 377 | 4-(3'-chloro-2-fluoro-5-methoxy-4-biphenylyl)-N-3-isothiazolyl-7-quinazolinesulfonamide | 527.0 | 111 | 0.09 | | |
| 378 | 4-(2-chloro-3'-fluoro-5-methoxy-4-biphenylyl)-N-1,3-thiazol-4-yl-7-quinazolinesulfonamide | 527.2 | 112 | 0.231 | | |
| 379 | 1-(2,4'-dichloro-5-methoxy-3'-methyl-4-biphenylyl)-N-1,3,4-thiadiazol-2-yl-6-isoquinolinesulfonamide | 557.0 | 113 | 0.014 | | |
| 380 | 1-(2-chloro-3',5'-difluoro-5-methoxy-4-biphenylyl)-N-1,3,4-thiadiazol-2-yl-6-isoquinolinesulfonamide | 545.0 | 114 | 0.019 | | |

Biological Assays

The following assays were used in testing the exemplary compounds of the invention. Data for those examples tested in accordance with the procedures described below are presented in Table 1 herein.

Nav 1.7 or Nav 1.5 IWQ In Vitro Assay

HEK 293 Cells stably transfected with either Nav 1.7 or Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the 26$^{th}$ pulse to −20 mV was subtracted from the peak current evoked by the 26$^{th}$ pulse to −20 mV to correct for leak current. Percent block was calculated for each concentration in duplicate, and IC$_{50}$ curves were fitted to percent block as a function of concentration.

Nav 1.7 In Vitro PX Assay

HEK 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and IC$_{50}$ curves were fitted to percent inhibition as a function of concentration.

Nav 1.5 In Vitro PX Assay 293 cells stably transfected with Nav 1.5 were recorded in whole cell voltage clamp mode with the PatchXpress automated electrophysiology system according the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. IC$_{50}$ curves were fitted to percent inhibition as a function of concentration.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 μL with a 30 g needle Immediately following injection, a small metal band can be affixed to the plantar side of the left hindpaw with a drop of LOCTITE (adhesive) Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (−(Individual score−Vehicle average score)/Vehicle average score))*100=% MPE Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57B1/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 µL with a 30 g needle Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/−standard error for each group.

Mouse Open Field Assay

Mice (Naïve, male C57B1/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. In a room separate from the testing room, animals were pretreated with the appropriate test compound either by oral gavage or intraperitoneal injection at the desired pretreatment time (typically two hours before test onset) and then returned to their home cages until the pretreatment has elapsed. At test time, animal were transferred to the open field testing room in their home cages. Each animal was placed in a separate testing chamber and the motion tracking system was started. The house lights in the testing room were turned off and the animals were allowed to explore the novel open field for 30 minutes. An automated motion tracker, made by Kinder Scientific, Poway, Calif., was used to capture animal exploration with the aid of infrared photo beams to detect animal movement. These behaviors include basic movement and vertical rearing, which were used as the primary endpoints for this assay. At the end of the test, house lights were turned on and the animals were removed from the testing apparatus.

Statistical analysis was performed by analysis of variance (ANOVA), with post-hoc analysis using the Dunnett post-hoc test compared to the vehicle group for any significant main effect. Data were represented as mean+/−standard error for each group. Data was also expressed as a percent change from the vehicle control using the following equation:

(1−(Test mean/Vehicle mean))*100=% Change.

CFA—Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean–Pre-Drug Mean)/(Baseline Mean–Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

What is claimed is:

1. A compound of Formula I, or a pharmaceutically acceptable salt thereof,

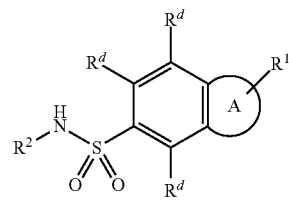

wherein:

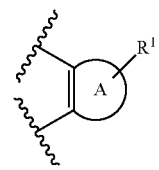

is

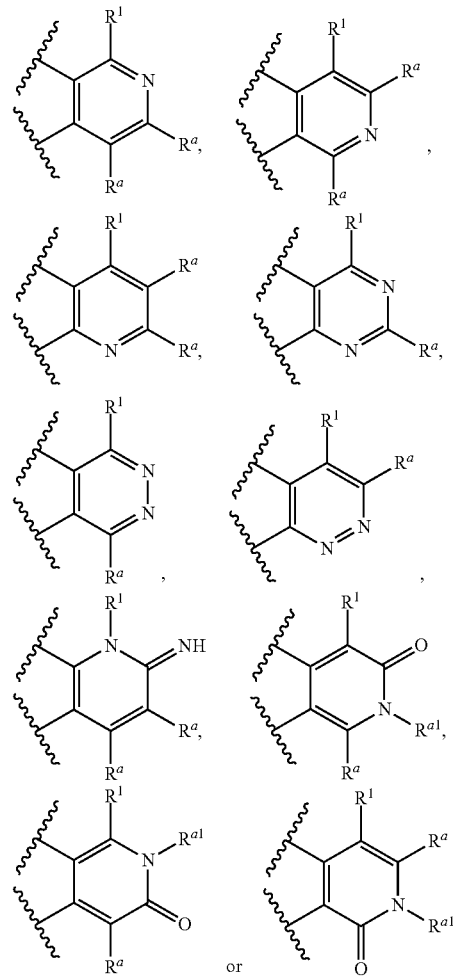

wherein each $R^a$ is independently H, halo, —$NR^cR^c$, —OH, hydroxy$C_{1-6}$alkyl, —$C_{1-6}$alkyl, —$OC_{1-6}$alkyl, —$C_{1-6}$haloalkyl, —$OC_{1-6}$haloalkyl or —CN, and $R^{a1}$ is H, —$C_{1-6}$alkyl or acetyl;

R[1] is a 6 membered aryl or heteroaryl, wherein the aryl or heteroaryl is substituted with from 1 to 4 substituents independently selected from halo, OH, —NR$^b$R$^b$, —C$_{1-6}$alkyl, —OC$_{1-6}$alkyl, —OC$_{1-6}$alkylCF$_3$, —OC$_{1-6}$alkylCN, —(CR$^e$R$^e$)$_m$CN,—C$_{1-6}$alkyl OC$_{1-6}$alkyl, —CF$_3$, —CHF$_2$, —CH$_2$F, —OCF$_3$, —OCHF$_2$, —OCH$_2$F, —(CR$^e$R$^e$)$_m$A, —N(R$^e$)(CR$^e$R$^e$)$_m$A, —O(CR$^e$R$^e$)$_m$A, —O(CR$^e$R$^e$)$_m$OA or —C(═O)A, provided at least one substituent on R[1] is —(CR$^e$R$^e$)$_m$A, —N(R$^e$)(CR$^e$R$^e$)$_m$A, —O(CR$^e$R$^e$)$_m$A, —O(CR$^e$R$^e$)$_m$OA or —C(═O)A;

A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —NR$^b$R$^b$, —C$_{1-6}$alkyl, —OC$_{1-6}$alkyl, —(CR$^e$R$^e$)$_m$OH, hydroxyC$_{1-6}$alkyl, —CF$_3$, —CHF$_2$, —CH$_2$F, —OCF$_3$, —OCHF$_2$, —OCH$_2$F, —CN, —C(═O)NR$^b$R$^b$, —O(CR$^e$R$^e$)$_m$B or —(CR$^e$R$^e$)$_m$B;

B is a 3 to 5 membered cycloalkyl group that can be unsubstituted or substituted with from 1 to 4 substituents independently selected from Cl, F, Br, —NHCH$_3$, —N(CH$_3$)$_2$, —C$_{1-4}$alkyl, —OC$_{1-4}$alkyl, —CF$_3$, —CHF$_2$, —CH$_2$F, —OCF$_3$, —OCHF$_2$, —OCH$_2$F or —CN;

R[2] is a 5 to 6 membered aryl or heteroaryl, where the heteroaryl can have from 1 to 3 heteroatoms independently selected from O, N or S, and the aryl and heteroaryl group can be unsubstituted or substituted with from 1 to 4 substituents independently selected from halo, —NR$^b$R$^b$, —C$_{1-6}$alkyl, —OC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(═O) NR$^b$R$^b$;

each R$^b$ is independently H or —C$_{1-6}$alkyl;
each R$^c$ is independently H or —C$_{1-6}$alkyl;
each R$^d$ is independently H, halo, —CN, —NR$^c$R$^c$, —OH, —C$_{1-6}$alkyl, —C$_{1-6}$haloalkyl, —OC$_{1-6}$haloalkyl or —OC$_{1-6}$alkyl;
each R$^e$ is independently H, halo, —CN, —NR$^c$R$^c$, —OH, —C$_{1-6}$alkyl or —OC$_{1-6}$alkyl;
each n is independently 0, 1, 2, 3 or 4; and
each m is independently 0, 1, 2, 3 or 4;
provided that the compound is not
1-(4-fluoro-2-(pyrimidin-5-yl)phenyl)-N-(thiazol-2-yl)isoquinoline-6-sulfonamide;
1-(4-fluoro-2-(pyrimidin-2-yloxy)phenyl)-N-(thiazol-2-yl)isoquinoline-6-sulfonamide;
5-methoxy-4-(2-methoxy-4-(trifluoromethyl)phenyl)-N-(thiazol-2-yl)quinoline-7-sulfonamide;
N-3-isoxazolyl-1-(3-methoxy-1-phenyl-1H-pyrazol-4-yl)-6-isoquinolinesulfonamide;
1-(2-methoxy-6-(tetrahydro-2H-pyran-4-yloxy)-3-pyridinyl)-N-4-pyrimidinyl-6-isoquinolinesulfonamide;
1-(2-(cyclohexylamino)-6-methoxy-3-pyridinyl)-N-4-pyrimidinyl-6-isoquinolinesulfonamide;
1-(2-((4,4-difluorocyclohexyl)amino)-6-methoxy-3-pyridinyl)-N-4-pyrimidinyl-6-isoquinolinesulfonamide;
1-(2-methoxy-6-(tetrahydro-2H-pyran-4-ylamino)-3-pyridinyl)-N-4-pyrimidinyl-6-isoquinolinesulfonamide;
1-(2-(4,4-difluoro-1-piperidinyl)-6-methoxy-3-pyridinyl)-N-4-pyrimidinyl-6-isoquinolinesulfonamide;
1-(6-methoxy-2-(1-pyrrolidinyl)-3-pyridinyl)-N-4-pyrimidinyl-6-isoquinolinesulfonamide;
1-(2-methoxy-6-(4-morpholinyl)-3-pyridinyl)-N-4-pyrimidinyl-6-isoquinolinesulfonamide;
1-(6-methoxy-2-(4-morpholinyl)-3-pyridinyl)-N-4-pyrimidinyl-6-isoquinolinesulfonamide;
1-(6-methoxy-2-(1-piperidinyl)-3-pyridinyl)-N-4-pyrimidinyl-6-isoquinolinesulfonamide;
1-(6-methoxy-2-(tetrahydro-2H-pyran-4-ylamino)-3-pyridinyl)-N-4-pyrimidinyl-6-isoquinolinesulfonamide;
1-(3',5'-difluoro-3-methoxy-4-biphenylyl)-N-(5-methoxy-4-pyrimidinyl)-6-isoquinolinesulfonamide; or
1-(2-methyl-5-(3-oxetanylmethoxy)phenyl)-N-4-pyrimidinyl-6-isoquinolinesulfonamide.

2. A compound in accordance with claim 1, or a pharmaceutically acceptable salt thereof, wherein

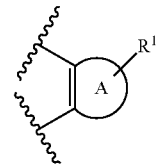

is

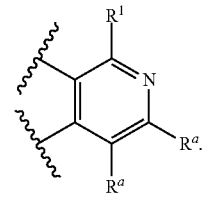

3. A compound in accordance with claim 1, or a pharmaceutically acceptable salt thereof, wherein

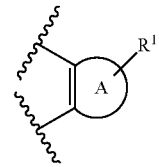

is

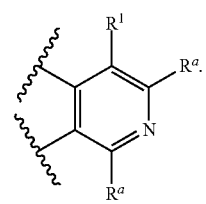

4. A compound in accordance with claim 1, or a pharmaceutically acceptable salt thereof, wherein

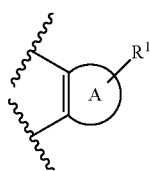

is

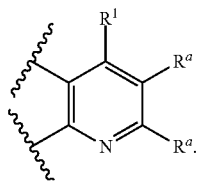

5. A compound in accordance with claim 1, or a pharmaceutically acceptable salt thereof, wherein

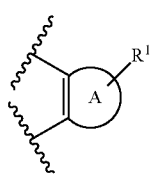

is

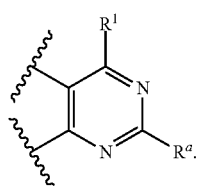

6. A compound in accordance with claim 1, or a pharmaceutically acceptable salt thereof, wherein

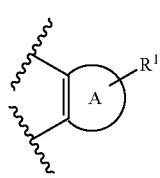

is

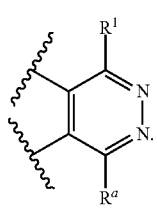

7. A compound in accordance with claim 1, or a pharmaceutically acceptable salt thereof, wherein

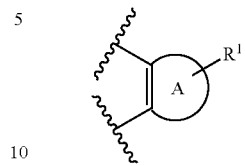

is

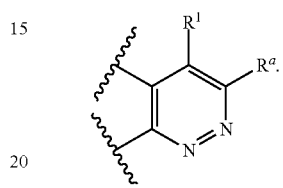

8. A compound in accordance with claim 1, or a pharmaceutically acceptable salt thereof, wherein

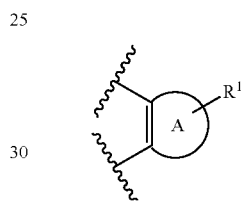

is

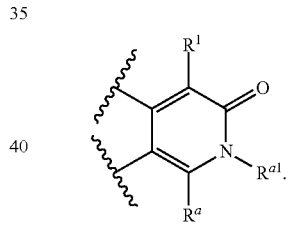

9. A compound in accordance with claim 1, or a pharmaceutically acceptable salt thereof, wherein

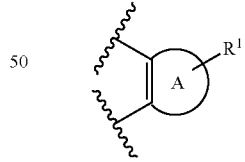

is

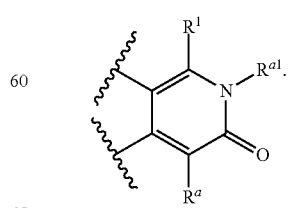

10. A compound in accordance with claim 1, or a pharmaceutically acceptable salt thereof, wherein is

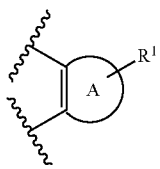

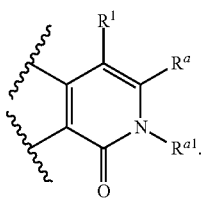

11. A compound in accordance with claim 1, or a pharmaceutically acceptable salt thereof, wherein each $R^d$ is independently H or F.

12. A compound in accordance with claim 1, or a pharmaceutically acceptable salt thereof, wherein
$R^1$ is a ring selected from phenyl, pyridinyl or pyrimidinyl, wherein the ring is substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, CN, —C(=O)$NR^bR^b$, —C(=O)$OR^b$, —OA or A, provided at least one substituent on $R^1$ is A or —OA; and
A is a 5 to 6 membered aryl or heteroaryl group, or a 4 to 6 membered N-linked heterocycloalkyl group, or a 3 to 6 membered cycloalkyl group, where the heteroaryl can have from 1 to 3 heteroatoms independently selected from O, N or S, the N-linked heterocycloalkyl can have 1 additional heteroatom independently selected from O, N or S, and the aryl, heteroaryl, heterocyclic and cycloalkyl group can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

13. A compound in accordance with claim 1, or a pharmaceutically acceptable salt thereof, wherein $R^1$ is a phenyl ring or pyridyl ring, wherein the ring is substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, CN, —C(=O)$NR^bR^b$ —C(=O)$OR^b$, —OA or A, provided at least one substituent on $R^1$ is A or —OA.

14. A compound in accordance with claim 1, or a pharmaceutically acceptable salt thereof, wherein A is a ring selected from phenyl, cyclopropyl, cyclopentyl, cyclohexyl, piperidinyl, piperazinyl, pyrrolidinyl, azetidinyl, pyridyl, pyrimidinyl, pyrazinyl or pyridazinyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

15. A compound in accordance with claim 1, or a pharmaceutically acceptable salt thereof, wherein
$R^1$ is a phenyl ring or pyridyl ring, wherein the ring is substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, CN, —C(=O)$NR^bR^b$ —C(=O)$OR^b$, —OA or A, provided at least one substituent on $R^1$ is A or —OA; and
A is a ring selected from phenyl, piperidinyl, piperazinyl, pyrrolidinyl, azetidinyl, cyclopentyl, pyridyl, pyrimidinyl, pyrazolyl or pyridazolyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

16. A compound in accordance with claim 1, or a pharmaceutically acceptable salt thereof, wherein
$R^1$ is a phenyl or pyridyl ring that is substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, CN, —C(=O)$NR^bR^b$, —C(=O)$OR^b$, —OA or A, provided at least one substituent on $R^1$ is A or —OA; and
A is a ring selected from phenyl or pyridyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

17. A compound in accordance with claim 1, or a pharmaceutically acceptable salt thereof, wherein $R^2$ is thiadiazolyl, substituted thiadiazolyl, thiazolyl, substituted thiazolyl, oxazolyl, substituted oxazolyl, oxadiazolyl, substituted oxadiazolyl, pyrimidinyl, substituted pyrimidinyl, isoxazolyl, substituted isoxazolyl, pyrazolyl, substituted pyrazolyl, pyridyl, substituted pyridyl, pyridazinyl, substituted pyridazinyl, pyrazinyl or substituted pyrazinyl.

18. A compound in accordance with claim 1, or a pharmaceutically acceptable salt thereof, wherein each $R^d$ is independently H.

19. A compound in accordance with claim 1, or a pharmaceutically acceptable salt thereof, wherein $R^2$ is a ring selected from 3-oxazolyl, 3-oxadiazolyl, 3-isoxazolyl, 2-thiazolyl, 4-thiazolyl, 2-thiadiazolyl, 3-isothiazolyl, 2-pyrimidinyl, 4-pyrimidinyl or 3-pyridazinyl, where the ring can be unsubstituted or substituted with from 1 to 4 substituents independently selected from F, Cl, —NH($CH_3$), —$CH_3$, —$CH_2CH_3$, propyl, isopropyl, —$OCH_3$, —$OCH_2CH_3$, propoxyl, —$CF_3$, —$CHF_2$, —$CH_2F$, —$OCF_3$, —$OCHF_2$, —$OCH_2F$ or —CN.

20. A compound in accordance with claim 1, or a pharmaceutically acceptable salt thereof, wherein

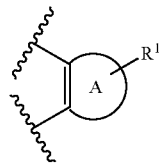

is

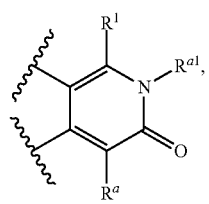 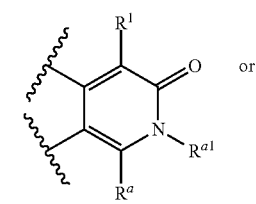

539

-continued

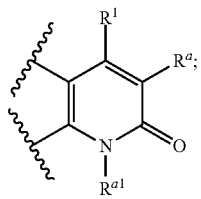

each $R^a$ is independently H, halo, —C$_{1-6}$alkyl, —OC$_{1-6}$alkyl, —C$_{1-6}$haloalkyl, —OC$_{1-6}$haloalkyl or —CN;

$R^1$ is a ring selected from phenyl or pyridyl, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on $R^1$ is A or —OA;

A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxy C$_{1-6}$alkyl —CF$_3$, —CHF$_2$, —CH$_2$F, —OCF$_3$, —OCHF$_2$, —OCH$_2$F, —CN or —C(=O)NR$^b$R$^b$;

$R^2$ is a ring selected from thiazolyl, isothiazolyl, thiadiazolyl, oxazolyl, isoxazolyl, oxadiazolyl, pyrazolyl, pyrimidinyl, pyridyl, pyridazinyl or pyrazinyl, where the ring can be unsubstituted or substituted with from 1 to 4 substituents independently selected from halo, —NR$^b$R$^b$, —C$_{1-6}$alkyl, —OC$_{1-6}$alkyl, hydroxy C$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F or —CN; and each $R^d$ is independently H.

21. A compound in accordance with claim 1, or a pharmaceutically acceptable salt thereof, wherein

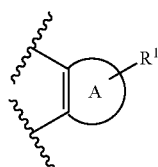

is

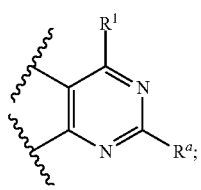

$R^a$ is independently H, halo, , —C$_{1-6}$alkyl, —OC$_{1-6}$alkyl, —C$_{1-6}$haloalkyl, —OC$_{1-6}$haloalkyl or —CN;

$R^1$ is a ring selected from phenyl or pyridyl, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on $R^1$ is A or —OA;

540

A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxy C$_{1-6}$alkyl —CF$_3$, —CHF$_2$, —CH$_2$F, —OCF$_3$, —OCHF$_2$, —OCH$_2$F, —CN, C$_{3-6}$cycloalkyl or —C(=O)NR$^b$R$^b$; and $R^2$ is a ring selected from thiazolyl, isothiazolyl, thiadiazolyl, oxazolyl, isoxazolyl, oxadiazolyl, pyrazolyl, pyrimidinyl, pyridyl, pyridazinyl or pyrazinyl, where the ring can be unsubstituted or substituted with from 1 to 4 substituents independently selected from halo, —NR$^b$R$^b$, —C$_{1-6}$alkyl, —OC$_{1-6}$alkyl, hydroxy C$_{1-6}$alkyl, —(CR$^c$R$^c$)$_n$R$^b$R$^b$, —CF$_3$, —CHF$_2$, —CH$_2$F, —OCF$_3$, —OCHF$_2$, —OCH$_2$F or —CN; and each $R^d$ is independently H.

22. A compound, or a pharmaceutically acceptable salt thereof, selected from:
- 1-(2-chloro-3'-fluoro-5-methoxy-4-biphenylyl)-7-fluoro-N-3-isoxazolyl-6-isoquinolinesulfonamide;
- 7-fluoro-1-(3'-fluoro-3-methoxy-4-biphenylyl)-N-1,2,4-thiadiazol-5-yl-6-isoquinolinesulfonamide;
- N-3-isoxazolyl-1-(3-methoxy-4-biphenylyl)-6-isoquinolinesulfonamide;
- 1-(3-methoxy-4-biphenylyl)-N-1,3,4-thiadiazol-2-yl-6-isoquinolinesulfonamide;
- 1-(6-(cyclohexylmethoxy)-2-methoxy-3-pyridinyl)-N-4-pyrimidinyl-6-isoquinolinesulfonamide;
- 1-(6-((4,4-difluorocyclohexyl)methoxy)-2-methoxy-3-pyridinyl)-N-4-pyrimidinyl-6-isoquinolinesulfonamide;
- 1-(6-(cyclohexylamino)-2-methoxy-3-pyridinyl)-N-4-pyrimidinyl-6-isoquinolinesulfonamide;
- 1-(4'-chloro-2-cyano-3'-fluoro-5-methoxy-4-biphenylyl)-N-3-isoxazolyl-6-isoquinolinesulfonamide;
- 1-(2-cyano-3'-fluoro-5-methoxy-5'-methyl-4-biphenylyl)-N-3-isoxazolyl-6-isoquinolinesulfonamide;
- 1-(3'-chloro-2-cyano-5-methoxy-4'-methyl-4-biphenylyl)-N-3-isoxazolyl-6-isoquinolinesulfonamide;
- 1-(2-cyano-5-methoxy-2'-methyl-4-biphenylyl)-N-3-isoxazolyl-6-isoquinolinesulfonamide;
- 1-(2-cyano-3',4'-difluoro-5-methoxy-4-biphenylyl)-N-3-isoxazolyl-6-isoquinolinesulfonamide;
- 1-(2-cyano-3'-fluoro-5-methoxy-4'-methyl-4-biphenylyl)-N-3-isoxazolyl-6-isoquinolinesulfonamide;
- 1-(4'-chloro-2-cyano-5-methoxy-3'-methyl-4-biphenylyl)-N-3-isoxazolyl-6-isoquinolinesulfonamide;
- 1-(5-cyano-4-(5-fluoro-2-methoxy-3-pyridinyl)-2-methoxyphenyl)-N-3-isoxazolyl-6-isoquinolinesulfonamide;
- 1-(3'-chloro-2-cyano-4'-fluoro-5-methoxy-4-biphenylyl)-N-3-isoxazolyl-6-isoquinolinesulfonamide;
- 1-(2-cyano-4'-fluoro-5-methoxy-3'-methyl-4-biphenylyl)-N-3-isoxazolyl-6-isoquinolinesulfonamide;
- 1-(3'-chloro-2-cyano-5'-fluoro-5-methoxy-4-biphenylyl)-N-3-isoxazolyl-6-isoquinolinesulfonamide;
- 1-(4'-chloro-2-fluoro-5-methoxy-3'-methyl-4-biphenylyl)-N-3-pyridazinyl-6-isoquinolinesulfonamide;
- 1-(4'-chloro-2-fluoro-5-methoxy-3'-methyl-4-biphenylyl)-N-2-pyrimidinyl-6-isoquinolinesulfonamide;
- 1-(2,4'-difluoro-5-methoxy-3'-methyl-4-biphenylyl)-N-3-isoxazolyl-6-isoquinolinesulfonamide;
- 1-(4'-chloro-2-fluoro-5-methoxy-3'-methyl-4-biphenylyl)-N-3-isoxazolyl-6-isoquinolinesulfonamide;
- 1-(3'-chloro-2-fluoro-5-methoxy-4'-methyl-4-biphenylyl)-N-3-isoxazolyl-6-isoquinolinesulfonamide;

1-(5-fluoro-4-(5-fluoro-2-methoxy-3-pyridinyl)-2-methoxyphenyl)-N-2-pyrimidinyl-6-isoquinolinesulfonamide;
1-(5-fluoro-4-(5-fluoro-2-methoxy-3-pyridinyl)-2-methoxyphenyl)-N-3-isoxazolyl-6-isoquinolinesulfonamide;
1-(2-chloro-4'-fluoro-5-methoxy-3'-methyl-4-biphenylyl)-N-3-isoxazolyl-6-isoquinolinesulfonamide;
1-(4'-chloro-2,3'-difluoro-5-methoxy-4-biphenylyl)-N-3-isoxazolyl-6-isoquinolinesulfonamide;
1-(2,3'-dichloro-5-methoxy-4'-methyl-4-biphenylyl)-N-3-isoxazolyl-6-isoquinolinesulfonamide;
1-(3'-chloro-2-fluoro-5-methoxy-4-biphenylyl)-N-2-pyrimidinyl-6-isoquinolinesulfonamide;
N-3-isoxazolyl-1-(2,3',5'-trifluoro-5-methoxy-4-biphenylyl)-6-isoquinolinesulfonamide;
1-(5-fluoro-4-(5-fluoro-2-methoxy-3-pyridinyl)-2-methoxyphenyl)-N-3-isothiazolyl-6-isoquinolinesulfonamide;
1-(2,4'-dichloro-3'-fluoro-5-methoxy-4-biphenylyl)-N-3-isoxazolyl-6-isoquinolinesulfonamide 1-(3',5'-difluoro-3-(1-methyl-1H-pyrazol-5-yl)-4-biphenylyl)-N-3-isoxazolyl-6-isoquinolinesulfonamide;
1-(5-chloro-4-(5-fluoro-2-methoxy-3-pyridinyl)-2-methoxyphenyl)-N-3-isoxazolyl-6-isoquinolinesulfonamide;
1-(2-cyano-4'-fluoro-5-methoxy-4-biphenylyl)-N-3-isoxazolyl-6-isoquinolinesulfonamide;
1-(2-cyano-3',5'-difluoro-5-methoxy-4-biphenylyl)-N-2-pyrimidinyl-6-isoquinolinesulfonamide;
1-(3',5'-difluoro-3-methoxy-4-biphenylyl)-N-3-isothiazolyl-6-isoquinolinesulfonamide;
N-3-isoxazolyl-1-(3-methoxy-3'-(trifluoromethyl)-4-biphenylyl)-6-isoquinolinesulfonamide;
1-(2-chloro-3'-fluoro-5-methoxy-4-biphenylyl)-N-2-pyrimidinyl-6-isoquinolinesulfonamide;
1-(2-cyano-3'-fluoro-5-methoxy-4-biphenylyl)-N-2-pyrimidinyl-6-isoquinolinesulfonamide;
1-(6-chloro-3'-fluoro-4-methoxy-3-biphenylyl)-N-1,3,4-thiadiazol-2-yl-6-isoquinolinesulfonamide;
1-(3'-chloro-2-cyano-5-methoxy-4-biphenylyl)-N-3-isoxazolyl-6-isoquinolinesulfonamide;
1-(2-cyano-5-methoxy-3'-methyl-4-biphenylyl)-N-3-isoxazolyl-6-isoquinolinesulfonamide;
1-(3'-chloro-2-cyano-5-methoxy-5'-methyl-4-biphenylyl)-N-3-isoxazolyl-6-isoquinolinesulfonamide;
1-(2-fluoro-5-methoxy-3'-(trifluoromethyl)-4-biphenylyl)-N-3-isoxazolyl-6-isoquinolinesulfonamide;
1-(3'-chloro-2-fluoro-5-methoxy-4-biphenylyl)-N-3-isoxazolyl-6-isoquinolinesulfonamide;
1-(4-bromo-5-chloro-2-methoxyphenyl)-N-3-isoxazolyl-6-isoquinolinesulfonamide;
1-(2-cyano-5-methoxy-3'-(trifluoromethyl)-4-biphenylyl)-N-1,2,4-oxadiazol-3-yl-6-isoquinolinesulfonamide;
1-(2,4'-dichloro-5-methoxy-3'-methyl-4-biphenylyl)-N-3-isoxazolyl-6-isoquinolinesulfonamide;
1-(2-chloro-3'-fluoro-5-methoxy-4-biphenylyl)-N-3-pyridazinyl-6-isoquinolinesulfonamide;
1-(6-chloro-3'-fluoro-4-methoxy-3-biphenylyl)-N-3-isoxazolyl-6-isoquinolinesulfonamide;
1-(2-chloro-3'-fluoro-5-methoxy-4-biphenylyl)-N-1,2,4-oxadiazol-3-yl-6-isoquinolinesulfonamide;
1-(6-chloro-3'-fluoro-4-methoxy-3-biphenylyl)-N-2-pyrimidinyl-6-isoquinolinesulfonamide;
1-(3',5'-difluoro-3-methoxy-4-biphenylyl)-N-2-pyrimidinyl-6-isoquinolinesulfonamide;
1-(3',5'-difluoro-3-methoxy-4-biphenylyl)-N-1,2,4-oxadiazol-3-yl-6-isoquinolinesulfonamide;
1-(3',5'-difluoro-3-methoxy-4-biphenylyl)-N-(5-fluoro-2-pyrimidinyl)-6-isoquinolinesulfonamide;
1-(3',5'-difluoro-3-methoxy-4-biphenylyl)-N-3-pyridazinyl-6-isoquinolinesulfonamide;
1-(3',5'-difluoro-3-methoxy-4-biphenylyl)-N-3-isoxazolyl-6-isoquinolinesulfonamide;
1-(2-cyano-3'-fluoro-5-methoxy-4-biphenylyl)-N-4-pyrimidinyl-6-isoquinolinesulfonamide;
1-(3-(hydroxymethyl)-3'-(trifluoromethyl)-4-biphenylyl)-N-3-isoxazolyl-6-isoquinolinesulfonamide;
1-(2-cyano-5-methoxy-4'-(trifluoromethyl)-4-biphenylyl)-N-3-isoxazolyl-6-isoquinolinesulfonamide;
1-(4-methoxy-4'-(trifluoromethyl)-3-biphenylyl)-N-4-pyrimidinyl-6-isoquinolinesulfonamide;
1-(2-cyano-5-methoxy-3'-(trifluoromethyl)-4-biphenylyl)-N-3-isoxazolyl-6-isoquinolinesulfonamide;
1-(4'-chloro-2-cyano-3'-fluoro-5-methoxy-4-biphenylyl)-N-4-pyrimidinyl-6-isoquinolinesulfonamide;
1-(2-cyano-4'-fluoro-5-methoxy-3'-methyl-4-biphenylyl)-N-4-pyrimidinyl-6-isoquinolinesulfonamide;
1-(2-cyano-5-methoxy-3'-methyl-4-biphenylyl)-N-4-pyrimidinyl-6-isoquinolinesulfonamide;
1-(2-cyano-5-methoxy-2'-methyl-4-biphenylyl)-N-4-pyrimidinyl-6-isoquinolinesulfonamide;
1-(3'-chloro-2-cyano-4'-fluoro-5-methoxy-4-biphenylyl)-N-4-pyrimidinyl-6-isoquinolinesulfonamide;
1-(3'-chloro-2-cyano-5-methoxy-4'-methyl-4-biphenylyl)-N-4-pyrimidinyl-6-isoquinolinesulfonamide;
1-(3'-chloro-2-cyano-5-methoxy-5'-methyl-4-biphenylyl)-N-4-pyrimidinyl-6-isoquinolinesulfonamide;
1-(4'-chloro-2-cyano-5-methoxy-3'-methyl-4-biphenylyl)-N-4-pyrimidinyl-6-isoquinolinesulfonamide;
1-(2-cyano-3'-fluoro-5-methoxy-4'-methyl-4-biphenylyl)-N-4-pyrimidinyl-6-isoquinolinesulfonamide;
1-(2-cyano-3'-fluoro-5-methoxy-5'-methyl-4-biphenylyl)-N-4-pyrimidinyl-6-isoquinolinesulfonamide;
1-(2-cyano-5-methoxy-2',4',5'-trimethyl-4-biphenylyl)-N-4-pyrimidinyl-6-isoquinolinesulfonamide;
1-(2-cyano-3',5'-difluoro-5-methoxy-4-biphenylyl)-N-4-pyrimidinyl-6-isoquinolinesulfonamide;
1-(4-(5-fluoro-2-methoxy-3-pyridinyl)-2-methoxyphenyl)-N-1,3,4-thiadiazol-2-yl-6-isoquinolinesulfonamide;
1-(5-chloro-4-(difluoromethyl)-2-methoxyphenyl)-N-3-isoxazolyl-6-isoquinolinesulfonamide;
1-(2-methoxy-4-(2-methylphenoxy)phenyl)-N-4-pyrimidinyl-6-isoquinolinesulfonamide;
1-(3',4'-difluoro-5-methoxy-2-methyl-4-biphenylyl)-N-1,3,4-thiadiazol-2-yl-6-isoquinolinesulfonamide;
1-(3',5'-difluoro-5-methoxy-2-methyl-4-biphenylyl)-N-1,3,4-thiadiazol-2-yl-6-isoquinolinesulfonamide;
1-(4-(4-fluorophenoxy)-2-methoxyphenyl)-N-1,3,4-thiadiazol-2-yl-6-isoquinolinesulfonamide;
1-(4-(3,4-difluorophenoxy)-2-methoxyphenyl)-N-4-pyrimidinyl-6-isoquinolinesulfonamide;
1-(4-(3,4-dimethylphenoxy)-2-methoxyphenyl)-N-4-pyrimidinyl-6-isoquinolinesulfonamide;
1-(4-(3-fluoro-4-methylphenoxy)-2-methoxyphenyl)-N-4-pyrimidinyl-6-isoquinolinesulfonamide;
1-(4-(3-fluoro-5-methylphenoxy)-2-methoxyphenyl)-N-4-pyrimidinyl-6-isoquinolinesulfonamide;
1-(2-methoxy-4-(3-methylphenoxy)phenyl)-N-4-pyrimidinyl-6-isoquinolinesulfonamide;
1-(2-methoxy-4-(3-methoxyphenoxy)phenyl)-N-4-pyrimidinyl-6-isoquinolinesulfonamide;

1-(2-cyano-5-methoxy-3'-(trifluoromethyl)-4-biphenylyl)-N-4-pyrimidinyl-6-isoquinolinesulfonamide;
1-(2-cyano-5-methoxy-4'-(trifluoromethyl)-4-biphenylyl)-N-4-pyrimidinyl-6-isoquinolinesulfonamide;
1-(2-cyano-4'-fluoro-5-methoxy-4-biphenylyl)-N-4-pyrimidinyl-6-isoquinolinesulfonamide;
1-(4-(2,5-difluorophenoxy)-2-methoxyphenyl)-N-1,3,4-thiadiazol-2-yl-6-isoquinolinesulfonamide;
1-(2-methoxy-4-(2-methoxy-5-methyl-3-pyridinyl)phenyl)-N-1,3,4-thiadiazol-2-yl-6-isoquinolinesulfonamide;
1-(4-(1H-indol-1-yl)-2-methoxyphenyl)-N-1,3,4-thiadiazol-2-yl-6-isoquinolinesulfonamide;
1-(4-(2-fluoro-5-methylphenoxy)-2-methoxyphenyl)-N-1,3,4-thiadiazol-2-yl-6-isoquinolinesulfonamide;
1-(4-(5-fluoro-2-methoxy-3-pyridinyl)-2-methoxyphenyl)-N-3-isoxazolyl-6-isoquinolinesulfonamide;
1-(4-(3-fluoro-4-methylphenoxy)-2-methoxyphenyl)-N-1,3,4-thiadiazol-2-yl-6-isoquinolinesulfonamide;
1-(4-(3-fluoro-5-methylphenoxy)-2-methoxyphenyl)-N-1,3,4-thiadiazol-2-yl-6-isoquinolinesulfonamide;
1-(2-cyano-3',4'-difluoro-5-methoxy-4-biphenylyl)-N-4-pyrimidinyl-6-isoquinolinesulfonamide;
1-(3-(cyanomethoxy)-3'-fluoro-4-biphenylyl)-N-4-pyrimidinyl-6-isoquinolinesulfonamide;
1-(2-cyano-5-methoxy-3'-methyl-4-biphenylyl)-N-1,3,4-thiadiazol-2-yl-6-isoquinolinesulfonamide;
1-(2-cyano-3'-fluoro-5-methoxy-4'-methyl-4-biphenylyl)-N-1,3,4-thiadiazol-2-yl-6-isoquinolinesulfonamide;
1-(2-cyano-5-methoxy-4'-(trifluoromethyl)-4-biphenylyl)-N-1,3,4-thiadiazol-2-yl-6-isoquinolinesulfonamide;
1-(2-cyano-4'-fluoro-5-methoxy-4-biphenylyl)-N-1,3,4-thiadiazol-2-yl-6-isoquinolinesulfonamide;
1-(2-cyano-5-methoxy-2'-methyl-4-biphenylyl)-N-1,3,4-thiadiazol-2-yl-6-isoquinolinesulfonamide;
1-(3'-chloro-2-cyano-4'-fluoro-5-methoxy-4-biphenylyl)-N-1,3,4-thiadiazol-2-yl-6-isoquinolinesulfonamide;
1-(2-chloro-3'-fluoro-5-methoxy-4-biphenylyl)-4-hydroxy-N-3-isoxazolyl-6-isoquinolinesulfonamide;
1-(2-cyano-3'-fluoro-5-methoxy-5'-methyl-4-biphenylyl)-N-1,3,4-thiadiazol-2-yl-6-isoquinolinesulfonamide;
1-(5-cyano-4-(5-fluoro-2-methoxy-3-pyridinyl)-2-methoxyphenyl)-N-1,3,4-thiadiazol-2-yl-6-isoquinolinesulfonamide;
1-(4'-chloro-2-cyano-3'-fluoro-5-methoxy-4-biphenylyl)-N-1,3,4-thiadiazol-2-yl-6-isoquinolinesulfonamide;
1-(3'-chloro-2-cyano-5-methoxy-5'-methyl-4-biphenylyl)-N-1,3,4-thiadiazol-2-yl-6-isoquinolinesulfonamide;
1-(4'-chloro-2-cyano-5-methoxy-3'-methyl-4-biphenylyl)-N-1,3,4-thiadiazol-2-yl-6-isoquinolinesulfonamide;
1-(3'-chloro-2-cyano-5-methoxy-4'-methyl-4-biphenylyl)-N-1,3,4-thiadiazol-2-yl-6-isoquinolinesulfonamide;
1-(2-cyano-4'-fluoro-5-methoxy-3'-methyl-4-biphenylyl)-N-1,3,4-thiadiazol-2-yl-6-isoquinolinesulfonamide;
1-(3-(cyanomethoxy)-3'-fluoro-4-biphenylyl)-N-3-isoxazolyl-6-isoquinolinesulfonamide;
1-(3-(cyanomethoxy)-3'-fluoro-4-biphenylyl)-N-1,3,4-thiadiazol-2-yl-6-isoquinolinesulfonamide;
1-(2-chloro-3'-fluoro-5-methoxy-4-biphenylyl)-4-cyano-N-3-isoxazolyl-6-isoquinolinesulfonamide;
1-(4-chloro-2-methoxy-5-methylphenyl)-N-3-isoxazolyl-6-isoquinolinesulfonamide;
1-(5-chloro-2-methoxy-4-(trifluoromethyl)phenyl)-N-3-isoxazolyl-6-isoquinolinesulfonamide;
1-(4'-chloro-5-methoxy-2,3'-dimethyl-4-biphenylyl)-N-3-isoxazolyl-6-isoquinolinesulfonamide;
1-(2-chloro-3'-fluoro-5-methoxy-4-biphenylyl)-N-3-isothiazolyl-6-isoquinolinesulfonamide;
1-(2-chloro-3'-fluoro-5-methoxy-4-biphenylyl)-N-1,3-oxazol-2-yl-6-isoquinolinesulfonamide;
N-3-isoxazolyl-1-(2-methoxy-5-methyl-4-(trifluoromethyl)phenyl)-6-isoquinolinesulfonamide;
1-(3',5'-difluoro-5-methoxy-2-methyl-4-biphenylyl)-N-3-isoxazolyl-6-isoquinolinesulfonamide;
1-(3',4'-difluoro-5-methoxy-2-methyl-4-biphenylyl)-N-3-isoxazolyl-6-isoquinolinesulfonamide;
1-(3'-fluoro-5-methoxy-2,5'-dimethyl-4-biphenylyl)-N-3-isoxazolyl-6-isoquinolinesulfonamide;
1-(4'-fluoro-5-methoxy-2,3'-dimethyl-4-biphenylyl)-N-3-isoxazolyl-6-isoquinolinesulfonamide;
N-3-isoxazolyl-1-(5-methoxy-2,2',4',5'-tetramethyl-4-biphenylyl)-6-isoquinolinesulfonamide;
N-3-isoxazolyl-1-(5-methoxy-2,3'-dimethyl-4-biphenylyl)-6-isoquinolinesulfonamide;
1-(3'-chloro-5-methoxy-2-methyl-4-biphenylyl)-N-3-isoxazolyl-6-isoquinolinesulfonamide;
N-3-isoxazolyl-1-(5-methoxy-2-methyl-3'-(trifluoromethyl)-4-biphenylyl)-6-isoquinolinesulfonamide;
1-(4-(5-fluoro-2-methoxy-3-pyridinyl)-2-methoxy-5-methylphenyl)-N-3-isoxazolyl-6-isoquinolinesulfonamide;
1-(5'-fluoro-2',5-dimethoxy-2-methyl-4-biphenylyl)-N-3-isoxazolyl-6-isoquinolinesulfonamide;
1-(5'-chloro-2',5-dimethoxy-2-methyl-4-biphenylyl)-N-3-isoxazolyl-6-isoquinolinesulfonamide;
1-(3'-chloro-5-methoxy-2,4'-dimethyl-4-biphenylyl)-N-3-isoxazolyl-6-isoquinolinesulfonamide;
1-(3'-chloro-5-methoxy-2,5'-dimethyl-4-biphenylyl)-N-3-isoxazolyl-6-isoquinolinesulfonamide;
1-(3'-chloro-4'-fluoro-5-methoxy-2-methyl-4-biphenylyl)-N-3-isoxazolyl-6-isoquinolinesulfonamide;
1-(3'-chloro-5'-fluoro-5-methoxy-2-methyl-4-biphenylyl)-N-3-isoxazolyl-6-isoquinolinesulfonamide;
1-(4'-chloro-3'-fluoro-5-methoxy-2-methyl-4-biphenylyl)-N-3-isoxazolyl-6-isoquinolinesulfonamide;
1-(3'-chloro-3-methoxy-4'-methyl-4-biphenylyl)-N-3 soxazolyl-6-isoquinolinesulfonamide;
1-(4'-chloro-3-methoxy-3'-methyl-4-biphenylyl)-N-3 soxazolyl-6-isoquinolinesulfonamide;
1-(4'-chloro-3'-fluoro-3-methoxy-4-biphenylyl)-N-3 soxazolyl-6-isoquinolinesulfonamide; or
3-cyano-1-(2,3'-difluoro-5-methoxy-4-biphenylyl)-N-3 soxazolyl-6-isoquinolinesulfonamide.

23. A compound, or a pharmaceutically acceptable salt thereof, selected from:
1-(2-fluoro-5-methoxy-3'-(trifluoromethyl)-4-biphenylyl)-N-3-isoxazolyl-6-phthalazinesulfonamide;
4-(2-fluoro-5-methoxy-3'-(trifluoromethyl)-4-biphenylyl)-N-3-isoxazolyl-7-quinazolinesulfonamide;
4-(4'-chloro-2-fluoro-5-methoxy-3'-methyl-4-biphenylyl)-N-3-isoxazolyl-7-quinazolinesulfonamide;
4-(3'-chloro-2-fluoro-5-methoxy-4-biphenylyl)-N-3-isoxazolyl-7-quinazolinesulfonamide;
1-(2-chloro-3'-fluoro-5-methoxy-4-biphenylyl)-N-3-isoxazolyl-6-phthalazinesulfonamide;
1-(2-chloro-3'-fluoro-5-methoxy-4-biphenylyl)-N-2-pyrimidinyl-6-phthalazinesulfonamide;

1-(2-chloro-3'-fluoro-5-methoxy-4-biphenylyl)-N-1,3,4-thiadiazol-2-yl-6-phthalazinesulfonamide;
4-(5'-fluoro-2',5-dimethoxy-2-methyl-4-biphenylyl)-N-3-isoxazolyl-7-quinazolinesulfonamide;
4-(4-(5-fluoro-6-methyl-2-pyridinyl)-2-methoxy-5-methylphenyl)-N-3-isoxazolyl-7-quinazolinesulfonamide;
4-(4-(5-fluoro-2-methoxy-3-pyridinyl)-2-methoxy-5-methylphenyl)-N-3-isoxazolyl-7-quinazolinesulfonamide;
4-(3',4'-difluoro-5-methoxy-2-methyl-4-biphenylyl)-N-3-isoxazolyl-7-quinazolinesulfonamide;
4-(5-cyano-4-(5-fluoro-2-methoxy-3-pyridinyl)-2-methoxyphenyl)-N-3-isoxazolyl-7-quinazolinesulfonamide;
4-(2-chloro-3'-fluoro-5-methoxy-4-biphenylyl)-N-3-pyridazinyl-7-quinazolinesulfonamide;
4-(2-cyano-3',5'-difluoro-5-methoxy-4-biphenylyl)-N-3-isoxazolyl-7-quinazolinesulfonamide;
4-(2-cyano-3'-fluoro-5-methoxy-4-biphenylyl)-N-3-isoxazolyl-7-quinazolinesulfonamide;
4-(2,3'-dichloro-4'-fluoro-5-methoxy-4-biphenylyl)-N-3-isoxazolyl-7-quinazolinesulfonamide;
4-(5-cyano-4-(5-fluoro-2-methoxy-3-pyridinyl)-2-methoxyphenyl)-N-1,3,4-thiadiazol-2-yl-7-quinazolinesulfonamide;
4-(2,4'-dichloro-5-methoxy-3'-methyl-4-biphenylyl)-N-3-isoxazolyl-7-quinazolinesulfonamide;
4-(2-chloro-3',5'-difluoro-5-methoxy-4-biphenylyl)-N-3-isoxazolyl-7-quinazolinesulfonamide;
4-(2-chloro-3'-fluoro-5-methoxy-4-biphenylyl)-N-1,2,5-thiadiazol-3-yl-7-quinazolinesulfonamide;
4-(2-cyano-5-methoxy-3'-(trifluoromethyl)-4-biphenylyl)-N-3-isoxazolyl-7-quinazolinesulfonamide;
4-(2-chloro-4'-fluoro-5-methoxy-3'-methyl-4-biphenylyl)-N-3-isoxazolyl-7-quinazolinesulfonamide;
4-(5-chloro-4-(5-fluoro-2-methoxy-3-pyridinyl)-2-methoxyphenyl)-N-3-isoxazolyl-7-quinazolinesulfonamide;
4-(2-cyano-3',5'-difluoro-5-methoxy-4-biphenylyl)-N-1,3,4-thiadiazol-2-yl-7-quinazolinesulfonamide;
4-(2-cyano-5-methoxy-3'-(trifluoromethyl)-4-biphenylyl)-N-1,3,4-thiadiazol-2-yl-7-quinazolinesulfonamide;
4-(2-chloro-3'-fluoro-5-methoxy-4-biphenylyl)-N-3-isoxazolyl-7-quinazolinesulfonamide;
4-(2-chloro-3'-fluoro-5-methoxy-4-biphenylyl)-N-1,2,4-oxadiazol-3-yl-7-quinazolinesulfonamide;
4-(2-cyano-3'-fluoro-5-methoxy-4-biphenylyl)-N-1,3,4-thiadiazol-2-yl-7-quinazolinesulfonamide;
4-(2-chloro-3'-fluoro-5-methoxy-4-biphenylyl)-N-2-pyrimidinyl-7-quinazolinesulfonamide;
1-(2,4'-dichloro-5-methoxy-3'-methyl-4-biphenylyl)-N-3-isoxazolyl-6-phthalazinesulfonamide;
1-(2,3'-dichloro-5-methoxy-4'-methyl-4-biphenylyl)-N-3-isoxazolyl-6-phthalazinesulfonamide;
4-(4-chloro-2-methoxy-5-methylphenyl)-N-3-isoxazolyl-7-quinazolinesulfonamide;
4-(4'-chloro-5-methoxy-2,3'-dimethyl-4-biphenylyl)-N-3-isoxazolyl-7-quinazolinesulfonamide;
1-(2-chloro-3'-fluoro-5-methoxy-4-biphenylyl)-N-3-isoxazolyl-4-methoxy-6-phthalazinesulfonamide;
1-(2,4'-dichloro-5-methoxy-3'-methyl-4-biphenylyl)-N-3-isothiazolyl-6-phthalazinesulfonamide;
1-(2-chloro-3',5'-difluoro-5-methoxy-4-biphenylyl)-N-3-isothiazolyl-6-phthalazinesulfonamide;
4-(5-chloro-2-methoxy-4-(trifluoromethyl)phenyl)-N-3-isoxazolyl-7-quinazolinesulfonamide;
4-(3',5'-difluoro-5-methoxy-2-methyl-4-biphenylyl)-N-3-isoxazolyl-7-quinazolinesulfonamide;
4-(3'-fluoro-5-methoxy-2,5'-dimethyl-4-biphenylyl)-N-3-isoxazolyl-7-quinazolinesulfonamide;
4-(4'-fluoro-5-methoxy-2,3'-dimethyl-4-biphenylyl)-N-3-isoxazolyl-7-quinazolinesulfonamide;
N-3-isoxazolyl-4-(5-methoxy-2,2',4',5'-tetramethyl-4-biphenylyl)-7-quinazolinesulfonamide;
N-3-isoxazolyl-4-(5-methoxy-2,3'-dimethyl-4-biphenylyl)-7-quinazolinesulfonamide;
4-(3'-chloro-5-methoxy-2-methyl-4-biphenylyl)-N-3-isoxazolyl-7-quinazolinesulfonamide;
N-3-isoxazolyl-4-(5-methoxy-2-methyl-3'-(trifluoromethyl)-4-biphenylyl)-7-quinazolinesulfonamide;
4-(5'-chloro-2',5-dimethoxy-2-methyl-4-biphenylyl)-N-3-isoxazolyl-7-quinazolinesulfonamide;
4-(3'-chloro-5-methoxy-2,4'-dimethyl-4-biphenylyl)-N-3-isoxazolyl-7-quinazolinesulfonamide;
4-(3'-chloro-5-methoxy-2,5'-dimethyl-4-biphenylyl)-N-3-isoxazolyl-7-quinazolinesulfonamide;
4-(3'-chloro-4'-fluoro-5-methoxy-2-methyl-4-biphenylyl)-N-3-isoxazolyl-7-quinazolinesulfonamide;
4-(3'-chloro-5'-fluoro-5-methoxy-2-methyl-4-biphenylyl)-N-3-isoxazolyl-7-quinazolinesulfonamide;
4-(4'-chloro-3'-fluoro-5-methoxy-2-methyl-4-biphenylyl)-N-3-isoxazolyl-7-quinazolinesulfonamide; or 4-(2-chloro-3'-fluoro-5-methoxy-4-biphenylyl)-N-(5-fluoro-2-pyrimidinyl)-7-quinazolinesulfonamide.

24. A pharmaceutical composition comprising a compound in accordance with claim 1, or a pharmaceutically acceptable salt thereof, and a pharmaceutically acceptable excipient.

* * * * *